US012595249B2

(12) United States Patent
Zhang et al.

(10) Patent No.: US 12,595,249 B2
(45) Date of Patent: Apr. 7, 2026

(54) ARYL ETHER-SUBSTITUTED HETEROCYCLIC COMPOUNDS AS GLPIR AGONISTS

(71) Applicant: MINDRANK AI LTD, Hangzhou (CN)

(72) Inventors: Long Zhang, Hangzhou (CN); Zhangming Niu, Hangzhou (CN); Bowen Tang, Hangzhou (CN)

(73) Assignee: MINDRANK AI LTD., Hangzhou (CN)

( * ) Notice: Subject to any disclaimer, the term of this patent is extended or adjusted under 35 U.S.C. 154(b) by 0 days.

(21) Appl. No.: 19/084,086

(22) Filed: Mar. 19, 2025

(65) Prior Publication Data

US 2025/0304553 A1 Oct. 2, 2025

Related U.S. Application Data

(63) Continuation of application No. 18/255,247, filed as application No. PCT/CN2022/075295 on Jan. 31, 2022.

(30) Foreign Application Priority Data

Aug. 30, 2021 (CN) ......................... 202111017657.5
Sep. 29, 2021 (CN) ......................... 202111168512.5

(51) Int. Cl.
*C07D 401/14* (2006.01)
*C07D 405/14* (2006.01)
*C07D 471/04* (2006.01)

(52) U.S. Cl.
CPC ......... *C07D 401/14* (2013.01); *C07D 405/14* (2013.01); *C07D 471/04* (2013.01)

(58) Field of Classification Search
CPC .................................................... C07D 401/14
USPC .......................................................... 514/303
See application file for complete search history.

(56) References Cited

U.S. PATENT DOCUMENTS

| | | | |
|---|---|---|---|
| 11,926,626 B2 | 3/2024 | Meng et al. | |
| 12,221,442 B2 | 2/2025 | Meng et al. | |
| 2020/0325121 A1 | 10/2020 | Zhong et al. | |
| 2021/0171499 A1 | 6/2021 | Ammann et al. | |
| 2022/0135588 A1 | 5/2022 | Yu et al. | |
| 2022/0396569 A1 | 12/2022 | Du et al. | |
| 2023/0002348 A1 | 1/2023 | Yoon et al. | |
| 2023/0089073 A1 | 3/2023 | Du et al. | |
| 2023/0126875 A1 | 4/2023 | Yang et al. | |
| 2023/0234968 A1 | 7/2023 | Chen | |
| 2024/0067630 A1* | 2/2024 | Zhang | A61K 31/506 |
| 2024/0246958 A1 | 7/2024 | Yang et al. | |
| 2024/0360110 A1 | 10/2024 | Zhai et al. | |

FOREIGN PATENT DOCUMENTS

| | | | |
|---|---|---|---|
| CN | 110325530 A | 10/2019 |
| CN | 111333714 A | 6/2020 |
| CN | 111548311 A | 8/2020 |
| CN | 113227068 A | 8/2021 |
| CN | 113480534 A | 10/2021 |
| CN | 113493447 A | 10/2021 |
| CN | 114728939 A | 7/2022 |
| CN | 114728940 A | 7/2022 |
| CN | 115521297 A | 12/2022 |
| CN | 115594669 A | 1/2023 |
| CN | 117043154 A | 11/2023 |
| TW | 202128658 A | 8/2021 |
| TW | 202128659 A | 8/2021 |
| WO | WO 2002/026228 A1 | 4/2002 |
| WO | WO 2008/019477 A1 | 2/2008 |
| WO | WO 2009/018656 A1 | 2/2009 |
| WO | WO 2018/056453 A1 | 3/2018 |
| WO | WO 2018/109607 A1 | 6/2018 |
| WO | WO 2018/200833 A1 | 11/2018 |
| WO | WO 2019/165374 A1 | 8/2019 |
| WO | WO 2019/239319 A1 | 12/2019 |
| WO | WO 2019/239371 A1 | 12/2019 |
| WO | WO 2020/043638 A1 | 3/2020 |
| WO | WO 2020/103815 A1 | 5/2020 |
| WO | 2020207474 A1 | 10/2020 |
| WO | WO 2020/263695 A1 | 12/2020 |
| WO | WO 2021/018023 A1 | 2/2021 |
| WO | WO 2021/081207 A1 | 4/2021 |
| WO | 2021096284 A1 | 5/2021 |
| WO | WO 2021/096304 A1 | 5/2021 |
| WO | 2021112538 A1 | 6/2021 |
| WO | WO 2021/130723 A1 | 7/2021 |
| WO | WO 2021/150673 A1 | 7/2021 |
| WO | WO 2021/154796 A1 | 8/2021 |
| WO | WO 2021/155841 A1 | 8/2021 |
| WO | WO 2021/160127 A1 | 8/2021 |
| WO | WO 2021/197464 A1 | 10/2021 |
| WO | WO 2021/219019 A1 | 11/2021 |
| WO | WO 2021/242807 A1 | 12/2021 |

(Continued)

OTHER PUBLICATIONS

Griffith, David A. et al.; "A small-molecule oral agonist of the human glucagon-like peptide-1 receptor"; bioRxiv preprint doi: https://doi.org/10.1101/2020.09.29.319483; Sep. 30, 2020; pp. 1-33.
Berge, Stephen M. et al., "Pharmaceutical Salts", Journal of Pharmaceutical Science; vol. 66, No. 1; Jan. 1977; pp. 1-19.

*Primary Examiner* — Niloofar Rahmani
(74) *Attorney, Agent, or Firm* — Jones Day

(57) ABSTRACT

A novel aryl ether substituted heterocyclic compound has GLP1R agonist activity. Specifically, the compound of formula (I) can be used as a GLP1R agonist. The pharmaceutically acceptable salt, solvate, hydrate, isotope substituent or isomer of the compound are also provided. A method for preventing and/or treating diseases related to the GLP1/GLP1R signaling pathway includes the step of administering to a patient a preventive or therapeutically effective amount the compound, a pharmaceutically acceptable salt, or an enantiomer thereof.

13 Claims, 3 Drawing Sheets

(56) References Cited

FOREIGN PATENT DOCUMENTS

| | | | |
|---|---|---|---|
| WO | WO 2021/242817 | A1 | 12/2021 |
| WO | WO 2021/244391 | A1 | 12/2021 |
| WO | WO 2021/244645 | A1 | 12/2021 |
| WO | WO 2021/249492 | A1 | 12/2021 |
| WO | WO 2021/254470 | A1 | 12/2021 |
| WO | WO 2021/259309 | A1 | 12/2021 |
| WO | WO 2022/007979 | A1 | 1/2022 |
| WO | WO 2022/028572 | A1 | 2/2022 |
| WO | WO 2022/042691 | A1 | 3/2022 |
| WO | WO 2022/048665 | A1 | 3/2022 |
| WO | WO 2022/052958 | A1 | 3/2022 |
| WO | WO 2022/068772 | A1 | 4/2022 |
| WO | WO 2022/078380 | A1 | 4/2022 |
| WO | WO 2022/078407 | A1 | 4/2022 |
| WO | WO 2022/165076 | A1 | 8/2022 |
| WO | WO 2022/235717 | A1 | 11/2022 |
| WO | WO 2022/268152 | A1 | 12/2022 |
| WO | WO 2023/000834 | A1 | 1/2023 |
| WO | WO 2023/222124 | A1 | 11/2023 |

* cited by examiner

ARYL ETHER-SUBSTITUTED HETEROCYCLIC COMPOUNDS AS GLPIR AGONISTS

This application is a continuation of U.S. patent application Ser. No. 18/255,247, filed on May 31, 2023, which is a U.S. national entry of PCT International Application No. PCT/CN2022/075295, filed on Jan. 31, 2022, which claims the priority of the previous applications submitted to the State Intellectual Property Office of China on Aug. 30, 2021, with the patent application number of 202111017657.5 and the name of "novel aromatic ether substituted heterocyclic compound as GLP1R agonist" and submitted to the State Intellectual Property Office of China on Sep. 29, 2021 with the patent application number of 202111168512.5 and the name of "novel aromatic ether substituted heterocyclic compound as GLP1R agonist". The full text of the earlier applications are incorporated herein by reference.

TECHNICAL FIELD

The invention belongs to the field of medicinal chemistry, specifically comprising novel aryl ether substituted heterocyclic compounds having GLP1R agonistic activity, compositions comprising the class of compounds and methods for applying the class of compounds to the preparation of drugs for the treatment or prevention of diseases associated with GLP1/GLP1R.

BACKGROUND OF THE INVENTION

With the improvement of living standards, overweight or obesity is becoming more and more common in modern society. The number of patients with obesity related complications such as diabetes and fatty liver is increasing. Reports from the World Health Organization (WHO) and ZhiYan advisory predict that the number of obese patients in the world will reach 3.26 billion by 2030; By 2029, the number of global patients with diabetes will exceed 500 million; The number of patients with nonalcoholic fatty liver disease in the world will exceed 1.5 billion. At present, there is no effective drug for fatty liver; There are only 6 drugs approved by FDA for the treatment of obesity, and most of them are controlled drugs with weak efficacy and strong side effects; Although many drugs for the treatment of type 2 diabetes have been approved for marketing, achieved optimal diabetes control-rate (HbAlc<7%), and the achieved optimal diabetes control-rate of even the most active combination drug is only about 45%. Therefore, for fatty liver, obesity or diabetes, new drugs need to be developed to meet the unmet needs of more patients.

Glucagon-like peptide-1 (GLP-1) is a long peptide hormone containing 30 or 31 amino acids. It is produced and secreted by enteroendocrine L cells and certain neurons in the nucleus tractus solitarius of the brainstem during feeding. GLP-1 stimulates insulin secretion, reduces glucagon secretion, inhibits gastric emptying, reduces appetite, and stimulates beta cell proliferation in a physiological and glucose-dependent manner. In non-clinical experiments, GLP-1 promotes β-cell persistence by stimulating transcription of genes important, for glucose-dependent insulin secretion and promoting β-cell regeneration (Meier, et al. Biodrugs. 2003; 17 (2): 93-102). The GLP1 receptor is a proven ideal target for the treatment of metabolic diseases such as obesity, diabetes, fatty liver, etc., and several GLP1R agonist peptide drugs such as dulaglutide, somalutamide have been approved abroad for the treatment of diabetes and weight loss.

However, these peptides need to be injected with poor compliance, high cost, poor accessibility, and heavy social medical burden. These peptides need to be refrigerated, which is inconvenient to carry and store. In addition, these peptides are difficult for combination use with existing oral small molecule drugs for diseases having complex causes and requiring treatment of multiple drug combinations, such as nonalcoholic fatty liver disease. Therefore, there is an urgent need to develop small-molecule oral GLP1R agonists.

Oral small molecule GLP1 agonists have been reported in a few literatures or patents: for example, Pfizer's PF-06882961 can achieve similar or better efficacy as GLP1 polypeptides (https://doi.org/10.1101/2020.09.29.319483). Although the efficacy and safety have been preliminarily verified, PF-06882961 has some druggability deficiencies, such as poor oral absorption, extremely low bioavailability, high clinical dosage, and heavy burden on gastrointestinal tract of patients (GI toxicity), which cannot achieve better glucose—and weight-lowering effect by further increasing the drug amount, and so on. Therefore, it is necessary to develop new small-molecule GLP1 agonists with better druggabilities to meet the needs of more patients.

TECHNICAL EFFECTS

The inventors unexpectedly found that some of the novel aryl ether-substituted heterocyclic compounds of formula (I) of the present invention not only have significant GLP1R agonistic activity, but also have better pharmacokinetics parameters (including longer T1/2, higher exposure) and bioavailability than the reference compound PF-06882961 with a known structure. These compounds are expected to have better human PK, and are more suitable as drug candidates for preventing or treating diseases related to GLP1/GLP1R target or signaling pathway.

SUMMARY OF INVENTION

The object of the present invention is to provide the compound represented by Formula (I) or its pharmaceutically acceptable salt, solvate, enantiomer and isotopic variations thereof.

Formula (I)

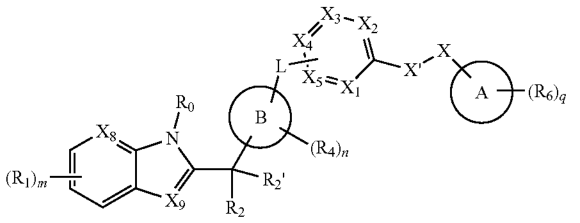

Wherein,

Ring A and ring B are optionally and independently selected from monocyclic or polycyclic structures of 3 to 18 carbons atoms, and the monocyclic or polycyclic structures can be optionally selected from aromatic rings, heteroaromatic rings, aliphatic rings, heterocyclic rings, fused, spirocyclic or bridged ring structures;

X and X' are each independently selected from —C($R_{d1}$)($R_{d2}$)—, —C(—O)N($R_{d3}$)—, —N($R_{d4}$)—, —C(═$NR_{d5}$)—, —S(═O)$_2$N($R_{d6}$)—, —N($R_{d7}$)—, —O—, —S—, —C(═O)O—, —OC(═O)—, —C(═O)—, —C(═S)—, —S(═O)—, or —S(═O)$_2$—;

L is independently selected from —C($R_{d1}$)($R_{d2}$)—, —OC($R_{d1}$)($R_{d2}$)—, —C($R_{d1}$)($R_{d2}$)O—, —C(═O)N($R_{d3}$)—, —N($R_{d4}$)—, —C(═$NR_{d5}$)—, —S(═O)$_2$ N($R_{d6}$)—, —N($R_{d7}$)—, —O—, —S—, —C(═O)O—, —OC(═O)—, —C(═O)—, —C(═S)—, —S(═O)—, or —S(═O)$_2$—;

$X_1$, $X_2$, $X_3$, $X_4$, $X_5$, $X_8$ and $X_9$, are each independently selected from —$CR_5$— or —N—;

$R_0$ is independently selected from hydrogen, deuterium, halogen, —CN, $C_{1-10}$ alkyl, $C_{2-10}$ alkenyl, $C_{2-10}$ alkynyl, $C_{1-10}$ alkoxy, —$NRd_8Rd_9$, 6- to 10-membered aryl, 5- to 8-membered heteroaryl, 3- to 8-membered saturated or partially saturated cycloalkyl and 3- to 8-membered saturated or partially saturated heterocyclyl, wherein $R_0$ representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally optimally substituted with one to multiple substituent groups, the substituent groups are optionally selected from hydrogen, deuterium, halogen, alkyl, haloalkyl, alkoxy, alkylamino, O═, CN, OH, —$NRd_8Rd_9$, $C_{3-10}$ saturated or partially saturated cycloalkyl, $C_{3-10}$ saturated or partially saturated heterocyclic group, 6- to 10-aryl and 5- to 8-membered heteroaryl; Wherein the aryl, heteroaryl, saturated or partially saturated cycloalkyl, saturated or partially saturated heterocyclyl are further optionally substituted with one to multiple substituents, and the substituents are optionally selected from hydrogen, deuterium, Halogen, alkyl, haloalkyl, cyano, cyanoethyl, O═, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with 1 to 3 substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate, preferably, the carboxyl surrogate is

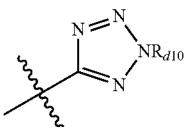
or
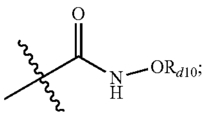

Wherein $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or, partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkylcarboxyl or carboxyl surrogates are optionally optimally substituted with one to more substituents selected from H, deuterium, halogen, $OCH_3$, Carboxyl, OH, CN and $NR_{d8}R_{d9}$; Or any two adjacent $R_1$ together with the carbon to which they are attached form a 5- to 6-membered heteroaryl, 3- to 8-membered saturated or partially saturated cycloalkyl, 3- to 8-membered saturated or partially saturated heterocyclyl, the hydrogen on the aryl, saturated or the partially saturated cycloalkyl, heterocycloalkyl is optionally substituted with hydrogen, deuterium, halogen, —CN, —OH, $CF_3$, $C_{1-6}$ alkyl, $C_{1-6}$ alkoxy, —$NH_2$, —$NHC_{1-6}$ alkyl, —N($C_{1-6}$ alkyl)$_2$, ═O, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl.

Each $R_2$, $R_2$' and $R_{d1}$, $R_{d2}$ is the same or different and is independently selected from hydrogen, deuterium, halogen, $C_{1-10}$ alkyl, $C_{2-10}$ alkenyl, $C_{2-10}$ alkynyl, $C_{1-10}$ alkylamino, N, N-di($C_{1-10}$ alkyl)amino, $C_{1-10}$ alkoxy, $C_{1-10}$ alkylacyl, $C_{1-10}$ alkoxy, $C_{1-10}$ alkylsulfonyl, $C_{1-10}$ alkylsulfinyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxyacetyl, $C_{3-10}$ cycloalkylsulfonyl and $C_{3-10}$ cycloalkylsulfinyl; and the alkyl, alkenyl, alkynyl, aryl, saturated or partially saturated cycloalkyl, heterocycloalkyl are optionally substituted with one to more selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —N($C_{1-6}$ alkyl)$_2$, oxy, and saturated or partially saturated $C_{3-6}$ cycloalkyl, and the $C_{1-6}$ alkyl and $C_{1-6}$ alkoxy are optionally further substituted with one to more selected from hydrogen, deuterium, halogen, oxo, CN, $CF_3$, OH, $OCH_3$, $OCH_2CH_3$ and saturated or partially saturated $C_{3-6}$ cycloalkyl; Or optionally $R_2$ and $R_2$: or Rai and $R_{d2}$ may together with the carbon to which they are attached form 5- to 6-membered aryl or heteroaryl, 3- to 8-membered saturated or partially saturated cycloalkyl, 3- to 8-membered saturated or partially saturated heterocyclic group, wherein the cycloalkyl and heterocycloalkyl are optionally substituted with one to more groups selected from hydrogen, deuterium, halogen, oxo, CN, $CF_3$, OH, $OCH_3$, $OCH_2CH_3$;

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy are optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ are the same or different and is independently selected from hydrogen, deuterium, halogen, CN, OH, SH, $NRd_8R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or heterocyclyl; Or any adjacent two $R_5$ or $R_6$ together with the carbon to which they are attached form 5- to 6-heteroaryl, 3- to 8-saturated or partially saturated cycloalkyl, 3- to 8-saturated or partially saturated heterocyclyl, and wherein the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

$R_{d3}$, $R_{d4}$, $R_{d5}$, $R_{d6}$, $R_{d7}$, $R_{d8}$, $R_{d9}$ and $R_{d10}$ are the same or different, and are optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

the hetero represents any heteroatom optionally and independently selected from O, N, S, P and isotopes thereof;

the halogen is optionally and independently selected from F, Cl, Br, I and isotopes thereof;

m is an integer optionally selected from 1, 2, 3 and 4;

n is an integer optionally selected from 0, 1, 2, 3, 4 and 5;

q is an integer optionally selected from 0, 1, 2, 3, 4 and 5.

In one embodiment of the present invention, the compound or a pharmaceutically acceptable salt, isotopic variations or isomer thereof has the structure of Formula (IA), Formula (IA)

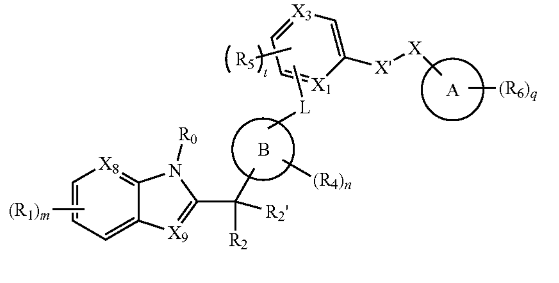

Wherein,

Ring A and ring B are optionally and independently selected from monocyclic or polycyclic structures of 3 to 18 carbons atoms, and the monocyclic or polycyclic structures can be optionally selected from aromatic rings, heteroaromatic rings, aliphatic rings, heterocyclic rings, fused, spirocyclic or bridged ring structures;

X and X' are each independently selected from —$C(R_{d1})(R_{d2})$—, —$C(=O)N(R_{d3})$—, —$N(R_{d4})$—, —$C(=NR_{d5})$—, —$S(—O)_2N(R_{d6})$—, —$N(R_{d7})$—, —O—, —S—, —C(=O)O—, —OC(=O)—, —C(=O)—, —C(=S)—, —S(=O)—, or —$S(=O)_2$—;

L is independently selected from —$C(R_{d1})(R_{d2})$—, —$OC(R_{d1})(R_{d2})$—, —$C(Rai)(R_{d2})O$—, —$C(=O)N(R_{d3})$—, —$N(R_{d4})$—, —$C(=NR_{d5})$—, —$S(=O)_2$ $N(R_{d6})$—, —$N(R_{d7})$—, —O—, —S—, —C(=O)O—, —OC(=O)—, —C(=O)—, —C(=S)—, —S(=O)—, or —$S(=O)_2$—;

$X_1$, $X_3$, $X_8$ and $X_9$ are each independently selected from —$CR_5$— or —N—;

$R_0$ is independently selected from hydrogen, deuterium, halogen, —CN, $C_{1-10}$ alkyl, $C_{2-10}$ alkenyl, $C_{2-10}$ alkynyl, $C_{1-10}$ alkoxy, —$NR_{d8}R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein $R_0$ representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally optimally substituted with one to multiple substituent groups, the substituent groups are optionally selected from hydrogen, deuterium, halogen, alkyl, haloalkyl, alkoxy, alkylamino, O=, CN, OH, —$NRd_8R_{d9}$, $C_{3-10}$ saturated or partially saturated cycloalkyl, $C_{3-10}$ saturated or partially saturated heterocyclic group, 6- to 10-aryl and 5- to 8-membered heteroaryl; Wherein the aryl, heteroaryl, saturated or partially saturated cycloalkyl, saturated or partially saturated heterocyclyl are further optionally substituted with one to multiple substituents, and the substituents are optionally selected from hydrogen, deuterium, halogen, alkyl, haloalkyl, cyano, cyanoethyl, O=, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally optimally substituted with 1 to 3 substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ Alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate,

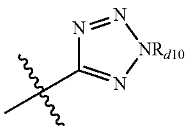 or 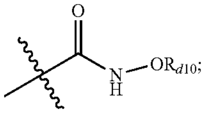

preferably, the carboxyl surrogate is Wherein $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkylcarboxyl or carboxyl surrogates are optionally optimally substituted with one to more substituents selected from H, Deuterium, Halogen, $OCH_3$, Carboxyl, OH, CN and $NRd_8R_{d9}$; Or any two adjacent $R_1$ together with the carbon to which they are attached form a 5- to 6-membered heteroaryl, 3- to 8-membered saturated or partially saturated cycloalkyl, 3- to 8-membered saturated or partially saturated heterocyclyl, hydrogen on the aryl, saturated or the partially saturated cycloalkyl, heterocycloalkyl is optionally substituted with hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, —O, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl.

Each $R_2$, $R_2$, and $R_{d1}$, $R_{d2}$ is the same or different and is independently selected from hydrogen, deuterium, halogen, $C_{1-10}$ alkyl, $C_{2-10}$ alkenyl, $C_{2-10}$ alkynyl, $C_{1-10}$ alkylamino, N, N-di($C_{1-10}$ alkyl)amino, $C_{1-10}$ alkoxy, $C_{1-10}$ alkylacyl, $C_{1-10}$ alkoxy, $C_{1-10}$ alkylsulfonyl, $C_{1-10}$ alkylsulfinyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxyacetyl, $C_{3-10}$ cycloalkylsulfonyl and $C_{3-10}$ cycloalkylsulfinyl; and the alkyl, alkenyl, alkynyl, aryl, saturated or partially saturated cycloalkyl, heterocycloalkyl are optionally substituted with one to more selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$ and saturated or partially saturated $C_{3-6}$ cycloalkyl; Or optionally $R_2$ and $R^2$ or Ral and $R_{d2}$ may together with the carbon to which they are attached form 5- to 6-membered aryl or heteroaryl, 3- to 8-membered saturated or partially saturated cycloalkyl, 3- to 8-membered saturated or partially saturated heterocyclic group, wherein the cycloalkyl and heterocycloalkyl are optionally substituted with one to more groups selected from hydrogen, deuterium, halogen, oxo, CN, $CF_3$, OH, $OCH_3$, $OCH_2CH_3$;

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy are optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and independently selected from the group consisting of hydrogen, deuterium, halogen, CN, OH, SH, $NR_{d8}R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl, wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or Heterocyclyl; Or any adjacent two $R_5$ or $R_6$ together with the carbon to which they are attached form 5- to 6-membered heteroaryl, 3- to 8-membered saturated or partially saturated cycloalkyl, 3- to 8-membered saturated or partially saturated heterocyclyl, and the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy is optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d3}$, $R_{d4}$, $R_{d5}$, $R_{d6}$, $R_{d7}$, $R_{d5}$, Rag and $R_{d10}$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof;

m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

In one embodiment of the present invention, the compound or a pharmaceutically acceptable salt, isotopic variations or isomer thereof has the structure of Formula (IB), Formula (IB)

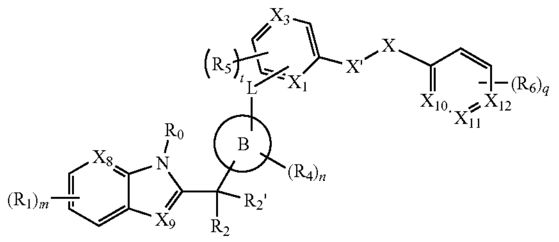

Wherein,

Ring B is optionally and independently selected from monocyclic or polycyclic structures of 3 to 18 carbons atoms, and the monocyclic or polycyclic structures can be optionally selected from aromatic rings, heteroaromatic rings, aliphatic rings, heterocyclic rings, fused, spirocyclic or bridged ring structures;

X and X' are independently selected from —C($R_{d1}$)($R_{d2}$)—, —C(═O)N($R_{d3}$)—, —N($R_{d4}$)—, —C(═N$R_{d5}$)—, —S(═O)$_2$N($R_{d6}$)—, —N($R_{d2}$)—, —O—, —S—, —C(═O)O—, —OC(═O)—, —C(═O)—, —C(═S)—, —S(═O)—, or —S(═O)$_2$—;

L is independently selected from —C($R_{d1}$)($R_{d2}$)—, —OC($R_{d1}$)($R_{d2}$)—, —C($R_{d1}$)($R_{d2}$)O—, —C(═O)N($R_{d3}$)—, —N($R_{d4}$)—, —C(═N$R_{d5}$)—, —S(═O)$_2$ N($R_{d6}$)—, —N($R_{d7}$)—, —O—, —S—, —C(═O)O—, —OC(═O)—, —C(═O)—, —C(═S)—, —S(═O)—, or —S(═O)$_2$—; $X_1$, $X_3$, $X_8$, $X_9$ $X_{10}$, $X_{11}$ and $X_{12}$ are independently selected from —$CR_5$— or —N—;

$R_0$ is independently selected from hydrogen, deuterium, halogen, —CN, $C_{1-10}$ alkyl, $C_{2-10}$ alkenyl, $C_{2-10}$ alkynyl, $C_{1-10}$ alkoxy, —N$R_{d8}R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein $R_0$ representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally substituted with one to multiple substituent groups, the substituent groups are optionally selected from hydrogen, deuterium, halogen, alkyl, Haloalkyl, carboxyl, alkoxy, alkylamino, O═, CN, OH, —NRd$_8R_{d9}$, $C_{3-10}$ saturated or partially saturated cycloalkyl, $C_{3-10}$ saturated or partially saturated heterocyclic group, 6- to 10-aryl and 5- to 8-membered heteroaryl; Wherein the aryl, heteroaryl, saturated or partially saturated cycloalkyl, saturated or partially saturated heterocyclyl are optionally substituted with one to multiple substituents, and the substituents are optionally selected from hydrogen, deuterium, Halogen, alkyl, haloalkyl, cyano, cyanoethyl, O═, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with one to three substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ Alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate, preferably, the carboxyl surrogate is

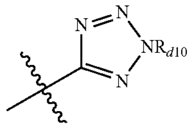

or

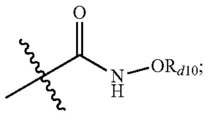

Wherein $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkylcarboxyl or carboxyl surrogates are optionally substituted with one to more groups selected from H, deuterium, Halogen, $OCH_3$, Carboxyl, OH, CN and NRd$_8R_{d9}$; Or any two adjacent $R_1$ together with the carbon to which they are attached form a 5- to 6-membered heteroaryl, 3- to 8-membered saturated or partially saturated cycloalkyl, 3- to 8-membered saturated or partially saturated heterocyclyl, and the aryl, saturated or the partially saturated cycloalkyl, heterocycloalkyl is optionally substituted with hydrogen, deuterium, halogen, —CN, —OH, $CF_3$, $C_{1-6}$ alkyl, $C_{1-6}$ alkoxy, —$NH_2$, —NH$C_{1-6}$ alkyl, —N($C_{1-6}$ alkyl)$_2$, ═O, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl.

Each $R_2$, $R_2$ and $R_{d1}$, $R_{d2}$ is the same or different and is independently selected from hydrogen, deuterium, halogen, $C_{1-10}$ alkyl, $C_{2-10}$ alkenyl, $C_{2-10}$ alkynyl, $C_{1-10}$ alkylamino, N, N-di($C_{1-10}$ alkyl)amino, $C_{1-10}$ alkoxy, $C_{1-10}$ alkylacyl, $C_{1-10}$ alkoxy, $C_{1-10}$ alkylsulfonyl, $C_{1-10}$ alkylsulfinyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxyacetyl, $C_{3-10}$ cycloalkylsulfonyl and $C_{3-10}$ cycloalkylsulfinyl; and the alkyl, alkenyl, alkynyl, aryl, saturated or partially saturated cycloalkyl, heterocycloalkyl are optionally substituted with one to more selected from hydrogen, deuterium, halogen, —CN, —OH, $CF_3$, $C_{1-6}$ alkyl, $C_{1-6}$ alkoxy, —$NH_2$, —NH$C_{1-6}$ alkyl, —N($C_{1-6}$ alkyl)$_2$, oxy, and saturated or partially saturated $C_{3-6}$ cycloalkyl, and the $C_{1-6}$ alkyl and $C_{1-6}$ alkoxy are optionally substituted with one to more selected from hydrogen, deuterium, halogen, oxo, CN, $CF_3$, OH, $OCH_3$, $OCH_2CH_3$ and saturated or partially saturated $C_{3-6}$ cycloalkyl; Or optionally $R_2$ and $R^2$ or Rai and $R_{d2}$ may together with the carbon to which they are attached form 5- to 6-membered aryl or heteroaryl, 3- to 8-membered saturated or partially saturated cycloalkyl, 3- to 8-membered saturated or partially saturated heterocyclic group, wherein the cycloalkyl and heterocycloalkyl are optionally substituted with one to more selected from hydrogen, deuterium, halogen, oxo, CN, $CF_3$, OH, $OCH_3$, $OCH_2CH_3$;

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy are optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and is independently hydrogen, deuterium, halogen, CN, OH, SH, $NRd_8R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or heterocyclyl; Or any adjacent two $R_5$ or $R_6$ together with the carbon to which they are attached form 5- to 6-membered heteroaryl, 3- to 8-membered saturated or partially saturated cycloalkyl, 3- to 8-membered saturated or partially saturated heterocyclyl, and the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d3}$, $R_{d4}$, $R_{d5}$, $R_{d6}$, $R_{d7}$, $R_{d8}$, $R_{d9}$ and $R_{d10}$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof;

m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

In one embodiment of the present invention, the compound or a pharmaceutically acceptable salt, isotopic variations or isomer thereof has the structure of Formula (IC), Formula (IC)

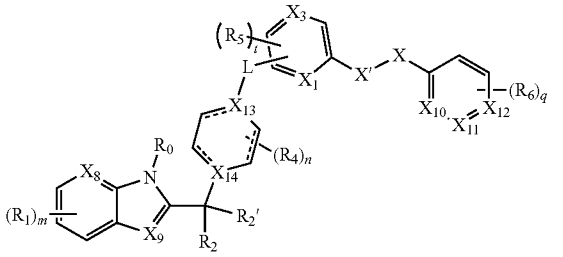

Wherein, $\overset{\text{-----}}{=}$ optionally represents a single bond or a double bond;

X and X' are independently selected from —$C(R_{d1})(R_{d2})$—, —C(═O)$N(R_{d3})$—, —$N(R_{d4})$—, —C(═$NR_{d5}$)—, —S(═O)$_2N(R_{d6})$—, —$N(R_{d7})$—, —O—, —S—, —C(═O)O—, —OC(═O)—, —C(═O)—, —C(═S)—, —S(═O)—, or —S(═O)$_2$—;

L is independently selected from —$C(R_{d1})(R_{d2})$—, —$OC(R_{d1})(R_{d2})$—, —$C(R_{d1})(R_{d2})O$—, —C(═O)$N(R_{d3})$—, —$N(R_{d4})$—, —C(═$NR_{d5}$)—, —S(═O)$_2$ $N(R_{d6})$—, —$N(R_{d7})$—, —O—, —S—, —C(═O)O—, —OC(═O)—, —C(═O)—, —C(═S)—, —S(═O)—, or —S(═O)$_2$—;

$X_1$, $X_3$, $X_8$, $X_9$ $X_{10}$, $X_{11}$, $X_{12}$, $X_{13}$ or $X_{14}$ are independently selected from —$CR_5$— or —N—;

$R_0$ is independently selected from hydrogen, deuterium, halogen, —CN, $C_{1-10}$ alkyl, $C_{2-10}$ alkenyl, $C_{2-10}$ alkynyl, $C_{1-10}$ alkoxy, —$NRd_8R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein $R_0$ representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally substituted with one to multiple substituent groups, the substituent groups are optionally selected from hydrogen, deuterium, halogen, alkyl, Haloalkyl, alkoxy, alkylamino, O═, CN, OH, —$NRd_8R_{d9}$, $C_{3-10}$ saturated or partially saturated cycloalkyl, $C_{3-10}$ saturated or partially saturated heterocyclic group, 6- to 10-aryl and 5- to 8-membered heteroaryl; Wherein the aryl, heteroaryl, saturated or partially saturated cycloalkyl, saturated or partially saturated heterocyclyl are further optionally substituted with one to multiple substituents, and the substituents are optionally selected from hydrogen, deuterium, Halogen, alkyl, haloalkyl, cyano, cyanoethyl, O═, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with one to three substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ Alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate, preferably, the carboxyl surrogate is

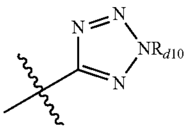 or 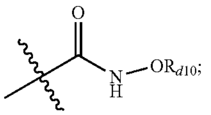

Wherein $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkylcarboxyl or carboxyl surrogates are optionally substituted with one to more substituents selected from H, Deuterium, Halogen, $OCH_3$, Carboxyl, OH, CN and $NRd_8R_{d9}$; Or any two adjacent $R_1$ together with the carbon to which they are attached form a 5-to 6-membered heteroaryl, 3- to 8-membered saturated or partially saturated cycloalkyl, 3- to 8-membered saturated or partially saturated heterocyclyl, and the hydrogen on the aryl, saturated or the partially saturated cycloalkyl, heterocycloalkyl is optionally substituted with hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, =O, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl.

Each $R_2$, $R_2$, and $R_{d1}$, $R_{d2}$ is the same or different and is independently selected from hydrogen, deuterium, halogen, $C_{1-10}$ alkyl, $C_{2-10}$ alkenyl, $C_{2-10}$ alkynyl, $C_{1-10}$ alkylamino, N, N-di($C_{1-10}$ alkyl)amino, $C_{1-10}$ alkoxy, $C_{1-10}$ alkylacyl, $C_{1-10}$ alkoxy, $C_{1-10}$ alkylsulfonyl, $C_{1-10}$ alkylsulfinyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxyacetyl, $C_{3-10}$ cycloalkylsulfonyl and $C_{3-10}$ cycloalkylsulfinyl; and the alkyl, alkenyl, alkynyl, aryl, saturated or partially saturated cycloalkyl, heterocycloalkyl are optionally substituted with one to more selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy are optionally substituted with one to more selected from hydrogen, deuterium, halogen, oxo, CN, $CF_3$, OH, $OCH_3$, $OCH_2CH_3$ and saturated or partially saturated $C_{3-6}$ cycloalkyl; Or optionally $R_2$ and $R^2$ or Ral and $R_{d2}$ may together with the carbon to which they are attached form 5- to 6-membered aryl or heteroaryl, 3- to 8-membered saturated or partially saturated cycloalkyl, 3- to 8-membered saturated or partially saturated heterocyclic group, wherein the cycloalkyl and heterocycloalkyl are optionally substituted with one to more selected from hydrogen, deuterium, halogen, oxo, CN, $CF_3$, OH, $OCH_3$, $OCH_2CH_3$;

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy are optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and is independently selected from hydrogen, deuterium, halogen, CN, OH, SH, $NRd_8R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or heterocyclyl; Or any adjacent two $R_5$ or Re together with the carbon to which they are attached form 5- to 6-membered heteroaryl, 3- to 8-membered saturated or partially saturated cycloalkyl, 3- to 8-membered saturated or partially saturated heterocyclyl, and the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy is optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d3}$, $R_{d4}$, $R_{d5}$, $R_{d6}$, $R_{d7}$, $R_{d8}$, $R_{d9}$ and $R_{d10}$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof;

m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

In one embodiment of the present invention, the compound or a pharmaceutically acceptable salt, isotopic variations or isomer thereof has the structure of Formula (ID), Formula (ID)

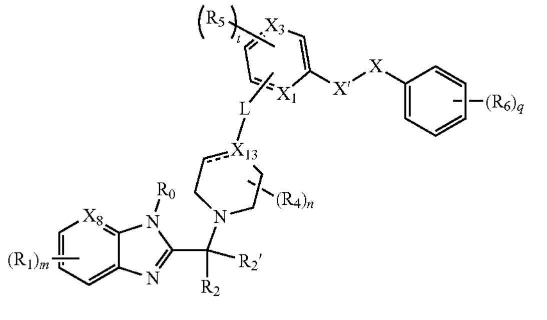

Wherein,

⩦ optionally represents a single bond or a double bond;

X and X' are independently selected from —C(Rai)($R_{d2}$)—, —C(═O)N($R_{d3}$)—, —N($R_{d4}$)—, —C(═$NR_{d5}$)—, —S(═$O)_2$N($R_{d6}$)—, —N($R_{d7}$)—, —O—, —S—, —C(═O)O—, —OC(═O)—, —C(═O)—, —C(═S)—, —S(═O)—, or —S(═$O)_2$—; preferred—C($R_{d1}$)($R_{d2}$)—, —N($R_{d4}$)—, —O—, —S—, —S(═O)— or —S(═$O)_2$—;

L is independently selected from —C($R_{d1}$)($R_{d2}$)—, —OC($R_{d1}$)($R_{d2}$)—, —C($R_{d1}$)($R_{d2}$)O—, —C(—O)N($R_{d3}$)—, —N($R_{d4}$)—, —C(═$NR_{d5}$)—, —S(═$O)_2$ N($R_{d6}$)—, —N($R_{d7}$)—, —O—, —S—, —C(═O)O—, —OC(═O)—, —C(═O)—, —C(═S)—, —S(═O)—, or —S(═$O)_2$—; preferred —OC($R_{d1}$)($R_{d2}$)—, —C($R_{d1}$)($R_{d2}$)O—, —O—, —S— or —N($R_{d4}$)—;

$X_1$, $X_3$, $X_8$ and $X_{13}$ are independently selected from —$CR_5$— or —N—;

$R_0$ is independently selected from hydrogen, deuterium, halogen, —CN, $C_{1-10}$ alkyl, $C_{2-10}$ alkenyl, $C_{2-10}$ alkynyl, $C_{1-10}$ alkoxy, —$NRd_8R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein $R_0$ representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally substituted with one to multiple substituent groups, the substituent groups are optionally selected from hydrogen, deuterium, halogen, alkyl, haloalkyl, alkoxy, alkylamino, O═, CN, OH, —$NRd_8R_{d9}$, $C_{3-10}$ saturated or partially saturated cycloalkyl, $C_{3-10}$ saturated or partially saturated heterocyclic group, 6- to 10-aryl and 5- to 8-membered heteroaryl; wherein the aryl, heteroaryl, saturated or partially saturated cycloalkyl, saturated or partially saturated heterocyclyl are further optionally substituted with one to multiple substituents, and the substituents are optionally selected from hydrogen, deuterium, Halogen, alkyl, haloalkyl, cyano, cyanoethyl, O—, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with one to three substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ Alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate; wherein $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkylcarboxyl or carboxyl surrogates are optionally substituted with one to more substituents selected from H, deuterium, halogen, $OCH_3$, carboxyl, OH, CN and $NR_{d8}R_{d9}$; Or any two adjacent $R_1$ together with the carbon to which they are attached form a 5- to 6-membered heteroaryl, 3- to 8-membered saturated or partially saturated cycloalkyl, 3- to 8-membered saturated or partially saturated heterocyclyl, a hydrogen on the aryl, saturated or the partially saturated cycloalkyl, or heterocycloalkyl is optionally substituted by hydrogen, deuterium, halogen, —CN, —OH, $CF_3$, $C_{1-6}$ alkyl, $C_{1-6}$ alkoxy, —$NH_2$, —$NHC_{1-6}$ alkyl, —N($C_{1-6}$ $alkyl)_2$, ═O, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl.

Each $R_2$, $R_2$ and $R_{d1}$, $R_{d2}$ is the same or different and is independently selected from hydrogen, deuterium, halogen, $C_{1-10}$ alkyl, $C_{2-10}$ alkenyl, $C_{2-10}$ alkynyl, $C_{1-10}$ alkylamino, N, N-di($C_{1-10}$ alkyl)amino, $C_{1-10}$ alkoxy, $C_{1-10}$ alkylacyl, $C_{1-10}$ alkoxy, $C_{1-10}$ alkylsulfonyl, $C_{1-10}$ alkylsulfinyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxyacetyl, $C_{3-10}$ cycloalkylsulfonyl and $C_{3-10}$ cycloalkylsulfinyl; and the alkyl, alkenyl, alkynyl, aryl, saturated or partially saturated cycloalkyl, heterocycloalkyl are optionally substituted with one to more selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —N($C_{1-6}$ $alkyl)_2$, oxy, and saturated or partially saturated $C_{3-6}$ cycloalkyl, and the $C_{1-6}$ alkyl and $C_{1-6}$ alkoxy are optionally further substituted with one to more selected from hydrogen, deuterium, halogen, oxo, CN, $CF_3$, OH, $OCH_3$, $OCH_2CH_3$ and saturated or partially saturated $C_{3-6}$ cycloalkyl; Or optionally $R_2$ and $R_2$ or $R_{d1}$ and $R_{d2}$ may together with the carbon to which they are attached form 5- to 6-membered aryl or heteroaryl, 3- to 8-membered saturated or partially saturated cycloalkyl, 3- to 8-membered saturated or partially saturated heterocyclic group, wherein the cycloalkyl and heterocycloalkyl are optionally substituted with one to more groups selected from hydrogen, deuterium, halogen, oxo, CN, $CF_3$, OH, $OCH_3$, $OCH_2CH_3$;

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and is independently hydrogen, deuterium, halogen, CN, OH, SH, $NR_{d8}R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ Cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or Heterocyclyl; Or any adjacent two $R_5$ or $R_6$ together with the carbon to which they are attached form 5- to 6-membered heteroaryl, 3- to 8-membered saturated or partially saturated cycloalkyl, 3- to 8-membered saturated or partially saturated heterocyclyl, and the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, $—NH_2$, $—NHC_{1-6}$ alkyl, $—N(C_{1-6}\ alkyl)_2$, oxy, and saturated or partially saturated $C_{3-6}$ cycloalkyl, and the $C_{1-6}$ alkyl and $C_{1-6}$ alkoxy is optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d4}$, $R_{d5}$, and $R_{d6}$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof;

m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

In one embodiment of the present invention, the compound or a pharmaceutically acceptable salt, isotopic variations or isomer thereof has the structure of Formula (IE), Formula (IE)

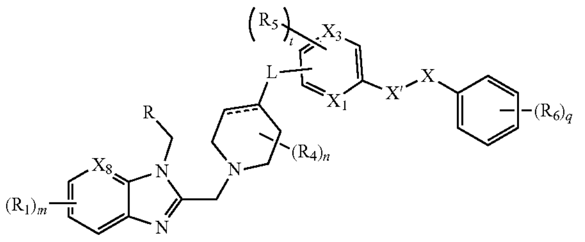

Wherein,

═══ optionally represents a single bond or a double bond;

X and X' are independently selected from $—C(R_{d1})(R_{d2})—$, $—N(R_{d4})—$, $—N(R_{d7})—$, —O—, —S—, —S(═O)— or $—S(═O)_2—$; preferred-$C(R_{d1})(R_{d2})—$, $—N(R_{d4})—$, —O—, —S—, —S(═O)— or $—S(═O)_2—$;

L is independently selected from $—C(R_{d1})(R_{d2})—$, $—OC(Rai)(R_{d2})—$, $—C(R_{d1})(R_{d2})O—$, $—C(═O)N(R_{d3})—$, $—N(R_{d4})—$, $—C(═NR_{d5})—$, $—S(═O)_2\ N(R_{d6})—$, $—N(R_{d7})—$, —O—, —S—, —C(═O)O—, —OC(═O)—, —C(═O)—, —C(═S)—, —S(═O)— or $—S(═O)_2—$; preferred $—OC(R_{d1})(R_{d2})—$, $—C(R_{d1})(R_{d2})O—$, —O—, —S— or $—N(R_{d4})—$;

$X_1$, $X_3$, $X_8$ and $X_{13}$ are independently selected from $—CR_5—$ or —N—;

R is independently selected from hydrogen, deuterium, halogen, —CN, $C_{1-10}$ alkyl, $C_{2-10}$ alkenyl, $C_{2-10}$ alkynyl, $C_{1-10}$ alkoxy, $—NR_{d8}R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein R representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally substituted with one to multiple substituent groups, the substituent groups are optionally selected from hydrogen, deuterium, halogen, alkyl, haloalkyl, alkoxy, alkylamino, O═, CN, OH, $—NRd_8R_{d9}$, $C_{3-10}$ saturated or partially saturated cycloalkyl, $C_{3-10}$ saturated or partially saturated heterocyclic group, 6- to 10-aryl and 5- to 8-membered heteroaryl; wherein the aryl, heteroaryl, saturated or partially saturated cycloalkyl, saturated or partially saturated heterocyclyl are optionally substituted with one to multiple substituents, and the substituents are optionally selected from hydrogen, deuterium, halogen, alkyl, haloalkyl, cyano, cyanoethyl, O═, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with one to three substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ Alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate; or any two adjacent $R_1$ together with the carbon to which they are attached form a 5- to 6-membered heteroaryl, 3- to 8-membered saturated or partially saturated cycloalkyl, 3- to 8-membered saturated or partially saturated heterocyclyl, and the hydrogen on the aryl, saturated or the partially saturated cycloalkyl, heterocycloalkyl is optionally substituted with hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, =O, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl.

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and is independently selected from hydrogen, deuterium, halogen, CN, OH, SH, $NR_{d8}R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or heterocyclyl; or any adjacent two $R_5$ or $R_6$ together with the carbon to which they are attached form 5- to 6-membered heteroaryl, 3- to 8-membered saturated or partially saturated cycloalkyl, 3- to 8-membered saturated or partially saturated heterocyclyl, and the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}$ alkyl$)_2$, oxy, and saturated or partially saturated $C_{3-6}$ cycloalkyl, and the $C_{1-6}$ alkyl and $C_{1-6}$ alkoxy are optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d1}$, $R_{d2}$, $R_{d4}$, $R_{d5}$ and $R_{d6}$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3.10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof;

m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

In one embodiment of the present invention, the compound or a pharmaceutically acceptable salt, isotopic variations or isomer thereof has the structure of Formula (IF-1) or (IF-2), Formula (IF-1)

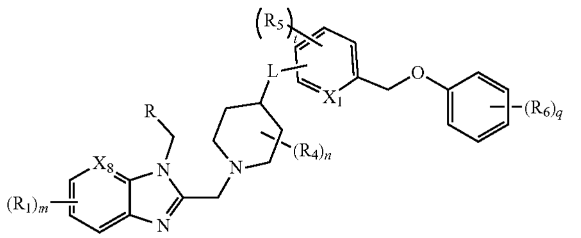

Formula (IF-2)

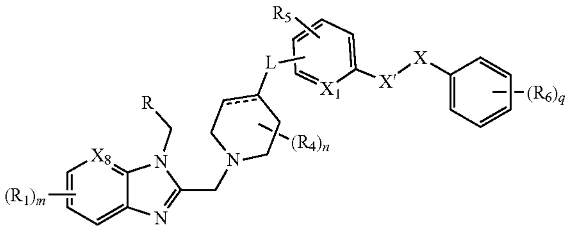

Wherein,

------ optionally represents a single bond or a double bond;

X and X' are independently selected from —$C(R_{d1})(R_{d2})$—, —$N(R_{d4})$—, —O—, —S—, —S(=O)— or —$S(=O)_2$—;

L is independently selected from —$OC(R_{d1})(R_{d2})$—, —$C(R_{d1})(R_{d2})O$—, —O—, —S— or —$N(R_{d4})$—;

$X_1$ and $X_8$ are independently selected from —$CR_5$— or —N—;

R is independently selected from hydrogen, deuterium, halogen, —CN, $C_{1-10}$ alkyl, $C_{2-10}$ alkenyl, $C_{2-10}$ alkynyl, $C_{1-10}$ alkoxy, —$NRd_8R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein R representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3- to 8-membered saturated or partially saturated cycloalkyl and 3- to 8-membered saturated or partially saturated heterocyclyl are optionally substituted with one to multiple substituent groups, the substituent groups are optionally selected from hydrogen, deuterium, halogen, alkyl, haloalkyl, alkoxy, alkylamino, O═, CN, OH, —$NRd_8R_{d9}$, $C_{3-10}$ saturated or partially saturated cycloalkyl, $C_{3-10}$ saturated or partially saturated heterocyclic group, 6- to 10-aryl and 5- to 8-membered heteroaryl; Wherein the aryl, heteroaryl, saturated or partially saturated cycloalkyl, saturated or partially saturated heterocyclyl are further optionally substituted with one to multiple substituents, and the substituents are optionally selected from hydrogen, deuterium, halogen, alkyl, haloalkyl, cyano, cyanoethyl, O═, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with one to three substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ Alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate;

Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy are optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and is independently hydrogen, deuterium, halogen, CN, OH, SH, $NRd_8R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or heterocyclyl; or any adjacent two $R_5$ or $R_6$ together with the carbon to which they are attached form 5- to 6-membered heteroaryl, 3- to 8-membered saturated or partially saturated cycloalkyl, 3- to 8-membered saturated or partially saturated heterocyclyl, and where in the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}\ alkyl)_2$, oxy, and saturated or partially saturated $C_{3-6}$ cycloalkyl, and the $C_{1-6}$ alkyl and $C_{1-6}$ alkoxy is optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d1}$, $R_{d2}$, $R_{d4}$, Ras and $R_4$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof; m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

In one embodiment of the present invention, the compound or a pharmaceutically acceptable salt, isotopic variations or isomer thereof has the structure of Formula (IG), Formula (IG)

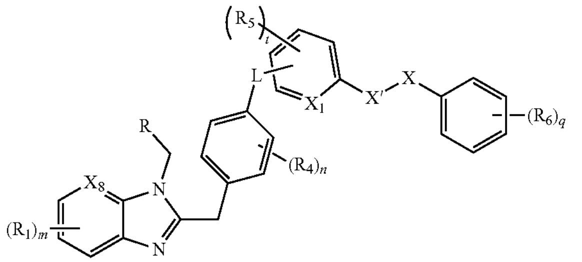

Wherein,

X and X' are independently selected from —$C(R_{d1})(R_{42})$—, —$N(R_{d4})$—, —O—, —S—, —S(═O)— or —$S(═O)_2$—; L is independently selected from —$OC(R_{d1})(R_{d2})$—, —$C(R_{d1})(R_{d2})O$—, —O—, —S— or —$N(R_{d4})$—; $X_1$ and $X_8$ are each independently selected from —$CR_5$— or —N—;

R is independently hydrogen, deuterium, halogen, —CN, $C_{1-10}$ alkyl, $C_{2-10}$ alkenyl, $C_{2-10}$ alkynyl, $C_{1-10}$ alkoxy, —$NR_{d8}R_{d9}$, 6- to 10-membered aryl, 5- to 8-membered heteroaryl, 3- to 8-membered saturated or partially saturated cycloalkyl and 3- to 8-membered saturated or partially saturated heterocyclyl, wherein R representing $C_{1-10}$ alkyl, $C_{2-10}$ alkenyl, $C_{2-10}$ alkynyl, $C_{1-10}$ alkoxy, 6- to 10-membered aryl, 5- to 8-membered heteroaryl, 3-to 8-membered saturated or partially saturated cycloalkyl and 3- to 8-membered saturated or partially saturated heterocyclyl are optionally substituted with one to multiple substituent groups, the substituent groups are optionally selected from hydrogen, deuterium, halogen, alkyl, haloalkyl, alkoxy, alkylamino, O═, CN, OH, —$NRd_8Rd_9$, $C_{3-10}$ saturated or partially saturated cycloalkyl, $C_{3-10}$ saturated or partially saturated heterocyclic group, 6- to 10-aryl and 5- to 8-membered heteroaryl; wherein the aryl, heteroaryl, saturated or partially saturated cycloalkyl, saturated or partially saturated heterocyclyl are optionally substituted with one to multiple substituents, and the substituents are optionally selected from hydrogen, deuterium, halogen, alkyl, haloalkyl, cyano, cyanoethyl, O═, OH, $C_{1-3}$ alkyl, $C_{1-3}$ alkoxy, saturated or partially saturated cycloalkyl or saturated or partially saturated heterocyclyl, wherein the $C_{1-3}$ alkyl group, $C_{1-3}$ alkoxy group, saturated or partially saturated cycloalkyl group or saturated or partially saturated heterocyclic group are optionally substituted with one to three substituent groups, the substituent groups are optionally selected from H, deuterium, halogen, haloalkyl, cyano, $OCH_3$ and OH.

Each $R_1$ is the same or different and is independently selected from the group consisting of hydrogen, deuterium, halogen, —CN, —OH, —SH and —$NH_2$, —COOH or from $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ saturated or partially saturated cycloalkyl, $C_{3-10}$ saturated or partially saturated heterocycloalkyl, $C_{1-10}$ alkyl substituted by $C_{3-10}$ cycloalkyl or $C_{3-10}$ heterocycloalkyl, $C_{2-10}$ heteroalkyl substituted by $C_{3-10}$ cycloalkyl, $C_{3-10}$ heterocyclyl, $C_{1-10}$ alkyl substituted with carboxyl or carboxyl surrogate; Each $R_4$ is the same or different and is optionally and independently selected from hydrogen, deuterium, halogen, CN, OH, SH and $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted $C_{3-10}$ cycloalkyl or $C_{3-10}$ heterocycloalkyl, and $C_{1-10}$ heteroalkyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy are optionally substituted with one to more groups selected from hydrogen, deuterium, halogen, oxo, CN, OH, and $C_{3-10}$ saturated or partially saturated cycloalkyl or heterocyclyl;

Each $R_5$ and $R_6$ is the same or different and is independently hydrogen, deuterium, halogen, CN, OH, SH, $NRd_8R_{d9}$, $NH_2$, —COOH or $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkenyl, $C_{2-10}$ alkynyl or $C_{1-10}$ alkoxy, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocycloalkyl substituted by $C_{3-10}$ cycloalkyl or $C_{3-10}$ heterocycloalkyl are optionally substituted with one to more groups selected from hydrogen, deuterium, halogen, oxo, CN, OH and $C_{3-10}$ saturated or partially substituted saturated cycloalkyl or Heterocyclyl; Or any adjacent two $R_5$ or $R_6$ together with the carbon to which they are attached form 5- to 6-membered heteroaryl, 3- to 8-membered saturated or partially saturated cycloalkyl, 3- to 8-membered saturated or partially saturated heterocyclyl, and the aryl, saturated or partially saturated cycloalkyl, heterocycloalkyl are optionally substituted with one to more groups selected from hydrogen, deuterium, halogen, —CN, —OH, $CF_3$, $C_{1-6}$ alkyl, $C_{1-6}$ alkoxy, —$NH_2$, —$NHC_{1-6}$ alkyl, —$N(C_{1-6}\ alkyl)_2$, oxy, and saturated or partially saturated $C_{3-6}$ cycloalkyl, and the $C_{1-6}$ alkyl and $C_{1-6}$ alkoxy is optionally substituted with one to more groups selected from hydrogen, deuterium, halogen, oxo, CN, $CF_3$, OH, $OCH_3$, $OCH_2CH_3$, saturated or partially saturated $C_{3-6}$ cycloalkyl;

Each $R_{d1}$, $R_{d2}$, $R_{d4}$, Ras and $R_4$ is the same or different, and is optionally and independently selected from hydrogen, deuterium, $NH_2$, $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl; wherein, the $C_{1-10}$ alkyl, $C_{2-10}$ alkynyl or $C_{1-10}$ alkoxy, $C_{1-10}$ alkylacyl, $C_{1-10}$ alkylsulfonyl, $C_{2-10}$ heteroalkyl, $C_{3-10}$ cycloalkyl, $C_{3-10}$ heterocycloalkyl, $C_{1-10}$ alkyl substituted by $C_{3-10}$ cycloalkyl, or $C_{3-10}$ heterocyclyl substituted by $C_{3-10}$ cycloalkyl or $C_{3-10}$ heterocycloalkyl are optionally substituted with one to multiple groups selected from hydrogen, deuterium, halogen, oxo, CN, OH and $C_{3-10}$ saturated or partially substituted saturated cycloalkyl or heterocyclyl;

The hetero represents any heteroatom independently selected from O, N, S, P and isotopes thereof;

The halogen is optionally and independently selected from F, Cl, Br, I and isotopes thereof; m is an integer optionally selected from 1, 2, 3 and 4;

n is an integer optionally selected from 0, 1, 2, 3, 4 and 5;

q is an integer optionally selected from 0, 1, 2, 3, 4 and 5;

t is an integer optionally selected from 0, 1, 2, 3, and 4.

According to an embodiment of the present invention, A is selected from unsubstituted or substituted $C_{6-20}$ aryl, 5- to 20-membered heteroaryl;

B is selected from unsubstituted or substituted 3- to 20-membered heterocyclyl, 6- to 18-membered spirocyclyl or bridged cyclyl, $C_{6-20}$ aryl;

X and X' are the same or different and are independently selected from —C(Rai)($R_{d2}$)—, —O—, —S—, —C(═O)O—, —OC(═O)—, —C(═O)—, —S(═O)— or —$S(═O)_2$—;

L is selected from —$C(R_{d1})(R_{d2})$—, $OC(R_{d1})(R_{d2})$—, —$C(R_{d1})(R_{d2})O$—, —O—, —S—, —NH—, —C(═O)O—, —OC(═O)—, —C(═O)—, —S(—O)— or —$S(═O)_2$—; Rai and $R_{d2}$ are the same or different and optionally independently selected from hydrogen, deuterium, halogen, $C_{1-10}$ alkyl, $C_{1-10}$ alkoxy;

$X_1$, $X_2$, $X_3$, $X_4$, $X_5$, $X_8$ and $X_9$ are the same or different and are independently selected from —$CR_5$— or —N—; each $R_5$ is the same or different and is independently selected from hydrogen, deuterium, halogen, CN, OH, SH, $NH_2$, —COOH, $C_{1-10}$ alkyl, $C_{1-10}$ alkoxy;

$R_0$ is selected from $C_{1-10}$ alkyl unsubstituted or optionally substituted with one, two or more $R_{01}$; each $R_{02}$ is the same or different and is independently selected from $C_{3-20}$ cycloalkyl, 3- to 20-membered heterocyclyl and 5- to 20-membered heteroaryl unsubstituted or optionally substituted with one, two or more $R_{01}$; each $R_{02}$ is the same or different, and is independently selected from halogen, deuterium, CN, oxo (═O), $C_{1-10}$ alkyl, halogenated $C_{1-10}$ alkyl, CN—$C_{1-10}$ alkyl, $C_{3-6}$ cycloalkyl-$C_{1-10}$ alkyl;

Each R is the same or different and is independently selected from hydrogen, deuterium, halogen, —CN, —OH, —SH, —$NH_2$, COOH, $C_{1-10}$ alkyl-COOH or —$C_{2-10}$ alkenyl-COOH unsubstituted or optionally substituted with one, two or more $R_1$; each Rn is the same or different and is independently selected from H, deuterium, halogen, $C_{1-10}$ alkyl, $C_{1-10}$ alkoxy;

Each $R_2$, $R_2$ is the same or different, and is independently selected from hydrogen, deuterium, halogen, oxo (═O), $C_{1-10}$ alkyl, $C_{1-10}$ alkoxy;

Each $R_4$ is the same or different and is optionally and independently selected from hydrogen, deuterium, halogen, oxo (═O), CN, OH, SH and $NH_2$, —COOH, $C_{1-10}$ alkyl, $C_{1-10}$ alkoxy;

Each $R_6$ is the same or different and is independently selected from the group consisting of hydrogen, deuterium, halogen, CN, OH, SH, $NH_2$, —COOH, $C_{1-10}$ alkyl, $C_{1-10}$ alkoxy, $C_{2-10}$ alkynyl, 5- to 14-membered heteroaryl;

$R_{d3}$, $R_{d4}$, $R_{d5}$, $R_{d6}$, Raz, $R_{d5}$, Ray and $R_{d10}$ are the same or different and are optionally and independently selected from hydrogen, deuterium, CN, OH, SH and $NH_2$, —COOH, $C_{1-10}$ alkyl, $C_{1-10}$ alkoxy;

10 m is an integer optionally selected from 1, 2, 3 and 4;

n is an integer optionally selected from 0, 1, 2, 3, 4 and 5;

q is an integer optionally selected from 0, 1, 2, 3, 4 and 5.

According to an embodiment of the present invention, A is selected from unsubstituted or substituted $C_{6-14}$ aryl, 5- to 14-membered heteroaryl;

B is selected from unsubstituted or substituted 3- to 14-membered heterocyclyl, 6- to 18-membered spirocyclyl or bridged cyclyl, $C_{6-14}$ aryl;

X and X' are the same or different and are independently selected from —C($R_{d1}$)($R_{d2}$)—, —O—, —S—;

L is selected from —C($R_{d1}$)($R_{d2}$)—, —OC($R_{d1}$)($R_{d2}$)—, —C($R_{d1}$)($R_{d2}$)O—, —O—, —S—, —NH—; $R_{d1}$ and $R_{d2}$ are the same or different, and are optionally and independently selected from hydrogen, deuterium, $C_{1-10}$ alkyl;

$X_1$, $X_2$, $X_3$, $X_4$, $X_5$, $X_8$ and $X_9$ are the same or different, independently selected from —$CR_5$— or —N—; each $R^5$ is the same or different, independently selected from hydrogen, deuterium, halogen, $C_{1-10}$ alkyl, $C_{1-10}$ alkoxy;

$R_0$ is selected from $C_{1-10}$ alkyl unsubstituted or optionally substituted with one, two or more $R_{01}$; each Rol is the same or different and is independently selected from $C_{3-20}$ cycloalkyl, 3- to 20-membered heterocyclyl and 5- to 20-membered heteroaryl unsubstituted or optionally substituted with one, two or more $R_{02}$; each $R_{02}$ is the same or different, independently selected from CN, deuterium, oxo (═O), $C_{1-10}$ alkyl, CN—$C_{1-10}$ alkyl, $C_{3-6}$ cycloalkyl-$C_{1-10}$ alkyl;

Each $R_1$ is the same or different and independently selected from, halogen, COOH, $C_{1-10}$ alkyl-COOH, —$C_{2-10}$ alkenyl-COOH unsubstituted or optionally substituted with one, two or more $R_{11}$; each Ru is the same or different, independently selected from H, deuterium, halogen, $C_{1-10}$ alkyl, $C_{1-10}$ alkoxy;

$R_2$, $R_2$ are the same or different, and are independently selected from hydrogen, deuterium, halogen, oxo (═O), $C_{1-10}$ alkyl, $C_{1-10}$ alkoxy;

Each $R_4$ is the same or different and is optionally and independently selected from hydrogen, deuterium, halogen, oxo (═O), CN, OH, SH and $NH_2$, —COOH, $C_{1-10}$ alkyl, $C_{1-10}$ alkoxy;

Each $R_6$ is the same or different and is independently selected from the group consisting of hydrogen, deuterium, halogen, CN, $C_{1-10}$ alkyl, $C_{1-10}$ alkoxy, $C_{2-10}$ alkynyl, 5- to 14-membered heteroaryl;

m is an integer optionally selected from an integer of 1, 2 and 3;

n is an integer optionally selected from 0, 1, 2, 3 and 4;

q is an integer optionally selected from 0, 1, 2, 3 and 4.

According to an embodiment of the present invention, A is selected from phenyl or pyridyl;

B is piperidinyl, azetidinyl, phenyl, (1R,5S)-3-azabicyclo[3.2.1]octyl, spirocyclic group or bridged cyclic group; the spirocyclic or the bridged ring contains one or more heteroatoms optionally and independently selected from N, O or S;

X and X' are the same or different and are independently selected from $CH_2$, O or S;

L can be selected from O, S, NH, $CH_2$, $OCH_2$, $CH_2O$;

$X_1$, $X_2$, $X_3$, $X_4$, $X_5$, $X_8$ and $X_9$ are the same or different and are independently selected from CH, C—F or N $R_0$ is selected from $C_{1-3}$ alkyl unsubstituted or substituted with imidazolyl, pyrazolyl, pyrrolyl, azetidinyl, oxetanyl, pyrrolidinyl or cyclopropyl; the imidazolyl, pyrazolyl, pyrrolyl, azetidinyl, oxetanyl, pyrrolidinyl or cyclopropyl may be unsubstituted or substituted with oxo (═O) or $C_{1-3}$ alkyl, CN—$C_{1-3}$ alkyl, $C_{3-6}$ cycloalkyl-$C_1$-3 alkyl;

Each $R_1$ is the same or different and is independently selected from COOH, F, —$C_{1-3}$ alkyl-COOH, —$C_{2-3}$ alkenyl-COOH;

$R_2$, $R_2$ are the same or different, and are independently selected from hydrogen, deuterium, halogen, oxo (═O), $C_{1-3}$ alkyl;

Each $R_4$ is the same or different and is optionally and independently selected from hydrogen, deuterium, halogen, oxo (—O), $C_{1-3}$ alkyl;

Each $R_6$ is the same or different and is independently selected from hydrogen, deuterium, F, Cl, Br, CN, ethynyl, imidazolyl;

m is optionally selected from 1 or 2;

n is optionally selected from 0, 1 or 2;

q is optionally selected from 0, 1 or 2.

According to an embodiment of the present invention,

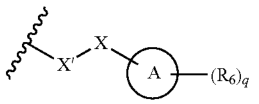

can be selected from the structures shown below
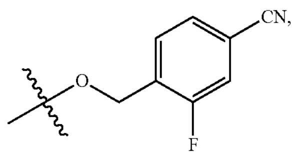
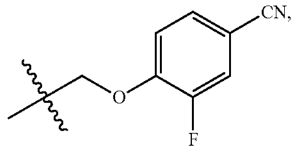
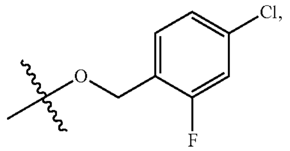
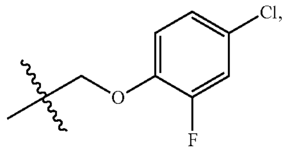
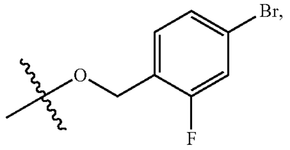
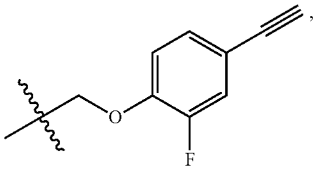
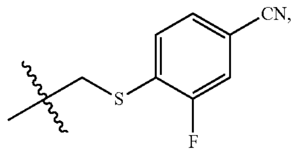
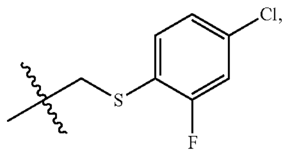
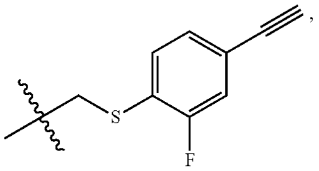
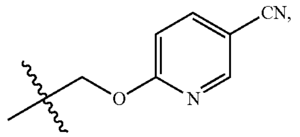
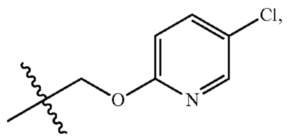
-continued
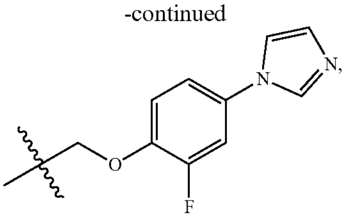
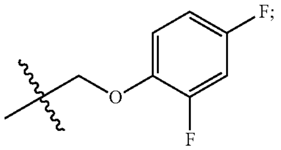
B can have the following structure
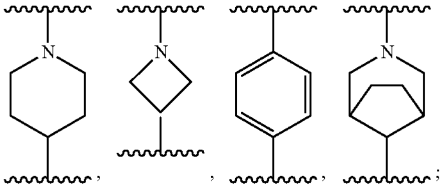
L can be selected from O, S, NH, $CH_2$, $OCH_2$, $CH_2O$;
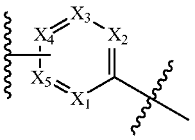
can be selected from the structures shown below
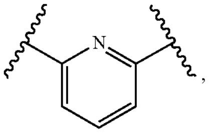
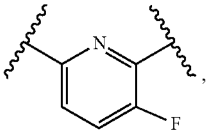
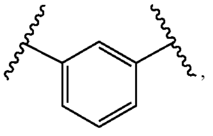
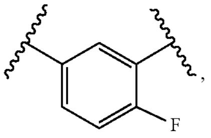
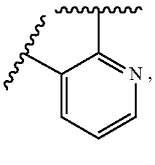
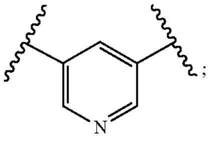

$R_0$ can be selected from the structures shown below

Methyl, 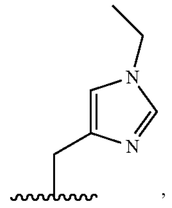, 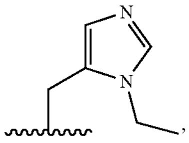, 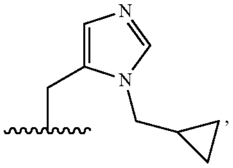, 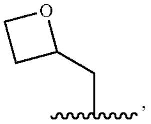, 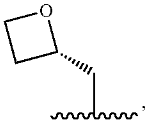, 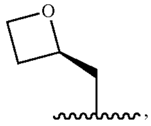, 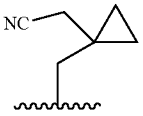, 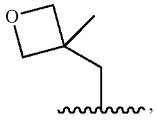, 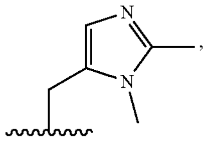, 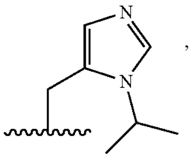, 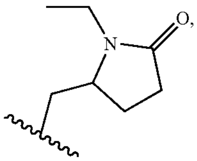, 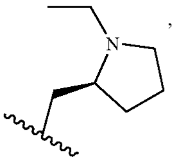, 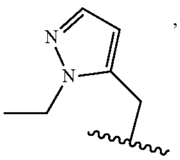, -continued

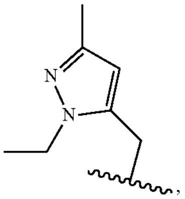, 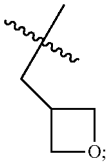;

$R_1$ can be selected from COOH, F,

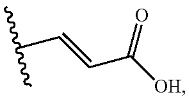, 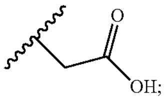;

Both $R_2$ and $R^2$ are H;

$R_4$ is H, F, methyl; X: is selected from CH or N; X, is selected from CH or N;

m is selected from 1 or 2; n is selected from 1 or 2.

In one embodiment of the present invention, the above-mentioned compound or a pharmaceutically acceptable salt thereof, or an enantiomer or isotopic variations thereof, is a compound selected from the following structures:

| Number | Structure |
|---|---|
| Compound 1 | 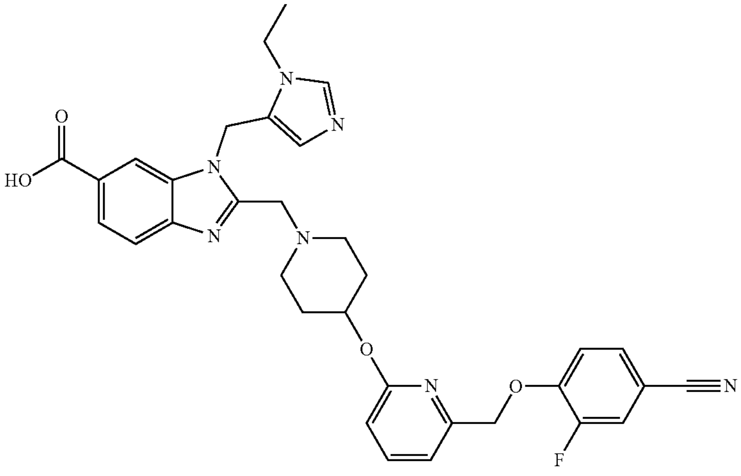 [SMILES: CCn1cncc1Cn1c(CN2CCC(Oc3cccc(COc4ccc(C#N)cc4F)n3)CC2)nc2ccc(C(=O)O)cc21] |

-continued
| Number | Structure |
|---|---|
| Compound 2 | 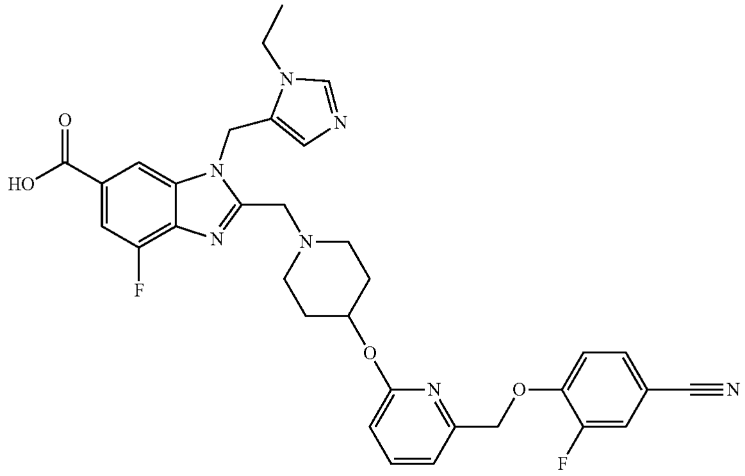 [SMILES: CCn1cncc1Cn1c(CN2CCC(Oc3cccc(COc4ccc(C#N)cc4F)n3)CC2)nc2c(F)cc(C(=O)O)cc21] |
| Compound 3 | 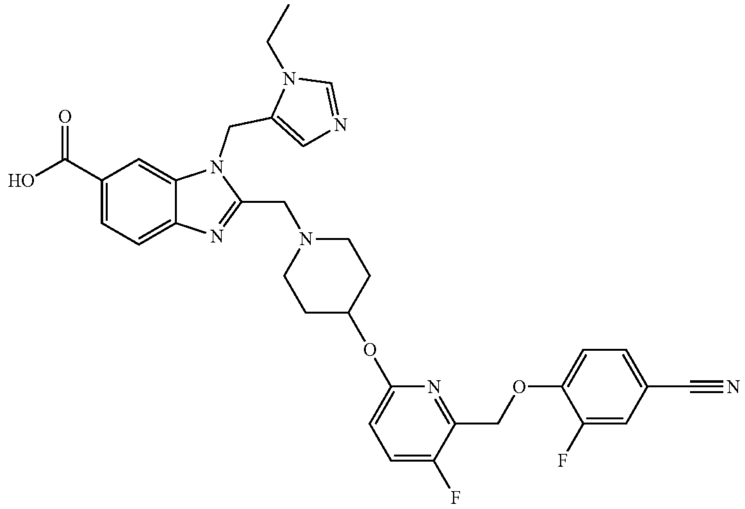 [SMILES: CCn1cncc1Cn1c(CN2CCC(Oc3ccc(F)c(COc4ccc(C#N)cc4F)n3)CC2)nc2ccc(C(=O)O)cc21] |
| Compound 4 | 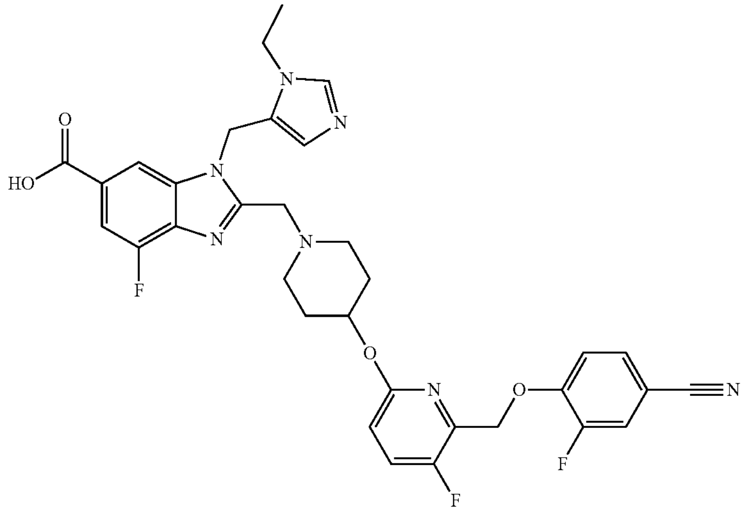 |

-continued
| Number | Structure |
| --- | --- |
| Compound 5 | 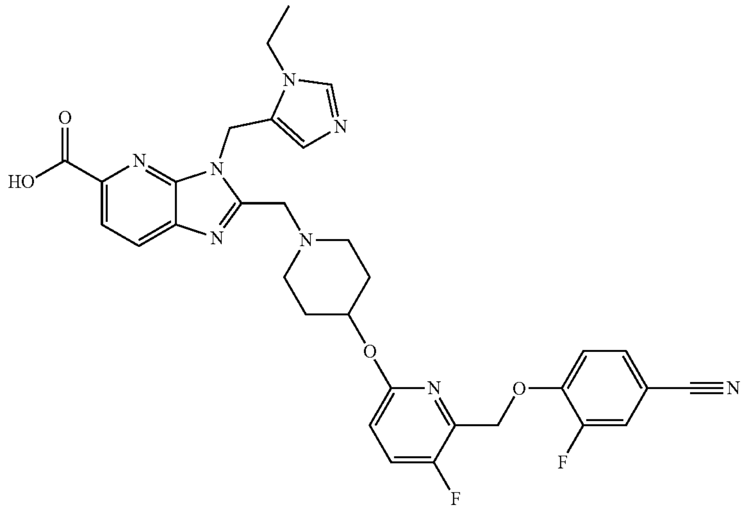 |
| Compound 6 | 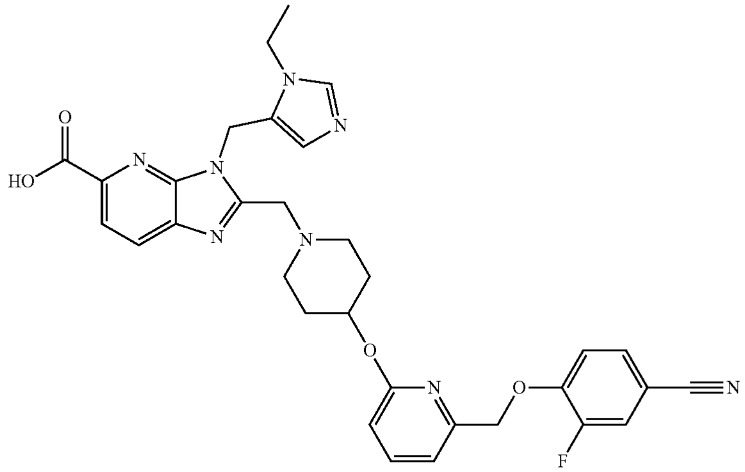 |
| Compound 7 | 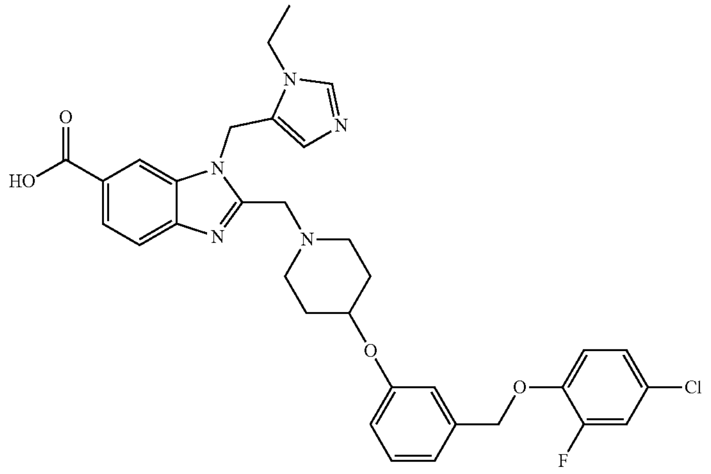 |

-continued
| Number | Structure |
| --- | --- |
| Compound 8 | 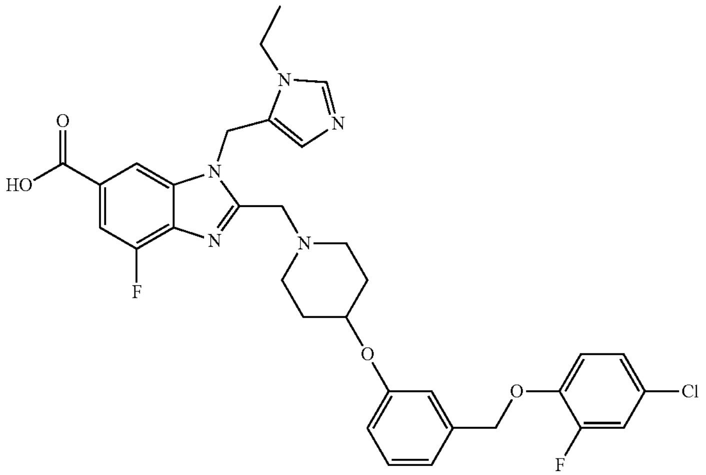 [SMILES: CCn1cncc1Cn1c(CN2CCC(Oc3cccc(COc4ccc(Cl)cc4F)c3)CC2)nc2c(F)cc(C(=O)O)cc21] |
| Compound 9 | 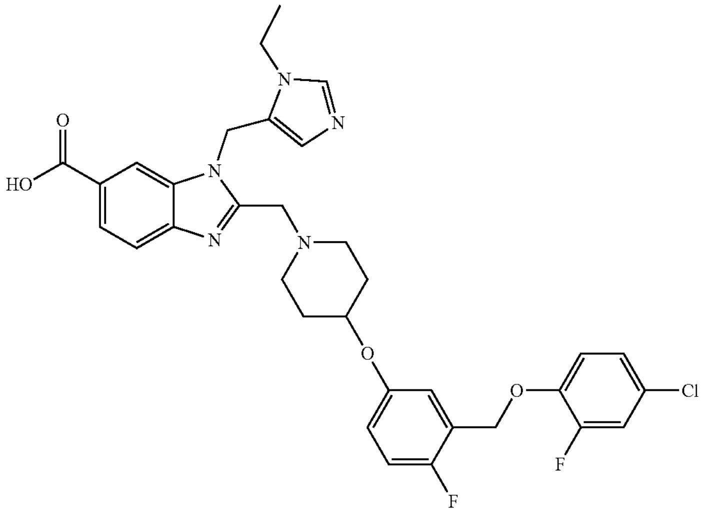 [SMILES: CCn1cncc1Cn1c(CN2CCC(Oc3ccc(F)c(COc4ccc(Cl)cc4F)c3)CC2)nc2ccc(C(=O)O)cc21] |
| Compound 10 | 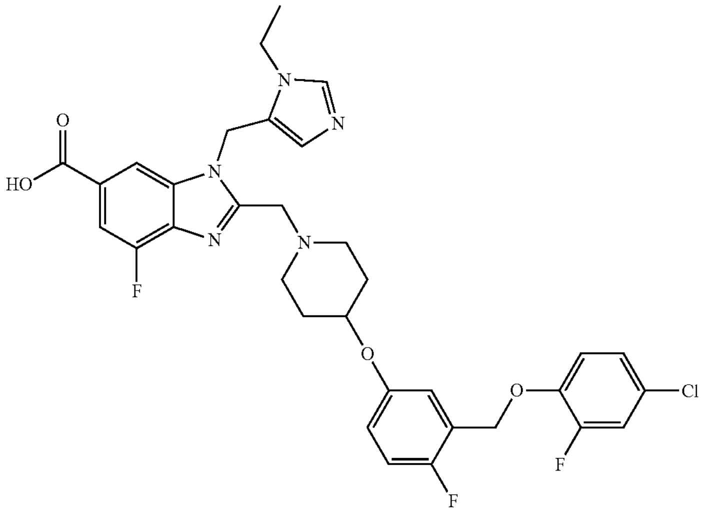 |

-continued
| Number | Structure |
| --- | --- |
| Compound 11 | 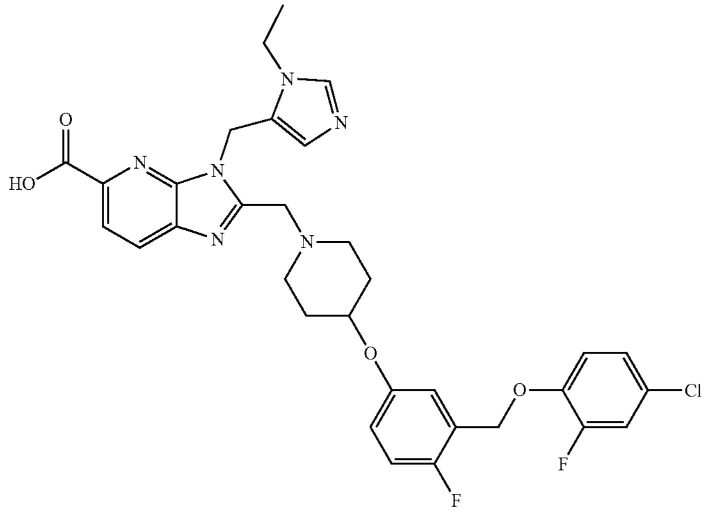 |
| Compound 12 | 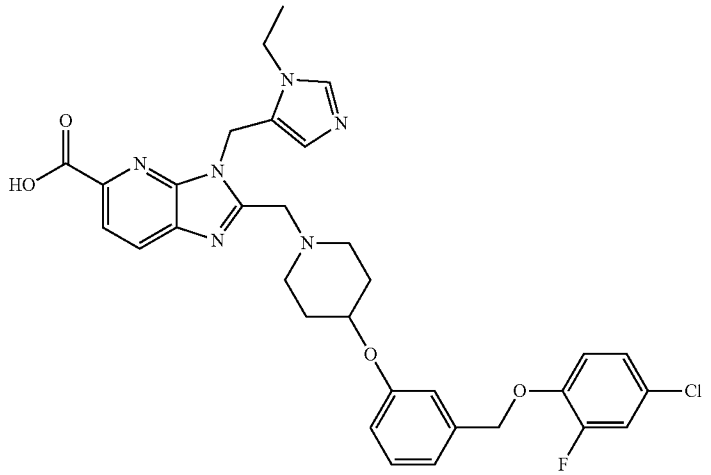 [SMILES: CCn1cncc1Cn1c(CN2CCC(Oc3cccc(COc4ccc(Cl)cc4F)c3)CC2)nc2ccc(C(=O)O)nc21] |
| Compound 13 | 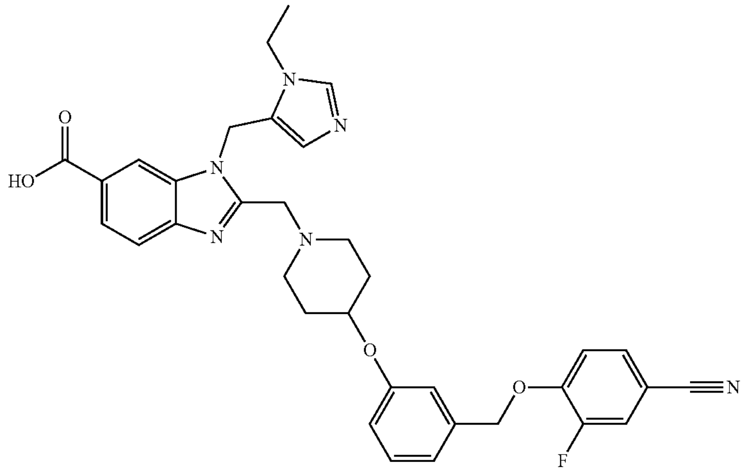 [SMILES: CCn1cncc1Cn1c(CN2CCC(Oc3cccc(COc4ccc(C#N)cc4F)c3)CC2)nc2ccc(C(=O)O)cc21] |

-continued
| Number | Structure |
|---|---|
| Compound 14 | 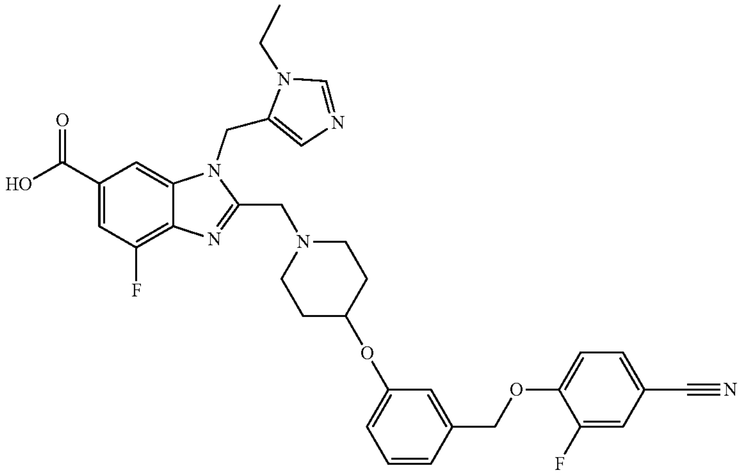 |
| Compound 15 | 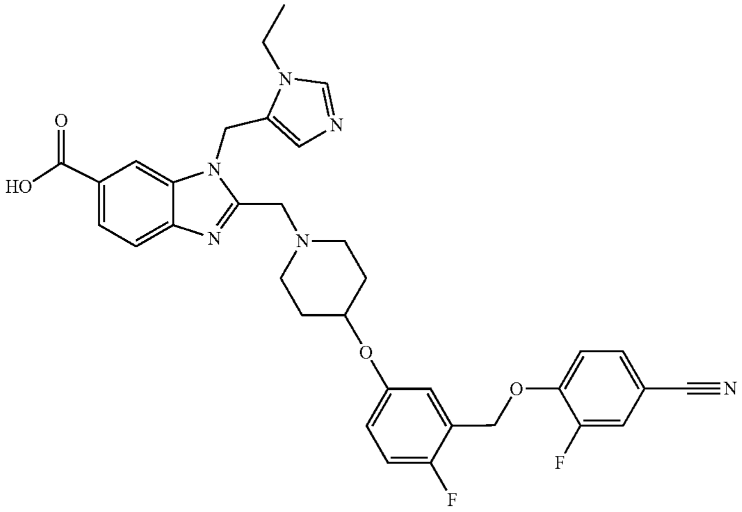 [SMILES: CCn1cncc1Cn1c(CN2CCC(Oc3ccc(F)c(COc4ccc(C#N)cc4F)c3)CC2)nc2ccc(C(=O)O)cc21] |
| Compound 16 | 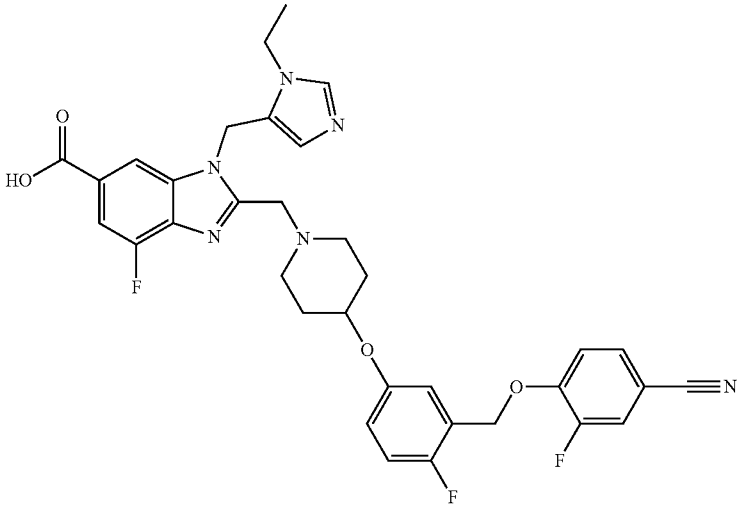 |

-continued
| Number | Structure |
|---|---|
| Compound 17 | 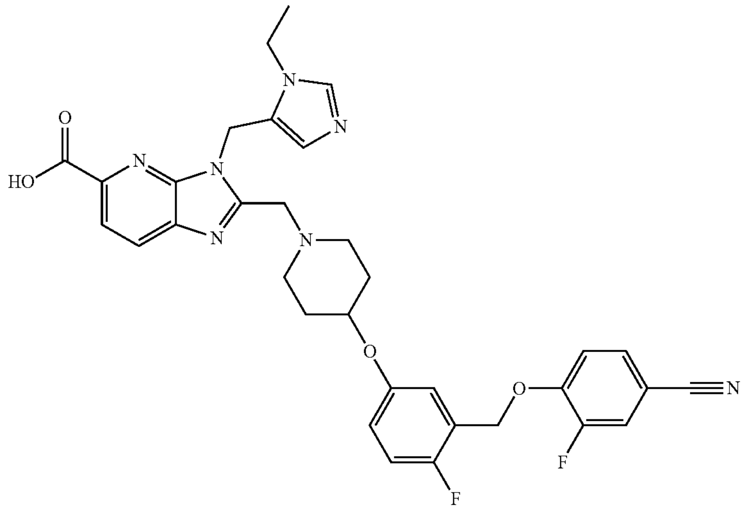 |
| Compound 18 | 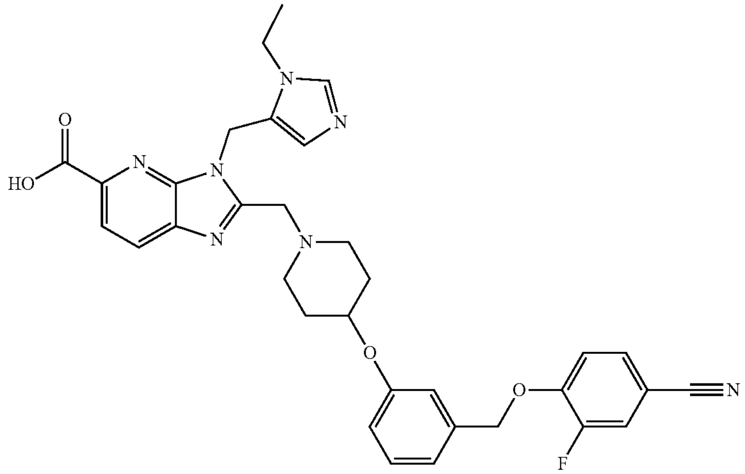 [SMILES: CCn1cncc1Cn1c(CN2CCC(Oc3cccc(COc4ccc(C#N)cc4F)c3)CC2)nc2ccc(C(=O)O)nc21] |
| Compound 19 | 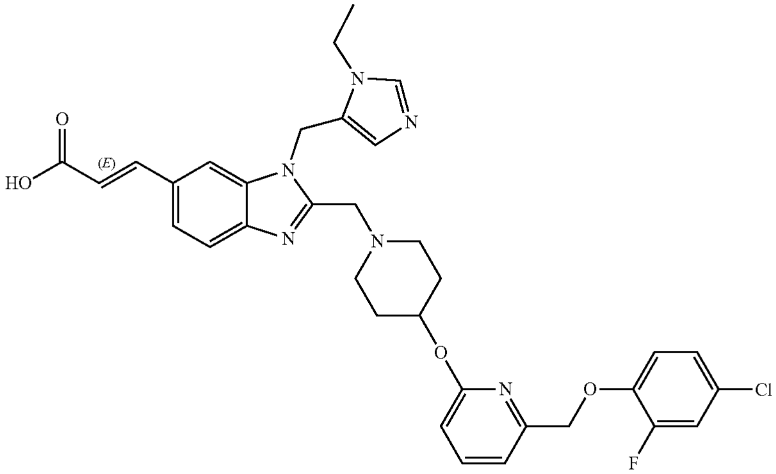 [SMILES: CCn1cncc1Cn1c(CN2CCC(Oc3cccc(COc4ccc(Cl)cc4F)n3)CC2)nc2ccc(/C=C/C(=O)O)cc21] |

-continued
| Number | Structure |
| --- | --- |
| Compound 20 | 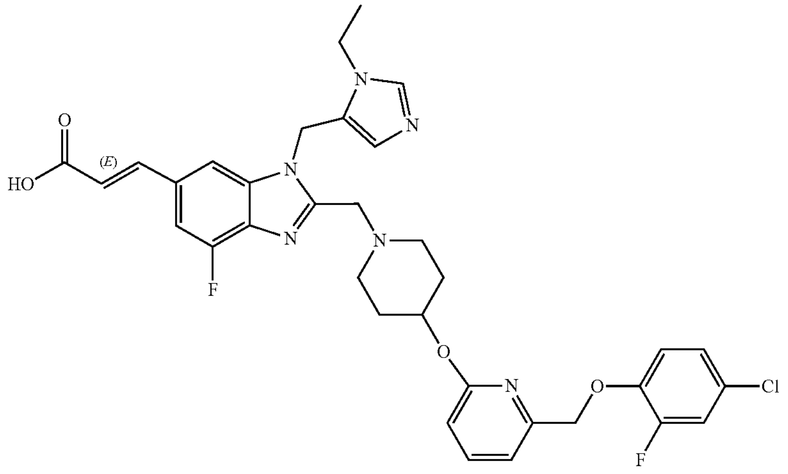 [SMILES: CCn1cncc1Cn1c(CN2CCC(Oc3cccc(COc4ccc(Cl)cc4F)n3)CC2)nc2c(F)cc(/C=C/C(=O)O)cc21] |
| Compound 21 | 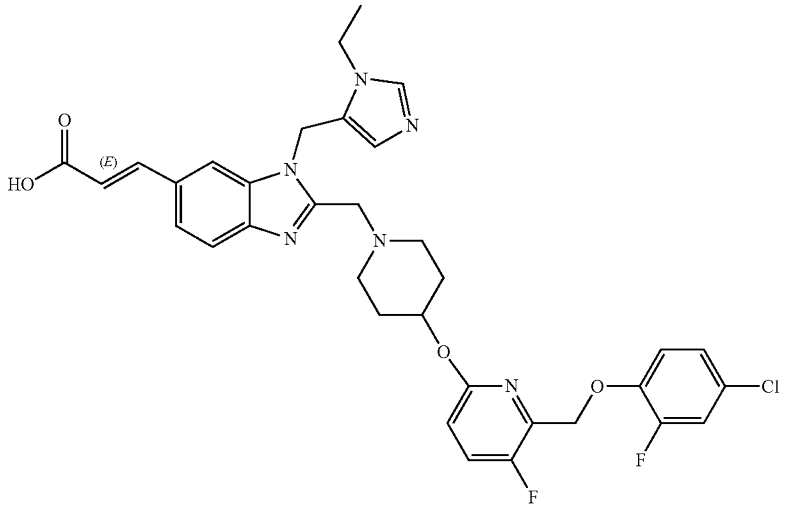 [SMILES: CCn1cncc1Cn1c(CN2CCC(Oc3ccc(F)c(COc4ccc(Cl)cc4F)n3)CC2)nc2ccc(/C=C/C(=O)O)cc21] |
| Compound 22 | 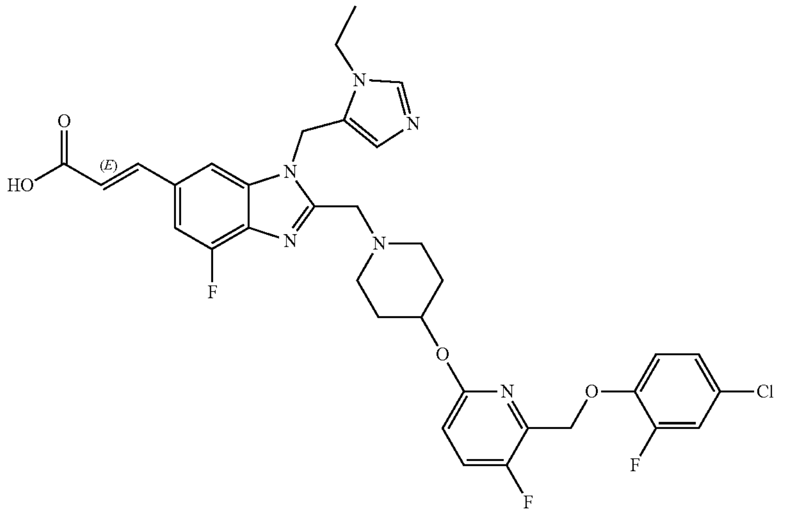 [SMILES: CCn1cncc1Cn1c(CN2CCC(Oc3ccc(F)c(COc4ccc(Cl)cc4F)n3)CC2)nc2c(F)cc(/C=C/C(=O)O)cc21] |

-continued
| Number | Structure |
| --- | --- |
| Compound 23 | 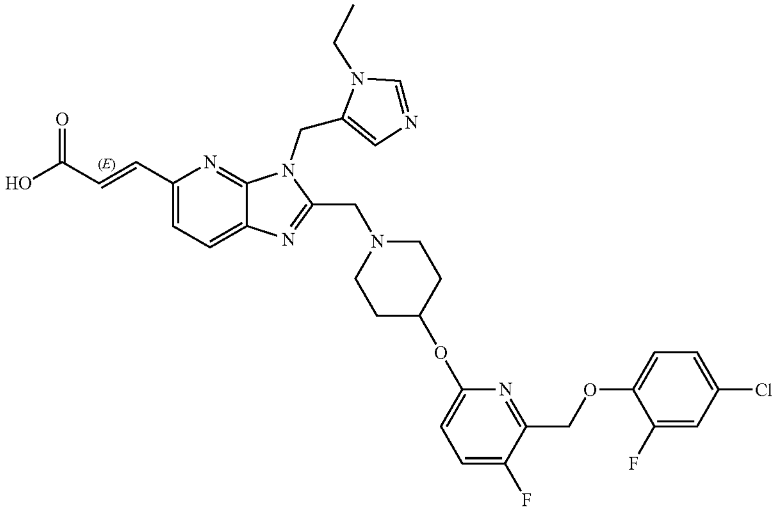 [SMILES: CCn1cncc1Cn1c(CN2CCC(Oc3ccc(F)c(COc4ccc(Cl)cc4F)n3)CC2)nc2ccc(/C=C/C(=O)O)nc21] |
| Compound 24 | 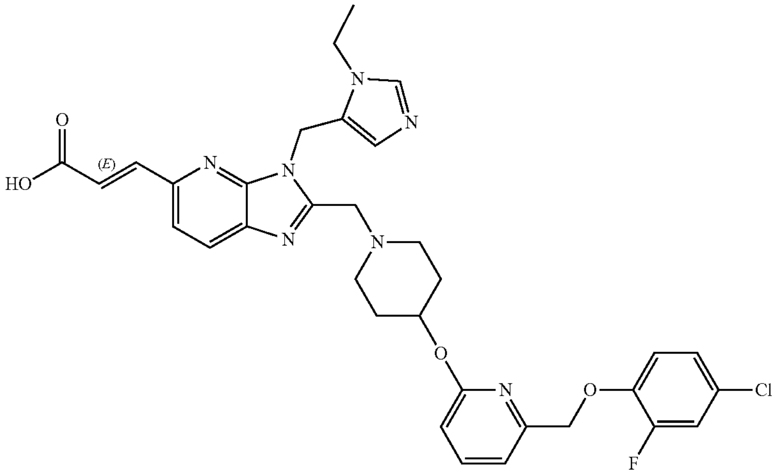 [SMILES: CCn1cncc1Cn1c(CN2CCC(Oc3cccc(COc4ccc(Cl)cc4F)n3)CC2)nc2ccc(/C=C/C(=O)O)nc21] |
| Compound 25 | 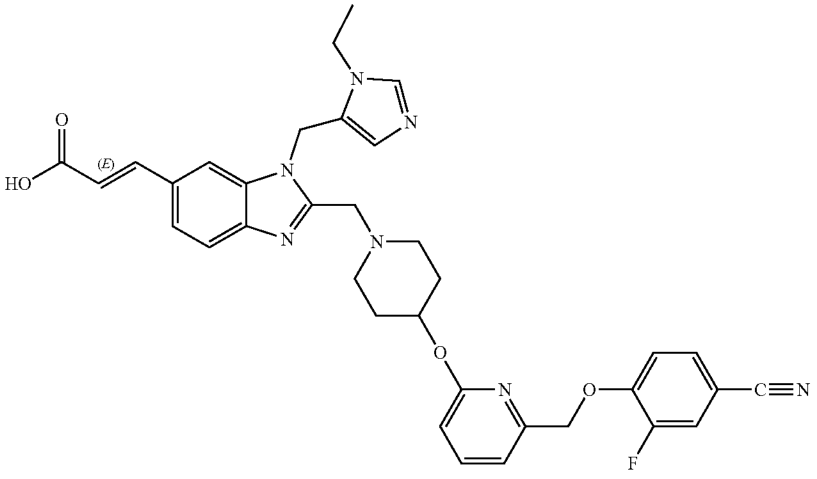 [SMILES: CCn1cncc1Cn1c(CN2CCC(Oc3cccc(COc4ccc(C#N)cc4F)n3)CC2)nc2ccc(/C=C/C(=O)O)cc21] |

-continued
| Number | Structure |
|---|---|
| Compound 26 | 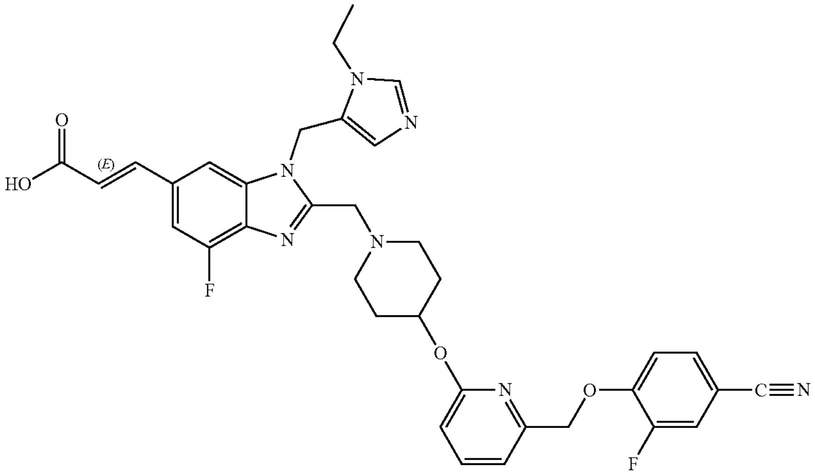 [SMILES: CCn1cncc1Cn1c(CN2CCC(Oc3cccc(COc4ccc(C#N)cc4F)n3)CC2)nc2c(F)cc(/C=C/C(=O)O)cc21] |
| Compound 27 | 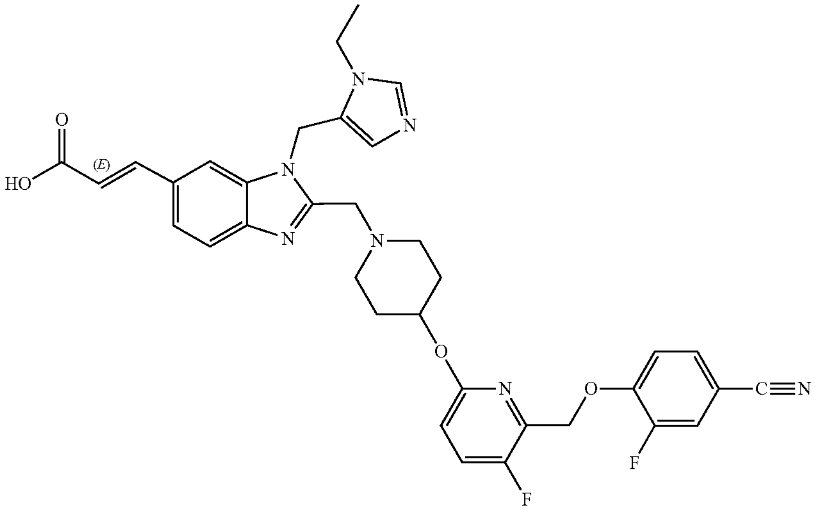 [SMILES: CCn1cncc1Cn1c(CN2CCC(Oc3ccc(F)c(COc4ccc(C#N)cc4F)n3)CC2)nc2ccc(/C=C/C(=O)O)cc21] |
| Compound 28 | 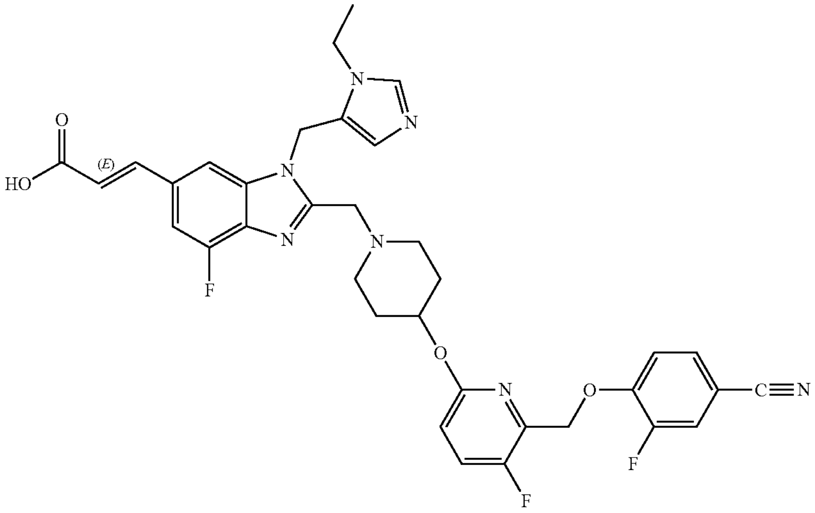 [SMILES: CCn1cncc1Cn1c(CN2CCC(Oc3ccc(F)c(COc4ccc(C#N)cc4F)n3)CC2)nc2c(F)cc(/C=C/C(=O)O)cc21] |

-continued
| Number | Structure |
| --- | --- |
| Compound 29 | 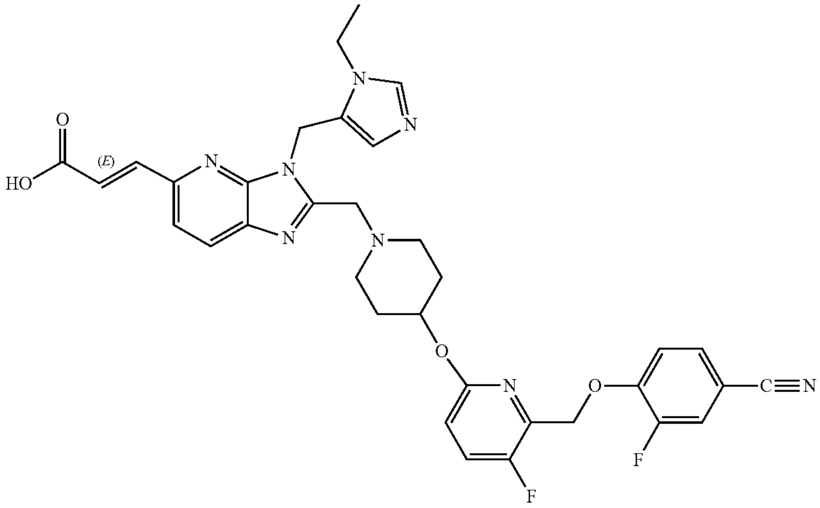 [SMILES: CCn1cncc1Cn1c(CN2CCC(Oc3ccc(F)c(COc4ccc(C#N)cc4F)n3)CC2)nc2ccc(/C=C/C(=O)O)nc21] |
| Compound 30 | 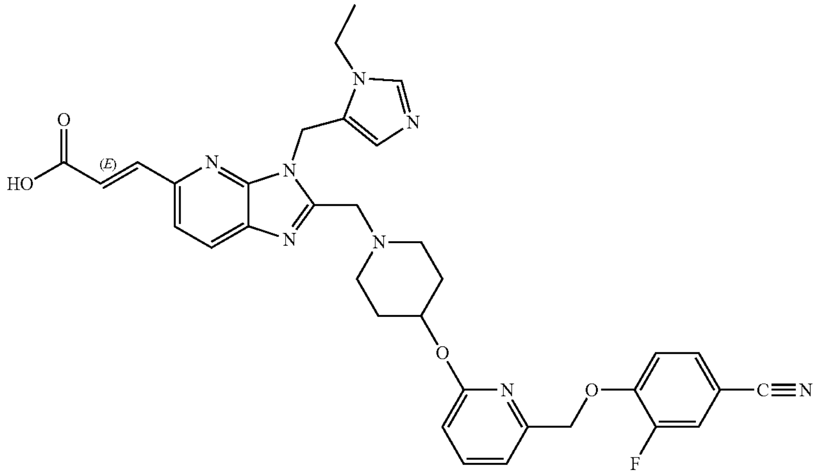 [SMILES: CCn1cncc1Cn1c(CN2CCC(Oc3cccc(COc4ccc(C#N)cc4F)n3)CC2)nc2ccc(/C=C/C(=O)O)nc21] |
| Compound 31 | 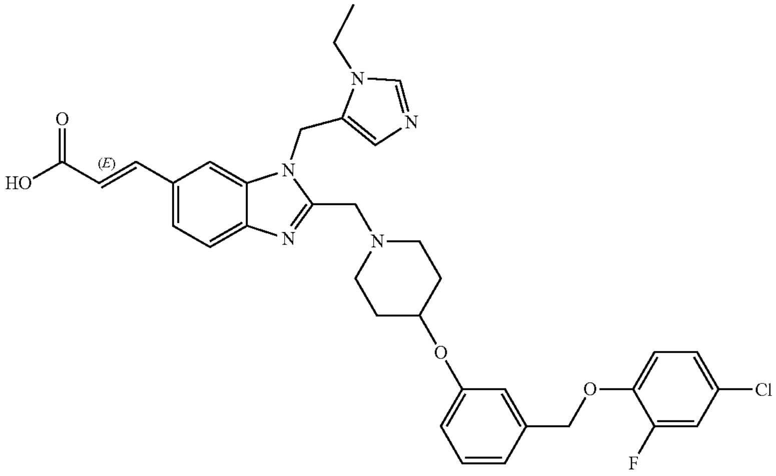 [SMILES: CCn1cncc1Cn1c(CN2CCC(Oc3cccc(COc4ccc(Cl)cc4F)c3)CC2)nc2ccc(/C=C/C(=O)O)cc21] |

-continued
| Number | Structure |
|---|---|
| Compound 32 | 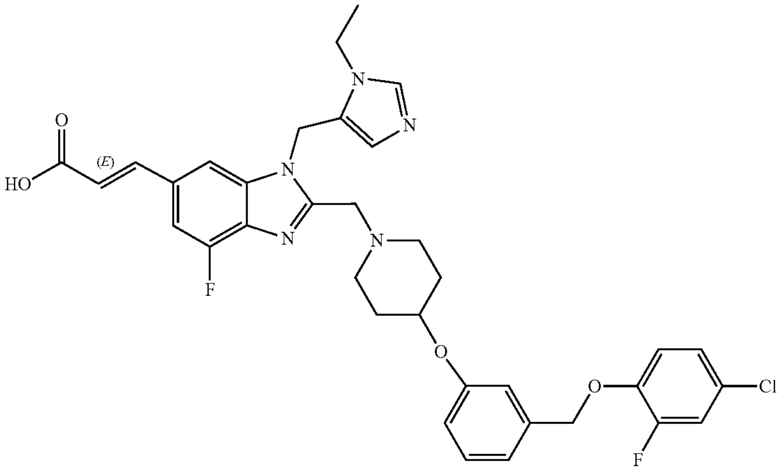 [SMILES: CCn1cncc1Cn1c(CN2CCC(Oc3cccc(COc4ccc(Cl)cc4F)c3)CC2)nc2c(F)cc(/C=C/C(=O)O)cc21] |
| Compound 33 | 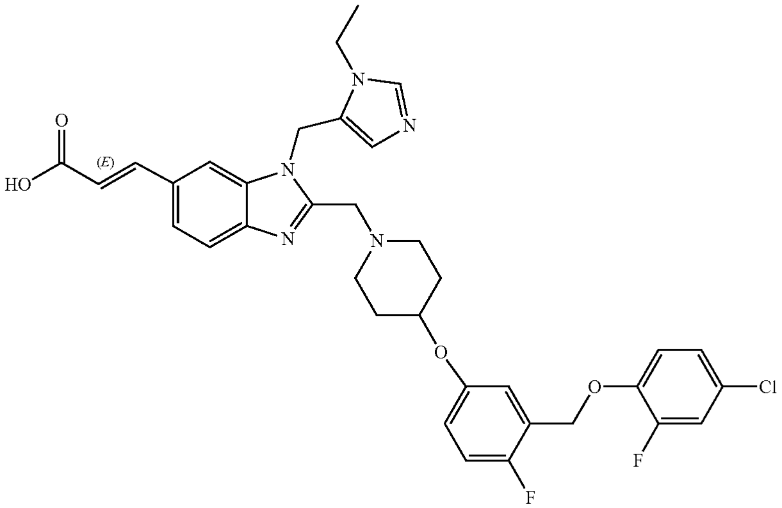 [SMILES: CCn1cncc1Cn1c(CN2CCC(Oc3ccc(F)c(COc4ccc(Cl)cc4F)c3)CC2)nc2ccc(/C=C/C(=O)O)cc21] |
| Compound 34 | 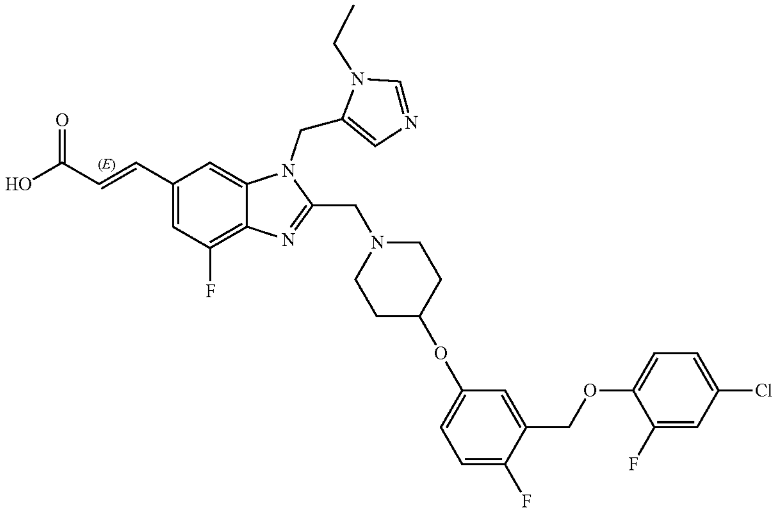 [SMILES: CCn1cncc1Cn1c(CN2CCC(Oc3ccc(F)c(COc4ccc(Cl)cc4F)c3)CC2)nc2c(F)cc(/C=C/C(=O)O)cc21] |

-continued
| Number | Structure |
|---|---|
| Compound 35 | 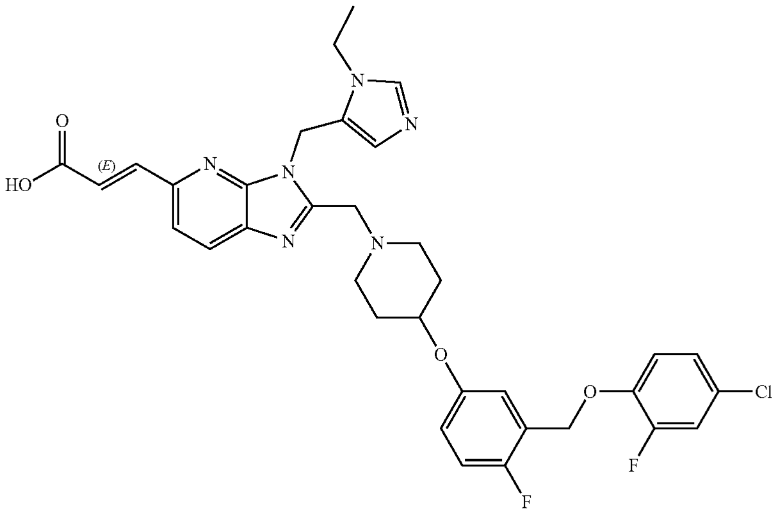 [SMILES: CCn1cncc1Cn1c(CN2CCC(Oc3ccc(F)c(COc4ccc(Cl)cc4F)c3)CC2)nc2ccc(/C=C/C(=O)O)nc21] |
| Compound 36 | 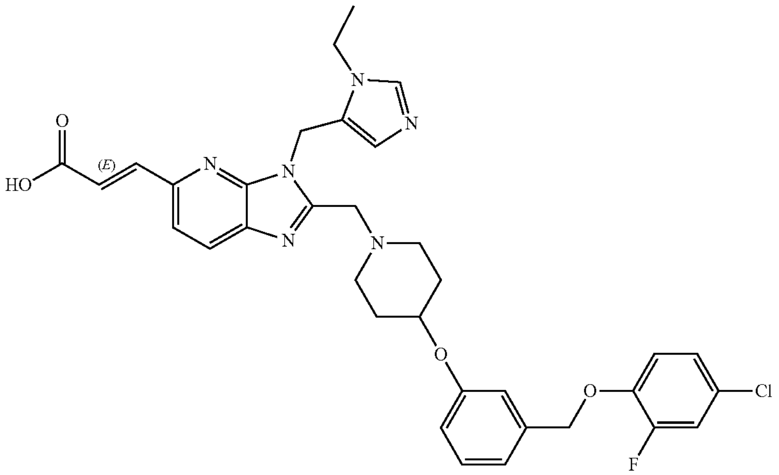 [SMILES: CCn1cncc1Cn1c(CN2CCC(Oc3cccc(COc4ccc(Cl)cc4F)c3)CC2)nc2ccc(/C=C/C(=O)O)nc21] |
| Compound 37 | 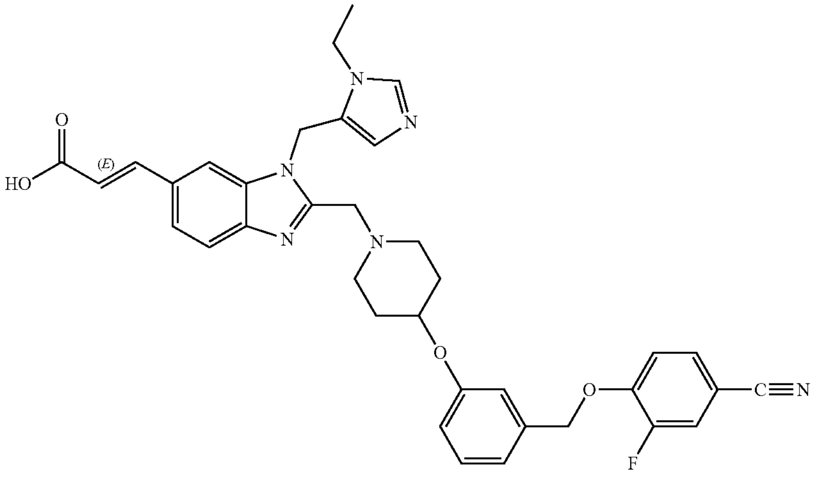 [SMILES: CCn1cncc1Cn1c(CN2CCC(Oc3cccc(COc4ccc(C#N)cc4F)c3)CC2)nc2ccc(/C=C/C(=O)O)cc21] |

-continued
| Number | Structure |
|---|---|
| Compound 38 | 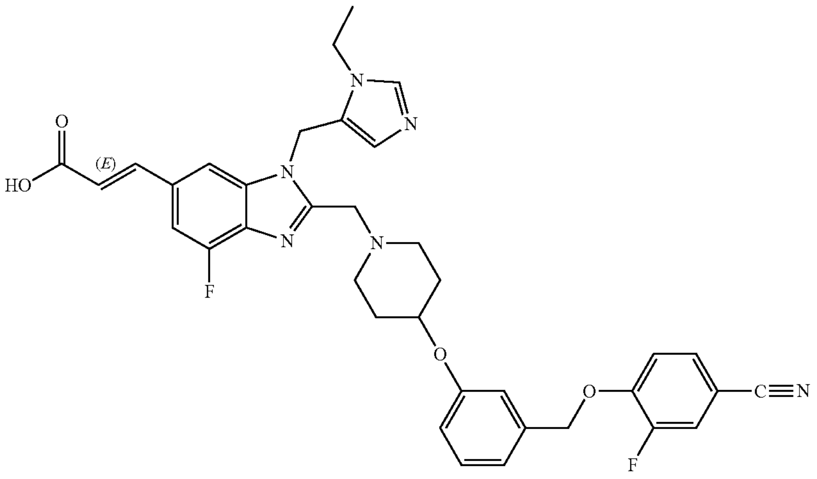 [SMILES: CCn1cncc1Cn1c(CN2CCC(Oc3cccc(COc4ccc(C#N)cc4F)c3)CC2)nc2c(F)cc(/C=C/C(=O)O)cc21] |
| Compound 39 | 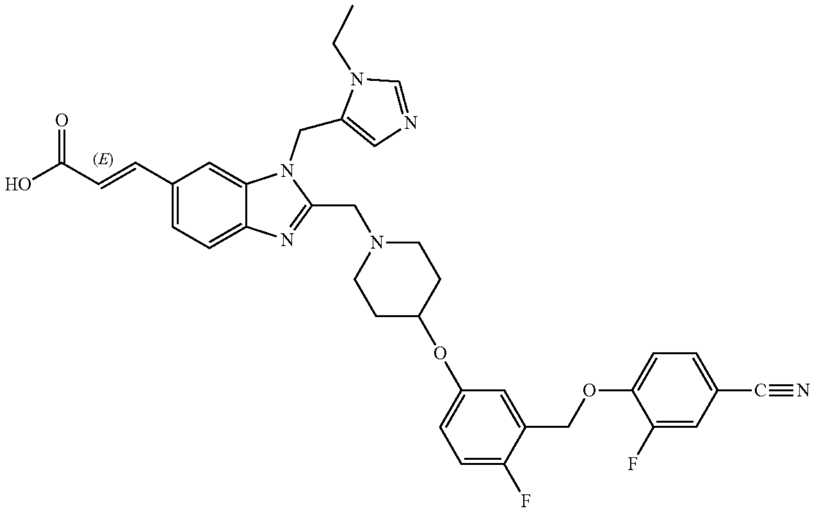 [SMILES: CCn1cncc1Cn1c(CN2CCC(Oc3ccc(F)c(COc4ccc(C#N)cc4F)c3)CC2)nc2ccc(/C=C/C(=O)O)cc21] |
| Compound 40 | 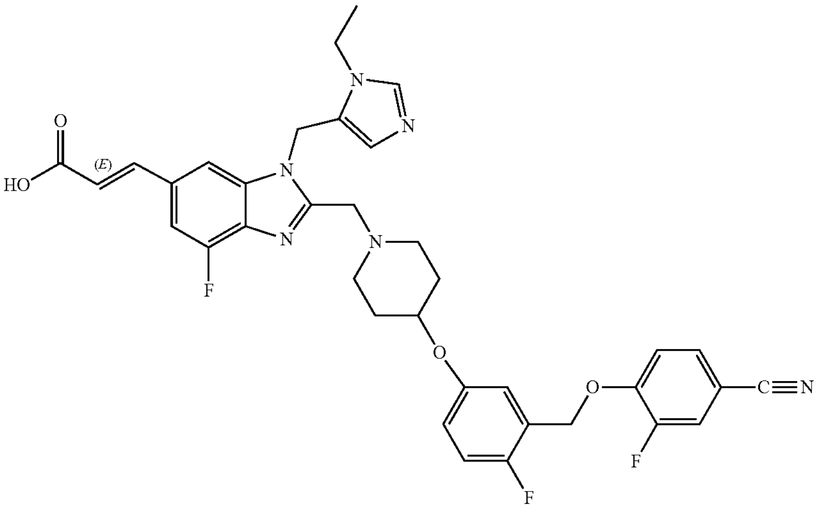 [SMILES: CCn1cncc1Cn1c(CN2CCC(Oc3ccc(F)c(COc4ccc(C#N)cc4F)c3)CC2)nc2c(F)cc(/C=C/C(=O)O)cc21] |

-continued
| Number | Structure |
|---|---|
| Compound 41 | 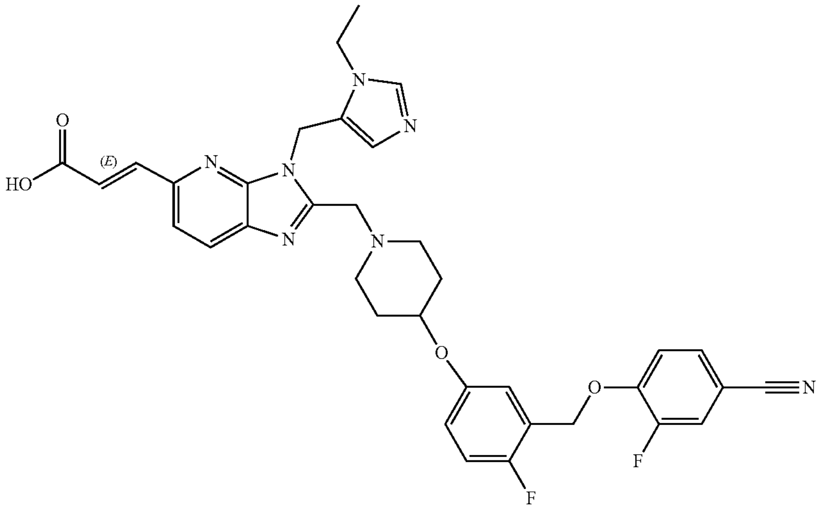 [SMILES: CCn1cncc1Cn1c(CN2CCC(Oc3ccc(F)c(COc4ccc(C#N)cc4F)c3)CC2)nc2ccc(/C=C/C(=O)O)nc21] |
| Compound 42 | 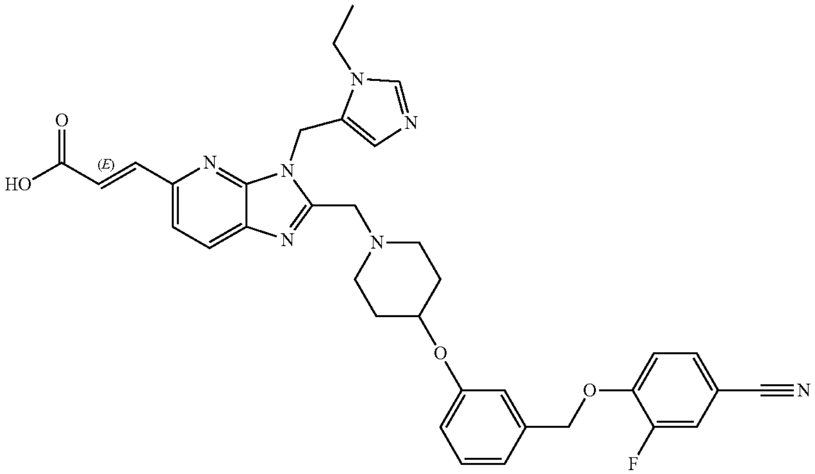 [SMILES: CCn1cncc1Cn1c(CN2CCC(Oc3cccc(COc4ccc(C#N)cc4F)c3)CC2)nc2ccc(/C=C/C(=O)O)nc21] |
| Compound 43 | 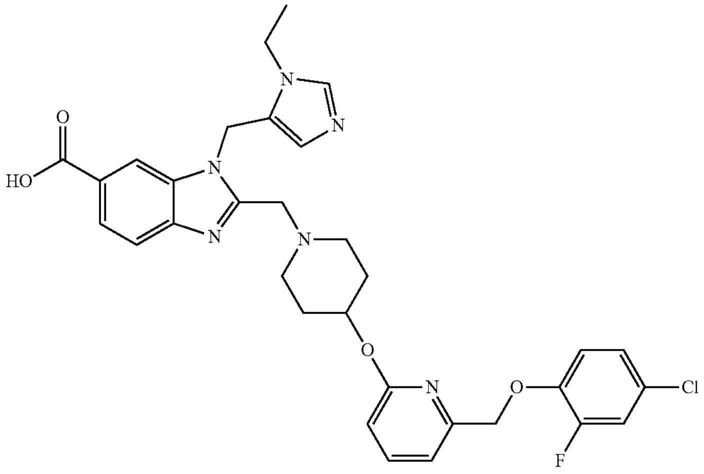 [SMILES: CCn1cncc1Cn1c(CN2CCC(Oc3cccc(COc4ccc(Cl)cc4F)n3)CC2)nc2ccc(C(=O)O)cc21] |

-continued
| Number | Structure |
| --- | --- |
| Compound 44 | 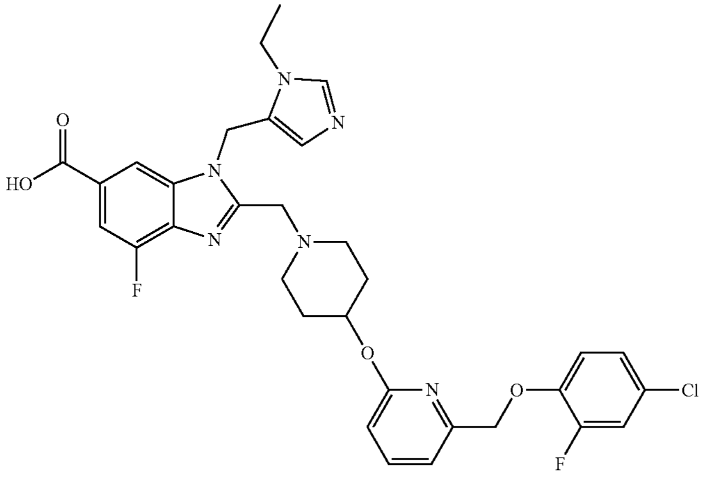 [SMILES: CCn1cncc1Cn1c(CN2CCC(Oc3cccc(COc4ccc(Cl)cc4F)n3)CC2)nc2c(F)cc(C(=O)O)cc21] |
| Compound 45 | 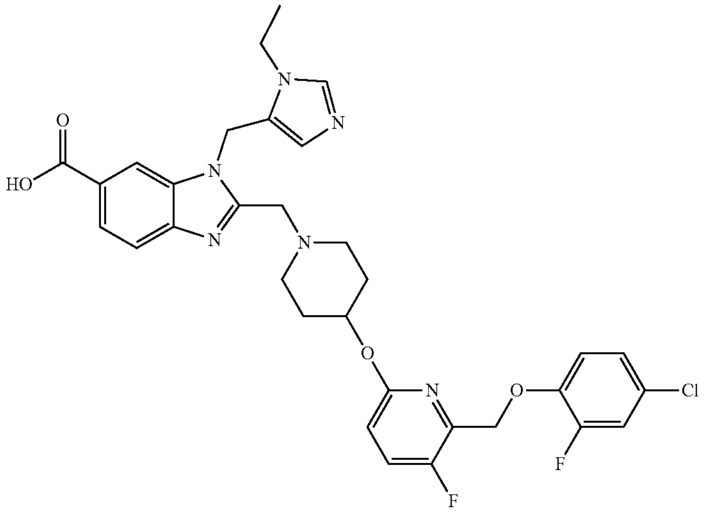 [SMILES: CCn1cncc1Cn1c(CN2CCC(Oc3ccc(F)c(COc4ccc(Cl)cc4F)n3)CC2)nc2ccc(C(=O)O)cc21] |
| Compound 46 | 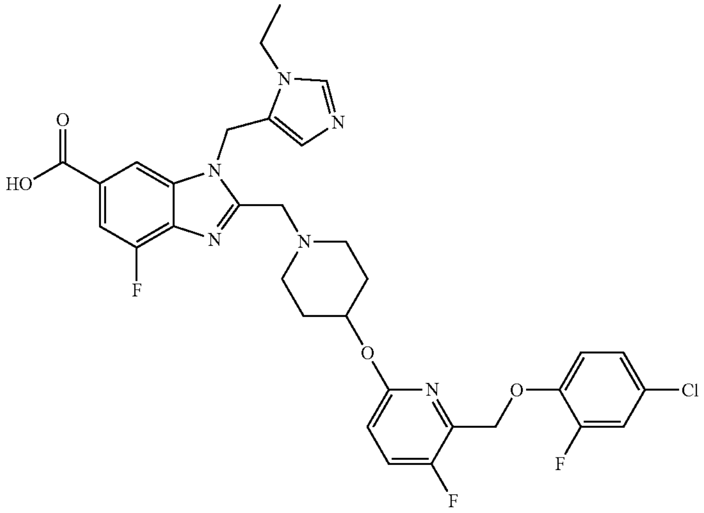 [SMILES: CCn1cncc1Cn1c(CN2CCC(Oc3ccc(F)c(COc4ccc(Cl)cc4F)n3)CC2)nc2c(F)cc(C(=O)O)cc21] |

-continued
| Number | Structure |
|---|---|
| Compound 47 | 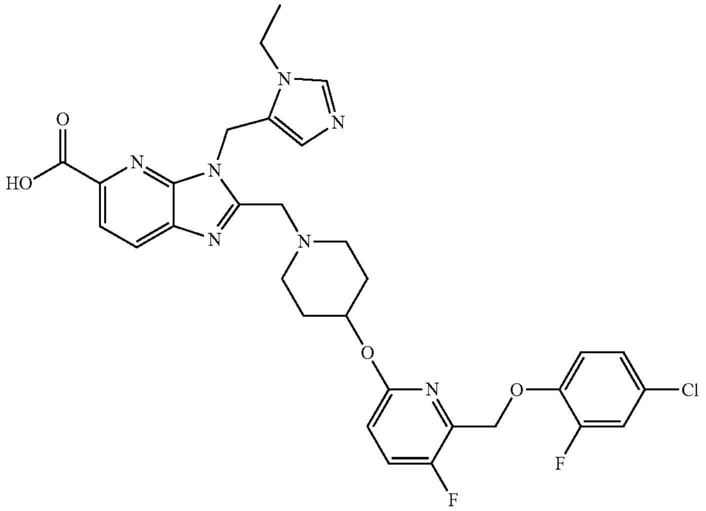 [SMILES: CCn1cncc1Cn1c(CN2CCC(Oc3ccc(F)c(COc4ccc(Cl)cc4F)n3)CC2)nc2ccc(C(=O)O)nc21] |
| Compound 48 | 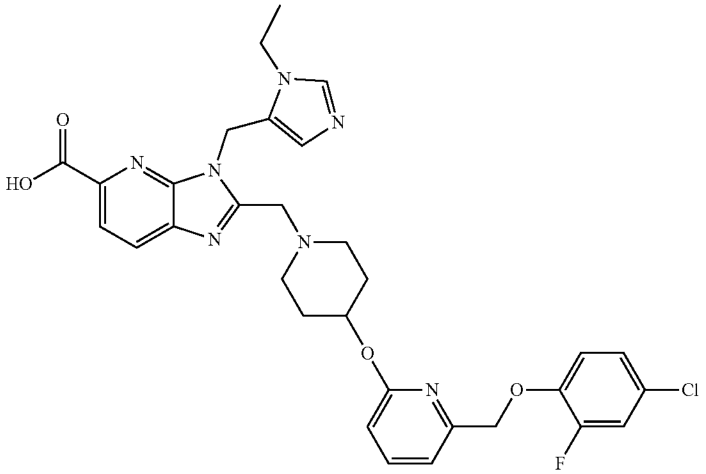 [SMILES: CCn1cncc1Cn1c(CN2CCC(Oc3cccc(COc4ccc(Cl)cc4F)n3)CC2)nc2ccc(C(=O)O)nc21] |
| Compound 49 | 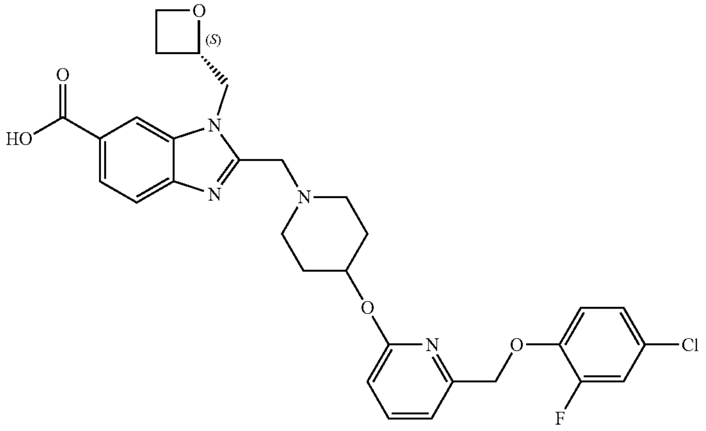 |

-continued
| Number | Structure |
|---|---|
| Compound 50 | 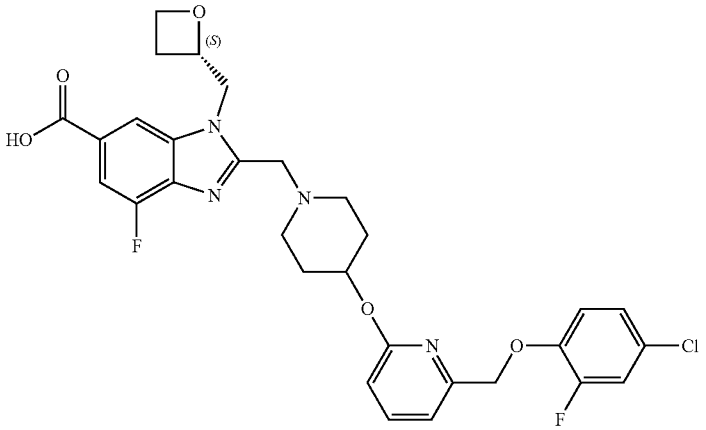 |
| Compound 51 | 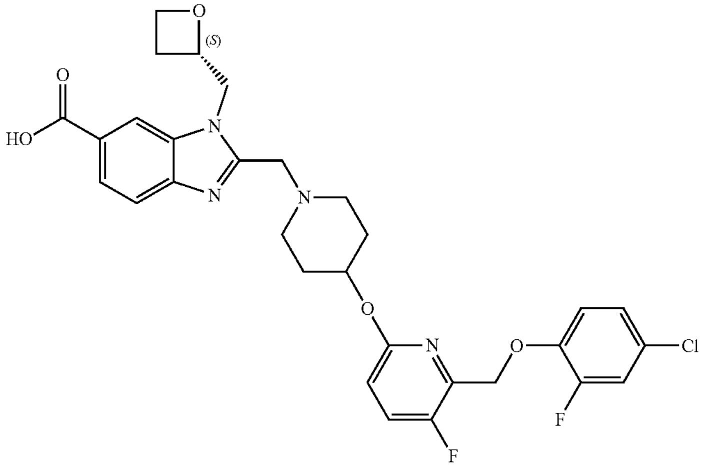 |
| Compound 52 | 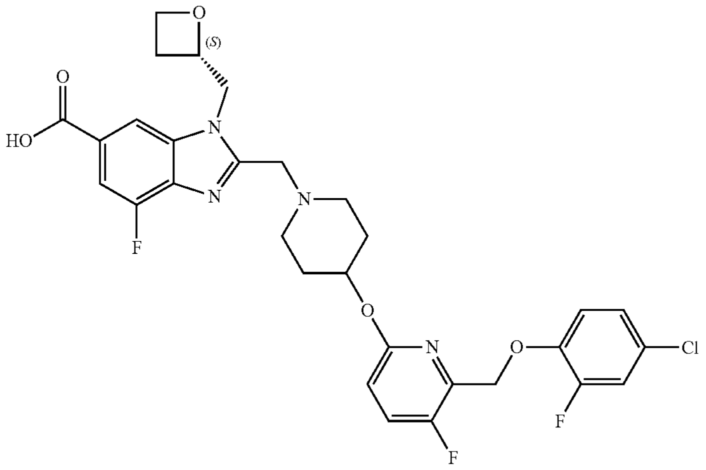 |

-continued
| Number | Structure |
|---|---|
| Compound 53 | 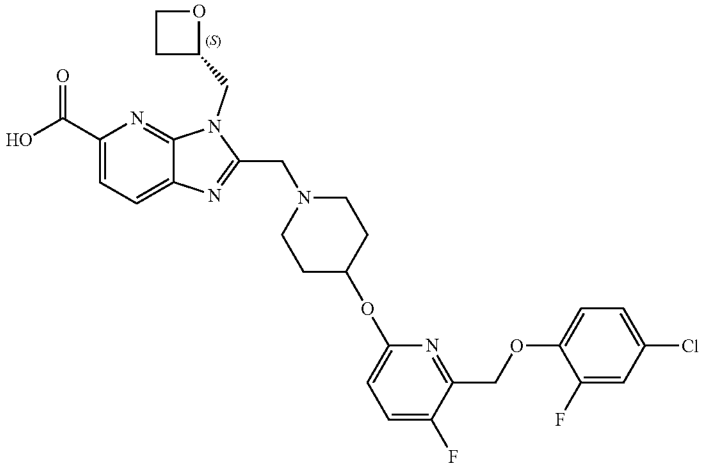 |
| Compound 54 | 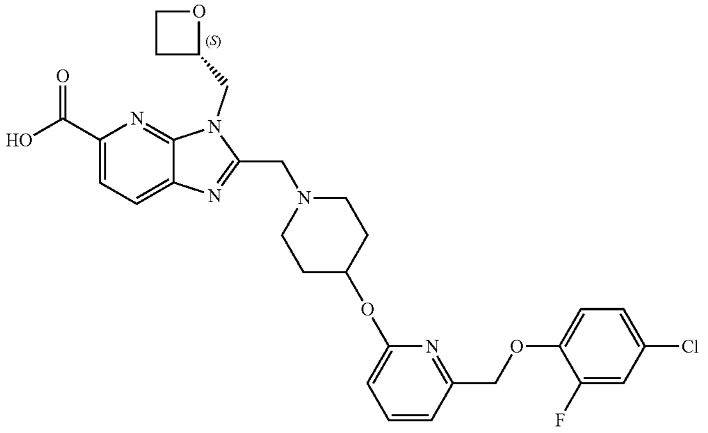 |
| Compound 55 | 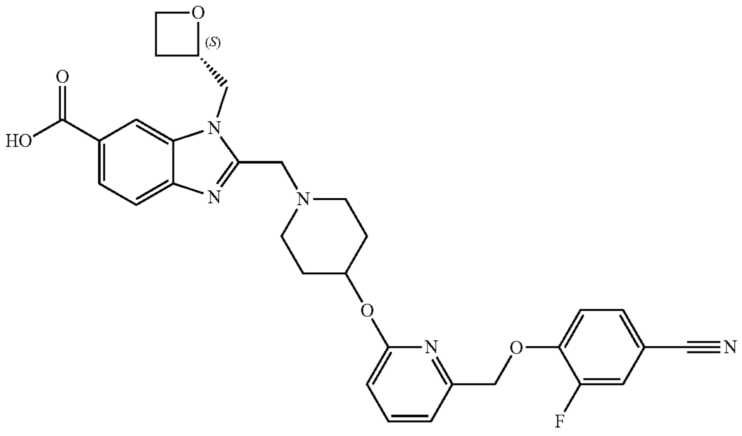 |

-continued
| Number | Structure |
| --- | --- |
| Compound 56 | 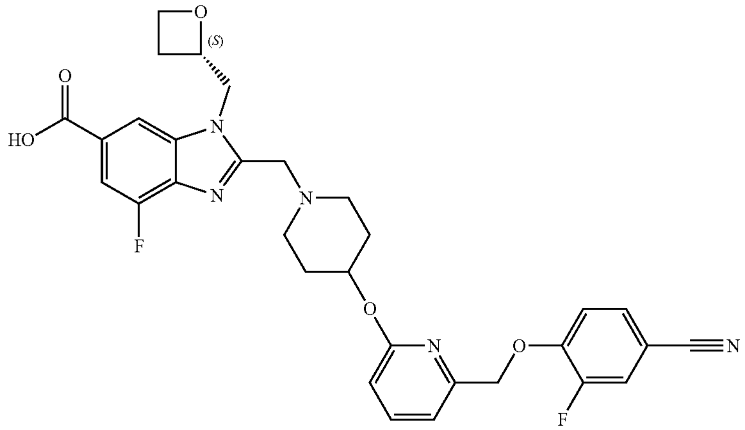 |
| Compound 57 | 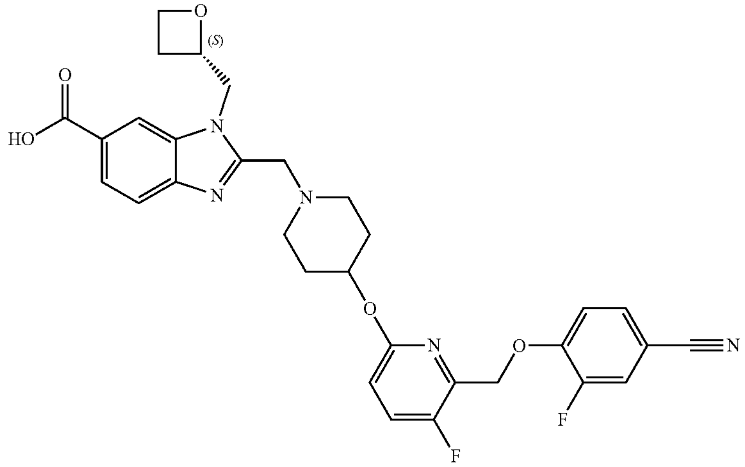 |
| Compound 58 | 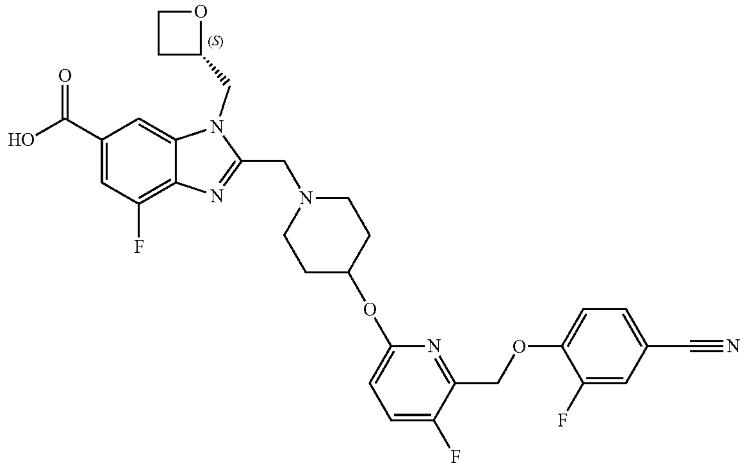 |

-continued
| Number | Structure |
|---|---|
| Compound 59 | 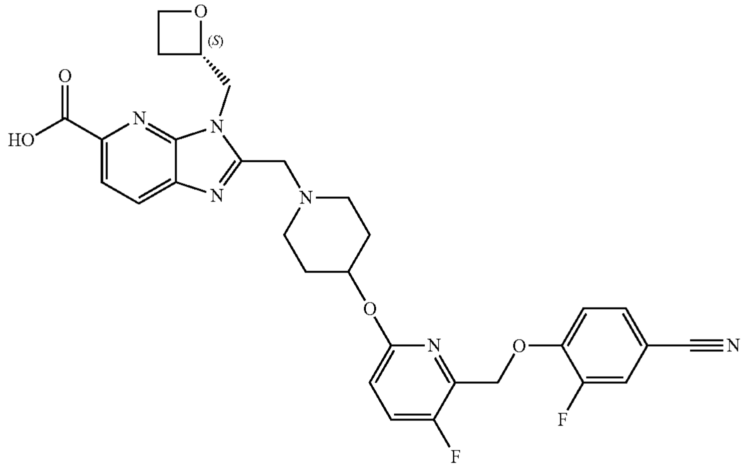 |
| Compound 60 | 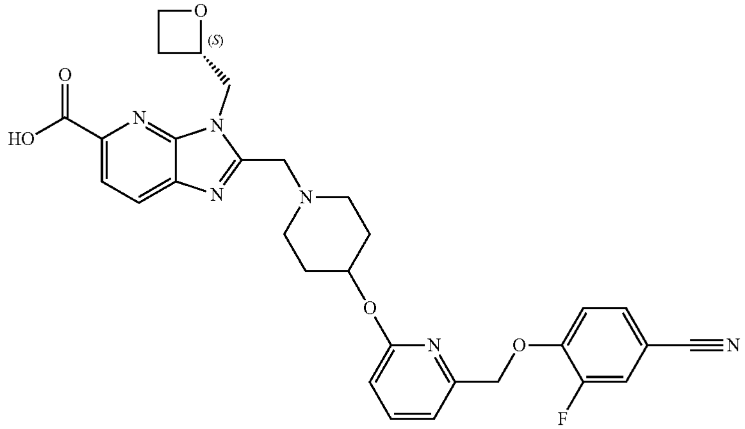 |
| Compound 61 | 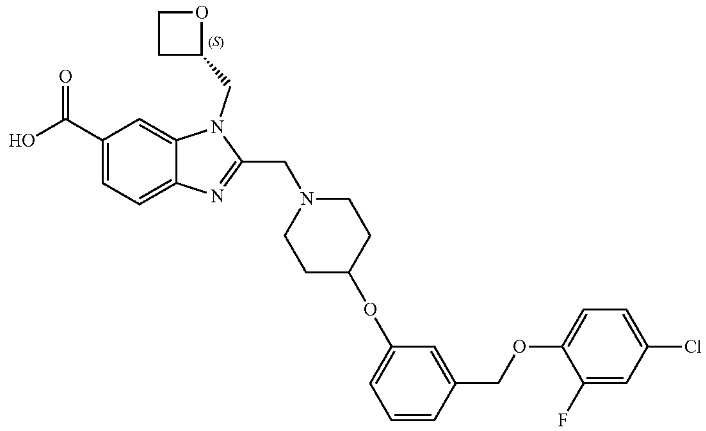 |

-continued
| Number | Structure |
|---|---|
| Compound 62 | 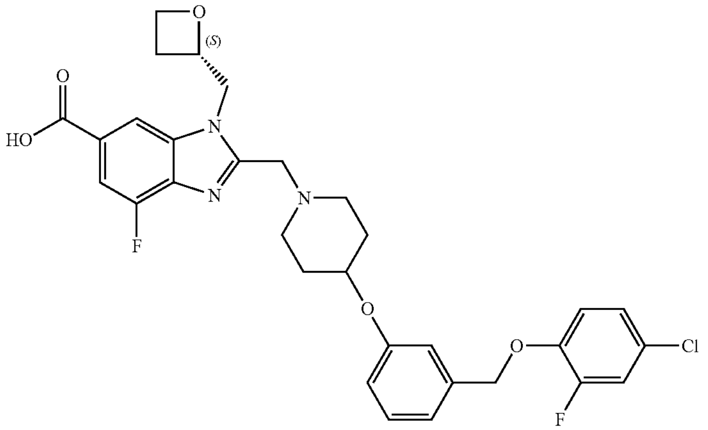 |
| Compound 63 | 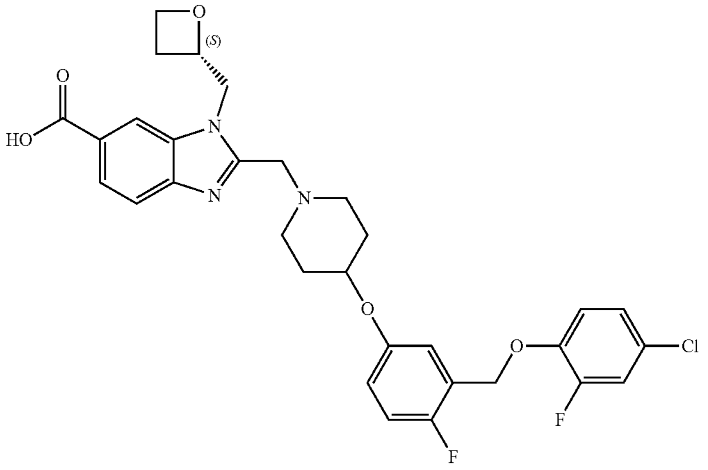 |
| Compound 64 | 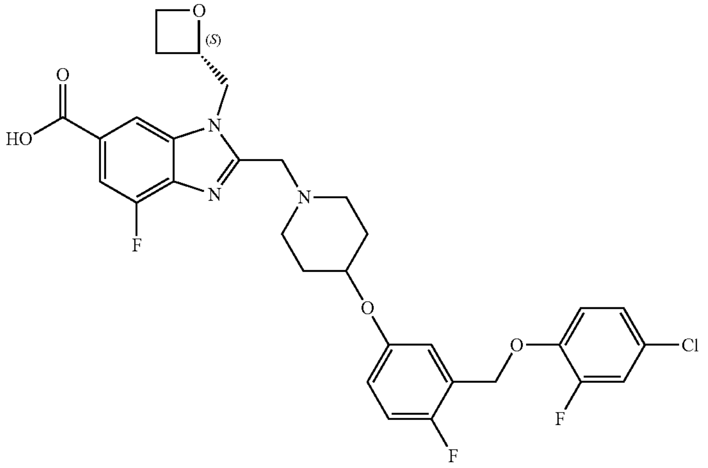 |

-continued
| Number | Structure |
|---|---|
| Compound 65 | 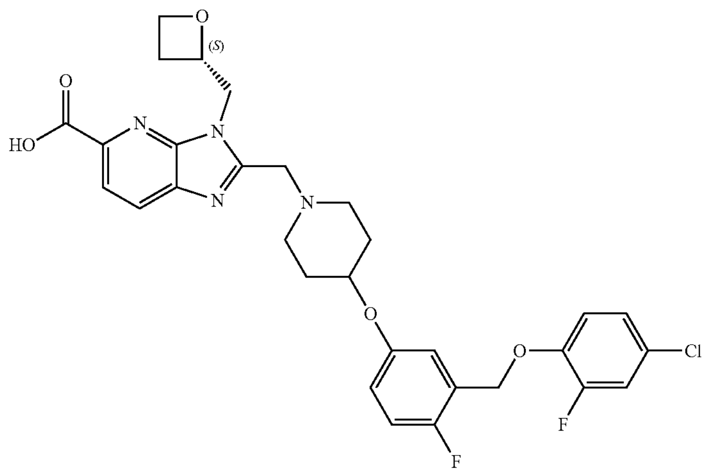 |
| Compound 66 | 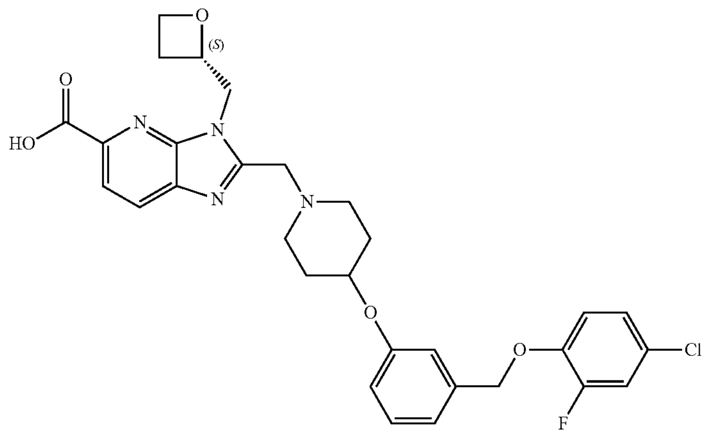 |
| Compound 67 | 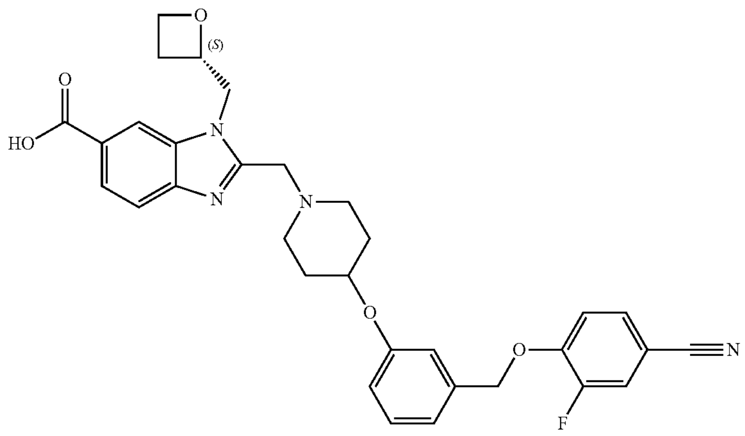 |

-continued
| Number | Structure |
|---|---|
| Compound 68 | 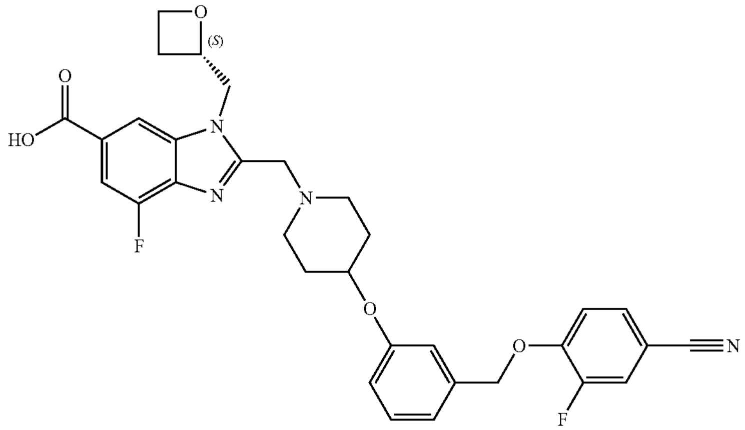 |
| Compound 69 | 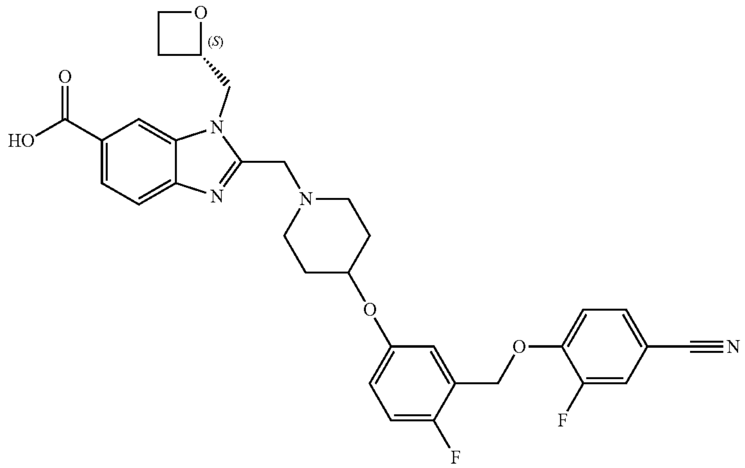 |
| Compound 70 | 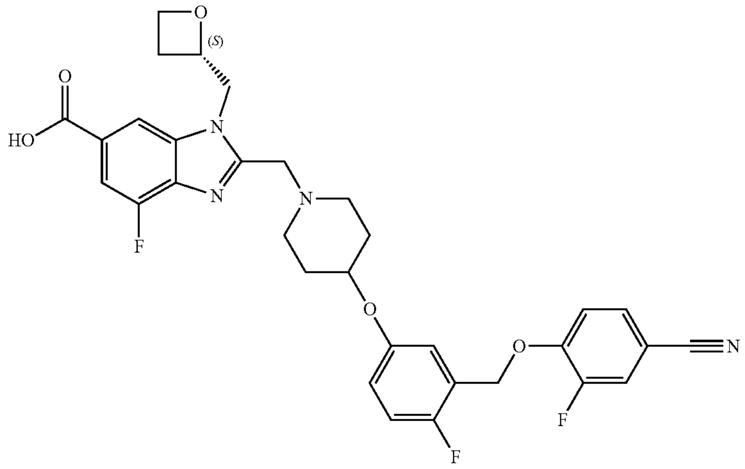 |

-continued
| Number | Structure |
| --- | --- |
| Compound 71 | 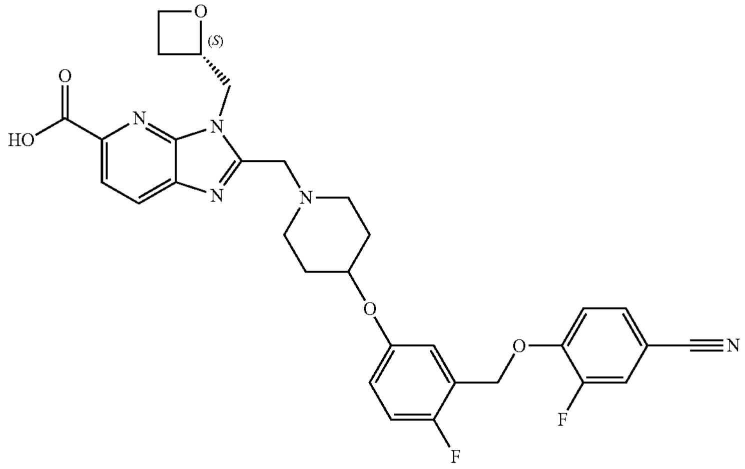 |
| Compound 72 | 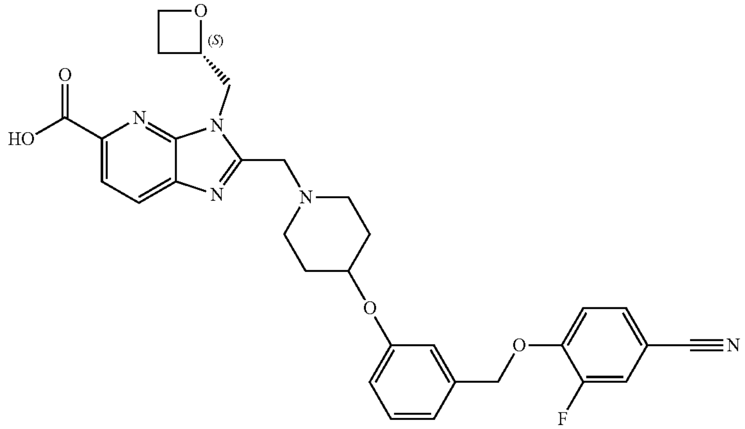 |
| Compound 73 | 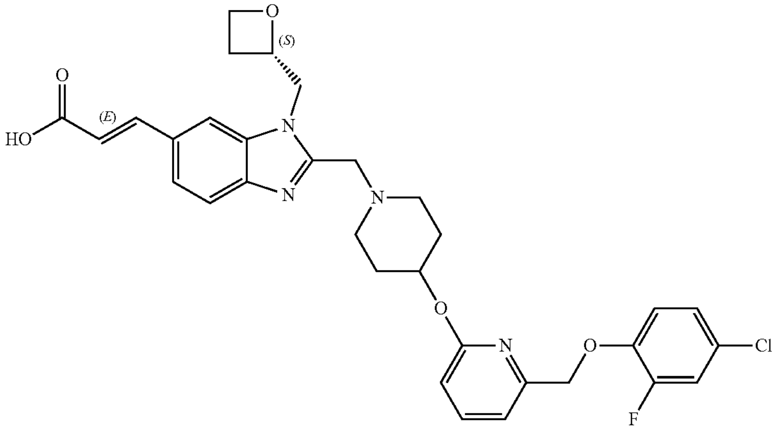 |

-continued
| Number | Structure |
|---|---|
| Compound 74 | 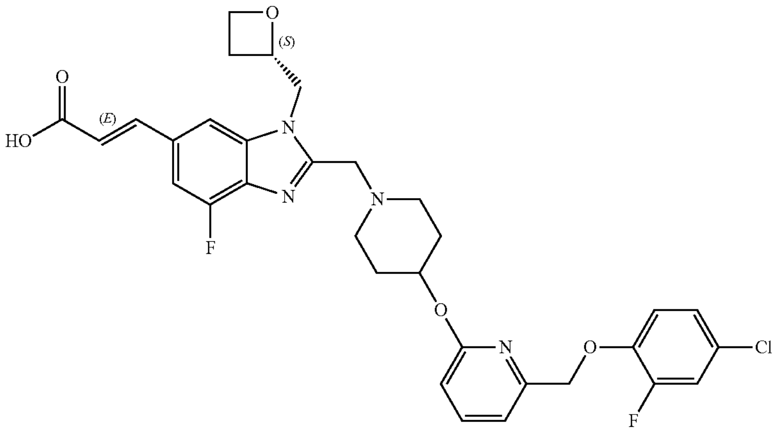 |
| Compound 75 | 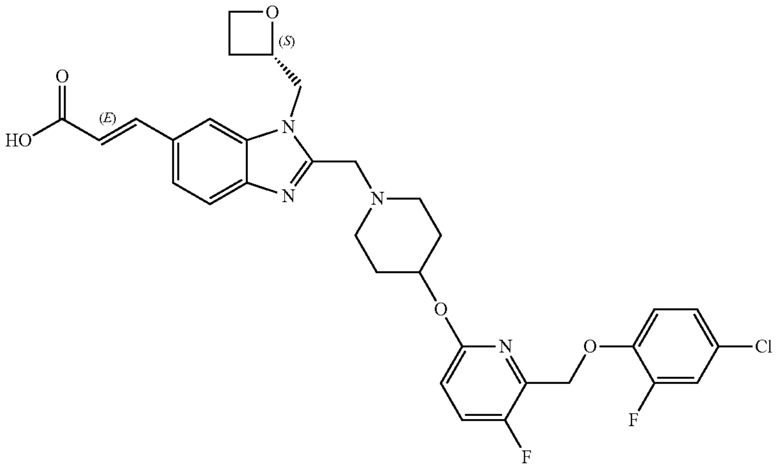 |
| Compound 76 | 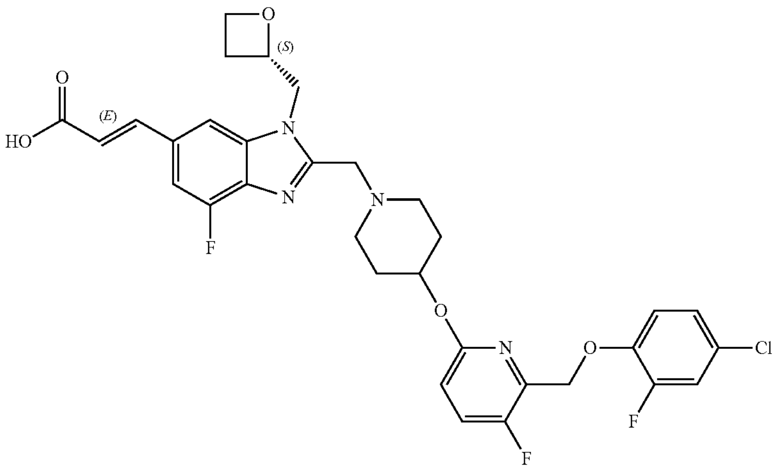 |

-continued
| Number | Structure |
|---|---|
| Compound 77 | 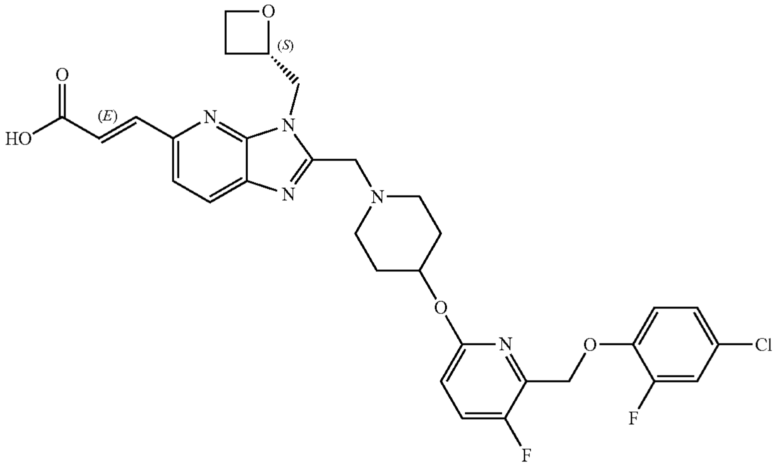 |
| Compound 78 | 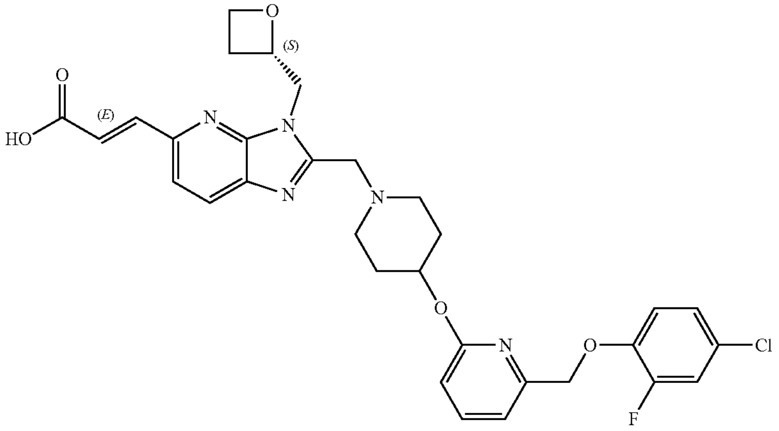 |
| Compound 79 | 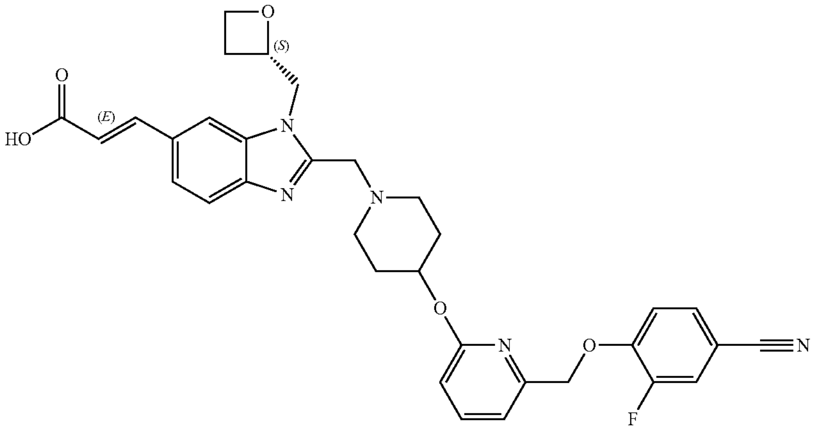 |

-continued
| Number | Structure |
|---|---|
| Compound 80 | 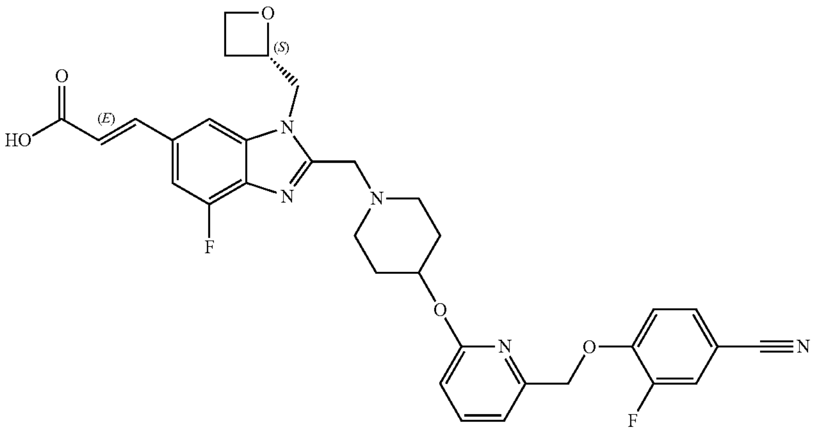 |
| Compound 81 | 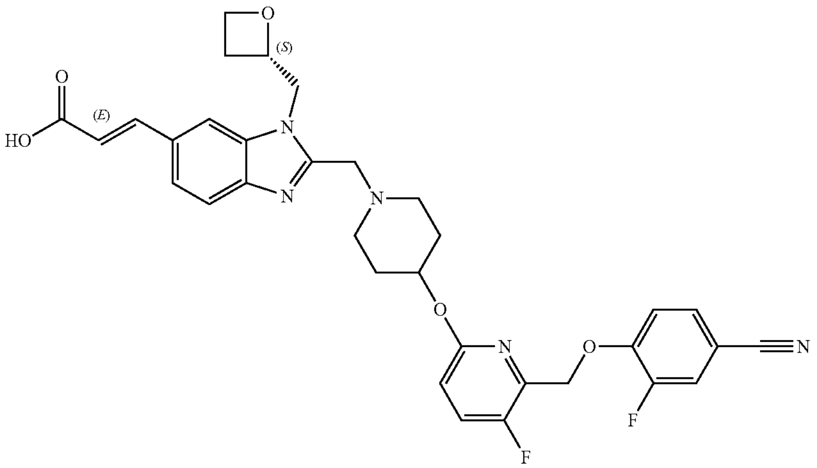 |
| Compound 82 | 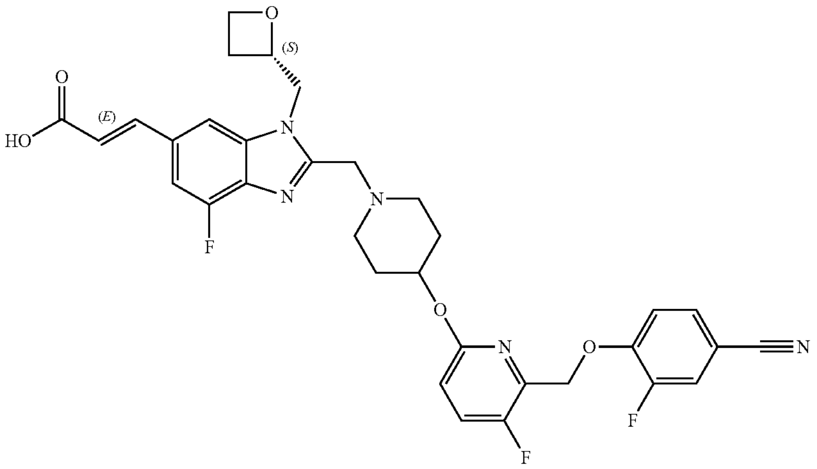 |

-continued
| Number | Structure |
| --- | --- |
| Compound 83 | 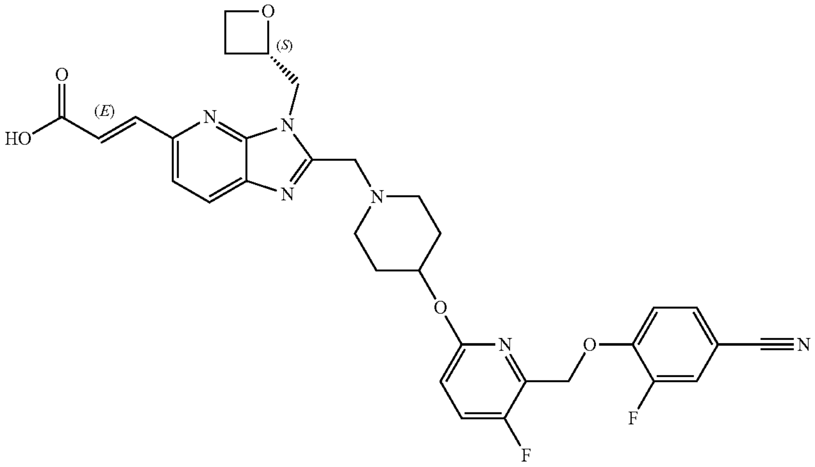 |
| Compound 84 | 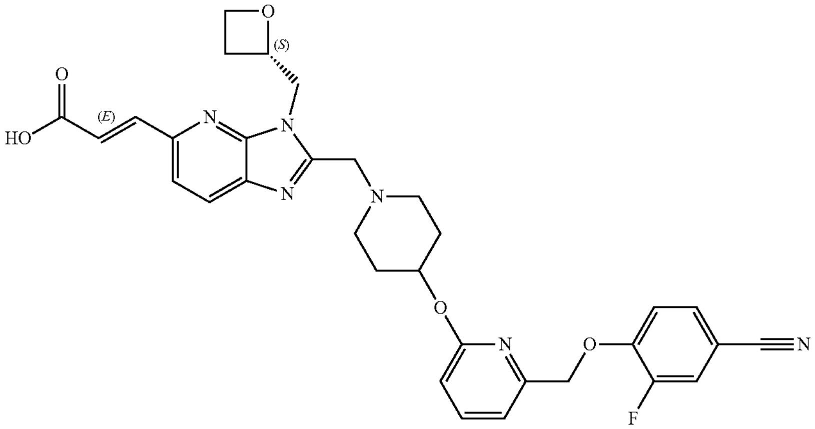 |
| Compound 85 | 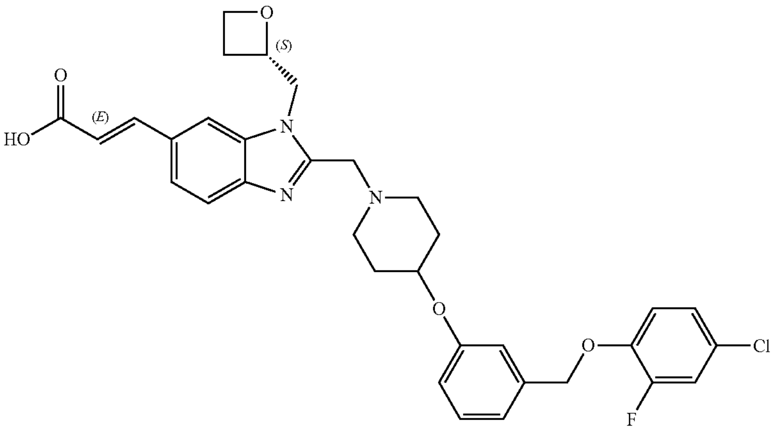 |

-continued
| Number | Structure |
|---|---|
| Compound 86 | 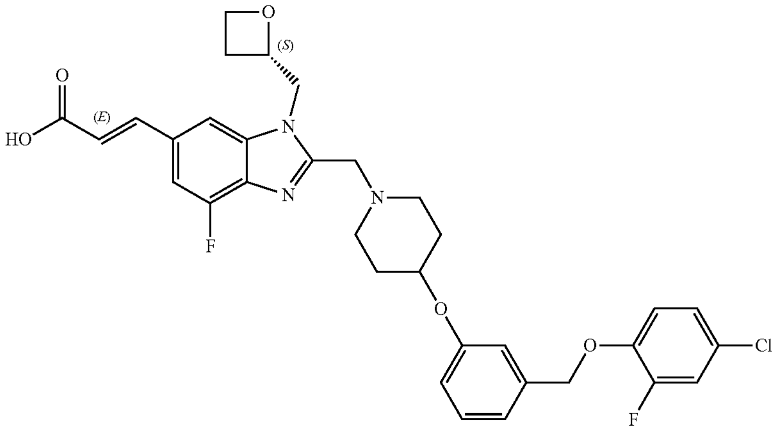 |
| Compound 87 | 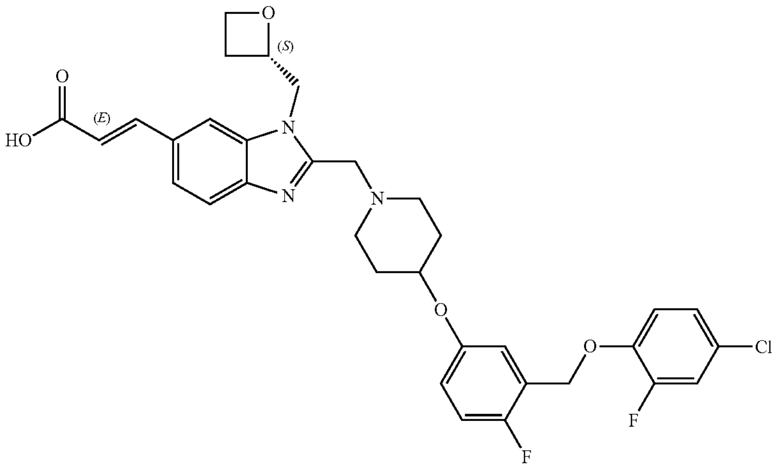 |
| Compound 88 | 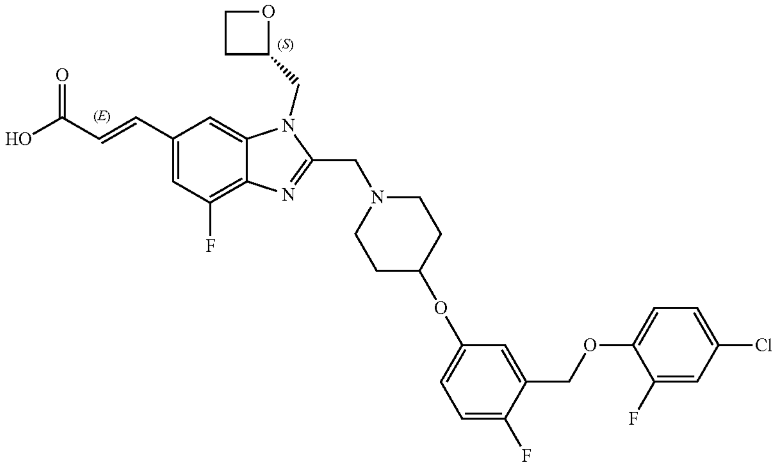 |

-continued
| Number | Structure |
|---|---|
| Compound 89 | 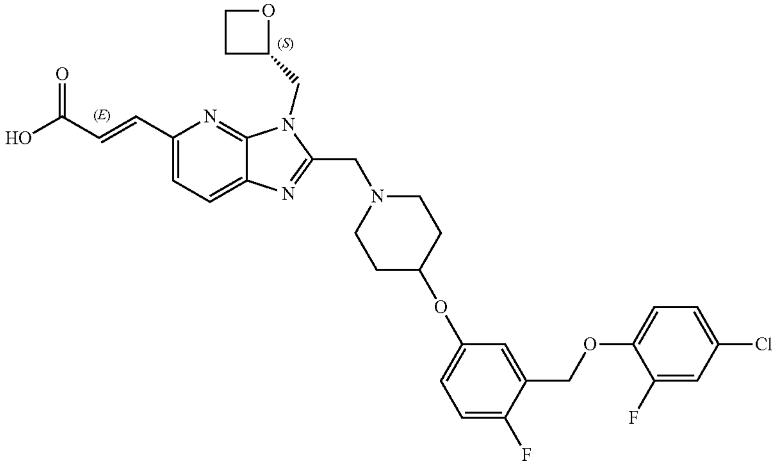 |
| Compound 90 | 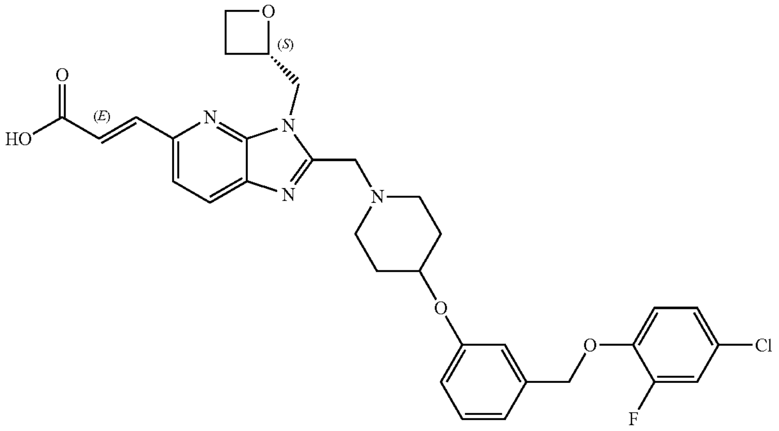 |
| Compound 91 | 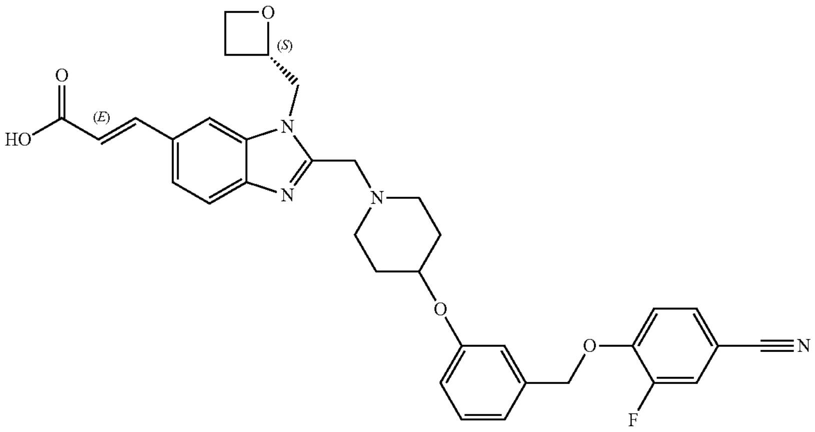 |

-continued
| Number | Structure |
|---|---|
| Compound 92 | 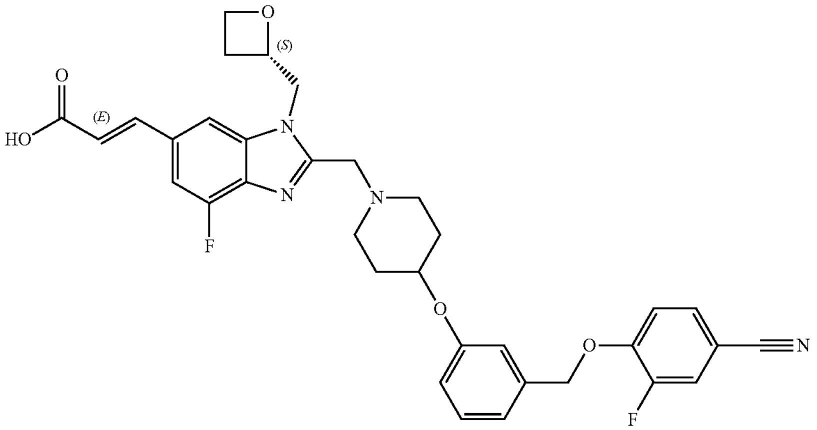 |
| Compound 93 | 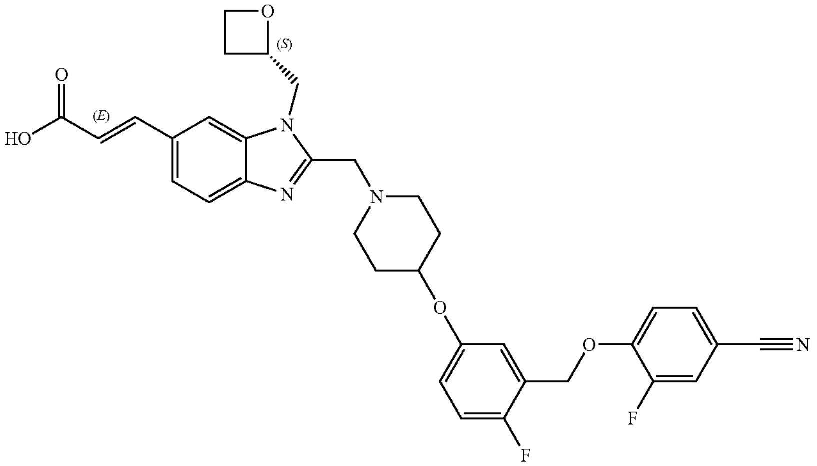 |
| Compound 94 | 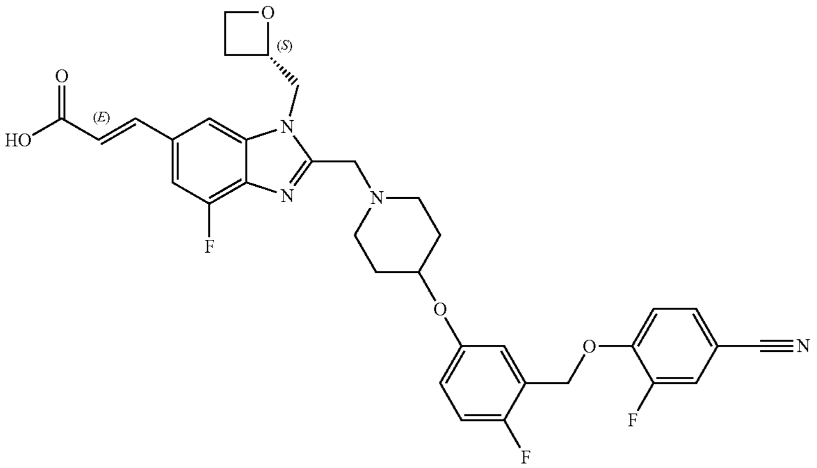 |

-continued
| Number | Structure |
| --- | --- |
| Compound 95 | 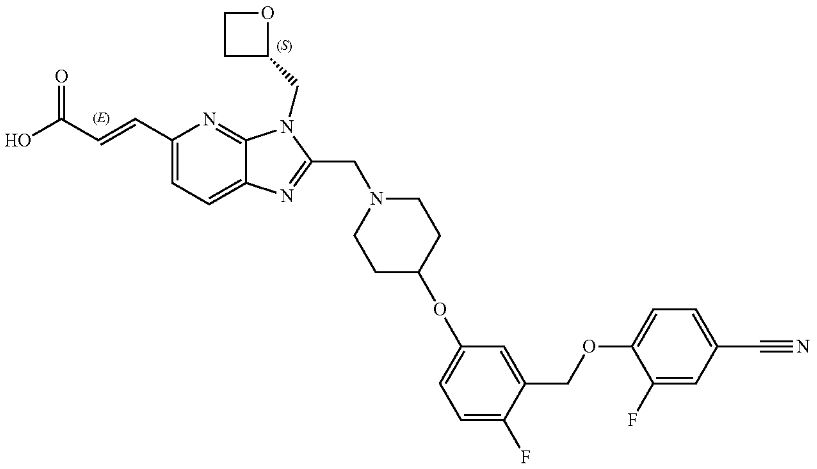 |
| Compound 96 | 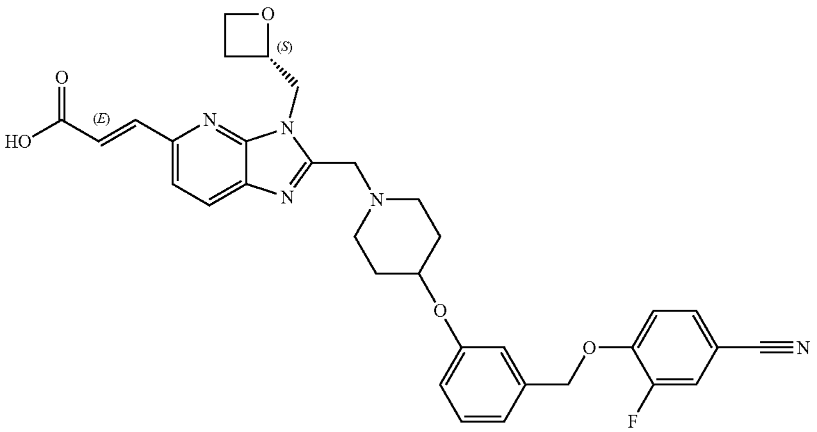 |
| Compound 97 | 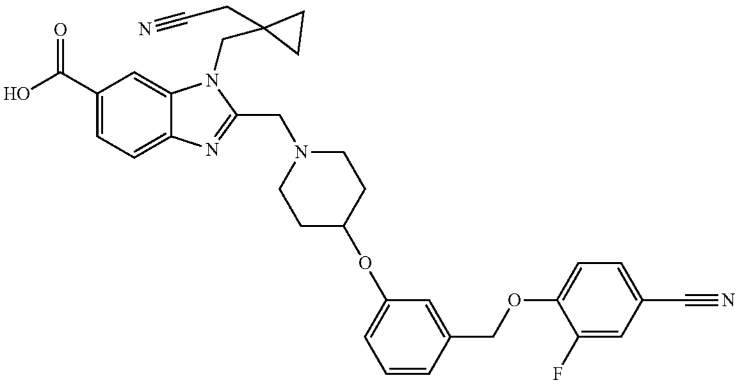 [SMILES: N#CCC1(Cn2c(CN3CCC(Oc4cccc(COc5ccc(C#N)cc5F)c4)CC3)nc3ccc(C(=O)O)cc32)CC1] |

-continued
| Number | Structure |
|---|---|
| Compound 98 | 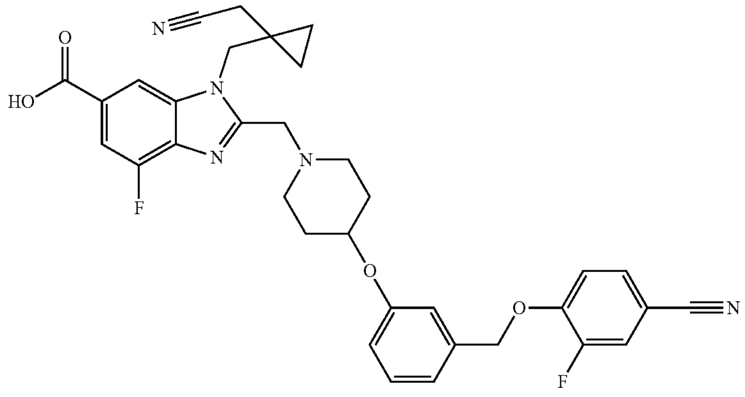 [SMILES: N#CCC1(Cn2c(CN3CCC(Oc4cccc(COc5ccc(C#N)cc5F)c4)CC3)nc3c(F)cc(C(=O)O)cc32)CC1] |
| Compound 99 | 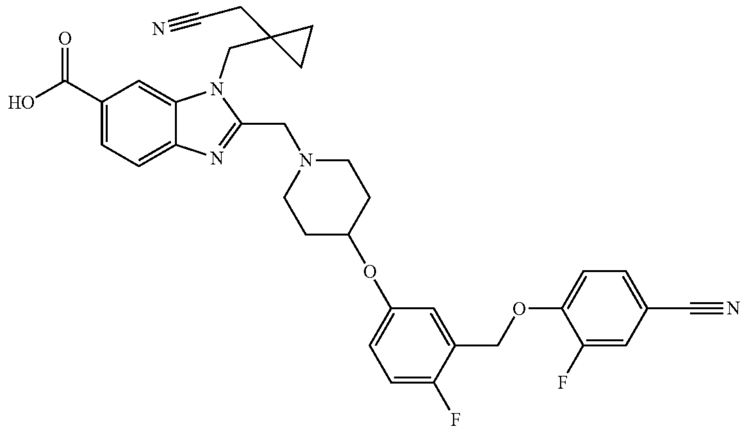 |
| Compound 100 | 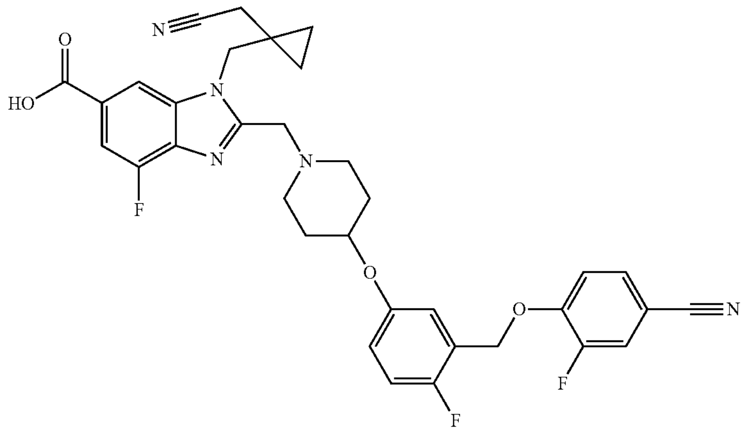 [SMILES: N#CCC1(Cn2c(CN3CCC(Oc4ccc(F)c(COc5ccc(C#N)cc5F)c4)CC3)nc3c(F)cc(C(=O)O)cc32)CC1] |

-continued
| Number | Structure |
|---|---|
| Compound 101 | 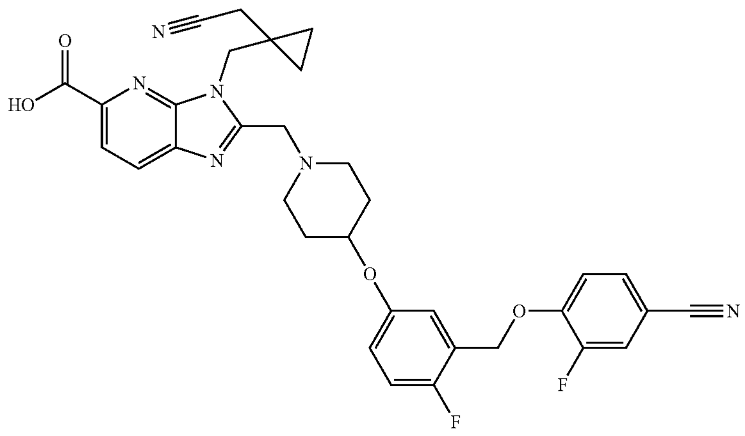 [SMILES: N#CCC1(Cn2c(CN3CCC(Oc4ccc(F)c(COc5ccc(C#N)cc5F)c4)CC3)nc3ccc(C(=O)O)nc32)CC1] |
| Compound 102 | 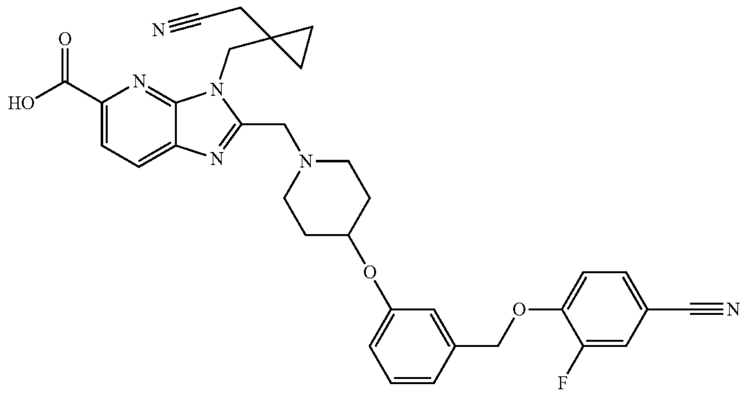 [SMILES: N#CCC1(Cn2c(CN3CCC(Oc4cccc(COc5ccc(C#N)cc5F)c4)CC3)nc3ccc(C(=O)O)nc32)CC1] |
| Compound 103 | 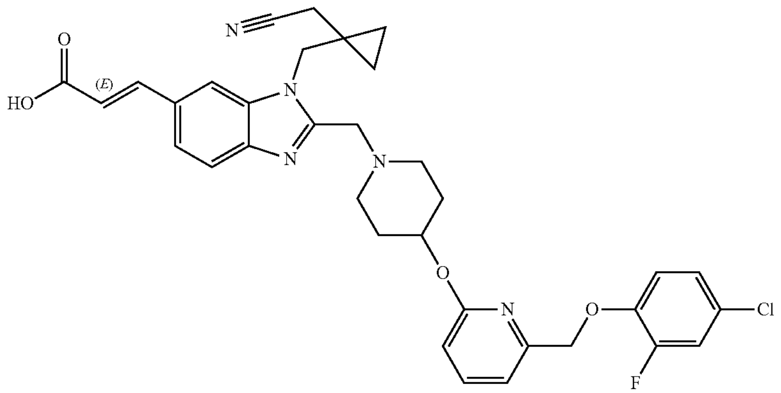 |
| Compound 104 | 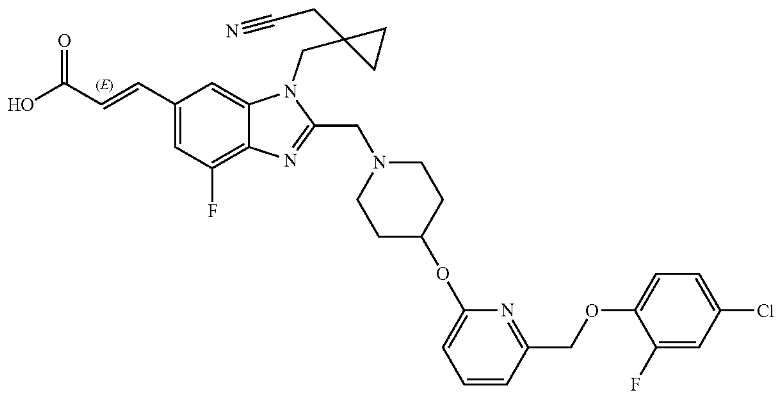 [SMILES: N#CCC1(Cn2c(CN3CCC(Oc4cccc(COc5ccc(Cl)cc5F)n4)CC3)nc3c(F)cc(/C=C/C(=O)O)cc32)CC1] |

-continued
| Number | Structure |
|---|---|
| Compound 105 | 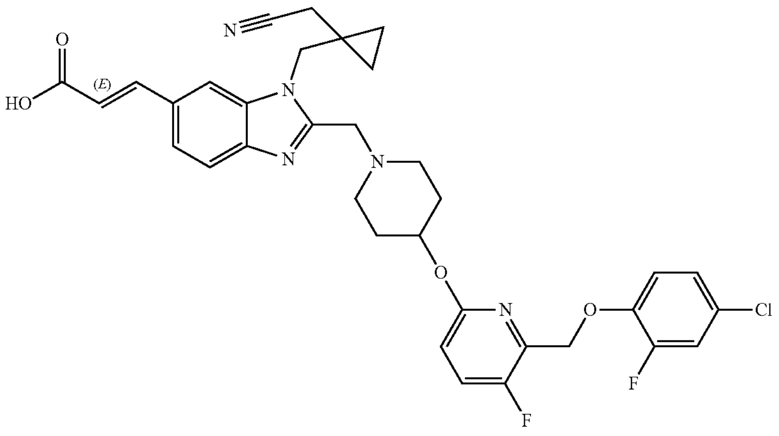 |
| Compound 106 | 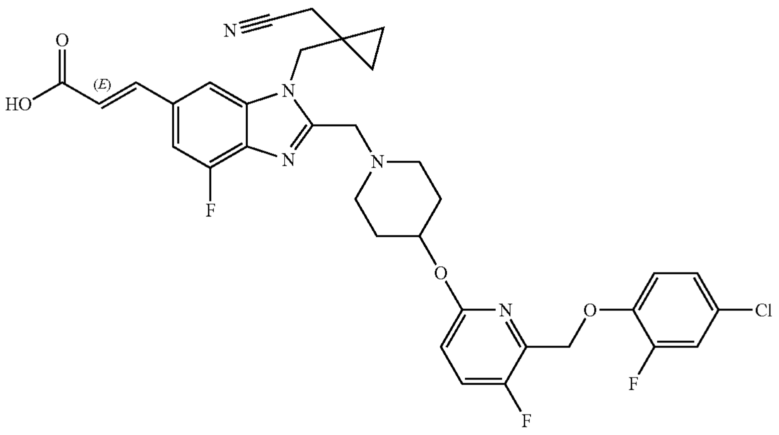 [SMILES: N#CCC1(Cn2c(CN3CCC(Oc4ccc(F)c(COc5ccc(Cl)cc5F)n4)CC3)nc3c(F)cc(/C=C/C(=O)O)cc32)CC1] |
| Compound 107 | 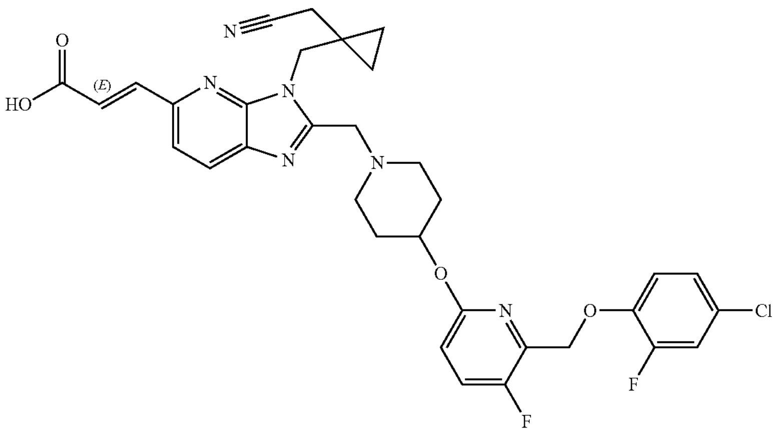 |

-continued
| Number | Structure |
| --- | --- |
| Compound 108 | 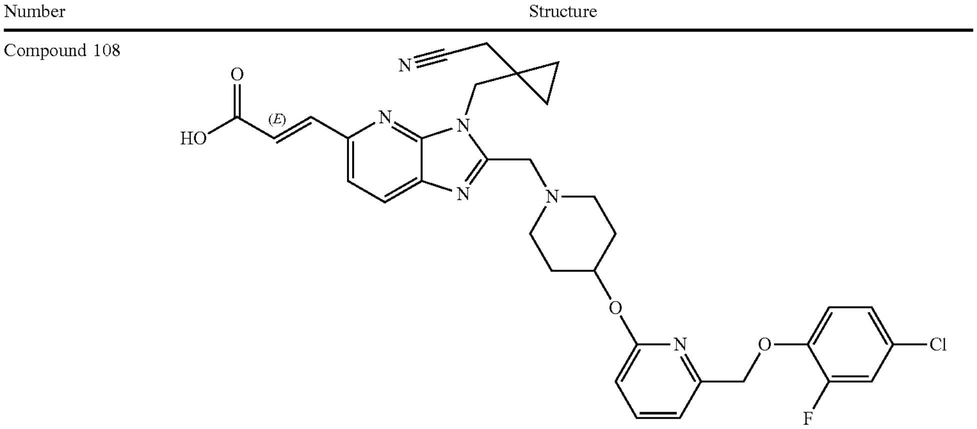 |
| Compound 109 | 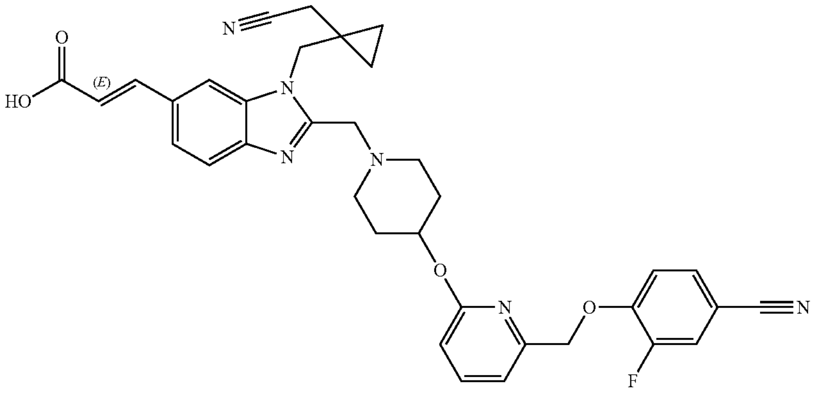 |
| Compound 110 | 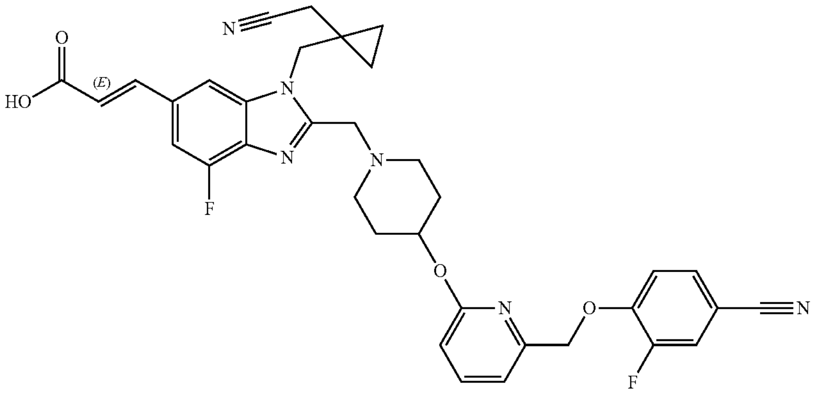 |
| Compound 111 | 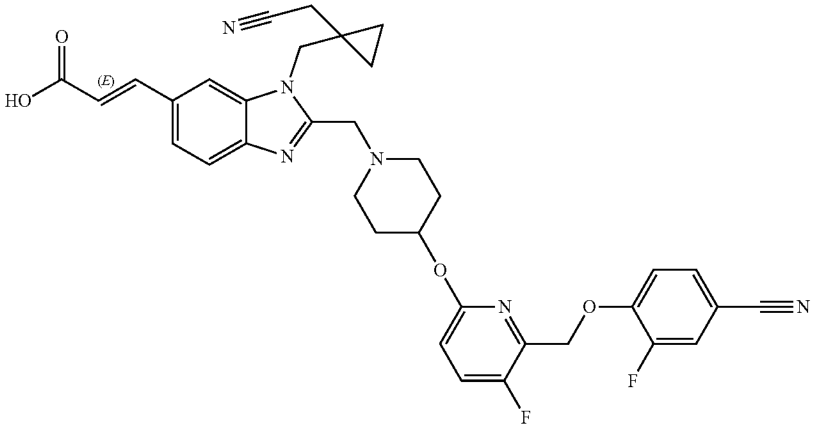 |

-continued
| Number | Structure |
|---|---|
| Compound 112 | 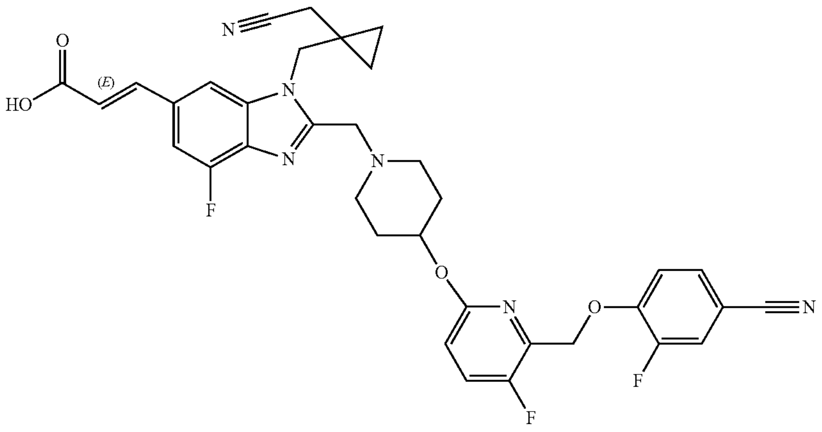 [SMILES: N#CCC1(Cn2c(CN3CCC(Oc4ccc(F)c(COc5ccc(C#N)cc5F)n4)CC3)nc3c(F)cc(/C=C/C(=O)O)cc32)CC1] |
| Compound 113 | 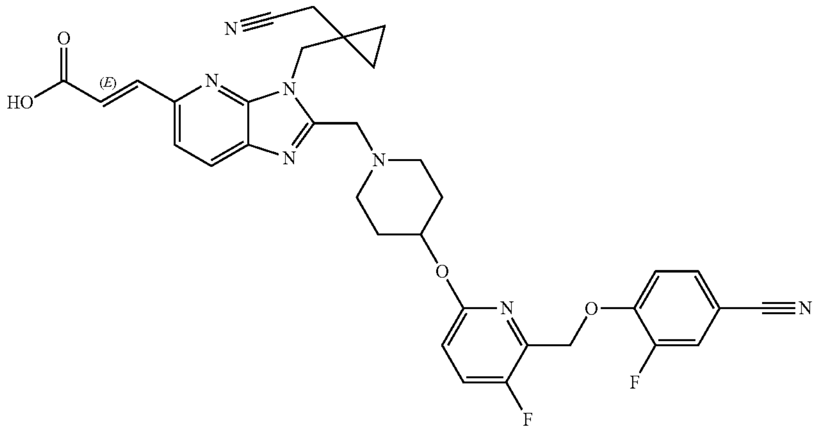 [SMILES: N#CCC1(Cn2c(CN3CCC(Oc4ccc(F)c(COc5ccc(C#N)cc5F)n4)CC3)nc3ccc(/C=C/C(=O)O)nc32)CC1] |
| Compound 114 | 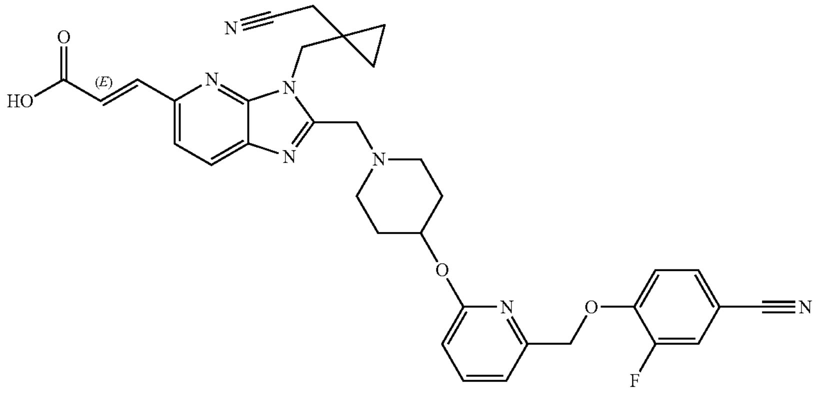 [SMILES: N#CCC1(Cn2c(CN3CCC(Oc4cccc(COc5ccc(C#N)cc5F)n4)CC3)nc3ccc(/C=C/C(=O)O)nc32)CC1] |

-continued
| Number | Structure |
| --- | --- |
| Compound 115 | 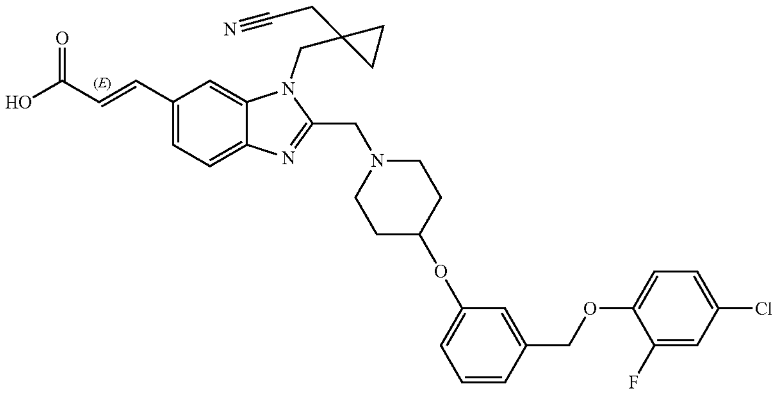 [SMILES: N#CCC1(Cn2c(CN3CCC(Oc4cccc(COc5ccc(Cl)cc5F)c4)CC3)nc3ccc(/C=C/C(=O)O)cc32)CC1] |
| Compound 116 | 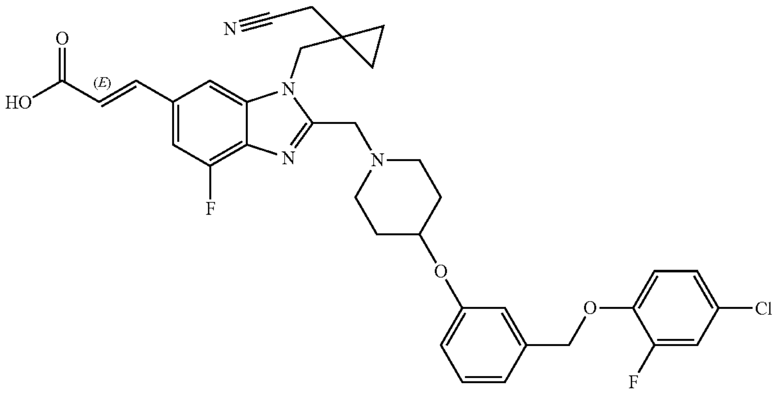 |
| Compound 117 | 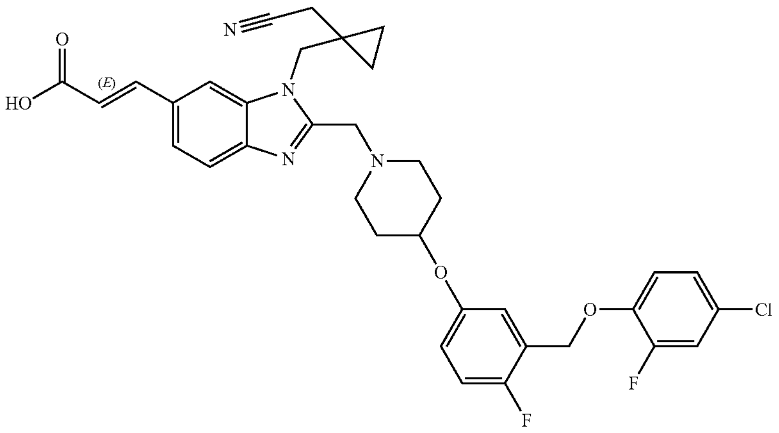 [SMILES: N#CCC1(Cn2c(CN3CCC(Oc4ccc(F)c(COc5ccc(Cl)cc5F)c4)CC3)nc3ccc(/C=C/C(=O)O)cc32)CC1] |

-continued
| Number | Structure |
|---|---|
| Compound 118 | 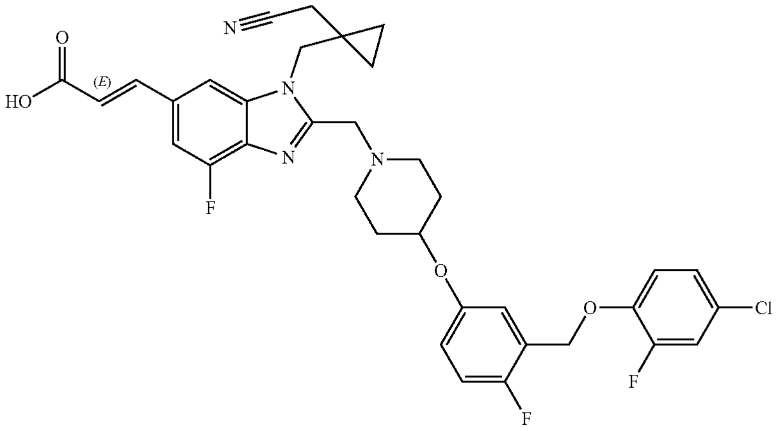 |
| Compound 119 | 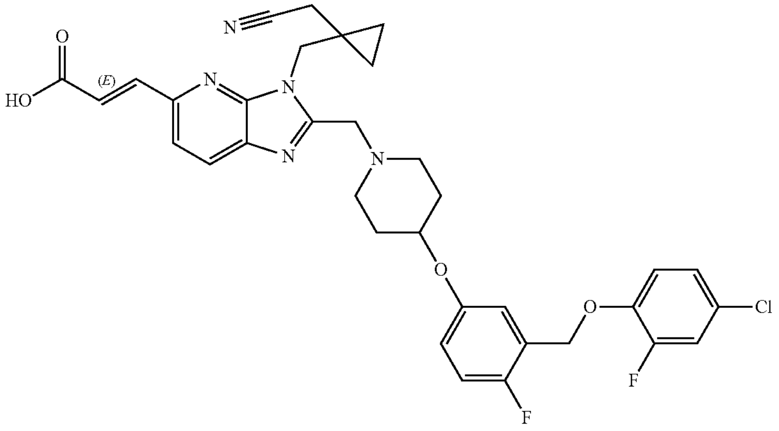 |
| Compound 120 | 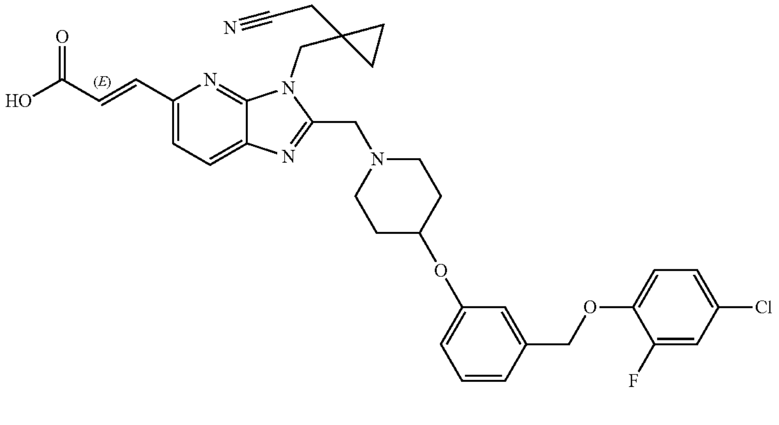 [SMILES: N#CCC1(Cn2c(CN3CCC(Oc4cccc(COc5ccc(Cl)cc5F)c4)CC3)nc3ccc(/C=C/C(=O)O)nc32)CC1] |

-continued
| Number | Structure |
|---|---|
| Compound 121 | 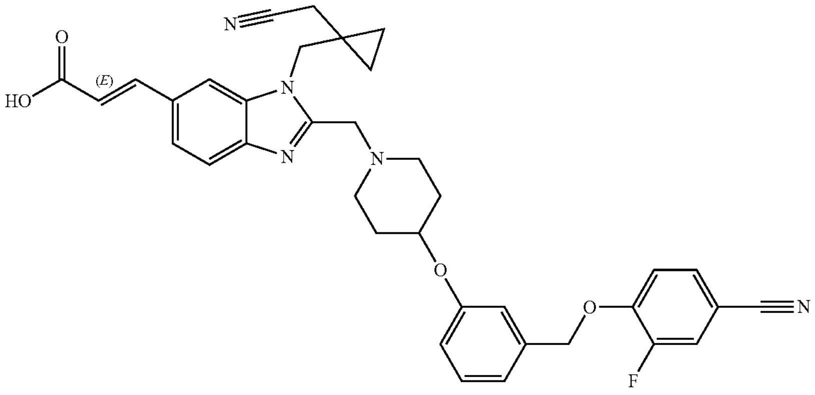 |
| Compound 122 | 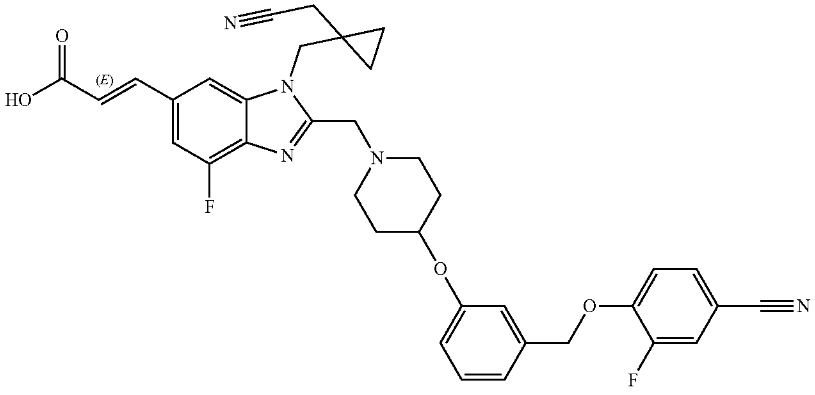 |
| Compound 123 | 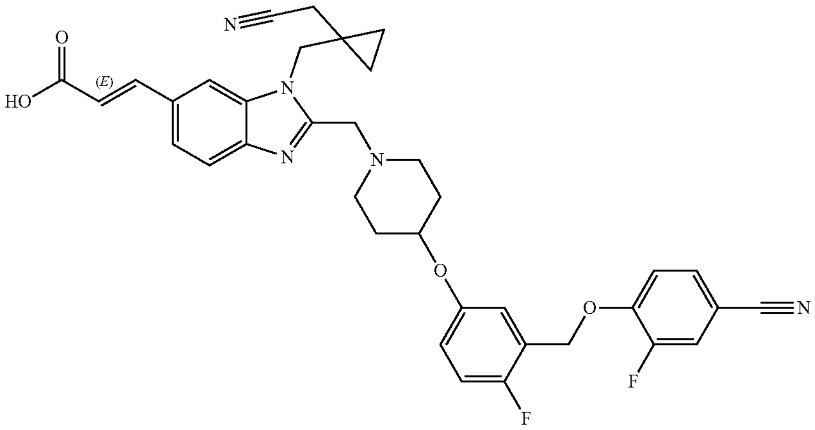 |

-continued
| Number | Structure |
| --- | --- |
| Compound 124 | 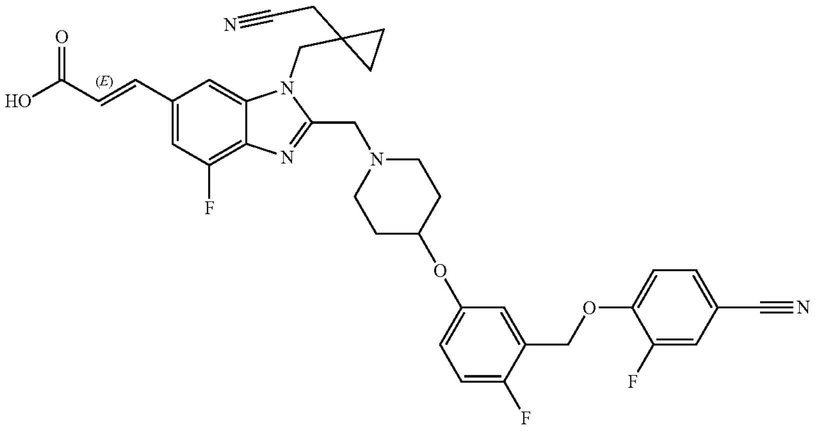 |
| Compound 125 | 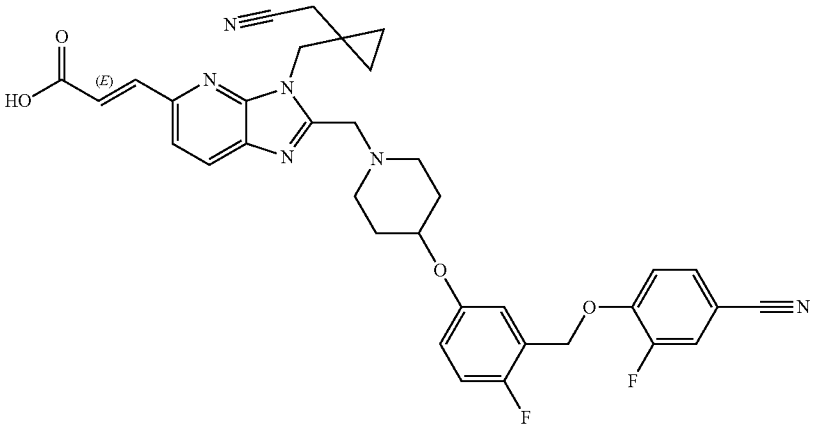 [SMILES: N#CCC1(Cn2c(CN3CCC(Oc4ccc(F)c(COc5ccc(C#N)cc5F)c4)CC3)nc3ccc(/C=C/C(=O)O)nc32)CC1] |
| Compound 126 | 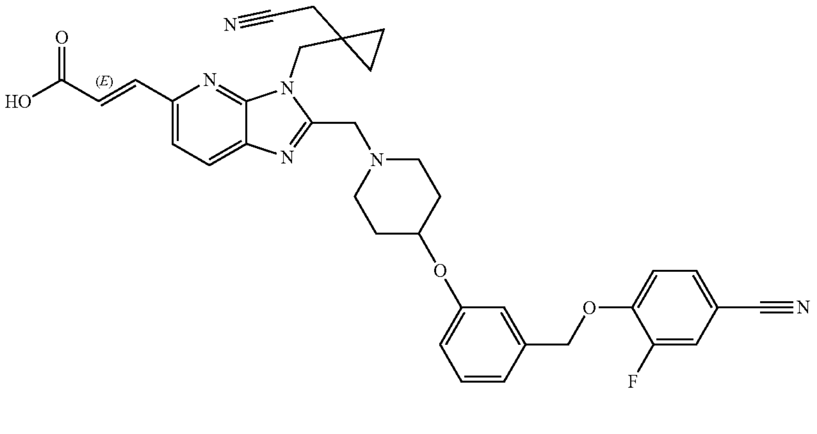 [SMILES: N#CCC1(Cn2c(CN3CCC(Oc4cccc(COc5ccc(C#N)cc5F)c4)CC3)nc3ccc(/C=C/C(=O)O)nc32)CC1] |

-continued
| Number | Structure |
|---|---|
| Compound 127 | 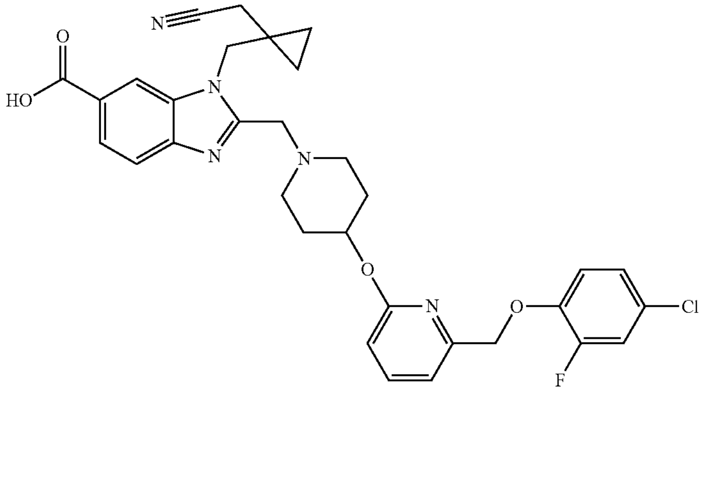 |
| Compound 128 | 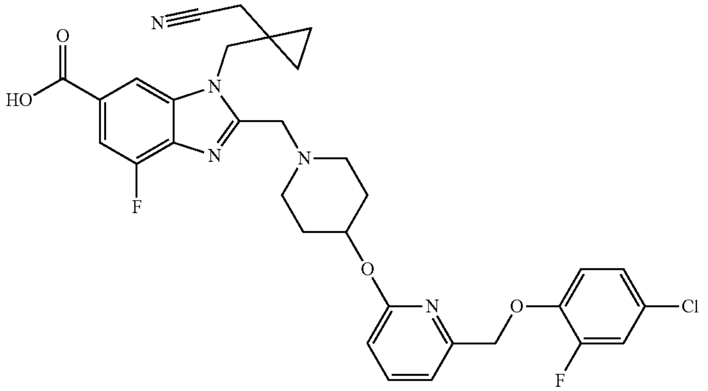 |
| Compound 129 | 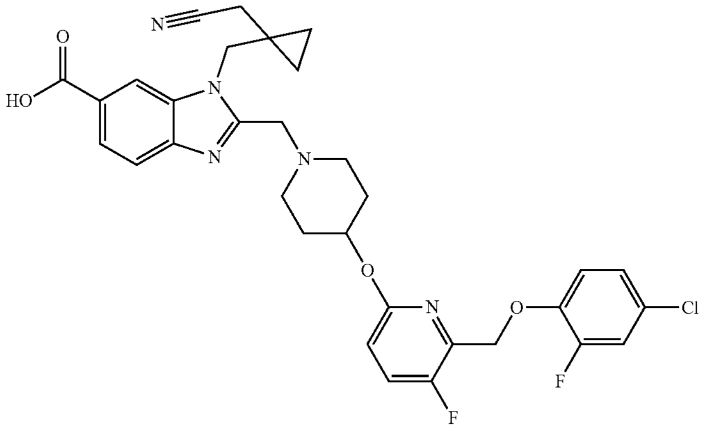 |

-continued
| Number | Structure |
|---|---|
| Compound 130 | 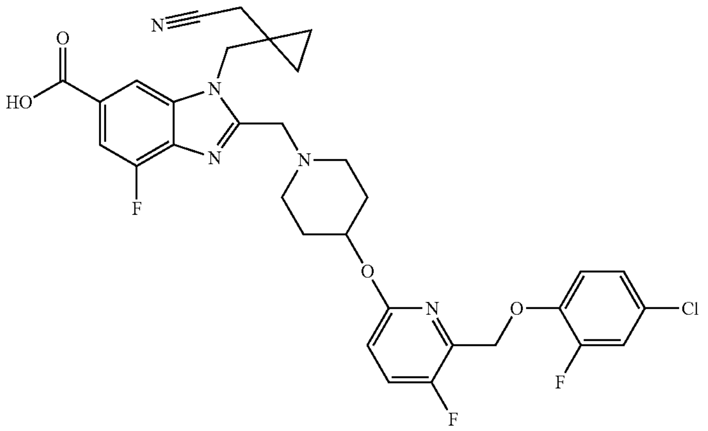 [SMILES: N#CCC1(Cn2c(CN3CCC(Oc4ccc(F)c(COc5ccc(Cl)cc5F)n4)CC3)nc3c(F)cc(C(=O)O)cc32)CC1] |
| Compound 131 | 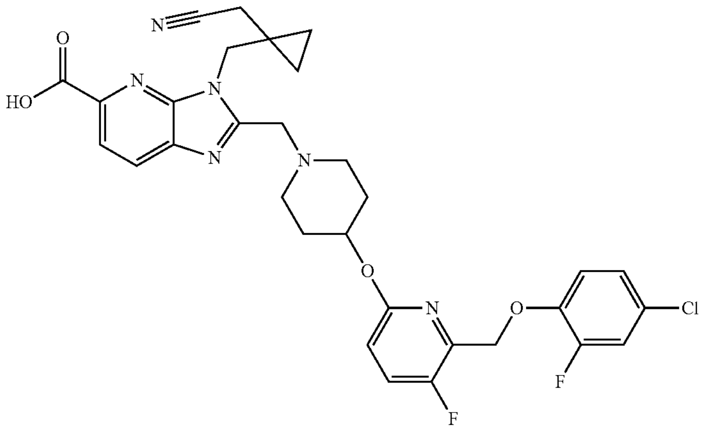 |
| Compound 132 | 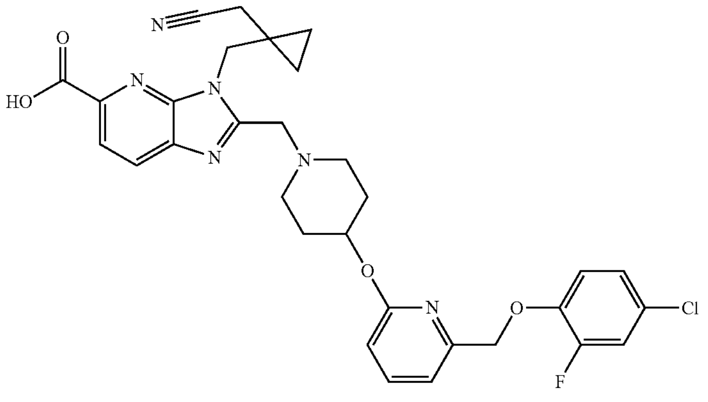 [SMILES: N#CCC1(Cn2c(CN3CCC(Oc4cccc(COc5ccc(Cl)cc5F)n4)CC3)nc3ccc(C(=O)O)nc32)CC1] |

-continued
| Number | Structure |
|---|---|
| Compound 133 | 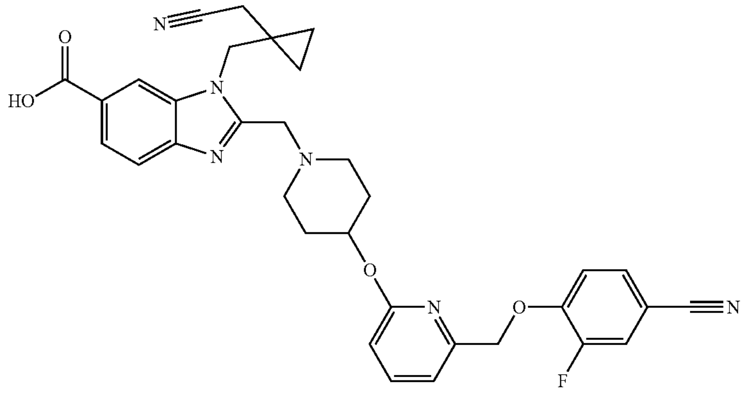 [SMILES: N#CCC1(Cn2c(CN3CCC(Oc4cccc(COc5ccc(C#N)cc5F)n4)CC3)nc3ccc(C(=O)O)cc32)CC1] |
| Compound 134 | 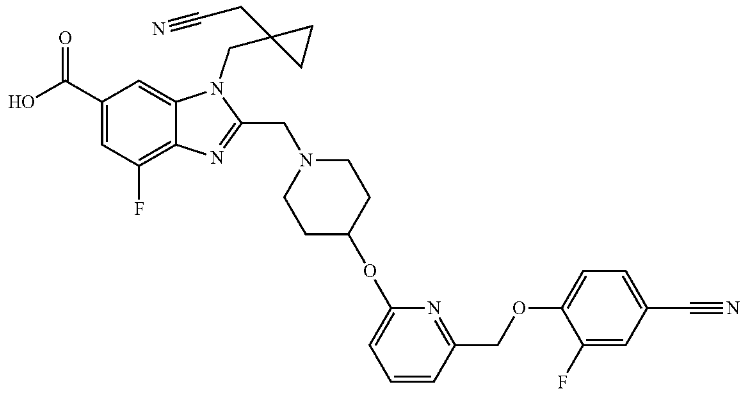 |
| Compound 135 | 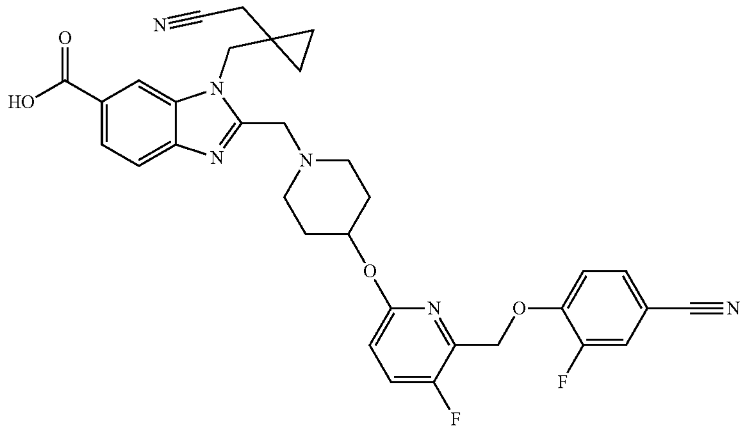 |

-continued
| Number | Structure |
| --- | --- |
| Compound 136 | 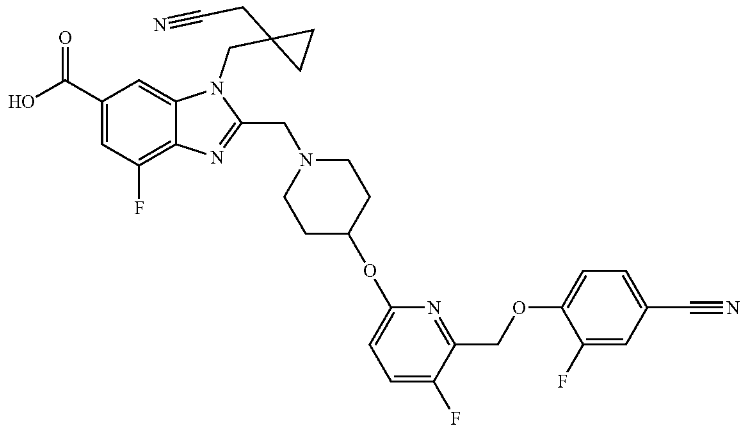 |
| Compound 137 | 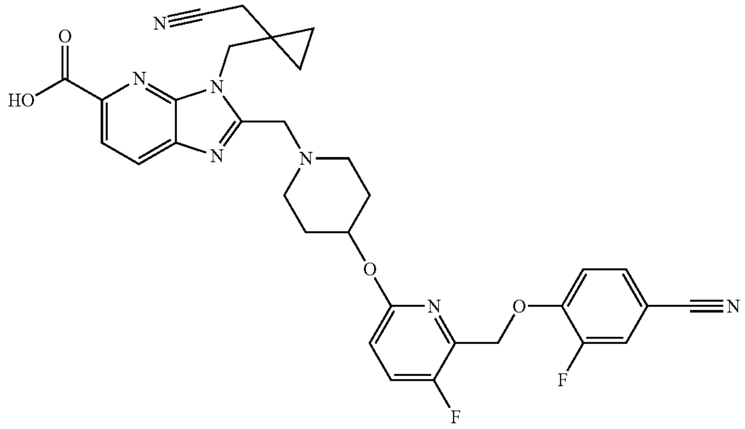 [SMILES: N#CCC1(Cn2c(CN3CCC(Oc4ccc(F)c(COc5ccc(C#N)cc5F)n4)CC3)nc3ccc(C(=O)O)nc32)CC1] |
| Compound 138 | 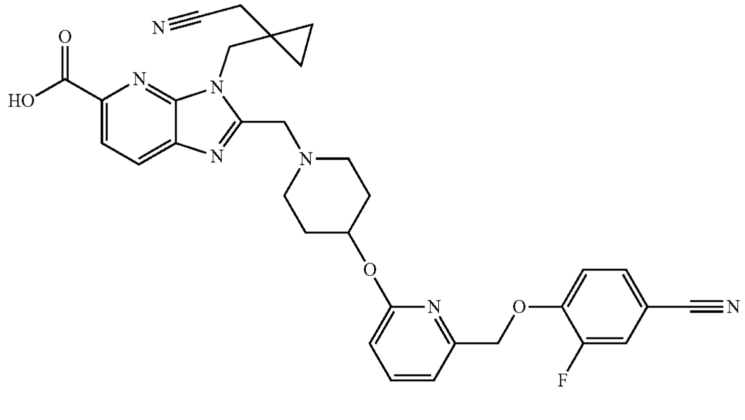 [SMILES: N#CCC1(Cn2c(CN3CCC(Oc4cccc(COc5ccc(C#N)cc5F)n4)CC3)nc3ccc(C(=O)O)nc32)CC1] |

-continued
| Number | Structure |
| --- | --- |
| Compound 139 | 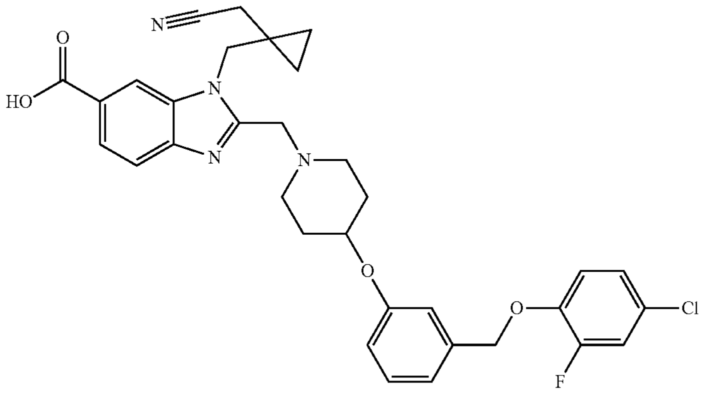 |
| Compound 140 | 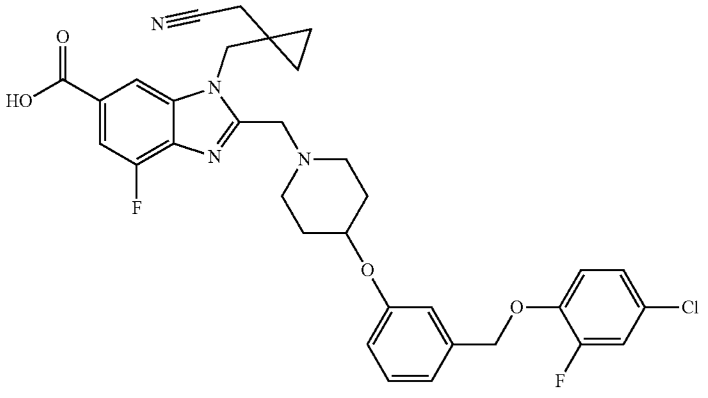 |
| Compound 141 | 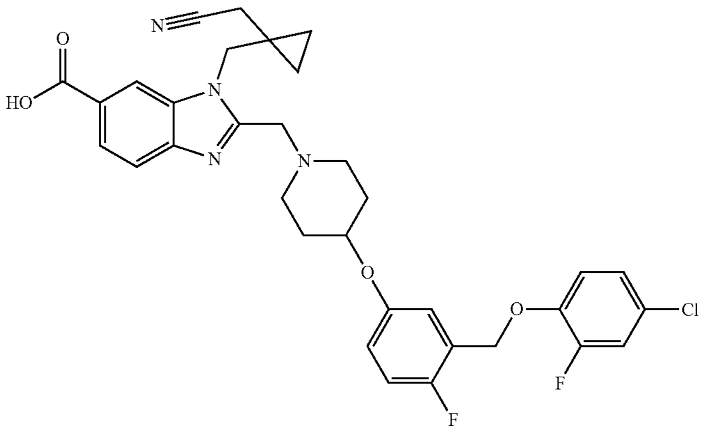 [SMILES: N#CCC1(Cn2c(CN3CCC(Oc4ccc(F)c(COc5ccc(Cl)cc5F)c4)CC3)nc3ccc(C(=O)O)cc32)CC1] |

-continued
| Number | Structure |
|---|---|
| Compound 142 | 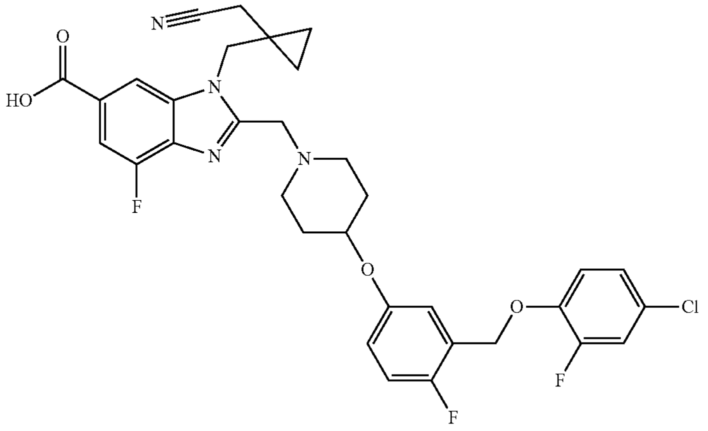 |
| Compound 143 | 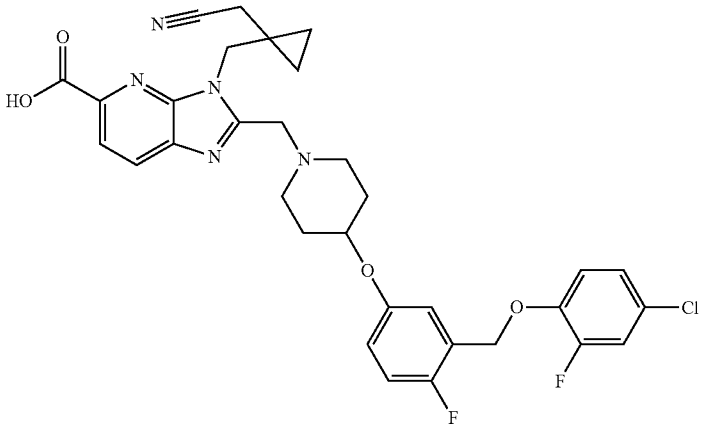 [SMILES: N#CCC1(Cn2c(CN3CCC(Oc4ccc(F)c(COc5ccc(Cl)cc5F)c4)CC3)nc3ccc(C(=O)O)nc32)CC1] |
| Compound 144 | 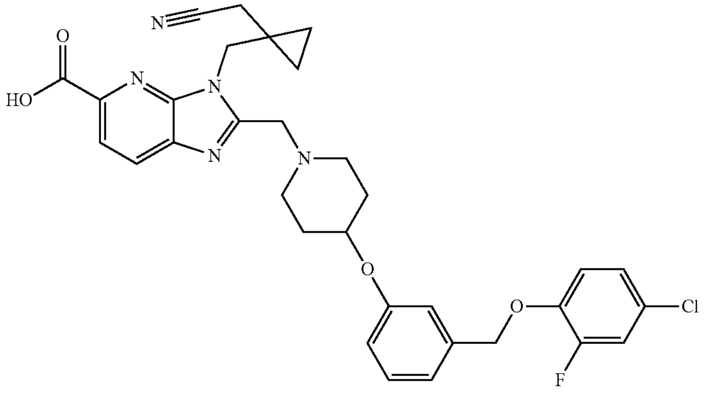 [SMILES: N#CCC1(Cn2c(CN3CCC(Oc4cccc(COc5ccc(Cl)cc5F)c4)CC3)nc3ccc(C(=O)O)nc32)CC1] |

-continued
| Number | Structure |
|---|---|
| Compound 145 | 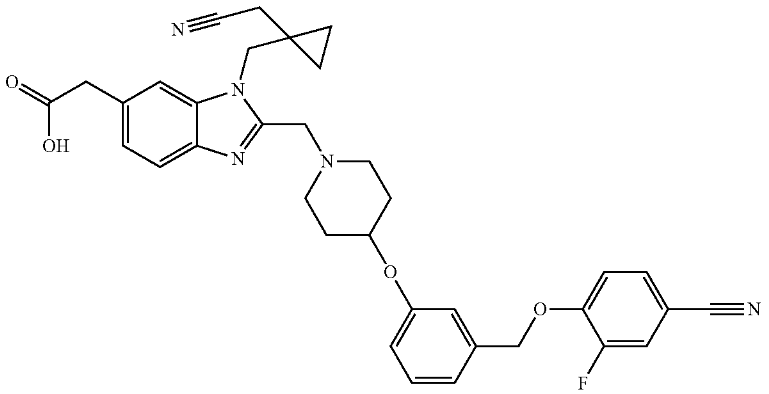 [SMILES: N#CCC1(Cn2c(CN3CCC(Oc4cccc(COc5ccc(C#N)cc5F)c4)CC3)nc3ccc(CC(=O)O)cc32)CC1] |
| Compound 146 | 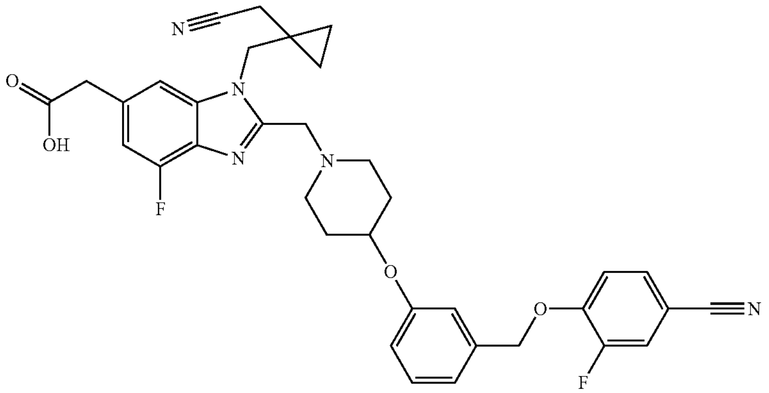 |
| Compound 147 | 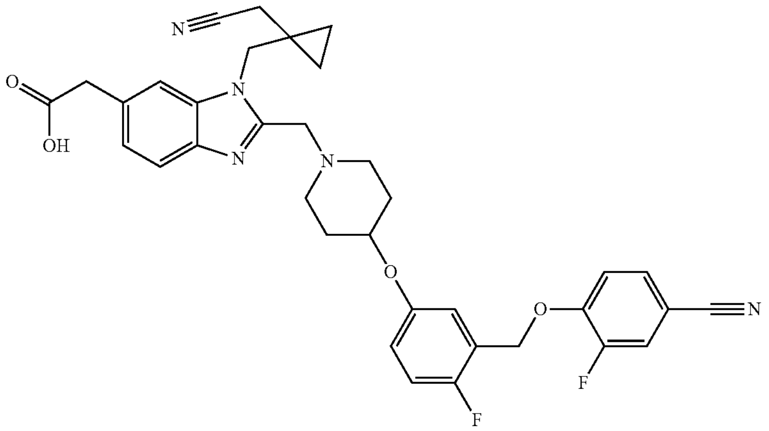 |

-continued
| Number | Structure |
|---|---|
| Compound 148 | 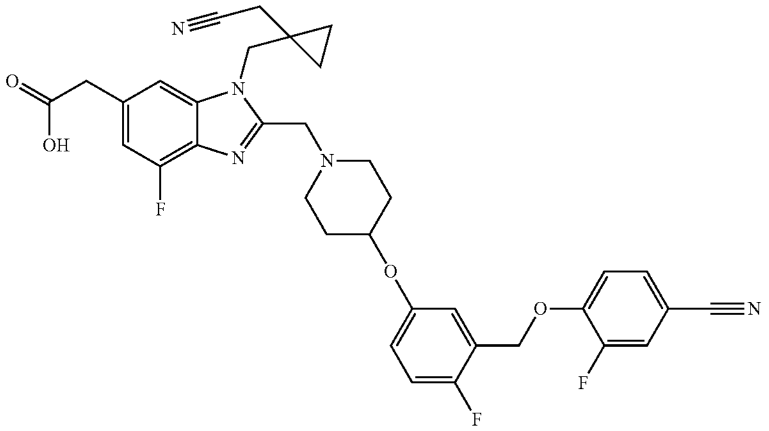 [SMILES: N#CCC1(Cn2c(CN3CCC(Oc4ccc(F)c(COc5ccc(C#N)cc5F)c4)CC3)nc3c(F)cc(CC(=O)O)cc32)CC1] |
| Compound 149 | 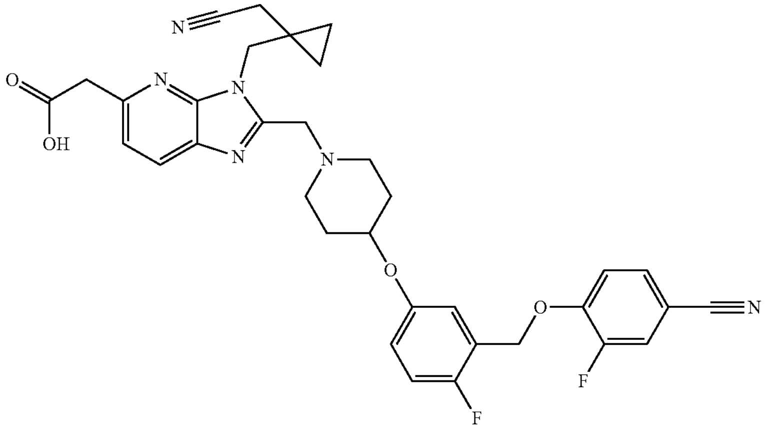 |
| Compound 150 | 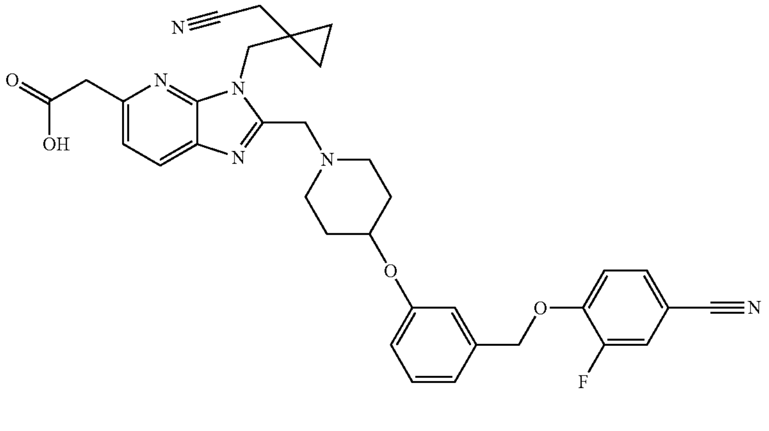 [SMILES: N#CCC1(Cn2c(CN3CCC(Oc4cccc(COc5ccc(C#N)cc5F)c4)CC3)nc3ccc(CC(=O)O)nc32)CC1] |

-continued
| Number | Structure |
|---|---|
| Compound 151 | 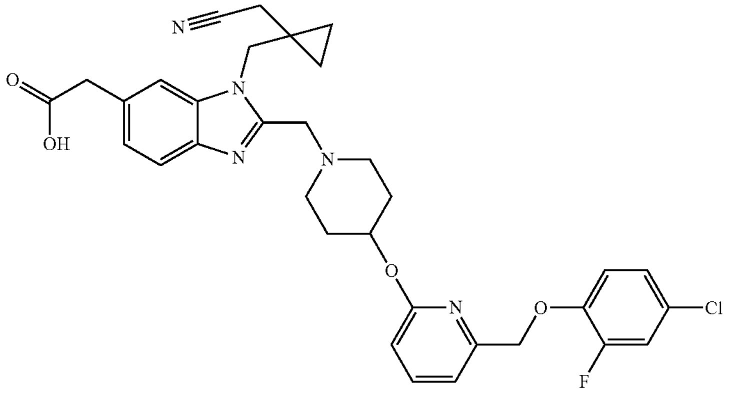 [SMILES: N#CCC1(Cn2c(CN3CCC(Oc4cccc(COc5ccc(Cl)cc5F)n4)CC3)nc3ccc(CC(=O)O)cc32)CC1] |
| Compound 152 | 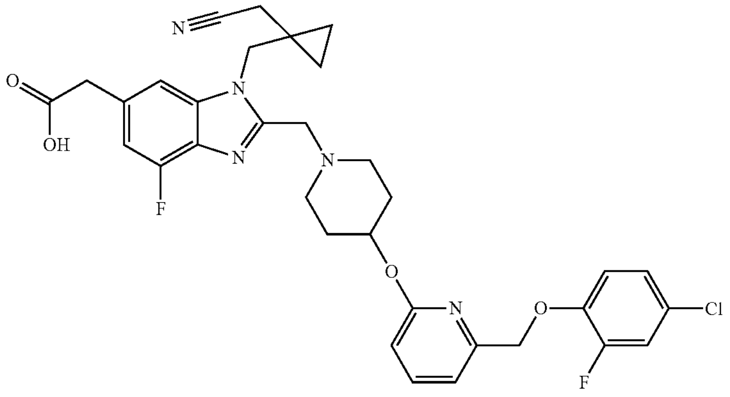 [SMILES: N#CCC1(Cn2c(CN3CCC(Oc4cccc(COc5ccc(Cl)cc5F)n4)CC3)nc3c(F)cc(CC(=O)O)cc32)CC1] |
| Compound 153 | 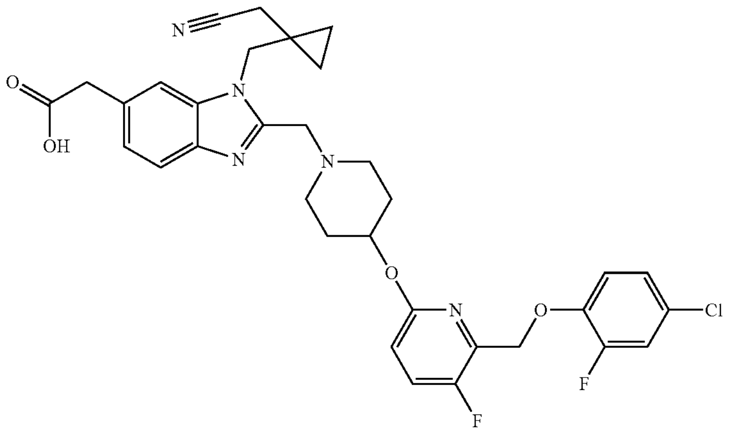 |

-continued
| Number | Structure |
| --- | --- |
| Compound 154 | 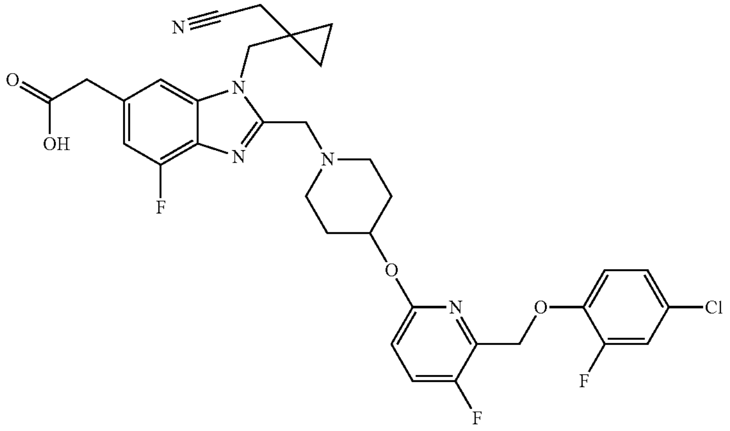 |
| Compound 155 | 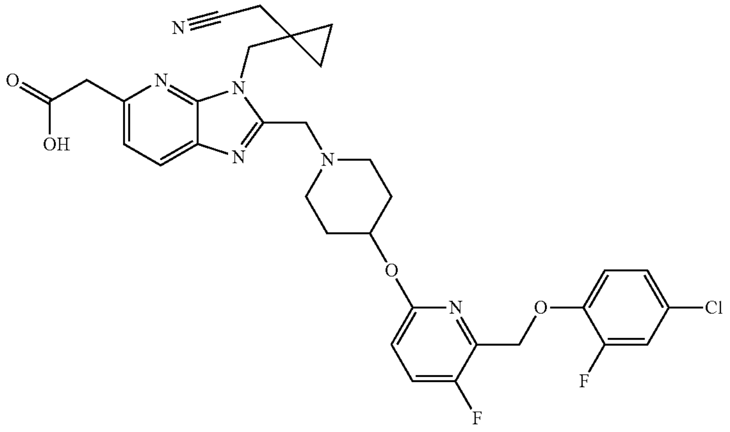 [SMILES: N#CCC1(Cn2c(CN3CCC(Oc4ccc(F)c(COc5ccc(Cl)cc5F)n4)CC3)nc3ccc(CC(=O)O)nc32)CC1] |
| Compound 156 | 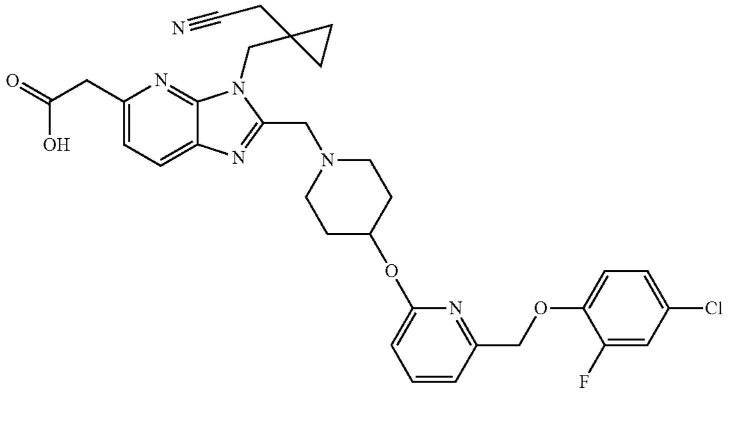 |

-continued
| Number | Structure |
|---|---|
| Compound 157 | 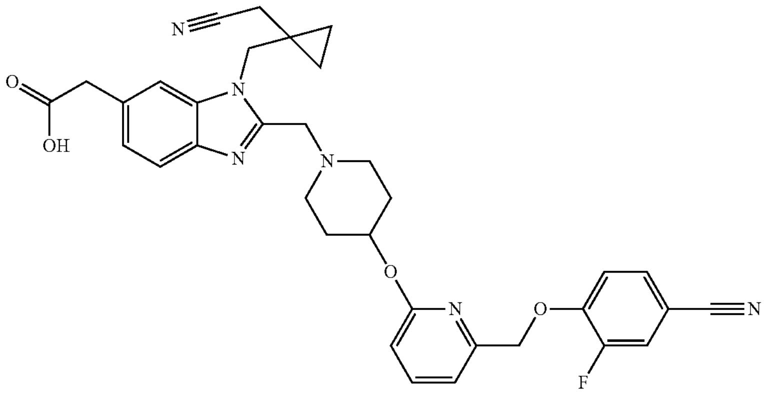 |
| Compound 158 | 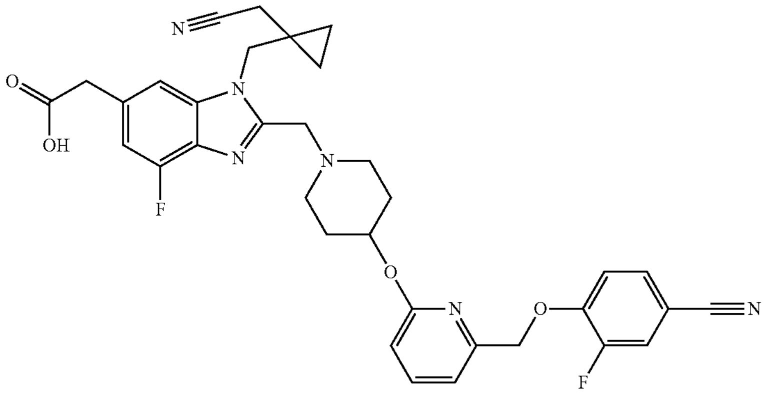 [SMILES: N#CCC1(Cn2c(CN3CCC(Oc4cccc(COc5ccc(C#N)cc5F)n4)CC3)nc3c(F)cc(CC(=O)O)cc32)CC1] |
| Compound 159 | 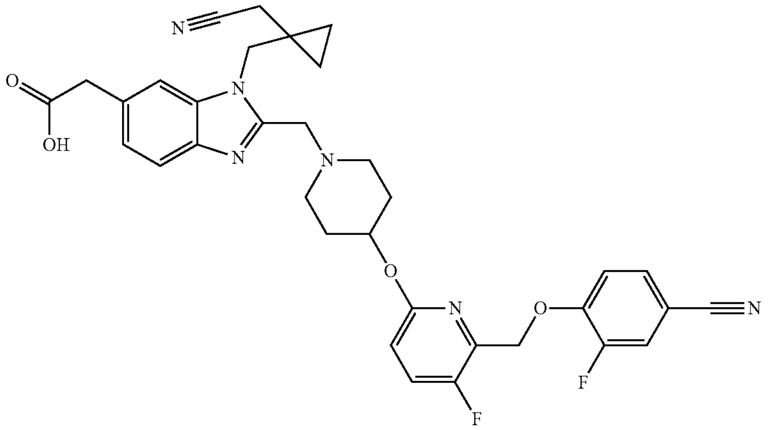 |

-continued
| Number | Structure |
| --- | --- |
| Compound 160 | 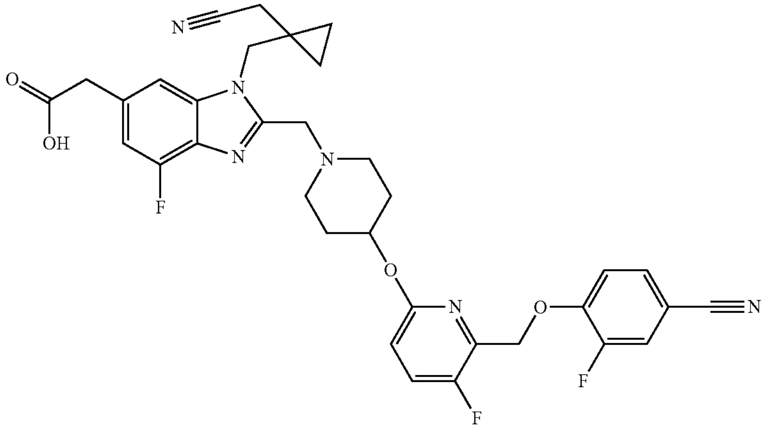 [SMILES: N#CCC1(Cn2c(CN3CCC(Oc4ccc(F)c(COc5ccc(C#N)cc5F)n4)CC3)nc3c(F)cc(CC(=O)O)cc32)CC1] |
| Compound 161 | 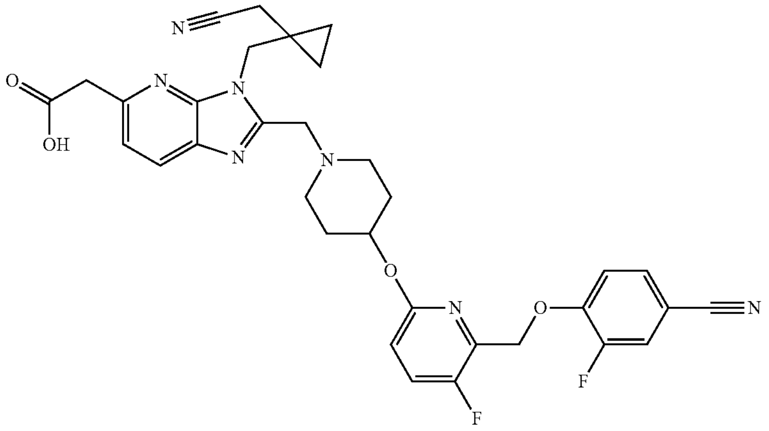 [SMILES: N#CCC1(Cn2c(CN3CCC(Oc4ccc(F)c(COc5ccc(C#N)cc5F)n4)CC3)nc3ccc(CC(=O)O)nc32)CC1] |
| Compound 162 | 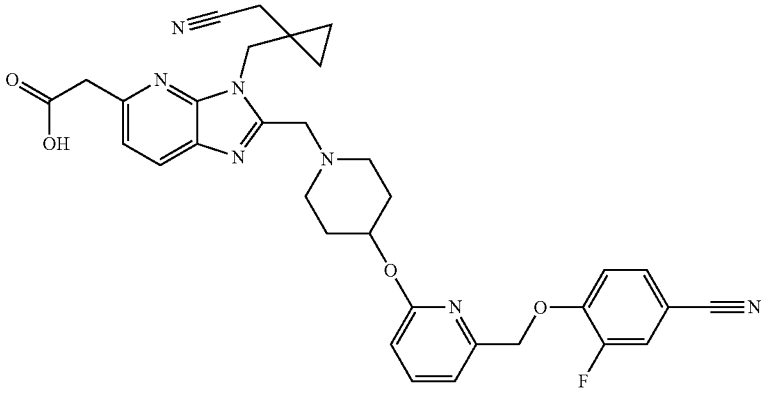 [SMILES: N#CCC1(Cn2c(CN3CCC(Oc4cccc(COc5ccc(C#N)cc5F)n4)CC3)nc3ccc(CC(=O)O)nc32)CC1] |

-continued
| Number | Structure |
| --- | --- |
| Compound 163 | 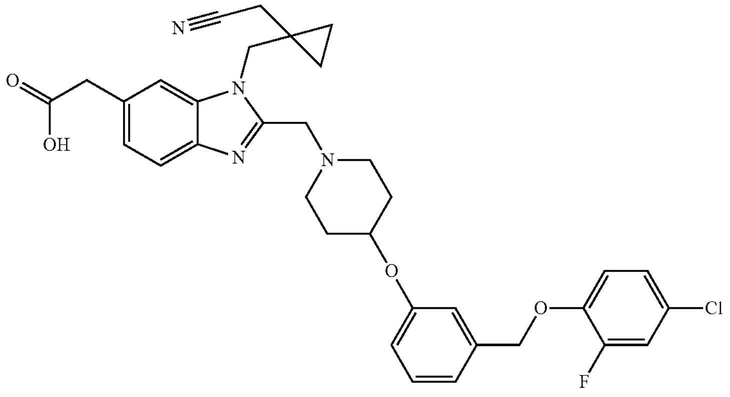 |
| Compound 164 | 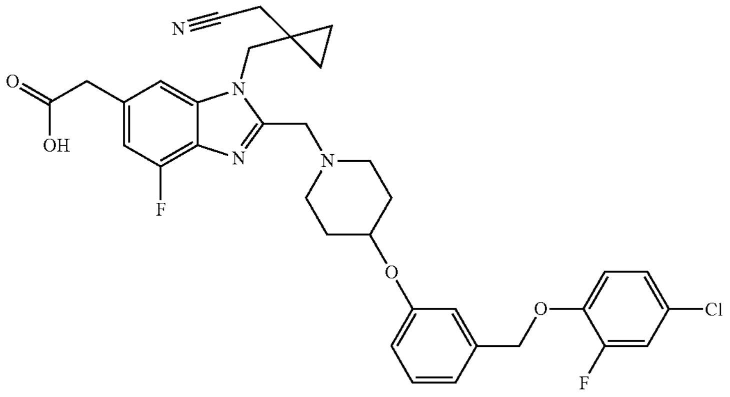 |
| Compound 165 | 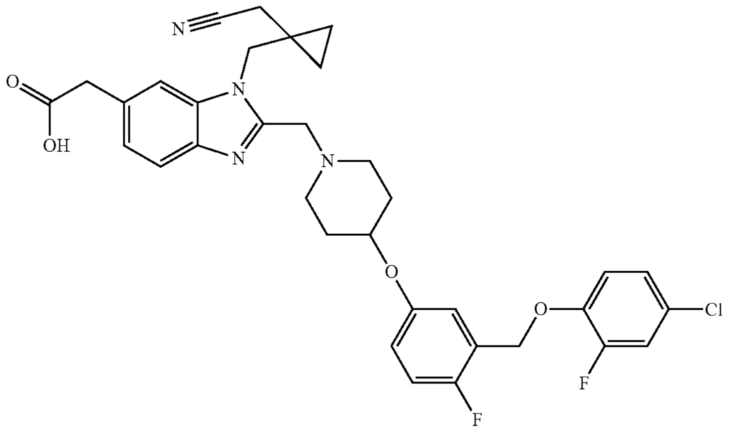 [SMILES: N#CCC1(Cn2c(CN3CCC(Oc4ccc(F)c(COc5ccc(Cl)cc5F)c4)CC3)nc3ccc(CC(=O)O)cc32)CC1] |

-continued
| Number | Structure |
|---|---|
| Compound 166 | 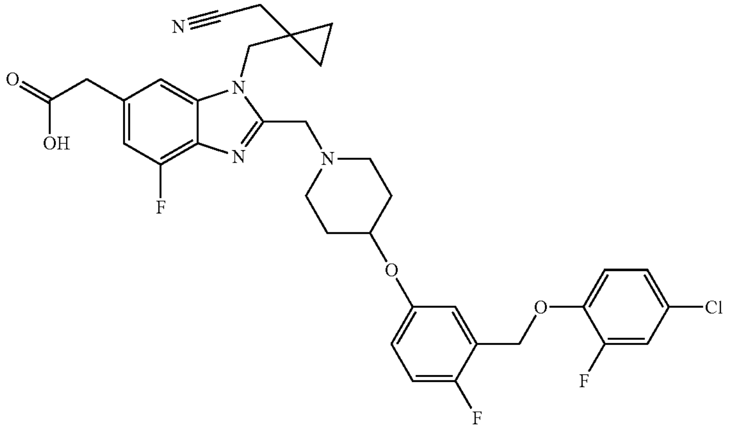 [SMILES: N#CCC1(Cn2c(CN3CCC(Oc4ccc(F)c(COc5ccc(Cl)cc5F)c4)CC3)nc3c(F)cc(CC(=O)O)cc32)CC1] |
| Compound 167 | 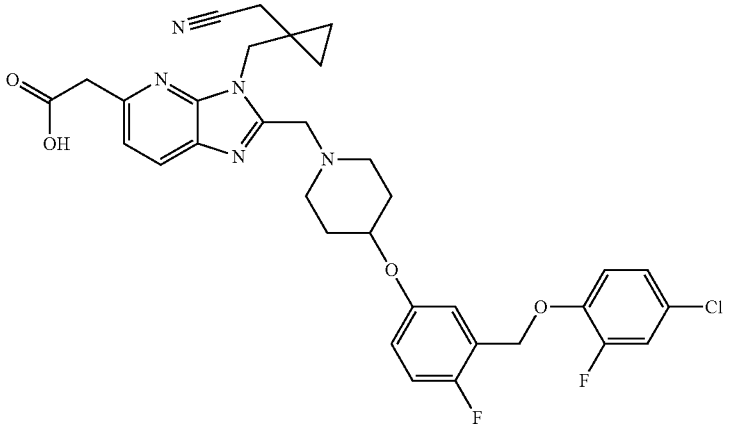 |
| Compound 168 | 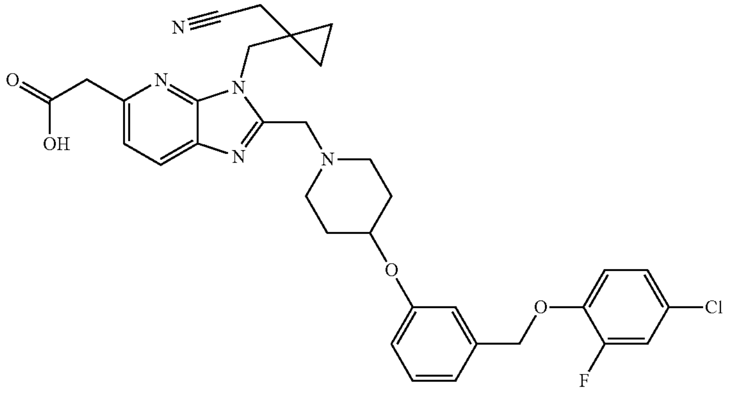 |

-continued
| Number | Structure |
| --- | --- |
| Compound 169 | 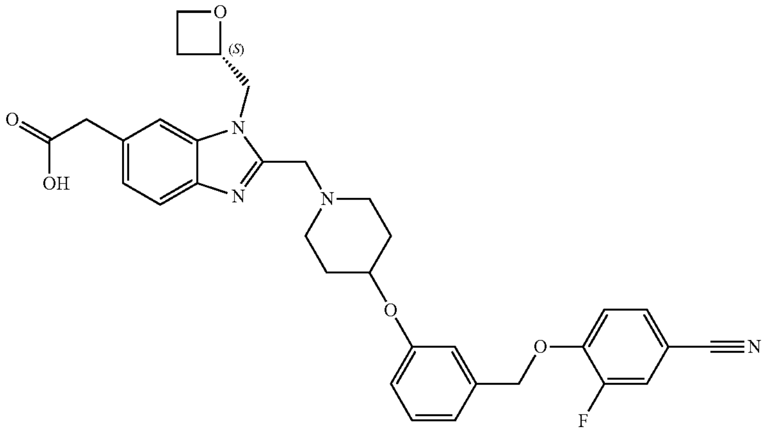 |
| Compound 170 | 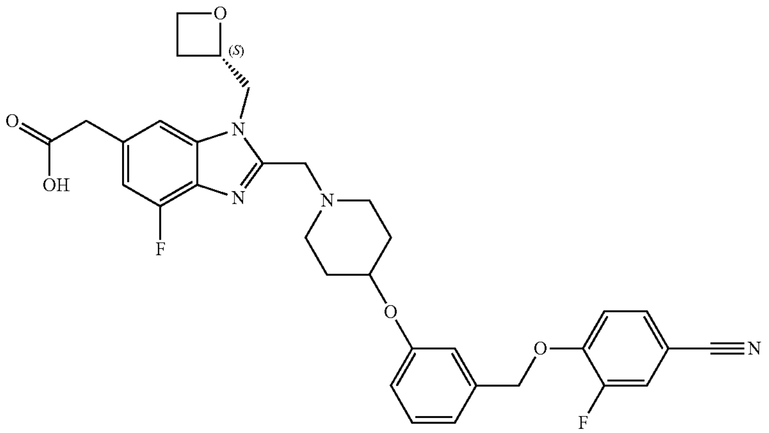 |
| Compound 171 | 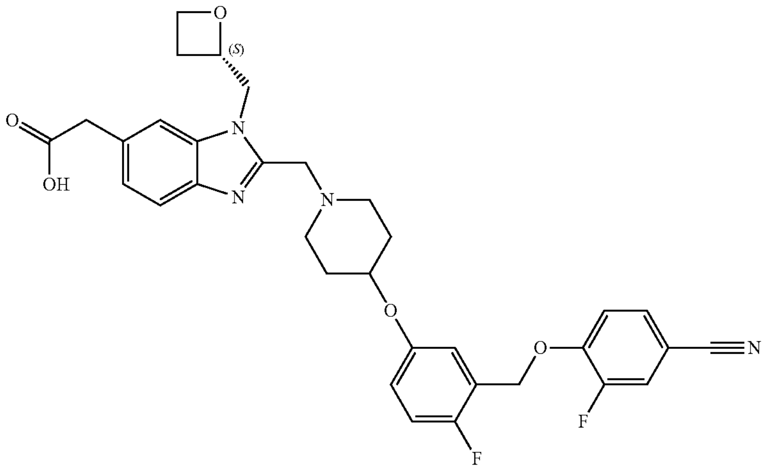 |

-continued
| Number | Structure |
| --- | --- |
| Compound 172 | 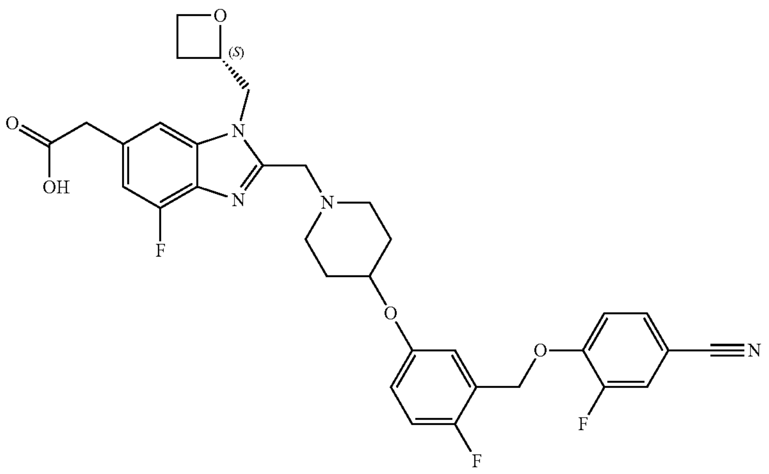 |
| Compound 173 | 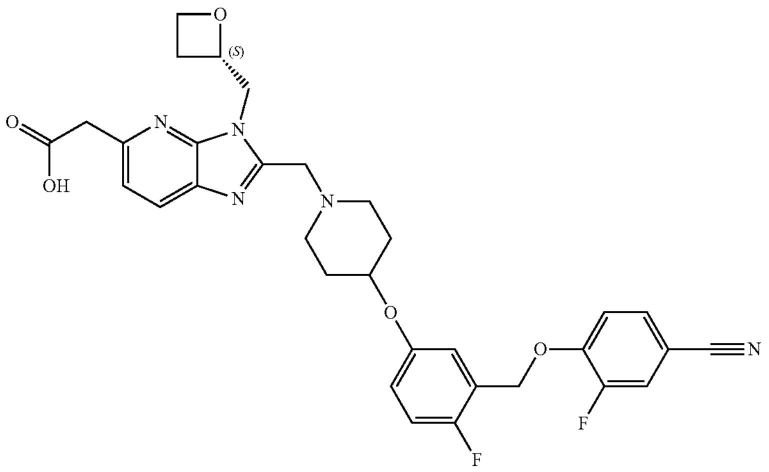 |
| Compound 174 | 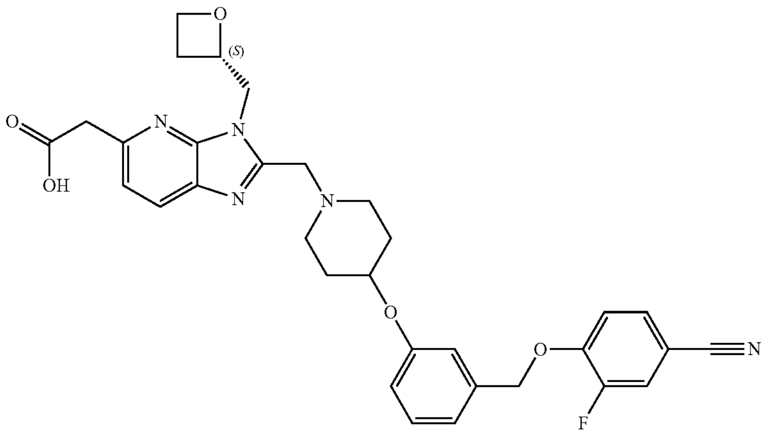 |

-continued
| Number | Structure |
|---|---|
| Compound 175 | 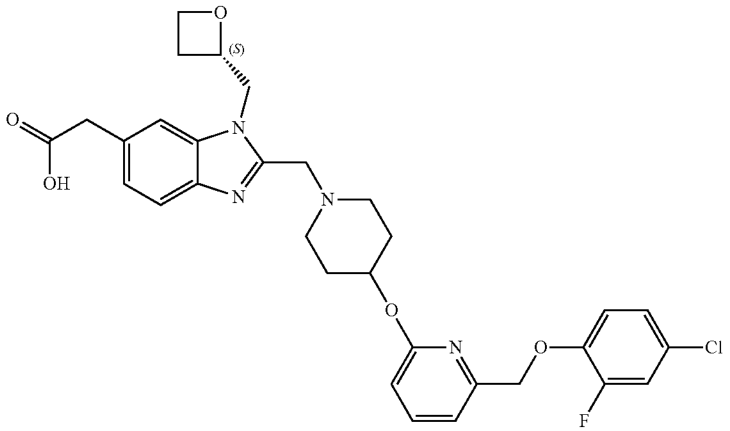 |
| Compound 176 | 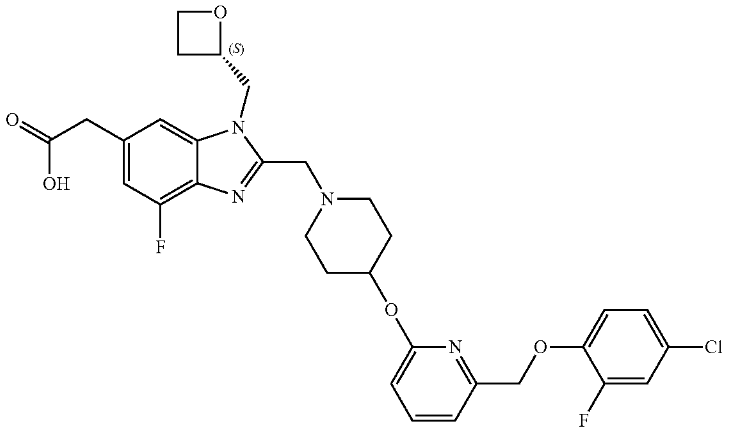 |
| Compound 177 | 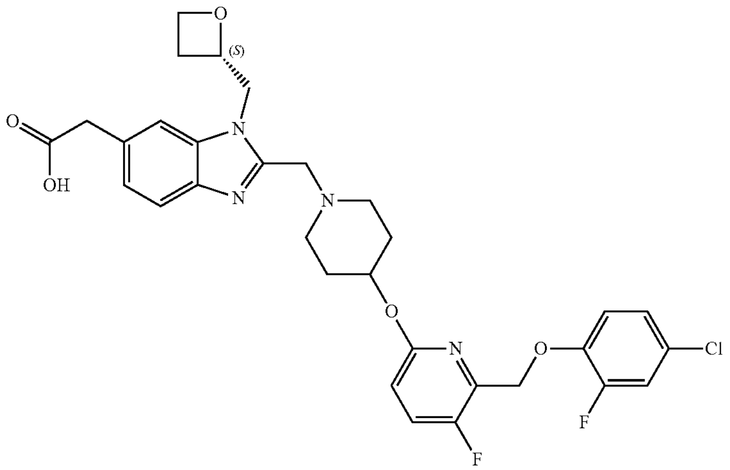 |

-continued
| Number | Structure |
| --- | --- |
| Compound 178 | 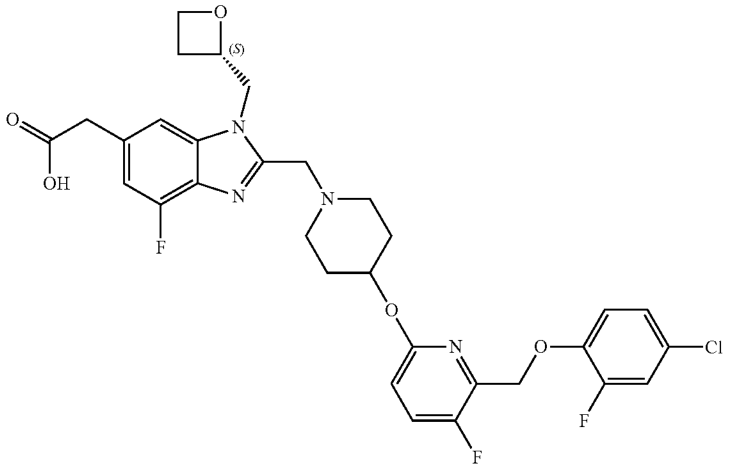 |
| Compound 179 | 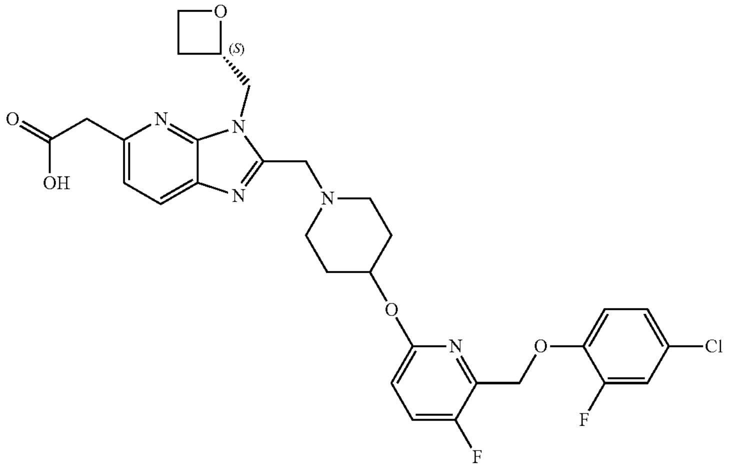 |
| Compound 180 | 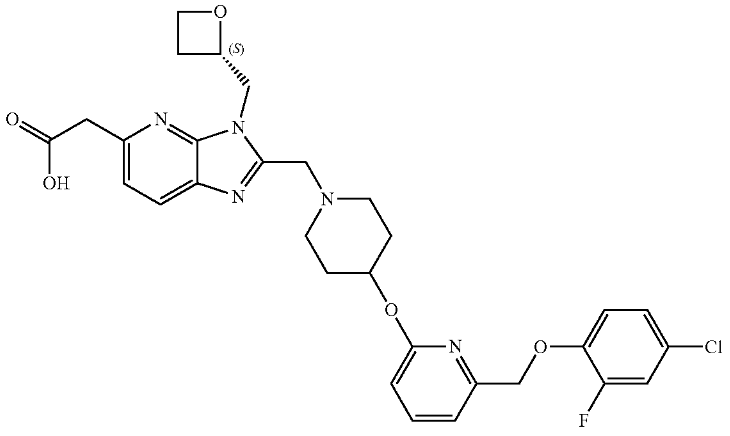 |

-continued
| Number | Structure |
|---|---|
| Compound 181 | 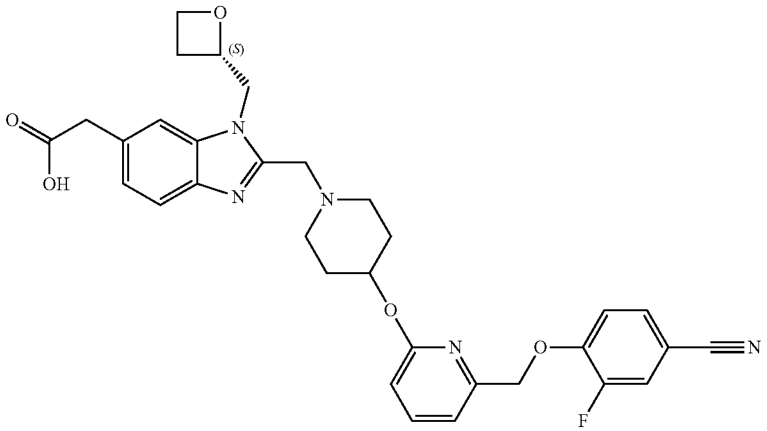 |
| Compound 182 | 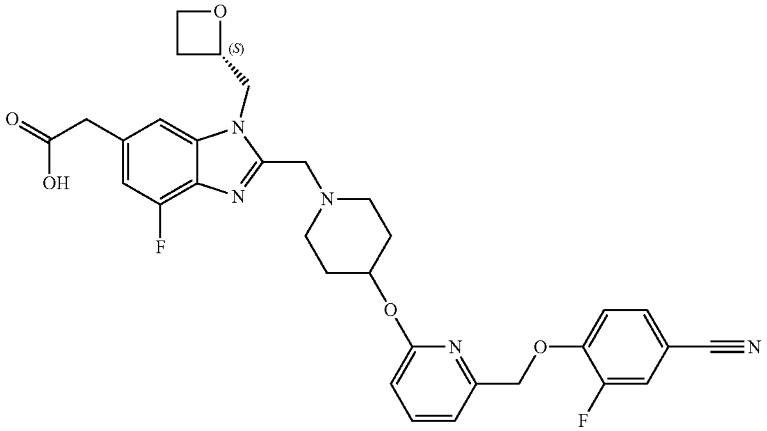 |
| Compound 183 | 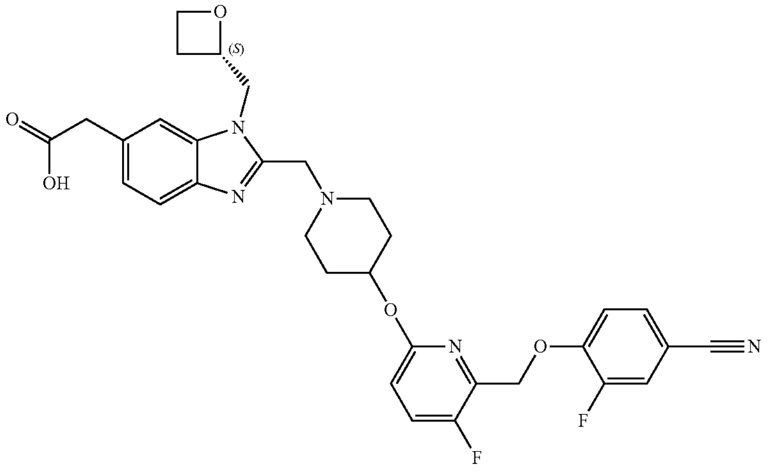 |

-continued
| Number | Structure |
|---|---|
| Compound 184 | 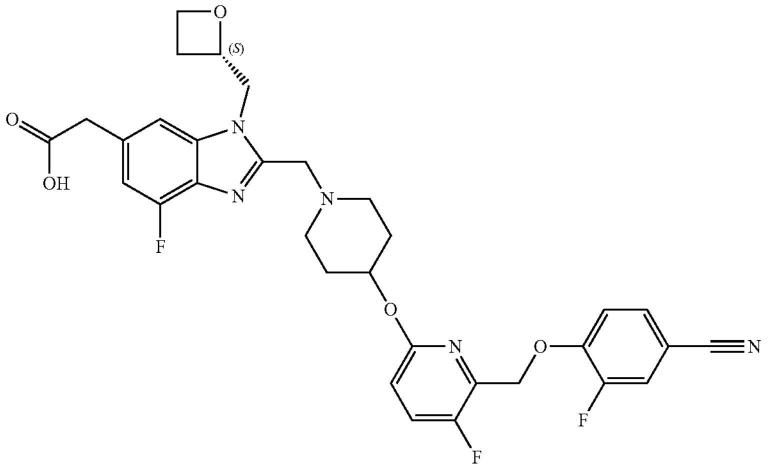 |
| Compound 185 | 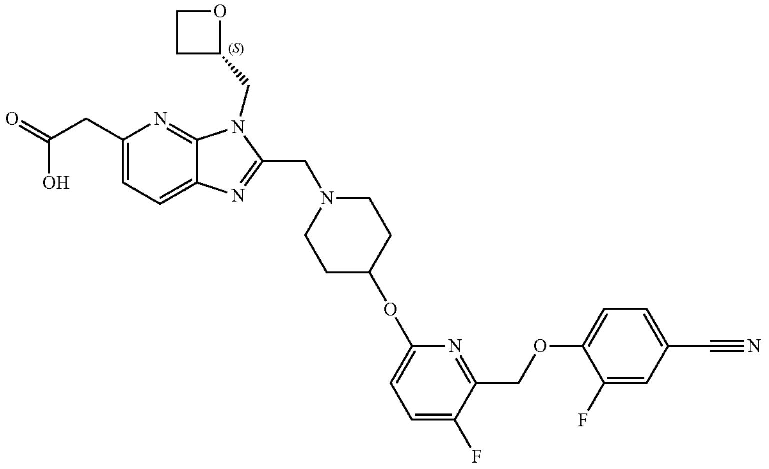 |
| Compound 186 | 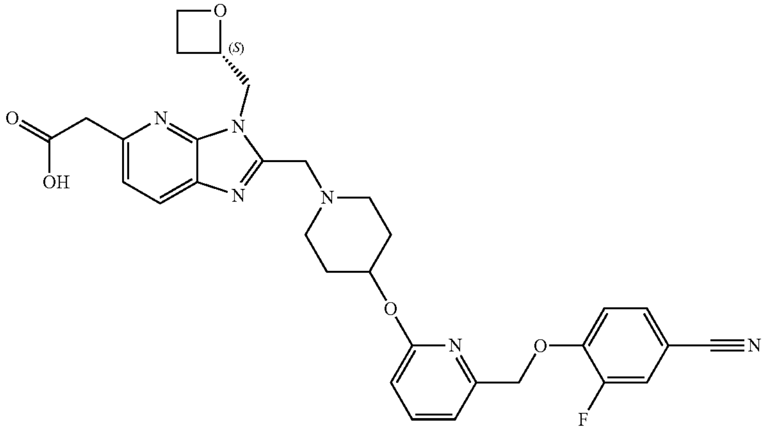 |

-continued
| Number | Structure |
| --- | --- |
| Compound 187 | 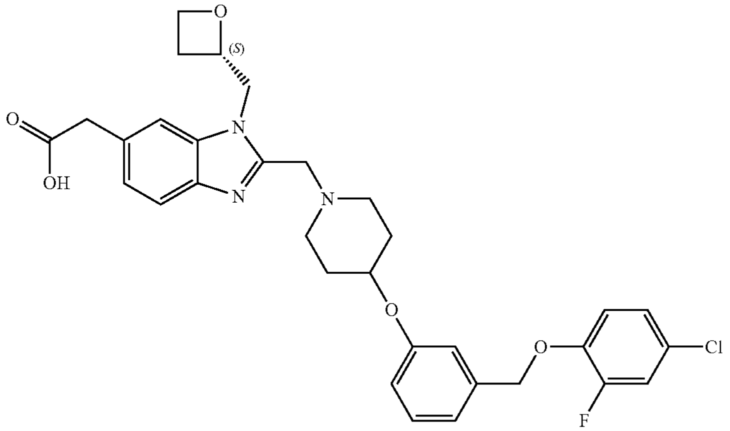 |
| Compound 188 | 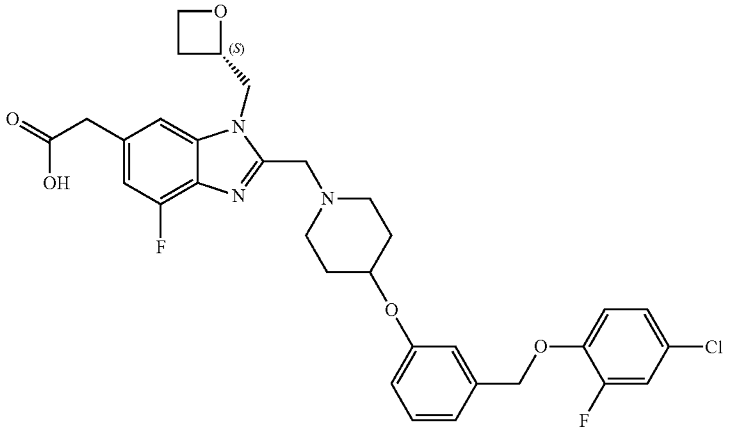 |
| Compound 189 | 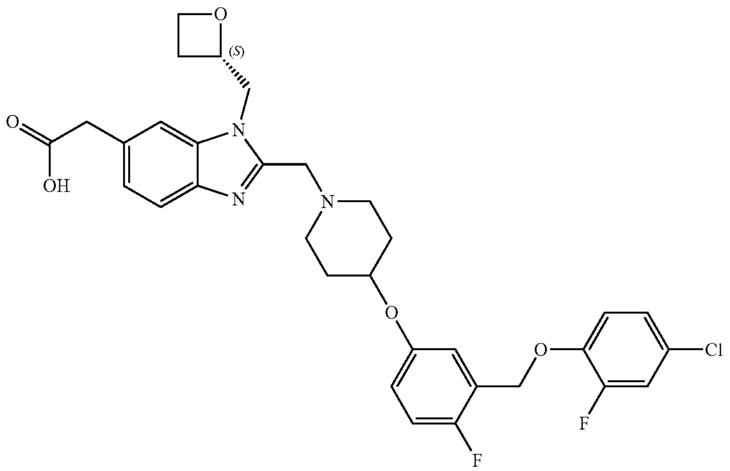 |

-continued
| Number | Structure |
| --- | --- |
| Compound 190 | 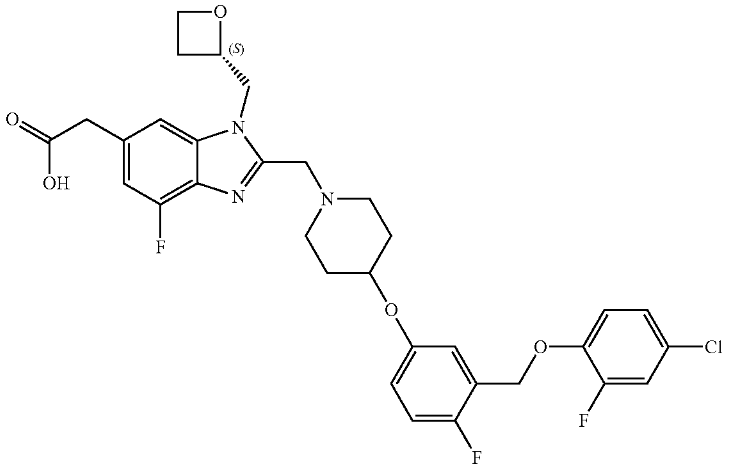 |
| Compound 191 | 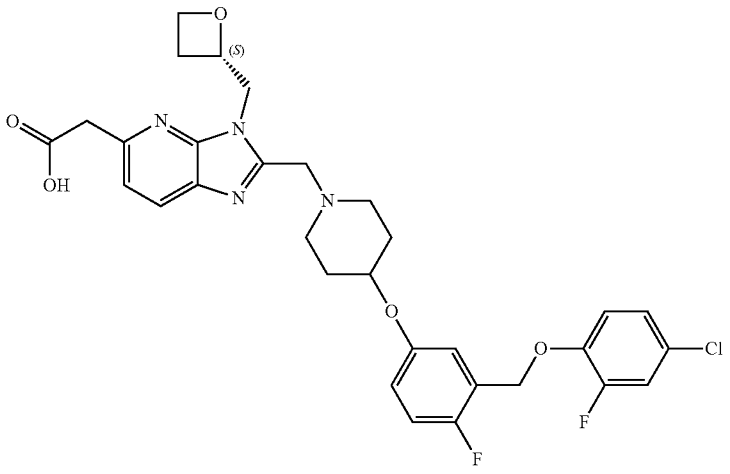 |
| Compound 192 | 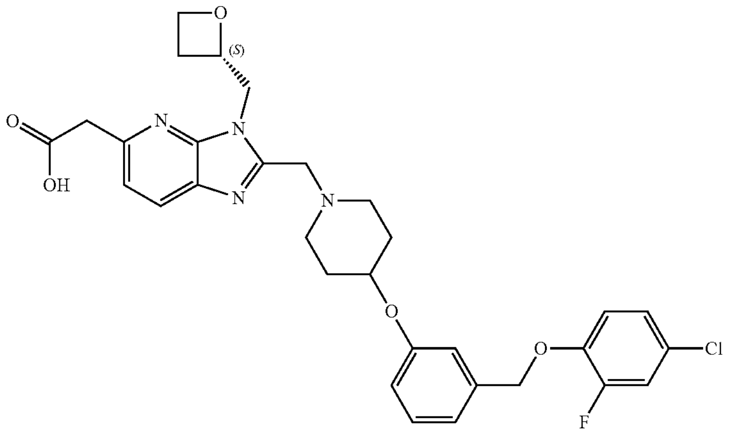 |

-continued
| Number | Structure |
|---|---|
| Compound 193 | 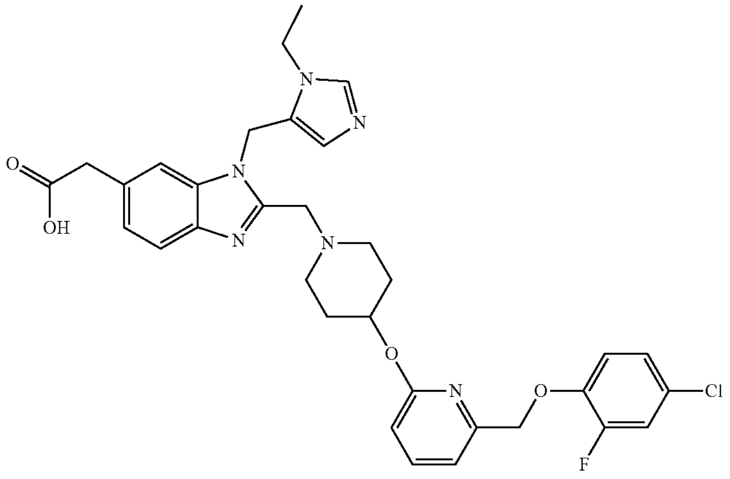 [SMILES: CCn1cncc1Cn1c(CN2CCC(Oc3cccc(COc4ccc(Cl)cc4F)n3)CC2)nc2ccc(CC(=O)O)cc21] |
| Compound 194 | 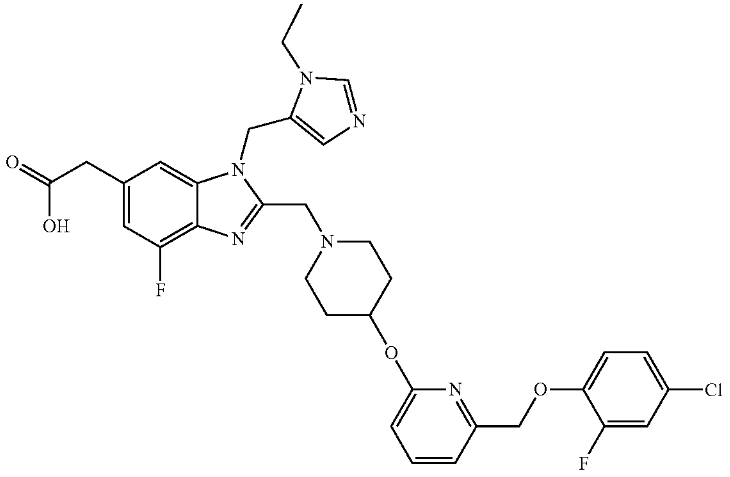 [SMILES: CCn1cncc1Cn1c(CN2CCC(Oc3cccc(COc4ccc(Cl)cc4F)n3)CC2)nc2c(F)cc(CC(=O)O)cc21] |
| Compound 195 | 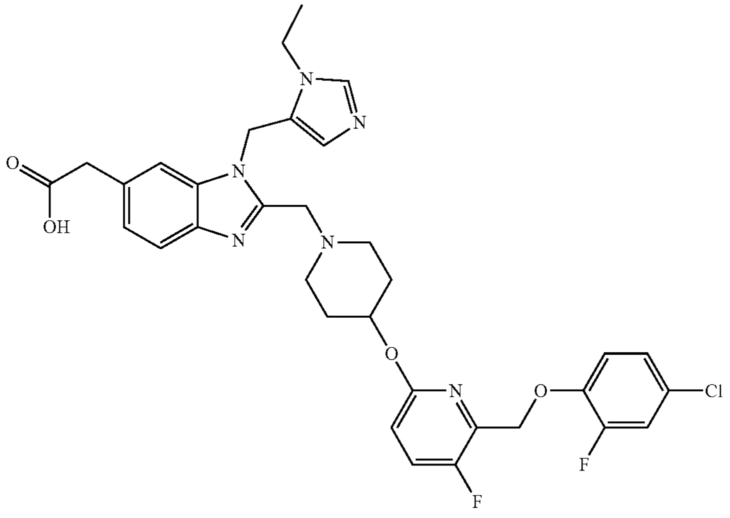 [SMILES: CCn1cncc1Cn1c(CN2CCC(Oc3ccc(F)c(COc4ccc(Cl)cc4F)n3)CC2)nc2ccc(CC(=O)O)cc21] |

-continued
| Number | Structure |
| --- | --- |
| Compound 196 | 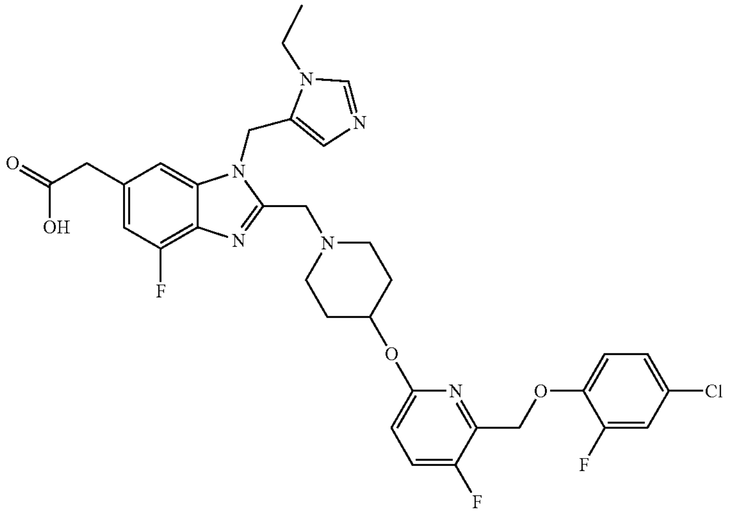 [SMILES: CCn1cncc1Cn1c(CN2CCC(Oc3ccc(F)c(COc4ccc(Cl)cc4F)n3)CC2)nc2c(F)cc(CC(=O)O)cc21] |
| Compound 197 | 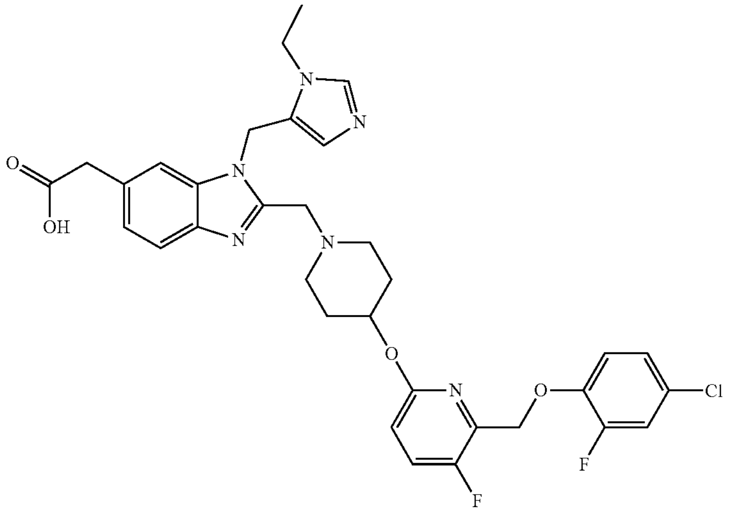 [SMILES: CCn1cncc1Cn1c(CN2CCC(Oc3ccc(F)c(COc4ccc(Cl)cc4F)n3)CC2)nc2ccc(CC(=O)O)cc21] |
| Compound 198 | 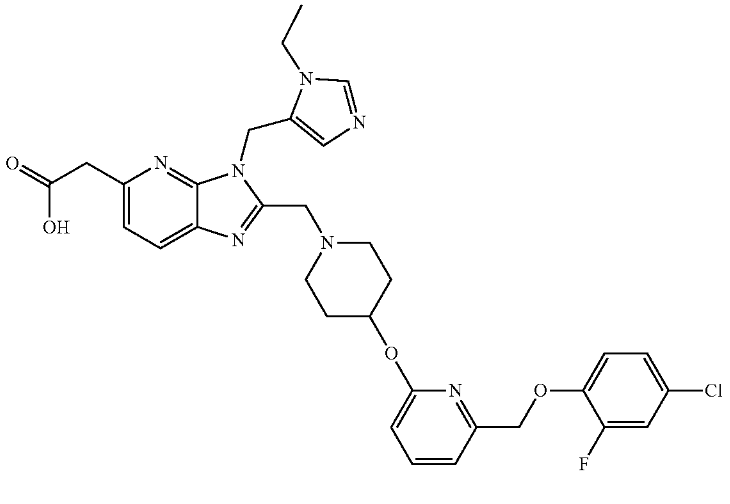 |

-continued
| Number | Structure |
|---|---|
| Compound 199 | 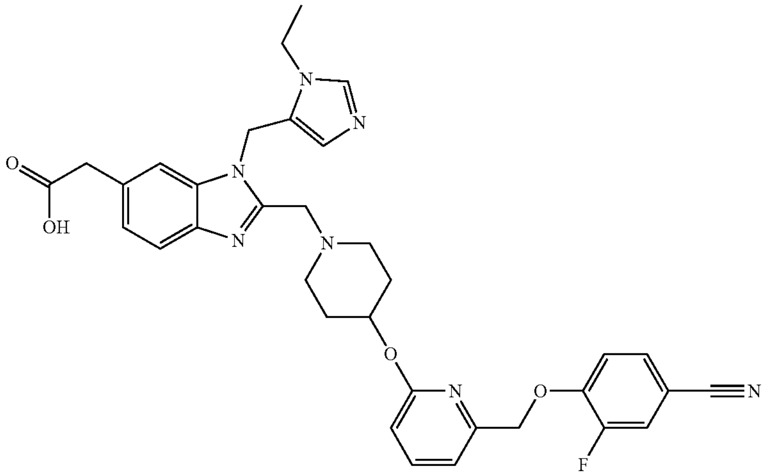 |
| Compound 200 | 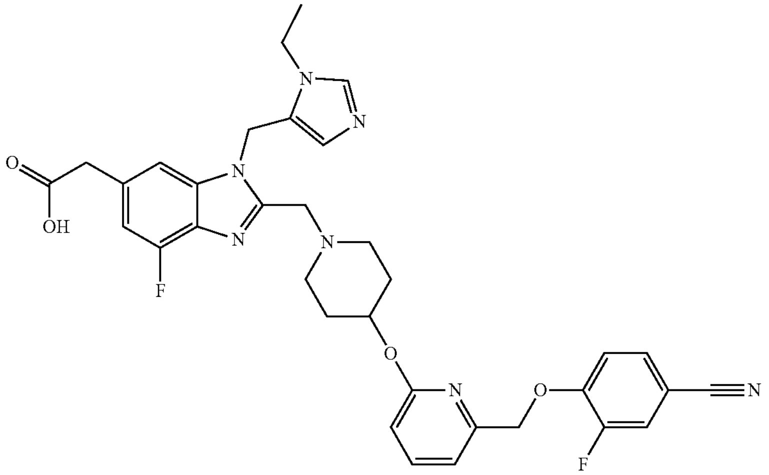 [SMILES: CCn1cncc1Cn1c(CN2CCC(Oc3cccc(COc4ccc(C#N)cc4F)n3)CC2)nc2c(F)cc(CC(=O)O)cc21] |
| Compound 201 | 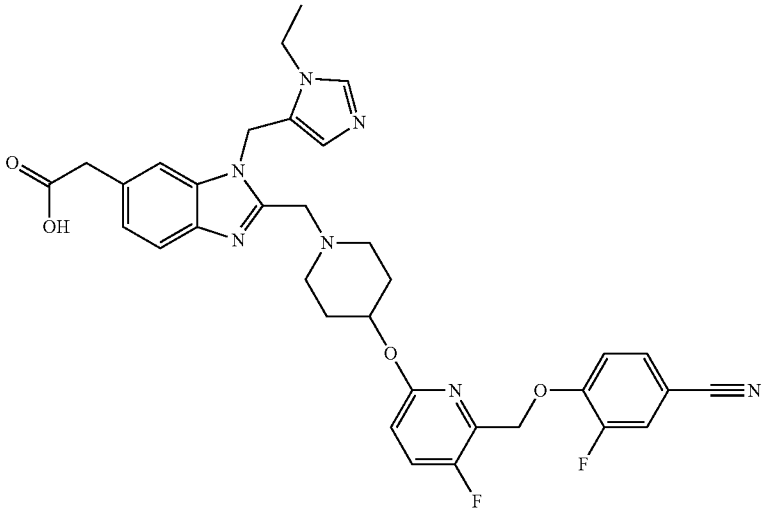 [SMILES: CCn1cncc1Cn1c(CN2CCC(Oc3ccc(F)c(COc4ccc(C#N)cc4F)n3)CC2)nc2ccc(CC(=O)O)cc21] |

-continued
| Number | Structure |
| --- | --- |
| Compound 202 | 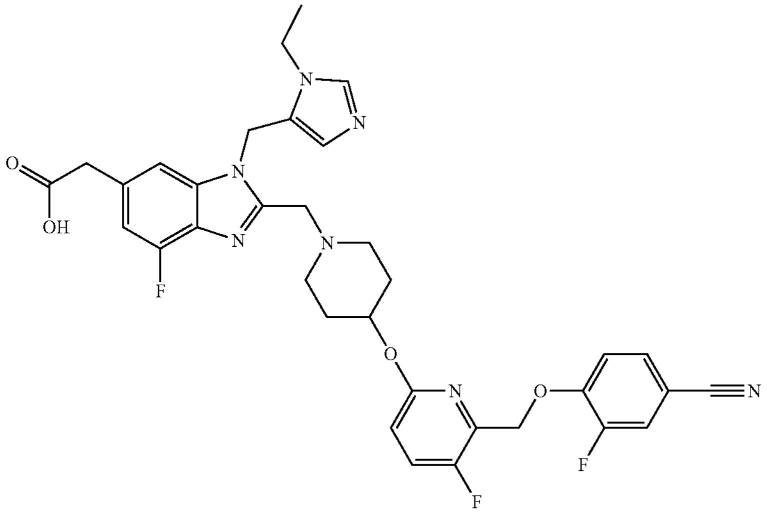 [SMILES: CCn1cncc1Cn1c(CN2CCC(Oc3ccc(F)c(COc4ccc(C#N)cc4F)n3)CC2)nc2c(F)cc(CC(=O)O)cc21] |
| Compound 203 | 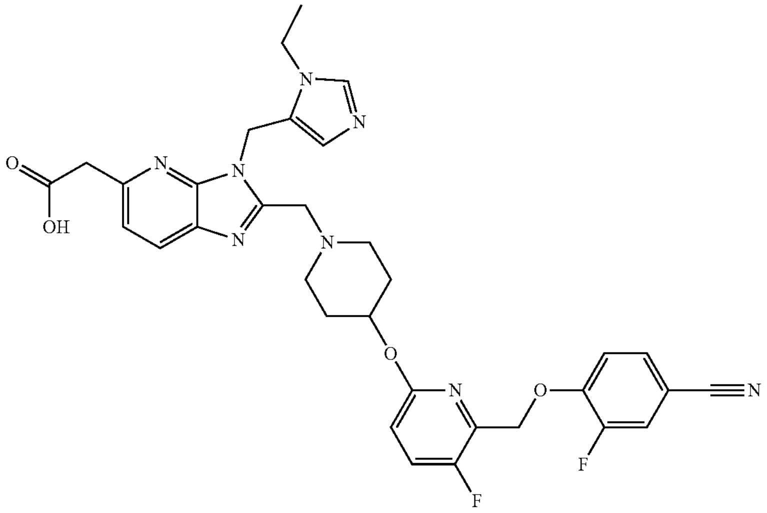 [SMILES: CCn1cncc1Cn1c(CN2CCC(Oc3ccc(F)c(COc4ccc(C#N)cc4F)n3)CC2)nc2ccc(CC(=O)O)nc21] |
| Compound 204 | 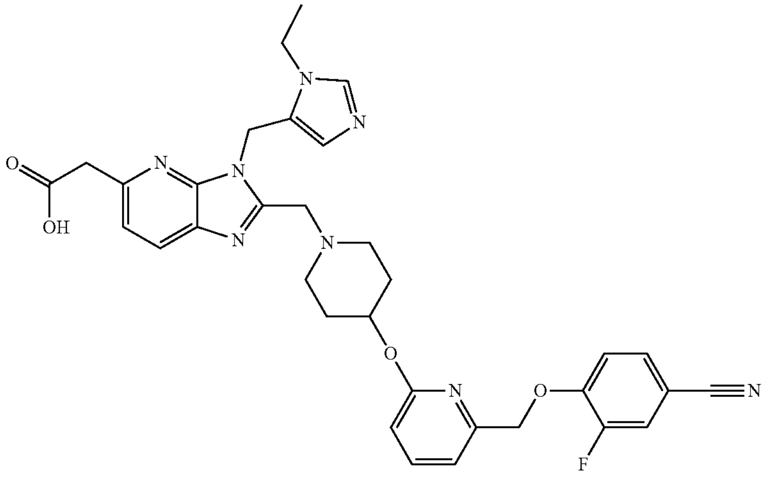 |

-continued
| Number | Structure |
| --- | --- |
| Compound 205 | 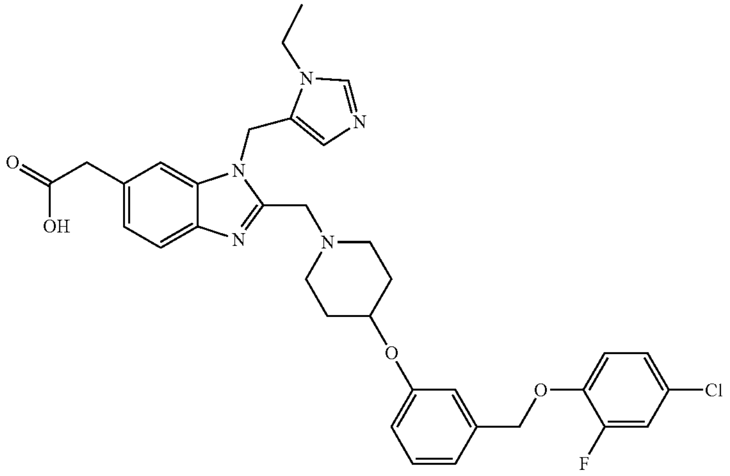 |
| Compound 206 | 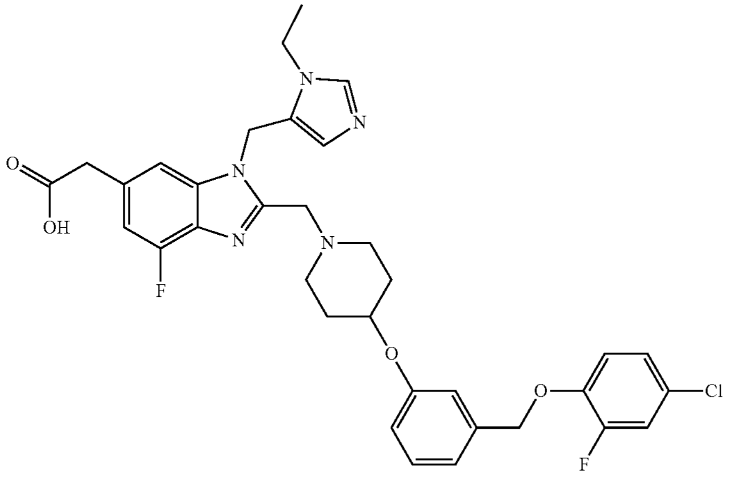 [SMILES: CCn1cncc1Cn1c(CN2CCC(Oc3cccc(COc4ccc(Cl)cc4F)c3)CC2)nc2c(F)cc(CC(=O)O)cc21] |
| Compound 207 | 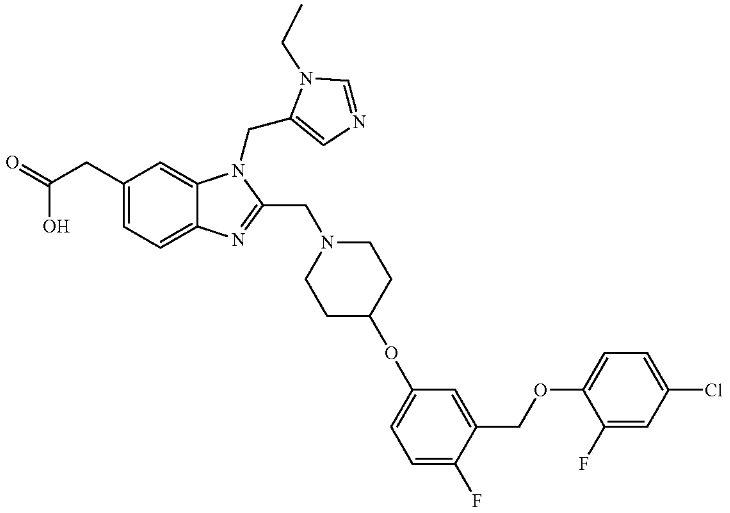 |

-continued
| Number | Structure |
| --- | --- |
| Compound 208 | 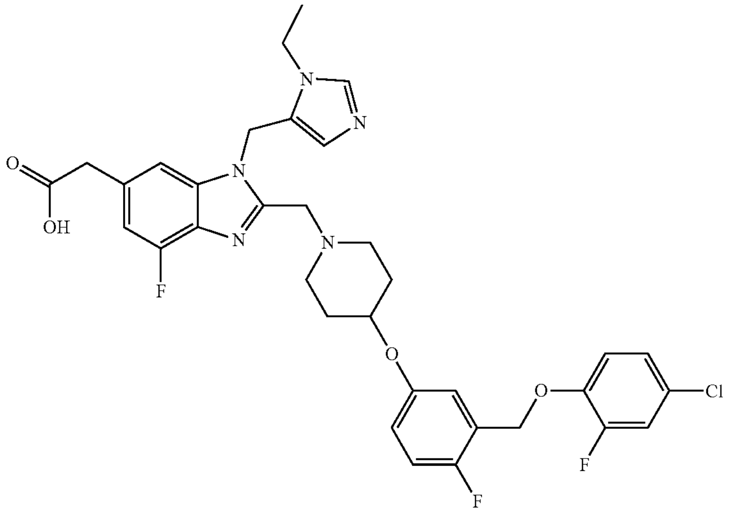 |
| Compound 209 | 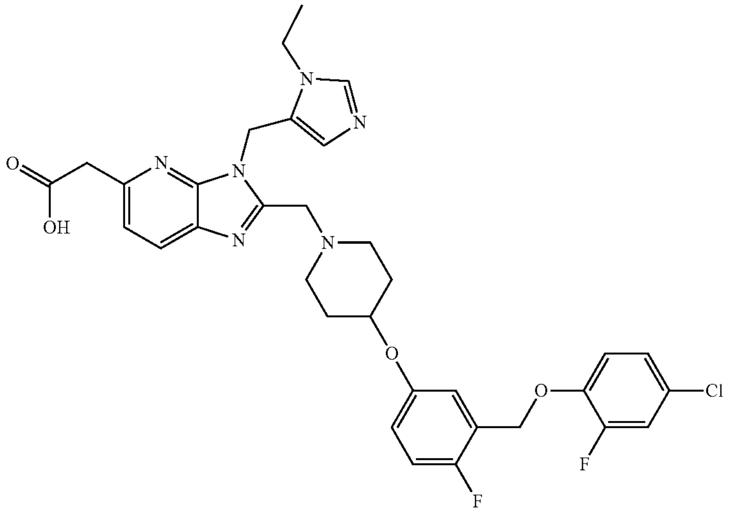 |
| Compound 210 | 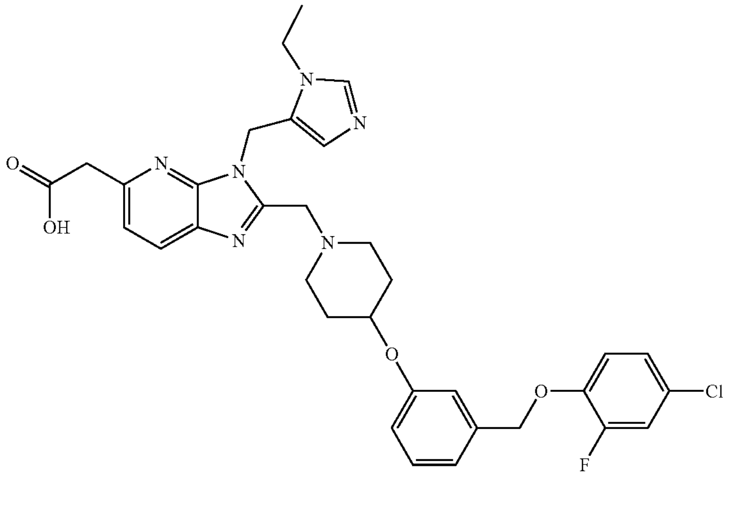 [SMILES: CCn1cncc1Cn1c(CN2CCC(Oc3cccc(COc4ccc(Cl)cc4F)c3)CC2)nc2ccc(CC(=O)O)nc21] |

-continued
| Number | Structure |
|---|---|
| Compound 211 | 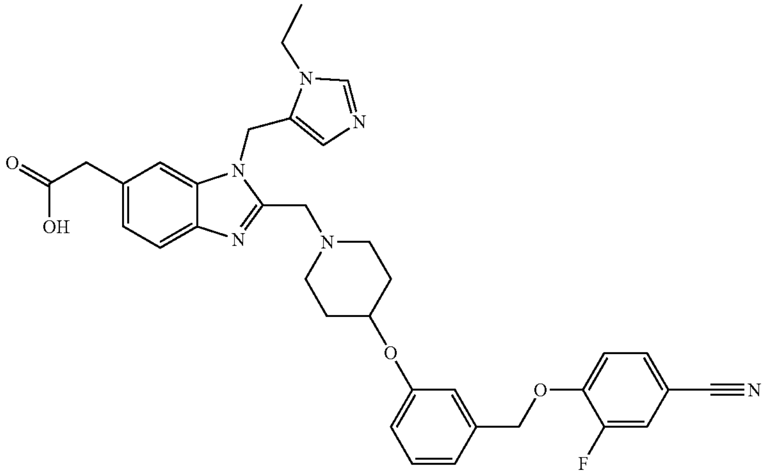 |
| Compound 212 | 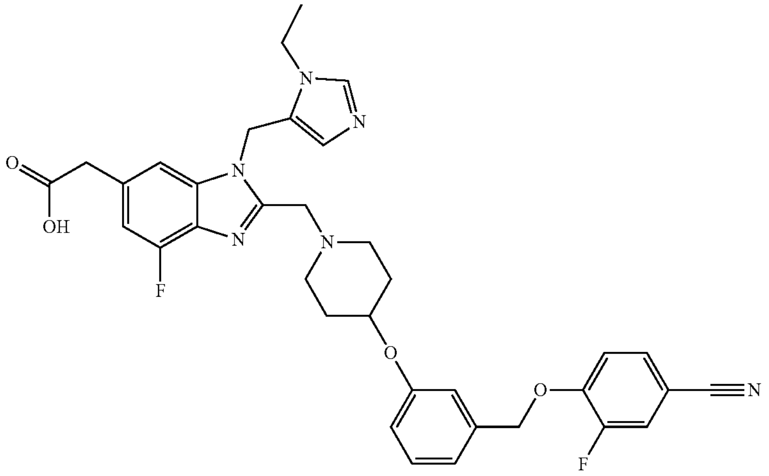 [SMILES: CCn1cncc1Cn1c(CN2CCC(Oc3cccc(COc4ccc(C#N)cc4F)c3)CC2)nc2c(F)cc(CC(=O)O)cc21] |
| Compound 213 | 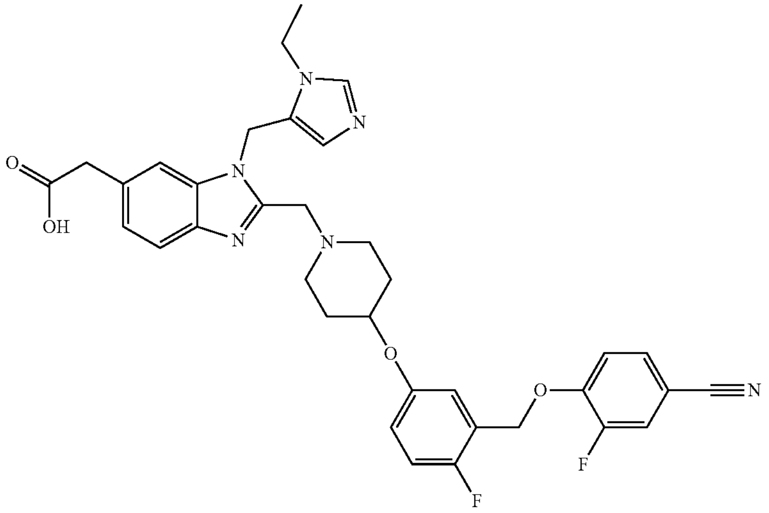 [SMILES: CCn1cncc1Cn1c(CN2CCC(Oc3ccc(F)c(COc4ccc(C#N)cc4F)c3)CC2)nc2ccc(CC(=O)O)cc21] |

-continued
| Number | Structure |
| --- | --- |
| Compound 214 | 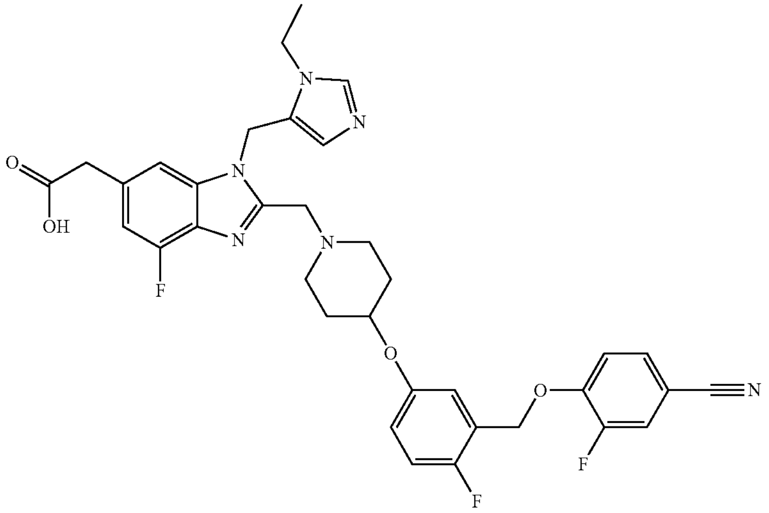 [SMILES: CCn1cncc1Cn1c(CN2CCC(Oc3ccc(F)c(COc4ccc(C#N)cc4F)c3)CC2)nc2c(F)cc(CC(=O)O)cc21] |
| Compound 215 | 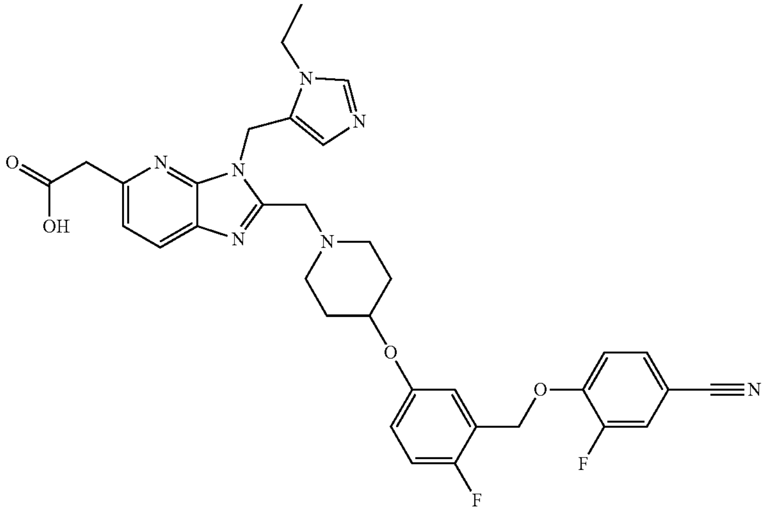 [SMILES: CCn1cncc1Cn1c(CN2CCC(Oc3ccc(F)c(COc4ccc(C#N)cc4F)c3)CC2)nc2ccc(CC(=O)O)nc21] |
| Compound 216 | 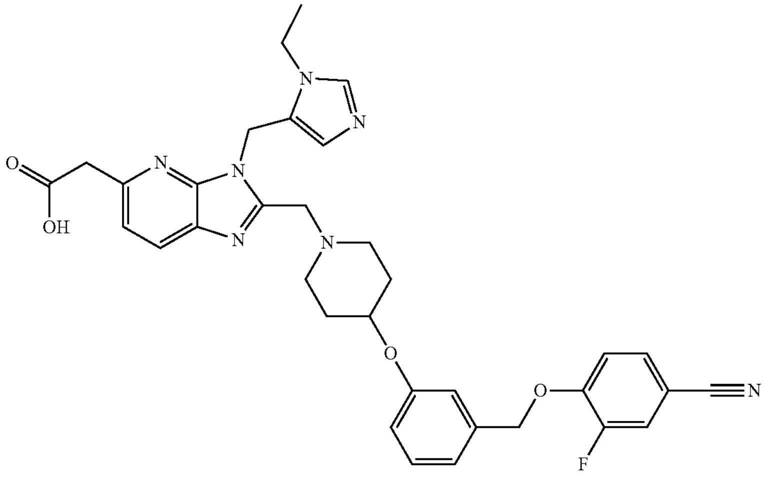 [SMILES: CCn1cncc1Cn1c(CN2CCC(Oc3cccc(COc4ccc(C#N)cc4F)c3)CC2)nc2ccc(CC(=O)O)nc21] |

| Number | Structure |
|---|---|
| Compound S1 | 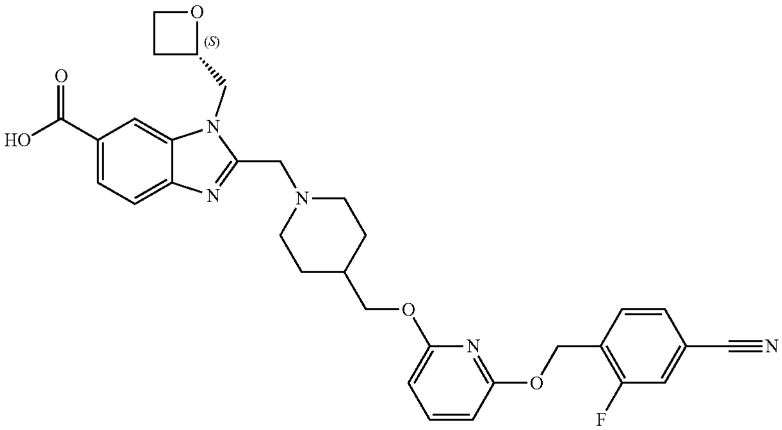 |
| Compound S2 | 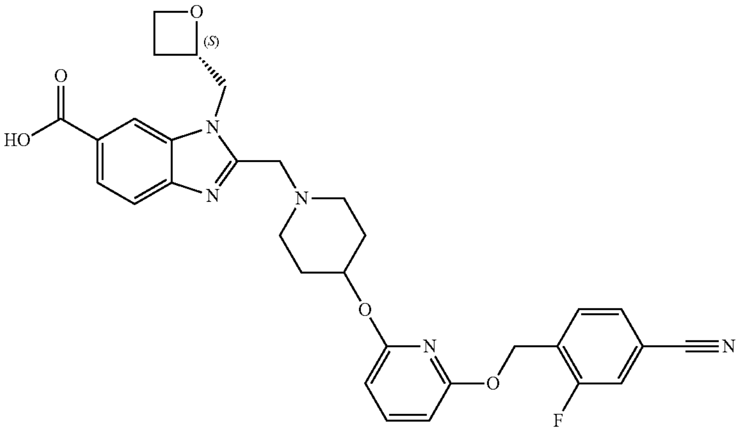 |
| Compound S3 | 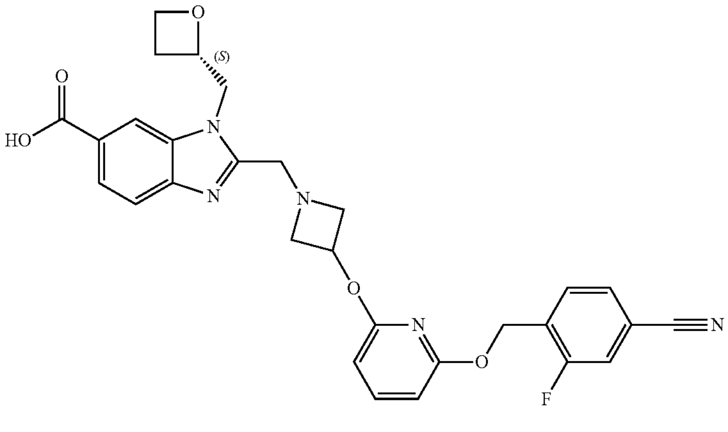 |

-continued
| Number | Structure |
| --- | --- |
| Compound S4 | 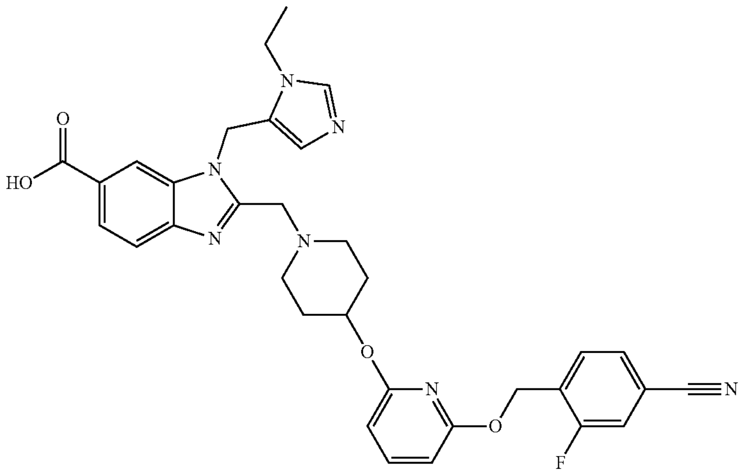 [SMILES: CCn1cncc1Cn1c(CN2CCC(Oc3cccc(OCc4ccc(C#N)cc4F)n3)CC2)nc2ccc(C(=O)O)cc21] |
| Compound S5 | 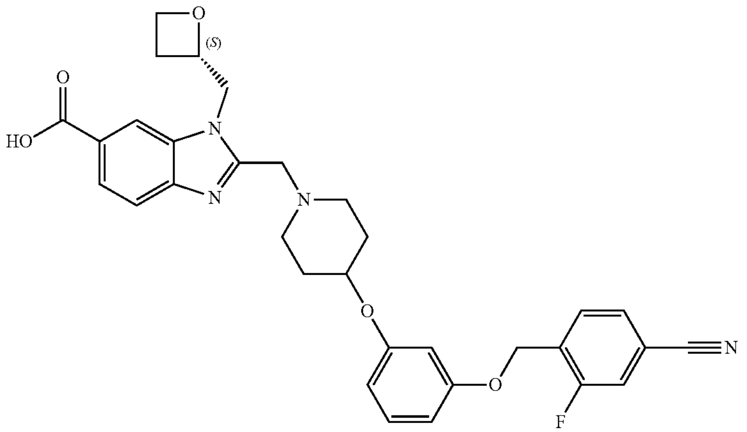 |
| Compound S6 | 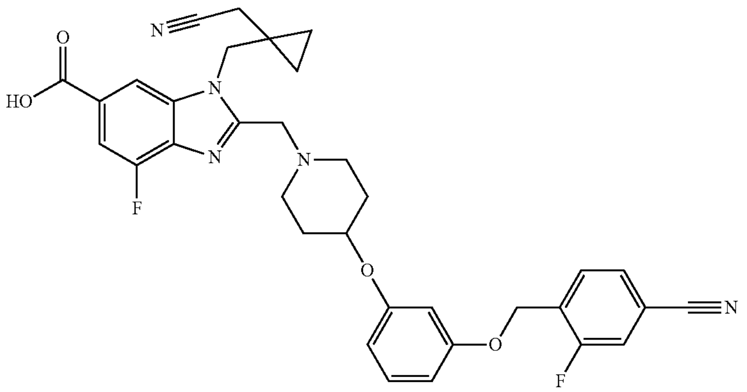 [SMILES: N#CCC1(Cn2c(CN3CCC(Oc4cccc(OCc5ccc(C#N)cc5F)c4)CC3)nc3c(F)cc(C(=O)O)cc32)CC1] |

-continued
| Number | Structure |
|---|---|
| Compound S7 | 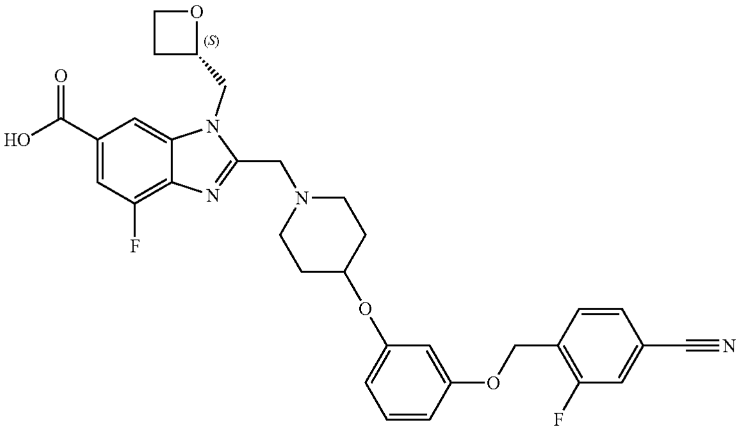 |
| Compound S8 | 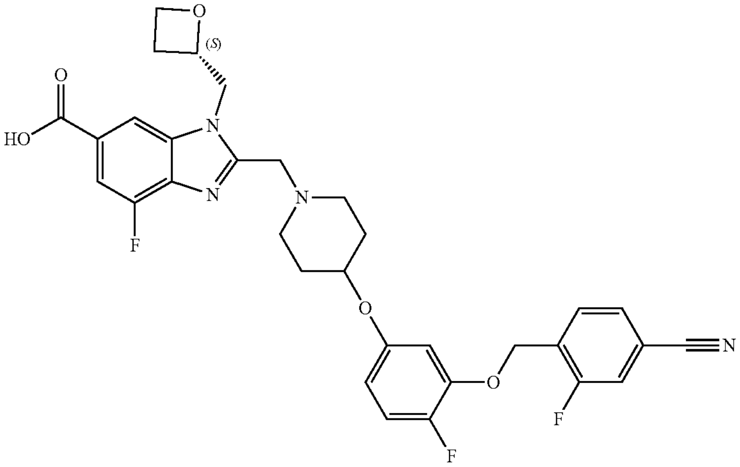 |
| Compound S9 | 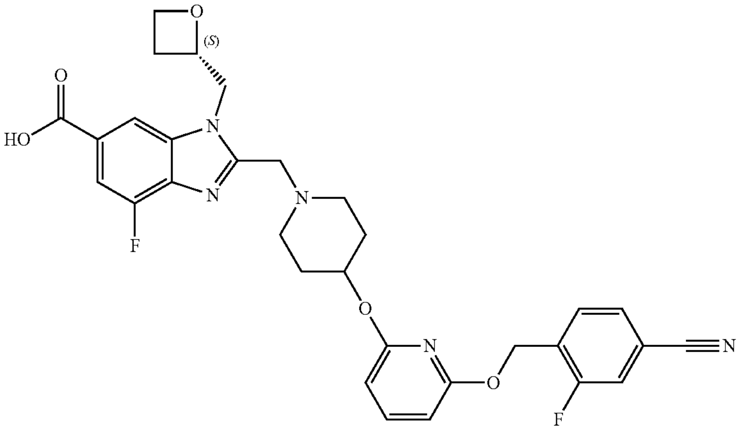 |

-continued
| Number | Structure |
|---|---|
| Compound S10 | 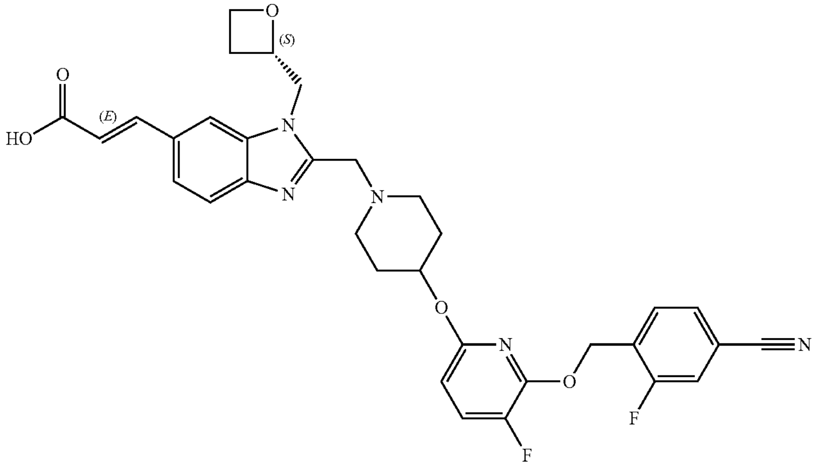 |
| Compound S11 | 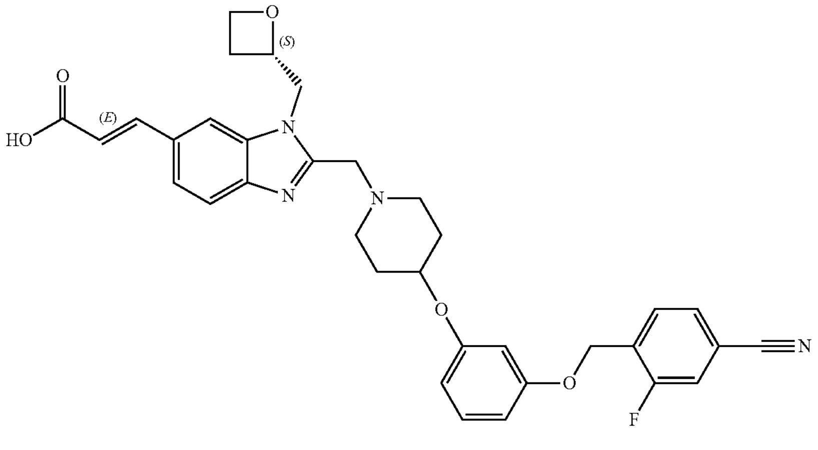 |
| Compound S14 | 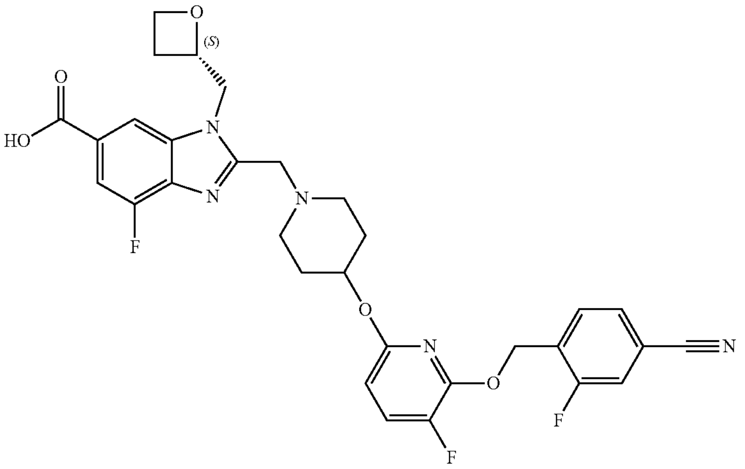 |

-continued
| Number | Structure |
| --- | --- |
| Compound S15 | 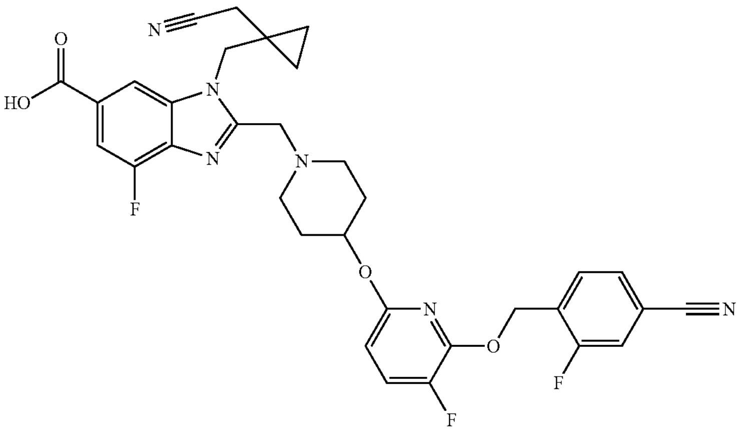 [SMILES: N#CCC1(Cn2c(CN3CCC(Oc4ccc(F)c(OCc5ccc(C#N)cc5F)n4)CC3)nc3c(F)cc(C(=O)O)cc32)CC1] |
| Compound S16 | 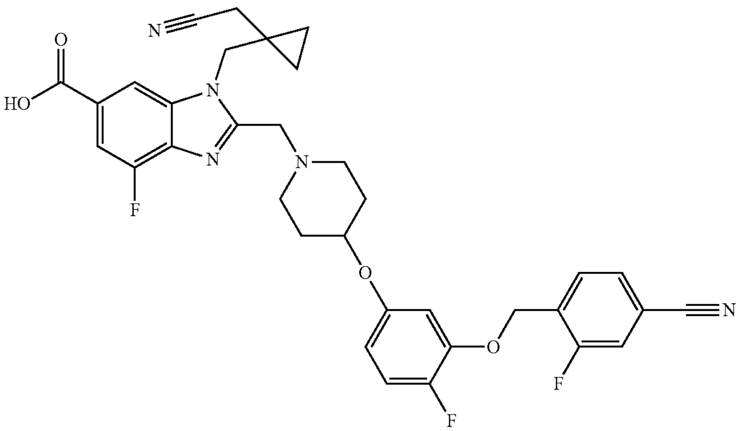 [SMILES: N#CCC1(Cn2c(CN3CCC(Oc4ccc(F)c(OCc5ccc(C#N)cc5F)c4)CC3)nc3c(F)cc(C(=O)O)cc32)CC1] |
| Compound S17 | 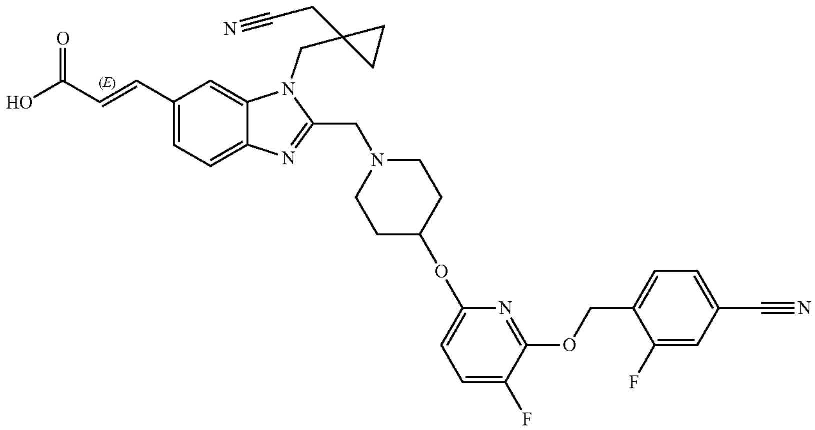 |

-continued
| Number | Structure |
|---|---|
| Compound S20 | 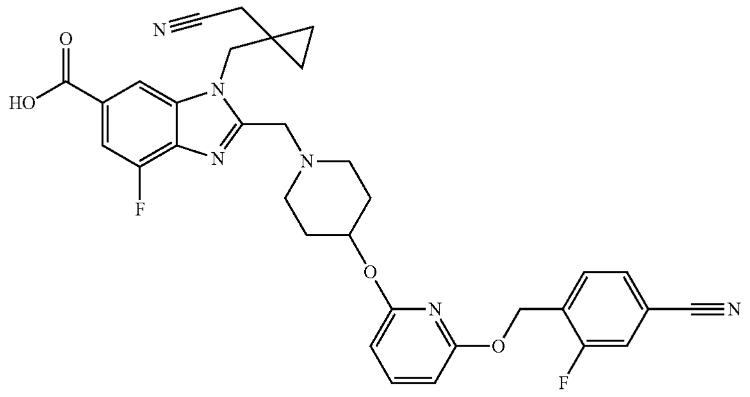 |
| Compound S21 | 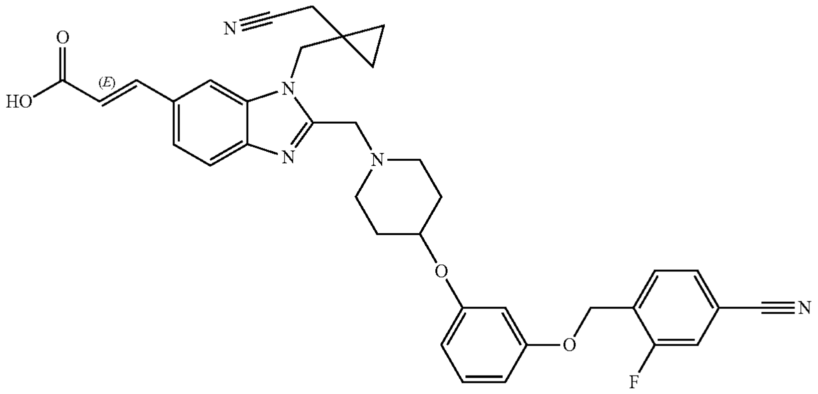 |
| Compound S22 | 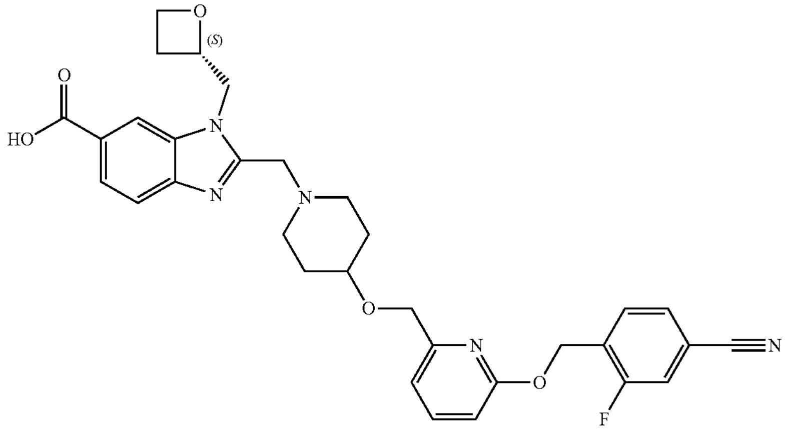 |

-continued
| Number | Structure |
|---|---|
| Compound S23 | 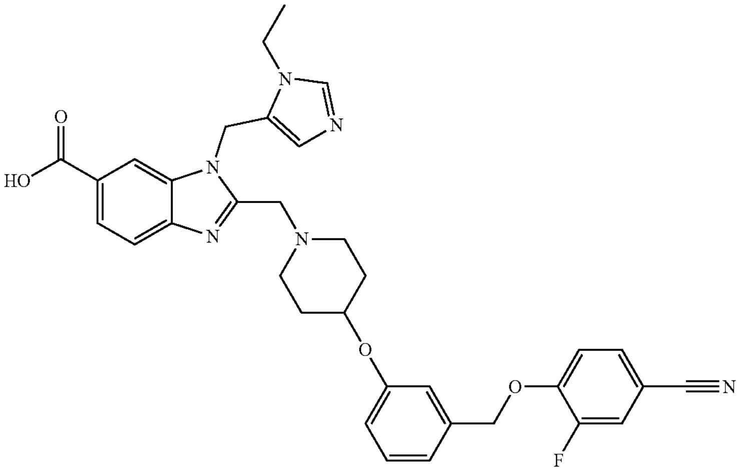 |
| Compound S24 | 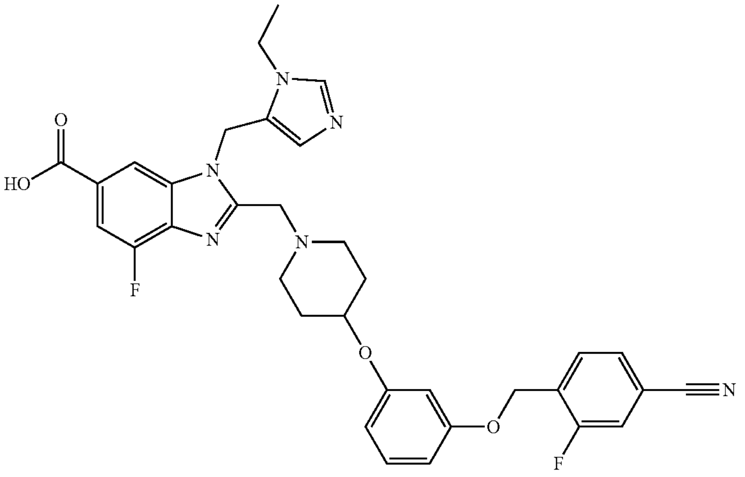 [SMILES: CCn1cncc1Cn1c(CN2CCC(Oc3cccc(OCc4ccc(C#N)cc4F)c3)CC2)nc2c(F)cc(C(=O)O)cc21] |
| Compound S25 | 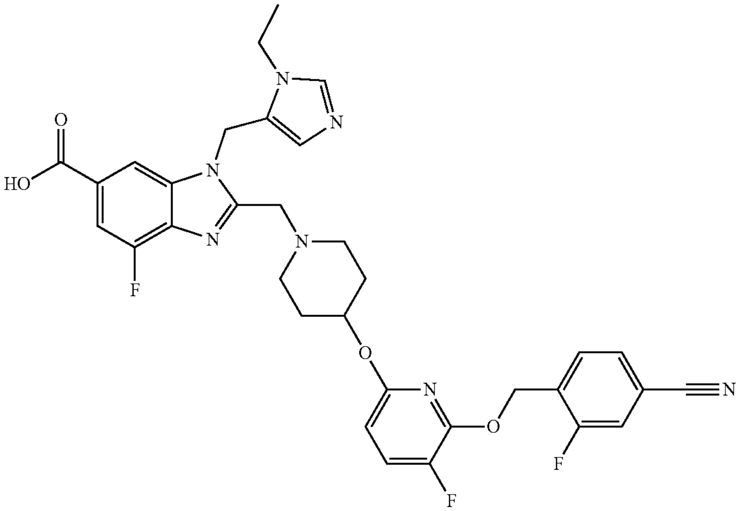 |

-continued
| Number | Structure |
|---|---|
| Compound S26 | 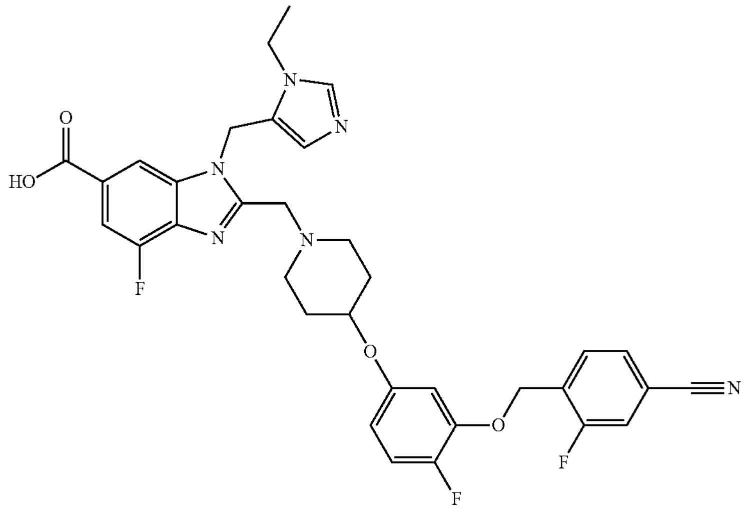 |
| Compound S27 | 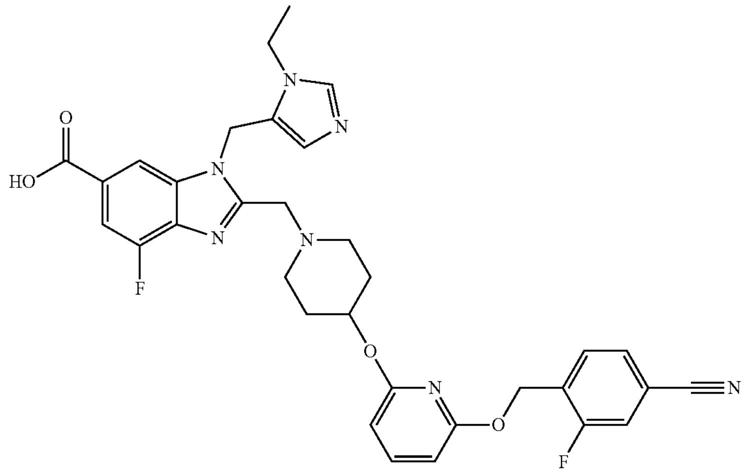 |
| Compound S28 | 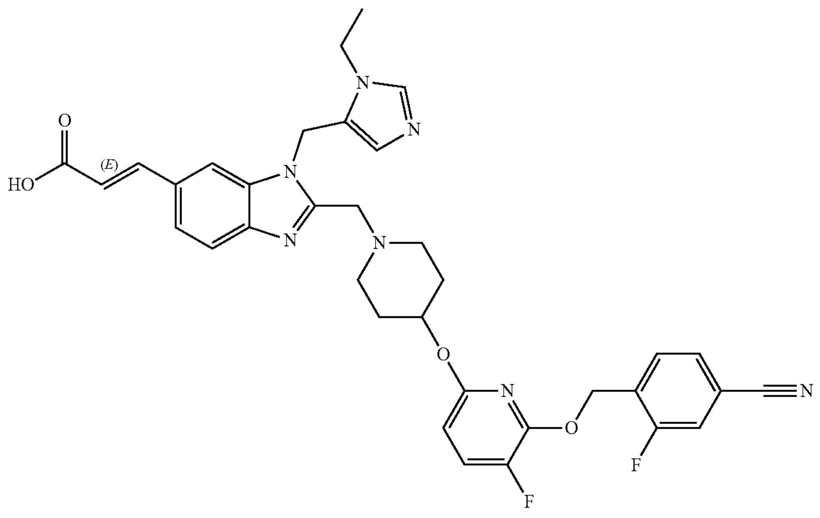 |

-continued
| Number | Structure |
| --- | --- |
| Compound S29 | 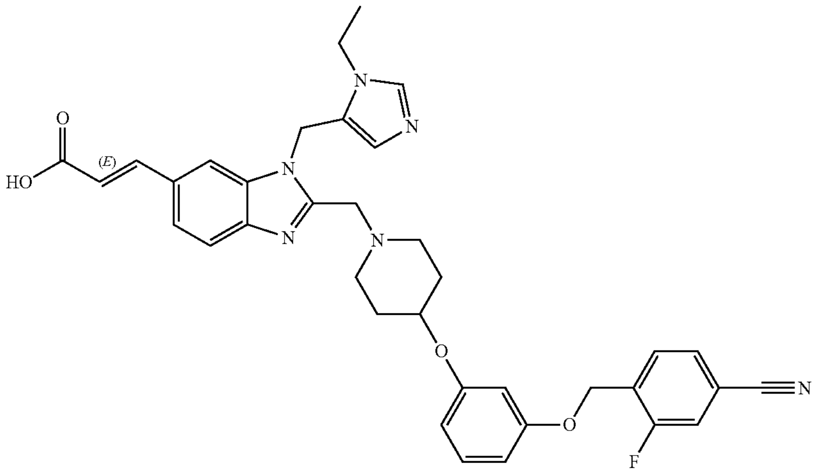 |
| Compound S32 | 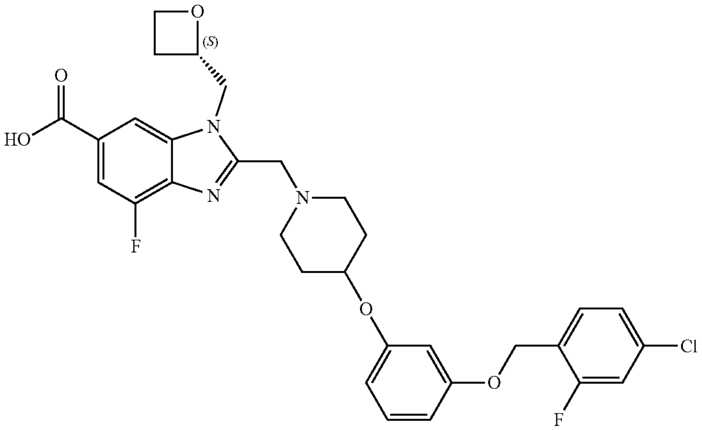 |
| Compound S33 | 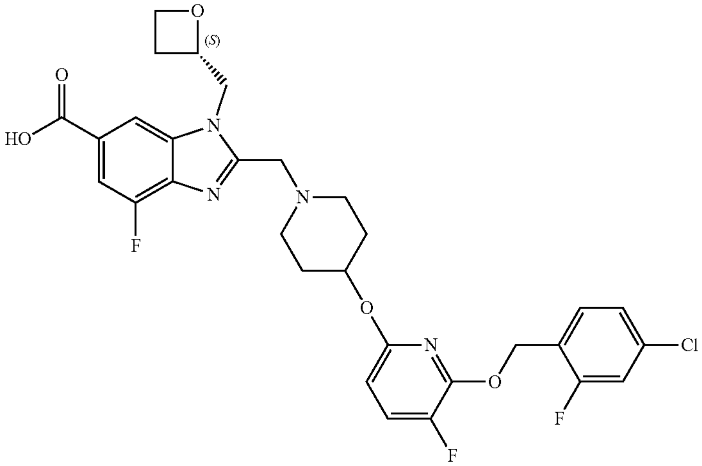 |

-continued
| Number | Structure |
|---|---|
| Compound S34 | 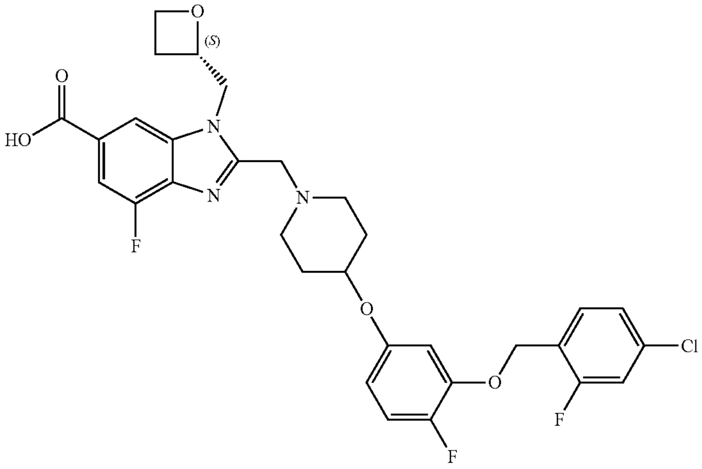 |
| Compound S35 | 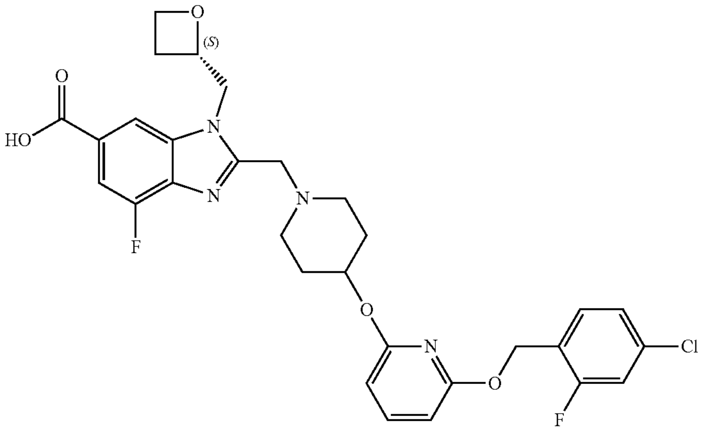 |
| Compound S36 | 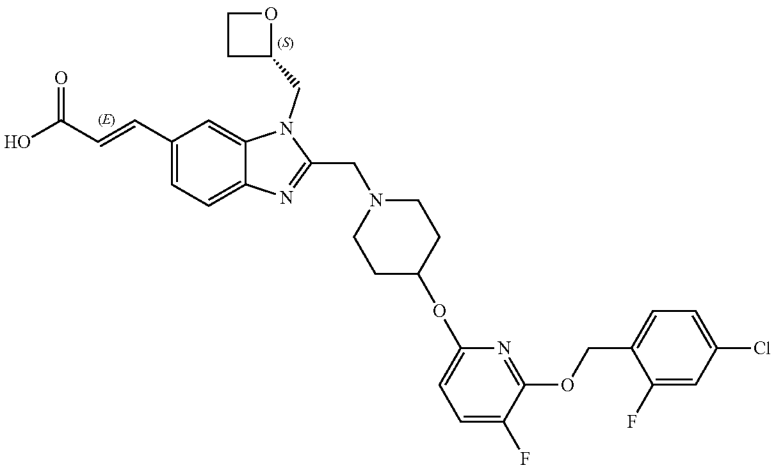 |

-continued
| Number | Structure |
|---|---|
| Compound S37 | 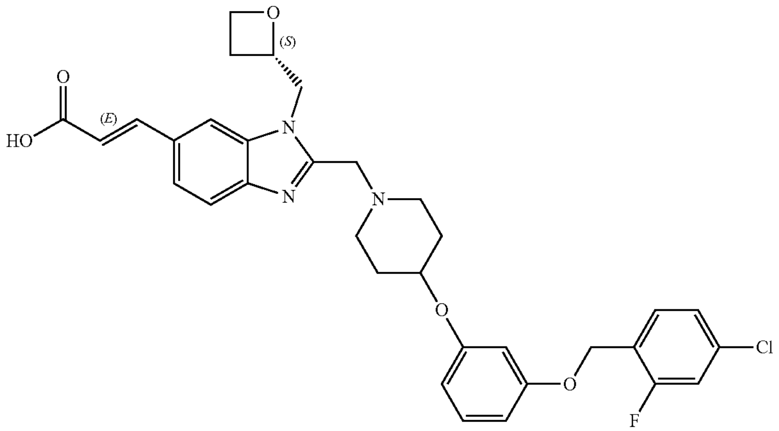 |
| Compound S40 | 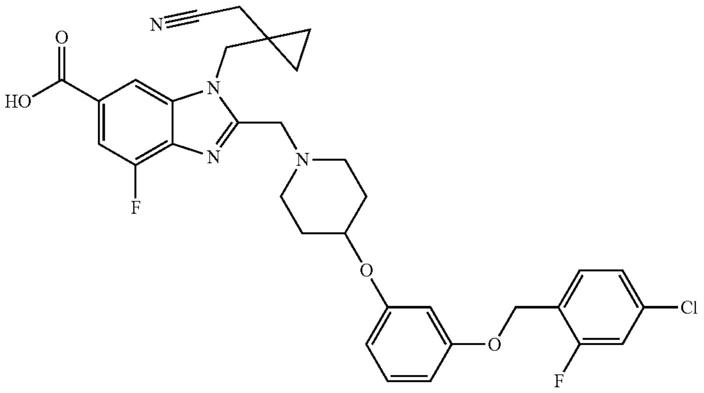 |
| Compound S41 | 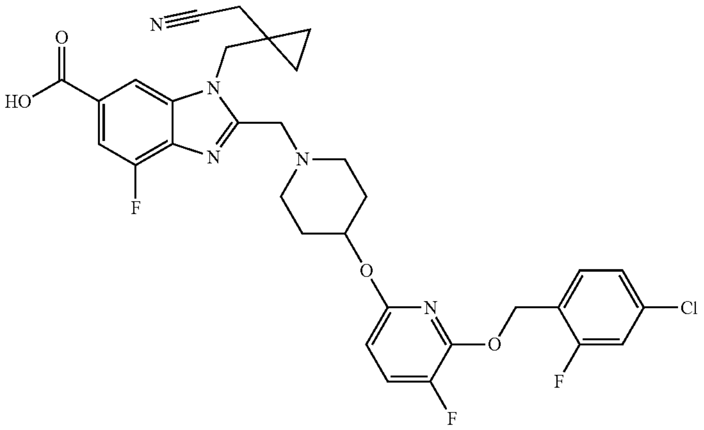 |

-continued
| Number | Structure |
|---|---|
| Compound S42 | 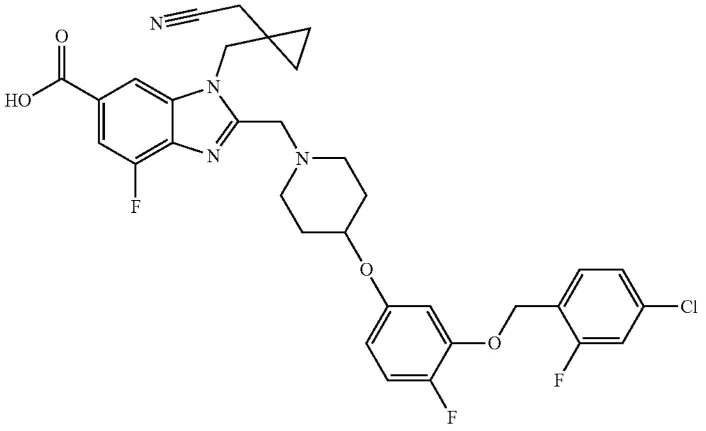 |
| Compound S43 | 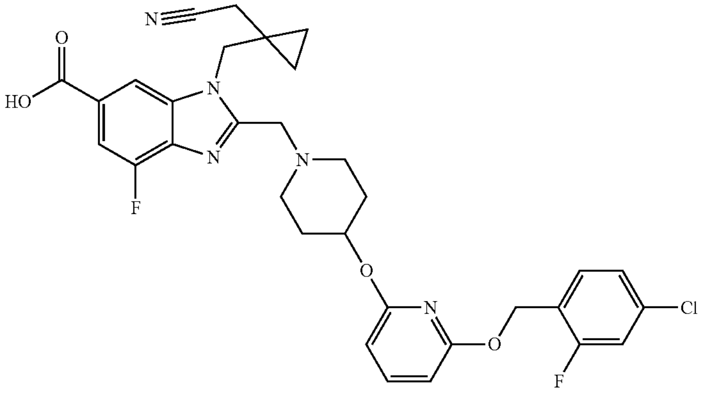 [SMILES: N#CCC1(Cn2c(CN3CCC(Oc4cccc(OCc5ccc(Cl)cc5F)n4)CC3)nc3c(F)cc(C(=O)O)cc32)CC1] |
| Compound S44 | 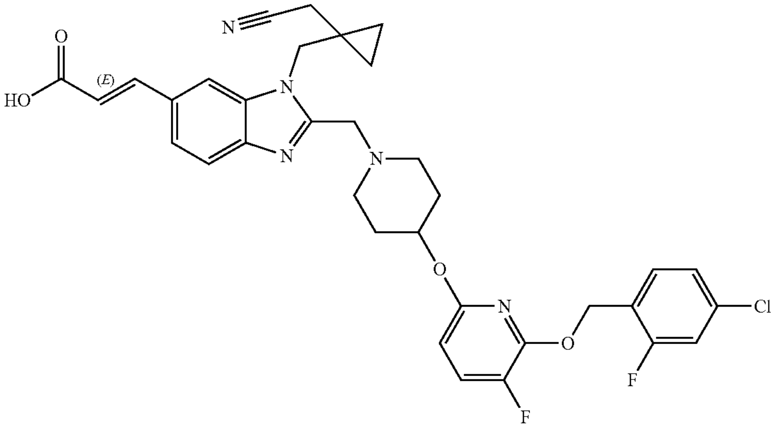 [SMILES: N#CCC1(Cn2c(CN3CCC(Oc4ccc(F)c(OCc5ccc(Cl)cc5F)n4)CC3)nc3ccc(/C=C/C(=O)O)cc32)CC1] |

-continued
| Number | Structure |
|---|---|
| Compound S45 | 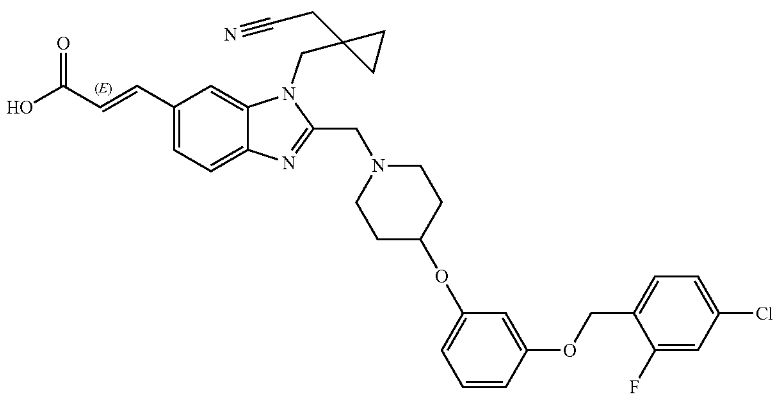 |
| Compound S48 | 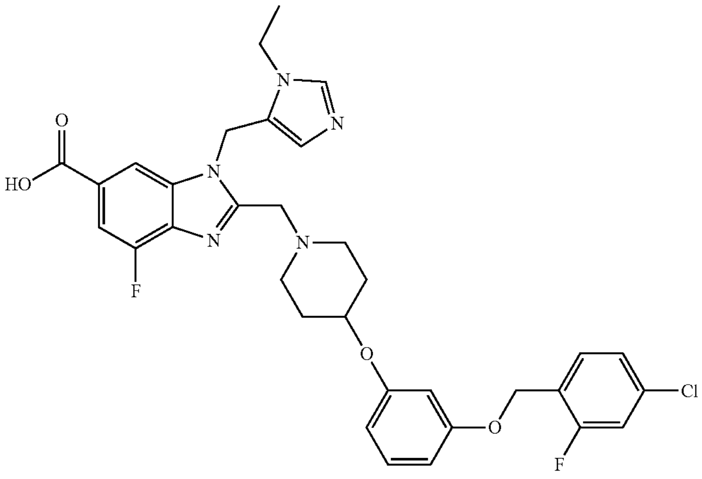 |
| Compound S49 | 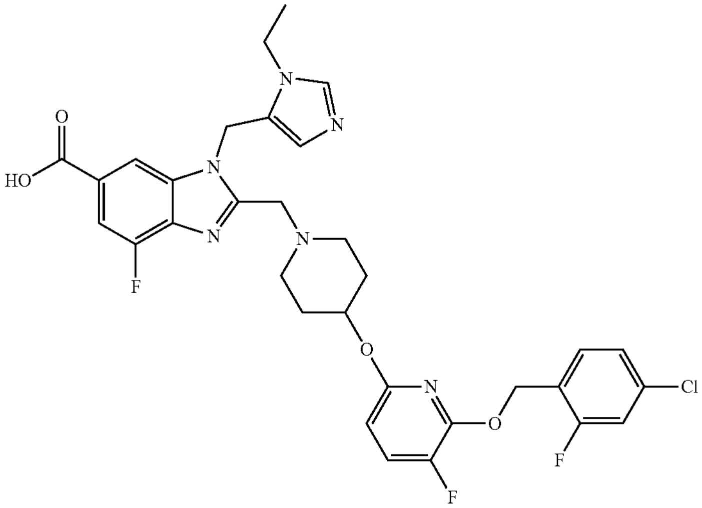 |

-continued
| Number | Structure |
| --- | --- |
| Compound S50 | 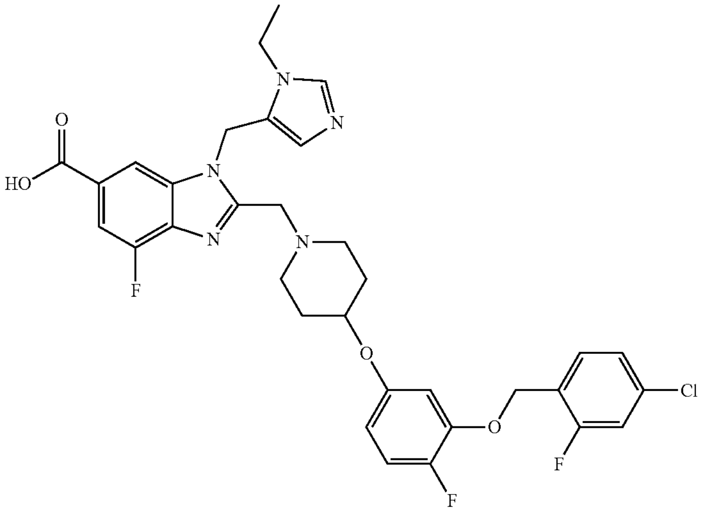 |
| Compound S51 | 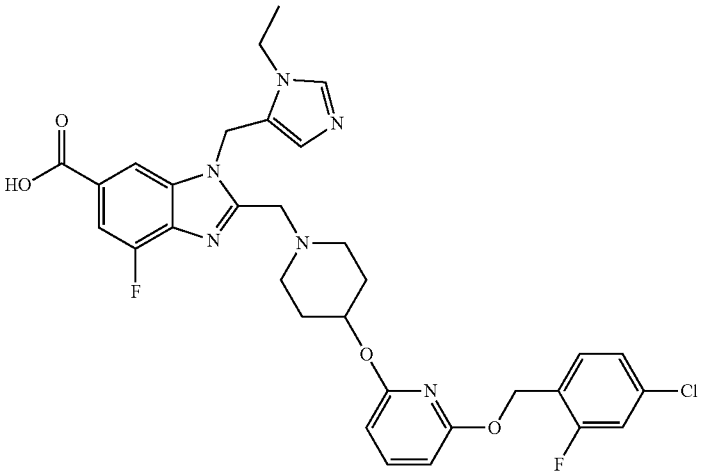 |
| Compound S52 | 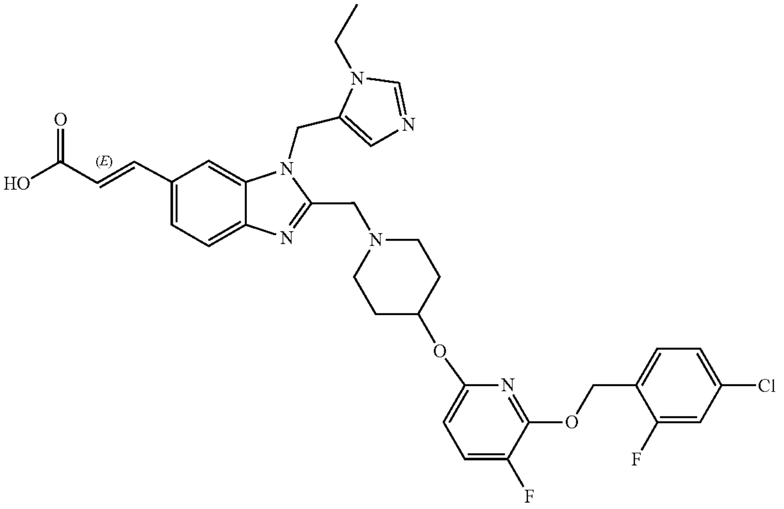 [SMILES: CCn1cncc1Cn1c(CN2CCC(Oc3ccc(F)c(OCc4ccc(Cl)cc4F)n3)CC2)nc2ccc(/C=C/C(=O)O)cc21] |

-continued
| Number | Structure |
|---|---|
| Compound S53 | 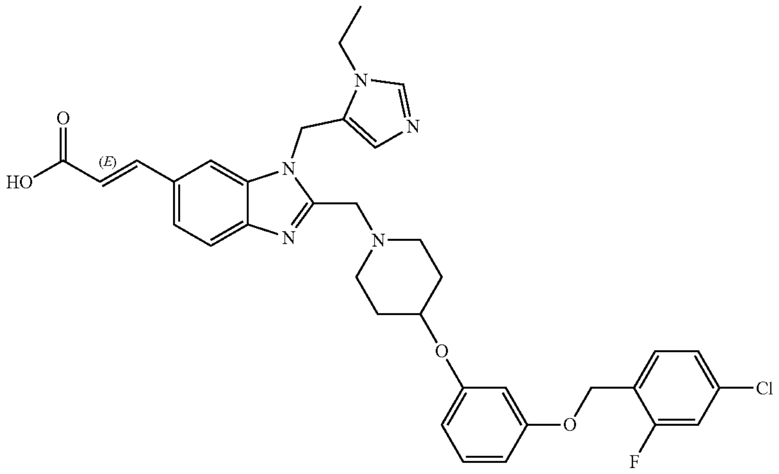 |
| Compound S56 | 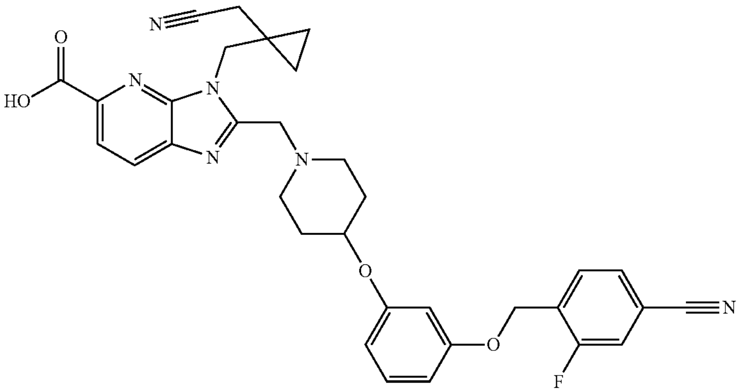 [SMILES: N#CCC1(Cn2c(CN3CCC(Oc4cccc(OCc5ccc(C#N)cc5F)c4)CC3)nc3ccc(C(=O)O)nc32)CC1] |
| Compound S57 | 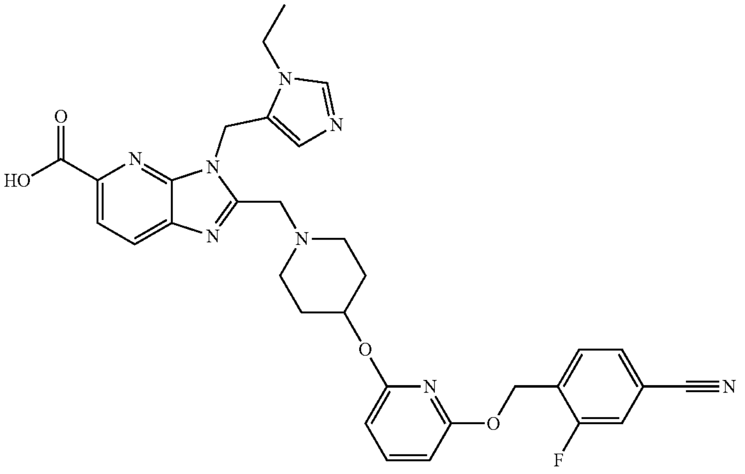 |

-continued
| Number | Structure |
| --- | --- |
| Compound S58 | 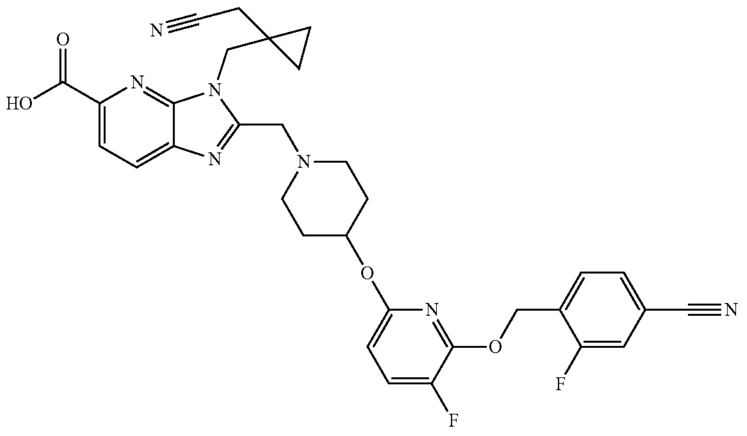 [SMILES: N#CCC1(Cn2c(CN3CCC(Oc4ccc(F)c(OCc5ccc(C#N)cc5F)n4)CC3)nc3ccc(C(=O)O)nc32)CC1] |
| Compound S59 | 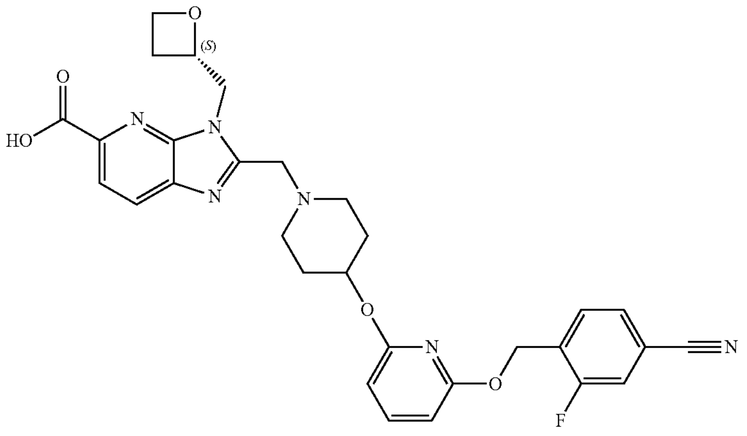 |
| Compound S60 | 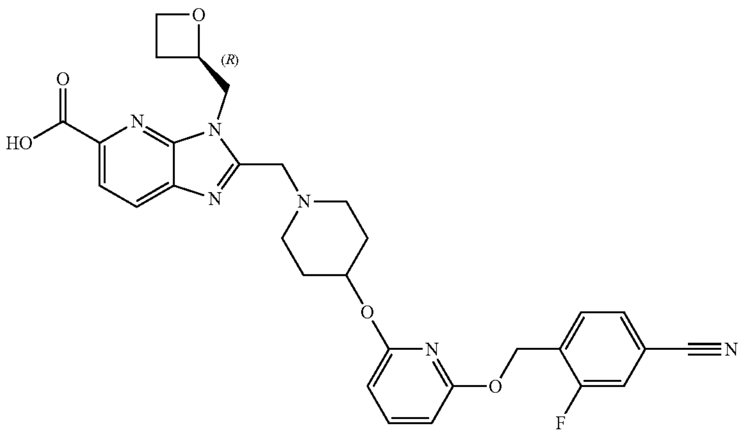 |

-continued
| Number | Structure |
|---|---|
| Compound S61 | 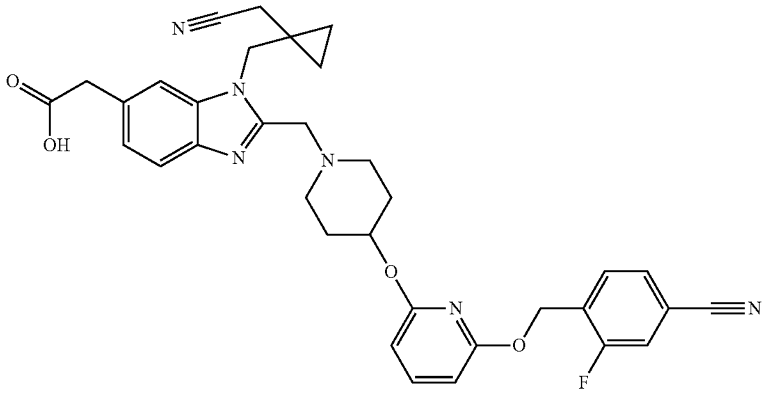 |
| Compound S62 | 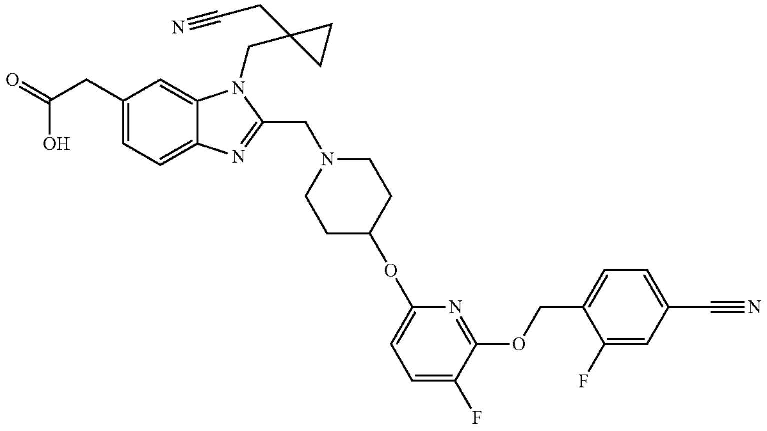 |
| Compound S63 | 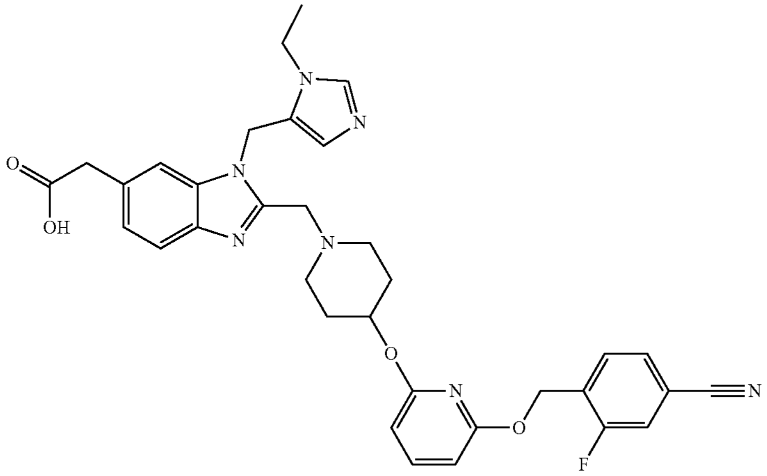 [SMILES: CCn1cncc1Cn1c(CN2CCC(Oc3cccc(OCc4ccc(C#N)cc4F)n3)CC2)nc2ccc(CC(=O)O)cc21] |

-continued
| Number | Structure |
|---|---|
| Compound S64 | 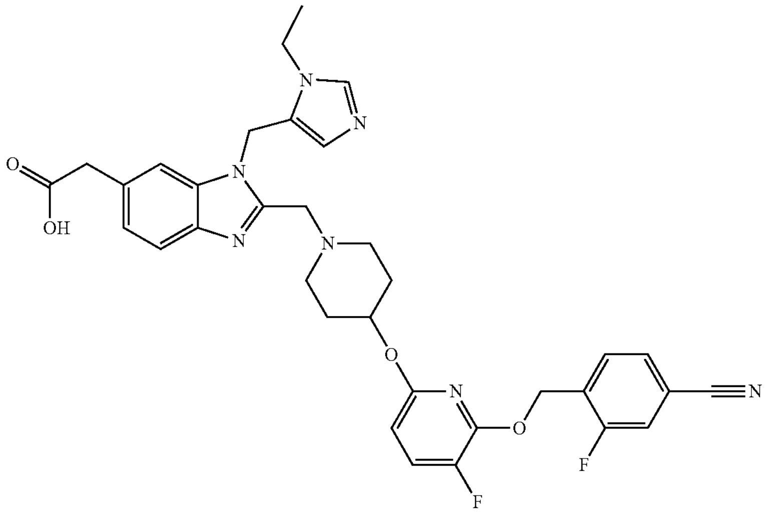 |
| Compound S65 | 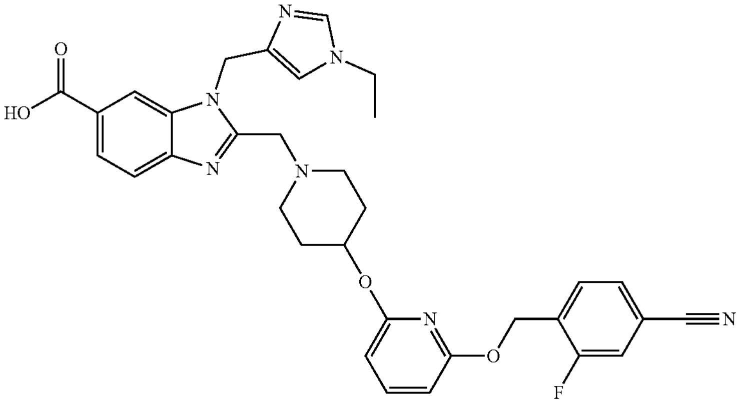 [SMILES: CCn1cnc(Cn2c(CN3CCC(Oc4cccc(OCc5ccc(C#N)cc5F)n4)CC3)nc3ccc(C(=O)O)cc32)c1] |
| Compound S66 | 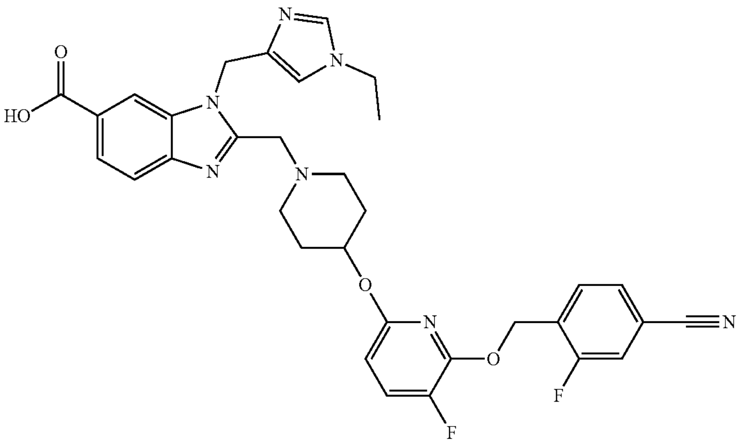 [SMILES: CCn1cnc(Cn2c(CN3CCC(Oc4ccc(F)c(OCc5ccc(C#N)cc5F)n4)CC3)nc3ccc(C(=O)O)cc32)c1] |

| Number | Structure |
| --- | --- |
| Compound C1 | 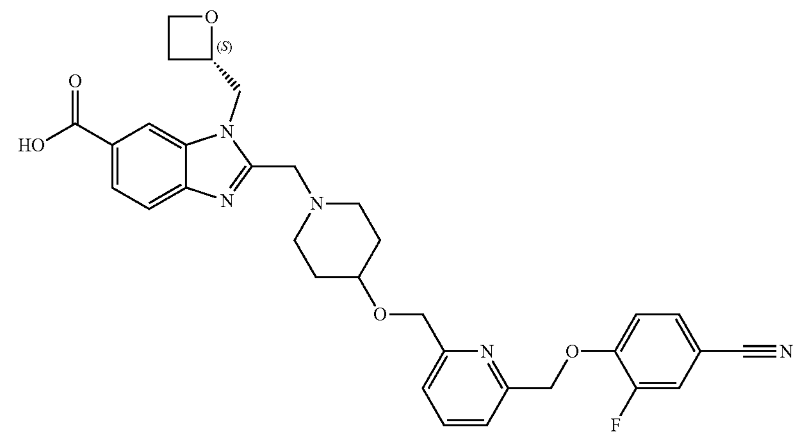 |
| Compound C2 | 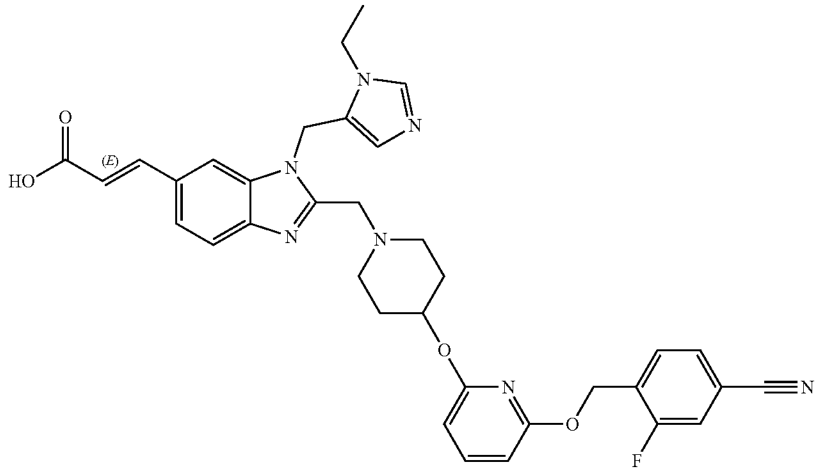 |
| Compound C3 | 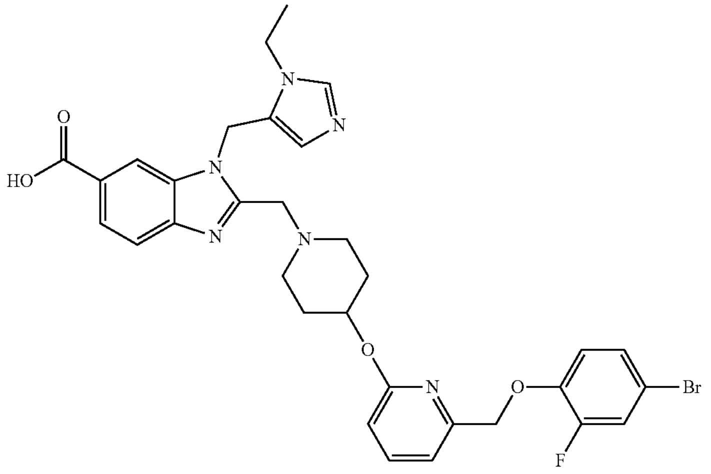 [SMILES: CCn1cncc1Cn1c(CN2CCC(Oc3cccc(COc4ccc(Br)cc4F)n3)CC2)nc2ccc(C(=O)O)cc21] |

-continued
| Number | Structure |
|---|---|
| Compound C4 | 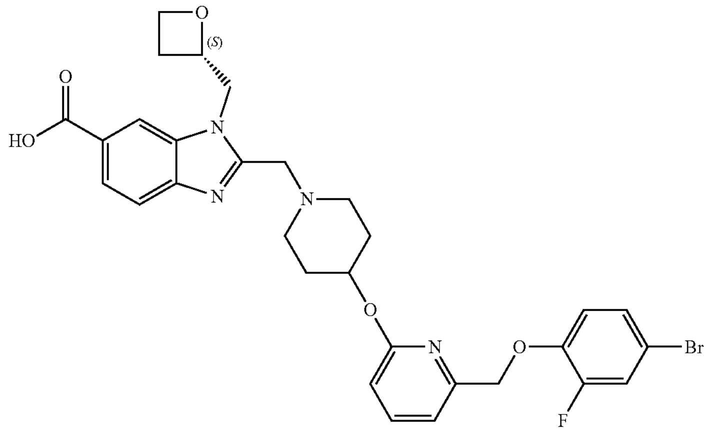 |
| Compound C5 | 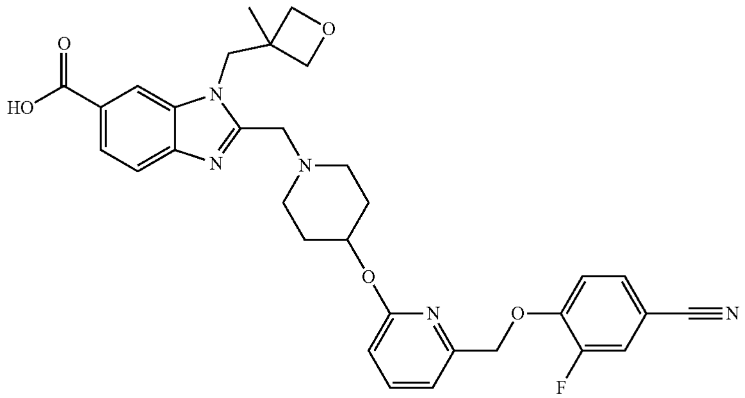 [SMILES: CC1(Cn2c(CN3CCC(Oc4cccc(COc5ccc(C#N)cc5F)n4)CC3)nc3ccc(C(=O)O)cc32)COC1] |
| Compound C6 | 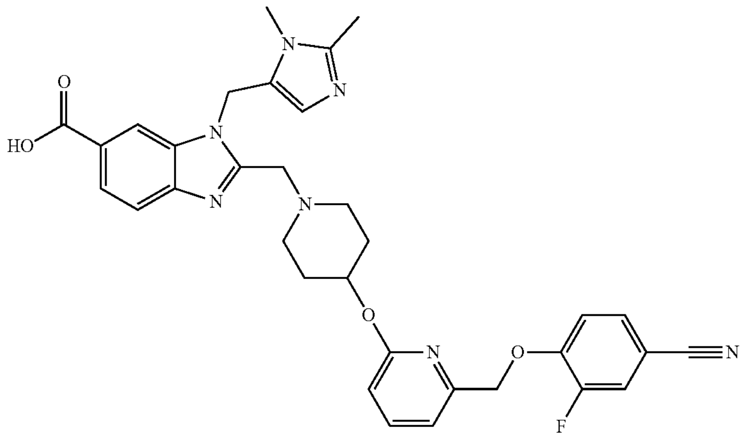 [SMILES: Cc1ncc(Cn2c(CN3CCC(Oc4cccc(COc5ccc(C#N)cc5F)n4)CC3)nc3ccc(C(=O)O)cc32)n1C] |

-continued
| Number | Structure |
|---|---|
| Compound C7 | 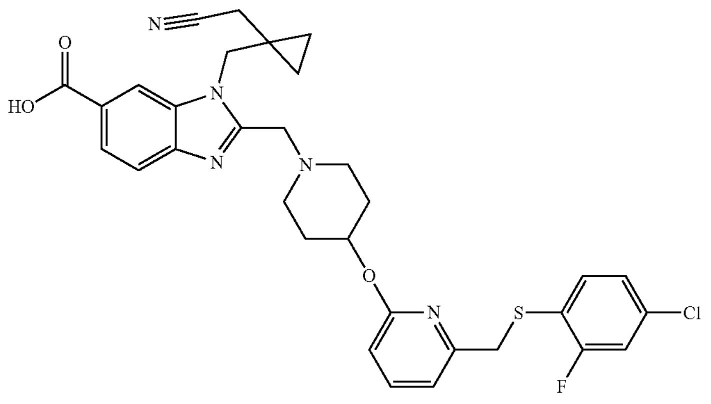 |
| Compound C8 | 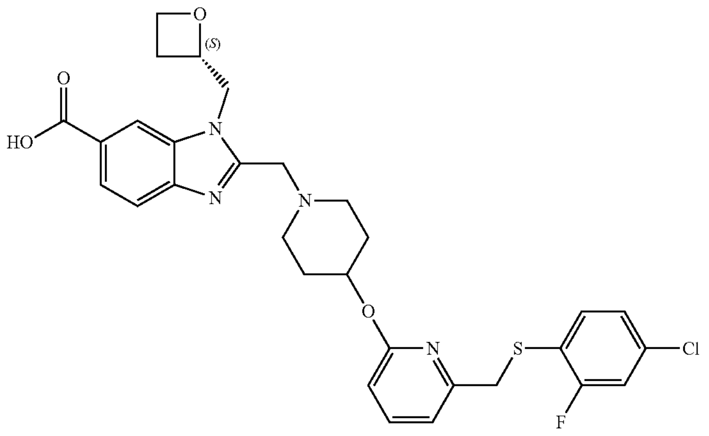 |
| Compound C9 | 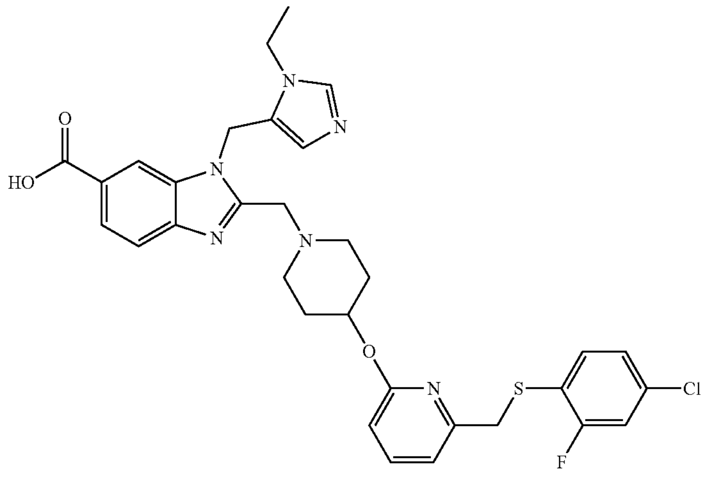 |

-continued
| Number | Structure |
| --- | --- |
| Compound C10 | 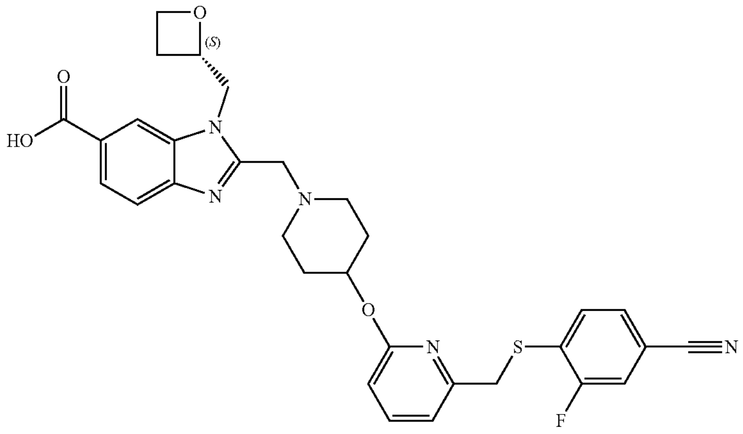 |
| Compound C11 | 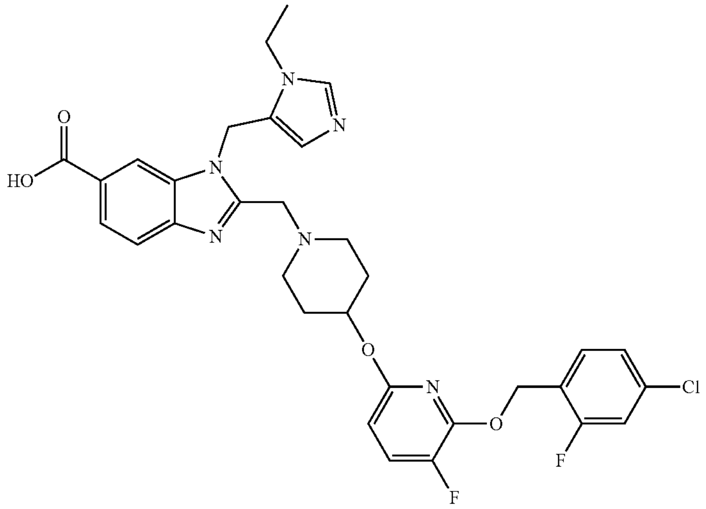 |
| Compound C12 | 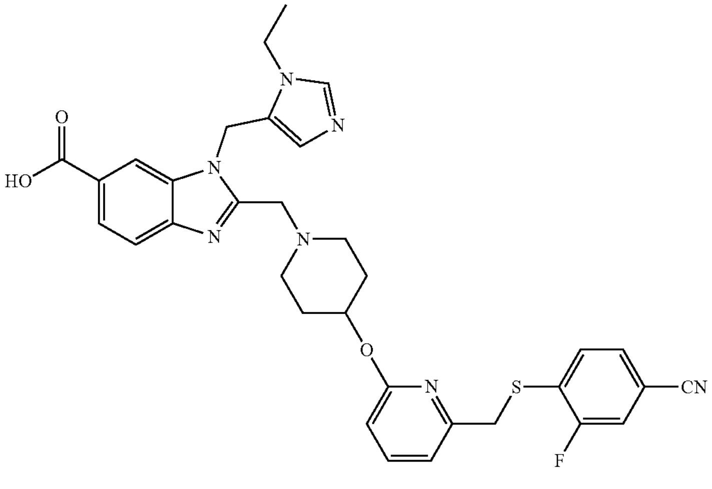 [SMILES: CCn1cncc1Cn1c(CN2CCC(Oc3cccc(CSc4ccc(C#N)cc4F)n3)CC2)nc2ccc(C(=O)O)cc21] |

-continued
| Number | Structure |
|---|---|
| Compound C13 | 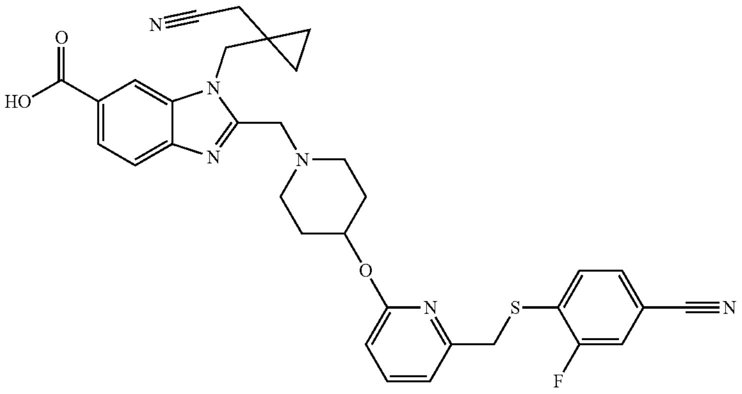 |
| Compound C14 | 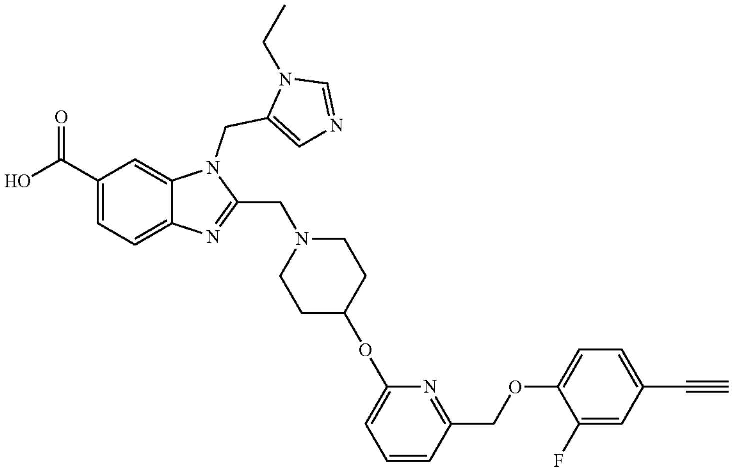 [SMILES: C#Cc1ccc(OCc2cccc(OC3CCN(Cc4nc5ccc(C(=O)O)cc5n4Cc4cncn4CC)CC3)n2)c(F)c1] |
| Compound C15 | 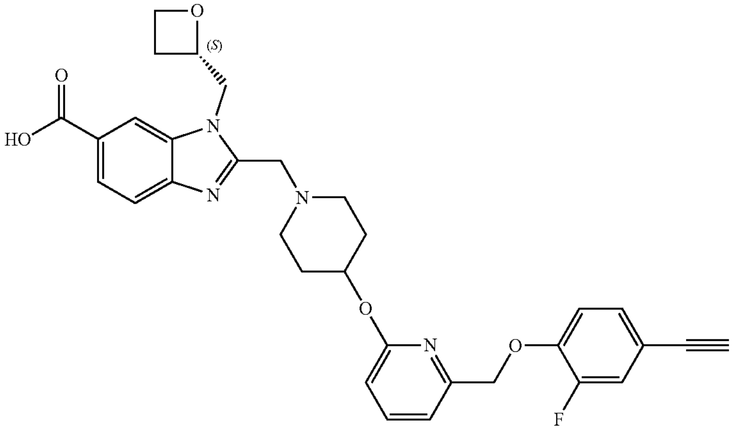 |

-continued
| Number | Structure |
|---|---|
| Compound C16 | 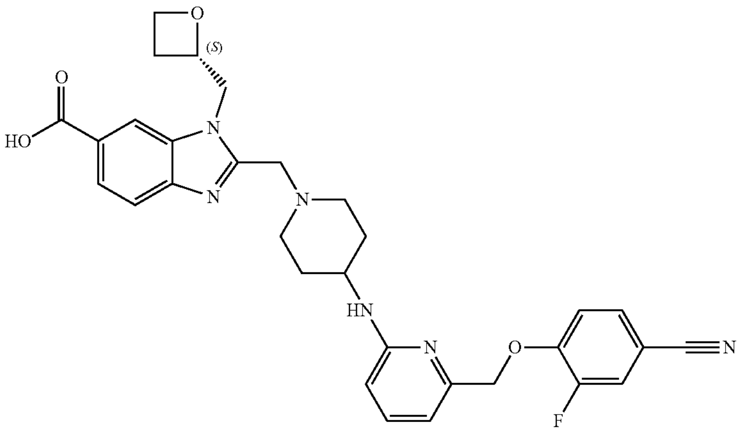 |
| Compound C17 | 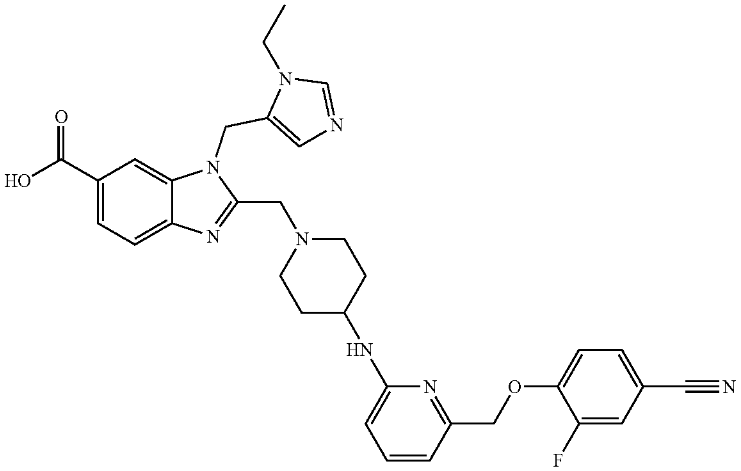 [SMILES: CCn1cncc1Cn1c(CN2CCC(Nc3cccc(COc4ccc(C#N)cc4F)n3)CC2)nc2ccc(C(=O)O)cc21] |
| Compound C18 | 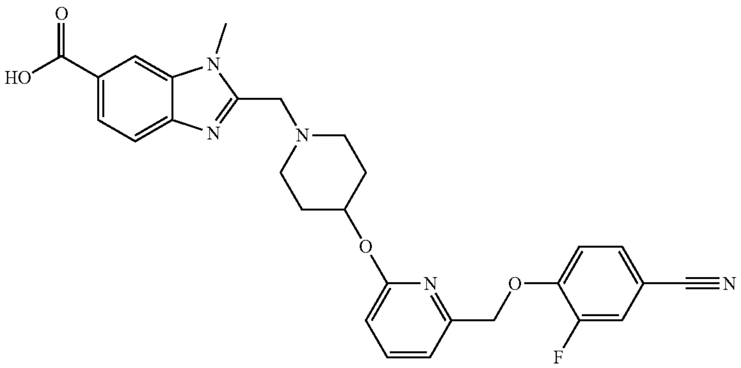 [SMILES: Cn1c(CN2CCC(Oc3cccc(COc4ccc(C#N)cc4F)n3)CC2)nc2ccc(C(=O)O)cc21] |

-continued
| Number | Structure |
| --- | --- |
| Compound C19 | 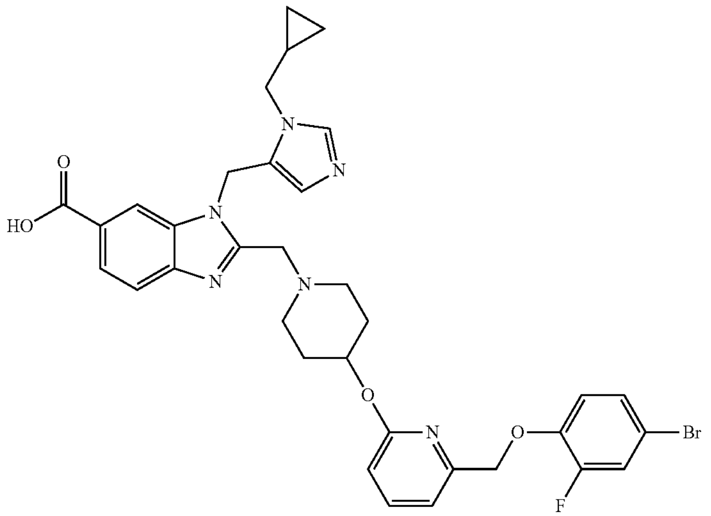 [SMILES: O=C(O)c1ccc2nc(CN3CCC(Oc4cccc(COc5ccc(Br)cc5F)n4)CC3)n(Cc3cncn3CC3CC3)c2c1] |
| Compound C20 | 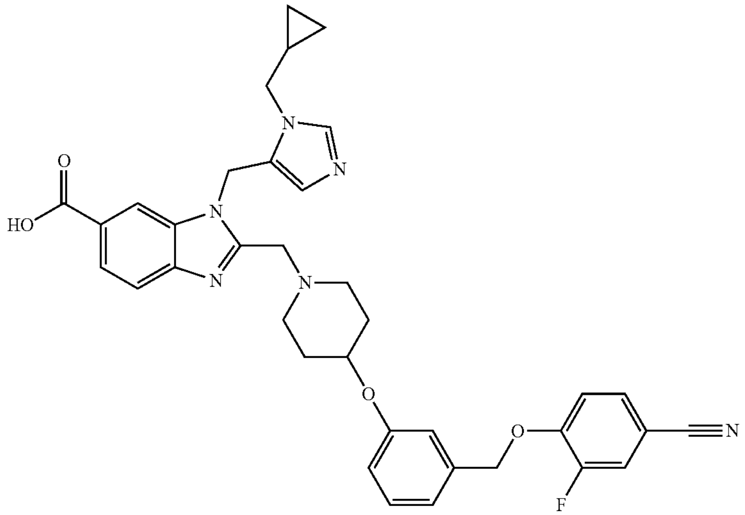 |
| Compound C21 | 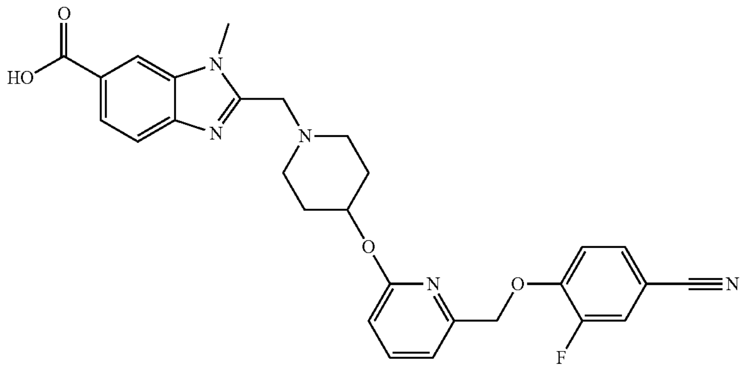 [SMILES: Cn1c(CN2CCC(Oc3cccc(COc4ccc(C#N)cc4F)n3)CC2)nc2ccc(C(=O)O)cc21] |

-continued
| Number | Structure |
| --- | --- |
| Compound C22 | 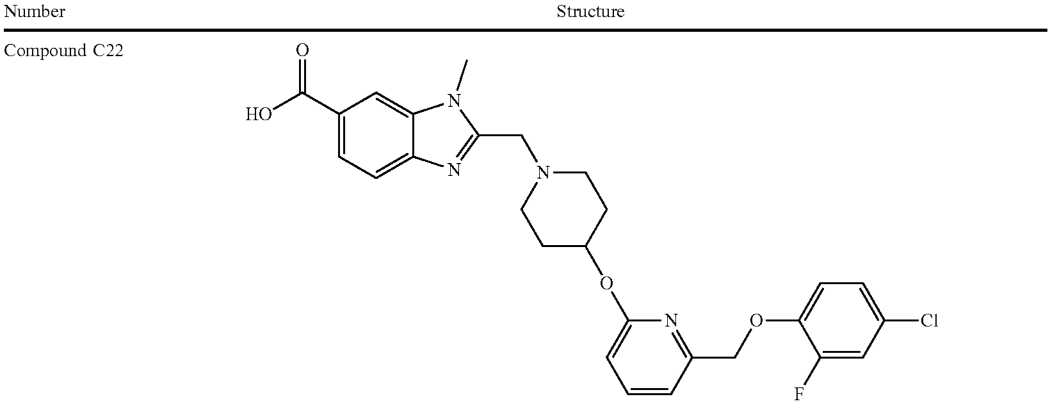 |
| Compound C23 | 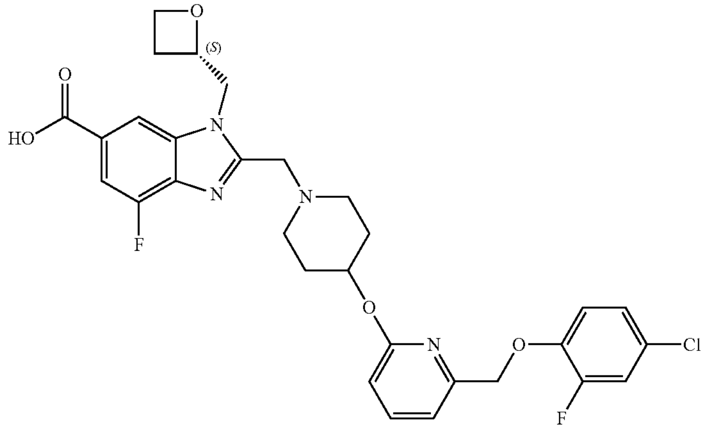 |
| Compound C24 | 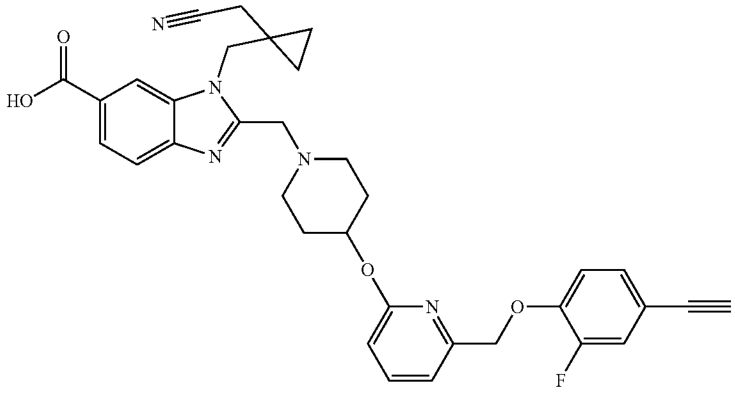 [SMILES: C#Cc1ccc(OCc2cccc(OC3CCN(Cc4nc5ccc(C(=O)O)cc5n4CC4(CC#N)CC4)CC3)n2)c(F)c1] |
| Compound C25 | 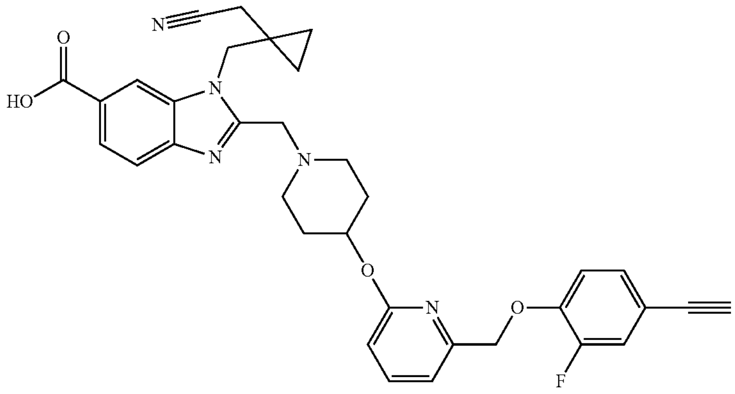 [SMILES: C#Cc1ccc(OCc2cccc(OC3CCN(Cc4nc5ccc(C(=O)O)cc5n4CC4(CC#N)CC4)CC3)n2)c(F)c1] |

-continued
| Number | Structure |
| --- | --- |
| Compound C26 | 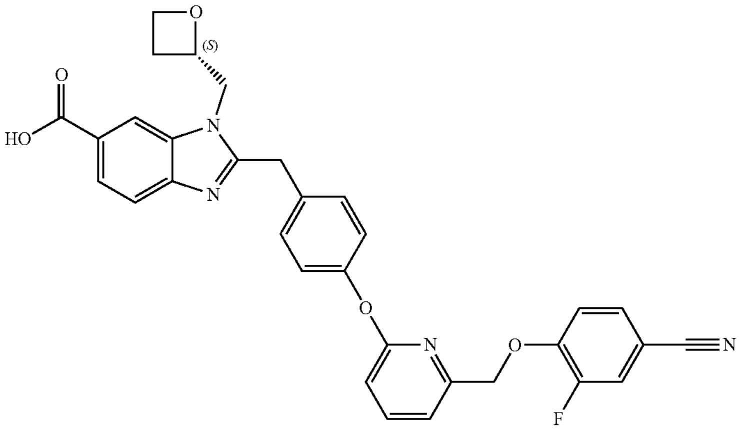 |
| Compound C27 | 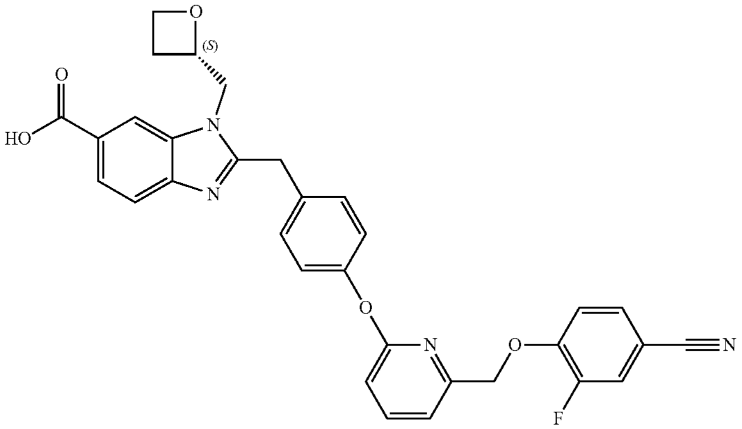 |
| Compound C28 | 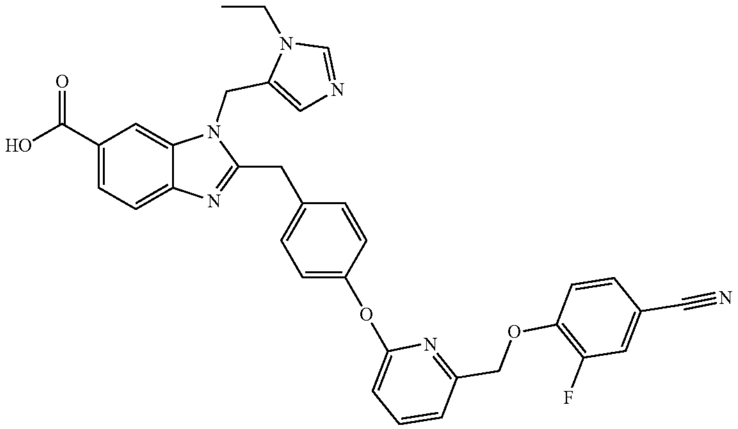 [SMILES: CCn1cncc1Cn1c(Cc2ccc(Oc3cccc(COc4ccc(C#N)cc4F)n3)cc2)nc2ccc(C(=O)O)cc21] |

-continued
| Number | Structure |
|---|---|
| Compound C29 | 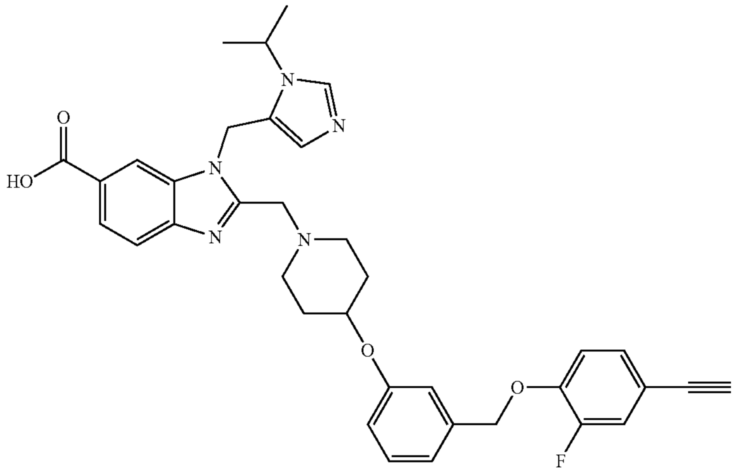 [SMILES: C#Cc1ccc(OCc2cccc(OC3CCN(Cc4nc5ccc(C(=O)O)cc5n4Cc4cncn4C(C)C)CC3)c2)c(F)c1] |
| Compound C30 | 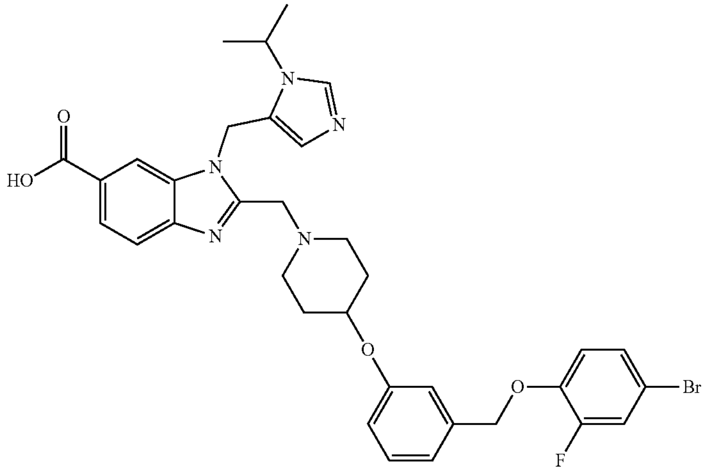 [SMILES: CC(C)n1cncc1Cn1c(CN2CCC(Oc3cccc(COc4ccc(Br)cc4F)c3)CC2)nc2ccc(C(=O)O)cc21] |
| Compound C31 | 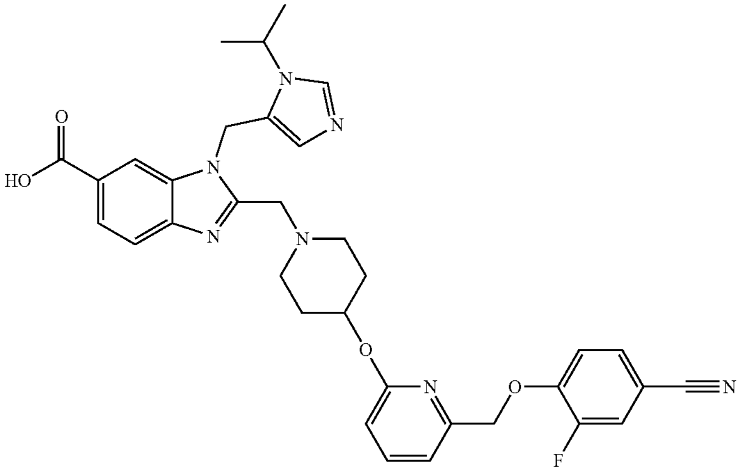 |

-continued
| Number | Structure |
|---|---|
| Compound C32 | 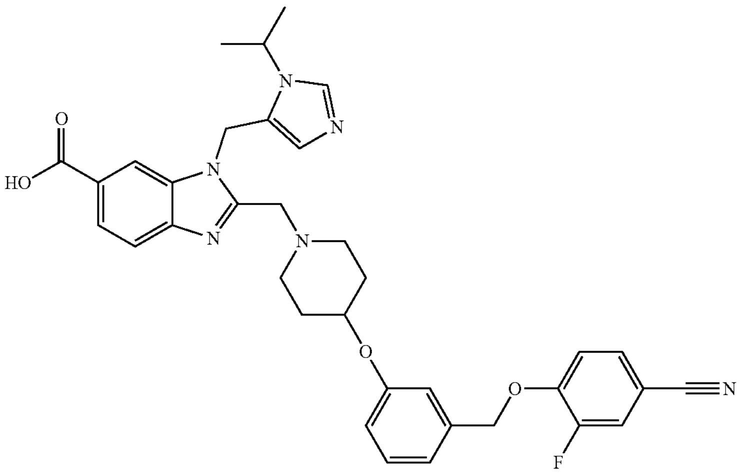 |
| Compound C33 | 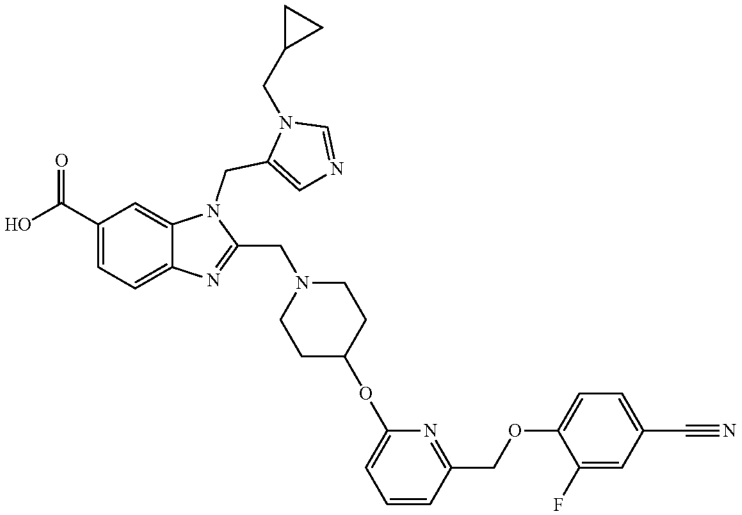 [SMILES: N#Cc1ccc(OCc2cccc(OC3CCN(Cc4nc5ccc(C(=O)O)cc5n4Cc4cncn4CC4CC4)CC3)n2)c(F)c1] |
| Compound C34 | 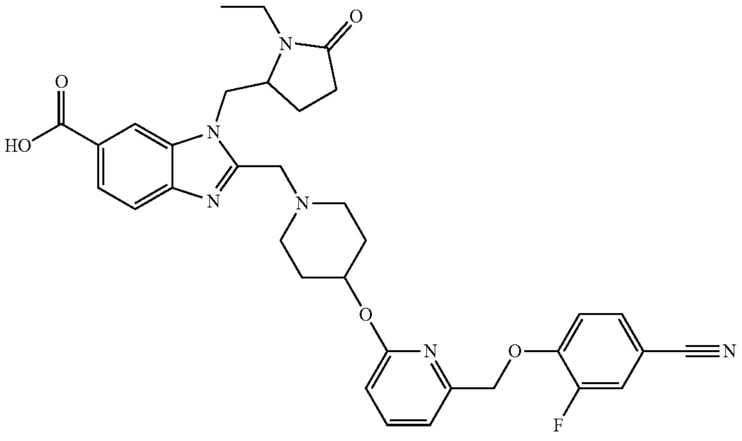 [SMILES: CCN1C(=O)CCC1Cn1c(CN2CCC(Oc3cccc(COc4ccc(C#N)cc4F)n3)CC2)nc2ccc(C(=O)O)cc21] |

-continued
| Number | Structure |
| --- | --- |
| Compound C35 | 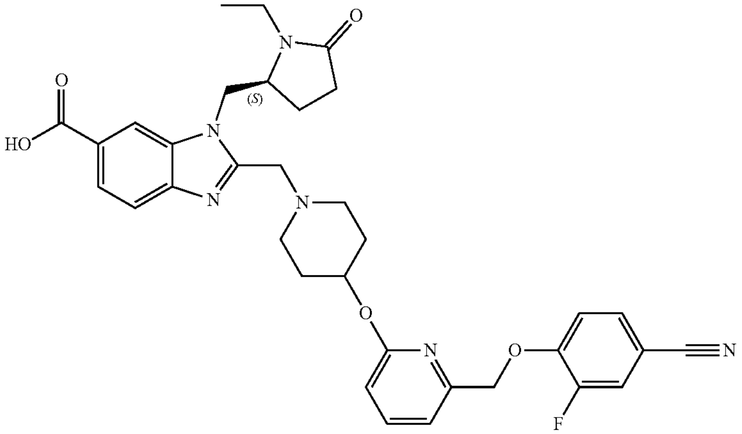 |
| Compound C36 | 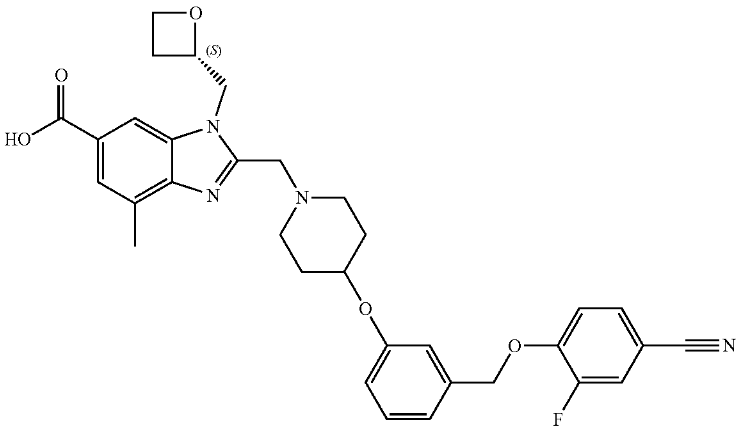 |
| Compound C37 | 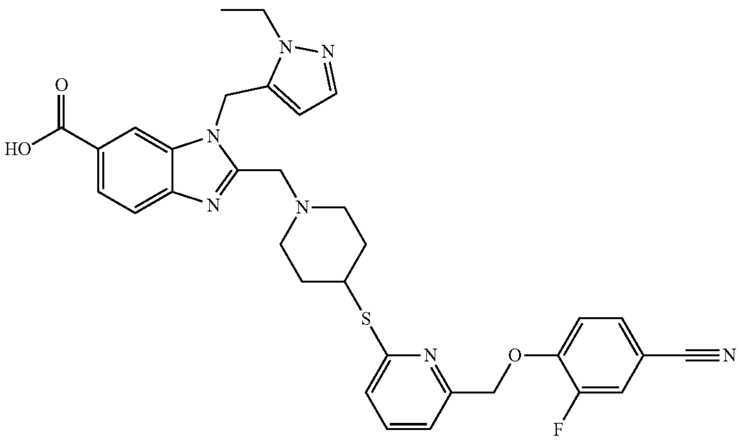 [SMILES: CCn1nccc1Cn1c(CN2CCC(Sc3cccc(COc4ccc(C#N)cc4F)n3)CC2)nc2ccc(C(=O)O)cc21] |

-continued
| Number | Structure |
|---|---|
| Compound C38 | 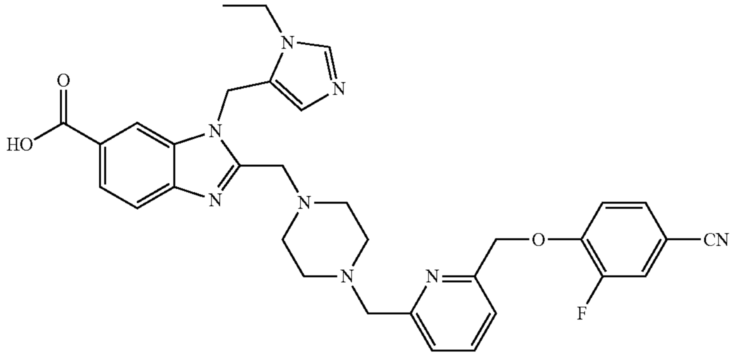 [SMILES: CCn1cncc1Cn1c(CN2CCN(Cc3cccc(COc4ccc(C#N)cc4F)n3)CC2)nc2ccc(C(=O)O)cc21] |
| Compound C39 | 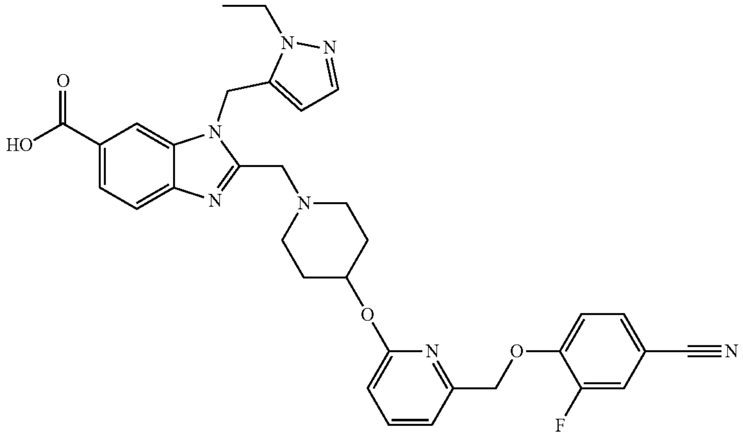 [SMILES: CCn1nccc1Cn1c(CN2CCC(Oc3cccc(COc4ccc(C#N)cc4F)n3)CC2)nc2ccc(C(=O)O)cc21] |
| Compound C40 | 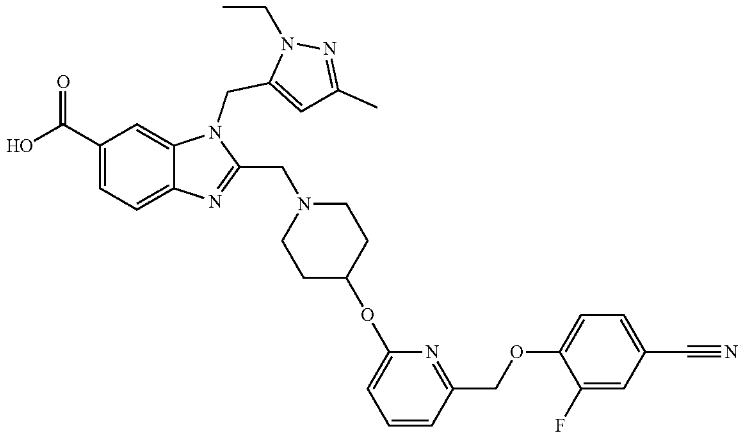 [SMILES: CCn1nc(C)cc1Cn1c(CN2CCC(Oc3cccc(COc4ccc(C#N)cc4F)n3)CC2)nc2ccc(C(=O)O)cc21] |

-continued
| Number | Structure |
|---|---|
| Compound C41 | 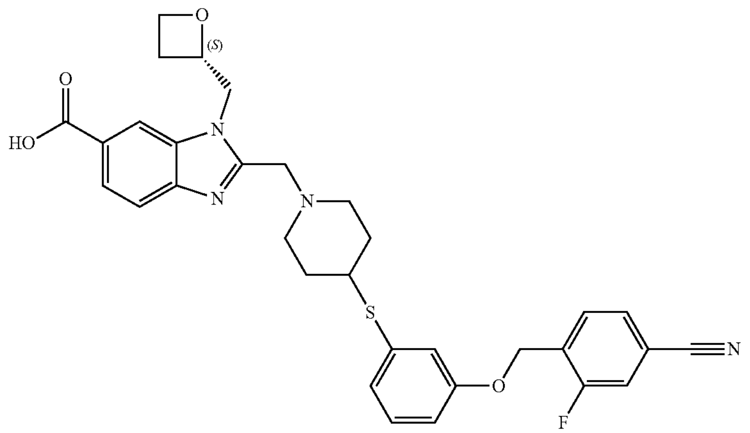 |
| Compound C42 | 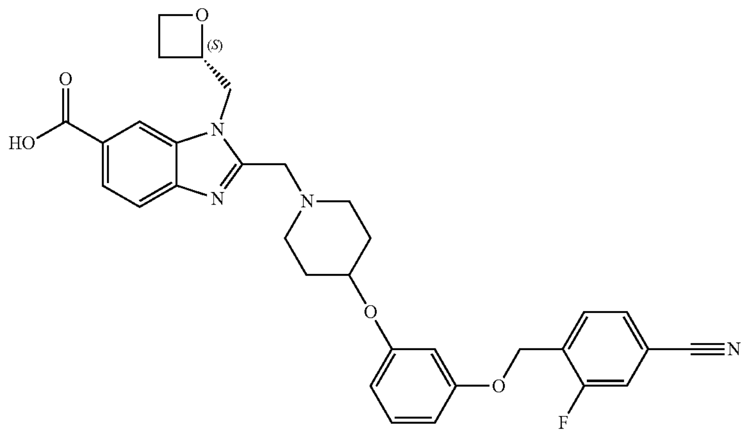 |
| Compound C43 | 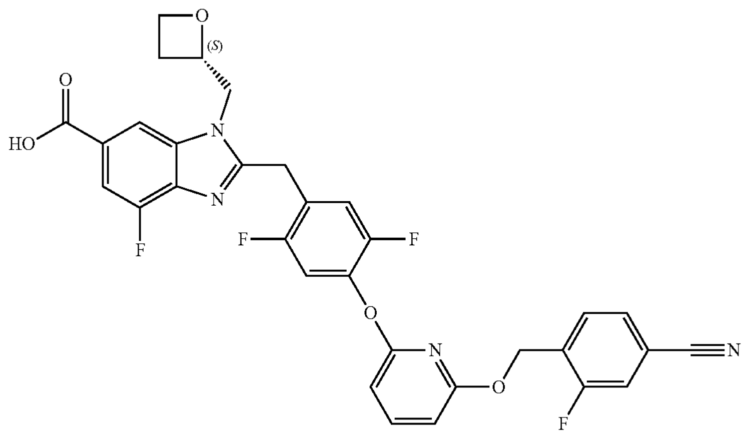 |

-continued
| Number | Structure |
|---|---|
| Compound C44 | 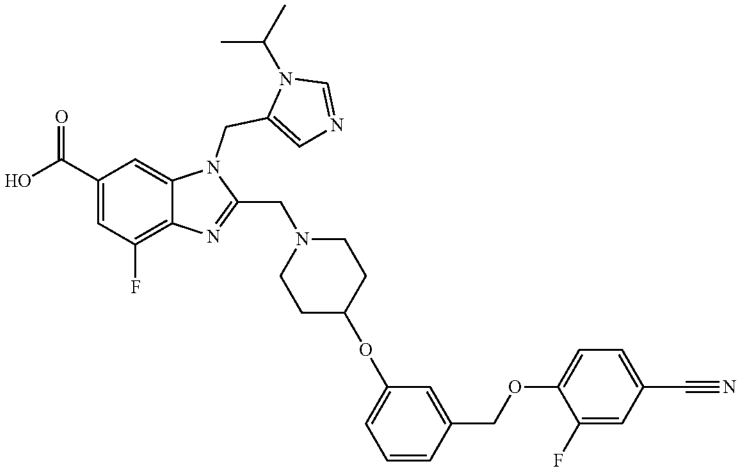 |
| Compound C45 | 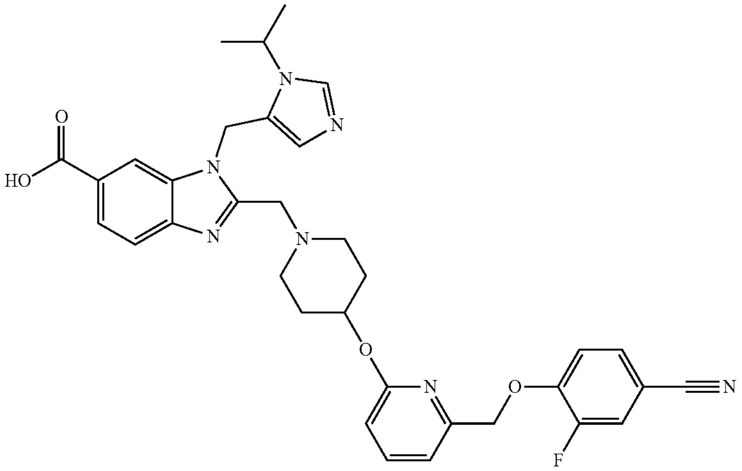 [SMILES: CC(C)n1cncc1Cn1c(CN2CCC(Oc3cccc(COc4ccc(C#N)cc4F)n3)CC2)nc2ccc(C(=O)O)cc21] |
| Compound C46 | 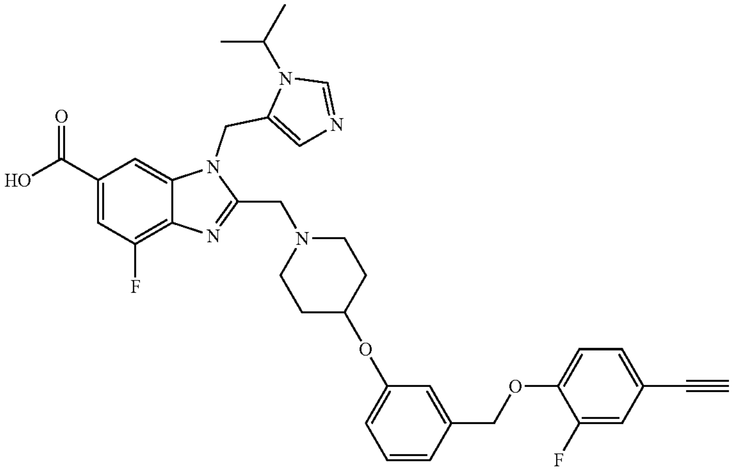 [SMILES: C#Cc1ccc(OCc2cccc(OC3CCN(Cc4nc5c(F)cc(C(=O)O)cc5n4Cc4cncn4C(C)C)CC3)c2)c(F)c1] |

-continued
| Number | Structure |
|---|---|
| Compound C47 | 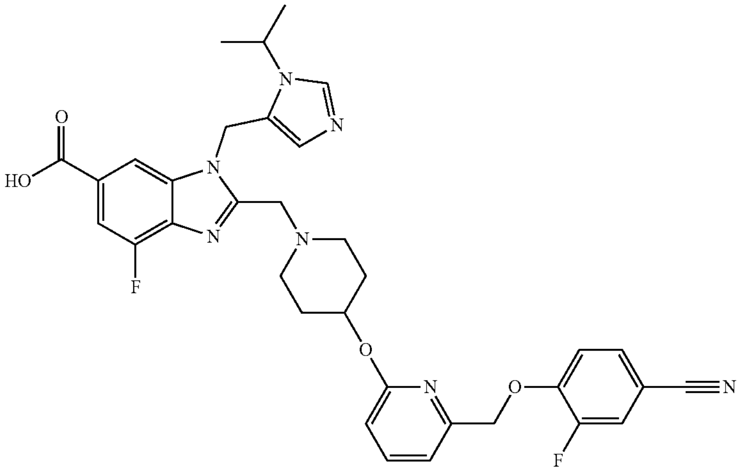 [SMILES: CC(C)n1cncc1Cn1c(CN2CCC(Oc3cccc(COc4ccc(C#N)cc4F)n3)CC2)nc2c(F)cc(C(=O)O)cc21] |
| Compound C48 | 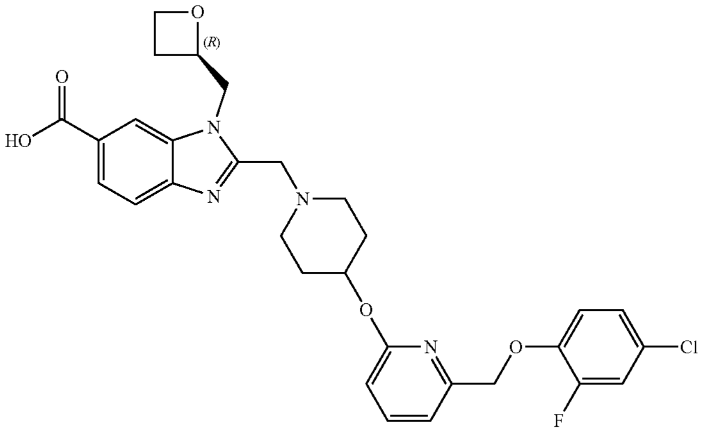 |
| Compound C49 | 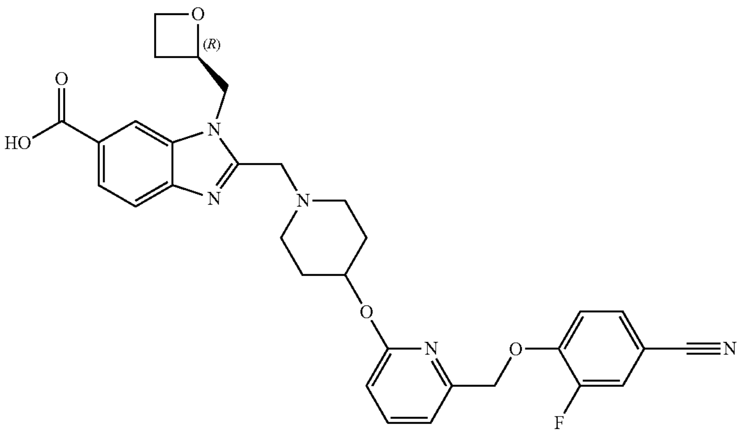 |

-continued
| Number | Structure |
| --- | --- |
| Compound C50 | 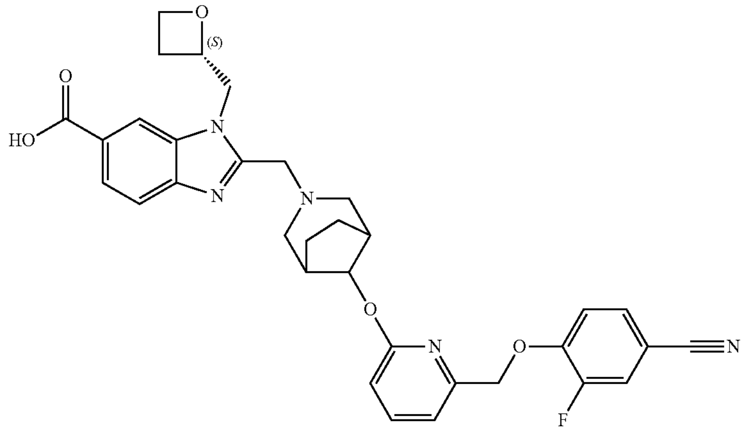 |
| Compound C51 | 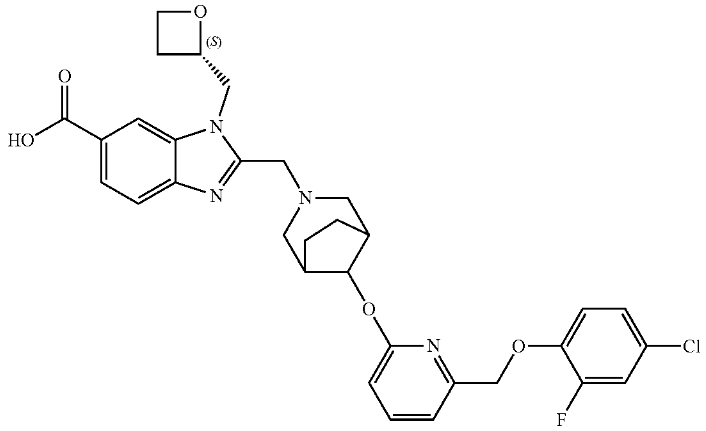 |
| Compound C52 | 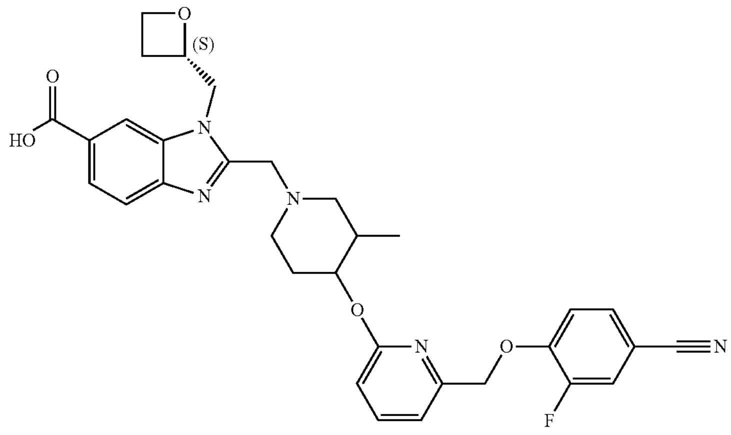 |

-continued
| Number | Structure |
|---|---|
| Compound C53 | 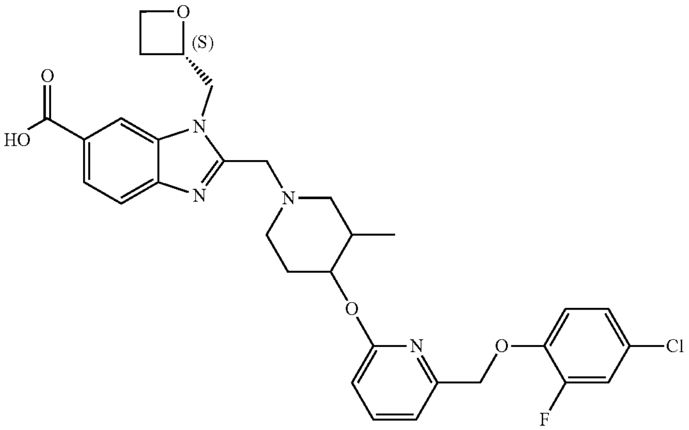 |
| Compound C54 | 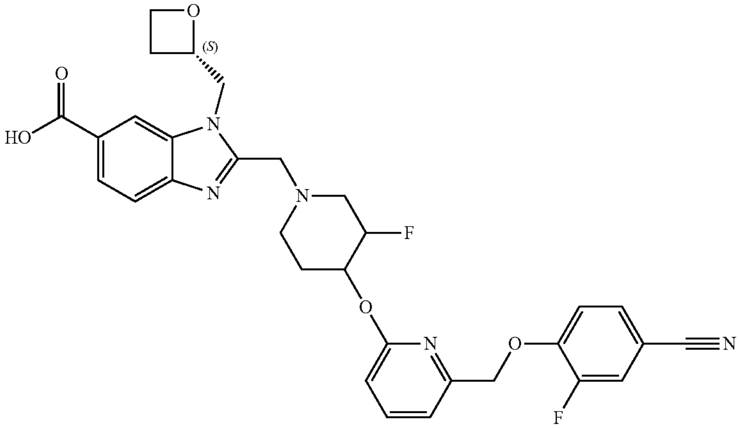 |
| Compound C55 | 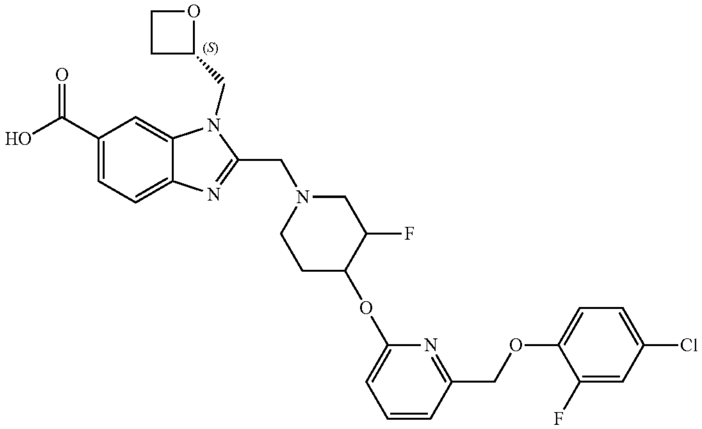 |

-continued
| Number | Structure |
| --- | --- |
| Compound C56 | 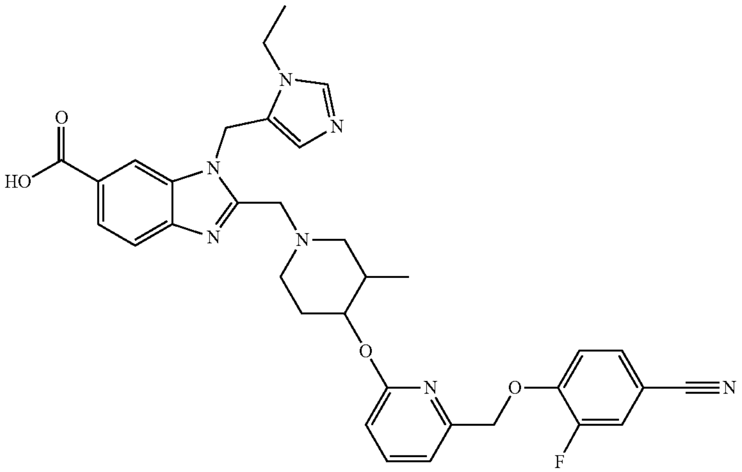 [SMILES: CCn1cncc1Cn1c(CN2CCC(Oc3cccc(COc4ccc(C#N)cc4F)n3)C(C)C2)nc2ccc(C(=O)O)cc21] |
| Compound C57 | 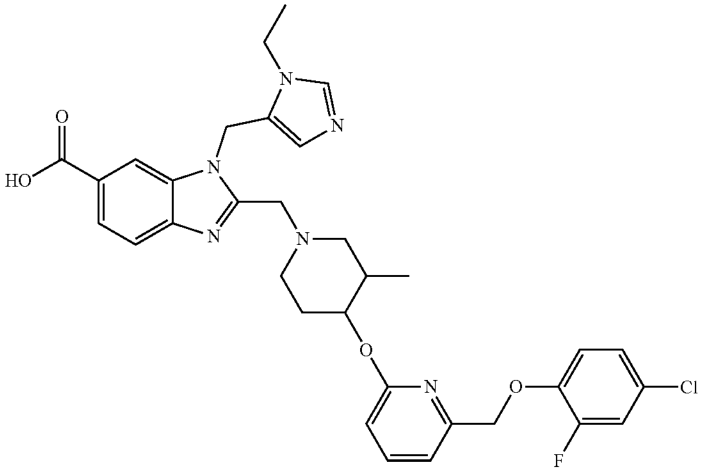 [SMILES: CCn1cncc1Cn1c(CN2CCC(Oc3cccc(COc4ccc(Cl)cc4F)n3)C(C)C2)nc2ccc(C(=O)O)cc21] |
| Compound C58 | 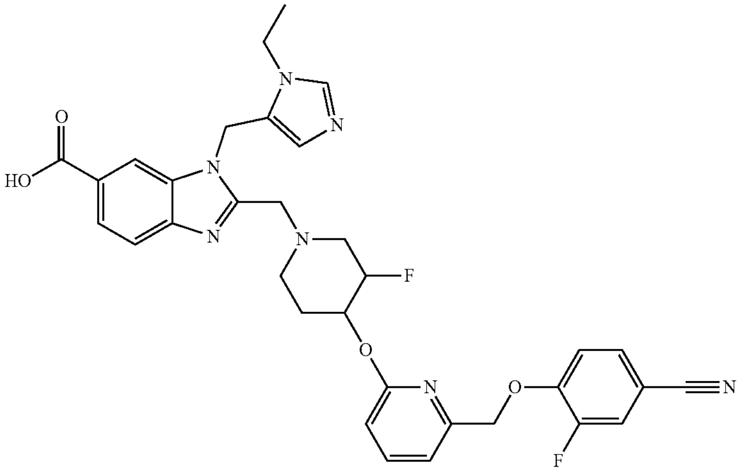 |

-continued
| Number | Structure |
| --- | --- |
| Compound C59 | 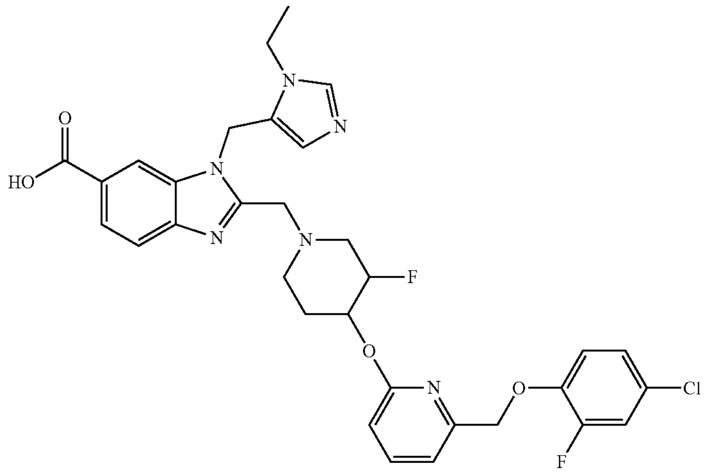 |
| Compound C60 | 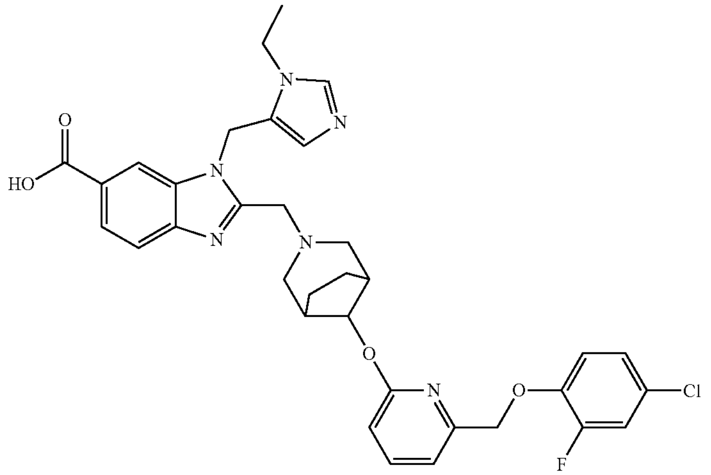 [SMILES: CCn1cncc1Cn1c(CN2CC3CCC(C2)C3Oc2cccc(COc3ccc(Cl)cc3F)n2)nc2ccc(C(=O)O)cc21] |
| Compound C61 | 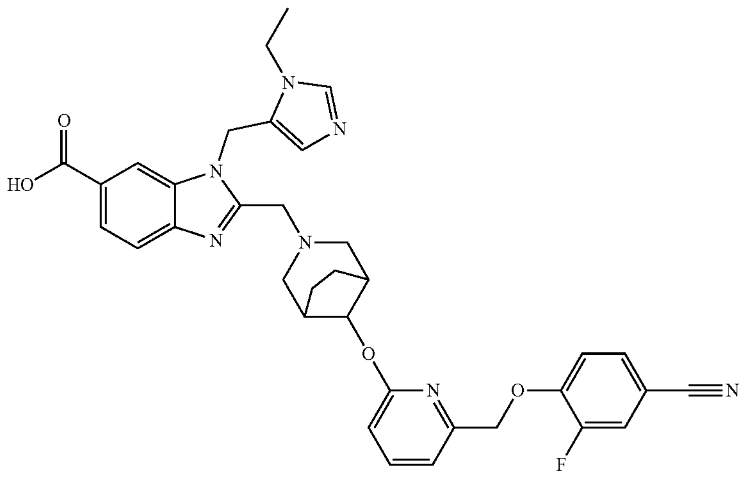 [SMILES: CCn1cncc1Cn1c(CN2CC3CCC(C2)C3Oc2cccc(COc3ccc(C#N)cc3F)n2)nc2ccc(C(=O)O)cc21] |

-continued
| Number | Structure |
| --- | --- |
| Compound C62 | 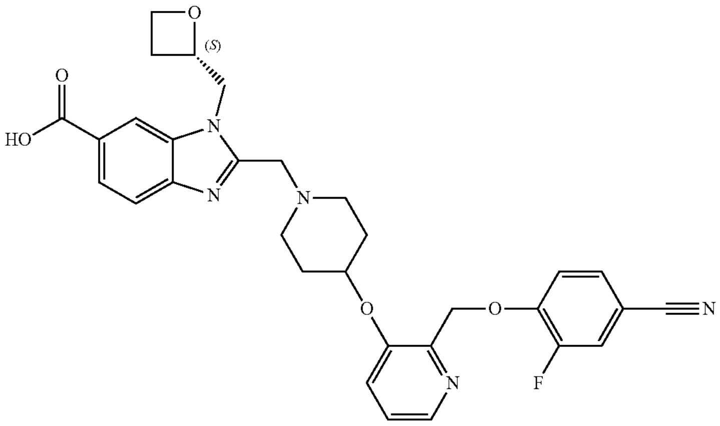 |
| Compound C63 | 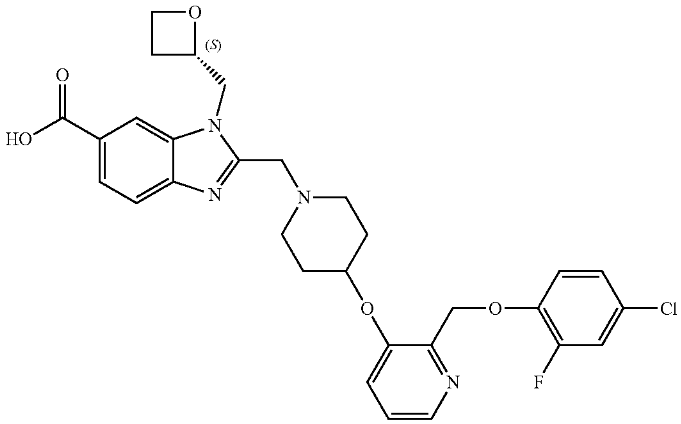 |
| Compound C64 | 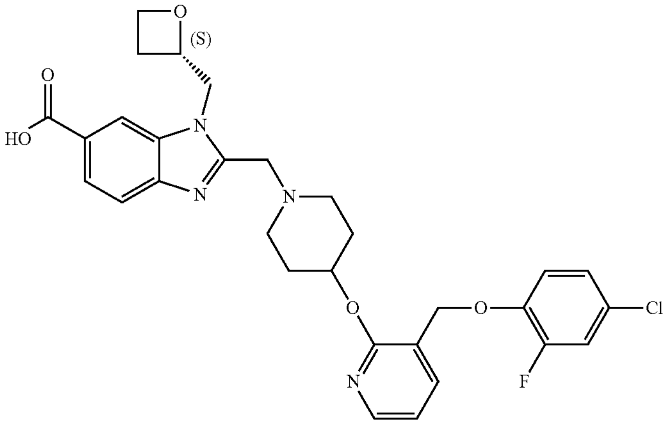 |

-continued
| Number | Structure |
| --- | --- |
| Compound C65 | 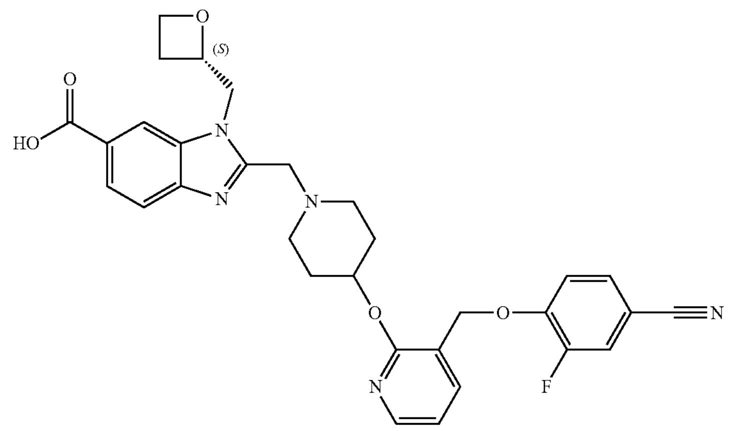 |
| Compound C66 | 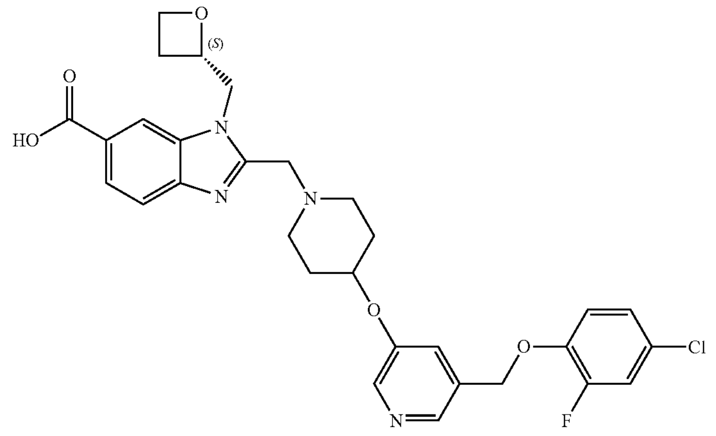 |
| Compound C67 | 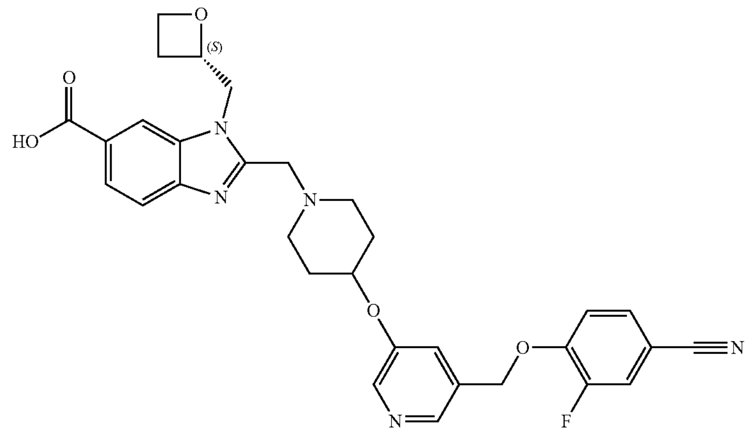 |

-continued
| Number | Structure |
| --- | --- |
| Compound C68 | 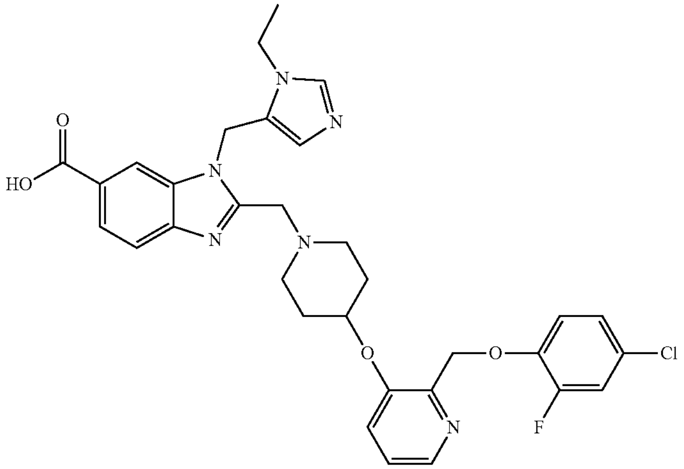 |
| Compound C69 | 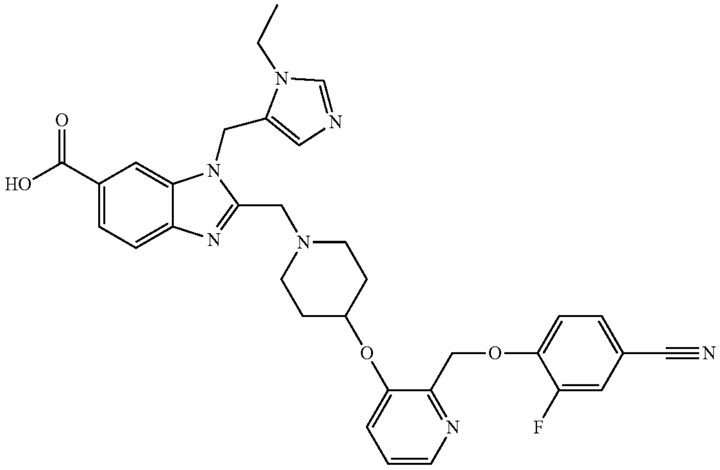 [SMILES: CCn1cncc1Cn1c(CN2CCC(Oc3cccnc3COc3ccc(C#N)cc3F)CC2)nc2ccc(C(=O)O)cc21] |
| Compound C70 | 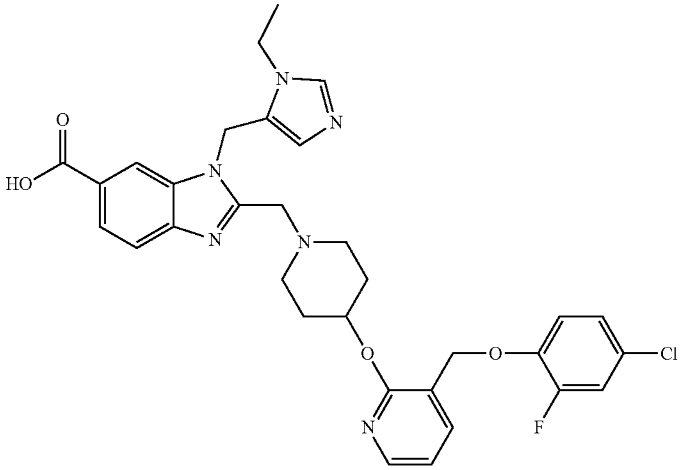 [SMILES: CCn1cncc1Cn1c(CN2CCC(Oc3ncccc3COc3ccc(Cl)cc3F)CC2)nc2ccc(C(=O)O)cc21] |

-continued
| Number | Structure |
| --- | --- |
| Compound C71 | 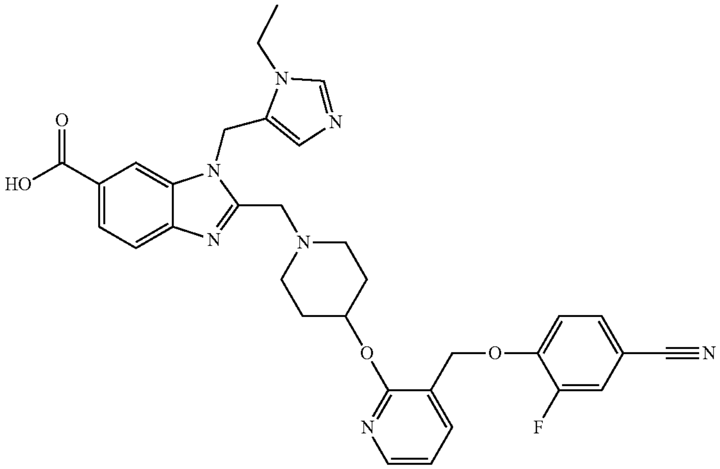 [SMILES: CCn1cncc1Cn1c(CN2CCC(Oc3ncccc3COc3ccc(C#N)cc3F)CC2)nc2ccc(C(=O)O)cc21] |
| Compound C72 | 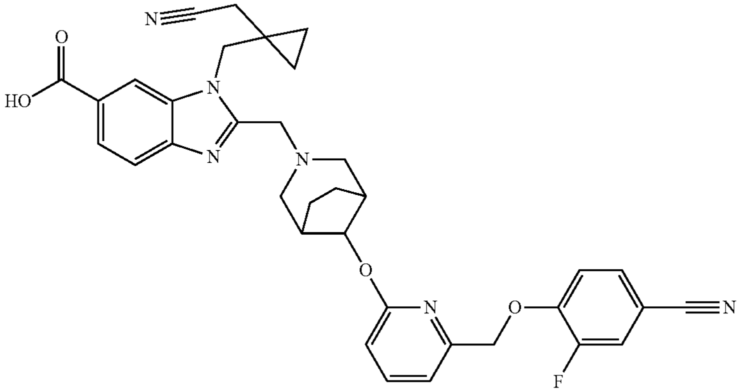 [SMILES: N#CCC1(Cn2c(CN3CC4CCC(C3)C4Oc3cccc(COc4ccc(C#N)cc4F)n3)nc3ccc(C(=O)O)cc32)CC1] |
| Compound C73 | 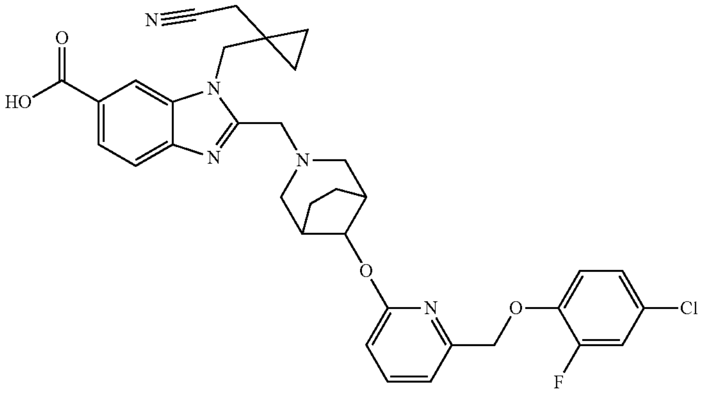 [SMILES: N#CCC1(Cn2c(CN3CC4CCC(C3)C4Oc3cccc(COc4ccc(Cl)cc4F)n3)nc3ccc(C(=O)O)cc32)CC1] |

-continued
| Number | Structure |
|---|---|
| Compound C74 | 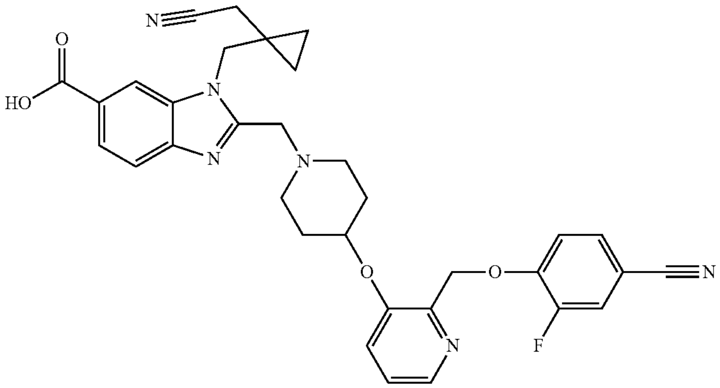 [SMILES: N#CCC1(Cn2c(CN3CCC(Oc4cccnc4COc4ccc(C#N)cc4F)CC3)nc3ccc(C(=O)O)cc32)CC1] |
| Compound C75 | 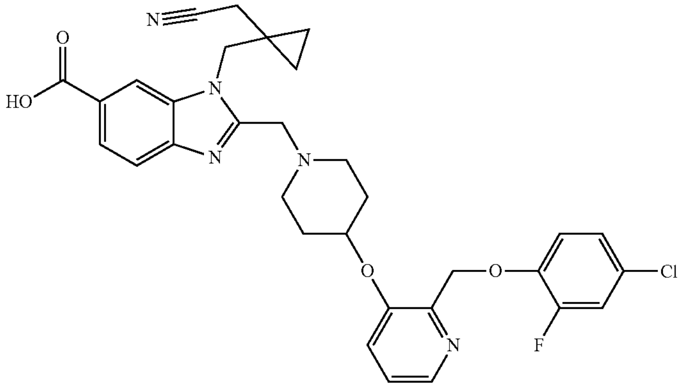 [SMILES: N#CCC1(Cn2c(CN3CCC(Oc4cccnc4COc4ccc(Cl)cc4F)CC3)nc3ccc(C(=O)O)cc32)CC1] |
| Compound C76 | 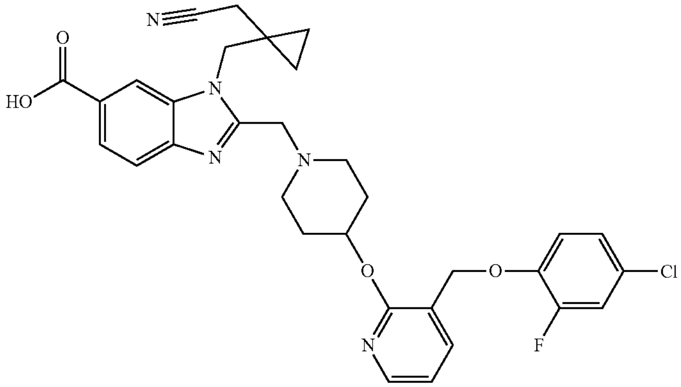 |
| Compound C77 | 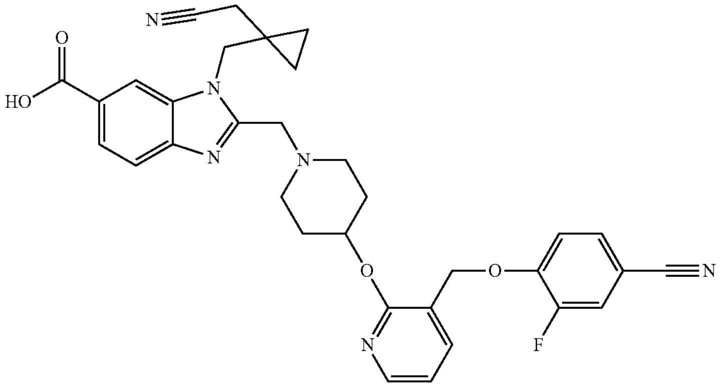 [SMILES: N#CCC1(Cn2c(CN3CCC(Oc4ncccc4COc4ccc(C#N)cc4F)CC3)nc3ccc(C(=O)O)cc32)CC1] |

-continued
| Number | Structure |
|---|---|
| Compound C78 | 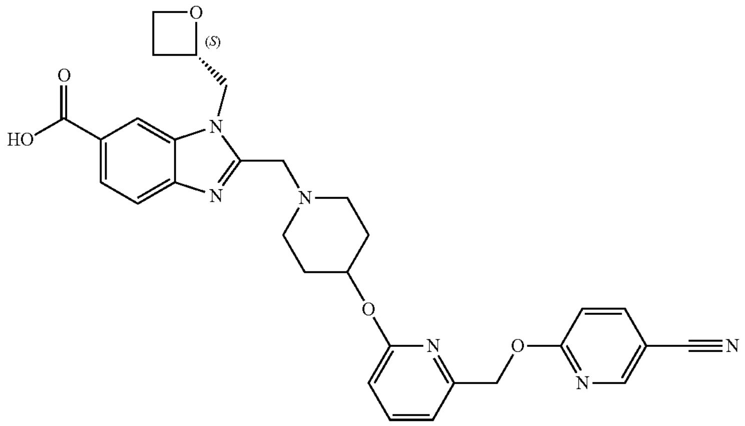 |
| Compound C79 | 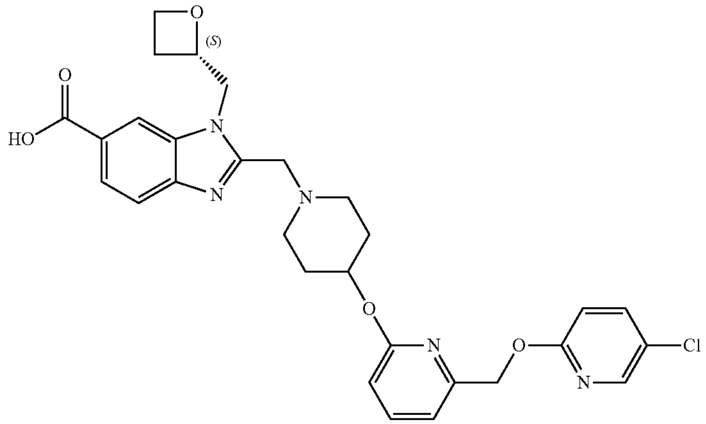 |
| Compound C80 | 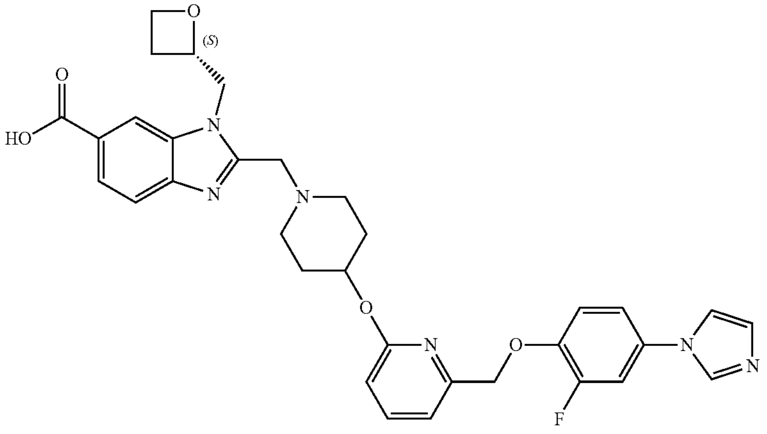 |

-continued
| Number | Structure |
|---|---|
| Compound C81 | 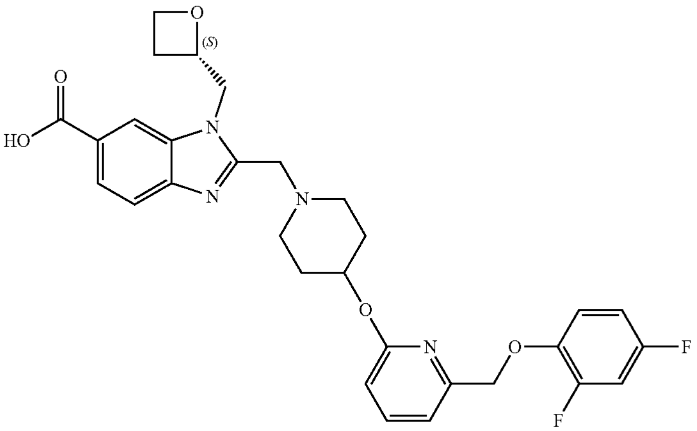 |
| Compound C82 | 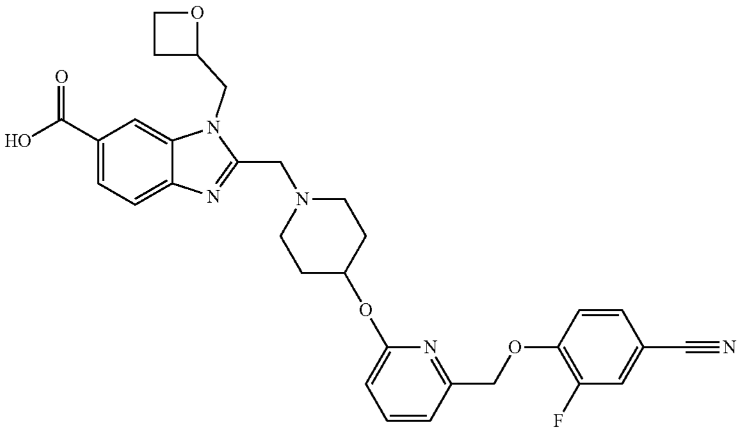 [SMILES: N#Cc1ccc(OCc2cccc(OC3CCN(Cc4nc5ccc(C(=O)O)cc5n4CC4CCO4)CC3)n2)c(F)c1] |
| Compound C83 | 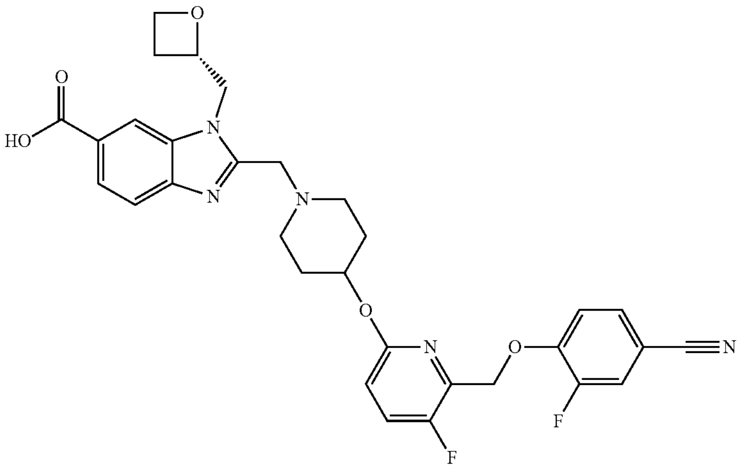 [SMILES: N#Cc1ccc(OCc2nc(OC3CCN(Cc4nc5ccc(C(=O)O)cc5n4C[C@@H]4CCO4)CC3)ccc2F)c(F)c1] |

-continued

| Number | Structure |
| --- | --- |
| Compound C84 | 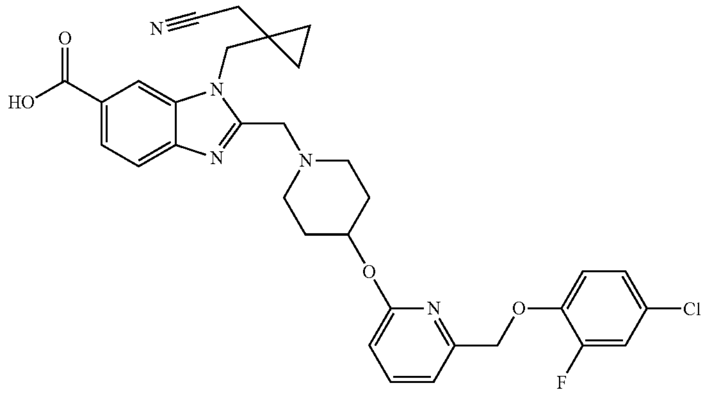 [SMILES: N#CCC1(Cn2c(CN3CCC(Oc4cccc(COc5ccc(Cl)cc5F)n4)CC3)nc3ccc(C(=O)O)cc32)CC1] |

The present invention also provides a pharmaceutical composition comprising a therapeutically effective amount of at least one of the compounds represented by Formula (I), its pharmaceutically acceptable salts, solvates, enantiomers, and isotopic variations.

According to an embodiment of the invention, the pharmaceutical composition is formulated for administration by a route selected from the group consisting of oral, injection, rectal, nasal, pulmonary, topical, buccal and sublingual, vaginal, parenteral, subcutaneous, intramuscular, intravenous, intradermal, intrathecal, and epidural.

According to an embodiment of the present invention, the pharmaceutical composition is preferably administered orally.

The oral dosage form is not particularly limited, and any oral dosage form well known in the art can be used, preferably including tablets, capsules, suspensions or oral solutions and other oral dosage forms known in the art. As an oral dosage form, the dosage standard used is, for example, 500-1500 mg/day, preferably 700-1200 mg/day, preferably 800-1000 mg/day, most preferably 1000 mg/day.

The administration time of the pharmaceutical composition according to the present invention may depend on the degree of the disease, preferably at least 1 month, for example, 1, 2, 3, 4, 5, or 6 months, and the longest may be lifelong medication due to the needs of the disease.

According to an embodiment of the present invention, the pharmaceutical composition may further comprise pharmaceutically acceptable excipients selected from at least one including but not limited to the following excipients: filler, disintegrant, binder, lubricant, surfactants, flavoring agents, wetting agents, pH regulators, solubilizers or cosolvents, osmotic pressure regulators. Those skilled in the art can easily determine how to select the corresponding excipients and their corresponding amounts according to the needs of specific dosage forms.

According to embodiments of the present invention, the pharmaceutical composition may further contain one or more additional therapeutic agents.

Another object of the present invention is to provide use of the above-mentioned compounds for manufacturing a medicament for preventing or treating GLP1/GLP1R signaling pathway related diseases. The GLP1/GLP1R signaling pathway related diseases include but are not limited to overweight, obesity, diabetes (T1 D and/or T2DM, including prediabetes), idiopathic T1 D (type 1B), latent autoimmune diabetes in adults (LADA), early-onset T2DM (EOD), youthful atypical diabetes mellitus (YOAD), maturity-onset diabetes mellitus (MODY), malnutrition-related diabetes mellitus, gestational diabetes mellitus, hyperglycemia, insulin resistance, hepatic insulin resistance, glucose tolerance Impairment, diabetic neuropathy, diabetic nephropathy, renal disease (e.g., acute kidney disease, renal tubular dysfunction, proinflammatory changes in proximal tubules), diabetic retinopathy, adipocyte dysfunction, visceral fat deposition, sleep apnea suspension, obesity (including hypothalamic and monogenic obesity) and associated comorbidities (e.g., osteoarthritis and urinary incontinence), eating disorders (including binge drinking syndrome, bulimia nervosa, and syndromic obesity such as Prader-Willi and Bardet-Biedl syndrome), weight gain due to use of other drugs (e.g., steroid and antipsychotic use), hyperglycemia, dyslipidemia (including hyperlipidemia, hypertriglyceridemia, total Increased cholesterol, high-density lipoprotein cholesterol, low-density lipoprotein cholesterol, hyperinsulinemia, NAFLD (including steatosis, NASH, fibrosis, liver cirrhosis, hepatocellular carcinoma and other related diseases), cardiovascular disease, atherosclerosis (including coronary artery disease), peripheral vascular disease, hypertension, endothelial dysfunction, impaired vascular compliance, congestive heart failure, myocardial infarction (e.g., necrosis and apoptosis), stroke, hemorrhagic stroke, ischemic stroke, Traumatic brain injury, pulmonary hypertension, restenosis after angioplasty, intermittent claudication, postprandial lipids, metabolic acidosis, ketosis, arthritis, osteoporosis, Parkinson's disease, left ventricular hypertrophy, peripheral artery disease, macular degeneration, cataract, glomerulosclerosis, chronic renal failure, metabolic syndrome, syndrome X, premenstrual syndrome, angina pectoris, thrombosis, atherosclerosis, transient ischemic attack, restenosis, sugar Impaired metabolism, impaired fasting glucose, hyperuricemia, gout, erectile dysfunction, skin and connective tissue disorders, psoriasis, foot ulcers, ulcerative colitis, hyperapolipoprotein B lipoproteinemia, Alzheimer's disease Prophylaxis or treatment of silent disease, schizophrenia, cognitive impairment, inflammatory bowel disease, short bowel syndrome, Crohn's disease, colitis, irritable bowel syndrome, polycystic ovary syndrome, and addiction treatment (e.g., alcohol and/or drug abuse) and other conditions.

The present invention also provides the use of the compound represented by the Formula (I), its pharmaceutically acceptable salts, solvates, enantiomers and isotopic variations, and the pharmaceutical compositions in the prevention and/or treatment of diseases related to GLP1/GLP1R signaling pathway. The GLP1/GLP1R signaling pathway-related diseases have the above-mentioned definitions.

The present invention also provides a method for preventing and/or treating diseases related to the GLP1/GLP1R signaling pathway, comprising administering to a patient a preventive or therapeutically effective amount of the compound represented by Formula (I), a pharmaceutically acceptable salt, a solvate, enantiomers and isotopic variations, thereof at least one of the compounds, or administering to the patient a prophylactically or therapeutically effective amount of the above-mentioned pharmaceutical composition. The GLP1/GLP1R signaling pathway-related diseases have the above-mentioned definitions.

In some embodiments, the patient is a mammal, preferably a human.

DETAILED DESCRIPTION OF THE INVENTION

Figure 1:
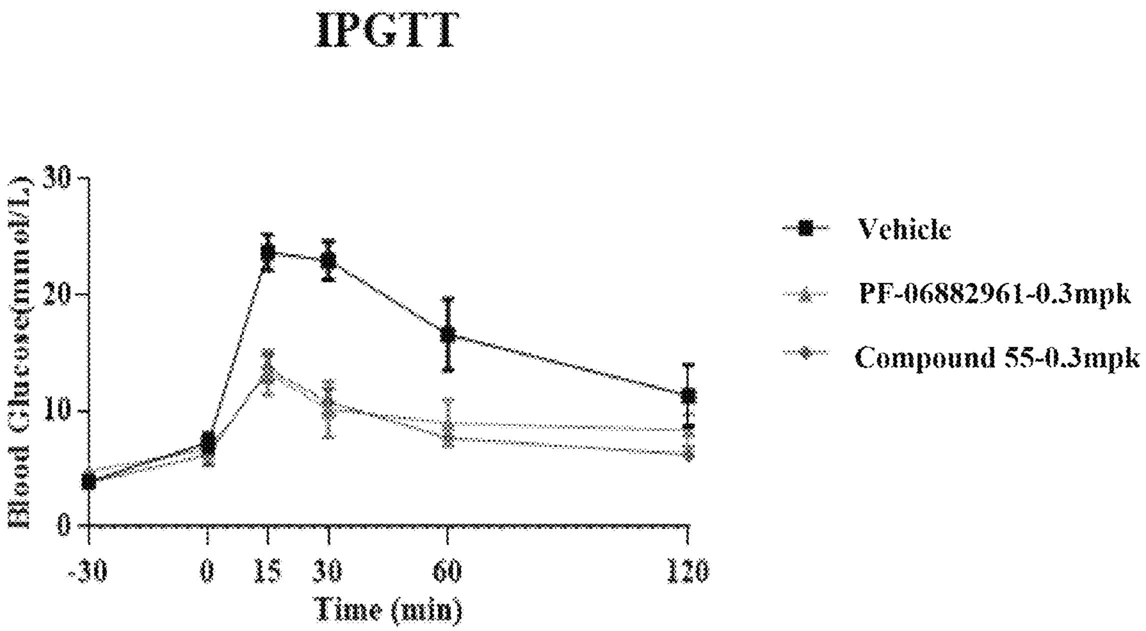
FIG. 1 shows comparison curve of the effects of the compounds of the present invention and known drugs on the IPGTT blood sugar of hGLP1R mice.

Definition and Description:

$C_{1-10}$ is selected from $C_1$, $C_2$, $C_3$, $C_4$, $C_5$, $C_6$, $C_7$, $C_8$, $C_9$ and $C_{10}$; $C_{2-10}$ is selected from $C_2$, $C_3$, $C_4$, $C_5$, $C_6$, $C_7$, $C_8$, $C_9$ and $C_{10}$; $C_{3-10}$ is selected from $C_3$, $C_4$, $C_5$, $C_6$, $C_7$, $C_8$, $C_9$, and $C_{10}$;

The term 'alkyl' as used herein refers to a linear or branched chain monovalent hydrocarbon group. Examples include, but are not limited to, methyl, ethyl, propyl, butyl, 2-methyl-propyl, 1,1-dimethylethyl, pentyl, and hexyl.

The term 'alkylene' as used herein refers to a linear or branched chain divalent hydrocarbon group of formula $—(CH_2)_n—$. Examples include, but are not limited to, ethylene and propylene.

The term 'one to more' or 'one to multiple' as used herein refers to more than 1, such as 1, 2, 3, 4, 5 or more.

The term 'carbocycle (radical)' or "cycloalkyl" refers to a saturated or partially unsaturated monocyclic or polycyclic hydrocarbon group, the carbocycle may contain 3 to 20 carbon atoms, preferably 3 to 12 (e.g. 3, 4, 5, 6, 7, 8, 9, 10, 11, 12) carbon atoms, more preferably 3 to 6 carbon atoms. The carbocycle may be monocyclic or polycyclic, it may be a saturated cycloalkyl or may optionally contain one, two or more double and/or triple bonds in its ring, thereby forming so-called cycloalkenyl or cycloalkynyl. Where carbocycles have multiple rings, the rings can form spiro, fused and bridged ring structures. For example, non-limiting examples of monocyclic carbocycles include cyclopropyl, cyclobutyl, cyclopentyl, cyclopentenyl, cyclohexyl, cyclohexenyl, cyclohexadienyl, cycloheptyl, cycloheptyl alkenyl, cyclooctyl, cyclooctatetraenyl, etc.; non-limiting examples of polycyclic carbocycles include decalin or isobornyl.

The term 'heterocycle (radical)' refers to a saturated or partially unsaturated monocyclic or polycyclic cyclic hydrocarbon substituent containing 3 to 20 ring atoms, wherein one or more of the ring atoms is a heteroatom or group of atoms selected from N, O, NH, S, S(O) or $S(O)_2$, but excluding ring parts of —O—O—, —O—S— or —S—S—, the remaining ring atoms are carbon. Preferably 3 to 12 ring atoms, of which 1 to 4 are heteroatoms, are comprised (e.g. 1, 2, 3 and 4); more preferably 3 to 6 ring atoms (e.g. 3, 4, 5, 6). A heterocyclyl group can be attached to the remainder of the molecule through any of the carbon atoms or a nitrogen atom (if present) or an oxygen or sulfur atom (especially in the case of an onium salt formation). The heterocyclyl group may include fused or bridged rings and/or spiro rings. Non-limiting examples of monocyclic heterocyclyl groups include azetidinyl, oxetanyl, pyrrolidinyl, imidazolidinyl, tetrahydrofuranyl, tetrahydrothienyl, dihydroimidazolyl, dihydrofuranyl, dihydropyrazolyl, dihydropyrrolyl, dioxolyl, tetrahydropyranyl, pyrroline, piperidinyl, piperazinyl, morpholinyl, thiomorpholinyl, dithianyl trithianyl, homopiperazinyl, diazepanyl, etc., preferably piperidinyl and pyrrolidinyl. Polycyclic heterocyclyls include spiro, fused and bridged heterocyclyls, and may also be benzo-fused heterocyclyls such as dihydroisoquinolinyl. The heterocyclyl may be bicyclic, non-limiting examples of which include hexahydrocyclopento [c]pyrrol-2 (1H)-yl, hexahydropyrrolo[1,2-a]pyrazin-2 (1H)-yl. Heterocyclyl can also be partially unsaturated, i.e. it can contain one or more double bonds, non-limiting examples of which include dihydrofuranyl, dihydropyranyl, 2,5-dihydro-1H-pyrrolyl, 4H-[1,3,4]thiadiazinyl, 4,5-dihydrooxazolyl or 4H-[1,4]thiazinyl.

Heterocyclyl may be optionally substituted or unsubstituted, and when substituted, the substituents are preferably one or more of the following groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkanethio, heterocycloalkylthio, oxo, carboxyl or carboxylate.

As used herein, the term 'heteroaryl/heteroaromatic ring' refers to a heteroaromatic system comprising 1 to 4 heteroatoms, 5 to 20 ring atoms, wherein the heteroatoms are selected from oxygen, sulfur, nitrogen and phosphorus. Heteroaryl is preferably 5- to 10-membered (e.g. 5-, 6-, 7-, 8-, 9— or 10-membered), more preferably 5— or 6-membered. Non-limiting examples of heteroaryl groups include, but are not limited to, thienyl, furyl, pyrrolyl, oxazolyl, thiazolyl, imidazolyl, pyrazolyl, isoxazolyl, isothiazolyl, oxadiazolyl, triazolyl oxazolyl, thiadiazolyl, thi-4H-pyrazolyl, etc. and their benzo derivatives such as benzofuranyl, benzothienyl, benzoxazolyl, benzisoxazolyl, benzoyl imidazolyl, benzotriazolyl, indazolyl, indolyl, isoindolyl, etc.; or pyridyl, pyridazinyl, pyrimidinyl, pyrazinyl, triazinyl, etc., and their benzo derivatives, such as quinolinyl, quinazolinyl, isoquinolinyl, etc; or azinyl, indozinyl, purinyl, etc., as well as their benzo derivatives; or cinolinyl, phthalazinyl, quinazolinyl, quinoxalinyl, naphthyridinyl, pteridinyl, carbazolyl, acridinyl, phenazinyl, phenothiazinyl, and/or phenoxazinyl, etc.

Heteroaryl/heteroaryl rings may be optionally substituted or unsubstituted, when substituted, the substituents are preferably one, two or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboxylate.

Unless otherwise stated, a heterocyclyl, heteroaryl or heteroaryl ring includes all possible isomeric forms thereof, e.g. positional isomers thereof. Thus, for some illustrative non-limiting examples, can be included in its 1-, 2-, 3—, 4-, 5-, 6-, 7-, 8-, 9-, 10-, 11-, 12- and etc. (if present) substituted at one, two or more positions, or bonded to other groups, including pyridin-2-yl, pyridin-2-yl, pyridin-3-yl, Pyridin-3-yl, pyridin-4-yl and pyridin-4-yl; thienyl or thienylene includes thien-2-yl, thien-2-yl, thien-3-yl and thien-3-base; pyrazol-1-yl, pyrazol-3-yl, pyrazol-4-yl, pyrazol-5-yl.

As used herein, the term 'pharmaceutically acceptable' refers to those compounds, materials, compositions and/or dosage forms that, within the scope of sound medical judgment, are suitable for use in contact with human and animal tissue, without excessive toxicity, irritation, allergic reactions or other problems or complications, commensurate with a reasonable benefit/risk ratio.

The term 'pharmaceutically acceptable salts' refers to salts of the compounds of the present invention, prepared from compounds with specific substituents discovered by the present invention and relatively non-toxic acids or bases. When the compounds of the present invention contain relatively acidic functional groups, base addition salts can be obtained by contacting the neutral forms of such compounds with a sufficient amount of base in neat solution or in a suitable inert solvent. Pharmaceutically acceptable base addition salts include sodium, potassium, calcium, ammonium, organic ammonia or magnesium salts or similar salts. When the compounds of the present invention contain relatively basic functional groups, acid addition salts can be obtained by contacting the neutral form of such compounds with a sufficient amount of acid in neat solution or in a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc.; and organic acid salts including, for example, acetic acid, propionic acid, isobutyric acid, maleic acid, malonic acid, benzoic acid, succinic acid, suberic acid, fumaric acid, lactic acid, mandelic acid, ortho Phthalic acid, benzenesulfonic acid, p-toluenesulfonic acid, citric acid, tartaric acid, methanesulfonic acid and similar acids; also includes salts of amino acids such as arginine, etc., and salts of organic acids such as glucuronic acid (See Berge et al., "Pharmaceutical Salts", Journal of Pharmaceutical Science 66:1-19 (1977)). Certain specific compounds of the present invention contain both basic and acidic functional groups and thus can be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

As used herein, "pharmaceutically acceptable salts" pertain to derivatives of compounds of the present invention wherein the parent compound is modified by salt formation with an acid or salt formation with a base. Examples of pharmaceutically acceptable salts include, but are not limited to, inorganic or organic acid salts of bases such as amines, alkali metal or organic salts of acid groups such as carboxylic acids, and the like. Pharmaceutically acceptable salts include conventional non-toxic salts such as Na salts, potassium salts, amine salts, quaternary ammonium salts of the parent compound, and the like. Conventional non-toxic salts include, but are not limited to, those derived from inorganic and organic acids, inorganic and organic bases selected from the group consisting of 2-acetoxybenzoic acid, 2-hydroxyethanesulfonic acid acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutaric acid Amino acid, glycolic acid, hydrobromic acid, hydrochloric acid, hydroiodide, hydroxy, hydroxynaphthalene, isethionic acid, lactic acid, lactose, dodecylsulfonic acid, maleic acid, malic acid, mandelic acid, methanesulfonic acid acid, nitric acid, oxalic acid, pamoic acid, pantothenic acid, phenylacetic acid, phosphoric acid, polygalacturonic acid, propionic acid, salicylic acid, stearic acid, acetic acid, succinic acid, sulfamic acid, p-aminobenzenesulfonic acid, sulfuric acid, tannin, tartaric acid and p-toluenesulfonic acid etc. described inorganic base and organic base are selected from Na, potassium, magnesium, calcium etc. or amine, diethylamine, triethylamine, ethanolamine etc.

The pharmaceutically acceptable salts of the present invention can be synthesized from the acid or base containing parent compound by conventional chemical methods. Generally, such salts are prepared by reacting the free acid or base form of these compounds with a stoichiometric amount of the appropriate base or acid in water or an organic solvent or a mixture of the two. Generally, non-aqueous media such as ether, ethyl acetate, ethanol, isopropanol or acetonitrile are preferred.

In addition to salt forms, the compounds provided herein also exist in prodrug forms. Prodrugs of the compounds described herein are readily chemically altered under physiological conditions to convert to the compounds of the present invention. In addition, prodrugs can be converted to the compounds of the present invention by chemical or biochemical methods in an in vivo environment.

Certain compounds of the present invention may exist in unsolvated as well as solvated forms, including hydrated forms. In general, solvated and unsolvated forms are equivalent and are intended to be included within the scope of the present invention. Certain compounds of the present invention may exist in multiple crystalline or amorphous forms.

As used herein, the term 'solvate' refers to an association of one or more solvent molecules with a compound of the present invention. Solvate-forming solvents include, but are not limited to, water, isopropanol, ethanol, methanol, dimethyl sulfoxide, ethyl acetate, acetic acid, and aminocthanol. Thus, the term 'hydrate' refers to an association in which the solvent molecule is water.

Certain compounds of the present invention may have asymmetric carbon atoms (optical centers) or double bonds. Racemates, diastereomers, geometric isomers and individual isomers are included within the scope of the present invention.

Schematic representations of racemates, ambiscalemic and scalemic or enantiomerically pure compounds herein are from Maehr, J. Chem. Ed. 1985, 62:114-120. 1985, 62:114-120. Unless otherwise stated, wedge and dashed bonds are used to indicate the absolute configuration of a stereocenter. When the compounds described herein contain olefinic double bonds or other centers of geometric asymmetry, they include E, Z geometric isomers unless otherwise specified. Likewise, all tautomeric forms are included within the scope of the present invention.

The compounds of the present invention may exist in specific geometric or stereoisomeric forms. The present invention contemplates all such compounds, including cis and trans isomers, (−)- and (+)-enantiomers, (R)- and(S)-enantiomers, diastereomers isomers, (D)-isomers, (L)-isomers, and racemic and other mixtures thereof, such as enantiomerically or diastereomerically enriched mixtures, all of which belong to within the scope of the present invention. Additional asymmetric carbon atoms may be present in substituents such as alkyl. All such isomers, as well as mixtures thereof, are included within the scope of the present invention.

Optically active (R)- and(S)-isomers as well as D and L isomers can be prepared by chiral synthesis or chiral reagents or other conventional techniques. If one enantiomer of a compound of the present invention is desired, it can be prepared by asymmetric synthesis or derivatization with a chiral auxiliary, wherein the resulting mixture of diastereomers is separated and the auxiliary group is cleaved to provide pure desired enantiomer. Alternatively, when the molecule contains basic functional groups (such as amino groups) or acidic functional groups (such as carboxyl groups), diastereomeric salts are formed with appropriate optically active acids or bases, followed by stepwise steps well known in the art. The diastereoisomers are resolved by crystallization or chromatography, followed by recovery of the pure enantiomers. In addition, separation of enantiomers and diastereomers is usually accomplished by the use of chromatography using a chiral stationary phase, optionally in combination with chemical derivatization (e.g., carbamate formation from amines).

The compounds of the present invention may contain unnatural proportions of atomic isotopes at one or more of the atoms that constitute the compound. For example, compounds may be labeled with radioactive isotopes, such as tritium ($^3H$), iodine-125 ($^{125}I$) or C-14 ($^{14}C$). All isotopic variations of the compounds of the invention, whether radioactive or not, are intended to be encompassed within the scope of the invention.

The term "pharmaceutically acceptable carrier" refers to any formulation or carrier medium that provides the appropriate delivery of an effective amount of an active agent as defined herein, does not negatively interfere with the effectiveness of the biological activity of the active agent, and that is sufficiently non-toxic to the host. Representative carriers include water, oils, both vegetable and mineral, cream bases, lotion bases, ointment bases and the like. These bases include suspending agents, thickeners, penetration enhancers, and the like. Their formulation is well known to those in the art of topical pharmaceuticals. Additional information concerning carriers can be found in Remington: The Science and Practice of Pharmacy. 21st Ed., Lippincott, Williams & Wilkins (2005) which is incorporated herein by reference.

When any variable (e.g., R) occurs more than once in the composition or structure of the compound, its definition in each case is independent. Thus, for example, if a group is substituted with 0-2R, the group may optionally be substituted with up to two R, and in each case the R has an independent option. In addition, the combination of substituents and/or their variants is allowed only if such a combination will produce a stable compound.

When a bond of a substituent could be cross-linked to two atoms on a ring, such substituent may be bonded to any atoms in the ring. Where the listed substituent does not specify through which atom it is connected to the general structure formula including the compound that is not specifically mentioned, the substituent may be bonded through any one of its atoms. The combination of substituents and/or variant thereof is allowed only if such a combination results in a stable compound.

The term "halo" or 'halogen' refers to fluorine, chlorine, bromine and iodine.

In order to illustrate the disclosure in more detail, the following examples are given, but the scope of the disclosure is not limited thereto. The compounds of the disclosure can be prepared by various synthetic methods well-known to those skilled in the art, including the embodiments described below, the embodiments combing the embodiments described below with other synthetic methods, and equivalent alternatives known to those skilled in the art. Preferred embodiments include but are not limited to those embodiments of the present invention.

Unless otherwise specified, all solvents used in the present invention are commercially available, and no further purification is required for use. The reaction is usually carried out using an anhydrous solvent under an inert atmosphere of nitrogen. NMR spectra were measured on a Bruker-Avance-400 (400 MHZ) spectrometer and chemical shifts are reported in 8 (ppm). Mass spectrometry was performed with an Agilent 1200 series (plus 6110/and 1956A) LC/MS or a Shimadzu MS(DAD: SPD-M20A (LC)) and a Shimadzu Micromass 2020 detector. The mass spectrometer is equipped with an electrospray ionization (ESI) source operating in positive and negative modes.

Abbreviations used are as follows: aq is aqueous; TLC is thin layer chromatography; RT is room temperature; MeOH is methanol; EtOH is ethanol; EtOAc is ethyl acetate; THF is tetrahydrofuran; eq for equivalent or equivalents; CDI is carbonyldiimidazole; DCM is Dichloromethane; PE is petroleum ether; DIAD is diisopropyl azodicarboxylate; DMF is N,N-dimethylformamide; DMSO is dimethyl sulfoxide; CBz is benzyloxycarbonyl; Boc is tert-butyl; HOAc is acetic acid; Ms is methylsulfonyl: NMP is N-methylpyrrolidone; DMAP is 4-(dimethylamino)pyridine; $Boc_2O$ is di-tert-butyl dicarbonate; TFA is trifluoroacetic acid; DIPEA is Diisopropylethylamine; $SOCl_2$ is thionyl chloride; $CS_2$ is carbon disulfide; TsOH is 4-toluenesulfonic acid; MTBE is tert-butyl methyl ether; FA is formic acid; ACN is acetonitrile; i-PrOH is 2-propanol.

Compounds can be named manually or by ChemDraw® software, or if purchased commercially the supplier's catalog name is used. Usually, TLC or LC-MS is used to determine whether the reaction is completed.

EXAMPLES

In order to illustrate the present invention in more detail, the following examples are given, but the scope of the present invention is not limited thereto.

Example 1-1. Synthesis of methyl(S,E)-3-(2-(chloromethyl)-1-(oxetan-2-ylmethyl)-1H-benzo[d]imidazol-6-yl)acrylate (intermediate A-1)

1). (E) Preparation of methyl (E)-3-(3-fluoro-4-nitrophenyl)acrylate

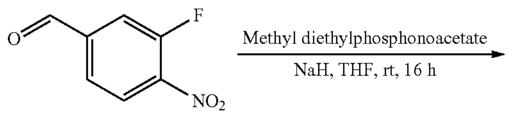

-continued

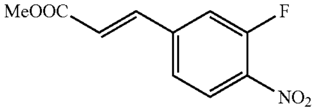

To a solution of methyl diethylphosphonateacetate (1 g, 4.76 mmol) in dry THF (10 mL) at 0° C. sodium hydride (60% w/w dispersed in mineral oil, 210 mg, 5.24 mmol) was added. The mixture was stirred at 0° C. for 30 mins, then 3-fluoro-4-nitrobenzaldehyde (885 mg, 5.24 mmol) was added slowly to above mixture, maintaining the reaction temperature around 0° C. After the addition was completed, the mixture was naturally warmed to room temperature and stirred for 16 hours. Cool to 0° C., the mixture was quenched with water (50 mL) and extracted with ethyl acetate (2×30 mL). The combined organic layer was concentrated in vacuo to give a residue. The residue was subjected to silica gel column chromatography (PE/EA=3/1) to obtain methyl (E)-3-(3-fluoro-4-nitrophenyl)acrylate (800 mg, 74.8% yield).

$^1$H NMR (400 MHZ, DMSO-$d_6$): δ8.18 (t, J=8.2 Hz, 1H), 8.05 (d, J=12.8 Hz, 1H), 7.80 (d, J=8.6 Hz, 1 H), 7.73 (d, J=16.0 Hz, 1H), 6.93 (d, J=16.0 Hz, 1H), 3.76 (s, 3H).

2). Synthesis of methyl(S,E)-3-(4-nitro-3-((oxetan-2-ylmethyl)amino)phenyl)acrylate

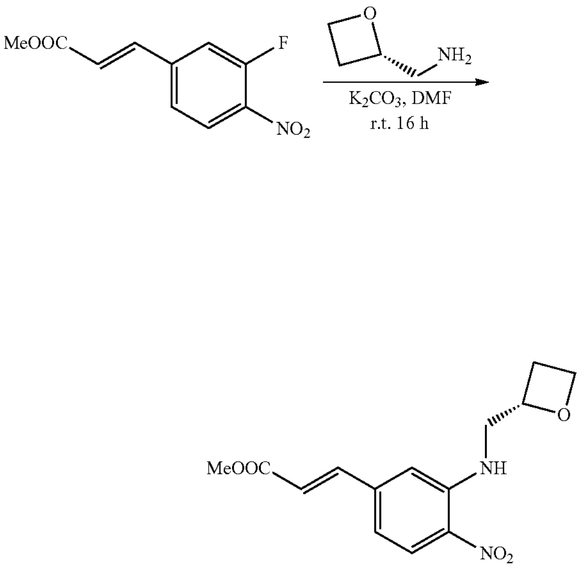

The mixture of methyl (E)-3-(3-fluoro-4-nitrophenyl) acrylate (300 mg, 1.33 mmol), (S)-oxetan-2-ylmethanamine (116 mg, 1.33 mmol) and $K_2CO_3$ (368 mg, 2.67 mmol) in N,N-dimethylformamide (5 mL) was stirred at room temperature for 16 hours. The mixture was diluted with water (50 mL) and extracted with EA (3×10 mL). The combined organic layers were washed with brine (50 mL), dried over $Na_2SO_4$, filtered, and concentrated in vacuo to give a residue. The residue was purified by pre-TLC (PE/EA=1/1) to give methyl(S,E)-3-(4-nitro-3-((oxetan-2-ylmethyl) amino)phenyl)acrylate (320 mg, 82.4% yield), LC-MS m/z: 293 [M+H]$^+$.

3). Synthesis of methyl(S,E)-3-(4-amino-3-((oxetan-2-ylmethyl)amino)phenyl)acrylate

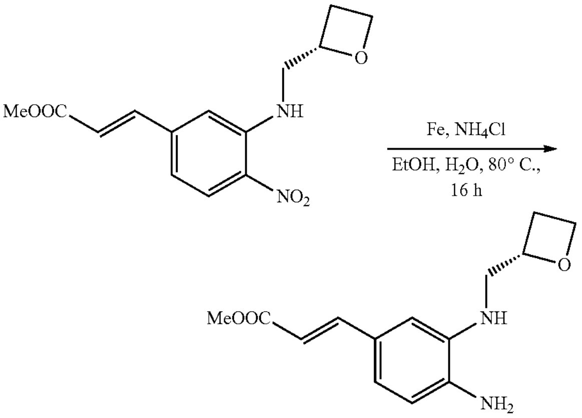

The mixture of methyl (S,E)(4-nitro-3-((oxetan-2-ylmethyl)amino)phenyl)acrylate (Intermediate 2)(320 mg, 1.1 mmol), Fe (173 mg) and $NH_4Cl$ (164 mg) in ethanol/water (v: v=10/1, 5 mL) was heated to 80° C. and stirred for 16 hours. The reaction mixture was cooled to room temperature, poured into saturated $NaHCO_3$ (30 mL), and then extracted with EA (3×10 mL). The combined organic layer was concentrated in vacuo to give a residue. The residue was purified by silica gel column chromatography (DCM/MeOH=20/1) to obtain methyl(S,E)-3-(4-amino-3-((oxetan-2-ylmethyl)amino)phenyl)acrylate (270 mg, 93.7% yield). LC-MS m/z: 263 [M+H]$^+$.

4). Synthesis of methyl(S,E)-3-(2-(chloromethyl)-1-(oxetan-2-ylmethyl)-1H-benzo[d]imidazol-6-15 yl)acrylate (intermediate A-1)

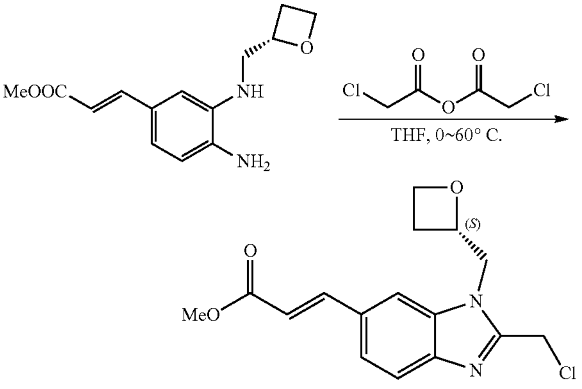

To a solution of methyl(S,E)-3-(4-amino-3-((oxetan-2-ylmethyl)amino)phenyl)acrylate (intermediate 3) in dry THF (5 mL) chloroacetic anhydride (173 mg, 1.01 mmol) was slowly added at 0° C. The reaction mixture was stirred at 0° C. for 30 mins, after which it was heated to 60° C. and stirred for 3 hours. Cooled to room temperature, quenched with water (20 ml) and extracted with EA (2×10 ml). The combined organic layer was directly concentrated in vacuo to give a residue. The residue was purified by silica gel column chromatography (DCM/MeOH=50/1) to obtain methyl(S,E)-3-(2-(chloromethyl)-1-(oxetan-2-ylmethyl)-1H-benzo[d]imidazol-6-yl)acrylate (intermediate A-1)(240 mg, 81.9% yield). LC-MS m/z: 321 $[M+H]^+$.

Example 1-2. Synthesis of methyl 4-(2-chloroacetamide)-3-(((1-ethyl-1H-imidazol-5-yl)methyl) amino)-benzoate (Intermediate A-2)

1). Synthesis of methyl 3-(((1-ethyl-1H-imidazol-5-yl)methyl)amino)-4-nitrobenzoate

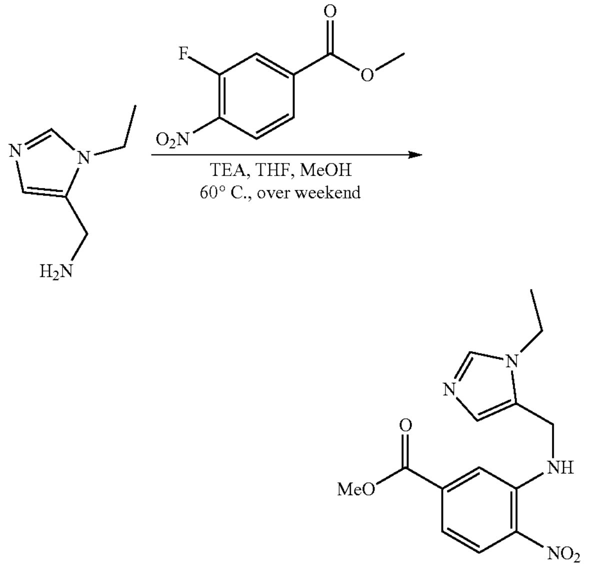

To a mixture of (1-ethyl-1H-imidazol-5-yl)methanamine (240 mg, 1.21 mmol) and methyl 3-fluoro-4-nitrobenzoate (241.2 mg, 1.21 mmol) in THF (6 mL) and MeOH (4 mL) TEA (1.2 g, 12.1 mmol) was added. The reaction mixture was warmed to 60° C. and stirred over weekend. The reaction mixture was poured into saturated brine (100 mL) and extracted with EA (2×80 mL). The organic layer was concentrated in vacuo to give a residue. The residue was purified by flash column chromatography on silica gel (eluted with EA/PE=3/1) to obtain methyl 3-(((1-ethyl-1H-imidazol-5-yl)methyl)amino)-4-nitrobenzoate (320 mg, 87.0% yield). LC-MS m/z: 305 $[M+H]^+$.

2). Synthesis of methyl 4-amino-3-(((1-ethyl-1H-imidazol-5-yl)methyl)amino)benzoate

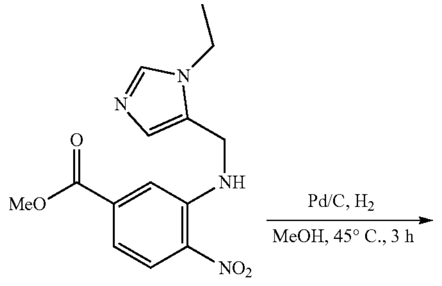

-continued

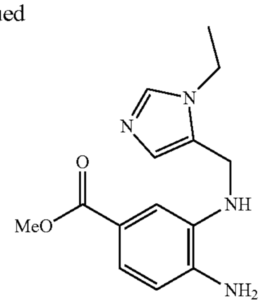

To a solution of methyl 3-(((1-ethyl-1H-imidazol-5-yl) methyl)amino)-4-nitrobenzoate (320 mg, 1.05 mmol) in MeOH (10 mL) wet Pd/C (50 mg) was added under $N_2$ atmosphere. The reaction solution was degassed with $H_2$ three times, and then raised to 45° C. for 3 hours under $H_2$ atmosphere. The mixture was filtered, and the filtrate was concentrated in vacuo to give a residue. The residue was purified by flash column chromatography on silica gel (eluted with DCM/MeOH=10/1) to obtain methyl 4-amino-3-((((1-ethyl-1H-imidazol-5-yl)methyl)amino)methyl)benzoate (270 mg, 93.8% yield). LC-MS m/z: 275 $[M+H]^+$.

3). Synthesis of methyl 4-(2-chloroacetamide)-3-(((1-ethyl-1H-imidazol-5-yl)methyl)amino)benzoate (Intermediate A-2)

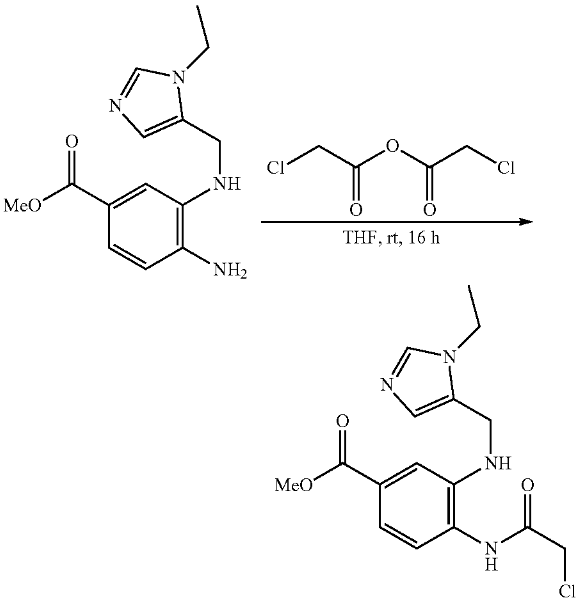

The solution of methyl 4-amino-3-(((1-ethyl-1H-imidazol-5-yl)methyl)amino)benzoate (230.0 mg, 0.84 mmol) and 2-chloroacetic anhydride (285.4 mg, 1.68 mmol) in THF (10 mL) was stirred at room temperature for 16 hours. The reaction solution was poured into saturated brine (100 mL) and extracted with DCM (2×80 mL). The combined organic layers were concentrated in vacuo to obtain methyl 4-(2-chloroacetamide)-3-(((1-ethyl-1H-imidazol-5-yl)methyl) amino)benzoate (230.0 mg, 78.2% yield), LC-MS m/z: 351 $[M+H]^+$.

Example 1-3. Synthesis of methyl(S)-2-(chloromethyl)-1-(oxetan-2-ylmethyl)-1H-benzo[d]imidazole-6-carboxylate (Intermediate A-3)

1). Synthesis of methyl(S)-4-nitro-3-((oxetan-2-ylmethyl)amino)benzoate

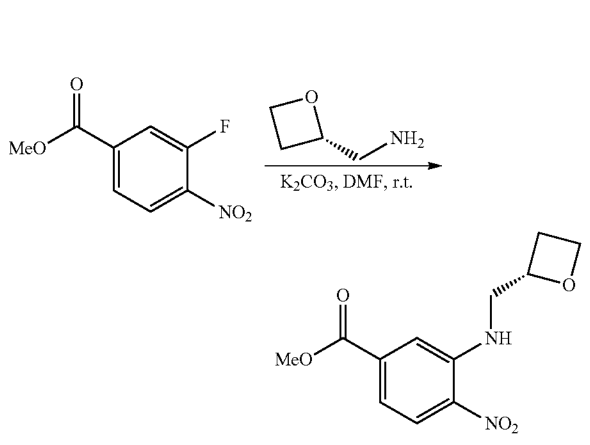

A solution of methyl 3-fluoro-4-nitrobenzoate (4.0 g, 20 mmol) and(S)-oxetan-2-ylmethanamine (1.7 g, 20 mmol) in DMF (40 mL) was added $K_2CO_3$ (5.5 g, 40 mmol). The reaction was stirred at room temperature for 12 hours. The reaction solution was poured into saturated brine (200 mL) and extracted with ethyl acetate (2×80 mL). The combined organic layers were washed with saturated brine (2×200 mL), dried over anhydrous sodium sulfate, and concentrated in vacuo to obtain crude product methyl(S)-4-nitro-3-((oxetan-2-ylmethyl)amino)benzoate (5.2 g). LC-MS m/z: 267 $[M+H]^+$.

2). Synthesis of methyl(S)-4-amino-3-((oxetan-2-ylmethyl)amino)benzoate

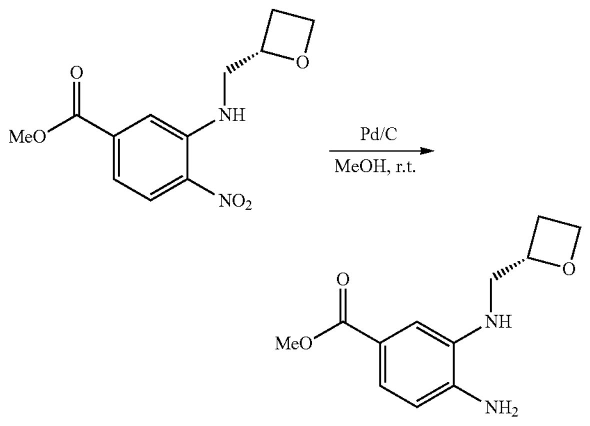

To a solution of methyl(S)-4-nitro-3-((oxetan-2-ylmethyl)amino)benzoate (5.2 g, 20 mmol) in methanol (50 mL) wet Pd/C (520 mg) was added under $N_2$ atmosphere. The mixture was degassed with $H_2$ three times, the reaction mixture was stirred at room temperature for 12 hours under $H_2$ atmosphere. The catalyst was removed by filtration, and the filtrate was concentrated in vacuo to obtain methyl(S)-4-amino-3-((oxetan-2-ylmethyl)amino)benzoate (3.9 g, 82.3% yield), LC-MS m/z: 237 $[M+H]^+$.

3). Synthesis of methyl(S)-2-(chloromethyl)-1-(oxetan-2-ylmethyl)-1H-benzo[d]imidazole-6— carboxylate (Intermediate A-3)

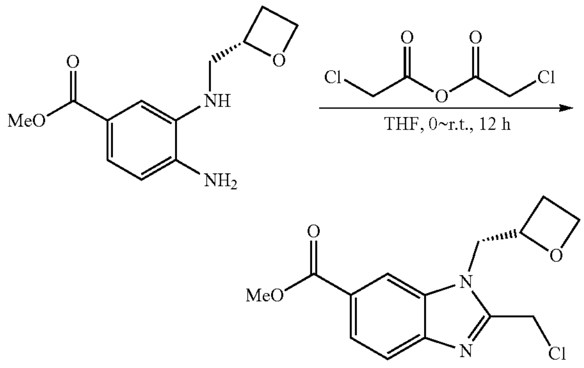

To a solution of methyl(S)-4-amino-3-((oxetan-2-ylmethyl)amino)benzoate (1.5 g, 6 mmol) in THF (12 mL) at 0° C. 2-chloroacetic anhydride (1.1 g, 6.6 mmol) was added. The reaction mixture was stirred at room temperature for 12 hours. The mixture was concentrated in vacuo and purified by silica gel column chromatography (EA/PE=1/1) to obtain methyl(S)-2-(chloromethyl)-1-(oxetan-2-ylmethyl)-1H-benzo[d]imidazole-6-carboxylate (Intermediate A-3)(1.6 g, 90% yield). LC-MS m/z: 295 $[M+H]^+$.

Example 1-4. Synthesis of methyl (E)-3-(4-(2-chloroacetamide)-3-(((1-ethyl-1H-imidazol-5-yl)methyl)amino)-phenyl)acrylate (Intermediate A-4)

1). Synthesis of methyl (E)-3-(3-((1-ethyl-1H-imidazol-5-yl)methyl)amino)-4-nitrophenyl)acrylate

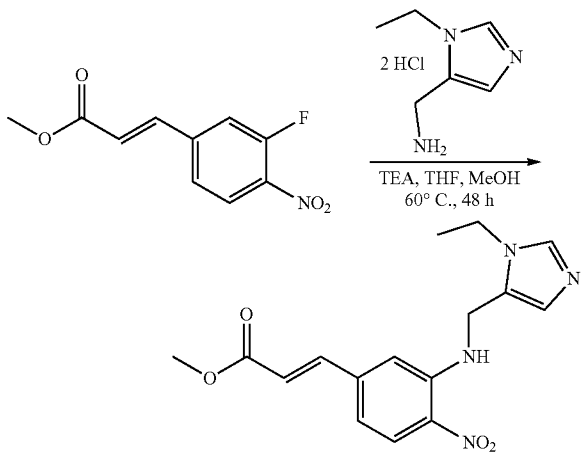

TEA (1.80 g, 17.80 mmol, 10.0 eq) was added to a mixture of methyl (E)-3-(3-fluoro-4-nitrophenyl)acrylate (Intermediate 1)(400 mg, 1.78 mmol) and (1-Ethyl-1H-imidazol-5-yl)methanamine (354 mg, 1.78 mmol) in THF (6 mL) and MeOH (4 mL). After stirring uniformly, the reaction mixture was heated to 60° C. and stirred for 48 hours. The resulting mixture was poured into brine (50 mL) and extracted with EA (2×20 mL). The combined organic layer was concentrated in vacuo and then purified by silica gel column chromatography (DCM/MeOH=10/1) to obtain methyl (E)-3-(3-((1-ethyl-1H-imidazol-5-yl)methyl)amino)-4-nitrophenyl)acrylate (400 mg, 68.1% yield). LC-MS m/z: 331 $[M+H]^+$.

2) Synthesis of methyl (E)-3-(3-((1-ethyl-1H-imidazol-5-yl)methyl)amino)-4-aminophenyl)acrylate

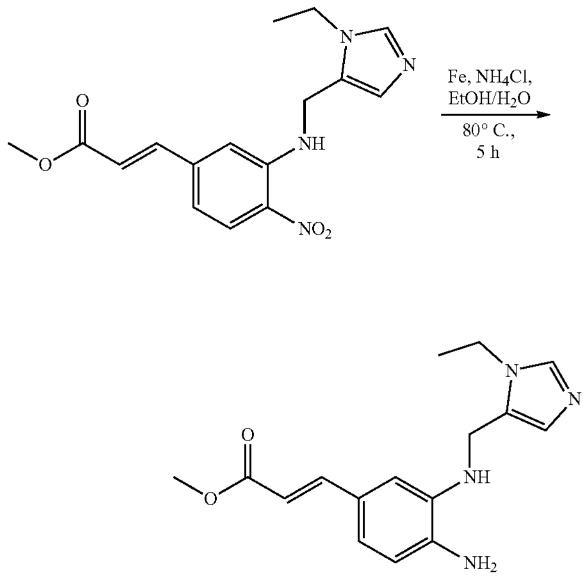 [SMILES: CCn1cncc1CNc1cc(/C=C/C(=O)OC)ccc1[N+](=O)[O-] ; CCn1cncc1CNc1cc(/C=C/C(=O)OC)ccc1N]

The mixture of methyl (E)-3-(3-((1-ethyl-1H-imidazol-5-yl)methyl)amino)-4-nitrophenyl)acrylate (400 mg, 1.21 mmol), iron powder (203 mg, 3.63 mmol) and $NH_1C_1$ (192 mg, 3.62 mmol) in $EtOH/H_2O$ (v/v=10/1, 5 mL) was raised to 80° C. and stirred for 5 hours. The reaction was cooled to room temperature, poured into saturated $NaHCO_3$ solution (30 mL) and extracted with EA (3×10 mL). The combined organic layers were washed with brine (3×10 mL), dried over $Na_2SO_4$, filtered, and concentrated in vacuo to give a residue. The residue was purified by silica gel column chromatography (DCM/MeOH=20/1) to obtain methyl (E)-3-(3-((1-ethyl-1H-imidazol-5-yl)methyl)amino)-4-aminophenyl)acrylate (60 mg, 16.5% yield). LC-MS m/z: 301 $[M+H]^+$.

3). Synthesis of methyl (E)-3-(4-(2-chloroacetamide)-3-(((1-ethyl-1H-imidazol-5-yl)methyl)amino)phenyl)-acrylate (Intermediate A-4)

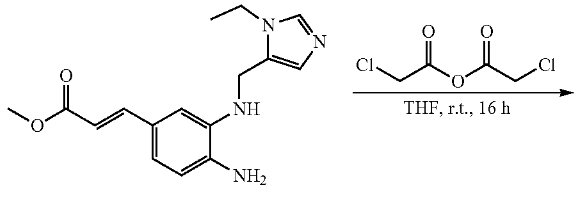

-continued

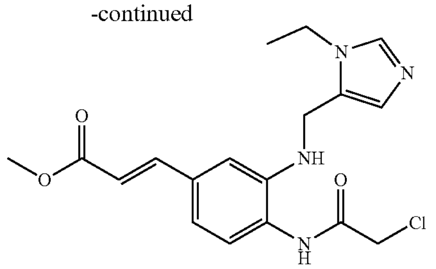

The mixture of methyl (E)-3-(3-((1-ethyl-1H-imidazol-5-yl)methyl)amino)-4-aminophenyl)acrylate (50 mg, 0.17 mmol) and 2-chloroacetic anhydride (58 mg, 0.34 mmol) in THF (2 mL) was stirred at room temperature for 16 hours. The resulting mixture was poured into brine (10 mL) and extracted with DCM (2×5 mL). The combined organic layer was directly concentrated to give methyl (E)-3-(4-(2-chloroacetamide)-3-(((1-ethyl-1H-imidazol-5-yl)methyl)-amino)phenyl)-acrylate (Intermediate A-4)(50 mg, 79.8% yield). LC-MS m/z: 377 $[M+H]^+$.

Example 1-5. Synthesis of methyl(S)-2-(2-(chloromethyl)-1-(oxetan-2-ylmethyl)-1H-benzo[d]imidazol-6-yl)acetate (intermediate A-5)

1). Synthesis of methyl 2-(3-fluoro-4-nitrophenyl)acetate

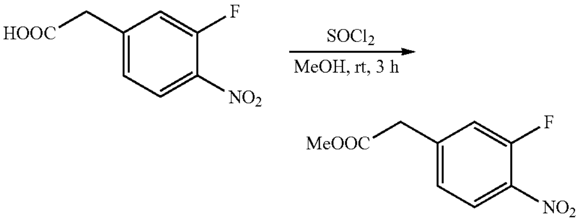

To a solution of 2-(3-fluoro-4-nitrophenyl)acetic acid (800 mg, 4.02 mmol) in methanol (10 mL) at 0° C. thionyl chloride (957 mg, 8.04 mmol) was slowly added. The mixture was stirred at room temperature for 3 hours, then the reaction mixture was quenched with water (50 mL) at 0° C. and then extracted with ethyl acetate (2×20 mL). The combined organic layers were dried over anhydrous sodium sulfate and filtered to give a filtrate. The filtrate was concentrated in vacuo to obtained methyl 2-(3-fluoro-4-nitrophenyl)acetate (840 mg, 98.1% yield).

$^1H$ NMR (400 MHZ, DMSO-$d_6$): δ8.13 (t, J=8.2 Hz, 1H), 7.55 (dd, J=12.4, 1.6 Hz, 1H), 7.37 (dd, J=8.4, 1.0 Hz, 1H), 3.90 (s, 2H), 3.65 (s, 3H).

2). Synthesis of methyl(S)-2-(4-nitro-3-((oxetan-2-ylmethyl)amino)phenyl)acetate

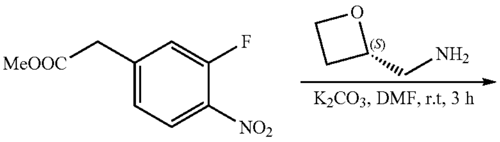

-continued

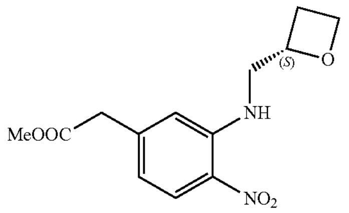

The mixture of methyl 2-(3-fluoro-4-nitrophenyl)acetate (1.05 g, 4.93 mmol), (S)-oxetan-2-ylmethanamine (468 mg, 5.38 mmol) and potassium carbonate (1.35 g, 9.78 mmol) in N, N-dimethylformamide (10 mL) was stirred at room temperature for 3 hours. The resulting mixture was diluted with water (100 mL) and extracted with dichloromethane (3x10 mL). The combined organic layers were washed with brine, dried over anhydrous sodium sulfate, filtered, and concentrated in vacuo to give a residue. The residue was purified by silica gel column chromatography (PE/EA=2/1) to obtain methyl(S)-2-(4-nitro)-3-((oxetan-2-ylmethyl)amino)phenyl)acetate (300 mg, 21.9% yield). LC-MS m/z: 280 $[M+H]^+$.

3). Synthesis of methyl(S)-2-(4-amino-3-((oxetan-2-ylmethyl)amino)phenyl)acetate

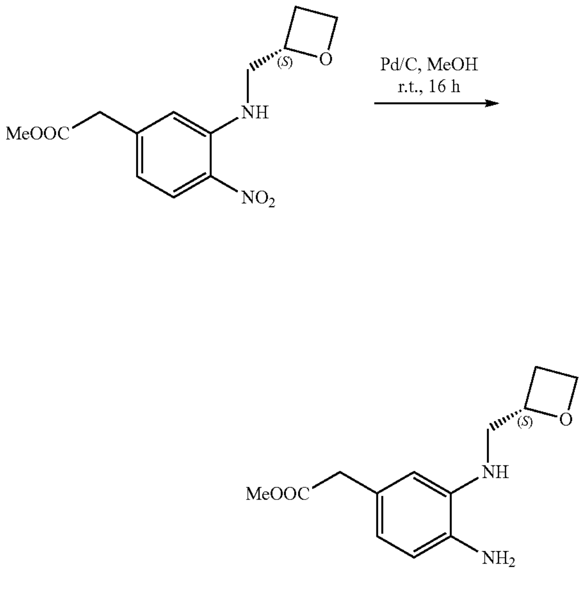

To a solution of methyl(S)-2-(4-nitro-3-((oxetan-2-ylmethyl)amino)phenyl)acetate (300 mg, 1.07 mmol) in methanol (10 mL) wet Pd/C (116 mg) was added under $N_2$ atmosphere solution. The mixture was degassed with $H_2$ three times and stirred at room temperature under $H_2$ atmosphere (1 atm) for 16 hours. T The reaction solution was filtered, and the filter cake was washed with methanol (50 mL). The filtrate was concentrated in vacuo and then purified by silica gel column chromatography (PE/EA=1/1) to obtain methyl(S)-2-(4-amino-3-((oxetan-2-ylmethyl)amino)phenyl)acetate (120 mg, 45.0% yield). LC-MS m/z: 251 $[M+H]^+$.

4). Synthesis of Methyl(S)-2-(2-(chloromethyl)-1-(oxetan-2-ylmethyl)-1H-benzo[d]imidazol-6-yl)acetate (Intermediate) A-5)

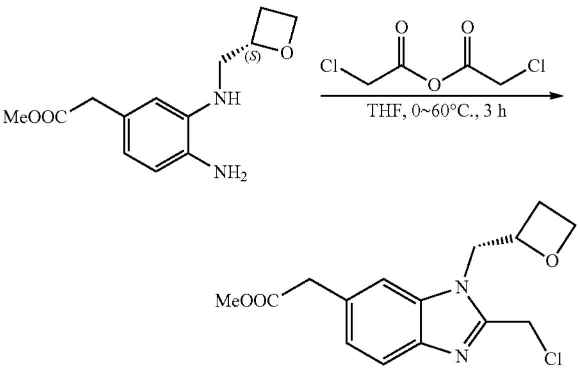

To a solution of methyl(S)-2-(4-amino-3-((oxetan-2-ylmethyl)amino)phenyl)acetate (120 mg, 0.48 mmol) in anhydrous THF (5 mL) 2-chloroacetic anhydride (91 mg, 0.53 mmol) was slowly added at 0° C. The mixture was stirred at 0° C. for 30 min, then heated to 60° C. for 3 h. Cooled to room temperature and quenched with water (20 mL), then extracted with ethyl acetate (2x10 mL). The combined organic layers were dried over $Na_2SO_4$, filtered, and concentrated in vacuo to give a residue. The residue was purified by silica gel column chromatography (DCM/MeOH=50/1) to obtain methyl(S)-2-(2-(chloromethyl)-1-(oxetane)-2-ylmethyl)-1H-benzo[d]imidazol-6-yl)acetate (Intermediate A-5) (100 mg, 67.6% yield). LC-MS m/z: 309 $[M+H]^+$.

Example 1-6. Synthesis of methyl 2-(chloromethyl)-1-(1-(cyanomethyl)cyclopropyl)methyl)-1H-benzo[d]-imidazole-6-carboxylate (Intermediate A-6)

1). Synthesis of (1-(cyanomethyl)cyclopropyl)methanesulfonate

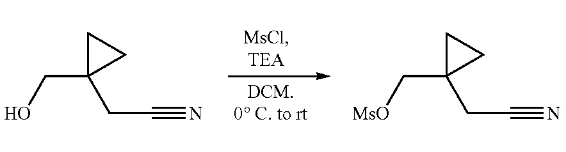

To a mixture of 2-(1-(hydroxymethyl)cyclopropyl)acetonitrile (2.00 g, 18.00 mmol) and triethylamine (4.00 g, 39.25 mmol) in DCM (20 mL) MsCI (3.12 g, 27.23 mmol) was added dropwise at 0° C. Then the mixture was stirred at 0° C. for 1 hour and then stirred at room temperature for 2 hours. The mixture was diluted with DCM (50 mL) and washed with brine (25 mL). The organic layer were dried over anhydrous sodium sulfate, filtered, and concentrated in vacuo to give (1-(cyanomethyl)cyclopropyl)methanesulfonate (3.26 g, 17.23 mmol).

$^1$HNMR (400 MHZ, $CDCl_3$) δ 4.15 (s, 2H), 3.08 (s, 3H), 2.59 (s, 2H), 0.82 (d, J=4.0 Hz, 4H).

2). Synthesis of 2-(1-(azidomethyl)cyclopropyl)acetonitrile

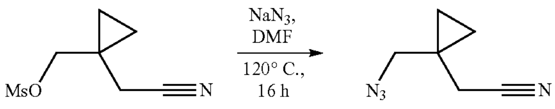

A solution of (1-(cyanomethyl)cyclopropyl)methanesulfonate (3.32 g, 17.54 mmol) and sodium azide (4.81 g, 73.99 mmol) in N, N-dimethylformamide (20 mL) was heated to 120° C. for 16 hours. The mixture was cooled to room temperature and quenched by the addition of water, extracted with dichloromethane (30 mL×3). The combined organic layers were washed with brine, dried over anhydrous sodium sulfate, filtered, and concentrated in vacuo to obtained 2-(1-(azidomethyl)cyclopropyl)acetonitrile (1.60 g, 11.75 mmol, 66.9% yield).

$^1$HNMR (400 MHZ, $CDCl_3$) δ 3.31 (s, 2H), 2.53 (s, 2H), 0.70 (d, J=1.2 Hz, 4H).

3). Synthesis of 2-(1-(aminomethyl)cyclopropyl)acetonitrile

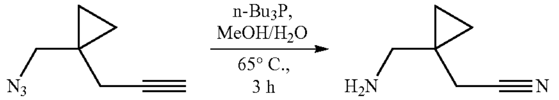

To a mixture of 2-(1-(azidomethyl)cyclopropyl)acetonitrile (1.60 g, 11.75 mmol) in methanol (15 mL)/water (9 mL) tributyl phosphine (7.13 g, 35.24 mmol) was added dropwise at room temperature. The resulting mixture was heated to 65° C. and stirred for 3 hours. The mixture was filtered, and the filter cake was washed with methanol (10 mL). The filtrate was concentrated in vacuo to obtained 2-(1-(aminomethyl)cyclopropyl)acetonitrile (821 mg, 7.45 mmol, 63.5% yield).

$^1$HNMR (400 MHZ, DMSO-$d_6$) δ2.39 (s, 2H), 2.25 (s, 2H), 0.22 (t, J=5.2 Hz, 2H), 0.17 (t, J=5.2 Hz, 2H).

4). Synthesis of methyl 3-((1-(cyanomethyl)cyclopropyl)methyl)amino)-4-nitrobenzoate

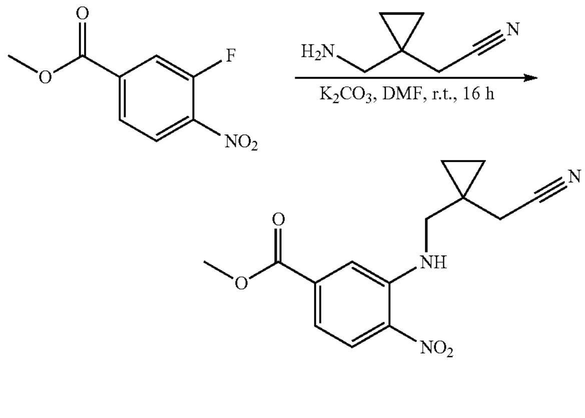

To a mixture of 3-fluoro-4-nitrobenzoate (300 mg, 1.51 mmol) and 2-(1-(aminomethyl)cyclopropyl)acetonitrile (166 mg, 1.51 mmol) in N,N-dimethylformamide (5 mL) potassium carbonate (625 mg, 4.53 mmol) was added. The mixture was stirred at room temperature for 16 hours. The reaction mixture was diluted with water (15 mL) and then extracted with ethyl acetate (3×30 mL). The combined organic layers were washed with brine (2×30 mL), dried over anhydrous sodium sulfate, filtered, and concentrated in vacuo to give a residue. The residue was purified by silica gel column chromatography (PE/EA=5/1) to give methyl 3-((1-(cyanomethyl)cyclopropyl)methyl)amino)-4-nitrobenzoate (250 mg, 0.86 mmol, 57.6% yield). LC-MS m/z: 290 $[M+H]^+$.

5). Synthesis of methyl 4-amino-3-((1-(cyanomethyl)cyclopropyl)methyl)amino)benzoate

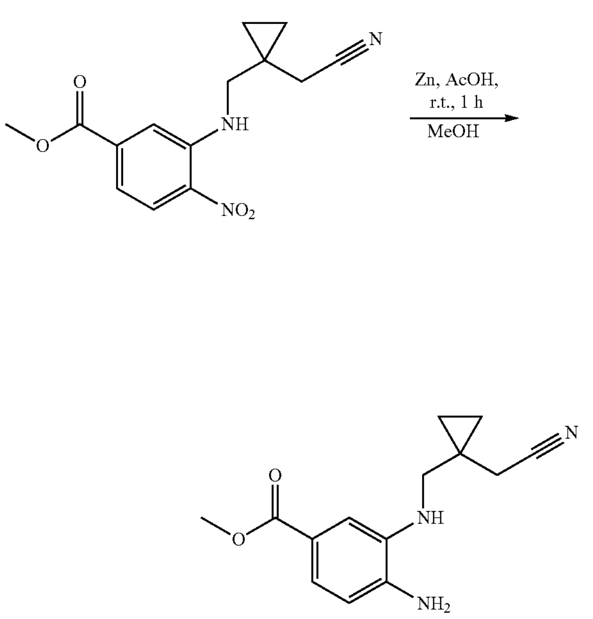

To a mixture of methyl 3-((1-(cyanomethyl)cyclopropyl)methyl)amino)-4-nitrobenzoate (200 mg, 0.69 mmol) dissolved in methanol (8 mL) zinc powder (449 mg, 6.87 mmol) and acetic acid (415 mg, 6.91 mmol) were added at room temperature. The mixture was stirred at room temperature for 1 hour. The mixture was diluted water (15 mL) and extracted with ethyl acetate (3×30 mL). The combined organic layers were washed with brine, dried over anhydrous $Na_2SO_4$, filtered, and concentrated to give a residue in vacuo. The residue was purified by reverse phase column chromatography with the following conditions: Column: Spherical C18, 20-40 μm, 120 g; Mobile Phase A: water (10 mM FA); Mobile Phase B: acetonitrile; Flow rate: 80 mL/min;

Gradient: 40% B-60% B within 20 minutes; detector: 254 nm. The fractions containing desired product were collected at 52% B and concentrated in vacuo to afford compound methyl 4-amino-3-((1-(cyanomethyl)cyclopropyl)methyl)amino)benzoate (141 mg, 0.54 mmol, 78.6% yield). LC-MS m/z: 260 $[M+H]^+$.

6). Synthesis of methyl 2-(chloromethyl)-1-(1-(cyanomethyl)cyclopropyl)methyl)-1H-benzo[d]imidazole-6-carboxylate (Intermediate A-6)

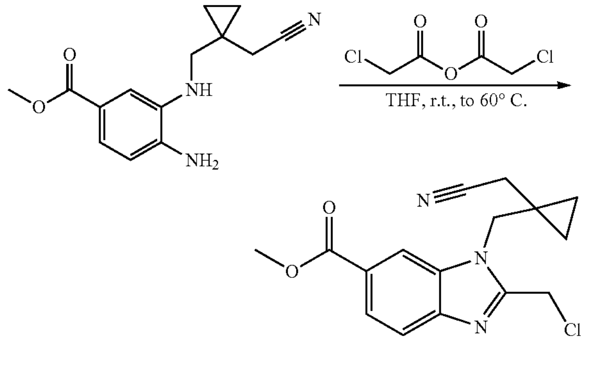

To a solution of methyl 4-amino-3-((1-(cyanomethyl) cyclopropyl)methyl)amino)benzoate (140 mg, 0.54 mmol) in dry THF (5 mL) 2-chloroacetic anhydride (92 mg, 0.54 mmol) was added batchwise at room temperature. The mixture was stirred at 60° C. for 16 hours. The reaction mixture was quenched by water (5 mL) and extracted with ethyl acetate (3x20 mL). The combined organic layers were combined and washed with brine, dried over anhydrous $Na_2SO_4$, filtered, and concentrated to give a residue in vacuo. The residue was purified by reverse phase flash chromatography with the following conditions: column: Spherical C18, 20-40 μm, 120 g; mobile phase A: water (10 mM FA); mobile phase B: acetonitrile; flow rate: 80 mL/min; gradient: 20 minutes 40%-60% B; detector: 254 nm). The mobile phase containing the desired product was collected under 50% B mobile phase and then concentrated in vacuo to obtained methyl 2-(chloromethyl)-1-(1-(cyanomethyl)cyclopropyl)methyl)-1H-benzo[d]imidazole-6-carboxylate (Intermediate A-6)(90 mg, 0.54 mmol, 52.5% yield). LC-MS m/z: 318 $[M+H]^+$.

Example 1-7. Synthesis of methyl 4-(2-chloroacetamide)-3-((1-(cyanomethyl)cyclopropyl)methyl) amino)-5-fluorobenzoate (Intermediate A-7)

1). Synthesis of 2-(1-((5-Bromo-3-fluoro-2-nitrophenyl)amino)methyl)cyclopropyl)acetonitrile

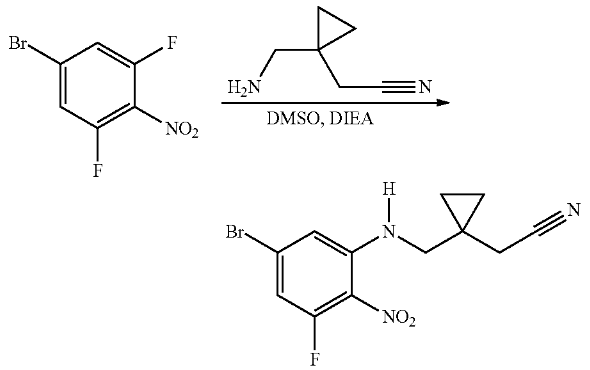

To a mixture of 5-bromo-1,3-difluoro-2-nitrobenzene (1.00 g, 4.20 mmol) and 2-(1-(aminomethyl)-cyclopropyl) acetonitrile (464.2 mg, 4.21 mmol) in dimethyl sulfoxide (20 mL) N,N-diisopropylethylamine (1.63 g, 12.61 mmol) was added. The mixture was stirred at 70° C. for 4 hours. The reaction mixture was diluted with water (15 mL) and extracted with ethyl acetate (3x30 mL). The combined organic layers were washed with brine (2x30 mL), dried over anhydrous sodium sulfate, filtered, and concentrated to give a residue in vacuo. The residue was purified by silica gel column chromatography (PE/EA=5/1) to obtain 2-(1-((5-bromo-3-fluoro-2-nitrophenyl)amino)methyl)-cyclopropyl)acetonitrile (542.0 mg, 1.65 mmol, 39.3% yield). LC-MS m/z: 328, 330 $[M+H]^+$.

2). Synthesis of 2-(1-((2-amino-5-bromo-3-fluorophenyl)amino)methyl)cyclopropyl)acetonitrile

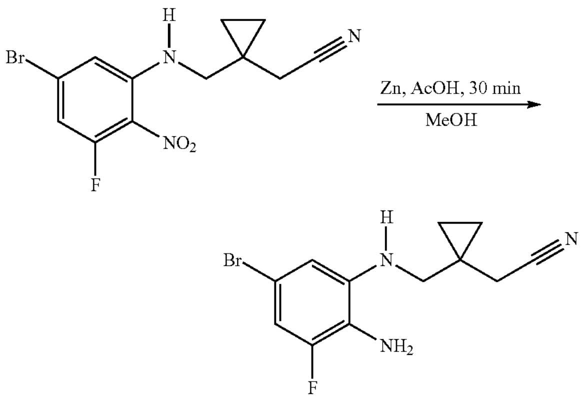

To a solution of 2-(1-((5-bromo-3-fluoro-2-nitrophenyl) amino)methyl)cyclopropyl)acetonitrile (542.0 mg, 1.65 mmol) in methanol (10 mL) was added zinc powder (1.08 g, 16.52 mmol) and acetic acid (996.0 mg, 16.59 mmol). The mixture was stirred at room temperature for 30 minutes. The reaction mixture was diluted with water (10 mL) and extracted with ethyl acetate (3x20 mL). The combined organic layers were washed with brine (2x20 mL), dried over anhydrous sodium sulfate, filtered, and concentrated to give a residue in vacuo. The residue was purified by silica gel column chromatography (PE/EA-2/1) to obtain 2-(1-((2-amino-5-bromo-3-fluorophenyl)amino)methyl)-cyclopropyl)acetonitrile (358.0 mg, 1.21 mmol, 72.9% yield). LC-MS m/z: 298 $[M+H]^+$.

3). Synthesis of methyl 4-amino-3-((1-(cyanomethyl)cyclopropyl)methyl)amino)-5-fluorobenzoate

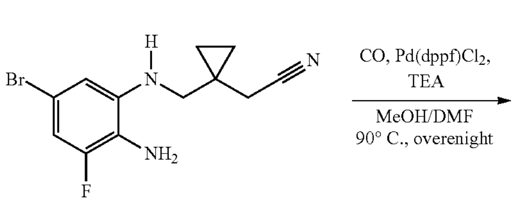

-continued

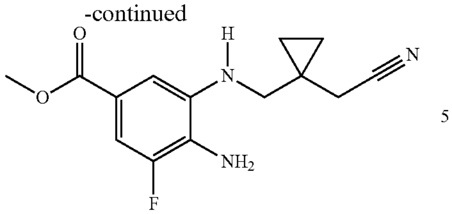

To a mixture of 2-(1-((2-amino-5-bromo-3-fluorophenyl) amino)methyl)cyclopropyl)acetonitrile (358.0 mg, 1.21 mmol) in N,N-dimethylformamide (3 mL)/methanol (10 mL) triethylamine (366.6 mg, 3.62 mmol) and 1,1'-bisdiphenylphosphinoferrocene palladium dichloride (88.5 mg, 0.12 mmol) were added at room temperature. The mixture was warmed to 90° C. for 16 hours under carbon monoxide atmosphere. Cooled to room temperature, the reaction mixture was diluted with water (15 mL) and extracted with ethyl acetate (30 mL××3). The combined organic layers were washed with brine (50 mL), dried over anhydrous sodium sulfate, filtered, and concentrated to give a residue in vacuo. The residue was purified by silica gel column chromatography (PE/EA=1/1) to obtain methyl 4-amino-3-((1-(cyanomethyl)cyclopropyl)-methyl)amino)-5-fluorobenzoate (100.0 mg, 0.36 mmol, 29.8% yield), LC-MS m/z: 278 $[M+H]^+$.

4). Synthesis of methyl 4-(2-chloroacetamide)-3-((1-(cyanomethyl)cyclopropyl)methyl)amino)-5-fluoro-benzoate (Intermediate A-7)

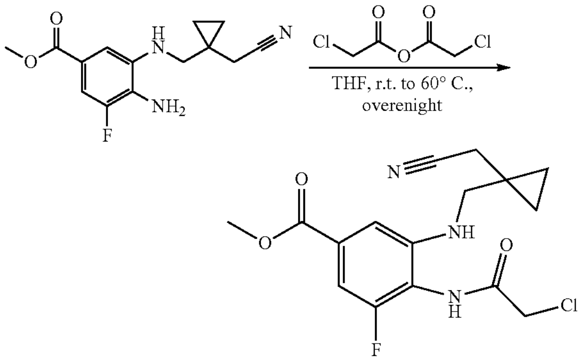

A solution of methyl 4-amino-3-((1-(cyanomethyl)cyclopropyl)methyl)amino)-5-fluorobenzoate (85.0 mg, 0.31 mmol) in THF (4 mL) 2-chloroacetic anhydride (52.5 mg, 0.31 mmol) was added dropwise at room temperature. The mixture was stirred at 60° C. for 16 hours. The mixture was quenched by adding water (5 mL) and extracted with ethyl acetate (3×20 mL). The combined organic layers were washed with brine, dried over anhydrous sodium sulfate, filtered, and concentrated to give a residue in vacuo. The residue was purified by reverse phase flash chromatography under the following conditions (column: Spherical C18, 20-40 um, 120 g; mobile phase A: water (10 mM FA); mobile phase B: acetonitrile; flow rate: 80 mL/min; Gradient: 40% B-60% B in 20 minutes; detector: 254 nm). The mobile phase containing the desired product was collected under 52% B mobile phase and concentrated in vacuo to obtain methyl 4-(2-chloroacetamide)-3-((1-(cyanomethyl) cyclopropyl)methyl)amino)-5-fluorobenzoate (Intermediate A-7)(141 mg, 0.54 mmol, 78.6% yield). LC-MS m/z: 354 $[M+H]^+$.

Example 1-8. Synthesis of methyl 2-(chloromethyl)-1-(oxetan-3-ylmethyl)-1H-benzo[d]imidazole-6-carboxylate (Intermediate A-8)

1). Synthesis of methyl 4-nitro-3-((oxetan-3-ylmethyl)amino)benzoate

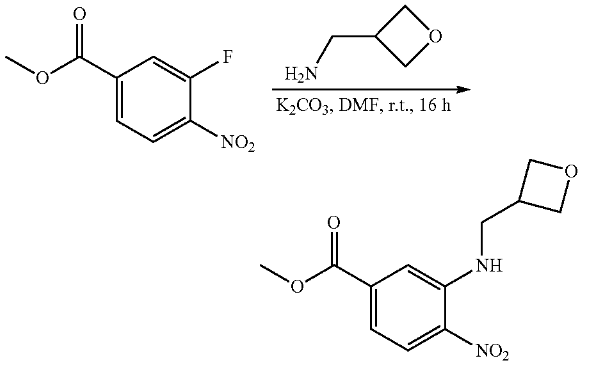

The mixture of methyl 3-fluoro-4-nitrobenzoate (1.60 g, 8.05 mmol), oxetan-3-ylmethanamine (700 mg, 8.05 mmol) and potassium carbonate (2.22 g, 16.10 mmol) in N, N-dimethylformamide (20 mL) was stirred at room temperature for 16 hours. The resulting mixture was diluted with water (200 mL) and extracted with ethyl acetate (50 mL×3). The combined organic layers were washed with brine (50 mL×3), dried over anhydrous sodium sulfate, filtered, and concentrated to give a residue in vacuo. The residue was purified by silica gel column chromatography (petroleum ether/ethyl acetate=1/2) to obtain methyl 4-nitro-3-((oxetan-3-ylmethyl)amino)benzoate (1.50 g, 70.1% yield). LC-MS m/z: 267 $[M+H]^+$.

2). Synthesis of methyl 4-amino-3-((oxetan-3-ylmethyl)amino)benzoate

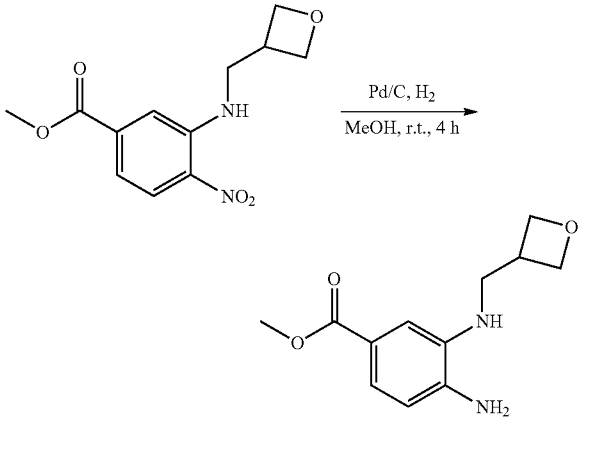

To a solution of methyl 4-nitro-3-((oxetan-3-ylmethyl) amino)benzoate (1.50 g, 5.64 mmol) in methanol (30 mL)

palladium on carbon (200 mg) was added under $N_2$ atmosphere. The resulting mixture was degassed $H_2$ three times and stirred at room temperature for 4 hours under $H_2$ atmosphere. The reaction was filtered, and the filter cake was washed with methanol (20 mL). The filtrate was concentrated to obtain methyl 4-amino-3-((oxetan-3-ylmethyl)amino)benzoate (1.20 g, 90.2% yield), which was used in the next reaction without purification. LC-MS m/z: 237 $[M+H]^+$.

3). Synthesis of methyl 2-(chloromethyl)-1-(oxetan-3-ylmethyl)-1H-benzo[d]imidazole-6-carboxylate

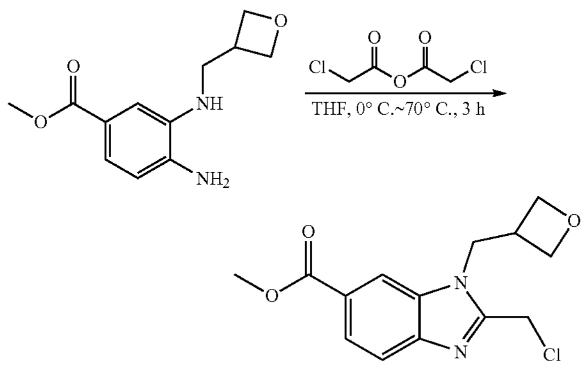

To a solution of methyl 4-amino-3-((oxetan-3-ylmethyl)amino)benzoate (1.20 g, 5.08 mmol) in dry THF (20 mL) 2-chloroacetic anhydride (869 mg, 5.08 mmol) was added slowly at 0° C. After stirred at 0° C. for 30 minutes, the mixture was heated to 70° C. and stirred for 3 hours. The mixture was quenched with water (100 mL) at room temperature and extracted with ethyl acetate (2×0 mL). The organic layer was concentrated in vacuo and purified by silica gel column chromatography (petroleum ether/ethyl acetate=1/1) to obtain methyl 2-(chloromethyl)-1-(oxetan-3-ylmethyl)-1H-benzo[d]imidazole-6-carboxylate (1.00 g, 67.0% yield), LC-MS m/z: 295 $[M+H]^+$.

Example 1-9. Synthesis of methyl 2-(chloromethyl)-1-((3-methyloxetan-3-yl)methyl)-1H-benzo[d]imidazole-6-carboxylate (Intermediate A-9)

1). Synthesis of methyl 3-((3-methoxy-3-yl)methyl)amino)-4-nitrobenzoate

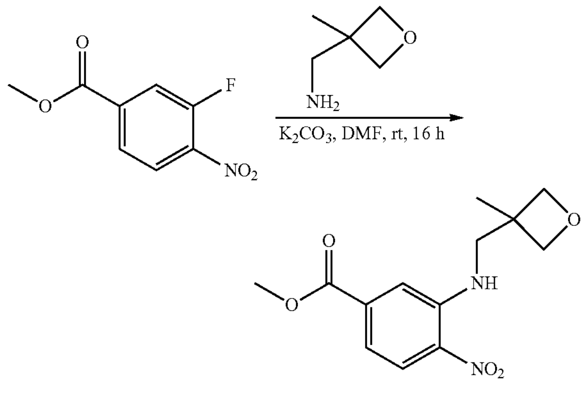

The mixture of methyl 3-fluoro-4-nitrobenzoate (2.00 g, 10.00 mmol), (3-methyloxan-3-yl)carboxamide (1.00 g, 10.00 mmol) and potassium carbonate (4.14 g, 30.00 mmol) in N,N-dimethylformamide (20 mL) was stirred at room temperature for 16 hours. The resulting mixture was diluted with water (200 mL) and extracted with ethyl acetate (50 mL×3). The combined organic layers were washed with brine (50 mL×3), dried over anhydrous sodium sulfate, filtered, and concentrated to give a residue in vacuo. The residue was purified by silica gel column chromatography (petroleum ether/ethyl acetate=2/1) to obtain methyl 3-((3-methoxy-3-yl)methyl)amino)-4-nitrobenzoate (1.96 g, 70.4% yield). LC-MS m/z: 281 $[M+H]^+$.

2). Synthesis of methyl 4-amino-3-((3-methyloxetan-3-yl)methyl)amino)benzoate

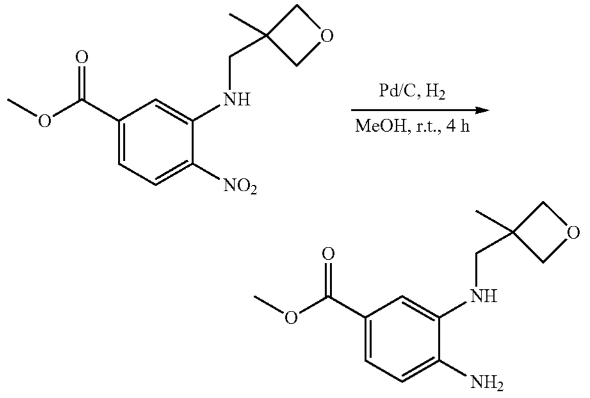

A solution of methyl 3-((3-methoxy-3-yl)methyl)amino)-4-nitrobenzoate (1.96 g, 7.04 mmol) in methanol (20 mL) was added palladium on carbon (400 mg). The resulting mixture was degassed and flushed with hydrogen three times, and then stirred at room temperature for 4 hours. The reaction was filtered, and the filter cake was washed with methanol (20 mL). The filtrate was concentrated to give methyl 4-amino-3-((3-methyloxetan-3-yl)methyl)amino)benzoate (1.55 g, 85.2% yield), which was directly used for the next step without further purification, LC-MS m/z: 251 $[M+H]^+$.

3). Synthesis of methyl 2-(chloromethyl)-1-((3-methyloxetan-3-yl)methyl)-1H-benzo[d]imidazole-6-carboxy-late (Intermediate A-10)

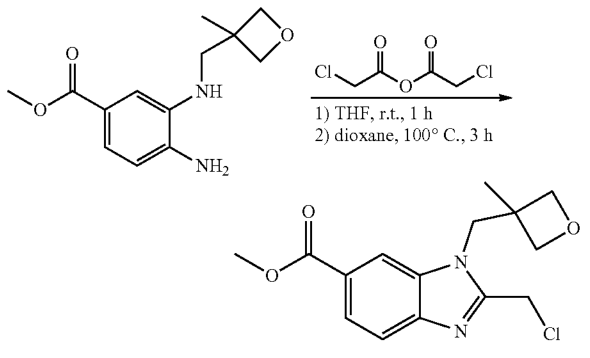

To a solution of methyl 4-amino-3-((3-methyloxetan-3-yl)methyl)amino)benzoate (200 mg, 0.80 mmol) in dry THF (5 mL) 2-chloroacetic anhydride (137 mg, 0.80 mmol) was added dropwise at 0° C. The mixture was stirred at room temperature for 1 hour. The solvent was removed by concentration in vacuo to give a residue. The residue was added dioxane (5 mL) then heated to 100° C. for 3 hours. The mixture was quenched with water (20 mL) at room temperature and extracted with ethyl acetate (2×10 mL). The combined organic layer was concentrated to give a residue in vacuo. The residue was purified by silica gel column chromatography (petroleum ether/ethyl acetate=1/1) to obtain methyl 2-(chloromethyl)-1-((3-methyloxetan-3-yl)methyl)-1H-benzo[d]imidazole-6-carboxy-late (Inthemediate A-10)(200 mg, 81.2% yield). LC-MS m/z: 309 [M+H]$^+$.

Example 1-10. Synthesis of methyl 4-(2-chloroacetamide)-3-((1,2-dimethyl-1H-imidazol-5-yl)methyl) amino)-benzoate (Intermediate A-10)

1). Synthesis of 1,2-dimethyl-1H-imidazole-5-carbaldehyde

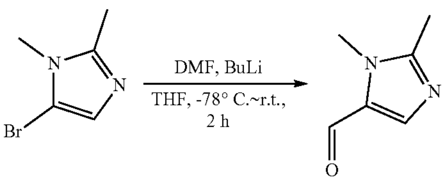

To a solution of 5-bromo-1,2-dimethyl-1H-imidazole (500 mg, 2.86 mmol) in dry tetrahydrofuran (10 mL) n-butyllithium (1.26 mL, 3.15 mmol, 2.5M in hexane) was added at −78° C. The mixture was stirred at −78° C. for 30 min, then N, N-dimethylformamide (626 mg, 8.58 mmol) was slowly added to the mixture at 0° C. The mixture was stirred at room temperature for 2 hours. When completion, the reaction was quenched with water (50 mL) at 0° C. and extracted with ethyl acetate (2×30 mL). The combined organic layer was concentrated in vacuo and purified by silica gel column chromatography (dichloromethane/methanol=20/1) to obtain 1,2-dimethyl-1H-imidazole-5-carbaldehyde (300 mg, 84.6 yield %), LC-MS m/z: 125 [M+H]$^+$.

2). Synthesis of (E)-N-((1,2-dimethyl-1H-imidazol-5-yl)methylene)-2-methylpropane-2-sulfinamide

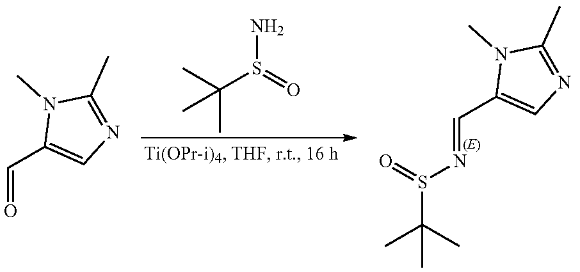

The mixture of 1,2-dimethyl-1H-imidazole-5-carbaldehyde (300 mg, 2.42 mmol), 2-methylpropane-2-sulfoxide (439 mg, 3.63 mmol) and tetraisopropyl titanate (2.06 g, 7.26 mmol) in THF (5 mL) was stirred at room temperature for 16 hours. The resulting mixture was diluted with water (2 mL) and filtered. The filtrate was concentrated in vacuo and purified by silica gel column chromatography (dichloromethane/methanol=20/1) to obtain (E)-N-((1,2-dimethylene)(500 mg, 91.0% yield). LC-MS m/z: 228 [M+H]$^+$.

3). Synthesis of N-((1,2-Dimethyl-1H-imidazol-5-yl)methyl)-2-methylpropane-2-sulfoxide amide

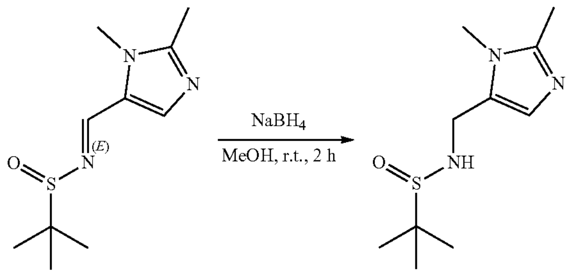

The mixture of (E)-N-((1,2-dimethyl-1H-imidazol-5-yl) methylene)-2-methylpropane-2-sulfoxide amide (500 mg, 2.20 mmol) and boron sodium hydride (167 mg, 4.40 mmol) in methanol (10 mL) was stirred at room temperature for 2 hours. When completion, the reaction was quenched with water (50 mL) at room temperature and extracted with dichloromethane (2×20 mL). The combined organic layer was concentrated in vacuo to obtain N-((1,2-dimethyl-1H-imidazol-5-yl)methyl)-2-methylpropane-2-sulfoxide amide (400 mg: 55.3% yield), which was directly used in the next step without further purification. LC-MS m/z: 230 [M+H]$^+$.

4). Synthesis of 1,2-Dimethyl-1H-imidazol-5-yl)methanamine hydrochloride

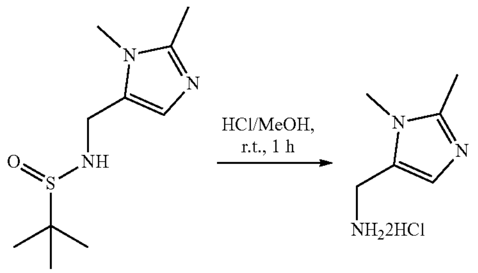

The mixture of N-((1,2-Dimethyl-1H-imidazol-5-yl) methyl)-2-methylpropane-2-sulfoxide amide (400 mg, 1.75 mmol) in HCl (5 mL, 3M in MeOH) was stirred at room temperature for 1 hour. The reaction was filtered to give (1,2-dimethyl-1H-imidazol-5-yl)methanamine hydrochloride (200 mg, 57.8% yield). $^1H$ NMR (400 MHZ, DMSO-$d_6$): δ8.86 (s, 2H), 7.63 (s, 1H), 4.19 (s, 2H), 3.77 (s, 3H), 2.63 (s, 3H).

5). Synthesis of methyl 3-((1,2-dimethyl-1H-imidazol-5-yl)methyl)amino)-4-nitrobenzoate

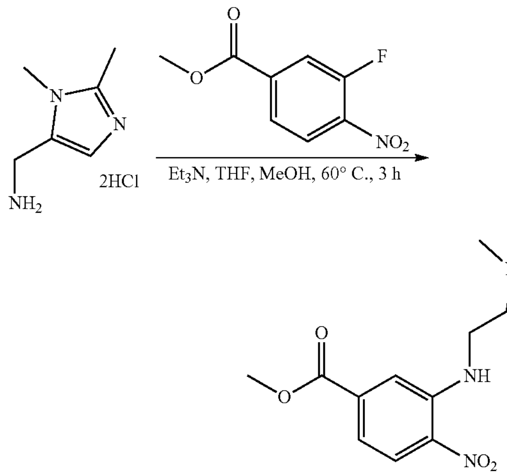

To a mixture of (1,2-dimethyl-1H-imidazol-5-yl)methanamine hydrochloride (200 mg, 1.01 mmol) and methyl 3-fluoro-4-nitrobenzoate (201 mg, 1.01 mmol) in THF (3 mL) and methanol (2 mL) triethylamine (510 mg, 5.05 mmol) was added. The mixture was stirred at 60° C. for 3 h. The resulting mixture was poured into brine (50 mL) and extracted with ethyl acetate (2×20 mL). The combined organic layer was concentrated in vacuo and purified by silica gel column chromatography (dichloromethane/methanol=20/1) to obtain 3-((1,2-dimethyl-1H-imidazol-5-yl)methyl)amino)-4-Nitrobenzoic acid methyl ester (200 mg, 65.1% yield). LC-MS m/z: 305 [M+H]$^+$.

6). Synthesis of methyl 4-amino-3-((1,2-dimethyl-1H-imidazol-5-yl)methyl)amino)benzoate

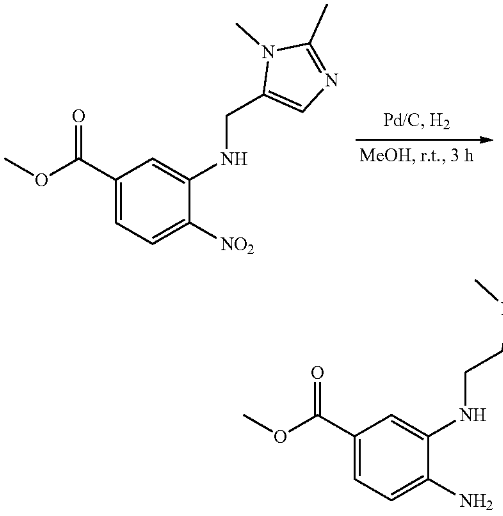

To a solution of methyl 3-((1,2-dimethyl-1H-imidazol-5-yl)methyl)amino)-4-nitrobenzoate (200 mg, 0.66 mmol) in methanol (10 ml) palladium on carbon (20 mg) was added. The resulting mixture was degassed and flushed with hydrogen three times and stirred at room temperature for 3 hours. The reaction mixture was filtered, and washed with methanol (50 mL). The filtrate was concentrated in vacuo to obtain methyl 4-amino-3-((1,2-dimethyl-1H-imidazol-5-yl)methyl)amino)benzoate (150 mg, 82.9% yield) that was directly used in the next step without purification. LC-MS m/z: 275 [M+H]$^+$.

7). Synthesis of methyl 4-(2-chloroacetamide)-3-((1,2-dimethyl-1H-imidazol-5-yl)methyl)amino) benzoate

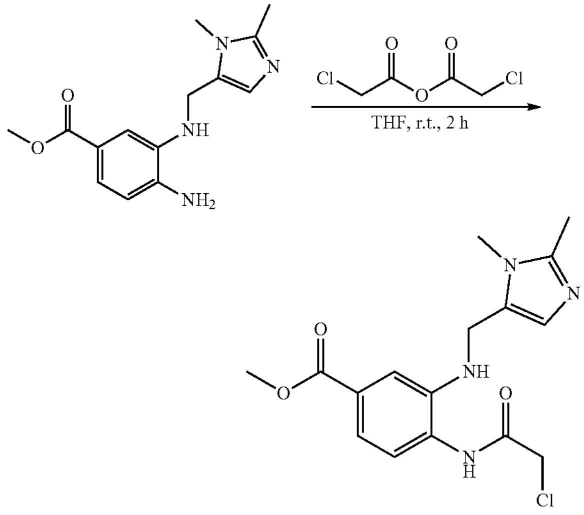

A solution of methyl 4-amino-3-((1,2-dimethyl-1H-imidazol-5-yl)methyl)amino)benzoate (150 mg, 0.55 mmol) and 2-chloroacetic anhydride (142 mg, 0.83 mmol) in THF (3 mL) was stirred at room temperature for 2 hours. The resulting mixture was concentrated in vacuo to give a residue. The residue was purified by silica gel column chromatography (dichloromethane/methanol-20/1) to obtain methyl 4-(2-chloroacetamide)-3-((1,2-dimethyl-1H-imidazol-5-yl)methyl)-amino)benzoate (150 mg, 77.9% yield), LC-MS m/z: 351 [M+H]$^+$.

Example 1-11. Synthesis of methyl 5-(2-chloroacetamide)-6-(1-(cyanomethyl)cyclopropyl)methyl) amino-picolinate 1). Synthesis of methyl 6-((1-(cyanomethyl)cyclopropyl)methyl)amino)-5-nitropicolinate

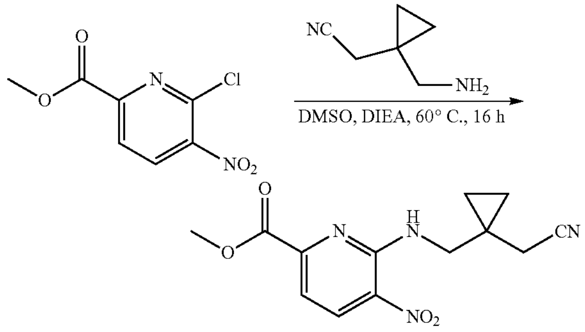

To a solution of methyl 6-chloro-5-nitropicolinate (850 mg, 3.94 mmol) and 2-(1-(aminomethyl) cyclopropyl)acetonitrile (433 mg, 3.94 mmol) in DMSO (10 mL) N,N-diisopropylethylamine (1.52 g, 11.81 mmol) was added. The reaction was stirred at 60° C. for 16 hours. The resulting mixture was poured into brine (20 mL) and extracted with ethyl acetate (20 mL×2). The combined organic layer was concentrated and purified by silica gel column chromatography (petroleum ether/ethyl acetate=1/1) to obtain methyl 6-((1-(cyanomethyl)cyclopropyl)methyl)amino)-5-nitropicolinate (190 mg, 16.7% yield). LC-MS m/z: 291 $[M+H]^+$.

2). Synthesis of methyl 5-amino-6-((1-(cyanomethyl)cyclopropyl)methyl)amino)picolinate

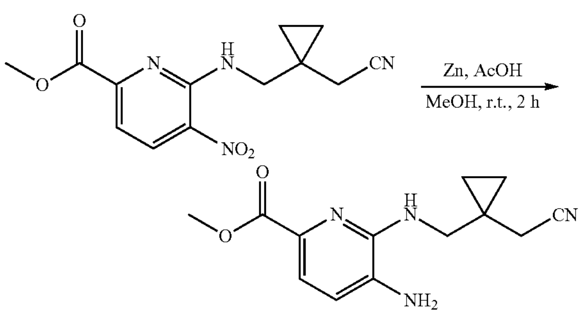

To a solution of methyl 6-((1-(cyanomethyl)cyclopropyl) methyl)amino)-5-nitropicolinate (190 mg, 0.65 mmol) in methanol (5 mL) zinc powder (428 mg, 6.55 mmol) and acetic acid (393 mg, 6.55 mmol) were added at room temperature and the resulting solution was stirred at room temperature for 2 hours. After completion, the resulting mixture was filtered, and concentrated to give a residue in vacuo. The residue was purified by silica gel column chromatography (petroleum ether/ethyl acetate=2/1) to obtain methyl 5-amino-6-((1-(cyanomethyl)cyclopropyl)methyl) amino)picolinate (130 mg, 53.7% yield). LC-MS m/z: 261 $[M+H]^+$.

3). Synthesis of methyl 5-(2-chloroacetamide)-6-(1-(cyanomethyl)cyclopropyl)methyl)aminopicolinate (Intermediate A-11)

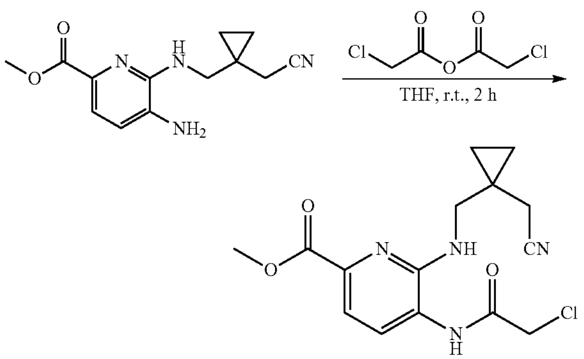

To a solution of methyl 5-amino-6-((1-(cyanomethyl) cyclopropyl)methyl)amino)picolinate (80 mg, 0.31 mmol) in tetrahydrofuran (5 mL) 2-chloroacetic anhydride (79 mg, 0.46 mmol) was added. The resulting mixture was stirred at room temperature for 2 hours. After completion, the mixture was concentrated to give a residue in vacuo. The residue was purified by silica gel column chromatography (petroleum ether/ethyl acetate=1/1) to obtain methyl 5-(2-chloroacetamido)-6-(((1-(cyanomethyl)cyclopropyl)methyl)amino)picolinate (Intermediate A-11)(150 mg, 88% yield). LC-MS m/z: 337 $[M+H]^+$.

Example 1-12. Synthesis of methyl(S)-2-(chloromethyl)-3-(oxetan-2-ylmethyl)-3H-imidazo[4,5-b]pyridine-5-carboxylate (Intermediate A-12)

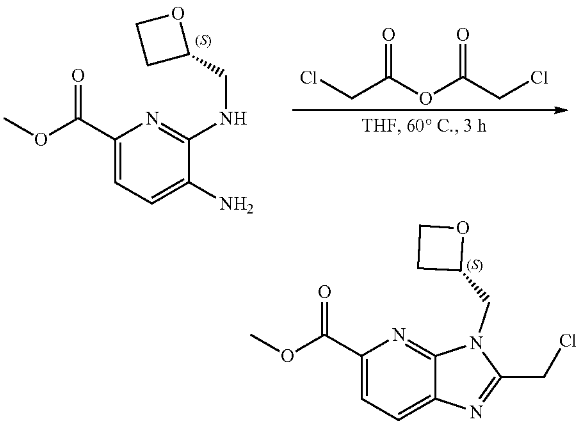

To a solution of methyl(S)-5-amino-6-((oxetan-2-ylmethyl)amino)picolinate (100 mg, 0.42 mmol) in tetrahydrofuran (10 mL) 2-chloroacetic anhydride (101 mg, 0.63 mmol) was added. The reaction mixture was stirred at 60° C. for 3 hours. The resulting mixture was directly concentrated in vacuo to give methyl(S)-2-(chloromethyl)-3-(oxetan-2-ylmethyl)-3H-imidazo[4,5-b]pyridine-5-carboxylate (Intermediate A-12)(140 mg).

Example 1-13. Synthesis of methyl 5-(2-chloroacetamide)-6-(1-ethyl-1H-imidazol-5-yl)methyl)amino-picolinate (Intermediate A-13)

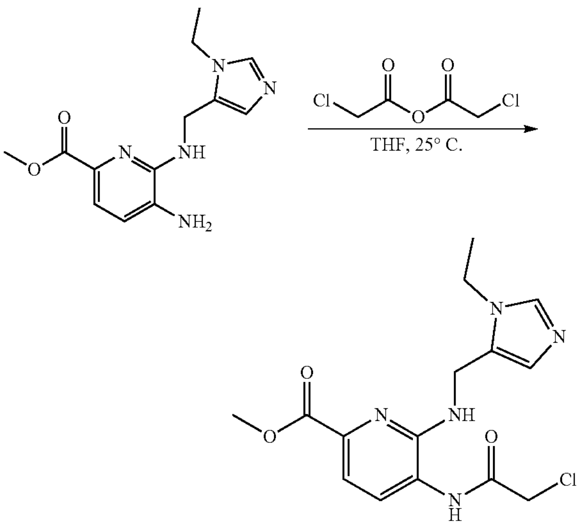

To a solution of methyl 5-amino-6-((1-ethyl-1H-imidazol-5-yl)methyl)amino)picolinate (150 mg, 0.54 mmol) in THF (5 mL) 2-chloroacetic anhydride (138 mg, 0.82 mmol) was added dropwise. The mixture was stirred at 25° C. for 16 hours. Then the mixture was concentrated to give a residue in vacuo. The residue was purified by silica gel column chromatography (dichloromethane/methanol=10/1) to obtain methyl 5-(2-chloroacetamide)-6-(1-ethyl-1H-imidazol-5-yl)methyl)amino-picolinate (180 mg, 94.7% yield). LC-MS m/z: 352 $[M+H]^+$.

Example 1-14. Synthesis of methyl 4-(2-chloroacetamide)-3-((1-(cyanomethyl)cyclopropyl)methyl) amino)-benzoate (Intermediate A-14)

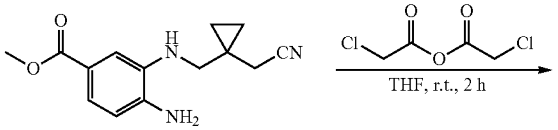

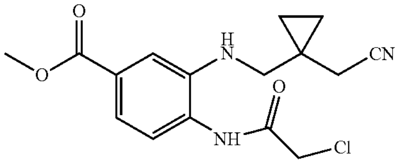

To a solution of methyl 4-amino-3-((1-(cyanomethyl) cyclopropyl)methyl)amino)benzoate (500 mg, 1.93 mmol) in THF (5 mL) 2-chloroacetic anhydride (494 mg, 2.89 mmol) was added. The mixture was stirred at room temperature for 2 hours. After completion, the mixture was concentrated and purified by silica gel column chromatography (petroleum ether/ethyl acetate-2/1) to obtain methyl 4-(2-chloroacetamide)-3-((1-(cyanomethyl)cyclopropyl) methyl)-amino)-benzoate (Intermediate A-14)(400 mg, 61.8% yield). LC-MS m/z: 336 $[M+H]^+$.

Example 1-15. Synthesis of(S)—N-(4-Bromo-2-fluoro-6-((oxetan-2-ylmethyl)amino)phenyl)-2-chloroacetamide e (Intermediate A-15)

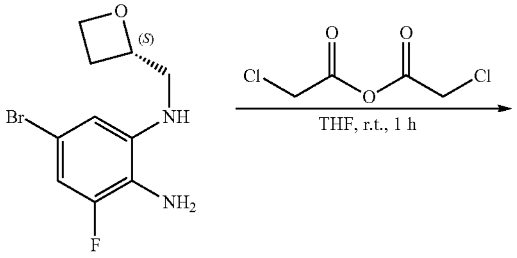

-continued

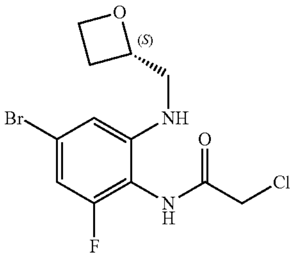

To a solution of(S)-5-bromo-3-fluoro-N1-(oxetan-2-ylmethyl)benzene-1,2-diamine (300 mg, 1.09 mmol) in dry THF (5 mL) 2-chloroacetic anhydride (241 mg, 1.42 mmol) was added. The mixture was stirred at room temperature for 1 hour. The mixture was diluted with water (10 mL) then extracted with ethyl acetate (10 mL×3). The combined organic layer was concentrated in vacuo and purified by silica gel column chromatography (petroleum ether/ethyl to acetate=1/1) obtain(S)—N-(4-bromo-2-fluoro-6-((oxetane-2-ylmethyl)amino)phenyl)-2-chloroacetamide (230 mg, 59.9% yield). LC-MS m/z: 353 $[M+H]^+$.

Example 1-16. Synthesis of N-(4-bromo-2-((1-(cyanomethyl)cyclopropyl)methyl)amino)-6-fluorophenyl)-2-chloroacetamide (Intermediate A-16)

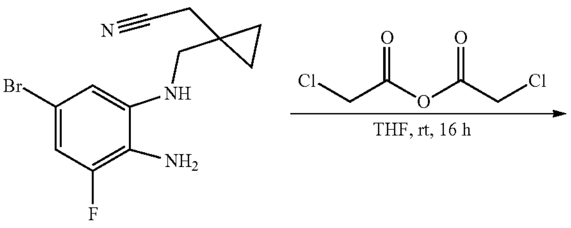

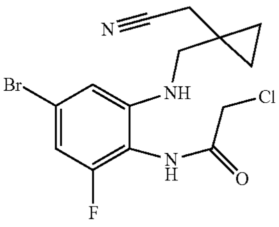

To a solution of 2-(1-((2-amino-5-bromo-3-fluorophenyl) amino)methyl)cyclopropyl)acetonitrile (150 mg, 0.50 mmol) in dry THF (5 mL) 2-chloroacetic anhydride (129 mg, 0.76 mmol) was slowly added. The mixture was stirred at room temperature for 1 hour. The mixture was diluted with water (10 mL) then extracted with ethyl acetate (3×10 mL). The combined organic layer was concentrated in vacuo and purified by silica gel column chromatography (petroleum ether/ethyl acetate=3/1) to give N-(4-bromo-2-((1-(cyanomethyl)cyclopropyl))methyl)amino)-6-fluorophenyl)-2-chloroacetamide (218 mg, crude). LC-MS m/z: 376 $[M+H]^+$.

Example 1-17. Synthesis of methyl 4-(2-chloroacetamide)-3-((1-ethyl-1H-imidazol-5-yl)methyl) amino)-5-fluorobenzoate (Intermediate A-17)

1). Synthesis of methyl 4-amino-3-((1-ethyl-1H-imidazol-5-yl)methyl)amino)-5-fluorobenzoate

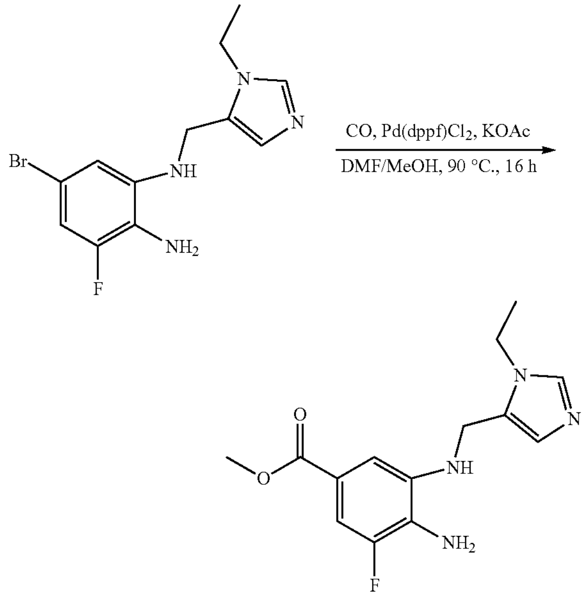

Potassium acetate (470 mg, 4.80 mmol) and 1,1'-bisdiphenylphosphinoferrocene palladium dichloride (117 mg, 0.16 mmol) were added to a mixture of 5-bromo-N1-((1-ethyl-1H-imidazol-5-yl)methyl)-3-fluorobenzene-1,2-diamine (500 mg, 1.60 mmol) in methanol (5 mL) and N,N-dimethylformamide (5 mL). The mixture was degassed with carbon monoxide three times and stirred at 90° C. for 16 hours under carbon monoxide atmosphere. After completion, the mixture was diluted with water (30 mL) and extracted with ethyl acetate (30 mL×2). The combined organic layers were washed with brine (20 mL×2), dried over anhydrous sodium sulfate, filtered, and concentrated to give a residue in vacuo. The residue was purified by silica gel column chromatography (dichloromethane/methanol=20/1) to give methyl 4-amino-3-((1-ethyl-1H-imidazol-5-yl)methyl)amino)-5-fluorobenzoate (150 mg, 32.1% yield). LC-MS m/z: 293 $[M+H]^+$.

2). Synthesis of methyl 4-(2-chloroacetamide)-3-((1-ethyl-1H-imidazol-5-yl)methyl)amino)-5-fluorobenzoate

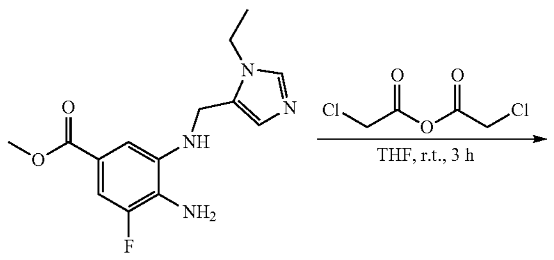

-continued

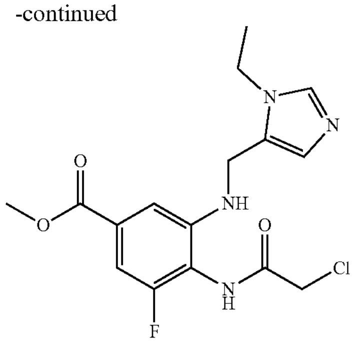

To a solution of methyl 4-amino-3-((1-ethyl-1H-imidazol-5-yl)methyl)amino)-5-fluorobenzoate (150 mg, 0.51 mmol) in THF (5 mL) 2-chloroacetic anhydride (176 mg, 1.02 mmol) was slowly added at room temperature. The reaction was stirred at room temperature for 3 hours. After completion, the reaction was quenched with water (30 mL) and extracted with ethyl acetate (2×20 mL). The organic phase was concentrated in vacuo and then purified by silica gel column chromatography (dichloromethane/methanol=20/1) to obtain methyl 4-(2-chloroacetamide)-3-((1-ethyl-1H-imidazol-5-yl)methyl)amino)-5-fluorobenzoate (130 mg, 69.3% yield). LC-MS m/z: 369 $[M+H]^+$.

Example 1-18. Synthesis of methyl 4-(2-chloroacetamido)-3-((1-(cyclopropylmethyl)-1H-imidazol-5-yl)-methyl)aminobenzoate (Intermediate A-18)

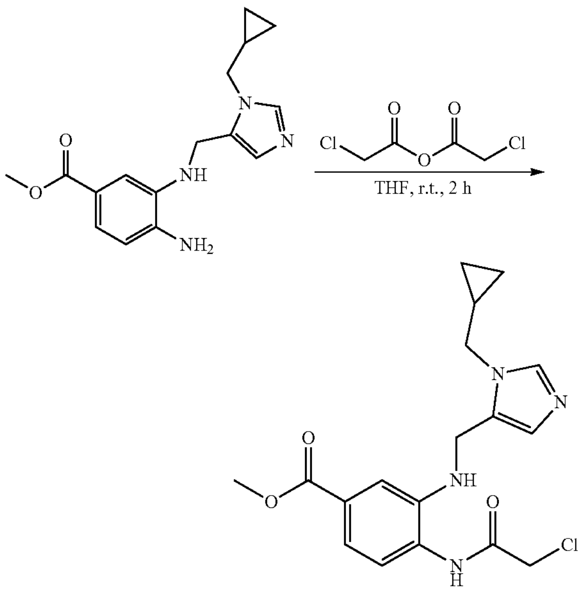

To a solution of methyl 4-amino-3-((1-(cyclopropylmethyl)-1H-imidazol-5-yl)methyl)aminobenzoate (500 mg, 1.67 mmol) in dry THF (10 mL) chloroacetic anhydride (715 mg, 4.18 mmol) was slowly added at room temperature. The resulting mixture was stirred at room temperature for 2 hours. After completion, the solvent was removed by concentration in vacuo, The residue was purified by silica gel column chromatography (dichloromethane/methanol=20/1) to obtain methyl 4-(2-chloroacetamide)-3-((1-(cyclopropylmethyl)-1H-imidazol-5-yl)-methyl)aminobenzoate (Intermediate A-18)(400 mg, 63.5% yield). LC-MS m/z: 377 [M+H]+.

Example 1-19. Synthesis of methyl 2-(chloromethyl)-1-((1-(cyclopropylmethyl)-1H-imidazol-5-yl)methyl)-1H-benzo[d]imidazole-6-carboxylate (IntermediateA-19)

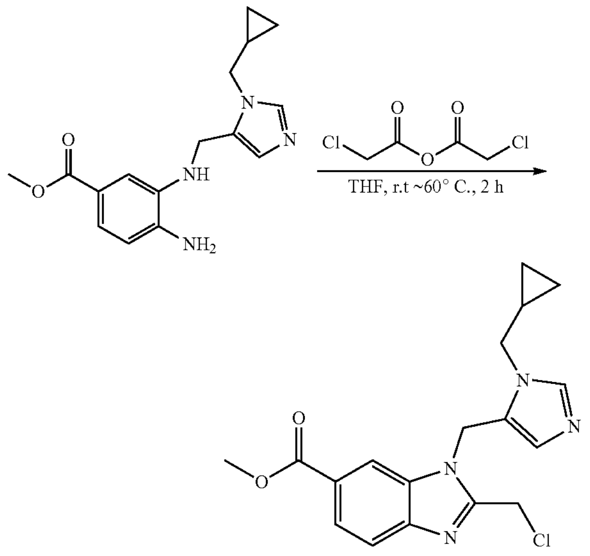

To a solution of methyl 4-amino-3-((1-(cyclopropylmethyl)-1H-imidazol-5-yl)methyl)aminobenzoate (500 mg, 1.67 mmol) in dry THF (10 mL) 2-chloroacetic anhydride (715 mg, 4.18 mmol) was added at room temperature solution. The resulting mixture was stirred at room temperature for 2 hours then raised to 60° C. stirred overnight. After completion, the solvent was removed by concentration in vacuo and the residue was purified by silica gel column chromatography (dichloromethane/methanol=20/1) to obtain methyl 2-(chloromethyl)-1-((1-(cyclopropylmethyl)-1H-imidazol-5-yl)methyl)-1H-benzo[d]imidazole-6-carboxylate (100 mg, 16.7% yield). LC-MS m/z: 359 [M+H]+.

Example 1-20. Synthesis of methyl 2-(chloromethyl)-1-methyl-1H-benzo[d]imidazole-6-carboxylate (Intermediate A-20)

1). Synthesis of methyl 3-(methylamino)-4-nitrobenzoate

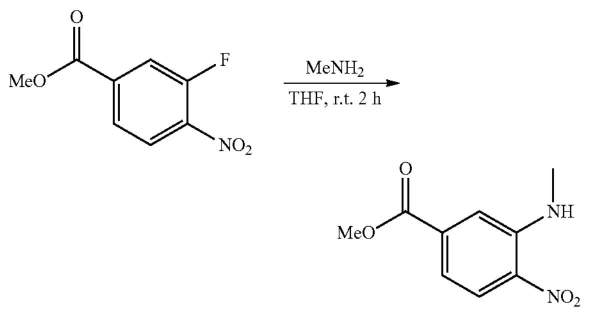

The solution of methyl 3-fluoro-4-nitrobenzoate (2.00 g, 10.00 mmol) and methylamine (10 mL, 2 M in tetrahydrofuran) in THF (30 mL) was stirred at room temperature for 2 hours. After completion, it was concentrated in vacuo and was purified by silica gel column chromatography (petroleum ether/ethyl acetate=1/1) to obtain methyl 3-(methylamino)-4-nitrobenzoate (1.80 g, 85.0% yield). LC-MS m/z: 211 [M+H]+.

2). Synthesis of methyl 4-amino-3-(methylamino)benzoate

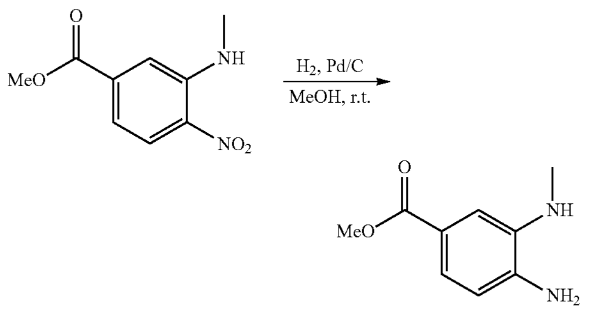

To a solution of methyl 3-(methylamino)-4-nitrobenzoate (1.80 g, 8.57 mmol) in methanol (20 mL) was added palladium on carbon (900 mg) at room temperature under $N_2$ atmosphere. The resulting mixture was degassed and flushed with hydrogen three times and stirred at room temperature for 3 hours. After completion, the reaction solution was filtered, and the filter cake was washed with methanol (20 mL). The filtrate was concentrated to give a residue in vacuo. The residue was purified by silica gel column chromatography (petroleum ether/ethyl acetate=16/9) to obtain methyl 4-amino-3-(methylamino)benzoate (1.2 g, 77.8% yield). LC-MS m/z: 181 [M+H]+.

3). Synthesis of methyl 2-(chloromethyl)-1-methyl-1H-benzo[d]imidazole-6-carboxylate

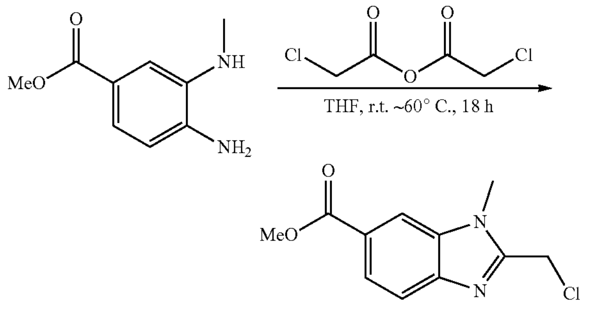

To a solution of methyl 4-amino-3-(methylamino)benzoate (1.2 g, 2.83 mmol) in dry THF (20 mL) was slowly added chloroacetic anhydride (2.27 g, 5.66 mmol) at room temperature. The reaction was stirred at room temperature for 2 hours, then the reaction mixture was heated to 60° C. for 16 hours. After completion, it was concentrated to give a residue in vacuo. The residue was purified by silica gel column chromatography (petroleum ether/ethyl acetate=3/1)

to obtain methyl 2-(chloromethyl)-1-methyl-1H-benzo[d]imidazole-6-carboxylate (1.4 g, 88.2% yield). LC-MS m/z: 239 $[M+H]^+$.

Example 1-21. Synthesis of methyl 4-(2-chloroacetamide)-3-((1-isopropyl-1H-imidazol-5-yl)methyl)amino)-benzoate (Intermediate A-21)

1). Synthesis of (E)-N-((1-isopropyl-1H-imidazol-5-yl)methylene)-2-methylpropane-2-sulfoxide amide

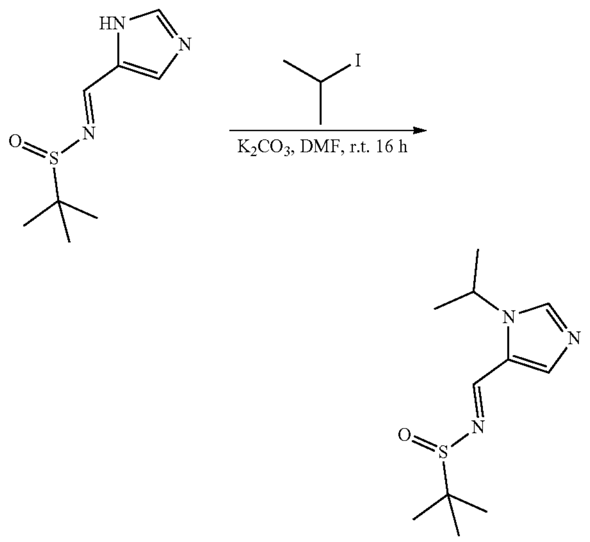

The mixture of (E)-N-((1H-imidazol-5-yl)methylene)-2-methylpropane-2-sulfoxide amide (5.00 g, 25.12 mmol), potassium carbonate (10.40 g, 75.36 mmol) and 2-iodopropane (8.54 g, 50.25 mmol) in N,N-dimethylacetamide (100 mL) was stirred at room temperature for 16 hours. After completion, it was diluted with water (200 mL) and extracted with ethyl acetate (50 mL×3). The combined organic layers were washed with brine (50 mL×3), dried over anhydrous sodium sulfate, filtered, and concentrated to give a residue in vacuo. The residue was purified by silica gel column chromatography (dichloromethane/methanol=12/1) to give (E)-N-((1-isopropyl-1H-imidazol-5-yl)methylene)-2-methan propane-2-sulfoxide amide (4.8 g, 73.4% yield). LC-MS m/z: 242 $[M+H]^+$.

2). Synthesis of N-((1-isopropyl-1H-imidazol-5-yl)methyl)-2-methylpropane-2-sulfoxide amide

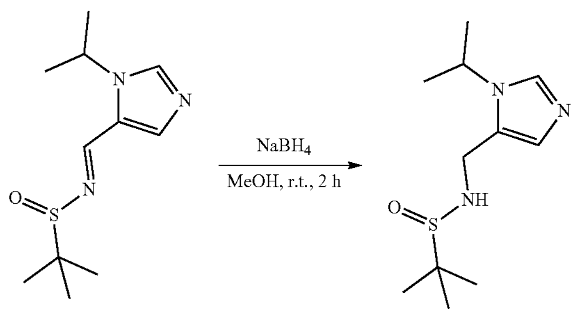 [SMILES: CC(C)n1cncc1/C=N/S(=O)C(C)(C)C ; "NaBH4" ; CC(C)n1cncc1CNS(=O)C(C)(C)C]

To a solution of (E)-N-((1-isopropyl-1H-imidazol-5-yl)methylene)-2-methylpropane-2-sulfoxide amide (4.80 g, 19.92 mmol) in methanol (30 mL) sodium borohydride (2.28 g, 59.75 mmol) was slowly added at room temperature. The resulting mixture was stirred at room temperature for 2 hours. After completion, water (200 mL×2) was added to quench the reaction, and extracted with ethyl acetate (200 mL). The combined organic layers were washed with brine (200 mL×2), dried over anhydrous sodium sulfate, filtered, and concentrated in vacuo to obtain N-((1-isopropyl-1H-imidazol-5-yl)methyl)-2-methylpropane-2-sulfoxide amide (4.5 g, 87.5% yield), LC-MS m/z: 244 $[M+H]^+$.

3). Synthesis of (1-isopropyl-1H-imidazol-5-yl)methanamine

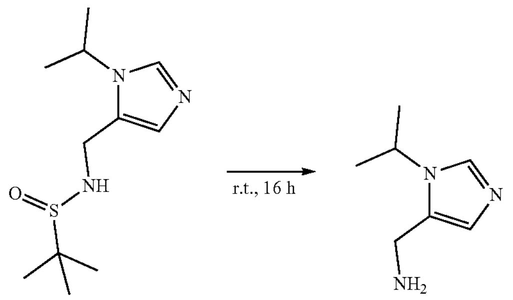

The mixture of N-((1-isopropyl-1H-imidazol-5-yl)methyl)-2-methylpropane-2-sulfoxide amide (4.50 g, 18.44 mmol) and AcOH (50 mL, 3 M in methanol) was stirred for 16 hours at room temperature. After completion, the reaction mixture was concentrated in vacuo to obtain (1-isopropyl-1H-imidazol-5-yl)methanamine (2.4 g, 93.6% yield). LC-MS m/z: 140 $[M+H]^+$.

4). Synthesis of methyl 3-((1-isopropyl-1H-imidazol-5-yl)methyl)amino)-4-nitrobenzoate

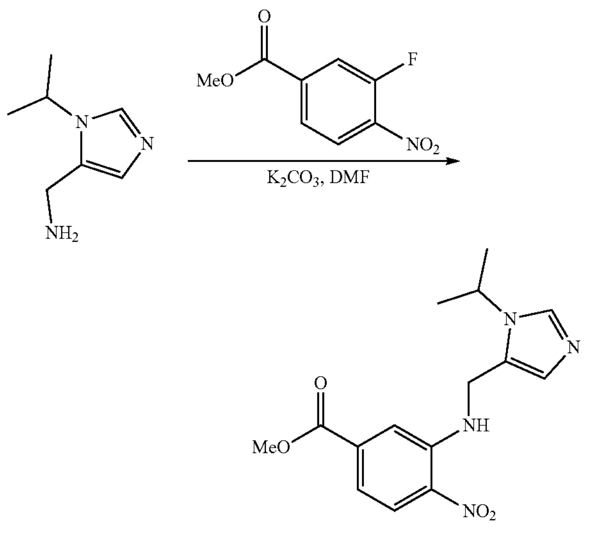

The mixture of (1-isopropyl-1H-imidazol-5-yl)methanamine (3.0 g, 17.27 mmol), methyl 3-fluoro-4-nitrobenzoate (4.14 g, 20.72 mmol) and potassium carbonate (4.79 g, 34.53 mmol) in N,N-dimethylformamide (50 mL) was stirred at room temperature for 16 hours. After completion, it was diluted with water (200 mL) and extracted with ethyl acetate (50 mL×3). The combined organic layers were washed with brine (50 mL×3), 10 dried over anhydrous sodium sulfate, filtered, and concentrated to give a residue in vacuo. The residue was purified by silica gel column chromatography (dichloromethane/methanol=12/1) to obtained methyl 3-((1-isopropyl-1H-imidazol-5-yl)methyl)amino)-4-nitrobenzoate (1.2 g, 21.9% yield). LC-MS m/z: 319 $[M+H]^+$. 5). Synthesis of methyl 4-amino-3-((1-isopropyl-1H-imidazol-5-yl)methyl)amino)benzoate

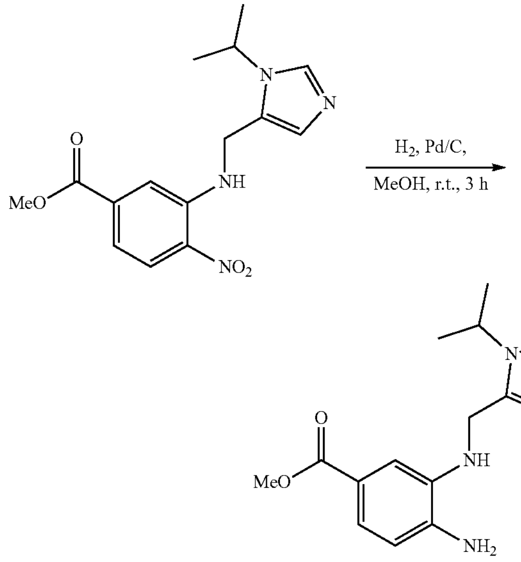

To a solution of methyl 3-((1-isopropyl-1H-imidazol-5-yl)methyl)amino)-4-nitrobenzoate (1.2 g, 3.78 mmol) in methanol (30 mL) palladium on carbon (600 mg. 5.6 mmol) was added at room temperature. The resulting mixture was degassed and flushed with hydrogen three times, and the reaction was stirred at room temperature for 3 hours under $H_2$ atmosphere. After completion, filter and wash the filter cake with methanol (50 mL). After the filtrate was concentrated to give a residue in vacuo, the residue was purified by silica gel column chromatography (dichloromethane/methanol=13/1) to obtain 4-amino-3-((1-isopropyl-1H-imidazol-5-20 yl)methyl)amino)methyl benzoate (750 mg, 69.0% yield). LC-MS m/z: 289 $[M+H]^+$.

6). Synthesis of methyl 4-(2-chloroacetamido)-3-((1-isopropyl-1H-imidazol-5-yl)methyl)amino)benzoate

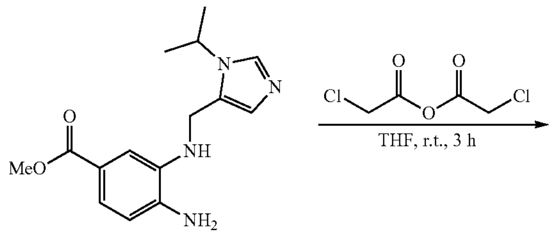

-continued

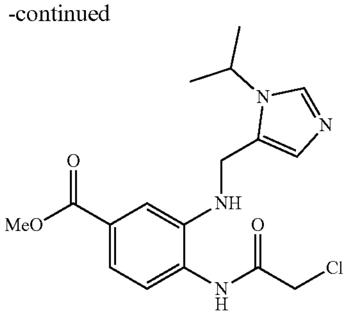

To a solution of methyl 4-amino-3-((1-isopropyl-1H-imidazol-5-yl)methyl)amino)benzoate (400 mg, 1.39 mmol) in dry THF (8 mL) added chloroacetic anhydride (595 mg, 3.48 mmol) was slowly at room temperature. The reaction was stirred at for 3 hours. After completion, the reaction solution was concentrated in vacuo, The residue was purified by silica gel column chromatography (dichloromethane/methanol=10/1) to obtain 4-(2-chloroacetamido)-3-((1-isopropyl-1H)-imidazol-5-yl)methyl)amino)methyl benzoate (450 mg, 88.8% yield). LC-MS m/z: 365 $[M+H]^+$.

Example 1-22. Synthesis of methyl 4-(2-chloroacetamido)-3-((1-(cyclopropylmethyl)-1H-imidazol-5-yl)methyl)aminobenzoate (Intermediate A-22)

1). Synthesis of (E)-N-((1H-imidazol-5-yl)methylene)-2-methylpropane-2-sulfoxide amide

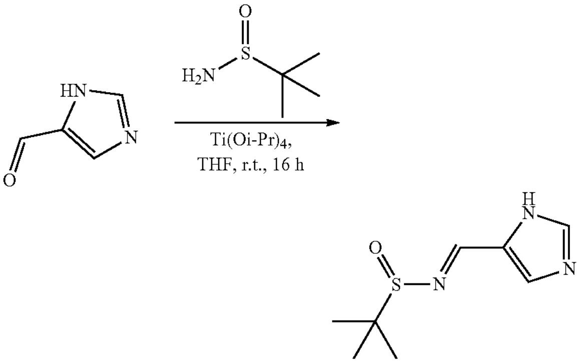

To a mixture of 1H-imidazole-5-carbaldehyde (5.00 g, 52.08 mmol) and 2-methylpropane-2-sulfoxide amide (9.39 g, 78.12 mmol) in THF (100 mL) titanium tetraisopropoxide (44.40 g, 156.25 mmol) was added at room temperature. The resulting mixture was stirred at room temperature for 16 hours. After completion, it was diluted with water (100 mL), filtered, and the filter cake was washed with ethyl acetate (150 mL). And the aqueous layer was extracted with ethyl acetate (100 mL×2). The combined organic layers were washed with brine (250 mL×3), dried over anhydrous sodium sulfate, filtered, and concentrated to give a residue in vacuo. The residue was purified by silica gel column chromatography (dichloromethane/methanol=12/1) to obtain (E)-N-((1H-imidazol-5-yl)methylene)-2-methylpropane-2-sulfoxide amide (9.00 g, 86.4% yield). LC-MS m/z: 200 $[M+H]^+$.

2). Synthesis of (E)-N-((1-(cyclopropylmethyl)-1H-imidazol-5-yl)methylene)-2-methylpropane-2-sulfoxide amide

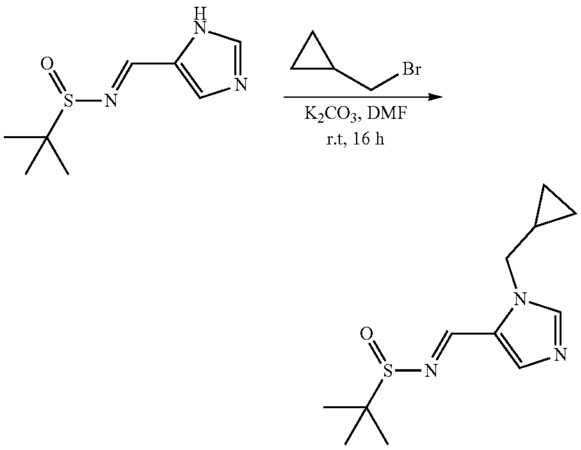

To a mixture of (E)-N-((1H-imidazol-5-yl)methylene)-2-methylpropane-2-sulfoxide amide (3.00 g, 15.10 mmol) and potassium carbonate (6.25 g, 45.30 mmol) in N,N-dimethylformamide (50 mL) (bromomethyl)cyclopropane (4.08 g, 30.20 mmol) was added. The resulting mixture was stirred at room temperature for 16 hours. After completion, the resulting mixture was diluted with water (200 mL) and extracted with ethyl acetate (150 mL×3). The combined organic layers were washed with brine (150 mL×3), dried over anhydrous sodium sulfate, filtered, and concentrated to give a residue in vacuo. The residue was purified by silica gel column chromatography (dichloromethane/methanol=13/1) to give (E)-N-((1-(cyclopropylmethyl)-1H-imidazol-5-yl)methylene-2-methylpropane-2-sulfoxide amide (2.8 g, yield 73.4%). LC-MS m/z: 254 [M+H]$^+$.

3). Synthesis of N-((1-(cyclopropylmethyl)-1H-imidazol-5-yl)methyl)-2-methylpropane-2-sulfoxide amide

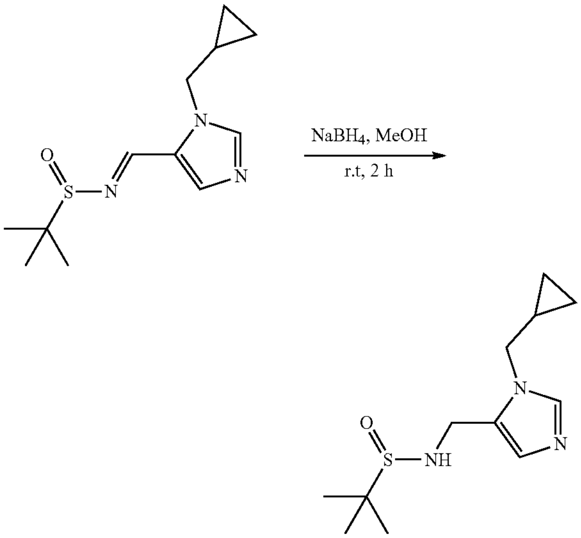

To a solution of (E)-N-((1-(cyclopropylmethyl)-1H-imidazol-5-yl)methylene)-2-methylpropane-2-sulfoxide amide (2.80 g, 11.60 mmol) in methanol (20 mL) sodium borohydride (1.26 g, 33.2 mmol) was added slowly. The reaction was stirred at room temperature for 2 hours. After completion, water (200 mL) was added to quench the reaction, and extracted with ethyl acetate (60 mL×3). The combined organic layers were washed with brine (200 mL×2), dried over anhydrous sodium sulfate, filtered, and concentrated in vacuo to obtain N-((1-(Cyclopropylmethyl)-1H-imidazol-5-yl)methyl)-2-methylpropane-2-sulfoxide amide (2.55 g, 90.9% yield). LC-MS m/z: 256 [M+H]$^+$.

4). Synthesis of (1-(cyclopropylmethyl)-1h-imidazol-5-yl)methylamine hydrochloride

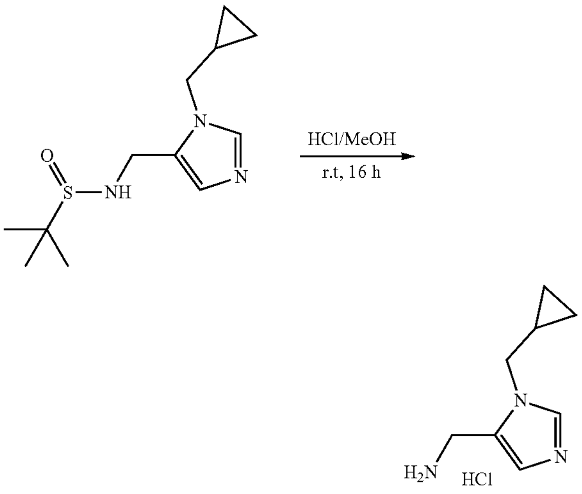

The mixture of N-((1-(cyclopropylmethyl)-1H-imidazol-5-yl)methyl)-2-methylpropane-2-sulfoxide amide (2.55 g, 10.00 mmol) and HCl (30 mL, 3 M in methanol) was stirred for 16 hours at room temperature. After completion, the mixture was concentrated to obtain (1-(cyclopropylmethyl)-1H-imidazol-5-yl)methanamine hydrochloride (1.87 g, 99.3% yield). LC-MS m/z: 152 [M+H]$^+$.

5). Synthesis of methyl 3-((1-(cyclopropylmethyl)-1H-imidazol-5-yl)methyl)amino)-4-nitrobenzoate

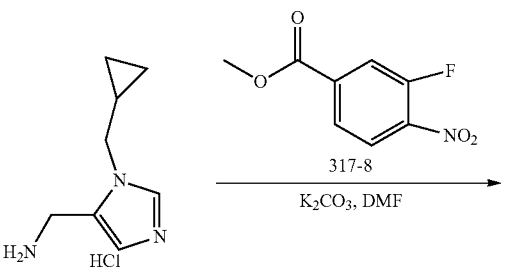

317-8

317-7

-continued

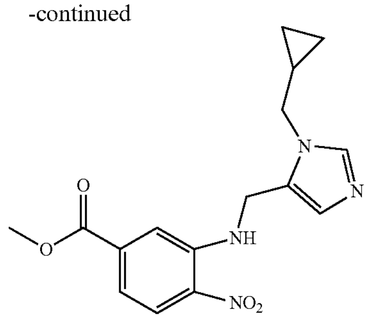

317-9

The mixture of (1-(cyclopropylmethyl)-1H-imidazol-5-yl)methanamine hydrochloride (1.87 g, 9.93 mmol), methyl 3-fluoro-4-nitrobenzoate (2.98 g, 14.90 mmol) and potassium carbonate (2.76 g, 19.87 mmol) in N,N-dimethylformamide (30 mL) was stirred at room temperature for 16 hours. After completion, the resulting mixture was diluted with water (200 mL) and extracted with ethyl acetate (50 mL×3). The combined organic layers were washed with brine (50 mL×3), dried over anhydrous sodium sulfate, filtered, and concentrated in vacuo. The residue was purified by silica gel column chromatography (dichloromethane/methanol=13/1) to obtain methyl 3-((1-(cyclopropylmethyl)-1H-imidazol-5-yl)methyl)amino)-4-nitrobenzoate (1.5 g, 45.7% yield). LC-MS m/z: 331 $[M+H]^+$.

6). Synthesis of methyl 4-amino-3-((1-(cyclopropylmethyl)-1H-imidazol-5-yl)methyl)aminobenzoate

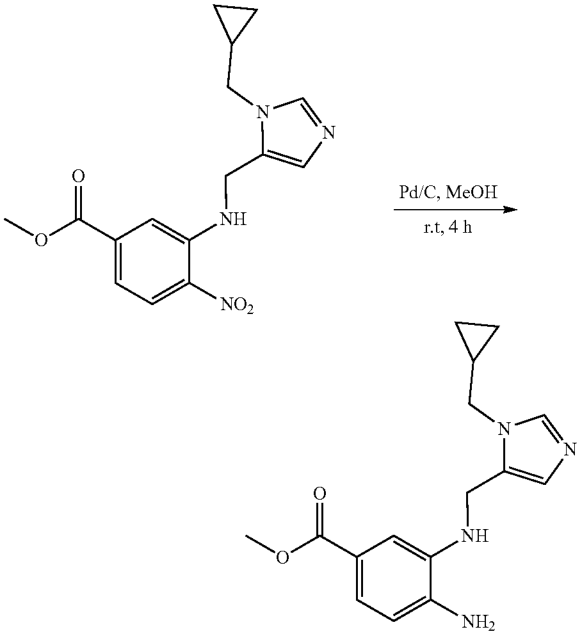

To a solution of methyl 3-((1-(cyclopropylmethyl)-1H-imidazol-5-yl)methyl)amino)-4-nitrobenzoate (1.50 g, 4.55 mmol) in methanol (40 mL) palladium on carbon (750 mg) was added at room temperature. The resulting mixture was degassed and flushed with hydrogen three times, and the reaction was stirred at room temperature for 4 hours. After completion, the reaction was filtered, and the filter cake was washed with methanol (50 mL). The filtrate was concentrated to give a residue in vacuo. The residue was purified by silica gel column chromatography (dichloromethane/methanol=13/1) to obtain 4-amino-3-((1-(cyclopropylmethyl)-1H-imidazol-5-yl))methyl)aminobenz-oate (1.1 g, 80.7% yield). LC-MS m/z: 301 $[M+H]^+$.

7). Synthesis of methyl 4-(2-chloroacetamide)-3-((1-(cyclopropylmethyl)-1H-imidazol-5-yl)methyl)-aminobenzoate

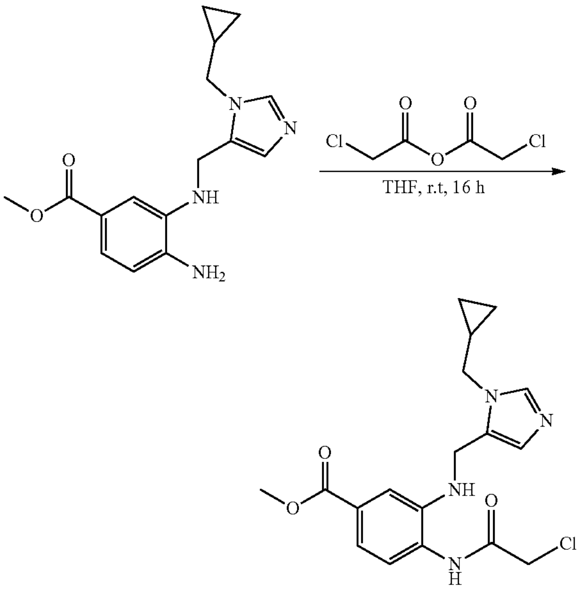

To a solution of methyl 4-amino-3-((1-(cyclopropylmethyl)-1H-imidazol-5-yl)methyl)aminobenzoate (150 mg, 0.50 mmol) in dry THF (5 ml) chloroacetic anhydride (257 mg, 1.50 mmol) was added at room temperature. The reaction was stirred at room temperature for 16 hours. After completion, the reaction solution was concentrated to give a residue in vacuo. The residue was purified by silica gel column chromatography (dichloromethane/methanol=15/1) to obtain methyl 4-(2-chloroacetamide)-3-((1-(cyclopropylmethyl)-1H-imidazol-5-yl)methyl)-aminobenzoate (180 mg, 95.5% yield). LC-MS m/z: 377 $[M+H]^+$.

Example 1-23. Synthesis of methyl 4-(2-chloroacetamide)-3-((1-ethyl-5-oxopyrrolidin-2-yl)methyl) amino-benzoate (Intermediate A-23)

1). Synthesis of dimethyl ethyl-L-glutamate

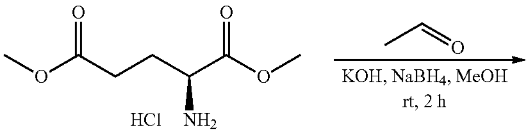

-continued

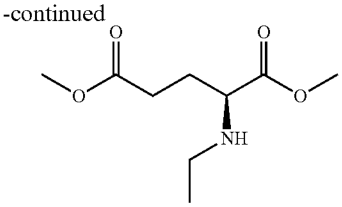

The mixture of dimethyl L-glutamate hydrochloride (5.00 g, 23.70 mmol) and potassium hydroxide (770 mg, 26.07 mmol) in methanol (100 mL) was stirred for 15 minutes at room temperature. Then acetaldehyde (1.56 g, 35.55 mmol) was added to the above mixture. The resulting mixture was stirred at room temperature for 2 hours. After completion, the reaction was quenched with water (200 mL) at room temperature, and extracted with ethyl acetate (100 mL×2). The combined organic layers were dried over anhydrous sodium sulfate, filtered, and concentrated to in vacuo to give dimethyl N-ethyl-L-glutamate (3.50 g, 72.7% yield) $^{1}H$ NMR (400 MHZ, $CDCl_3$): δ 3.73 (s, 3H), 3.67 (s, 3H), 2.65-12.59 (m, 1H), 2.50-2.42 (m, 3H), 2.01-1.86 (m, 2H), 1.07 (t, J=7.2 Hz, 3H).

2). Synthesis of methyl 1-ethyl-5-oxopyrrolidine-2-carboxylate

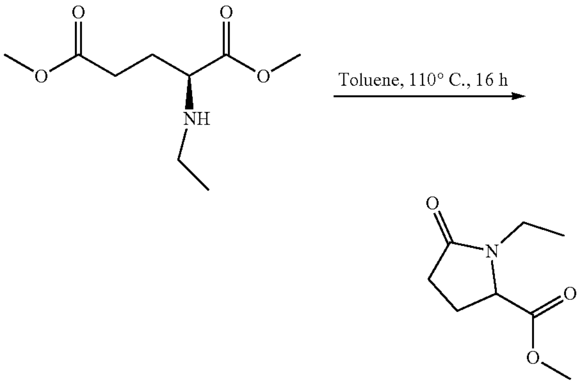

The solution of dimethyl ethyl-L-glutamate (3.50 g, 17.24 mmol) in toluene (50 mL) was stirred at 110° C. for 16 hours at room temperature. After completion, the solvent was removed in vacuo to obtain methyl 1-ethyl-5-oxopyrrolidine-2-carboxylate (2.00 g, 67.8% yield). LC-MS m/z: 172 $[M+H]^+$.

3). Synthesis of 1-ethyl-5-(hydroxymethyl) pyrrolidin-2-one

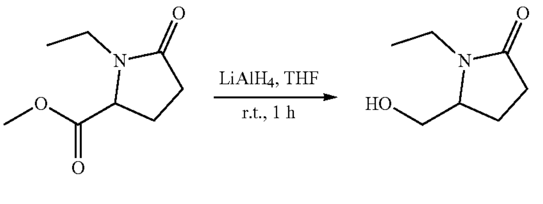

To a solution of methyl 1-ethyl-5-oxopyrrolidine-2-carboxylate (1.00 g, 5.85 mmol) in tetrahydrofuran (10 mL) at 0° C. lithium aluminum hydride (222 mg, 5.85 mmol) was added. The resulting mixture was stirred at room temperature for 1 hour. Upon completion of the reaction, the reaction mixture was quenched by adding water (2 mL) and aqueous sodium hydroxide (2 mL, 15%). The reaction was filtered and concentrated under reduced pressure to give 1-ethyl-5-(hydroxymethyl) pyrrolidin-2-one (600 mg, 71.7% yield). LC-MS m/z: 144 $[M+H]^+$.

4). Synthesis of methyl (1-ethyl-5-oxopyrrolidin-2-yl) sulfonate

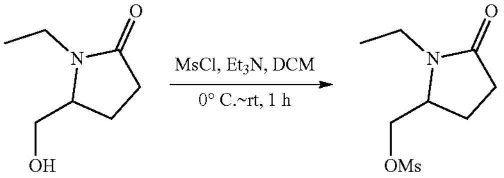

To a solution of 1-ethyl-5-(hydroxymethyl) pyrrolidin-2-one (600 mg, 4.20 mmol) in dichloromethane (10 mL) triethylamine (848 mg, 8.40 mmol) and methanesulfonyl chloride (580 mg, 5.04 mmol) was added at 0° C. The resulting mixture was stirred at room temperature for 1 hour. After completion, the reaction mixture was quenched with water (20 mL) at room temperature, and then extracted with dichloromethane (10 mL×2). The combined organic layers were dried over with anhydrous sodium sulfate, filtered, and concentrated in vacuo to give methyl (1-ethyl-5-oxypyrrolidin-2-yl) sulfonate (500 mg, 53.9% yield). LC-MS m/z: 222 $[M+H]^+$. 5). Synthesis of 5-(azidomethyl)-1-ethylpyrrolidin-2-one

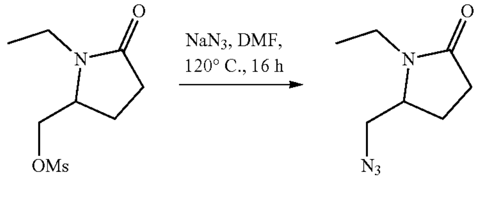

The mixture of methyl (1-ethyl-5-oxopyrrolidin-2-yl) sulfonate (500 mg, 2.26 mmol) and sodium azide (220 mg, 3.39 mmol) in N,N-dimethylformamide (10 mL) was stirred at 120° C. for 16 hours. After completion, it was diluted with saturated sodium bicarbonate (50 mL) solution at room temperature and extracted with ethyl acetate (10 mL×3). The combined organic layers were washed with brine (20 mL×3), dried over anhydrous sodium sulfate, filtered, and concentrated to give a residue in vacuo to obtain 5-(azidomethyl)-1-ethylpyrrolidin-2-one (500 mg, crude). LC-MS m/z: 169 $[M+H]^+$.

6). Synthesis of 5-(aminomethyl)-1-ethylpyrrolidin-2-one

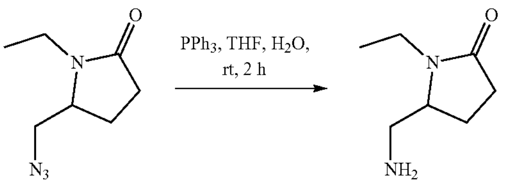

To a mixture of 5-(azidomethyl)-1-ethylpyrrolidin-2-one (500 mg, 2.98 mmol) in THF (10 mL) and water (2 mL) triphenylphosphine (1.56 g, 5.96 mmol) was added at room temperature. The resulting mixture was stirred at room temperature for 2 hours. After completion, the solvent was removed by concentration. The residue was purified by silica gel column chromatography to obtain 5-(aminomethyl)-1-ethylpyrrolidin-2-one (265 mg, 99.9% yield). LC-MS m/z: 143 $[M+H]^+$.

7). Synthesis of methyl 3-((1-ethyl-5-oxypyrrolidin-2-yl)methyl)amino)-4-nitrobenzoate

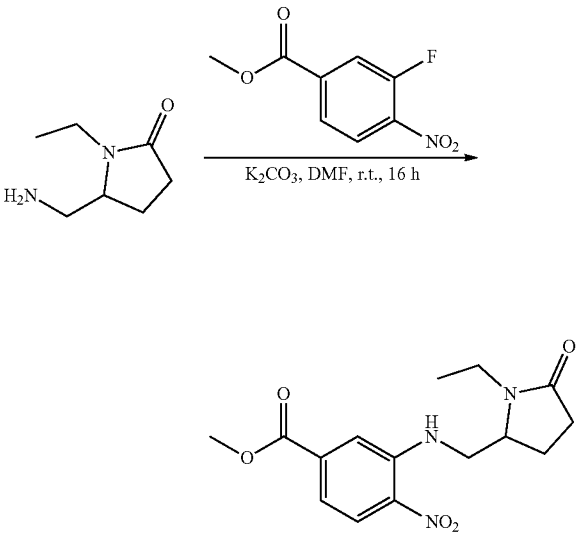

The mixture of 5-(aminomethyl)-1-ethylpyrrolidin-2-one (500 mg, 3.52 mmol), methyl 3-fluoro-4-nitrobenzoate (700 mg, 3.52 mmol) and potassium carbonate (972 mg, 7.04 mmol) in N, N-dimethylformamide (10 mL) was stirred at room temperature for 16 hours. After completion, the resulting mixture was diluted with water (100 mL) and extracted with ethyl acetate (20 mL×2). The combined organic layers were washed with brine (50 mL×3), dried over anhydrous sodium sulfate, filtered, and concentrated to give a residue in vacuo. The residue was purified by silica gel column chromatography (dichloromethane/methanol=20/1) to obtain methyl 3-((1-ethyl-5-oxypyrrolidin-2-yl)methyl)amino)-4-nitrobenzoate (120 mg, 10.6% yield). 8). Synthesis of methyl 4-amino-3-((1-ethyl-5-oxopyrrolidin-2-yl)methyl)amino)benzoate

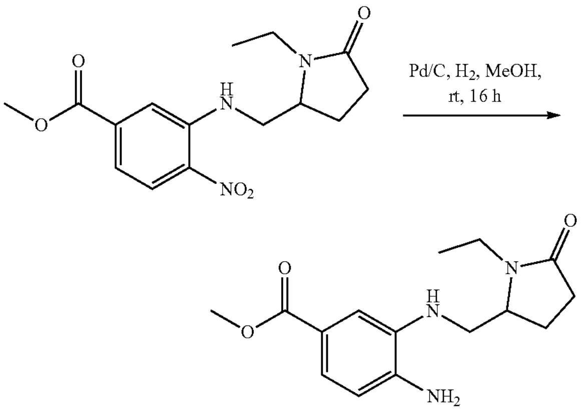

To a solution of to a solution of methyl 3-((1-ethyl-5-oxypyrrolidin-2-yl)methyl)amino)-4-nitrobenzoate (120 mg, 0.37 mmol) in methanol (10 mL) Pd/C (20 mg) was added at room temperature. The resulting mixture was degassed and flushed with hydrogen three times, and the reaction was stirred at room temperature for 16 hours. The reaction solution was filtered by celite with washed with MeOH (30 mL) and concentrated in vacuo to obtain methyl 4-amino-3-((1-ethyl-5-oxypyrrolidin-2-yl)methyl)amino) benzoate (100 mg, 92.9% yield). LC-MS m/z: 292 $[M+H]^+$.

9). Synthesis of methyl methyl 4-(2-chloroacetamide)-3-((1-ethyl-5-oxypyrrolidin-2-yl)methyl) aminobenzoate

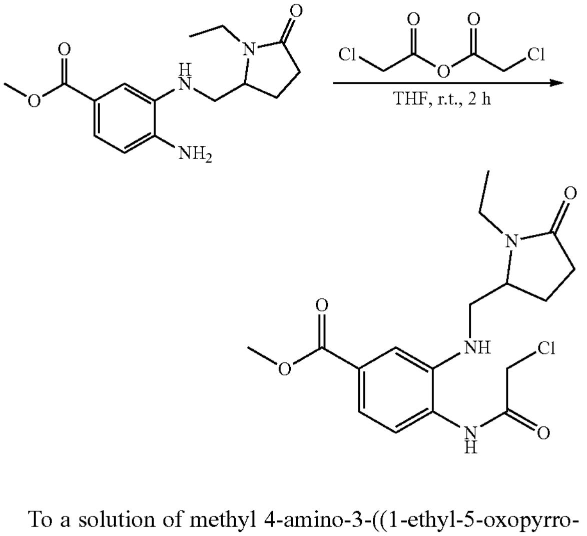

To a solution of methyl 4-amino-3-((1-ethyl-5-oxopyrrolidin-2-yl)methyl)amino)benzoate (100 mg, 0.31 mmol) in dry THF (3 mL) chloroacetic anhydride (106 mg, 0.62 mmol) was slowly added. The reaction was stirred at room temperature for 2 hours. After completion, the reaction mixture was directly concentrated to give a residue in vacuo. The residue was purified by silica gel column chromatography (dichloromethane/methanol=20/1) to obtain methyl 4-(2-chloroacetamide)-3-((1-ethyl-5-oxypyrrolidin-2-yl) methyl)aminobenzoate (100 mg, 87.9% yield). LC-MS m/z: 368 $[M+H]^+$.

Example 1-24. Synthesis of methyl(S)-4-(2-chloroacetamide)-3-((1-ethylpyrrolidin-2-yl)methyl)aminobenzoate (Intermediate A-24)

1). Synthesis of methyl(S)-3-((1-ethylpyrrolidin-2-yl)methyl)amino)-4-nitrobenzoate

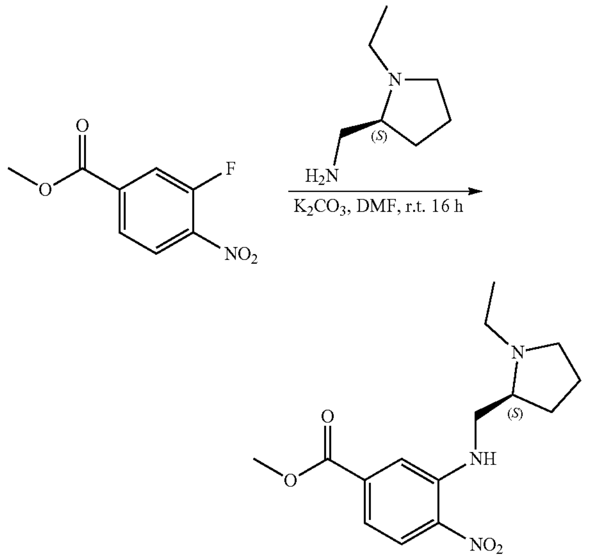

The mixture of methyl 3-fluoro-4-nitrobenzoate (7.77 g, 39.04 mmol), (S)—(1-ethylpyrrolidin-2-yl)carboxamide (5.00 g, 39.04 mmol) and potassium carbonate (16.16 g, 117.12 mmol) in N,N-dimethylformamide (70 mL) was stirred at room temperature for 16 hours. After completion, it was diluted with water (200 mL) and extracted with ethyl acetate (50 mL×3). The combined organic layers were washed with brine (50 mL×3), dried over anhydrous sodium sulfate, filtered, and concentrated to give a residue in vacuo. The residue was purified by silica gel column chromatography (dichloromethane:methanol=10:1) to obtain methyl (S)-3-((1-ethylpyrrolidin-2-yl)methyl)amino)-4-nitrobenzoate (9.30 g, 77.7% yield). LC-MS m/z: 308 $[M+H]^+$.

2). Synthesis of methyl(S)-4-amino-3-((1-ethylpyrrolidin-2-yl)methyl)aminobenzoate

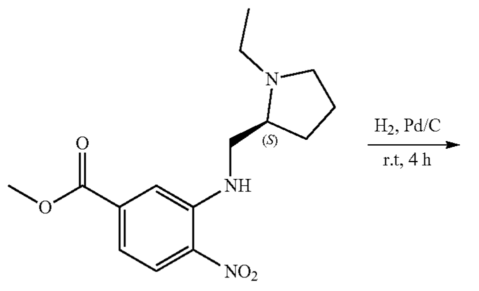

-continued

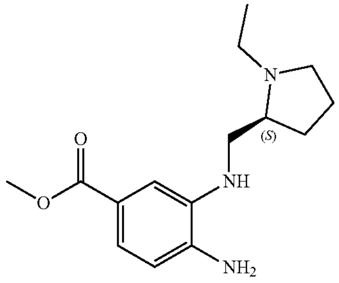

To a solution of methyl(S)-3-((1-ethylpyrrolidin-2-yl) methyl)amino)-4-nitrobenzoate (3.07 g, 10.00 mmol) in methanol (50 mL) palladium on carbon (1.50 g, 14.00 mmol) was added at room temperature. The resulting mixture was degassed and flushed with hydrogen three times, and the reaction was stirred at room temperature for 4 hours. After completion, filtered, and washed the filter cake with methanol (50 mL). The filtrate was concentrated in vacuo to give a residue. The residue was purified by silica gel column chromatography (dichloromethane/methanol=20/1) to obtain methyl(S)-4-amino-3-((1-ethylpyrrolidin-2-yl) methyl)aminobenzoate (2.3 g, 80.0% yield). LC-MS m/z: 278 $[M+H]^+$.

3). Synthesis of methyl(S)-4-(2-chloroacetamide)-3-((1-ethylpyrrolidin-2-yl)methyl)aminobenzoate

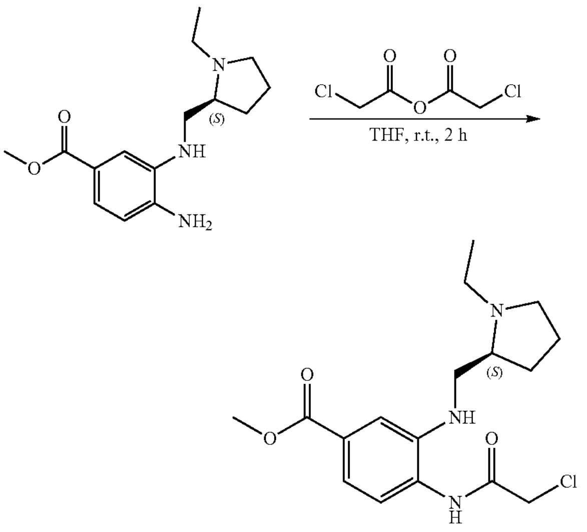

To a solution of methyl(S)-4-amino-3-((1-ethylpyrrolidin-2-yl)methyl)aminobenzoate (120 mg, 0.43 mmol) in dry THF (20 mL) chloroacetic anhydride (111 mg, 0.65 mmol) was slowly added at room temperature. The mixture was stirred at room temperature for 2 hours. After completion, the mixture was concentrated to give a residue in vacuo. The residue was purified by silica gel column chromatography (dichloromethane/methanol=20/1) to obtain(S)-4-(2-chloroacetamide)-3-((1-ethylpyrrolidin-2-yl)methyl)aminobenzoate (140 mg, 91.5% yield). LC-MS m/z: 354 $[M+H]^+$.

Example 1-25. Synthesis of(S)—N-(4-Bromo-2-methyl-6-((oxetan-2-ylmethyl)amino)phenyl)-2-chloroacetamide (Intermediate A-25)

1). Synthesis of(S)-5-bromo-3-methyl-2-nitro-N-(oxetan-2-ylmethyl)aniline

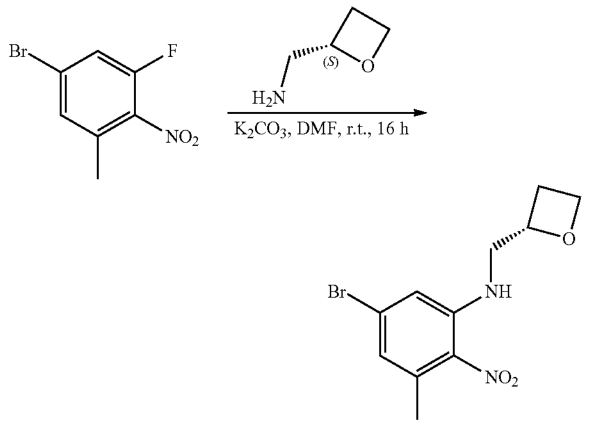

The mixture of 5-bromo-1-fluoro-3-methyl-2-nitrobenzene (500 mg, 2.14 mmol), (S)-oxetan-2-yl-methanamine (186 mg, 2.14 mmol) and potassium carbonate (590 mg, 4.28 mmol) in N, N-dimethylformamide (5 mL) was stirred at room temperature for 16 hours. After completion, water (5 mL) was added to quench the reaction, and it was extracted with ethyl acetate (20 mL×3). The combined organic layers were washed with brine (20 mL×3), dried over anhydrous sodium sulfate, filtered, and concentrated to give a residue in vacuo. The residue was purified by silica gel column chromatography (petroleum ether/ethyl acetate=4/1) to obtain(S) -5-bromo-3-methyl-2-nitro-N-(oxetan-2-ylmethyl)aniline (490 mg, 6.2% yield). LC-MS m/z: 301 $[M+H]^+$.

2). Synthesis of(S)-5-bromo-3-methyl-N-(oxetan-2-ylmethyl)benzene-1,2-diamine

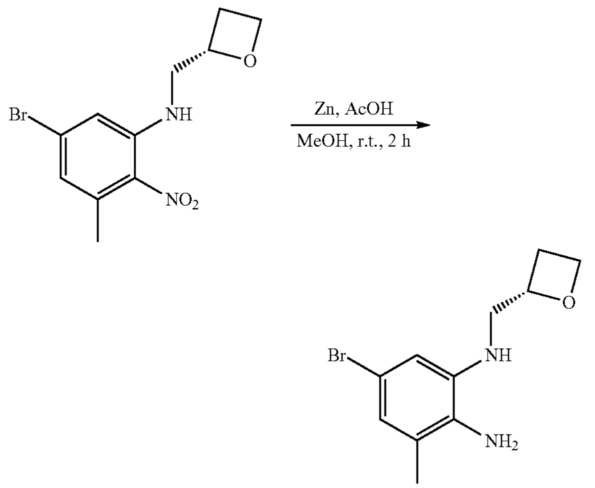

To a solution of(S)-5-bromo-3-methyl-2-nitro-N-(oxetan-2-ylmethyl)aniline (490 mg, 1.63 mmol) in methanol (5 mL) was added zinc dust (1:06 g, 16.30 mmol). The resulting mixture was stirred at room temperature for 2 hours. After completion, the reaction solution was filtered, and then the filtrate was adjusted to pH=7-8 with aqueous ammonia. After this, the mixture was concentrated to give a residue in vacuo. The residue was purified by silica gel column chromatography (dichloromethane/methanol=20/1) to obtain(S)-5-bromo-3-methyl-N-(oxetan-2-ylmethane) yl)benzene-1,2-diamine (269 mg, 60.7% yield), LC-MS m/z: 271 $[M+H]^+$.

3). Synthesis of(S)—N-(4-bromo-2-methyl-6-((oxetan-2-ylmethyl)amino)phenyl)-2-chloroacetamide

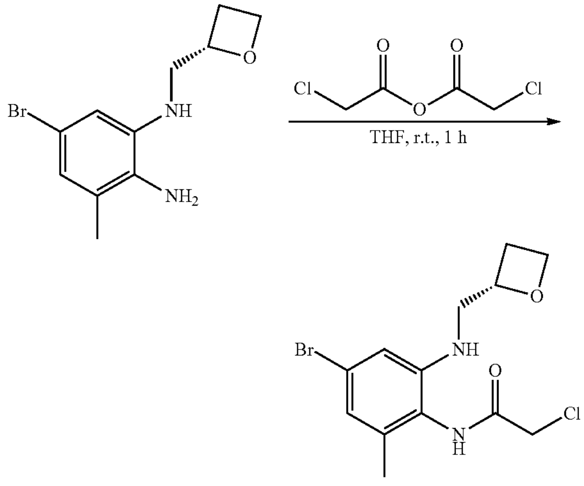

To a solution of(S)-5-bromo-3-methyl-N-(oxetan-2-ylmethyl)benzene-1,2-diamine (109 mg, 0.40 mmol) in THF (3 mL) chloroacetic anhydride (75 mg, 0.44 mmol) was added dropwise at room temperature. The resulting mixed solution was stirred and reacted at room temperature for 1 hour. After completion, the reaction solution was concentrated, and then was purified by silica gel column chromatography (petroleum ether/ethyl acetate=1/1) to obtain(S)—N-(4-bromo-2-methyl-6-((oxetan-2-ylmethyl)amino)phenyl)-2-chloroacetamide (98 mg, 70.4% yield), LC-MS m/z: 349 $[M+H]^+$.

Example 1-26. Synthesis of methyl(S)-2-(chloromethyl)-4-methyl-1-(oxetan-2-ylmethyl)-1H-benzo[d] imidazo-le-6-carboxylate (intermediate A-26)

1). Synthesis of methyl(S)-4-amino-3-methyl-5-((oxetan-2-ylmethyl)amino)benzoate

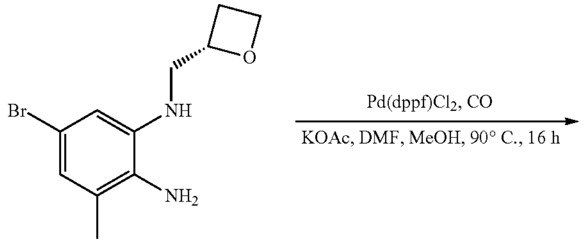

-continued

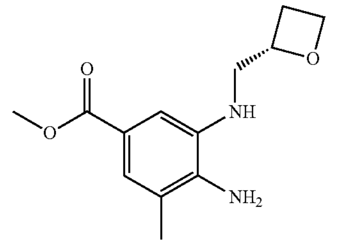

The solution of(S)-5-bromo-3-methyl-N-(oxetan-2-ylmethyl)benzene-1,2-diamine (130 mg, 0.48 mmol), 1,1'-bis-diphenylphosphinoferrocene palladium dichloride (37 mg, 0.05 mmol) and potassium acetate (141 mg, 1.44 mmol) in N,N-dimethylformamide (2 mL) and methanol (2 mL) was stirred at 90° C. for 16 hours under CO atmosphere (58.76 psi). After completion, the reaction solution was concentrated to give a residue in vacuo. The residue was purified by silica gel column chromatography (dichloromethane/methanol=20/1) to obtain methyl(S)-4-amino-3-methyl-5-((oxetan-2-ylmethyl)amino)benzoate (50 mg, 41.5% yield). LC-MS m/z: 251 $[M+H]^+$.

2). Synthesis of methyl(S)-2-(chloromethyl)-4-methyl-1-(oxetan-2-ylmethyl)-1H-benzo[d]imidazole-6-carboxylate

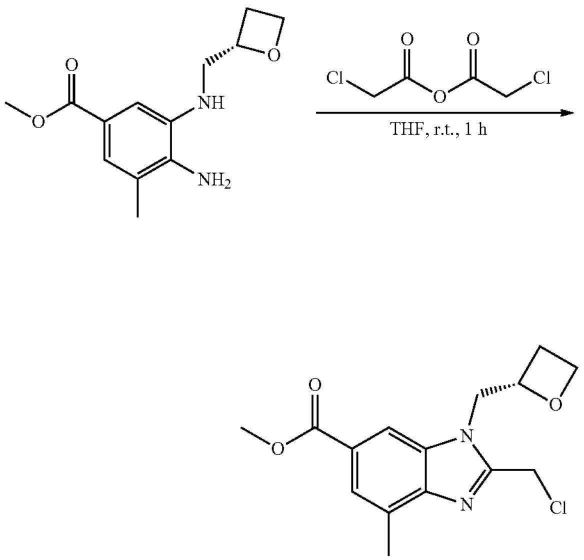

To a solution of methyl(S)-4-amino-3-methyl-5-((oxetan-2-ylmethyl)amino)benzoate (50 mg, 0.20 mmol) in THF (2 mL) chloroacetic anhydride (51 mg, 0.30 mmol) was added dropwise. The resulting mixture solution was stirred at room temperature for 1 hour. After completion, the reaction solution was concentrated to give a residue in vacuo. The residue was purified by silica gel column chromatography (petroleum ether/ethyl(S) -2-(chloromethyl)-4-methyl-1-(oxetan-2-ylmethyl)-1H-benzo[d]imidazole-6-acetate=1/1) to obtain carboxylate (20 mg, 32.6% yield). LC-MS m/z: 309 $[M+H]^+$.

Example 1-27. Synthesis of methyl 4-(2-chloroacetamide)-3-(1-ethyl-1H-pyrazol-5-yl)methyl)amino-benzoate (Intermediate A-27)

1). Synthesis of methyl 1-ethyl-1H-pyrazole-5-carboxylate

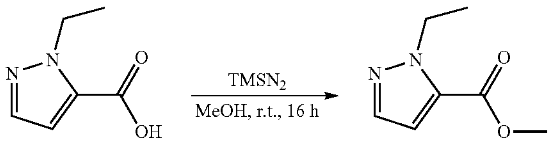

To a solution of 1-Ethyl-1H-pyrazole-5-carboxylic acid (770 mg, 5.50 mmol) in methanol (8 mL) (diazomethyl) trimethylsilane (27.5 mL, 55.00 mmol, 2.0 M in tetrahydrofuran) was dropwise added at 0° C. The resulting mixture was stirred at room temperature for 1 hour, then quenched with water (100 mL) and extracted with ethyl acetate (50 mL×2). The combined organic layers were washed with brine (50 mL×2), dried over anhydrous sodium sulfate, filtered, and concentrated in vacuo to obtain methyl 1-ethyl-1H-pyrazole-5-carboxylate (600 mg, 70.8% yield), LC-MS m/z: 155 $[M+H]^+$.

2). Synthesis of (1-ethyl-1H-pyrazol-5-yl)methanol

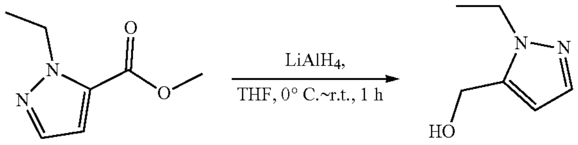

To a solution methyl 1-ethyl-1H-pyrazole-5-carboxylate (600 mg, 3.90 mmol) in dry THF (8 mL) lithium aluminum hydride powder (296 mg, 7.80 mmol) was added at 0° C. The reaction was stirred at room temperature for 1 hour. After completion, the reaction was quenched with water (2 mL) and aqueous sodium hydroxide (2 mL, 15%). The mixture was filtered, and concentrated in vacuo to give (1-ethyl-1H-pyrazol-5-yl)methanol (400 mg, 81.4% yield). LC-MS m/z: 127 $[M+H]^+$.

3). Synthesis of 5-(chloromethyl)-1-ethyl-1H-pyrazole

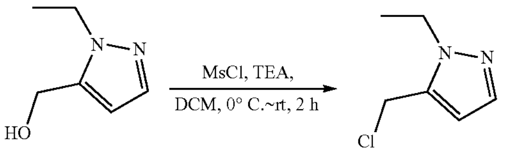

To a solution of (1-Ethyl-1H-pyrazol-5-yl)methanol (400 mg, 3.17 mmol) in dichloromethane (20 mL) triethylamine (640 mg, 6.34 mmol) and methanesulfonyl chloride (729 mg, 6.34 mmol) were added at 0° C. The reaction was stirred at room temperature for 2 hours. After completion, the reaction was quenched with water (100 mL) and extracted with dichloromethane (50 mL×2). The combined organic layer was washed with brine (50 mL×2), dried over anhydrous sodium sulfate, filtered, and concentrated in vacuo to obtain 5-(chloromethyl)-1-ethyl-1H-pyrazole (400 mg, 87.0% yield), LC-MS m/z: 145 [M+H]$^+$.

4). Synthesis of 5-(azidomethyl)-1-ethyl-1H-pyrazole

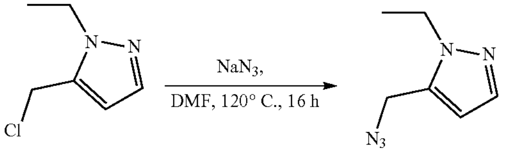

The mixture of 5-(chloromethyl)-1-ethyl-1H-pyrazole (400 mg, 2.76 mmol) and sodium azide (359 mg, 5.52 mmol) in N, N-dimethyl formamide was stirred at 120° C. for 16 hours. After completion, it was diluted with saturated sodium bicarbonate solution (10 mL) and extracted with ethyl acetate (10 mL×3). The combined organic layers were washed with brine (10 mL×3), dried over anhydrous sodium sulfate, filtered, and concentrated in vacuo to obtain 5-(azidomethyl)-1-ethyl-1H-pyrazole (370 mg, 88.8% yield). LC-MS m/z: 152 [M+H]$^+$.

5). Synthesis of (1-ethyl-1H-pyrazol-5-yl)methanamine

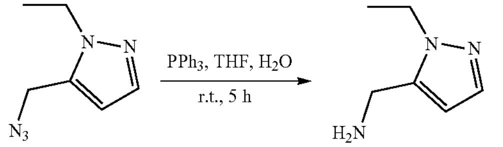

To a mixture of 5-(Azidomethyl)-1-ethyl-1H-pyrazole (320 mg, 2.12 mmol) in THF (4 mL) and water (0.4 mL) triphenylphosphine (1.1 g, 4.24 mmol) was added at room temperature. The reaction was stirred at room temperature for 5 hours. After completion, the solvent was removed by concentration in vacuo to obtain (1-ethyl-1H-pyrazol-5-yl) methanamine (265 mg, 99.9% yield).

6). Synthesis of methyl 3-((1-ethyl-1H-pyrazol-5-yl)methyl)amino)-4-nitrobenzoate

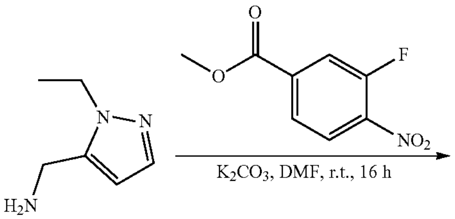

-continued

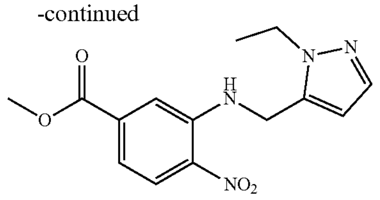

The mixture of (1-ethyl-1H-pyrazol-5-yl)methanamine (265 mg, 2.12 mmol), methyl 3-fluoro-4-nitrobenzoate (422 mg, 2.12 mmol) and potassium carbonate (585 mg, 4.24 mmol) in N,N-dimethylformamide (7 mL) was stirred at room temperature for 16 hours. After completion, it was diluted with water (60 mL) and extracted with ethyl acetate (20 mL×3). The combined organic layers were washed with brine (20 mL×3), dried over anhydrous sodium sulfate, filtered, and concentrated to give a residue in vacuo. The residue was purified by silica gel column chromatography (dichloromethane/methanol=20/1) to give methyl 3-((1-ethyl-1H-pyrazol-5-yl)methyl)amino)-4-nitrobenzoate (100 mg, 15.5% yield). LC-MS m/z: 346 [M+H]$^+$.

7). Synthesis of methyl 4-amino-3-((1-ethyl-1H-pyrazol-5-yl)methyl)amino)benzoate

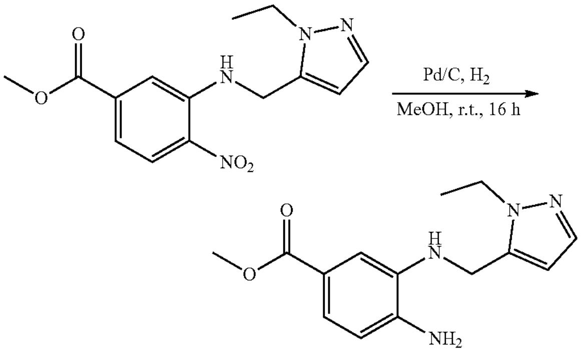

To solution of methyl 3-((1-ethyl-1H-pyrazol-5-yl) methyl)amino)-4-nitrobenzoate (130 mg, 0.43 mmol) in methanol (12 mL) palladium on carbon (50 mg, 30.42 mmol) was added at room temperature. The resulting mixture was degassed and flushed with hydrogen three times, and the reaction was stirred at room temperature for 16 hours. After completion, the reaction solution was filtered, the filter cake was rinsed with methanol. The filtrate was concentrated in vacuo to obtain methyl 4-amino-3-((1-ethyl-1H-pyrazol-5-yl)methyl)amino)benzoate (70 mg, 59.4% yield), LC-MS m/z: 275 [M+H]$^+$.

8). Synthesis of methyl 4-(2-chloroacetamide)-3-(1-ethyl-1H-pyrazol-5-yl)methyl)aminobenzoate

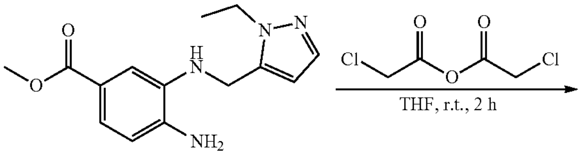

-continued

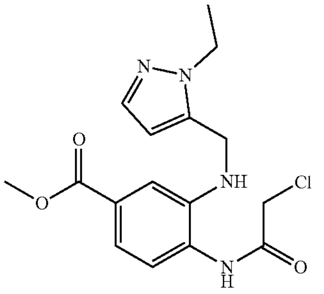

To a solution of methyl 4-amino-3-((1-ethyl-1H-pyrazol-5-yl)methyl)amino)benzoate (70 mg, 0.26 mmol) in tetrahydrofuran (3 mL) chloroacetic anhydride (111 mg, 0.65 mmol) was slowly added. The reaction was stirred at room temperature for 2 hours. After completion, the solvent was removed by concentration in vacuo to give a residue. The residue was purified by silica gel column chromatography (dichloromethane/methanol=20/1) to obtain methyl 4-(2-chloroacetamido)-3-(1-ethyl-1H-pyrazol-5-yl)methyl)aminobenzoate (60 mg, 65.7% yield). LC-MS m/z: 351 $[M+H]^+$.

Example 1-28. Synthesis of methyl 4-(2-chloroacetamide)-3-((1-ethyl-3-methyl-1H-pyrazol-5-yl)methyl)-amino)benzoate (Intermediate A-28)

1). Synthesis of methyl 1-ethyl-3-methyl-1H-pyrazole-5-carboxylate

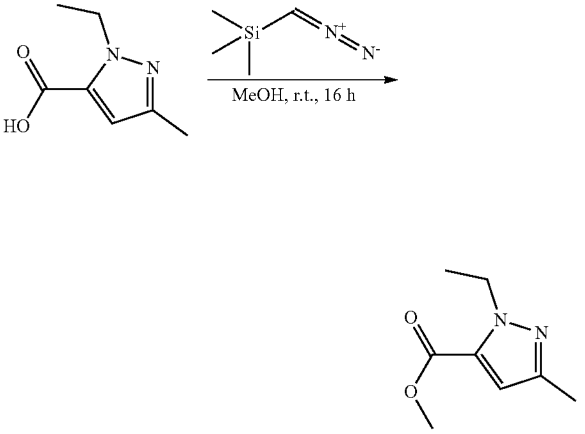

To a solution of 1-Ethyl-3-methyl-1H-pyrazole-5-carboxylic acid (1.00 g, 6.49 mmol) in methanol (10 mL) (diazomethyl)trimethylsilane (32.45 mL, 64.90 mmol, 2.0 M in THF) was added dropwise at 0° C. The resulting mixture was stirred at room temperature for 1 hour, After completion, the mixture was quenched with water (300 mL) and extracted with ethyl acetate (100 mL×3). The combined organic layers were washed with brine (100 mL×3), dried over anhydrous sodium sulfate, filtered, and concentrated in vacuo to give methyl 1-ethyl-3-methyl-1H-pyrazole-5-carboxylate (800 mg, 73.4% yield). LC-MS m/z: 169 $[M+H]^+$.

2). Synthesis of (1-ethyl-3-methyl-1H-pyrazol-5-yl)methanol

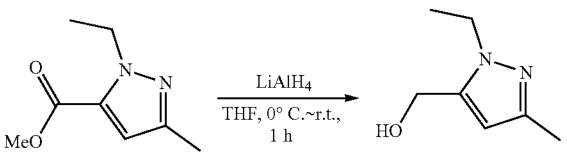

To solution of methyl 1-ethyl-3-methyl-1H-pyrazole-5-carboxylate (800 mg, 4.76 mmol) in dry THF (10 mL) Aluminum lithium hydride (543 mg, 14.28 mmol) was added at 0° C. The reaction was stirred at room temperature for 1 hour. After completion, the mixture was quenched with water (2 mL) and aqueous sodium hydroxide solution (2 mL, 15% w/w). The mixture was filtered, and the filtrate was concentration in vacuo to give (1-ethyl-3-methyl-1H-pyrazol-5-yl)methanol (550 mg, 82.5% yield). LC-MS m/z: 141. $[M+H]^+$.

3). Synthesis of 5-(chloromethyl)-1-ethyl-3-methyl-1H-pyrazole

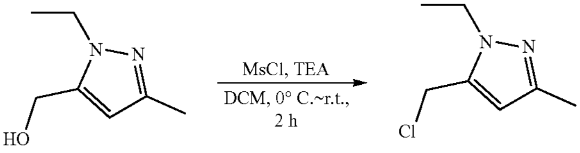

To a mixture of (1-ethyl-3-methyl-1H-pyrazol-5-yl)methanol (550 mg, 3.93 mmol) in dichloromethane (20 mL) triethylamine (794 mg, 7.86 mmol) and methanesulfonyl chloride (679 mg, 5.90 mmol) was added at 0° C. The reaction was stirred at room temperature for 2 hours. After completion, the mixture was quenched with water (100 mL) and extracted with dichloromethane (50 mL×2). The combined organic layer was washed with brine (50 mL×2), dried over anhydrous sodium sulfate, filtered, and concentrated in vacuo to obtain 5-(chloromethyl)-1-ethyl-3-methyl-1H-pyrazole (500 mg, 80.0% yield). LC-MS m/z: 159 $[M+H]^+$.

4). Synthesis of 5-(azidomethyl)-1-ethyl-3-methyl-1H-pyrazole

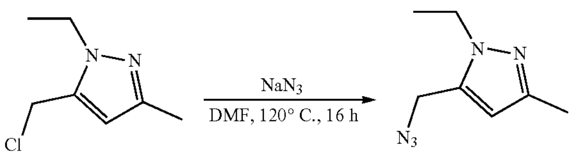

The mixture of 5-(chloromethyl)-1-ethyl-3-methyl-1H-pyrazole (450 mg, 2.83 mmol) and sodium azide (368 mg, 5.66 mmol) in N, N-dimethylformamide (4 mL) was stirred at 120° C. for 16 hours. After completion, it was diluted with saturated sodium bicarbonate solution (10 mL) and extracted with ethyl acetate (10 mL×3). The combined organic layers were washed with brine (10 mL×3), dried over anhydrous sodium sulfate, filtered, and concentrated in vacuo to obtain 5-(azidomethyl)-1-ethyl-3-methyl-1H-pyrazole (350 mg, 75.0% yield). LC-MS m/z: 166 $[M+H]^+$.

5). Synthesis of (1-ethyl-3-methyl-1H-pyrazol-5-yl)methanamine

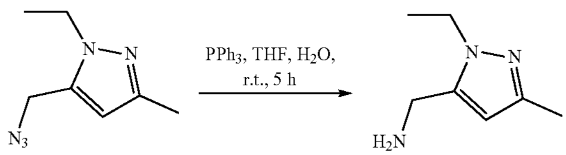

To a mixture of 5-(azidomethyl)-1-ethyl-3-methyl-1H-pyrazole (350 mg, 2.12 mmol) in THF (7 mL) and water (0.7 mL) triphenylphosphine (1.1 g, 4.24 mmol) was added, then stirred at room temperature for 5 hours. After completion, the solvent was removed in vacuo to obtain a colorless oil compound (1-ethyl-3-methyl-1H-pyrazol-5-yl)methanamine (286 mg, 97.1% yield). LC-MS m/z: 140 $[M+H]^+$.

6) Synthesis of methyl 3-((1-ethyl-3-methyl-1H-pyrazol-5-yl)methyl)amino)-4-nitrobenzoate

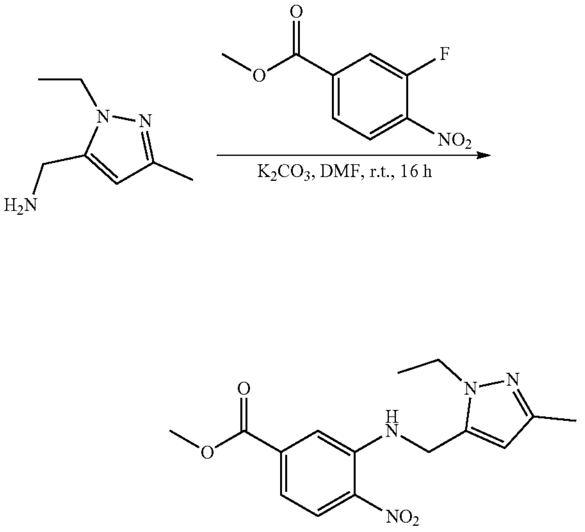

The mixture of (1-ethyl-3-methyl-1H-pyrazol-5-yl)methanamine (286 mg, 2.06 mmol), methyl 3-fluoro-4-nitrobenzoate (410 mg, 2.06 mmol) and potassium carbonate (569 mg, 4.12 mmol) in N,N-dimethylformamide (8 mL), was stirred at room temperature for 16 hours. After completion, it was diluted with water (50 mL) and extracted with ethyl acetate (25 mL×2). The combined organic layers were washed with brine (25 mL×2), dried over anhydrous sodium sulfate, filtered, and concentrated to give a residue in vacuo. The residue was purified by silica gel column chromatography (dichloromethane/methanol=20/1) to give methyl 3-((1-ethyl-3-methyl-1H-pyrazol-5-yl)methyl)amino)-4-nitrobenzoate (300 mg, 45.8% yield). LC-MS m/z: 319 $[M+H]^+$.

7). Synthesis of methyl 4-amino-3-((1-ethyl-3-methyl-1H-pyrazol-5-yl)methyl)amino)benzoate

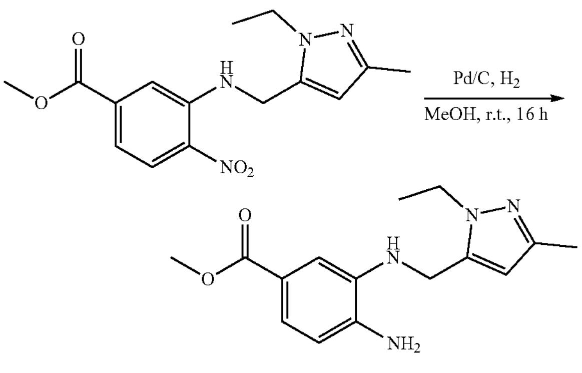

To a solution of methyl 3-((1-ethyl-3-methyl-1H-pyrazol-5-yl)methyl)amino)-4-nitrobenzoate (330 mg, 1.04 mmol) dissolved in methanol (24 mL) palladium on carbon (50 mg, 30.42 mmol) was added at room temperature. The resulting mixture was degassed and flushed with hydrogen three times and stirred at room temperature for 16 hours. After completion, the reaction solution was filtered, the filter cake was rinsed with methanol. The filtrate was concentrated in vacuo to obtain methyl 4-amino-3-((1-ethyl-3-methyl-1H-pyrazol-5-yl)methyl)amino)benzoate (200 mg, 67.1% yield), LC-MS m/z: 289 $[M+H]^+$.

8). Synthesis of methyl 4-(2-chloroacetamide)-3-((1-ethyl-3-methyl-1H-pyrazol-5-yl)methyl)amino) benzoate

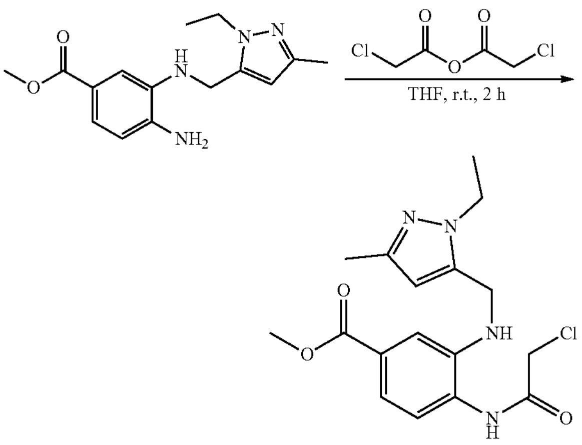

To a solution of methyl 4-amino-3-((1-ethyl-3-methyl-1H-pyrazol-5-yl)methyl)amino)benzoate (200 mg, 0.69 mmol) in THF (4 mL) chloroacetic anhydride (296 mg, 1.73 mmol) was slowly added at room temperature. The reaction was stirred at room temperature for 2 hours. After completion, the solvent was removed in vacuo 5 to give a residue, residue was purified by silica gel column chromatography (dichloromethane/methanol-20/1) to obtain methyl 4-(2-chloroacetamide)-3-((1-ethyl-3-methyl-1H-pyrazol-5-yl) methyl)amino)benzoate (200 mg, 79.4% yield). LC-MS m/z: 365 $[M+H]^+$.

Example 1-29. Synthesis of other Part A Intermediates

The following intermediates can be obtained with similar to the synthetic steps of each intermediate from Example 1-1 to Example 1-28

| Number | Structure | Name | MS m/z [M + H]+ |
|---|---|---|---|
| Intermediate A-29 | 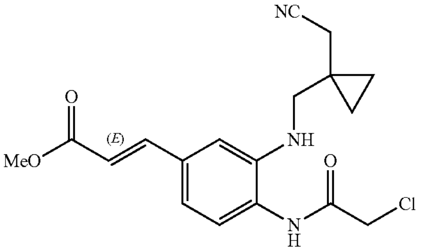 [SMILES: COC(=O)/C=C/c1ccc(NC(=O)CCl)c(NCC2(CC#N)CC2)c1] | Methyl (E)-3-(4-(2-chloroacetamido)-3-(((1-(cyano-methyl)cyclo-propyl)meth-yl)amino)phenyl)acrylate | 362 |
| Intermediate A-30 | 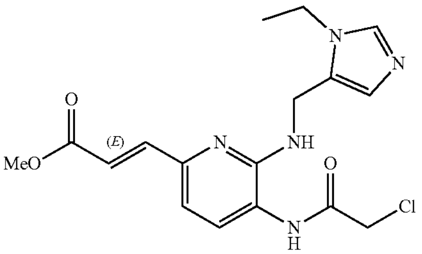 [SMILES: CCn1cncc1CNc1nc(/C=C/C(=O)OC)ccc1NC(=O)CCl] | Methyl (E)-3-(5-(2-chloroacetamido)-6-(((1-ethyl-1H-imidazol-5-yl)methyl)amino)pyridin-2-yl)acrylate | 378 |
| Intermediate A-31 | 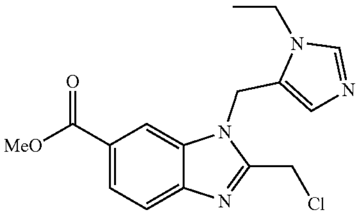 [SMILES: CCn1cncc1Cn1c(CCl)nc2ccc(C(=O)OC)cc21] | Methyl 2-(chloromethyl)-1-((1-ethyl-1H-imidazol-4-yl)methyl)-1H-benzo[d]imidazole-6-carboxylate | 333 |
| Intermediate A-32 | 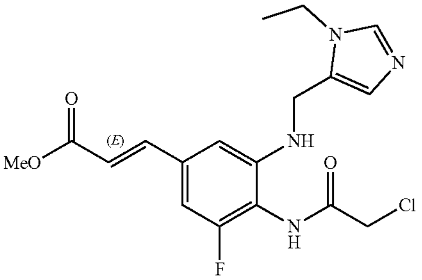 [SMILES: CCn1cncc1CNc1cc(/C=C/C(=O)OC)cc(F)c1NC(=O)CCl] | Methyl (E)-3-(4-(2-chloroacetamido)-3-((1-ethyl-1H-imidazol-5-yl)methyl)amino)-5-fluorophenyl)acrylate | 395 |
| Intermediate A-33 | 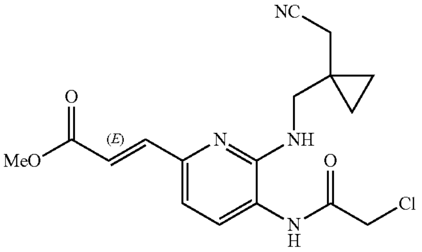 [SMILES: COC(=O)/C=C/c1ccc(NC(=O)CCl)c(NCC2(CC#N)CC2)n1] | Methyl (E)-3-(5-(2-chloroacetamido)-6-((((1-(cyanomethyl)cyclo-propyl)meth-yl)amino)pyridin-2-yl)acrylate | 363 |

-continued

| Number | Structure | Name | MS m/z [M + H]+ |
|---|---|---|---|
| Intermediate A-34 | 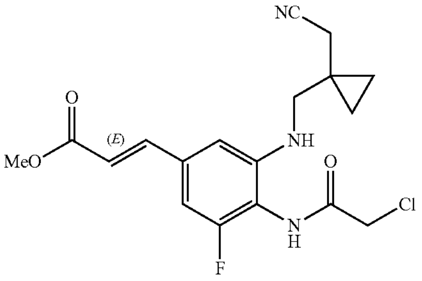 [SMILES: COC(=O)/C=C/c1cc(F)c(NC(=O)CCl)c(NCC2(CC#N)CC2)c1] | Methyl (E)-3-(4-(2-chloroacetamido)-3-((1-(cyanomethyl)cyclopropyl)methyl)amino)-5-fluorophenyl)acrylate | 380 |
| Intermediate A-35 | 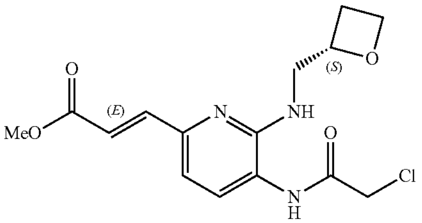 | Methyl (S,E)-3-(5-(2-chloroacetamido)-6-((oxetan-2-ylmethyl)amino)pyridin-2-yl)acrylate | 340 |
| Intermediate A-36 | 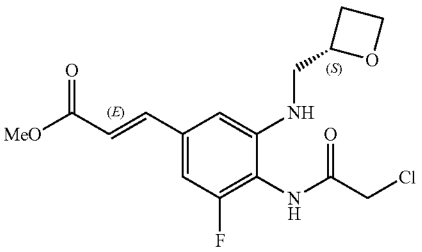 | Methyl (S,E)-3-(4-(2-chloroacetamido)-3-fluoro-5-((oxetan-2-ylmeth-yl)amino)phenyl)acrylate | 357 |
| Intermediate A-37 | 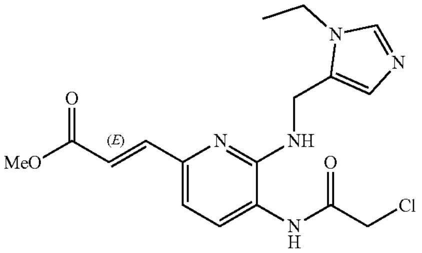 [SMILES: CCn1cncc1CNc1nc(/C=C/C(=O)OC)ccc1NC(=O)CCl] | Methyl (E)-3-(5-(2-chloroacetamido)-6-(((1-ethyl-1H-imidazol-5-yl)methyl)amino)pyridin-2-yl)acrylate | 378 |
| Intermediate A-38 | 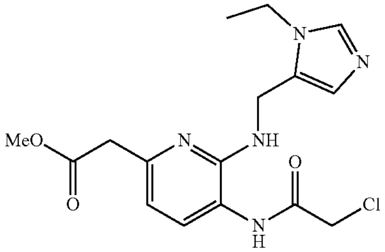 [SMILES: CCn1cncc1CNc1nc(CC(=O)OC)ccc1NC(=O)CCl] | Methyl 2-(5-(2-chloroacetamido)-6-(((1-ethyl-1H-imidazol-5-yl)methyl)aminopyridin-2-yl)acetate | 366 |
| Intermediate A-39 | 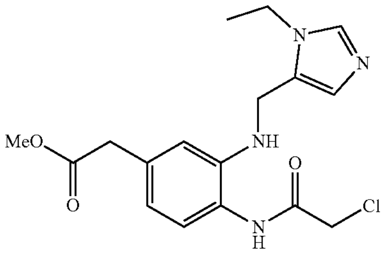 [SMILES: CCn1cncc1CNc1cc(CC(=O)OC)ccc1NC(=O)CCl] | Methyl 2-(4-(2-chloroacetamido)-3-(((1-ethyl-1H-imidazol-5-yl)meth-yl)amino)phenyl)acetate | 365 |

-continued

| Number | Structure | Name | MS m/z [M + H]+ |
|---|---|---|---|
| Intermediate A-40 | 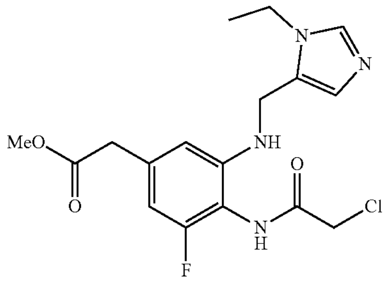 [SMILES: CCn1cncc1CNc1cc(CC(=O)OC)cc(F)c1NC(=O)CCl] | Methyl 2-(4-(2-chloroacetamido)-3-(((1-ethyl-1H-imidazol-5-yl)methyl)amino)-5-fluorophenyl)acetate | 383 |
| Intermediate A-41 | 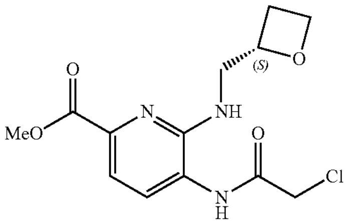 | (S)-Methyl 5-(2-chloroacetamido)-6-((oxetan-2-ylmethyl)amino)-picolinate | 314 |
| Intermediate A-42 | 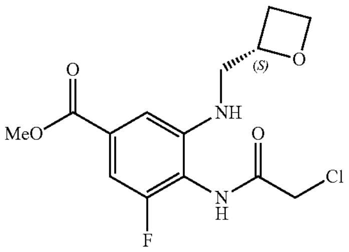 | Methyl (S)-4-(2-chloroacetamido)-3-fluoro-5-((oxetan-2-ylmethyl)amino)-benzoate | 331 |
| Intermediate A-43 | 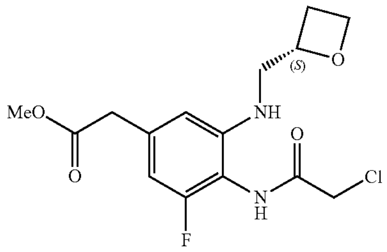 | Methyl (S)-2-(4-(2-chloroacetamido)-3-fluoro-5-((oxetan-2-ylmethyl)amino)phenyl)-acetate | 345 |
| Intermediate A-44 | 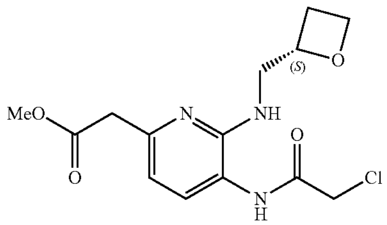 | Methyl (S)-2-(5-(2-chloroacetamido)-6-((oxetan-2-ylmethyl)amino)pyridin-2-yl)acetate | 328 |
| Intermediate A-45 | 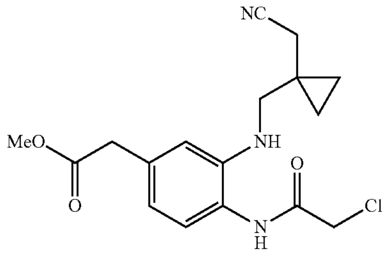 [SMILES: COC(=O)Cc1ccc(NC(=O)CCl)c(NCC2(CC#N)CC2)c1] | Methyl 2-(4-(2-chloroacetamido)-3-(((1-(cyanomethyl)cyclo-propyl)meth-yl)amino)phenyl)acetate | 350 |

-continued

| Number | Structure | Name | MS m/z [M + H]+ |
|---|---|---|---|
| Intermediate A-46 | 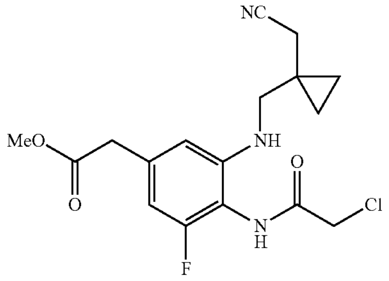 [SMILES: COC(=O)Cc1cc(F)c(NC(=O)CCl)c(NCC2(CC#N)CC2)c1] | Methyl 2-(4-(2-chloroacetamido)-3-((((1-(cyanomethyl)-cyclopropyl)meth-yl)amino)-5-fluorophenyl)acetate | 368 |
| Intermediate A-47 | 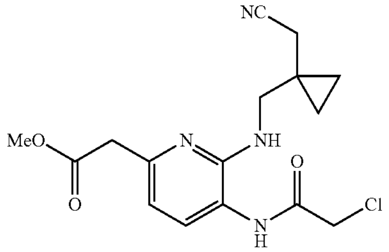 [SMILES: COC(=O)Cc1ccc(NC(=O)CCl)c(NCC2(CC#N)CC2)n1] | Methyl 2-(5-(2-chloroacetamido)-6-(((1-(cyanomethyl)cyclo-propyl)methyl)amino-pyridin-2-yl)acetate | 351 |
| Intermediate A-48 | 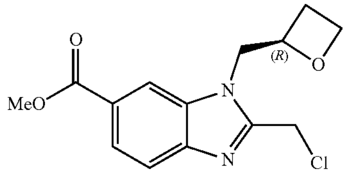 | Methyl (R)-2-(chloromethyl)-1-(oxetan-2-ylmethyl)-1H-benzo[d]imidazole-6-carboxylate | 295 |
| Intermediate A-49 | 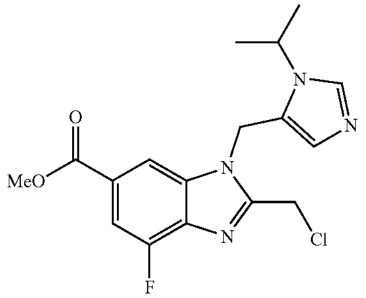 [SMILES: COC(=O)c1cc(F)c2nc(CCl)n(Cc3cncn3C(C)C)c2c1] | 2-(chloromethyl)-4-fluoro-1-((1-isopropyl-1H-imidazol-5-yl)methyl)-1H-benzo[d]imidazole-6-carboxylic acid | 351 |
| Intermediate A-50 | 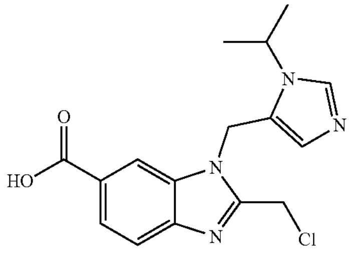 [SMILES: CC(C)n1cncc1Cn1c(CCl)nc2ccc(C(=O)O)cc21] | 2-(chloromethyl)-1-(1-isopropyl-1H-imidazol-5-yl)methyl)-1H-benzo[d]imidazole-6-carboxylic acid | 333 |

Example 2-1. Synthesis of 3-fluoro-4-((6-(piperidin-4-oxy)pyridin-2-yl)methoxy)benzonitrile (Intermediate B-1)

1). Synthesis of tert-butyl 4-(6-bromopyridin-2-yl)oxy)piperidine-1-carboxylate

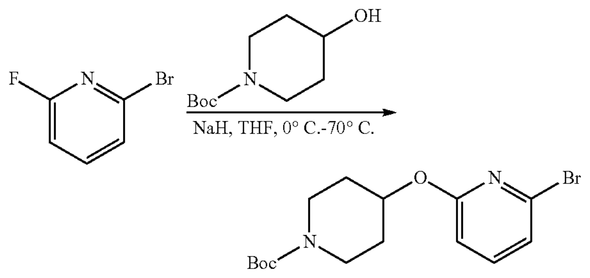

To a solution of compound tert-butyl 4-hydroxypiperidine-1-carboxylate (2.00 g, 9.95 mmol) in tetrahydrofuran (30 mL) sodium hydride (60% w/w dispersed in mineral oil, 597 mg, 14.93 mmol) was added at 0° C. The mixture was stirred at 0° C. for 30 min, then 2-bromo-6-fluoropyridine (2.09 g, 11.94 mmol) was added slowly to the mixture. The reaction mixture was stirred at 70° C. for 4 hours. After completion, the reaction was quenched with water (30 mL) at room temperature and extracted with ethyl acetate (50 mL×3). The combined organic layers were washed with brine (30 mL×2), dried over anhydrous sodium sulfate, filtered, and concentrated to give a residue in vacuo. The residue was purified by silica gel column chromatography (petroleum ether/ethyl acetate=10/1) to obtain tert-butyl 4-(6-bromopyridin-2-yl)oxy)piperidine-1-carboxylate (1.80 g, 5.06 mmol, 50.9% yield). LC-MS m/z: 356.9, 358.9 $[M+H]^+$.

2). Synthesis of methyl 6-((1-(tert-butoxycarbonyl)piperidin-4-yl)oxy)picolinate

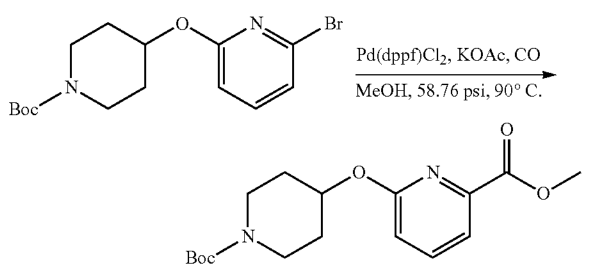

To a solution of 4-(6-bromopyridin-2-yl)oxy)piperidine-1-carboxylic acid tert-butyl ester (1.80 g, 5.06 mmol) in methanol (5 mL) potassium acetate (1.49 g, 15.18 mmol) and 1,1'-bisdiphenylphosphinoferrocene palladium dichloride (373 mg, 0.51 mmol) were added. The mixture was stirred at 90° C. for 16 h under CO (58.76 psi) atmosphere. The reaction was quenched by water (15 mL) and then extracted ethyl acetate (30 mL×3). The combined organic layers were washed with brine (30 ml×2), dried over anhydrous sodium sulfate, filtered, and concentrated in vacuo. The residue was purified by reverse-phase flash chromatography under the following conditions: (Column: spherical C18, 20-40 um, 120 g; mobile phase A: 10 mM $NH_4OH$ in water); Mobile Phase B: Acetonitrile; Flow rate: 80 mL/min; Gradient: 60% B-80% B in 20 minutes; detector: 254 nm.) The mobile phase containing the desired product was collected at 70% B and then concentrated in vacuo to give methyl 6-((1-(tert-butoxycarbonyl)piperidin-4-yl)oxy)picolinate (1.50 g, 4.46 mmol, 88.1% yield). LC-MS m/z: 337 $[M+H]^+$.

3). Synthesis of tert-butyl 4-(6-(hydroxymethyl)pyridin-2-yl)oxy)piperidine-1-carboxylate

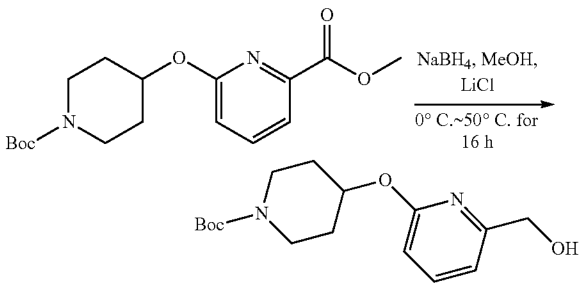

To a solution of methyl 6-((1-(tert-butoxycarbonyl)piperidin-4-yl)oxy)picolinate (500 mg, 1.49 mmol) in methanol (5 mL) sodium borohydride (170 mg, 4.47 mmol) and lithium chloride (6 mg, 0.15 mmol) were added at 0° C. The mixture was stirred at 50° C. for 16 hours. The reaction was quenched by water (5 mL) and then extracted with ethyl acetate (20 mL×3). The combined organic layers were washed with brine (10 mL×2), dried over anhydrous sodium sulfate, filtered, and concentrated to give a residue in vacuo. The residue was purified by reverse-phase flash chromatography under the following conditions: (Column: spherical C18, 20-40 μm, 120 g; Mobile Phase A: 10 mM $NH_4OH$ in water; Mobile Phase B: acetonitrile; Flow rate: 80 mL/min; Gradient: 60% B-80% B in 20 minutes; detector: 254 nm) The mobile phase containing the desired product was collected and concentrated in vacuo to give tert-butyl 4-(6-(hydroxymethyl)pyridin-2-yl)oxy)piperidine-1-carboxylate (200 mg, 0.65 mmol, 43.6% yield). LC-MS m/z: 309 $[M+H]^+$.

4). Synthesis of tert-butyl 4-(6-((4-cyano-2-fluorophenoxy)methyl)pyridin-2-yl)oxy)piperidine-1-carboxylate

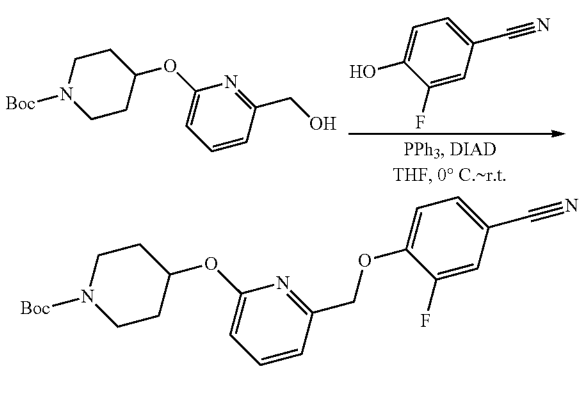

To a solution of tert-butyl 4-(6-(hydroxymethyl)pyridin-2-yl)oxy)piperidine-1-carboxylate (200 mg, 0.65 mmol) and 3-fluoro-4-hydroxybenzonitrile (89 mg, 0.65 mmol) in tetrahydrofuran (10 mL) triphenylphosphine (257 mg, 0.98 mmol) was added at 0° C. Diisopropyl azodicarboxylate (198 mg, 0.98 mmol) was added dropwise at 0° C. . . . The mixture was then stirred at room temperature for 16 hours. The resulting mixture was concentrated and purified by silica gel column chromatography (ethyl acetate/petroleum ether=1/1) to obtain tert-butyl 4-(6-((4-cyano-2-fluorophenoxy)methyl)pyridine-2-yl)oxy)piperidine-1-carboxylate (250 mg, 0.59 mmol, 90.8% yield). LC-MS m/z: 428 $[M+H]^+$.

5). Synthesis of 3-fluoro-4-((6-(piperidin-4-oxy) pyridin-2-yl)methoxy)benzonitrile (Intermediate B-1)

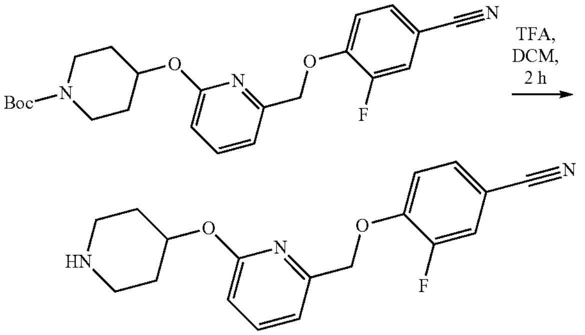

To a solution of tert-butyl 4-(6-((4-cyano-2-fluorophenoxy)methyl)pyridin-2-yl)oxy)piperidine-1-carboxylate (250 mg, 0.59 mmol) in dichloromethane (15 mL) dropwise trifluoroacetic acid (3 mL) was added at room temperature. The mixture stirred at room temperature for 2 hours. After completion, the mixture was concentrated in vacuo to give the crude product, which was further purified by reverse-phase flash chromatography under the following conditions: (Column: spherical C18, 20-40 um, 120 g; Mobile Phase A: 10 mM $NH_4OH$ in water; Mobile phase B: acetonitrile; Flow rate: 80 mL/min; Gradient: 40% B-60% B in 20 minutes; Detector: 254 nm.) The mobile phase containing the desired product at 52% B was collected and concentrated in vacuo to obtain 3-fluoro-4-((6-(piperidin-4-oxy)pyridin-2-yl) methoxy)benzonitrile (180 mg, 0.55 mmol, 93.2% yield), LC-MS m/z: 328 $[M+H]^+$.

Example 2-2. Synthesis of 3-fluoro-4-((6-((piperidin-4-yloxy)methyl)pyridin-2-yloxy)methyl)benzonitrile (Intermediate B-2)

1). Synthesis of tert-butyl 4-(6-fluoropyridin-2-yl) methoxy)piperidine-1-carboxylate

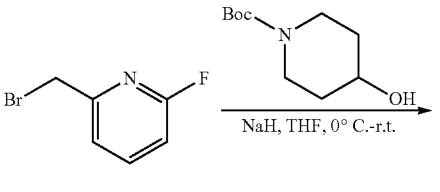

-continued

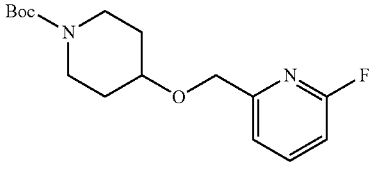

To a solution of tert-butyl 4-hydroxypiperidine-1-carboxylate (1.06 g, 5.26 mmol) in tetrahydrofuran (15 mL) sodium hydride (252 mg, 6.31 mmol, 60% w/w dispersed in mineral oil) was added at 0° C. Then the mixture was stirred for 30 min. After this, the 2-(bromomethyl)-6-fluoropyridine (500 mg, 2.63 mmol) was added slowly to above mixture. The mixture was stirred at room temperature for 16 hours, quenched with methanol (10 mL) at room temperature and concentrated to give a residue in vacuo. The residue was purified by silica gel column chromatography (dichloromethane/methanol=10/1) to give tert-butyl 4-(6-fluoropyridin-2-yl)methoxy)piperidine-1-carboxylate (447 mg, 54.8% yield), LC-MS m/z: 311 $[M+H]^+$.

2). Synthesis of tert-butyl 4-(6-((4-cyano-2-fluorobenzyl)oxy)pyridin-2-yl)methoxy)piperidine-1-carboxylate

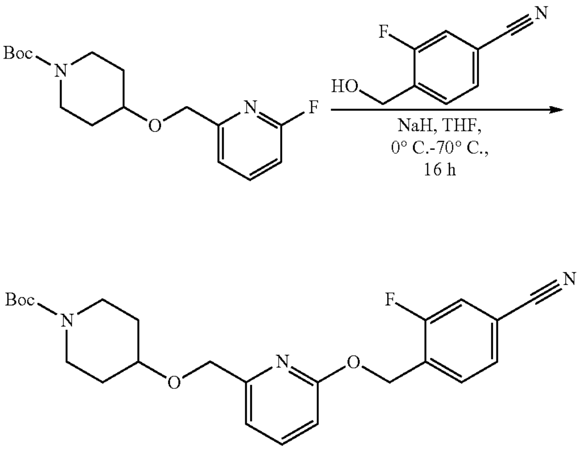

To a solution of 3-fluoro-4-(hydroxymethyl)benzonitrile (581 mg, 3.85 mmol) in tetrahydrofuran (10 mL) sodium hydride (185 mg, 4.62 mmol, 60% w/w dispersed in mineral oil) was added at 0° C., the mixture was stirred for 30 min, then the tert-butyl 4-(6-fluoropyridin-2-yl)methoxy)piperidine-1-carboxylate (240 mg, 0.77 mmol) was added slowly at 0° C. The mixture was stirred at 70° C. for 16 hours. After completion, the mixture was quenched with water (20 mL) at room temperature and extracted with ethyl acetate (20 mL×2). The combined organic layers were washed with brine (10 mL×2), dried over anhydrous sodium sulfate, filtered, and concentrated to give a residue in vacuo. The residue was purified by silica gel column chromatography (dichloromethane/methanol=20/1) to give tert-butyl 4-(6-((4-cyano-2-fluorobenzyl)oxy)pyridin-2-yl) methoxy)piperidine-1-carboxylate (281 mg, 82.4% yield). LC-MS m/z: 442 $[M+H]^+$ 3). Synthesis of 3-fluoro-4-((6-((piperidin-4-yloxy)methyl)pyridin-2-yloxy)methyl)benzonitrile

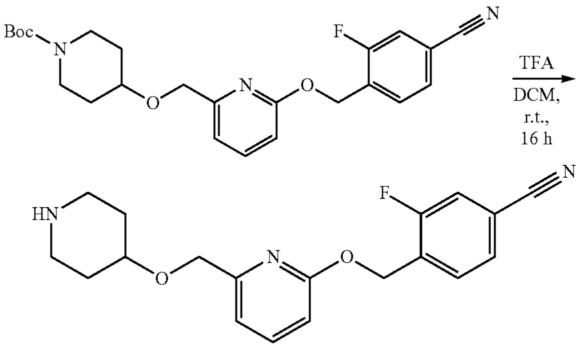

To a solution of tert-butyl 4-(6-((4-cyano-2-fluorobenzyl)oxy)pyridin-2-yl)methoxy)piperidine-1-carboxylate (400 mg, 0.91 mmol) in dichloromethane (2 mL) trifluoroacetic acid (1 mL) was added. The mixture was stirred at room temperature for 16 hours. After complete, the mixture was concentrated to remove the dichloromethane and then adjusted pH to 8-9 with $NH_3$/MeOH (7 M). After this, the mixture was directly concentrated to give a residue in vacuo. The residue was purified by silica gel column chromatography (dichloromethane/methanol=10/1) to give 3-fluoro-4-((6-((piperidin-4-yloxy)methyl)pyridin-2-yl oxy)methyl)benzonitrile (301 mg, 97.4% yield). LC-MS m/z: 342 $[M+H]^+$.

Example 2-3. Synthesis of 3-fluoro-4-((6-(piperidin-4-ylmethoxy)pyridin-2-yl)oxy)methyl)benzonitrile (Intermediate B-3)

1). Synthesis of tert-butyl 4-((6-fluoropyridin-2-yl)oxy)methyl)piperidine-1-carboxylate

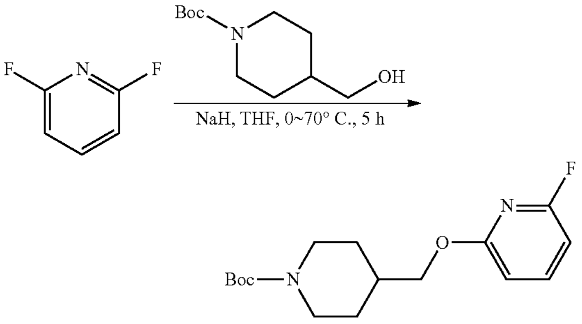

To a solution of tert-butyl 4-(hydroxymethyl)piperidine-1-carboxylate (3.0 g, 13.93 mmol) in dry THF (50 mL) sodium hydride (837 mg, 20.93 mmol, 60% w/w dispersion in mineral oil) was added at 0° C. The mixture was stirred at 0° C. for 30 minutes, then 2,6-difluoropyridine (2.41 g, 20.94 mmol) was slowly added at 0° C. The mixture was stirred at 70° C. for 5 hours. After completion, the mixture was quenched with water (200 mL) at 0° C. and extracted with dichloromethane (50 mL×3). The combined organic layer was concentrated to give a residue in vacuo. The residue was purified by silica gel column chromatography (PE/EA=4/1) to give tert-butyl 4-((6-fluoropyridin-2-yl)oxy)methyl)piperidine-1-carboxylate (2.0 g, 6.44 mmol, 46.2% yield). LC-MS m/z: 311 $[M+H]^+$.

2). Synthesis of tert-butyl 4-((6-((4-cyano-2-fluorobenzyl)oxy)pyridin-2-yl)oxy)methyl)piperidine-1-carboxylate

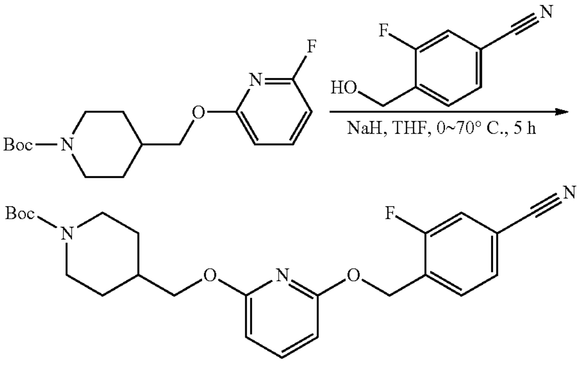

To a solution of 3-fluoro-4-(hydroxymethyl)benzonitrile (365 mg, 2.41 mmol) in dry THF (50 mL) sodium hydride (97 mg, 2.42 mmol, 60% w/w dispersion in mineral oil) was added at 0° C. The mixture was stirred at 0° C. for 30 min, then the tert-butyl 4-((6-fluoropyridin-2-yl)oxy)methyl)piperidine-1-carboxylate (500 mg, 1.61 mmol) was slowly added to above mixture at 0° C. The mixture was stirred at 70° C. for 5 hours. After this, the mixture was quenched with water (30 mL) at 0° C. and extracted with dichloromethane (10 mL×3). The combined organic layer was concentrated to give a residue in vacuo. The residue was purified by silica gel column chromatography (PE/EA=5/1) to give tert-butyl 4-((6-((4-cyano-2-fluorobenzyl)oxy)pyridin-2-yl)oxy)methyl)piperidine-1-carboxylate (400 mg, 0.91 mmol, 56.3% yield). LC-MS m/z: 442 $[M+H]^+$.

3). Synthesis of 3-fluoro-4-((6-(piperidin-4-ylmethoxy)pyridin-2-yl)oxy)methyl)benzonitrile

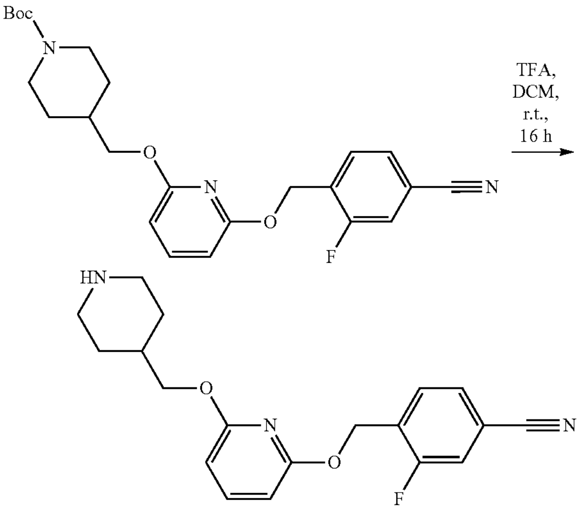

To a solution of tert-butyl 4-((6-((4-cyano-2-fluorobenzyl)oxy)pyridin-2-yl)oxy)methyl)piperidine-1-carboxylate (400 mg, 0.91 mmol) in dichloromethane (5 mL) trifluoroacetic acid (1 mL) was added and stirred at room temperature for 16 hours. When completed, The reaction was quenched with saturated sodium bicarbonate (30 mL) solution and then extracted with dichloromethane (10 mL×2). The combined organic layer was concentrated to give a residue in vacuo. The residue was purified by silica gel column chromatography (DCM/MeOH=10/1) to give 3-fluoro-4-((6-(piperidin-4-ylmethoxy)pyridin-2-yl)) oxy) methyl)benzonitrile (250 mg, 0.73 mmol, 80.6% yield). LC-MS m/z: 342 $[M+H]^+$.

Example 2-4. Synthesis of 3-fluoro-4-((6-(piperidin-4-oxy)pyridin-2-yl)oxy)methyl)benzonitrile (Intermediate B-4)

1). Synthesis of tert-butyl 4-((6-fluoropyridin-2-yl) oxy)piperidine-1-carboxylate

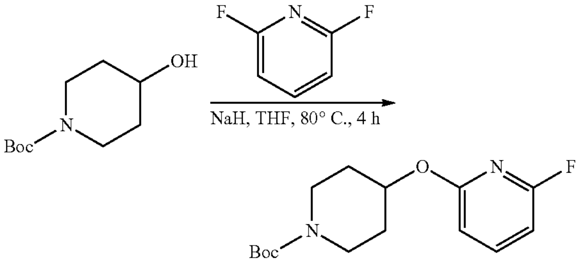

To a solution of tert-butyl 4-hydroxypiperidine-1-carboxylate (3.50 g, 17.39 mmol) in dry tetrahydrofuran (20 mL) sodium hydride (870 mg, 21.74 mmol, 60% w/w dispersion in mineral oil) was added at 0° C. The mixture was stirred at 0° C. for 30 min, then 2,6-difluoropyridine (2.00 g, 17.38 mmol) was slowly added to above mixture at 0° C. The mixture was warmed to 80° C. and stirred for 4 hours. The mixture was quenched with water (20 mL) at room temperature and then extracted with ethyl acetate (20 mL×2). The combined organic layers were washed with brine (10 mL×2), dried over anhydrous sodium sulfate, filtered, and concentrated to give a residue in vacuo. The residue was purified by silica gel column chromatography (PE/EA=10/1) to obtain tert-butyl 4-((6-fluoropyridin-2-yl) oxy)piperidine-1-carboxylate (5.10 g, 17.21 mmol, 99.2% yield).

$^1H$ NMR (400 MHZ, DMSO-$d_6$) δ 7.86 (dd, J=16.8, 8.0 Hz, 1H), 6.73 (dd, J=8.0, 1.6 Hz, 1H), 6.68 (dd, J=7.6, 2.4 Hz, 1H), 5.06-5.02 (m, 1H), 3.70-3.64 (m, 2H), 3.20-3.15 (m, 2H), 1.96-1.90 (m, 2H), 1.58-1.49 (m, 2H), 1.40 (s, 9H).

2). Synthesis of tert-butyl 4-((6-((4-cyano-2-fluorobenzyl)oxy)pyridin-2-yl)oxy)piperidine-1-carboxylate

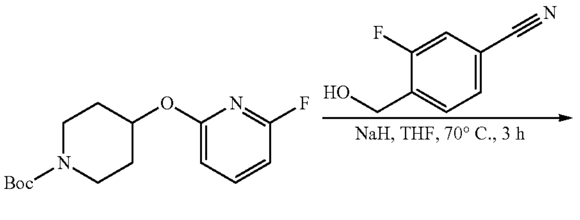

-continued

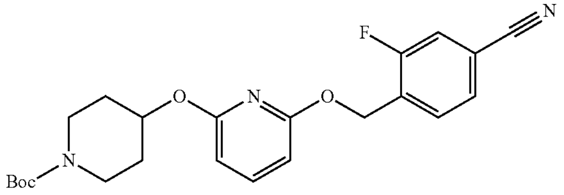

Sodium hydride (541 mg, 13.52 mmol, 60% w/w dispersion in mineral oil) was added to a solution of 3-fluoro-4-(hydroxymethyl)benzonitrile (1.22 g, 8.07 mmol) in dry THF (20 mL). The mixture was stirred at 0° C. for 30 minutes, then the tert-butyl 4-((6-fluoropyridin-2-yl)oxy) piperidine-1-carboxylate (2.00 g, 6.75 mmol) was slowly added to the above mixture at 0° C. The reaction mixture was warmed to 70° C. and stirred for 3 hours. After completion, the reaction solution was cooled to room temperature, quenched with water (20 mL), and extracted with EA (20 mL×2). The combined organic layers were washed with brine (10 mL×2), dried over anhydrous sodium sulfate, filtered, and concentrated to give a residue in vacuo. The residue was purified by silica gel column chromatography (PE/EA=10/1) to give tert-butyl 4-((6-((4-Cyano-2-fluorobenzyl)oxy)pyridin-2-yl)oxy)piperidine-1-carboxylate (1.52 g, 3.56 mmol, 55.6% yield). LC-MS m/z: 428 $[M+H]^+$.

3). Synthesis of 3-fluoro-4-((6-(piperidin-4-oxy) pyridin-2-yl)oxy)methyl)benzonitrile

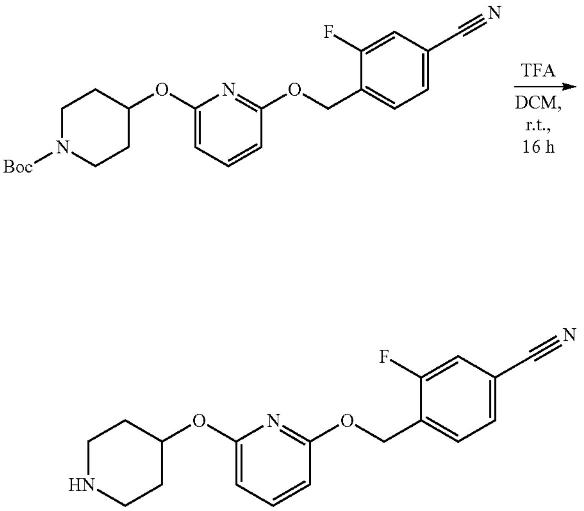

To a solution of tert-butyl 4-((6-((4-cyano-2-fluorobenzyl)oxy)pyridin-2-yl)oxy)piperidine-1-carboxylate (1.52 g, 3.56 mmol) in dichloromethane (15 mL) trifluoroacetic acid (3 mL) was added. The reaction solution was stirred at room temperature for 16 hours. After completion, the reaction mixture was adjusted pH to 8-9 with $NH_3$/MeQH (7M) and then concentrated to give a residue in vacuo. The residue was purified by silica gel column chromatography (DCM/MeOH=10/1) to give 3-fluoro-4-((6-(piperidin-4-oxy)pyridin-2-yl)oxy)methyl)benzonitrile (1.00 g, 3.05 mmol, 86.2% yield). LC-MS m/z: 328 $[M+H]^+$

Example 2-5. Synthesis of 3-fluoro-4-((6-((piperidin-4-oxy)methyl)pyridin-2-yl)methoxy)benzonitrile (Intermediate B-5)

1). Synthesis of methyl 6-(chloromethyl)picolinate

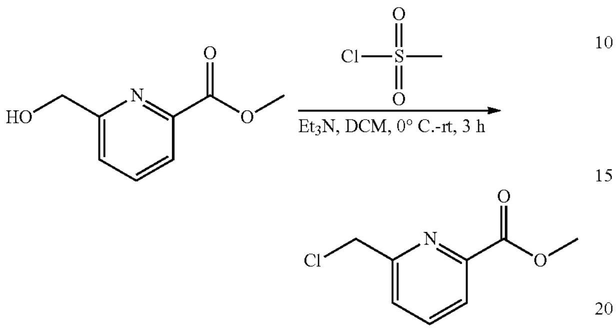

To a solution of methyl 6-(hydroxymethyl)picolinate (2.00 g, 11.98 mmol) in dichloromethane (20 mL) triethylamine (2.42 g, 23.96 mmol) and methanesulfonyl chloride (1.65 g, 14.38 mmol) was sequentially added at 0° C. slowly. The mixture was stirred at room temperature for 3 hours. The mixture was quenched with water (10 mL) and then extracted with dichloromethane (20 mL×2). The combined organic layers were washed with brine (10 ml×2), dried over anhydrous sodium sulfate, filtered, and concentrated in vacuo. The residue was purified by silica gel column chromatography (petroleum ether/ethyl acetate=4/1) to obtain methyl 6-(chloromethyl)picolinate (1.2 g, 54.2% yield). LC-MS m/z: 188 $[M+H]^+$.

2). Synthesis of 6-((1-(tert-butoxycarbonyl)piperidin-4-yl)oxy)methyl)picolinic acid

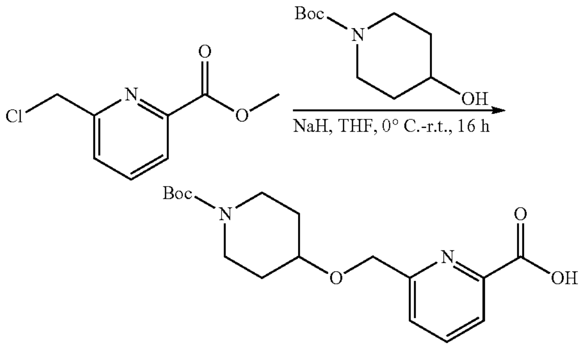

To a solution of tert-butyl 4-hydroxypiperidine-1-carboxylate (4.92 g, 24.50 mmol) in tetrahydrofuran (50 mL) sodium hydride (1.18 g, 29.40 mmol, 60% w/w dispersed in mineral oil) was added at 0° C. The mixture was stirred for 30 min, then the methyl 6-(chloromethyl)picolinate (454 mg, 2.45 mmol) was slowly added above mixture at 0° C. The mixture was stirred at room temperature for 16 hours. The reaction was then quenched with water (10 mL) at room temperature and extracted with ethyl acetate (20 mL×2). The combined organic layers were washed with brine (10 mL×2), dried over anhydrous sodium sulfate, filtered, and concentrated to give a residue in vacuo. The residue was purified by silica gel column chromatography (dichloromethane/methanol=10/1) to give 6-((1-(tert-butoxycarbonyl)piperidin-4-yl)oxy)methyl)picolinic acid (356 mg, 43.2% yield). LC-MS m/z: 337 $[M+H]^+$.

3). Synthesis of methyl 6-((piperidine-4-oxy)methyl)picolinate

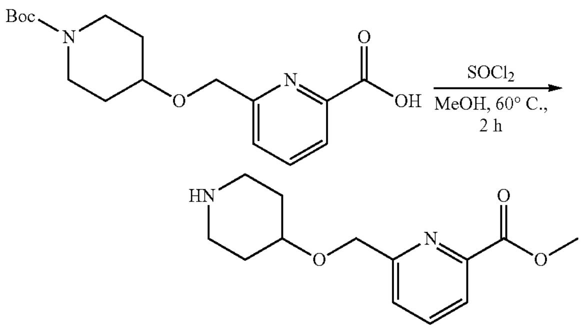

To a solution of 6-((1-(tert-butoxycarbonyl)piperidin-4-yl)oxy)methyl)picolinic acid (356 mg, 1.06 mmol) in methanol (5 mL) thionyl chloride (189 mg, 1.59 mmol) was added dropwise at 0° C. The mixture was stirred at 60° C. for 2 hours. The mixture was quenched with water (10 mL) at room temperature and extracted with ethyl acetate (10 mL×2). The combined organic layers were washed with saturated sodium bicarbonate (10 mL), brine (10 mL), dried over anhydrous sodium sulfate, filtered, and concentrated to give a residue in vacuo. The residue was purified by silica gel column chromatography (dichloromethane/methanol=10/1) to obtain methyl 6-((piperidin-4-oxy)methyl)picolinate (260 mg, 98.1% yield). LC-MS m/z: 251 $[M+H]^+$.

4). Synthesis of methyl 6-((1-(tert-butoxycarbonyl) piperidin-4-yl)oxy)methyl)picolinate

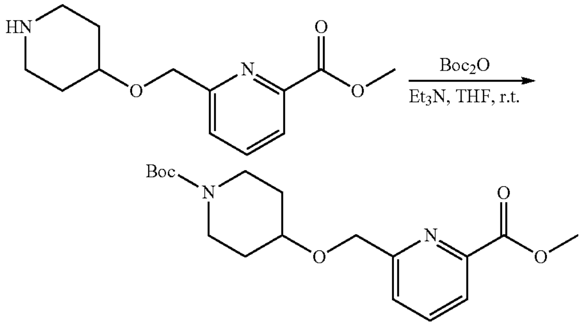

To a mixture of methyl 6-((piperidin-4-oxy)methyl)picolinate (260 mg, 1.04 mmol) and triethylamine (315 mg, 3.12 mmol) in THF (3 mL) di-tert-butyl dicarbonate (453 mg, 2.08 mmol) was added at room temperature. The mixture was stirred at room temperature for 16 hours. The mixture was quenched with water (10 mL) at room temperature and then extracted with ethyl acetate (10 mL×2). The combined organic layers were washed with brine (10 mL×2), dried over anhydrous sodium sulfate, filtered, and concentrated to give a residue in vacuo. The residue was purified by silica gel column chromatography (petroleum ether/ethyl acetate=1/1) to obtain methyl 6-((1-(tert-butoxycarbonyl)piperidin-4-yl)oxy)methyl)picolinate ester (255 mg, 70.1% yield). LC-MS m/z: 351 $[M+H]^+$.

5). Synthesis of tert-butyl 4-(6-(hydroxymethyl)pyridin-2-yl)methoxy)piperidine-1-carboxylate

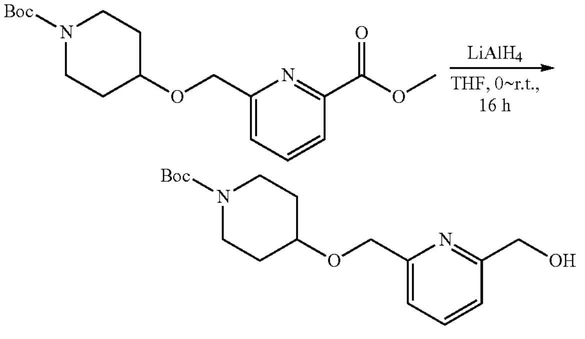

To a solution of methyl 6-((1-(tert-butoxycarbonyl)piperidin-4-yl)oxy)methyl)picolinate (244 mg, 0.70 mmol) in tetrahydrofuran (3 mL) Aluminum lithium hydride (27 mg, 0.70 mmol) was added at 0° C. The mixture was stirred at room temperature for 16 hours. The mixture was quenched with water (10 mL) at room temperature and extracted with ethyl acetate (10 mL×2). The combined organic layers were washed with brine (10 mL×2), dried over anhydrous sodium sulfate, filtered, and concentrated to give residue in vacuo. The residue was purified by silica gel column chromatography (petroleum ether/ethyl acetate=1/1) to obtain tert-butyl 4-(6-(hydroxymethyl)pyridin-2-yl)methoxy)piperidine-1-carboxylate (107 mg, 39.6% yield). LC-MS m/z: 323 $[M+H]^+$.

6). Synthesis of tert-butyl 4-(6-(chloromethyl)pyridin-2-yl)methoxy)piperidine-1-carboxylate

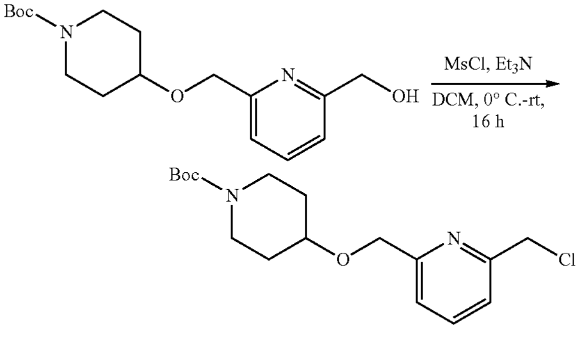

To a solution of tert-butyl 4-(6-(hydroxymethyl)pyridin-2-yl)methoxy)piperidine-1-carboxylate (47 mg, 0.15 mmol) in dichloromethane (1 mL) triethylamine (30 mg, 0.30 mmol) and methanesulfonyl chloride (21 mg, 0.18 mmol) was added sequentially at 0° C. The mixture was stirred at room temperature for 16 hours. After completion, water (10 mL) was added to mixture and then extracted with DCM (20 mL×2). The combined organic layers were washed with brine (10 mL×2), dried over anhydrous sodium sulfate, filtered, and concentrated to give a residue under reduced pressure. The residue was purified by silica gel column chromatography (petroleum ether/ethyl acetate=1/1) to obtain tert-butyl 4-(6-(chloromethyl)pyridin-2-yl)methoxy)piperidine-1-carboxylate (40 mg, 80.6% yield). LC-MS m/z: 341 $[M+H]^+$.

7). Synthesis of tert-butyl 4-(6-((4-cyano-2-fluorophenoxy)methyl)pyridin-2-yl)methoxy)piperidine-1-carboxylate

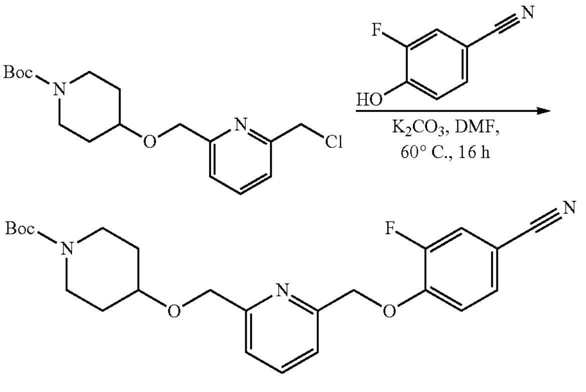

To a mixture of tert-butyl 4-(6-(chloromethyl)pyridin-2-yl)methoxy)piperidine-1-carboxylate (40 mg, 0.12 mmol) and 3-fluoro-4-hydroxybenzonitrile (33 mg, 0.24 mmol) in N,N-dimethylformamide (1 mL) potassium carbonate (541 mg, 13.52 mmol) was added at room temperature. The mixture was stirred at 60° C. for 16 hours. The mixture was quenched with water (10 mL) at room temperature and extracted with ethyl acetate (10 mL×2). The combined organic layers were washed with saturated ammonium chloride (20 mL×3), brine (10 mL×2), dried over anhydrous sodium sulfate, filtered, and concentrated to give a residue in vacuo. The residue was purified by silica gel column chromatography (petroleum ether/ethyl acetate=4/1) to obtain tert-butyl 4-(6-((4-cyano-2-fluorophenoxy)methyl)pyridin-2-yl)methoxy)piperidine-1-carboxylate (35 mg, 67.4% yield). LC-MS m/z: 442 $[M+H]^+$.

8). Synthesis of 3-fluoro-4-((6-((piperidin-4-oxy)methyl)pyridin-2-yl)methoxy)benzonitrile

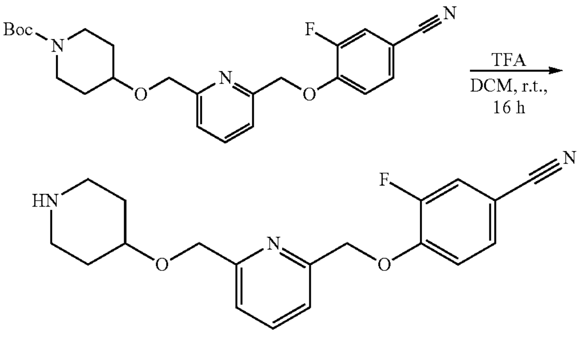

To a solution of tert-butyl 4-(6-((4-cyano-2-fluorophenoxy)methyl)pyridin-2-yl)methoxy)piperidine-1-carboxylate (35 mg, 0.08 mmol) in dichloromethane (2 mL) trifluoroacetic acid (1 mL) was added. The mixture was stirred at room temperature for 16 hours. The reaction mixture was adjusted to pH=8-9 with $NH_3$/MeOH (7 M) and then concentrated to give a residue under reduced pressure. The residue was purified by silica gel column chromatography (dichloromethane/methanol=10/1) to give 3-fluoro-4-((6-((piperidin-4-oxy)methyl)pyridin-2-yl)methoxy)benzonitrile (27 mg, 99% yield). LC-MS m/z: 342 $[M+H]^+$.

Example 2-6. Synthesis of 4-((6-(azetidin-3-yloxy)pyridin-2-yloxy)methyl)-3-fluorobenzonitrile (Intermediate B-6)

1). Synthesis of tert-butyl 3-(6-fluoropyridin-2-yl)oxy) azetidine-1-carboxylate

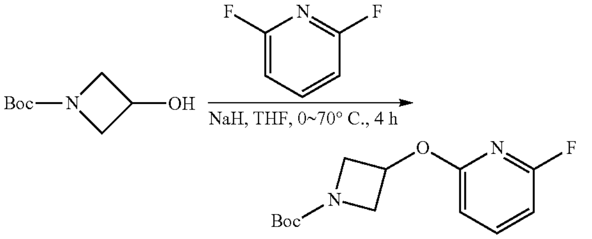

To a solution of tert-butyl 3-hydroxyazetidine-1-carboxylate (2.00 g, 11.55 mmol) in dry THF (30 mL) sodium hydride (694 mg, 17.34 mmol, 60% w/w dispersion in mineral oil) was added at 0° C. The mixture was stirred at 0° C. for 30 min, then the 2,6-difluoropyridine (1.60 g, 13.90 mmol) was added slowly to the mixture at 0° C. The mixture was warmed to 70° C. and stirred for 4 hours. After completion, it was quenched with water (20 mL) at room temperature and extracted with ethyl acetate (2×20 mL). The combined organic layers were washed with brine, dried over anhydrous sodium sulfate, filtered, and concentrated to give a residue in vacuo. The residue was purified by silica gel column chromatography (petroleum ether/ethyl acetate=10/1) to obtain tert-butyl 3-(6-fluoropyridin-2-yl)oxy) azetidine-1-carboxylate (3.00 g, 11.18 g mmol, 96.7% yield). LC-MS m/z: 269 $[M+H]^+$.

2). Synthesis of tert-butyl 3-(6-((4-cyano-2-fluorobenzyl)oxy)pyridin-2-yl)oxy) azetidine-1-carboxylate

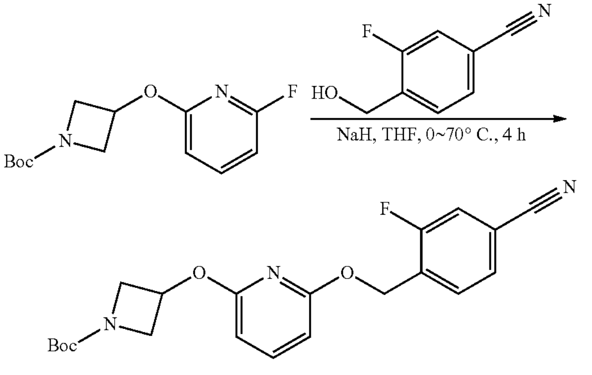

To a solution of 3-fluoro-4-(hydroxymethyl)benzonitrile (1.00 g, 6.62 mmol) in dry THF (20 mL) sodium hydride (397 mg, 9.93 mmol, 60% w/w dispersion in mineral oil) was added at 0° C. The mixture was stirred at 0° C. for 30 minutes, then the tert-butyl 3-(6-fluoropyridin-2-yl)oxy) azetidine-1-carboxylate (1.33 g, 4.96 mmol) was added to above mixture. The mixture was stirred at 70° C. for 4 hours. The reaction mixture was quenched with water (20 mL) at room temperature and extracted with ethyl acetate (2×20 mL). The combined organic layers were washed with brine (2×20 mL), dried over anhydrous sodium sulfate, filtered, and concentrated in vacuo. The residue was purified by silica gel column chromatography (petroleum ether/ethyl acetate=5/1) to give 3-(6-((4-cyano-2-fluorobenzyl)oxy)pyridin-2-yl)oxy) azetidine-1-carboxylate tert-butyl ester (1.52 g, 3.81 mmol, 57.4% yield), LC-MS m/z: 400 $[M+H]^+$.

3). Synthesis of 4-((6-(azetidin-3-yloxy)pyridin-2-yloxy)methyl)-3-fluorobenzonitrile

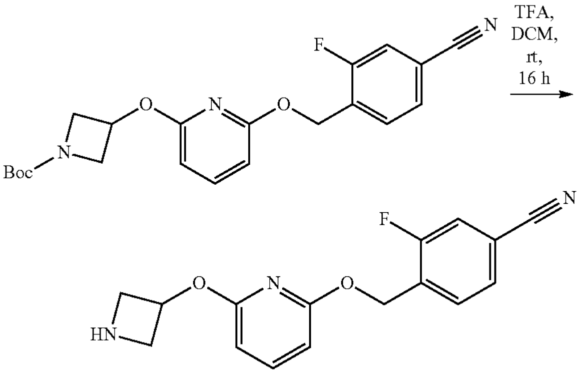

To a solution of tert-butyl 3-(6-((4-cyano-2-fluorobenzyl)oxy)pyridin-2-yl)oxy) azetidine-1-carboxylate (900 mg, 2.25 mmol) in dichloromethane (10 mL) trifluoroacetic acid (2 mL) was added. The reaction mixture was stirred at room temperature for 16 hours. The reaction mixture was adjusted to pH-8-9 with $NH_3$/MeOH (7M) and then concentrated to give a residue in vacuo. The residue was purified by silica gel column chromatography (DCM/MeOH=10/1) to obtain 4-((6-(azetidin-3-yloxy)pyridin-2-yloxy)methyl)-3-fluorobenzonitrile (650 mg, 2.17 mmol, 96.0% yield). LC-MS m/z: 300 $[M+H]^+$.

Example 2-7. Synthesis of 3-fluoro-4-((3-(piperidin-4-oxy)phenoxy)methyl)benzonitrile (Intermediate B-7)

1). Synthesis of 3-fluoro-4-((3-hydroxyphenoxy)methyl)benzonitrile

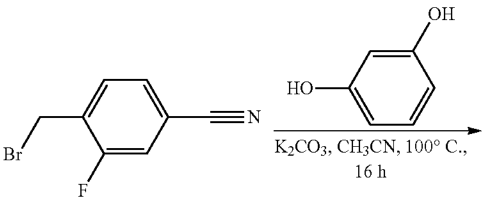

-continued

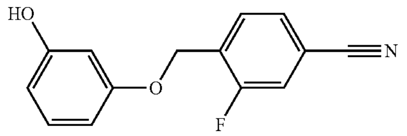

The mixture of resorcinol (1.04 g, 9.52 mmol), potassium carbonate (1.31 g, 9.52 mmol) and 4-bromomethyl-3-fluorobenzonitrile (1.00 g, 4.76 mmol) in acetonitrile (10 mL) was stirred at 100° C. for 16 hours and cooled to room temperature. The mixture was diluted with water (20 mL) and then extracted with ethyl acetate (30 mL×3). The combined organic layers were washed with brine, dried over anhydrous sodium sulfate, filtered, and concentrated to give a residue in vacuo. The residue was purified by silica gel column chromatography (petroleum/ethyl acetate=4/1) to obtain 3-fluoro-4-((3-hydro-xyphenoxy)methyl)benzonitrile (514 mg, 44.0% yield). LC-MS m/z: 244 $[M+H]^+$.

2). Synthesis of tert-butyl 4-(3-((4-cyano-2-fluorobenzyl)oxy)phenoxy)piperidine-1-carboxylate

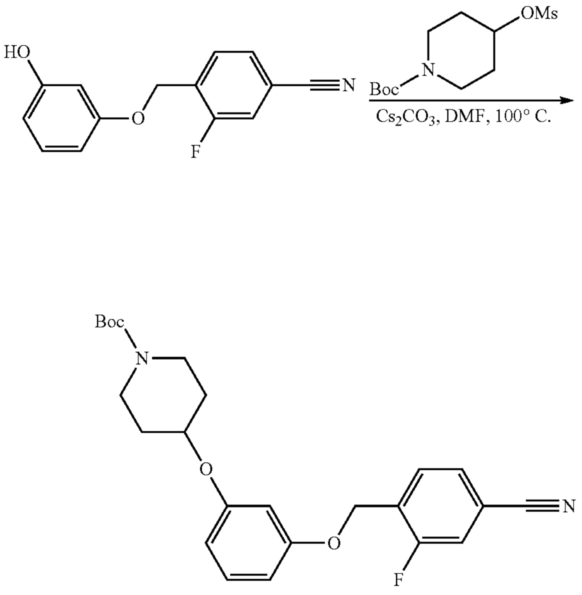

The mixture of 3-fluoro-4-((3-hydroxyphenoxy)methyl) benzonitrile (200 mg, 0.82 mmol), tert-butyl 4-((methylsulfonyl)oxy)piperidine-1-carboxylate (919 mg, 3.29 mmol) and $Cs_2CO_3$ (805 mg, 2.47 mmol) in N,N-dimethylformamide (5 mL) was stirred at 100° C. for 16 hours. The mixture was concentrated in vacuo and purified by reverse-phase flash chromatography (Column: Spherical C18, 20-40 μm, 120 g; Mobile Phase A: water 10 mM $NH_4OH$ in water, Mobile Phase B: acetonitrile; Flow rate: 80 mL/min; Gradient: 40% B-80% B in 20 minutes; Detector: 254 nm). The fractions containing the desired product were collected at 65% B and concentrated in vacuo to give tert-butyl 4-(3-((4-cyano-2-fluorobenzyl)oxy)phenoxy)piperidine-1-carboxylate (180.0 mg, 79.8% yield). LC-MS m/z: 371 $[M+H]^+$.

3). Synthesis of 3-fluoro-4-((3-(piperidin-4-oxy) phenoxy)methyl)benzonitrile

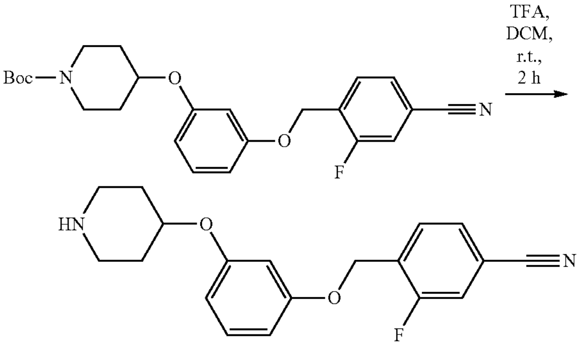

To a solution of tert-butyl 4-(3-((4-cyano-2-fluorobenzyl) oxy)phenoxy)piperidine-1-carboxylate (120.0 mg, 0.282 mmol) in DCM (3 mL) trifluoroacetic acid (1 mL) was added dropwise. The reaction mixture was stirred at room temperature for 2 hours. The mixture was quenched with saturated sodium bicarbonate (30 mL), then extracted with DCM (2×10 mL). The combined organic layers were concentrated in vacuo and purified by silica gel column chromatography (DCM/MeOH=20/1) to obtain 3-fluoro-4-((3-(piperidin-4-oxy)phenoxy)methyl)benzonitrile (89.0 mg, 96.8% yield). LC-MS m/z: 327 $[M+H]^+$.

Example 2-8. Synthesis of 2-((4-Chloro-2-fluorobenzyl)oxy)-3-fluoro-6-(piperidin-4-oxy)pyridine (Intermediate B-8)

1). Synthesis of tert-butyl 4-(6-((4-chloro-2-fluorobenzyl)oxy)-5-fluoropyridin-2-yl)oxypiperidine-1-carboxylate

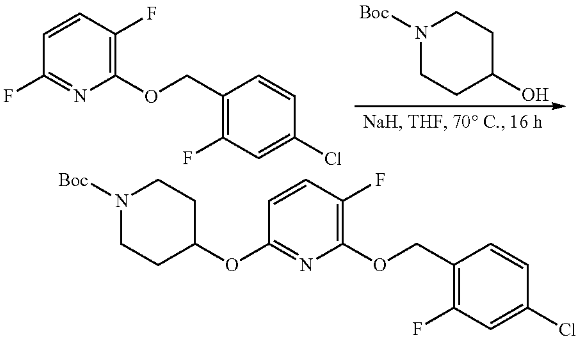

The sodium hydride (264 mg, 0.56 mmol) was added to solution of tert-butyl 4-hydroxypiperidine-1-carboxylate (1.10 g, 5.50 mmol) in tetrahydrofuran (15 mL) at 0° C. The mixture was stirred at 0° C. for 30 minutes. Then 2-((4-chloro-2-fluorobenzyl)oxy)-3,6-difluoropyridine (100 mg, 0.28 mmol) was added to above mixture at 0° C. The mixture was warmed to 70° C. and stirred for 16 hours. The desired product was detected by LC-MS, then the reaction was quenched with methanol (10 mL) and extracted with ethyl acetate (20 mL×3). The combined organic layers were washed with brine (20 mL×2), dried over anhydrous sodium sulfate, filtered, and concentrated to give a residue under reduced pressure. The residue was purified by silica gel column chromatography (petroleum ether:ethyl acetate=5:1) to obtain tert-butyl 4-(6-((4-chloro-2-fluorobenzyl)oxy)-5-fluoropyridine-2-yl)oxypiperidine-1-carboxylate (447 mg, 53.7% yield). LC-MS m/z: 399 $[M+H]^+$.

2). Synthesis of 2-((4-Chloro-2-fluorobenzyl)oxy)-3-fluoro-6-(piperidin-4-oxy)pyridine

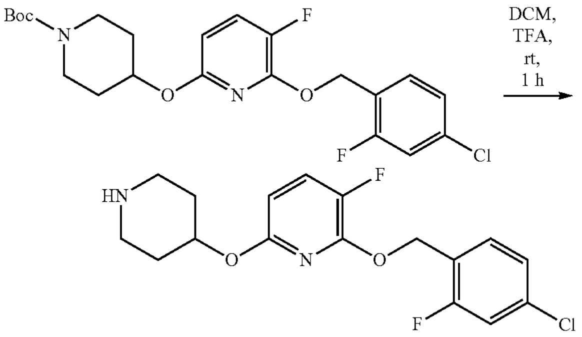

To a solution of tert-butyl 4-(6-((4-chloro-2-fluorobenzyl)oxy)-5-fluoropyridin-2-yl)oxypiperidine-1-carboxylate (447 mg, 0.98 mmol) in dichloromethane (10 mL) trifluoroacetic acid (3 mL) was added. The mixture was stirred at room temperature for 1 hour. The desired product was detected by LC-MS, then the mixture was quenched with water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane: methanol=10:1) to give 2-((4-chloro-2-fluorobenzyl)oxy)-3-fluoro-6-(piperidin-4-oxy)pyridine (199 mg, 57.2% yield). LC-MS m/z: 355 [M+H]+

Example 2-9. Synthesis of 3-fluoro-4-((3-fluoro-6-(piperidin-4-oxy)pyridin-2-yl)methoxy)benzonitrile (Intermediate B-9)

1). Synthesis of methyl 3,6-difluoropicolinate

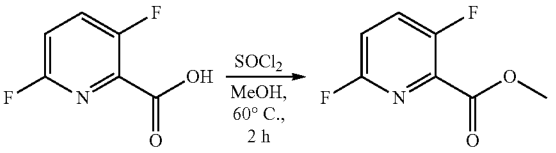

To a solution of 3,6-difluoropicolinic acid (3.6 g, 22.64 mmol) in methanol (80 mL) thionyl chloride (4.0 g, 33.96 mmol) was added. The mixture was stirred at 60° C. for 2 hours. The reaction mixture was directly concentrated in vacuo and then purification by silica gel column chromatography (petroleum ether/ethyl acetate=4/1) to obtain methyl 3,6-difluoropicolinate (3.15 g, 80.4% yield). LC-MS m/z: 174 $[M+H]^+$. 2). Synthesis of (3,6-difluoropyridin-2-yl)methanol

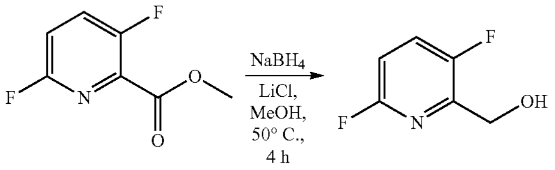

To a solution of methyl 3,6-difluoropicolinate (3.15 g, 18.21 mmol) in methanol (55 mL) sodium borohydride (2.07 g, 54.63 mmol) and lithium chloride (153 mg, 3.64 mmol) was added. The solution was stirred at 50° C. for 4 hours. The reaction mixture was concentrated to give a residue in vacuo. The residue was purified by silica gel column chromatography (petroleum ether/ethyl acetate=2:1) to obtain (3,6-difluoropyridin-2-yl)methanol (2.0 g, 91.1% yield). LC-MS m/z: 146 $[M+H]^+$.

3). Synthesis of methyl (3,6-difluoropyridin-2-yl)methanesulfonate

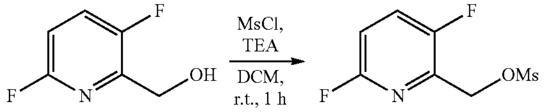 [SMILES: OCc1nc(F)ccc1F ; CS(=O)(=O)OCc1nc(F)ccc1F]

To a solution of (3,6-difluoropyridin-2-yl)methanol (300 mg, 2.07 mmol) in dry dichloromethane (20 mL) triethylamine (460 mg, 4.55 mmol) and methanesulfonyl chloride (358 mg, 3.11 mmol) was added slowly. The mixture was stirred at 0° C. for 1 hour and then stirred at room temperature for another 2 hours. The mixture was diluted with dichloromethane (50 mL) and washed with brine (25 mL). The organic layer was dried over anhydrous sodium sulfate, filtered, and concentrated to give a residue in vacuo. The residue was purified by silica gel column chromatography (petroleum ether/ethyl acetate=2/1) to obtain methyl (3,6-difluoropyridin-2-yl)methanesulfonate (272 mg, 58.9% yield). LC-MS m/z: 224 $[M+H]^+$.

4). Synthesis of 4-((3,6-difluoropyridin-2-yl)methoxy)-3-fluorobenzonitrile

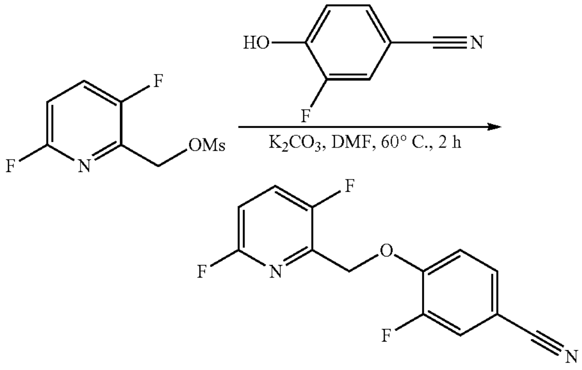

To a mixture of methyl (3,6-difluoropyridin-2-yl)methanesulfonate (272 mg, 1.22 mmol) and 3-fluoro-4-hydroxybenzonitrile (167 mg, 1.22 mmol) in N,N-dimethylformamide (5 mL) potassium carbonate (505 mg, 3.66 mmol) was added. The reaction mixture was stirred at 60° C. for 2 hours. The reaction mixture was quenched by adding water (15 mL), then was extracted with ethyl acetate (30 mL×3). The combined organic layers were washed with brine (30 mL×2), dried over anhydrous sodium sulfate, filtered, and concentrated to give a residue in vacuo. The residue was purified by silica gel column chromatography (petroleum ether/ethyl acetate=2/1) to obtain 4-((3,6-difluoropyridin-2-yl)methoxy)-3-fluorobenzonitrile (270 mg, 83.6% yield). LC-MS m/z: 265 $[M+H]^+$.

5). Synthesis of tert-butyl 4-(6-((4-cyano-2-fluorophenoxy)methyl)-5-fluoropyridin-2-yl)oxypiperidine-1-carboxylate

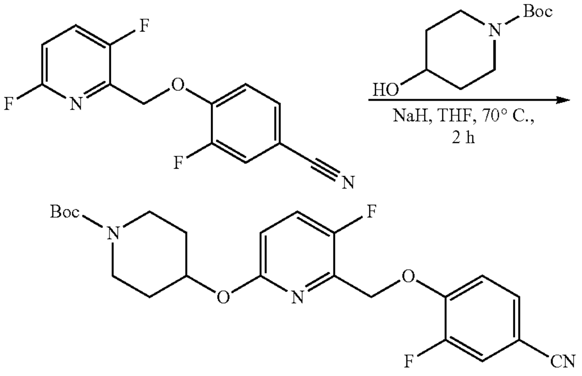

To a solution of tert-butyl 4-hydroxypiperidine-1-carboxylate (246 mg, 1.22 mmol) in THF (30 mL) sodium hydride (61 mg, 1.53 mmol, 60% w/w dispersed in mineral oil) was added at 0° C. The mixture was stirred at 0° C. for 30 minutes, then 4-((3,6-difluoropyridin-2-yl)methoxy)-3-fluorobenzonitrile (270 mg, 1.02 mmol) was added to above mixture. The mixture was stirred at 70° C. for 2 hours. After this, the mixture was quenched with water (20 mL) and extracted with ethyl acetate (20 mL×2). The combined organic layers were washed with brine (10 mL×2), dried over anhydrous sodium sulfate, filtered, and concentrated to give a residue in vacuo. The residue was purified by silica gel column chromatography (petroleum ether/ethyl acetate=2/1) to obtain tert-butyl 4-(6-((4-cyano-2-fluorophenoxy)methyl)-5-fluoropyridin-2-yl)oxypiperidine-1-carboxylate (200 mg, 36.9% yield). LC-MS m/z: 390 $[M+H]^+$.

6). Synthesis of 3-fluoro-4-((3-fluoro-6-(piperidin-4-oxy)pyridin-2-yl)methoxy)benzonitrile

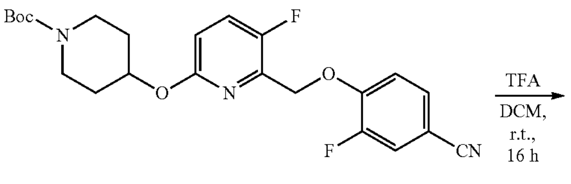

-continued

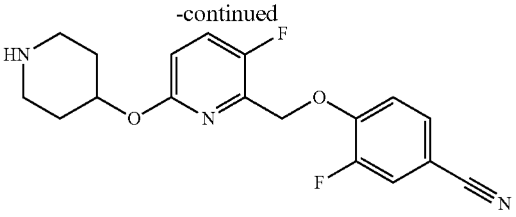

To a solution of tert-butyl 4-(6-((4-cyano-2-fluorophenoxy)methyl)-5-fluoropyridin-2-yl)oxypiperidine-1-carboxylate (200 mg, 0.45 mmol) in dichloromethane (10 mL) trifluoroacetic acid (2 mL) was added. The mixture was stirred at room temperature for 16 hours. The reaction mixture was adjusted to pH-8-9 with $NH_3$/MeOH (7M) and then concentrated to give a residue in vacuo. The residue was purified by silica gel column chromatography (dichloromethane/methanol=10/1) to obtain 3-fluoro-4-((3-fluoro-6-(piperidin-4-oxy)pyridin-2-yl)methoxy)benzonitrile (140 mg, 91.1% yield). LC-MS m/z: 346 $[M+H]^+$.

Example 2-10. Synthesis of 2-((4-Chloro-2-fluorophenylthio)methyl)-6-(piperidin-4-oxy)pyridine (Intermediate B-10)

1) Synthesis of 1,2-bis(4-chloro-2-fluorophenyl) disulfane

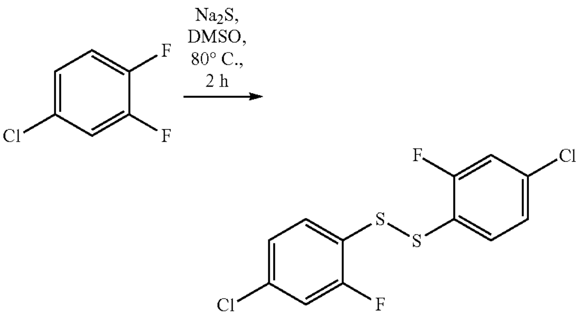

The mixture of 4-chloro-1,2-difluorobenzene (1.00 g, 6.76 mmol) and sodium sulfide (1.05 g, 13.52 mmol) in dimethylsulfoxide (10 mL) was stirred at 80° C. for 2 hours. The mixture was quenched with water (100 mL) and then extracted with dichloromethane (50 mL×2). The aqueous phase was acidified with HCl to pH=2, and extracted with ethyl acetate (50 mL×3). The combined organic layers were washed with brine (100 mL×3), dried over anhydrous sodium sulfate, filtered, and concentrated in vacuo to give 1,2-bis(4-chloro-2-fluorophenyl) disulfane (700 mg, 32.1% yield).

2). Synthesis of 4-chloro-2-fluorobenzenethiol

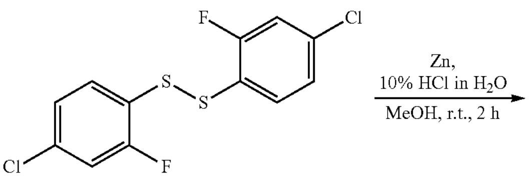

-continued

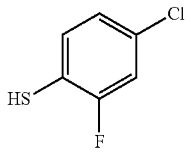

The mixture of 1,2-bis(4-chloro-2-fluorophenyl) disulfane (700 mg, 2.17 mmol) and zinc powder (423 mg, 6.51 mmol) in methanol (10 mL) and HCl (10 mL, 10% in $H_2O$) was as stirred at room temperature for 2 hours. The mixture was diluted with water (50 mL) and then extracted with dichloromethane (20 mL×3). The combined organic layer was concentrated in vacuo to obtain 4-chloro-2-fluorobenzenethiol (400 mg, 56.9% yield), LC-MS m/z: 161 $[M+H]^+$.

3). Synthesis of tert-butyl 4-(6-((4-chloro-2-fluorophenyl)thio) methyl)pyridin-2-yl)oxypiperidine-1-carboxylate

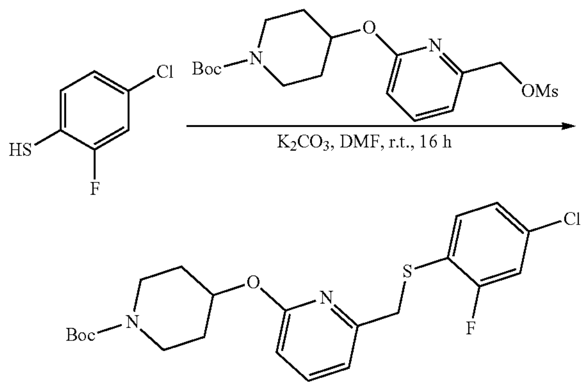

The mixture of 4-chloro-2-fluorobenzenethiol (400 mg, 2.47 mmol), potassium carbonate (682 mg, 4.94 mmol) and tert-butyl 4-((6-((methylsulfonyl)oxy)methyl)pyridine-2-yl) oxy)piperidine-1-carboxylate (956 mg, 2.47 mmol) in N,N-dimethylformamide (20 mL) was stirred at room temperature for 16 hours. The resulting mixture was diluted with water (200 mL) and then extracted with ethyl acetate (80 mL×3). The combined organic layers were washed with saturated brine (100 mL×3), dried over anhydrous sodium sulfate, filtered, and concentrated to give a residue in vacuo. The residue was purified by silica gel column chromatography (ethyl acetate/petroleum ether-1/4) to obtain 4-(6-((4-chloro-2-fluorophenyl)thio) methyl)pyridin-2-yl) Oxypiperidine-1-carboxylate tert-butyl ester (1.00 g, 89.6% yield), LC-MS m/z: 453 $[M+H]^+$.

4). Synthesis of 2-((4-chloro-2-fluorophenylthio) methyl)-6-(piperidin-4-oxy)pyridine

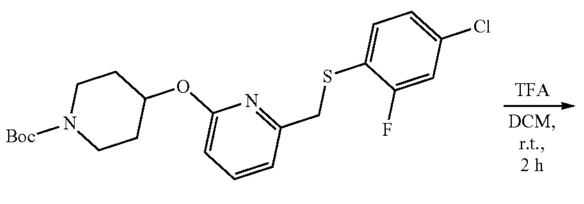

-continued

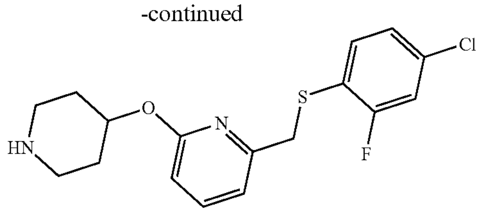

To a solution of tert-butyl 4-(6-((4-chloro-2-fluorophenylthio)methyl)pyridin-2-yl)oxypiperidine-1-carboxylate (1.00 g, 2.21 mmol) in dichloromethane (10 mL) trifluoroacetic acid (3 mL) was added. The solution was stirred at room temperature for 2 hours. The mixture was quenched with saturated sodium bicarbonate (50 mL), then extracted with dichloromethane (20 mL×3). The combined organic layer was concentrated to give a residue in vacuo. The residue was purified by silica gel column chromatography (dichloromethane/methanol=20/1) to obtain 2-((4-chloro-2-fluorophenylthio)methyl)-6-(piperidin-4-oxy)pyridine (700 mg, 90.0% yield). LC-MS m/z: 353 $[M+H]^+$.

Example 2-11. Synthesis of 3-fluoro-4-((6-(piperidin-4-oxy)pyridin-2-yl)methyl)thio) benzonitrile (Inter-mediate B-11)

1). Synthesis of 4,4'-dithioylbis(3-fluorobenzonitrile)

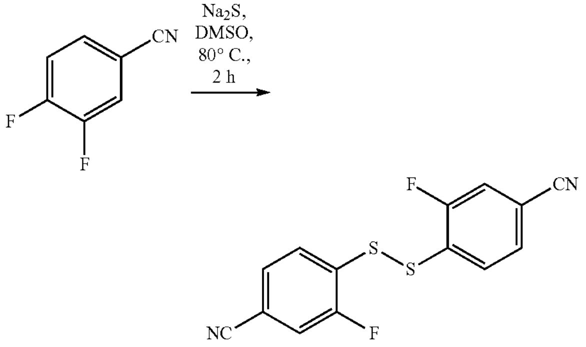

To a solution of 3,4-difluorobenzonitrile (10.00 g, 71.89 mmol) in dimethylsulfoxide (100 mL) was added sodium sulfide (11.22 g, 143.88 mmol). The resulting mixture was stirred at 80° C. for 2 hours. After completion, the reaction was quenched with water (500 mL) and extracted with dichloromethane (200 mL×2). The aqueous phase was acidified to pH=2 with aqueous hydrochloric acid, and extracted with ethyl acetate (200 mL×3). The combined organic layers were washed with brine (400 mL×3), dried over anhydrous sodium sulfate, filtered, and concentrated in vacuo to give 4,4'-dithioylbis(3-fluorobenzonitrile)(5.70 g, 26.1% yield).

2). Synthesis of 3-fluoro-4-mercaptobenzonitrile

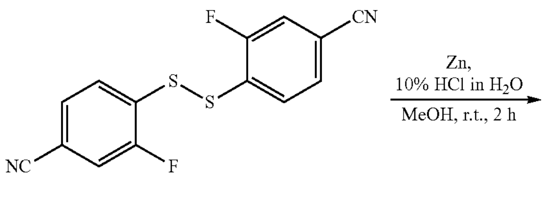

-continued

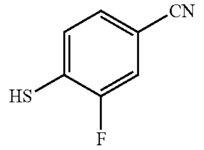

To a mixture of of 4,4'-dithionylbis(3-fluorobenzonitrile) (2.00 g, 6.57 mmol) in methanol (10 mL) and hydrochloric acid (10% in water, 10 ml) zinc powder (1.28 g, 19.58 mmol) was added and the mixture was stirred at room temperature for 2 hours. After this, the mixture was diluted with water (200 mL) and then extracted with dichloromethane (80 mL×3). The organic layer was concentrated to give 3-fluoro-4-mercaptobenzonitrile (1.20 g, 59.6% yield).

3). Synthesis of tert-butyl 4-((6-((4-cyano-2-fluorophenyl)thio) methyl)pyridin-2-yl)oxy)piperidine-1-carboxylate

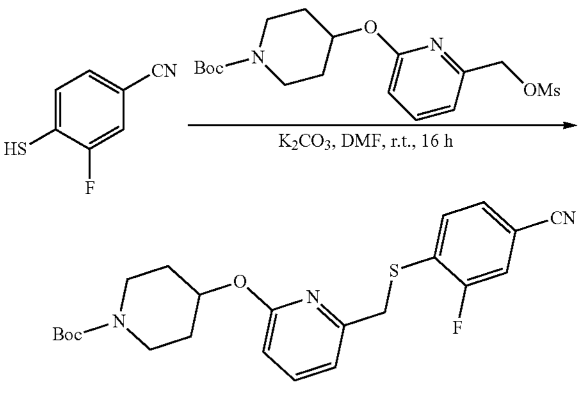

To a mixture of 3-fluoro-4-mercaptobenzonitrile (474 mg, 3.10 mmol) and tert-butyl 4-((6-((methylsulfonyl)oxy) methyl)pyridin-2-yl)oxy)piperidine-1-carboxylate in N,N-dimethylformamide (20 mL) potassium carbonate (856 mg, 6.20 mmol) was added. The mixture was stirred at room temperature for 16 hours. The mixture was diluted with water (200 mL) and then extracted with ethyl acetate (80 mL×3). The combined organic layers were washed with brine (100 mL×3), dried over anhydrous sodium sulfate, filtered, and concentrated in vacuo. The residue was purified by silica gel column chromatography (ethyl acetate/petroleum ether=1/4) to obtain 4-((6-((4-cyano-2-fluorophenylthio)methyl)pyridin-2-yl)oxy)piperidine-1-carboxylate tert-butyl ester (600 mg, 43.7% yield). LC-MS m/z: 444 $[M+H]^+$.

4). Synthesis of 3-fluoro-4-((6-(piperidin-4-oxy) pyridin-2-yl)methylthio) benzonitrile

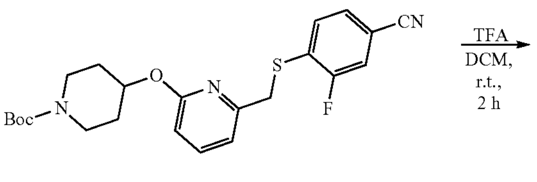

-continued

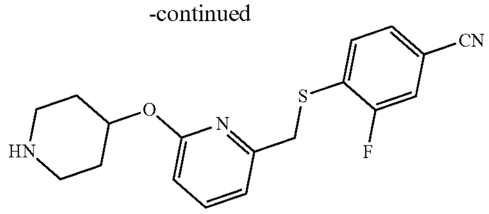

To a solution of tert-butyl 4-((6-((4-cyano-2-fluorophenylthio)methyl)pyridin-2-yl)oxy)piperidine-1-carboxylate (500 mg, 1.13 mmol) in dichloromethane (5 mL) 2,2,2-trifluoroacetic acid (1 mL) was added. The mixture was stirred at room temperature for 2 hours. After completion, the reaction mixture was quenched with saturated sodium bicarbonate (10 mL) and extracted with dichloromethane (5 mL×3). The combined layer was concentrated and then purified by silica gel column chromatography (dichloromethane/methanol=20/1) to give 3-fluoro-4-((6-(piperidin-4-oxy)pyridin-2-yl)methylthio) benzonitrile (334 mg, 86.4% yield). LC-MS m/z: 344 $[M+H]^+$.

Example 2-12. Synthesis of 3-fluoro-4-((3-(piperidin-4-oxy)benzyl)oxy)benzonitrile (Intermediate B-12)

1). Synthesis of tert-butyl 4-(3-(methoxycarbonyl) phenoxy)piperidine-1-carboxylate

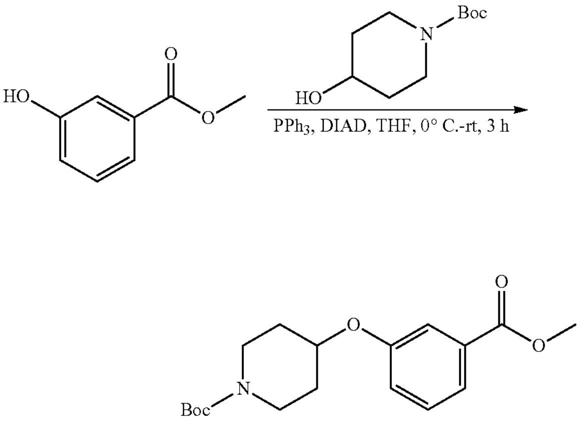

To a mixture of methyl 3-hydroxybenzoate (3.00 g, 19.73 mmol), tert-butyl 4-hydroxypiperidine-1-carboxylate (3.97 g, 19.73 mmol) and triphenylphosphine (7.76 g, 29.60 mmol) in tetrahydrofuran (30 mL) diisopropyl azodicarboxylate (5.98 g, 29.60 mmol) was added at 0° C. The mixture was stirred at room temperature for 3 hours. After completion, water (50 mL) was added to quench the reaction, and extracted with ethyl acetate (50 mL×2). The combined organic layers were washed with brine (20 mL×2), dried over anhydrous sodium sulfate, filtered, and concentrated to give a residue in vacuo. The residue was purified by silica gel column chromatography (petroleum ether/ethyl acetate=5/1) to give tert-butyl 4-(3-(methoxycarbonyl) phenoxy)piperidine-1-carboxylate (2.44 g, 36.9% yield). LC-MS m/z: 358 $[M+H]^+$.

2). Synthesis of tert-butyl 4-(3-(hydroxymethyl) phenoxy)piperidine-1-carboxylate

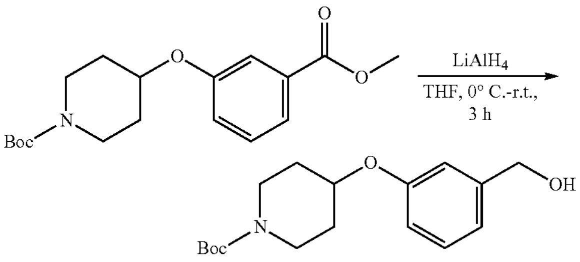

To a solution of tert-butyl 4-(3-(methoxycarbonyl) phenoxy)piperidine-1-carboxylate (1.40 g, 4.18 mmol) in tetrahydrofuran (15 mL) lithium aluminum hydride (238 mg, 6.27 mmol) was slowly added at 0° C. The resulting mixture was stirred at room temperature for 3 hours. After completion, water (5 mL) was added to quench the reaction, then extracted with ethyl acetate (20 mL×2). The combined organic layers were dried over anhydrous sodium sulfate, filtered, and concentrated to give a residue in vacuo. The residue was purified by silica gel column chromatography (petroleum ether/ethyl acetate-5/1) to obtain tert-butyl 4-(3-(hydroxymethyl) phenoxy)piperidine-1-carboxylate (400 mg, 31.2% yield).

3). Synthesis of tert-butyl 4-(3-((4-cyano-2-fluoro-phenoxy)methyl) phenoxy)piperidine-1-carboxylate

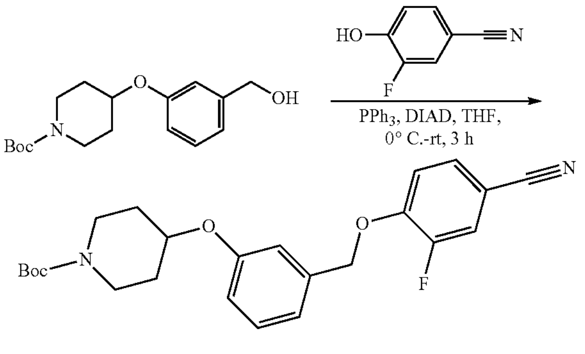

To a mixture of 3-fluoro-4-hydroxybenzonitrile (178 mg, 1.30 mmol), triphenylphosphine (409 mg, 1.56 mmol) and tert-butyl 4-(3-(hydroxymethyl) phenoxy)piperidine-1-carboxylate (400 mg, 1.30 mmol) in tetrahydrofuran (15 mL) azodicarboxylate (315 mg, 1.56 mmol) was added diisopropyl at 0° C. The mixture was stirred at room temperature for 3 hours. After completion, the mixture was diluted with water (20 mL) and then extracted with ethyl acetate (30 mL×2). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain tert-butyl 4-(3-((4-cyano-2-fluorophenoxy)methyl) phenoxy)piperidine-1-carboxylate (312 mg, 56.3% yield). LC-MS m/z: 371 [M+H−56]+.

4). Synthesis of 3-fluoro-4-((3-(piperidin-4-oxy) benzyl)oxy)benzonitrile

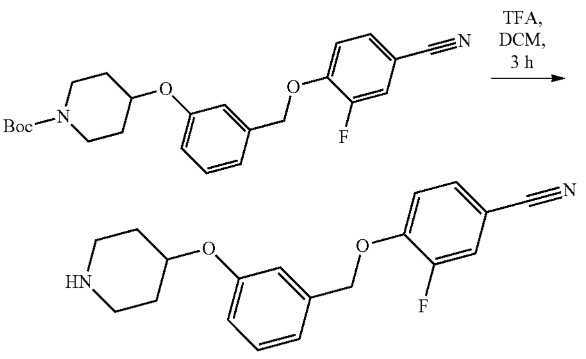

To a solution of tert-butyl 4-(3-((4-cyano-2-fluorophenoxy)methyl) phenoxy)piperidine-1-carboxylate (312 mg, 0.73 mmol) in dichloromethane (5 mL) trifluoroacetic acid (1 mL) was added at room temperature. The mixture was stirred at room temperature for 3 hours. After completion, the mixture was diluted with water (20 mL), and then extracted with ethyl acetate (20 mL×2). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to give 3-fluoro-4-((3-(piperidin-4-oxy)benzyl) oxy)benzonitrile (230 mg, 96.6% yield). LC-MS m/z: 327 $[M+H]^+$.

Example 2-13. Synthesis of 4-(3-((4-chloro-2-fluorophenoxy)methyl) phenoxy)piperidine (Intermediate B-13)

1). Synthesis of tert-butyl 4-(3-((4-chloro-2-fluoro-phenoxy)methyl) phenoxy)piperidine-1-carboxylate

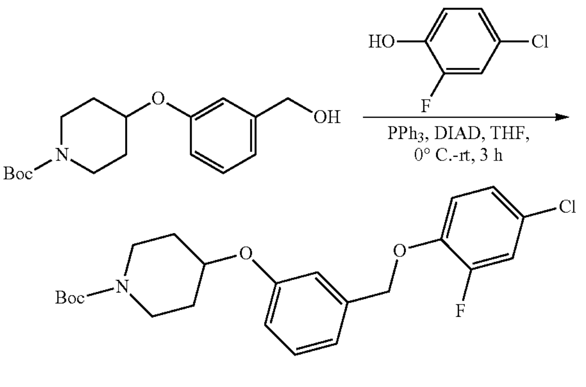

To a mixture of 4-chloro-2-fluorophenol (144 mg, 0.98 mmol), triphenylphosphine (308 mg, 1.18 mmol) and tert-butyl 4-(3-(hydroxymethyl) phenoxy)piperidine-1-formate (300 mg, 0.98 mmol) in tetrahydrofuran (8 mL) diisopropyl azodicarboxylate (238 mg, 1.18 mmol) was added slowly at 0° C. The mixture was stirred at room temperature for 3 hours. After completion, water (20 mL) was added to quench the reaction. The mixture was extracted with ethyl acetate (20 mL×2). The combined organic layers were washed with brine (20 mL×2), dried over anhydrous sodium sulfate, filtered, and concentrated to give a residue in vacuo. The residue was purified by silica gel column chromatography (petroleum ether/ethyl acetate=5/1) to obtain tert-butyl 4-(3-((4-chloro-2-fluorophenoxy)methyl)-phenoxy)piperidine-1-carboxylate (381 mg, 89.2% yield).

2). Synthesis of 4-(3-((4-chloro-2-fluorophenoxy) methyl) phenoxy)piperidine

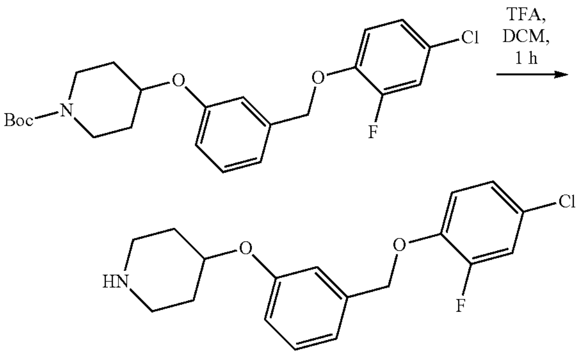

To a solution of tert-butyl 4-(3-((4-chloro-2-fluorophenoxy)methyl) phenoxy)piperidine-1-carboxylate (381 mg, 0.88 mmol) in dichloromethane (5 mL) trifluoroacetic acid (1 mL) was added at room temperature. The resulting mixture was stirred at room temperature for 1 hour. After completion, the mixture was adjusted to pH=7-8 with $NH_3$/MeOH (7 M). The reaction solution was concentrated to give a residue in vacuo. The residue was purified by silica gel column chromatography (dichloromethane/methanol=10/1) to obtain 4-(3-((4-Chloro-2-fluorophenoxy) methyl) phenoxy)-piperidine (271 mg, 91.6% yield). LC-MS m/z: 336 $[M+H]^+$.

Example 2-14. Synthesis of methyl 2-(4-((6-((methylsulfonyl)oxy)methyl)pyridin-2-yl)oxy)phenyl) acetate (Intermediate B-14)

1). Synthesis of methyl 2-(4-((6-bromopyridin-2-yl) oxy)phenyl)acetate

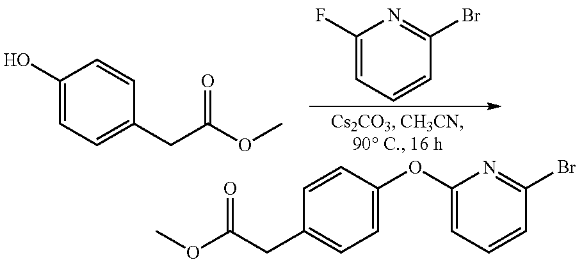

To a solution of methyl 2-(4-hydroxyphenyl)acetate (2.00 g, 12.05 mmol) in acetonitrile (20 mL) added 2-bromo-6-fluoropyridine (2.53 g, 14.46 mmol) and cesium carbonate (5.89 g, 18.07 mmol) was at room temperature. The mixture was stirred at 90° C. for 16 hours. After completion, it was diluted by water (5 mL) and then extracted with ethyl acetate (40 mL×3). The combined organic layers were washed with brine (30 mL×2), dried over anhydrous sodium sulfate, filtered, and concentrated in vacuo. The residue was purified by silica gel column chromatography (petroleum ether/ethyl acetate=10/1) to give methyl 2-(4-((6-bromopyridin-2-yl) oxy)phenyl)acetate (3.17 g: 81.7% yield). LC-MS m/z: 322, 324 $[M+H]^+$.

2). Synthesis of 2-(4-((6-Bromopyridin-2-yl)oxy) phenyl)acetic acid

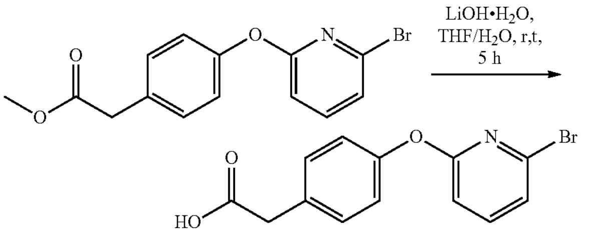

To a mixture of methyl 2-(4-((6-bromopyridin-2-yl)oxy) phenyl)acetate (3.17 g, 9.84 mmol) in tetrahydrofuran (20 mL) and water (15 mL) lithium hydroxide monohydrate (4.13 g, 98.40 mmol) was added at room temperature. The mixture was stirred at room temperature for 5 hours. After completion, the mixture was diluted with water (5 mL), and then extracted with ethyl acetate (40 mL×3). The combined organic layers were washed with brine (30 mL×2), dried over anhydrous sodium sulfate, filtered, and concentrated to give a residue in vacuo. The residue was purified by silica gel column chromatography (dichloromethane/methanol-20/1) to give 2-(4-((6-bromopyridin-2-yl)oxy)-phenyl)acetic acid (1.8 g, 59.4% yield). LC-MS m/z: 308, 310 $[M+H]^+$.

3). Synthesis of 2-(4-((6-(methylcarboxylate) pyridin-2-yl)oxy)phenyl)acetic acid

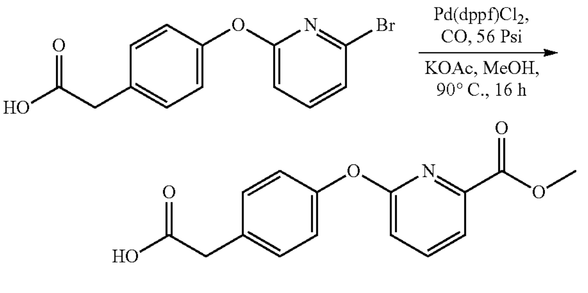

The mixture of 2-(4-((6-bromopyridin-2-yl)oxy)phenyl) acetic acid (900 mg, 2.92 mmol), 1,1'-bisdiphenyl-phosphinoferrocene palladium dichloride (213 mg, 0.29 mmol) and potassium acetate (859 mg, 8.76 mmol) in methanol (10 mL) was degassed with CO three times at room temperature. The mixture was warmed up to 90° C. and stirred for 16 hours under CO (56 Psi) atmosphere. After completion, water (5 mL) was added to quench the reaction. The mixture was extracted with ethyl acetate (40 mL×3). The combined organic layers were washed with brine (30 mL×2), dried over anhydrous sodium sulfate, filtered, and concentrated to give residue in vacuo. The residue was purified by silica gel column chromatography (dichloromethane/methanol=10/1)

to give 2-(4-((6-(methylcarboxylate) pyridin-2-yl)oxy)phenyl)acetic acid (385 mg, 45.9% yield). LC-MS m/z: 288 $[M+H]^+$.

4). Synthesis of 2-(4-((6-(hydroxymethyl)pyridin-2-yl)oxy)phenyl)acetic acid

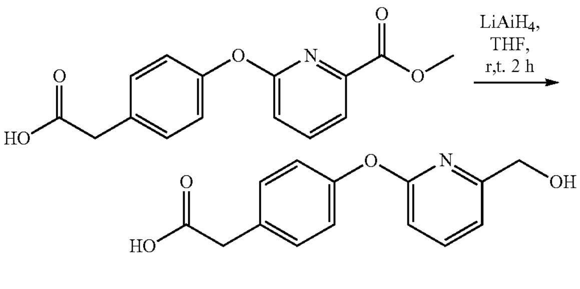

To a solution of 2-(4-((6-(methylcarboxylate) pyridin-2-yl)oxy)phenyl)acetic acid (385 mg, 1.34 mmol) in tetrahydrofuran (5 mL) lithium aluminum hydride (76 mg, 2.01 mmol) was added at 0° C. The mixture was stirred at room temperature for an additional 2 hours. After completion, the mixture was adjusted to pH=5-6 with hydrochloric acid (1M), and then extracted with ethyl acetate (20 mL×3). The combined organic layer were washed with brine (20 mL), dried over anhydrous sodium sulfate, filtered, and concentrated to give a residue in vacuo. The residue was purified by silica gel column chromatography (dichloromethane/methanol=10/1) to obtain 2-(4-((6-(hydroxymethyl)pyridin-2-yl)oxy)phenyl)acetic acid (118 mg, 33.9% yield). LC-MS m/z: 260 $[M+H]^+$.

5). Synthesis of methyl 2-(4-(6-(hydroxymethyl)pyridin-2-yl)oxy)phenyl)acetate

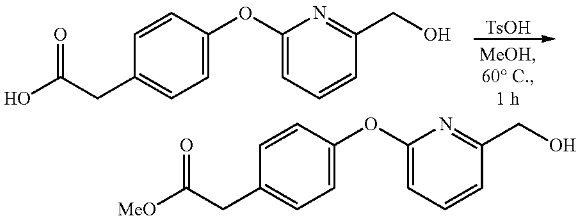

To a solution of 2-(4-((6-(Hydroxymethyl)pyridin-2-yl)oxy)phenyl)acetic acid (118 mg, 0.45 mmol) in methanol (3 mL) p-toluenesulfonic acid (12 mg, 0.32 mmol) was added at room temperature. The resulting mixture was stirred at 60° C. for 1 hour. When completion, the reaction mixture was quenched by adding water (5 mL) and then was extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=15/1) to obtain methyl 2-(4-(6-(hydroxymethyl)pyridin-2-yl)oxy)phenyl)acetate (89 mg, 72.4% yield). LC-MS m/z: 274 $[M+H]^+$.

6). Synthesis of methyl 2-(4-((6-((methylsulfonyl)oxy)methyl)pyridin-2-yl)oxy)phenyl)acetate

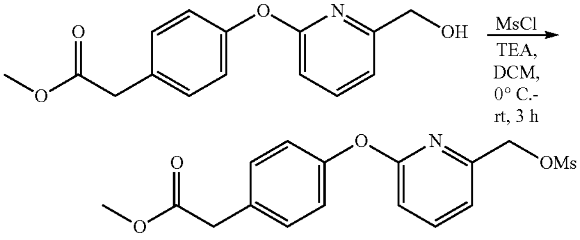

To a mixture of 2-(4-(6-(hydroxymethyl)pyridin-2-yl)oxy)phenyl)acetate (89 mg, 0.33 mmol) and triethylamine (74 mg, 0.73 mmol) mmol) in dichloromethane (3 mL), methanesulfonyl chloride was added slowly at 0° C. The reaction mixture was stirred at room temperature for 3 hours. After completion, the reaction was quenched by adding water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (petroleum ether/ethyl acetate=4/1) to obtain 2-(4-((6-((methylsulfonyl)oxy)methyl)-pyridin-2-yl) oxy (56 mg, 48.3% yield). LC-MS m/z: 352 $[M+H]^+$.

Example 2-15. Synthesis of other B intermediates

The following intermediates can be obtained with similar to the synthetic steps of each intermediate from example 2-1 to Example 2-14

| Number | Structure | Name | MS m/z: [M + H]+ |
|---|---|---|---|
| Intermediate B-15 | 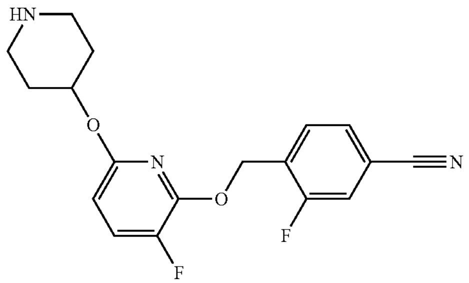 [SMILES: N#Cc1ccc(COc2nc(OC3CCNCC3)ccc2F)c(F)c1] | 3-Fluoro-4-(((3-fluoro-6-(piperidin-4-oxy)pyridin-2-yl)oxy)-methyl)benzonitrile | 346 |

-continued

| Number | Structure | Name | MS m/z: [M + H]+ |
|---|---|---|---|
| Intermediate B-16 | 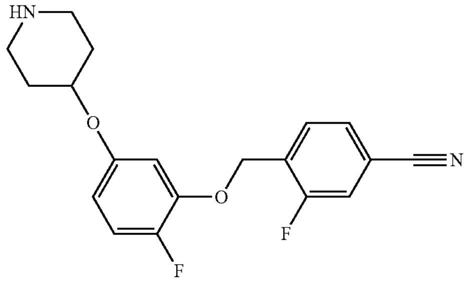 [SMILES: N#Cc1ccc(COc2cc(OC3CCNCC3)ccc2F)c(F)c1] | 3-Fluoro-4-((2-fluoro-5-(piperidin-4-oxy)phenoxy)methyl)benzonitrile | 345 |
| Intermediate B-17 | 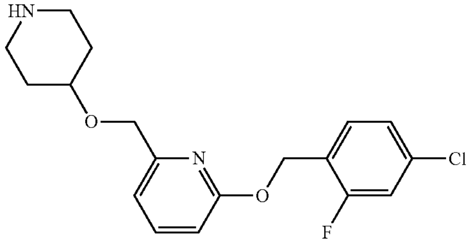 [SMILES: Fc1cc(Cl)ccc1COc1cccc(COC2CCNCC2)n1] | 2-((4-Chloro-2-fluorobenzyl)oxy)-6-((piperidin-4-oxy)methyl)pyridine | 351 |
| Intermediate B-18 | 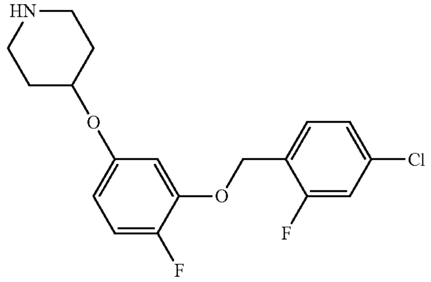 [SMILES: Fc1cc(Cl)ccc1COc1cc(OC2CCNCC2)ccc1F] | 4-(3-((4-Chloro-2-fluorobenzyl)oxy)-4-fluoro-phenoxy)piperidine | 354 |
| Intermediate B-19 | 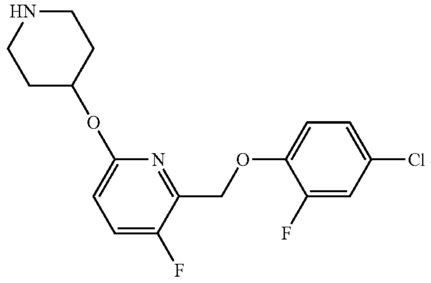 [SMILES: Fc1cc(Cl)ccc1OCc1nc(OC2CCNCC2)ccc1F] | 2-((4-Chloro-2-fluorophenoxy)methyl)-3-fluoro-6-(piperidin-4-oxy)pyridine | 355 |
| Intermediate B-20 | 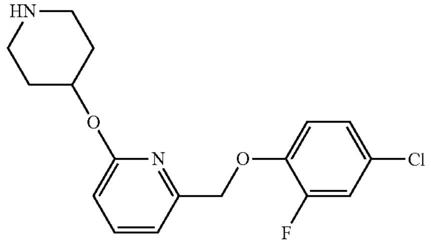 [SMILES: Fc1cc(Cl)ccc1OCc1cccc(OC2CCNCC2)n1] | 2-((4-Chloro-2-fluorophenoxy)methyl)-6-(piperidin-4-oxy)pyridine | 337 |

-continued

| Number | Structure | Name | MS m/z: [M + H]+ |
|---|---|---|---|
| Intermediate B-21 | 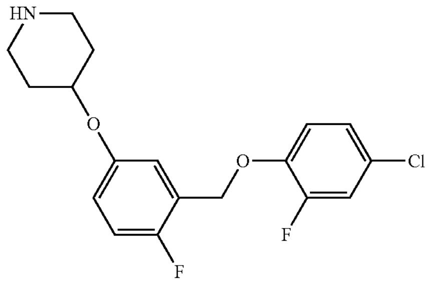 [SMILES: Fc1ccc(OC2CCNCC2)cc1COc1ccc(Cl)cc1F] | 4-(3-((4-Chloro-2-fluorophenoxy)methyl)-4-fluoro-phenoxy)piperidine | 354 |
| Intermediate B-22 | 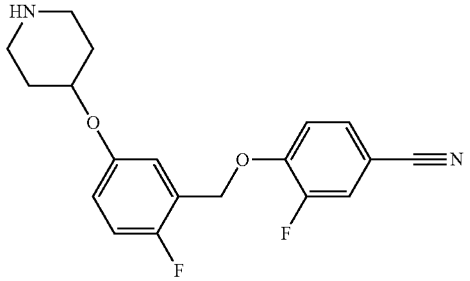 [SMILES: N#Cc1ccc(OCc2cc(OC3CCNCC3)ccc2F)c(F)c1] | 3-Fluoro-4-((2-fluoro-5-(piperidin-4-oxy)benzyl)oxy)-benzonitrile | 345 |
| Intermediate B-23 | 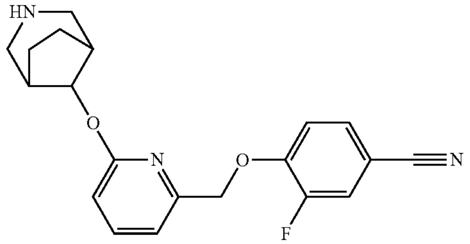 [SMILES: N#Cc1ccc(OCc2cccc(OC3C4CCC3CNC4)n2)c(F)c1] | 4-((6-((3-azabicyclo[3.2.1]octan-8-yl)oxy)pyridin-2-yl)methoxy)-3-fluorobenzonitrile | 354 |
| Intermediate B-24 | 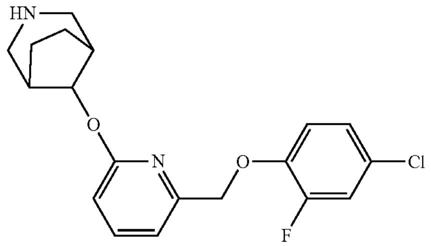 [SMILES: Fc1cc(Cl)ccc1OCc1cccc(OC2C3CCC2CNC3)n1] | 8-((6-((4-Chloro-2-fluorophenoxy)meth-yl)pyridin-2-yl)oxy)-3-azabicyclo[3.2.1]octane | 363 |
| Intermediate B-25 | 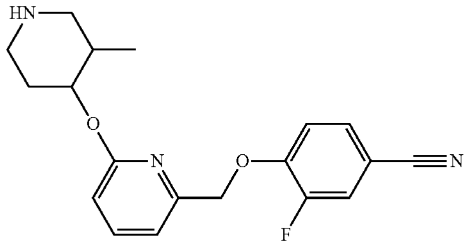 [SMILES: CC1CNCCC1Oc1cccc(COc2ccc(C#N)cc2F)n1] | 3-Fluoro-4-((6-((3-methylpiperidin-4-yl)oxy)pyridin-2-yl)methoxy)benzonitrile | 342 |
| Intermediate B-26 | 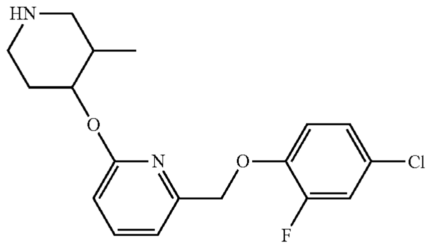 [SMILES: CC1CNCCC1Oc1cccc(COc2ccc(Cl)cc2F)n1] | 2-((4-Chloro-2-fluorophenoxy)methyl)-6-((3-methylpiperidin-4-yl)oxy)pyridine | 351 |

-continued

| Number | Structure | Name | MS m/z: [M + H]+ |
|---|---|---|---|
| Intermediate B-27 | 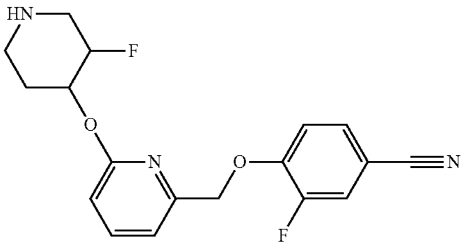 [SMILES: N#Cc1ccc(OCc2cccc(OC3CCNCC3F)n2)c(F)c1] | 3-Fluoro-4-((6-((3-fluoropiperidin-4-yl)oxy)pyridin-2-yl)methoxy)benzonitrile | 346 |
| Intermediate B-28 | 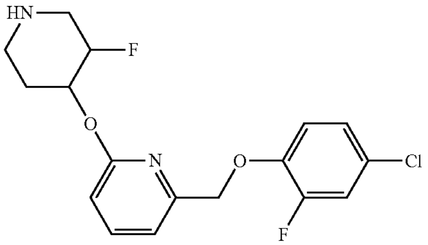 [SMILES: Fc1cc(Cl)ccc1OCc1cccc(OC2CCNCC2F)n1] | 2-((4-Chloro-2-fluorophenoxy)methyl)-6-((3-fluoropiperidin-4-yl)oxy)pyridine | 355 |
| Intermediate B-29 | 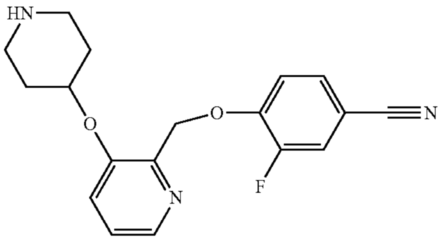 [SMILES: N#Cc1ccc(OCc2ncccc2OC2CCNCC2)c(F)c1] | 3-Fluoro-4-((3-(piperidin-4-oxy)pyridin-2-yl)methoxy)benzonitrile | 328 |
| Intermediate B-30 | 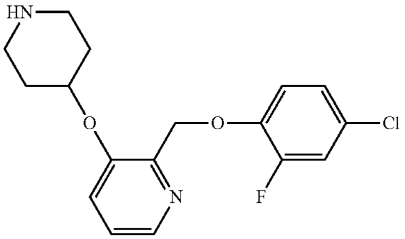 [SMILES: Fc1cc(Cl)ccc1OCc1ncccc1OC1CCNCC1] | 2-((4-Chloro-2-fluorophenoxy)methyl)-3-(piperidin-4-oxy)pyridine | 337 |
| Intermediate B-31 | 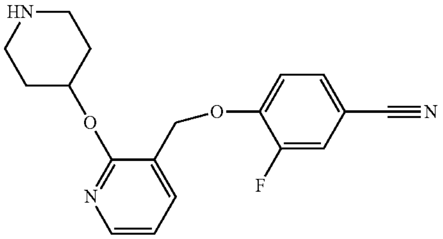 [SMILES: N#Cc1ccc(OCc2cccnc2OC2CCNCC2)c(F)c1] | 3-Fluoro-4-((2-(piperidin-4-oxy)pyridin-3-yl)methoxy)-benzonitrile | 328 |
| Intermediate B-32 | 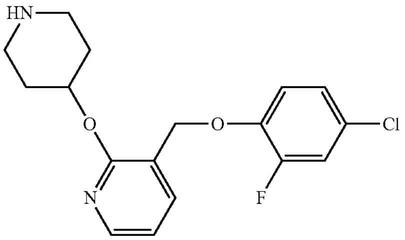 [SMILES: Fc1cc(Cl)ccc1OCc1cccnc1OC1CCNCC1] | 3-((4-Chloro-2-fluorophenoxy)methyl)-2-(piperidin-4-oxy)-pyridine | 337 |

-continued

| Number | Structure | Name | MS m/z: [M + H]+ |
|---|---|---|---|
| Intermediate B-33 | 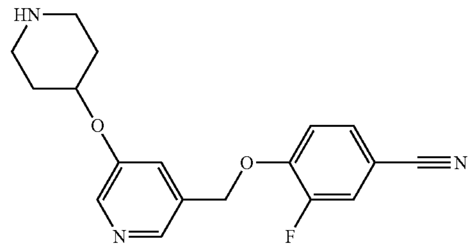 [SMILES: N#Cc1ccc(OCc2cncc(OC3CCNCC3)c2)c(F)c1] | 3-Fluoro-4-((5-(piperidin-4-oxy)pyridin-3-yl)methoxy)-benzonitrile | 328 |
| Intermediate B-34 | 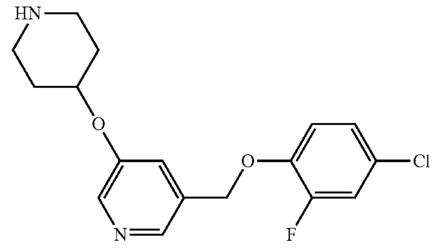 [SMILES: Fc1cc(Cl)ccc1OCc1cncc(OC2CCNCC2)c1] | 3-((4-Chloro-2-fluorophenoxy)methyl)-5-(piperidin-4-oxy)pyridine | 337 |
| Intermediate B-35 | 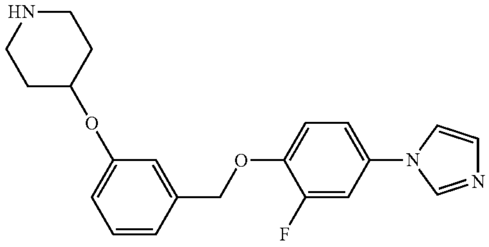 [SMILES: Fc1cc(-n2ccnc2)ccc1OCc1cccc(OC2CCNCC2)c1] | 4-(3-((2-Fluoro-4-(1H-imidazol-1-yl)phenoxy)meth-yl)phenoxy)piperidine | 368 |
| Intermediate B-36 | 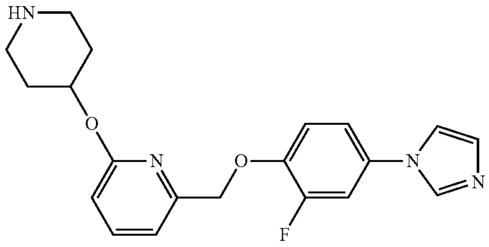 | 2-((2-Fluoro-4-(1H-imidazol-1-yl)phenoxy)methyl)-6-(piperidin-4-oxy)pyridine | 369 |
| Intermediate B-37 | 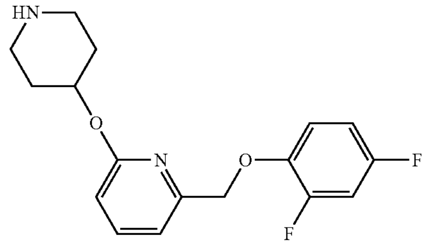 [SMILES: Fc1ccc(OCc2cccc(OC3CCNCC3)n2)c(F)c1] | 2-((2,4-Difluoro-phenoxy)methyl)-6-(piperidin-4-oxy)pyridine | 321 |
| Intermediate B-38 | 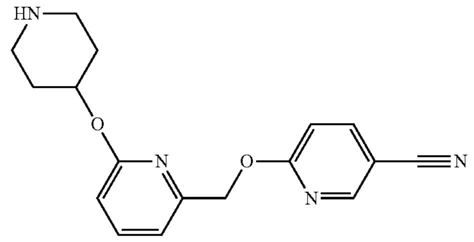 [SMILES: N#Cc1ccc(OCc2cccc(OC3CCNCC3)n2)nc1] | 6-((6-(Piperidin-4-oxy)pyridin-2-yl)methoxy)-nicotinonitrile | 311 |

-continued

| Number | Structure | Name | MS m/z: [M + H]+ |
|---|---|---|---|
| Intermediate B-39 | 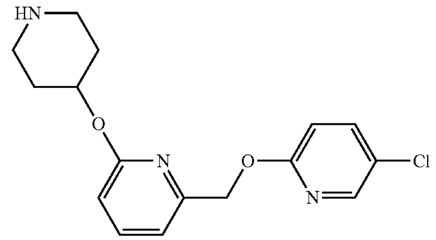 [SMILES: Clc1ccc(OCc2cccc(OC3CCNCC3)n2)nc1] | 5-Chloro-2-((6-(piperidin-4-oxy)-pyridin-2-yl)methoxy)-pyridine | 320 |

Example 3. Synthesis of 2-((4-((6-((4-cyano-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylic acid (compound 1)

1). Synthesis of methyl 4-(2-(4-((6-((4-cyano-2-fluorophenoxy)methyl)pyridin-2-yl)oxy)piperidin-1-yl)acetamide)-3-((1-ethyl-1H-imidazol-5-yl)methyl)amino)benzoate

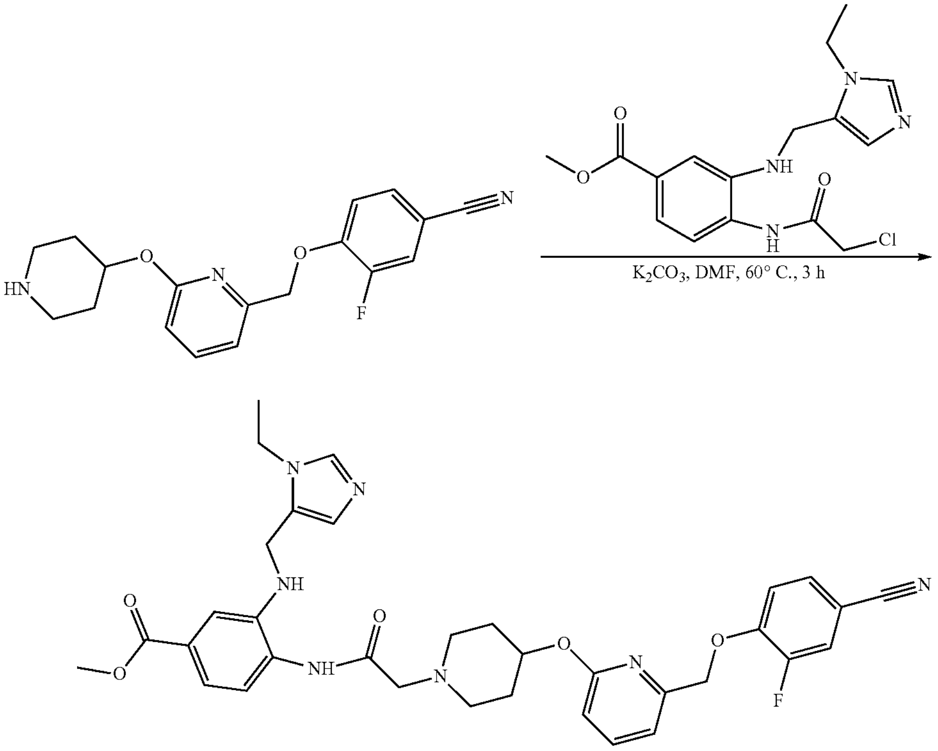

To a mixture of 3-fluoro-4-((6-(piperidin-4-oxy)pyridin-2-yl)methoxy)benzonitrile (100 mg, 0.31 mmol) and methyl 4-(2-chloroacetamido)-3-(((1-ethyl-1H-imidazol-5-yl)methyl)amino)benzoate (109 mg, 0.31 mmol) in N,N-dimethylformamide (2 mL) potassium carbonate (86 mg, 0.62 mmol) was added. The mixture was stirred at 60° C. for 3 hours. The resulting mixture was poured into brine (20 mL) and extracted with dichloromethane (5 mL×2). The combined organic layer was concentrated in vacuo and purified by reverse-phase flash chromatography under the following conditions (Column: spherical C18, 20-40 um, 120 g; Mobile Phase A: 0.1% $NH_4OH$ in Water; Mobile Phase B: Acetonitrile; Flow rate: 80 mL/min; Gradient: 0% B-95% B over 30 minutes; Detector: 254 nm). The fractions containing desired product were collected at 72% B and concentrated vacuo to afford methyl 4-(2-(4-((6-((4-cyano-2-fluorophenoxy)methyl)pyridin-2-yl)oxy)piperidin-1-yl)acetamide)-3-((1-ethyl-1H-imidazol-5-yl)methyl)amino)benzoate (40 mg, 20.1% yield). LC-MS m/z: 642.5 $[M+H]^+$.

2). Synthesis of methyl 2-((4-((6-((4-cyano-2-fluorophenoxy)methyl)pyridin-2-yl)oxy)piperidin-1-yl)methyl)-1-(1-ethyl-1H-imidazol-5-yl)methyl)-1H-benzo[d]imidazole-6-carboxylate

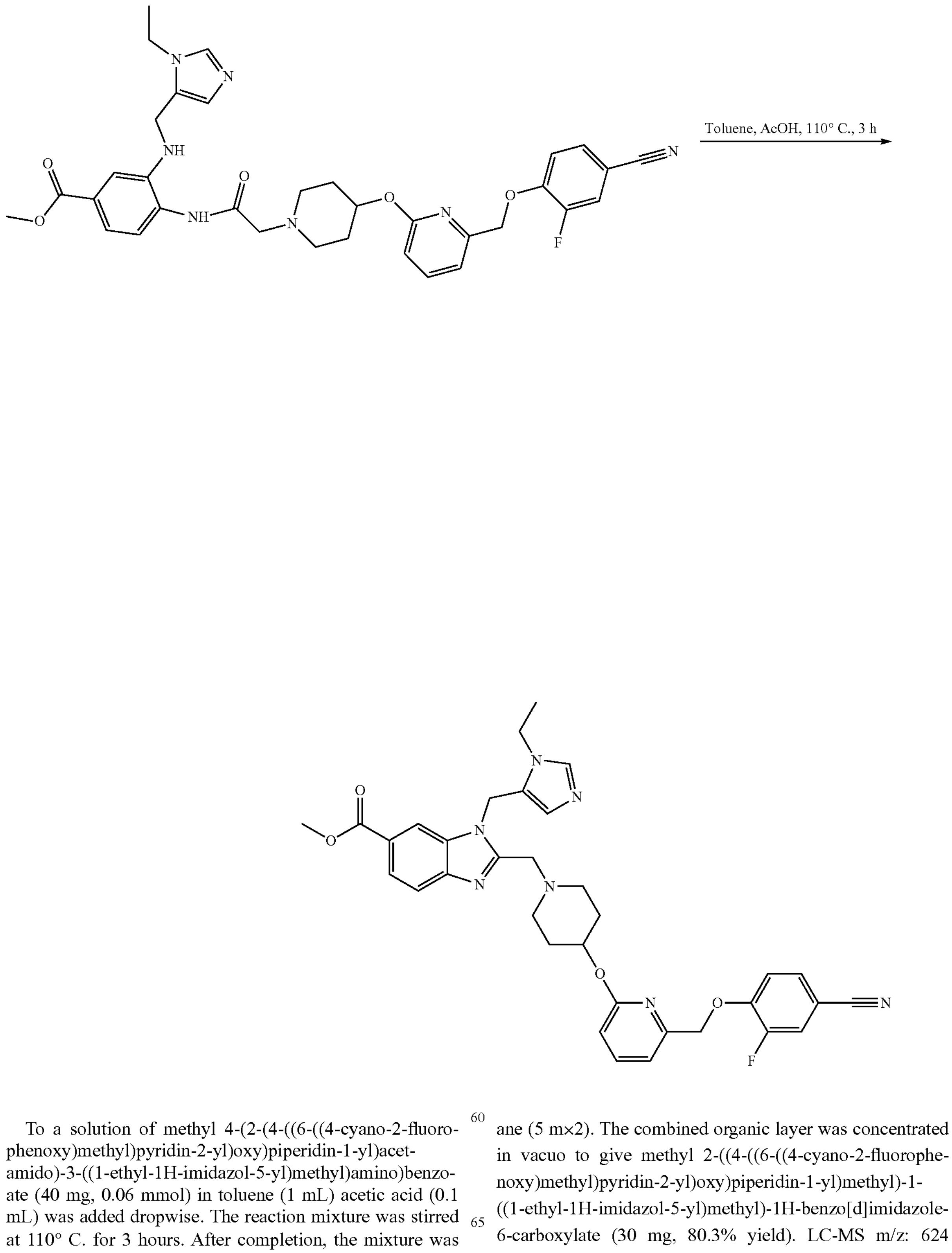

To a solution of methyl 4-(2-(4-((6-((4-cyano-2-fluorophenoxy)methyl)pyridin-2-yl)oxy)piperidin-1-yl)acetamido)-3-((1-ethyl-1H-imidazol-5-yl)methyl)amino)benzoate (40 mg, 0.06 mmol) in toluene (1 mL) acetic acid (0.1 mL) was added dropwise. The reaction mixture was stirred at 110° C. for 3 hours. After completion, the mixture was poured into brine (10 mL) and extracted with dichloromethane (5 m×2). The combined organic layer was concentrated in vacuo to give methyl 2-((4-((6-((4-cyano-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate (30 mg, 80.3% yield). LC-MS m/z: 624 $[M+H]^+$.

3). Synthesis of 2-((4-((6-((4-cyano-2-fluorophenoxy)methyl)pyridin-2-yl)oxy)piperidin-1-yl) methyl)-1-((1-ethyl-1H-imidazol-5-yl)methyl)-1H-benzo[d]imidazole-6-carboxylic acid

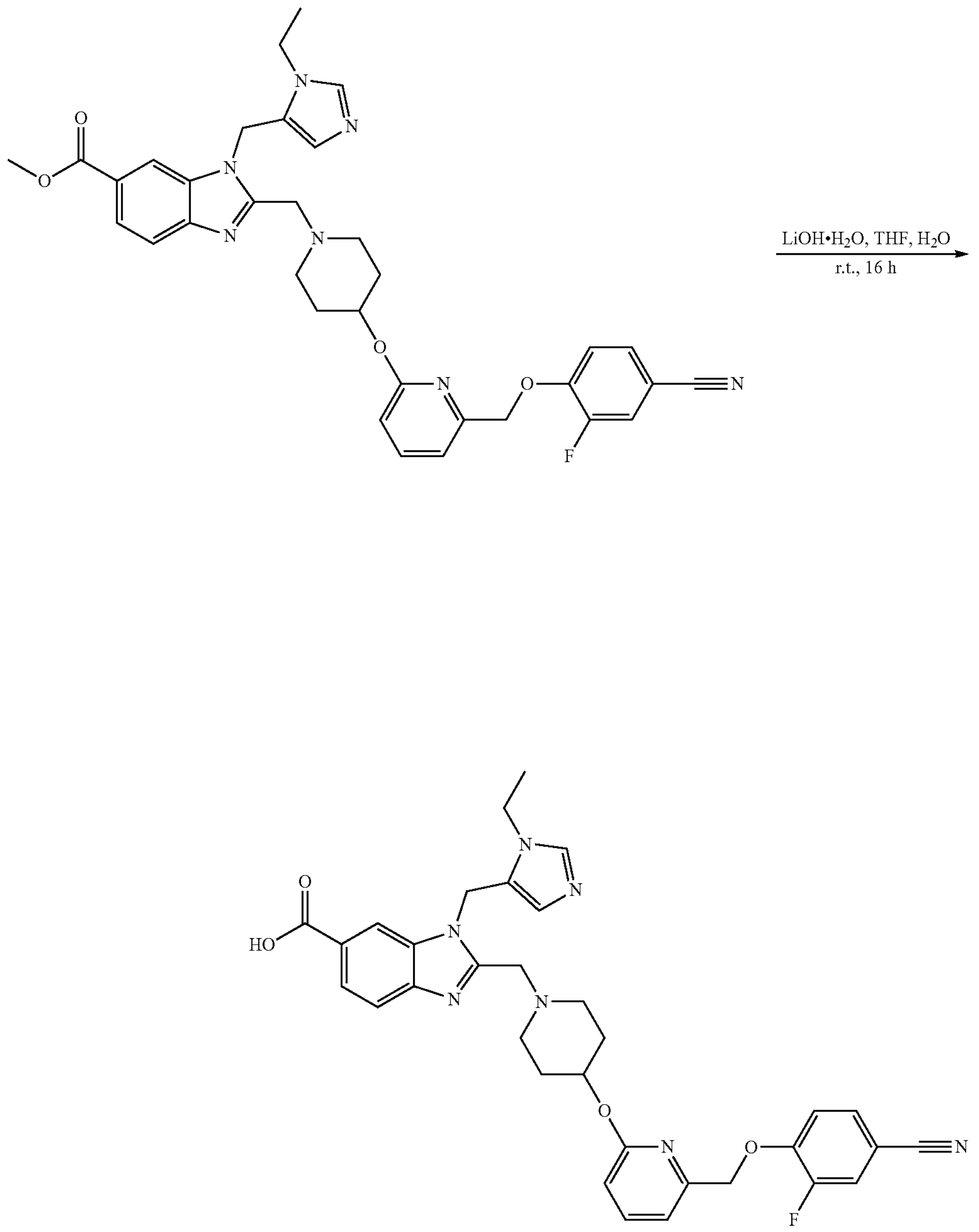

To a mixture of methyl 2-((4-((6-((4-cyano-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate (30 mg, 0.05 mmol) in THF (1 mL) and water (1 mL) lithium hydroxide (2.4 mg, 0.10 mmol) was added. The mixture was stirred at room temperature for 16 hours. The reaction mixture was directly concentrated in vacuo to remove the solvent, and then purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidin-1-yl) methyl)-1-((1-ethyl-1H-imidazol-5-yl)methyl)-1H-benzo[d] imid-azole-6-carboxylic acid (7.67 mg, 25.2% yield). LC-MS m/z: 610 $[M+H]^+$.

$^1$H NMR (400 MHZ, DMSO-$d_6$): δ8.04 (s, 1H), 7.89-7.80 (m, 2H), 7.74-7.60 (m, 4H), 7.43 (m, 1H), 7.04 (d, J-7.2 Hz, 1H), 6.72 (d, J-8.0 Hz, 1H), 6.39 (s, 1H), 5.69 (s, 2H), 5.30 (s, 2H), 4.88-4.83 (m, 1H), 4.01-4.00 (m, 2H), 3.79 (s, 2H), 2.68-2.65 (m, 2H), 2.25-2.20 (m, 2H), 1.81-1.76 (m, 2H), 1.47-1.44 (m, 2H), 1.16 (t, J=7.2 Hz, 3H).

Example 4. Synthesis of(S)-2-((4-((6-((4-cyano-2-fluorobenzyl)oxy)pyridin-2-yl)methoxy)piperidin-1-yl)methyl)-1-(oxetan-2-ylmethyl)-1H-benzo[d]imidazole-6-carboxylic acid (compound S22)

1). Synthesis of methyl(S)-2-((4-((6-((4-cyano-2-fluorobenzyl)oxy)pyridin-2-yl)methoxy)piperidin-1-yl)-methyl)-1-(oxetan-2-ylmethyl)-1H-benzo[d]imidazole-6-carboxylate

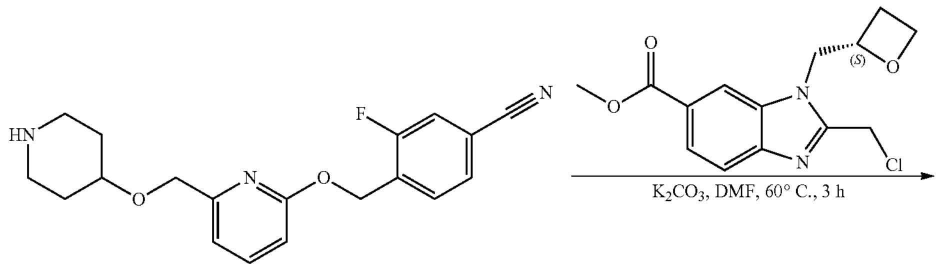

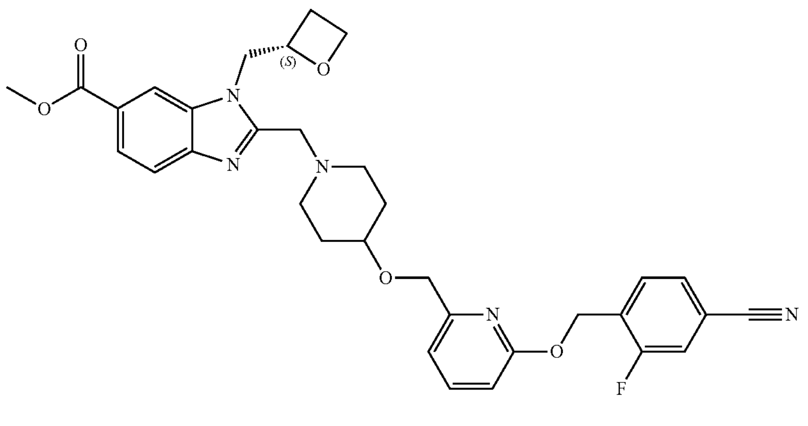

The mixture of methyl(S)-2-(chloromethyl)-1-(oxetan-2-ylmethyl)-1H-benzo[d]imidazole-6-carboxylate (150 mg, 0.51 mmol), 3-fluoro-4-((6-((piperidin-4-yloxy)methyl)pyridin-2-yloxy)methyl)benzonitrile (173 mg, 0.51 mmol) and potassium carbonate (140 mg, 1.02 mmol) in N,N-dimethylformamide (2 mL) was stirred at 60° C. for 3 hours. The mixture was diluted with water (10 mL) and extracted with ethyl acetate (20 mL×2). The combined organic layers were washed successively with saturated ammonium chloride (20 mL×3) and brine (10 mL×2) in turn, dried over anhydrous sodium sulfate, filtered, and concentrated to give a residue in vacuo. The residue was purified by silica gel column chromatography (dichloromethane/methanol=20/1) to give methyl(S)-2-((4-((6-((4-cyano-2-fluorobenzyl)oxy)pyridin-2-yl)methoxy)-piperidin-1-yl)methyl)-1-(oxetan-2-ylmethyl)-1H-benzo[d]imidazole-6-carboxylate (100 mg, 32.9% yield). LC-MS m/z: 600 [M+H]$^+$.

2). Synthesis of(S)-2-((4-((6-((4-cyano-2-fluorobenzyl)oxy)pyridin-2-yl)methoxy)piperidin-1-yl) methyl)-1-(oxetan-2-ylmethyl)-1H--benzo[d]imidazole-6-carboxylic acid

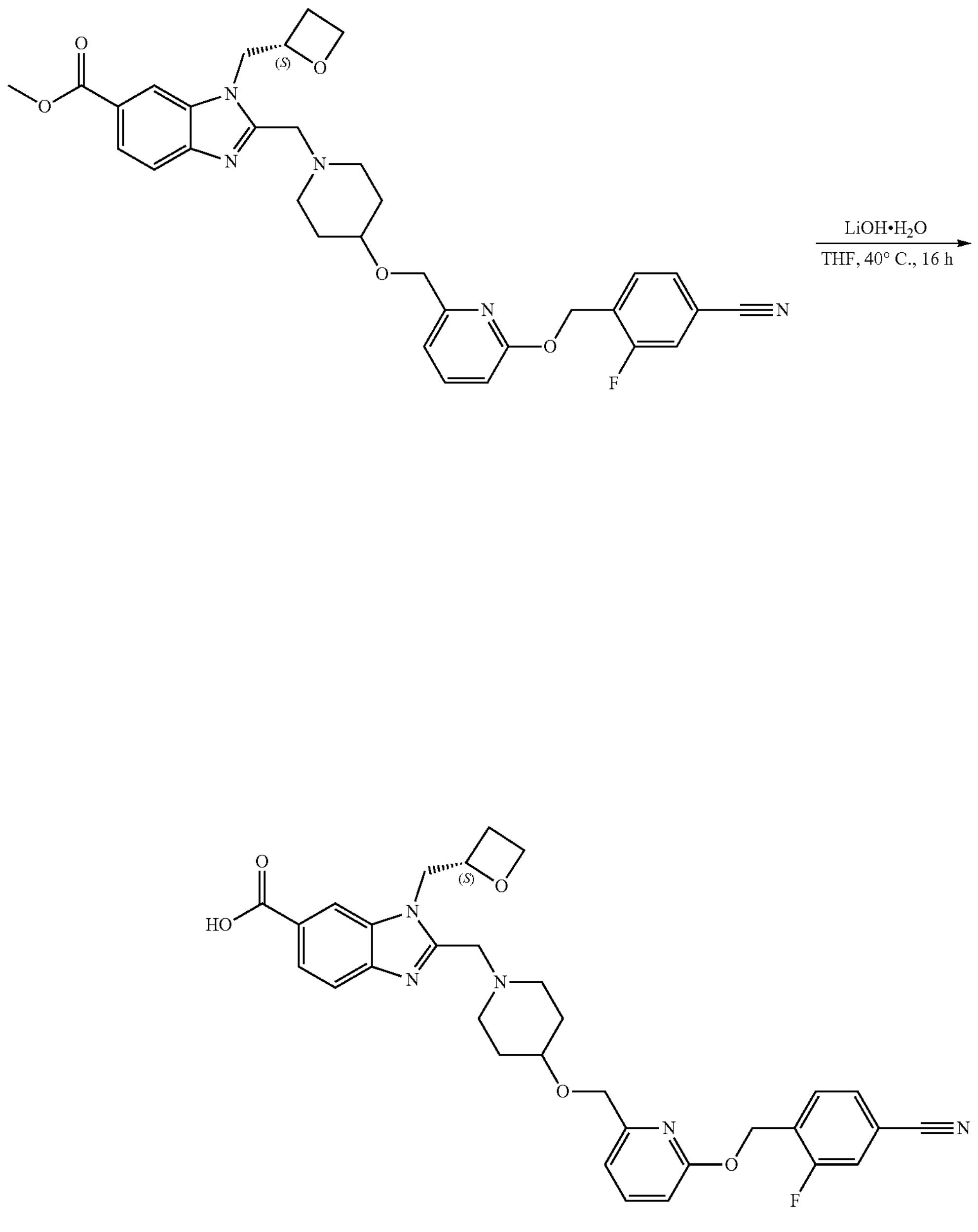

To a mixture of methyl(S)-2-((4-((6-((4-cyano-2-fluorobenzyl)oxy)pyridin-2-yl)methoxy)piperidin-1-yl)methyl)-1-(oxetan-2-ylmethyl)-1H-benzo[d]imidazole-6-carboxylate (100 mg, 0.17 mmol) in water (4 mL) and THF (4 mL) lithium hydroxide monohydrate (12 mg, 0.51 mmol) was added. The reaction mixture was stirred at 40° C. for 16 hours. The reaction mixture was adjusted to pH-5-6 with formic acid. The solvent was removed in vacuo and the residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain(S)-2-((4-((6-((4-cyano-2-fluorobenzyl)oxy)pyridine-2-yl)methoxy)piperidin-1-yl)methyl)-1-(oxetan-2-ylmethyl)-1H-benzo-[d]imidazole-6-carboxylic acid (Compound S22)(19.26 mg, 19.7% yield). LC-MS m/z: 586 [M+H]+1HNMR (400 MHZ, DMSO-$d_6$): 8.08-8.06 (m, 1H), 7.90 (d, J=10.0 Hz, 1H), 7.77-7.70 (m, 4H), 7.46-7.44 (m, 1H), 7.07 (d, J=7.2 Hz, 1H), 6.80 (d, J=8.4 Hz, 1H), 5.44 (s, 2H), 5.10-5.05 (m, 1H), 4.73-4.68 (m, 1 H), 4.59-4.51 (m, 1H), 4.49-4.46 (m, 3H), 4.39-4.34 (m, 1H), 3.86 (d, J=13.2 Hz, 1H), 3.73-3.69 (m, 1H), 3.47-3.41 (m, 1H), 2.76-2.64 (m, 3H), 2.49-2.41 (m, 1H), 2.23-2.17 (m, 2H), 1.89-1.85 (m, 2H), 1.56-1.49 (m, 2H).

Example 5. Synthesis of(S)-2-((4-((6-((4-cyano-2-fluorobenzyl)oxy)pyridin-2-yl)oxy)methyl)piperidin-1-yl)methyl)-1-(oxetan-2-ylmethyl)-1H-benzo[d]imidazole-6-carboxylic acid (Compound S1)

1). Synthesis of methyl(S)-2-((4-((6-((4-cyano-2-fluorobenzyl)oxy)pyridin-2-yl)oxy)methyl)piperidin-1-yl)methyl)-1-(oxetan-2-ylmethyl)-1H-benzo[d]imidazole-6-carboxylate

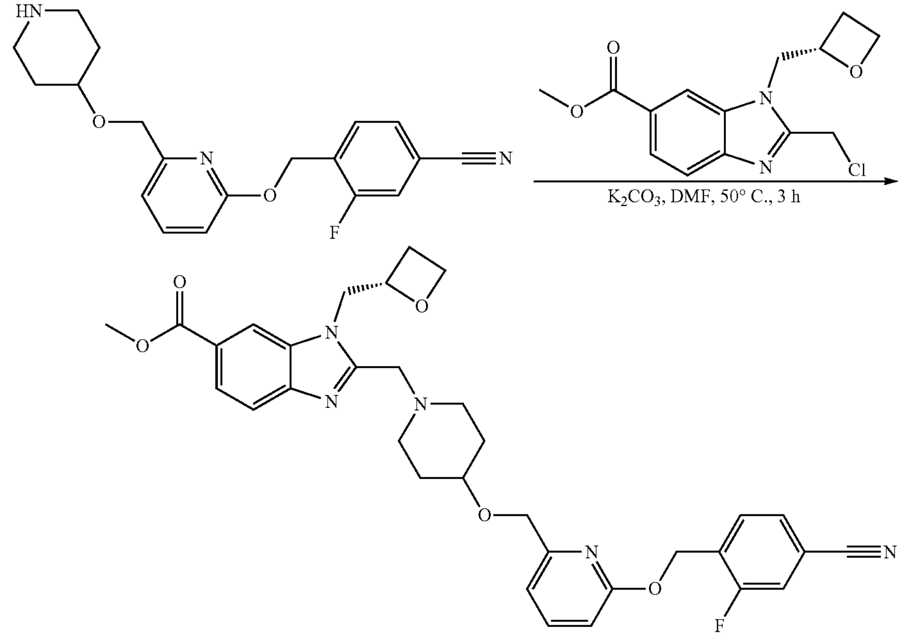

The mixture of 3-fluoro-4-((6-(piperidin-4-ylmethoxy)pyridin-2-yl)oxy)methyl)benzonitrile (100 mg, 0.29 mmol), methyl(S)-2-(chloromethyl)-1-(oxetan-2-ylmethyl)-1H-benzo[d]imidazole-6-carboxylate (85 mg, 0.29 mmol) and potassium carbonate (80 mg, 0.58 mmol) in N,N-dimethylformamide (2 mL) was heated to 50° C. and stirred for 3 hours. After completion, the resulting mixture was diluted with water (20 mL) and extracted with ethyl acetate (10 mL×2). The combined organic layers were washed with brine (30 mL), dried over sodium sulfate, filtered, and concentrated to give a residue in vacuo. The residue was purified by silica gel column chromatography (DCM/MeOH=20/1) to give methyl(S)-2-((4-((6-((4-cyano-2-fluorobenzyl)oxy)pyridine-2-yl)oxy)methyl)piperidin-1-yl)methyl)-1-(oxetan-2-ylmethyl)-1H-benzo[d]imidazole-6-carboxylate (100 mg, 0.17 mmol, 57.6% yield). LC-MS m/z: 600 $[M+H]^+$.

2). Synthesis of(S)-2-((4-((6-((4-cyano-2-fluorobenzyl)oxy)pyridin-2-yl)oxy)methyl)piperidin-1-yl)methyl)-1-(oxetan-2-ylmethyl)-1H-benzo[d]imidazole-6-carboxylic acid

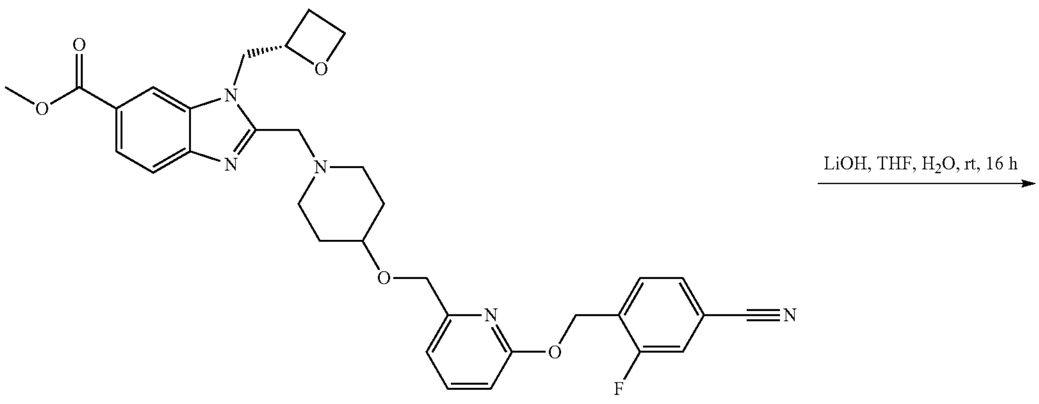

-continued

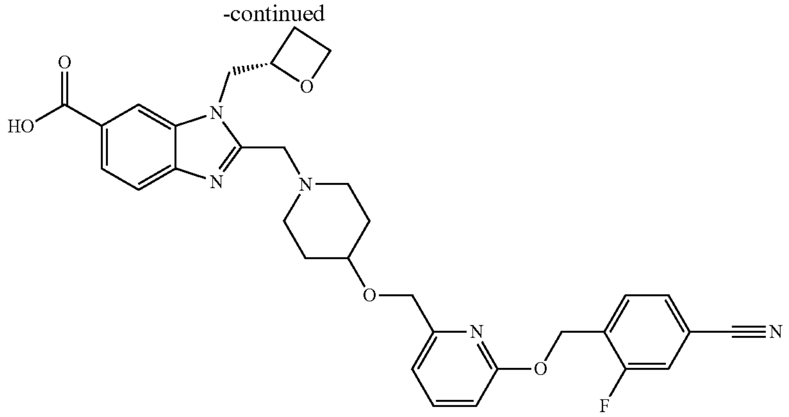

To a mixture of methyl(S)-2-((4-((6-((4-cyano-2-fluorobenzyl)oxy)pyridin-2-yl)oxy)methyl)piperidine-1-yl) methyl)-1-(oxetan-2-ylmethyl)-1H-benzo[d]imidazole-6-carboxylate (100 mg, 0.17 mmol) in water (1.0 mL) and THF (1.0 mL) lithium hydroxide (8 mg, 0.33 mmol) was added. The reaction mixture was stirred at room temperature for 16 hours. The solvent was removed in vacuo and the residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelengths: 254 nm/214 nm; Flow rate: 20 mL/min) to give(S)-2-((4-((6-((4-cyano-2-fluorobenzyl)oxy)pyridin-2-yl) oxy yl)methyl)piperidin-1-yl)methyl)-1-(oxetan-2-ylmethyl)-1H-benzo[d]imidazole-6-carboxylic acid (15.48 mg, 15.6% yield). LC-MS m/z: 586 $[M+H]^+$.

$^1$H NMR (400 MHZ, DMSO-$d_6$): δ 8.28 (s, 1H), 8.24 (s, 1H), 7.92-7.87 (m, 1H), 7.80 (d, J=8.4 Hz, 1H), 7.71 (dd, J=7.6, 1.2 Hz, 1H), 7.66 (d, J=6.4 Hz, 1H), 7.64-7.60 (m, 2H), 6.46 (d, J-8.0 Hz, 1H), 6.37 (d, J-8.0 Hz, 1H), 5.45 (s, 2H), 5.11-5.03 (m, 1H), 4.80-4.72 (m, 1H), 4.66-4.58 (m, 1H), 4.52-4.45 (m, 1H), 4.40-4.33 (m, 1H), 4.00 (d, J=6.0 Hz, 2H), 3.89 (d, J=13.6 Hz, 1H), 3.73 (d, J=13.6 Hz, 1H), 2.90 (d, J=10.4 Hz, 1 H), 2.80-2.70 (m, 1H), 2.72-2.64 (m, 1H), 2.45-2.37 (m, 1H), 2.13-1.95 (m, 2H), 1.70-1.60 (m, 3H), 1.27-1.13 (m, 2H).

Example 6. Synthesis of(S)-2-((4-((6-((4-cyano-2-fluorobenzyl)oxy)pyridin-2-yl)oxy)piperidin-1-yl) methyl)-1-(oxetan-2-ylmethyl)-1H-benzo[d]imidazole-6-carboxylic acid (compound S2)

1). Synthesis of methyl(S)-2-((4-((6-((4-cyano-2-fluorobenzyl)oxy)pyridin-2-yl)oxy)piperidin-1-yl) methyl)-1-(oxetan-2-ylmethyl)-1H-benzo[d]imidazole-6-carboxylate

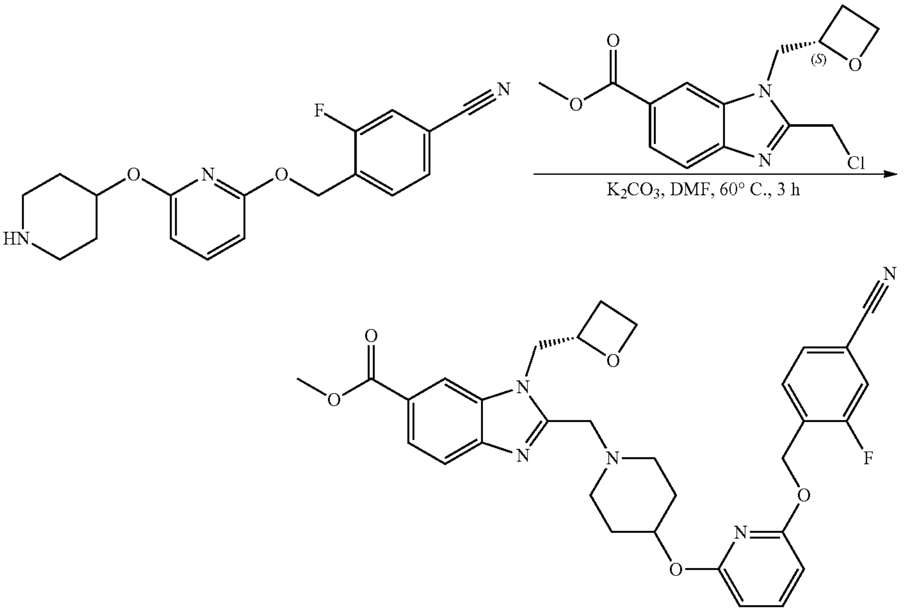

The mixture of methyl(S)-2-(chloromethyl)-1-(oxetan-2-ylmethyl)-1H-benzo[d]imidazole-6-carboxylate (200 mg, 0.68 mmol), 3-fluoro-4-((6-(piperidin-4-oxy)pyridin-2-yl) oxy)methyl)benzonitrile (245 mg, 0.75 mmol) and potassium carbonate (188 mg, 1.36 mmol) in N,N-dimethylformamide (2 mL) was stirred at 60° C. for 3 hours. The resulting mixture was diluted with water (10 mL) and extracted with ethyl acetate (20 mL×2). The combined organic layers were washed successively with saturated ammonium chloride (20 mL×3) and brine (10 mL×2), then dried over anhydrous sodium sulfate, filtered, and concentrated to give a residue in vacuo. The residue was purified by silica gel column chromatography (DCM/MeOH=20/1) to give methyl(S)-2-((4-((6-((4-cyano-2-fluorobenzyl)oxy)pyridine-2-yl)oxy)piperidin-1-yl)methyl)-1-(oxetan-2-ylmethyl)-1H-benzo[d]imidazole-6-carboxylate (205 mg, 0.35 mmol, 51.5% yield). LC-MS m/z: 586 $[M+H]^+$.

2). Synthesis of(S)-2-((4-((6-((4-cyano-2-fluorobenzyl)oxy)pyridin-2-yl)oxy)piperidin-1-yl)methyl)-1-(oxetan-2-ylmethyl)-1H-benzo[d]imidazole-6-carboxylic acid

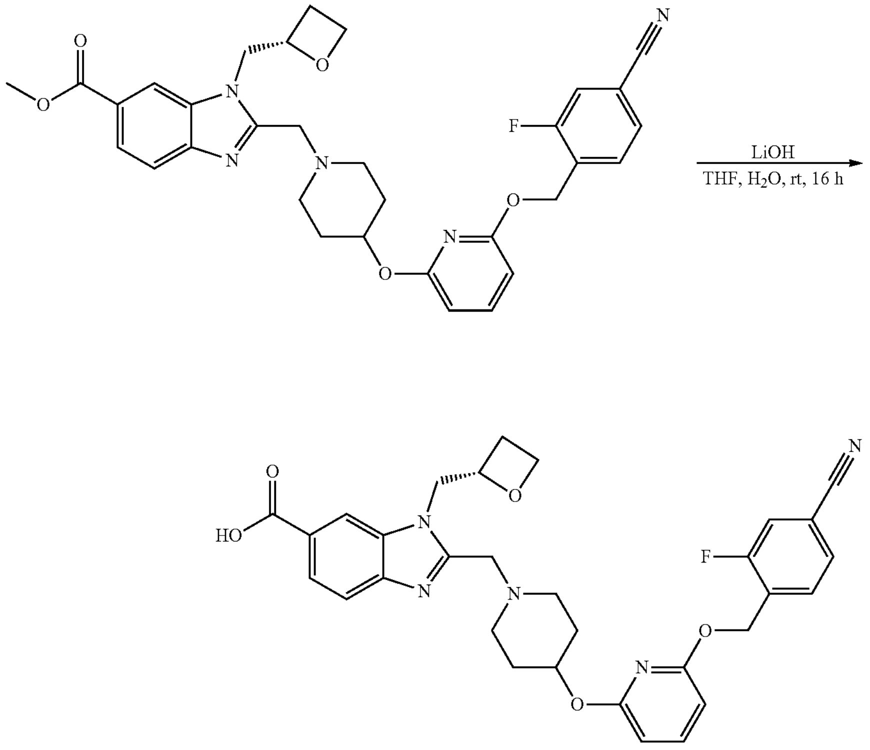

-

To a mixture of methyl(S)-2-((4-((6-((4-cyano-2-fluorobenzyl)oxy)pyridin-2-yl)oxy)piperidin-1-yl)methyl)-1-(oxetan-2-ylmethyl)-1H-benzo[d]imidazole-6-carboxylate (150 mg, 0.26 mmol) in water (1 mL) and THF (1 mL) lithium hydroxide (62 mg, 2.59 mmol) was added. The reaction mixture was stirred at room temperature for 16 hours. The reaction mixture was adjusted to pH=5-6 with formic acid. Then the solvent was removed by concentration in vacuo to give a residue. The residue was purified prep-HPLC (Waters 2767/2545/2489 system; Column: SunFire Prep C8 OBD 10 um 19×250 mm; Gradient elution with ACN/0.1% FA in $H_2O$ solvent system; Detection Wavelength 254 nm/214 nm; Flow rate: 20 mL/min) to give(S)-2-((4-((6-((4-cyano-2-fluorobenzyl)oxy)pyridin-2-yl)oxy)piperidin-1-yl)methyl)-1-(oxetan-2-ylmethyl)-1H-benzo[d]imidazole-6-carboxylic acid (38.01 mg, 0.07 mmol, 26.0% yield). LC-MS m/z: 572 $[M+H]^+$.

$^1H$ NMR (400 MHZ, DMSO-$d_6$): δ8.26 (s, 1H), 7.93-7.90 (m, 1H), 7.80 (d, J=8.0 Hz, 1H), 7.72-7.69 (m, 1 H), 7.65-7.61 (m, 3H), 6.46 (d, J-7.6 Hz, 1H), 6.36 (d, J=8.0 Hz, 1H), 5.45 (s, 2H), 5.09-5.07 (m, 1H), 4.81-4.75 (m, 2H), 4.66-4.61 (m, 1H), 4.52-4.47 (m, 1H), 4.40-4.36 (m, 1H), 3.94 (d, J=13.6 Hz, 1H), 3.78 (d, J=13.6 Hz, 1H), 2.78-2.67 (m, 3H), 2.45-2.41 (m, 1H), 2.31-2.27 (m, 2H), 1.86-1.83 (m, 2H), 1.58-1.53 (m, 2H).

Example 7. Synthesis of(S)-2-((4-((6-((4-cyano-2-fluorophenoxy)methyl)pyridin-2-yl)methoxy)piperidin-1-yl)methyl)-1-(oxetan-2-ylmethyl)-1H-benzo[d]imidazole-6-carboxylic (compound C1)

1): Synthesis of methyl(S)-2-((4-((6-((4-cyano-2-fluorophenoxy)methyl)pyridin-2-yl)methoxy)piperidin-1-yl)methyl)-1-(oxetan-2-ylmethyl)-1H-benzo[d]imidazole-6-carboxylate

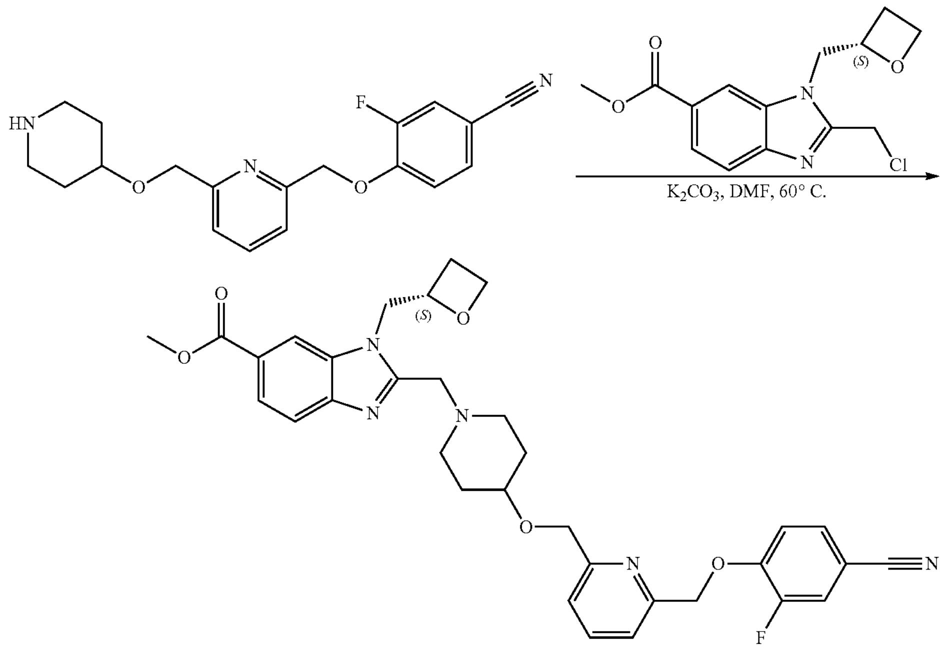

The mixture of 3-fluoro-4-((6-((piperidin-4-oxy)methyl)pyridin-2-yl)methoxy)benzonitrile (27 mg, 0.08 mmol), methyl(S)-2-(chloromethyl)-1-(oxyethane-2-ylmethyl)-1H-benzo[d]imidazole-6-carboxylate (24 mg, 0.08 mmol) and potassium carbonate (22 mg, 0.16 mmol) in N,N-dimethylformamide (1 mL) was stirred at 60° C. for 3 hours. The resulting mixture was diluted with water (10 mL) and extracted with ethyl acetate (20 mL×2). The combined organic layers were combined, washed with saturated ammonium chloride (20 mL×3) and brine (10 mL×2) in turn, dried over anhydrous sodium sulfate, filtered, and concentrated to give a residue in vacuo. The residue was purified by silica gel column chromatography (dichloromethane/methanol=20/1) to obtain methyl(S)-2-((4-((6-((4-cyano-2-fluorophenoxy)methyl)-pyridin-2-yl)methoxy)piperidin-1-yl)methyl)-1-(oxetan-2-ylmethyl)-1H-benzo[d]imidazole-6-carboxylate (23 mg, 47.0% yield). LC-MS m/z: 600 $[M+H]^+$.

2). Synthesis of(S)-2-((4-((6-((4-cyano-2-fluorophenoxy)methyl)pyridin-2-yl)methoxy)piperidin-1-yl)methyl)-1-(oxetan-2-ylmethyl)-1H-benzo[d]imidazole-6-carboxylic acid

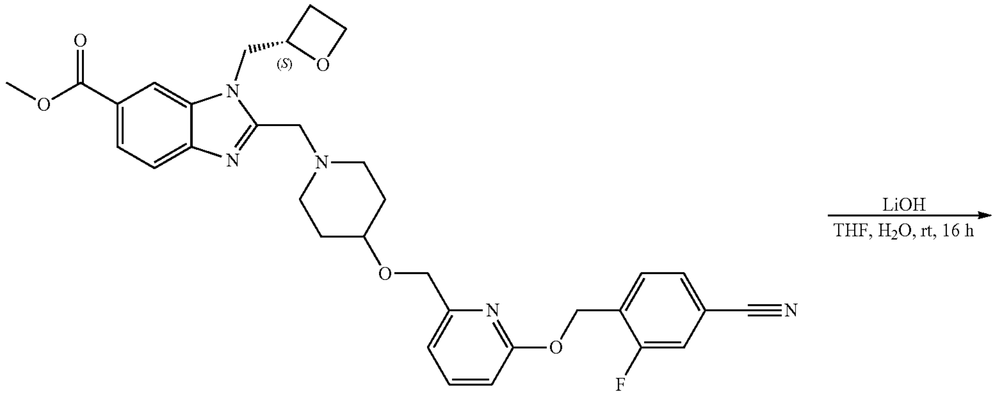

-continued

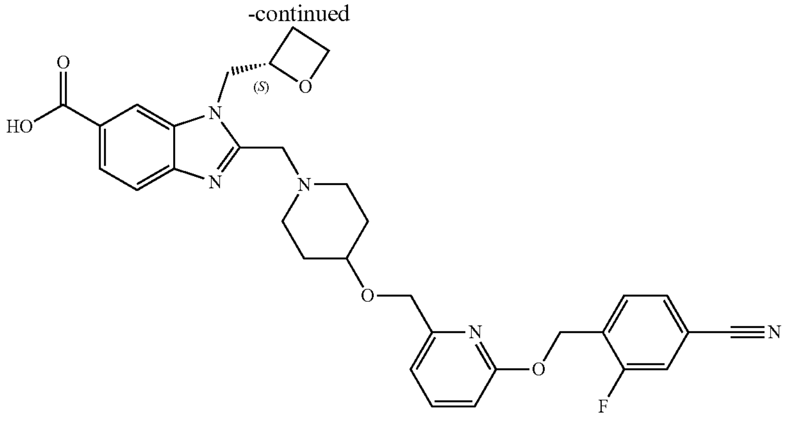

To a mixture of methyl(S)-2-((4-((6-((4-cyano-2-fluorophenoxy)methyl)pyridin-2-yl)methoxy)piperidin-1-yl) methyl)-1-(oxetan-2-ylmethyl)-1H-benzo[d]imidazole-6-carboxylate (23 mg, 0.04 mmol) in water (1 mL) and THF (1 mL) lithium hydroxide (10 mg, 0.40 mmol) was added. The reaction mixture was stirred at room temperature for 16 hours. The reaction mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to give(S)-2-((4-((6-((4-cyano-2-fluorophenoxy)methyl)pyridin-2-yl) methoxy)piperidine-1-yl)methyl)-1-(oxetan-2-ylmethyl)-1H-benzo[d]imidazole-6-carboxylic acid (14.73 mg, 65.5% yield). LC-MS m/z: 586 $[M+H]^+$.

$^1$H NMR (400 MHZ, DMSO-$d_6$) δ 8.26 (s, 1H), 8.22 (s, 1H), 7.91-7.86 (m, 2H), 7.82-7.79 (m, 1H), 7.69 (d, J=8.8 Hz, 1H), 7.63 (d, J=8.4 Hz, 1H), 7.46-7.42 (m, 3H), 5.35 (s, 2H), 5.10-5.08 (m, 1H), 4.81-4.76 (m, 1H), 4.66-4.59 (m, 3H), 4.52-4.47 (m, 1H), 4.40-4.35 (m, 1H), 3.92 (d, J=13.6 Hz, 1H), 3.75 (d, J=13.6 Hz, 1H), 3.51-3.46 (m, 1H), 2.79-2.67 (m, 3H), 2.46-2.41 (m, 1H), 2.27-2.24 (m, 2H), 1.91-1.89 (m, 2H), 1.56-1.51 (m, 2H).

Example 8. Synthesis of(S)-2-((3-((6-((4-cyano-2-fluorobenzyl)oxy)pyridin-2-yl)oxy) azetidin-1-yl) methyl)-1-(oxetan-2-ylmethyl)-1H-benzo[d]imidazole-6-carboxylic acid (Compound S3)

1). Synthesis of methyl(S)-2-((3-((6-((4-cyano-2-fluorobenzyl)oxy)pyridin-2-yl)oxy) azetidin-1-yl) methyl)-1-(oxetan-2-ylmethyl)-1H-benzo[d]imidazole-6-carboxylate

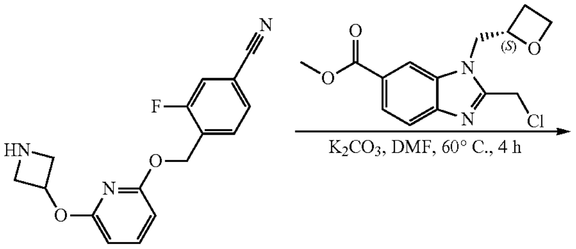

-continued

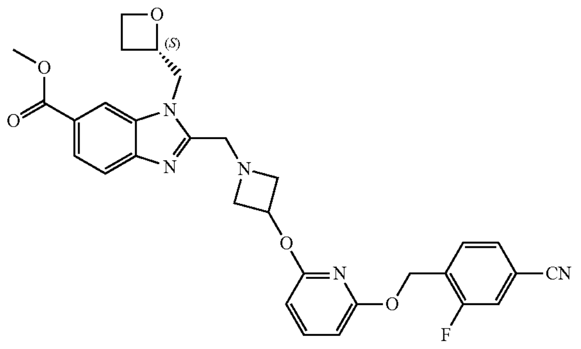

The mixture of methyl(S)-2-(chloromethyl)-1-(oxetan-2-ylmethyl)-1H-benzo[d]imidazole-6-carboxylate (150 mg, 0.51 mmol), 4-((6-(azetidin-3-yloxy)pyridin-2-yloxy) methyl)-3-fluorobenzonitrile (153 mg, 0.51 mmol) and potassium carbonate (211 mg, 1.530 mmol) in N,N-dimethylformamide (2 mL) was warmed to 60° C. for 4 hours. The resulting mixture was diluted with water (10 mL) and extracted with ethyl acetate (2×20 mL). The combined organic layers was washed sequentially with saturated ammonium chloride (30 mL) and brine (2×20 mL), dried over anhydrous sodium sulfate, filtered, and concentrated to give a residue in vacuo.

The residue was purified by silica gel column chromatography (DCM/MeOH=20/1) to give methyl(S)-2-((3-((6-((4-cyano-2-fluorobenzyl)oxy)pyridine-2-yl)oxy) azetidine-1-yl)methyl)-1-(oxetan-2-yl-methyl)-1H benzo[d] imidazole-6-carboxylate (180.0 mg, 0.32 mmol, 63.3% yield). LC-MS m/z: 558 $[M+H]^+$.

2). Synthesis of(S)-2-((3-((6-((4-cyano-2-fluorobenzyl)oxy)pyridin-2-yl)oxy) azetidin-1-yl)methyl)-1-(oxetan-2-ylmethyl)-1H-benzo[d]imidazole-6-carboxylic acid

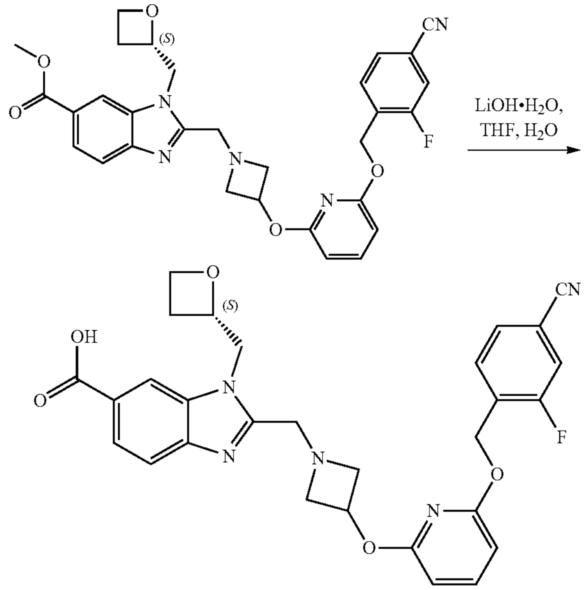

To a mixture of methyl(S)-2-((3-((6-((4-cyano-2-fluorobenzyl)oxy)pyridin-2-yl)oxy) azetidine-1-(yl)methyl)-1-(oxetan-2-ylmethyl)-1H-benzo[d]imidazole-6-carboxylate (90 mg, 0.16 mmol) in water (4 mL) and THF (4 mL) lithium hydroxide monohydrate (68 mg, 1.63 mmol) was added. The reaction mixture was stirred at room temperature for 16 hours. The reaction mixture was adjusted to pH=5-6 with formic acid. The solvent was removed to give a residue in vacuo. The residue was purified by prep-HPLC (Waters 2767/2545/2489 system; Column: SunFire Prep C8 OBD 10 um 19×250 mm; Gradient elution with ACN/0.1% $NH_4OH$ in $H_2O$ solvent system; Detection Wavelength: 254 nm/214 nm; Flow rate: 20 mL/min) to obtain(S)-2-((3-((6-((4-cyano-2-fluorobenzyl)oxy)pyridin-2-yl)oxy) azetidine-1-yl) methyl)-1-(oxetan-2-ylmethyl)-1H-benzo[d]imidazole-6-carboxylic acid (compound S3)(10.23 mg, 11.7% yield). LC-MS m/z: 544 $[M+H]^+$.

$^1$HNMR (400 MHZ, DMSO-$d_6$): δ12.56 (brs, 1H), 8.24 (d, J-0.8 Hz, 1H), 7.86-7.78 (m, 2H), 7.71-7.63 (m, 4H), 6.49 (d, J-7.6 Hz, 1H), 6.42 (d, J-7.6 Hz, 1H), 5.41 (s, 2H), 5.08-5.02 (m, 2H), 4.72 (dd, J=15.4, 7.2 Hz, 1H), 4.59 (dd, J=15.4, 2.8 Hz, 1H), 4.47-4.43 (m, 1H), 4.33-4.28 (m, 1H), 4.05 (d, J=13.6 Hz, 1H), 3.95 (d, J=13.6 Hz, 1H), 3.77-3.69 (m, 2H), 3.20-3.16 (m, 2H), 2.70-2.66 (m, 1H), 2.40-2.35 (m, 1H).

Example 9. Synthesis of(S)-2-((4-(3-((4-cyano-2-fluorobenzyl)oxy)phenoxy)piperidin-1-yl)methyl)-1-(oxetan-2-ylmethyl)-1H-benzo[d]imidazole-6-carboxylic acid (compound S5)

1). Synthesis of methyl(S)-2-((4-(3-((4-cyano-2-fluorobenzyl)oxy)phenoxy)piperidin-1-yl)methyl)-1-(oxetan-2-ylmethyl)-1H-benzo[d]imidazole-6-carboxylate

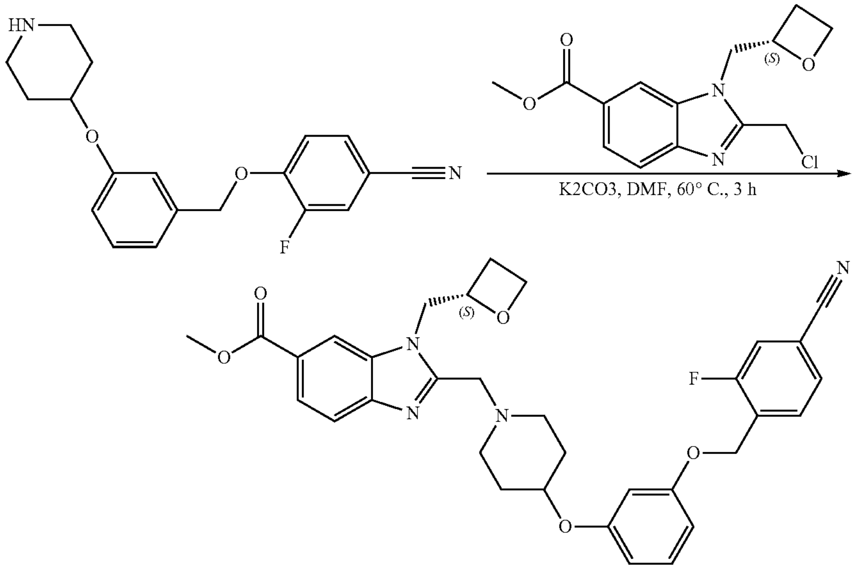

To a mixture of 3-fluoro-4-((6-(piperidin-4-oxy)pyridin-2-yl)oxy)methyl)benzonitrile (89.0 mg, 0.273 mmol) and methyl(S)-2-(chloromethyl)-1-(oxetan-2-ylmethyl)-1H-benzo[d]imidazole-6-carboxylate (80.3 mg, 0.273 mmol) in N,N-dimethylformamide (4 mL) potassium carbonate (113.0 mg, 0.819 mmol) was added. The mixture was heated to 60° C. for 3 hours. The mixture was diluted with water (5 mL) and extracted with EA (3×20 mL). The combined organic layers were washed with brine, dried over anhydrous $Na_2SO_4$, filtered, and concentrated to give a residue in vacuo. The residue was purified by silica gel column chromatography (dichloromethane/methanol=20/1) to give methyl(S)-2-((4-(3-((4-cyano-2-fluorobenzyl)oxy)phenoxy))-piperidin-1-yl)methyl)-1-(oxetan-2-ylmethyl)-1H-benzo[d]imidazole-6-carboxylate (94 mg, 59.0% yield). LC-MS m/z: 585 $[M+H]^+$.

2). (S)-2-((4-(3-((4-cyano-2-fluorobenzyl)oxy)phenoxy)piperidin-1-yl)methyl)-1-(oxetan-2-ylmethyl)-1H-benzo[d]imidazole-6-carboxylic acid

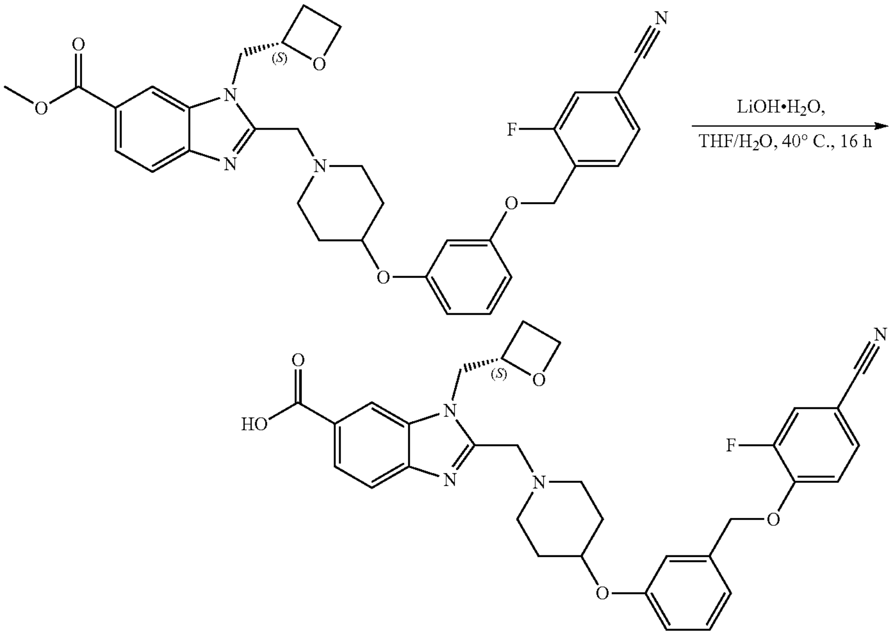

To a mixture of methyl(S)-2-((4-(3-((4-cyano-2-fluorobenzyl)oxy)phenoxy)piperidin-1-yl)methyl)-1-(oxetan-2-ylmethyl)-1H-benzo[d]imidazole-6-carboxylate (94 mg, 0.16 mmol) in THF (4 mL) and $H_2O$ (4 mL) $LiOH{\cdot}H_2O$ (68 mg, 1.60 mmol) was added. The mixture was warmed to 40° C. and stirred for 16 hours. The mixture was adjusted to pH-5-6 with hydrochloric acid (1 M) and extracted with ethyl acetate (10 mL×3). The combined organic layers were washed with brine (10 mL), dried over anhydrous $Na_2SO_4$, filtered, and concentrated to give a residue in vacuo. The residue was purified by reverse phase column chromatography (Spherical C18 column, 20-40 um, 40 g; Mobile Phase A: 10 mM in $NH_3{\cdot}H_2O$ water; Mobile Phase B: acetonitrile; Flow rate: 40 mL/min; Gradient: 20% B-50% B in 20 minutes; Detector: 254 nm). The mobile phase containing the desired product was collected under 32% B and then concentrated in vacuo to give(S)-2-((4-(3-((4-cyano-2-fluorobenzyl)oxy)phenoxy)yl)piperidin-1-yl)methyl)-1-(oxetan-2-ylmethyl)-1H-benzo[d]imidazole-6-carboxylic acid (26.27 mg, 28.6% yield). LC-MS m/z: 571 $[M+H]^{+1}$H NMR (400 MHz, DMSO-$d_6$) δ 8.16 (s, 1H), 7.92 (d, J-8.0 Hz, 1H), 7.80-7.77 (m, 1H), 7.76-7.75 (m, 2H), 7.53-7.51 (m, 1H), 7.17 (t, J-8.0 Hz, 1H), 6.62-6.57 (m, 3H), 5.21 (s, 2H), 5.11-5.06 (m, 1H), 4.77-4.71 (m, 1H), 4.63-4.59 (m, 1H), 4.52-4.47 (m, 1H), 4.40-4.36 (m, 2H), 3.90 (d, J=13.6 Hz, 1H), 3.76 (d, J=13.5 Hz, 1 H), 2.78-2.68 (m, 3H), 2.50-2.33 (m, 3H), 1.93-1.91 (m, 2H), 1.62-1.58 (m, 2H).

Example 10. Synthesis of 2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazole-6-carboxylic acid (compound S4)

1). Synthesis of methyl 4-(2-(4-((6-((4-cyano-2-fluorobenzyl)oxy)pyridin-2-yl)oxy)piperidin-1-yl)acetamido)-3-(((1-ethyl-1H-imidazol-5-yl)methyl)amino)benzoate

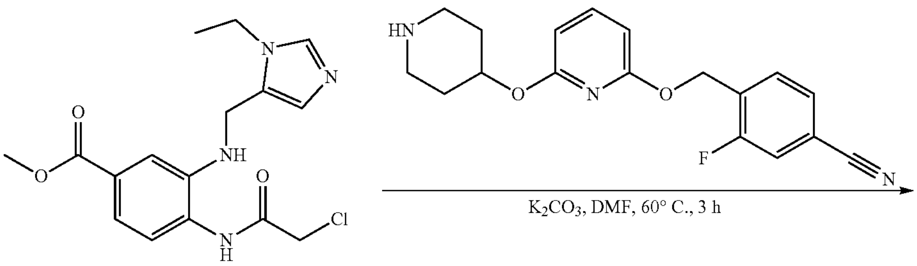

-continued

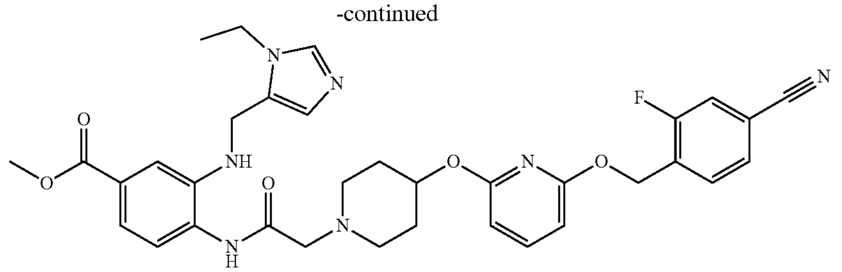

To a mixture of methyl 4-(2-chloroacetamido)-3-(((1-ethyl-1H-imidazol-5-yl)methyl)amino)benzoate (140 mg, 0.40 mmol) and 3-fluoro-4-(((6-(piperidin-4-yloxy)pyridin-2-yl)oxy)methyl)benzonitrile (131 mg, 0.40 mmol) in N,N-dimethylformamide (3 mL) potassium carbonate (110 mg, 0.80 mmol) was added. The mixture was stirred at 60° C. for 3 hours. The resulting mixture was poured into brine (50 mL) and extracted with DCM (10 mL×2). After the combined organic phases were concentrated to give a residue in vacuo. The residue was purified by silica gel column chromatography (DCM/MeOH=10/1) to obtain methyl 4-(2-(4-((6-((4-cyano-2-fluorobenzyl)) oxy)pyridin-2-yl)oxy)piperidin-1-yl)acetamido)-3-(((1-ethyl-1H-imidazol-5-yl)methyl) amino)benzoate (140 mg, 54.6% yield). LC-MS m/z: 642 $[M+H]^+$.

2). Synthesis of 4-(2-(4-((6-((4-cyano-2-fluorobenzyl)oxy)pyridin-2-yl)oxy)piperidin-1-yl)acetamido)-3-(((1-ethyl-1H-imidazol-5-yl)methyl)amino)benzoic acid To a mixture of methyl 4-(2-(4-((6-((4-cyano-2-fluorobenzyl)) oxy)pyridin-2-yl)oxy)piperidin-1-yl)acetamido)-3-(((1-ethyl-1H-imidazol-5-yl)methyl)amino)benzoate (140 mg, 0.22 mmol) in THF (1 mL) and $H_2O$ (1 mL) lithium hydroxide (11 mg, 0.46 mmol) was added. The mixture was stirred at room temperature for 5 hours. The resulting mixture was poured into brine (10 mL) and extracted with DCM (5 mL×2). The combined organic layer was concentrated to give a residue in vacuo. The residue was purified by silica gel column chromatography (DCM/MeOH=10/1) to obtain 4-(2-(4-((6-((4-cyano-2-fluorobenzyl)) oxy)pyridin-2-yl)oxy)piperidin-1-yl)acetamido)-3-(((1-ethyl-1H-imidazol-5-yl)methyl)amino)benzoic acid (80 mg, 58.0% yield). LC-MS m/z: 628 $[M+H]^+$.

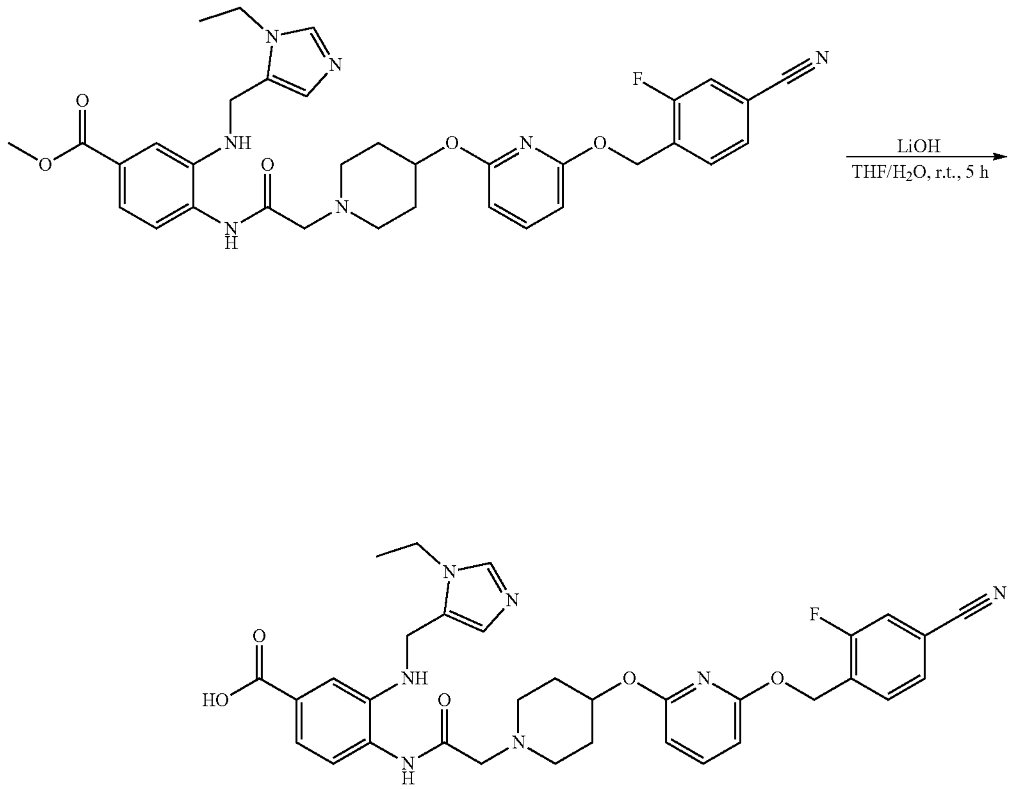 [SMILES: CCn1cncc1CNc1cc(C(=O)OC)ccc1NC(=O)CN1CCC(Oc2cccc(OCc3ccc(C#N)cc3F)n2)CC1 ; "LiOH" ; CCn1cncc1CNc1cc(C(=O)O)ccc1NC(=O)CN1CCC(Oc2cccc(OCc3ccc(C#N)cc3F)n2)CC1]

3). Synthesis of 2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazole-6-carboxylic acid (compound 4)

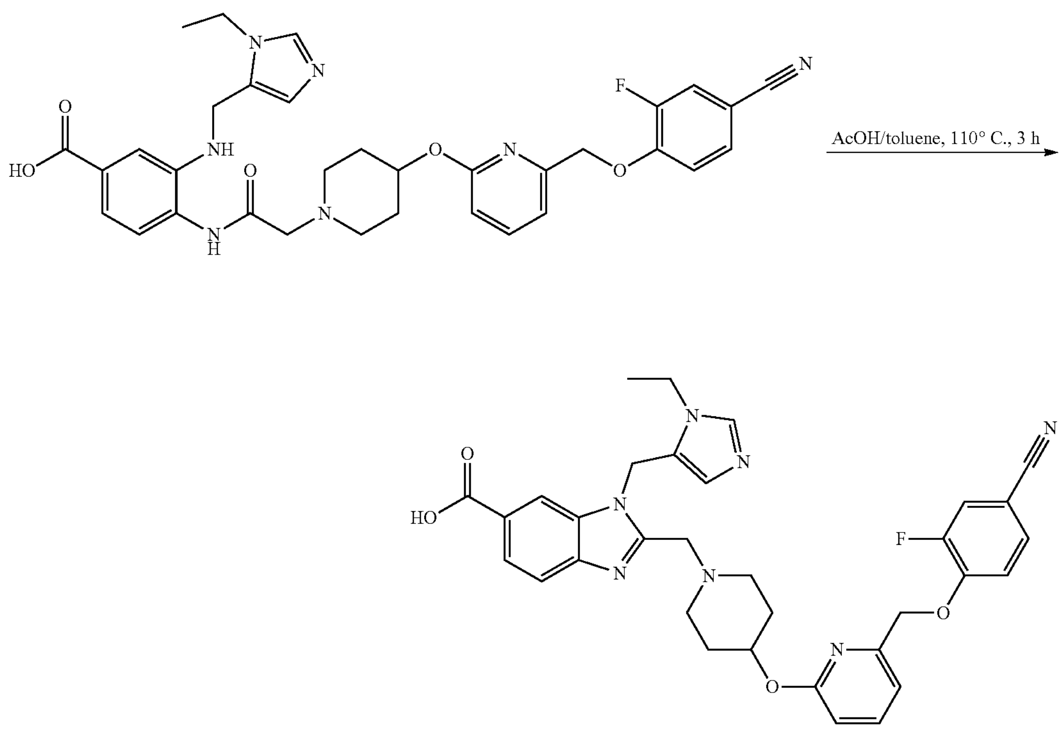 [SMILES: CCn1cncc1CNc1cc(C(=O)O)ccc1NC(=O)CN1CCC(Oc2cccc(COc3ccc(C#N)cc3F)n2)CC1 ; "AcOH/toluene, 110° C., 3 h" ; CCn1cncc1Cn1c(CN2CCC(Oc3cccc(COc4ccc(C#N)cc4F)n3)CC2)nc2ccc(C(=O)O)cc21]

The mixture of 4-(2-(4-((6-((4-cyano-2-fluorobenzyl)oxy)pyridin-2-yl)oxy)piperidin-1-yl)acetamido)-3-(((1-ethyl-1H-imidazol-5-yl)methyl)amino)benzoic acid (80 mg, 0.13 mmol) in toluene (1 mL) and AcOH (0.2 mL), stirred at 110° C. for 3 hours. The solvent was removed in vacuo to give a residue. The residue was purified by prep-HPLC (Waters 2767/2545/2489 system; Column: SunFire Prep C8 OBD 10 um 19×250 mm; Gradient eluted ACN/0.1% $NH_4OH$ in $H_2O$ solvent system; Detection Wavelength 254 nm/214 nm; Flow rate 20 mL/min) to obtain 2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazole-6-carboxylic acid (compound S4)(20.72 mg, 26.2% yield). LC-MS m/z: 610 $[M+H]^+$.

$^1$H NMR (400 MHZ, DMSO-$d_6$): δ8.07 (s, 1H), 7.92-7.89 (m, 1H), 7.83-7.80 (m, 1H), 7.71-7.67 (m, 3H), 7.64-7.59 (m, 2H), 6.45 (d, J=8.0 Hz, 1H), 6.41 (s, 1H), 6.34 (d, J-8.0 Hz, 1H), 5.71 (s, 2H), 5.43 (s, 2H), 4.73-4.71 (m, 1H), 4.03-3.97 (m, 2H), 3.81 (s, 2H), 2.68-2.65 (m, 2H), 2.25-2.20 (m, 2H), 1.75-1.71 (m, 2H), 1.43-1.39 (m, 2H), 1.16 (t, J=7.2 Hz, 3H).

Example 11. Synthesis of 2-((4-(3-((4-cyano-2-fluorobenzyl)oxy)phenoxy)piperidin-1-yl)methyl)-1-((1-ethyl-1H-imidazol-5-yl)methyl)-1H-benzo[d]imidazole-6-carboxylic acid (compound S23)

1). Synthesis of methyl 4-(2-(4-(3-((4-cyano-2-fluorobenzyl)oxy)phenoxy)piperidin-1-yl)acetamido)-3-((1-ethyl)-1H-imid-azol-5-yl)methyl)amino)benzoate

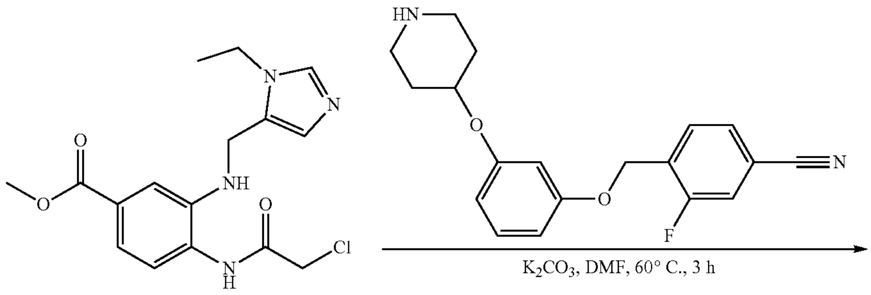

-continued

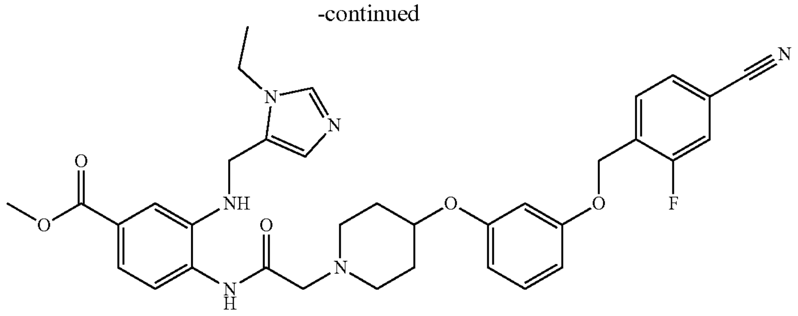

To a mixture of methyl 4-(2-chloroacetamido)-3-((1-ethyl-1H-imidazol-5-yl)methyl)amino)benzoate (100 mg, 0.29 mmol) and 3-fluoro-4-((3-(piperidin-4-oxy)phenoxy)methyl)benzonitrile (95 mg, 0.29 mmol) in N,N-dimethylformamide (5 mL) potassium carbonate (120 mg, 0.87 mmol) was added at room temperature. The mixture was stirred at 60° C. for 3 hours. The reaction was diluted with water (5 mL) and extracted with ethyl acetate (20 mL×3). The combined organic layers were washed with brine (20 mL×2), dried over anhydrous sodium sulfate, filtered, and concentrated in vacuo, The residue was purified by silica gel column chromatography (dichloromethane/methanol=15/1) to obtain methyl 4-(2-(4-(3-((4-cyano-2-fluorobenzyl)oxy)phenoxy)piperidin-1-yl)acetamido)-3-((1-ethyl-1H-imidazol-5-yl)methyl)amino)benzoate (45 mg, 24.1% yield). LC-MS m/z: 641 $[M+H]^+$.

2). Synthesis of methyl 2-((4-(3-((4-cyano-2-fluorobenzyl)oxy)phenoxy)piperidin-1-yl)methyl-1-((1-ethyl-1H-imi-dazol-5-yl)methyl)-1H-benzo[d]imidazole-6-carboxylate

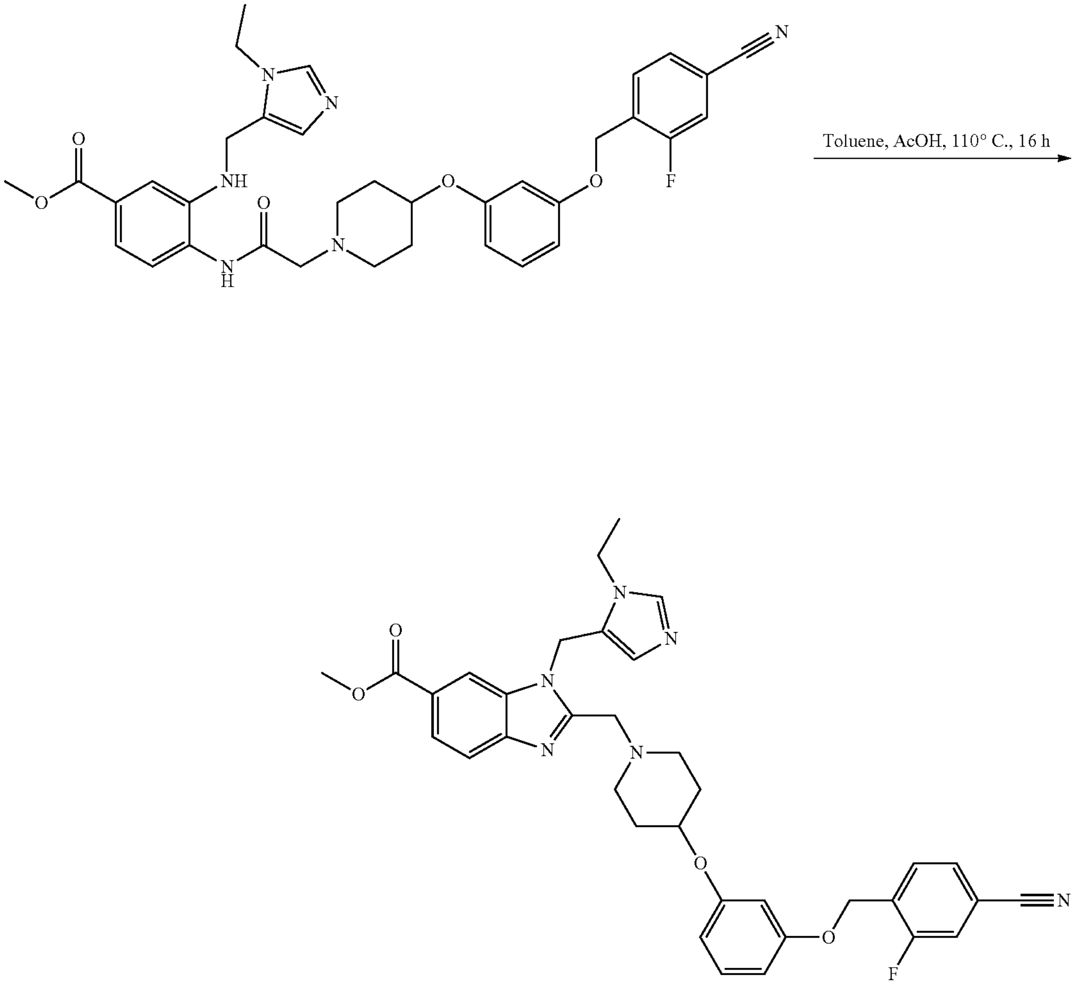

To a solution of methyl 4-(2-(4-(3-((4-cyano-2-fluorobenzyl)oxy)phenoxy)piperidin-1-yl)acetamido)-3-((1-ethyl-1H-imidazol-5-yl)methyl)amino)benzoate (45 mg, 0.07 mmol) in toluene (10 mL) acetic acid (2 mL) was added. The mixture was stirred at 110° C. for 16 hours. The mixture was concentrated to give the crude product, which was further purified by reverse-phase flash chromatography under the following conditions: (Column: spherical C18, 20-40, 120 g; Mobile Phase A: 10 mM $NH_3$ $H_2O$ in water; Mobile Phase B: acetonitrile; Flow rate: 80 mL/min; Gradient: 60% B-80% B in 20 minutes; Monitor: 254 nm.). The mobile phase containing desired product was collected at 72% B and concentrated in vacuo to obtain methyl 2-((4-(3-((4-cyano-2-fluorobenzyl)oxy)phenoxy)piperidin-1-yl)methyl-1-((1-ethyl-1H-imidazole-5-yl)methyl)-1H-benzo[d]imidazole-6-carboxylate (22 mg, 57.1% yield). LC-MS m/z: 623 $[M+H]^+$.

3). Synthesis of 2-((4-(3-((4-cyano-2-fluorobenzyl)oxy)phenoxy)piperidin-1-yl)methyl)-1-((1-ethyl-1H-imidazol-5-yl)methyl)-1H-benzo[d]imidazole-6-carboxylic acid

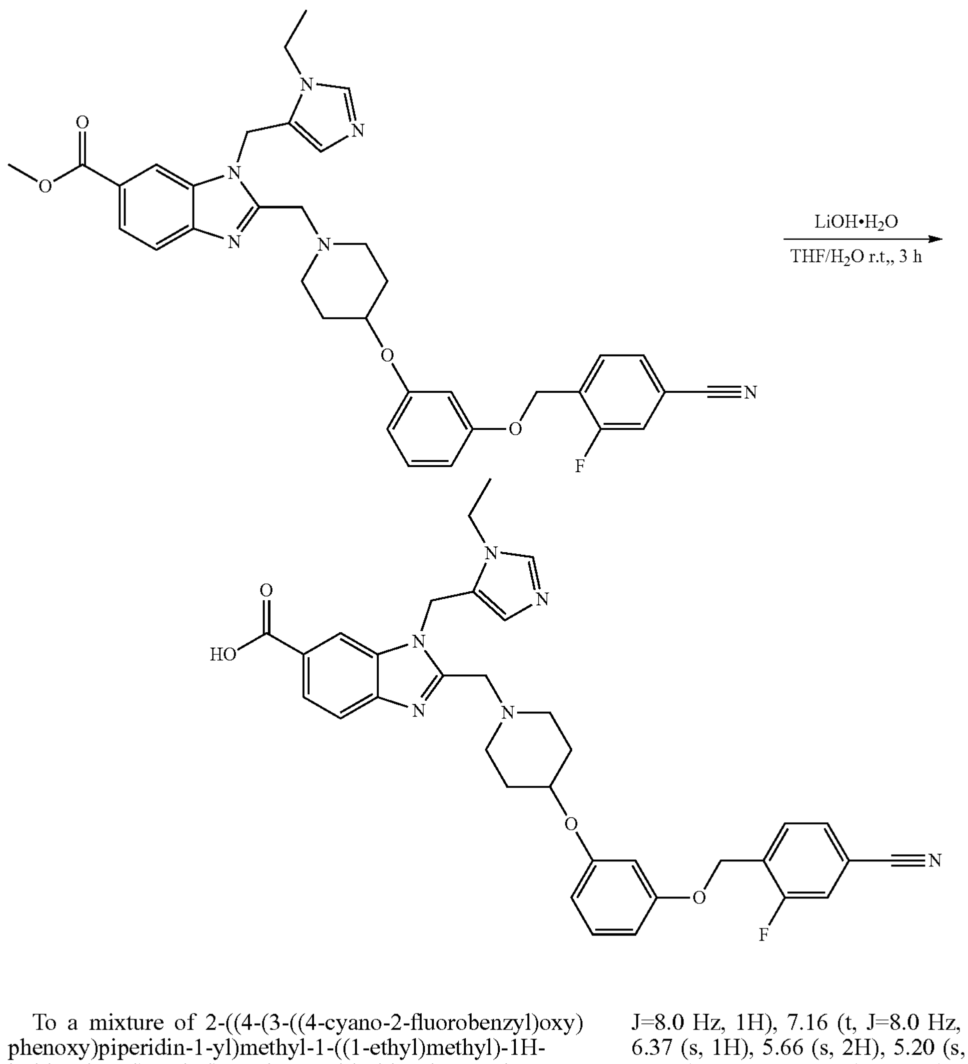

To a mixture of 2-((4-(3-((4-cyano-2-fluorobenzyl)oxy)phenoxy)piperidin-1-yl)methyl-1-((1-ethyl)methyl)-1H-imidazol-5-yl)methyl)-1H-benzo[d]imidazole-6-carboxylate (22 mg, 0.04 mmol) in THF (4 mL) and water (4 mL) lithium hydroxide monohydrate (17 mg, 0.40 mmol) was added. The mixture was stirred at room temperature for 3 hours. The resulting mixture was adjusted to pH=5-6 with hydrochloric acid solution (1 N) and extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions: (Column: spherical C18, 20-40 μm, 40 g; Mobile Phase A: 10 mM $NH_3$ $H_2O$ in water; Mobile Phase B: acetonitrile; Flow rate: 40 mL/min; Gradient: 20% B-50% B in 20 minutes; Detector: 254 nm.). The mobile phase containing the desired product was collected at 29% B and concentrated in vacuo to obtain 2-((4-(3-((4-cyano-2-fluorobenzyl)oxy)phenoxy)yl)piperidin-1-yl)methyl)-1-((1-ethyl-1H-imidazol-5-yl)methyl)-1H-benzo[d]im-idazole-6-carboxylic acid (11.42 mg, 0.019 mmol, 47.5% yield). LC-MS m/z: 609 $[M+H]^+$.

$^1H$ NMR (400 MHZ, DMSO-$d_6$) δ 8.00 (s, 1H), 7.91 (d, J=9.6 Hz, 1H), 7.80-7.73 (m, 3H), 7.66 (s, 1H), 7.52 (d, J=8.0 Hz, 1H), 7.16 (t, J=8.0 Hz, 1H), 6.60-6.54 (m, 3H), 6.37 (s, 1H), 5.66 (s, 2H), 5.20 (s, 2H), 4.36-4.32 (m, 1H), 4.00 (q, J=7.2 Hz, 2H), 3.76 (s, 2H), 2.67-2.65 (m, 2H), 2.31-2.26 (m, 2H), 1.82-1.79 (m, 2H), 1.49-1.37 (m, 2H), 1.17 (t, J=7.2 Hz, 3H).

Example 12. Synthesis of (S,E)-3-(2-((4-((6-((4-chloro-2-fluorobenzyl)oxy)-5-fluoropyridin-2-yl)oxy)piperidin-1-yl)methyl)-1-(oxetan-2-ylmethyl)-1H-benzo[d]imidazol-6-yl)acrylic acid formate 1). Synthesis of methyl(S,E)-3-(2-((4-((6-((4-chloro-2-fluorobenzyl)oxy)-5-fluoropyridin-2-yl)oxy)piperidin-1-yl)methyl)-1-(oxetan-2-ylmethyl)-1H-benzo[d]imidazol-6-yl)acrylate

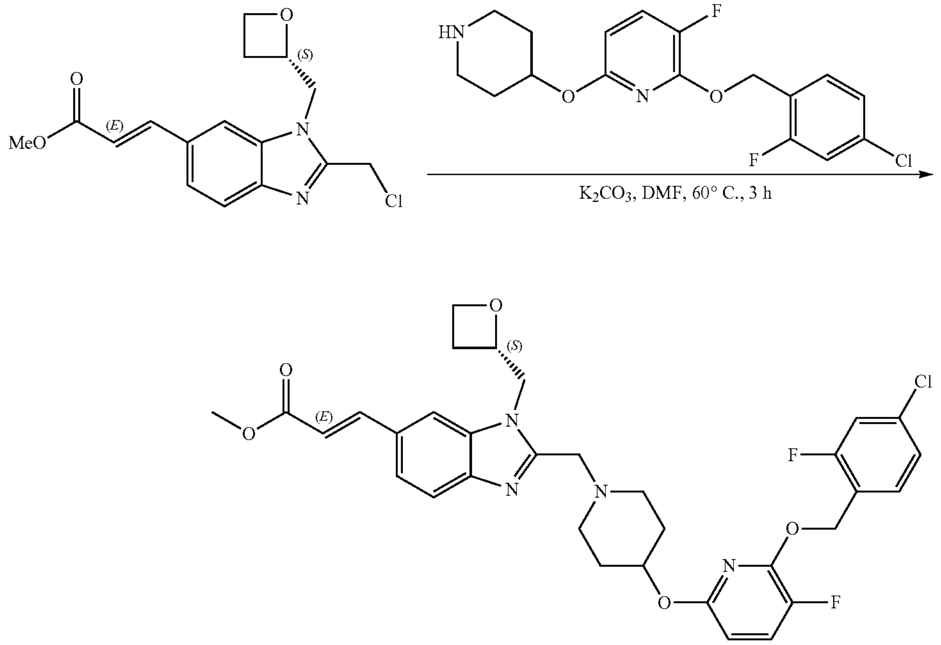

To a mixture of methyl (methyl(S,E)-3-(2-(chloromethyl)-1-(oxetan-2-ylmethyl)-1H-benzo[d]imidazol-6-yl) acrylate (90 mg, 0.28 mmol) and 2-((4-chloro-2-fluorobenzyl)oxy)-3-fluoro-6-(piperidin-4-oxy)pyridine (100 mg, 0.28 mmol) in N,N-dimethylformamide (3 mL) potassium carbonate (78 mg, 0.56 mmol) was added. The mixture was stirred at 60° C. for 3 hours. The desired product was detected by LC-MS. The mixture was quenched by adding water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane: methanol=10:1) to obtain methyl(S,E)-3-(2-((4-((6-((4-chloro-2-fluorobenzyl)oxy)-5-fluoropyridin-2-yl)oxy)piperidin-1-yl)methyl)-1-(oxetan-2-ylmethyl)-1H-benzo[d]imidazol-6-yl)acrylate (60 mg, 33.5% yield). LC-MS m/z: 639 $[M+H]^+$.

2). Synthesis of (S,E)-3-(2-((4-((6-((4-chloro-2-fluorobenzyl)oxy)-5-fluoropyridin-2-yl)oxy)piperidin-1-yl)-methyl)-1-(oxetan-2-ylmethyl)-1H-benzo[d]imidazol-6-yl)acrylic acid formate salt

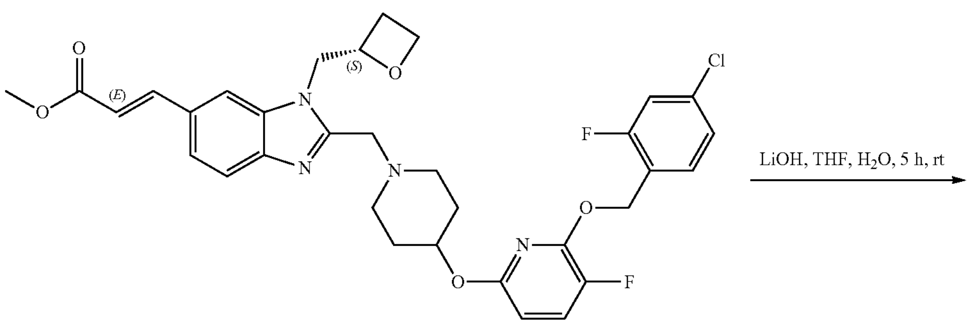

-continued

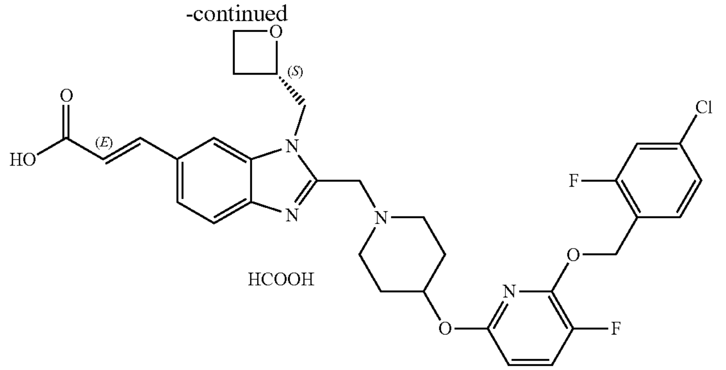

To a mixture of methyl(S,E)-3-(2-((4-((6-((4-chloro-2-fluorobenzyl)oxy)-5-fluoropyridin-2-yl)oxy)piperidin-1-yl)methyl)-1-(oxetan-2-ylmethyl)-1H-benzo[d]imidazol-6-yl)acrylate (60 mg, 0.094 mmol) in THF (2 mL) and water (2 2 mL) lithium hydroxide monohydrate (6 mg, 0.24 mmol) was added. The mixture was stirred at room temperature for 5 hours. The resulting mixture was adjusted to pH=5-6 with formic acid. The mixture was concentrated to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ Solvent system; Detection Wavelength 254 nm/214 nm; Flow rate: 20 mL/min) to obtain (S,E)-3-(2-((4-((6-((4-chloro-2-fluorobenzyl)oxy)-5-fluoropyridin-2-yl)oxy)piperidin-1-yl)methyl)-1-(oxetan-2-ylmethyl)-1H-benzo[d]imidazol-6-yl)acrylic acid formate salt (13.10 mg, 27% yield). LC-MS m/z: 625 $[M+H]^+$.

$^1$H NMR (400 MHZ, DMSO-$d_6$): δ8.27 (s, 1H), 8.00 (s, 1H), 7.66-7.47 (m, 6H), 7.32 (dd, J-10.0 Hz, 2.0 Hz, 1H), 6.54 (d, J=15.6 Hz, 1H), 6.34 (dd, J=8.8 Hz, 2.0 Hz, 1H), 5.44 (s, 2H), 5.11-5.09 (m, 1H), 4.79-4.75 (m, 2H), 4.62-4.58 (m, 1H), 4.51-4.40 (m, 2H), 3.95-3.92 (m, 1H), 3.80-3.76 (m, 1H), 2.80-2.68 (m, 3H), 2.50-2.41 (m, 1H), 2.36-2.29 (m, 2H), 1.91-1.89 (m, 2H), 1.62-1.57 (m, 2H).

Example 13. Synthesis of (E)-3-(2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazol-6-yl)acrylic acid (compound C2)

1). Synthesis of methyl (E)-3-(4-(2-(4-((6-((4-cyano-2-fluorobenzyl)oxy)pyridin-2-yl)oxy)piperidin-1-yl)acetamido)-3-(((1-ethyl-1H-imidazol-5-yl)methyl)amino)phenyl)acrylate

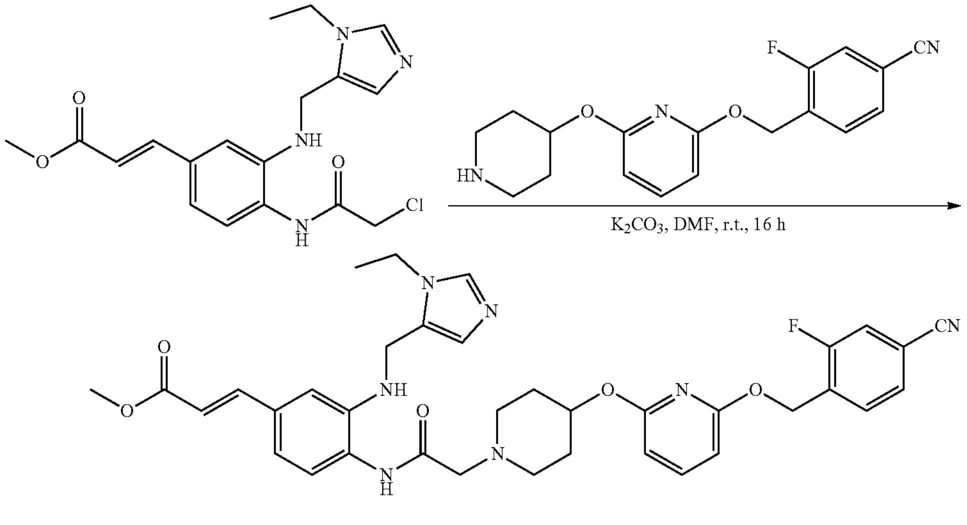

To a mixture of methyl (E)-3-(4-(2-chloroacetamido)-3-((1-ethyl-1H-imidazol-5-yl)methyl)amino)phenyl)acrylate (100 mg, 0.27 mmol) and 3-fluoro-4-((6-(piperidin-4-yloxy)pyridin-2-yl)oxy)methyl)benzonitrile (88 mg, 0.27 mmol) in N,N-dimethylformamide (5 mL) potassium carbonate (75 mg, 0.54 mmol) was added. The mixture was stirred at room temperature for 16 hours. The resulting mixture was poured into brine (50 mL) and extracted with ethyl acetate (2×15 mL). The combined organic was concentrated to give a residue in vacuo. The residue was purified by silica gel column chromatography (dichloromethane/methanol=20/1) to obtain methyl (E)-3-(4-(2-(4-((6-((4-cyano-2-fluorobenzyl)oxy)pyridin-2-yl)oxy)piperidin-1-yl)acetamido)-3-((1-ethyl-1H-imidazol-5-yl)methyl)amino)phenyl)acrylate (100 mg, 55.5% yield). LC-MS m/z: 668 $[M+H]^+$.

2). Synthesis of methyl (E)-3-(2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazol-6-yl)acrylate

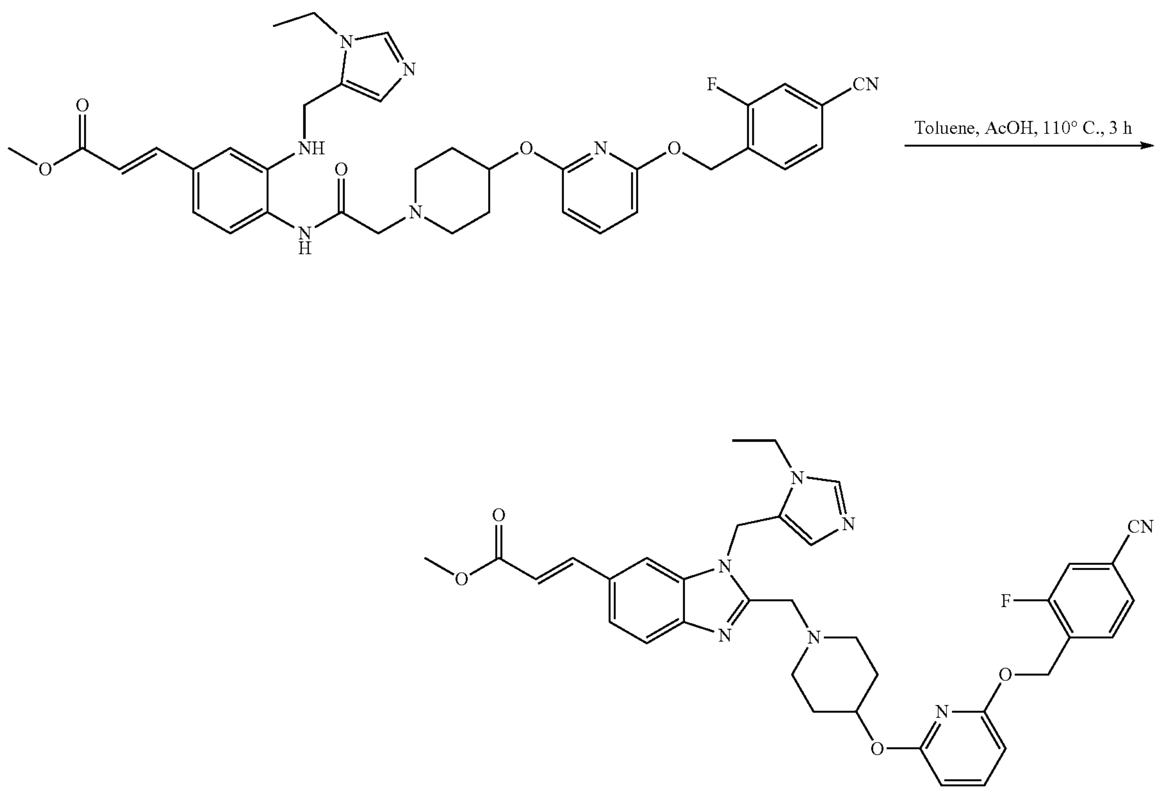

The mixture of methyl (E)-3-(4-(2-(4-((6-((4-cyano-2-fluorobenzyl)oxy)pyridin-2-yl)oxy)piperidine-1-yl)acetamido)-3-((1-ethyl-1H-imidazol-5-yl)methyl)amino)phenyl)acrylate (100 mg, 0.15 mmol) in toluene (2 mL) and acetic acid (0.2 mL) was stirred at 110° C. for 3 hours. The resulting mixture was poured into brine (20 mL) and extracted with dichloromethane (3x5 mL). The combined organic layer was concentrated to give a residue in vacuo. The residue was purified by silica gel column chromatography (dichloromethane/methanol-20/1) to give methyl (E)-3-(2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazol-6-yl)acrylate (70 mg, 71.9% yield). LC-MS m/z: 650 $[M+H]^+$.

3). Synthesis of (E)-3-(2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazol-6-yl)acrylic acid

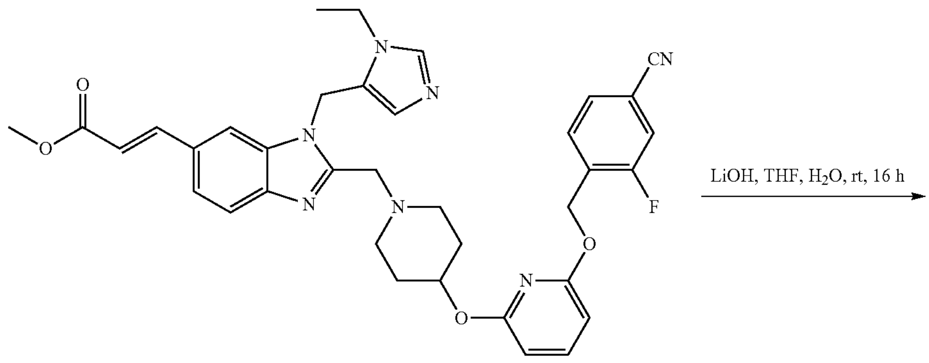

-continued

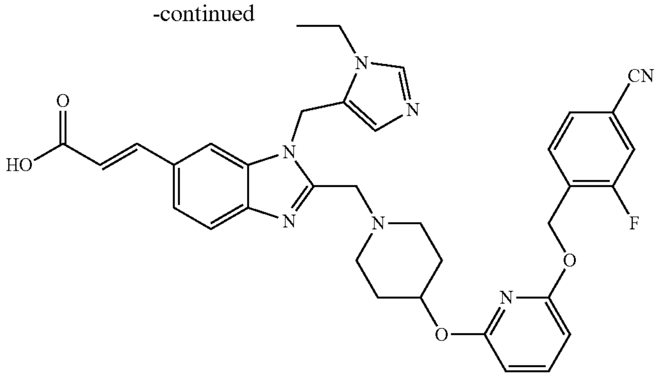

To A mixture of methyl (E)-3-(2-((4-((6-((4-cyano-2-fluorobenzyl)oxy)pyridin-2-yl)oxy)piperidin-1-yl)methyl)-1-((1-ethyl-1H-imidazol-5-yl)methyl)-1H-benzo[d]imidazol-6-yl)acrylate (70 mg, 0.11 mmol) in THF (2 mL) and water (2 mL) lithium hydroxide (5 mg, 0.21 mmol) was added. The mixture was stirred at room temperature for 16 hours. The mixture was concentrated to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to give (E)-3-(2-((4-((6-((4-cyano-2-fluorobenzyl)oxy)pyridin-2-yl)oxy)piperidin-1-yl) methyl)-1-((1-ethyl-1H-imidazol-5-yl)methyl)-1H-benzo[d] imidazol-6-yl)acrylic acid (13.86 mg, 19.8% yield). LC-MS m/z: 636 $[M+H]^+$.

$^1$H NMR (400 MHZ, DMSO-$d_6$): δ7.91 (d, J=9.6 Hz, 1H), 7.81 (s, 1H), 7.71-7.69 (m, 2H), 7.64-7.59 (m, 4 H), 7.52-7.50 (m, 1H), 6.50 (d, J=8.4 Hz, 1H), 6.45 (d, J=7.6 Hz, 1H), 6.34 (d, J-8.0 Hz, 1H), 5.66 (s, 2H), 5.43 (s, 2H), 4.74-4.70 (m, 1H), 4.00-3.95 (m, 2H), 3.76 (s, 2H), 2.67-2.64 (m, 2H), 2.23-2.19 (m, 2H), 1.76-1.73 (m, 2H), 1.44-1.38 (m, 2H), 1.14-1.10 (m, 3H).

Example 14. Synthesis of 2-((4-((6-((4-bromo-2-fluorophenoxy)methyl)pyridin-2-yl)oxy)piperidin-1-yl)meth-yl)-1-((1-ethyl-1H-imidazol-5-yl)methyl)-1H-benzo[d]imidazole-6-carboxylic acid (compound C3)

1). Synthesis of methyl 4-(2-(4-((6-((4-bromo-2-fluorophenoxy)methyl)pyridin-2-yl)oxy)piperidin-1-yl)acetamido)-3-((1-ethyl-1H-imidazol-5-yl)methyl) amino)benzoate

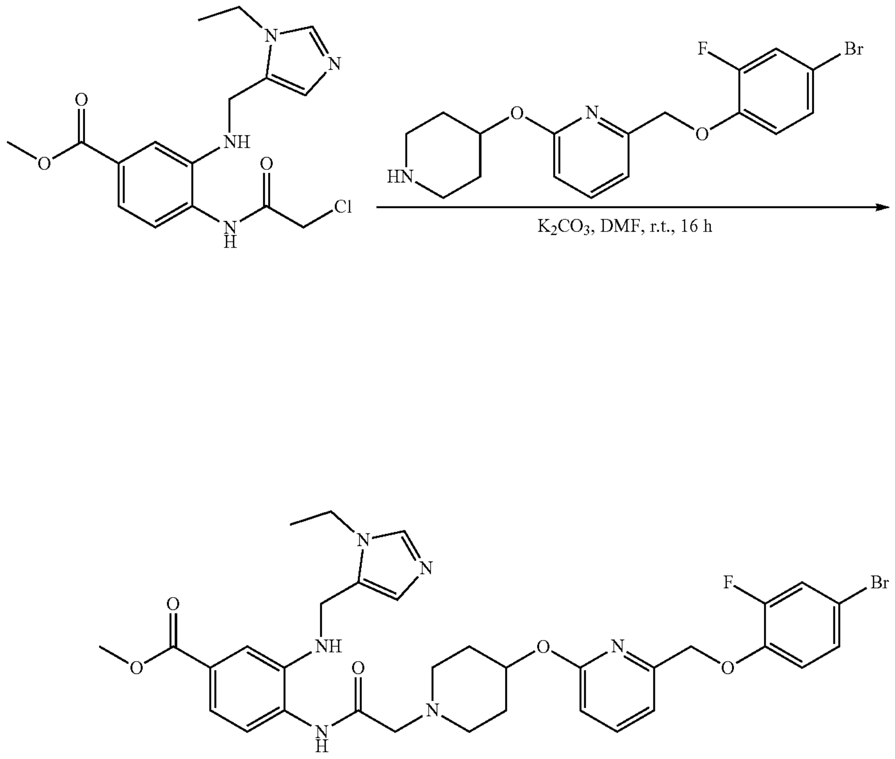

The mixture of methyl 4-(2-chloroacetamido)-3-((1-ethyl-1H-imidazol-5-yl)methyl)amino)benzoate (540 mg, 1.54 mmol), 2-((4-bromo-2-fluorophenoxy)methyl)-6-(piperidin-4-oxy)pyridine (586 mg, 1.54 mmol) and potassium carbonate (637 mg, 4.62 mmol) in dry N,N-dimethylformamide (15 mL) was stirred at room temperature for 16 hours. After completion, the reaction was quenched with water (10 mL) and extracted with ethyl acetate (3×10 mL). The combined organic layer was concentrated to give a residue in vacuo. The residue was purified by silica gel column chromatography (dichloromethane/methanol=10/1) to obtain methyl 4-(2-(4-((6-((4-bromo-2-fluorophenoxy)methyl)pyridin-2-yl)oxy)piperidin-1-yl)acetamido)-3-((1-ethyl-1H-imidazol-5-yl)methyl)amino)benzoate (500 mg, 46.8% yield). LC-MS m/z: 695 [M+H]+.

2). Synthesis of methyl 2-((4-((6-((4-bromo-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate

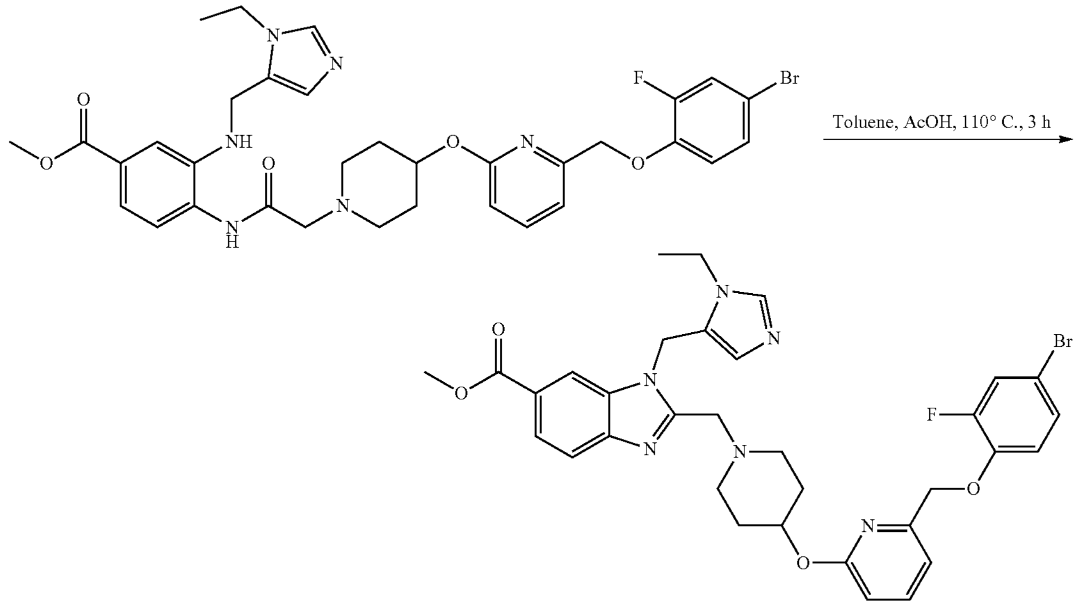

The mixture of methyl 4-(2-(4-((6-((4-bromo-2-fluorophenoxy)methyl)pyridin-2-yl)oxy)piperidin-1-yl)acetamido)-3-((1-ethyl-1H-imidazol-5-yl)methyl)amino)benzoate (500 mg, 0.72 mmol) in toluene (6 mL) and acetic acid (1 mL) was stirred at 110° C. for 3 hours. The mixture was concentrated to give a residue in vacuo. The residue was purified by silica gel column chromatography (dichloromethane/methanol=10/1) to obtain methyl 2-((4-((6-((4-bromo-2-fluorophenoxy)methyl)pyridin-2-yl)oxy)piperidin-1-yl)methyl)-1-((1-ethyl-1H-imidazol-5-yl)methyl)-1H-benzo[d]imid-azole-6-carboxylate (470 mg, 96.5% yield). LC-MS m/z: 679 [M+H]+.

3). Synthesis of 2-((4-((6-((4-bromo-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylic acid

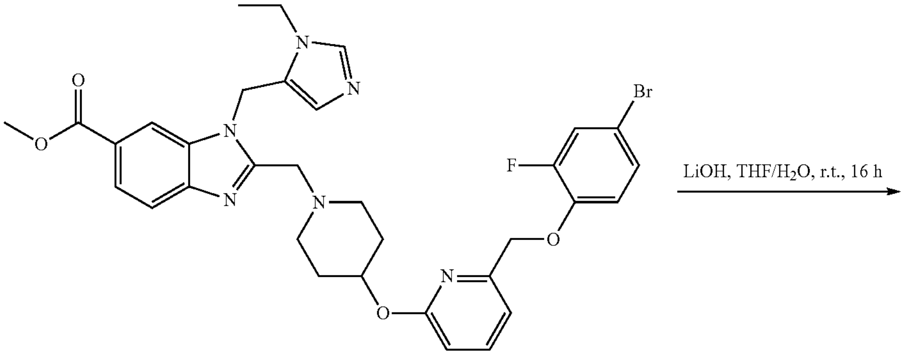

-continued

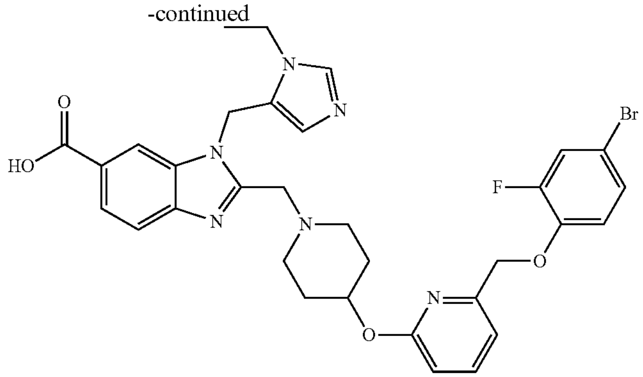

To a mixture of methyl 2-((4-((6-((4-bromo-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate (80 mg, 0.12 mmol) in THF (1 mL) and water (1 mL) lithium hydroxide (9 mg, 0.36 mmol) was added. The reaction mixture was stirred at room temperature for 16 hours. The reaction mixture was adjusted to pH=5-6 with formic acid. The mixture was concentrated to give a residue in vacuo. The residue was eluted by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to give 2-((4-((6-((4-bromo-2-fluorophenoxy)methyl)pyridin-2-yl)oxy)piperidin-1-yl) methyl)-1-((1-ethyl-1H-imidazol-5-yl)methyl)-1H-benzo[d] imidazole-6-carboxylic acid (30.96 mg, 39% yield). LC-MS m/z: 665 $[M+H]^+$.

$^1$H NMR (400 MHZ, DMSO-$d_6$): δ8.19 (s, 1H), 8.07 (s, 1H), 7.81 (dd, J=8.8 Hz, 1.6 Hz, 1H), 7.72-7.67 (m, 3H), 7.54 (dd, J-6.8 Hz, 2.4 Hz, 1 H), 7.30 (d, J=8.8 Hz, 1H), 7.21 (t, J=8.8 Hz, 1H), 7.03 (d, J=7.2 Hz, 1H), 6.70 (d, J=8.4 Hz, 1H), 6.41 (s, 1H), 5.72 (s, 2H), 5.17 (s, 2H), 4.88-4.86 (m, 1H), 4.03-3.98 (m, 2H), 3.81 (s, 2 H), 2.69-2.67 (m, 2H), 2.33-2.23 (m, 2H), 1.81-1.78 (m, 2H), 1.47-1.44 (m, 2H), 1.16 (t, J-7.2 Hz, 3H).

Example 15. Synthesis of(S)-2-((4-((6-((4-bromo-2-fluorophenoxy)methyl)pyridin-2-yl)oxy)piperidin-1-yl)methyl)-1-(oxetan-2-ylmethyl)-1H-benzo[d]imidazole-6-carboxylic acid (compound C4)

1). Synthesis of methyl(S)-2-((4-((6-((4-bromo-2-fluorophenoxy)methyl)pyridin-2-yl)oxy)piperidin-1-yl)methyl)-1-(oxetan-2-ylmethyl)-1H-benzo[d]imidazole-6-carboxylate

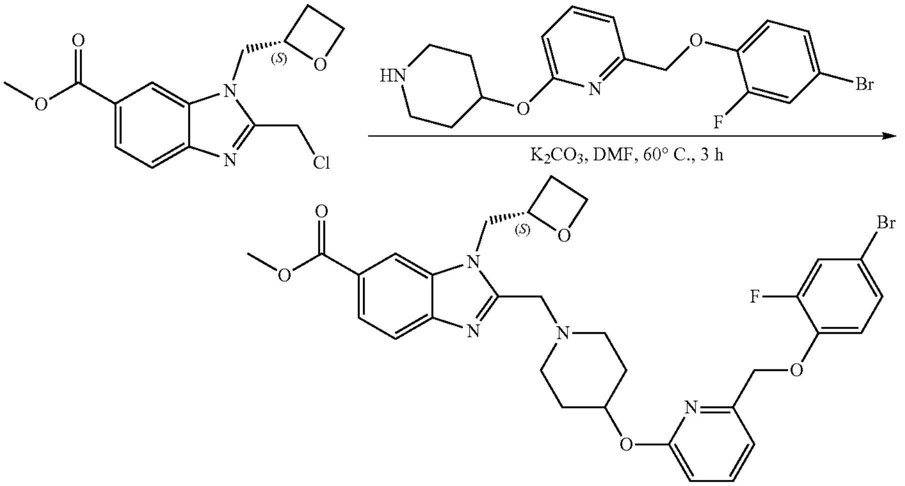

The mixture of methyl(S)-2-(chloromethyl)-1-(oxetan-2-ylmethyl)-1H-benzo[d]imidazole-6-carboxylate (100 mg, 0.34 mmol), 2-((4-bromo-2-fluorophenoxy)methyl)-6-(piperidin-4-oxy)pyridine (130 mg, 0.34 mmol) and potassium carbonate (140 mg, 1.02 mmol)) in N,N-dimethylformamide (4 mL) was stirred at 60° C. for 3 hours. The mixture was quenched with water (10 mL) and extracted with ethyl acetate (3×10 mL). The combined organic layer was concentrated to give a residue in vacuo. The residue was purified by silica gel column chromatography (dichloromethane/methanol=10/1) to obtain methyl(S)-2-((4-((6-((4-bromo-2-fluorophenoxy)yl)methyl) pyridin-2-yl)oxy)piperidin-1-yl) methyl)-1-(oxetan-2-ylmethyl)-1H-benzo[d]imidazole-6-carboxylate (100 mg, 46.1% yield). LC-MS m/z: 639 $[M+H]^+$.

2). Synthesis of(S)-2-((4-((6-((4-bromo-2-fluorophenoxy)methyl)pyridin-2-yl)oxy)piperidin-1-yl) methyl)-1-(oxetan-2-ylmethyl)-1H-benzo[d]imidazole-6-carboxylate

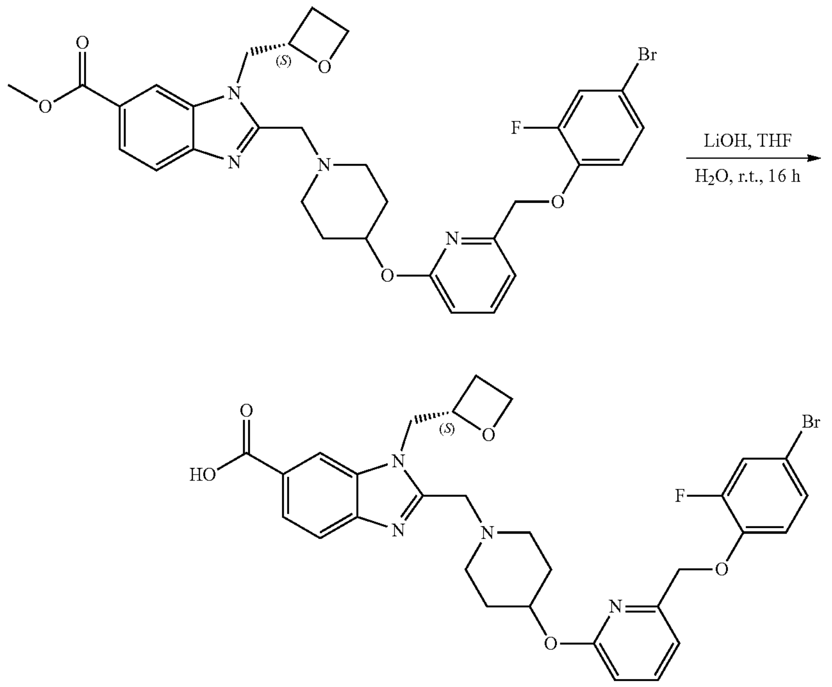

To a mixture of methyl(S)-2-((4-((6-((4-bromo-2-fluorophenoxy)methyl)pyridin-2-yl)oxy)piperidin-1-yl)methyl)-1-(oxetan-2-ylmethyl)-1H-benzo[d]imidazole-6-carboxylate (100 mg, 0.16 mmol) in THF (2 mL) and water (2 mL) lithium hydroxide (12 mg, 0.48 mmol) was added. The reaction mixture was stirred at room temperature for 16 hours. The reaction mixture was adjusted to pH=5-6 with formic acid. The solvent was removed by concentration to give residue in vacuo. The residue purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain(S)-2-((4-((6-((4-bromo-2-fluorophenoxy)methyl)pyridin-2-yl)oxy)pyridin-1-yl)methyl)-1-(oxetan-2-ylmethyl)-1H-benzo[d]imidazole-6-carboxylic acid (20.08 mg, 20.5% yield). LC-MS m/z: 627 $[M+H]^+$.

$^1$H NMR (400 MHZ, DMSO-$d_6$): δ8.28-8.23 (m, 1H), 7.80 (d, J-8.8 Hz, 1H), 7.71 (t, J=7.6 Hz, 1H), 7.63 (d, J=8.4 Hz, 1H), 7.54 (dd, J=10.4 Hz, 2.0 Hz, 1H), 7.31 (d, J=9.2 Hz, 1H), 7.22 (t, J=8.8 Hz, 1H), 7.04 (d, J=7.2 Hz, 1H), 6.72 (d, J=8.4 Hz, 1H), 5.18 (s, 2H), 5.13-5.06 (m, 1H), 4.97-4.89 (m, 1H), 4.83-4.73 (m, 1H), 4.68-4.60 (m, 1H), 4.54-4.46 (m, 1H), 4.41-4.33 (m, 1H), 3.98-3.90 (m, 1H), 3.82-3.75 (m, 1H), 2.82-2.66 (m, 4H), 2.46-2.36 (m, 1H), 2.33-2.26 (m, 2H), 1.97-1.88 (m, 2H), 1.66-1.56 (m, 2H).

Example 16. Synthesis of 2-((4-((6-((4-cyano-2-fluorophenoxy)methyl)pyridin-2-yl)oxy)piperidin-1-yl)methyl)-1-(oxetan-3-ylmethyl)-1H-benzo[d]imidazole-6-carboxylic acid (compound C82)

1). Synthesis of methyl 2-((4-((6-((4-cyano-2-fluorophenoxy)methyl)pyridin-2-yl)oxy)piperidin-1-yl) methyl)-1-(oxetan-3-ylmethyl)-1H-benzo[d]imidazole-6-carboxylate

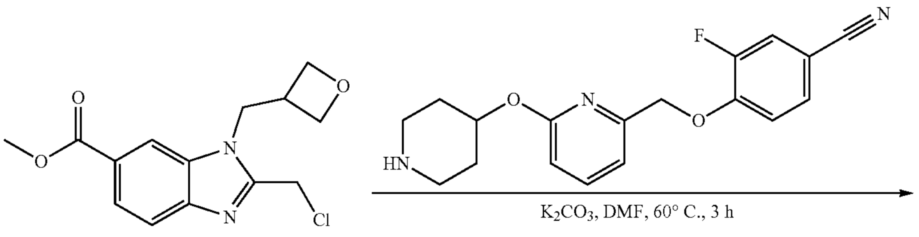

-continued

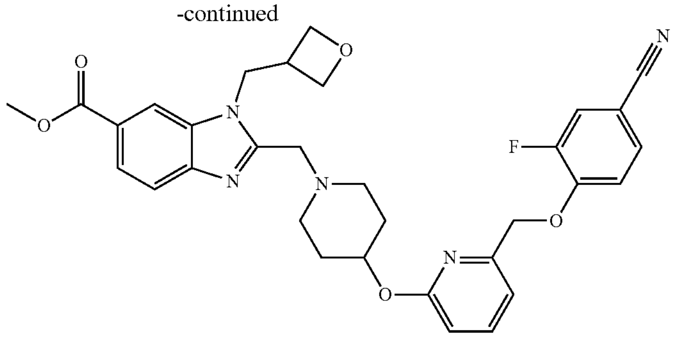

The mixture of methyl 2-(chloromethyl)-1-(oxetan-3-ylmethyl)-1H-benzo[d]imidazole-6-carboxylate (100 mg, 0.34 mmol), 3-fluoro-4-((6-(piperidin-4-oxy)pyridin-2-yl)methoxy)benzonitrile (111 mg, 0.34 mmol) and potassium carbonate (94 mg, 0.68 mmol) in N,N-dimethylformamide (2 mL) was stirred at 60° C. for 3 hours. The resulting mixture was diluted with water (30 mL) and extracted with ethyl acetate (10 mL×3). The combined organic layers were washed with brine (30 mL), concentrated under to give a residue reduced pressure.

The residue was purified by silica gel column chromatography (dichloromethane/methanol=20/1) to obtain methyl 2-((4-((6-((4-cyano-2-fluorophenoxy)methyl)pyridin-2-yl)oxy)piperidin-1-yl)methyl)-1-(oxetan-3-ylmethyl))-1H-benzo[d]imidazole-6-carboxylate (100 mg, 50.3% yield). LC-MS m/z: 586 $[M+H]^+$. 2). Synthesis of 2-((4-((6-((4-cyano-2-fluorophenoxy)methyl)pyridin-2-yl)oxy)piperidin-1-yl)methyl)-1-(oxetan-3-ylmethyl)-1H-benzo[d]imidazole-6-carboxylic acid:

To a mixture of methyl 2-((4-((6-((4-cyano-2-fluorophenoxy)methyl)pyridin-2-yl)oxy)piperidin-1-yl)methyl)-1-(oxetan-3-ylmethyl)-1H-benzo[d]imidazole-6-carboxylate (100 mg, 0.17 mmol) in THF (1.0 mL) and water (1.0 mL) lithium hydroxide (8 mg, 0.34 mmol) was added. The reaction mixture was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidin-1-yl)methyl)-1-(oxetan-3-ylmethyl)-1H-benzo[d]imidazole-6-carboxylic acid (25.81 mg, 26.6% yield). LC-MS m/z: 572 $[M+H]^+$. $^1H$ NMR (400 MHZ, DMSO-$d_6$): δ8.22 (s, 1H), 7.88 (dd, J=11.2, 2.0 Hz, 1H), 7.81 (dd, J=8.4, 1.2 Hz, 1 H), 7.73 (t, J-8.0 Hz, 1H), 7.67-7.61 (m, 2H), 7.45 (t, J-8.4 Hz, 1H), 7.06 (d, J=7.2 Hz, 1H), 6.74 (d, J=8.4 Hz, 1H), 5.31 (s, 2H), 4.94-4.91 (m, 1H), 4.72 (d, J=7.6 Hz, 2H), 4.64-4.61 (m, 2H), 4.56-4.53 (m, 2H), 3.81 (s, 2 H), 3.67-3.61 (m, 1H), 2.80-2.77 (m, 2H), 2.33-2.27 (m, 2H), 1.93-1.90 (m, 2H), 1.64-1.59 (m, 2H).

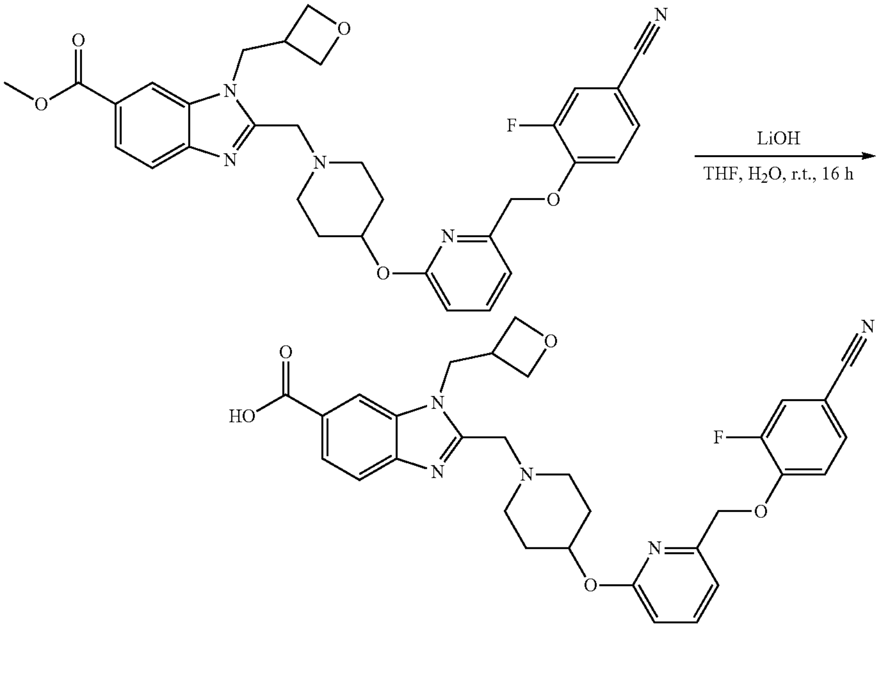

Example 17. Synthesis of 2-((4-((6-((4-cyano-2-fluorophenoxy)methyl)pyridin-2-yl)oxy)piperidin-1-yl)methyl)-1-((3-methyloxetan-3-yl)methyl)-1H-benzo[d]imidazole-6-carboxylic acid (compound C5)

1). Synthesis of methyl 2-((4-((6-((4-cyano-2-fluorophenoxy)methyl)pyridin-2-yl)oxy)piperidin-1-yl)methyl)-1-((3-methyloxetan-3-yl)methyl)-1H-benzo[d]imidazole-6-carboxylate

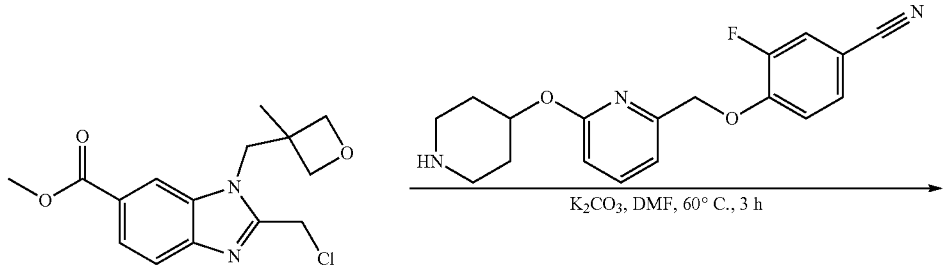

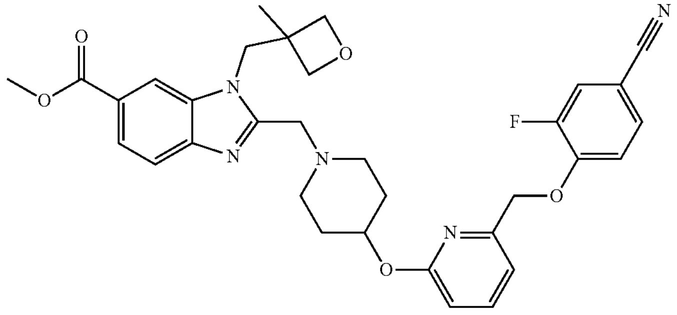

The mixture of methyl 2-(chloromethyl)-1-((3-methyloxetan-3-yl)methyl)-1H-benzo[d]imidazole-6-carboxylate (100 mg, 0.32 mmol), 3-fluoro-4-((6-(piperidin-4-oxy)pyridin-2-yl)methoxy)benzonitrile (105 mg, 0.32 mmol) and potassium carbonate (88 mg, 0.64 mmol) in N,N-dimethylformamide (2 mL) was stirred at 60° C. for 3 hours. The resulting mixture was diluted with water (30 mL) and extracted with ethyl acetate (10 mL×3). The combined organic layers were washed with saturated brine (30 mL) and concentrated to give a residue in vacuo. The residue was purified by silica gel column chromatography (dichloromethane/methanol=20/1) to obtain methyl 2-((4-((6-((4-cyano-2-fluorophenoxy)methyl)-pyridin-2-yl)oxy)piperidin-1-yl)methyl)-1-((3-methyloxetan-3-yl)methyl)-1H-benzo[d]imidazole-6-carboxylate (50 mg, 26.0% yield). LC-MS m/z: 600 $[M+H]^+$.

2). Synthesis of 2-((4-((6-((4-cyano-2-fluorophenoxy)methyl)pyridin-2-yl)oxy)piperidin-1-yl)methyl)-1-((3-methyloxetan-3-yl)methyl)-1H-benzo[d]imidazole-6-carboxylic acid

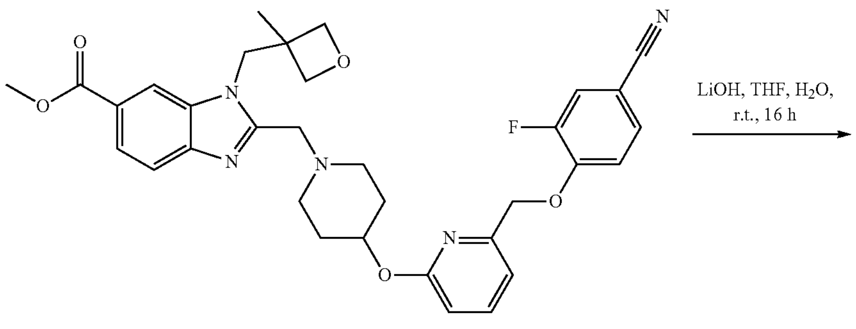

-continued

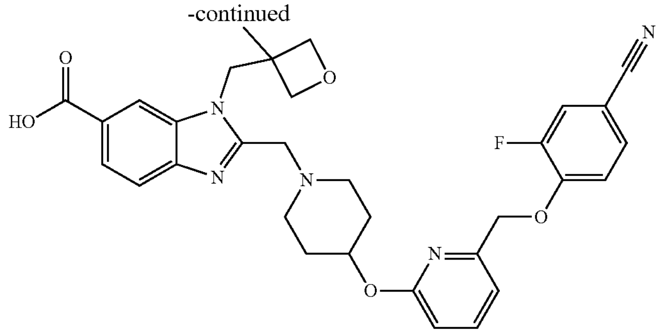

To a mixture of methyl 2-((4-((6-((4-cyano-2-fluorophenoxy)methyl)-pyridin-2-yl)oxy)piperidin-1-yl)methyl)-1-((3-methyloxetan-3-yl)methyl)-1H-benzo[d]imidazole-6-carboxylate (50 mg, 0.08 mmol) in THF (5 mL) and water (5 mL) lithium hydroxide (10 mg, 0.42 mmol) was added. The mixture was stirred at room temperature for 16 hours. The solvent was removed to give a residue by concentration in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidin-1-yl)methyl)-1-((3-methyloxetan-3-yl)methyl)-1H-benzo[d]imidazole-6-carboxylic acid (9.50 mg, 20.3% yield). LC-MS m/z: 586 $[M+H]^+$.

$^1H$ NMR (400 MHZ, DMSO-$d_6$): δ8.21 (s, 1H), 7.88 (dd, J=11.2, 1.6 Hz, 1H), 7.81 (d, J=9.2 Hz, 1H), 7.73 (t, J=8.0 Hz, 1H), 7.66 (d, J-8.4 Hz, 2H), 7.44 (t, J=8.8 Hz, 1H), 7.05 (d, J=7.2 Hz, 1H), 6.73 (d, J=8.4 Hz, 1H), 5.30 (s, 2H), 4.92-4.90 (m, 1H), 4.65-4.61 (m, 4H), 4.22 (d, J-6.0 Hz, 1H), 3.78 (s, 2H), 2.76-2.74 (m, 2H), 2.31-2.26 (m, 2H), 1.92-1.87 (m, 2H), 1.62-1.58 (m, 2H), 1.25 (s, 3H).

Example 18. Synthesis of(S)-2-((4-(3-((4-cyano-2-fluorophenoxy)methyl) phenoxy)piperidin-1-yl) methyl)-1-(oxetan-2-ylmethyl)-1H-benzo[d]imidazole-6-carboxylic acid (compound 67)

1). Synthesis of methyl(S)-2-((4-(3-((4-cyano-2-fluorophenoxy)methyl) phenoxy)piperidin-1-yl) methyl)-1-(oxetan-2-ylmethyl)-1H-benzo[d]imidazole-6-carboxylate

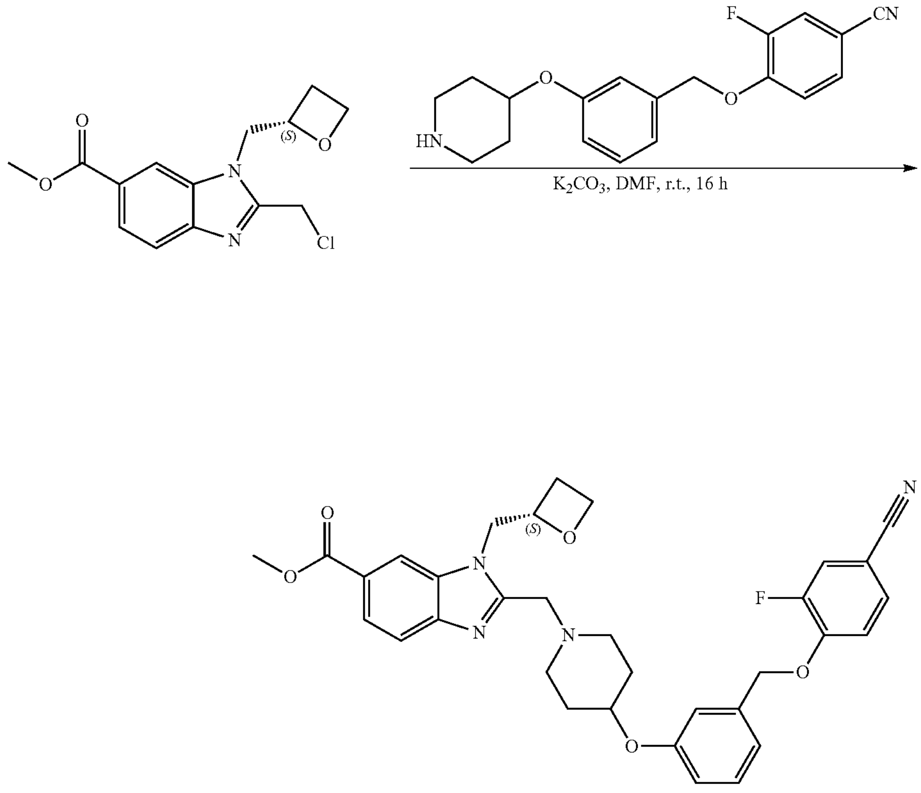

To A mixture of methyl(S)-2-(chloromethyl)-1-(oxetan-2-ylmethyl)-1H-benzo[d]imidazole-6-carboxylate (100 mg, 0.34 mmol) and 3-fluoro-4-((3-(piperidin-4-oxy)benzyl)oxy)benzonitrile (122 mg, 0.37 mmol) in N,N-dimethylformamide (5 mL) potassium carbonate (94 mg, 0.68 mmol) was added. The mixture was stirred at room temperature for 16 hours. The mixture was quenched by adding water (5 mL) and extracted with ethyl acetate (40 mL×3). The combined organic layers were washed with brine (30 mL×2), dried over anhydrous sodium sulfate, filtered, and concentrated to give a residue in vacuo. The residue was purified by silica gel column chromatography (dichloromethane/methanol=10/1) to obtain methyl(S)-2-((4-(3-((4-cyano-2-fluorophenoxy)methyl) phenoxy)piperidin-1-yl)methyl)-1-(oxetan-2-ylmethyl)-1H-benzo[d]imidazole-6-carboxylate (71 mg, 35.8% yield). LC-MS m/z: 585 [M+H]$^+$.

2). Synthesis of(S)-2-((4-(3-((4-cyano-2-fluorophenoxy)methyl) phenoxy)piperidin-1-yl)methyl)-1-(oxetan-2-ylmethyl)-1H-benzo[d]imidazole-6-carboxylic acid

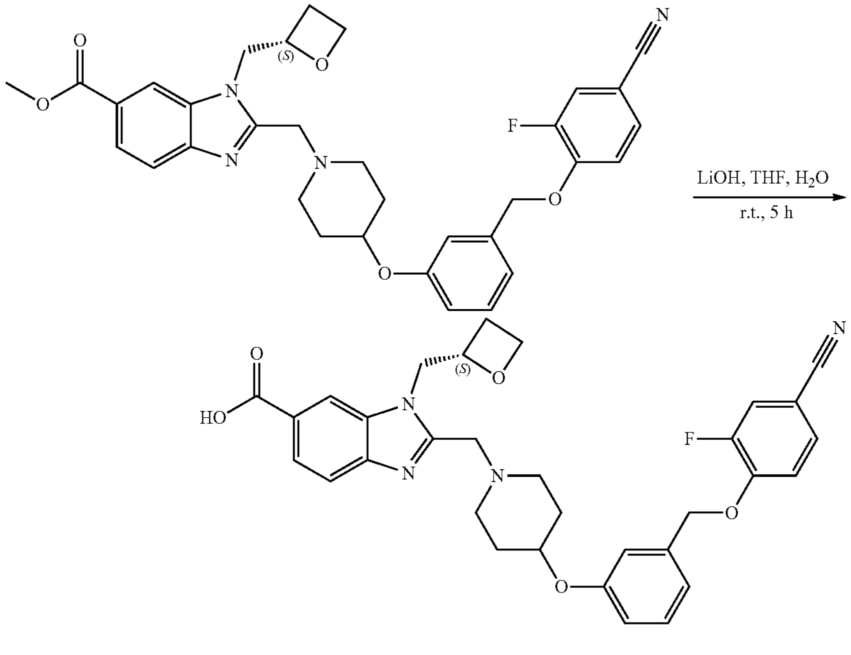

-

To a mixture of methyl(S)-2-((4-(3-((4-cyano-2-fluorophenoxy)methyl) phenoxy)piperidin-1-yl)methyl)-1-(oxetan-2-ylmethyl)-1H-benzo[d]imidazole-6-carboxylate (71 mg, 0.12 mmol) in THF (2 mL) and water (2 mL) lithium hydroxide monohydrate (50 mg, 1.20 mmol) was added at room temperature. The reaction was stirred at room temperature for 5 hours. The resulting mixture was adjusted to pH=5-6 with hydrochloric acid (1M), and then extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_3$ $H_2O$ in water; Mobile Phase B: acetonitrile; Flow rate: 40 mL/min; Gradient: 20% B-50% B in 20 minutes; Detector: 254 nm) to obtain(S)-2-((4-(3-((4-cyano-2-fluorophenoxy)methyl) phenoxy)piperidin-1-yl)methyl)-1-(oxetan-2-ylmethyl)-1 H-benzo[d]imi-dazole-6-carboxylic acid (4.69 mg, 7.3% yield). LC-MS m/z: 571 [M+H]$^+$.

$^1$H NMR (400 MHZ, DMSO-$d_6$) 8.25 (s, 1H), 7.88-7.80 (m, 2H), 7.68 (d, J=8.4 Hz, 1H), 7.61 (d, J-8.0 Hz, 1H), 7.42 (t, J=8.4 Hz, 1H), 7.30 (t, J-7.6 Hz, 1H), 7.05-6.93 (m, 3H), 5.25 (s, 2H), 5.10-5.07 (m, 1H), 4.80-4.75 (m, 1H), 4.63 (d, J=13.2 Hz, 1H), 4.52-4.47 (m, 1H), 4.42-4.35 (m, 2H), 3.94 (d, J=13.2 Hz, 1H), 3.78 (d, J=13.2 Hz, 1H), 2.79-2.67 (m, 3H), 2.46-2.35 (m, 3H), 1.95-1.93 (m, 2H), 1.64-1.60 (m, 2H).

Example 19. Synthesis of 2-((4-((6-((4-cyano-2-fluorophenoxy)methyl)pyridin-2-yl)oxy)piperidin-1-yl)methyl)-1-((1,2-dimethyl-1H-imidazol-5-yl)methyl)-1H-benzo[d]imidazole-6-carboxylic acid (compound C6)

1). Synthesis of methyl 4-(2-(4-((6-((4-cyano-2-fluorophenoxy)methyl)pyridin-2-yl)oxy)piperidin-1-yl)acetamido)-3-((1,2-dimethyl-1H-imidazol-5-yl)methyl)amino)benzoate

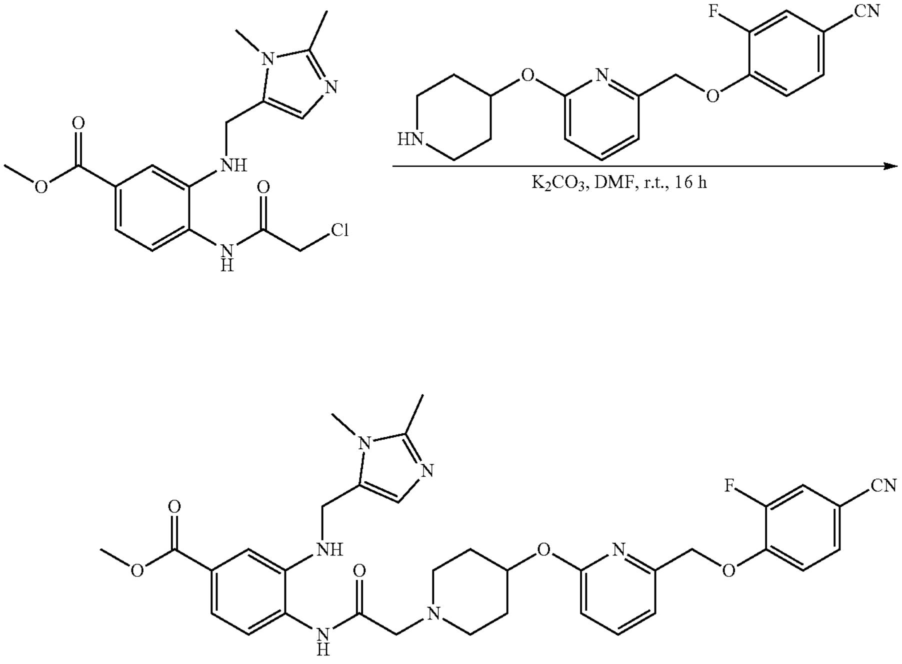 [SMILES: COC(=O)c1ccc(NC(=O)CCl)c(NCc2cnc(C)n2C)c1 ; N#Cc1ccc(OCc2cccc(OC3CCNCC3)n2)c(F)c1 ; COC(=O)c1ccc(NC(=O)CN2CCC(Oc3cccc(COc4ccc(C#N)cc4F)n3)CC2)c(NCc2cnc(C)n2C)c1]

To a mixture of methyl 4-(2-chloroacetamido)-3-((1,2-dimethyl-1H-imidazol-5-yl)methyl)amino)benzoate (150 mg, 0.43 mmol) and 3-fluoro-4-((6-(piperidin-4-oxy)pyridin-2-yl)methoxy)benzonitrile (141 mg, 0.43 mmol) in N,N-dimethylformamide (5 mL) potassium carbonate (119 mg, 0.86 mmol) was added. The mixture was stirred at room temperature for 16 hours. After completion, the mixture was poured into brine (50 mL) and extracted with ethyl acetate (2×20 mL). The combined organic layer was concentrated to give a residue in vacuo. The residue was purified by silica gel column chromatography (dichloromethane/methanol=20/1) to obtain methyl 4-(2-(4-((6-((4-cyano-2-fluorophenoxy))methyl)pyridin-2-yl)oxy)piperidin-1-yl)acetamido)-3-((1,2-dimethyl-1H-imidazol-5-yl)methyl)amino) benzoate (150 mg, 54.3% yield). LC-MS m/z: 642 $[M+H]^+$.

2). Synthesis of methyl 2-((4-((6-((4-cyano-2-fluorophenoxy)methyl)pyridin-2-yl)oxy)piperidin-1-yl) methyl)-1-((1,2-dimethyl-1H-imidazol-5-yl)methyl)-1H-benzo[d]imidazole-6-carboxylate

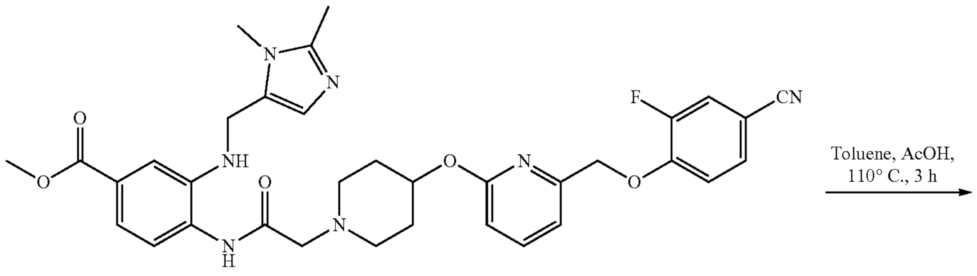

-continued

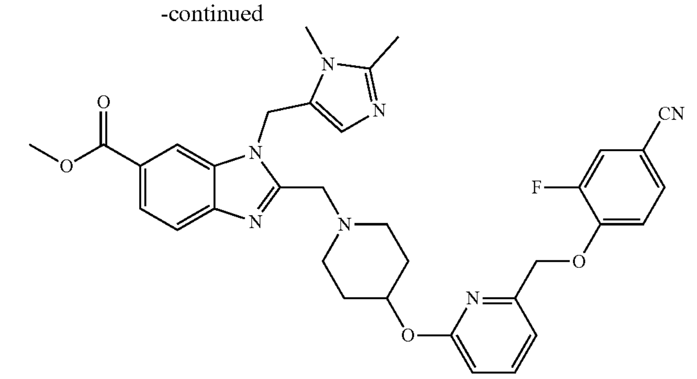

The mixture of methyl 4-(2-(4-((6-((4-cyano-2-fluorophenoxy)methyl)pyridin-2-yl)oxy)piperidin-1-yl)acetamido)-3-((1,2-dimethyl-1H-imidazol-5-yl)methyl)amino) benzoate (150 mg, 0.08 mmol) in toluene (5 mL) and acetic acid (1 mL) was stirred at 110° C. for 3 hours. The mixture was poured into brine (20 mL) and extracted with dichloromethane (2×10 mL). The combined organic layer was concentrated in vacuo to give methyl 2-((4-((6-((4-cyano-2-fluorophenoxy)methyl)pyridin-2-yl)oxy)piperidin-1-yl)methyl)-1-((1,2-dimethyl-1H-imidazol-5-yl)methyl)-1H-benzo-[d]imidazole-6-carboxylate (100 mg, 69.8% yield). LC-MS m/z: 624 $[M+H]^+$.

3). Synthesis of 2-((4-((6-((4-cyano-2-fluorophenoxy)methyl)pyridin-2-yl)oxy)piperidin-1-yl)methyl)-1-((1,2-dimethyl-1H-imidazol-5-yl)methyl)-1H-benzo[d]imidazole-6-carboxylic acid formate salt

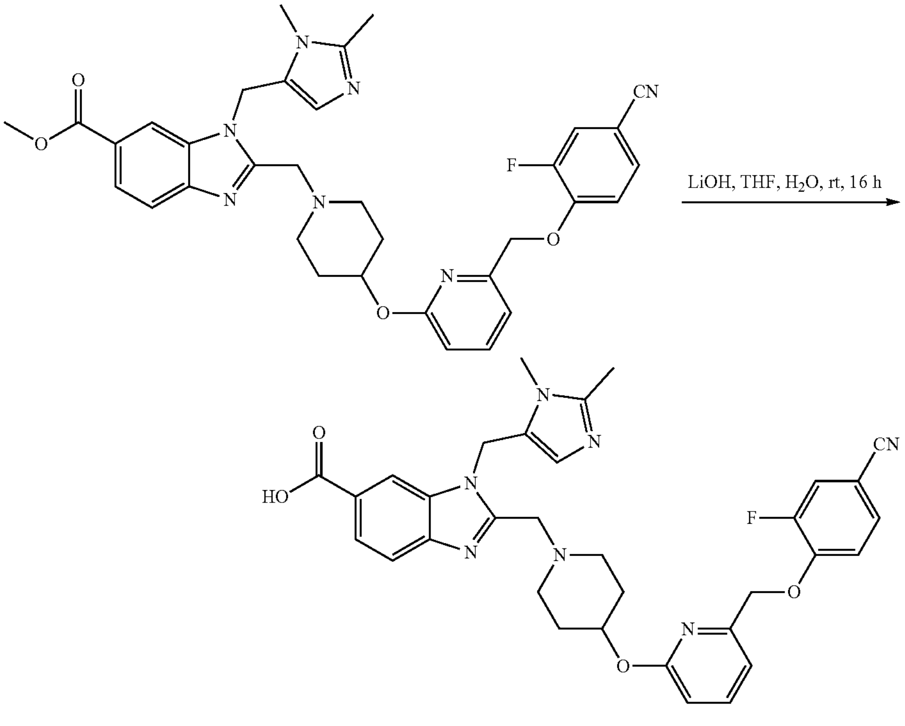

To a mixture of methyl 2-((4-((6-((4-cyano-2-fluorophenoxy)methyl)pyridin-2-yl)oxy)piperidin-1-yl)methyl)-1-((1,2-dimethyl-1H-imidazol-5-yl)methyl)-1H-benzo-[d]imidazole-6-carboxylate (100 mg, 0.17 mmol) in THF (5 mL) and water (5 mL) lithium hydroxide (8 mg, 0.34 mmol) was added. The reaction mixture was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtained 2-((4-((6-((4-cyano-2-fluorophenoxy)methyl)pyridin-2-yl)oxy)piperidine-1-yl)methyl)-1-((1,2-dimethyl-1H-imidazol- 5-yl)me-thyl)-1H-benzo[d]imidazole-6-carboxylic acid formate salt (71.07 mg, 68.6% yield). LC-MS m/z: 610 $[M+H]^+$.

$^1H$ NMR (400 MHZ, DMSO-$d_6$): δ8.16 (s, 2H), 8.09 (s, 1H), 7.88 (dd, J=11.2, 1.6 Hz, 1H), 7.81 (dd, J=8.4, 1.2 Hz, 1H), 7.74-7.65 (m, 3H), 7.44 (t, J=8.4 Hz, 1H), 7.05 (d, J=7.2 Hz, 1H), 6.72 (d, J=8.4 Hz, 1H), 6.41 (s, 1H), 5.67 (s, 2H), 5.30 (s, 2H), 4.90-4.86 (m, 1H), 3.82 (s, 2H), 3.44 (s, 3H), 2.72-2.69 (m, 2H), 2.33-2.24 (m, 5H), 1.84-1.82 (m, 2H), 1.54-1.47 (m, 2H).

Example 20. Synthesis of 2-((4-((6-((4-cyano-2-fluorophenoxy)methyl)-5-fluoropyridin-2-yl)oxy)piperidin-1-yl)methyl)-1-((1-(cyanomethyl)cyclopropyl)methyl)-1H-benzo[d]imidazole-6-carboxylic acid (compound 135)

1). Synthesis of methyl 2-((4-((6-((4-cyano-2-fluorophenoxy)methyl)-5-fluoropyridin-2-yl)oxy)piperidin-1-yl)methyl)-1-((1-(cyanomethyl)cyclopropyl)methyl)-1H-benzo[d]imidazole-6-carboxylate

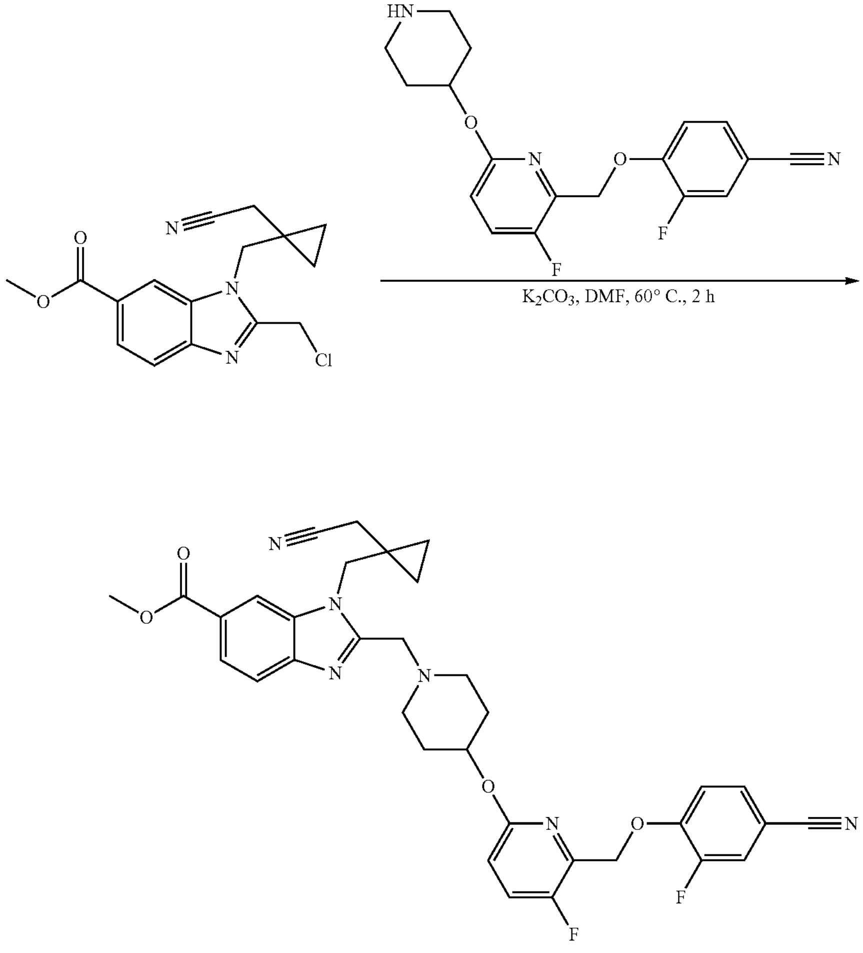

To a mixture of methyl 2-(chloromethyl)-1-(1-(cyanomethyl)cyclopropyl)methyl)-1H-benzo[d]imidazole-6-carboxylate (160 mg, 0.50 mmol) and 3-fluoro-4-((3-fluoro-6-(piperidin-4-oxy)pyridin-2-yl)methoxy)benzonitrile (173 mg, 0.50 mmol) in N,N-dimethylformamide (4 mL) potassium carbonate (207 mg, 1.50 mmol) was added at room temperature. The mixture was stirred at 60° C. for 2 hours. The mixture was quenched with water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain methyl 2-((4-((6-((4-cyano-2-fluorophenoxy)methyl)-5-fluoropyridin-2-yl)oxy)piperidin-1-yl)methyl)-1-((1-(cyanomethyl)cyclopropyl)methyl)-1H-benzo[d]imidazole-6-carboxylate (17 mg, 6.0% yield). LC-MS 20 m/z: 627 $[M+H]^+$.

2). Synthesis of 2-((4-((6-((4-cyano-2-fluorophenoxy)methyl)-5-fluoropyridin-2-yl)oxy)piperidin-1-yl)methyl)-1-((1-(cyanomethyl)cyclopropyl)methyl)-1H-benzo[d]imidazole-6-carboxylic acid

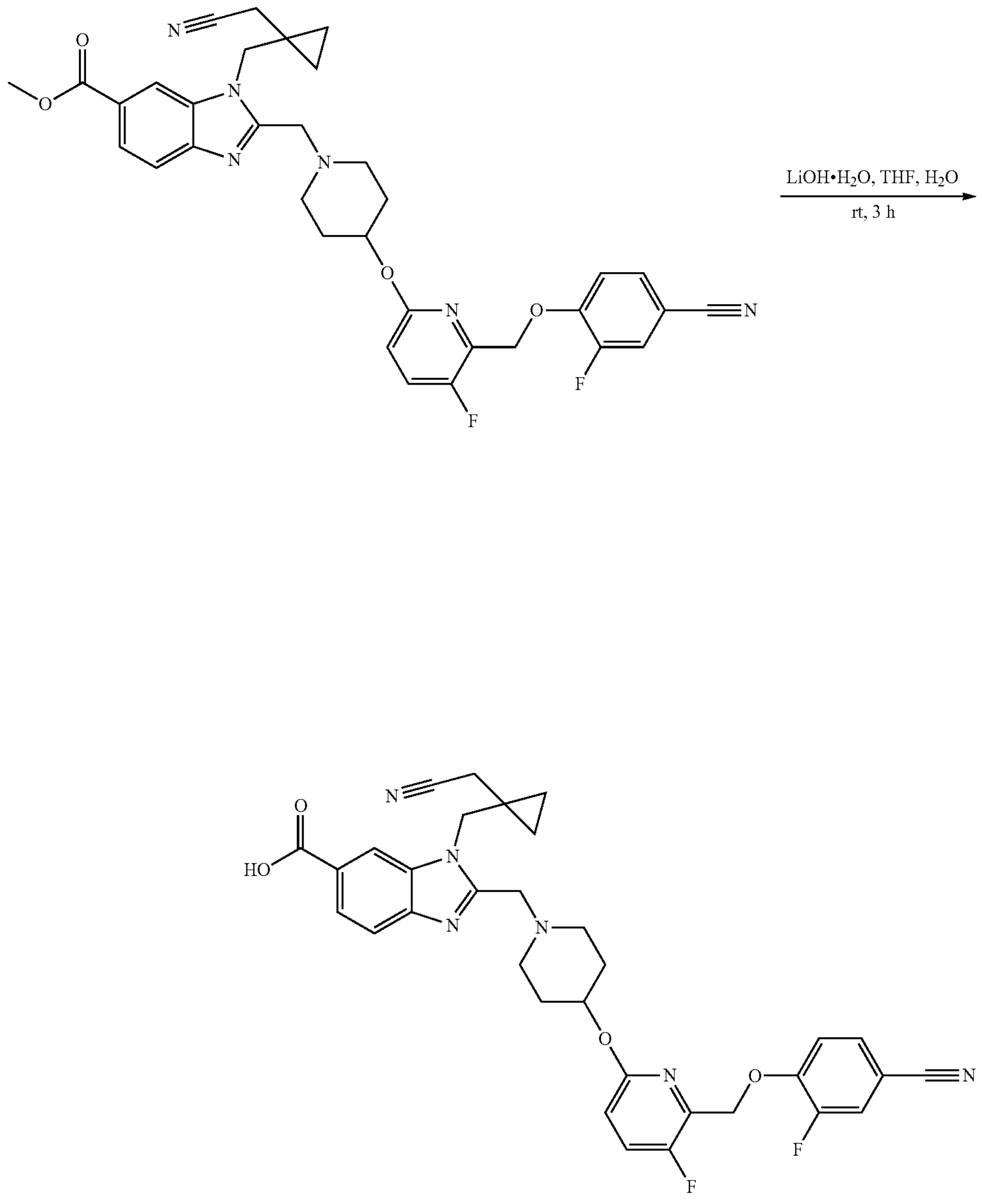

To a mixture of methyl 2-((4-((6-((4-cyano-2-fluorophenoxy)methyl)-5-fluoropyridin-2-yl)oxy)piperidin-1-yl)methyl)-1-((1-(cyanomethyl)cyclopropyl)methyl)-1H-benzo[d]imidazole-6-carboxylate (17 mg, 0.03 mmol) in THF (3 mL) and water (10 mL) lithium hydroxide monohydrate (12 mg, 0.30 mmol) was added. The mixture was stirred at room temperature for 3 hours. The resulting mixture was adjusted to pH=5-6 with hydrochloric acid (1 M), and then extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: 10 mM $NH_3$ $H_2O$ in water); Mobile Phase B: acetonitrile; Flow rate: 80 mL/min; Gradient: 30% B-50% B in 20 minutes; Detector: 254 nm) to obtain 2-((4-((6-((4-cyano-2-fluorophenoxy)methyl)-5-fluoropyridin-2-yl)oxy)piperidin-1-yl)methyl)-1-((1-(cyanomethyl)cyclopropyl)methyl)-1H-benzo[d]imidazole-6-carboxylic acid (7.02 mg, 33.3% yield). LC-MS m/z: 613 $[M+H]^+$.

$^1$H NMR (400 MHZ, DMSO-$d_6$) δ 8.23 (s, 1H), 7.87 (dd, J=11.2, 1.6 Hz, H), 7.82-7.80 (m, 1H), 7.74-7.63 (m, 3H), 7.51 (t, J=8.4 Hz, 1H), 6.84 (dd, J=8.8, 2.8 Hz, 1H), 5.40 (s, 2H), 4.74-4.72 (m, 1H), 4.59 (s, 2H), 3.83 (s, 2H), 2.78-2.75 (m, 2H), 2.68 (s, 2H), 2.24 (t, J-9.2 Hz, 2H), 1.84 (d, J=10.0 Hz, 2H), 1.60-1.55 (m, 2H), 0.74-0.67 (m, 4H).

Example 21. Synthesis of(S)-2-((4-((6-((4-cyano-2-fluorophenoxy)methyl)-5-fluoropyridin-2-yl)oxy)piperidin-1-yl)methyl)-1-(oxetan-2-ylmethyl)-1H-benzo[d]imidazole-6-carboxylic acid (compound C83)

1). Synthesis of methyl(S)-2-((4-((6-((4-cyano-2-fluorophenoxy)methyl)-5-fluoropyridin-2-yl)oxy)piperidin-1-yl)methyl)-1-(oxetan-2-ylmethyl)-1H-benzo[d]imidazole-6-carboxylate

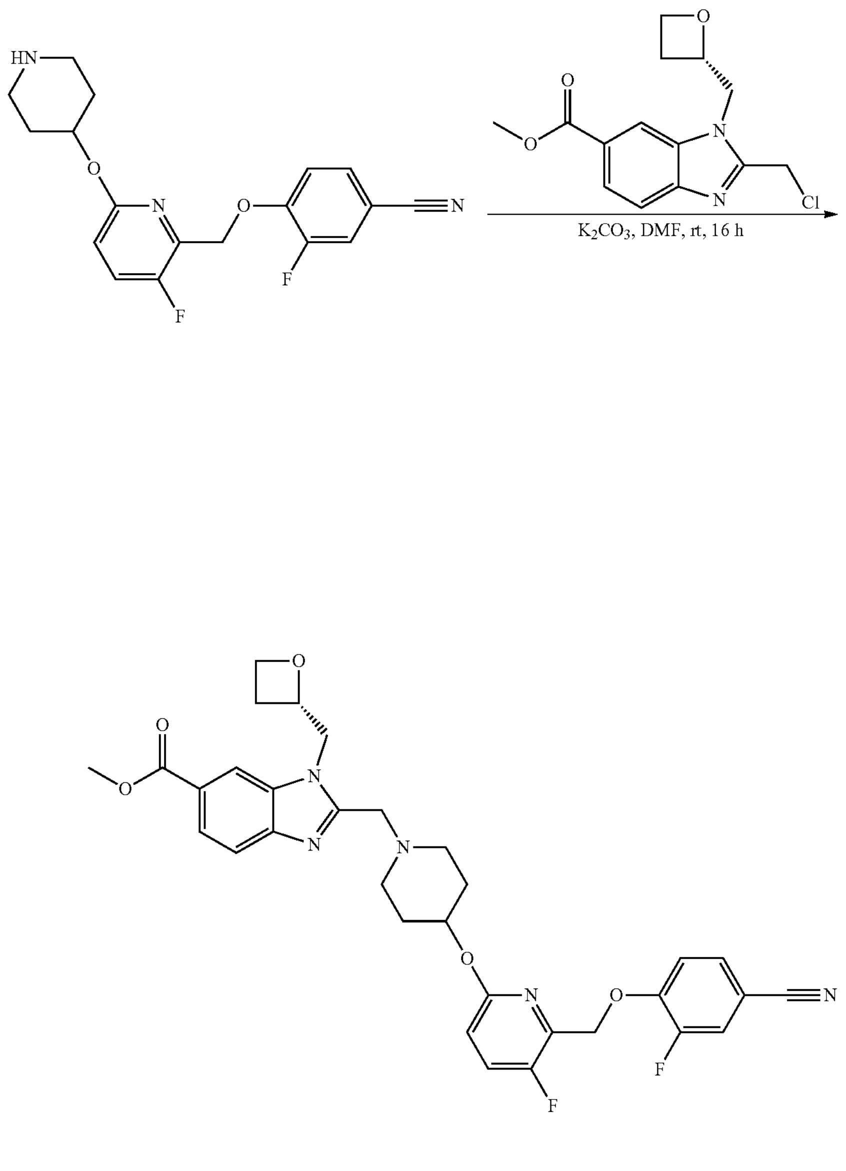

To a mixture of 3-fluoro-4-((3-fluoro-6-(piperidin-4-oxy)pyridin-2-yl)methoxy)benzonitrile (90 mg, 0.26 mmol) and methyl(S)-2-(chloromethyl)-1-(oxetan-2-ylmethyl)-1H-benzo[d]imidazole-6-carboxylate (81 mg, 0.26 mmol) in N,N-dimethylformamide (4 mL) potassium carbonate (108 mg, 0.78 mmol) was added at room temperature. The mixture was stirred at room temperature for 16 hours. The reaction was quenched with water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: 10 mM hexachlorocyclohexane in water; Mobile Phase B: acetonitrile; Flow rate: 80 mL/min; Gradient: 30% B-50% B in 20 minutes; Detector: 254 nm) to obtain methyl(S)-2-((4-((6-((4-cyano-2-fluorophenoxy)methyl)-5-fluoropyridin-2-yl)oxy)piperidine-1-yl)methyl)-1-(oxetan-2-ylmeth-yl)-1H-benzo[d]imidazole-6-carboxylate (85 mg, 53.8% yield). LC-MS m/z: 604 $[M+H]^+$.

2). (S)-2-((4-((6-((4-cyano-2-fluorophenoxy) methyl)-5-fluoropyridin-2-yl)oxy)piperidin-1-yl) methyl)-1-(oxetan-2-ylmethyl)-1H-benzo[d]imidazole-6-carboxylic acid

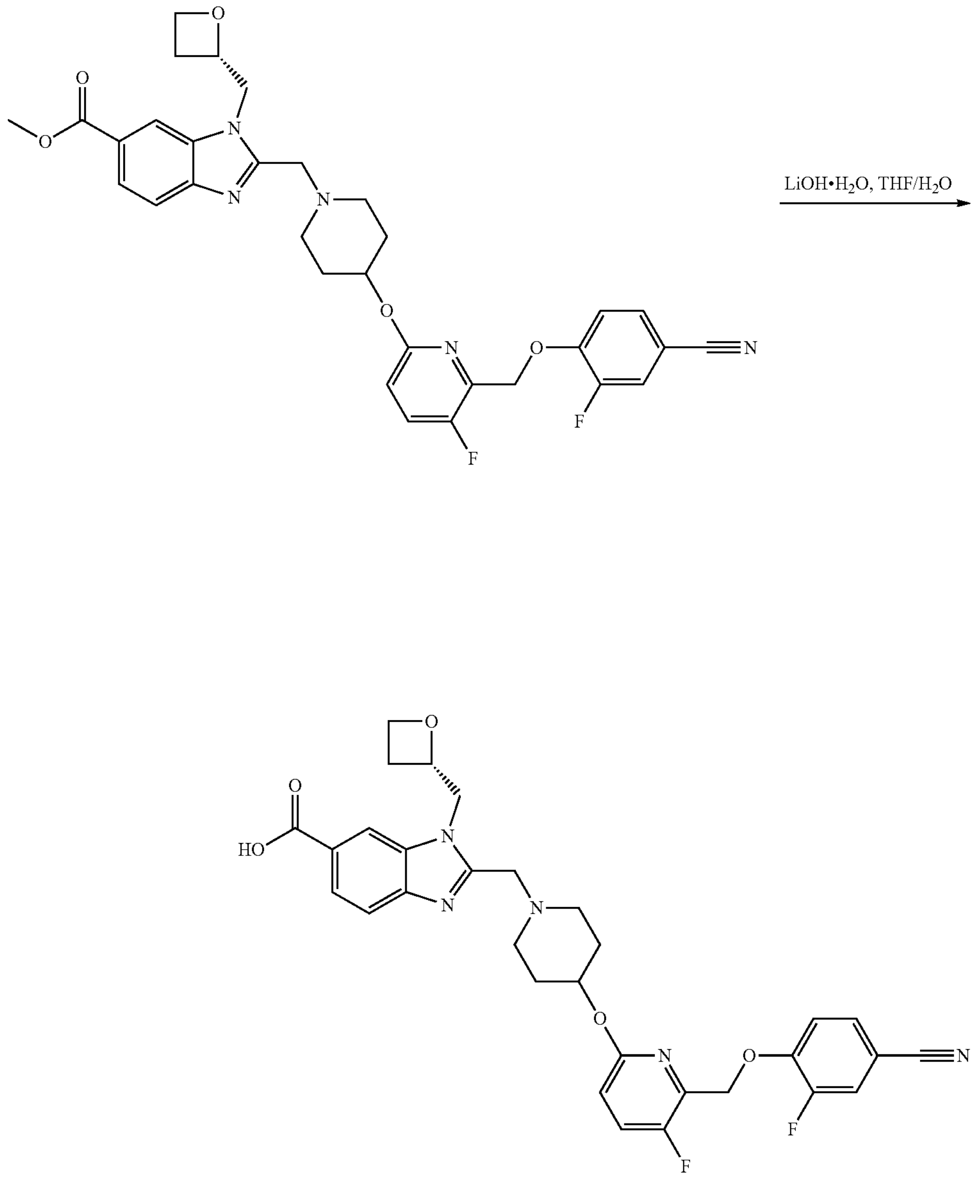

To a mixture of methyl(S)-2-((4-((6-((4-cyano-2-fluorophenoxy)methyl)-5-fluoropyridin-2-yl)oxy)piperidine-1-yl) methyl)-1-(oxetan-2-ylmethyl)-1H-benzo[d]imidazole-6-carboxylate (85 mg, 0.14 mmol) in THF (3 mL) and water (3 mL) lithium hydroxide monohydrate (56 mg, 1.4 mmol) was added. The reaction was stirred at room temperature for 3 hours. The resulting mixture was adjusted to pH=5-6 with hydrochloric acid (1M), and then extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: water 10 mMNH3 $H_2O$ in water; Mobile Phase B: acetonitrile; Flow rate: 80 mL/min; Gradient: 30% B-50% B in 20 minutes; Detector: 254 nm) to obtain(S)-2-((4-((6-((4-cyano-2-fluorophenoxy) methyl)-5-fluoropyridin-2-yl)oxy)piperidin-1-yl)methyl)-1-(oxetan-2-ylmethyl)-1H-benzo[d]imidazole-6-carboxylic acid (50.26 mg, 64.3% yield). LC-MS m/z: 590 $[M+H]^+$.

$^1H$ NMR (400 MHZ, DMSO-$d_6$) δ 8.25 (s, 1H), 7.88 (dd, J=11.2, 1.6 Hz, 1H), 7.79 (dd, J=8.4, 1.6 Hz, 1H), 7.74-7.67 (m, 2H), 7.63 (d, J=8.4 Hz, 1H), 7.50 (t, J=8.8 Hz, 1H), 6.84 (dd, J=8.8, 3.2 Hz, 1H), 5.41 (s, 2H), 5.09-5.07 (m, 1H), 4.80-4.70 (m, 2H), 4.62 (dd, J=16.0, 2.8 Hz, 1H), 4.49 (q, J=7.6, 1H), 4.39-4.34 (m, 1H), 3.92 (d, J=13.6 Hz, 1H), 3.76 (d, J=13.6 Hz, 1H), 2.76-2.66 (m, 3H), 2.45-2.40 (m, 1H), 2.25-2.20 (m, 1H), 1.84-1.81 (m, 2H), 1.57-1.53 (m, 2H).

Example 22. Synthesis of 2-((4-((6-((4-cyano-2-fluorophenoxy)methyl)-5-fluoropyridin-2-yl)oxy)piperidin-1-yl)methyl)-1-((1-ethyl-1H-imidazol-5-yl)methyl)-1H benzo[d]imidazole-6-carboxylic acid (compound 3)

1). methyl 4-(2-(4-((6-((4-cyano-2-fluorophenoxy)methyl)-5-fluoropyridin-2-yl)oxy)piperidin-1-yl)acetamido)-3-(((1-ethyl-1H-imidazol-5-yl)methyl)amino)benzoate

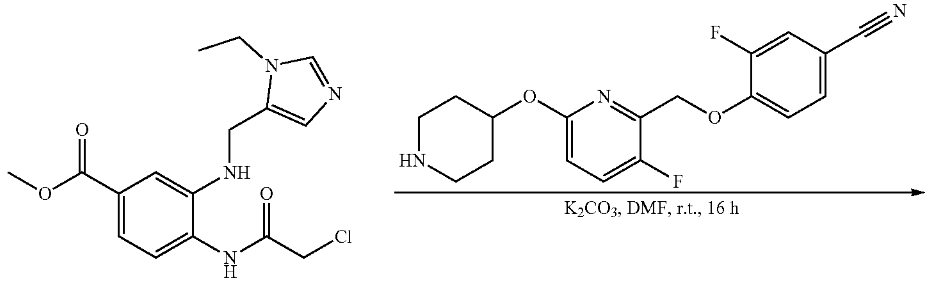

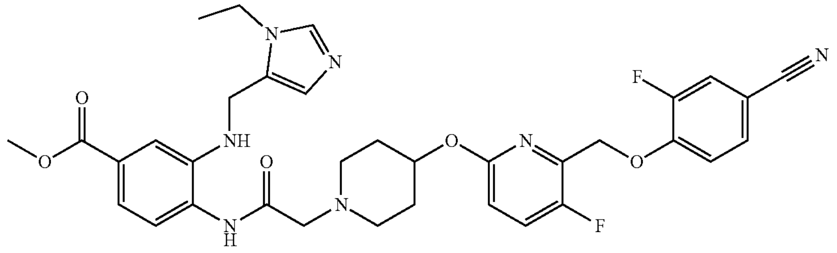

To a mixture of methyl 4-(2-chloroacetamido)-3-((1-ethyl-1H-imidazol-5-yl)methyl)amino)benzoate (130 mg, 0.37 mmol) and 3-fluoro-4-((3-fluoro-6-(piperidin-4-oxy)pyridin-2-yl)methoxy)benzonitrile (128 mg, 0.37 mmol) in N,N-dimethylformamide (4 mL) potassium carbonate (153 mg, 1.11 mmol) was added at room temperature. The mixture was stirred at room temperature for 16 hours, The reaction was quenched with water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to give methyl 4-(2-(4-((6-((4-cyano-2-fluorophenoxy)methyl)-5-fluoropyridin-2-yl)oxy)-piperidin-1-yl)acetamido)-3-((1-ethyl-1H-imidazol-5-yl)methyl)amino)benzoate (116 mg, 48.6% yield). LC-MS m/z: 660 $[M+H]^+$.

2). methyl 2-((4-((6-((4-cyano-2-fluorophenoxy)methyl)-5-fluoropyridin-2-yl)oxy)piperidin-1-yl)methyl)-1-((1-ethyl-1H-imidazol-5-yl)methyl)-1H-benzo[d]imidazole-6-carboxylate

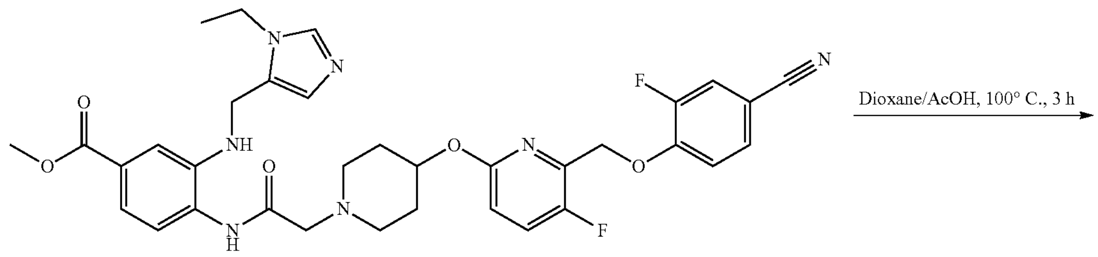

-continued

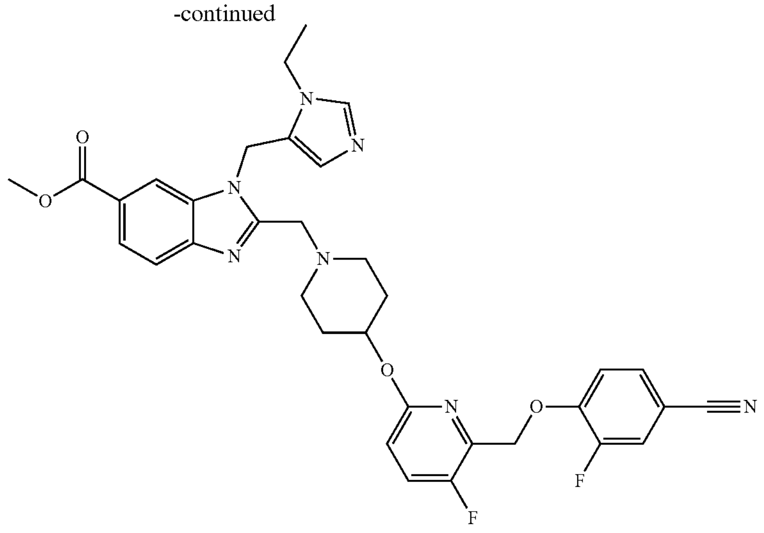

To a solution of methyl 4-(2-(4-((6-((4-cyano-2-fluorophenoxy)methyl)-5-fluoropyridin-2-yl)oxy)piperidin-1-yl)acetamido)-3-((1-ethyl-1H-imidazol-5-yl)methyl)amino)benzoate (116 mg, 0.18 mmol) in dioxane (6 mL) acetic acid (2 mL) was added at room temperature. The mixture was stirred at 100° C. for 3 hours. The reaction was quenched with water (5 mL) and extracted with ethyl acetate (40 mL×3). The combined organic layers were washed with brine (40 mL×2), dried over anhydrous sodium sulfate, filtered, and concentrated to give a residue in vacuo. The residue was purified by silica gel column chromatography (dichloromethane/methanol=10/1) to obtain methyl 2-((6-((4 ((4-cyano-2-fluorophenoxy)methyl)-5-fluoropyridin-2-yl)oxy)piperidin-1-yl)methyl)-1-((1-ethyl-1H-imidazol-5-yl)methyl)-1H-benzo[d]imidazole-6-carboxylate (18 mg, 15.6% yield). LC-MS m/z: 642 $[M+H]^+$.

3). Synthesis of 2-((4-((6-((4-cyano-2-fluorophenoxy)methyl)-5-fluoropyridin-2-yl)oxy)piperidin-1-yl)methyl)-1-((1-ethyl-1H-imidazol-5-yl)methyl)-1H-benzo[d]imidazole-6-carboxylic acid

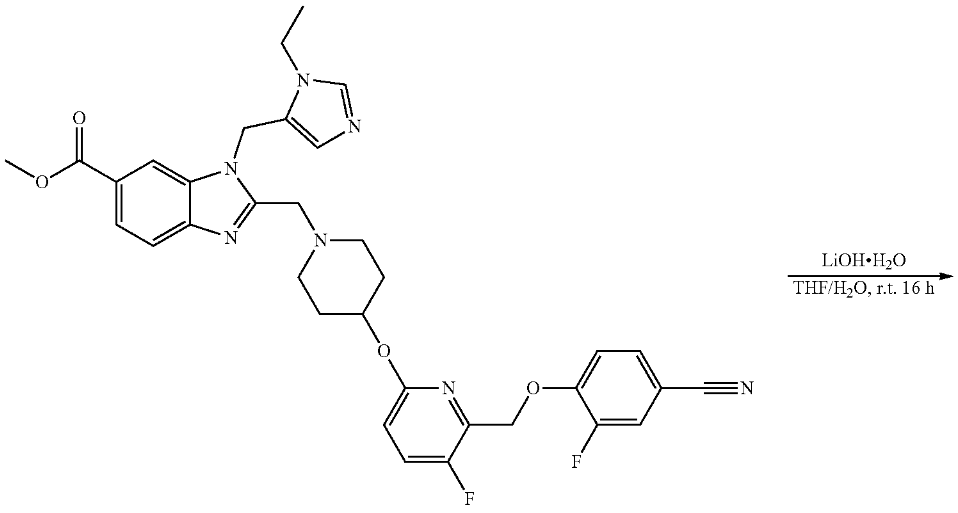

-continued

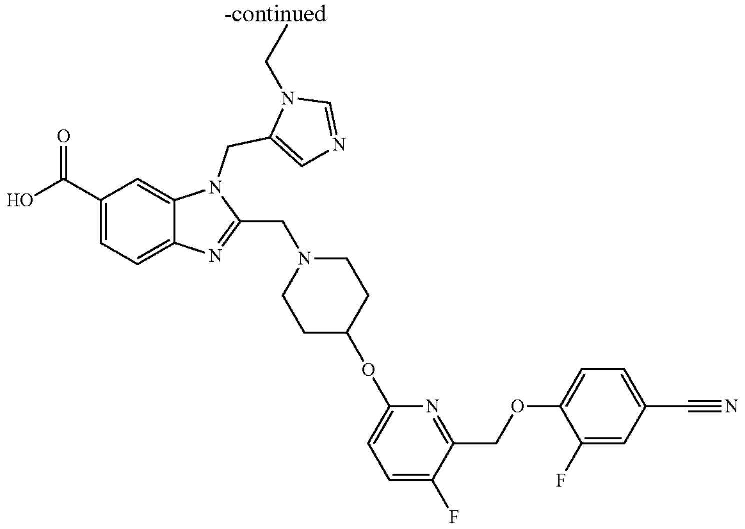

To a mixture of methyl 2-((4-((6-((4-cyano-2-fluorophenoxy)methyl)-5-fluoropyridin-2-yl)oxy)piperidin-1-yl) methyl)-1-((1-ethyl-1H-imidazol-5-yl)methyl)-1H-benzo[d] imidazole-6-carboxylate (18 mg, 0.028 mmol) in THF (3 mL) and water (3 mL) lithium hydroxide monohydrate (11 mg, 0.28 mmol) was added. The mixture was stirred at room temperature for 3 hours. The resulting mixture was adjusted to pH=5-6 with hydrochloric acid 1 (1 M) and then extracted with ethyl acetate (10 mL×3). The combined organic layers were washed with brine (10 mL), dried over anhydrous sodium sulfate, filtered, and concentrated to give a residue in vacuo. The residue was purified by reversed-phase flash chromatography under the following conditions (Column: Spherical C18, 20-40 μm, 120 g; Mobile Phase A: 10 mM $NH_3$ $H_2O$ in water; Mobile Phase B: acetonitrile; Flow rate: 80 mL/min; Gradient: 30% B-50% B in 20 min; Detector: 254 nm) to obtain 2-((4-((6-((4-cyano-2-fluorophenoxy) methyl)-5-fluoropyridin-2-yl)oxy)piperidin-1-yl)methyl)-1-((1-ethyl-1H-imidazol-5-yl)methyl)-1H-benzo[d]imidazol-6-carboxylic acid (5.37 mg, 32% yield). LC-MS m/z: 628 $[M+H]^+$.

$^1H$ NMR (400 MHZ, DMSO-$d_6$) 8.06 (s, 1H), 7.87 (dd, J=11.6, 2.0 Hz, 1H), 7.81 (d, J=8.4 Hz, 1H), 7.73-7.66 (m, 4H), 7.49 (t, J=8.4 Hz, 1H), 6.83 (dd, J=9.2, 2.8 Hz, 1H), 6.40 (s, 1H), 5.70 (s, 2H), 5.40 (s, 2H), 4.67-4.65 (m, 1H), 4.02-3.97 (m, 2H), 3.80 (s, 2H), 2.67-2.63 (m, 2H), 2.19-2.15 (m, 2H), 1.72-1.70 (m, 2H), 1.43-1.34 (m, 2H), 1.16 (t, J=7.2 Hz, 3H).

Example 23. Synthesis of 2-((4-((6-((4-cyano-2-fluorophenoxy)methyl)pyridin-2-yl)oxy)piperidin-1-yl)methyl)-3-((1-(cyanomethyl)cyclopropyl)methyl)-3H-imidazo[4,5-b]pyridine-5-carboxylic acid (compound 138)

1). Synthesis of methyl 5-(2-(4-((6-((4-cyano-2-fluorophenoxy)methyl)pyridin-2-yl)oxy)piperidin-1-yl)acetamido)-6-((1-(cyanomethyl)cyclopropyl) methyl)amino)picolinate

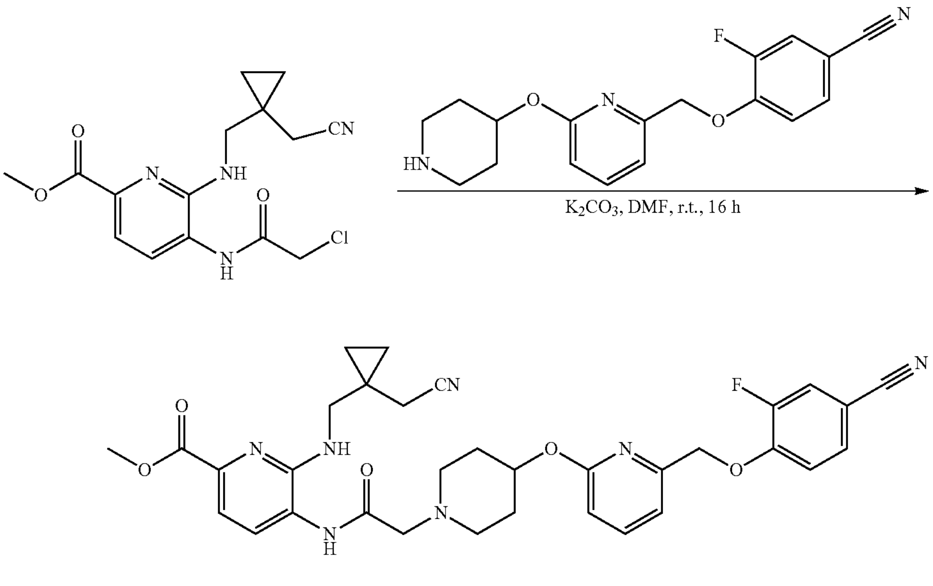

To a mixture of methyl 5-(2-chloroacetamido)-6-(1-(cyanomethyl)cyclopropyl)methyl)amino)picolinate (150 mg, 0.45 mmol) and 3-fluoro-4-((6-(piperidin-4-oxy)pyridin-2-yl)methoxy)benzonitrile (175 mg, 0.54 mmol) in N,N-dimethylformamide (5 mL) potassium carbonate (185 mg, 1.34 mmol) was added. The mixture was stirred at room temperature for 16 hours. The resulting mixture was poured into brine (20 mL) and extracted with ethyl acetate (20 mL×2). The combined organic layers were concentrated to give a residue in vacuo. The residue was purified by silica gel column chromatography (dichloromethane/methanol=20/1) to obtain methyl 5-(2-(4-((6-((4-cyano-2-fluorophenoxy)methyl)pyridin-2-yl)oxy)piperidin-1-yl)acetamido)-6-((1-(cyanomethyl)cyclopropyl)methyl)amino)picolinate: (220 mg, 78.6% yield). LC-MS m/z: 628 [M+H]+.

2). Synthesis of methyl 2-((4-((6-((4-cyano-2-fluorophenoxy)methyl)pyridin-2-yl)oxy)piperidin-1-yl)methyl)-3-((1-(cyanomethyl)cyclopropyl)methyl)-3H-imidazo[4,5-b]pyridine-5-carboxylate

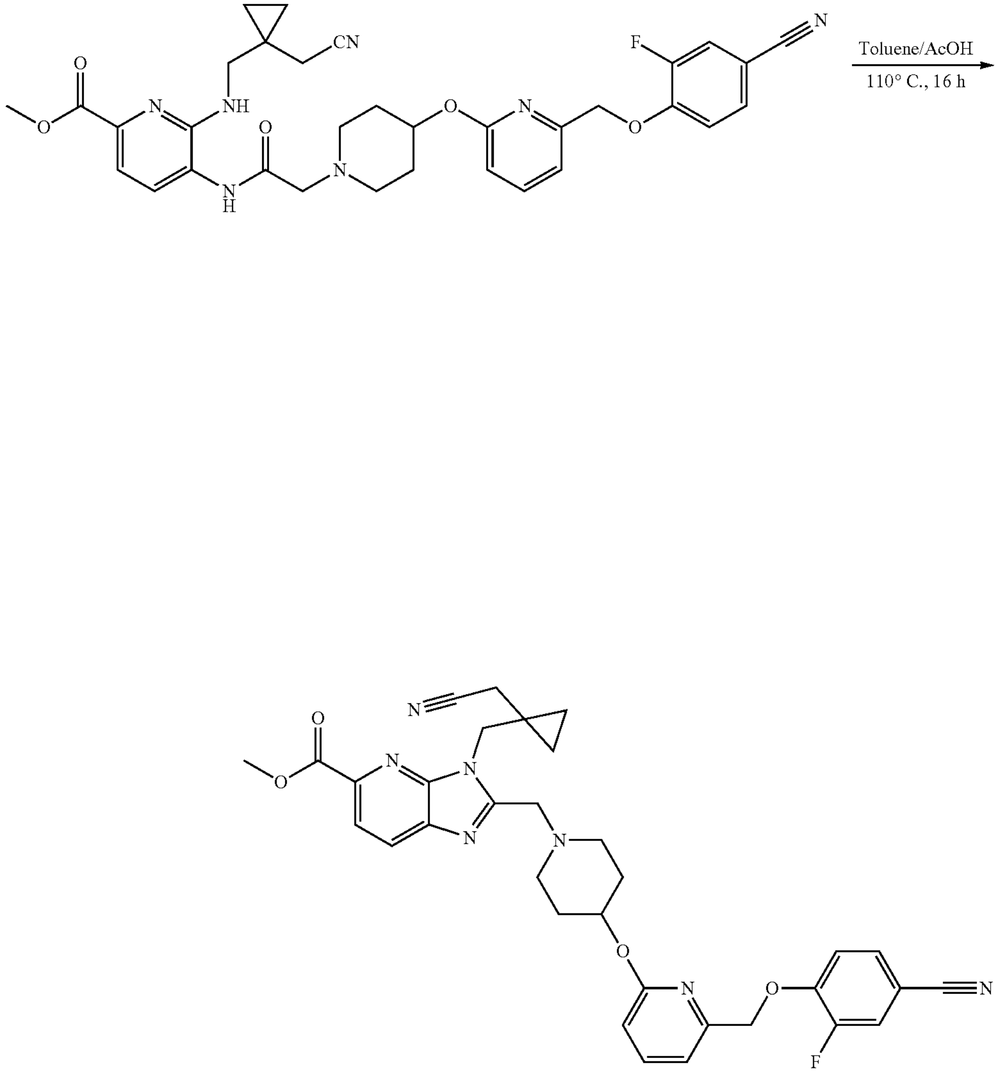

The mixture of methyl 5-(2-(4-((4-cyano-2-fluorophenoxy)methyl)pyridin-2-yl)oxy)piperidin-1-yl)acetamido)-6-((1-(cyanomethyl)cyclopropyl)methyl)amino)picolinate (220 mg, 0.35 mmol) in toluene (10 mL) and acetic acid (10 mL) was stirred at 110° C. for 16 h under nitrogen atmosphere. After completion, the resulting mixture was filtered, and concentrated to give a residue in vacuo. The residue was purified by silica gel column chromatography (dichloromethane/methanol=40/1) to obtain methyl 2-((4-((6-((4-cyano-2-fluorophenoxy)-methyl)pyridin-2-yl)oxy)-piperidin-1-yl)methyl)-3-((1-(cyanomethyl)cyclopropyl)methyl)-3H-imidazo[4,5-b]pyridine-5-carboxylate (200 mg, 93.5% yield). LC-MS m/z: 610 [M+H]+.

3). Synthesis of 2-((4-((6-((4-cyano-2-fluorophenoxy)methyl)pyridin-2-yl)oxy)piperidin-1-yl)methyl)-3-((1-(cyanomethyl)cyclopropyl)methyl)-3H-imidazo[4,5-b]pyridine-5-carboxylic acid

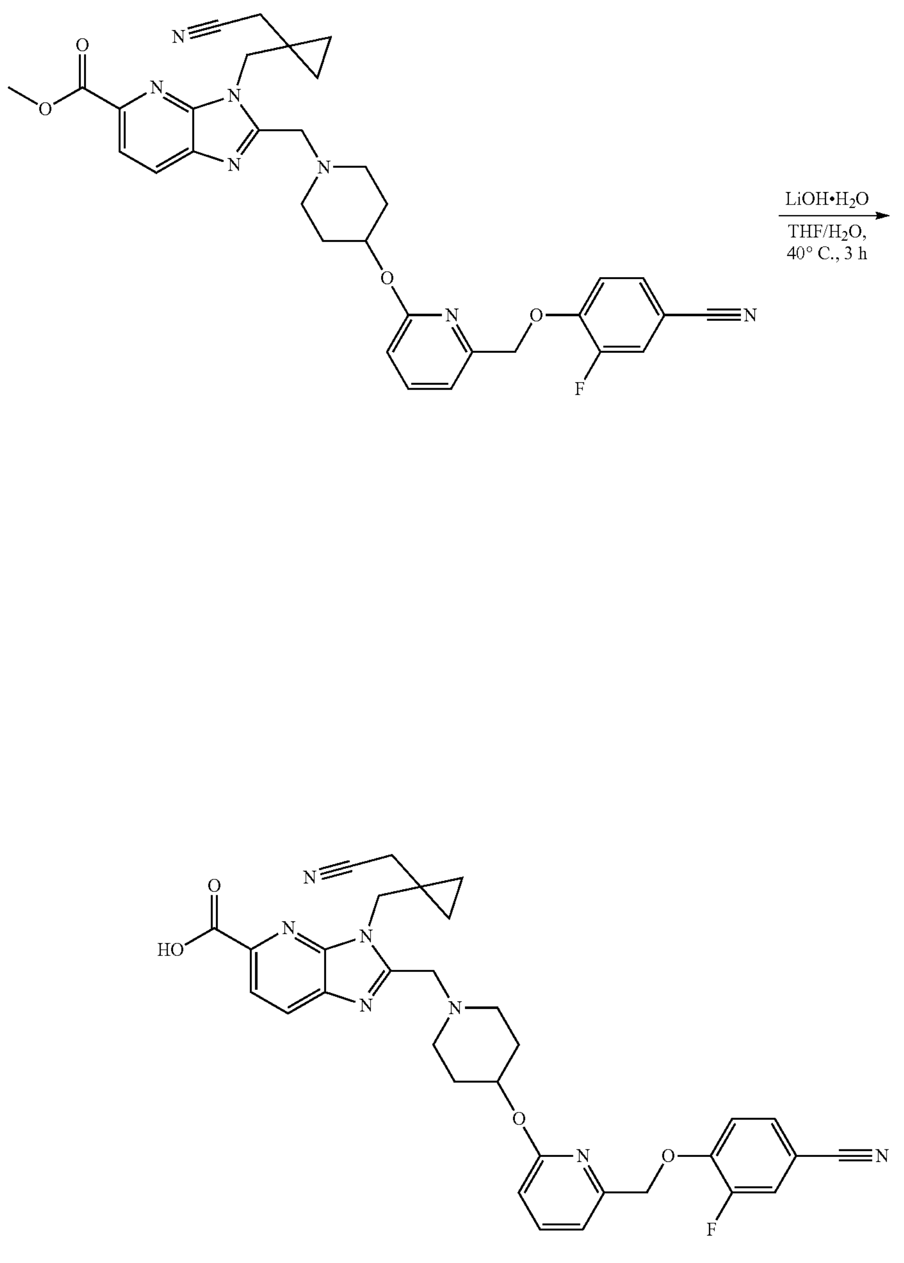

To a mixture of methyl 2-((4-((6-((4-cyano-2-fluorophenoxy)-methyl)pyridin-2-yl)oxy)-piperidin-1-yl)methyl)-3-((1-(cyanomethyl)cyclopropyl)methyl)-3H-imidazo[4,5-b]pyridine-5-carboxylate (100 mg, 0.16 mmol) in THF (5 mL) and water (5 mL) lithium hydroxide monohydrate (69 mg, 1.60 mmol) was added. The mixture was stirred at 40° C. for 3 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.05% $NH_4OH$ in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidine-1-yl)methyl)-3-((1-(cyanomethyl)cyclopropyl)methyl)-3H-imidazo[4,5-b]pyridine-5-carboxylic acid (48.10 mg, 49.2% yield). LC-MS m/z: 596 $[M+H]^+$. $^1H$ NMR (400 MHZ, DMSO-$d_6$) δ 8.03 (d, J=8.4 Hz, 1H), 7.94-7.86 (m, 2H), 7.73 (t, J=8.0 Hz, 1H), 7.66 (d, J-8.8 Hz, 1H), 7.45 (t, J-8.8 Hz, 1H), 7.05 (d, J=7.2 Hz, 1H), 6.73 (d, J=8.4 Hz, 1H), 5.31 (s, 2H), 4.94-4.90 (m, 1H), 4.52 (s, 2H), 3.86 (s, 2H), 2.83-2.76 (m, 4H), 2.33-2.29 (m, 2H), 1.93-1.91 (m, 2H), 1.66-1.59 (m, 2H), 1.05 (s, 2H), 0.62-0.61 (m, 2H).

Example 24. Synthesis of(S)-2-((4-((6-((4-cyano-2-fluorophenoxy)methyl)pyridin-2-yl)oxy)piperidin-1-yl)methyl)-3-(oxetan-2-ylmethyl)-3H-imidazo[4,5-b]pyridine-5-carboxylic acid (compound 60)

1). Synthesis of methyl(S)-2-((4-((6-((4-cyano-2-fluorophenoxy)methyl)pyridin-2-yl)oxy)piperidin-1-yl)methyl)-3-(oxetan-2-ylmethyl)-3H-imidazo[4,5-b]pyridine-5-carboxylate

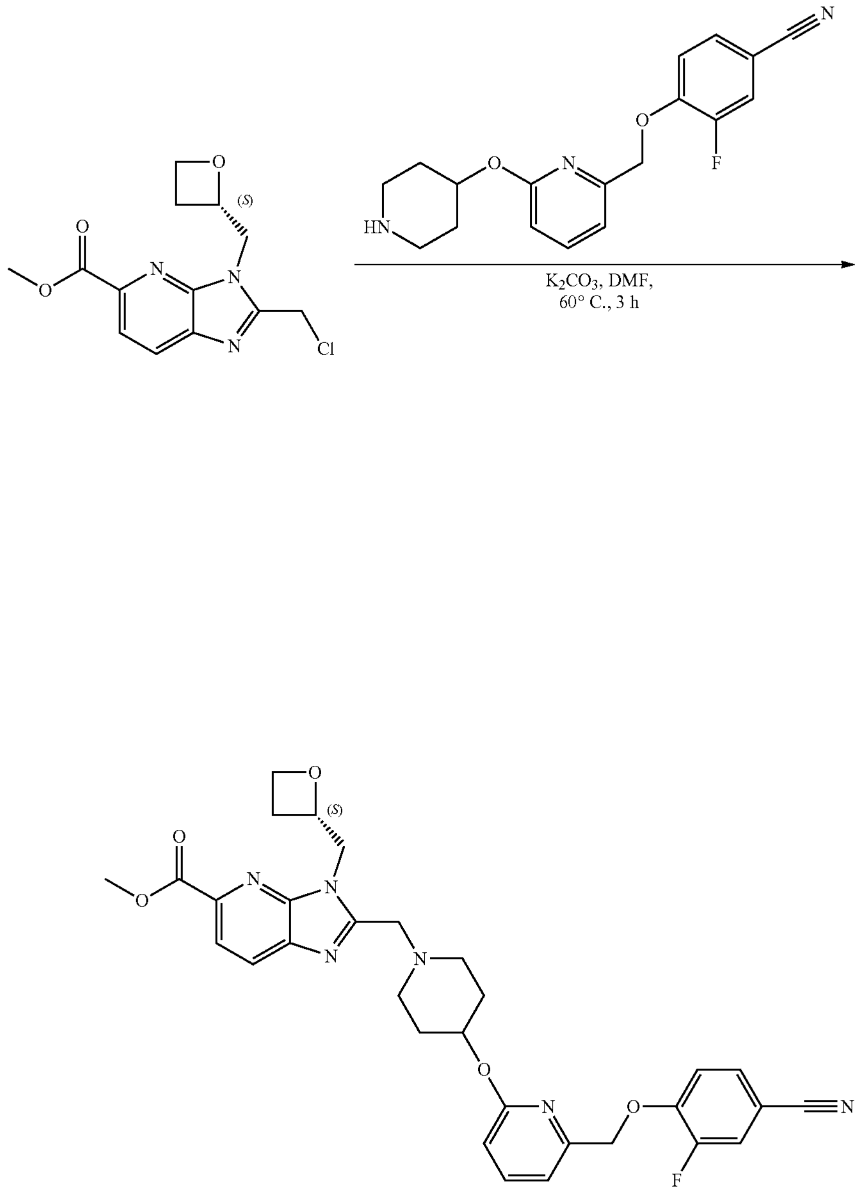

To a mixture of methyl(S)-2-(chloromethyl)-3-(oxetan-2-ylmethyl)-3H-imidazo[4,5-b]pyridine-5-carboxylate (180 mg, 0.61 mmol) and potassium carbonate (248 mg, 1.83 mmol) in N,N-dimethylformamide (5 mL) 3-fluoro-4-((6-(piperidine-4-oxy)pyridin-2-yl)methoxy)benzonitrile (216 mg, 0.67 mmol) was added. The mixture was stirred at 60° C. for 3 hours under nitrogen atmosphere. After completion, the mixture was poured into water (10 mL) and extracted with ethyl acetate (10 mL×2). The combined organic layers were washed with saturated brine (10 mL×2), dried over anhydrous sodium sulfate, filtered, and concentrated to give a residue in vacuo. The residue was purified by silica gel column chromatography (dichloromethane/methanol=10/1) to obtain methyl(S)-2-((4-((6-((4-cyano-2-fluorophenoxy)-methyl)pyridin-2-yl)oxy)piperidin-1-yl)methyl)-3-(oxetan-2-ylmethyl)-3H-imidazo[4,5-b]pyridine-5-carboxylate (190 mg, 48.7% yield). LCMS m/z: 587 $[M+H]^+$.

2). Synthesis of(S)-2-((4-((6-((4-cyano-2-fluorophenoxy)methyl)pyridin-2-yl)oxy)piperidin-1-yl)methyl)-3-(oxetan-2-ylmethyl)-3H-imidazo[4,5-b]pyridine-5-carboxylic acid

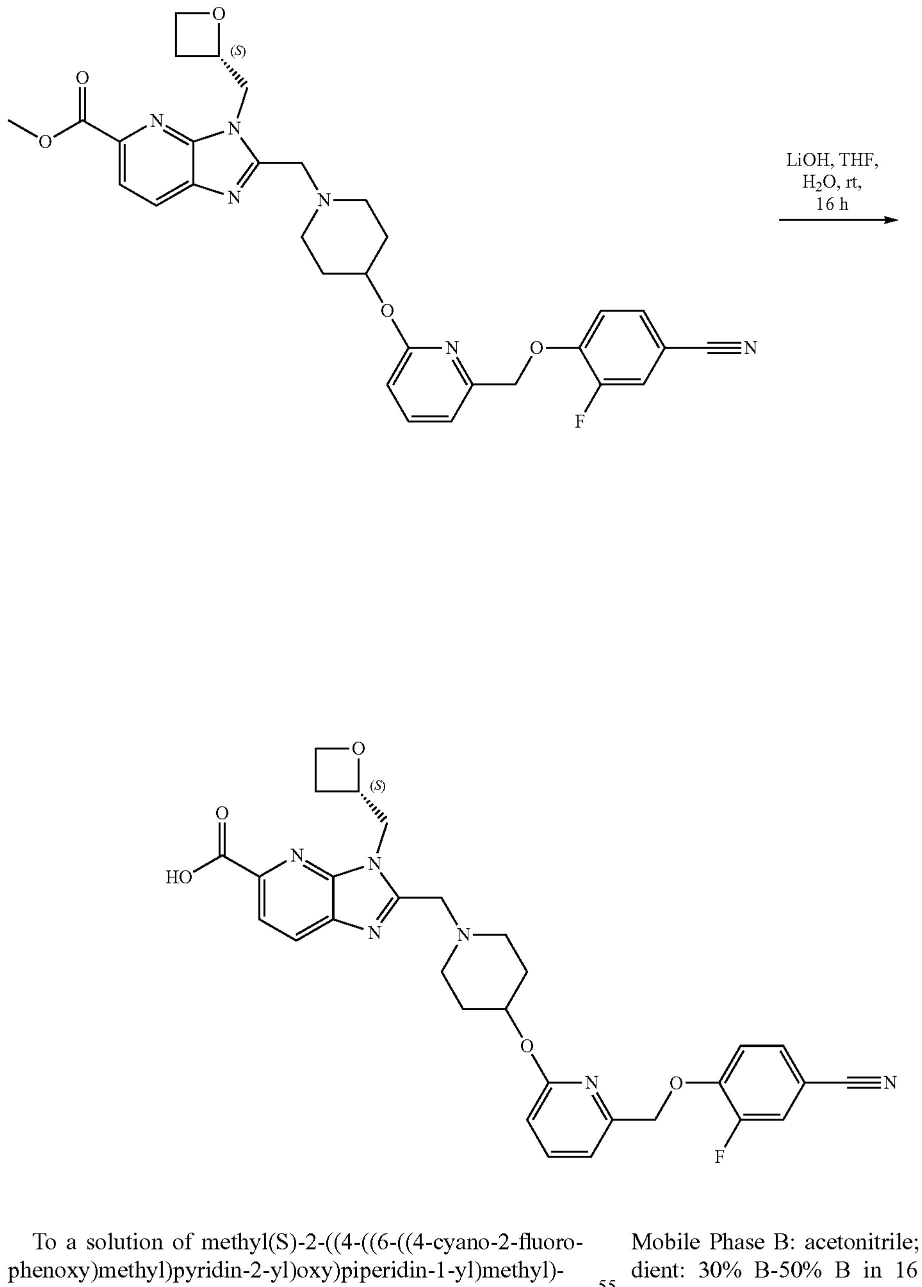

To a solution of methyl(S)-2-((4-((6-((4-cyano-2-fluorophenoxy)methyl)pyridin-2-yl)oxy)piperidin-1-yl)methyl)-3-(oxetan-2-ylmethyl)-3H-imidazo[4,5-b]pyridine-5-carboxylate (90 mg, 0.15 mmol) in THF (3 mL) and water (3 mL) with lithium hydroxide (36 mg, 1.50 mmol) was added. The reaction was stirred at 25° C. for 16 hours. The resulting mixture was adjusted to pH=5-6 with formic acid, and then extracted with ethyl acetate (10 mL×2). The combined organic layers were washed with saturated brine (5 mL×2), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: Water 10 mM formic acid in Water); Mobile Phase B: acetonitrile; Flow rate: 80 mL/min; Gradient: 30% B-50% B in 16 min; Detector: 254 nm) to obtain(S)-2-((4-((6-((4-cyano-2-fluorophenoxy)methyl)yl)pyridin-2-yl)oxy)piperidin-1-yl)methyl)-3-(oxetan-2-ylmethyl)-3H-imidazo[4,5-b]pyridine-5-carboxylic acid (10.82 mg, 13.8% yield). LC-MS m/z: 573 $[M+H]^+$.

$^1$HNMR (400 MHZ, DMSO-$d_6$) δ 8.12 (d, J=8.4 Hz, 1H), 7.98 (d, J=8.4 Hz, 1H), 7.88 (dd, J=11.6 Hz, 2.0 Hz, 1H), 7.73 (t, J=8.0 Hz, 1H), 7.66 (d, J=8.8 Hz, 1H), 7.45 (t, J=8.4 Hz, 1H), 7.05 (d, J=7.6 Hz, 1H), 6.74 (d, J=8.4 Hz, 1H), 5.31 (s, 2H), 5.18-5.15 (m, 1H), 4.94-4.81 (m, 2H), 4.74-4.69 (m, 1H), 4.52-4.47 (m, 1H), 4.38-4.33 (m, 1H), 4.00-3.90 (m, 2H), 2.76-2.67 (m, 4 H), 2.35-2.31 (m, 2H), 1.93-1.91 (m, 2H), 1.66-1.62 (m, 2H).

Example 25. Synthesis of 2-((4-((6-((4-cyano-2-fluorophenoxy)methyl)pyridin-2-yl)oxy)piperidin-1-yl)methyl)-3-((1-ethyl-1H-imidazol-5-yl)methyl)-3H-imidazo[4,5-b]pyridine-5-carboxylic acid (compound 6)

1). Synthesis of methyl 5-(2-(4-((6-((4-cyano-2-fluorophenoxy)methyl)pyridin-2-yl)oxy)piperidin-1-yl)acetamido)-6-(((1-ethyl-1H-imidazol-5-yl)methyl)amino)picolinate

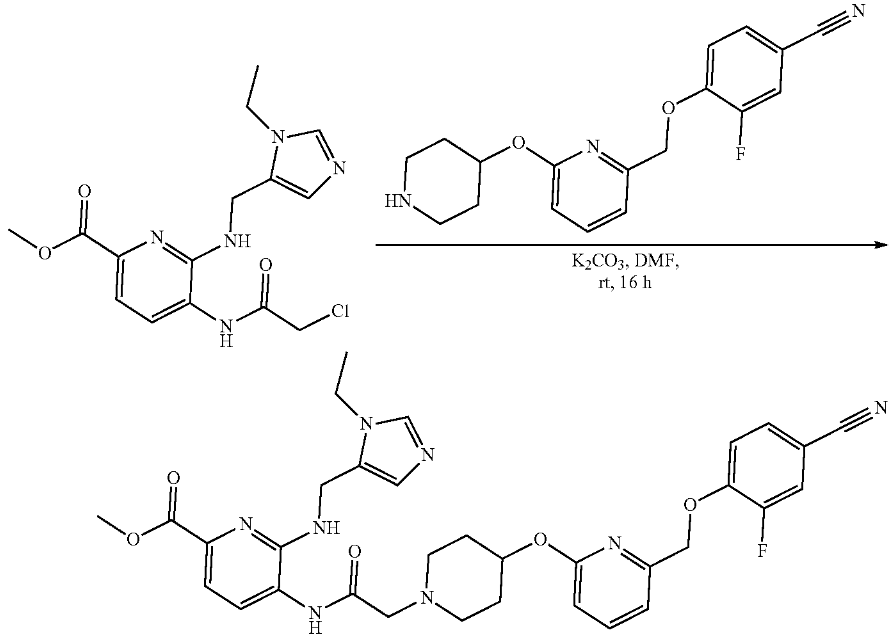

To a mixture of methyl 5-(2-chloroacetamido)-6-(((1-ethyl-1H-imidazol-5-yl)methyl)amino)picolinate (180 mg, 0.51 mmol) and 3-fluoro-4-((6-(piperidin-4-oxy)pyridin-2-yl)methoxy)benzonitrile (167 mg, 0.51 mmol) in N,N-dimethylformamide (10 mL) potassium carbonate (211 mg, 1.53 mmol) was added at room temperature. The mixture was stirred at 25° C. for 16 hours. The reaction mixture was quenched with $H_2O$ (5 mL) and extracted with ethyl acetate (20 mL×3). The combined organic layers were washed with saturated brine (20 mL×2), dried over anhydrous sodium sulfate, filtered, and concentrated to give residue in vacuo. The residue was purified by silica gel column chromatography (dichloromethane/methanol=10/1) to obtain methyl 5-(2-(4-((6-((4-cyano-2-fluorophenoxy)methyl)pyridin-2-yl)oxy)piperidin-1-yl)acetamido)-6-(((1-ethyl-1H-imidazol-5-yl)methyl)amino)picolinate (230 mg, 71.6% yield). LC-MS m/z: 643 $[M+H]^+$.

2). methyl 2-((4-((6-((4-cyano-2-fluorophenoxy)methyl)pyridin-2-yl)oxy)piperidin-1-yl)methyl)-3-((1-ethyl-1H-imidazol-5-yl)methyl)-3H-imidazo[4,5-b]pyridine-5-carboxylate

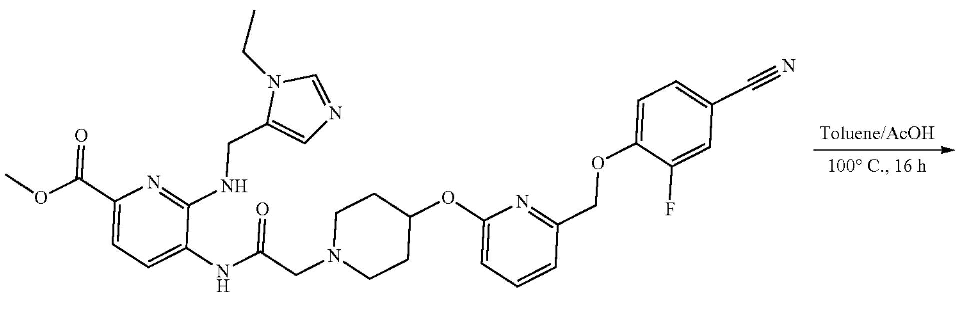

-continued

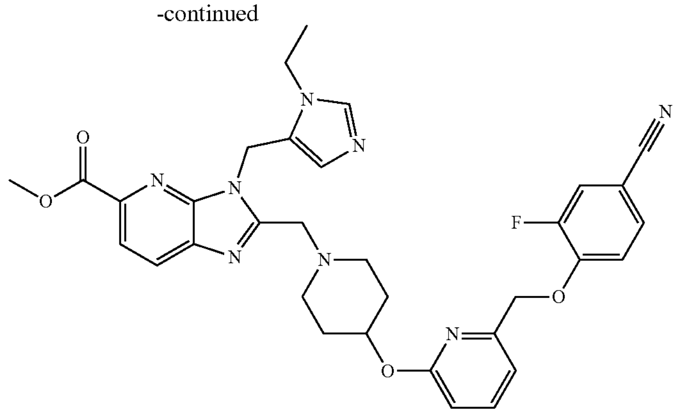

The mixture of methyl 5-(2-(4-((6-((4-cyano-2-fluorophenoxy)methyl)pyridin-2-yl)oxy)piperidin-1-yl)acetamido)-6-(((1-ethyl-1H-imidazol-5-yl)methyl)amino)picolinate (230 mg, 0.36 mmol) in toluene (3 mL) and acetic acid (0.5 mL) was stirred at 100° C. for 16 hours. The resulting mixture was poured into saturated brine (10 mL) and extracted with dichloromethane (5 mL×2). The combined organic layer was concentrated to give methyl 2-((4-((6-((4-cyano-2-fluorophenoxy)methyl)pyridin-2-yl)oxy)piperidin-1-yl)methyl)-3-((1-ethyl-1H-imidazol-5-yl)methyl)-3H-imidazo[4,5-b]pyridine-5-carboxylate (180 mg, 81% yield). LC-MS m/z: 625 $[M+H]^+$.

3). Synthesis of 2-((4-((6-((4-cyano-2-fluorophenoxy)methyl)pyridin-2-yl)oxy)piperidin-1-yl)methyl)-3-((1-ethyl-1h-imidazol-5-yl)methyl)-3H imidazole [4,5-b]pyridin-5-carboxylic acid

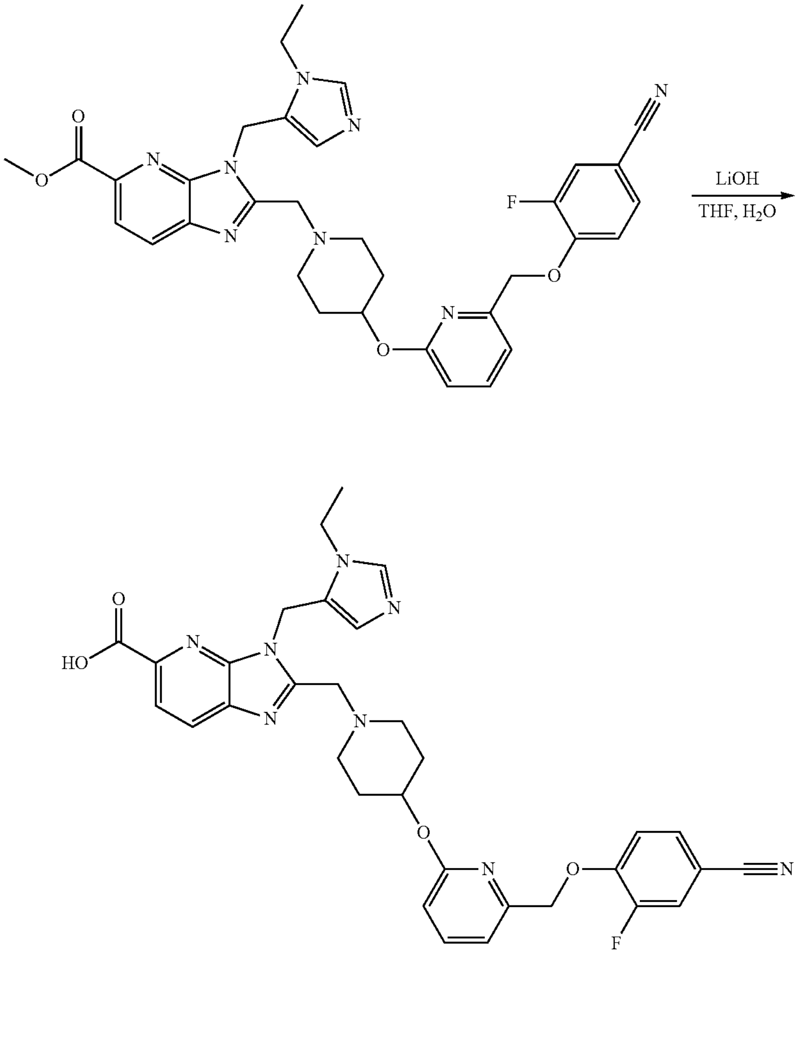

To a mixture of methyl 2-((4-((6-((4-cyano-2-fluorophenoxy)methyl)pyridin-2-yl)oxy)piperidin-1-yl)methyl)-3-((1-ethyl-1h-imidazol-5-yl)methyl)-3H imidazole [4,5-b] pyridine-5-carboxylate (130 mg, 0.20 mmol) in THF (3 mL) and water (3 mL) lithium hydroxide (32 mg, 2.0 mmol) was added. The mixture was stirred at room temperature for 16 hours. The resulting mixture was adjusted to pH 5-6 with hydrochloric acid (1 M) and extracted with ethyl acetate (10 ml×3) The combined organic layers were washed with saturated brine (10 ml), dried over anhydrous sodium sulfate, filtered, and concentrated to give a residue in vacuo. The residue was purified by reversed-phase flash chromatography (Column: sphere C18, 20-40 μm, 120 g; Mobile phase A: 10 mm $NH_3$ $H_2O$ in water; Mobile phase B: acetonitrile; Flow rate: 80 ml/min; Gradient: 30% B-50% B in 20 min; Detector: 254 nm) to obtain 2-((4-((6-((4-cyano-2-fluorophenoxy)methyl)pyridin-2-yl)oxy)piperidin-1-yl) methyl)-3-((1-ethyl-1h-imidazol-5-yl)methyl)-3H-imidazole [4,5-b]pyridine-5-carboxylic acid (30.28 mg, 24.5% yield). LC-MS m/z: 611 $[M+H]^+$.

$^1$HNMR (400 MHZ, DMSO-$d_6$) δ 8.16-8.13 (m, 1H), 8.02-7.99 (m, 1H), 7.88 (d, J=11.6 Hz, 1H), 7.74-7.70 (m, 1H), 7.67-7.65 (m, 2H), 7.46-7.42 (m, 1H), 7.05 (d, J=7.6 Hz, 1H), 6.74-6.71 (m, 2H), 5.72 (s, 2H), 5.30 (s 2H), 4.90-4.87 (m, 1H), 4.17-4.12 (m, 2H), 3.80 (s, 2H), 2.73-2.67 (m, 2H), 2.28-2.24 (m, 2H), 1.87-1.84 (m, 2H), 1.57-1.55 (m, 2H), 1.12-1.08 (m, 3H).

Example 26. Synthesis of 2-((4-((6-((4-chloro-2-fluorophenylthio)methyl)pyridin-2-yl)oxy)piperidin-1-yl)methyl)-1-((1-(cyanomethyl)cyclopropyl) methyl)-1H-benzo[d]imidazole-6-carboxylic acid (compound C7)

1). Synthesis of methyl 4-(2-(4-((6-((4-chloro-2-fluorophenylthio)methyl)pyridin-2-yl)oxy)piperidin-1-yl)acetamido)-3-((1-(cyanomethyl)cyclopropyl) methyl)amino)benzoate

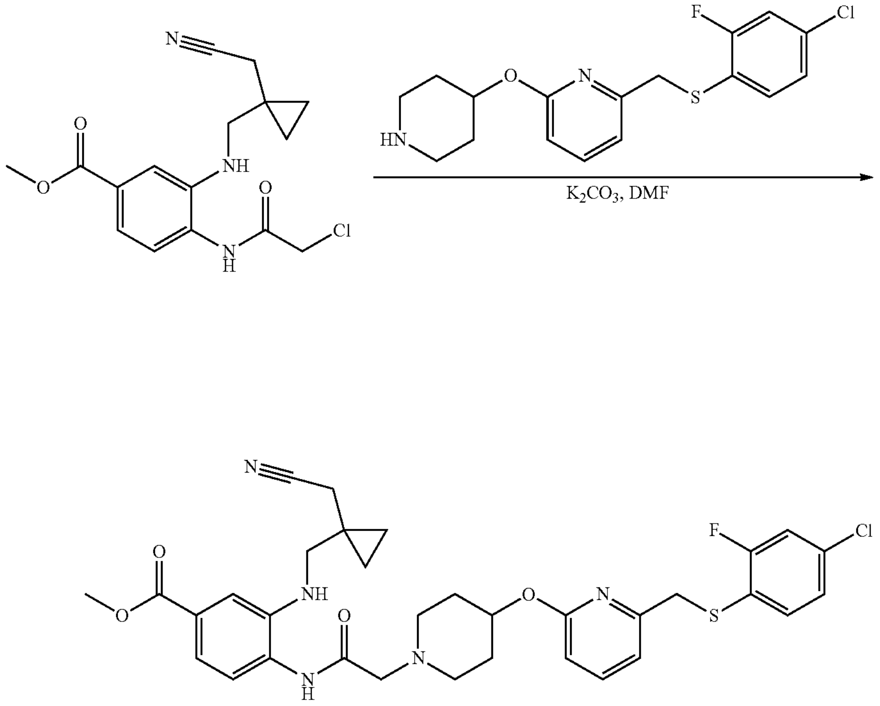

To a mixture of methyl 4-(2-chloroacetamido)-3-((1-(cyanomethyl)cyclopropyl)methyl)amino)benzoate (200 mg, 0.60 mmol) and 2-((4-chloro-2-fluorophenylthio)methyl)-6-(piperidin-4-oxy)pyridine (210 mg, 0.60 mmol) in N,N-dimethylformamide (4 mL) potassium carbonate (247 mg, 1.80 mmol) was added. The reaction was stirred at room temperature for 16 hours. After completion, the resulting mixture was poured into brine (10 mL) and extracted with ethyl acetate (2×5 mL). The combined organic layer was concentrated to give residue in vacuo. The residue was purified by silica gel column chromatography (dichloromethane/methanol=20/1) to obtain methyl 4-(2-(4-((6-((4-chloro-2-fluorophenylthio)methyl)pyridin-2-yl)oxy)piperidin-1-yl)acetamido)-3-((1-(cyanomethyl)cyclopropyl) methyl)amino)benzoate (300 mg, 77.3% yield). LC-MS m/z: 652 $[M+H]^+$.

2). Synthesis of methyl 2-((4-((6-((4-chloro-2-fluorophenylthio)methyl)pyridin-2-yl)oxy)piperidin-1-yl)methyl)-1-((1-(cyanomethyl)cyclopropyl)methyl)-1H-benzo[d]imidazole-6-carboxylate

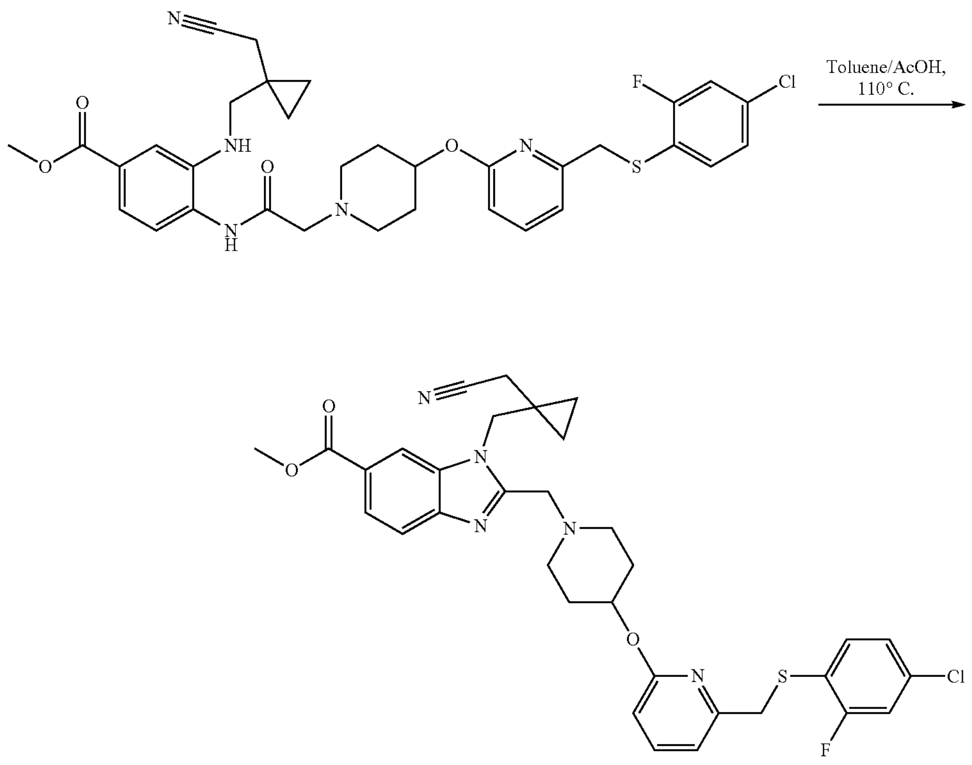

The mixture of methyl 4-(2-(4-((6-((4-chloro-2-fluorophenylthio)methyl)pyridin-2-yl)oxy)piperidin-1-yl)acetamido)-3-((1-(cyanomethyl)cyclopropyl)methyl)amino) benzoate (300 mg, 0.46 mmol) in toluene (10 mL) and acetic acid (4 mL) was stirred at 110° C. for 16 hours under nitrogen atmosphere. After completion, the mixture was concentrated to give a residue in vacuo. The residue was purified by silica gel column chromatography (dichloromethane/methanol=10/1) to obtain methyl 2-((4-((6-((4-chloro-2-fluorophenylthio)methyl)-pyridin-2-yl)oxy)piperidin-1-yl)methyl)-1-((1-(cyanomethyl)cyclopropyl)methyl)-1H-benzo[d]imidazole-6-carboxylate (210 mg, 80.0% yield). LC-MS m/z: 634 [M+H]+.

3). Synthesis of 2-((4-((6-((4-Chloro-2-fluorophenylthio)methyl)pyridin-2-yl)oxy)piperidin-1-yl) methyl)-1-((1-(cyanomethyl)cyclopropyl)methyl)-1H-benzo[d]imidazole-6-carboxylic acid

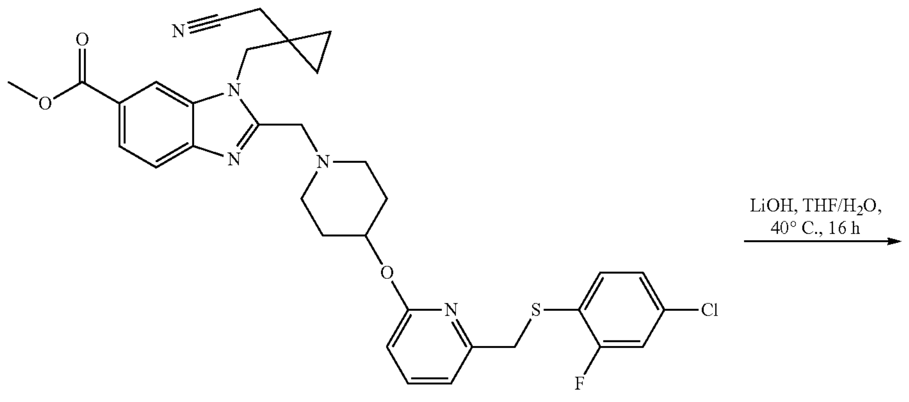

-continued

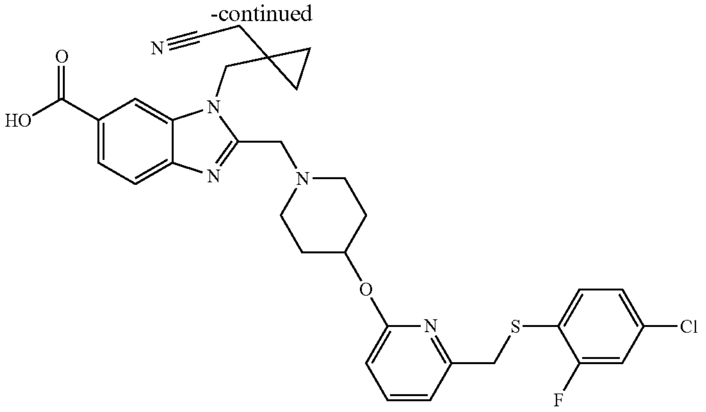

To a mixture of methyl 2-((4-((6-((4-chloro-2-fluorophenylthio)methyl)pyridin-2-yl)oxy)piperidin-1-yl)methyl)-1-((1-(cyanomethyl)cyclopropyl)methyl)-1H-benzo[d]imidazole-6-carboxylate (210 mg, 0.33 mmol) in THF (1 mL) and water (1 mL) lithium hydroxide (79 mg, 3.30 mmol) was added. The mixture was stirred at 40° C. for 16 hours. The solvent was removed by concentration in vacuo. The residue was purified by prep-HPLC (Waters 2767/2545/2489 system; Column: SunFire Prep C8 OBD 10 um 19×250 mm; Gradient elution with ACN/0.05% $NH_4OH$ in $H_2O$ solvent system; Detection Wavelength: 254 nm/214 nm; Flow rate: 2-((4-((6-((4-chloro-2-fluorophenylthio)methyl)pyridin-2-yl)oxy)piperidine-1-20 mL/min) to obtain yl)methyl)-1-((1-(cyanomethyl)cyclopropyl)methyl)-1H-benzo-[d]imidazole-6-carboxylic acid (19.36 mg, 9.4% yield). LC-MS m/z: 620 $[M+H]^+$.

$^1H$ NMR (400 MHZ, DMSO-$d_6$) δ 8.23 (s, 1H), 7.81 (d, J=8.8 Hz, 1H), 7.65-7.61 (m, 3H), 7.29-7.21 (m, 2H), 6.98 (d, J=7.2 Hz 1 H), 6.63 (d, J-8.4 Hz, 1H), 4.87-4.85 (m, 1H), 4.59 (s, 2H), 4.30 (s, 2H), 3.83 (s, 2H), 2.78-2.75 (m, 2H), 2.68 (d, J=6.8 Hz, 2H), 2.32-2.28 (m, 2H), 1.90-1.88 (m, 2H), 1.60-1.57 (m, 2H), 0.74-0.67 (m, 4H).

Example 27. Synthesis of 2-((4-((6-((4-cyano-2-fluorophenoxy)methyl)pyridin-2-yl)oxy)piperidin-1-yl)methyl)-1-((1-(cyanomethyl)cyclopropyl)methyl)-1H-benzo[d]imidazole-6-carboxylic acid (compound 133)

1). Synthesis of methyl 4-(2-(4-((6-((4-cyano-2-fluorophenoxy)methyl)pyridin-2-yl)oxy)piperidin-1-yl)acetamido)-3-((1-(cyanomethyl)cyclopropyl)methyl)amino)benzoate

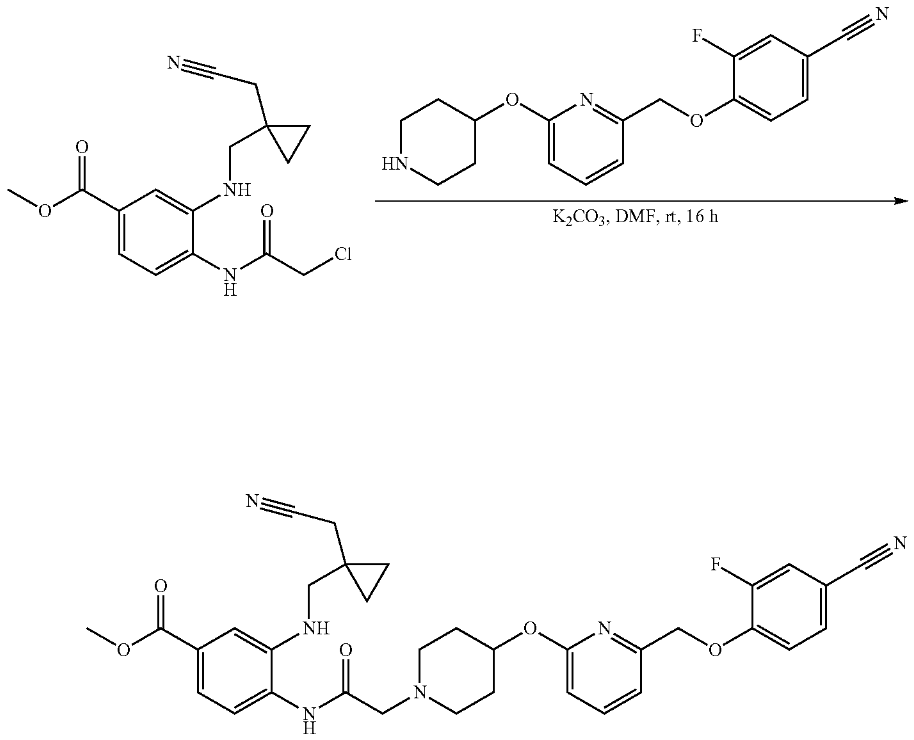

To a mixture of methyl 4-(2-chloroacetamido)-3-((1-(cyanomethyl)cyclopropyl)methyl)amino)benzoate (160 mg, 0.48 mmol) and 3-fluoro-4-((6-(Piperidin-4-oxy)pyridin-2-yl)methoxy)benzonitrile (187 mg, 0.57 mmol) in N,N-dimethylformamide (10 mL) potassium carbonate (197 mg, 1.43 mmol) was added. The reaction mixture was stirred at room temperature for 16 hours. The mixture was poured into brine (20 mL) and extracted with ethyl acetate (2×20 mL). The combined organic layer was concentrated to give a residue in vacuo. The residue was purified by silica gel column chromatography (dichloromethane/methanol=20/1) to give methyl 4-(2-(4-((6-((4-cyano-2-fluorophenoxy))methyl) pyridin-2-yl)oxy)-piperidin-1-yl)acetamido)-3-((1-(cyanomethyl)cyclopropyl)methyl)amino)benzoate (290 mg, 94.2% yield). LC-MS m/z: 627 $[M+H]^+$. 2). Synthesis of methyl 2-((4-((6-((4-cyano-2-fluorophenoxy)methyl)pyridin-2-yl)oxy)piperidin-1-yl)methyl)-1-((1-(cyanomethyl) cyclopropyl)methyl)-1H-benzo[d]imidazole-6-carboxylate

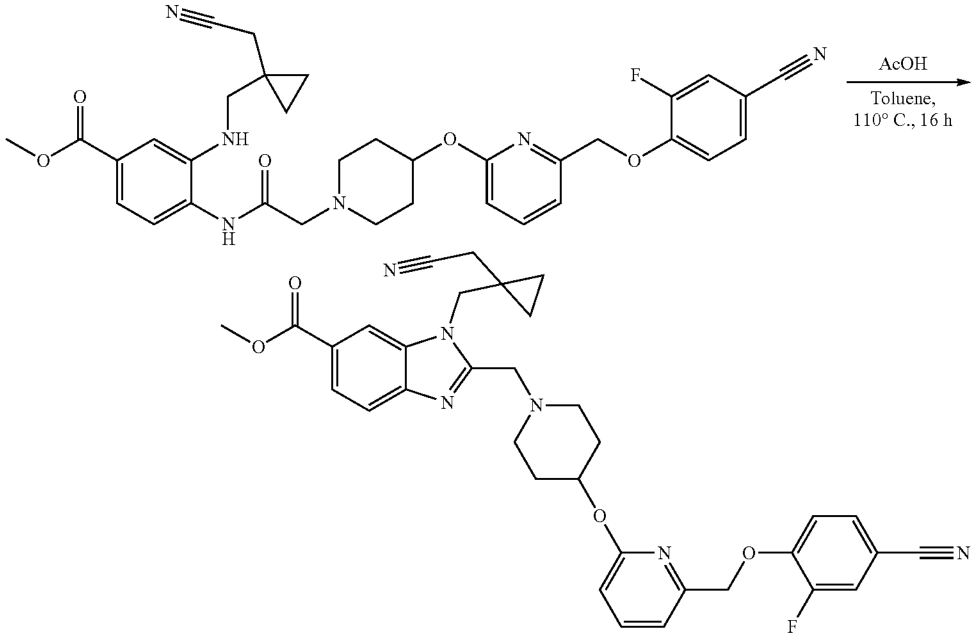

The mixture of methyl 4-(2-(4-((6-((4-cyano-2-fluorophenoxy)methyl)pyridin-2-yl)oxy)piperidin-1-yl)acetamido)-3-((1-(cyanomethyl)cyclopropyl)methyl)amino) benzoate (290 mg, 0.46 mmol) in toluene (10 mL) and acetic acid (10 mL) was stirred at 110° C. for 16 hours under nitrogen atmosphere. The mixture was concentrated and purified by silica gel column chromatography (dichloromethane/methanol=40/1) to obtain 2-((4-((6-((4-cyano-2-fluorophenoxy)-methyl)pyridin-2-yl)oxy)piperidin-1-yl) methyl)-1-((1-methyl (cyanomethyl)cyclopropyl)methyl)-1H-benzo[d]imidazole-6-carboxylate (250 mg, 88.9% yield). LC-MS m/z: 609 $[M+H]^+$.

3). Synthesis of 2-((4-((6-((4-cyano-2-fluorophenoxy)methyl)pyridin-2-yl)oxy)piperidin-1-yl) methyl)-1-((1-(cyanomethyl)cyclopropyl)methyl)-1H-benzo[d]imidazole-6-carboxylic acid

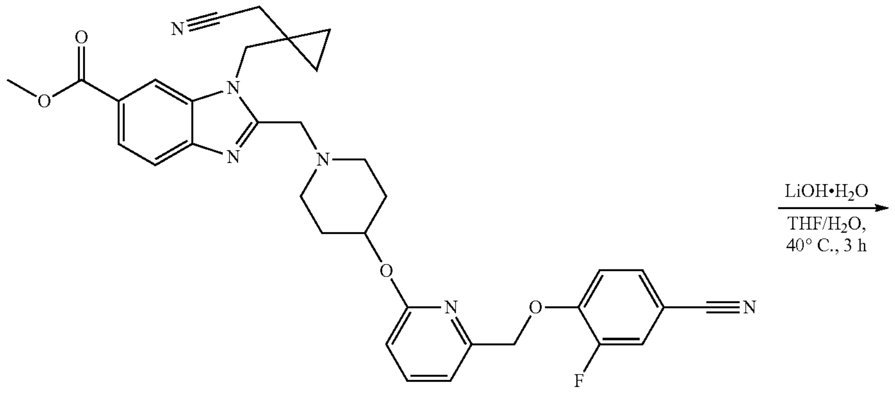

-continued

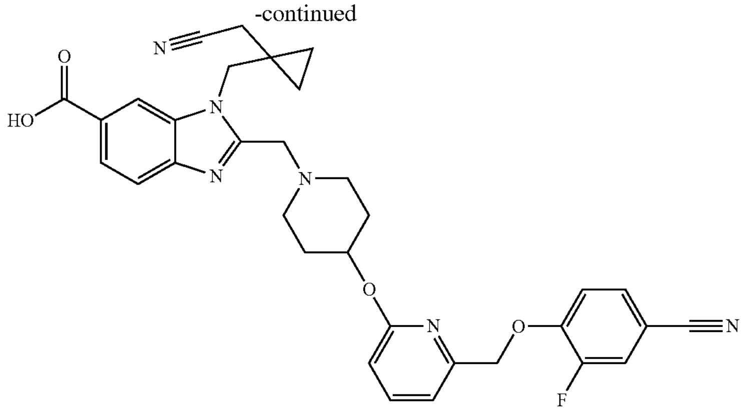

To a mixture of methyl 2-((4-((6-((4-cyano-2-fluorophenoxy)-methyl)pyridin-2-yl)oxy)piperidin-1-yl)methyl)-1-((1-(cyanomethyl)cyclopropyl)methyl)-1H-benzo[d]imidazole-6-carboxylate (125 mg, 0.21 mmol) in THF (5 mL) and water (5 mL) lithium hydroxide monohydrate (86 mg, 2.10 mmol) was added. The mixture was stirred at 40° C. for 3 hours. The solvent was removed by concentration to give a residue in vacuo. The residue was purified by prep-HPLC (Waters 2767/2545/2489 system; Column: SunFire Prep C8 OBD 10 μm 19×250 mm; Gradient elution with ACN/0.05% $NH_4OH$ in $H_2O$ solvent system; Detection Wavelength 254 nm/214 nm; Flow rate 20 mL/min) to obtain 2-((4-((6-((4-cyano-2-fluorophenoxy)methyl)pyridin-2-yl)oxy)piperidine-1-yl)methyl)-1-((1-(cyanomethyl)cyclopropyl)methyl)-1H-benzo[d]imidazole-6-carboxylic acid (40.09 mg, 32.8% yield). LC-MS m/z: 595 $[M+H]^+$.

$^1H$ NMR (400 MHZ, DMSO-$d_6$) δ 8.22 (s, 1H), 7.89-7.86 (m, 1H), 7.81 (d, J=8.4 Hz, 1H), 7.73 (t, J=7.6 Hz, 1H), 7.67-7.61 (m, 2H), 7.45 (t, J=8.8 Hz, 1H), 7.05 (d, J=7.6 Hz, 1H), 6.73 (d, J=8.0 Hz, 1H), 5.31 (s, 2H), 4.94-4.90 (m, 1H), 4.60 (s, 2H), 3.84 (s, 2H), 2.80-2.77 (m, 2H), 2.70 (s, 2H), 2.33-2.28 (m, 2H), 1.92-1.90 (m, 2H), 1.65-1.58 (m, 2H), 0.74-0.69 (m, 4H).

Example 28. Synthesis of(S)-2-((4-((6-((4-cyano-2-fluorophenoxy)methyl)pyridin-2-yl)oxy)piperidin-1-yl)methyl)-4-fluoro-1-(oxetan-2-ylmethyl)-1H-benzo[d]imidazole-6-carboxylic acid (compound 56)

1). Synthesis of(S)—N-(4-bromo-2-fluoro-6-((oxetan-2-ylmethyl)amino)phenyl)-2-(4-((6-((4-cyano-2-fluoro-phenoxy)methyl)pyridin-2-yl)oxy)piperidin-1-yl)acetamido

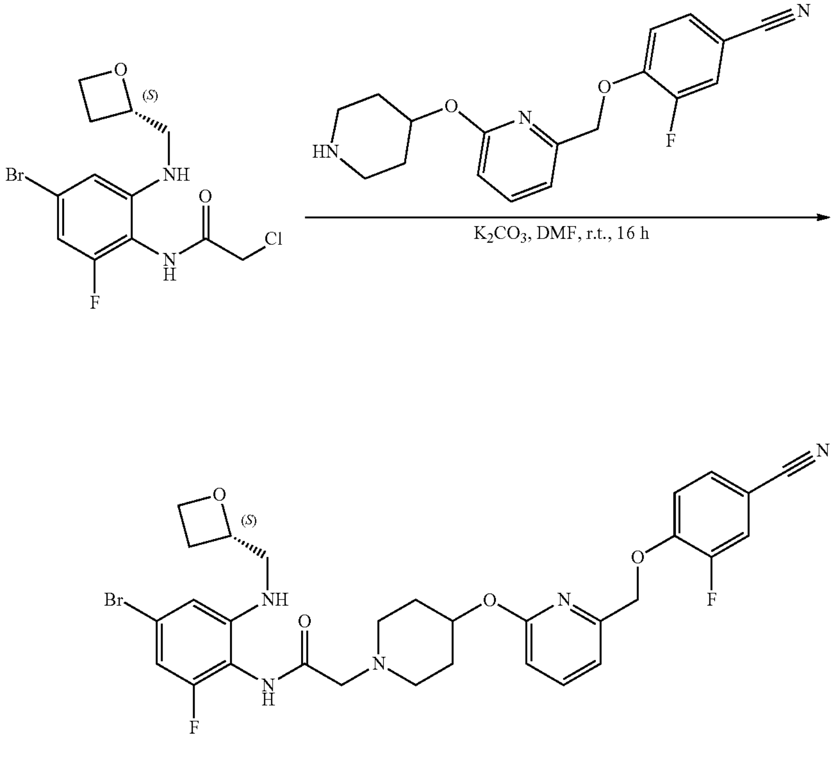

The mixture of(S)—N-(4-bromo-2-fluoro-6-((oxetan-2-ylmethyl)amino)phenyl)-2-chloroacetamido (230 mg, 0.65 mmol), 3-fluoro-4-((6-(piperidin-4-oxy)pyridin-2-yl)methoxy)benzonitrile (214 mg, 0.65 mmol) and potassium carbonate (271 mg, 1.95 mmol) in dry N,N-dimethylformamide (7 mL) was stirred at room temperature for 16 hours. After completion, the reaction mixture was quenched with water (10 mL) and extracted with ethyl acetate (3×10 mL). The combined organic layer was concentrated to give a residue in vacuo. The residue was purified by silica gel column chromatography (dichloromethane/methanol=10/1) to give(S)—N-(4-bromo-2-fluoro-6-((oxetan-2-ylmethyl)amino)phenyl)-2-(4-((6-((4-cyano-2-fluorophenoxy)methyl)pyridin-2-yl)oxy)piperidin-1-yl)acetamido (300 mg, 71.9% yield). LC-MS m/z: 644 [M+H]$^+$.

2). Synthesis of(S)-4-((6-((1-((6-bromo-4-fluoro-1-(oxetan-2-ylmethyl)-1H-benzo[d]imidazole-2-yl)methyl)piperidin-4-yl)oxy)pyridin-2-yl)methoxy)-3-fluorobenzonitrile

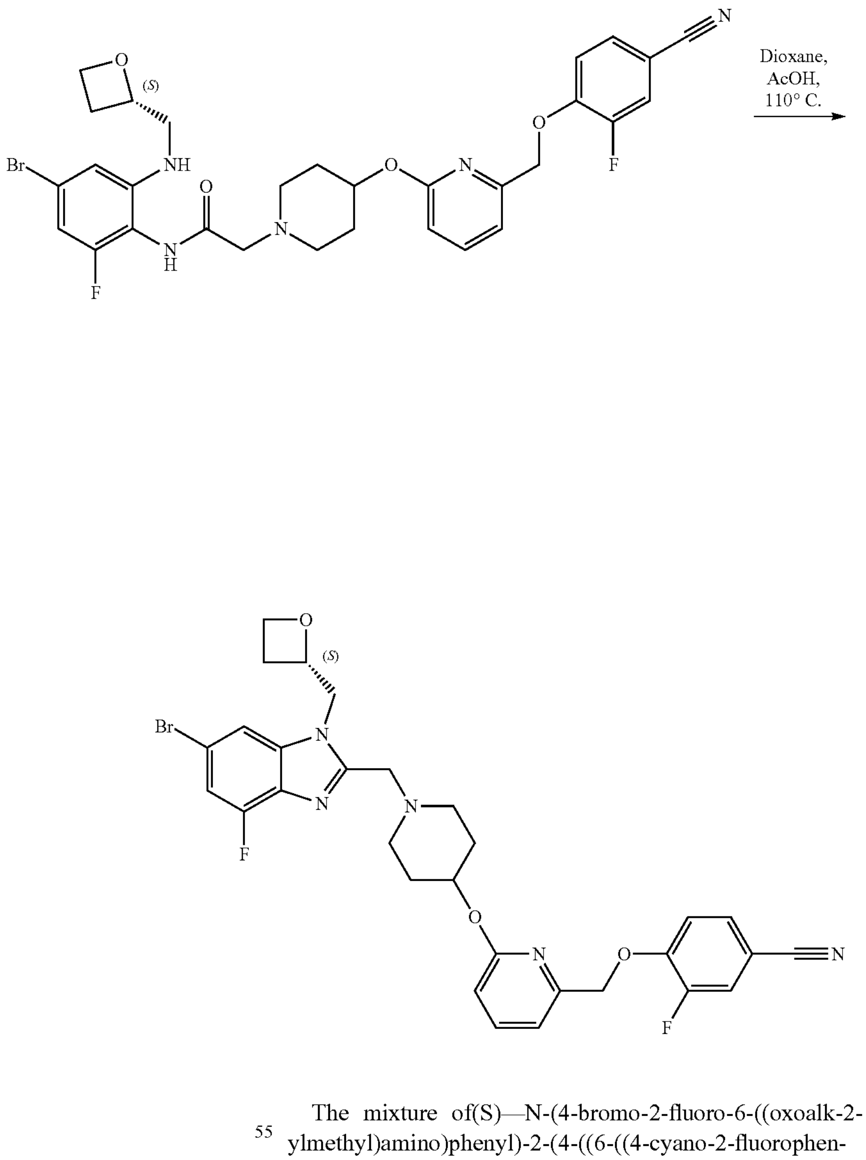

The mixture of(S)—N-(4-bromo-2-fluoro-6-((oxoalk-2-ylmethyl)amino)phenyl)-2-(4-((6-((4-cyano-2-fluorophenoxy)methyl)pyridin-2-yl)oxy)piperidin-1-yl)acetamido (230 mg, 0.36 mmol) in dioxane (5 mL) and acetic acid (0.5 mL) was stirred at 110° C. for 16 hours. The mixture was concentrated to give a residue in vacuo. The residue was purified by silica gel column chromatography (dichloromethane/methanol=20/1) to obtain(S)-4-((6-((1-((6-bromo-4-fluoro-1)-(oxetan-2-ylmethyl)-1H-benzo[d]imidazol-2-yl)methyl)piperidin-4-yl)oxy)pyridin-2-yl)methoxy)-3-fluoroben-zonitrile (80 mg, 35.7% yield). LC-MS m/z: 626 [M+H]$^+$.

3). Synthesis of methyl(S)-2-((4-((6-((4-cyano-2-fluorophenoxy)methyl)pyridin-2-yl)oxy)piperidin-1-yl)methyl)-4-fluoro-1-(oxetan-2-ylmethyl)-1H-benzo[d]imidazole-6-carboxylate

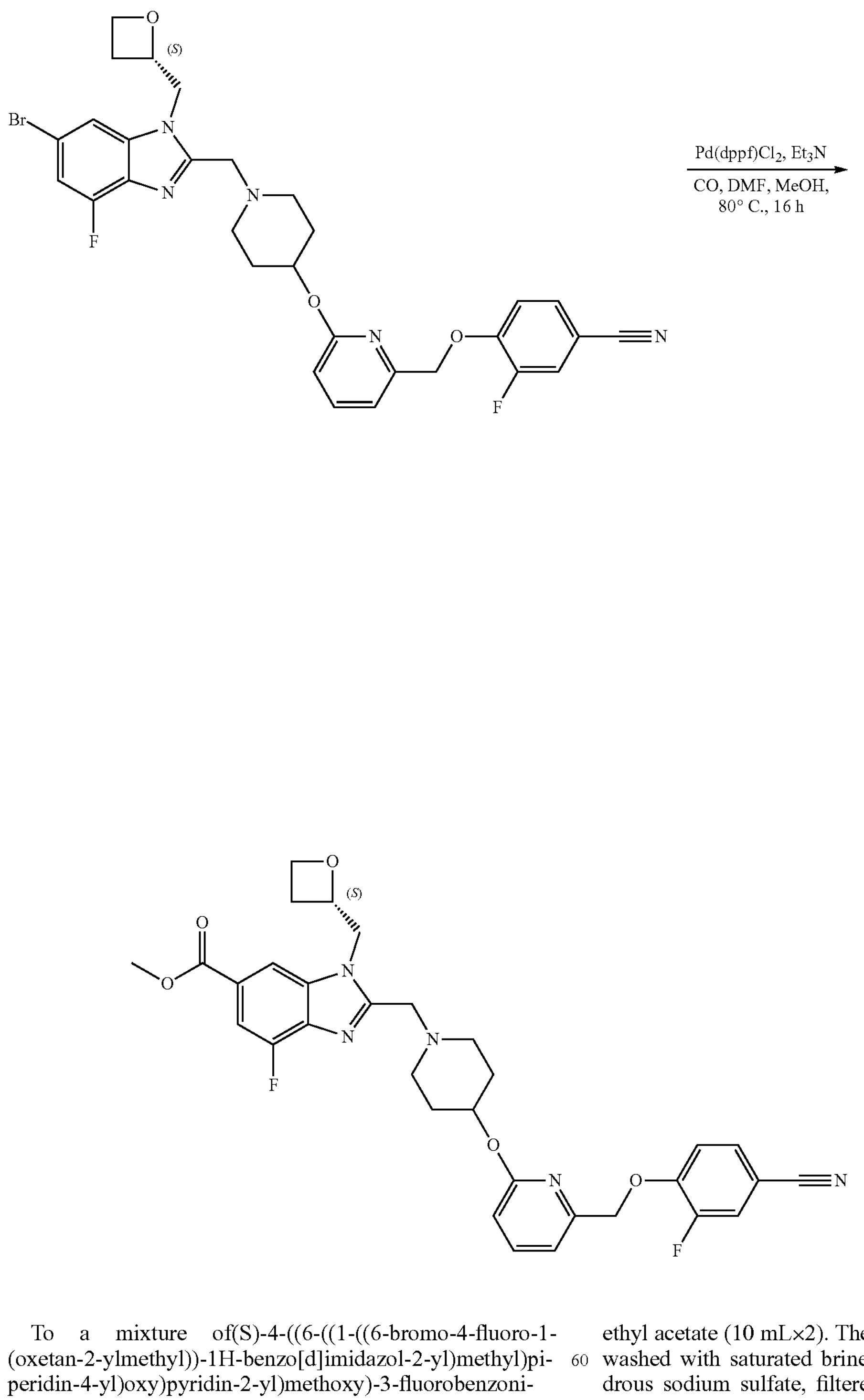

To a mixture of(S)-4-((6-((1-((6-bromo-4-fluoro-1-(oxetan-2-ylmethyl))-1H-benzo[d]imidazol-2-yl)methyl)piperidin-4-yl)oxy)pyridin-2-yl)methoxy)-3-fluorobenzonitrile (61 mg, 0.10 mmol) in N,N-dimethylformamide (2 mL) and methanol (2 mL) triethylamine (30 mg, 0.30 mmol) and 1,1'-bisdiphenylphosphinoferrocene palladium dichloride (7 mg, 0.01 mmol) were added. The mixture was stirred at 80° C. for 16 hours under carbon monoxide atmosphere. The mixture was diluted with water (5 ml) and extracted with ethyl acetate (10 mL×2). The combined organic layers were washed with saturated brine (10 mL×3), dried over anhydrous sodium sulfate, filtered, and concentrated to give a residue in vacuo. The residue was purified by silica gel column chromatography (petroleum ether/ethyl acetate=1/1) to obtain methyl(S)-2-((4-((6-((4-cyano-2-fluorophenoxy)methyl)pyridin-2-yl)oxy)piperidin-1-yl)methyl)-4-fluoro-1-(oxetan-2-ylmethyl)-1H-benzo[d]imidazole-6-carboxylate (30 mg, 50.8% yield). LC-MS m/z: 604 $[M+H]^+$.

4). Synthesis of(S)-2-((4-((6-((4-cyano-2-fluorophenoxy)methyl)pyridin-2-yl)oxy)piperidin-1-yl) methyl)-4-fluoro-1-(oxetan-2-ylmethyl)-1H-benzo [d]imidazole-6-carboxylic acid

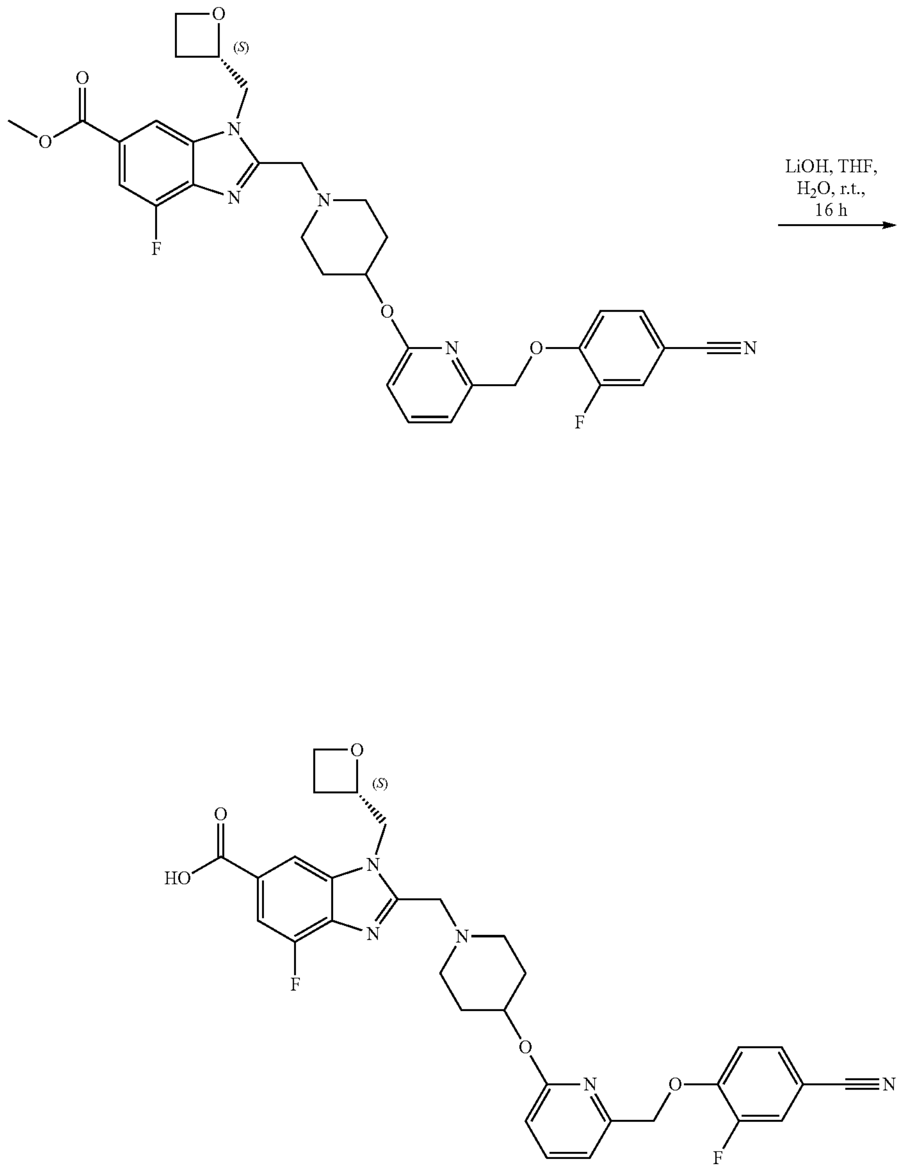

To a mixture of methyl(S)-2-((4-((6-((4-cyano-2-fluorophenoxy)methyl)pyridin-2-yl)oxy)piperidin-1-yl)methyl)-4-fluoro-1-(oxetan-2-ylmethyl)-1H-benzo[d]imidazole-6-carboxylate (37 mg, 0.06 mmol) in water (1 mL) and THF (1 mL) lithium hydroxide (14 mg, 0.60 mmol) was added. The reaction mixture was stirred at room temperature for 16 hours. The reaction solution was adjusted to pH=5-6 with formic acid and extracted with ethyl acetate (10 mL×2). The combined organic layers were washed saturated brine (10 mL×2), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: 10 mmol FA in water; Mobile Phase B: acetonitrile; Flow rate: 80 mL/min; Gradient: 30% B-50% B in 20 min; Detector: 254 nm) to obtain(S)-2-((4-((6-((4-cyano-2-fluorophenoxy)methyl)yl) pyridin-2-yl) oxy)piperidin-1-yl)methyl)-4-fluoro-1-(oxetan-2-ylmethyl)-1H-benzo[d]imidaz-ole-6-carboxylic acid (6.63 mg, 18.3% yield). LC-MS m/z: 590 $[M+H]^+$.

$^1H$ NMR (400 MHZ, DMSO-$d_6$): δ8.09 (s, 1H), 7.89 (dd, J-11.2 Hz, 1.6 Hz 1H), 7.75-7.66 (m, 2H), 7.52-7.43 (m, 2H), 7.06 (d, J=7.6 Hz, 1H), 6.74 (d, J-8.4 Hz, 1H), 5.31 (s, 2H), 5.11-5.06 (m, 1H), 4.95-4.89 (m, 1H), 4.81-4.76 (m, 1H), 4.66-4.63 (m, 1H), 4.52-4.47 (m, 1H), 4.40-4.34 (m, 1H), 3.96-3.92 (m, 1H), 3.81-3.78 (m, 1H), 2.79-2.67 (m, 3H), 2.46-2.41 (m, 1H), 2.33-2.27 (m, 2H), 1.93-1.89 (m, 2H), 1.64-1.57 (m, 2H).

Example 29. Synthesis of(S)-2-((4-((6-((4-chloro-2-fluorophenyl)thio) methyl)pyridin-2-yl)oxy)piperidin-1-yl)methyl)-1-(oxetan-2-ylmethyl)-1H-benzo[d] imidazole-6-carboxylic acid (compound C8)

1). Synthesis of methyl(S)-2-((4-((6-((4-chloro-2-fluorophenylthio)methyl)pyridin-2-yl)oxy)piperidin-1-yl)methyl)-1-(oxetan-2-ylmethyl)-1H-benzo[d] imidazole-6-carboxylate

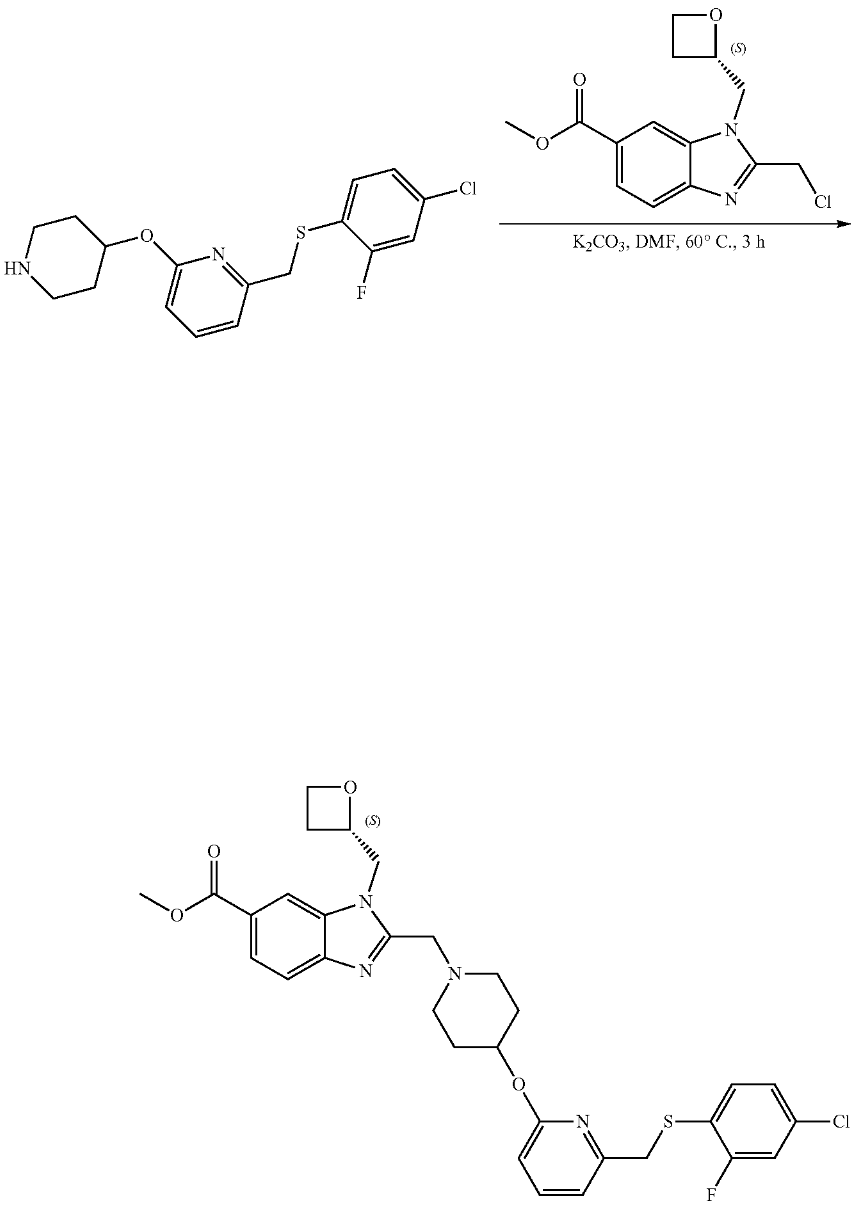

The mixture of 2-((4-chloro-2-fluorophenylthio)methyl)-6-(piperidin-4-oxy)pyridine (144 mg, 0.41 mmol), methyl (S)-2-(chloromethyl)-1-(oxetan-2-ylmethyl)-1H-benzo[d] imidazole-6-carboxylate (120 mg, 0.41 mmol) and potassium carbonate (168 mg, 1.23 mmol) in N,N-dimethylformamide (4 mL) was stirred at 60° C. for 3 hours. The mixture was diluted with water (30 mL) and extracted with ethyl acetate (10 mL×3). The combined organic layers were washed with brine (10 mL×3), dried over anhydrous sodium sulfate, filtered, and concentrated to give residue in vacuo. The residue was purified by silica gel column chromatography (dichloromethane/methanol=20/1) to give methyl(S)-2-((4-((6-((4-chloro-2-fluorophenylthio)methyl)pyridin-2-yl)oxy)piperidin-1-yl)methyl)-1-(oxetan-2-ylmethyl)-1H-benzo[d]imidazole-6-carbo-xylate (80 mg, 32.0% yield). LC-MS m/z: 611 $[M+H]^+$.

2). Synthesis of(S)-2-((4-((6-((4-chloro-2-fluorophenyl)thio) methyl)pyridin-2-yl)oxy)piperidin-1-yl) methyl)-1-(oxetan-2-ylmethyl)-1H-benzo[d]imidazole-6-carboxylic acid

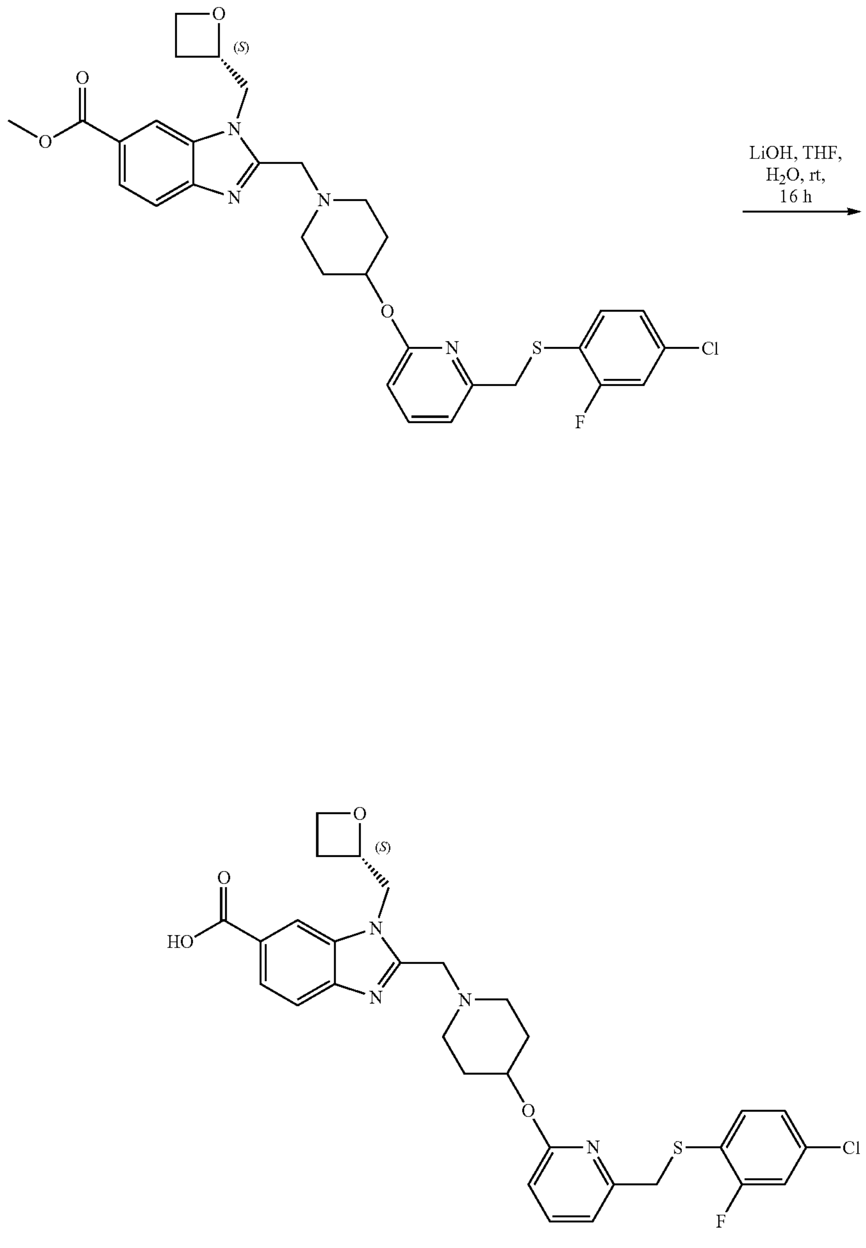

To a mixture of methyl(S)-2-((4-((6-((4-chloro-2-fluorophenylthio)methyl)pyridin-2-yl)oxy)piperidin-1-yl)methyl yl)-1-(oxetan-2-ylmethyl)-1H-benzo[d]imidazole-6-carboxylate (80 mg, 0.13 mmol) in water (1.0 mL) and THF (1.0 mL) lithium hydroxide (9 mg, 0.39 mmol) was added. The reaction mixture was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain(S)-2-((4-((6-((4-chloro-2-fluorophenylthio)methyl)pyridin-2-yl)oxy)piperidin-1-yl)methyl)-1-(oxetan-2-ylmethyl)-1H-benzo[d] imidazole-6-carboxylic acid (20.29 mg, 26.2% yield). LC-MS m/z: 597 $[M+H]^+$.

$^1H$ NMR (400 MHZ, DMSO-$d_6$): δ8.26 (s, 1H), 7.81-7.79 (m, 1H), 7.65-7.61 (m, 3H), 7.28-7.22 (m, 2H), 6.98 (d, J=7.2 Hz, 1H), 6.64 (d, J=8.0 Hz, 1H), 5.10-5.07 (m, 1H), 4.86 (s, 1H), 4.81-4.75 (m, 1H), 4.65-4.61 (m, 1H), 4.51-4.49 (m, 1H), 4.38-4.34 (m, 1H), 4.30 (s, 2H), 3.93 (d, J=13.6 Hz, 1H), 3.77 (d, J=13.6 Hz, 1H), 2.75-2.67 (m, 3H), 2.46-2.39 (m, 1H), 2.31-2.26 (m, 2H), 1.88-1.87 (m, 2H), 1.60-1.56 (m, 2H).

Example 30. Synthesis of(S)-2-((4-((6-((4-cyano-2-fluorophenoxy)methyl)pyridin-2-yl)oxy)piperidin-1-yl)methyl)-1-(oxetan-2-ylmethyl)-1H-benzo[d]imidazole-6-carboxylic acid (compound 55)

1). Synthesis of methyl(S)-2-((4-((6-((4-cyano-2-fluorophenoxy)methyl)pyridin-2-yl)oxy)piperidin-1-yl)methyl)-1-(oxetan-2-ylmethyl)-1H-benzo[d]imidazole-6-carboxylate

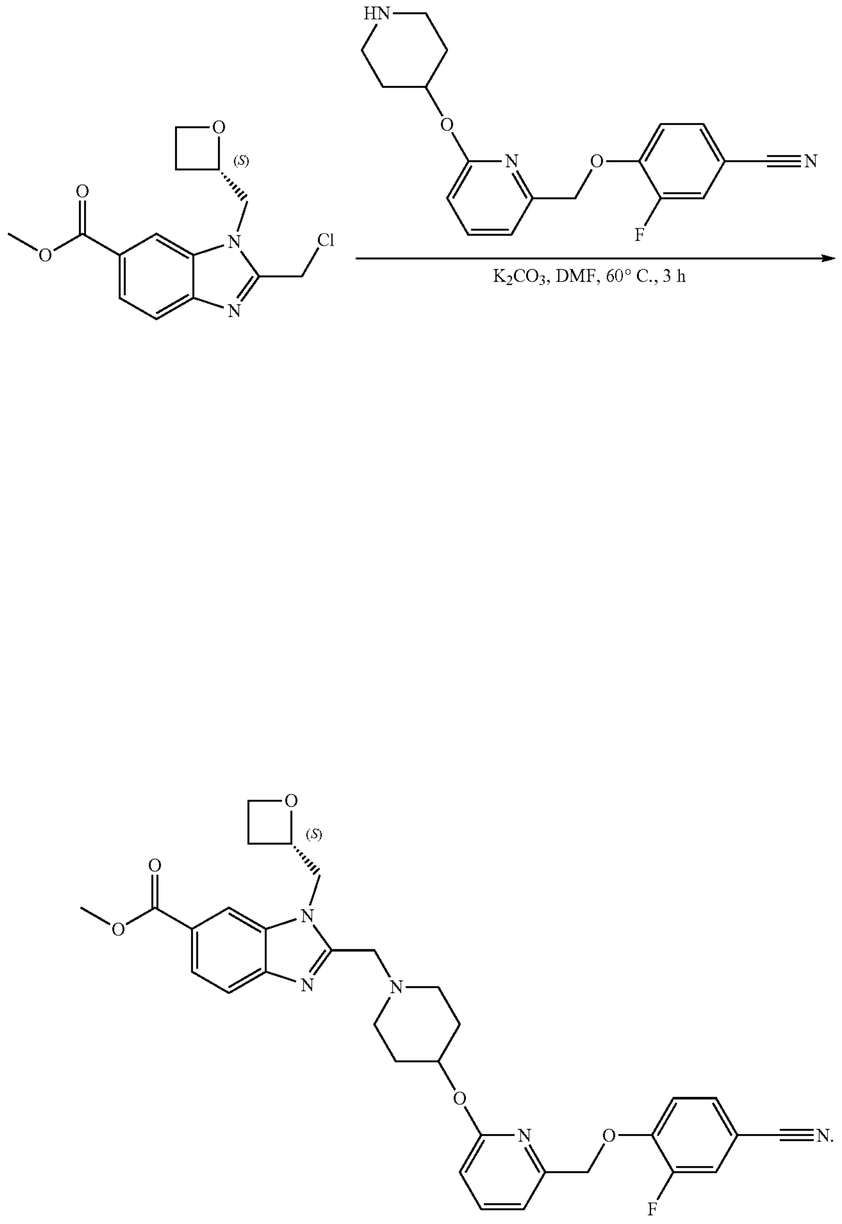

The mixture methyl(S)-2-(chloromethyl)-1-(oxetan-2-ylmethyl)-1H-benzo[d]imidazole-6-carboxylate (150 mg, 0.51 mmol), 3-fluoro-4-((6-(piperidin-4-oxy)pyridin-2-yl)methoxy)benzonitrile (184 mg, 0.56 mmol) and potassium carbonate (176 mg, 1.27 mmol)) in N,N-dimethylformamide (8 mL) was stirred at 60° C. for 3 hours. The mixture was quenched with water (10 mL) and extracted with ethyl acetate (10 mL×3). The combined organic layers were washed with brine (10 mL×3), dried over anhydrous sodium sulfate, filtered, and concentrated to give a residue in vacuo. The residue was purified by silica gel column chromatography (dichloromethane/methanol=20/1) to obtain methyl (S)-2-((4-((6-((4-cyano-2-fluorophenoxy)methyl)) pyridin-2-yl)oxy)piperidin-1-yl)methyl)-1-(oxetan-2-ylmethyl)-1H-benzo[d]imidazole-6-carbox-ylate (100 mg, 33.5% yield). LCMS m/z: 586 $[M+H]^+$.

2). Synthesis of(S)-2-((4-((6-((4-cyano-2-fluorophenoxy)methyl)pyridin-2-yl)oxy)piperidin-1-yl) methyl)-1-(oxetan-2-ylmethyl)-1H-benzo[d]imidazole-6-carboxylic acid

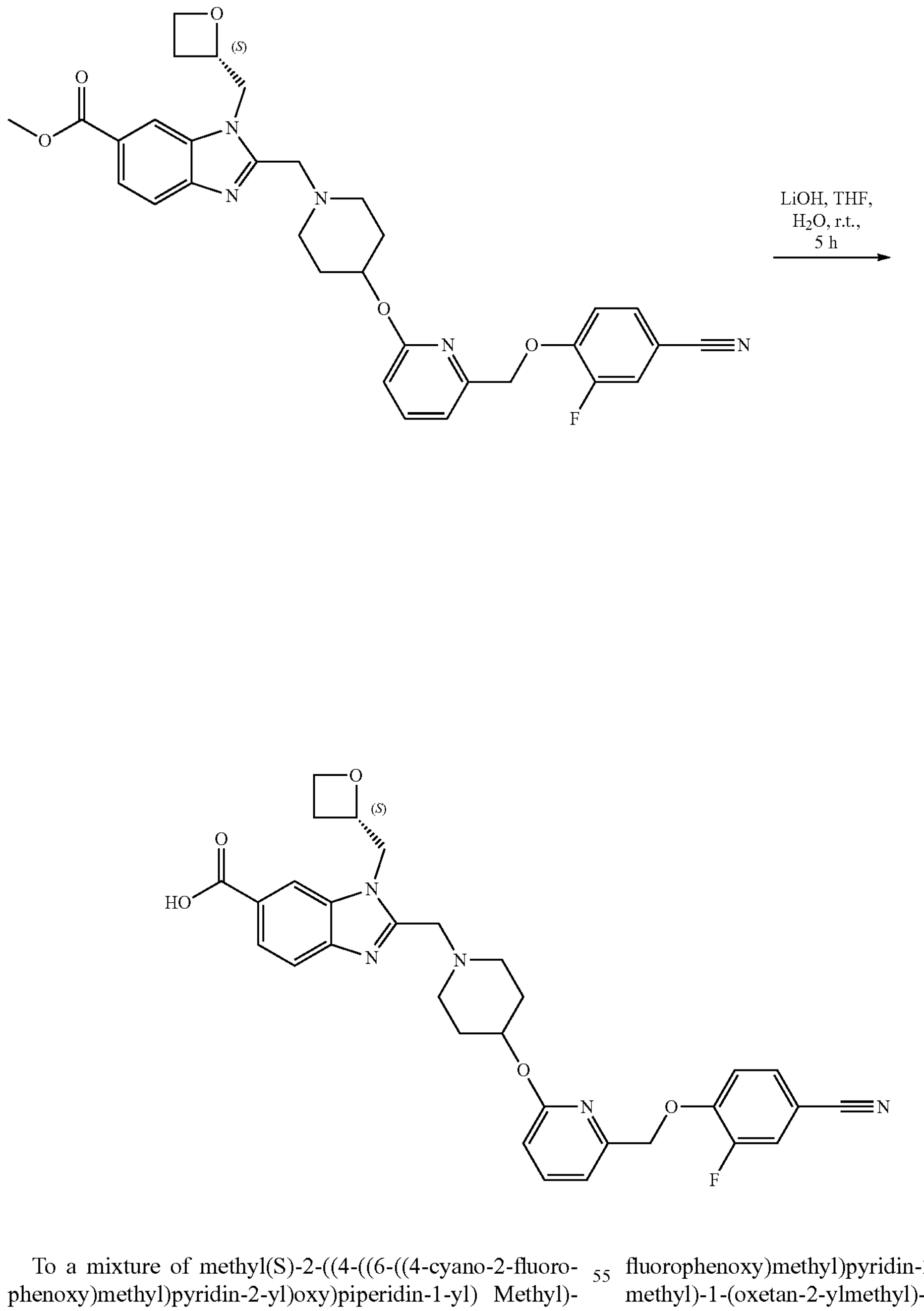

To a mixture of methyl(S)-2-((4-((6-((4-cyano-2-fluorophenoxy)methyl)pyridin-2-yl)oxy)piperidin-1-yl) Methyl)-1-(oxetan-2-ylmethyl)-1H-benzo[d]imidazole-6-carboxylate (100 mg, 0.17 mmol) in THF (2 mL) and water (2 mL) lithium hydroxide (13 mg, 0.51 mmol) was added. The reaction was stirred at room temperature for 16 hours. The resulting mixture was adjusted to pH=5-6 with formic acid. The solvent was removed by concentration to give a residue in vacuo. The residue was eluted by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength 254 nm/214 nm; Flow rate: 20 mL/min) to obtain(S)-2-((4-((6-((4-cyano-2-fluorophenoxy)methyl)pyridin-2-yl)oxy)piperidin-1-yl) methyl)-1-(oxetan-2-ylmethyl)-1H-benzo[d]imidazole-6-carboxylic acid (56.80 mg, 58.6% yield). LC-MS m/z: 572 $[M+H]^+$.

$^1$HNMR (400 MHZ, DMSO-$d_6$): δ8.23 (s, 1H), 7.88 (dd, J-2.0 Hz, 11.6 Hz, 1H), 7.80 (dd, J=1.6, 8.8 Hz, 1H), 7.73 (t, J=8.0 Hz, 1H), 7.67 (d, J=8.4 Hz, 1H), 7.60 (d, J=8.8 Hz, 1H), 7.45 (t, J=8.4 Hz, 1H), 7.06 (d, J=7.6 Hz, 1H), 6.74 (d, J=8.4 Hz, 1H), 5.31 (s, 2H), 5.10-5.08 (m, 1H), 4.92-4.90 (m, 1H), 4.80-4.74 (m, 1H), 4.65-4.61 (m, 1H), 4.50-4.47 (m, 1H), 4.40-4.35 (m, 1H), 3.93 (d, J=13.6 Hz, 1H), 3.78 (d, J=13.6 Hz, 1H), 2.79-2.67 (m, 3H), 2.51-2.41 (m, 1H), 2.32-2.27 (m, 2H), 1.92-1.89 (m, 2H) 1.63-1.58 (m, 2H).

Example 31. Synthesis of 2-((4-((6-((4-chloro-2-fluorobenzyl)oxy)-5-fluoropyridin-2-yl)oxy)piperidin-1-yl)methyl)-1-((1-(cyanomethyl)cyclopropyl)methyl)-4-fluoro-1H-benzo[d]imidazole-6-carboxylic acid (Compound S41)

1). Synthesis of N-(4-bromo-2-((1-(cyanomethyl)cyclopropyl)methyl)amino)-6-fluorophenyl)-2-(4-((6-((4-chloro-2-fluorobenzyl)oxy)-5-fluoropyridin-2-yl)oxy)piperidin-1-yl)acetamide

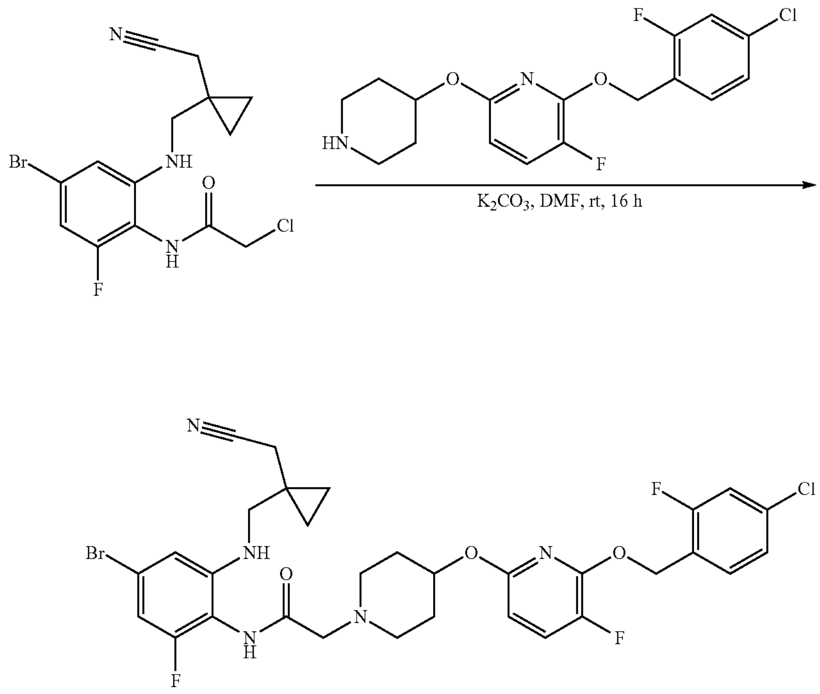

The mixture of N-(4-bromo-2-((1-(cyanomethyl)cyclopropyl)methyl)amino)-6-fluorophenyl)-2-chloroacetamide (189 mg, 0.50 mmol), 2-((4-chloro-2-fluorobenzyl)oxy)-3-fluoro-6-(piperidin-4-oxy)pyridine (90 mg, 0.50 mmol) and potassium carbonate (140 mg, 1.00 mmol) in dry N,N-dimethylformamide (4 mL) was stirred at room temperature for 16 hours. When completion, it was quenched with water (10 mL) and extracted with dichloromethane (3×10 mL). The combined organic layer was concentrated to give a residue in vacuo. The residue was purified by silica gel column chromatography (dichloromethane/methanol=10/1) to give N-(4-bromo-2-((1-(cyanomethyl)-cyclopropyl)methyl)) amino)-6-fluorophenyl)-2-(4-((6-((4-chloro-2-fluorobenzyl)oxy)-5-fluoropyridin-2-yl)oxy)piperid-ine-1-yl)acetamide (218 mg, 62.6% yield). LC-MS m/z: 694 $[M+H]^+$.

2). Synthesis of 2-(1-((6-bromo-2-((4-((4-chloro-2-fluorobenzyl)oxy)-5-fluoropyridin-2-yl)oxy)piperidine-1-yl)methyl)-4-fluoro-1H-benzo[d]imidazol-1-yl)methyl)cyclopropyl)acetonitrile

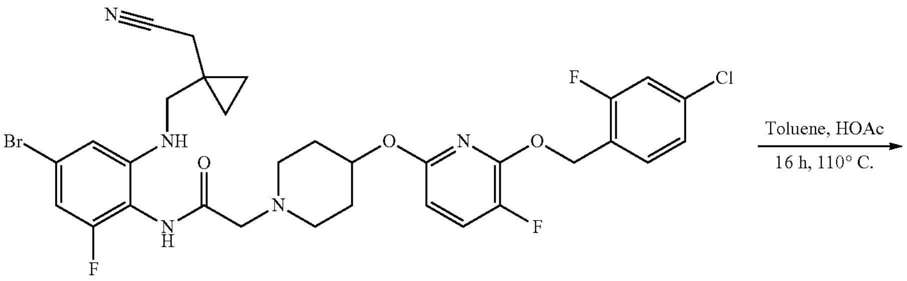

-continued

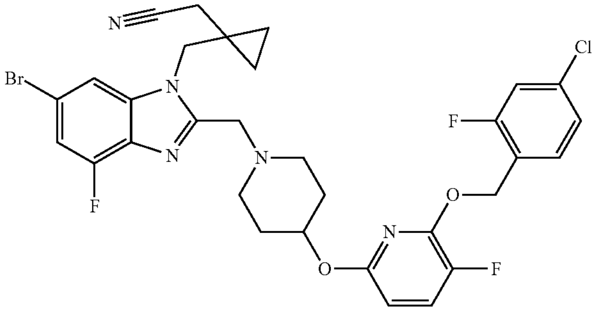

The mixture of N-(4-bromo-2-((1-(cyanomethyl)cyclopropyl)methyl)amino)-6-fluorophenyl)-2-(4-((6-((4-chloro-2-fluoro-benzyl)oxy)-5-fluoropyridin-2-yl)oxy)piperidin-1-yl)acetamide (218 mg, 3.17 mmol) in toluene (4 mL) and acetic acid (1 mL)) was stirred at 110° C. for 16 hours. The solvent was removed by concentration to give a residue in vacuo. The residue was purified by silica gel column chromatography (dichloromethane/methanol=10/1) to obtain 2-(1-((6-bromo-2-((4-((4-chloro-2-fluorobenzyl)oxy)-5-fluoropyridin-2-yl)oxy)piperidin-1-yl)methyl)-4-fluoro-1H-benzo[d]-imidazol-1-yl)methyl)cyclopropyl)acetonitrile (45 mg, 21.2% yield). LC-MS m/z: 676 [M+H]$^+$.

3). Synthesis of methyl 2-((4-((6-((4-chloro-2-fluorobenzyl)oxy)-5-fluoropyridin-2-yl)oxy)piperidin-1-yl)methyl)-1-((1-(cyanomethyl)cyclopropyl)methyl)-4-fluoro-1H-benzo[d]imidazole-6-carboxylate

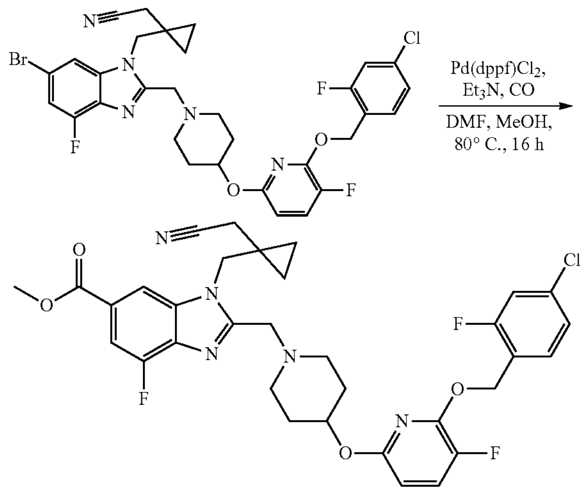

To a mixture of 2-(1-((6-bromo-2-((4-((6-((4-chloro-2-fluorobenzyl)oxy)-5-fluoropyridin-2-yl) oxy)piperidin-1-yl) methyl)-4-fluoro-1H-benzo[d]imidazol-1-yl)methyl)cyclopropyl)acetonitrile (220 mg, 0.33 mmol) in N,N-dimethylformamide (10 mL) and methanol (10 mL) triethylamine (60 mg, 0.6 mmol) and 1,1'-bisdiphenylphosphinoferrocene palladium dichloride (20 mg, 0.03 mmol) were added under carbon monoxide atmosphere. The mixture was stirred at 80° C. for 16 hours, diluted with water (50 mL) and extracted with ethyl acetate (100 mL×2). The combined organic layers were washed with brine (50 mL×3), dried over anhydrous sodium sulfate, filtered, and concentrated to give a residue in vacuo. The residue was purified by silica gel column chromatography (petroleum ether/ethyl acetate-2/1) to obtain methyl 2-((4-((6-((4-chloro-2-fluorobenzyl)oxy)-5-fluoropyridin-2-yl)oxy)piperidin-1-yl)methyl)-1-((1-(cyanomethyl)cyclopropyl) methyl)-4-fluoro-1H-benzo[d]imidazole-6-carboxylate (93.7 mg, 43.5% yield). LC-MS m/z: 654 [M+H]$^+$.

4). Synthesis of 2-((4-((6-((4-chloro-2-fluorobenzyl) oxy)-5-fluoropyridin-2-yl)oxy)piperidin-1-yl) methyl)-1-((1-(cyanomethyl)cyclopropyl)methyl)-4-fluoro-1H-benzo[d]imidazole-6-carboxylic acid

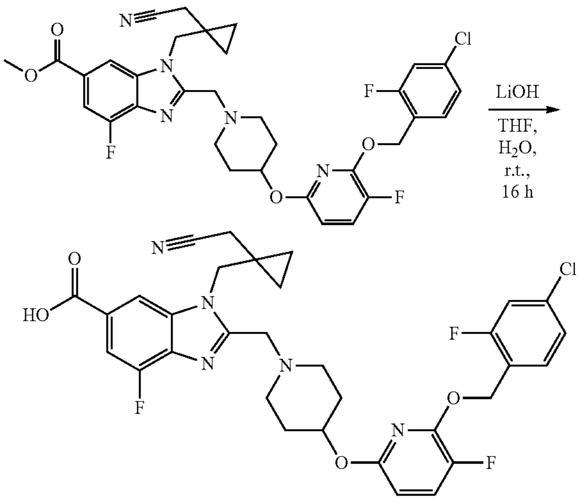

To a mixture of methyl 2-((4-((6-((4-chloro-2-fluorobenzyl)oxy)-5-fluoropyridin-2-yl)oxy)piperidin-1-yl)methyl)-1-((1-(cyanomethyl)cyclopropyl)methyl)-4-fluoro-1H-benzo[d]imidazole-6-carboxylate (18 mg, 0.03 mmol) in THF (Im L) and water (1 mL) lithium hydroxide (7 mg, 0.30 mmol) was added. The reaction mixture was stirred at room temperature for 16 hours. The reaction mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient eluted ACN/0.1% FA in $H_2O$ solvent system; Detection Wavelength: 254 nm/214 nm; Flow rate: 20 mL/min) to obtain 2-((4-((6-((4-chloro-2-fluorobenzyl)oxy)-5-fluoropyridin-2-yl)oxy)piperidine-1-yl)methyl)-1-((1-(cyanomethyl)cyclopropyl)methyl)-4-fluoro-1H-benzo[d]imidazole-6-carboxylic acid (4.84 mg, 27.5% yield). LC-MS m/z: 640 [M+H]$^+$.

$^{1}$H NMR (400 MHZ, DMSO-$d_6$): δ8.07 (s, 1H), 7.66-7.61 (m, 1H), 7.54-7.47 (m, 3H), 7.32 (dd, J=8.4 Hz, 2.0 Hz 1H), 6.34 (dd, J=8.8 Hz, 2.0 Hz 1H), 5.44 (s, 2H), 4.81-4.76 (m, 1H), 4.60 (s, 2H), 3.86 (s, 2H), 2.81-2.78 (m, 2H), 2.70 (s, 2H), 2.36-2.32 (m, 2H), 1.92-1.90 (m, 2H), 1.64-1.56 (m, 2H), 0.76-0.69 (m, 4H).

Example 32. Synthesis of 2-((4-((6-((4-chloro-2-fluorophenyl)thio) methyl)pyridin-2-yl)oxy)piperidin-1-yl)methyl)-1-((1-ethyl-1H-imidazol-5-yl) methyl)-1H-benzo[d]imidazole-6-carboxylic acid (compound C9)

1). Synthesis of 4-(2-(4-((6-(((4-chloro-2-fluorophenyl)thio) methyl)pyridin-2-yl)oxy)piperidin-1-yl) acetamido)-3-((1-ethyl-1H-imidazol-5-yl)methyl) amino)benzoate

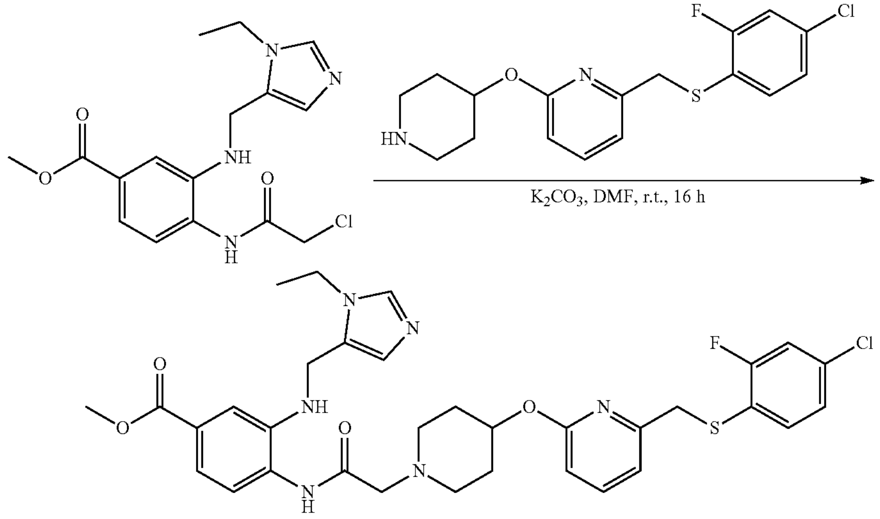

To a mixture of methyl 4-(2-chloroacetamido)-3-((1-ethyl-1H-imidazol-5-yl)methyl)amino)benzoate (190 mg, 0.54 mmol) and 2-((4-chloro-2-fluorophenylthio)methyl)-6-(piperidin-4-oxy)pyridine (190 mg, 0.54 mmol) in N,N-dimethylformamide (5 mL) potassium carbonate (224 mg, 1.62 mmol) was added. The reaction was stirred at room temperature for 16 hours. After completion, the mixture was quenched with water (5 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain methyl 4-(2-(4-((6-(((4-chloro-2-fluorophenyl)thio) methyl)pyridine-2-yl) oxy)piperidin-1-yl)acetamido)-3-((1-ethyl-1H-imidazol-5-yl)methyl)amino)benzoate (149 mg, 41.5% yield). LC-MS m/z: 667 [M+H]$^+$.

2). Synthesis of methyl 2-((4-((6-(((4-chloro-2-fluorophenyl)thio) methyl)pyridin-2-yl)oxy)piperidin-1-yl)methyl)-1-((1-ethyl-1H-imidazol-5-yl)methyl)-1H-benzo[d]imidazole-6-carboxylate

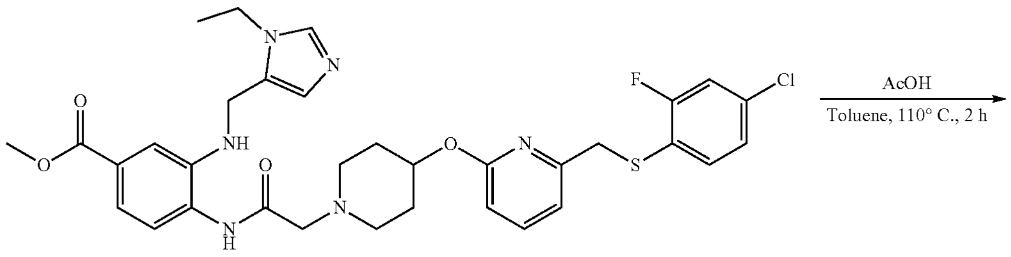

-continued

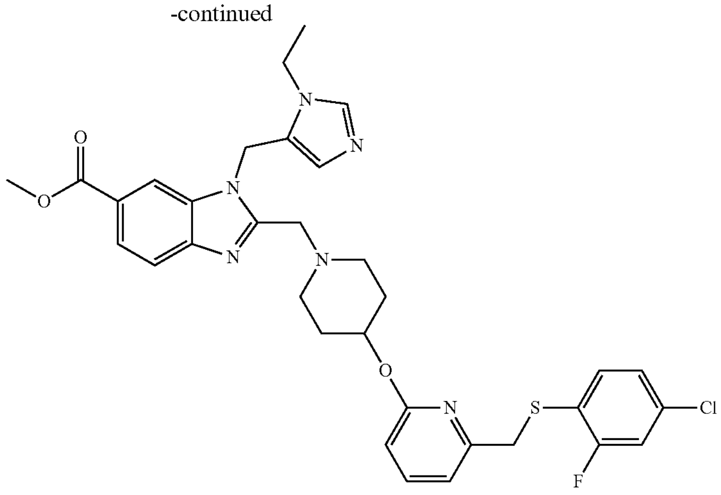

The mixture of methyl 4-(2-(4-((6-(((4-chloro-2-fluorophenyl)thio) methyl)pyridine-2-yl)oxy)piperidin-1-yl)acetamido)-3-((1-ethyl-1H-imidazol-5-yl)methyl)amino)benzoate (149 mg, 0.22 mmol) in toluene (6 mL) and acetic acid (1 mL) was stirred at 110° C. for 2 hours. The resulting mixture was poured into water (10 mL) and extracted with ethyl acetate (10 mL×2). The combined organic layers were washed successively with saturated sodium bicarbonate (10 mL×2), brine (10 mL×2), dried over anhydrous sodium sulfate, filtered, and concentrated to give a residue in vacuo. The residue was purified by silica gel column chromatography (dichloromethane/methanol=15/1) to obtain methyl 2-((4-((6-(((4-chloro-2-fluorophenyl)thio) methyl)pyridin-2-yl)oxy)piperidin-1-yl)methyl)-1-((1-ethyl-1H-imida-zol-5-yl)methyl)-1H-benzo[d]imidazole-6-carboxylate (129 mg, 90.5% yield). LC-MS m/z: 649 $[M+H]^+$.

3). Synthesis of 2-((4-((6-((4-Chloro-2-fluorophenylthio)methyl)pyridin-2-yl)oxy)piperidin-1-yl) methyl)-1-((1-ethyl-1H-imidazol-5-yl)methyl)-1H-benzo[d]imidazole-6-carboxylic acid

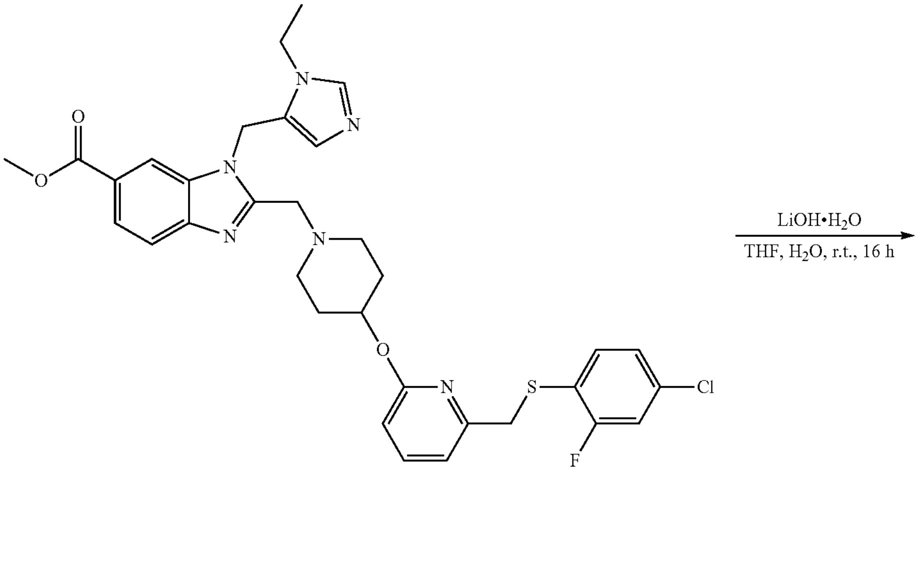

-continued

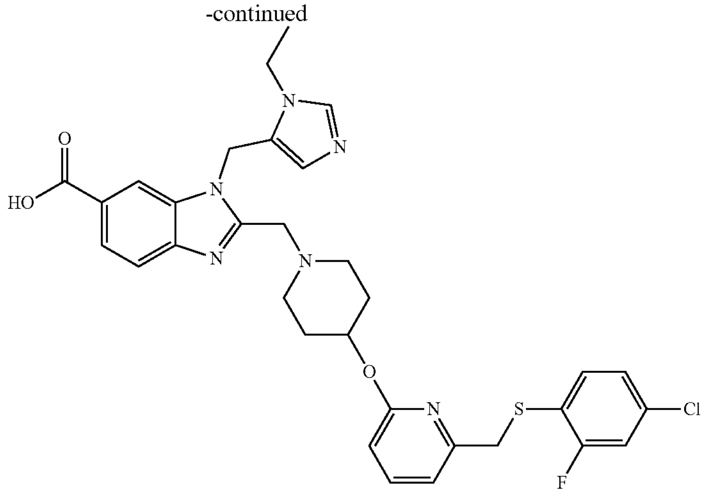

To a mixture of methyl 2-((4-((4-chloro-2-fluorophenylthio)methyl)pyridin-2-yl)oxypiperidin-1-yl)methyl)-1-((1-ethyl-1H-imidazol-5-yl)methyl)-1 H-benzo[d]imidazole-6-carboxylate (129 mg, 0.20 mmol) in THF (4 mL) and water (4 mL) lithium hydroxide monohydrate (47 mg, 1.99 mmol) was added. The reaction was stirred at room temperature for 16 hours. The resulting mixture was adjusted to pH=5-6 with hydrochloric acid (1M) and extracted with ethyl acetate (10 mL×3). The combined organic layers were washed with brine (10 mL), dried over anhydrous sodium sulfate, filtered, and concentrated in vacuo. The residue was purified by reverse-phase flash chromatography under the following conditions (Column: spherical C18, 20-40 μm, 120 g; Mobile Phase A: 10 mM $NH_4OH$ in water; Mobile Phase B: acetonitrile; Flow rate: 80 mL/min; Gradient: 30% B-50% B in 20 min; Detector: 254 nm) to obtain 2-((4-((6-((4-chloro-2-fluorophenylthio)methyl)pyridine-2-yl)oxy)piperidin-1-yl)methyl)-1-((1-ethyl-1H-imidazol-5-yl)methyl)-1H-benzo-[d]imidazole-6-carboxylic acid (58.36 mg, 0.09 mmol, 46% yield). LC-MS m/z: 635 $[M+H]^+$.

$^1H$ NMR (400 MHZ, DMSO-$d_6$) δ 8.08 (s, 1H), 7.82 (dd, J=8.4 Hz, 1.2 Hz, 1H), 7.69-7.67 (m, 2H), 7.64-7.60 (m, 2H), 7.30-7.22 (m, 2H), 6.98 (d, J=7.2 Hz, 1H), 6.62 (d, J=8.4 Hz, 1H), 6.41 (s, 1H), 5.72 (s, 2H), 4.83-4.78 (m, 1H), 4.29 (s, 2H), 4.03-3.98 (m, 2H), 3.80 (s, 2H), 2.66-2.63 (m, 2H), 2.25-2.21 (m, 2H), 1.74 (s, 2H), 1.45-1.42 (m, 2H), 1.16 (t, J-7.2 Hz, 3H).

Example 33. Synthesis of 2-((4-((6-((4-chloro-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylic acid (compound 43)

1) Synthesis of methyl 4-(2-(4-((6-((4-chloro-2-fluorophenoxy)methyl)pyridin-2-yl)oxy)piperidin-1-yl)acetamido)-3-((1-ethyl-1H-imidazol-5-yl)methyl) amino)benzoate

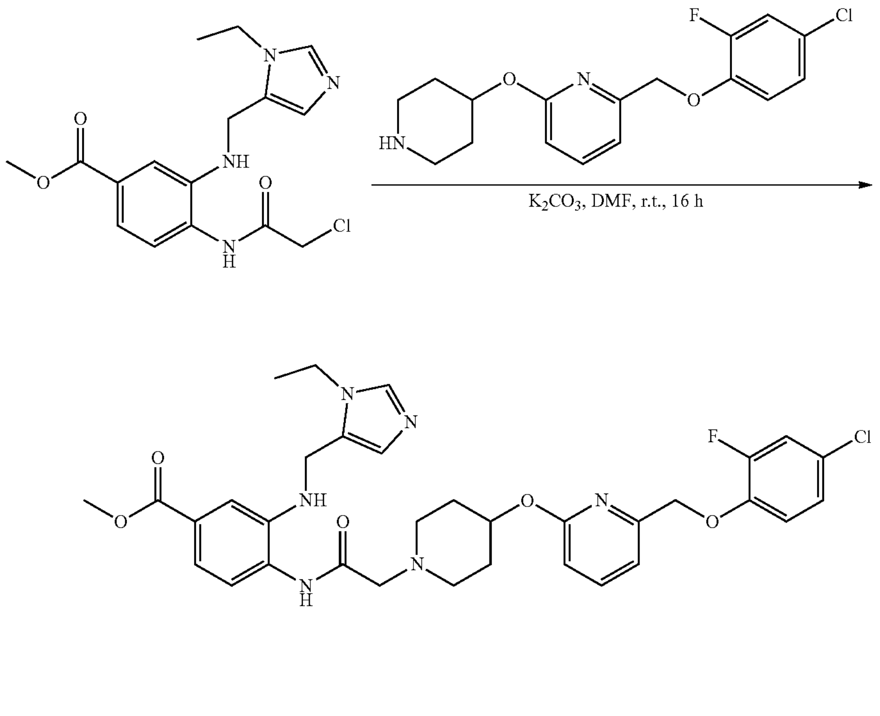

To a mixture of methyl 4-(2-chloroacetamido)-3-((1-ethyl-1H-imidazol-5-yl)methyl)amino)benzoate (190 mg, 0.54 mmol) and 2-((4-chloro-2-fluorophenoxy)methyl)-6-(piperidin-4-acyloxy)pyridine (181 mg, 0.54 mmol)) in N,N-dimethylformamide (4 mL) potassium carbonate (224 mg, 1.62 mmol) was added at room temperature. The mixture was stirred for 16 hours at room temperature. After completion, the water (5 mL) was added to quench the reaction mixture, and extracted with ethyl acetate (20 mL×3). The combined organic layers were washed with brine (20 mL×2), dried over anhydrous sodium sulfate, filtered, and concentrated in vacuo. The residue was purified by silica gel column chromatography (dichloromethane/methanol=15/1) to obtain methyl 4-(2-(4-((6-((4-chloro-2-fluoro phenoxy)methyl)pyridine-2-yl)oxy)piperidin-1-yl)acetamido)-3-((1-ethyl-1H-imidazol-5-yl)methyl)amino)benzoate (241 mg, 0.37 mmol, 68.5% yield). LC-MS m/z: 651 $[M+H]^+$.

2). Synthesis of methyl 2-((4-((6-((4-chloro-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate

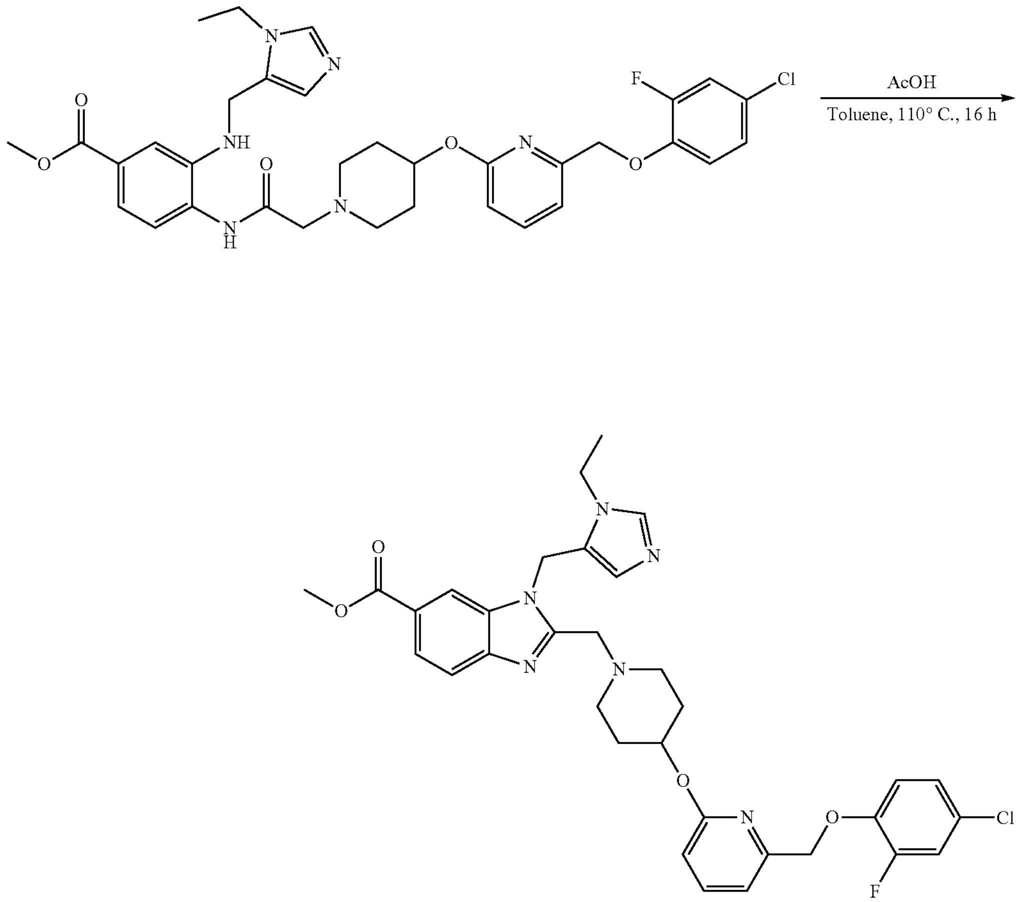

To a mixture of methyl 4-(2-(4-((6-((4-chloro-2-fluorophenoxy)methyl)pyridin-2-yl)oxy)piperidine-1-yl)acetamido)-3-((1-ethyl-1H-imidazol-5-yl)methyl)amino)benzoate (241 mg, 0.37 mmol) in toluene (10 mL) acetic acid (1 mL) was added, and the reaction mixture was stirred at 110° C. for 16 hours. After completion, the obtained mixture was poured into water (10 mL) and extracted with ethyl acetate (10 mL×2). The organic layer were washed successively with saturated sodium bicarbonate (10 mL×2) and brine (10 mL×2), dried over anhydrous sodium sulfate, filtered, and concentrated to give a residue in vacuo. The residue was purified by silica gel column chromatography (dichloromethane/methanol=15/1) to obtain methyl 2-((4-((6-((4-chloro-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate (87 mg, 37.8% yield). LC-MS m/z: 633 $[M+H]^+$.

3). Synthesis of 2-((4-((6-((4-chloro-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylic acid

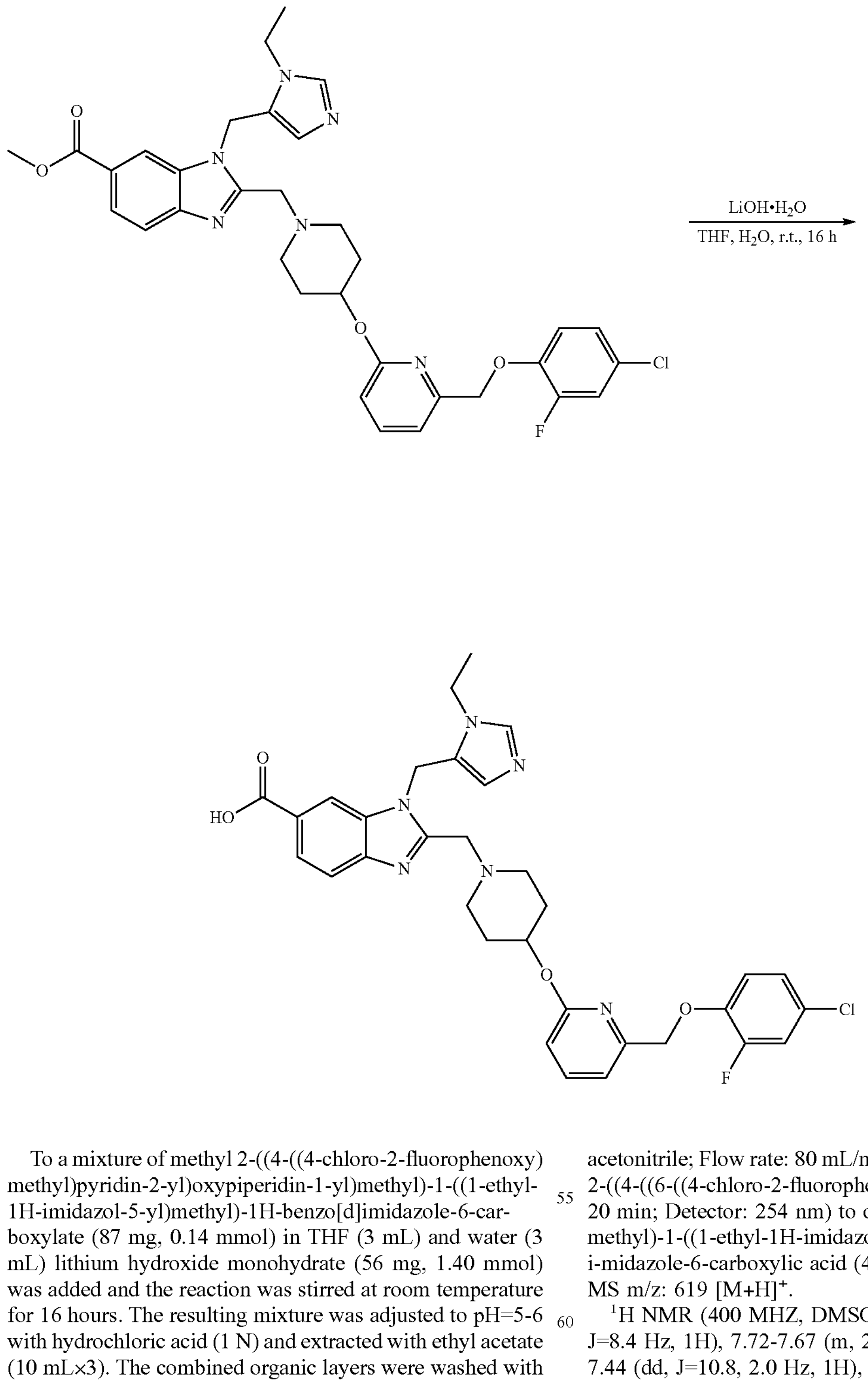

To a mixture of methyl 2-((4-((4-chloro-2-fluorophenoxy)methyl)pyridin-2-yl)oxypiperidin-1-yl)methyl)-1-((1-ethyl-1H-imidazol-5-yl)methyl)-1H-benzo[d]imidazole-6-carboxylate (87 mg, 0.14 mmol) in THF (3 mL) and water (3 mL) lithium hydroxide monohydrate (56 mg, 1.40 mmol) was added and the reaction was stirred at room temperature for 16 hours. The resulting mixture was adjusted to pH=5-6 with hydrochloric acid (1 N) and extracted with ethyl acetate (10 mL×3). The combined organic layers were washed with brine (10 mL), dried over anhydrous sodium sulfate, filtered, and concentrated in vacuo. The residue was purified by reverse-phase flash chromatography under the following conditions (Column: Spherical C18, 20-40 μm, 120 g; Mobile Phase A: 10 mM $NH_4OH$ in water; Mobile Phase B: acetonitrile; Flow rate: 80 mL/min; Gradient: 30% B-50% B 2-((4-((6-((4-chloro-2-fluorophenoxy)methyl)pyridine-2-in 20 min; Detector: 254 nm) to obtain yl)oxy)piperidin-1-yl)methyl)-1-((1-ethyl-1H-imidazol-5-yl)methyl)-1H-benzo[d]i-midazole-6-carboxylic acid (46.87 mg, 55.4% yield). LC-MS m/z: 619 $[M+H]^+$.

$^1H$ NMR (400 MHZ, DMSO-$d_6$) δ8.02 (s, 1H), 7.80 (d, J=8.4 Hz, 1H), 7.72-7.67 (m, 2H), 7.56 (d, J=8.4 Hz, 1H), 7.44 (dd, J=10.8, 2.0 Hz, 1H), 7.27 (t, J=9.2 Hz, 1H), 7.18 (d, J=8.8 Hz, 1H), 7.03 (d, J-7.2 Hz, 1H), 6.70 (d, J-8.4 Hz, 1H), 6.38 (s, 1H), 5.67 (s, 2H), 5.17 (s, 2H), 4.89-4.86 (m, 1H), 4.00 (q, J=7.2 Hz, 2H), 3.78 (s, 2H), 2.67 (s, 2H), 2.24 (t, J=8.0 Hz, 2H), 1.79 (d, J-9.6 Hz, 2H), 1.46 (m, 2H), 1.17 (t, J=7.2 Hz, 3H).

Example 34. Synthesis of(S)-2-((4-((6-((4-chloro-2-fluorophenoxy)methyl)pyridin-2-yl)oxy)piperidin-1-yl)methyl)-1-(oxetan-2-ylmethyl)-1H-benzo[d]imidazole-6-carboxylic acid (compound 49)

1). Synthesis of methyl(S)-2-((4-((6-((4-chloro-2-fluorophenoxy)methyl)pyridin-2-yl)oxy)piperidin-1-yl)methyl)-1-(oxetan-2-ylmethyl)-1H-benzo[d]imidazole-6-carboxylate

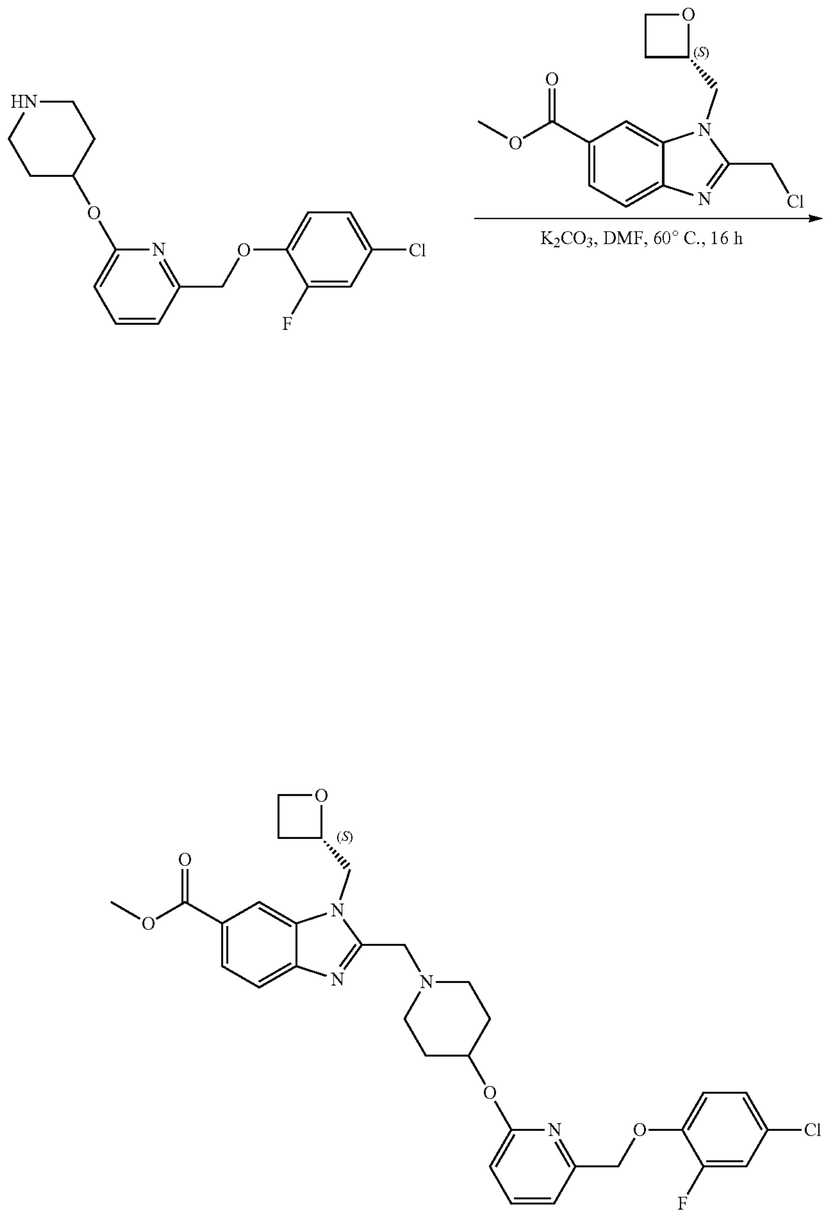

The mixture of 2-((4-chloro-2-fluorophenoxy)methyl)-6-(piperidin-4-oxy)pyridine (115 mg, 0.34 mmol), (S)-2-(chloromethyl)-1-(oxetan-2-ylmethyl)-1H-benzo[d]imidazole-6-carboxylate (100 mg, 0.34 mmol) and potassium carbonate (140 mg, 1.02 mmol)) in N,N-dimethylformamide (4 mL) was stirred at 60° C. for 16 hours. After completion, the resulting mixture was diluted with water (40 mL) and extracted with ethyl acetate (20 mL×2). The organic layers were washed with brine (20 mL×2), dried over anhydrous sodium sulfate, filtered, and concentrated in vacuo. The residue was purified by silica gel column chromatography (dichloromethane/methanol=20/1) to obtain methyl(S)-2-((4-((6-((4-chloro-2-fluorophenoxy)methyl)) pyridin-2-yl) oxy)piperidin-1-yl)methyl)-1-(oxetan-2-ylmethyl)-1H-benzo[d]imidazole-6-carboxylate (110 mg, 54.5% yield). LC-MS m/z: 595 $[M+H]^+$.

2). Synthesis of(S)-2-((4-((6-((4-chloro-2-fluorophenoxy)methyl)pyridin-2-yl)oxy)piperidin-1-yl)methyl)-1-(oxetan-2-ylmethyl)-1H-benzo[d]imidazole-6-carboxylate

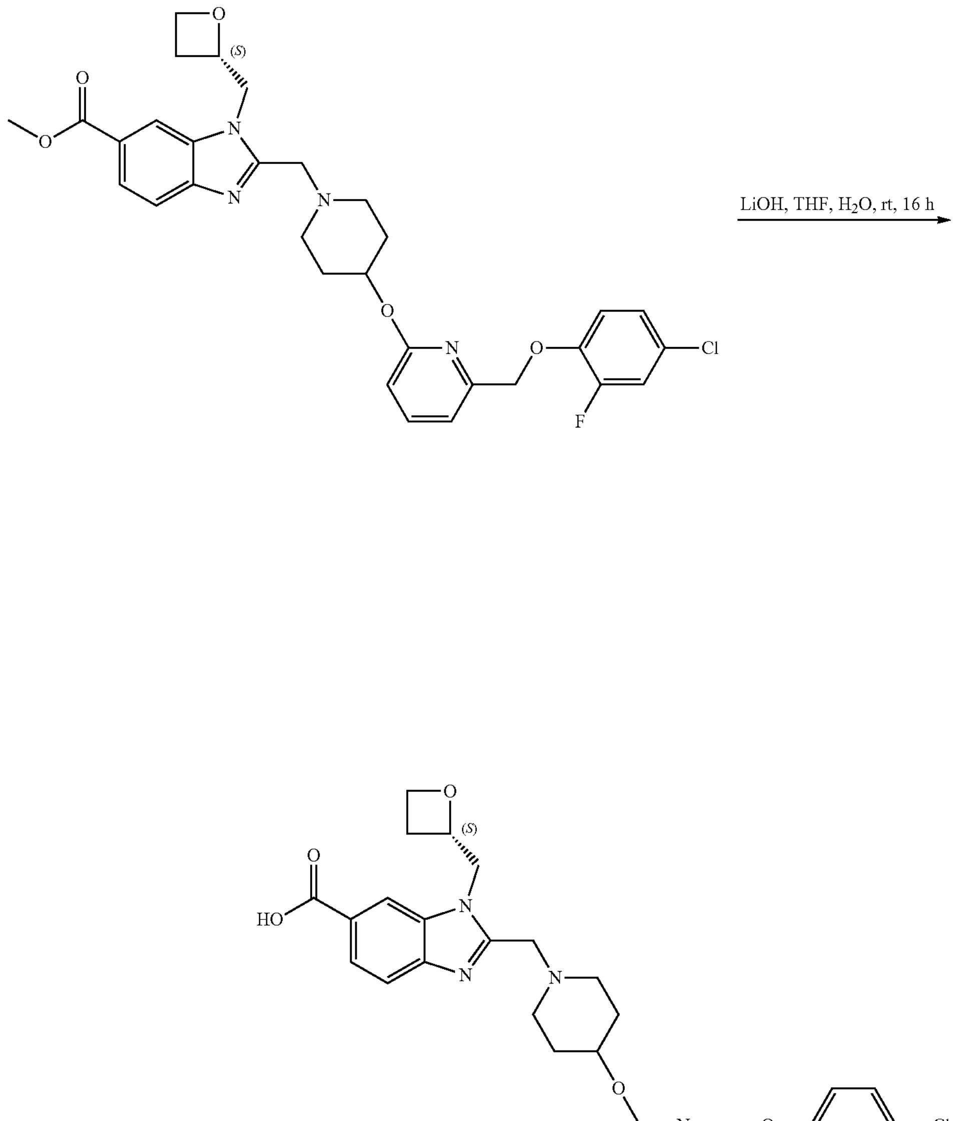

To a mixture of methyl(S)-2-((4-((6-((4-chloro-2-fluorophenoxy)methyl)pyridin-2-yl)oxy)piperidin-1-yl)methyl yl)-1-(oxetan-2-ylmethyl)-1H-benzo[d]imidazole-6-carboxylate (110 mg, 0.19 mmol) in THF (2 mL) and water (2 mL) lithium hydroxide (9 mg, 0.38 mmol) was added, and the reaction mixture was stirred at room temperature for 16 hours. After completion, the solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain(S)-2-((4-((6-((4-chloro-2-fluorophenoxy)methyl)pyridin-2-yl)oxy)piperidin-1-yl)methyl)-1-(oxetan-2-ylmethyl)-1H-benzo[d]imidazole-6-carboxylic acid (52.13 mg, 47.2% yield). LC-MS m/z: 581 $[M+H]^+$.

$^1$H NMR (400 MHZ, DMSO-$d_6$): δ8.27 (s, 1H), 7.80 (dd, J-8.4 Hz, 1.2 Hz, 1H), 7.72 (t, J-7.6 Hz, 1H), 7.64 (d, J=8.4 Hz, 1H), 7.44 (dd, J=11.2 Hz, 2.0 Hz, 1H), 7.28 (t, J=8.8 Hz, 1H), 7.18 (d, J=8.4 Hz, 1H), 7.04 (d, J=7.2 Hz, 1H), 6.72 (d, J=8.0 Hz, 1H), 5.18 (s, 2H), 5.12-5.06 (m, 1H), 4.95-4.93 (m, 1H), 4.81-4.76 (m, 1H), 4.66-4.62 (m, 1H), 4.51-4.49 (m, 1H), 4.38-4.36 (m, 1H), 3.94 (d, J=13.6 Hz, 1H), 3.78 (d, J=13.6 Hz, 1H), 2.79-2.67 (m, 2H), 2.46-2.41 (m, 1H), 2.32 (s, 2H), 1.92-1.91 (m, 2H), 1.63-1.59 (m, 2H).

Example 35. Synthesis of 2-((4-((6-((4-cyano-2-fluorophenoxy)methyl)pyridin-2-yl)oxy)piperidin-1-yl)methyl)-1-((1-ethyl-1H-imidazol-5-yl)methyl)-4-fluoro-1H-benzo[d]imidazole-6-carboxylic acid (compound 2)

1). Synthesis of methyl 4-(2-(4-((6-((4-cyano-2-fluorophenoxy)methyl)pyridin-2-yl)oxy)piperidin-1-yl)acetamido)-3-(((1-ethyl-1H-imidazol-5-yl)methyl)amino)-5-fluorobenzoate

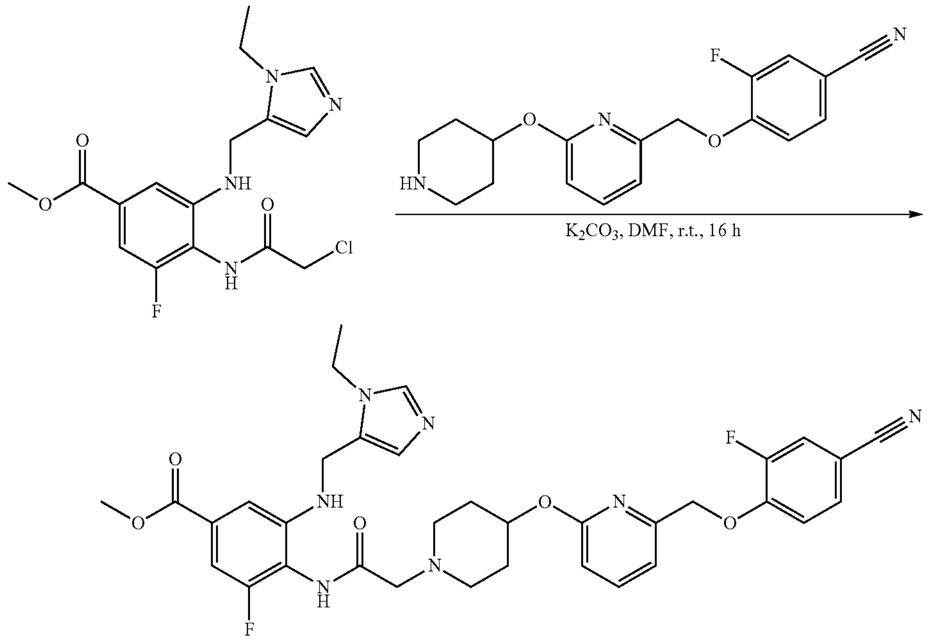

The mixture of methyl 4-(2-chloroacetamido)-3-((1-ethyl-1H-imidazol-5-yl)methyl)amino)-5-fluorobenzoate (130 mg, 0.35 mmol), 3-fluoro-4-((6-(piperidin-4-oxy)pyridin-2-yl)methoxy)benzonitrile (115 mg, 0.35 mmol) and potassium carbonate (146 mg, 1.05 mmol) in N,N-dimethylformamide (5 mL) was stirred at room temperature for 16 hours. The resulting mixture was diluted with water (50 mL) and extracted with ethyl acetate (10 mL×3). The organic layer were washed with brine (10 mL×3), and concentrated to give a residue in vacuo. The residue was purified by column chromatography (dichloromethane/methanol=20/1) to obtain methyl 4-(2-(4-((6-((4-cyano-2-fluorophenoxy)methyl)pyridin-2-yl)oxy)piperidin-1-yl)acetamido)-3-(((1-ethyl-1H-imidazol-5-yl)methyl)amino)-5-fluorobenzoate (70 mg, 30.3% yield). LC-MS m/z: 660 $[M+H]^+$.

2). Synthesis of methyl 2-((4-((6-((4-cyano-2-fluorophenoxy)methyl)pyridin-2-yl)oxy)piperidin-1-yl)methyl)-1-((1-ethyl-1H-imidazol-5-yl)methyl)-4-fluoro-1H-benzo[d]imidazole-6-carboxylate

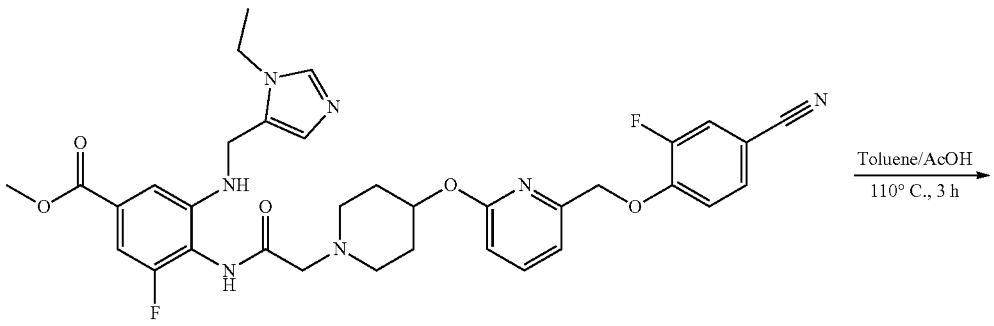

-continued

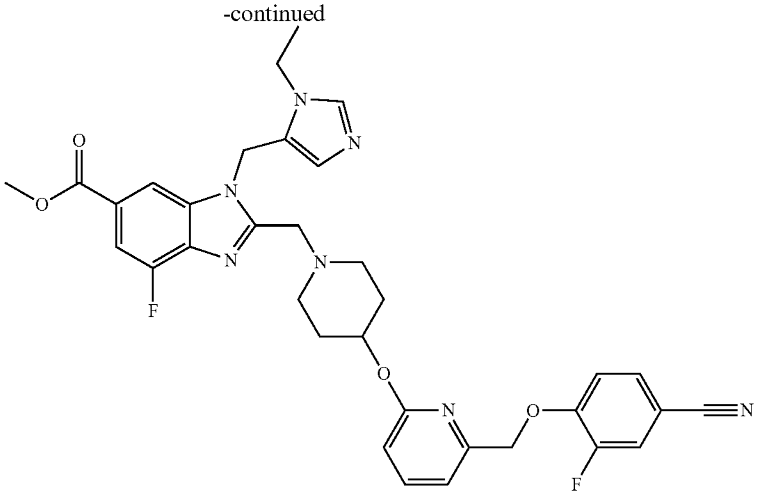

The mixture of methyl 4-(2-(4-((6-((4-cyano-2-fluorophenoxy)methyl)pyridin-2-yl)oxy)piperidin-1-yl)acetamido)-3-((1-ethyl-1H-imidazol-5-yl)methyl)amino)-5-fluorobenzoate (70 mg, 0.11 mmol) in toluene (2 mL) and acetic acid (0.5 mL) was stirred at 110° C. for 3 hours. After completion, The mixture was diluted with water (20 mL) and extracted with dichloromethane (2×25 mL). The organic phase was concentrated to give methyl 2-((4-((6-((4-cyano-2-fluorophenoxy)methyl)pyridin-2-yl)oxy)piperidin-1-yl)methyl)-1-((1-ethyl-1H-imidazol-5-yl)methyl)-4-fluoro-1H-benz-o [d]imidazole-6-carboxylate (40 mg, 56.7% yield). LC-MS m/z: 642 [M+H]$^+$.

3). Synthesis of 2-((4-((6-((4-cyano-2-fluorophenoxy)methyl)pyridin-2-yl)oxy)piperidin-1-yl)methyl)-1-((1-ethyl-1H-imidazol-5-yl)methyl)-4-fluoro-1H-benzo[d]imidazole-6-carboxylic acid

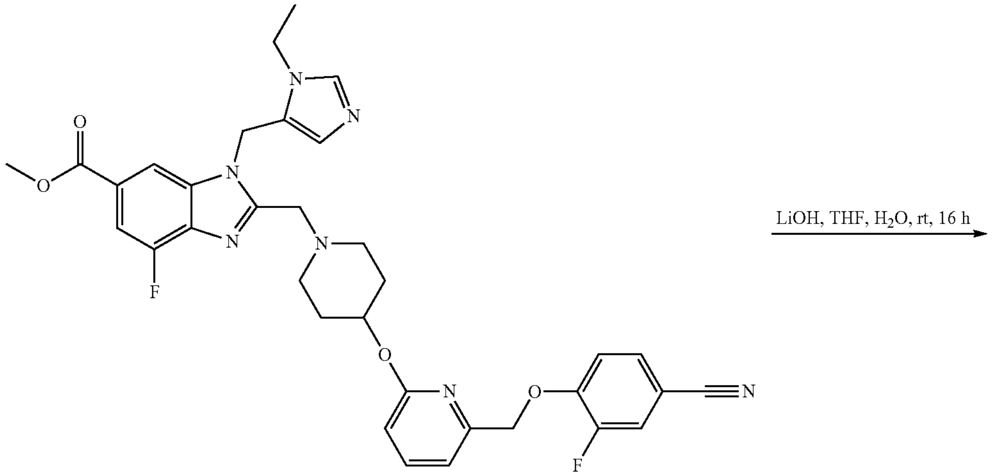

-continued

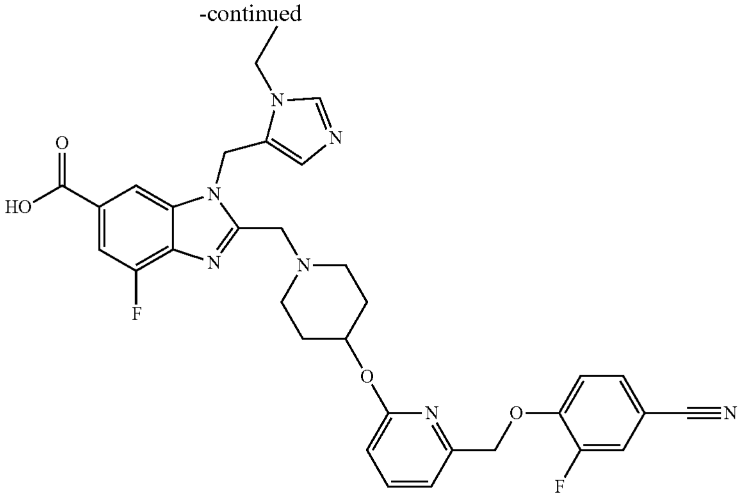

To a mixture of methyl 2-((4-((4-cyano-2-fluorophenoxy) methyl)pyridin-2-yl)oxypiperidin-1-yl)methyl)-1-((1-ethyl-1H-imidazol-5-yl)methyl)-4-fluoro-1H-benzo[d]imidazole-6-carboxylate (40 mg, 0.062 mmol) in THF (4 mL) and water (4 mL) lithium hydroxide (4 mg) was added, and the reaction was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidine-1-yl) methyl)-1-((1-ethyl-1H-imidazol-5-yl)methyl)-4-fluoro-1H-benzo[d]imidazole-6-carboxylic acid (8.49 mg, 22.6% yield). LC-MS m/z: 628 $[M+H]^+$.

$^1H$ NMR (400 MHz, DMSO-$d_6$): δ 8.20 (s, 1H), 7.93-7.86 (m, 2H), 7.74-7.65 (m, 3H), 7.52 (d, J=11.6 Hz 1 H), 7.43 (t, J=8.4 Hz 1 H), 7.04 (d, J=7.2 Hz 1 H), 6.72 (d, J=8.0 Hz 1 H), 6.42 (s, 1H), 5.74 (s, 2H), 5.30 (s, 2 H), 4.86-4.84 (m, 1H), 4.03-3.98 (m, 2H), 3.83 (s, 2H), 2.67 (s, 2H), 2.27-2.22 (m, 2H), 1.79-1.76 (m, 2H), 1.46-1.44 (m, 2H), 1.17 (t, J-7.2 Hz, 3H).

Example 36. Synthesis of(S)-2-((4-((6-((4-cyano-2-fluorophenylthio)methyl)pyridin-2-yl)oxy)piperidin-1-yl)methyl)-1-(oxetan-2-ylmethyl)-1H-benzo[d] imidazole-6-carboxylic acid (compound C10)

1). Synthesis of methyl(S)-2-((4-((6-((4-cyano-2-fluorophenyl)thio) methyl)pyridin-2-yl)oxy)piperidin-1-yl)methyl)-1-(oxetan-2-ylmethyl)-1H-benzo[d] imidazole-6-carboxylate

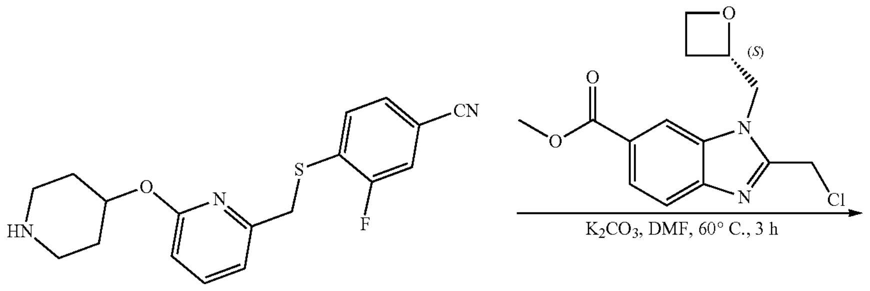

-continued

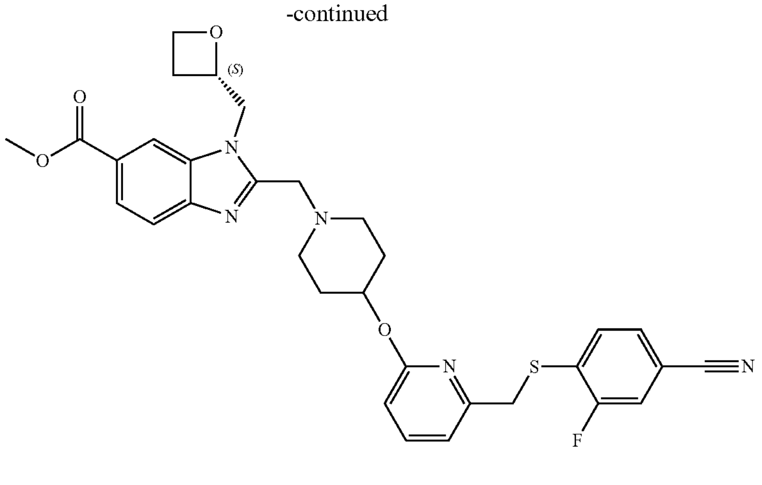

The mixture of 3-fluoro-4-((6-(piperidin-4-oxy)pyridin-2-yl)methylthio) benzonitrile (152 mg, 0.44 mmol), methyl (S)-2-(chloromethyl)-1-(oxetan-2-ylmethyl)-1H-benzo[d]imidazole-6-carboxylate (100 mg, 0.34 mmol) and potassium carbonate (140 mg, 1.02 mmol) in N,N-dimethylformamide (4 mL) was stirred at 60° C. for 3 hours. The resulting mixture was diluted with water (30 mL) and extracted with ethyl acetate (10 mL×3). The combined organic layers were washed with brine (10 mL×3), dried over anhydrous sodium sulfate, filtered, and concentrated to give a residue in vacuo. The residue was purified by silica gel column chromatography (dichloromethane/methanol=20/1) to give methyl(S)-2-((4-((6-((4-cyano-2-fluorophenylthio)methyl)) pyridin-2-yl)oxy)piperidin-1-yl) methyl)-1-(oxetan-2-ylmethyl)-1H-benzo[d]imidazole-6-carboxylate (150 mg, 56.6% yield). LC-MS m/z: 602 $[M+H]^+$.

2). Synthesis of(S)-2-((4-((6-((4-cyano-2-fluorophenylthio)methyl)pyridin-2-yl)oxy)piperidin-1-yl) methyl)-1-(oxetan-2-ylmethyl)-1H-benzo[d]imidazole-6-carboxylic acid

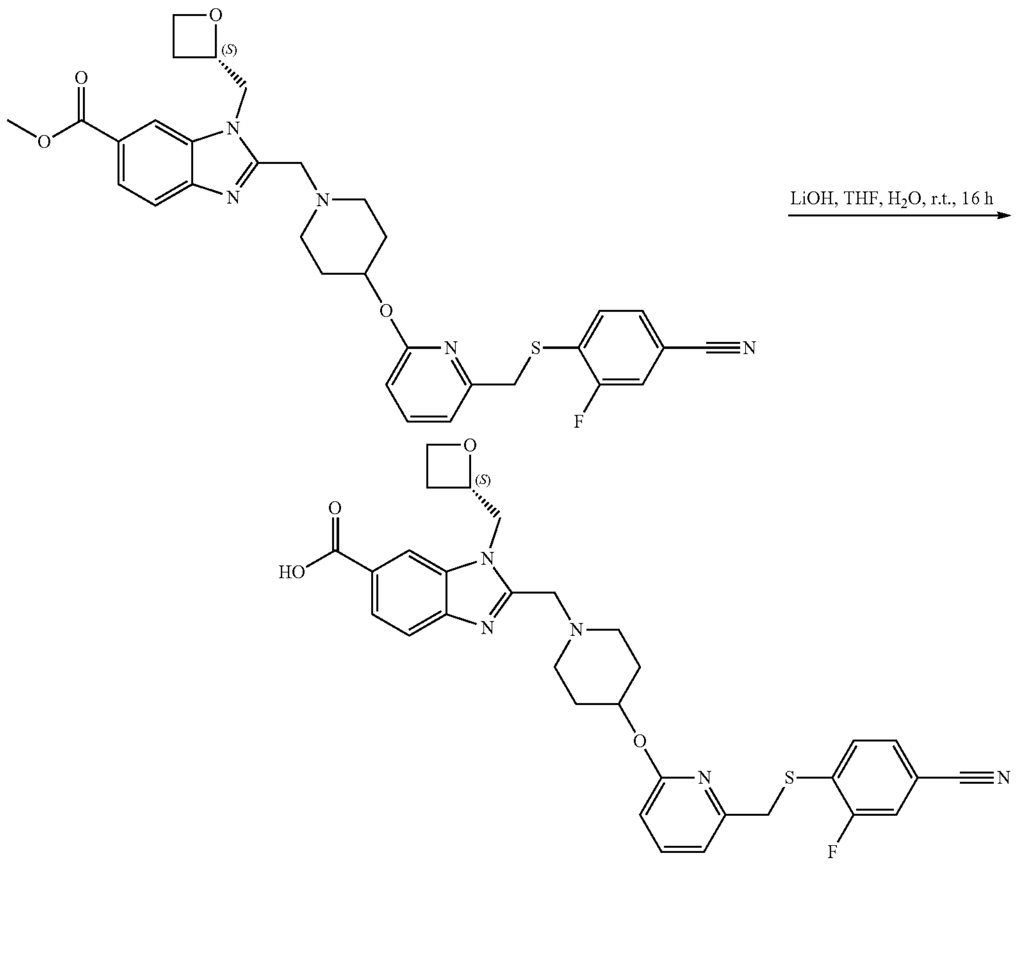

To a mixture of methyl(S)-2-((4-((6-((4-cyano-2-fluorophenylthio)methyl)pyridin-2-yl)oxy)piperidin-1-yl) methyl)-1-(oxetan-2-ylmethyl)-1H-benzo[d]imidazole-6-carboxylate (150 mg, 0.25 mmol) in THF (2 mL) and water (2 mL) lithium hydroxide (10 mg, 0.75 mmol) was added. The mixture was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain(S)-2-((4-((6-((4-cyano-2-fluorophenylthio)methyl)pyridin-2-yl)oxy)piperidin-1-yl)methyl)-1-(oxetan-2-ylmethyl)-1H-benzo[d]imidazole-6-carbo-xylic acid (40.33 mg, 27.4% yield). LC-MS m/z: 588 $[M+H]^+$. $^1H$ NMR (400 MHZ, DMSO-$d_6$): δ8.26 (s, 1H), 7.84-7.75 (m, 3H), 7.68-7.62 (m, 3H), 7.02 (d, J=7.2 Hz, 1 H), 6.65 (d, J=8.4 Hz, 1H), 5.10-5.08 (m, 1H), 4.81-4.75 (m, 2H), 4.66-4.61 (m, 1H), 4.53-4.47 (m, 1H), 4.41 (s, 2H), 4.39-4.36 (m, 1H), 3.93 (d, J=13.6, 1H), 3.77 (d, J=13.6 Hz, 1H), 2.77-2.67 (m, 4H), 2.46-2.41 (m, 1H), 2.28-2.23 (m, 2H), 1.91-1.86 (m, 2H), 1.59-1.55 (m, 2H).

Example 37. Synthesis of 2-((4-(3-((4-cyano-2-fluorobenzyl)oxy)phenoxy)piperidin-1-yl)methyl)-1-((1-(cyanomethyl)yl)cyclopropyl)methyl)-4-fluoro-1H-benzo[d]imidazole-6-carboxylic acid (compound S6)

1). Synthesis of N-(4-bromo-2-(((1-(cyanomethyl) cyclopropyl)methyl)amino)-6-fluorophenyl)-2-(4-(3-((4-cyano-2-fluorobenzyl)oxy)phenoxy)piperidin-1-yl)acetamido

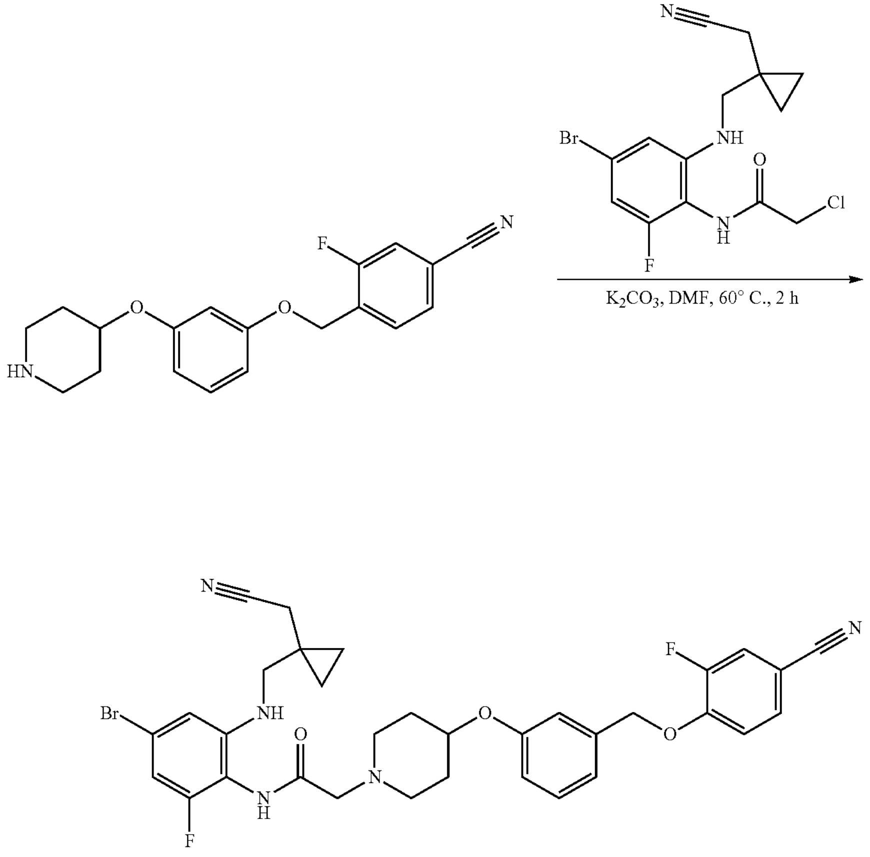 [SMILES: N#Cc1ccc(COc2cccc(OC3CCNCC3)c2)c(F)c1 ; N#CCC1(CNc2cc(Br)cc(F)c2NC(=O)CCl)CC1 ; N#CCC1(CNc2cc(Br)cc(F)c2NC(=O)CN2CCC(Oc3cccc(COc4ccc(C#N)cc4F)c3)CC2)CC1]

To a mixture of 3-fluoro-4-((3-(piperidin-4-oxy)phenoxy) methyl)benzonitrile (130 mg, 0.40 mmol) and N-(4-bromo-2-((1-(cyanomethyl)cyclopropyl)methyl)amino)-6-fluorophenyl)-2-chloroacetamido (149 mg, 0.40 mmol) in N,N-dimethylformamide (4 mL) K2$CO_3$ (165 mg, 1.20 mmol) was added. The mixture was stirred at 60° C. for 2 hours. The mixture was diluted with water (5 mL) and extracted with EA (2×30 mL).

The combined organic phases were washed with brine (20 mL), dried over anhydrous $Na_2SO_4$, filtered, and concentrated in vacuo to give N-(4-bromo-2-(((1-(cyanomethyl) cyclopropyl)methyl)amino)-6-fluorophenyl)-2-(4-(3-(((4-cyano-2-fluorobenzyl)oxy)phenoxy)piperidin-1-yl) acetamido (180 mg, 67.9% yield). LC-MS m/z: 666, 664 $[M+H]^+$.

2). Synthesis of 4-((3-((1-((6-bromo-1-((1-(cyanomethyl)cyclopropyl)methyl)-4-fluoro-1H-benzo[d]imidazole-2-yl)methyl)piperidin-4-yl)oxy)phenoxy)methyl)-3-fluorobenzonitrile

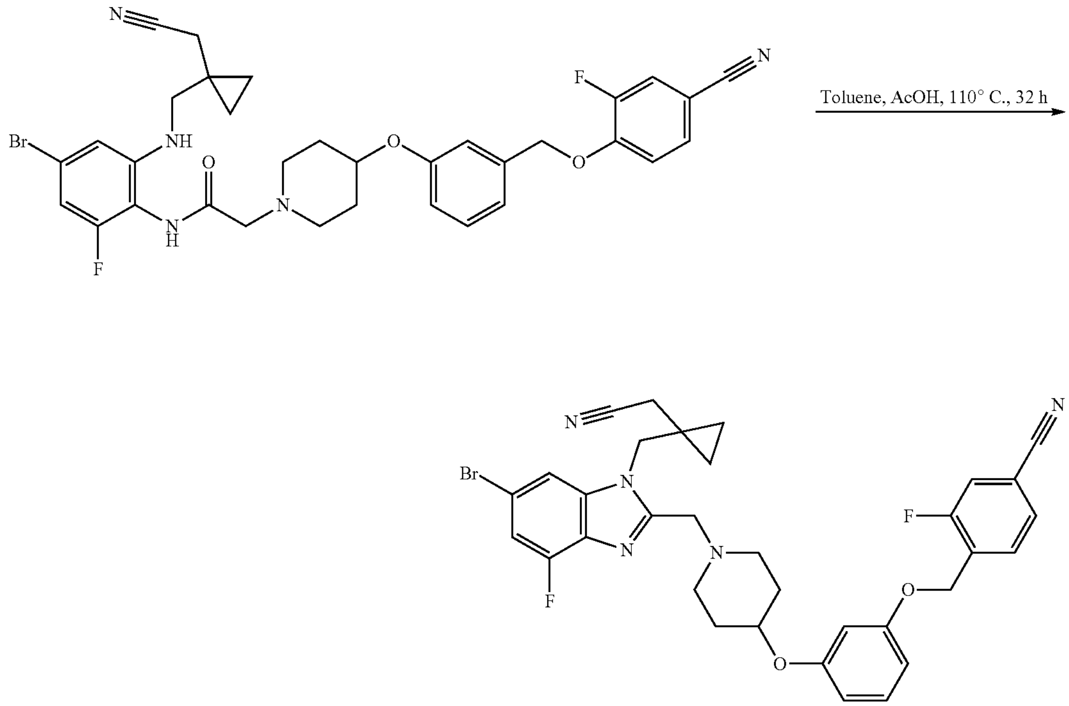 [SMILES: N#CCC1(CNc2cc(Br)cc(F)c2NC(=O)CN2CCC(Oc3cccc(COc4ccc(C#N)cc4F)c3)CC2)CC1 ; N#CCC1(Cn2c(CN3CCC(Oc4cccc(OCc5ccc(C#N)cc5F)c4)CC3)nc3c(F)cc(Br)cc32)CC1]

To a mixture of N-(4-bromo-2-((1-(cyanomethyl)cyclopropyl)methyl)amino)-6-fluorophenyl)-2-(4-(3-(((4-cyano-2-fluorobenzyl)oxy)phenoxy)piperidin-1-yl)acetamido (160 mg, 0.24 mmol) in toluene (6 mL) AcOH (1 mL) was added, and the mixture was stirred at 110° C. for 32 hours. The resulting mixture was poured into $H_2O$ (10 mL) and extracted with EA (2×10 mL). The combined organic layers were sequentially washed with saturated $NaHCO_3$ (2×10 mL), brine (10 mL×2), dried over anhydrous $Na_2SO_4$, filtered, and concentrated to give residue in vacuo. The residue was purified by reverse-phase column chromatography (Column: Spherical $C_{18}$ column, 20-40 μm, 120 g; Mobile Phase A: 10 mM $NH_4OH$ in water; Mobile Phase B: Acetonitrile; Flow Rate: 80 mL/min; Gradient: 60% B-80% B in 20 min; Detector: 254 nm). The fractions containing the desired product were collected at 69% B and concentrated in vacuo to obtain 4-((3-((1-((6-bromo-1-((1-(cyanomethyl)cyclopropyl)methyl)-4-fluoro-1H-benzo[d]imidazol-2-yl)methyl)piperidin-4-yl)oxy)phenoxy)methyl)-3-fluorobenzonitrile (142 mg, 91.3% yield). LC-MS m/z: 646, 648 $[M+H]^+$.

3). Synthesis of methyl 2-((4-(3-((4-cyano-2-fluorobenzyl)oxy)phenoxy)piperidin-1-yl)methyl)-1-((1-(cyanomethyl)-cyclopropyl)methyl)-4-fluoro-1H-benzo[d]imidazole-6-carboxylate

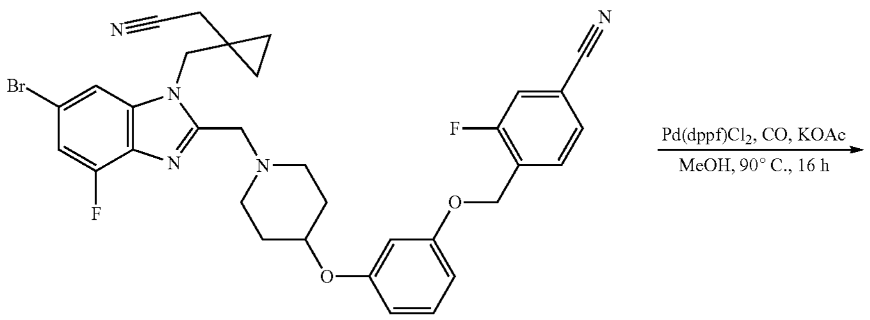

-continued

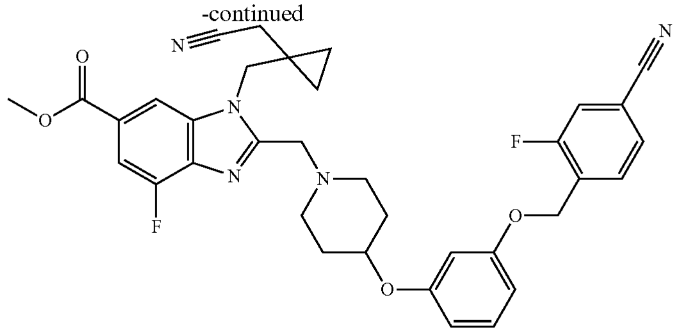

To a mixture of 4-((3-((1-((6-bromo-1-((1-(cyanomethyl) cyclopropyl)methyl)-4-fluoro-1H-benzo[d]imidazol-2-yl) methyl)piperidin-4-yl)oxy)phenoxy)methyl)-3-fluorobenzonitrile (130 mg, 0.20 mmol) in methanol (5 mL)) KOAc (59 mg, 0.60 mmol) and Pd (dppf) $C_12$ (15 mg, 0.02 mmol) were added at room temperature under carbon monoxide atmosphere. The mixture was stirred at 90° C. for 16 hours. The mixture was diluted with water (15 mL) and extract with ethyl acetate (3x30 mL). The combined organic layers were washed with brine (30 mL), dried over anhydrous $Na_2SO_4$, filtered, and concentrated to give a residue in vacuo.

The residue was purified by reverse phase column chromatography (Column: Spherical $C_{18}$ column, 20-40 μm, 120 g; Mobile Phase A: 10 mM $NH_4OH$ in water; Mobile Phase B: acetonitrile; Flow rate: 80 mL/min; Gradient: 60% B-80% B in 20 min; Detector: 254 nm) to obtain methyl 2-((4-(3-((4-cyano-2-fluorobenzyl)oxy)phenoxy)piperidin-1-yl)methyl)-1-((1-(cyanomethyl)cyclopropyl)methyl)-4-fluoro-1H-benzo[d]imidazole-6-carboxylate (60 mg, 47.5% yield). LC-MS m/z: 626 $[M+H]^+$.

4). Synthesis 2-((4-(3-((4-cyano-2-fluorobenzyl) oxy)phenoxy)piperidin-1-yl)methyl)-1-((1-(cyanomethyl)cyclopropyl)methyl)-4-fluoro-1H-benzo[d] imidazole-6-carboxylic acid

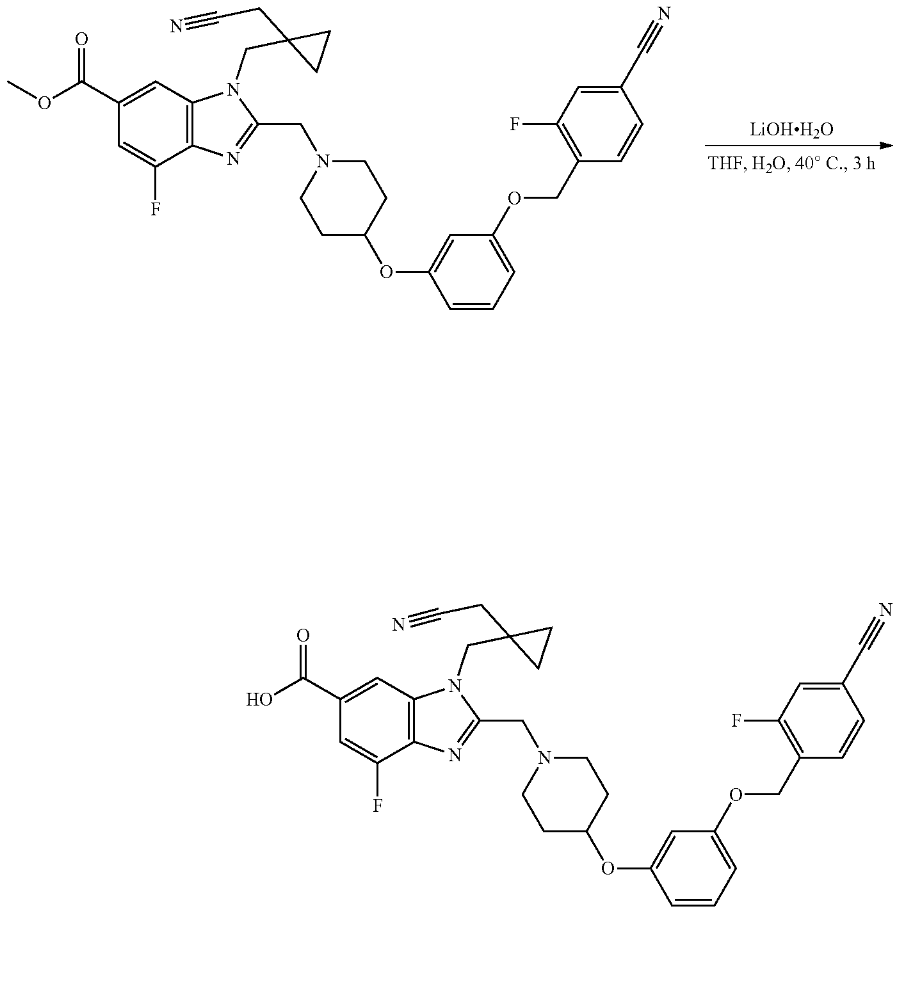

To a mixture of methyl 2-((4-(3-((4-cyano-2-fluorobenzyl)oxy)phenoxy)piperidin-1-yl)methyl)-1-((1-(cyanomethyl)cyclopropyl)methyl)-4-fluoro-1H-benzo[d]imidazole-6-carboxylate (60 mg, 0.10 mmol) in THF (2 mL) and $H_2O$ (2 mL) lithium hydroxide monohydrate (40 mg, 1.00 mmol) was added and stirred at 40° C. for 3 hours. The resulting mixture was adjusted to pH=5-6 with HCl (1 M) and extracted with EA (3× mL). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile Phase B: acetonitrile; Flow rate: 40 ml/min; Gradient: 20% B-50% B in 20 min; Detection Wavelength: 254 nm) to obtain 2-((4-(3-((4-cyano-2-fluorobenzyl)oxy)phenoxy))piperidin-1-yl) methyl)-1-((1-(cyanomethyl)cyclopropyl)methyl)-4-fluoro-1H-benzo[d]imidazole-6-carboxylic acid (26.23 mg, 43.5% yield). LC-MS m/z: 612 $[M+H]^+$. $^1H$ NMR (400 MHZ, DMSO-$d_6$) δ 8.04 (s, 1H), 7.91 (d, J=10.4 Hz, 1H), 7.75 (d, J=3.2 Hz, 2H), 7.49 (d, J=11.2 Hz, 1H), 7.17 (t, J=8.0 Hz, 1H), 6.62-6.57 (m, 3H), 5.21 (s, 2H), 4.60 (s, 2H), 4.42-4.40 (m, 1H), 3.85 (s, 2H), 2.79-2.77 (m, 2H), 2.70 (s, 2H), 2.38 (t, J-10.0 Hz, 2H), 1.93 (d, J=10.8 Hz, 2H), 1.64-1.60 (m, 2H), 0.75-0.67 (m, 4H).

Example 38. Synthesis of 2-((4-((6-((4-chloro-2-fluorobenzyl)oxy)-5-fluoropyridin-2-yl)oxy)piperidin-1-yl)methyl)-1-((1-ethyl-1H-imidazol-5-yl) methyl)-1H-benzo[d]imidazole-6-carboxylic acid (compound C11)

1). Synthesis of methyl 4-(2-(4-((6-((4-chloro-2-fluorobenzyl)oxy)-5-fluoropyridin-2-yl)oxy)piperidin-1-yl)acetamido)-3-((1-ethyl-1H-imidazol-5-yl) methyl)amino)benzoate

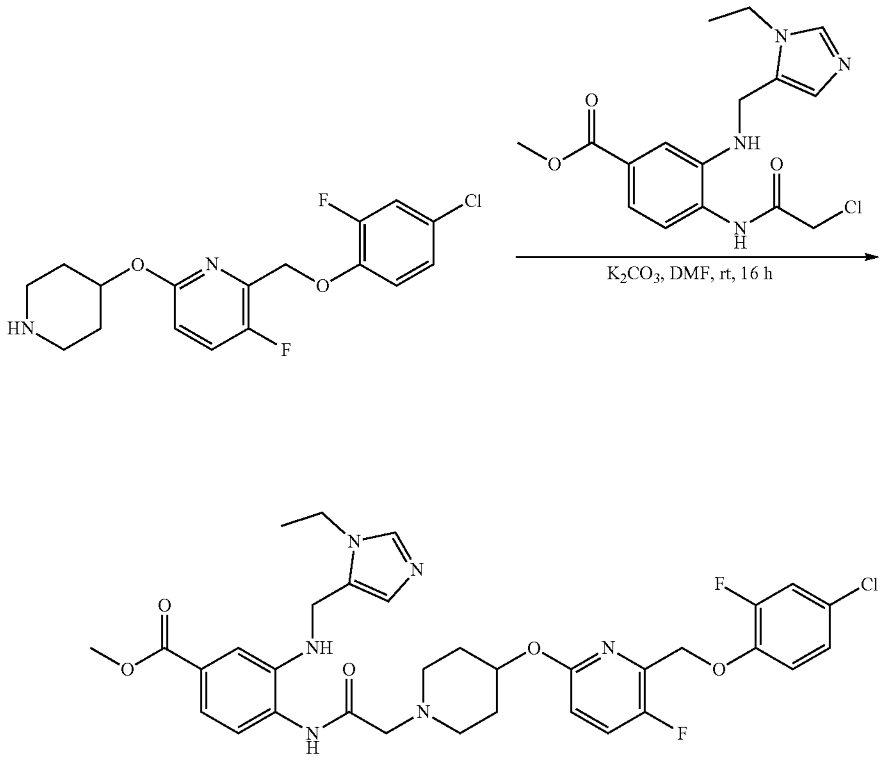 [SMILES: Fc1cc(Cl)ccc1OCc1nc(OC2CCNCC2)ccc1F ; CCn1cncc1CNc1cc(C(=O)OC)ccc1NC(=O)CCl ; CCn1cncc1CNc1cc(C(=O)OC)ccc1NC(=O)CN1CCC(Oc2ccc(F)c(COc3ccc(Cl)cc3F)n2)CC1]

The mixture of 2-((4-chloro-2-fluorobenzyl)oxy)-3-fluoro-6-(piperidin-4-oxy)pyridine (175 mg, 0.49 mmol), methyl 4-(2-chloroacetamido)-3-((1-ethyl-1H-imidazol-5-yl)methyl)amino)benzoate (184 mg, 0.49 mmol) and potassium carbonate (144 mg, 1.04 mmol) in N,N-dimethylformamide (5 mL) was stirred at room temperature for 16 hours. The resulting mixture was diluted with water (50 mL) and extracted with ethyl acetate (10 mL×3). The combined organic layers were washed with brine (10 mL×3), dried over anhydrous sodium sulfate, filtered, and concentrated to give a residue in vacuo. The residue was purified by silica gel column chromatography (dichloromethane/methanol=20/1) to obtain methyl 4-(2-(4-((6-((4-chloro-2-fluorobenzyl)oxy)-5-fluoropyridin-2-yl)oxy)piperidin-1-yl)acetamido)-3-((1-ethyl-1H-imidazol-5-yl)methyl)amino) benzoate (180 mg, 51.82% yield). LC-MS m/z: 669 $[M+H]^+$.

2). Synthesis of methyl 2-((4-((6-((4-chloro-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylate

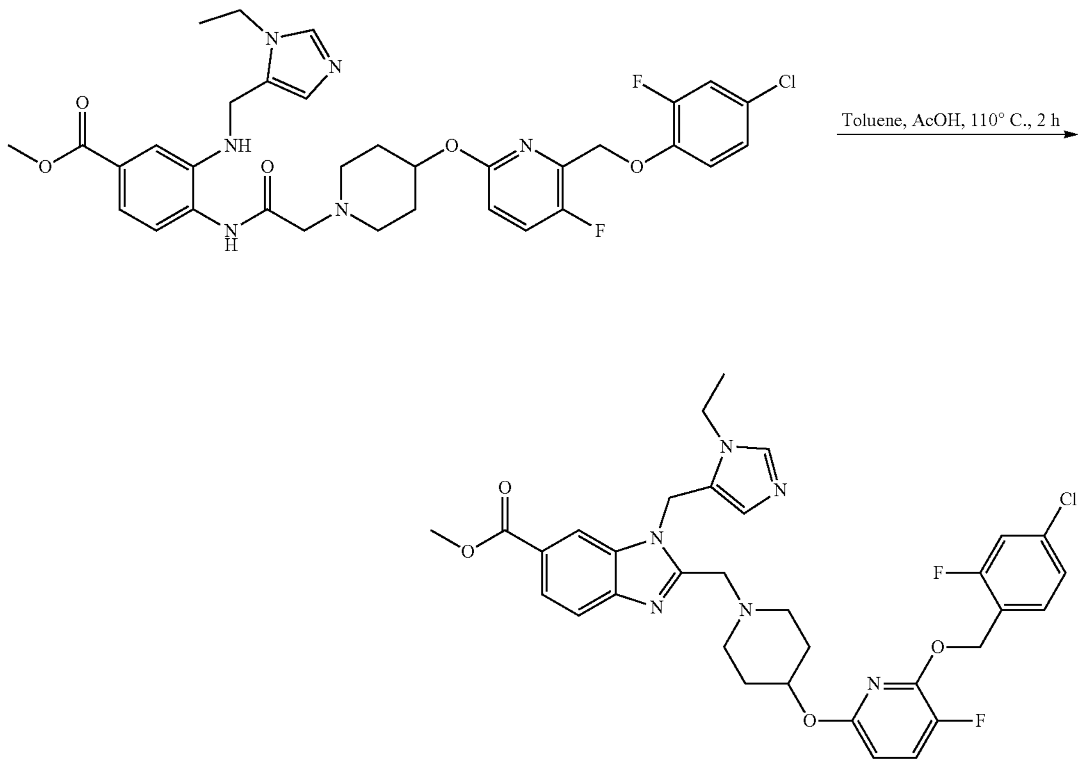

The mixture of methyl 4-(2-(4-((6-((4-chloro-2-fluorobenzyl)oxy)-5-fluoropyridin-2-yl)oxy)piperidin-1-yl)acetamido)-3-((1-ethyl-1H-imidazol-5-yl)methyl)amino)benzoate (180 mg, 0.27 mmol) in toluene (3 mL) and acetic acid (1 mL) was stirred at 110° C. for 2 hours. The resulting mixture was poured into brine (20 mL) and extracted with dichloromethane (2×10 mL). The combined organic layer was concentrated to give a residue in vacuo to obtain methyl 2-((4-((6-((4-chloro-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylate (140 mg, 77.9% yield). LC-MS m/z: 651 $[M+H]^+$.

3). Synthesis of 2-((4-((6-((4-chloro-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylic acid

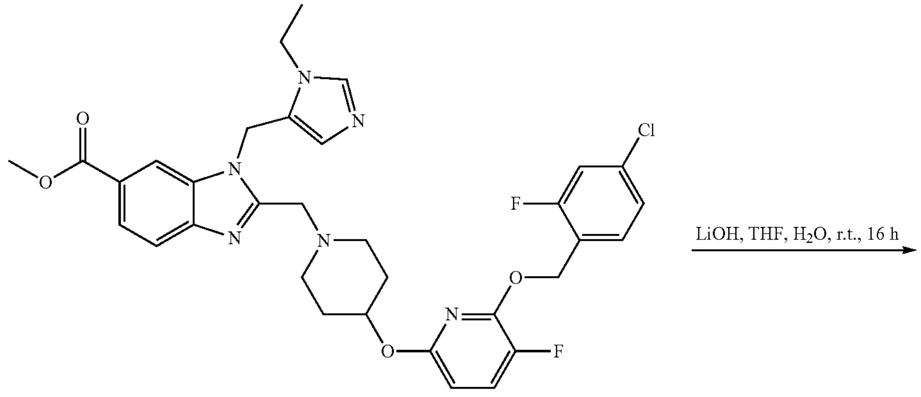

-continued

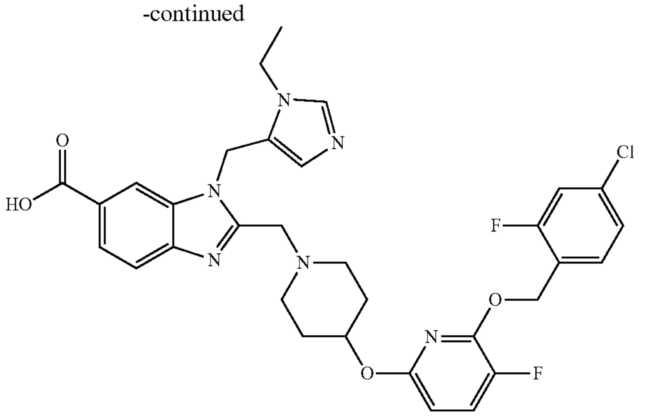

To a mixture of methyl 2-((4-((6-((4-chloro-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylate (70 mg, 0.11 mmol) in THF (4 mL) and water (4 mL) lithium hydroxide (8 mg, 0.33 mmol) was added. The mixture was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength 254 nm/214 nm; Flow rate 20 mL/min) to give 2-((4-((6-((4-chloro-2-fluorobenzyl)oxy)-5-fluoropyridin-2-yl)oxy)piperidine-1-yl)methyl)-1-((1-ethyl-1H-imidazol-5-yl)methyl)-1H-benzo[d]imidazole-6-carboxylic acid (37.86 mg, 54.1% yield). LC-MS m/z: 637 $[M+H]^+$.

$^1$H NMR (400 MHZ, DMSO-$d_6$): δ8.08 (s, 1H), 7.82 (d, J-8.4 Hz, 1H), 7.69-7.60 (m, 3H), 7.53-7.46 (m, 2 H), 7.31 (dd, J=8.4 Hz, 2.0 Hz, 1H), 6.42 (s, 1H), 6.33 (dd, J=8.8 Hz, 2.0 Hz, 1H), 5.72 (s, 2H), 5.43 (s, 2H), 4.74-4.71 (m, 1H), 4.03-3.98 (m, 2H), 3.82 (s, 2H), 2.69-2.67 (m, 2H), 2.29-2.24 (m, 2H), 1.79-1.77 (m, 2H), 1.46-1.42 (m, 2H), 1.16 (t, J-7.2 Hz, 3H).

Example 39. Synthesis of 2-((4-((6-((4-cyano-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylic acid (compound S66)

1). Synthesis of 2-((4-((6-((4-cyano-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylate

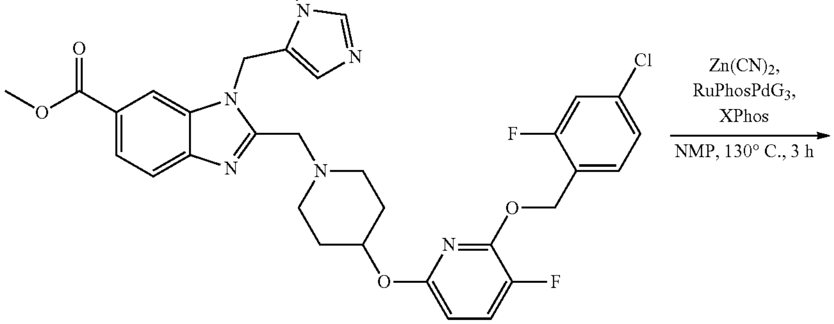

-continued

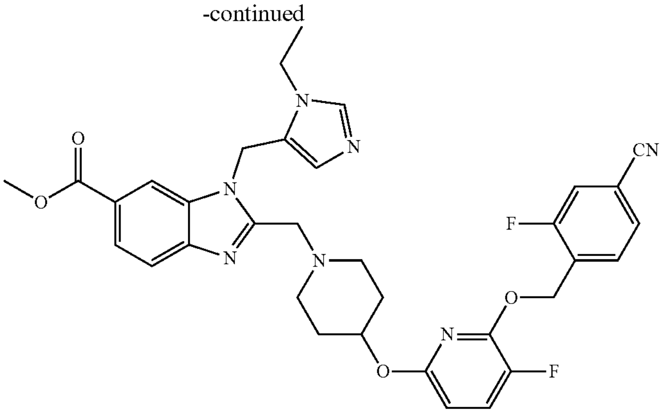

To a mixture of methyl 2-((4-((6-((4-chloro-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylate (132 mg, 0.20 mmol) and zinc cyanide (234 mg, 2.00 mmol) in N-methylpyrrolidone (2 mL) methanesulfonato (2-dicyclohexylphosphino-2',6'-di-1-propoxy-1,1'-biphenyl)(2'-amino-1,1'-biphenyl-2-yl) palladium (II) (17 mg, 0.02 mmol) and 2-dicyclohexylphosphine-2',4',6'-triiso propylbiphenyl (10 mg, 0.02 mmol) were added. The reaction mixture was stirred at 130° C. for 3 hours. After completion, the mixture was diluted with water (10 mL) and extracted with ethyl acetate (10 mL×2). The combined organic layers were washed with brine (10 mL×2), dried over anhydrous sodium sulfate, filtered, and concentrated to give a residue in vacuo. The residue was purified by pre-TLC chromatography (dichloromethane/methanol=20/1) to give methyl 2-((4-((6-((4-cyano-2-fluorobenzyl)oxy)-5-fluoropyridine-2-yl)oxy)piperidin-1-yl)methyl)-1-((1-ethyl-1H-imidazol-5-yl)methyl)-1H-benzo[d]imidazol-6-carboxylate (40 mg, 31.2% yield). LC-MS m/z: 642 $[M+H]^+$.

2). Synthesis of 2-((4-((6-((4-cyano-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylic acid

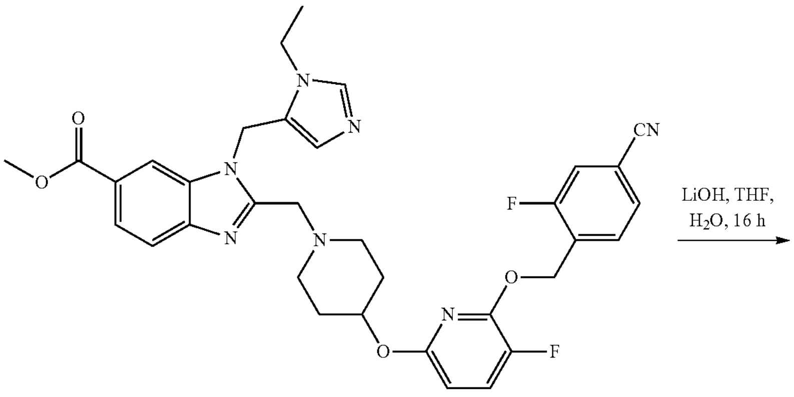

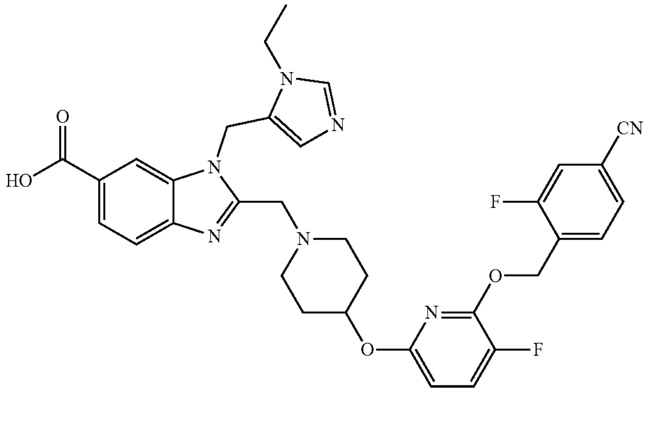

To a mixture of methyl 2-((4-((6-((4-cyano-2-fluorobenzyl)oxy)-5-fluoropyridin-2-yl)oxy)piperidin-1-yl)methyl)-1-((1-ethyl-1H-imidazol-5-yl)methyl)-1H-benzo[d]imidazole-6-carboxylate (40 mg, 0.06 mmol) in THF (4 mL) and water (4 mL) lithium hydroxide (4 mg, 0.17 mmol) was added. The mixture was stirred at room temperature for 16 hours. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength 254 nm/214 nm; Flow rate: 20 mL/min) to give 2-((4-((6-((4-cyano-2-fluorobenzyl)oxy)-5-fluoropyridin-2-yl)oxy)piperidin-1-yl)methyl)-1-((1-ethyl-1H-imidazol-5-yl)methyl)-1H-benzo[d]-imidazole-6-carboxylic acid (6.35 mg, 16.9% yield). LC-MS m/z: 628 $[M+H]^+$.

$^1$H NMR (400 MHZ, DMSO-$d_6$): δ8.07 (s, 1H), 7.93 (dd, J=9.6 Hz, 0.8 Hz, 1H), 7.81 (dd, J=8.4 Hz, 1.2 Hz, 1H), 7.73-7.62 (m, 5H), 6.40 (s, 1H), 6.34 (dd, J=8.4 Hz, 2.0 Hz, 1H), 5.71 (s, 2H), 5.52 (s, 2H), 4.65-4.63 (m, 1H), 4.03-3.97 (m, 2H), 3.81 (s, 2H), 2.67-2.65 (m, 2H), 2.25-2.20 (m, 2H), 1.74-1.71 (m, 2H), 1.43-1.36 (m, 2H), 1.16 (t, J=7.2 Hz, 3H).

Example 40. Synthesis of 2-((4-((6-(((4-cyano-2-fluorophenyl)thio) methyl)pyridin-2-yl)oxy)piperidin-1-yl)methyl)-1-((1-ethyl-1H-imidazol-5-yl) methyl)-1H-benzo[d]imidazole-6-carboxylic acid (compound C12)

1). Synthesis of methyl 4-(2-(4-((6-((4-cyano-2-fluorophenyl)thio) methyl)pyridin-2-yl)oxy)piperidin-1-yl)acetamido)-3-((1-ethyl-1H-imidazol-5-yl) methyl)amino)benzoate

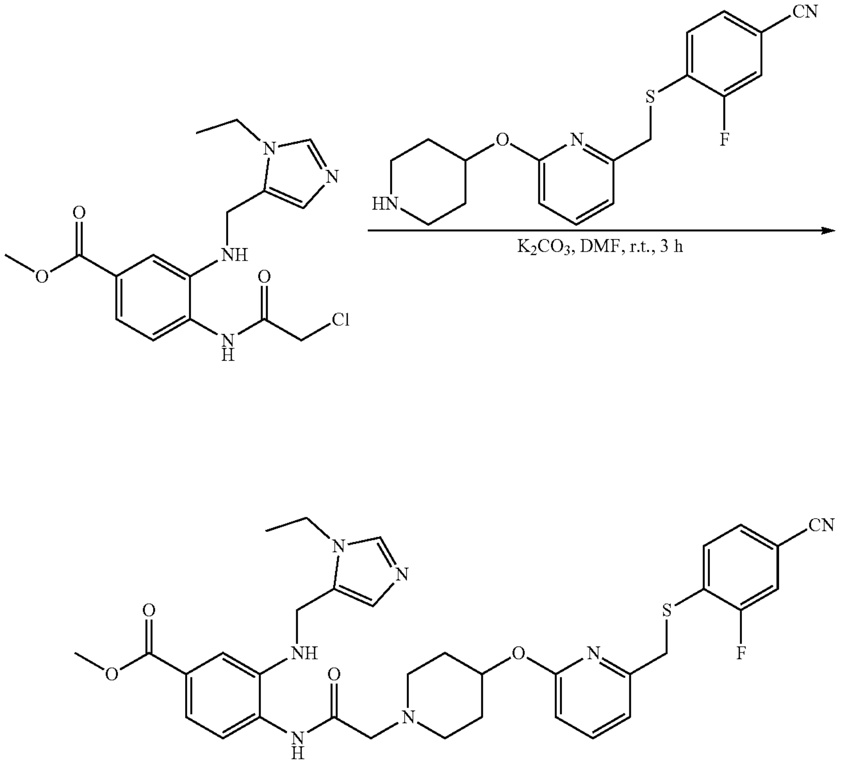 [SMILES: CCn1cncc1CNc1cc(C(=O)OC)ccc1NC(=O)CCl ; N#Cc1ccc(SCc2cccc(OC3CCNCC3)n2)c(F)c1 ; CCn1cncc1CNc1cc(C(=O)OC)ccc1NC(=O)CN1CCC(Oc2cccc(CSc3ccc(C#N)cc3F)n2)CC1]

To a solution of methyl 4-(2-chloroacetamido)-3-((1-ethyl-1H-imidazol-5-yl)methyl)amino)benzoate (176 mg, 0.50 mmol) in N,N-dimethylformamide (5 mL) potassium carbonate (138 mg, 1.00 mmol) and 3-fluoro-4-((6-(piperidin-4-oxy)pyridin-2-yl)methyl) sulfanyl)benzonitrile were added at room temperature (223 mg, 0.65 mmol). The mixture was stirred at room temperature for 3 hours. After completion, water (10 mL) was added to quench the reaction, and then it was extracted with ethyl acetate (15 mL×2). The combined organic layers were washed with brine (15 mL×2), dried over anhydrous sodium sulfate, filtered, and concentrated to give a residue in vacuo. The residue was purified by silica gel column chromatography (dichloromethane/methanol=10/1) to obtain methyl 4-(2-(4-((6-((4-cyano-2-fluorophenylthio)-methyl)) pyridin-2-yl)oxy)piperidin-1-yl)acetamido)-3-((1-ethyl-1H-imidazol-5-yl) methyl)amino)benzoate (141 mg, 42.9% yield). LC-MS m/z: 658 $[M+H]^+$.

2). Synthesis of methyl 2-((4-((6-(((4-cyano-2-fluorophenyl)thio) methyl)pyridin-2-yl)oxy)piperidin-1-yl)methyl)-1-((1-ethyl-1H-imidazol-5-yl)methyl)-1H-benzo[d]imidazole-6-carboxylate

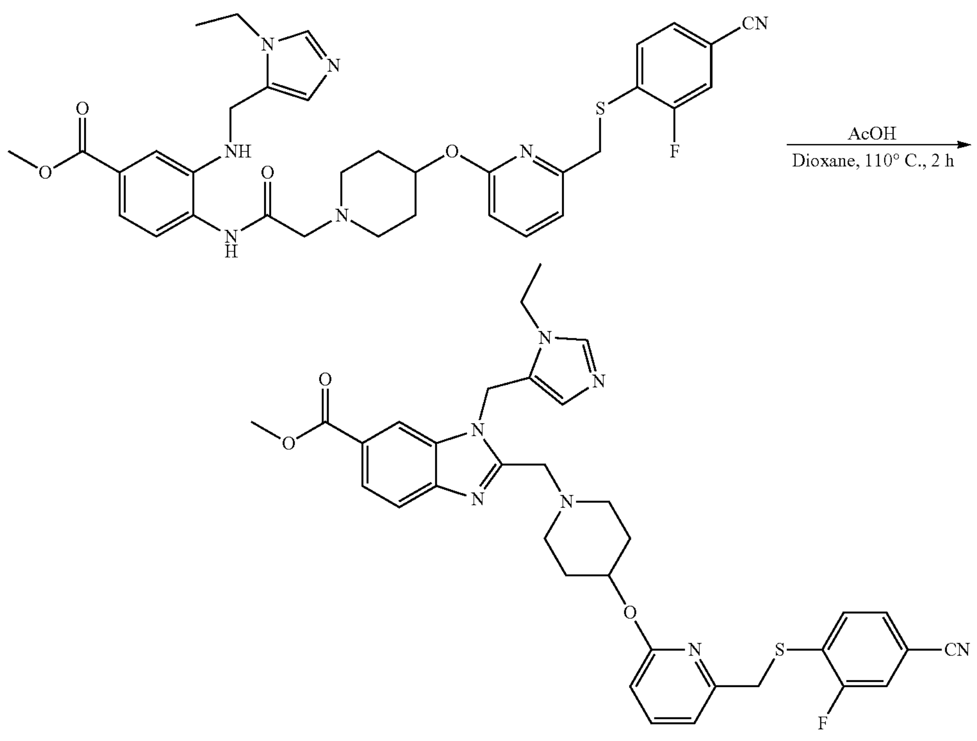

To a mixture of 4-(2-(4-((6-(((4-cyano-2-fluorophenyl) thio) methyl)pyridin-2-yl)oxy)piperidin-1-yl)acetamido)-3-((1-ethyl-1H-imidazol-5-yl)methyl)amino)benzoate (141 mg, 0.21 mmol) in dioxane (5 mL) acetic acid (0.5 mL) was added at room temperature. The mixture was stirred at 100° C. for 2 hours. After completion, the mixture was diluted with water (15 mL) and extracted with ethyl acetate (20 mL×2). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain methyl, 2-((4-((6-(((4-cyano-2-fluorophenyl)thio) methyl)pyridin-2-yl) oxy)piperidin-1-yl)methyl)-1-((1-ethyl-1H-imidazol-5-yl) methyl)-1H-be-nzo [d]imidazole-6-carboxylate (130 mg, 96.7% yield). LC-MS m/z: 640 $[M+H]^+$.

3). Synthesis of 2-((4-((6-(((4-cyano-2-fluorophenyl)thio) methyl)pyridin-2-yl)oxy)piperidin-1-yl) methyl)-1-((1-ethyl-1H-imidazol-5-yl)methyl)-1H-benzo[d]imidazole-6-carboxylic acid

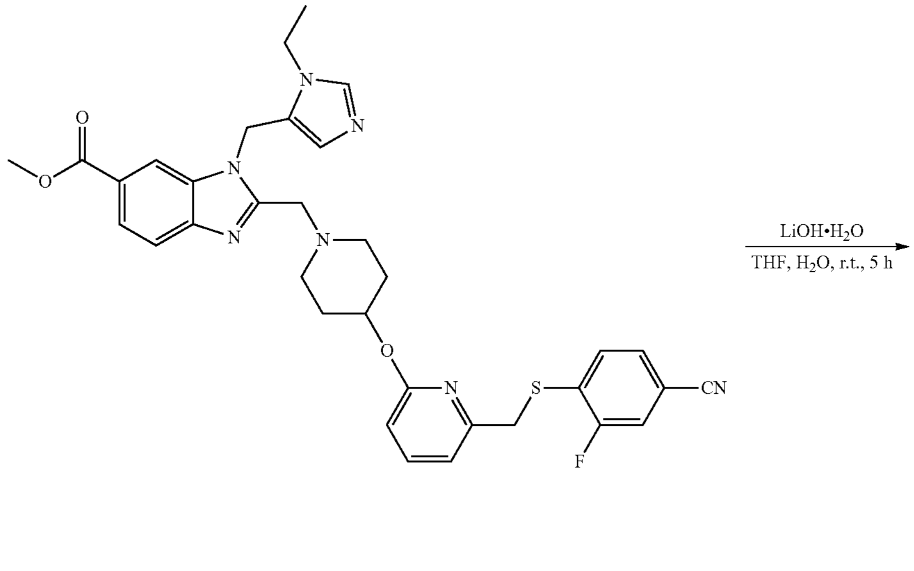

-continued

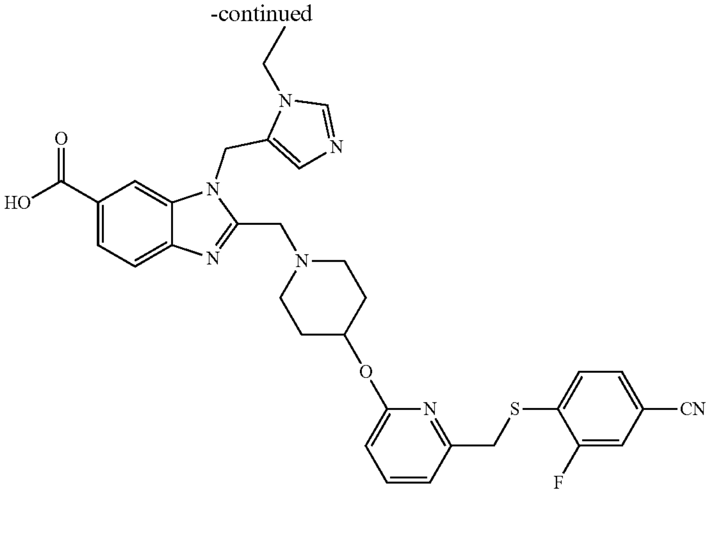

To a mixture of methyl 2-((4-((6-(((4-cyano-2-fluorophenyl)thio) methyl)pyridine-2-yl)oxy)piperidin-1-yl)methyl)-1-((1-ethyl-1H-imidazol-5-yl)methyl)-1H-benzo[d]imidazole-6-carboxylate (130 mg, 0.20 mmol) in THF (2 mL) and water (2 mL) lithium hydroxide monohydrate (85 mg, 2.00 mmol) was added at room temperature. The mixture was stirred at room temperature for 5 hours. After completion, the mixture was adjusted to pH=5-6 with formic acid, and extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile Phase B: acetonitrile; Flow rate: 40 mL/min; Gradient: 20% B-50% B in 20 min; Detector: 254 nm) to obtain 2-((4-((6-(((4-cyano-2-fluorophenyl)thio) methyl)pyridin-2-yl)oxy)piperidin-1-yl) methyl)-1-((1-ethyl-1H-imidazol-5-yl)methyl)-1H-benzo[d] imidazole-6-carboxylic acid (29.92 mg, 23.9% yield). LC-MS m/z: 626 $[M+H]^+$.

$^1H$ NMR (400 MHZ, DMSO-$d_6$) δ 8.07 (s, 1H), 7.83 (d, J=8.8 Hz, 2H), 7.76 (t, J=8.0 Hz, 1H), 7.69-7.61 (m, 4H), 7.02 (d, J=7.2 Hz, 1H), 6.64 (d, J=8.4 Hz, 1H), 6.41 (s, 1H), 5.71 (s, 2H), 4.75-4.74 (m, 1H), 4.40 (s, 2H), 4.04-3.98 (m, 2H), 3.80 (s, 2H), 2.67-2.64 (m, 2H), 2.21-2.17 (m, 2H), 1.76-1.74 (m, 2H), 1.44-1.41 (m, 2H), 1.16 (t, J=7.2 Hz, 3H).

Example 41. Synthesis of 2-((4-((6-(((4-cyano-2-fluorobenzyl)oxy)pyridin-2-yl)oxy)piperidin-1-yl) methyl)-1-((1-(cyanomethyl)cyclopropyl)methyl)-4-fluoro-1H-benzo[d]imidazole-6-carboxylic acid (compound S20)

1). Synthesis of N-(4-bromo-2-(((1-(cyanomethyl) cyclopropyl)methyl)amino)-6-fluorophenyl)-2-(4-((6-((4-cyano-2-fluorobenzyl)oxy)pyridin-2-yl)oxy) piperidin-1-yl)acetamide

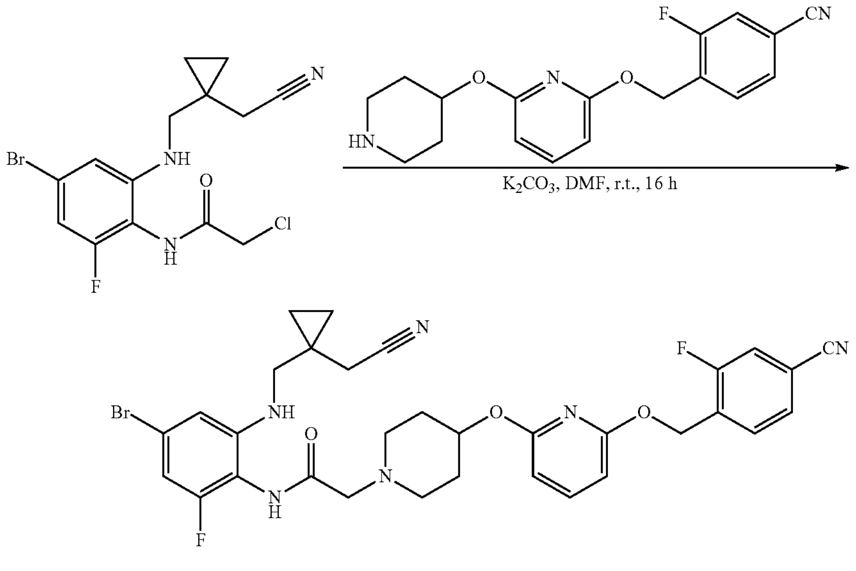

To a solution of N-(4-bromo-2-((1-(cyanomethyl)cyclopropyl)methyl)amino)-6-fluorophenyl)-2-chloroacetamide (100 mg, 0.27 mmol) in N,N-dimethylformamide (5 mL) 3-fluoro-4-((6-(piperidin-4-oxy)pyridin-2-yl)oxy)methyl) benzonitrile (88 mg, 0.27 mmol) and potassium carbonate (112 mg, 0.81 mmol) was added at room temperature. The mixture was stirred at room temperature for 16 hours. LCMS indicated the mixture was completed. The reaction was quenched by adding water (5 mL) and extracted with ethyl acetate (20 mL×3). The combined organic layers were washed with brine (20 mL×2), dried over anhydrous sodium sulfate, filtered, and concentrated to give N-(4-bromo-2-((1-(cyano-methyl)cyclopropyl))methyl)amino)-6-fluorophenyl)-2-(4-((6-((4-cyano-2-fluorobenzyl)oxy)pyridin-2-yl) oxy)-piperidi-ne-1-yl)acetamide (120 mg, 66.7% yield). LC-MS m/z: 665, 667 $[M+H]^+$.

2). Synthesis of 4-((6-((1-((6-bromo-1-((1-(cyanomethyl)cyclopropyl)methyl)-4-fluoro-1H-benzo[d] imidazole-2-yl)methyl)piperidin-4-yl)oxy)pyridin-2-yl)oxy)methyl)-3-fluorobenzonitrile

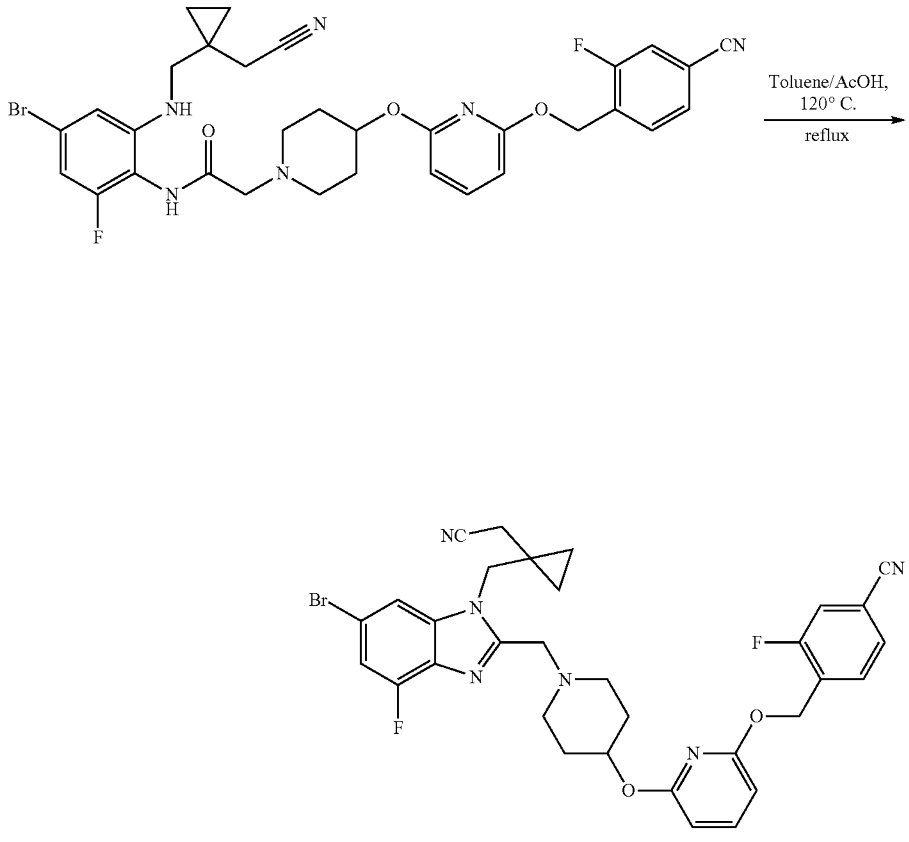

To a mixture of N-(4-bromo-2-((1-(cyanomethyl)cyclopropyl)methyl)amino)-6-fluorophenyl)-2-(4-((6-((4-cyano-2-fluorobenzyl)oxy)pyridin-2-yl)oxy)piperidin-1-yl)acetamide (120 mg, 0.18 mmol) in toluene (6 mL) acetic acid (1 mL) was added. The mixture was stirred at 120° C. for overnight. After completion, the mixture was poured into water (10 mL) and extracted with ethyl acetate (10 mL×2). The combined organic layer was washed with saturated sodium bicarbonate (10 mL×2) and brine (10 mL×2), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: 10 mM $NH_4OH$ in water; Mobile Phase B: acetonitrile; Flow rate: 80 mL/min; Gradient: 60% B-80% B in 20 min; Detector: 254 nm) to obtain 4-((6-((1-((6-bromo-1-((1-(cyanomethyl)cyclopropyl))methyl)-4-fluoro-1H-benzo[d]imidazol-2-yl)methyl)piperidin-4-yl)oxy)pyridin-2-yl)-oxy) methyl)-3-fluorobenzonitrile (100 mg, 83.3% yield). LC-MS m/z: 647, 649 $[M+H]^+$.

3). Synthesis of methyl 2-((4-((6-((4-cyano-2-fluorobenzyl)oxy)pyridin-2-yl)oxy)piperidin-1-yl)methyl)-1-((1-(cyanomethyl)cyclopropyl)methyl)-4-fluoro-1H-benzo[d]imidazole-6-carboxylate

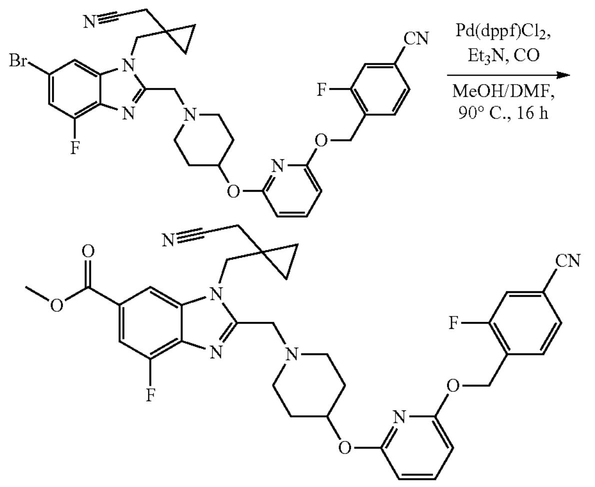

To a solution of 4-((6-((1-((6-bromo-1-((1-(cyanomethyl)cyclopropyl)methyl)-4-fluoro-1H-Benzo [d]imidazol-2-yl)methyl)piperidin-4-yl)oxy)pyridin-2-yl)oxy)methyl)-3-fluorobenzonitrile (100 mg, 0.15 mmol) in methanol/N,N-dimethylformamide (5 mL/5 mL) triethylamine (45 mg, 0.45 mmol) and 1,1'-bisdiphenylphosphinoferrocene palladium dichloride (15 mg, 0.02 mmol) were added at room temperature. The mixture was stirred at 90° C. for 16 hours under carbon monoxide atmosphere. After completion, water (15 ml) was added to quench the reaction. The mixture was extracted with ethyl acetate (30 mL×3). The combined organic layers were washed with brine (30 mL×2), dried over anhydrous sodium sulfate, filtered, and concentrated under reduced pressure. The residue was purified by reverse-phase flash chromatography under the following conditions (Column: Spherical C18, 20-40 μm, 120 g; Mobile Phase A: water 10 mM $NH_4OH$ in water; Mobile Phase B: acetonitrile; Flow rate: 80 mL/min; Gradient: 60% B-80% B in 20 min; Detector: 254 nm) to obtain methyl 2-((4-((6-((4-cyano-2-fluorobenzyl)oxy)pyridin-2-yl)oxy)piperidin-1-yl)methyl)-1-((1-(cyanomethyl)cyclopropyl)methyl)-4-fluoro-1H-benzo[d]imidazole-6-carboxylate (60 mg, 66.7% yield). LC-MS m/z: 627 $[M+H]^+$.

4). Synthesis of 2-((4-((6-((4-cyano-2-fluorobenzyl)oxy)pyridine-2-yl)oxy)piperidin-1-yl)methyl)-1-((1-(cyano-methyl)cyclopropyl)methyl)-4-fluoro-1H-benzo[d]imidazole-6-carboxylic acid

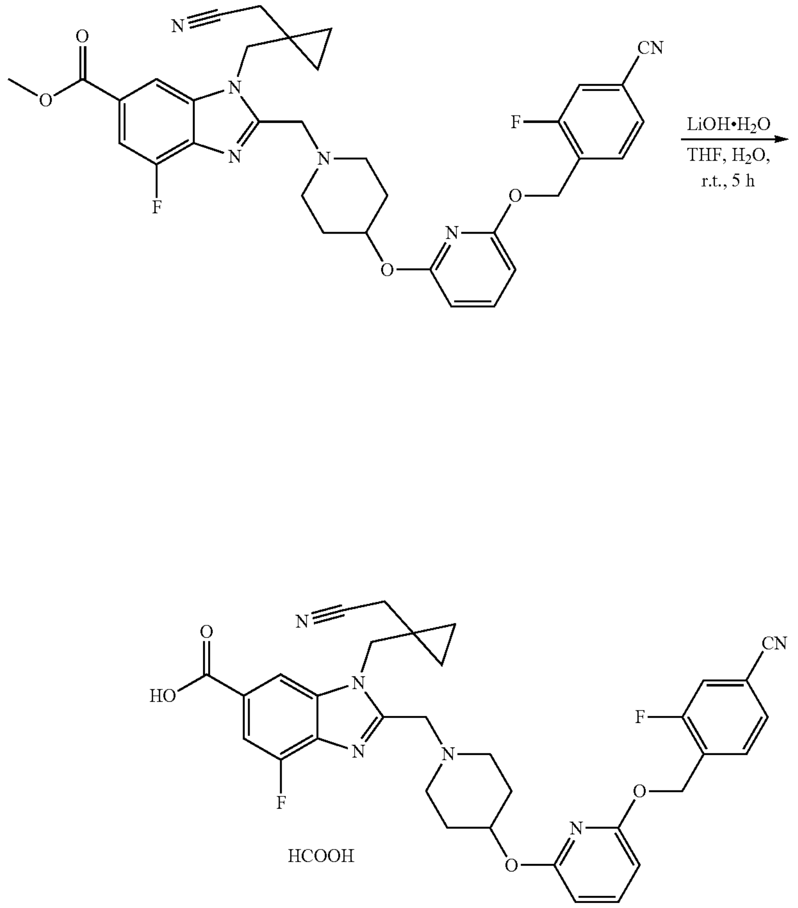

To a mixture of methyl 2-((4-((6-((4-cyano-2-fluorobenzyl)oxy)pyridin-2-yl)oxy)piperidin-1-yl)methyl)-1-((1-(cyanomethyl)cyclopropyl)methyl)-4-fluoro-1H-benzo[d]imidazole-6-carboxylate (60 mg, 0.10 mmol) in THF (3 mL) and water (3 mL) lithium hydroxide monohydrate (32 mg, 1.0 mmol) was added. The mixture was stirred at room temperature for 5 hours. After completion, the resulting mixture was adjusted to pH=5-6 with hydrochloric acid (1 M) and extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 120 g; Mobile Phase A: 10 mM $NH_4OH$ in water; Mobile Phase B: acetonitrile; Flow rate: 80 mL/min; Gradient: 30% B-50% B in 20 min; Detector: 254 nm) to obtain 2-((4-((6-((4-cyano-2-fluorobenzyl)oxy)pyridine-2-yl)oxy)piperidin-1-yl)methyl)-1-((1-(cyano-methyl)cyclopropyl)methyl)-4-fluoro-1H-benzo[d]imidazole-6-carboxylic acid (19.01 mg, 30% yield). LC-MS m/z: 613 $[M+H]^+$.

$^1H$ NMR (400 MHZ, DMSO-$d_6$): δ8.10 (s, 1H), 7.91 (dd, J=10.4, 1.6 Hz, 1H), 7.70 (dd, J=8.0, 1.2 Hz, 1 H), 7.63 (t, J=8.0 Hz, 2H), 7.53 (d, J=11.2 Hz, 1H), 6.45 (d, J=8.0 Hz, 1H), 6.35 (d, J=8.0 Hz, 1H), 5.45 (s, 2 H), 4.81-4.77 (m, 1H), 4.61 (s, 2H), 3.87 (s, 2H), 2.80-2.77 (m, 2H), 2.70 (s, 2H), 2.30 (t, J-9.6 Hz, 2H), 1.87 (d, J=9.6 Hz, 2H), 1.60-1.54 (m, 2H), 0.77-0.68 (m, 4H).

Example 42. Synthesis of 2-((4-((6-(((4-cyano-2-fluorophenyl)thio) methyl)pyridin-2-yl)oxy)piperidin-1-yl)methyl)-1-((1-(cyanomethyl)cyclopropyl) methyl)-1H-benzo[d]imidazole-6-carboxylic acid (compound C13)

1). Synthesis of methyl 4-(2-(4-((6-(((4-cyano-2-fluorophenyl)thio) methyl)pyridin-2-yl)oxy)piperidin-1-yl)acetamido)-3-((1-(cyanomethyl)cyclopropyl)methyl)amino)benzoate

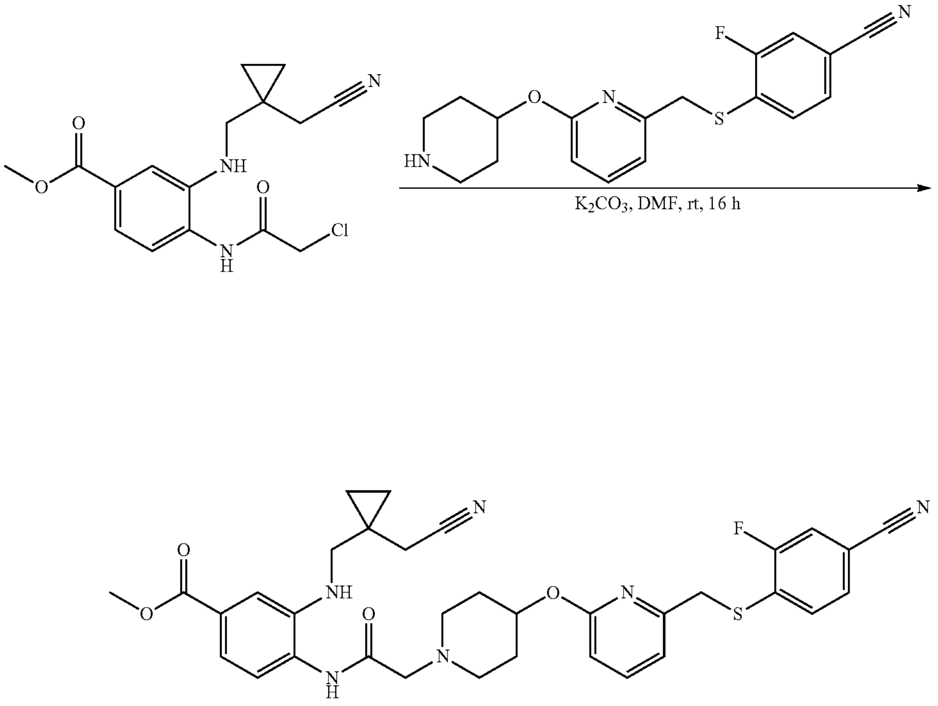

The mixture of methyl 4-(2-chloroacetamido)-3-((1-(cyanomethyl)cyclopropyl)methyl)amino)benzoate (210 mg, 0.63 mmol), 3-fluoro-4-((6-(piperidin-4-oxy)pyridin-2-yl) methyl)thio) benzonitrile (214 mg, 0.63 mmol) and potassium carbonate (259 mg, 1.89 mmol) in N,N-dimethylformamide (5 mL) was stirred at room temperature for 16 hours. After completion, the resulting mixture was diluted with water (40 mL) and extracted with ethyl acetate (20 mL×2). The combined organic layers were washed brine (20 mL×2) and concentrated to give a residue in vacuo. The residue was purified by silica gel column chromatography (dichloromethane/=20/1) to obtain methyl 4-(2-(4-((6-(((4-cyano-2-fluorophenyl)thio) methyl)pyridin-2-yl)oxy)piperidin-1-yl)acetamido)-3-((1-(cyanomethyl)cyclopropyl) methyl)amino)-benzoate (300 mg, 28.6% yield). LC-MS m/z: 643 $[M+H]^+$.

2). Synthesis of methyl 2-((4-((6-(((4-cyano-2-fluorophenyl)thio) methyl)pyridin-2-yl)oxy)piperidin-1-yl)methyl)-1-((1-(cyanomethyl)cyclopropyl)methyl)-1H-benzo[d]imidazole-6-carboxylate

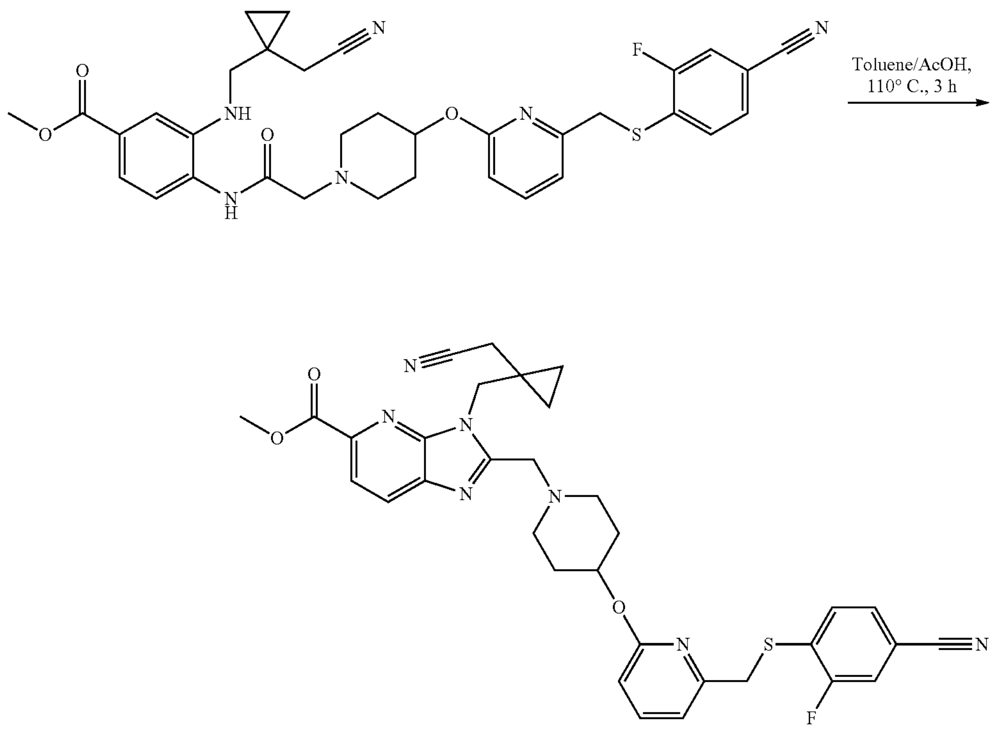

The mixture of methyl 4-(2-(4-((6-(((4-cyano-2-fluorophenyl)thio) methyl)pyridin-2-yl)oxy)piperidin-1-yl)-acetamido)-3-((1-(cyanomethyl)cyclopropyl)methyl)amino) benzoate (300 mg, 0.47 mmol) in toluene (5 mL) and acetic acid (0.5 mL) was stirred at 110° C. for 3 hours. After completion, the resulting mixture was diluted with water (60 mL) and extracted with ethyl acetate (30 mL×2). The combined organic layers were washed with brine (30 mL×2), and concentrated to give a residue in vacuo. The residue was purified by silica gel column chromatography (dichloromethane/methanol=20/1) to obtain methyl 2-((4-((6-(((4-cyano-2-fluorophenyl)thio) methyl)pyridin-2-yl) oxy)-piperidin-1-yl)methyl)-1-((1-(cyanomethyl)cyclopropyl)methyl)-1H-benzo[d]imidazole-6-carboxylate (200 mg, 68.1% yield). LC-MS m/z: 625 [M+H]$^+$.

3). Synthesis of 2-((4-((6-(((4-cyano-2-fluorophenyl)thio) methyl)pyridin-2-yl)oxy)piperidin-1-yl) methyl)-1-((1-(cyanomethyl)cyclopropyl)methyl)-1H-benzo[d]imidazole-6-carboxylic acid

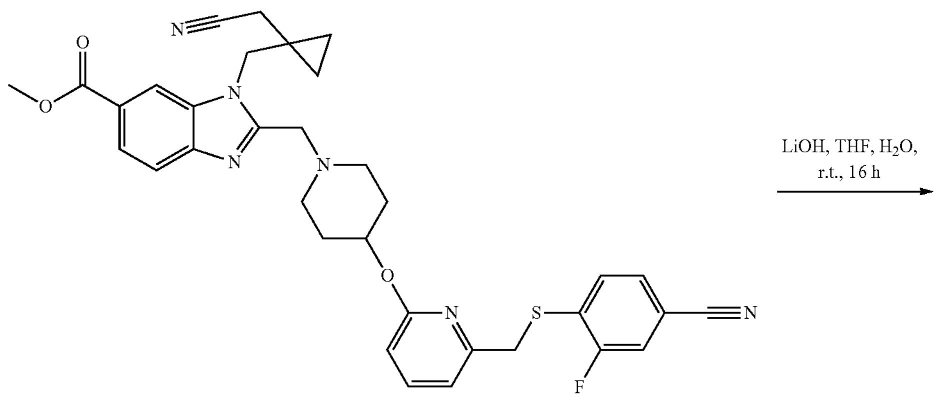

-continued

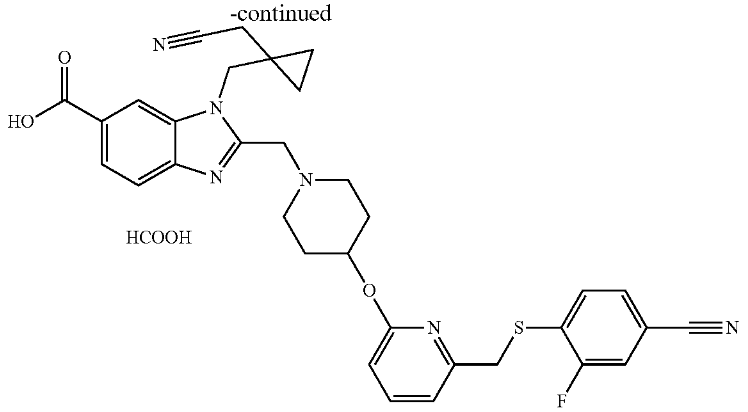

To a mixture of methyl 2-((4-((6-((4-cyano-2-fluorosulfanyl)methyl) pyridin-2-yl)oxy)piperidin-1-yl)methyl)-1-((1-(cyanomethyl)cyclopropyl)methyl)-1H-benzo[d]imidazole-6-carboxylate (200 mg, 0.33 mmol) in THF (2 mL) and water (2 mL) lithium hydroxide (24 mg, 0.99 mmol) was added at room temperature. The mixture was stirred at room temperature for 16 hours. After completion, the solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) purification to obtain 2-((4-((6-(((4-cyano-2-fluorophenyl)thio) methyl)pyridin-2-yl)oxy)piperidin-1-yl) methyl)-1-((1-(cyanomethyl)cyclopropyl)methyl)-1H-benzo[d]imidazole-6-carboxylic acid formic salt (51.79 mg, 25.7% yield). LC-MS m/z: 611 $[M+H]^+$. $^1H$ NMR (400 MHZ, DMSO-$d_6$): δ8.25 (s, 1H), 8.19 (s, 1H), 7.84-7.75 (m, 3H), 7.68-7.62 (m, 3H), 7.02 (d, J-6.8 Hz, 1H), 6.65 (d, J=8.0 Hz, 1H), 4.83-4.79 (m, 1H), 4.60 (s, 2H), 4.41 (s, 2H), 3.85 (s, 2H), 2.79-2.76 (m, 2H), 2.68 (s, 2H), 2.29-2.24 (m, 2H), 1.89-1.87 (m, 2H), 1.61-1.55 (m, 2H), 0.75-0.68 (m, 4H).

Example 43. Synthesis of 1-((1-ethyl-1H-imidazol-5-yl)methyl)-2-((4-((4-ethynyl-2-fluorophenoxy)-methyl)pyridin-2-yl)oxypiperidin-1-yl)methyl)-1H-benzo[d]imidazole-6-carboxylic acid (compound C14)

1). Synthesis of 1-((1-ethyl-1H-imidazol-5-yl) methyl)-2-((4-((6-((2-fluoro-4-((trimethylsilyl)ethynyl)benzene)methyl)oxy)methyl)pyridin-2-yl)oxy) piperidin-1-yl)methyl)-1H-benzo[d]imidazole-6-carboxylate

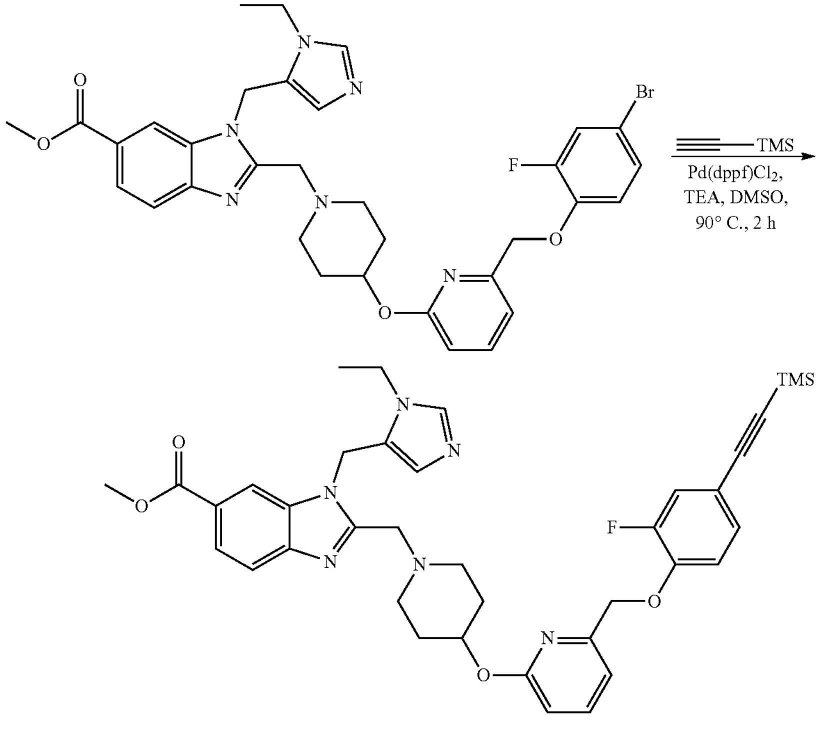

The mixture of methyl 2-((4-((6-((4-bromo-2-fluorophenoxy)methyl)pyridin-2-yl)oxy)piperidin-1-yl)methyl)-1-((1-ethyl-1H-imidazol-5-yl)methyl)-1H-benzo[d]imidazole-6-carboxylate (240 mg, 0.35 mmol), ethynyltrimethylsilane (343 mg, 3.50 mmol), 1,1'-bisdiphenylphosphinoferrocene palladium dichloride (26 mg, 0.035 mmol) and triethylamine (354 mg, 3.50 mmol) was stirred at 90° C. for 2 hours. After the reaction mixture was completed, it was diluted with water (10 mL) and extracted with ethyl acetate (10 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain methyl 1-((1-ethyl-1H-imidazol-5-yl)methyl)-2-((4-((6-((2-fluoro-4-((trimethylsilyl) ethynyl) phenoxy)methyl)pyridin-2-yl)oxy)piperidin-1-yl)methyl)-1H-benzene [d]-imidazole-6-carboxylate (190 mg, 77.2% yield). LC-MS m/z: 695 $[M+H]^+$.

2). Synthesis of 1-((1-ethyl-1H-imidazol-5-yl) methyl)-2-((4-((4-ethynyl-2-fluorophenoxy)methyl) pyridin-2-yl)oxypiperidin-1-yl)methyl)-1H-benzo[d] imidazole-6-carboxylic acid

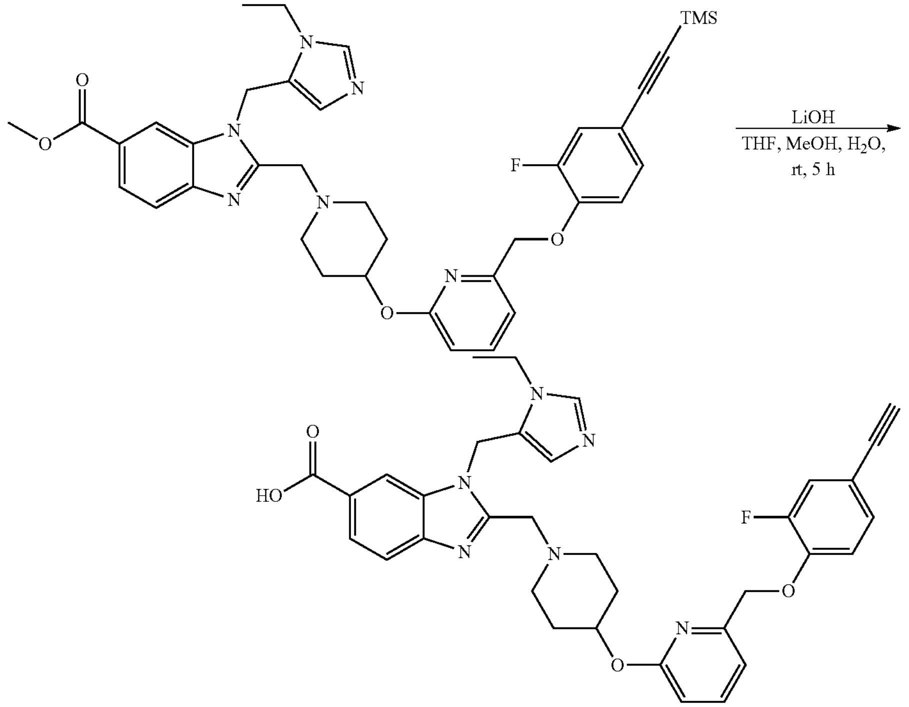

To a mixture of methyl 1-((1-ethyl-1H-imidazol-5-yl) methyl)-2-((4-((6-((2-fluoro-4-((trimethylsilyl)) ethynyl) phen-oxy)methyl)pyridin-2-yl)oxy)piperidin-1-yl) methyl)-1 H-benzo[d]imidazole-6-carboxylate (160 mg, 0.23 mmol) in methanol (1.0 mL), water (1.0 mL) and THF (1.0 mL) lithium hydroxide (44 mg, 1.84 mmol) was added. The reaction mixture was stirred at room temperature for 5 hours. After the completion of the reaction, the reaction mixture was adjusted to pH=5-6 by with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to give 1-((1-ethyl-1H-imidazol-5-yl)methyl)-2-((4-((4-ethynyl-2-fluorophenoxy))methyl) pyridin-2-yl)oxypiperidin-1-yl)methyl)-1H-benzo[d]imidazole-6-carboxylic acid (14.25 mg, 10.2% yield). LC-MS m/z: 609 $[M+H]^+$.

$^1H$ NMR (400 MHZ, DMSO-$d_6$): δ8.06 (s, 1H), 7.81 (dd, J=8.4 Hz, J=1.2 Hz, 1H), 7.73-7.65 (m, 3H), 7.39-7.36 (m, 1H), 7.24-7.23 (m, 2H), 7.03 (d, J=7.2 Hz, 1H), 6.71 (d, J=8.0 Hz, 1H), 6.41 (s, 1H), 5.71 (s, 2 H), 5.20 (s, 2H), 4.92-4.84 (m, 1H), 4.11 (s, 1H), 4.01-3.99 (m, 2H), 3.81 (s, 2H), 2.68-2.66 (m, 2H), 2.26-2.20 (m, 2H), 1.83-1.75 (m, 2H), 1.52-1.42 (m, 2H), 1.16 (t, J=7.2 Hz, 3H).

Example 44. Synthesis of(S)-2-((4-((6-((4-ethynyl-2-fluorophenoxy)methyl)pyridin-2-yl)oxy)piperidin-1-yl)methyl)-1-(oxetan-2-ylmethyl)-1H-benzo[d]imidazole-6-carboxylic acid (compound C15)

1). Synthesis of methyl(S)-2-((4-((6-((2-fluoro-4-((trimethylsilyl) ethynyl) phenoxy)methyl)pyridin-2-yl)oxy)pi-peridin-1-yl)methyl)-1-(oxetan-2-ylm-ethyl)-1H-benzo[d]imidazole-6-carboxylate

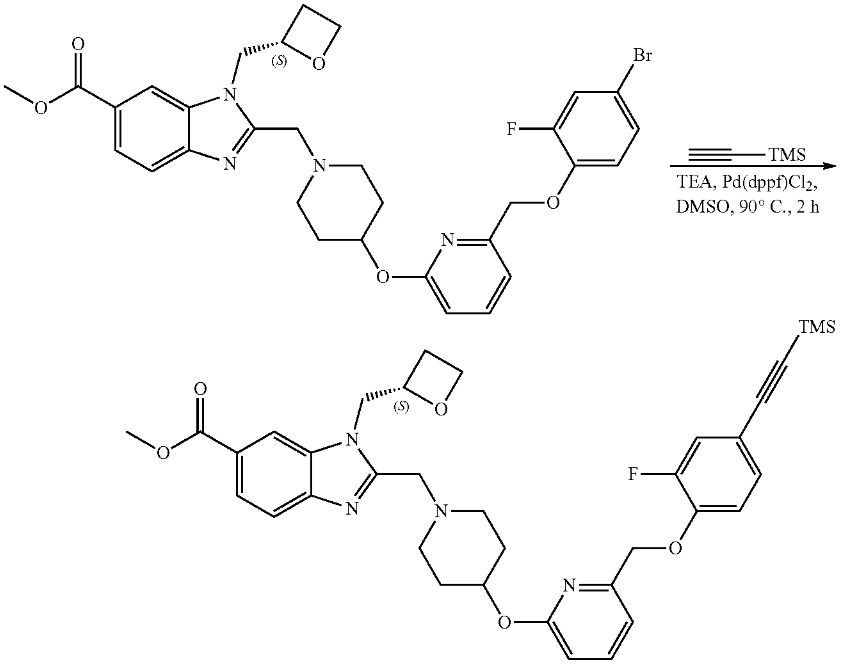

The mixture of ethynyltrimethylsilane (304 mg, 3.10 mmol), triethylamine (313 mg, 3.10 mmol) and 1,1'-bisdiphenylphosphinoferrocene palladium dichloride (22 mg, 0.03 mmol) and methyl(S)-2-((4-((6-((4-bromo-2-fluorophenoxy)methyl)pyridin-2-yl)oxy)piperidin-1-yl)methyl)-1-(oxetan-2-ylmethyl)-1H-benzo[d]imidazole-6-carboxylate (200 mg, 0.31 mmol) in DMSO (6 mL)) was stirred at 90° C. for 2 hours. After completion, the reaction was quenched with water (10 mL) at room temperature, and extracted with ethyl acetate (10 mL×3). The combined organic layers were washed with brine (10 mL×2), dried over anhydrous sodium sulfate, filtered, and concentrated to give a residue in vacuo. The residue was purified by silica gel column chromatography (dichloromethane/methanol=10/1) to obtain methyl(S)-2-((4-((6-((2-fluoro-4-((trimethylsilyl)) ethynyl) phenoxy)methyl)-pyridin-2-yl)oxy)piperidin-1-yl)methyl)-1-(oxetan-2-ylmethyl)-1H-benzo[d]imidazole-6-carboxylate (260 mg, crude). LC-MS m/z: 657 $[M+H]^+$.

2). Synthesis of(S)-2-((4-((6-((4-ethynyl-2-fluorophenoxy)methyl)pyridin-2-yl)oxy)piperidin-1-yl)methyl)-1-(oxetan-2-ylmethyl)-1H-benzo[d]imidazole-6-carboxylic acid

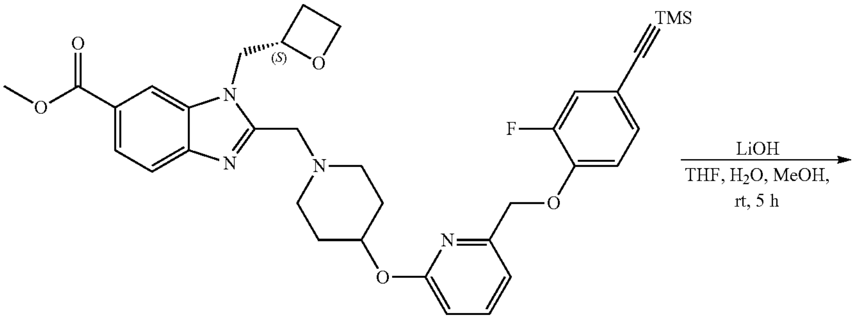

-continued

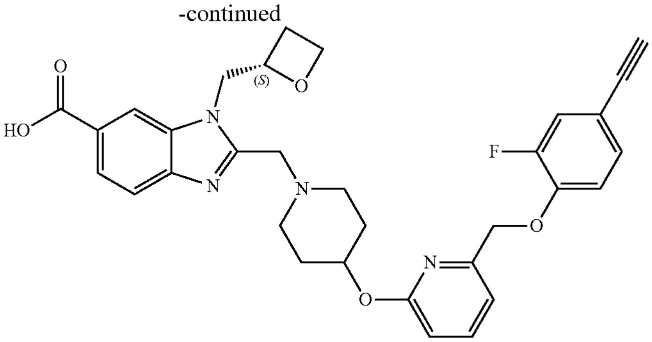

To a mixture of methyl(S)-2-((4-((6-((2-fluoro-4-((trimethylsilyl) ethynyl) phenoxy)methyl)pyridin-2-yl)oxy)piperidin-1-yl)methyl)-1-(oxetan-2-ylmethyl)-1H-benzo[d] imidazole-6-carboxylate (210 mg, 0.32 mmol) in water (1 mL), THF (1 mL) and methanol (1 mL) lithium hydroxide (61 mg, 2.56 mmol) was added. The reaction mixture was stirred at room temperature for 5 hours. After the completion of the reaction, the reaction mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$solvent system; Detection Wavelength: 254 nm/214 nm; Flow rate: 20 mL/min) to obtain (S)-2-((4-((6-((4-ethynyl-2-fluorophenoxy)methyl)pyridin-2-yl)oxy)piperidin-1-yl)methyl)-1-(oxetan-2-ylmethyl)-1H-benzo[d]im-idazole-6-carboxylic acid (10.76 mg, 5.9% yield). LC-MS m/z: 571 $[M+H]^+$.

$^1H$ NMR (400 MHZ, DMSO-$d_6$): δ8.27 (s, 1H), 7.80 (d, J=8.0 Hz, 1H), 7.74-7.70 (m, 1H), 7.64 (d, J=8.8 Hz, 1H), 7.38 (d, J=11.2 Hz, 1H), 7.25 (s, 2H), 7.05 (d, J-6.8 Hz, 1H), 6.73 (d, J=8.0 Hz, 1H), 5.21 (s, 2H), 5.10-5.08 (m, 1H), 4.96-4.94 (m, 1H), 4.79-4.75 (m, 1H), 4.64 (d, J=15.2 Hz, 1H), 4.52-4.49 (m, 1H), 4.38-4.36 (m, 1H), 4.13 (d, J=2.8 Hz, 1H), 3.94 (d, J=14.0 Hz, 1H), 3.78 (d, J=13.2 Hz, 1H), 2.79-2.69 (m, 3H), 2.44-2.32 (m, 3H), 1.93-1.87 (m, 2H), 1.63-1.61 (m, 2H).

Example 45. Synthesis of 2-((4-(3-((4-cyano-2-fluorophenoxy)methyl) phenoxy)piperidin-1-yl) methyl)-1-((1-ethyl-1H-imidazol-5-yl)methyl)-1H-benzo[d]imidazole-6-carboxylic acid (compound 13)

1). Synthesis of methyl 4-(2-(4-(3-((4-cyano-2-fluorophenoxy)methyl) phenoxy)piperidin-1-yl)acetamido)-3-((1-ethyl)-1H-imidazol-5-yl)methyl) amino)benzoate

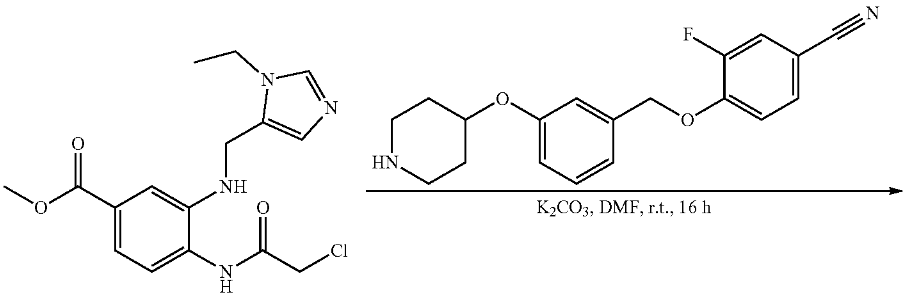

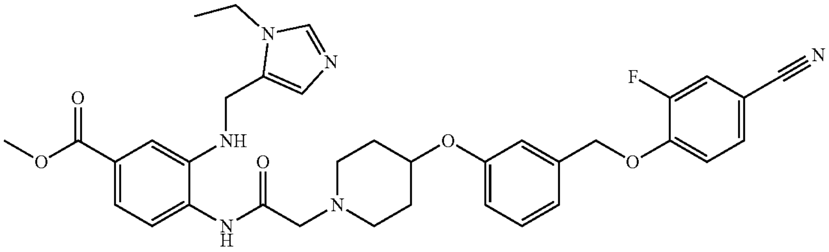

To a solution of methyl 4-(2-chloroacetamido)-3-((1-ethyl-1H-imidazol-5-yl)methyl)amino)benzoate (190 mg, 0.54 mmol) in N,N-dimethylformamide (5 mL) 3-fluoro-4-((3-(piperidin-4-oxy)benzyl)oxy)benzonitrile (196 mg, 0.60 mmol) and potassium carbonate (149 mg, 1.08 mmol) were added at room temperature. The mixture was stirred at room temperature for 16 hours. After completion, the mixture was diluted with water (20 mL) and extracted with ethyl acetate (20 mL×3). The combined organic layers were washed with brine (20 mL×2), dried over anhydrous sodium sulfate, filtered, and concentrated in vacuo. The residue was purified by silica gel column chromatography (dichloromethane/methanol=10/1) to obtain methyl 4-(2-(4-(3-((4-cyano-2-fluorophenoxy)methyl) phenoxy)piperidin-1-yl)acetamido)-3-((1-ethyl-1H-imidazol-5-yl)methyl)amino)benzoate (60 mg, 17.4% yield). LC-MS m/z: 641 [M+H]$^+$.

2). Synthesis of methyl 2-((4-(3-((4-cyano-2-fluorophenoxy)methyl) phenoxy)piperidin-1-yl)methyl)-1-((1-ethyl-1H-imidazol-5-yl)methyl)-1H-benzo[d] imidazole-6-carboxylate

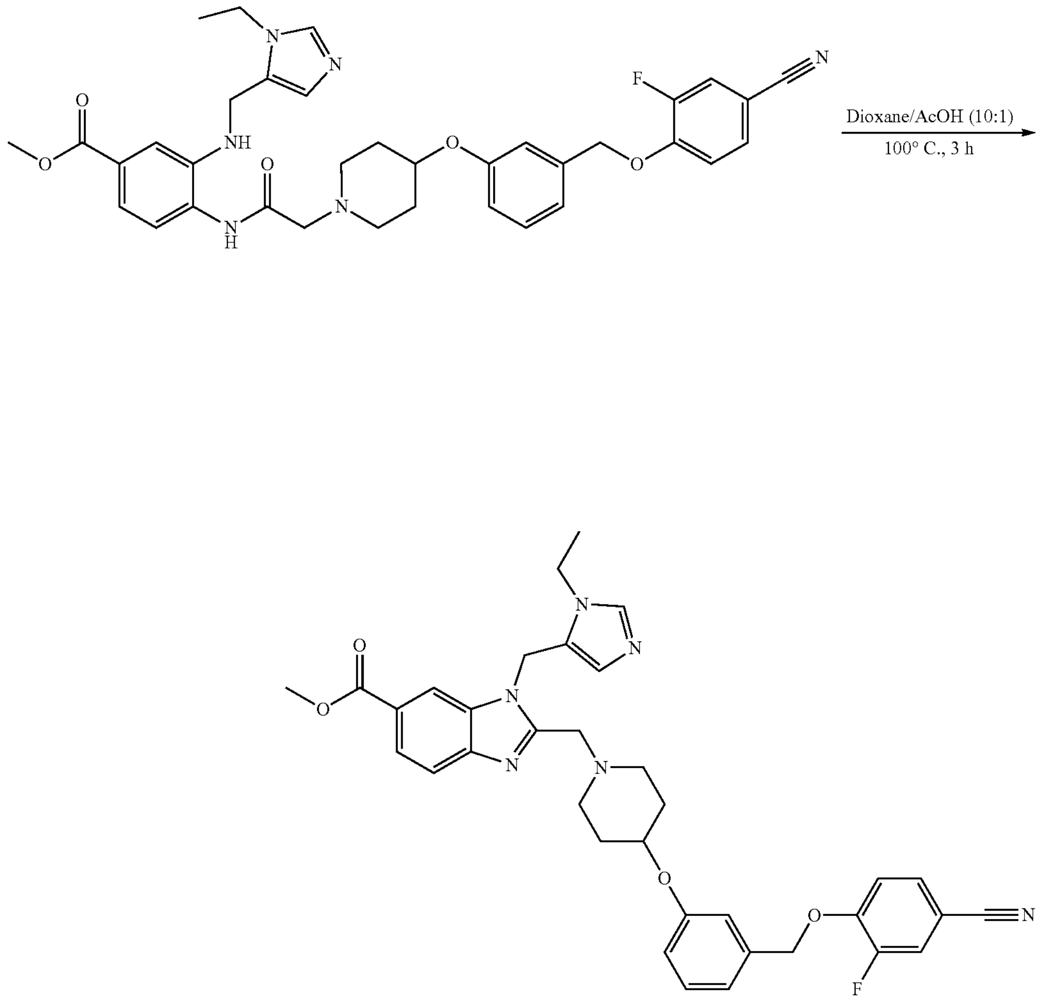

To a mixture of methyl 4-(2-(4-(3-((4-cyano-2-fluorophenoxy)methyl) phenoxy)piperidin-1-yl)acetamido)-3-((1-ethyl-1H-imidazol-5-yl)methyl)amino)benzoate (60 mg, 0.09 mmol,) in dioxane (5 mL) acetic acid (0.5 mL) was added. The resulting mixture was stirred and reacted at 100° C. for 3 hours. After completion, the mixture was diluted with water (20 mL) and extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain methyl 2-((4-(3-((4-cyano-2-fluorophenoxy)methyl) phenoxy)piperidin-1-yl)methyl)-1-((1-ethyl-1H-imidazol-5-yl)methyl)-1H-benzo[d]-imidazole-6-carboxylate (50 mg, 89.2% yield). LC-MS m/z: 623 [M+H]$^+$.

3). Synthesis of 2-((4-(3-((4-cyano-2-fluorophenoxy)methyl) phenoxy)piperidin-1-yl)methyl)-1-((1-ethyl-1H-imidazol-5-yl)methyl)-1H-benzo[d]imidazole-6-carboxylic acid

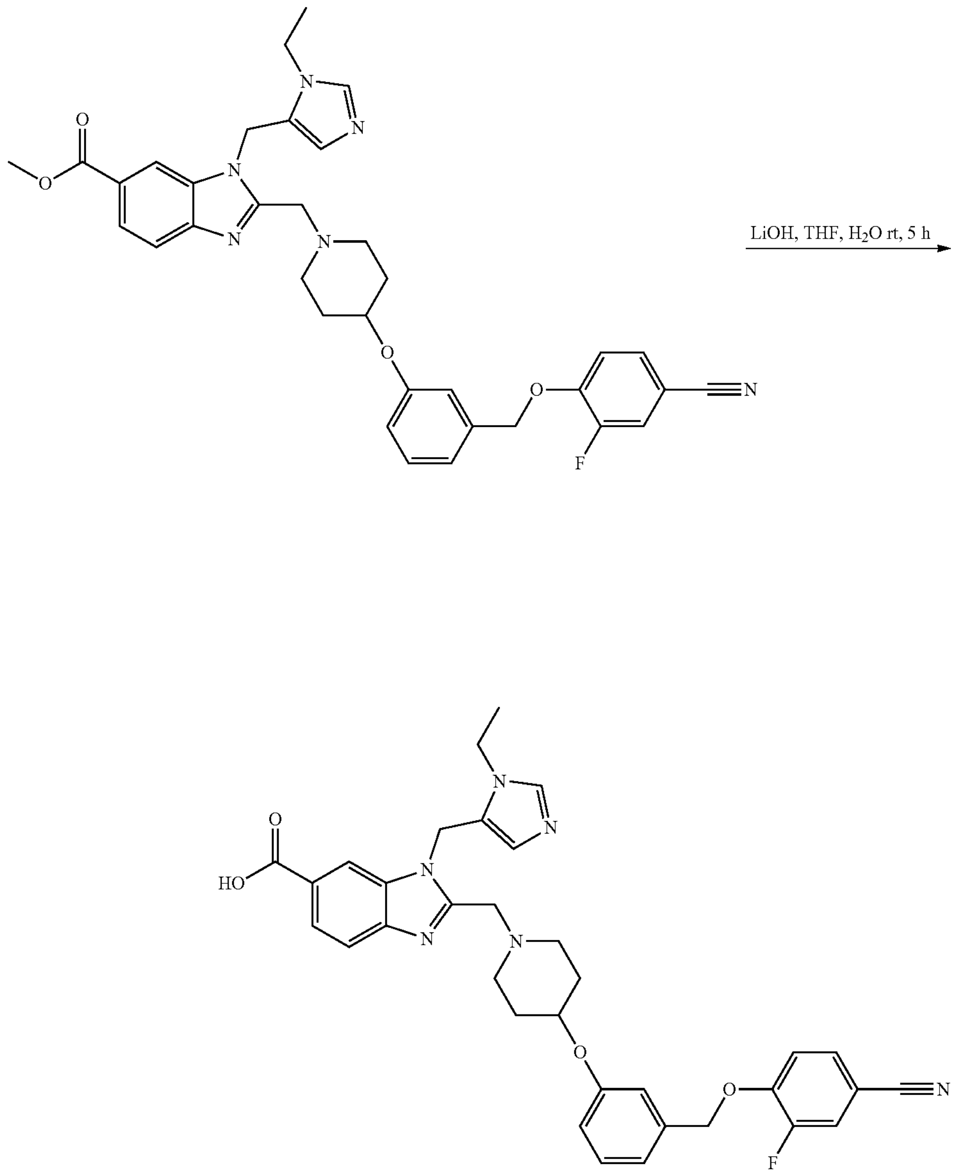

To a mixture of methyl 2-((4-(3-((4-cyano-2-fluorophenoxy)methyl) phenoxy)piperidin-1-yl)methyl)-1-((1-ethyl-1H-imidazol-5-yl)methyl)-1H-benzo[d]imidazole-6-carboxylate (50 mg, 0.08 mmol) in THF (5 mL) and water (4 mL) lithium hydroxide monohydrate (34 mg, 0.80 mmol) was added. The resulting mixture was stirred at room temperature for 5 hours. After completion, the resulting mixture was adjusted to pH=5-6 with hydrochloric acid (1 N) and extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following condition (Column: Spherical C18, 20-40 μm, 40 g; Mobile Phase A: 10 mM $NH_4OH$ in water); Mobile Phase B: acetonitrile; Flow rate: 40 mL/min; Gradient: 20% B-50% B in 20 min; Detector: 254 nm) to obtain 2-((4-(3-((4-cyano-2-fluorophenoxy)methyl) phenoxy)piperidin-1-yl)methyl)-1-((1-ethyl-1H-imidazol-5-yl)methyl)-1H-benzo[d]imidazole-6-carboxylic acid (10.33 mg, 21.2% yield). LC-MS m/z: 609 $[M+H]^+$.

$^1H$ NMR (400 MHZ, DMSO-$d_6$) δ 8.06 (s, 1H), 7.88-7.80 (m, 2H), 7.69-7.64 (m, 3H), 7.42 (t, J=8.8 Hz, 1 H), 7.29 (t, J=8.0 Hz, 1H), 7.02-6.98 (m, 2H), 6.92 (dd, J=8.0 Hz, 2.0 Hz, 1H), 6.41 (s, 1H), 5.71 (s, 2H), 5.24 (s, 2H), 4.36-4.35 (m, 1H), 4.03-3.97 (m, 2H), 3.81 (s, 2H), 2.69-2.67 (m, 2H), 2.33-2.28 (m, 2H), 1.83-1.81 (m, 2H), 1.49-1.47 (m, 2H), 1.15 (t, J=7.2 Hz, 3H).

Example 46. Synthesis of 2-((4-((6-((4-cyano-2-fluorophenoxy)methyl)pyridin-2-yl)oxy)piperidin-1-yl)methyl)-1-((1-(cyanomethyl)cyclopropyl)methyl)-4-fluoro-1H-benzimidazole-6-carboxylic acid (compound 134)

1). Synthesis of N-(4-bromo-2-(((1-(cyanomethyl) cyclopropyl)methyl)amino)-6-fluorophenyl)-2-(4-((6-((4-cyano-2-fluorophenoxy)methyl)pyridin-2-yl) oxy)piperidin-1-yl)acetamide

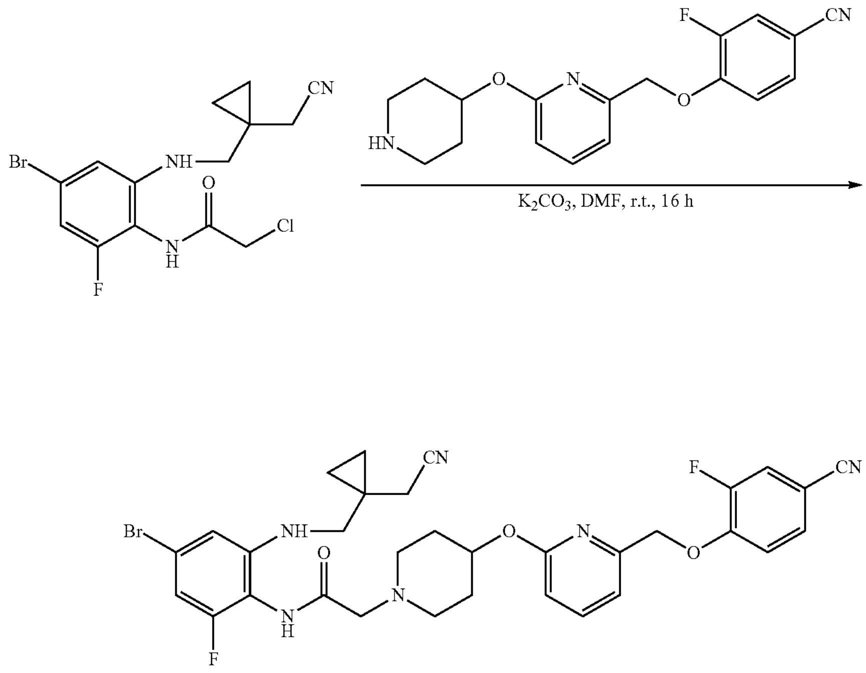

The mixture of N-(4-bromo-2-(((1-(cyanomethyl)cyclopropyl)methyl)amino)-6-fluorophenyl)-2-chloroacetamide (350 mg, 1.04 mmol), 3-fluoro-4-((6-(piperidin-4-oxy)pyridin-2-yl)methoxy)benzonitrile (389 mg, 1.04 mmol) and potassium carbonate (287 mg, 2.08 mmol)) in N, N-dimethylformamide (8 mL) was stirred at room temperature for 16 hours. Upon completion of the reaction, the resulting mixture was poured into brine (20 mL) and extracted with ethyl acetate (2×20 mL). The combined organic layers were concentrated to give a residue in vacuo. The residue was purified by silica gel column chromatography (dichloromethane/methanol=20/1) to obtain N-(4-bromo-2-(((1-(cyanomethyl)cyclopropyl)methyl)) amino)-6-fluorophenyl)-2-(4-((6-((4-cyano-2-fluorophenoxy)methyl)pyridin-2-yl)oxy)piperidine-1-yl)acetamide (693 mg, 99.0% yield). LC-MS m/z: 667 $[M+H]^+$.

2). Synthesis of 4-((6-((1-((6-bromo-1-((1-(cyanomethyl)cyclopropyl)methyl)-4-fluoro-1H-benzo[d] imidazole-2-yl)methyl)piperidin-4-yl)oxy)pyridin-2-yl)methoxy)-3-fluorobenzonitrile

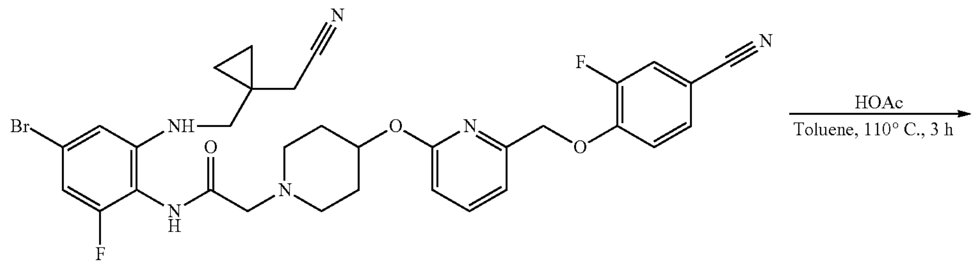

-continued

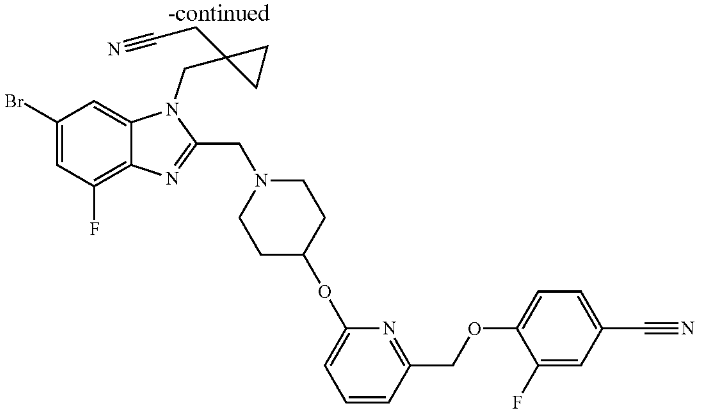

The mixture of N-(4-bromo-2-(((1-(cyanomethyl)cyclopropyl)methyl)amino)-6-fluorophenyl)-2-(4-((6-((4-cyano-2-fluorophenoxy)methyl)pyridin-2-yl)oxy)piperidin-1-yl) acetamide (690 mg, 1.04 mmol) in toluene (12 mL) and acetic acid (2 mL)) was warmed to 110° C. and stirred for 3 hours under nitrogen atmosphere. After completion, the resulting mixture was concentrated to give a residue. The residue was purified by silica gel column chromatography (petroleum ether/ethyl acetate=1/1) to obtain 4-((6-((1-((6-bromo-1-((1-(cyanomethyl)cyclopropyl)methyl)-4-fluoro-1H-benzo[d]imidazol-2-yl)methyl)piperidin-4-yl)oxy)pyridin-2-yl)methoxy)-3-fluorobenzonitrile (330 mg, 49.1% yield). LC-MS m/z: 649 $[M+H]^+$.

3). Synthesis of methyl 2-((4-((6-((4-cyano-2-fluorophenoxy)methyl)pyridin-2-yl)oxy)piperidin-1-yl)methyl)-1-((1-(cyanomethyl)cyclopropyl)methyl)-4-fluoro-1H-benzo[d]imidazole-6-carboxylate

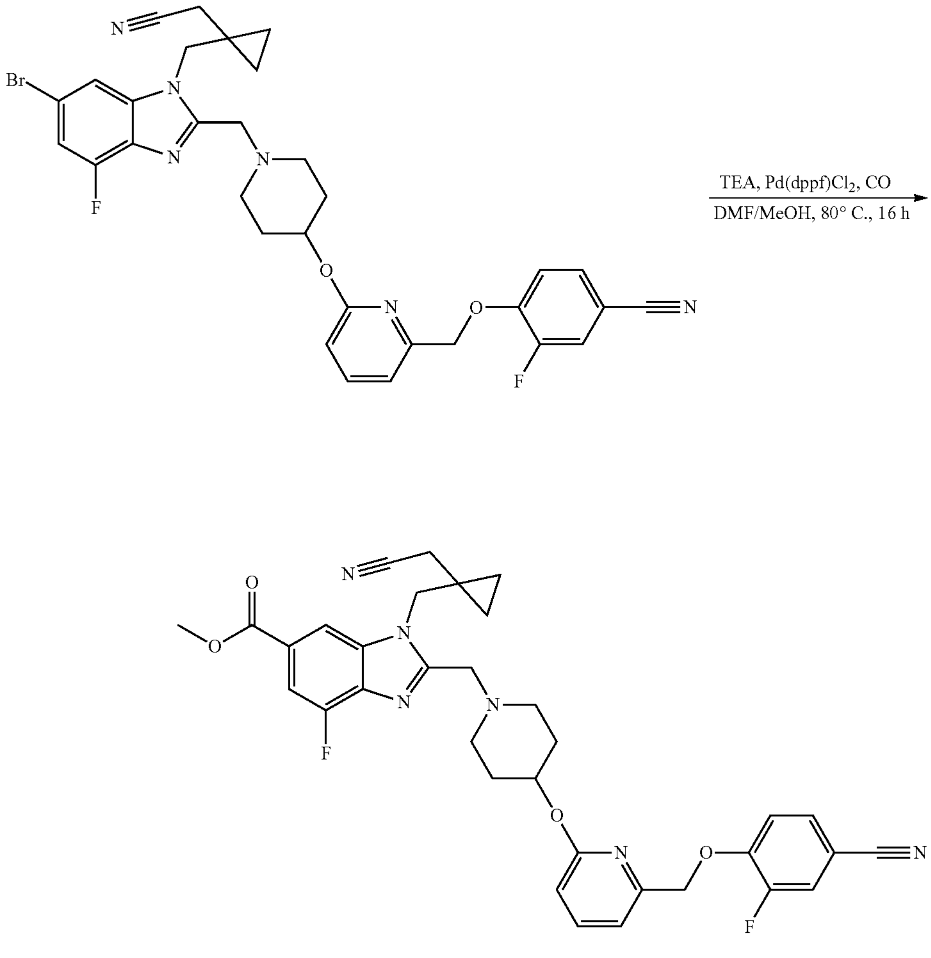

To a solution of 4-((6-((1-((6-bromo-1-((1-(cyanomethyl) cyclopropyl)methyl)-4-fluoro-1H-benzo[d]imidazole-2-yl) methyl)-pip-eridin-4-yl)oxy)pyridin-2-yl)methoxy)-3-fluorobenzonitrile (200 mg, 0.31 mmol) in N,N-dimethylformamide (10 mL) and methanol (10 mL) triethylamine (94 mg, 0.93 mmol) and 1,1'-bisdiphenylphosphinoferrocene palladium dichloride (25 mg, 0.03 mmol) were added at room temperature under carbon monoxide atmosphere. The mixture was stirred at 80° C. for 16 hours. After completion, the mixture was diluted with water (5 mL) and extracted with ethyl acetate (10 mL×2). The combined organic layers were washed with brine (10 mL×3), dried over anhydrous sodium sulfate, filtered, and concentrated in vacuo. The residue was purified by silica gel column chromatography (petroleum ether/ethyl acetate=1/1) to obtain methyl 2-((4-((6-((4-cyano-2-fluorophenoxy)methyl)pyridin-2-yl)oxy)piperidin-1-yl)methyl)-1-((1-(cyanomethyl) cyclopropyl)methyl)-4-fluoro-1H-benzo[d]imidazole-6-carboxylate (150 mg, 77.5% yield). LC-MS m/z: 627 $[M+H]^+$.

4). Synthesis of 2-((4-((6-((4-cyano-2-fluorophenoxy)methyl)pyridin-2-yl)oxy)piperidin-1-yl) methyl)-1-((1-(cyanomethyl)cyclopropyl)methyl)-4-fluoro-1H-benzimidazole-6-carboxylic acid

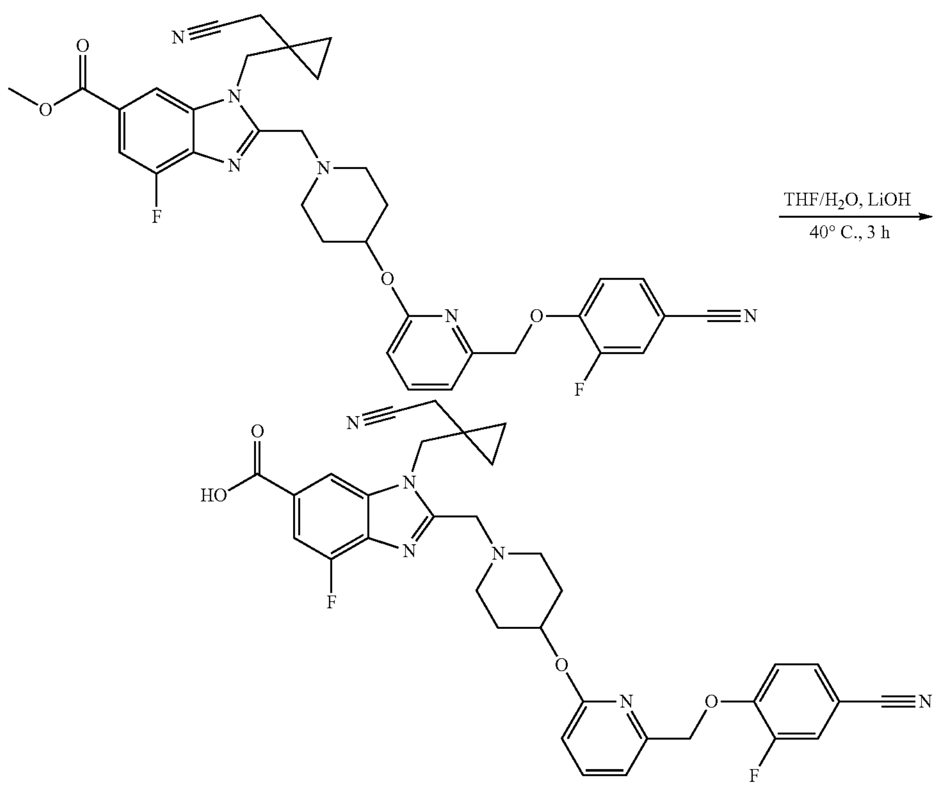

-

To a mixture of methyl 2-((4-((6-((4-cyano-2-fluorophenoxy)methyl)pyridin-2-yl)oxy)piperidin-1-yl)methyl)-1-(((1-(cyanomethyl)cyclopropyl)methyl)-4-fluoro-1H-benzo [d]imidazole-6-carboxylate (150 mg, 0.24 mmol) in THF (3 mL) water (3 mL) lithium hydroxide (57 mg, 2.40 mmol) was added at room temperature. The resulting mixture was stirred and reacted at 40° C. for 3 hours. After completion, the solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% $NH_4OH$ in $H_2O$ solvent system; Detection Wavelength 254 nm/214 nm; Flow rate: 20 mL/min) purification to give 2-((4-((6-((4-cyano-2-fluorophenoxy)methyl)pyridin-2-yl)oxy)piperidin-1-yl)methyl)-1-((1-(cyanomethyl)cyclopropyl) methyl)-4-fluoro-1H-benzimidazole-6-carboxylic acid (16.90 mg, 11.5% yield). LC-MS m/z: 613 $[M+H]^+$.

$^1H$ NMR (400 MHZ, DMSO-$d_6$) δ 8.07 (s, 1H), 7.88 (dd, J=11.2 Hz, 1.6 Hz, 1H), 7.73 (d, J=8.0 Hz, 1H), 7.66 (d, J-8.8 Hz, 1H), 7.52-7.43 (m, 2H), 7.05 (d, J=7.2 Hz, 1H), 6.73 (d, J=8.4 Hz, 1H), 5.31 (s, 2H), 4.95-4.90 (m, 1H), 4.61 (s, 2H), 3.86 (s, 2H), 2.81-2.78 (m, 2H), 2.70 (s, 2H), 2.34-2.29 (m, 2H), 1.94-1.91 (m, 2H), 1.66-1.61 (m, 2H), 0.76-0.67 (m, 4H).

Example 47. Synthesis of 2-((4-((6-((4-chloro-2-fluorophenoxy)methyl)pyridin-2-yl)oxy)piperidin-1-yl)methyl)-1-((1-(cyanomethyl)cyclopropyl)methyl)-1H-benzo[d]imidazole-6-carboxylic acid (compound C84)

1). Synthesis of methyl 2-((4-((6-((4-chloro-2-fluorophenoxy)methyl)pyridin-2-yl)oxy)piperidin-1-yl) methyl)-1-((1-(cyanomethyl))-1H-benzo[d]imidazole-6-carboxylate

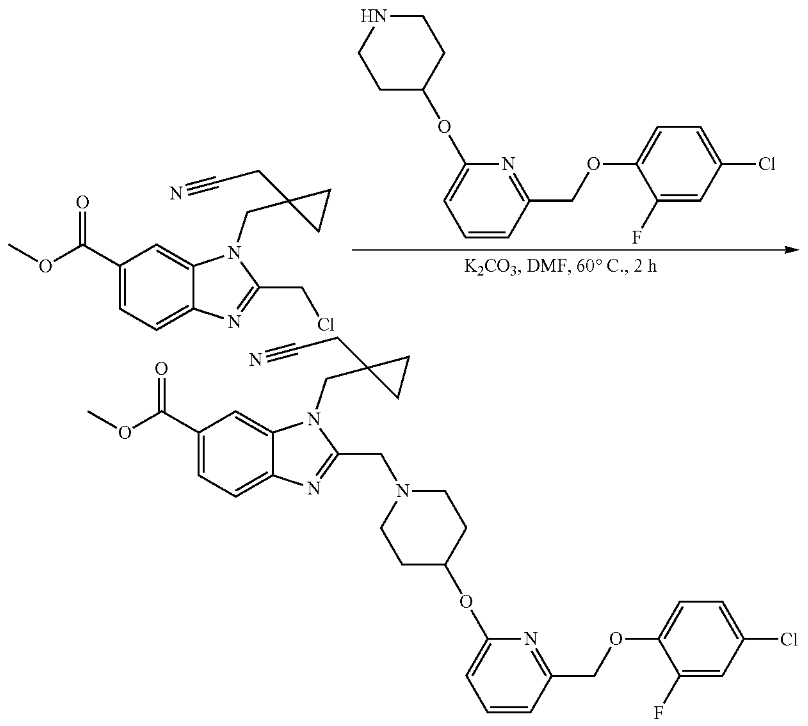

The mixture of methyl 2-(chloromethyl)-1-(1-(cyanomethyl)cyclopropyl)methyl)-1H-benzo[d]imidazole-6-carboxylate (57 mg, 0.18 mmol), 2-((4-chloro-2-fluorophenoxy)methyl)-6-(piperidin-4-acyloxy)pyridine (61 mg, 0.18 mmol), and potassium carbonate (50 mg, 0.36 mmol) in N, N-dimethylformamide (5 mL) was stirred at to 60° C. for 2 hours. After completion, the resulting mixture was poured into brine (20 mL) and extracted with ethyl acetate (2×20 mL). The combined organic layer was concentrated to give a residue in vacuo. The residue was purified by silica gel column chromatography (dichloromethane/methanol=20/1) to methyl 2-((4-((6-((4-chloro-2-fluorophenoxy)-methyl) pyridine-2-yl)oxypiperidin-1-yl)methyl)-1-((1-(cyanomethyl)cyclopropyl)methyl)-1H-benzo[d]imidazole-6-carboxylate (20 mg, 18.0% yield). LC-MS m/z: 618 $[M+H]^+$.

2). Synthesis of 2-((4-((6-((4-chloro-2-fluorophenoxy)methyl)pyridin-2-yl)oxy)piperidin-1-yl) methyl)-1-((1-(cyanomethyl)cyclopropyl)methyl)-1H-benzo[d]imidazole-6-carboxylic acid

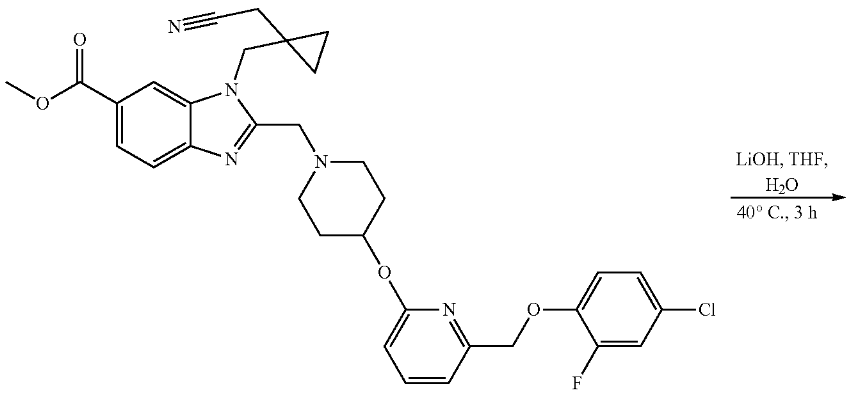

-continued

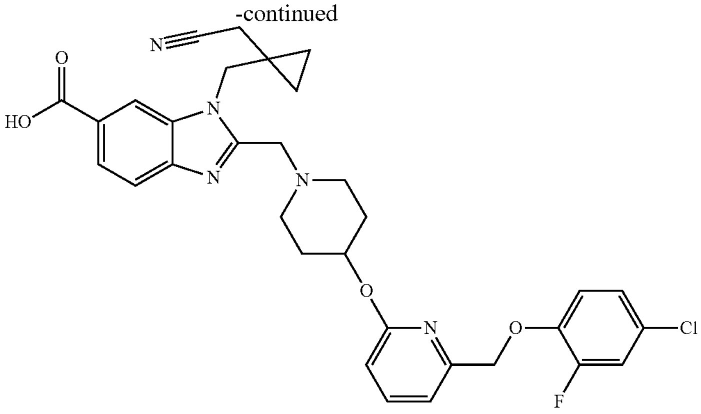

The mixture of methyl 2-((4-((6-((4-chloro-2-fluorophenoxy)methyl)pyridin-2-yl)oxy)piperidin-1-yl)methyl)-1-((1-(cyanomethyl)cyclopropyl)methyl)-1H-benzo[d]imidazole-6-carboxylate (20 mg, 0.03 mmol) and lithium hydroxide (7 mg, 0.30 mmol) in THF (2 mL) and (2 mL) was stirred at 40° C. and stirred for 3 hours. After completion, the solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% $NH_4OH$ in $H_2O$solvent system; Detection Wavelength 254 nm/214 nm; Flow rate: 20 ml/min) to obtain 2-((4-((6-((4-chloro-2-fluorophenoxy)methyl)pyridin-2-yl)oxy)piperidin-1-yl)methyl)-1-((1-(cyanomethyl)cyclopropyl)methyl)-1H-benzo[d]imidazole-6-carboxylic acid (16.58 mg, 84.8% yield). LC-MS m/z: 604 $[M+H]^+$.

$^1$H NMR (400 MHZ, DMSO-$d_6$) δ 8.26 (s, 1H), 7.82 (d, J=8.4 Hz, 1H), 7.74-7.66 (m, 2H), 7.44 (d, J=11.2 Hz, 1H), 7.28 (t, J=8.4 Hz, 1H), 7.19 (d, J=8.8 Hz, 1H), 7.05 (d, J-6.8 Hz, 1H), 6.72 (d, J=8.4 Hz, 1H), 5.19 (s, 2H), 4.98-4.92 (m, 1H), 4.61 (s, 2H), 3.86 (s, 2H), 2.81-2.79 (m, 2H), 2.69 (s, 2H), 2.36-2.31 (m, 2H), 1.94-1.92 (m, 2H), 1.66-1.59 (m, 2H), 0.76-0.70 (m, 4H).

Example 48. Synthesis of 2-((4-(3-((4-chloro-2-fluorophenoxy)methyl) phenoxy)piperidin-1-yl) methyl)-1-((1-ethyl-1H-imidazol-5-yl)methyl)-1H-benzo[d]imidazole-6-carboxylic acid (Compound 7)

1). Synthesis of methyl 4-(2-(4-(3-((4-chloro-2-fluorophenoxy)methyl) phenoxy)piperidin-1-yl)acetamido)-3-((1-ethyl-1H-imidazol-5-yl)methyl)amino) methyl benzoate

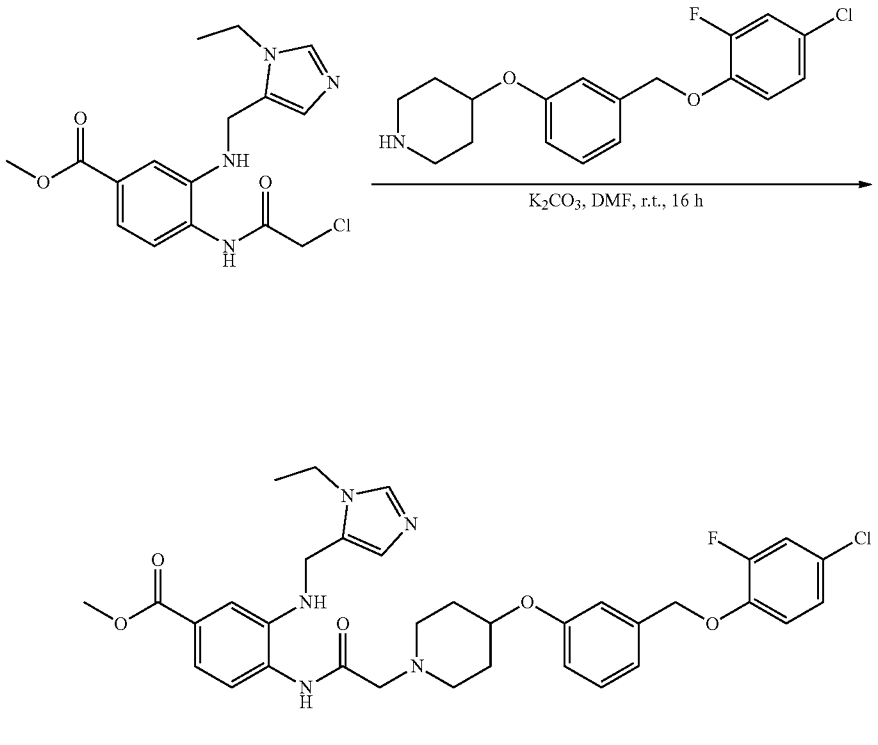

The mixture of 4-(3-((4-chloro-2-fluorophenoxy)methyl) phenoxy)piperidine (198 mg, 0.59 mmol), methyl 4-(2-chloroacetamido)-3-((1-ethyl-1H-imidazol-5-yl)methyl) amino)benzoate (190 mg, 0.54 mmol) and potassium carbonate (149 mg, 1.08 mmol) in N,N-dimethylformamide (7 mL) was stirred at room temperature for 16 hours. After completion, water (20 mL) was added to quench the reaction. The mixture was extracted with ethyl acetate (20 mL×3). The combined organic layers were washed with brine (20 mL×2), dried over anhydrous sodium sulfate, filtered, and concentrated to give a residue in vacuo. The residue was purified by silica gel column chromatography (dichloromethane/methanol=10/1) to obtain methyl 4-(2-(4-(3-((4-chloro-2-fluorophenoxy)methyl) phenoxy))piperidin-1-yl)acetamido)-3-((1-ethyl-1H-imidazol-5-yl)methyl) amino)benzoate (210 mg, 59.8% yield). LC-MS m/z: 650 $[M+H]^+$.

2). Synthesis of methyl 2-((4-(3-((4-chloro-2-fluorophenoxy)methyl) phenoxy)piperidin-1-yl)methyl)-1-((1-ethyl-1H-imidazol-5-yl)methyl)-1H-benzo[d] imidazole-6-carboxylate

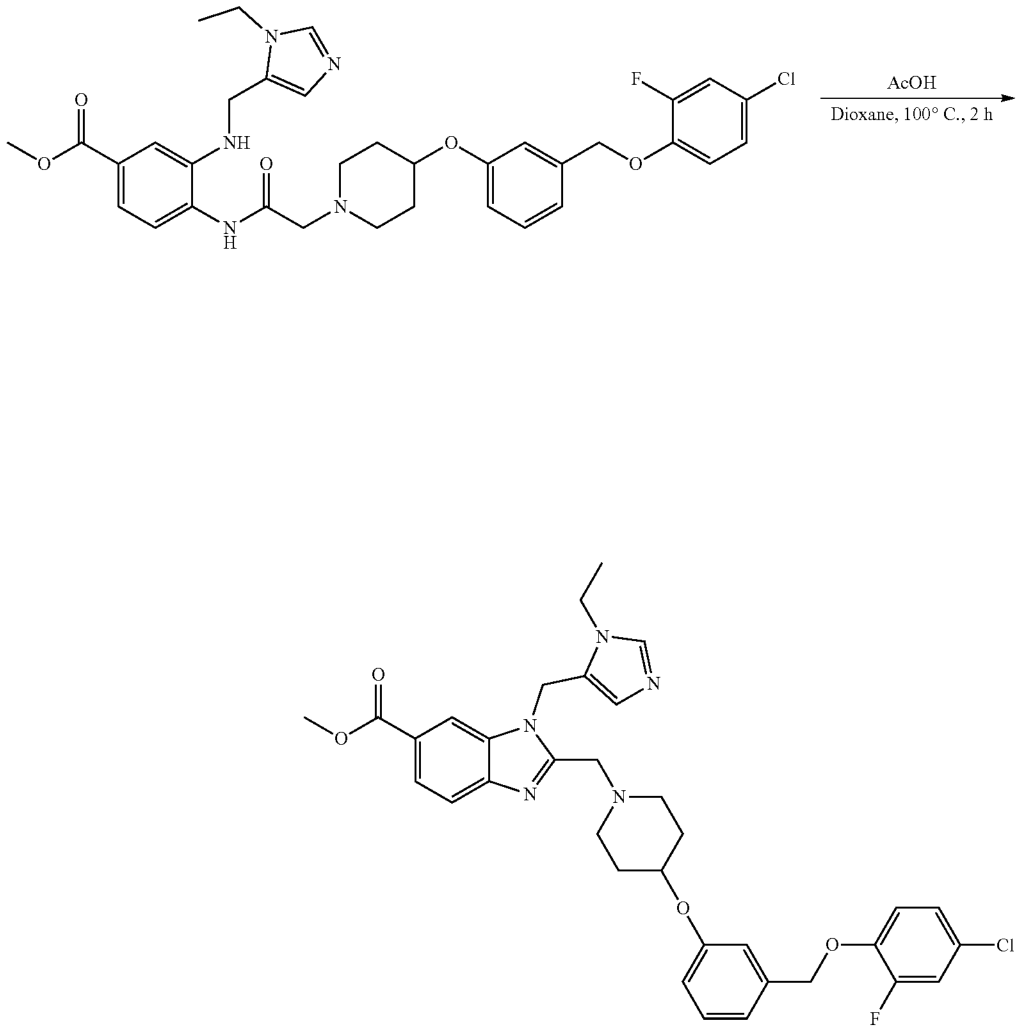

The mixture of methyl 4-(2-(4-(3-((4-chloro-2-fluorophenoxy)methyl) phenoxy)piperidin-1-yl)acetamido)-3-((1-ethyl-1H-imidazol-5-yl)methyl)amino)benzoate (210 mg, 0.32 mmol) was dioxane (10 mL) and acetic acid (1 mL) was stirred at 100° C. for 2 hours. After completion, the reaction solution was concentrated to give a residue. The residue was purified by silica gel column chromatography (dichloromethane/methanol=10/1) to obtain methyl 2-((4-(3-((4-chloro-2-fluorophenoxy))methyl) phenoxy)piperidin-1-yl) methyl)-1-((1-ethyl-1H-imidazol-5-yl)methyl)-1H-benz-o [d]imidazol-6-carboxylate (158 mg, 78.1% yield). LC-MS m/z: 632 $[M+H]^+$.

3). Synthesis of 2-((4-(3-((4-chloro-2-fluorophenoxy)methyl) phenoxy)piperidin-1-yl)methyl)-1-((1-ethyl-1H-imidazol-5-yl)methyl)-1H-benzo[d]imidazole-6-carboxylic acid

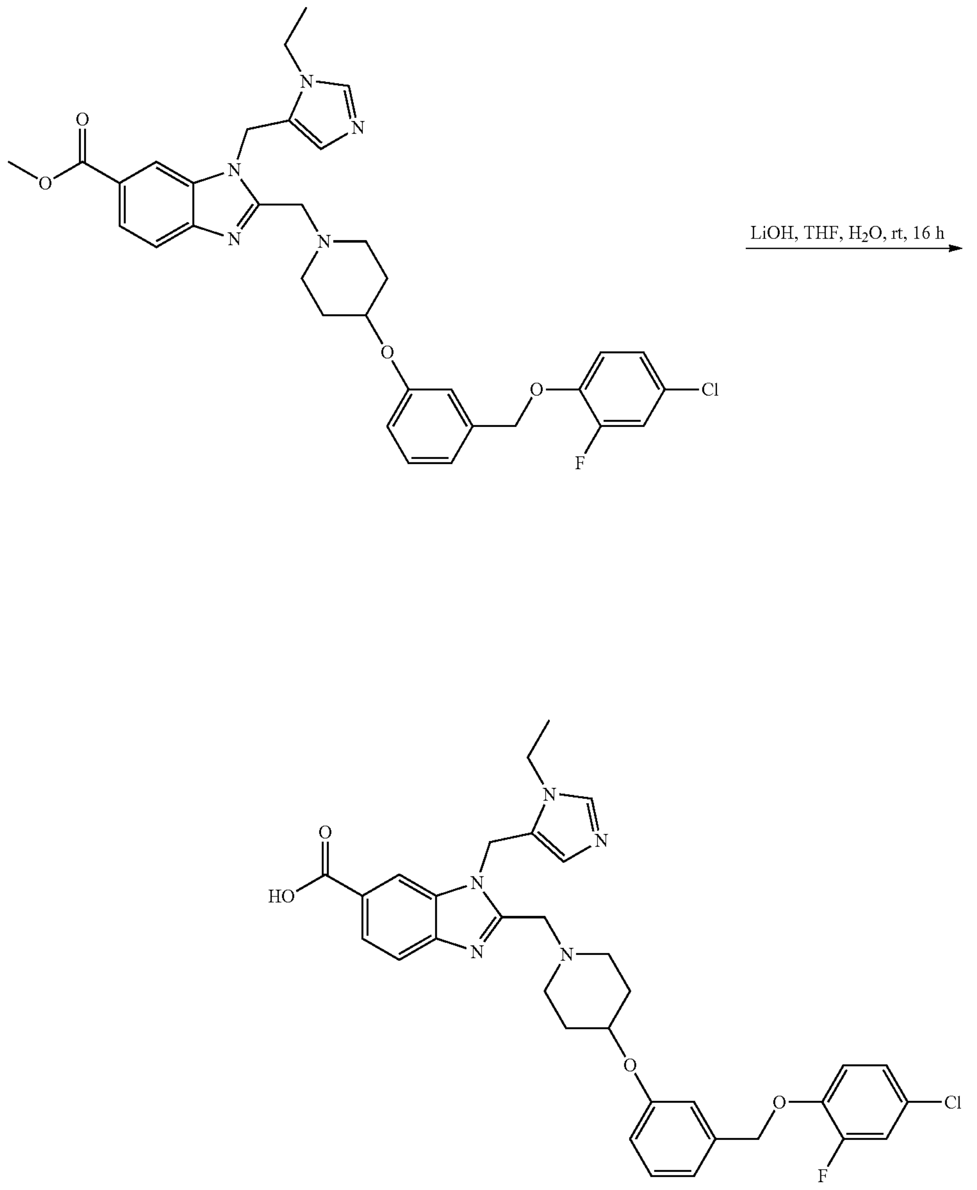

The mixture of lithium hydroxide monohydrate (105 mg, 2.50 mmol) and methyl 2-((4-(3-((4-chloro-2-fluorophenoxy)methyl) phenoxy)piperidine-1-yl)methyl)-1-((1-ethyl-1H-imidazol-5-yl)methyl)-1H-benzo[d]imidazole-6-carboxylate (158 mg, 0.25 mmol) in THF (5 mL) and water (4 mL) was stirred at room temperature for 16 hours. After completion, the resulting mixture was adjusted to pH=5-6 with hydrochloric acid (1M) and extracted with ethyl acetate (10 mL×3). The combined organic phases were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile Phase B: Acetonitrile; Flow rate: 40 mL/min; Gradient: 20% B-50% B in 20 min; Detector: 254 nm) to obtain 2-((4-(3-((4-chloro-2-fluorophenoxy)methyl) phenoxy)piperidin-1-yl)methyl)-1-((1-ethyl-1H-imidazol-5-yl)methyl)-1H-benzo [d]imidazole-6-carboxylic acid formic acid (10.32 mg, 6.7% yield). LC-MS m/z: 618 $[M+H]^+$.

$^1H$ NMR (400 MHZ, DMSO-$d_6$) δ 8.17 (s, 1H), 8.07 (s, 1H), 7.81 (dd, J-8.4, 1.2 Hz, 1H), 7.68 (d, J=8.4 Hz, 2H), 7.43 (dd, J=11.6, 2.8 Hz, 1H), 7.30-7.18 (m, 3H), 6.99-6.96 (m, 2H), 6.90 (dd, J=8.0, 1.6 Hz, 1H), 6.42 (s, 1H), 5.72 (s, 2H), 5.14 (s, 2H), 4.37-4.34 (m, 1H), 4.03-3.97 (m, 2H), 3.81 (s, 2H), 2.70-2.67 (m, 2H), 2.33-2.29 (m, 2H), 1.83-1.80 (m, 2H), 1.49-1.46 (m, 2H), 1.16 (t, J=7.2 Hz, 3H).

Example 49. Synthesis of(S)-2-((4-((6-((4-cyano-2-fluorophenoxy)methyl)pyridin-2-yl)amino)piperidin-1-yl)methyl)-1-(oxetan-2-ylmethyl)-1H-benzo[d]imidazole-6-carboxylic acid (compound C16)

1). Synthesis of methyl(S)-2-((4-((6-((4-cyano-2-fluorophenoxy)methyl)pyridin-2-yl)amino)piperidin-1-yl)methyl)-1-(oxetan-2-ylmethyl)-1H-benzo[d]imidazole-6-carboxylate

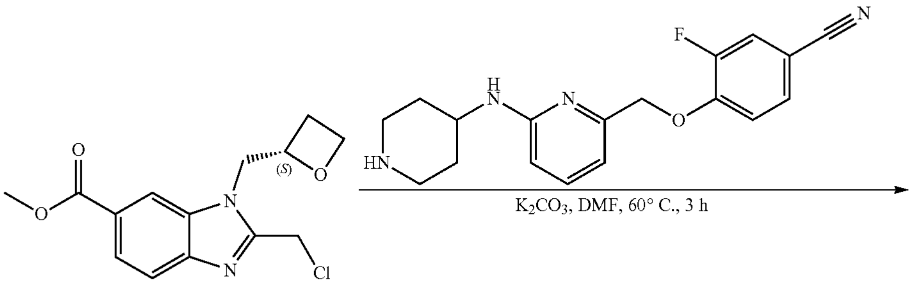

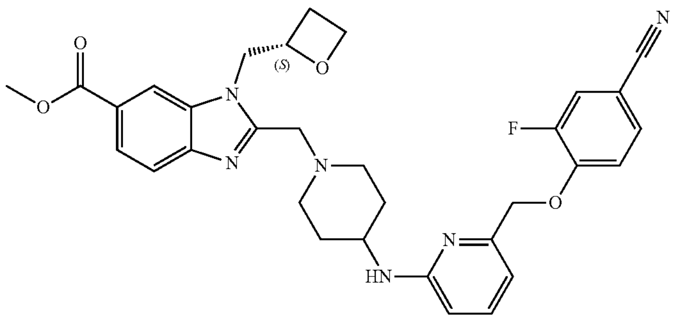

The mixture of methyl(S)-2-(chloromethyl)-1-(oxetan-2-ylmethyl)-1H-benzo[d]imidazole-6-carboxylate (100 mg, 0.34 mmol), 3-fluoro-4-((6-(piperidin-4-ylamino)pyridin-2-yl)methoxy)benzonitrile (110 mg, 0.34 mmol) and potassium carbonate (94 mg, 0.68 mmol) in N,N-dimethylformamide (4 mL) was stirred and reacted at 60° C. for 3 hours. After completion, the mixture was diluted with water (10 mL) and extracted with ethyl acetate (10 mL×3). The combined organic layers were washed with brine (10 mL×3), dried over anhydrous sodium sulfate, filtered, and concentrated to give a residue in vacuo. The residue was purified by silica gel column chromatography (dichloromethane/methanol=10/1) to obtain methyl(S)-2-((4-((6-((4-cyano-2-fluorophenoxy)methyl)) pyridin-2-yl)amino)piperidin-1-yl)methyl)-1-(oxetan-2-ylmethyl)-1H-benzo[d]imidazole-6-carboxylate (120 mg, 63.2% yield). LC-MS m/z: 585 [M+H]$^+$.

2). Synthesis of(S)-2-((4-((6-((4-cyano-2-fluorophenoxy)methyl)pyridin-2-yl)amino)piperidin-1-yl)methyl)-1-(oxetan-2-ylmethyl)-1H-benzo[d]imidazole-6-carboxylic acid

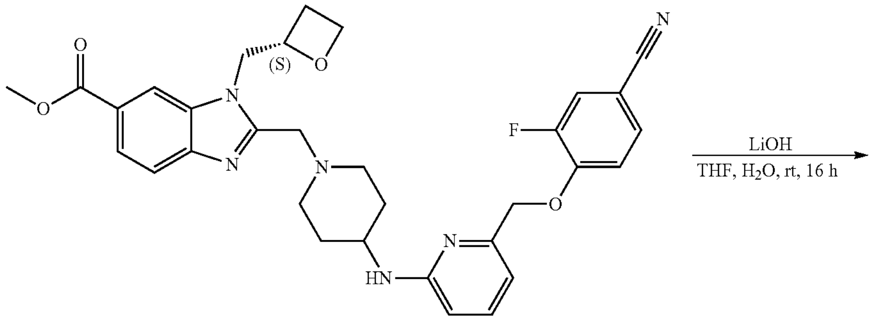

-continued

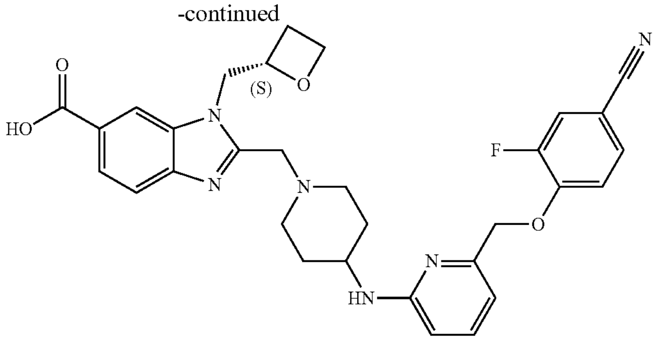

To a mixture of of methyl(S)-2-((4-((6-((4-cyano-2-fluorophenoxy)methyl)pyridin-2-yl)amino)piperidin-1-yl) methyl)-1-(oxetan-2-ylmethyl)-1H-benzo[d]imidazole-6-carboxylate (120 mg, 0.21 mmol) in THF (3 mL) and water (3 mL) lithium hydroxide (25 mg, 1.05 mmol) was added. The reaction was stirred at room temperature for 16 hours. After completion, the resulting mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to give(S) -2-((4-((6-((4-cyano-2-fluorophenoxy) methyl)pyridin-2-yl)amino)piperidin-1-yl)methyl)-1-(oxetan-2-ylmethyl)-1H-benzo[d]imidazole-6-carboxylic acid (16.75 mg, 14.1% yield). LC-MS m/z: 571 $[M+H]^+$.

$^1$HNMR (400 MHZ, DMSO-$d_6$): δ8.27 (s, 1H), 7.88-7.79 (m, 2H), 7.66-7.64 (m, 2H), 7.45-7.34 (m, 2H), 6.55-6.51 (m, 1H), 6.39 (d, J=8.4 Hz, 1H), 5.15 (s, 2H), 5.10-5.09 (m, 1H), 4.81-4.76 (m, 1H), 4.64 (d, J=15.6 Hz, 1H), 4.51-4.49 (m, 1H), 4.40-4.38 (m, 1H), 3.93 (d, J=13.2 Hz, 1H), 3.75 (d, J=12.8 Hz, 1H), 3.63-3.62 (m, 1H), 2.87-2.84 (m, 1H), 2.74-2.67 (m, 2H), 2.46-2.41 (m, 1H), 2.21-2.11 (m, 2H), 1.85-1.82 (m, 2H), 1.40-1.34 (m, 2H).

Example 50. Synthesis of 2-((4-((6-((4-cyano-2-fluorophenoxy)methyl)pyridin-2-yl)amino)piperidin-1-yl)methyl)-1-((1-ethyl-1H-imidazol-5-yl)methyl)-1H-benzo[d]imidazole-6-carboxylic acid (Compound C17)

1). Synthesis of methyl 4-(2-(4-((6-((4-cyano-2-fluorophenoxy)methyl)pyridin-2-yl)amino)piperidin-1-yl)acetamido)-3-((1-ethyl-1H-imidazol-5-yl) methyl)amino)benzoate

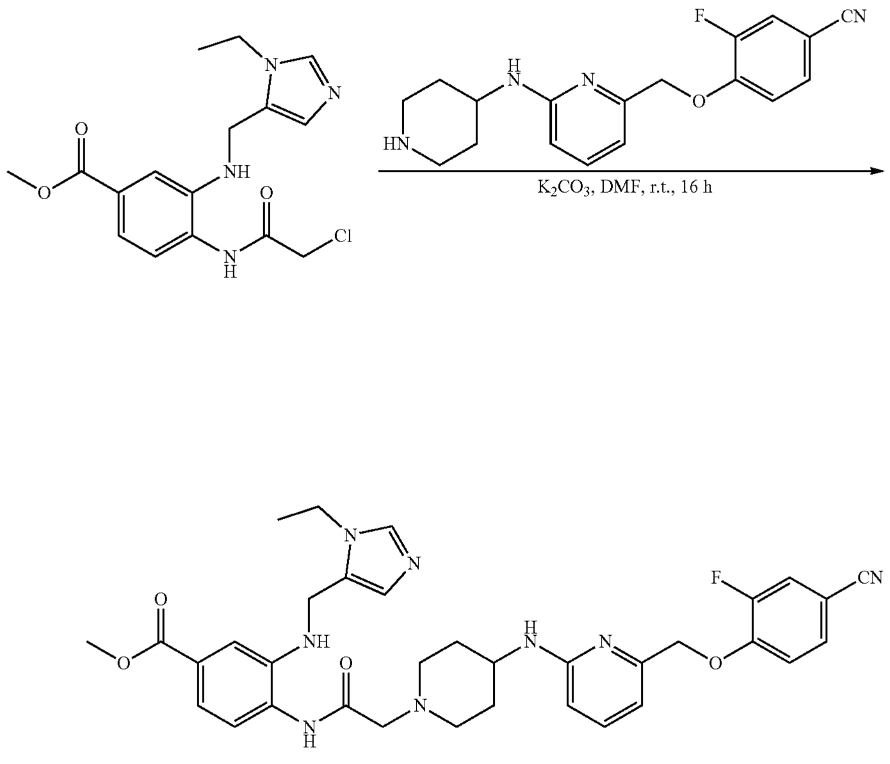

To a mixture of methyl 4-(2-chloroacetamido)-3-((1-ethyl-1H-imidazol-5-yl)methyl)amino)benzoate (170 mg, 0.48 mmol) and 3-fluoro-4-((6-(piperidin-4-ylamino)pyridin-2-yl)methoxy)benzonitrile (158 mg, 0.48 mmol) in N,N-dimethylformamide (5 mL) potassium carbonate (132 mg, 0.96 mmol) was added at room temperature. The mixture was stirred at room temperature for 16 hours. After completion, the mixture was extracted with ethyl acetate (10 mL×3). The combined organic layers were washed with brine (20 mL), dried over anhydrous sodium sulfate, filtered, and concentrated to give a residue in vacuo. The residue was purified by silica gel column chromatography (dichloromethane/methanol=10/1) to obtain methyl 4-(2-(4-((6-((4-cyano-2-fluorophenoxy)methyl)pyridin-2-yl)amino)piperidin-1-yl)acetamido)-3-((1-ethyl-1H-imidazol-5-yl)methyl)amino)benzoate (65 mg, 41.8% yield). LC-MS m/z: 641 [M+H]$^+$.

2). Synthesis of methyl 2-((4-((6-((4-cyano-2-fluorophenoxy)methyl)pyridin-2-yl)amino)piperidin-1-yl)methyl)-1-((1-ethyl-1H-imidazol-5-yl)methyl)-1H-benzo[d]imidazole-6-carboxylate

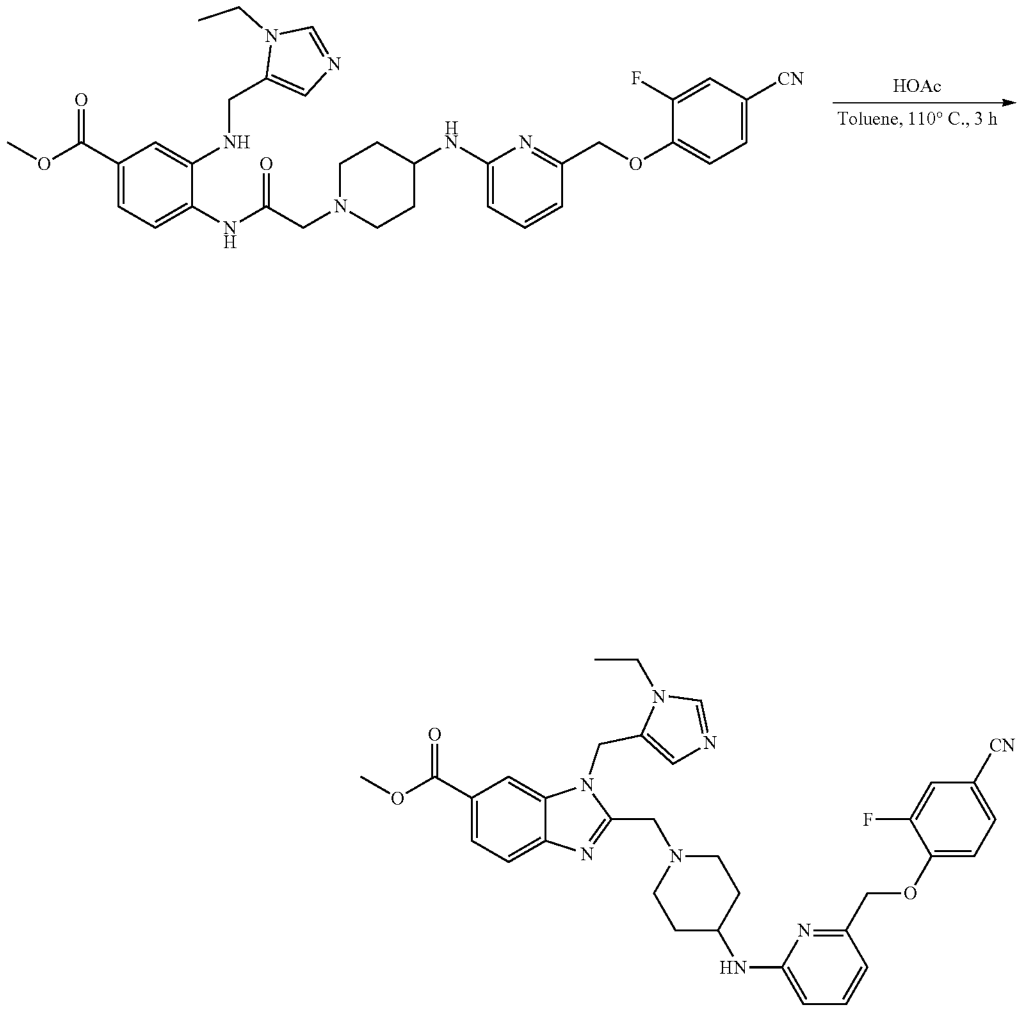

The mixture of methyl 4-(2-(4-((6-((4-cyano-2-fluorophenoxy)methyl)pyridin-2-yl)amino)piperidin-1-yl)acetamido)-3-((1-ethyl-1H-imidazol-5-yl)methyl)amino)benzoate (65 mg, 0.10 mmol) in toluene (3 mL) and acetic acid (0.5 mL) was stirred at 110° C. for 3 hours. After the completion of the reaction, the reaction solution was concentrated to give a residue in vacuo. The residue was purified by silica gel column chromatography (dichloromethane/methanol=10/1) to obtain methyl 2-((4-((6-((4-cyano-2-fluorophenoxy)methyl)pyridin-2-yl)amino)piperidin-1-yl)methyl)-1-((1-ethyl-1H-imidazol-5-yl)methyl)-1H-benzo[d]imidazol-6-carboxylate (45 mg, 71.4% yield). LC-MS m/z: 623 [M+H]$^+$.

3) Synthesis of 2-((4-((6-((4-cyano-2-fluorophenoxy)methyl)pyridin-2-yl)amino)piperidin-1-yl)methyl)-1-((1-ethyl-1H-imidazol-5-yl)methyl)-1H-benzo[d]imidazole-6-carboxylic acid

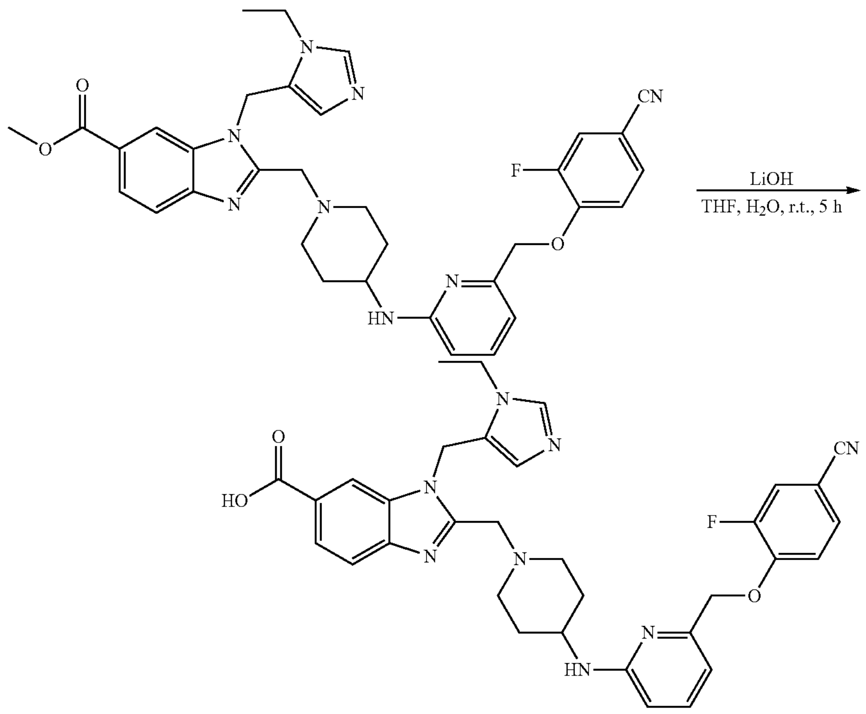

To a mixture of methyl 2-((4-((4-cyano-2-fluorophenoxy)methyl)pyridin-2-yl)aminopiperidin-1-yl)methyl)-1-((1-ethyl-1H-imidazol-5-yl)methyl)-1H-benzo[d]imidazole-6-carboxylate (45 mg, 0.07 mmol) in water (3.0 mL) and THF (3.0 mL) lithium hydroxide (7 mg, 0.28 mmol) was added. The reaction mixture was stirred at room temperature for 5 hours. After the completion of the reaction, the reaction mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)amino)piperidin-1-yl)methyl)-1-((1-ethyl-1H-imidazol-5-yl)methyl)-1H-benzo[d]-imidazole-6-carboxylic acid (14.70 mg, 33.5% yield). LC-MS m/z: 609 $[M+H]^+$.

$^1H$ NMR (400 MHZ, DMSO-$d_6$): δ8.05 (s, 1H), 7.87-7.79 (m, 2H), 7.68-7.63 (m, 3H), 7.44-7.34 (m, 2H), 6.53 (d, J-7.2 Hz, 1H), 6.47-6.44 (m, 2H), 6.40-6.38 (m, 1H), 5.72-5.69 (m, 2H), 5.14 (s, 2H), 4.02-3.97 (m, 2H), 3.78-3.76 (m, 2H), 3.59-3.54 (m, 1H), 2.76-2.67 (m, 2H), 2.14-2.07 (m, 2H), 1.77-1.72 (m, 2H), 1.29-1.20 (m, 2H), 1.14 (t, J=7.2 Hz, 3H).

Example 51. Synthesis of 1-((1-(cyclopropylmethyl)-1H-imidazol-5-yl)methyl)-2-(((4-((6-((4-ethynyl-2-fluoro-phenoxy))methyl)pyridin-2-yl)oxy)piperidin-1-yl)methyl)-1H-benzo[d]imidazole-6-carboxylic acid (compound C18)

1). Synthesis of methyl 4-(2-(4-((6-((4-bromo-2-fluorophenoxy)methyl)pyridin-2-yl)oxy)piperidin-1-yl)acetamido)-3-(((1-(cyclopropylmethyl)-1H-imidazol-5-yl)methyl)amino)benzoate

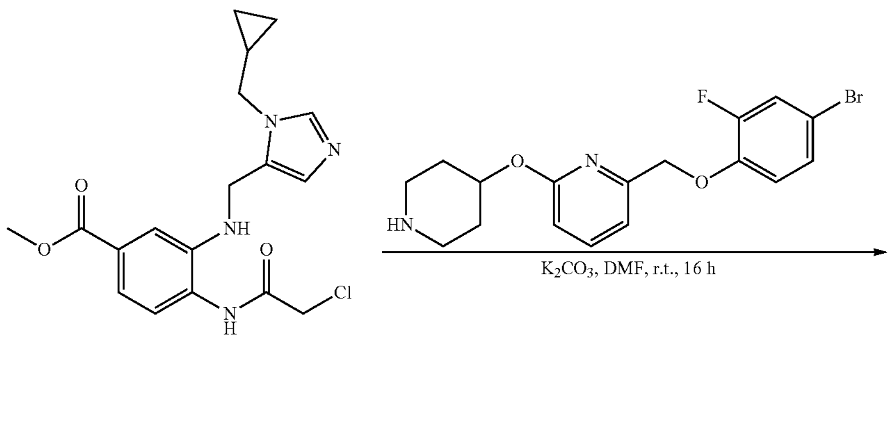

-continued

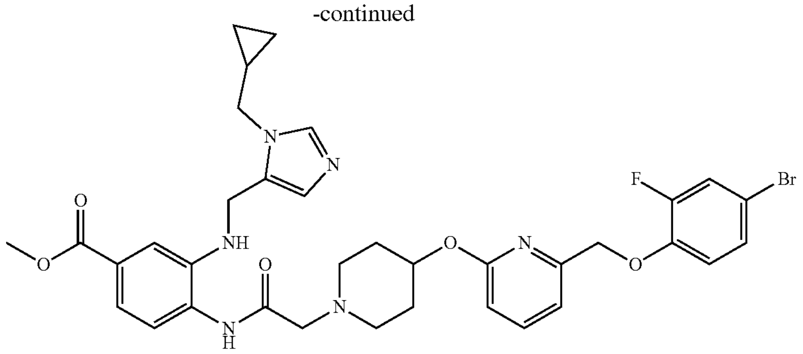

The mixture of methyl 4-(2-chloroacetamido)-3-((1-(cyclopropylmethyl)-1H-imidazol-5-yl)methyl)aminobenzoate (300 mg, 0.80 mmol), 2-((4-bromo-2-fluorophenoxy) methyl)-6-(piperidin-4-oxy)pyridine (305 mg, 0.80 mmol) and potassium carbonate (221 mg, 1.60 mmol)) in N,N-dimethylformamide (8 mL) was stirred at room temperature for 16 hours. After completion, the resulting mixture was diluted with water (30 mL) and extracted with ethyl acetate (10 mL×3). The combined organic layers were washed with brine (10 mL×3), dried over anhydrous sodium sulfate, filtered, and concentrated to give a residue in vacuo. The residue was purified by silica gel column chromatography (dichloromethane/methanol=20/1) to obtain methyl 4-(2-(4-((6-((4-bromo-2-fluorophenoxy)methyl)pyridin-2-yl)oxy) piperidin-1-yl)acetamido)-3-((1-(cyclopropylmethyl)-1H-imidazol-5-yl)methyl)amino)benzoate (350 mg, 60.6% yield). LC-MS m/z: 723 $[M+H]^+$.

2). Synthesis of methyl 2-((4-((6-((4-bromo-2-fluorophenoxy)methyl)pyridin-2-yl)oxy)piperidin-1-yl) methyl)-1-((1-(cyclopropylmethyl)-1H-imidazol-5-yl)methyl)-1H-benzo[d]imidazole-6-carboxylate

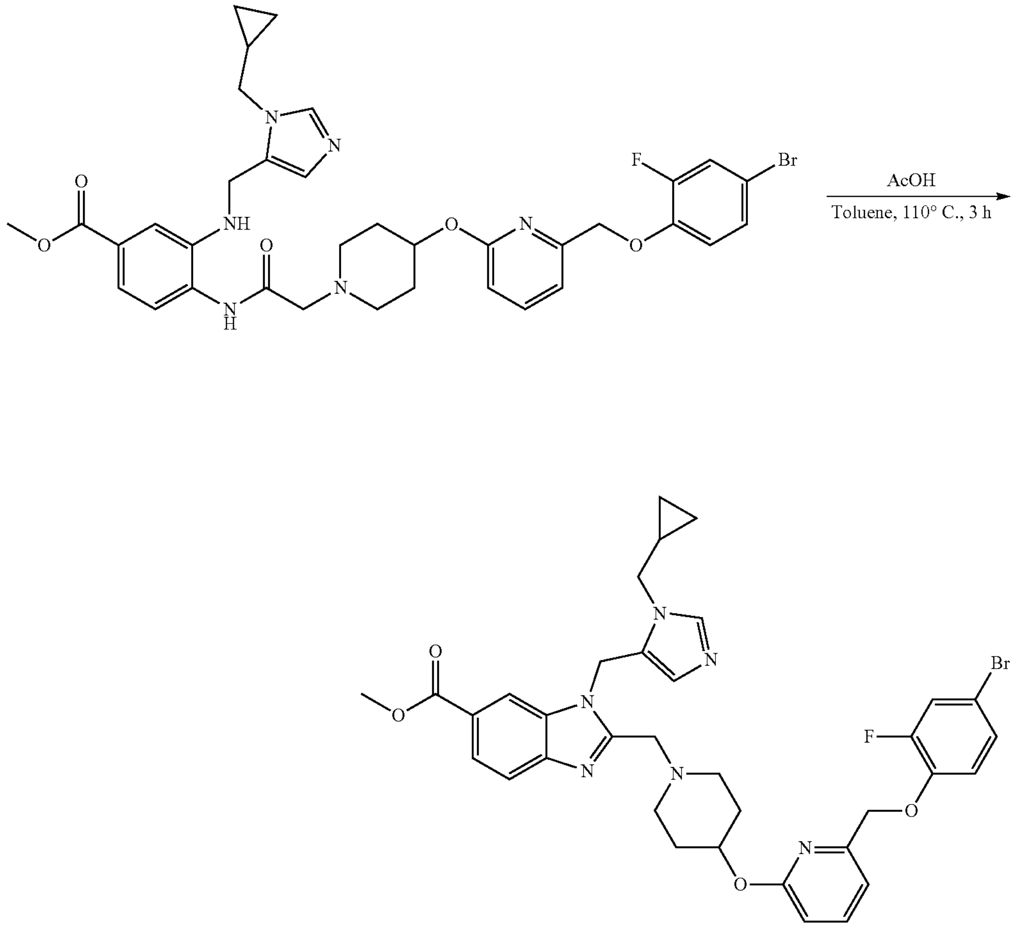

The mixture of methyl 4-(2-(4-((6-((4-bromo-2-fluorophenoxy)methyl)pyridin-2-yl)oxy)piperidin-1-yl)acetamido)-3-((1-(cyclopropylmethyl)-1H-imidazol-5-yl)methyl)amino)benzoate (350 mg, 0.48 mmol) in toluene (4 mL) and acetic acid (0.4 mL) was stirred at 110° for 3 hours. After completion, the solvent was removed by concentration to give a residue in vacuo. The residue was purified by silica gel column chromatography (dichloromethane/methanol=20/1) to obtain methyl 2-((4-((6-((4-bromo-2-fluorophenoxy)methyl)pyridin-2-yl)oxy)piperidin-1-yl)methyl)-1-((1-(cyclopropylmethyl)-1H-imidazol-5-yl)methyl)-1H-beno [d]imidazole-6-carboxylate (300 mg, 89.6% yield). LC-MS m/z: 705 [M+H]+.

3). Synthesis of methyl 1-((1-(cyclopropylmethyl)-1H-imidazol-5-yl)methyl)-2-((4-((6-((2-fluoro-4-((trimethylsilyl) ethynyl) phenoxy)methyl)pyridin-2-yl)oxy)piperidin-1-yl)methyl)-1H-benzo[d] imidazole-6-carboxylate

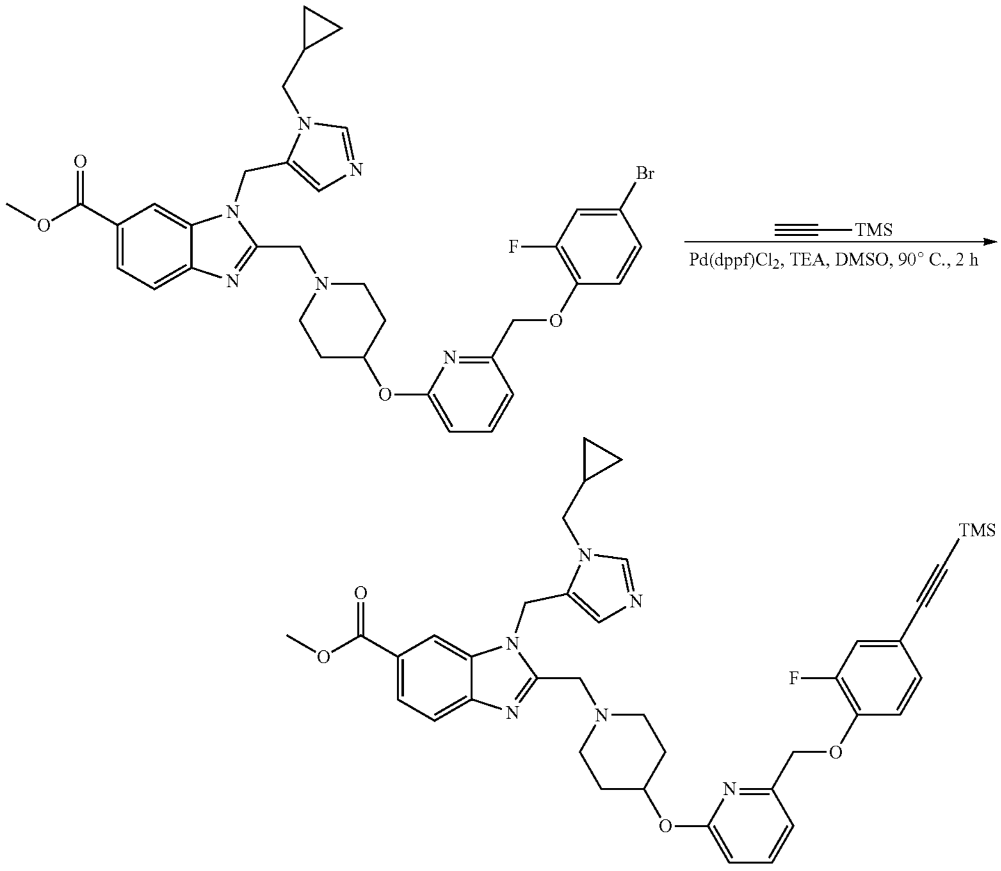

The mixture of methyl 2-((4-((6-((4-bromo-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylate (150 mg, 0.21 mmol), ethynyltrimethylsilane (206 mg, 2.10 mmol), triethylamine (212 mg, 2.10 mmol) and 1,1'-bisdiphenylphosphinoferrocene palladium dichloride (15 mg, 0.02 mmol) in dry DMSO (5 mL) was purged with nitrogen at room temperature. The resulting mixture was warmed to 90° C. and stirred at 90° C. for 2 hours. After completion, the reaction solution was cooled to room temperature and quenched with water (60 mL), and then extracted with ethyl acetate (20 mL×3). The combined organic layers were washed with brine (20 mL×3), dried over anhydrous sodium sulfate, filtered, and concentrated to give residue in vacuo. The residue was purified by silica gel column chromatography (dichloromethane/methanol=15/1) to give methyl 1-((1-(cyclopropylmethyl)-1H-imidazol-5-yl)methyl)-2-(((cyclopropylmethyl)-1H-imidazol-5-yl)methyl)-2-((4-((6-((2-fluoro-4-((trimethylsilyl) ethynyl) phenoxy)methyl)pyridin-2-yl)oxy) piperidin-1-yl)methyl)-1H-benzo[d]imidazole-6-carboxylate (80 mg, 52.8% yield). LC-MS m/z: 721 [M+H]+.

4). Synthesis of 1-((1-(cyclopropylmethyl)-1H-imidazol-5-yl)methyl)-2-((4-((6-((4-ethynyl-2-fluorophenoxy)-methyl)pyridin-2-yl)oxy)piperidin-1-yl)methyl)-1H-benzo[d]imidazole-6-carboxylic acid

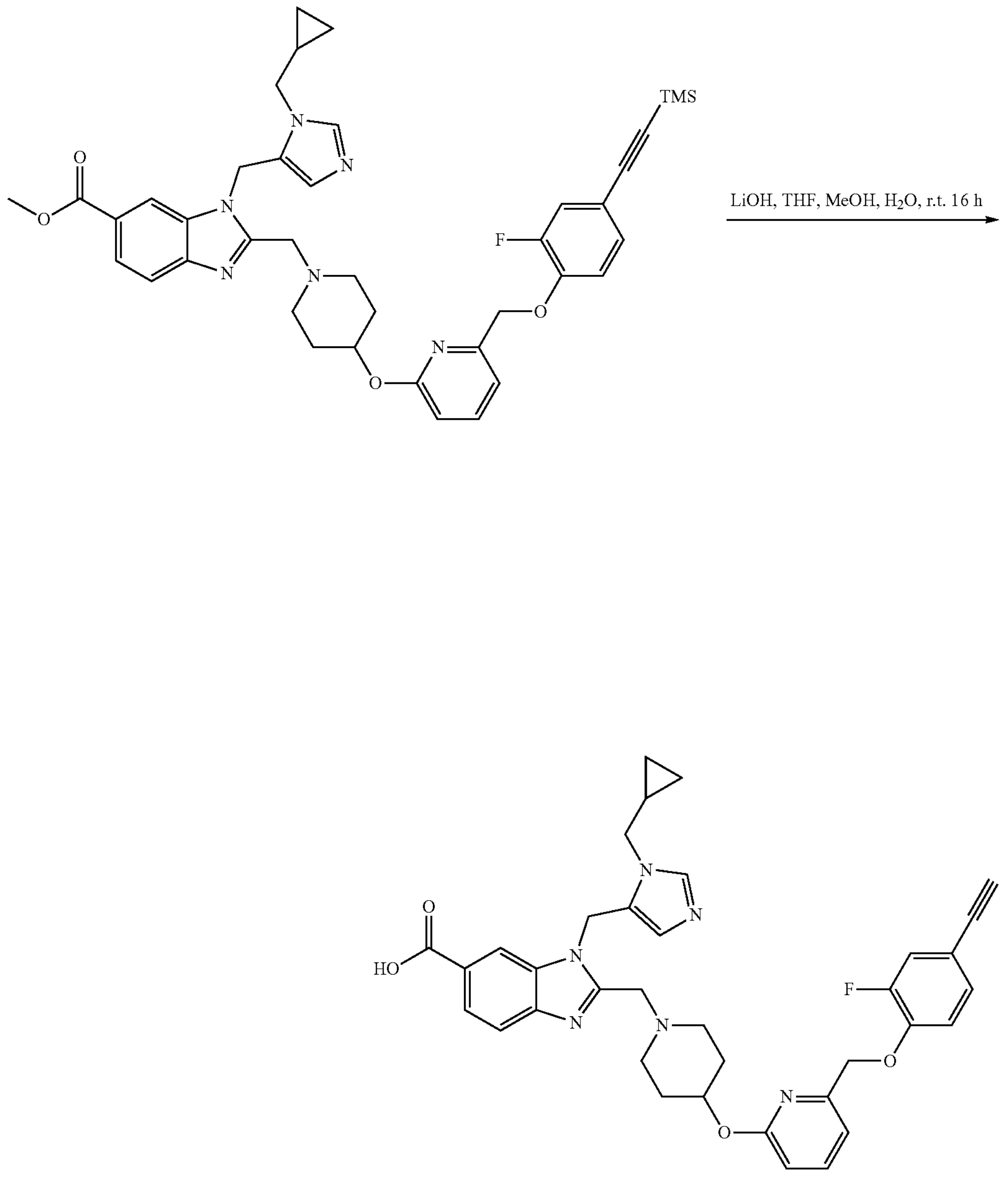

To a mixture of methyl 1-((1-(cyclopropylmethyl)-1H-imidazol-5-yl)methyl)-2-((4-((6-((2-fluoro-4-(((trimethylsilyl) ethynyl) phenoxy)methyl)pyridin-2-yl)oxy)piperidin-1-yl)methyl)-1H-benzo[d]imidazole-6-carboxylate (80 mg, 0.11 mmol) in THF (2 mL), water (2 mL) and MeOH (2 mL) lithium hydroxide (8 mg, 0.33 mmol) was added at room temperature. The resulting mixture was stirred at room temperature for 16 hours. After completion, the solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 1-((1-(cyclopropylmethyl)-1H-imidazol-5-yl)methyl)-2-((4-((6-((4-ethynyl-2-fluorophenoxy)-methyl)pyridin-2-yl)oxy)piper-idin-1-yl)methyl)-1H-benzo[d]imidazole-6-carboxylic acid (3.59 mg, 5.1% yield). LC-MS m/z: 635 $[M+H]^+$.

$^1H$ NMR (400 MHZ, DMSO-$d_6$): δ 8.05 (s, 1H), 7.82 (dd, J=8.4 Hz, 1.2 Hz, 1H), 7.73-7.65 (m, 3H), 7.39-7.36 (m, 1H), 7.24-7.23 (m, 2H), 7.03 (d, J=7.2 Hz, 1H), 6.71 (d, J=8.0 Hz, 1H), 6.36 (s, 1H), 5.74 (s, 2H), 5.20 (s, 2H), 4.88 (s, 1H), 4.11 (s, 1H), 3.89-3.82 (m, 4H), 2.70-2.67 (m, 2H), 2.28-2.24 (m, 2H), 1.81-1.79 (m, 2H), 1.48-1.46 (m, 2H), 1.06-0.97 (m, 1H), 0.49-0.46 (m, 2H), 0.34-0.31 (m, 2H).

Example 52. Synthesis of 2-((4-((6-((4-bromo-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylicacid (compound C19)

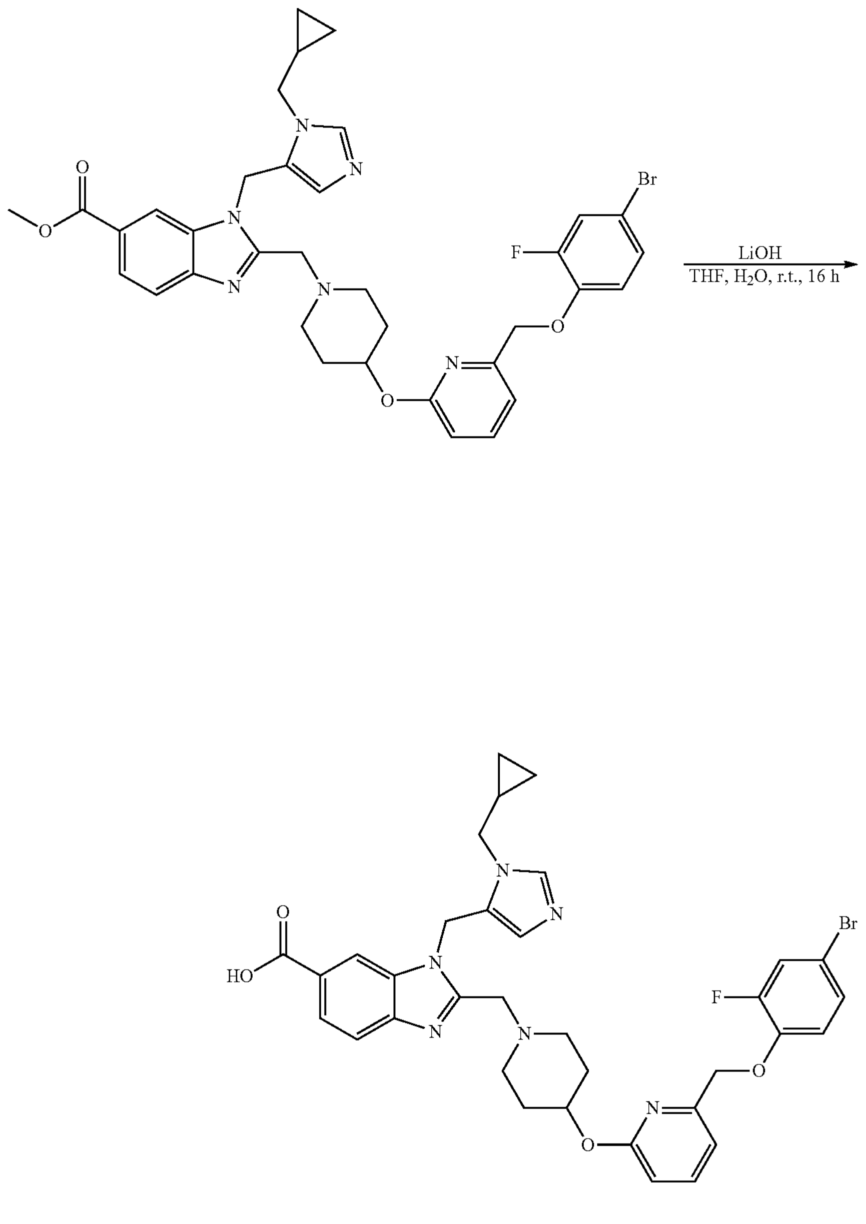

To a mixture of methyl 2-((4-((4-bromo-2-fluorophenoxy)methyl)pyridin-2-yl)oxypiperidin-1-yl)methyl)-1-((1-(cyclopropylmethyl)-1H-imidazol-5-yl)methyl)-1H-benzo[d]imidazole-6-carboxylate (60 mg, 0.09 mmol) in THF (4 mL) and water (4 mL) lithium hydroxide (6 mg, 0.27 mmol) was added at room temperature. The mixture was stirred at room temperature for 16 hours. After completion, the solvent was removed by concentration to give a residue in vacuo. The residue was purified prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; flow rate 20 ml/min) to obtain 2-((4-((6-((4-bromo-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylic acid (19.27 mg, 31.0% yield). LC-MS m/z: 691 $[M+H]^+$.

$^1H$ NMR (400 MHZ, DMSO-$d_6$): δ8.17 (s, 1H), 8.06 (s, 1H), 7.81 (dd, J-8.4 Hz, 1.2 Hz, 1H), 7.72-7.67 (m, 3H), 7.54 (dd, J=10.8 Hz, 2.0 Hz, 1H), 7.30 (d, J=9.2 Hz, 1H), 7.21 (t, J=9.2 Hz, 1H), 7.03 (d, J=7.2 Hz, 1H), 6.70 (d, J=8.4 Hz, 1H), 6.36 (s, 1H), 5.75 (s, 2H), 5.17 (s, 2H), 4.88-4.87 (m, 1H), 3.87-3.83 (m, 4H), 2.70-2.67 (m, 2H), 2.28-2.23 (m, 2H), 1.80-1.78 (m, 2H), 1.47-1.45 (m, 2H), 1.06-0.97 (m, 1H), 0.51-0.46 (m, 2H), 0.34-0.32 (m, 2H).

Example 53. Synthesis of 2-((4-(3-((4-cyano-2-fluorophenoxy)methyl) phenoxy)piperidin-1-yl) methyl)-1-((1-(cyclopropyl methyl)-1H-imidazol-5-yl)methyl)-1H-benzo[d]imidazole-6-carboxylic acid (compound C20)

1). Synthesis of methyl 2-((4-(3-((4-cyano-2-fluorophenoxy)methyl) phenoxy)piperidin-1-yl)methyl)-1-((1-(cyclopropylmethyl)-1H-imidazol-5-yl)methyl)-1H-benzo[d]imidazole-6-carboxylate

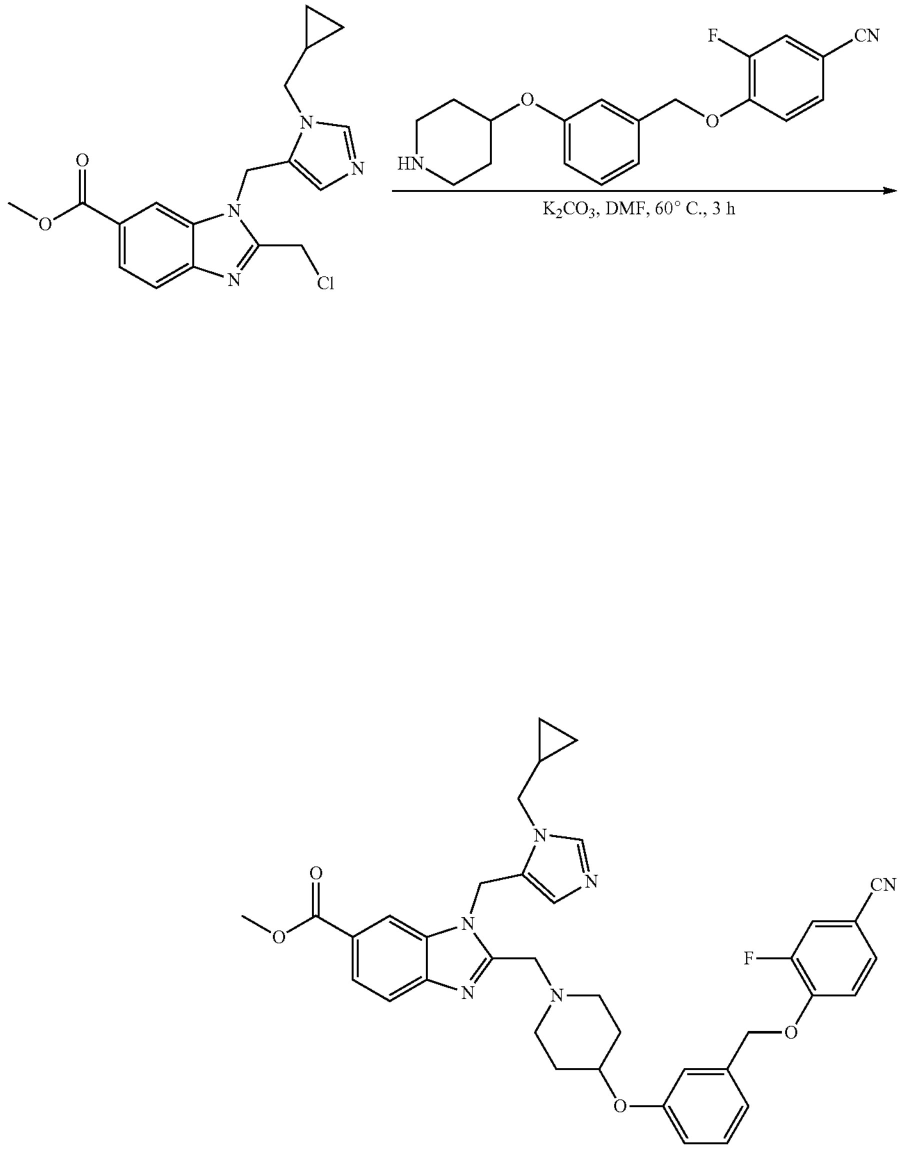

The mixture of methyl 2-(chloromethyl)-1-((1-(cyclopropylmethyl)-1H-imidazol-5-yl)methyl)-1H-benzo[d]imidazole-6-carboxylate (100 mg, 0.28 mmol), 3-fluoro-4-((3-(piperidin-4-oxy)benzyl)oxy)benzonitrile (92 mg, 0.28 mmol) and potassium carbonate (77 mg, 0.56 mmol) in N,N-dimethylformamide (3 mL) was warmed to 60° C. and stirred at 60° C. for 3 hours. After completion, the mixture was diluted with water (20 mL) and extracted with ethyl acetate (10 mL×2). The combined organic layers were washed with brine (10 mL×2), dried over anhydrous sodium sulfate, filtered, and concentrated to give a residue in vacuo. The residue was purified by silica gel column chromatography (dichloromethane/methanol=20/1) to obtain methyl 2-((4-(3-((4-cyano-2-fluorophenoxy)methyl) phenoxy)piperidin-1-yl)methyl-1-((1-(cyclopropylmethyl)-1H-imidazol-5-yl)methyl)-1H-benzo[d]imidazole-6-carboxylate (30 mg, 16.5% yield).

LC-MS m/z: 649 [M+H]$^+$.

2). Synthesis of 2-((4-(3-((4-cyano-2-fluorophenoxy)methyl) phenoxy)piperidin-1-yl)methyl)-1-((1-(cyclo-propylmethyl)-1H-imidazol-5-yl)methyl)-1H-benzo[d]imidazole-6-carboxylic acid

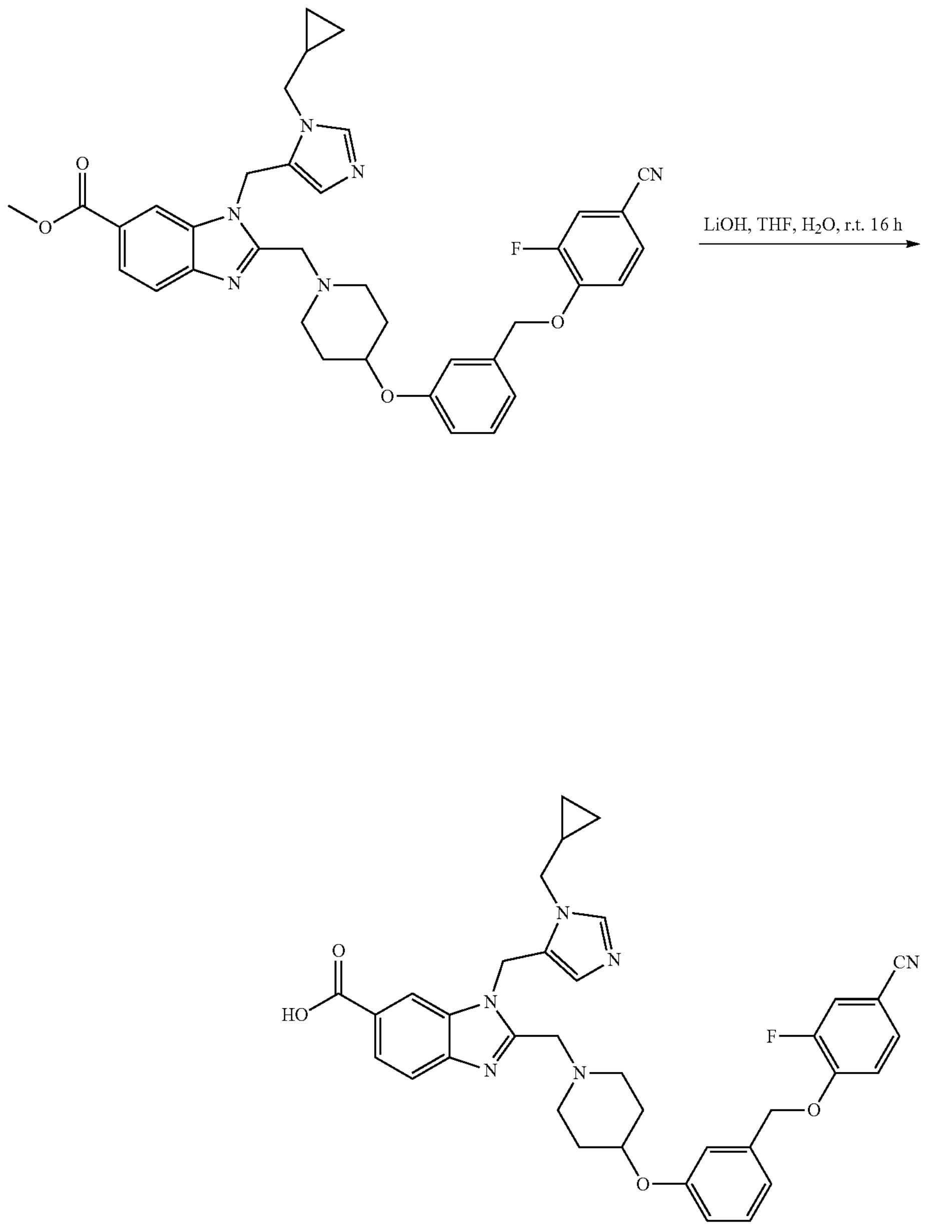

To a mixture of methyl 2-((4-(3-((4-cyano-2-fluorophenoxy)methyl) phenoxy)piperidin-1-yl)methyl-1-((1-(Cyclopropylmethyl)-1H-imidazol-5-yl)methyl)-1H-benzo[d]imidazole-6-carboxylate (30 mg, 0.046 mmol) in THF (2 mL) and water (2 mL) lithium hydroxide (4 mg, 0.15 mmol) was added. The reaction was stirred at room temperature for 16 hours. After completion, the solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-(3-((4-cyano-2-fluorophenoxy) methyl) phenoxy)piperidin-1-yl)methyl)-1-((1-(cyclopropyl-methyl)-1H-imidazol-5-yl)methyl)-1H-benzo[d]imidazole-6-carboxylic acid (5.16 mg, 16.3% yield). LC-MS m/z: 635 $[M+H]^+$.

$^1H$ NMR (400 MHZ, DMSO-$d_6$): δ8.19 (s, 1H), 8.05 (s, 1H), 7.88-7.80 (m, 2H), 7.72-7.66 (m, 3H), 7.42 (t, J=8.8 Hz, 1H), 7.29 (t, J-8.4 Hz, 1H), 7.02-6.98 (m, 2H), 6.93-6.91 (m, 1H), 6.36 (s, 1H), 5.75 (s, 2 H), 5.24 (s, 2H), 4.36 (s, 1H), 3.86-3.82 (m, 4H), 2.70-2.67 (m, 2H), 2.33-2.29 (m, 2H), 1.83-1.80 (m, 2H), 1.48-1.46 (m, 2H), 1.06-0.99 (m, 1H), 0.49-0.46 (m, 2H), 0.34-0.31 (m, 2H).

Example 54. Synthesis of 2-((4-((6-((4-cyano-2-fluorophenoxy)methyl)pyridin-2-yl)oxy)piperidin-1-yl)methyl)-1-methyl-1H-benzo[d]imidazole-6-carboxylic acid (compound C21)

1). Synthesis of methyl 2-((4-((6-((4-cyano-2-fluorophenoxy)methyl)pyridin-2-yl)oxy)piperidin-1-yl)methyl)-1-methyl-1H-benzo[d]imidazole-6-carboxylate

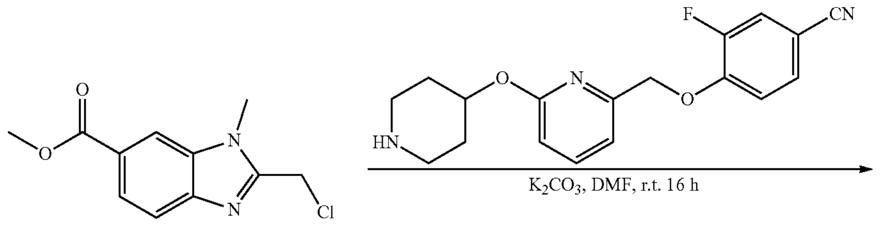

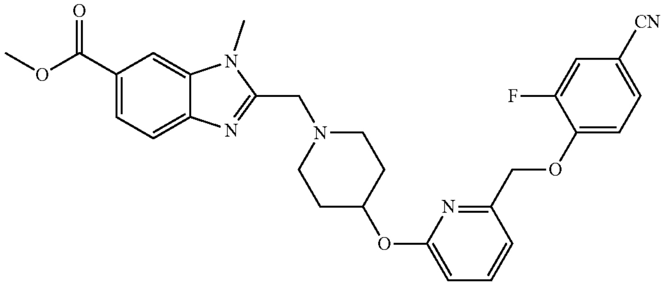

The mixture of methyl 2-(chloromethyl)-1-methyl-1H-benzo[d]imidazole-6-carboxylate (120 mg, 0.50 mmol), 3-fluoro-4-((6-(piperidin-4-oxy)pyridin-2-yl)methoxy)benzonitrile (163 mg, 0.50 mmol) and potassium carbonate (138 mg, 1.0 mmol) in N,N-dimethylformamide (5 mL) was stirred at room temperature for 16 hours. After completion, the mixture was concentrated to give a residue in vacuo. The residue was purified by silica gel column chromatography (dichloromethane/methanol=20/1) to obtain methyl 2-((4-((6-((4-cyano-2-fluorophenoxy)methyl)-pyridin-2-yl)oxy)piperidin-1-yl)methyl)-1-methyl-1H-benzo[d]imidazole-6-carboxylate (135 mg, 50.7% yield). LC-MS m/z: 530 $[M+H]^+$.

2). Synthesis of 2-((4-((6-((4-cyano-2-fluorophenoxy)methyl)pyridin-2-yl)oxy)piperidin-1-yl)methyl)-1-methyl-1H-benzo[d]imidazole-6-carboxylic acid

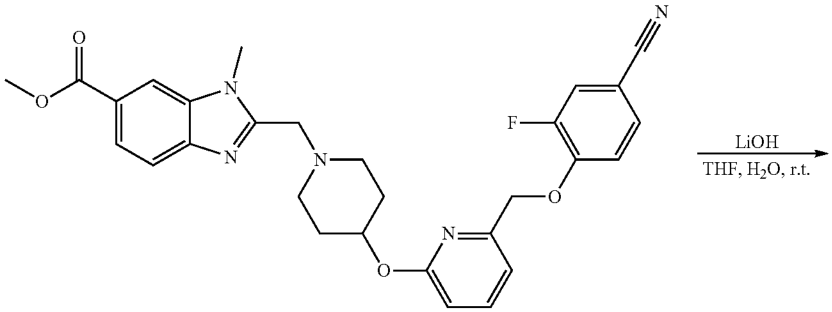

-continued

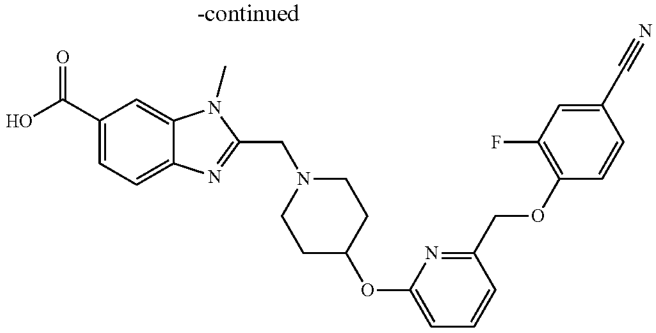

To a mixture of methyl 2-((4-((6-((4-cyano-2-fluorophenoxy)methyl)pyridin-2-yl)oxy)piperidin-1-yl)methyl)-1-methyl-1H-benzo[d]imidazole-6-carboxylate (135 mg, 0.25 mmol) in water (5 mL) and THF (5 mL) hydroxide lithium (60 mg, 2.50 mmol) was added at room temperature. The resulting mixture was stirred at room temperature for 16 hours. After completion, the solvent was removed by concentration to give a residue in vacuo. The residue was purified by Prep HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) purification to give 2-((4-((6-((4-cyano-2-fluorophenoxy)methyl)pyridin-2-yl)oxy)piperidin-1-yl)methyl)-1-methyl-1H-benzo[d]imidazole-6-carboxylic acid (72.01 mg: 55.9% yield). LC-MS m/z: 516 $[M+H]^+$. $^1H$ NMR (400 MHZ, DMSO-$d_6$): δ12.75 (s, 1H), 8.16-8.15 (m, 1H), 7.90-7.87 (m, 1H), 7.81 (dd, J=8.4, 1.6 Hz, 1H), 7.73 (t, J=8.0 Hz, 1H), 7.68-7.64 (m, 2H), 7.45 (t, J-8.4 Hz, 1H), 7.06 (d, J=7.2 Hz, 1H), 6.74 (d, J=8.4 Hz, 1H), 5.31 (s, 2H), 4.94-4.89 (m, 1H), 3.92 (s, 3H), 3.84 (s, 2H), 2.77-2.74 (m, 2H), 2.33-2.29 (m, 2H), 1.92-1.90 (m, 2H), 1.65-1.59 (m, 2H).

Example 55.: Synthesis of 2-((4-((6-((4-chloro-2-fluorophenoxy)methyl)pyridin-2-yl)oxy)piperidin-1-yl)methyl)-1-methyl-1H-benzo[d]imidazole-6-carboxylic acid (compound C22)

1). Synthesis of methyl 2-((4-((6-((4-Chloro-2-fluorophenoxy)methyl)pyridin-2-yl)oxy)piperidin-1-yl) methyl)-1-methyl-1H-benzo[d]imidazole-6-carboxylate

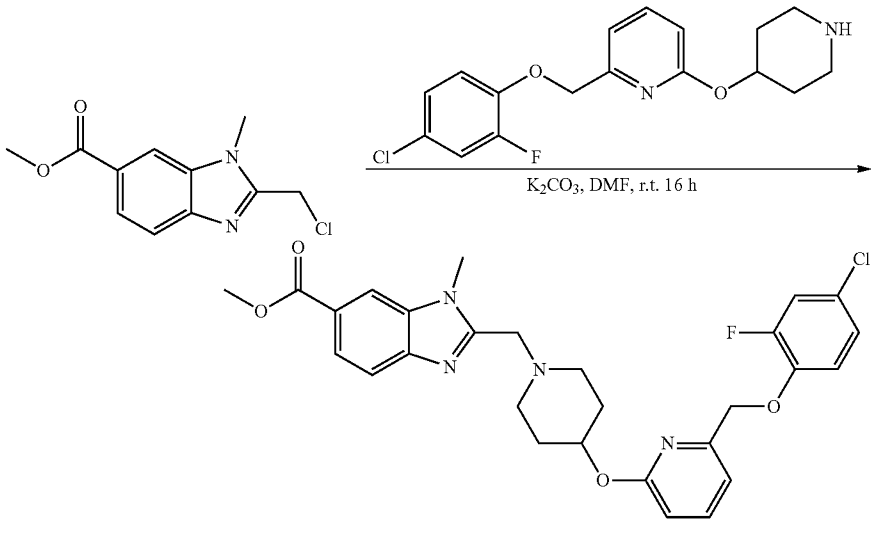

The mixture of methyl 2-(chloromethyl)-1-methyl-1H-benzo[d]imidazole-6-carboxylate (120 mg, 0.50 mmol), 2-((4-chloro-2-fluorophenoxy)methyl)-6-(piperidin-4-oxy) pyridine (170 mg, 0.50 mmol) and potassium carbonate (210 mg, 1.05 mmol) in N,N-dimethylformamide (10 mL) was stirred at room temperature for 16 hours. After completion, the mixture was concentrated to give a residue in vacuo. The residue was separated and purified by silica gel column (dichloromethane/methanol=19/1) to obtain methyl 2-((4-((6-((4-chloro-2-fluorophenoxy)methyl)pyridin-2-yl)) oxy) piperidin-1-yl)methyl)-1-methyl-1H-benzo[d]imidazole-6-carboxylate (120 mg, 44.3% yield). LC-MS m/z: 539 $[M+H]^+$.

2). Synthesis of 2-((4-((6-((4-chloro-2-fluorophenoxy)methyl)pyridin-2-yl)oxy)piperidin-1-yl)methyl)-1-methyl-1H-benzo[d]imidazole-6-carboxylic acid

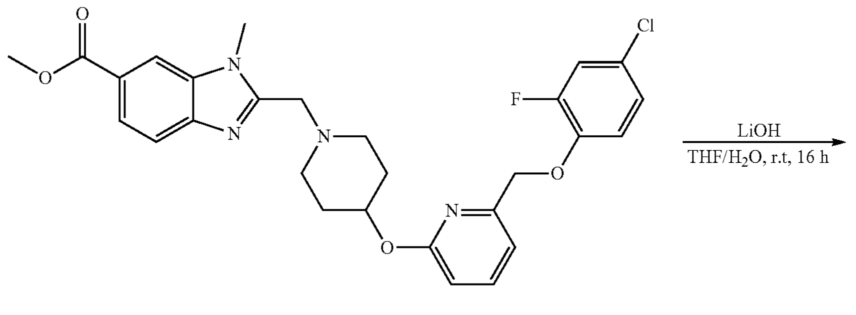

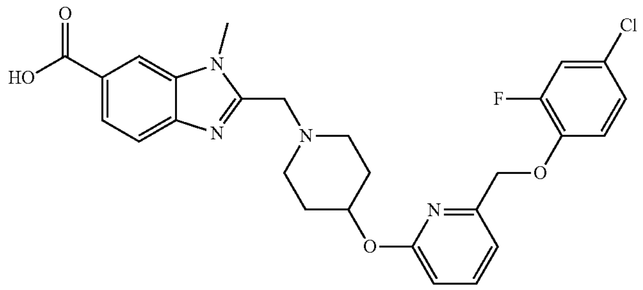

To a mixture of methyl 2-((4-((6-((4-chloro-2-fluorophenoxy)methyl)pyridin-2-yl)oxy)piperidin-1-yl)methyl)-1-methyl-1H-benzo[d]imidazole-6-carboxylate (120 mg, 0.22 mmol) in water (4 mL) and THF (4 mL) lithium hydroxide (53 mg, 2.20 mmol) was added at room temperature. The reaction mixture was stirred at room temperature for 16 hours. After completion, the solvent was removed by concentration to give a residue in vacuo, The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-chloro-2-fluorophenoxy)methyl)pyridin-2-yl)oxy)piperidine pyridin-1-yl)methyl)-1-methyl-1H-benzo[d]imidazole-6-carboxylic acid (89.02 mg, 77.2% yield). LC-MS m/z: 525 $[M+H]^+$.

$^1$H NMR (400 MHZ, DMSO-$d_6$): δ8.15 (s, 1H), 7.81 (dd, J-8.4 Hz, 1.6 Hz, 1H), 7.71 (t, J=8.0 Hz, 1H), 7.64 (d, J-8.4 Hz, 1H), 7.44 (dd, J=11.2 Hz, 2.4 Hz, 1H), 7.28 (t, J-9.2 Hz, 2H), 7.18 (d, J=8.8 Hz, 1H), 7.04 (d, J-7.2 Hz, 1H), 6.71 (d, J-8.4 Hz, 1H), 5.18 (s, 2H), 4.94-4.92 (m, 1H), 3.92 (s, 3H), 3.83 (s, 2H), 2.77-2.74 (m, 2H), 2.34-2.29 (m, 2H), 1.93-1.91 (m, 2H), 1.65-1.61 (m, 2H).

Example 56. Synthesis of(S)-2-((4-((6-((4-chloro-2-fluorophenoxy)methyl)pyridin-2-yl)oxy)piperidin-1-yl)methyl)-4-fluoro-1-(oxetan-2-ylmethyl)-1H-benzo[d]imidazole-6-carboxylic acid (compound C23)

1). Synthesis of(S)—N-(4-bromo-2-fluoro-6-((oxetan-2-ylmethyl)amino)phenyl)-2-(4-((6-((4-chloro-2-fluorophenoxy)methyl)pyridin-2-yl)oxy)piperidin-1-yl)acetamide

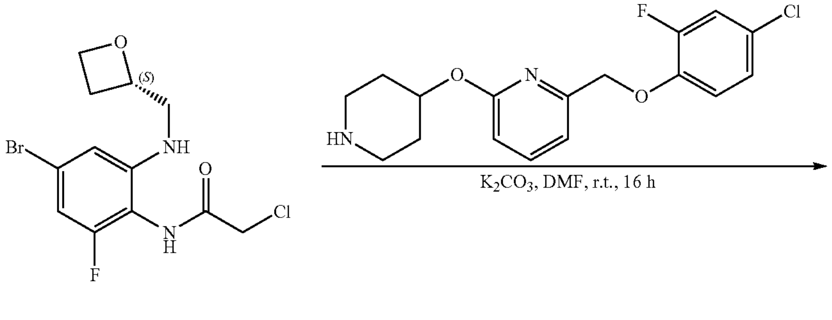

-continued

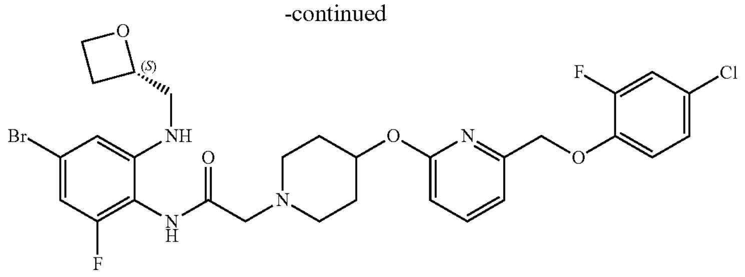

The mixture of 2-((4-chloro-2-fluorophenoxy)methyl)-6-(piperidin-4-oxy)pyridine (1.63 g, 4.85 mmol), (S)—N-(4-bromo-2-fluoro-6-((oxetan-2-yl-methyl)amino)phenyl)-2-chloroacetamido (1.70 g, 4.85 mmol) and potassium carbonate (1.34 g, 9.70 mmol) in N,N-dimethylformamide (20 mL) was stirred at room temperature for 16 hours. After completion, the mixture was diluted with ethyl acetate (100 mL) and washed with saturated ammonium chloride (20 mL×3) and brine (20 mL×3), dried over anhydrous sodium sulfate, filtered, and reduced in pressure concentrate. The residue was purified by silica gel column chromatography (petroleum ether/ethyl acetate=1/1) to obtain(S)—N-(4-bromo-2-fluoro-6-((oxetan-2-yl-methyl)amino)phenyl)-2-(4-((6-((4-chloro-2-fluorophenoxy)methyl)pyridin-2-yl)oxy)piperidin-1-yl)acetamide (2.10 g, 66.6% yield). LC-MS m/z: 653 $[M+H]^+$.

2). Synthesis of methyl(S)-6-Bbomo-2-((4-((6-((4-chloro-2-fluorophenoxy)methyl)pyridin-2-yl)oxy)piperidin-1-yl))-4-fluoro-1-(oxetan-2-yl-methyl)-1H-benzo[d]imidazole

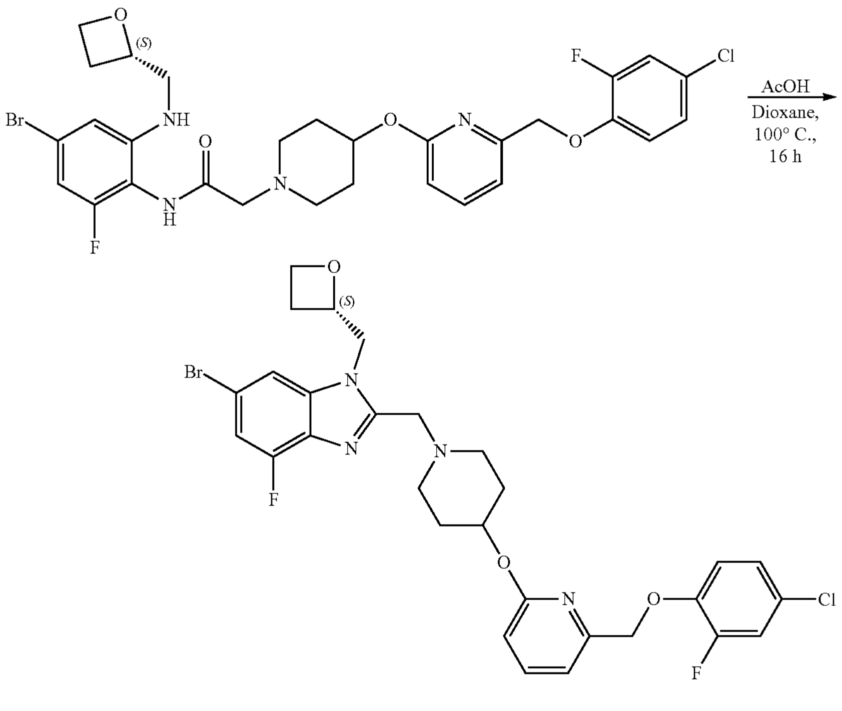

To a solution of(S)—N-(4-bromo-2-fluoro-6-((oxetan-2-yl-methyl)amino)phenyl)-2-(4-((6-((4-chloro-2-fluorophenoxy)methyl)pyridin-2-yl)oxy)piperidin-1-yl)acetamide (500 mg, 0.77 mmol) in dioxane (10 mL) acetic acid (1 mL) was added at room temperature. The resulting mixture was stirred for at 100° C. 16 hours. After completion, the reaction solution was concentrated to give a residue in vacuo. The residue was purified by silica gel column chromatography (petroleum ether/ethyl acetate=1/1) to obtain(S)-6-bromo-2-((4-((6-((4-chloro-2-fluorophenoxy)methyl)pyridin-2-yl)oxy)piperidin-1-yl)methyl)-4-fluoro-1-(oxetane-2-yl-methyl)-1H-benzo[d]imidazole (220 mg, 45.2% yield). LC-MS m/z: 635 $[M+H]^+$.

3). Synthesis of methyl(S)-2-((4-((6-((4-chloro-2-fluorophenoxy)methyl)pyridin-2-yl)oxy)piperidin-1-yl)methyl)-4-fluoro-1-(oxetan-2-yl-methyl)-1H-benzo[d]imidazole-6-carboxylate

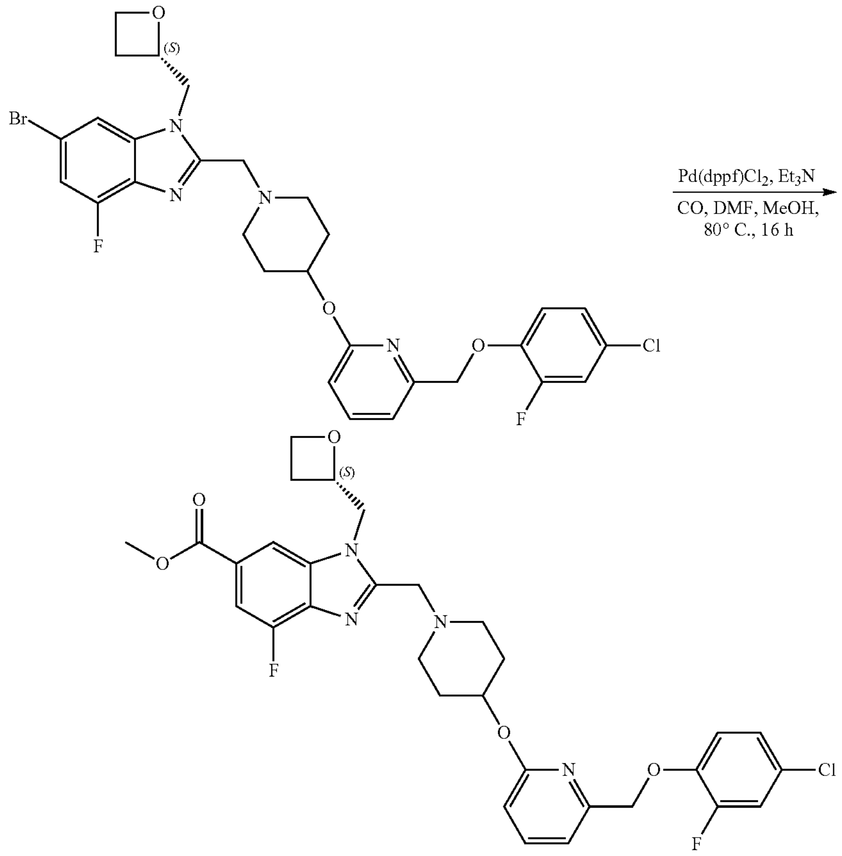

To a mixture of(S)-6-bromo-2-((4-((6-((4-chloro-2-fluorophenoxy)methyl)pyridin-2-yl)oxy)piperidin-1-yl) methyl)-4-fluoro-1-(oxetan-2-yl-methyl)-1H-benzo[d]imidazole (100 mg, 0.16 mmol) in N,N-dimethylformamide (5 mL) and methanol (5 mL) triethylamine (48 mg, 0.48 mmol) and 1,1'-bisdiphenylphosphinoferrocene palladium dichloride (15 mg, 0.02 mmol) were added at room temperature under carbon monoxide atmosphere. The mixture was stirred at 80° C. for 16 hours. After completion, the mixture was concentrated to give a residue in vacuo. The residue was purified by silica gel column chromatography (petroleum ether/ethyl acetate=1/1) to obtain methyl(S)-2-((4-((6-((4-chloro-2-fluorophenoxy)methyl)pyridin-2-yl)oxy)piperidin-1-yl)methyl)-4-fluoro-1-(oxetan-2-yl-methyl)-1H-benzo[d] imidazole-6-carboxylate (48 mg, 50.0% yield). LC-MS m/z: 613 $[M+H]^+$.

4). Synthesis of(S)-2-((4-((6-((4-chloro-2-fluorophenoxy)methyl)pyridin-2-yl)oxy)piperidin-1-yl) methyl)-4-fluoro-1-(oxetan-2-ylmethyl)-1H-benzo [d]imidazole-6-carboxylic acid

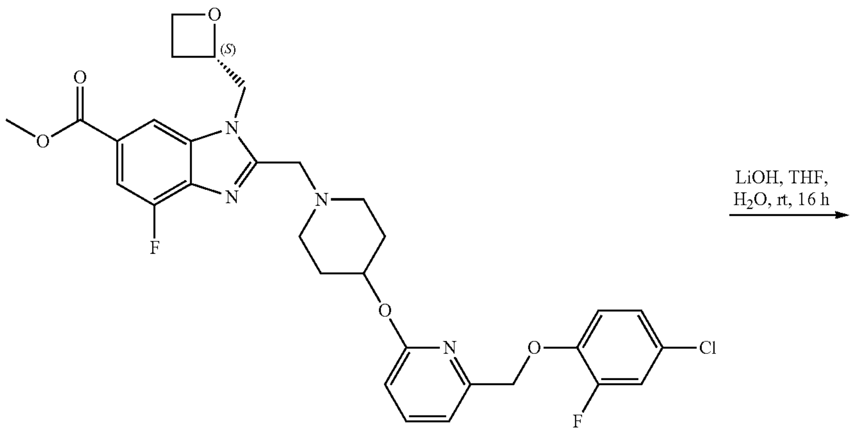

-continued

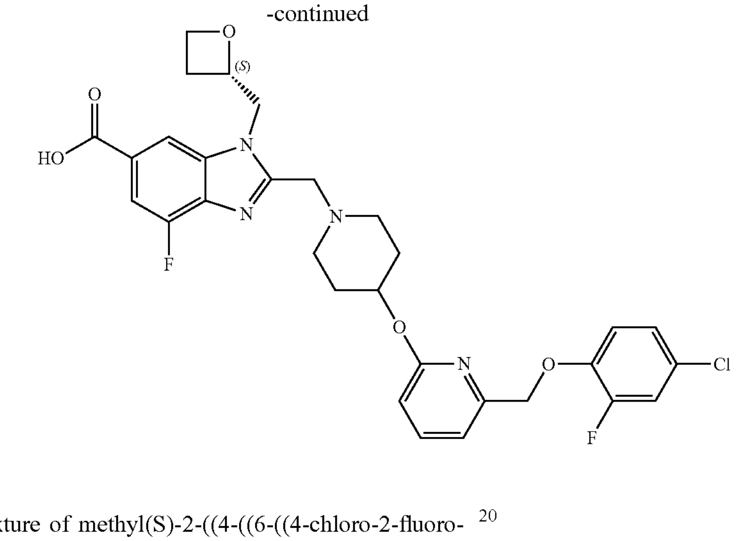

To a mixture of methyl(S)-2-((4-((6-((4-chloro-2-fluorophenoxy)methyl)pyridin-2-yl)oxy)piperidin-1-yl)methyl)-4-fluoro-1-(oxetan-2-yl-methyl)-1H-benzo[d]imidazole-6-carboxylate (48 mg, 0.08 mmol) in THF (2 mL) and water (2 mL) lithium hydroxide monohydrate (34 mg, 0.80 mmol) was added at room temperature. The resulting mixture was stirred at room temperature for 5 hours. After completion, the resulting mixture was adjusted to pH=5-6 with hydrochloric acid (1 M) and extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile Phase B: acetonitrile; Flow rate: 40 mL/min; Gradient: 20% B-50% B in 20 min; Detector: 254 nm) to give(S)-2-((4-((6-((4-chloro-2-fluorophenoxy)methyl)pyridin-2-yl)oxy)piperidin-1-yl)methyl)-4-fluoro-1-(oxetan-2-ylmethyl)-1H-benzo[d]imidazole-6-carboxylic acid (20.87 mg, 43.6% yield). LC-MS m/z: 599 $[M+H]^+$.

$^1H$ NMR (400 MHZ, DMSO-$d_6$) δ 8.11 (s, 1H), 7.72 (t, J=7.6 Hz, 1H), 7.54 (d, J=11.6 Hz, 1H), 7.45 (dd, J=11.2 Hz, 2.8 Hz, 1H), 7.28 (t, J=9.2 Hz, 1H), 7.20-7.17 (m, 1H), 7.04 (d, J=7.2 Hz, 1H), 6.72 (d, J-8.4 Hz, 1H), 5.19 (s, 2H), 5.12-5.07 (m, 1H), 4.97-4.92 (m, 1H), 4.82-4.76 (m, 1H), 4.65 (d, J=12.8 Hz, 1H), 4.52-4.47 (m, 1H), 4.39-4.34 (m, 1H), 3.94 (d, J=13.6 Hz, 1H), 3.79 (d, J=13.6 Hz, 1H), 2.80-2.67 (m, 3H), 2.46-2.41 (m, 1H), 2.35-2.32 (m, 2H), 1.93-1.91 (m, 2H), 1.63-1.59 (m, 2H).

Example 57. Synthesis of 2-(4-((6-((4-chloro-2-fluorophenoxy)methyl)pyridin-2-yl)oxy)benzyl)-1-((1-ethyl-1H-imidazole-5-yl)methyl)-1H-benzo[d]imidazole-6-carboxylic acid (compound C24)

1). Synthesis of methyl 2-(4-((6-((4-chloro-2-fluorophenoxy)methyl)pyridin-2-yl)oxy)phenyl)acetate

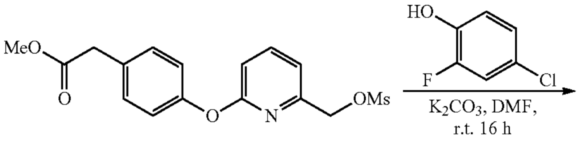

-continued

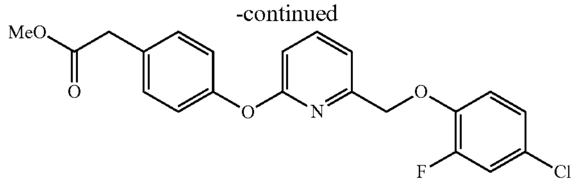

The mixture of methyl 2-(4-((6-((methylsulfonyl)oxy)methyl)pyridin-2-yl)oxy)phenyl)acetate (410 mg, 1.17 mmol), 3-fluoro-4-hydroxybenzonitrile (171 mg, 1.17 mmol) and potassium carbonate (323 mg, 2.34 mmol) in N,N-dimethylformamide (6 mL) was stirred at room temperature for 16 hours. After completion, water (5 mL) was added to dilute the mixture, and extracted with ethyl acetate (20 mL×3). The combined organic layers were washed with brine (15 mL×2), dried over anhydrous sodium sulfate, filtered, and concentrated to give a residue in vacuo. The residue was purified by silica gel column chromatography (dichloromethane/methanol=20/1) to obtain methyl 2-(4-((6-((4-chloro-2-fluorophenoxy)methyl)pyridin-2-yl)) oxy) phenyl)acetate (406 mg, 86.4% yield). LC-MS m/z: 402 $[M+H]^+$.

2). Synthesis of 2-(4-((6-((4-Chloro-2-fluorophenoxy)methyl)pyridin-2-yl)oxy)phenyl)acetic acid

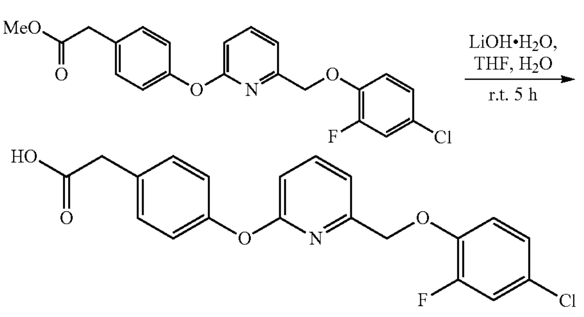

To a mixture of methyl 2-(4-((6-((4-chloro-2-fluorophenoxy)methyl)pyridine-2-yl)oxy)phenyl)acetate (406 mg, 1.01 mmol) in THF (5 mL) and water (5 mL) lithium hydroxide monohydrate (424 mg, 10.10 mmol) was added at room temperature. The resulting mixture was stirred at room temperature for 5 hours. After completion, the resulting mixture was adjusted to pH=5-6 with hydrochloric acid (1 M). The mixtures was concentrated to give a residue in vacuo. The residue was purified by silica gel column chromatography (dichloromethane/methanol=10/1) to obtain 2-(4-((6-((4-chloro-2-fluorophenoxy)methyl)pyridin-2-yl)oxy)phenyl)acetic acid (248 mg, 63.3% yield). LC-MS m/z: 388 [M+H]$^+$.

3). Synthesis of methyl 4-(2-(4-((6-((4-chloro-2-fluorophenoxy)methyl)pyridin-2-yl)oxy)phenyl)acetamido)-3-((1-ethyl-1H-imidazol-5-yl)methyl)amino)benzoate

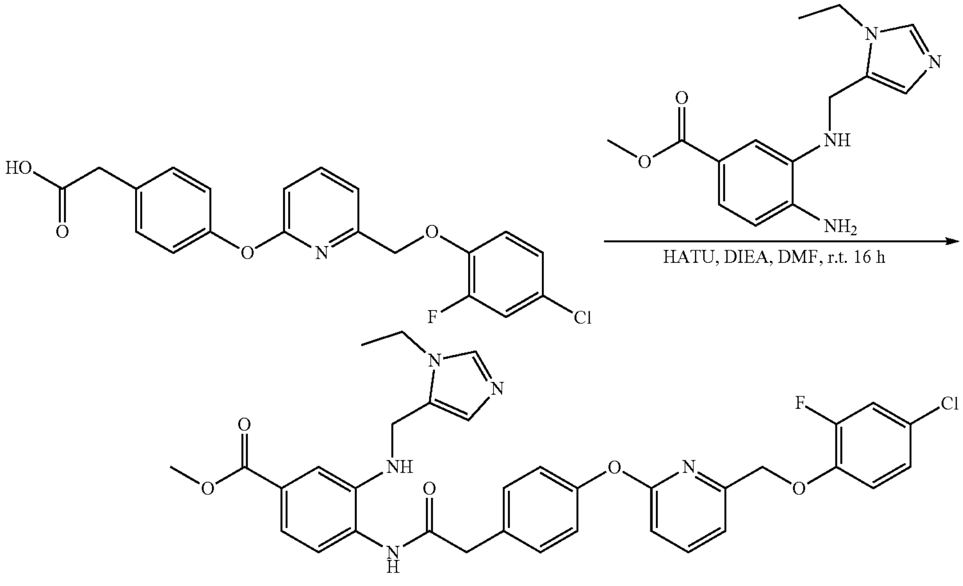

To a mixture of 2-(4-((6-((4-chloro-2-fluorophenoxy)methyl)pyridin-2-yl)oxy)phenyl)acetic acid (248 mg, 0.64 mmol), 2-(3H-[1,2,3]triazolo[4,5-b]pyridin-3-yl)-1,1,3,3-tetramethyluronium hexafluorophosphate (V) (365 mg, 0.96 mmol) and N,N-diisopropylethylamine (330 mg, 2.56 mmol) in N,N-dimethylformamide (3 mL) methyl 4-amino-3-(((1-ethyl-1H-imidazol-5-yl)methyl)amino)benzoate (175 mg, 0.64 mmol) was added at room temperature. The mixture was stirred at room temperature for 16 hours. After completion, the reaction was quenched by adding water (5 mL) and extracted with ethyl acetate (20 mL×2). The combined organic layers washed with brine (20 mL×3), dried over anhydrous sodium sulfate, filtered, and concentrated to give a residue in vacuo. The residue was purified by silica gel column chromatography (dichloromethane/methanol=10/1) to obtain methyl 4-(2-(4-((6-((4-chloro-2-fluorophenoxy)methyl)pyridine)-2-yl)oxy)phenyl)acetamido)-3-((1-ethyl-1H-imidazol-5-yl)methyl)amino)benzoate (232 mg, 56.3% yield). LC-MS m/z: 644 [M+H]$^+$.

4). Synthesis of methyl 2-(4-((6-((4-chloro-2-fluorophenoxy)methyl)pyridin-2-yl)oxy)benzyl)-1-((1-ethyl-1H-imidazole-5-yl)methyl)-1H-benzo[d]imidazole-6-carboxylate

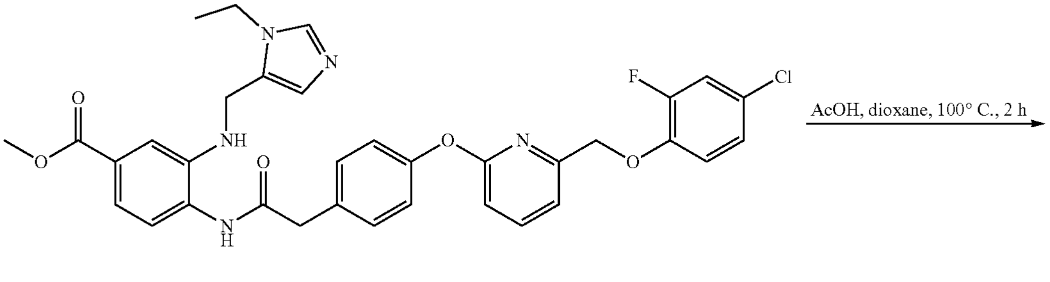

-continued

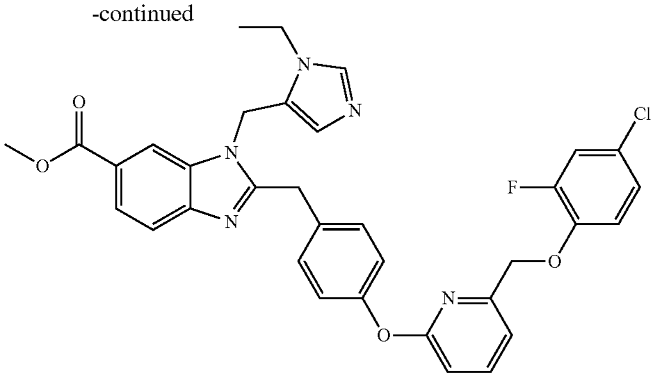

To a solution of methyl 4-(2-(4-((6-((4-chloro-2-fluorophenoxy)methyl)pyridin-2-yl)oxy)phenyl)acetamido)-3-((1-ethyl-1H-imidazol-5-yl)methyl)amino)benzoate (232 mg, 0.36 mmol) in dioxane (5 mL) acetic acid (0.5 mL) was added at room temperature. The resulting mixture was stirred at 100° C. for 2 hours. After completion, the reaction solution was concentrated to give a residue in vacuo. The residue was purified by silica gel column chromatography (dichloromethane/methanol=10/1) to obtain methyl 2-(4-((6-((4-chloro-2-fluorophenoxy)methyl)pyridin-2-yl)oxy)benzyl)-1-((1-ethyl-1H-imidazol-5-yl)methyl)-1H-benzo[d]imidazol-6-carboxylate (190 mg, 84.3% yield). LC-MS m/z: 626 $[M+H]^+$.

5). Synthesis of -2-(4-((6-((4-chloro-2-fluorophenoxy)methyl)pyridin-2-yl)oxy)benzyl)-1-((1-ethyl-1H-imidazole-5-yl)methyl)-1H-benzo[d]imidazole-6-carboxylic acid

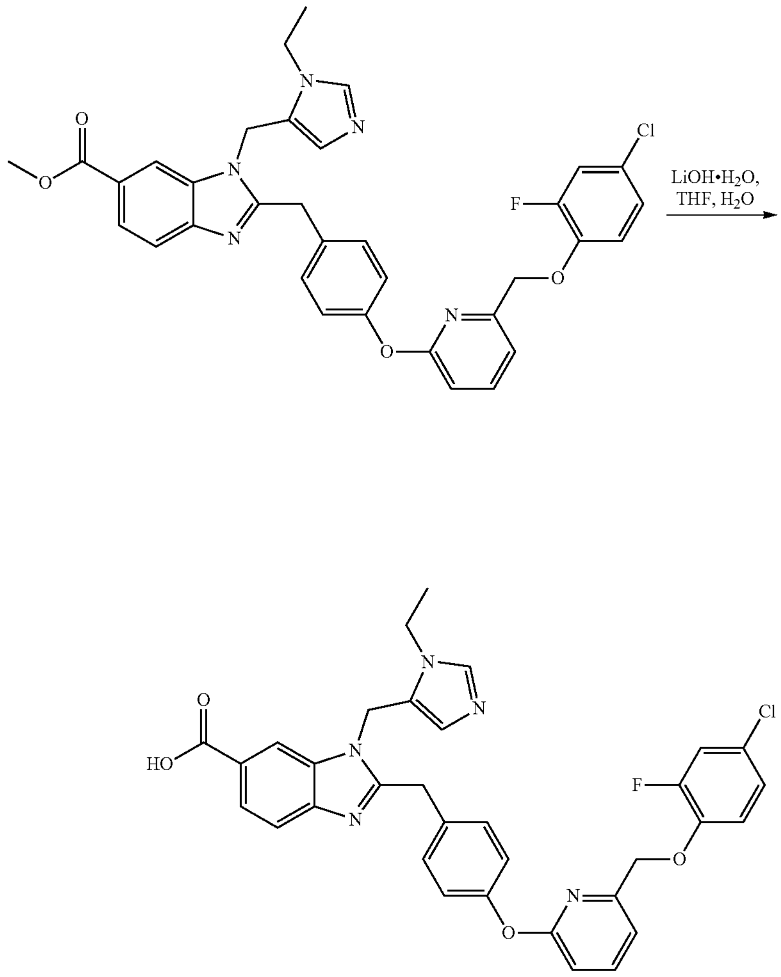

To a solution of methyl 2-(4-((6-((4-chloro-2-fluorophenoxy)methyl)pyridin-2-yl)oxy)benzyl)-1-((1-ethyl)-1H-imidazol-5-yl)methyl)-1H-benzo[d]imidazole-6-carboxylate (190 mg, 0.30 mmol) dissolved in THF (2 mL) and water (2 mL) lithium hydroxide monohydrate (128 mg, 3.00 mmol) was added at room temperature. The resulting mixture was stirred at room temperature for 5 hours. After completion, the resulting mixture was adjusted to pH=5-6 with hydrochloric acid (1 M) and extracted with ethyl acetate (10 mL×3). The combined organic layers were washed with brine (10 mL), dried over anhydrous sodium sulfate, filtered, and concentrated to give a residue in vacuo. The residue was purified by prep-HPLC (Gilson CA 258 system; Column: Agilent Prep C18 OBD 10 um 21.2×250 mm; Gradient elution with ACN/0.1% $NH_4OH$ solvent system;

Detection Wavelength: 254 nm/214 nm; Flow rate: 20 mL/min) to obtain 2-(4-((6-((4-chloro-2-fluorophenoxy)methyl)pyridin-2-yl)oxy)benzyl)-1-((1-ethyl-1H-imidazol-5-yl)methyl)-1H-benzo[d]imidazole-6-carboxylic acid (20.10 mg, 10.9% yield). LC-MS m/z: 612 $[M+H]^+$.

$^1H$ NMR (400 MHZ, DMSO-$d_6$) δ 8.03 (s, 1H), 7.88 (t, J=8.0 Hz, 1H), 7.79 (dd, J=8.4 Hz, 1.6 Hz, 1H), 7.63-7.58 (m, 2H), 7.43 (dd, J=11.2 Hz, 2.4 Hz, 1H), 7.30 (d, J-8.4 Hz, 2H), 7.24-7.14 (m, 3H), 7.04 (d, J=8.8 Hz, 2H), 6.91 (d, J=8.4 Hz, 1H), 6.35 (s, 1H), 5.62 (s, 2H), 5.10 (s, 2H), 4.35 (s, 2H), 3.93-3.87 (m, 2H), 1.11 (t, J=7.6 Hz, 3H).

Example 58. Synthesis of 1-((1-(cyanomethyl)cyclopropyl)methyl)-2-((4-((6-((4-ethynyl-2-fluorophenoxy)-methyl)pyridine-2-yl)oxy)piperidin-1-yl) methyl)-1H-benzo[d]imidazole-6-carboxylic acid (compound C25)

1). Synthesis of methyl 4-(2-(4-((6-((4-bromo-2-fluorophenoxy)methyl)pyridin-2-yl)oxy)piperidin-1-yl)acetamido)-3-((1-(cyanomethyl)cyclopropyl) methyl)amino)benzoate

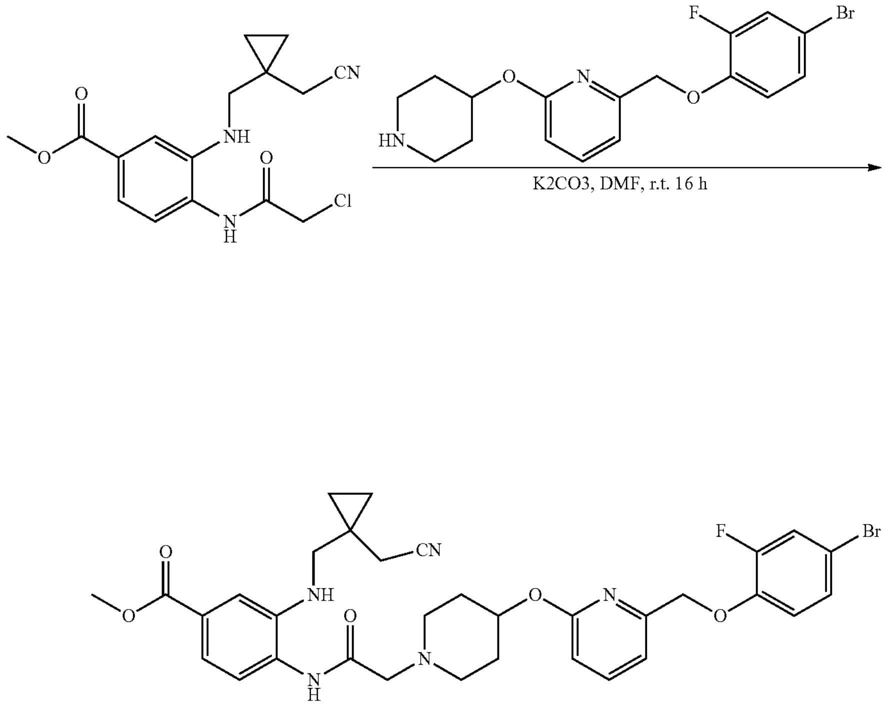 [SMILES: COC(=O)c1ccc(NC(=O)CCl)c(NCC2(CC#N)CC2)c1 ; Fc1cc(Br)ccc1OCc1cccc(OC2CCNCC2)n1 ; COC(=O)c1ccc(NC(=O)CN2CCC(Oc3cccc(COc4ccc(Br)cc4F)n3)CC2)c(NCC2(CC#N)CC2)c1]

The mixture of methyl 4-(2-chloroacetamido)-3-((1-(cyanomethyl)cyclopropyl)methyl)amino)benzoate (513 mg, 2.50 mmol), 2-((4-bromo-2-fluorophenoxy)methyl)-6-(piperidin-4-oxy)pyridine (950 mg, 2.50 mmol) and potassium carbonate (1.00 g, 7.50 mmol) in N,N-dimethylformamide (10 mL) was stirred at room temperature for 16 hours. Upon completion of the reaction, the resulting mixture was poured into brine (20 mL) and extracted with ethyl acetate (2×20 mL). The combined organic layer was concentrated to give a residue in vacuo. The residue was purified by silica gel column chromatography (petroleum ether/ethyl acetate=1/1) to obtain methyl 4-(2-(4-((6-((4-Bromo-2-fluorophenoxy) methyl)pyridin-2-yl)oxy)piperidin-1-yl)acetamido)-3-((1-(cyanomethyl)cyclopropyl)methyl)amino)-benzoate (347 mg, 28.0% yield). LC-MS m/z: 680 $[M+H]^+$.

2). Synthesis of methyl 2-((4-((6-((4-bromo-2-fluorophenoxy)methyl)pyridin-2-yl)oxy)piperidin-1-yl)methyl)-1-((1-(cyanomethyl)cyclopropyl))methyl)-1H-benzo[d]imidazole-6-carboxylate

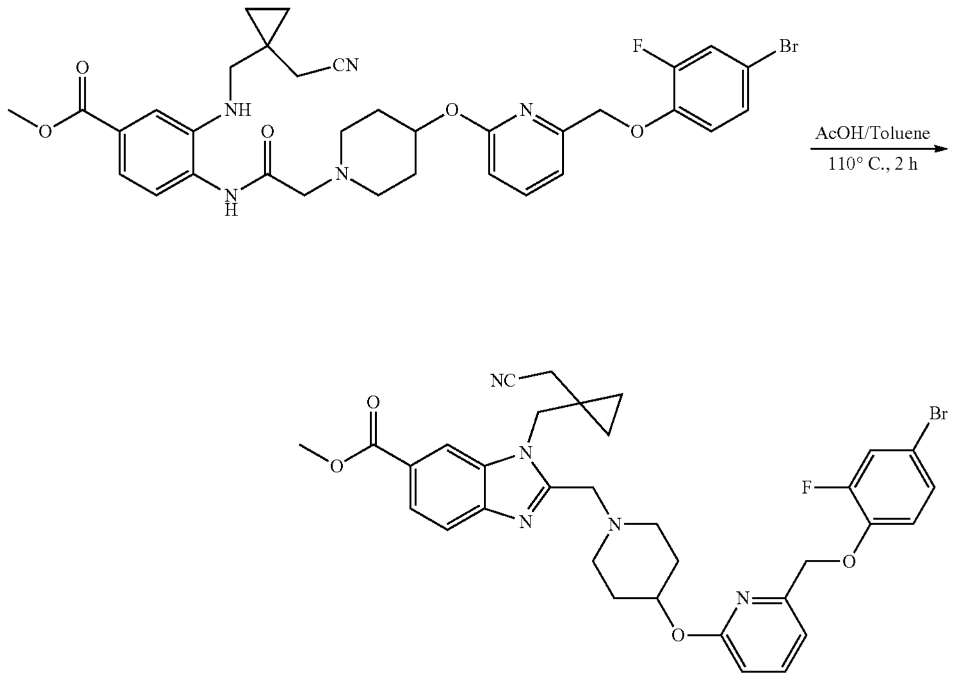 [SMILES: COC(=O)c1ccc(NC(=O)CN2CCC(Oc3cccc(COc4ccc(Br)cc4F)n3)CC2)c(NCC2(CC#N)CC2)c1 ; COC(=O)c1ccc2nc(CN3CCC(Oc4cccc(COc5ccc(Br)cc5F)n4)CC3)n(CC3(CC#N)CC3)c2c1]

To a solution of methyl 4-(2-(4-((6-((4-bromo-2-fluorophenoxy)methyl)pyridin-2-yl)oxy)piperidine-1-yl)acetamido)-3-((1-(cyanomethyl)cyclopropyl)methyl)amino) benzoate (347 mg, 0.51 mmol) in toluene (6 mL) acetic acid (1 mL) was added at room temperature. The resulting mixture was stirred for 2 hours at 110° C. under $N_2$ atmosphere. After completion, the reaction solution was concentrated to give a residue. The residue was purified by silica gel column chromatography (dichloromethane/methanol=10/1) to obtain methyl 2-((4-((6-((4-bromo-2-fluorophenoxy))methyl)pyridin-2-yl)oxy)piperidin-1-yl)methyl)-1-((1-(cyanomethyl)cyclopropyl))methyl)-1H-benzo[d]-imidazole-6-carboxylate (336 mg, 99.7% yield). LC-MS m/z: 664 $[M+H]^+$.

3). Synthesis of 1-((1-(cyanomethyl)cyclopropyl)methyl)-2-((4-((6-((2-fluoro-4-((trimethylsilyl) ethynyl) phenoxy)methyl)methyl) pyridin-2-yl)oxy)piperidin-1-yl)methyl)-1H-benzo[d]imidazole-6-carboxylate

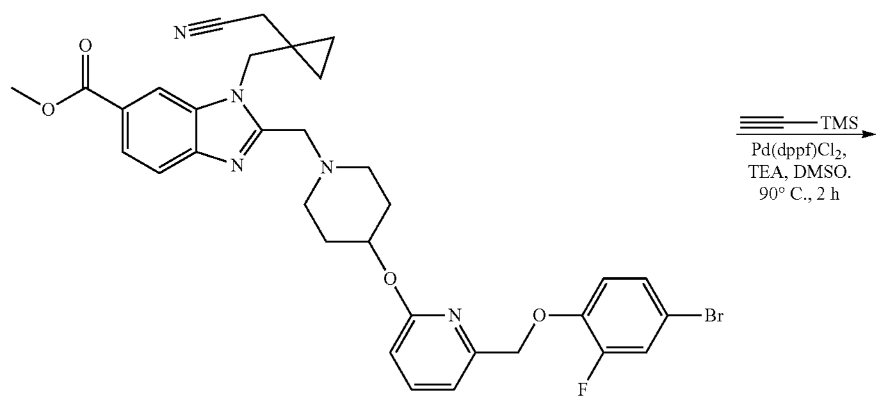

-continued

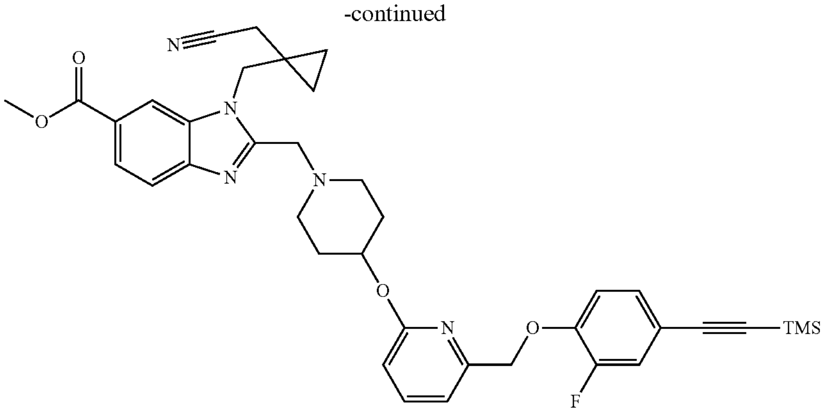

The mixture of methyl 2-((4-((6-((4-bromo-2-fluorophenoxy)methyl)pyridin-2-yl)oxy)piperidin-1-yl)methyl)-1-((1-(cyanomethyl)cyclopropyl))methyl)-1H-benzo[d]imidazole-6-carboxylate (336 mg, 0.51 mmol), ethynyltrimethylsilane (500 mg, 5.10 mmol), triethylamine (515 mg, 5.10 mmol) and 1,1'-bisdiphenylphosphinoferrocene palladium dichloride (37 mg, 0.05 mmol) in DMSO (5 mL) was stirred for 2 hours at 90° C. under nitrogen protection. After completion, the resulting mixture was diluted with water (10 mL) at room temperature, and extracted with ethyl acetate (10 mL×3). The combined organic layers were washed with brine (10 mL×2), dried over anhydrous sodium sulfate, filtered, and concentrated to give a residue in vacuo. The residue was purified by silica gel column chromatography (dichloromethane/methanol=10/1) to obtain methyl 1-((1-(cyanomethyl)cyclopropyl)methyl)-2-((4-((6-((2-fluoro-4-((trimethylsilyl) ethynyl) phenoxy)methyl)pyridin-2-yl)oxy)piperidin-1-yl)methyl)-1H-benzo[d]imidazole-6-carboxylate (258 mg, 76.1% yield). LC-MS m/z: 680 $[M+H]^+$.

4) Synthesis of 1-((1-(cyanomethyl)cyclopropyl) methyl)-2-((4-((6-((4-ethynyl-2-fluorophenoxy) methyl)pyridine-2-yl)oxy)piperidin-1-yl)methyl)-1H-benzo[d]imidazole-6-carboxylic acid

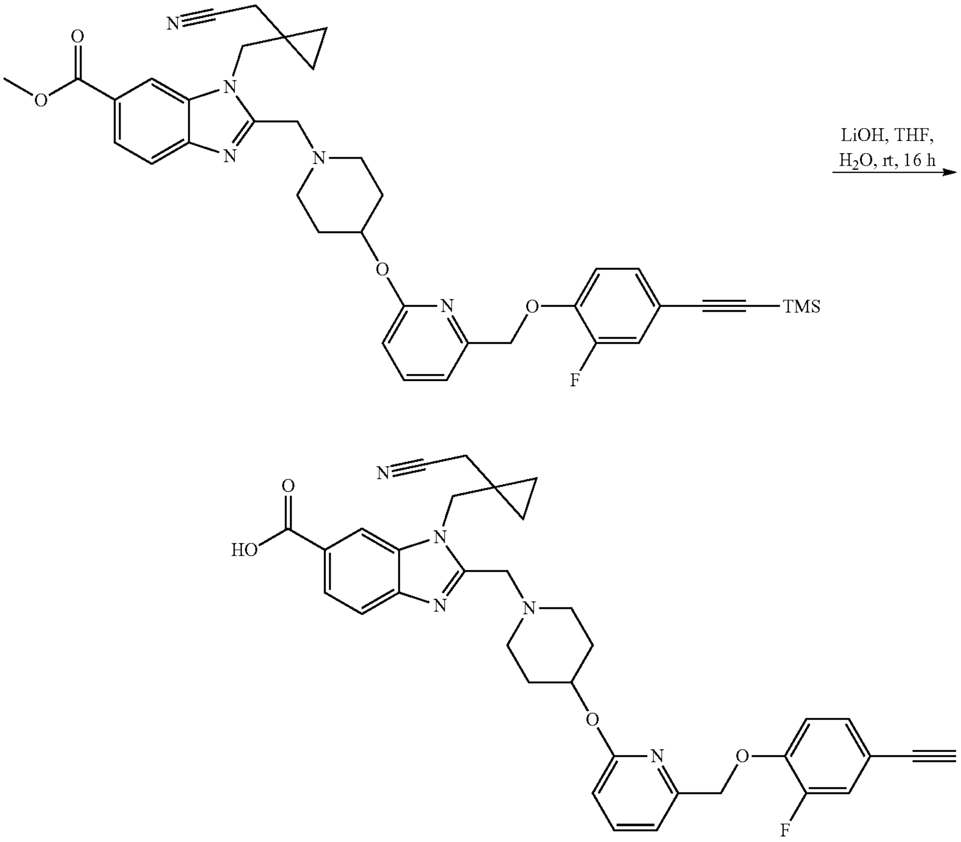

To a mixture of methyl 1-((1-(cyanomethyl)cyclopropyl) methyl)-2-((4-((6-((2-fluoro-4-((trimethylsilyl)acetylene) yl) phenoxy)methyl)pyridin-2-yl)oxy)piperidin-1-yl) methyl)-1H-benzo[d]imidazole-6-carboxylate (50 mg, 0.08 mmol) in THF (1 mL), water (1 mL) and methanol (1 mL) lithium hydroxide (19 mg, 0.80 mmol) was added at room temperature. The resulting mixture was stirred at room temperature for 16 hours. After completion, the solvent was removed by concentration to give a residue in vacuo. The residue was purified by prep-HPLC (Waters 2767/2545/2489 system; Column: SunFire Prep C8 OBD 10 um 19×250 mm Column; Gradient elution with ACN/0.05% $NH_4OH$ in $H_2O$solvent system;

Detection Wavelength: 254 nm/214 nm; Flow rate: 20 mL/min) to obtain 1-((1-(cyanomethyl)cyclopropyl) methyl)-2-((4-((6-((4-ethynyl)-2-fluorophenoxy) methyl)pyridin-2-yl)oxy)piperidin-1-yl)me-thyl)-1H-benzo[d]imidazole-6-carboxylic acid (3.20 mg, 6.7% yield). LC-MS m/z: 594 $[M+H]^+$.

$^1H$ NMR (400 MHZ, DMSO-$d_6$) δ 8.24 (s, 1H), 7.82 (d, J-8.0 Hz, 1H), 7.72 (t, J-8.4 Hz, 1H), 7.64 (d, J=8.4 Hz, 1H), 7.40-7.37 (m, 1H), 7.26-7.25 (m, 2H), 7.05 (d, J=7.6 Hz, 1H), 6.73 (d, J=8.0 Hz, 1H), 5.22 (s, 2H), 4.98-4.94 (m, 1H), 4.61 (s, 2H), 4.12 (s, 1H), 3.86 (s, 2H), 2.82-2.79 (m, 2H), 2.69 (s, 2H), 2.37-2.32 (m, 2H), 1.95-1.91 (m, 2H), 1.66-1.59 (m, 2H), 0.76-0.68 (m, 4H).

Example 59. Synthesis of 2-((4-((6-((4-bromo-2-fluorophenoxy)methyl)pyridin-2-yl)oxy)piperidin-1-yl)methyl)-1-((1-(cyanomethyl)cyclopropyl)methyl)-1H-benzo[d]imidazole-6-carboxylic acid (compound C26)

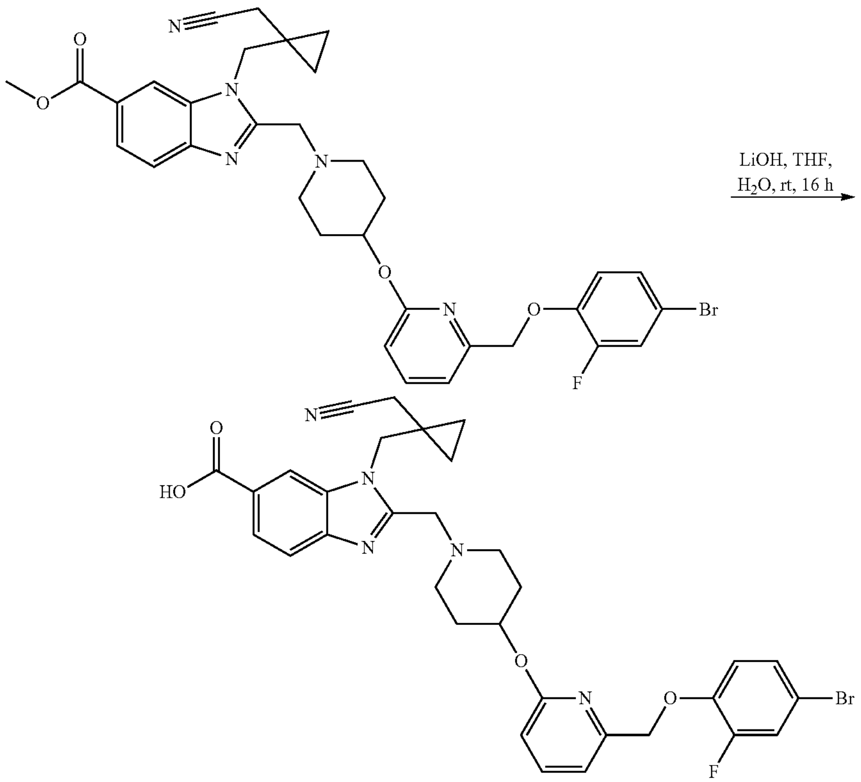

To a mixture of 2-((4-((6-((4-bromo-2-fluorophenoxy) methyl)pyridin-2-yl)oxy)piperidin-1-yl)methyl)-1-((1-(cyanomethyl)cyclopropyl))methyl)-1H-benzo[d]imidazole-6-carboxylate (50 mg, 0.08 mmol) in THF (3 mL) and water (3 mL) lithium hydroxide (19 mg, 0.80 mmol) was added at room temperature. The resulting mixture was stirred at room temperature for 16 hours. After completion, the residue was purified by prep-HPLC (Waters 2767/2545/2489 system; Column: SunFire Prep C8 OBD 10 um 19×250 mm; Gradient elution with ACN/0.05% $NH_4OH$ in $H_2O$ solvent system; Detection Wavelength: 254 nm/214 nm; Flow rate: 20 mL/min) to obtain 2-((4-((6-((4-bromo-2-fluorophenoxy) methyl)pyridin-2-yl)oxy)piperidin-1-yl)methyl)-1-((1-(cyanomethyl)cyclopropyl)methyl)-1H-benzo[d]-imidazole-6-carboxylic acid (16.81 mg, 32.5% yield). LC-MS m/z: 650 $[M+H]^+$.

$^1$H NMR (400 MHZ, DMSO-$d_6$) δ 8.22 (s, 1H), 7.81 (d, J=8.4 Hz, 1H), 7.71 (t, J-8.0 Hz, 1H), 7.61 (d, J=8.4 Hz, 1H), 7.54 (dd, J=11.2 Hz, 2.0 Hz, 1H), 7.30 (d, J-8.4 Hz, 1H), 7.22 (t, J=8.8 Hz, 1H), 7.03 (d, J=7.2 Hz, 1H), 6.72 (d, J=8.0 Hz, 1H), 5.18 (s, 2H), 4.96-4.92 (m, 1H), 4.60 (s, 2H), 3.85 (s, 2H), 2.81-2.78 (m, 2H), 2.69 (s, 2H), 2.35-2.30 (m, 2H), 1.94-1.91 (m, 2H), 1.66-1.61 (m, 2H), 0.72-0.67 (m, 4H).

Example 60. Synthesis of(S)-2-(4-((6-((4-cyano-2-fluorophenoxy)methyl)pyridin-2-yl)oxy)benzyl)-1-(oxetan-2-ylmethyl)-1H-benzo[d]imidazole-6-carboxylic acid (Compound C27): methyl(S)-4-(2-(4-((6-((4-cyano-2-fluorophenoxy)methyl)pyridin-2-1). Synthesis of yl)oxy)phenyl)acetamido)-3-((oxetan-2-ylmethyl)amino)benzoate

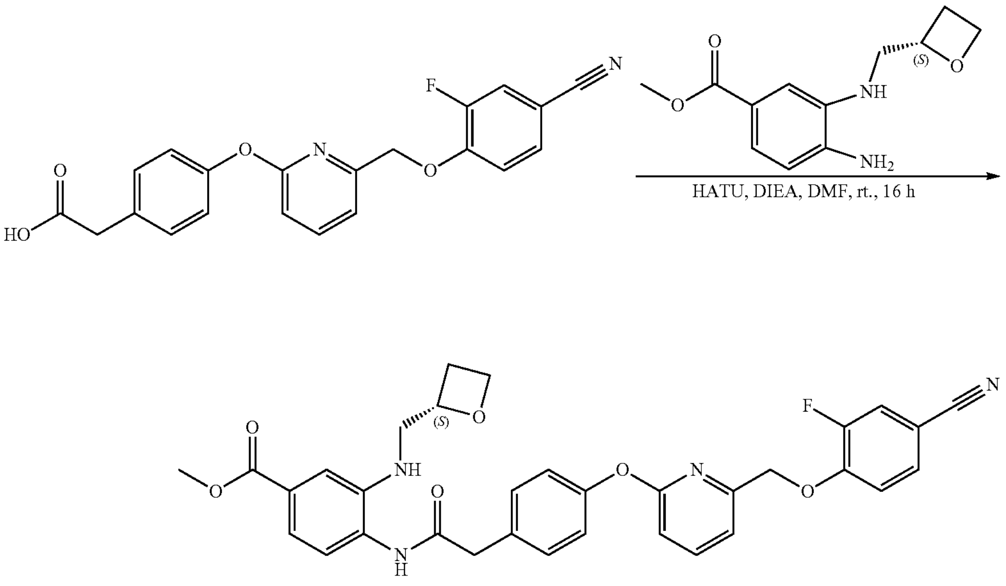

To a mixture of 2-(4-((6-((4-cyano-2-fluorophenoxy) methyl)pyridin-2-yl)oxy)phenyl)acetic acid (288 mg, 0.76 mmol) 2-(3H-[1,2,3]triazolo[4,5-b]pyridin-3-yl)-1,1,3,3-tetramethyluronium hexafluorophosphate (V) (433 mg, 1.14 mmol) and N,N-diisopropylethylamine (392 mg, 3.04 mmol) in N,N-dimethylformamide (3 mL)methyl(S)-4-amino-3-((oxetane-2-ylmethyl)amino)benzoate (179 mg, 0.76 mmol) was added at room temperature. The resulting mixture was stirred at room temperature for 16 hours. After completion, the mixture was quenched by adding water (5 mL) and extracted with ethyl acetate (20 mL×2). The combined organic layers were washed with brine (20 mL×3), dried over anhydrous sodium sulfate, filtered, and concentrated to give a residue in vacuo. The residue was purified by silica gel column chromatography (dichloromethane/methanol=10/1) to obtain methyl(S)-4-(2-(4-((6-((4-cyano-2-fluorophenoxy))methyl)pyridin-2-yl)oxy)phenyl)acetamido)-3-((oxetan-2-ylmethyl)amino)benzoate (301 mg, 66.6% yield)). LC-MS m/z: 597 [M+H]$^+$.

2). Synthesis of methyl(S)-2-(4-((6-((4-cyano-2-fluorophenoxy)methyl)pyridin-2-yl)oxy)benzyl)-1-(oxetan-2-ylmethyl)-1H-benzo[d]imidazole-6-carboxylate

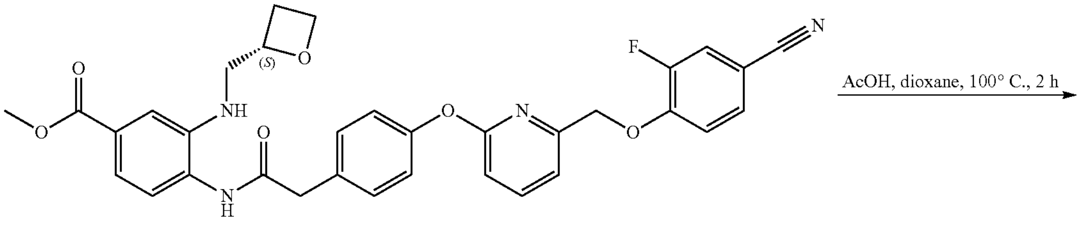

-continued

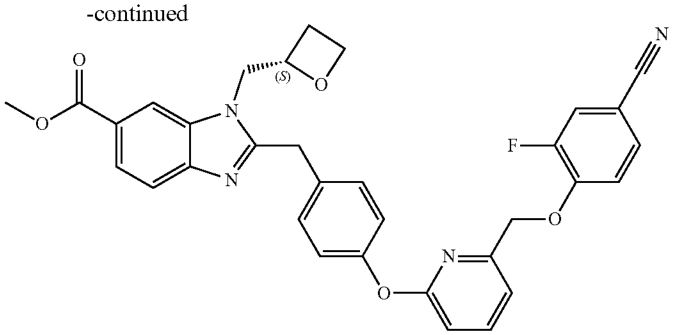

To a mixture of(S)-4-(2-(4-((6-((4-cyano-2-fluorophenoxy)methyl)pyridin-2-yl)oxy)phenyl)acetamido)-3-((oxetan-2-ylmethyl)amino)benzoate (301 mg, 0.51 mmol) in dioxane (10 mL) acetic acid (1 mL) was added at room temperature. The resulting mixture was stirred and reacted at 100° C. for 2 hours. After completion, the reaction solution was concentrated to give a residue in vacuo. The residue was purified by silica gel column chromatography (dichloromethane/methanol=10/1) to obtain methyl(S)-2-(4-((6-((4-cyano-2-fluorophenoxy)methyl)pyridin-2-yl)oxy)benzyl)-1-(oxetan-2-ylmethyl)-1H-benzo[d]imidazole-6-carboxylate (223 mg, 75.6% yield). LC-MS m/z: 579 $[M+H]^+$.

3). Synthesis of(S)-2-(4-((6-((4-cyano-2-fluorophenoxy)methyl)pyridin-2-yl)oxy)benzyl)-1-(oxetan-2-ylmethyl)-1H-benzo[d]imidazole-6-carboxylic acid

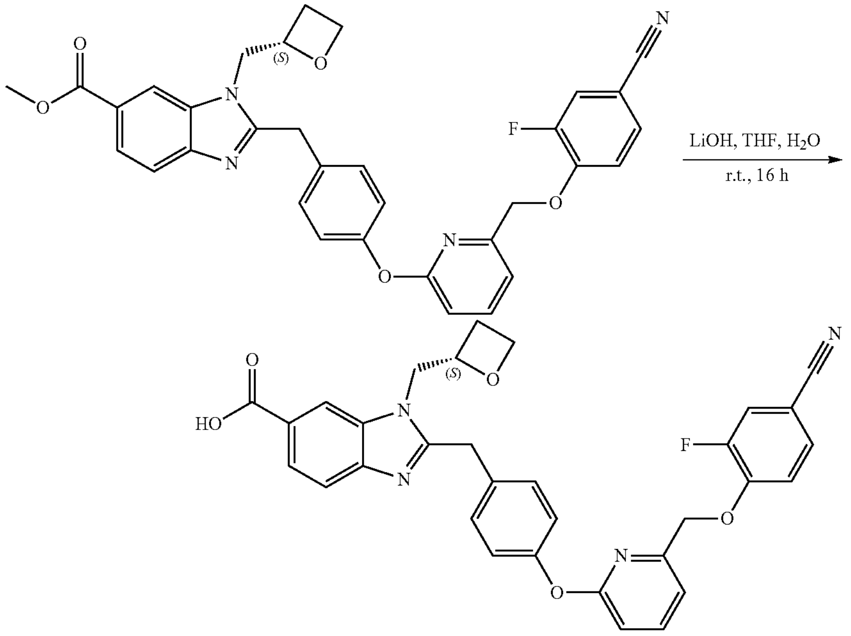

To a mixture of methyl(S)-2-(4-((6-((4-cyano-2-fluorophenoxy)methyl)pyridine-2-yl)oxy)benzyl)-1-(oxetan-2-ylmethyl)-1H-benzo[d]imidazole-6-carboxylate (223 mg, 0.39 mmol) in THF (2 mL) and water (2 mL) lithium hydroxide (93 mg, 3.90 mmol) was added. The resulting mixture was stirred at room temperature for 5 hours. After completion, the obtained mixture was adjusted to pH=5-6 with formic acid, and extracted with ethyl acetate (10 mL×3). The combined organic layers were washed with brine (10 mL), dried over anhydrous sodium sulfate, filtered, and concentrated in vacuo. The residue was purified by prep-HPLC (Gilson CA 258 system; Column: Agilent Prep C18 OBD 10 um 21.2×250 mm; Gradient elution with ACN/0.1% $NH_3.H_2O$ solvent system; Detection Wavelength: 254 nm/214 nm; Flow rate: 20 mL/min) to obtain (S)-2-(4-((6-((4-cyano-2-fluorophenoxy)methyl)pyridin-2-yl)oxy)benzyl)-1-(oxetan-2-ylmethyl)-1H-benzo[d]imidazole-6-carboxylic acid (75.28 mg, 34.2% yield). LC-MS m/z: 565 $[M+H]^+$.

$^1$H NMR (400 MHZ, DMSO-$d_6$) δ 8.14 (s, 1H), 7.90 (t, J=7.6 Hz, 1H), 7.84 (dd, J=11.2 Hz, 2.0 Hz, 1H), 7.79 (dd, J=8.4 Hz, 1.2 Hz, 1H), 7.62 (d, J=8.8 Hz, 1H), 7.53 (d, J-8.4 Hz, 1H), 7.38-7.33 (m, 3H), 7.25 (d, J=7.2 Hz, 1H), 7.07 (d, J=8.8 Hz, 2H), 6.97 (d, J=8.0 Hz, 1H), 5.21 (s, 2H), 4.97-4.92 (m, 1H), 4.65-4.59 (m, 1H), 4.53-4.43 (m, 2H), 4.39-4.32 (m, 3H), 2.68-2.58 (m, 1H), 2.38-2.30 (m, 1H).

Example 61. Synthesis of 2-(4-((6-((4-cyano-2-fluorophenoxy)methyl)pyridin-2-yl)oxy)benzyl)-1-((1-ethyl-1H-imidazol-5-yl)methyl)-1H-benzo[d]imidazole-6-carboxylic acid (compound C28)

1). Synthesis of methyl 2-(4-((6-((4-cyano-2-fluorophenoxy)methyl)pyridin-2-yl)oxy)phenyl)acetate

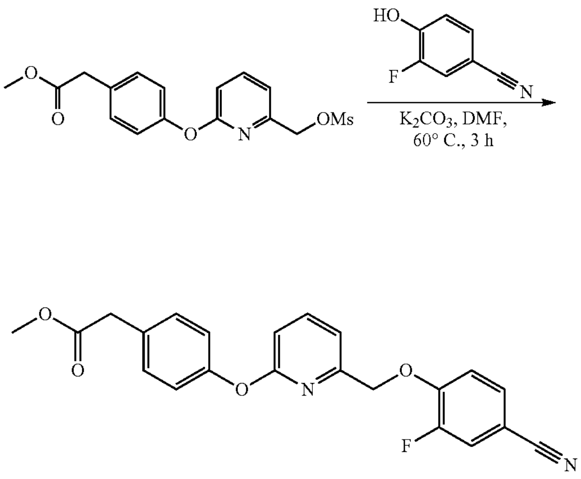

The mixture of 3-fluoro-4-hydroxybenzonitrile (22 mg, 0.16 mmol), potassium carbonate (44 mg, 0.32 mmol) and methyl 2-(4-((6-((methylsulfonyl)oxy))methyl)pyridin-2-yl) oxy)phenyl)acetate in N,N-dimethylformamide (2 mL) was stirred and reacted at 60° C. for 3 hours. After completion, the mixture was diluted with water (5 mL) and extracted with ethyl acetate (20 mL×3). The combined organic layers were washed with brine (15 mL×2), dried over anhydrous sodium sulfate, filtered, and concentrated to give a residue in vacuo. The residue was purified by silica gel column chromatography (petroleum ether/ethyl acetate=7/3) to obtain 2-(4-((6-((4-cyano-2-fluorophenoxy)methyl)pyridine-2-yl) oxy)phenyl)acetate (31 mg, 49.4% yield). LC-MS m/z: 393 $[M+H]^+$.

2). Synthesis of 2-(4-((6-((4-cyano-2-fluorophenoxy)methyl)pyridin-2-yl)oxy)phenyl)acetic acid

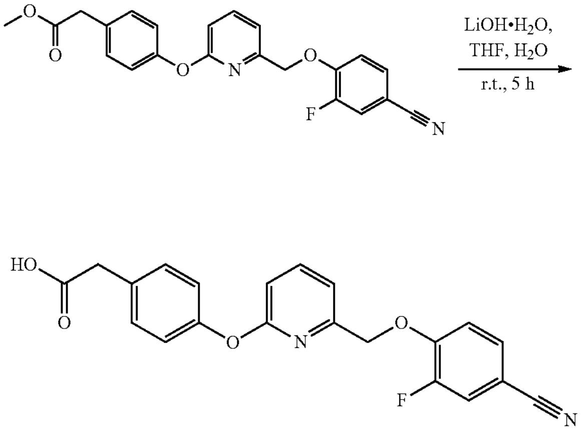

To a solution of methyl 2-(4-((6-((4-cyano-2-fluorophenoxy)methyl)pyridin-2-yl)oxy)phenyl)acetate (31 mg, 0.08 mmol) in THF (1.5 mL) and water (1.5 mL) lithium hydroxide monohydrate (33 mg, 0.80 mmol) was added at room temperature. The resulting mixture was stirred at room temperature for 5 hours. After completion, the resulting mixture was adjusted to pH=5-6 with hydrochloric acid (1 M), then concentrated to give a residue. The residue was purified by silica gel column chromatography (dichloromethane/methanol=10/1) to obtain 2-(4-((6-((4-cyano-2-fluorophenoxy)methyl)pyridin-2-yl)oxy)phenyl)acetic acid (30 mg, 99.2% yield). LC-MS m/z: 379 $[M+H]^+$.

3). Synthesis of methyl 4-(2-(4-((6-((4-cyano-2-fluorophenoxy)methyl)pyridin-2-yl)oxy)phenyl) acetamido)-3-((1-ethyl-1H-imidazol-5-yl)methyl) amino)benzoate

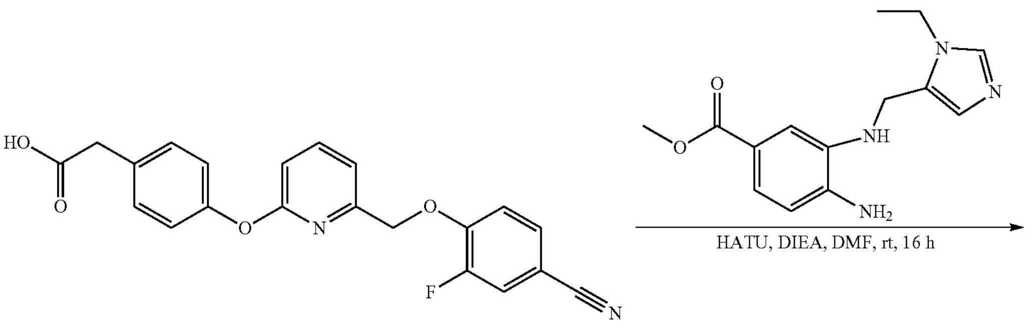

-continued

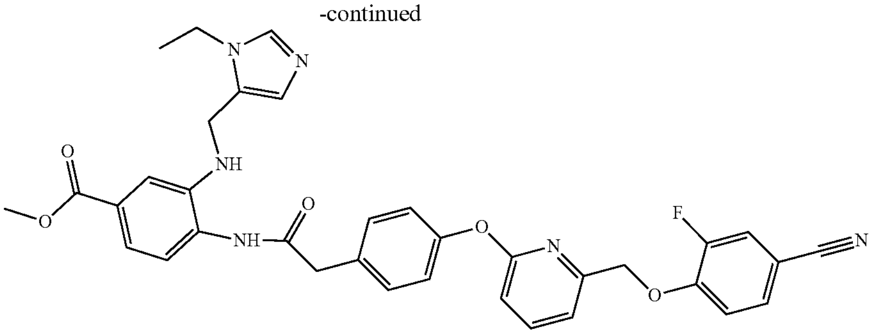

To a mixture of 2-(4-((6-((4-cyano-2-fluorophenoxy) methyl)pyridin-2-yl)oxy)phenyl)acetic acid (30 mg, 0.08 mmol)), 2-(3H-[1,2,3]triazolo[4,5-b]pyridin-3-yl)-1,1,3,3-tetramethyluronium hexafluorophosphate (V) (65 mg, 0.12 mmol) and N,N-diisopropylethylamine (57 mg, 0.32 mmol) in N,N-dimethylformamide (2 mL) methyl 4-amino-3-((1-ethyl-1H-imidazole-5-yl)methyl)aminobenzoate (22 mg, 0.08 mmol) was added at room temperature. The resulting mixture was stirred at room temperature for 16 hours. When completion, the mixture was quenched by adding water (5 mL) and extracted with ethyl acetate (20 mL×3). The combined organic layers were washed with brine (15 mL×2), dried over anhydrous sodium sulfate, filtered, and concentrated to give a residue in vacuo. The residue was purified by silica gel column chromatography (petroleum ether: ethyl acetate=1/1) to obtain methyl 4-(2-(4-((6-((4-cyano-2-fluoropheno-xy)methyl))pyridin-2-yl)oxy)phenyl) acetamido)-3-((1-ethyl-1H-imidazol-5-yl)methyl)amino) benzoate (27 mg, 54.7% yield). LC-MS m/z: 635 $[M+H]^+$.

4). Synthesis of methyl 2-(4-((6-((4-cyano-2-fluoro-phenoxy)methyl)pyridin-2-yl)oxy)benzyl)-1-((1-ethyl-1H-imidazol-5-yl)methyl)-1H-benzo[d]imidazole-6-carboxylate

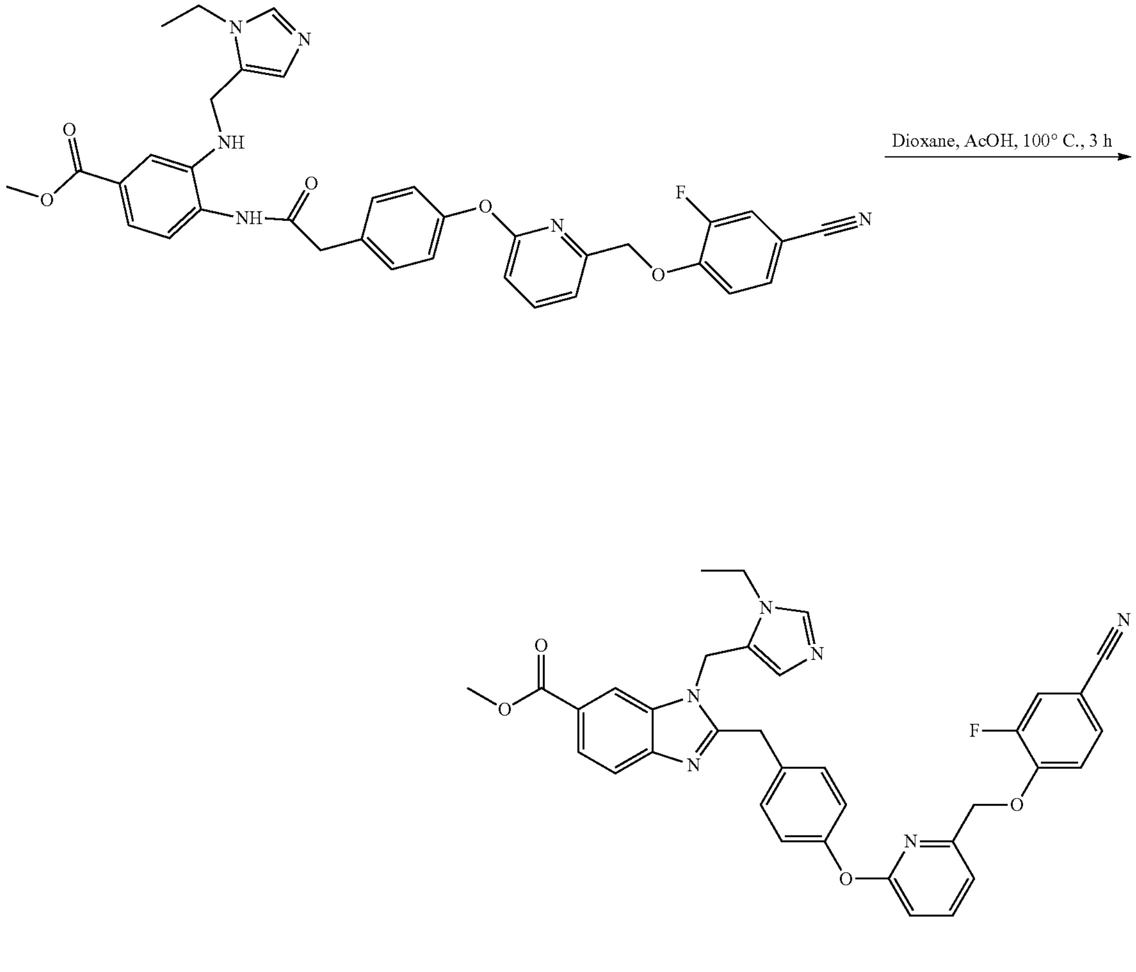

To a solution of methyl 4-(2-(4-((6-((4-cyano-2-fluorophenoxy)methyl)pyridin-2-yl)oxy)phenyl)acetamido)-3-((1-ethyl-1H-imidazol-5-yl)methyl)amino)benzoate (27 mg, 0.04 mmol) in dioxane (3 mL) acetic acid (0.3 mL) was added at room temperature. The resulting mixture solution was stirred at 100° C. for 3 hours. After completion, the reaction solution was concentrated to give a residue under reduced pressure. The residue was purified by silica gel column chromatography (dichloromethane/methanol=10/1) to obtain methyl 2-(4-((6-((4-cyano-2-fluorophenoxy))-methyl)pyridin-2-yl)oxy)benzyl)-1-((1-ethyl-1H-imidazol-5-yl)methyl)-1H-benzo[d]imidazole-6-carboxylate (20 mg, 76.3% yield). LC-MS m/z: 617 $[M+H]^+$. 5). Synthesis of 2-(4-((6-((4-cyano-2-fluorophenoxy)methyl)pyridin-2-yl)oxy)benzyl)-1-((1-ethyl-1H-imidazol-5-yl)methyl)-1H-benzo[d]imidazole-6-carboxylic acid:

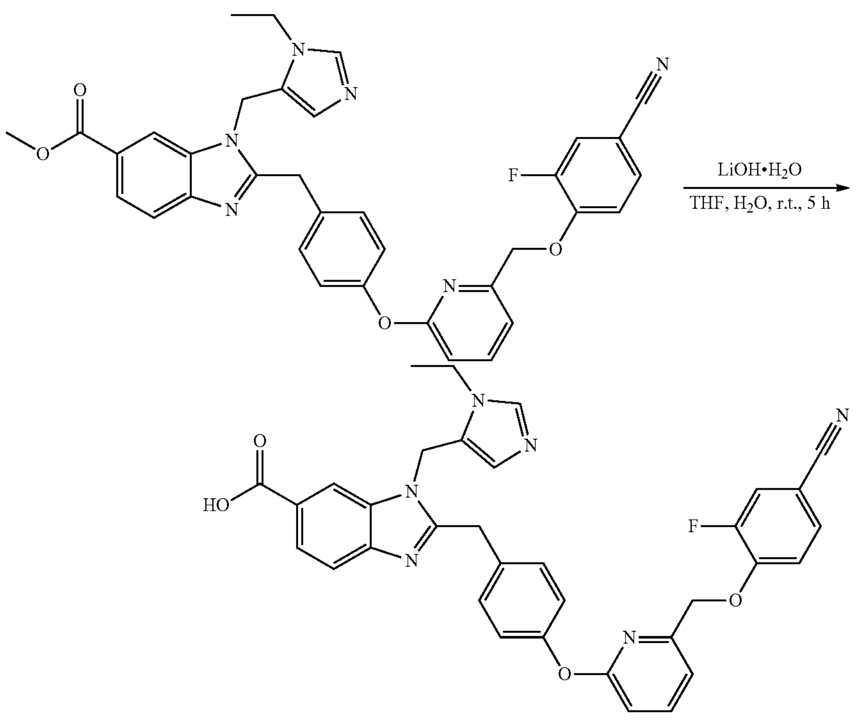

To a mixture of (4 mg, 0.09 mmol) methyl 2-(4-((6-((4-cyano-2-fluorophenoxy)methyl)pyridine-2-yl)oxy)benzyl)-1-((1-ethyl-1H-imidazol-5-yl)methyl)-1H benzo[d]imidazole-6-carboxylate (20 mg, 0.03 mmol) in THF (2 mL) and water (2 mL) lithium hydroxide monohydrate was added at room temperature. The resulting mixture solution was stirred at room temperature for 5 hours. After completion, the resulting mixture was adjusted to pH=5-6 with hydrochloric acid (1 M) and extracted with ethyl acetate (10 mL×3). The combined organic phases were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; mobile phase A: 10 mM $NH_4OH$ in water; Mobile Phase B: acetonitrile; Flow rate: 40 mL/min; Gradient: 20% B-50% B in 20 min; Detector: 254 nm to obtain 2-(4-((6-((4-cyano-2-fluorophenoxy)methyl)pyridine-2-yl)oxy)benzyl)-1-((1-ethyl-1H-imidazol-5-yl)methyl)-1H-benzo[d]imidazole-6-carboxylic acid (2.77 mg, 15.1% yield). LC-MS m/z: 603 $[M+H]^+$. $^1H$ NMR (400 MHZ, DMSO-$d_6$) δ 7.93 (s, 1H), 7.89 (t, J-8.0 Hz, 1H), 7.84 (dd, J=11.2 Hz, 2.0 Hz, 1H), 7.78 (dd, J=8.0 Hz, 0.8 Hz, 1H), 7.64-7.61 (m, 2H), 7.43 (d, J=8.0 Hz, 1H), 7.37 (t, J=8.4 Hz, 1H), 7.29 (d, J=8.4 Hz, 2H), 7.24 (d, J=7.6 Hz, 1H), 7.02 (d, J=8.8 Hz, 2H), 6.92 (d, J=8.4 Hz, 1H), 6.29 (s, 1H), 5.53 (s, 2H), 5.22 (s, 2H), 4.30 (s, 2H), 3.95-3.90 (m, 2H), 1.14 (t, J=7.2 Hz, 3H).

Example 62. Synthesis of 2-((4-(3-((4-ethynyl-2-fluorophenoxy)methyl) phenoxy)piperidin-1-yl) methyl)-1-((1-isopropyl-1H-imidazol-5-yl)methyl)-1H-benzo[d]imidazole-6-carboxylic acid (compound C29)

1). Synthesis s of methyl 4-(2-(4-(3-((4-bromo-2-fluorophenoxy)methyl) phenoxy)piperidin-1-yl)acetamido)-3-((1-isopropyl-1H-imidazol-5-yl)methyl) amino)benzoate

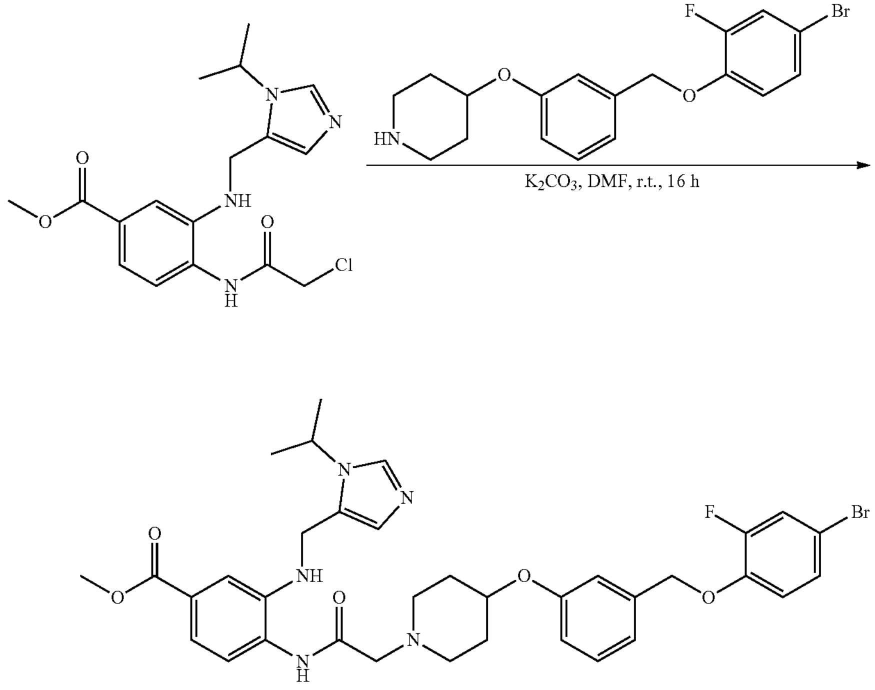 [SMILES: COC(=O)c1ccc(NC(=O)CCl)c(NCc2cncn2C(C)C)c1 ; Fc1cc(Br)ccc1OCc1cccc(OC2CCNCC2)c1 ; COC(=O)c1ccc(NC(=O)CN2CCC(Oc3cccc(COc4ccc(Br)cc4F)c3)CC2)c(NCc2cncn2C(C)C)c1]

The mixture of methyl 4-(2-chloroacetamido)-3-((1-isopropyl-1H-imidazol-5-yl)methyl)amino)benzoate (450 mg, 1.23 mmol), 4-(3-((4-bromo-2-fluorophenoxy)methyl) phenoxy)piperidine (467 mg, 1.23 mmol) and potassium carbonate (339 mg, 2.46 mmol) in dry N,N-dimethylformamide (10 mL) was stirred at room temperature for 16 hours. After completion, the reaction was quenched with water (10 mL) and extracted with ethyl acetate (3×10 mL). The combined organic layers were washed with brine (10 mL×2), dried over anhydrous sodium sulfate, filtered, and concentrated in vacuo. The residue was purified by silica gel column chromatography (dichloromethane/methanol=10/1) to obtain methyl 4-(2-(4-(3-((4-bromo-2-fluorophenoxy)methyl) phenoxy))piperidin-1-yl)acetamido)-3-((1-isopropyl-1H-imidazol-5-yl)methyl)amino)benzoate (400 mg, 51.4% yield). LC-MS m/z: 710 $[M+H]^+$.

2). Synthesis of methyl 2-((4-(3-((4-bromo-2-fluorophenoxy)methyl) phenoxy)piperidin-1-yl)-1-((1-isopropyl-1H-imidazole-5-yl)methyl)-1H-benzo[d] imidazole-6-carboxylate

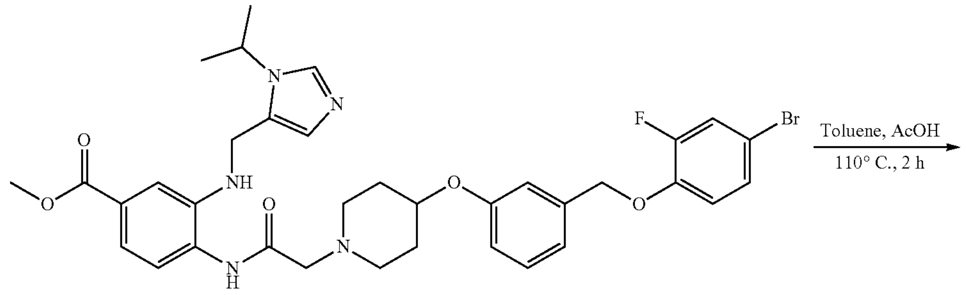

-continued

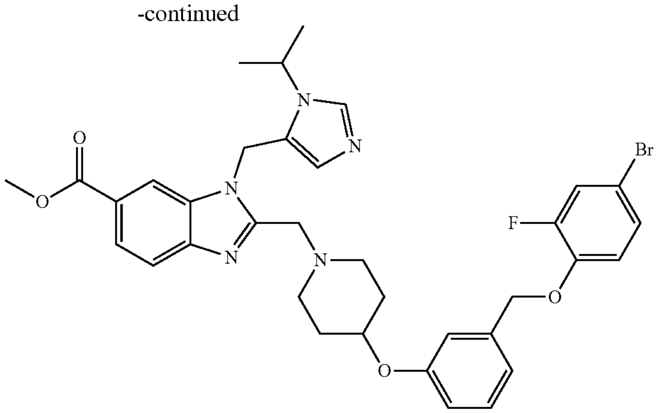

To a solution of methyl 4-(2-(4-(3-((4-bromo-2-fluorophenoxy)methyl) phenoxy)piperidin-1-yl)acetamido)-3-((1-isopropyl-1H-imidazol-5-yl)methyl)amino)benzoate (400 mg, 0.56 mmol) in toluene (5 mL) acetic acid (0.5 mL) was added at room temperature. The resulting mixed solution was stirred and reacted at 110° C. for 2 hours. After completion, the reaction solution was concentrated to give a residue in vacuo. The residue was purified by silica gel column chromatography (dichloromethane/methanol=10/1) to obtain methyl 2-((4-(3-((4-bromo-2-fluorophenoxy)yl) methyl) phenoxy)piperidin-1-yl)-1-((1-isopropyl-1H-imidazol-5-yl)methyl)-1H-benzo[d]imidazol-6-carboxylate (380 mg, 97.4% yield). LC-MS m/z: 692 [M+H]$^+$.

3). Synthesis of methyl 2-((4-(3-((2-fluoro-4-((trimethylsilyl) ethynyl) phenoxy)phenoxy)piperidin-1-yl)methyl)-1-((1-isopropyl-1H-imidazol-5-yl) methyl)-1H-benzo[d]imidazole-6-carboxylate

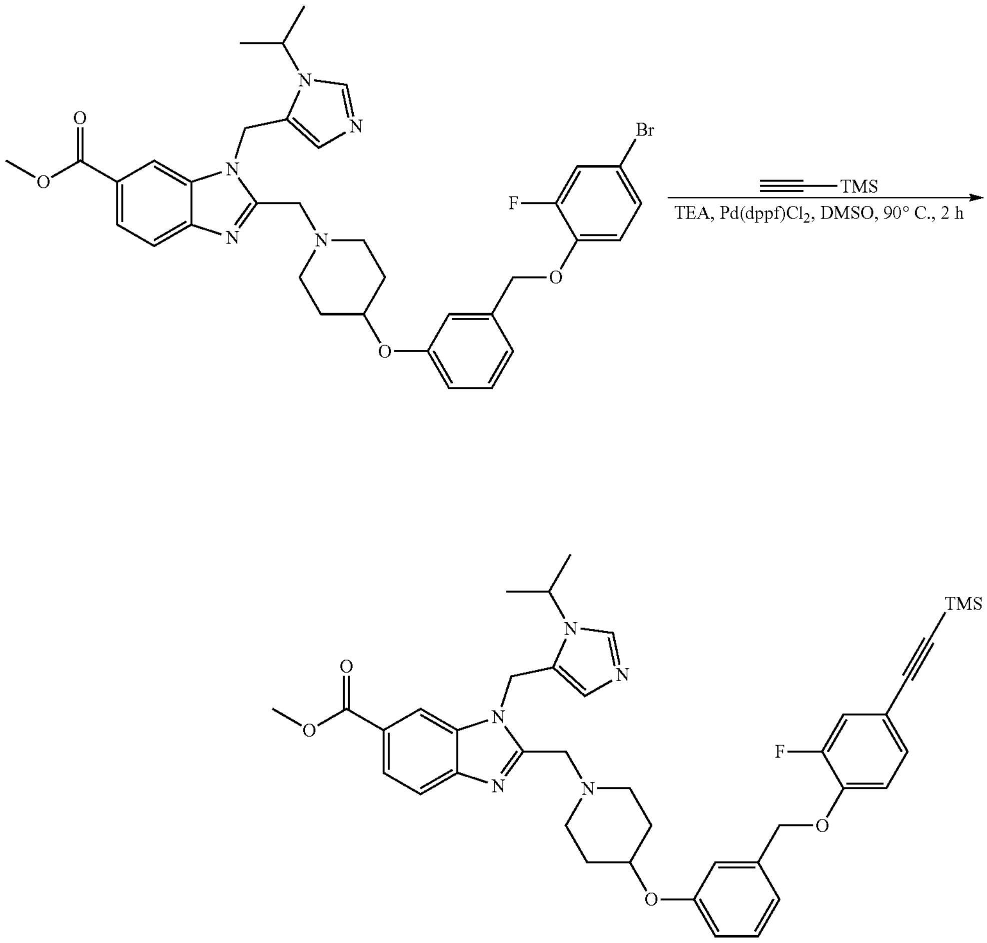

The mixture of methyl 2-((4-(3-((4-bromo-2-fluorophenoxy)methyl) phenoxy)piperidin-1-yl)-1-(((1-isopropyl-1H-imidazol-5-yl)methyl)-1H-benzo[d]imidazole-6-carboxylate (280 mg, 0.41 mmol), ethynyltrimethylsilane (402 mg, 4.10 mmol), triethylamine (414 mg, 4.10 mmol) and 1,1'-bisdiphenylphosphinoferrocene palladium dichloride (29 mg, 0.04 mmol) in DMSO (6 mL) was stirred at 90° C. for 2 hours under $N_2$ atmosphere. After completion, the reaction was quenched with water (10 mL) and extracted with ethyl acetate (10 mL×3). The combined organic layers were washed with brine (10 mL×2), dried over anhydrous sodium sulfate, filtered, and concentrated to give a residue in vacuo. The residue was purified by silica gel column chromatography (dichloromethane/methanol=10/1) to obtain methyl 2-((4-(3-(((2)-fluoro-4-((trimethylsilyl) ethynyl) phenoxy) phenoxy)piperidin-1-yl)methyl)-1-((1-isopropyl-1H-imidazole-5 I yl)methyl)-1H benzo[d]imidazole-6-carboxylate (420 mg, crude). LC-MS m/z: 708 $[M+H]^+$.

4). Synthesis of 2-((4-(3-((4-ethynyl-2-fluorophenoxy)methyl) phenoxy)piperidin-1-yl)methyl)-1-((1-isopropyl-1H-imidazol-5-yl)methyl)-1H-benzo[d]imidazole-6-carboxylic acid

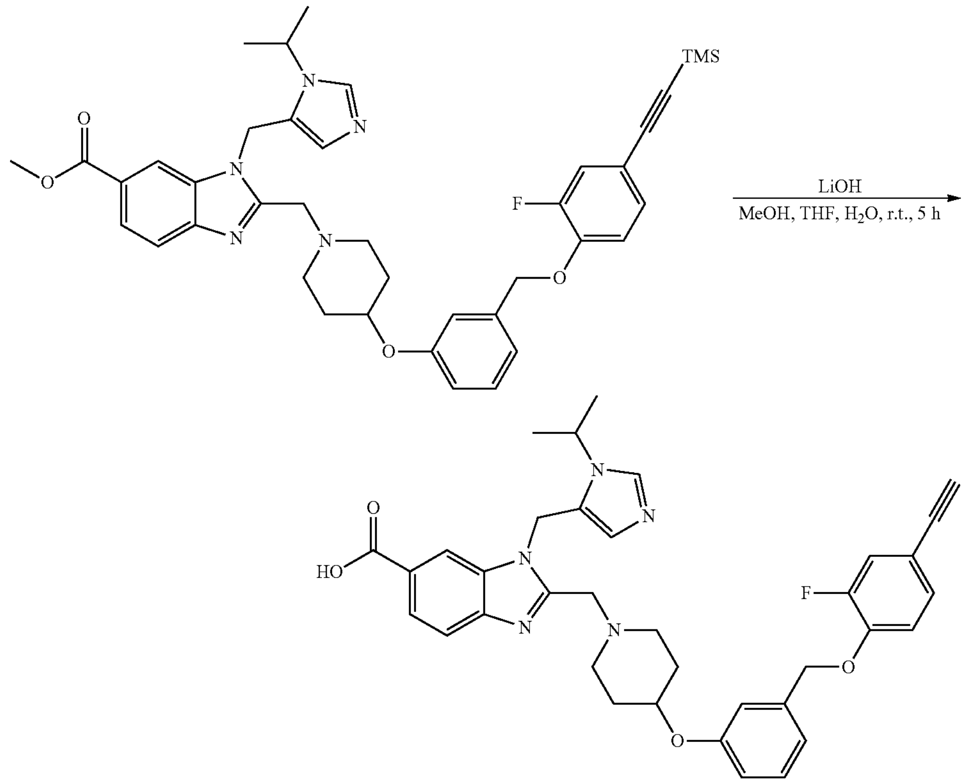

To a mixture of methyl 2-((4-(3-((2-fluoro-4-((trimethylsilyl) ethynyl) phenoxy)phenoxy)piperidin-1-yl)methyl)-1-((1-Isopropyl-1H-imidazol-5-yl)methyl)-1H-benzo[d]imidazole-6-carboxylate (420 mg, 0.59 mmol) in methanol (1 mL), water (1 mL) and THF (1 mL) lithium hydroxide (113 mg, 4.72 mmol) was added at room temperature. The reaction mixture was stirred at room temperature for 5 hours. After completion, the reaction mixture was adjusted to pH with formic acid=5-6. The mixture was concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Phase B: acetonitrile; Flow rate: 40 mL/min; gradient: 20% B-50% B in 20 min; Detector: 254 nm) to obtain 2-((4-(3-((4-ethynyl-2-fluorophenoxy) methyl) phenoxy)piperidin-1-yl)methyl)-1-((1-isopropyl-1H-imidazol-5-yl)methyl)-1H-benzo[d]Imidazole-6-carboxylic acid (23.6 mg, 6.4% yield). LC-MS m/z: 622 $[M+H]^+$.

$^1H$ NMR (400 MHZ, DMSO-$d_6$): δ8.02 (s, 1H), 7.81-7.78 (m, 2H), 7.65 (d, J=7.6 Hz, 1H), 7.38-7.35 (m, 1H), 7.30-7.20 (m, 3H), 7.01-6.97 (m, 2H), 6.92-6.89 (m, 1H), 6.37 (s, 1H), 5.72 (s, 2H), 5.16 (s, 2H), 4.45-4.35 (m, 2H), 4.12 (s, 1H), 3.80 (s, 2H), 2.70-2.65 (m, 2H), 2.35-2.27 (m, 2H), 1.86-1.79 (m, 2H), 1.51-1.44 (m, 2H), 1.33-1.27 (m, 6H).

Example 63. Synthesis of 2-((4-(3-((4-bromo-2-fluorophenoxy)methyl) phenoxy)piperidin-1-yl) methyl)-1-((1-isopropyl-1H-imidazol-5-yl)methyl)-1H-benzo[d]imidazole-6-carboxylic acid (compound C30)

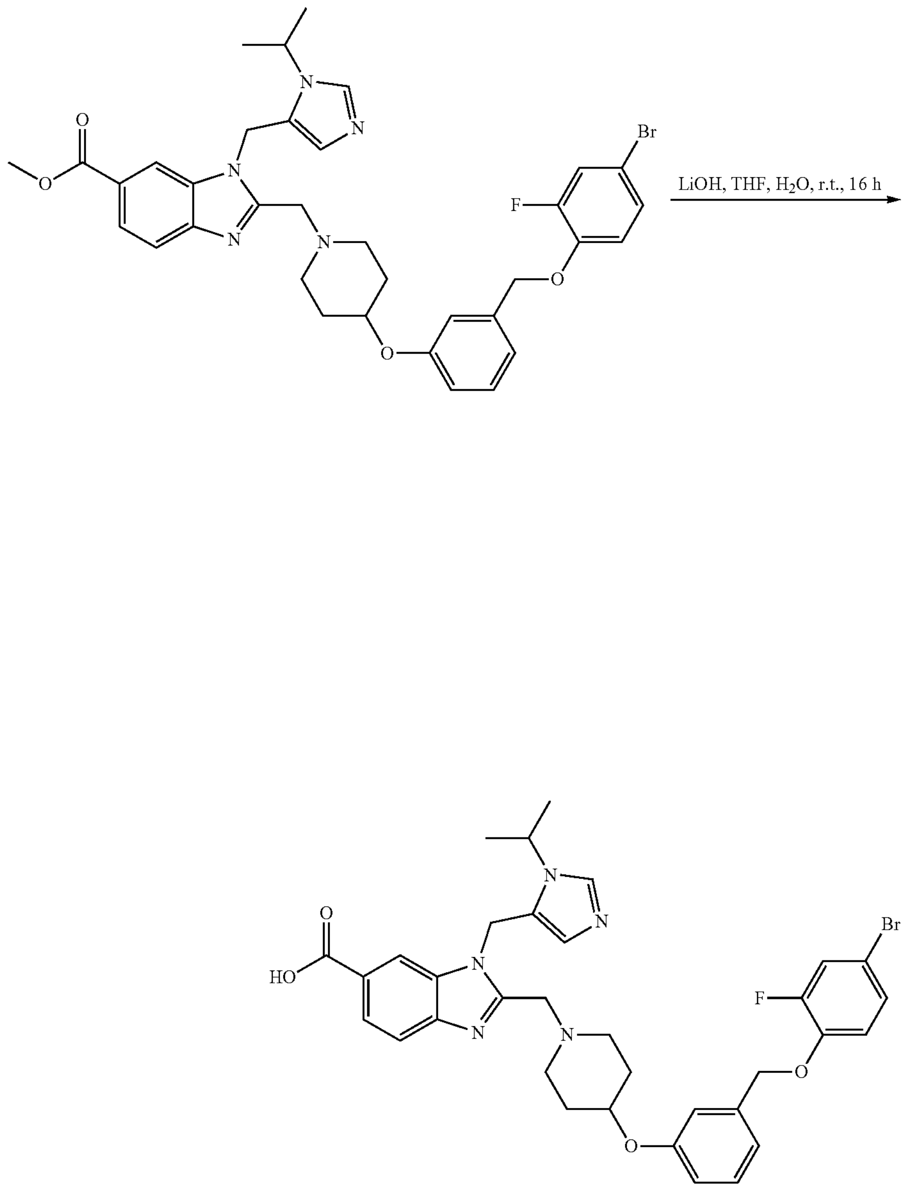

To a solution of 2-((4-(3-((4-bromo-2-fluorophenoxy) methyl) phenoxy)piperidin-1-yl)-1-((1-isopropyl-1 H-imidazol-5-yl)methyl)-1H-benzo[d]imidazole-6-carboxylate (100 mg, 0.16 mmol) in water (1 mL) and THF (1 mL), lithium hydroxide (10 mg, 0.42 mmol) was added at room temperature. The reaction mixture was stirred at room temperature for 16 hours. After completion, the reaction mixture was adjusted to pH=5-6 with formic acid. The mixture was concentrated to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-(3-((4-bromo-2-fluorophenoxy) methyl) phenoxy)piperidin-1-yl)methyl)-1-((1-isopropyl-1H-imidazol-5-yl)methyl)-1H-benzo[d]imidaz-ole-6-carboxylic acid (13.21 mg, 12.2% yield). LC-MS m/z: 678 $[M+H]^+$.

$^1H$ NMR (400 MHZ, DMSO-$d_6$): δ8.02 (s, 1H), 7.81-7.79 (m, 2H), 7.65 (d, J=8.4 Hz, 1H), 7.54 (dd, J=10.8 Hz, 2.4 Hz, 1H), 7.33-7.26 (m, 2H), 7.22-7.18 (m, 1H), 6.99-6.96 (m, 2H), 6.91-6.89 (m, 1H), 6.37 (s, 1H), 5.72 (s, 2H), 5.14 (s, 2H), 4.46-4.36 (m, 2H), 3.80 (s, 2H), 2.70-2.65 (m, 2H), 2.33-2.29 (m, 2H), 1.82-1.80 (m, 2H), 1.49-1.43 (m, 2H), 1.36-1.30 (m, 6H).

Example 64. Synthesis of 2-((4-((6-((4-cyano-2-fluorophenoxy)methyl)pyridin-2-yl)oxy)piperidin-1-yl)methyl)-1-((1-isopropyl-1H-imidazol-5-yl)methyl)-1H-benzo[d]imidazole-6-carboxylic acid (compound C31)

1). Synthesis of methyl 4-(2-(4-((6-((4-cyano-2-fluorophenoxy)methyl)pyridin-2-yl)oxy)piperidin-1-yl)acetamido)-3-((1-isopropyl-1H-imidazol-5-yl)methyl)amino)benzoate

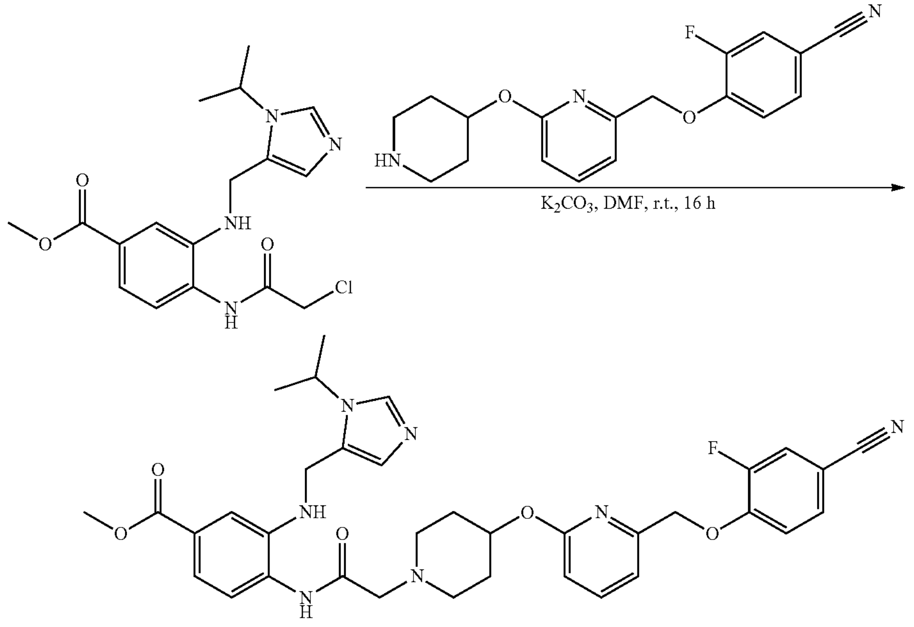

The mixture of 3-fluoro-4-((6-(piperidin-4-oxy)pyridin-2-yl)methoxy)benzonitrile (160 mg, 0.49 mmol), methyl 4-(2-chloroacetamido))-3-((1-isopropyl-1H-imidazol-5-yl)methyl)amino)benzoate (178 mg, 0.49 mmol) and potassium carbonate (135 mg, 0.98 mmol) in N,N-dimethylformamide (5 mL) was stirred at room temperature for 16 hours. After completion, water (5 mL) was added to quench the reaction, and extracted with ethyl acetate (40 mL×3). The combined organic layers were washed with brine (30 mL×2), dried over anhydrous sodium sulfate, filtered, and concentrated to give a residue in vacuo. The residue was purified by silica gel column chromatography (dichloromethane/methanol=10/1) to obtain methyl 4-(2-(4-((6-((4-cyano-2-fluorophenoxy)methyl)-pyridine)-2-yl)oxy)piperidin-1-yl)acetamido)-3-((1-isopropyl-1H-imidazol-5-yl)methyl)amino)benzoate (155 mg, 48.3% yield). LC-MS m/z: 656 $[M+H]^+$.

2). Synthesis of methyl 2-((4-((6-((4-cyano-2-fluorophenoxy)methyl)pyridin-2-yl)oxy)piperidin-1-yl)methyl)-1-((1-isopropyl-1H-imidazol-5-yl)methyl)-1H-benzo[d]imidazole-6-carboxylate

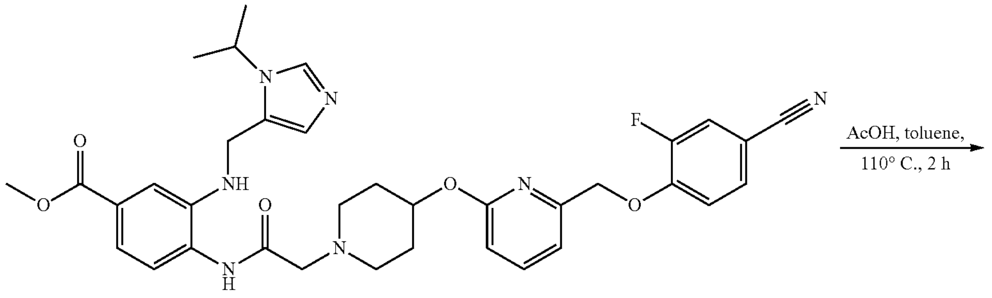

-continued

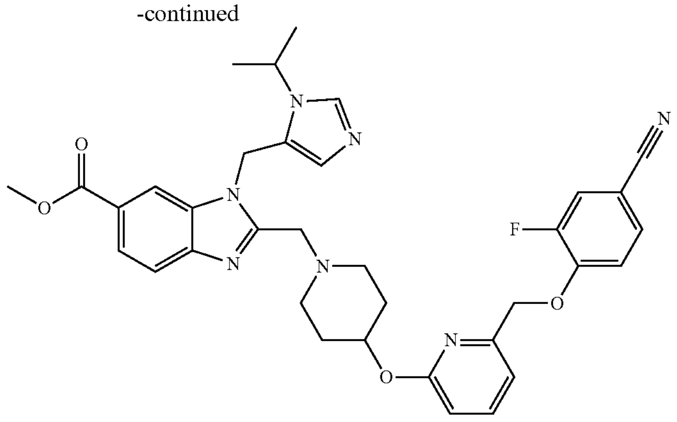

To a solution of methyl 4-(2-(4-((6-((4-cyano-2-fluorophenoxy)methyl)pyridin-2-yl)oxy)piperidin-1-yl)acetamido)-3-((1-isopropyl-1H-imidazol-5-yl)methyl)amino) benzoate (155 mg, 0.27 mmol) in toluene (3 mL) acetic acid (0.5 mL) was added at room temperature. The reaction was stirred at 110° C. for 2 hours. After completion, water (5 mL) was added to quench the reaction, and extracted with ethyl acetate (40 mL×3). The combined organic layers were washed with brine (40 mL×2), dried over anhydrous sodium sulfate, filtered, and concentrated to give a residue in vacuo. The residue was purified by silica gel column chromatography (dichloromethane/methanol=10/1) to obtain methyl 2-((4-((6-((4-cyano-2-fluorophenoxy)methyl)pyridin-2-yl)oxy)piperidin-1-yl)methyl)-1-((1-isopropyl-1H-imidazol-5-yl)methyl)-1H-benzo[d]imidazole-6-carboxylate (131 mg, yield: 87.3%). LC-MS m/z: 638 [M+H]$^+$.

3). Synthesis of 2-((4-((6-((4-cyano-2-fluorophenoxy)methyl)pyridin-2-yl)oxy)piperidin-1-yl)methyl)-1-((1-isopropyl-1H-imidazol-5-yl)methyl)-1H-benzo[d]imidazole-6-carboxylic acid

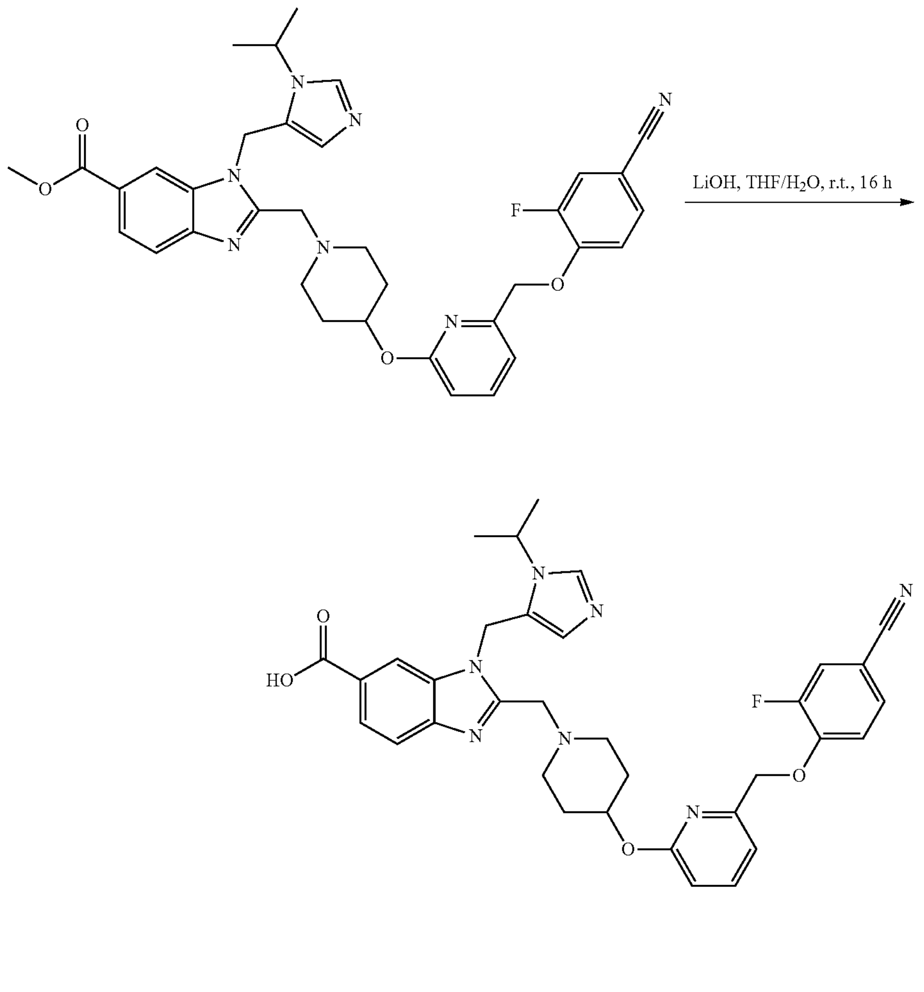 [SMILES: COC(=O)c1ccc2nc(CN3CCC(Oc4cccc(COc5ccc(C#N)cc5F)n4)CC3)n(Cc3cncn3C(C)C)c2c1 ; CC(C)n1cncc1Cn1c(CN2CCC(Oc3cccc(COc4ccc(C#N)cc4F)n3)CC2)nc2ccc(C(=O)O)cc21]

To a mixture of methyl 2-((4-((6-((4-cyano-2-fluorophenoxy)methyl)pyridin-2-yl)oxypiperidin-1-yl)methyl)-1-((1-Isopropyl-1H-imidazol-5-yl)methyl)-1H-benzo[d]imidazole-6-carboxylate (131 mg, 0.20 mmol) in THF (2 mL) and water (2 mL) lithium hydroxide (15 mg, 0.60 mmol) was added at room temperature. The mixture was stirred at room temperature for 16 hours. After completion, the resulting mixture was adjusted to pH=5-6 with acetic acid (1M), and then extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile phase B: acetonitrile; Flow rate: 40 mL/min; Gradient: 20% B-50% B in 20 min; Detector: 254 nm) to give 2-((4-((6-((4-cyano-2-fluorophenoxy)methyl)pyridin-2-yl)oxy)piperidin-1-yl)methyl)-1-((1-isopropyl-1H-imidazol-5-yl)methyl)-1H-benzo[d]imidazole-6-carboxylic acid (35.02 mg, 28.0% yield). LC-MS m/z: 624 $[M+H]^+$. $^1H$ NMR (400 MHz, DMSO-$d_6$) δ 8.03 (s, 1H), 7.89-7.78 (m, 3H), 7.74-7.64 (m, 3H), 7.44 (t, J=8.4 Hz, 1 H), 7.05 (d, J=7.2 Hz, 1H), 6.72 (d, J=8.4 Hz, 1H), 6.37 (s, 1H), 5.73 (s, 2H), 5.30 (s, 2H), 4.88-4.82 (m, 1 H), 4.46-4.40 (m, 1H), 3.81 (s, 2H), 2.74-2.57 (m, 2H), 2.27-2.22 (m, 2H), 1.86-1.79 (m, 2H), 1.48-1.46 (m, 2H), 1.34-1.29 (m, 6H).

Example 65. Synthesis of 2-((4-(3-((4-cyano-2-fluorophenoxy)methyl) phenoxy)piperidin-1-yl) methyl)-1-((1-ethyl-1H-imidazol-5-yl)methyl)-1H-benzo[d]imidazole-6-carboxylic acid (compound C32)

1). Synthesis of methyl 4-(2-(4-(3-((4-cyano-2-fluorophenoxy)methyl) phenoxy)piperidin-1-yl)acetamido-3-((1-isopropyl-1H-imidazol-5-yl)methyl) amino)benzoate

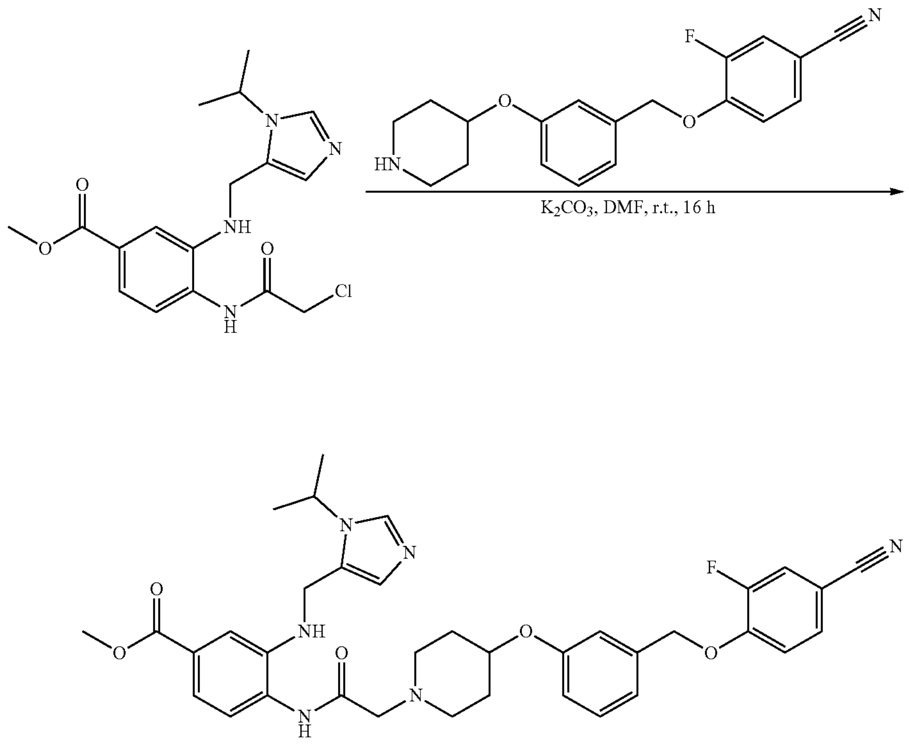 [SMILES: COC(=O)c1ccc(NC(=O)CCl)c(NCc2cncn2C(C)C)c1 ; N#Cc1ccc(OCc2cccc(OC3CCNCC3)c2)c(F)c1 ; COC(=O)c1ccc(NC(=O)CN2CCC(Oc3cccc(COc4ccc(C#N)cc4F)c3)CC2)c(NCc2cncn2C(C)C)c1]

-

The mixture of methyl 4-(2-chloroacetamido)-3-((1-isopropyl-1H-imidazol-5-yl)methyl)amino)benzoate (120 mg, 0.33 mmol), 3-fluoro-4-((3-(piperidin-4-oxy)benzyl)oxy) benzonitrile (108 mg, 0.33 mmol) and potassium carbonate (91 mg, 0.66 mmol) in dry N,N-dimethylformamide (5 mL) was stirred at room temperature for 16 hours. After completion, the reaction was quenched with water (10 mL) and extracted with ethyl acetate (3×10 mL). The combined organic layers were washed with brine (10 mL×2), dried over anhydrous sodium sulfate, filtered, and concentrated to give a residue in vacuo. The residue was purified by silica gel column chromatography (dichloromethane/methanol=10/1) to obtain methyl 4-(2-(4-(3-((4-cyano-2-fluorophenoxy)methyl) phenoxy)piperidin-1-yl)acetamido-3-((1-isopropyl-1H-imidazol-5-yl)methyl)amino)benzoate (130 mg, 60.5% yield). LC-MS m/z: 655 $[M+H]^+$.

2). Synthesis of methyl 2-((4-(3-((4-cyano-2-fluorophenoxy)methyl) phenoxy)piperidin-1-yl)-1-((1-isopropyl-1H-imidazol-5-yl)methyl)-1H-benzo[d]imidazole-6-carboxylate

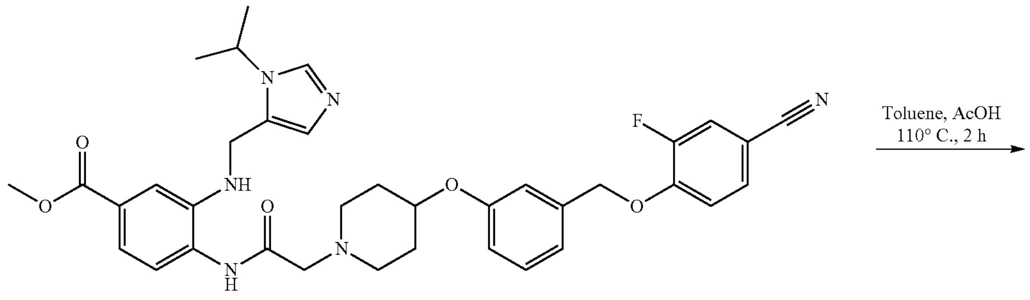

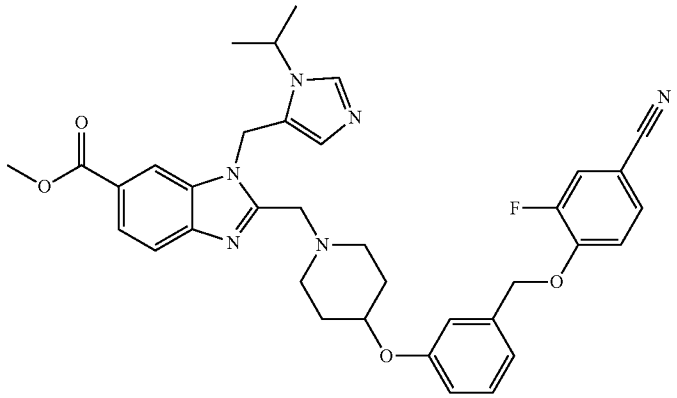

To a solution of methyl 4-(2-(4-(3-((4-cyano-2-fluorophenoxy)methyl) phenoxy)piperidin-1-yl)acetamido-3-((1-isopropyl-1H-imidazol-5-yl)methyl)amino)benzoate (130 mg, 0.20 mmol) in toluene (3 mL) acetic acid (0.5 mL) was added at room temperature. The mixture was stirred at 110° C. for 2 hours. After completion, the reaction solution was concentrated to give a residue in vacuo. The residue was purified by silica gel column chromatography (dichloromethane/methanol=10/1) to obtain methyl 2-((4-(3-((4-cyano-2-fluorobenzene oxy)methyl) phenoxy)piperidin-1-yl)-1-((1-isopropyl-1H-imidazol-5-yl)methyl)-1H-benzo[d]imidazol-6-carboxylate (100 mg, 79.4% yield). LC-MS m/z: 637 $[M+H]^+$.

3). Synthesis of 2-((4-(3-((4-cyano-2-fluorophenoxy)methyl) phenoxy)piperidin-1-yl)methyl)-1-((1-ethyl-1H-imidazol-5-yl)methyl)-1H-benzo[d]imidazole-6-carboxylic acid

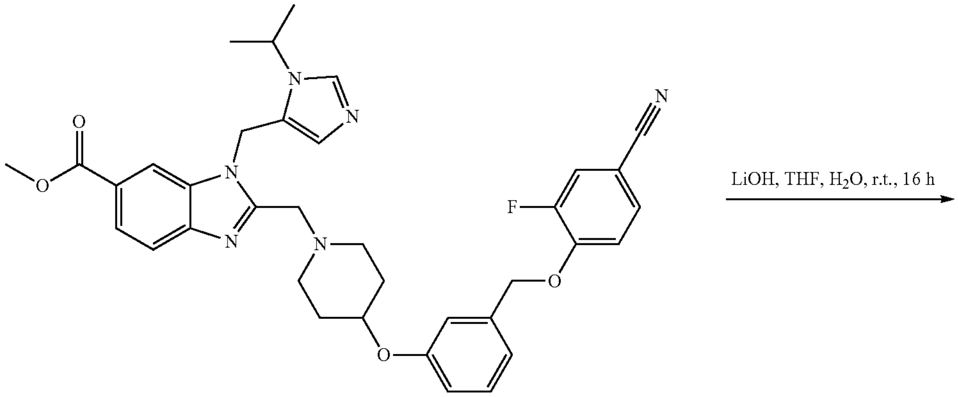

-continued

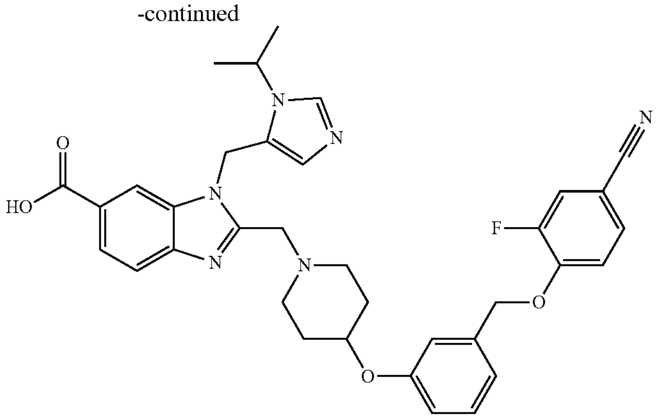

To a mixture of methyl 2-((4-(3-((4-cyano-2-fluorophenoxy)methyl) phenoxy)piperidin-1-yl)-1-((1-isopropyl)(1H-imidazol-5-yl)methyl)-1H-benzo[d]imidazole-6-carboxylate (100 mg, 0.16 mmol) in water (2 mL) and THF (2 mL) lithium hydroxide (12 mg, 0.48 mmol) was added at room temperature. The reaction mixture was stirred at room temperature for 16 hours. After completion, the reaction mixture was adjusted pH to 5-6 with formic acid. The mixture was concentrated to give a residue in vacuo. The residue was purified by prep-PLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-(3-((4-cyano-2-fluorophenoxy) methyl) phenoxy)piperidin-1-yl)methyl)-1-((1-ethyl)-1H-imidazol-5-yl)methyl)-1H-benzo[d]imidazole-6-carboxylic acid (17.60 mg, 18.0% yield). LC-MS m/z: 623 $[M+H]^+$.

$^1$H NMR (400 MHZ, DMSO-$d_6$): δ8.03 (s, 1H), 7.88-7.80 (m, 3H), 7.67 (t, J=8.8 Hz, 2H), 7.42 (t, J-8.4 Hz, 1H), 7.29 (t, J=7.6 Hz, 1H), 7.03-6.98 (m, 2H), 6.93 (d, J=8.4 Hz, 1H), 6.38 (s, 1H), 5.73 (s, 2H), 5.24 (s, 2H), 4.45-4.37 (m, 2H), 3.81 (s, 2H), 2.69-2.68 (m, 2H), 2.34-2.29 (m, 2H), 1.82 (s, 2H), 1.49-1.47 (m, 2H), 1.34-1.32 (m, 6H).

Example 66. Synthesis of 2-((4-((6-((4-cyano-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylic acid (Compound C33)

1). Synthesis of methyl 4-(2-(4-((6-((4-cyano-2-fluorophenoxy)methyl)pyridin-2-yl)oxy)piperidin-1-yl)acetamido)-3-((1-(cyclopropylmethyl)-1H-imidazol-5-yl)methyl)amino)benzoate

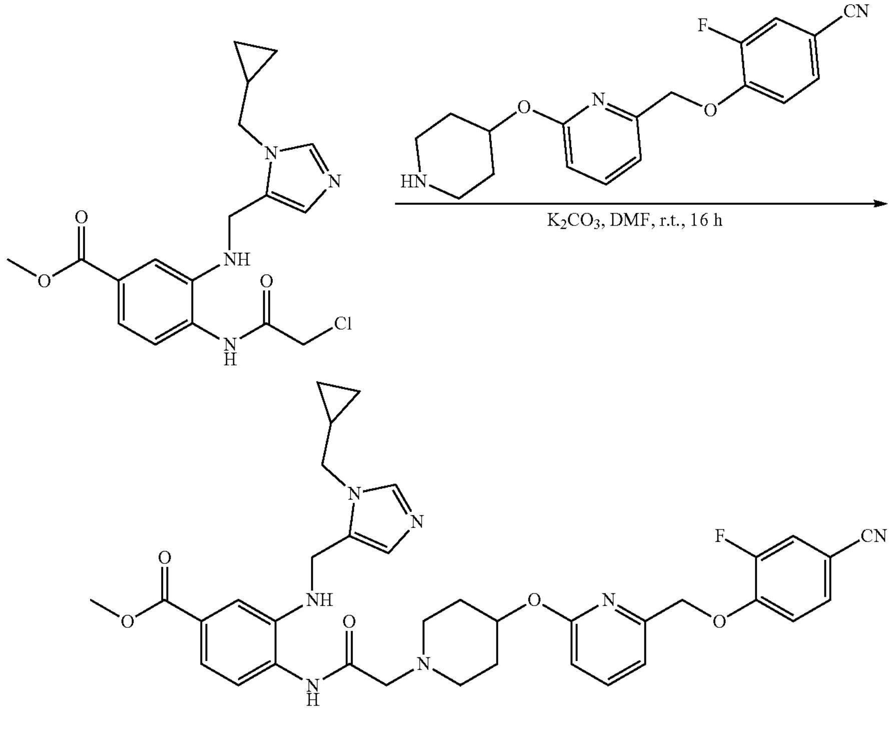

The mixture of methyl 4-(2-chloroacetamido)-3-((1-(cyclopropylmethyl)-1H-imidazol-5-yl)methyl)aminobenzoate (180 mg, 0.48 mmol), 3-fluoro-4-((6-(piperidin-4-oxy)pyridin-2-yl)methoxy)benzonitrile (156 mg, 0.48 mmol) and potassium carbonate (133 mg, 0.96 mmol) in N,N-dimethylformamide (5 mL) was stirred at room temperature for 16 hours. After completion, it was diluted with water (30 mL) and extracted with ethyl acetate (20 mL×3). The combined organic layers were washed with brine (30 mL) and concentrated to give a residue in vacuo. The residue was purified by silica gel column chromatography (dichloromethane/methanol=15/1) to obtain methyl 4-(2-(4-((6-((4-cyano-2-fluorophenoxy)methyl)pyridin-2-yl)oxy)piperidin-1-yl)acetamido)-3-((1-(cyclopropylmethyl)-1H-imidazol-5-yl)meth-yl)amino)benzoate (200 mg, 62.8% yield). LC-MS m/z: 668 $[M+H]^+$.

2). Synthesis of methyl 2-((4-((6-((4-cyano-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylate

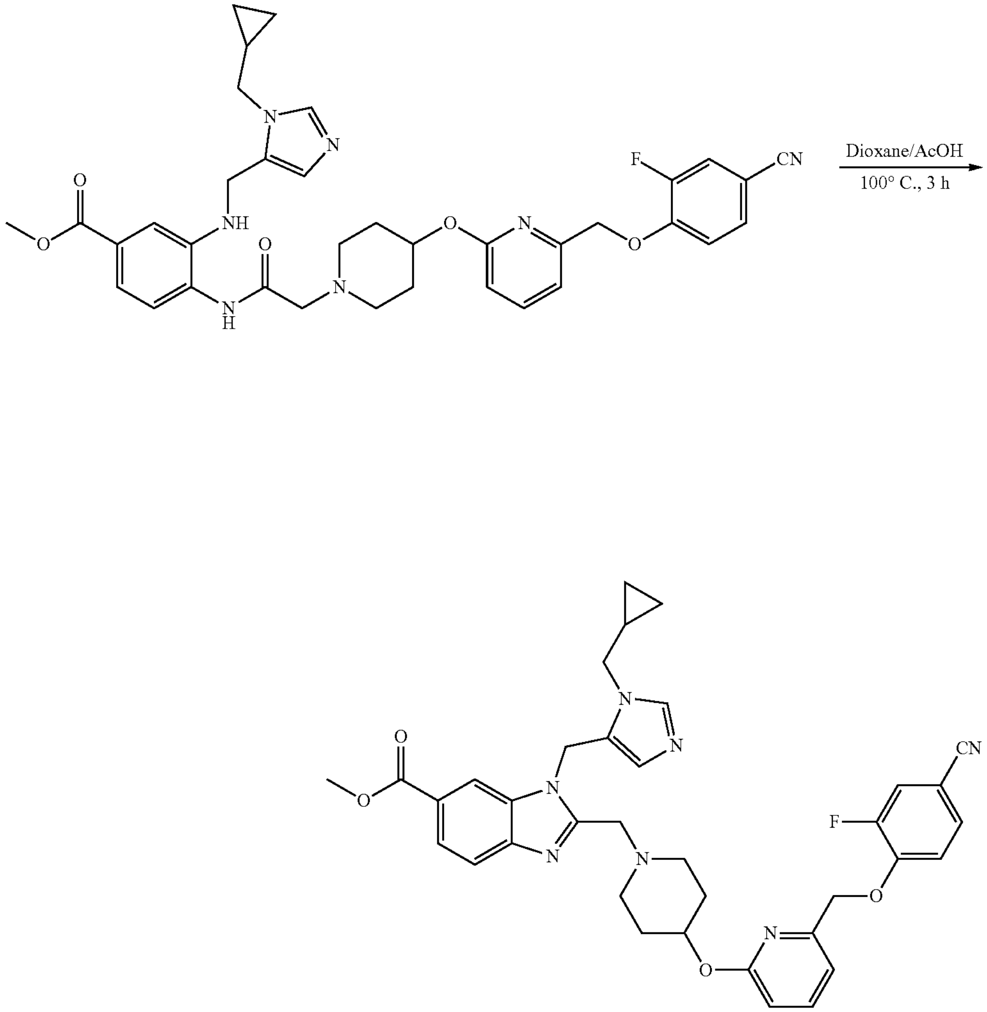

To a solution of methyl 4-(2-(4-((6-((4-cyano-2-fluorophenoxy)methyl)pyridin-2-yl)oxy)piperidin-1-yl)acetamido)-3-((1-(cyclopropylmethyl)-1H-imidazol-5-yl)methyl)amino)benzoate (200 mg, 0.30 mmol) in dioxane (10 mL) acetic acid (1 mL) was added at room temperature. The resulting mixture was stirred and reacted at 100° C. for 3 hours. After completion, the reaction solution was concentrated to give a residue in vacuo. The residue was purified by silica gel column chromatography (dichloromethane/methanol=15/1) to obtain methyl 2-((4-((6-((4-cyano-2-fluorophenoxy)methyl)pyridin-2-yl)oxy)piperidin-1-yl)methyl)-1-((1-(cyclopropylmethyl)-1 H-imidazol-5-yl)methyl)-1H-benzo[d]imidazole-6-carboxylate (150 mg, 77.1% yield). LC-MS m/z: 650 $[M+H]^+$.

3). Synthesis of 2-((4-((6-((4-cyano-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylic acid

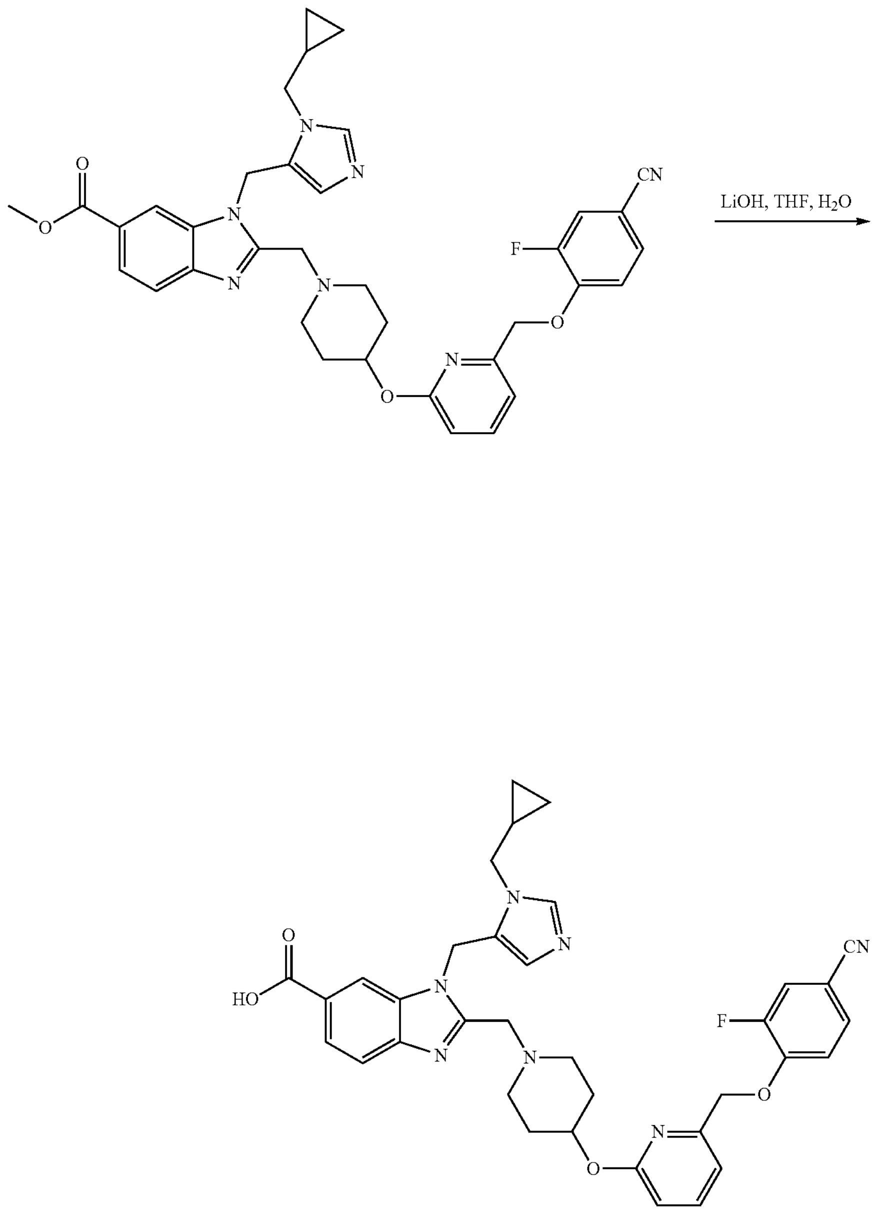

To a mixture of methyl 2-((4-((6-((4-cyano-2-fluorophenoxy)methyl)pyridin-2-yl)oxypiperidin-1-yl)methyl)-1-(((1-(cyclopropylmethyl)-1H-imidazol-5-yl)methyl)-1H-benzo[d]imidazole-6-carboxylate (150 mg, 0.23 mmol) in water (5 mL) and THF (5 mL) lithium hydroxide (56 mg, 2.30 mmol) was added at room temperature. The reaction mixture was stirred at room temperature for 16 hours. After completion, the reaction was adjusted to pH=5-6 with formic acid. The mixture was concentrated to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidin-1-yl)methyl)-1-((1-(cyclopropylmethyl)-1H-imidazol-5-yl)methyl)-1H-benzo[d]imidazole-6-carboxylic acid (77.69 mg, 53.1% yield). LC-MS m/z: 636 $[M+H]^+$.

$^1H$ NMR (400 MHZ, DMSO-$d_6$): δ12.76 (br, 1H), 8.06 (s, 1H), 7.90-7.81 (m, 2H), 7.74-7.65 (m, 4H), 7.44 (t, J-8.4 Hz, 1H), 7.05 (d, J=7.2 Hz, 1H), 6.72 (d, J=8.0 Hz, 1H), 6.37 (s, 1H), 5.75 (s, 2H), 5.30 (s, 2H), 4.85-4.84 (m, 1H), 3.87-3.83 (m, 4H), 2.69-2.67 (m, 2H), 2.27-2.22 (m, 2H), 1.79-1.77 (m, 2H), 1.47-1.41 (m, 2H), 1.04-1.00 (m, 1H), 0.51-0.46 (m, 2H), 0.35-0.31 (m, 2H).

Example 67. Synthesis of 2-((4-((6-((4-cyano-2-fluorophenoxy)methyl)pyridin-2-yl)oxy)piperidin-1-yl)methyl)-1-((1-ethyl-5-oxopyrrolidin-2-yl)methyl)-1H-benzo[d]imidazole-6-carboxylic acid (Compound C34)

1). Synthesis of methyl 4-(2-(4-((6-((4-cyano-2-fluorophenoxy)methyl)pyridin-2-yl)oxy)piperidin-1-yl)acetamido)-3-(((1-ethyl)-5-oxopyrrolidin-2-yl)methyl)amino)benzoate

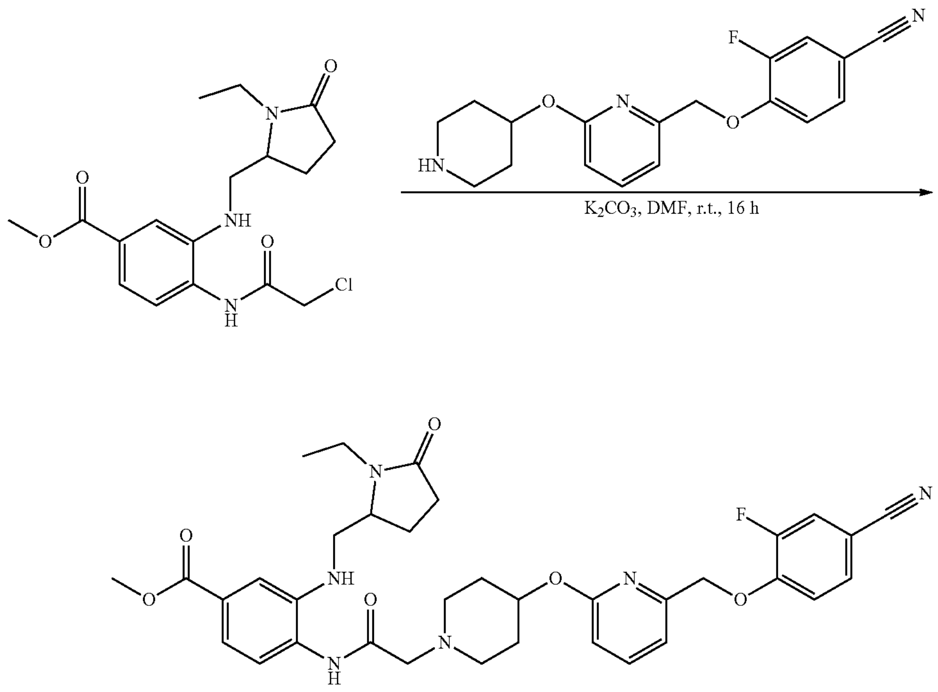

The mixture of methyl 4-(2-chloroacetamido)-3-((1-ethyl-5-oxopyrrolidin-2-yl)methyl)aminobenzoate (100 mg, 0.27 mmol), 3-fluoro-4-((6-(piperidin-4-oxy)pyridin-2-yl)methoxy)benzonitrile (88 mg, 0.27 mmol) and potassium carbonate (75 mg, 0.54 mmol) in N,N-dimethylformamide (2 mL) was stirred at room temperature for 16 hours. After completion, the mixture was diluted with water (30 mL) and extracted with ethyl acetate (10 mL×2). The combined organic layers were washed with brine (20 mL×3), dried over anhydrous sodium sulfate, filtered, and concentrated to give a residue in vacuo. The residue was purified by silica gel column chromatography (dichloromethane/methanol-20/1) to obtain methyl 4-(2-(4-((6-((4-cyano-2-fluorophenoxy)methyl)pyridin-2-yl)oxy)piperidin-1-yl)acetamido)-3-(((1-ethyl)-5-oxopyrrolidin-2-yl)methyl)amino)benzoate (90 mg, 50.7% yield). LC-MS m/z: 659 $[M+H]^+$.

2). Synthesis of methyl 2-((4-((6-((4-cyano-2-fluorophenoxy)methyl)pyridin-2-yl)oxy)piperidin-1-yl)methyl)-1-((1-ethyl-5-oxopyrrolidin-2-yl)methyl)-1H-benzo[d]imidazole-6-carboxylate

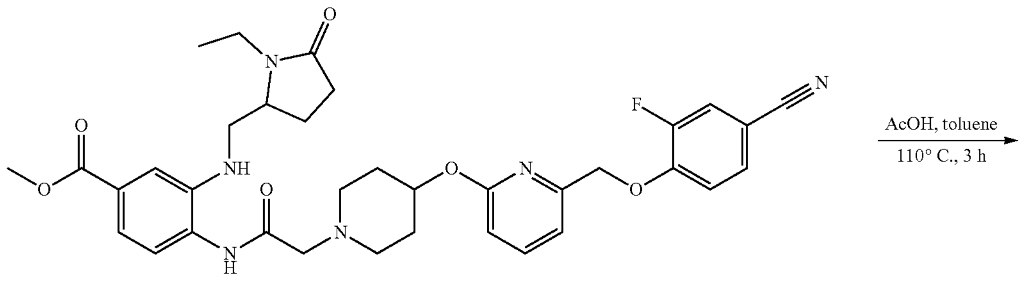

-continued

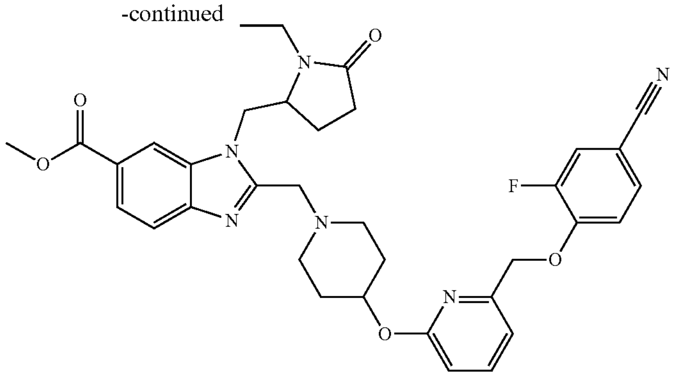

The mixture of 4-(2-(4-((6-((4-cyano-2-fluorophenoxy)methyl)pyridin-2-yl)oxy)piperidin-1-yl)acetamido)-3-(((1-ethyl)-5-oxopyrrolidin-2-yl)methyl)amino)benzoate (90 mg, 0.14 mmol) in toluene (3 mL) and acetic acid (0.5 mL) was stirred at 110° C. for 3 hours. After completion, the solvent was removed by concentration to give a residue in vacuo. The residue was purified by silica gel column chromatography (dichloromethane/methanol=20/1) to obtain methyl 2-((4-((6-((4-cyano-2-fluorophenoxy)methyl)pyridin-2-yl)oxy)piperidin-1-yl)methyl)-1-((1-ethyl-5-oxopyrrolidin-2-yl)methyl)-1H-benzo[d]imidazole-6-carboxylate (70 mg, 78.1% yield). LC-MS m/z: 641 $[M+H]^+$.

3). Synthesis of 2-((4-((6-((4-cyano-2-fluorophenoxy)methyl)pyridin-2-yl)oxy)piperidin-1-yl)methyl)-1-((1-ethyl-5-oxopyrrolidin-2-yl)methyl)-1H-benzo[d]imidazole-6-carboxylic acid

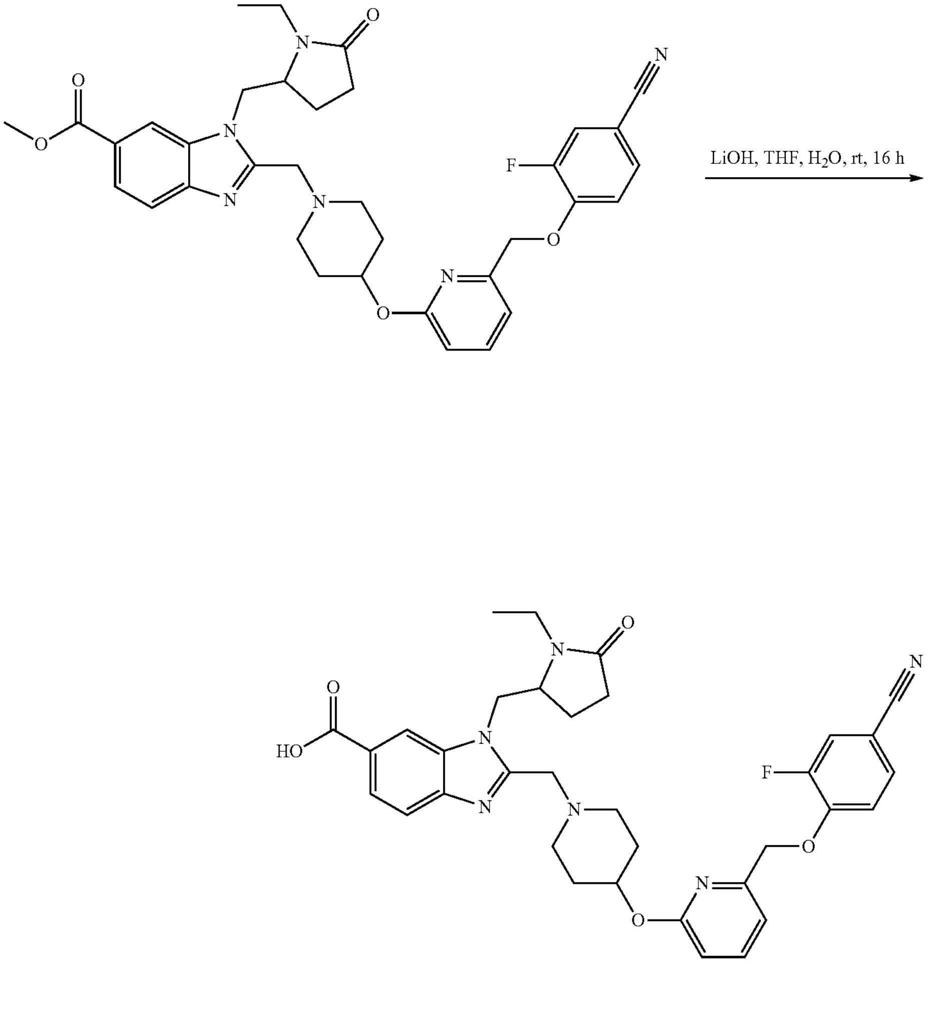

To a mixture of methyl 2-((4-((4-cyano-2-fluorophenoxy)methyl)pyridin-2-yl)oxypiperidin-1-yl)methyl)-1-(((1-ethyl-5-oxopyrrolidin-2-yl)methyl)-1H-benzo[d]imidazole-6-carboxylate (70 mg, 0.11 mmol) in THF (5 mL) and water (5 mL) lithium hydroxide (8 mg, 0.33 mmol) was added at room temperature. The reaction was stirred at room temperature for 16 hours. After completion and concentrated to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidin-1-yl)methyl)-1-((1-ethyl-5-oxopyrrolidin-2-yl)methyl)-1H-benzo[d]imidazole-6-carboxylic acid (32.33 mg, 46.9% yield). LC-MS m/z: 627 $[M+H]^+$.

$^1$H NMR (400 MHZ, DMSO-$d_6$): δ8.27 (s, 1H), 7.90-7.82 (m, 2H), 7.75-7.66 (m, 3H), 7.45 (t, J=8.8 Hz, 1H), 7.06 (d, J=7.2 Hz, 1H), 6.74 (d, J=8.4 Hz, 1H), 5.31 (s, 2H), 4.93-4.91 (m, 1H), 4.77-4.72 (m, 1H), 4.51-4.46 (m, 1H), 4.33-4.31 (m, 1H), 3.91-3.81 (m, 2H), 3.51-3.46 (m, 1H), 2.76-2.67 (m, 3H), 2.47-2.39 (m, 1H), 2.34-2.30 (m, 2H), 2.16-2.14 (m, 1H), 1.94-1.79 (m, 4H), 1.62-1.55 (m, 2H), 1.00 (t, J=7.2 Hz, 3 H).

Example 68. Synthesis of(S)-2-((4-((6-((4-cyano-2-fluorophenoxy)methyl)pyridin-2-yl)oxy)piperidin-1-yl)methyl)-1-((1-ethylpyrrolidin-2-yl)methyl)-1H-benzo[d]imidazole-6-carboxylic acid (Compound C35)

1). Synthesis of methyl(S)-4-(2-(4-((6-((4-cyano-2-fluorophenoxy)methyl)pyridin-2-yl)oxy)piperidin-1-yl)acetamido)-3-((1-ethylpyrrolidin-2-yl)methyl)amino)benzoate

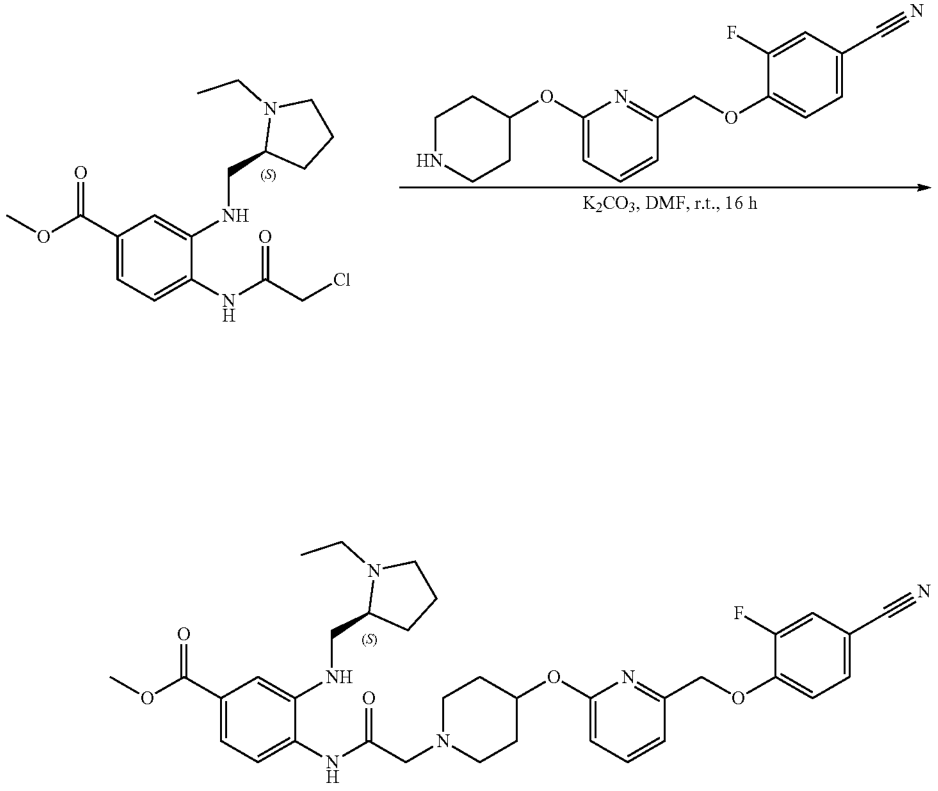

The mixture of methyl(S)-4-(2-chloroacetamido)-3-((1-ethylpyrrolidin-2-yl)methyl)aminobenzoate (140 mg, 0.40 mmol), 3-fluoro-4-((6-(piperidin-4-oxy)pyridin-2-yl)methoxy)benzonitrile (142 mg, 0.44 mmol) and potassium carbonate (165 mg, 1.20 mmol) in N,N-dimethylformamide (5 mL) was stirred at room temperature for 16 hours. After completion, it was diluted with water (50 mL) and extracted with ethyl acetate (50 mL×3). The combined organic layers washed with brine (120 mL×2). The organic layer was concentrated in vacuo and purified by silica gel column chromatography (dichloromethane/methanol=13/1) to give methyl(S)-4-(2-(4-((6-((4-cyano-2-fluorophenoxy)methyl)-pyridin-2-yl)oxy)piperidin-1-yl)acetamido)-3-((1-ethylpyrrolidin-2-yl)methyl)amino)benzoate (180 mg, 70.4% yield). LC-MS m/z: 645 $[M+H]^+$.

2). Synthesis of methyl(S)-2-((4-((6-((4-cyano-2-fluorophenoxy)methyl)pyridin-2-yl)oxy)piperidin-1-yl)methyl)-1-((1-ethylpyrrolidin-2-yl)methyl)-1H-benzo[d]imidazole-6-carboxylate

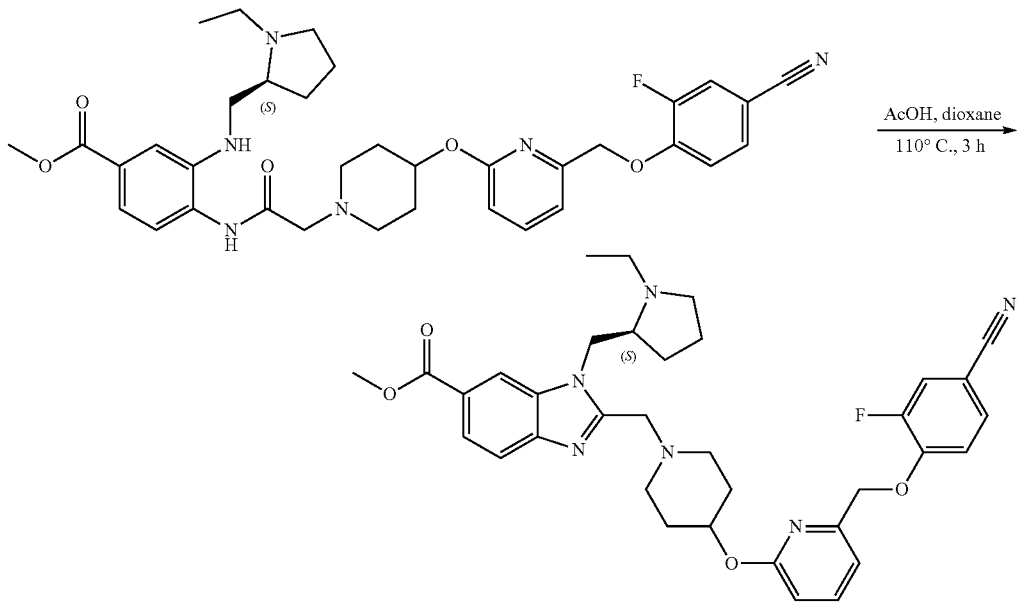

To a mixture of methyl(S)-4-(2-(4-((6-((4-cyano-2-fluorophenoxy)methyl)pyridin-2-yl)oxy)piperidin-1-yl)acetamido)-3-((1-ethylpyrrolidin-2-yl)methyl)amino)benzoate (180 mg, 0.28 mmol) in dioxane (10 mL) acetic acid (2 mL) was added. The resulting mixture was stirred and reacted at 100° C. for 3 hours. After completion, the reaction mixture was concentrated to give a residue in vacuo. The residue was purified by silica gel (dichloromethane/methanol=10/1) to obtain methyl(S)-2-((4-((6-((4-cyano-2-fluorophenoxy)methyl)pyridin-2-yl)oxy)piperidin-1-yl)methyl)-1-((1-ethylpyrrolidin-2-yl)methyl)-1H-benzo[d]imidazole-6-carboxylate (80 mg, 45.7% yield). LC-MS m/z: 627 [M+H]$^+$.

3). Synthesis of(S)-2-((4-((6-((4-cyano-2-fluorophenoxy)methyl)pyridin-2-yl)oxy)piperidin-1-yl)methyl)-1-((1-ethylpyrrolidin-2-yl)methyl)-1H-benzo[d]imidazole-6-carboxylic acid

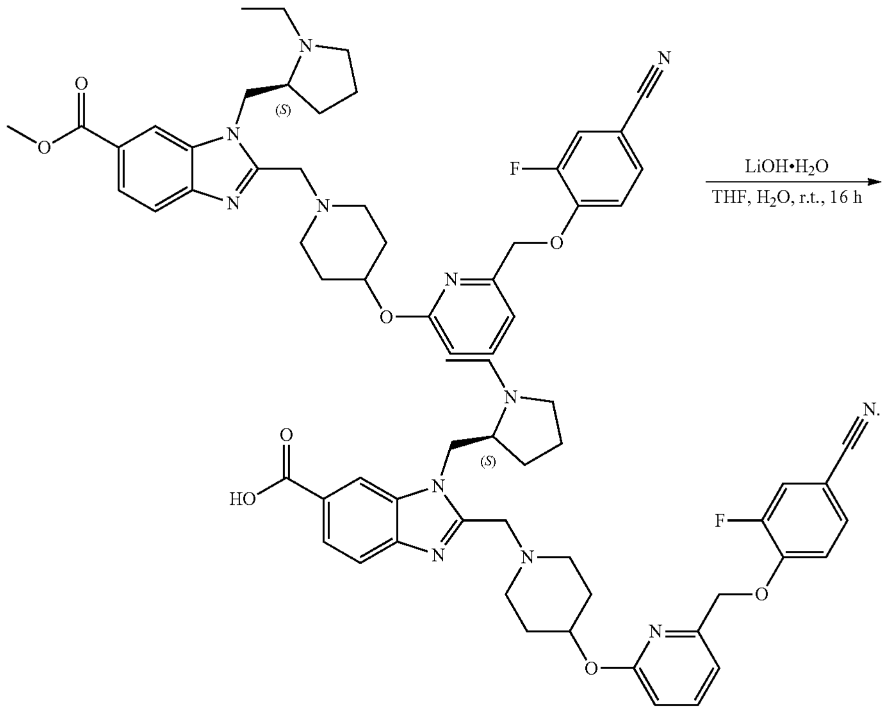

To a mixture of methyl(S)-2-((4-((6-((4-cyano-2-fluoro-phenoxy)methyl)pyridin-2-yl)oxypiperidin-1-yl)methyl)-1-((1-ethylpyrrolidin-2-yl)methyl)-1H-benzo[d]imidazole-6-carboxylate (80 mg, 0.13 mmol) was dissolved in $H_2O$ (4 mL) and THF (4 mL) lithium hydroxide (32 mg, 1.30 mmol) was added at room temperature.

The reaction mixture was stirred at room temperature for 16 hours. After completion, the reaction solution was adjusted to pH-5-6 with formic acid. The mixture was concentrated to give a residue in vacuo to remove the solvent. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain(S)-2-((4-((6-((4-cyano-2-fluorophenoxy)methyl)pyridin-2-yl)oxy)piperidin-1-yl)methyl)-1-((1-ethylpyrrolidin-2-yl)methyl)-1H-benzo[d]imidazole-6-carboxylic acid (19.20 mg, 24.6% yield). LC-MS m/z: 613 $[M+H]^+$.

$^1H$ NMR (400 MHZ, DMSO-$d_6$): δ8.21 (s, 1H), 7.88 (dd, J=11.2 Hz, 2.0 Hz, 1H), 7.79 (dd, J=8.8 Hz, 1.2 Hz, 1H), 7.73 (t, J-8.0 Hz, 1H), 7.68-7.62 (m, 2H), 7.45 (t, J-8.8 Hz, 1H), 7.06 (d, J-7.6 Hz, 1H), 6.74 (d, J=8.4 Hz, 1H), 5.31 (s, 2H), 4.93-4.89 (m, 1H), 4.44-4.39 (m, 1H), 4.33-4.28 (m, 1H), 4.04 (d, J=13.2 Hz, 1H), 3.76 (d, J=13.2 Hz, 1H), 3.11-3.07 (m, 2H), 2.77-2.70 (m, 2H), 2.34-2.26 (m, 2H), 2.22-2.14 (m, 2H), 1.91-1.89 (m, 2H), 1.80-1.62 (m, 3H), 1.61-1.55 (m, 3H), 0.80 (t, J-7.2 Hz, 3H).

Example 69. Synthesis of(S)-2-((4-(3-((4-cyano-2-fluorophenoxy)methyl) phenoxy)piperidin-1-yl) methyl)-4-methyl-1-(oxan-2-ylmethyl)-1H benzo[d] imidazole-6-carboxylic acid (compound C36)

1). Synthesis of(S)—N-(4-bromo-2-methyl-6-((oxetan-2-ylmethyl)amino)phenyl)-2-(4-(3-((4-cyano-2-fluoro-phenoxy)methyl) phenoxy)piperidin-1-yl)acetamide

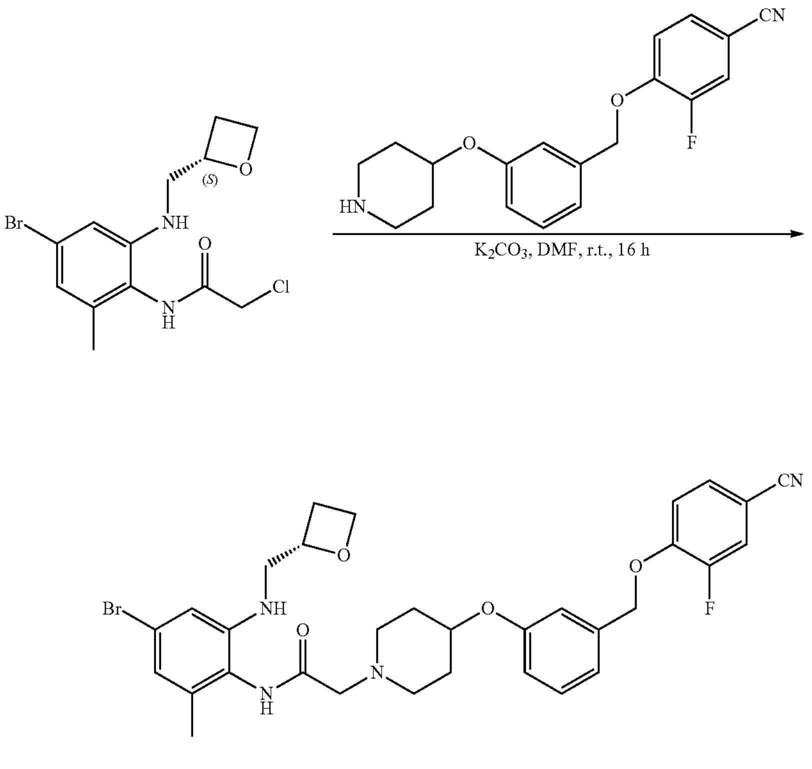

The mixture of(S)—N-(4-bromo-2-methyl-6-((oxetan-2-ylmethyl)amino)phenyl)-2-chloroacetamide (98 mg, 0.28 mmol), 3-fluoro-4-((3-(piperidin-4-oxy)benzyl)oxy)benzonitrile (119 mg, 0.37 mmol) and potassium carbonate (77 mg, 0.56 mmol) in N,N-dimethylformamide (3 mL) was stirred at room temperature for 16 hours. After completion, the reaction was quenched by adding water (5 mL) and extracted with ethyl acetate (20 mL×3). The combined organic layers were washed with brine (20 mL×3), dried over anhydrous sodium sulfate, filtered, and concentrated to give a residue in vacuo. The residue was purified by silica gel column chromatography (dichloromethane/methanol=10/1) to obtain(S)—N-(4-bromo-2-methyl-6-((oxetan-2-ylmethyl)amino)phenyl)-2-(4-(3-((4-cyano-2-fluorophenoxy)methyl)-phenoxy)piperidin-1-yl)acetamide (65 mg, 35.7% yield) as yellow solid. LC-MS m/z: 639 $[M+H]^+$.

2). Synthesis of(S)-4-((3-((1-((6-bromo-4-methyl-1-(oxetan-2-ylmethyl)-1H-benzo[d]imidazole-2-yl) methyl)-piperidin-4-yl)oxy)benzyl)oxy)-3-fluorobenzonitrile

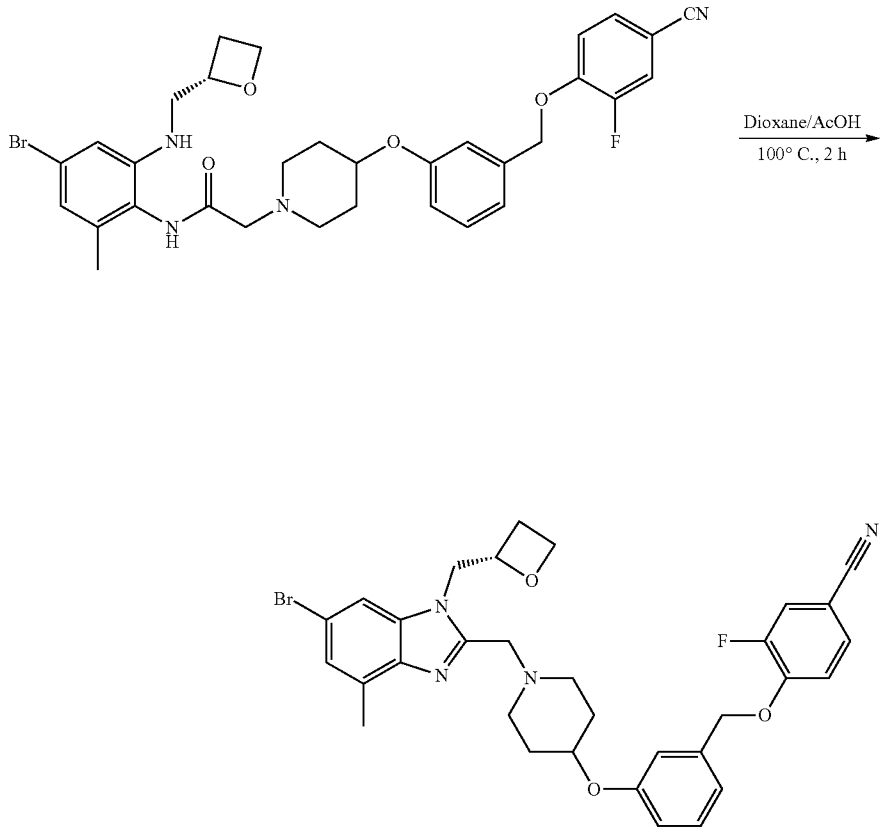

To a solution of(S)—N-(4-bromo-2-methyl-6-((oxetan-2-ylmethyl)amino)phenyl)-2-(4-(3-((4-cyano-2-fluorophenoxy)-methyl) phenoxy)piperidin-1-yl)acetamide (65 mg, 0.10 mmol) in dioxane (5 mL) acetic acid (0.5 mL) was added at room temperature. The resulting mixed solution was stirred at 100° C. for 2 hours. After completion, the reaction solution was concentrated to give a residue under reduced pressure. The residue was purified by silica gel column chromatography (dichloromethane/methanol=10/1) to obtain compound(S)-4-((3-((1-((6-bromo-4-methyl-1-(oxetan-2-ylmethyl)-1H-benzo[d]imidazol-2-yl)methyl)piperidin-4-yl)oxy)benzyl)oxy)-3-fluorobenzonitrile (60 mg: 96.9% yield) as yellow solid. LC-MS m/z: 621 $[M+H]^+$.

3). Synthesis of methyl(S)-2-((4-(3-((4-cyano-2-fluorophenoxy)methyl) phenoxy)piperidin-1-yl) methyl)-4-methyl-1-(oxetan-2-ylmethyl)-1H-benzo [d]imidazole-6-carboxylate

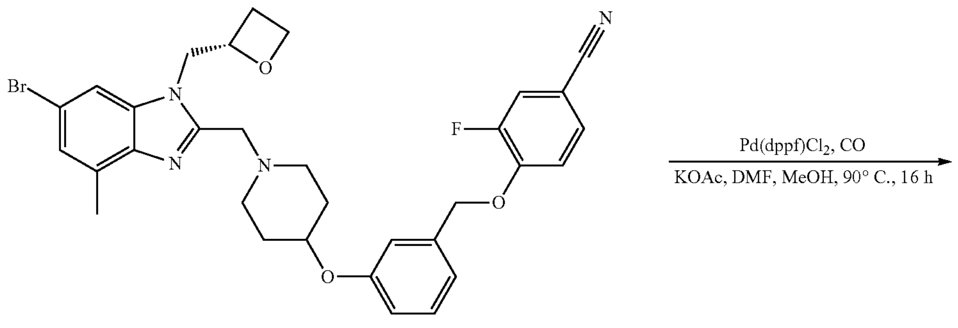

-continued

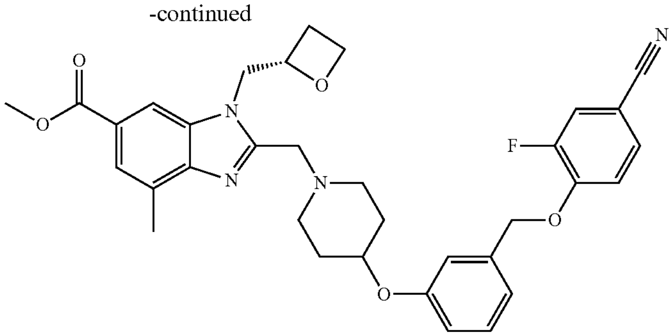

The mixture of(S)-4-((3-((1-((6-bromo-4-methyl-1-(oxetan-2-ylmethyl)-1H-benzo[d]imidazol-2-yl)methyl)piperi-din-4-yl)oxy)benzyl)oxy)-3-fluorobenzonitrile (60 mg, 0.10 mmol), 1,1'-bisdiphenylphosphinoferrocenepalladium dichloride (7 mg, 0.01 mmol) and potassium acetate (29 mg, 0.30 mmol) in N,N-dimethylformamide (1 mL) and methanol (1 mL) was stirred at 90° C. for 16 hours under carbon monoxide (58.76 psi) atmosphere. After completion, the reaction mixture was concentrated to give a residue. The residue was purified by silica gel column chromatography (dichloromethane/methanol=20/1) to obtain methyl(S)-2-((4-(3-((4-cyano-2-fluorophenoxy)methyl) phenoxy)piperi-din-1-yl)methyl)-4-methyl-1-(oxetan-2-ylmethyl)-1H-benzo[d]imidazole-6-carboxylate (11 mg, 17.8% yield). LC-MS m/z: 599 $[M+H]^+$.

4). Synthesis of(S)-2-((4-(3-((4-cyano-2-fluorophenoxy)methyl) phenoxy)piperidine-1-yl)methyl)-4-methyl-1-(oxocyclobutan-2-ylmethyl)-1H-benzo[d] imidazole-6-carboxylic acid methyl ester

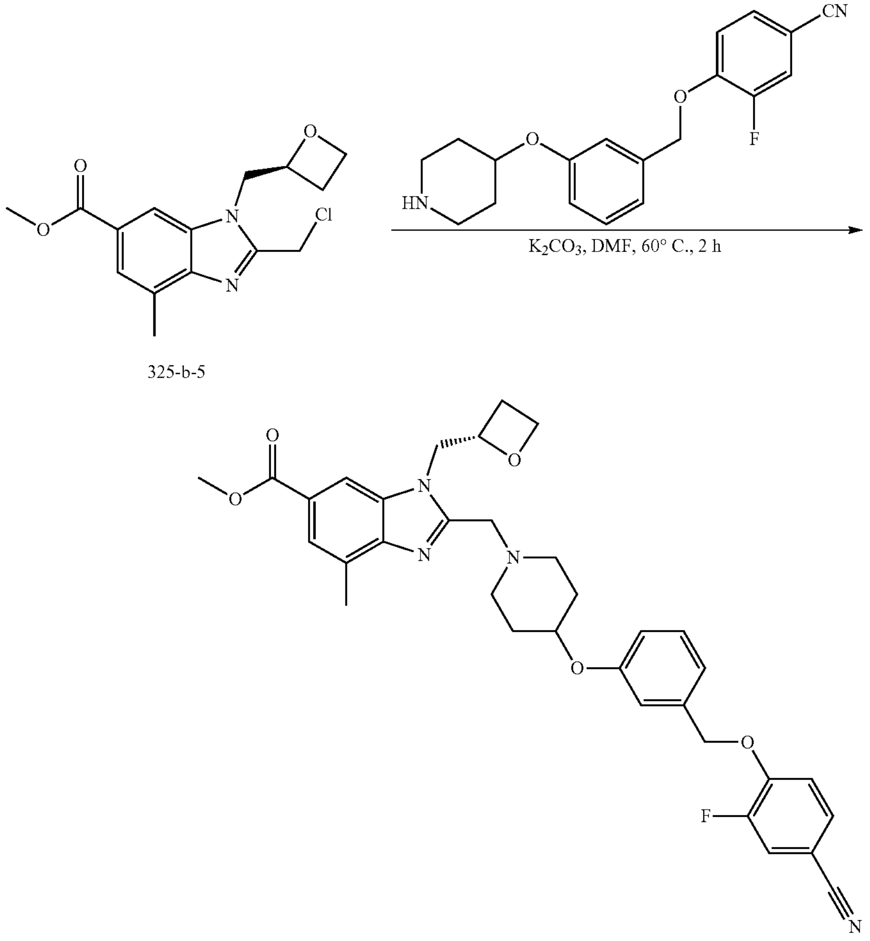

325-b-5

325-7

The mixture of(S)-2-(chloromethyl)-4-methyl-1-(oxocyclobutan-2-ylmethyl)-1H-benzo[d]imidazole-6-carboxylic acid methyl ester (20 mg, 0.07 mmol), 3-fluoro-4-(3-(piperidin-4-oxy)benzyl)oxy)benzonitrile (30 mg, 0.09 mmol) and potassium carbonate (29 mg, 0.21 mmol) in N, N-dimethylformamide (1 mL) was stirred at 60° C. for 2 hours. After completion, the mixture was diluted with water (3 mL), and extract with ethyl acetate (15 mL×3). The combined organic layer was washed with brine (10 mL×3), dried over anhydrous sodium sulfate, filtered, and concentrated to give a residue in vacuo. The residue was purified by silica gel column chromatography (dichloromethane/methanol=20/1) obtain(S)-2-((4-(3-((4-cyano-2-to fluorophenoxy) methyl) phenoxy)piperidine-1-yl)methyl)-4-methyl-1-(oxocyclobutan-2-yl methyl)-1H-benzo[d]imidazole-6-carboxylic acid methyl ester (11 mg, yield: 28.6%). LC-MS m/z: 599 [M+H]+.

5). Synthesis of(S)-2-((4-(3-((4-cyano-2-fluorophenoxy)methyl) phenoxy)piperidin-1-yl)methyl)-4-methyl-1-(oxetan-2-ylmethyl)-1H-benzo[d]imidazole-6-carboxylic acid

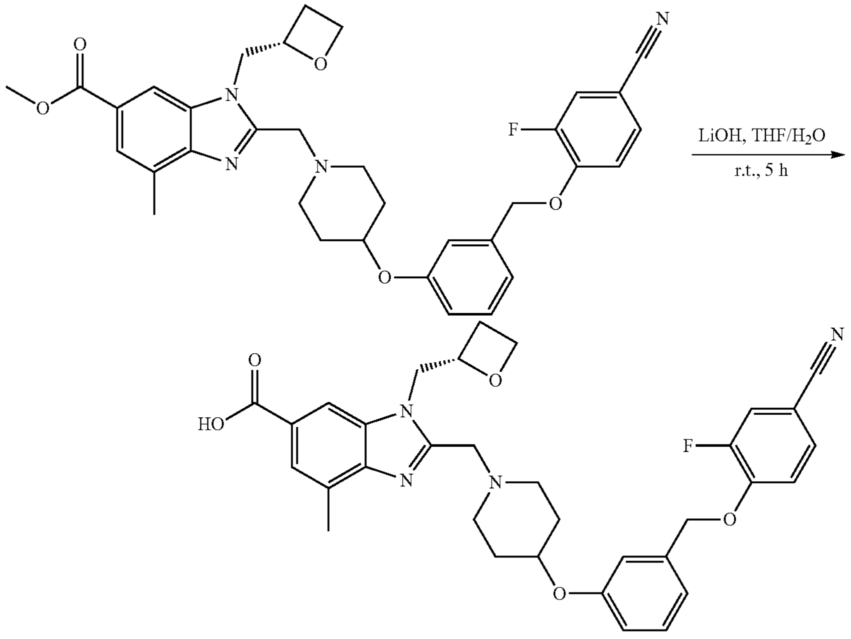

To a mixture of methyl(S)-2-((4-(3-((4-cyano-2-fluorophenoxy)methyl) phenoxy)piperidin-1-yl)methyl)-4-methyl-1-(oxetan-2-ylmethyl)-1H-benzo[d]imidazole-6-carboxylate (22 mg, 0.04 mmol) in THF (4 mL) and water (4 mL) lithium hydroxide (16 mg, 0.40 mmol) was added at room temperature. The resulting mixture solution was stirred and reacted at room temperature for 5 hours. After completion, the resulting mixture was adjusted to pH=5-6 with acetic acid (1 M) and extracted with ethyl acetate (10 mL×3). The combined organic layers were washed with brine (10 mL), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile Phase B: acetonitrile; Flow rate: 40 mL/min; Gradient: 20% B-50% B in 20 min; Detector: 254 nm) to obtain(S)-2-((4-(3-((4-cyano-2-fluorophenoxy)methyl)) phenoxy)piperidin-1-yl)methyl)-4-methyl-1-(oxetan-2-ylmethyl)-1H-benzo[d]imidazole-6-carboxylic acid (9.33 mg, 39.9% yield). LC-MS m/z: 585 [M+H]+.

$^1H$ NMR (400 MHZ, DMSO-$d_6$) δ 7.90-7.85 (m, 2H), 7.69-7.63 (m, 2H), 7.42 (t, J-8.4 Hz, 1H), 7.30 (t, J-8.0 Hz, 1H), 7.05 (m, 1H), 7.00 (d, J=7.2 Hz, 1H), 6.95 (dd, J-8.0 Hz, 1.6 Hz, 1H), 5.25 (s, 2H), 5.11-5.05 (m, 1H), 4.70-4.65 (m, 1H), 4.58-4.54 (m, 1H), 4.51-4.45 (m, 1H), 4.41-4.33 (m, 2H), 3.89 (d, J=13.6 Hz, 1H), 3.77 (d, J=13.6 Hz, 1H), 2.74-2.63 (m, 3H), 2.49 (s, 3H), 2.45-2.35 (m, 3H), 1.93 (s, 2H), 1.64-1.60 (m, 2H).

Example 70. Synthesis of 2-((4-((6-((4-cyano-2-fluorophenoxy)methyl)pyridin-2-yl)thio)piperidin-1-yl)methyl)-1-((1-ethyl-1H-imidazol-5-yl)methyl)-1H-benzo[d]imidazole-6-carboxylic acid (compound C37)

1). Synthesis of methyl 4-(2-(4-((6-((4-cyano-2-fluorophenoxy)methyl)pyridin-2-yl)mercapto)piperidin-1-yl)acetamido)-3-((1-ethyl-1H-imidazol-5-yl)methyl)amino)benzoate

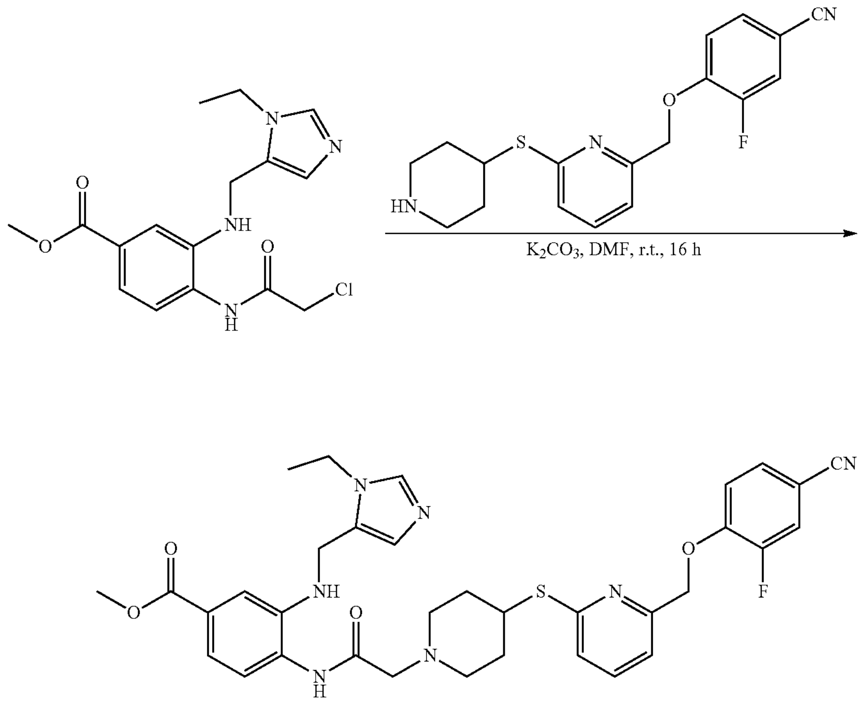

The mixture of methyl 4-(2-chloroacetamide)-3-((1-ethyl-1H-imidazol-5-yl)methyl)amino)benzoate (100 mg, 0.29 mmol), 3-fluoro-4-((6-(piperidin-4-ylthio)pyridin-2-yl)methoxy)benzonitrile (99 mg, 0.29 mmol) and potassium carbonate (80 mg, 0.58 mmol) in N,N-dimethylformamide (5 mL) was stirred at room temperature for 16 hours. After completion, the resulting mixture was poured into saturated ammonium chloride solution (20 mL) and extracted with ethyl acetate (10 mL×2). The combined organic layers were washed with brine (20 mL×3) and concentrated to give a residue in vacuo. The residue was purified by silica gel column chromatography (dichloromethane/methanol=20/1) to obtain methyl 4-(2-(4-((6-((4-cyano-2-fluorophenoxy)methyl)pyridin-2-yl)mercapto)piperidin-1-yl)acetamido)-3-((1-ethyl-1H-imidazol-5-yl)methyl)amino)benzoate (70 mg, 38.1% yield). LC-MS m/z: 658 $[M+H]^+$.

2). Synthesis of methyl 12-((4-((6-((4-cyano-2-fluorophenoxy)methyl)pyridin-2-yl)mercapto)piperidin-1-yl)methyl)-1-((-ethyl-1H-imidazol-5-yl)methyl)-1H-benzo[d]imidazole-6-carboxylate

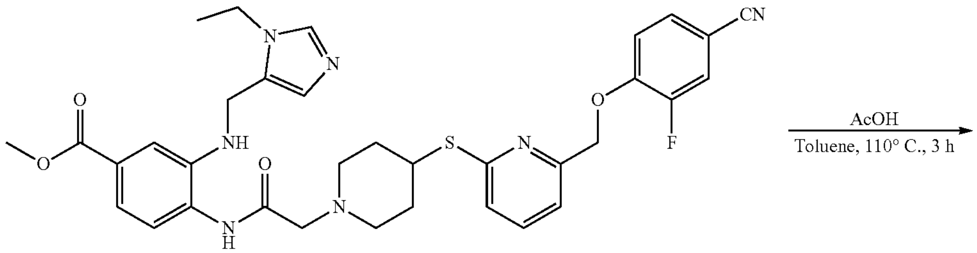

-continued

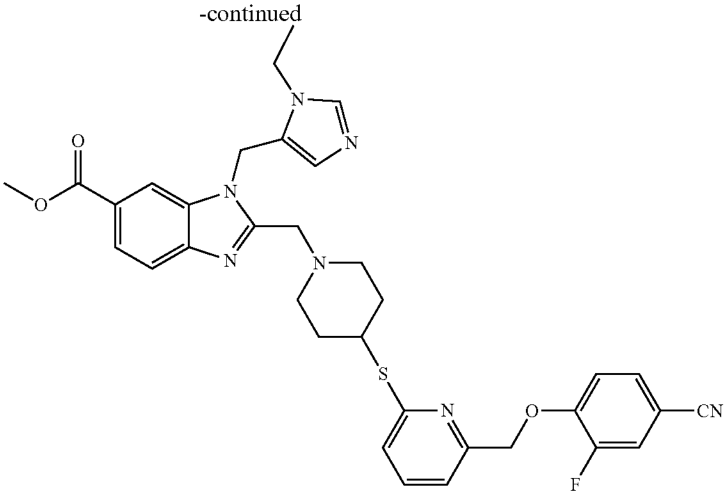

To a mixture of methyl 4-(2-(4-((6-((4-cyano-2-fluorophenoxy)methyl)pyridin-2-yl)mercapto)piperidin-1-yl)acetamido)-methyl 3-((1-ethyl-1H-imidazol-5-yl)methyl) amino)benzoate (70 mg, 0.11 mmol) in toluene (5 mL) acetic acid (1 mL) was added at room temperature. The resulting mixture was stirred at 110° C. for 3 hours. After completion, the solvent was removed by concentration to give a residue in vacuo. The residue was purified by preparative thin layer chromatography (dichloromethane/methanol=30/1) to give methyl 2-((4-((6-((4-cyano-2-fluorophenoxy)methyl)pyridin-2-yl)mercapto)piperidin-1-yl) methyl)-1-((1-ethyl-1H-imidazol-5-yl)methyl)-1H-benzo[d] imidazole-6-carboxylate (60 mg, 85.4% yield). LC-MS m/z: 640 $[M+H]^+$. 3). Synthesis of 2-((4-((6-((4-cyano-2-fluorophenoxy)methyl)pyridin-2-yl)mercapto)piperidin-1-yl) methyl)-1-((1-ethyl-1H-imidazol-5-yl)methyl)-1H-benzo[d] imidazole-6-carboxylic acid

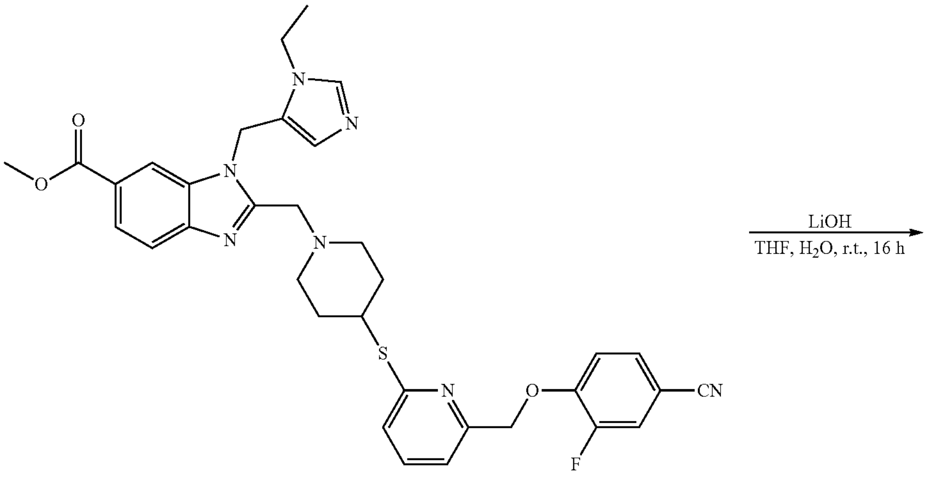

-continued

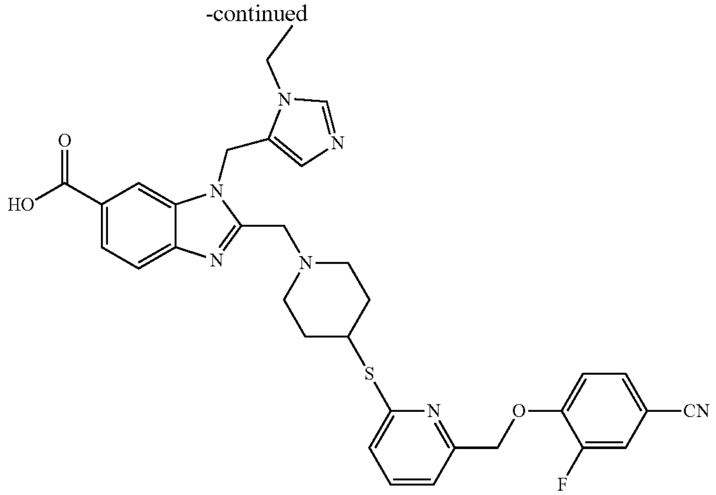

To a solution of methyl 2-((4-((6-((4-cyano-2-fluorophenoxy)methyl)pyridin-2-yl)mercapto)piperidin-1-yl)methyl)-1-((1-ethyl-1H-imidazol-5-yl)methyl)-1H-benzo[d]imidazole-6-carboxylate (60 mg, 0.09 mmol) in $H_2O$(5 mL) and THF (5 mL) lithium hydroxide (7 mg, 0.27 mmol) was added at room temperature. The reaction mixture was stirred at room temperature for 16 hours; after completion concentrated to give a residue in vacuo. The residue was purified by prep-HPLC (Waters 2767/2545/2489 system; Column: SunFire Prep C8

OBD 10 um 19×250 mm; Gradient elution with ACN/0.1% $NH_4OH$ in $H_2O$ solvent system; Detection Wavelength 254 nm/214 nm; Flow rate 20 mL/min to obtain 2-((4-((6-((4-cyano-2-fluorophenoxy)-methyl)pyridin-2-yl)mercapto)piperidin-1-yl)methyl)-1-((1-ethyl-1H-imidazol-5-yl)methyl)-1H-benzo[d]imidazole-6-carboxylic acid (28.45 mg, 50.6% yield). LC-MS m/z: 626 $[M+H]^+$.

$^1H$ NMR (400 MHZ, DMSO-$d_6$): δ8.06 (s, 1H), 7.89 (dd, J=11.2 Hz, 2.0 Hz, 1H), 7.81 (dd, J=8.8 Hz, 1.6 Hz, 1H), 7.69-7.65 (m, 4H), 7.41 (t, J-8.8 Hz, 1H), 7.22-7.19 (m, 2H), 6.38 (s, 1H), 5.69 (s, 1H), 5.36 (s, 2H), 4.02-3.96 (m, 2H), 3.79 (s, 2H), 3.68-3.60 (m, 1H), 2.71-2.68 (m, 2H), 2.19-2.14 (m, 2H), 1.86-1.84 (m, 2H), 1.41-1.32 (m, 2H), 1.16 (t, J=7.2 Hz, 3H).

Example 71. Synthesis of 2-((4-((6-((4-cyano-2-fluorophenoxy)methyl)pyridin-2-yl)methyl)piperazin-1-yl)methyl)-1-((1-ethyl-1H-imidazol-5-yl)methyl)-1H-benzo[d]imidazole-6-carboxylic acid (compound C38)

1). Synthesis of methyl 4-(2-(4-((6-((4-Cyano-2-fluorophenoxy)methyl)pyridin-2-yl)methyl)piperazin-1-yl)acetamido)-3-((1-ethyl-1H-imidazol-5-yl)methyl)amino)benzoate

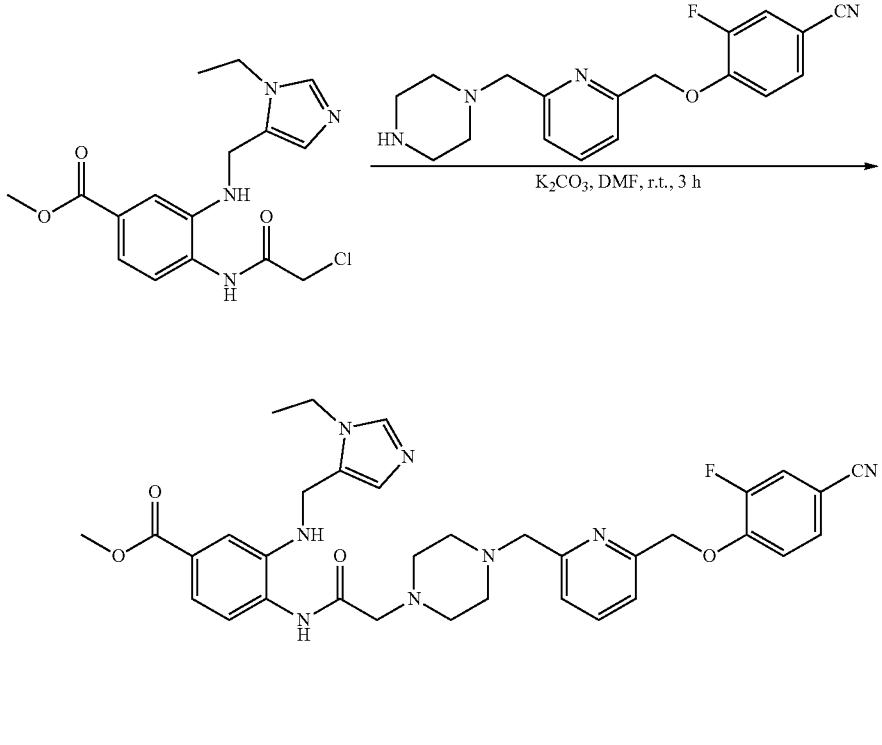

The mixture of potassium carbonate (135 mg, 0.98 mmol), methyl 4-(2-chloroacetamide)-3-((1-ethyl-1H-imidazol-5-yl)amino)benzoate (172 mg, 0.49 mmol) and 3-fluoro-4-((6-(piperazin-1-ylmethyl)pyridin-2-yl)methoxy)benzonitrile (176 mg, 0.54 mmol) in N,N-dimethylformamide (5 mL) was stirred and reacted at room temperature for 3 hours. After completion, the mixture was diluted with water (5 mL) and extracted with ethyl acetate (40 mL×3). The combined organic layers were washed with brine (30 mL×2), dried over anhydrous sodium sulfate, filtered, and concentrated to give a residue in vacuo. The residue was purified by silica gel column chromatography (dichloromethane/methanol=10/1) to obtain methyl 4-(2-(4-((6-((4-cyano-2-fluorophenoxy)methyl)pyridin-2-yl)methyl)piperazin-1-yl)acetamido)-3-((1-ethyl-1H-imidazol-5-yl)methyl)amino)benzoate (120 mg, 38.3% yield). LC-MS m/z: 641 $[M+H]^+$.

2). Synthesis of methyl 2-((4-((6-((4-cyano-2-fluorophenoxy)methyl)pyridin-2-yl)methyl)piperazin-1-yl)methyl)-1-((1-ethyl-1H-imidazol-5-yl)methyl)-1H-benzo[d]imidazole-6-carboxylate

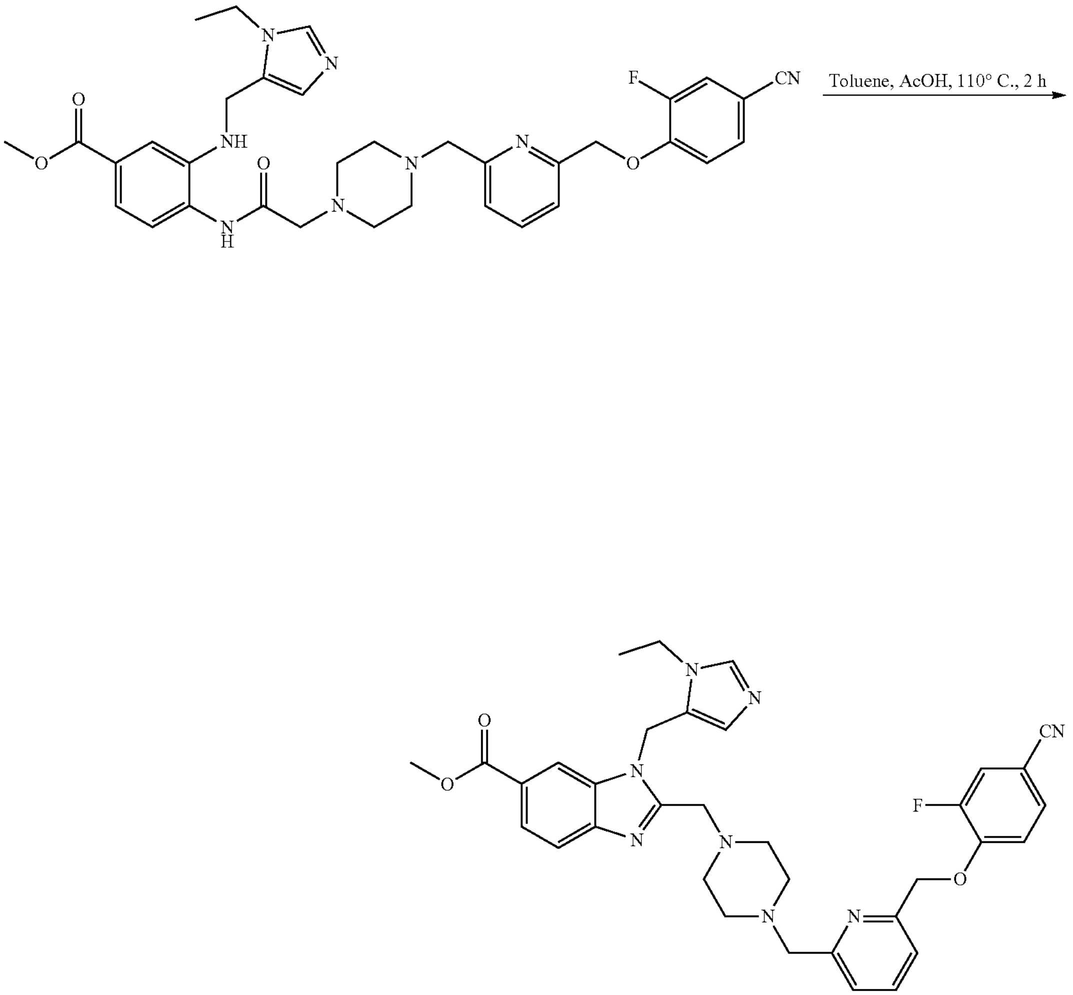

To a solution of methyl 4-(2-(4-((6-((4-cyano-2-fluorophenoxy)methyl)pyridin-2-yl)methyl)piperazin-1-yl)acetamido)-3-((1-ethyl-1H-imidazol-5-yl)methyl)amino)benzoate (120 mg, 0.19 mmol) in toluene (6 mL) acetic acid (1 mL) was added at room temperature. The resulting mixture solution was stirred and reacted at 110° C. for 2 hours. After completion, the reaction solution was concentrated to give a residue in vacuo. The residue was purified by silica gel column chromatography (dichloromethane/methanol=10/1) to obtain methyl 2-((4-((6-((4-cyano-2-fluorophenoxy)methyl)pyridin-2-yl)methyl)piperazin-1-yl)methyl)-1-((1-ethyl-1H-imidazol-5-yl)methyl)-1H-benzo-[d]imidazole-6-carboxylate (100 mg, 84.5% yield). LC-MS m/z: 623 $[M+H]^+$.

3). Synthesis of 2-((4-((6-((4-cyano-2-fluorophenoxy)methyl)pyridin-2-yl)methyl)piperazin-1-yl) methyl)-1-((1-ethyl-1H-imidazol-5-yl)methyl)-1H-benzo[d]imidazole-6-carboxylic acid

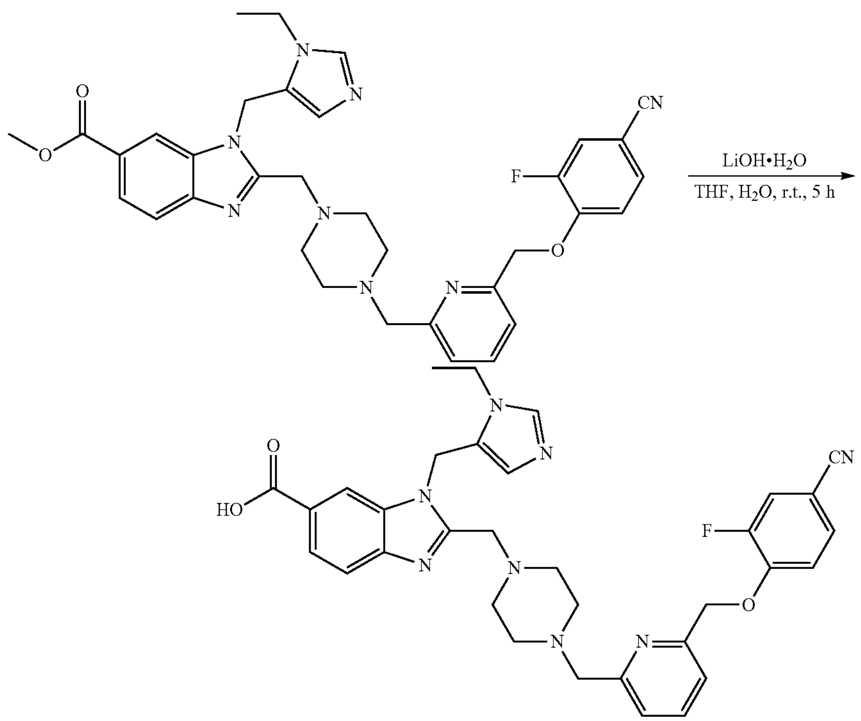

To a mixture of methyl 2-((4-((4-cyano-2-fluorophenoxy) methyl)pyridin-2-ylmethyl)piperazin-1-ylmethyl)-1-((1-ethyl-1H-imidazol-5-yl)methyl)-1H-benzo[d]imidazole-6-carboxylate (100 mg, 0.16 mmol) in water (3.0 mL) and THF (3.0 mL) lithium hydroxide monohydrate (67 mg, 1.60 mmol) was added at room temperature. The resulting mixture solution was stirred and reacted at room temperature for 5 hours. After completion, the resulting mixture was adjusted to pH=5-6 using hydrochloric acid (IM) and concentrated to give a residue in vacuo. The residue was purified by prep-HPLC (Waters 2767/2545/2489 system; Column: SunFire Prep C8 OBD 10 um 19×250 mm; Gradient elution with ACN/0.1% $NH_4OH$ in $H_2O$ solvent system; Detection Wavelength: 254 nm/214 nm); Flow rate: 20 mL/min) to obtain 2-((4-((6-((4-cyano-2-fluorophenoxy)methyl)pyridin-2-yl)methyl)piperazin-1-yl)methyl)-1-((1-ethyl-1H-imidazol-5-yl)methyl)-1H-benzo[d]imidazole-6-carboxylic acid (18.66 mg, 19.2% yield). LC-MS m/z: 609 $[M+H]^+$.

$^1H$ NMR (400 MHZ, DMSO-$d_6$) δ 8.05 (s, 1H), 7.90-7.79 (m, 3H), 7.68-7.62 (m, 3H), 7.46-7.38 (m, 3 H), 6.38 (s, 1H), 5.68 (s, 2H), 5.33 (s, 2H), 4.00-3.95 (m, 2H), 3.79 (s, 2H), 3.53 (s, 2H), 2.50-2.42 (m, 4 H), 2.33-2.28 (m, 4H), 1.15 (t, J=7.2 Hz, 3H).

Example 72. Synthesis of 2-((4-((6-((4-cyano-2-fluorophenoxy)methyl)pyridin-2-yl)oxy)piperidin-1-yl)methyl)-1-((1-ethyl-1H-pyrazol-5-yl)methyl)-1H-benzo[d]imidazole-6-carboxylic acid (compound C39)

1). Synthesis of 4-(2-(4-((6-((4-cyano-2-fluorophenoxy)methyl)pyridin-2-yl)oxy)piperidin-1-yl)acetamido)-3-((1-ethyl-1H-pyrazol-5-yl)methyl)amino) methyl benzoate

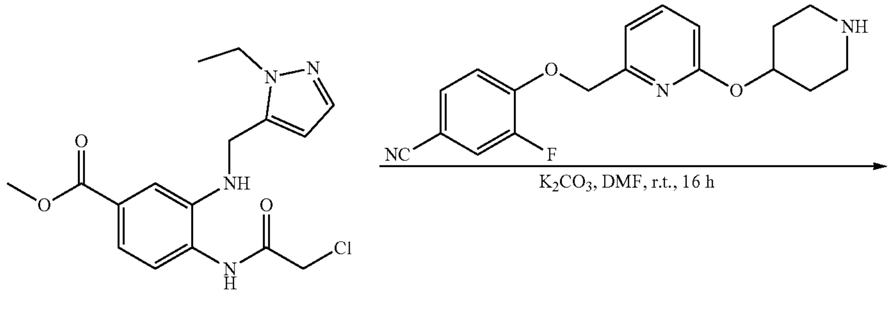

-continued

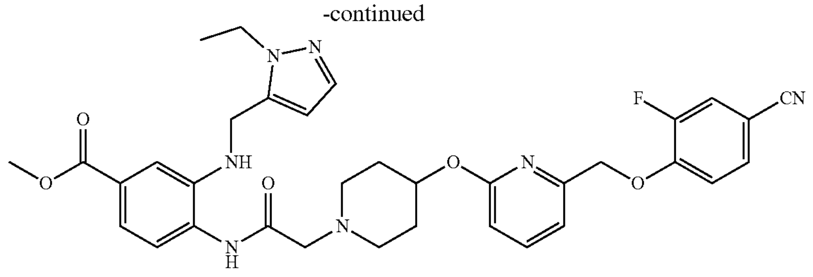

The mixture of methyl 4-(2-chloroacetamide)-3-(1-ethyl-1H-pyrazol-5-yl)methyl)aminobenzoate (50 mg, 0.14 mmol), 3-fluoro-4-((6-(piperidin-4-oxy)pyridin-2-yl) methoxy)benzonitrile (46 mg, 0.14 mmol) and potassium carbonate (39 mg, 0.28 mmol) in N,N-dimethylformamide (2 mL) was stirred at room temperature for 16 hours. After completion, it was diluted with water (10 mL) and extracted with ethyl acetate (5 mL×2). The combined organic layers were washed with brine (5 mL×2), dried over anhydrous sodium sulfate, filtered, and concentrated to give a residue in vacuo. The residue was purified by silica gel column chromatography (dichloromethane/methanol=20/1) to obtain methyl 4-(2-(4-((6-((4-cyano-2-fluorophenoxy)methyl)pyridin-2-yl)oxy)piperidin-1-yl)acetamide)-3-((1-ethyl-1H-pyrazol-5-yl)met-hyl)amino)benzoate (60 mg, 66.8% yield). LC-MS m/z: 642 $[M+H]^+$.

2). Synthesis of methyl 2-((4-((6-((4-cyano-2-fluorophenoxy)methyl)pyridin-2-yl)oxy)piperidin-1-yl) methyl)-1-((1-ethyl-1H-pyrazol-5-yl)methyl)-1H-benzo[d]imidazole-6-carboxylate

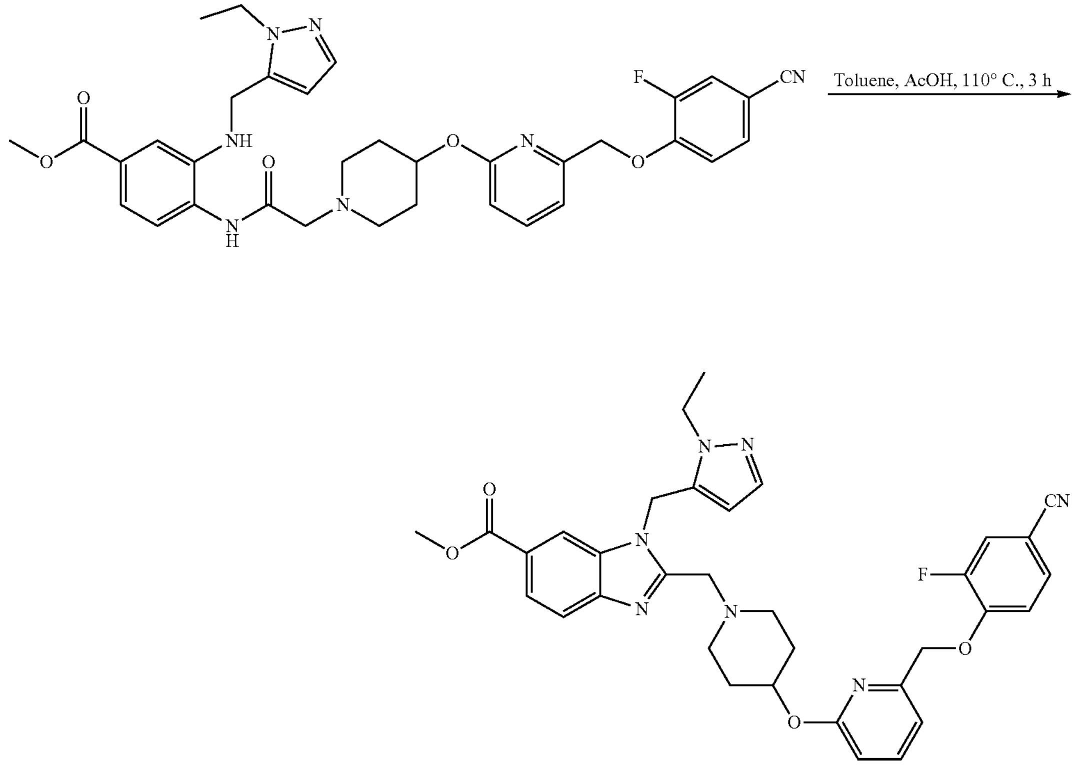

The mixture of methyl 4-(2-(4-((6-((4-cyano-2-fluorophenoxy)methyl)pyridin-2-yl)oxy)piperidin-1-yl)acetamido)-3-((1-ethyl-1H-pyrazol-5-yl)methyl)amino)benzoate (60 mg, 0.09 mmol) in toluene (2 mL) and acetic acid (0.5 mL) was stirred at 110° C. for 3 hours. After completion, the solvent was removed to give a residue in vacuo. The residue was purified by silica gel column chromatography (dichloromethane/methanol=20/1) to obtain methyl 2-((4-((6-((4-cyano-2-fluorophenoxy)methyl)pyridin-2-yl)oxy)piperidin-1-yl)methyl)-1-((1-ethyl-1H-pyrazol-5-yl)methyl)-1H-benzo[d]imidazol-6-carboxylate (50 mg, 89.0% yield). LC-MS m/z: 624 $[M+H]^+$.

3). Synthesis of 2-((4-((6-((4-cyano-2-fluorophenoxy)methyl)pyridin-2-yl)oxy)piperidin-1-yl)methyl)-1-((1-ethyl-1H-pyrazol-5-yl)methyl)-1H-benzo[d]imidazole-6-carboxylic acid

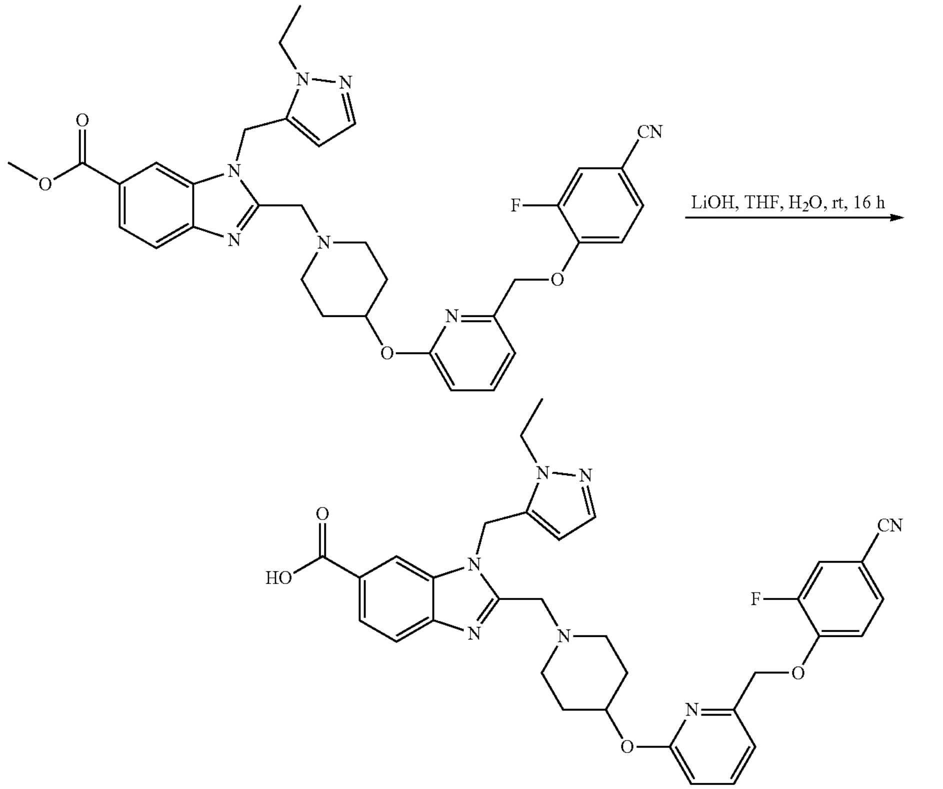

To a mixture of methyl 2-((4-((6-((4-cyano-2-fluorophenoxy)methyl)pyridin-2-yl)oxy)piperidin-1-yl)methyl)-1-((1-ethyl-1H-pyrazol-5-yl)methyl)-1H-benzo[d]imidazole-6-carboxylate (50 mg, 0.08 mmol) in THF (5 mL) and water (5 mL) lithium hydroxide (6 mg, 0.24 mmol) was added at room temperature. The reaction was stirred at room temperature for 16 hours. After completion, the resulting mixture was adjusted to pH=5-6 with formic acid. The mixture was concentrated to give a residue. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm); Flow rate: 20 mL/min) to obtain 2-((4-((6-((4-cyano-2-fluorophenoxy)methyl)pyridin-2-yl)oxy)piperidine-1-yl)methyl)-1-((1-ethyl-1H-pyrazol-5-yl)methyl)-1H-benzo[d]imidazole-6-carboxylic acid (14.38 mg, 29.5% yield). LC-MS m/z: 610 $[M+H]^+$.

$^1$H NMR (400 MHZ, DMSO-$d_6$): δ8.06 (s, 1H), 7.89-7.82 (m, 2H), 7.73-7.64 (m, 3H), 7.43 (t, J=8.4 Hz, 1H), 7.29 (s, 1H), 7.04 (d, J=7.2 Hz, 1H), 6.71 (d, J-8.4 Hz, 1H), 5.80 (s, 2H), 5.51 (s, 1H), 5.29 (s, 2H), 4.81 (s, 1H), 4.25-4.20 (m, 2H), 3.82 (s, 2H), 2.65-2.62 (m, 2H), 2.22-2.17 (m, 2H), 1.73-1.71 (m, 2H), 1.39-1.37 (m, 2H), 1.30 (t, J=7.2 Hz, 3H).

Example 73. Synthesis of 2-((4-((6-((4-cyano-2-fluorophenoxy)methyl)pyridin-2-yl)oxy)piperidin-1-yl)methyl)-1-((1-ethyl-3-methyl-1H-pyrazol-5-yl)methyl)-1H-benzo[d]imidazole-6-carboxylic acid (compound C40)

1). Synthesis of methyl 4-(2-(4-((6-((4-cyano-2-fluorophenoxy)methyl)pyridin-2-yl)oxy)piperidin-1-yl)acetamido)-3-(((1-ethyl-3-methyl-1H-pyrazol-5-yl)methyl)amino)benzoate

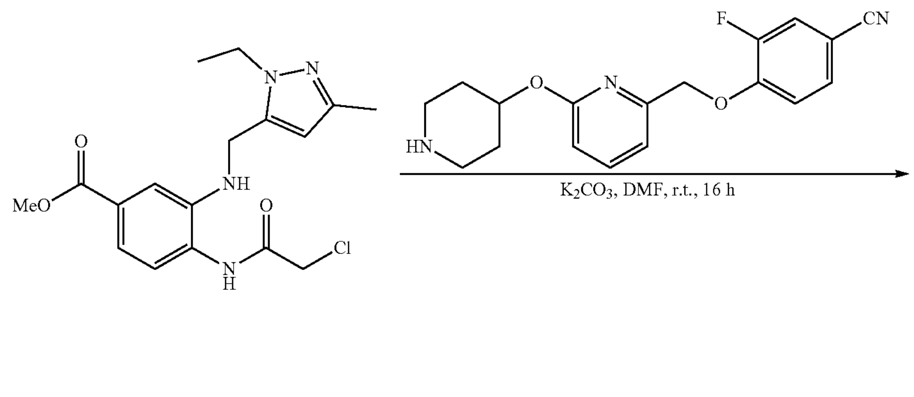

-continued

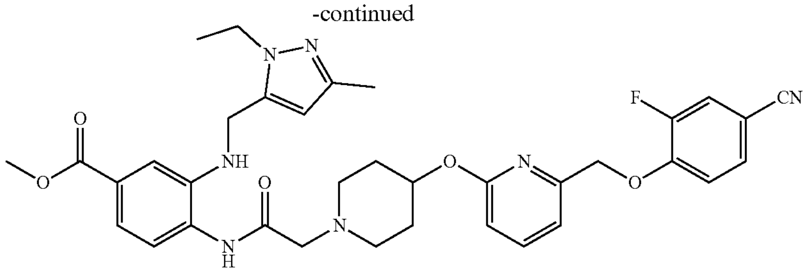

The mixture of methyl 4-(2-chloroacetamide)-3-((1-ethyl-3-methyl-1H-pyrazol-5-yl)methyl)amino)benzoate (200 mg, 0.55 mmol), 3-fluoro-4-((6-(piperidin-4-oxy)pyridin-2-yl)methoxy)benzonitrile (180 mg, 0.55 mmol) and potassium carbonate (152 mg, 1.10 mmol) in N,N-dimethylformamide (5 mL) was stirred at room temperature for 16 hours. After completion, it was diluted with water (30 mL) and extracted with ethyl acetate (10 mL×3). The combined organic layers were washed with brine (10 mL×3), dried over anhydrous sodium sulfate, filtered, and concentrated to give a residue in vacuo. The residue was purified by silica gel column chromatography (dichloromethane/methanol=20/1) to obtain 4-(2-(4-((6-((4-cyano-2-fluorophenoxy)methyl)pyridin-2-yl)oxy)piperidin-1-yl)acetamido)-3-((1-methyl ethyl-3-methyl-1H-pyrazol-5-yl)methyl)amino) benzoate (200 mg, 55.4% yield). LC-MS m/z: 656 $[M+H]^+$.

2). Synthesis of methyl 2-((4-((6-((4-cyano-2-fluorophenoxy)methyl)pyridin-2-yl)oxy)piperidin-1-yl)methyl)-1-((1-ethyl-3-methyl-1H-pyrazol-5-yl)methyl)-1H-benzo[d]imidazole-6-carboxylate

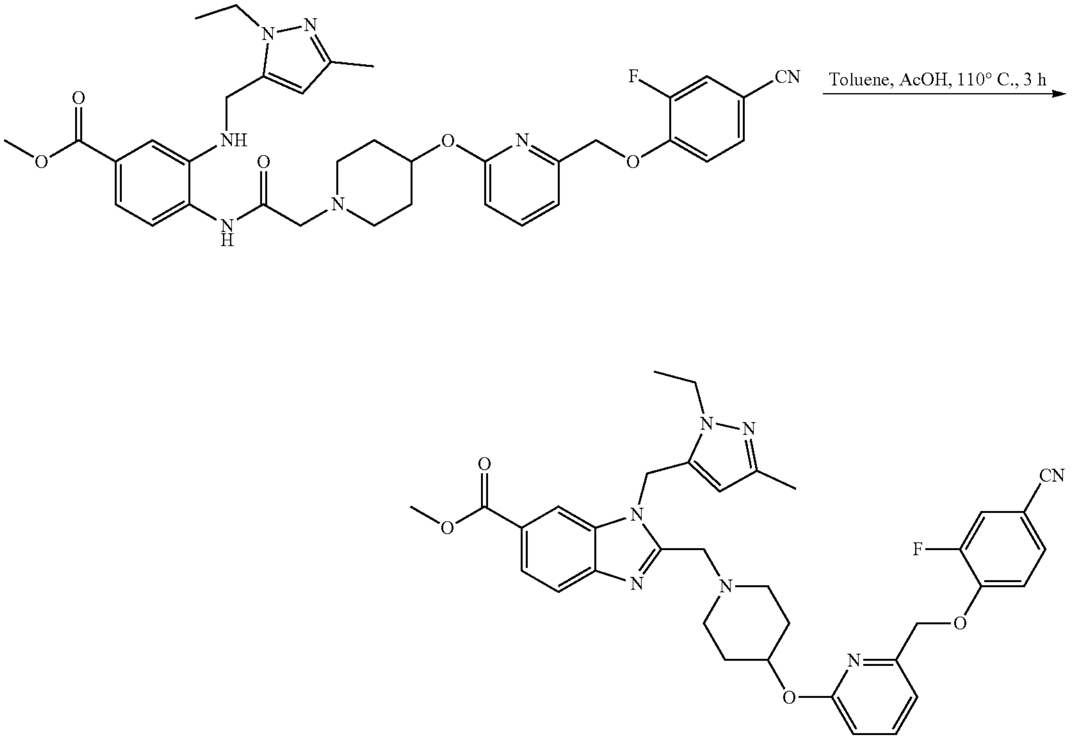

The mixture of methyl 4-(2-(4-((6-((4-cyano-2-fluorophenoxy)methyl)pyridin-2-yl)oxy)piperidin-1-yl)acetamido)-3-((1-ethyl-3-methyl-1H-pyrazol-5-yl)methyl)amino)benzoate (200 mg, 0.30 mmol) in toluene (2 mL) and acetic acid (0.5 mL) was stirred at 110° C. for 3 hours. After completion, the solvent was removed by concentration to give a residue in vacuo. The residue was purified by silica gel column chromatography (dichloromethane/methanol=20/1) to obtain 2-((4-((6-((4-cyano-2-fluorophenoxy)methyl)pyridin-2-yl)oxy)piperidin-1-yl)methyl)-1-((1-ethyl-3-methyl-1H-pyrazol-5-yl)methyl)-1H-benzo[d]imidazol-6-carboxylate (150 mg, 78.4% yield). LC-MS m/z: 638 $[M+H]^+$.

3). Synthesis of 2-((4-((6-((4-cyano-2-fluorophenoxy)methyl)pyridin-2-yl)oxy)piperidin-1-yl)methyl)-1-((1-ethyl-3-methyl-1H-pyrazol-5-yl)methyl)-1H-benzo[d]imidazole-6-carboxylic acid

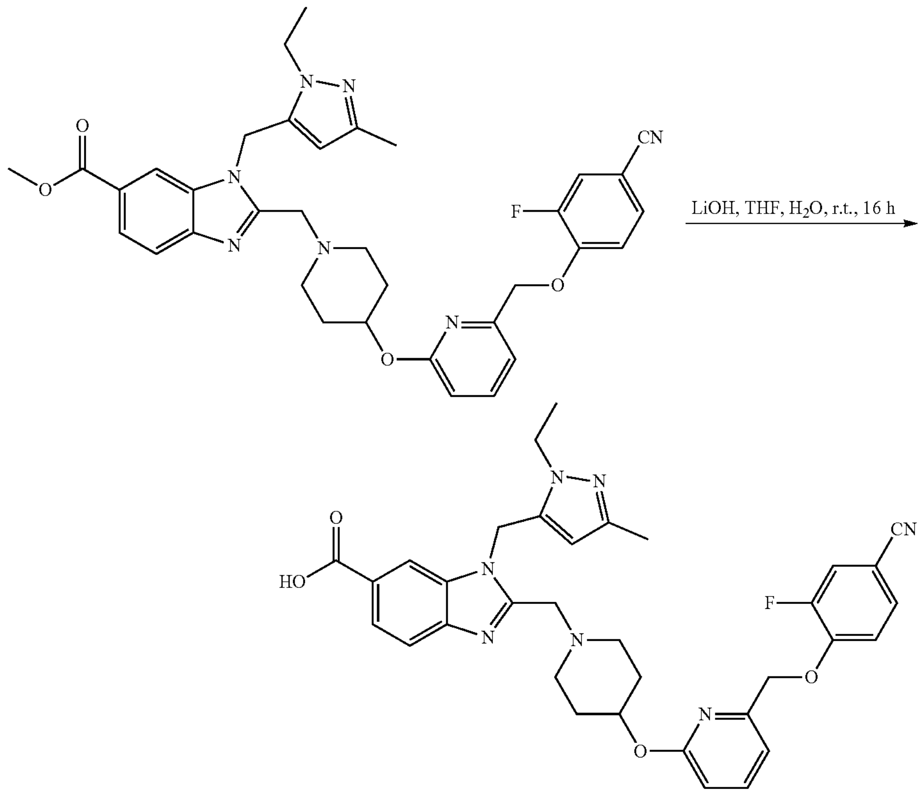

To a mixture of methyl 2-((4-((4-cyano-2-fluorophenoxy)methyl)pyridin-2-yl)oxypiperidin-1-yl)methyl)-1-((1-ethyl-3-methyl-1H-pyrazol-5-yl)methyl)-1H-benzo[d]imidazole-6-carboxylate (150 mg, 0.24 mmol) in THF (5 mL) and water (5 mL) lithium hydroxide (6 mg, 0.24 mmol) was added at room temperature and the reaction was stirred at room temperature for 16 hours. After completion, the resulting mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% FA in $H_2O$ solvent system; Detection Wavelength: 254 nm/214 nm; Flow rate: 20 mL/min) to obtain 2-((4-((6-((4-cyano-2-fluorophenoxy)methyl)pyridin-2-yl)oxy)piperidin-1-yl)methyl)-1-((1-ethyl-3-methyl-1H-pyrazol-5-yl)methyl)-1H-benzo[d]imidazole-6-carboxylic acid (59.70 mg, 39.9% yield). LC-MS m/z: 624 $[M+H]^+$. $^1H$ NMR (400 MHZ, DMSO-$d_6$): δ8.09 (s, 1H), 7.89-7.82 (m, 2H), 7.74-7.64 (m, 3H), 7.43 (t, J=8.8 Hz, 1H), 7.05 (d, J-7.2 Hz, 1H), 6.72 (d, J-8.0 Hz, 1H), 5.75 (s, 2H), 5.30 (s, 2H), 5.26 (s, 1H), 4.83 (s, 1H), 4.16-4.11 (m, 2H), 3.81 (s, 2H), 2.66-2.63 (m, 2H), 2.23-2.19 (m, 2H), 2.00 (s, 3H), 1.75-1.73 (m, 2H), 1.43-1.40 (m, 2H), 1.29 (t, J-7.2 Hz, 3H).

Example 74. Synthesis of(S)-2-((4-((6-((4-cyano-2-fluorophenoxy)methyl)pyridin-2-yl)thio)piperidin-1-yl)methyl)-1-(oxetan-2-ylmethyl)-1H-benzo[d]imidazole-6-carboxylic acid (compound C41)

1). Synthesis of methyl(S)-2-((4-((6-((4-cyano-2-fluorophenoxy)methyl)pyridin-2-yl)thio)piperidin-1-yl)methyl)-1-(oxetan-2-ylmethyl)-1H benzo[d]imidazole-6-carboxylate

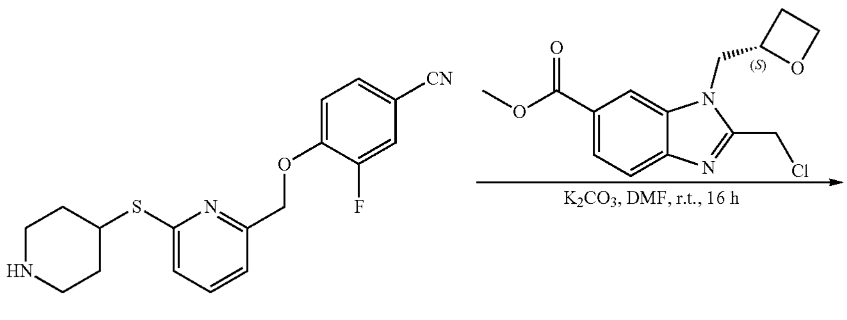

-continued

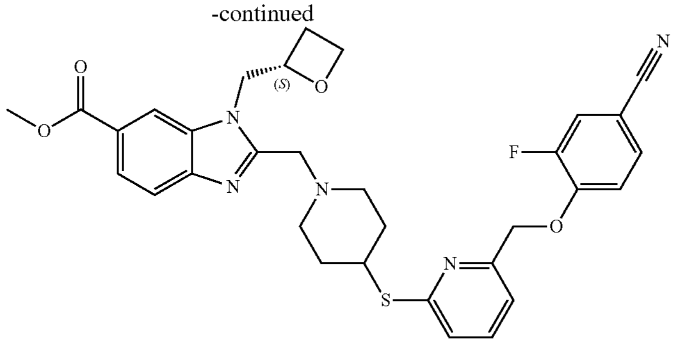

A mixture of 3-fluoro-4-((6-(piperidin-4-ylmercapto) pyridin-2-yl)methoxy)benzonitrile (86 mg, 0.29 mmol) and methyl(S)-2-(chloromethyl)-1-(oxetan-2-ylmethyl)-1H-benzo[d]imidazole-6-carboxylate (100 mg, 0.29 mmol) in N,N-dimethylformamide (5 mL) potassium carbonate (80 mg, 0.58 mmol) was added at room temperature. The reaction was stirred at room temperature for 16 hours. Upon completion of the reaction, the resulting mixture was poured into brine (20 mL) and extracted with ethyl acetate (20 mL×2) The combined organic layers were concentrated and then purified by silica gel column chromatography (dichloromethane/methanol=10/1) to give methyl(S)-2-((4-((6-((4-cyano-2-fluoro-phenoxy))methyl)pyridin-2-yl)thio)piperidin-1-yl)methyl)-1-(oxetan-2-ylmethyl)-1H-benzo[d]imidazole-6-carboxylate (100 mg, 57.5% yield). LC-MS m/z: 602 [M+H]$^+$.

2). Synthesis of(S)-2-((4-((6-((4-cyano-2-fluorophenoxy)methyl)pyridin-2-yl)thio)piperidin-1-yl)methyl)-1-(oxetan-2-ylmethyl)-1H-benzo[d]imidazole-6-carboxylic acid

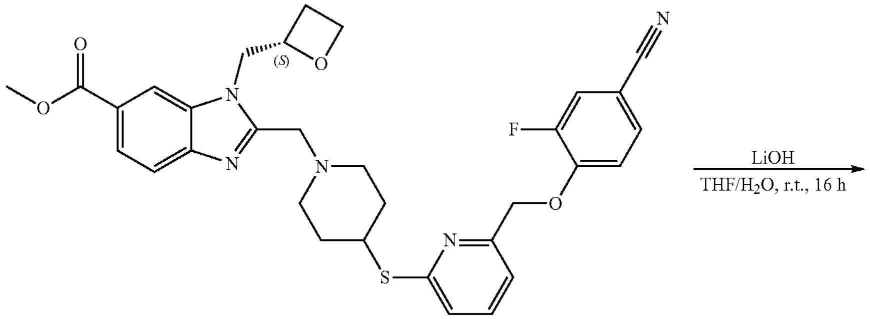

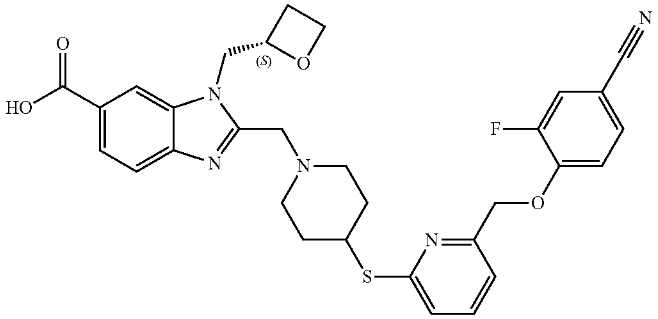

To a mixture of methyl(S)-2-((4-((6-((4-cyano-2-fluorophenoxy)methyl)pyridin-2-yl)mercapto)piperidin-1-yl)methyl)-1-(oxetan-2-ylmethyl)-1H-benzo[d]imidazole-6-carboxylate (100 mg, 0.17 mmol) in THF (5 mL) and water (5 mL) lithium hydroxide (40 mg, 1.70 mmol) was added at room temperature. The reaction was stirred at room temperature for 16 hours. After completion, the resulting mixture was adjusted to pH=5-6 using hydrochloric acid (1M). The solvent was removed by concentration to give a residue in vacuo. The residue was purified by prep-HPLC (Waters 2767/2545/2489 system; Column: SunFire Prep C8 OBD 10 um 19×250 mm; Gradient elution with ACN/0.1% $NH_4OH$ in $H_2O$ solvent system; Detection Wavelength: 254 nm/214 nm; Flow rate: 20 mL/min) to obtain(S)-2-((4-((6-((4-cyano-2-fluorophenoxy)methyl)pyridin-2-yl)thio)piperidin-1-yl)methyl)-1-(oxetan-2-ylmethyl)-1H-benzo[d]imidazole-6-carboxylic acid (37.32 mg, 37.4% yield). LC-MS m/z: 588 $[M+H]^+$.

$^1$H NMR (400 MHZ, DMSO-$d_6$) δ 8.26 (s, 1H), 7.89 (dd, J=11.2 Hz, 1.6 Hz, 1H), 7.81 (d, J=8.4 Hz, 1 H), 7.70-7.63 (m, 3H), 7.43 (t, J=8.4 Hz, 1H), 7.22 (t, J=8.4 Hz, 2H), 5.37 (s, 2H), 5.08-5.06 (m, 1H), 4.80-4.75 (m, 1H), 4.65-4.61 (m, 1H), 4.50-4.48 (m, 1H), 4.38-4.35 (m, 1H), 3.92 (d, J=13.6 Hz 1 H), 3.78-3.70 (m, 2H), 2.82-2.68 (m, 3H), 2.42-2.38 (m, 1H), 2.30-2.23 (m, 2H), 1.94 (s, 2H), 1.58-1.53 (m, 2H).

Example 75. Synthesis of 2-((4-((6-((4-cyano-2-fluorophenoxy)methyl)pyridin-2-yl)oxy)piperidin-1-yl)methyl)-1-(oxetan-2-ylmethyl)-1H-indole-6-carboxylic acid (compound C42)

1). Synthesis of oxetan-2-ylmethanesulfonate

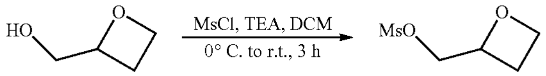 [SMILES: OCC1CCO1 ; "0° C. to r.t., 3 h" ; "MsCl, TEA, DCM" ; CS(=O)(=O)OCC1CCO1]

To a mixture of oxetan-2-ylmethanol (250 mg, 2.84 mmol) and triethylamine (574 mg, 5.68 mmol) in anhydrous dichloromethane (15 mL) methanesulfonyl chloride (557 mg, 5.68 mmol) was added dropwise at 0° C. under nitrogen atmosphere. The mixture was stirred at for 3 hours. After completion, water (10 mL) was added to quench the reaction, and it was extracted with ethyl acetate (20 mL×3). The combined organic layers were washed with brine (20 mL×3), dried over anhydrous sodium sulfate, filtered, and concentrated to give a residue in vacuo to obtain oxetan-2-ylmethanesulfonate (300 mg, yield: 63.7%). 1H-NMR (400 MHz, $CDCl_3$) δ 5.05-5.01 (m, 1H), 4.70-4.66 (m, 1H), 4.61-4.56 (m, 1H), 4.36 (d, J=4.0 Hz, 2H), 3.11 (s, 3H), 2.81-2.74 (m, 1H), 2.66-2.61 (m, 1H).

2). Synthesis of 1-(tert-butyl) 2-methyl 6-bromo-1H-indole-1,2-dicarboxylate

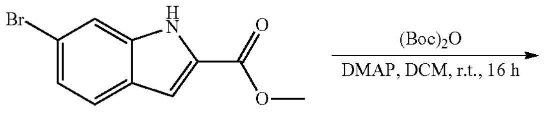

-continued

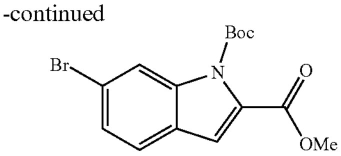

To a solution of methyl 6-bromo-1H-indole-2-carboxylate (2.00 g, 7.91 mmol) in dichloromethane (30 mL) 4-dimethylaminopyridine (193 mg, 1.58 mmol) and di-tert-butyl dicarbonate (2.41 g, 11.07 mmol) were added at room temperature. The resulting mixture was stirred at room temperature for 16 hours. After completion, the mixture was concentrated in vacuo to obtain a crude product. The crude product was further purified by silica gel column chromatography (petroleum ether/ethyl acetate=5/1) to obtain 1-(tert-butyl) 2-methyl 6-bromo-1H-ndole-1,2-dicarboxylate (2.2 g, 78.8% yield).

$^1$HNMR (400 MHZ, $CDCl_3$) δ8.31 (s, 1H), 7.46 (d, J-8.4 Hz, 1H), 7.38 (dd, J=8.4, 2.0 Hz, 1H), 7.05 (d, J=0.8 Hz, 1H), 3.92 (s, 3H), 1.62 (s, 9H).

3). Synthesis of tert-butyl 6-bromo-2-(hydroxymethyl)-1H-indole-1-carboxylate

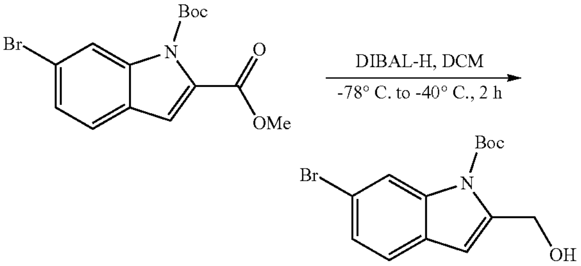

To a solution of 1-(tert-butyl) 2-methyl 6-bromo-1H-indole-1,2-dicarboxylate (1.00 g, 2.83 mmol) in dichloromethane (15 mL) diisobutylaluminum hydride (7 mL, 7.08 mol) was slowly added at −78° C. under nitrogen atmosphere. The resulting mixture was stirred at −40° C. for 2 hours. After completion, the reaction was quenched by adding methanol (15 mL) and water (9 mL) and then extracted with ethyl acetate (30 mL×3). The combined organic layers were washed with brine (50 mL×2), dried over anhydrous sodium sulfate, filtered, and concentrated to give a residue in vacuo. The residue was purified by silica gel column chromatography (petroleum ether/ethyl acetate=1/1) to obtain tert-butyl 6-bromo-2-(hydroxymethyl)-1H-indole-1-carboxylate (650 mg, 70.7% yield). 1HNMR (400 MHZ, $CDCl_3$) δ8.18 (d, J-0.8 Hz, 1H), 7.37-7.32 (m, 2H), 6.54 (s, 1H), 4.79 (d, J=5.6 Hz, 2H), 3.62 (s, 1H), 1.73 (s, 9H).

4). Synthesis of tert-butyl ester 6-bromo-2-(chloromethyl)-1H-indole-1-carboxylate

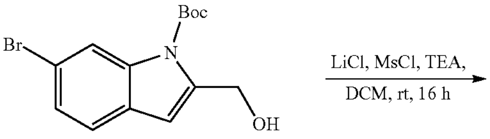

-continued

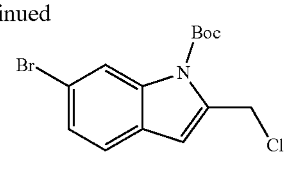

To a mixture of tert-butyl 6-bromo-2-(hydroxymethyl)-1H-indole-1-carboxylate (650 mg, 2.00 mmol), triethylamine (343 mg, 3.40 mmol), and lithium chloride (840 mg, 20.00 mmol) in dichloromethane (20 mL) methanesulfonyl chloride (333 mg, 3.40 mmol) was slowly added at room temperature. The resulting mixture was stirred at room temperature for 16 hours. After completion, water (10 mL) was added to quench the reaction, and the mixture was extracted with ethyl acetate (30 mL×3). The combined organic layers were washed with brine (50 mL×2), dried over anhydrous sodium sulfate, filtered, and concentrated to give a residue in vacuo. The residue was purified by silica gel column chromatography (dichloromethane/methanol=15/1) to obtain tert-butyl 6-bromo-2-(chloromethyl)-1H-indole-1-carboxylate (500 mg, 73.0% yield).

$^1$HNMR (400 MHZ, $CDCl_3$) δ8.39 (s, 1H), 7.36-7.35 (m, 2H), 6.66 (d, J=0.8 Hz, 1H), 4.95 (dd, J=0.4 Hz, 2H), 1.73 (s, 9H).

5). Synthesis of tert-butyl 6-bromo-2-((4-((6-((4-cyano-2-fluorophenoxy)methyl)pyridin-2-yl)oxy)piperidin-1-yl)methyl)-1H-indole-1-carboxylate

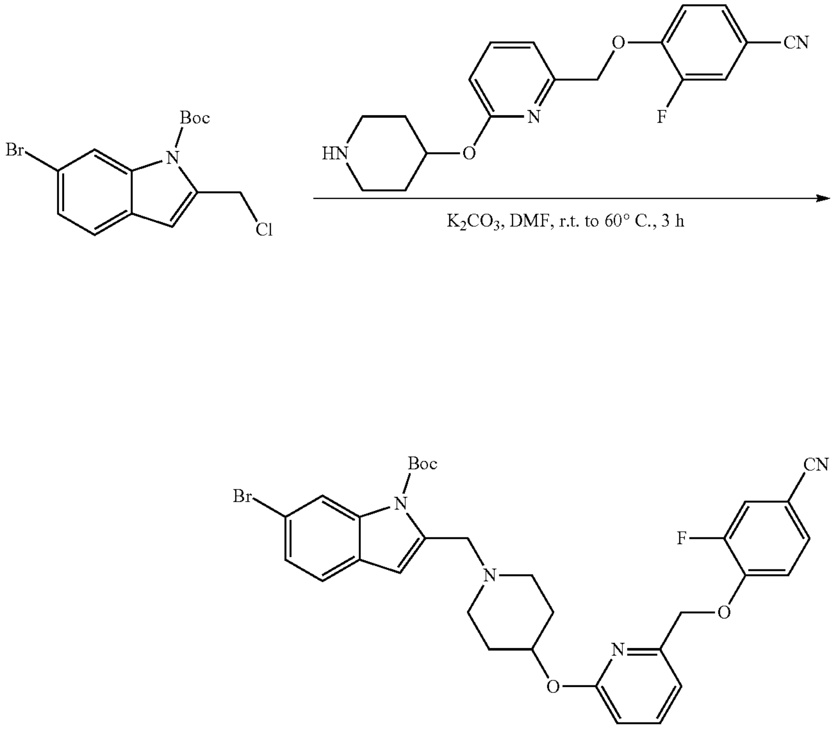 [SMILES: CC(C)(C)OC(=O)n1c(CCl)cc2ccc(Br)cc21 ; N#Cc1ccc(OCc2cccc(OC3CCNCC3)n2)c(F)c1 ; "K2CO3, DMF, r.t. to 60° C., 3 h" ; CC(C)(C)OC(=O)n1c(CN2CCC(Oc3cccc(COc4ccc(C#N)cc4F)n3)CC2)cc2ccc(Br)cc21]

The mixture of tert-butyl 6-bromo-2-(chloromethyl)-1H-indole-1-carboxylate (300 mg, 0.87 mmol), 3-fluoro-4-((6-(piperidine-4-oxy)pyridin-2-yl)methoxy)benzonitrile (284 mg, 0.87 mmol), and potassium carbonate (360 mg, 2.61 mmol) in N,N-dimethylformamide (5 mL) was stirred and reacted at 60° C. for 3 hours. After completion, the resulting mixture was cooled to room temperature, then poured into brine (5 mL) and extracted with ethyl acetate (2×20 mL). The combined organic layers were washed with brine (2×20 mL) and concentrated to give a residue in vacuo. The residue was purified by silica gel column chromatography (petroleum ether/ethyl acetate=1/1) to obtain tert-butyl 6-bromo-2-((4-((6-((4-cyano-2-fluorophenoxy)methyl)pyridine-2-yl)oxy)piperidin-1-yl)methyl)-1H-indole-1-carboxylate (400 mg, 63.1% yield). LC-MS m/z: 635 $[M+H]^+$. 1HNMR (400 MHZ, $CDCl_3$) δ8.26 (s, 1H), 7.58 (t, J=8.0 Hz, 1H), 7.40-7.30 (m, 4H), 7.10 (t, J-8.0 Hz, 1H), 7.00 (d, J=7.2 Hz, 1H), 6.66 (d, J=8.0 Hz, 1H), 6.55 (s, 1H), 5.18 (s, 2H), 5.05-5.03 (m, 1H), 3.86 (s, 2H), 2.85-2.82 (m, 2H), 2.40-2.36 (m, 2H), 2.05-2.00 (m, 2H), 1.82-1.78 (m, 2H), 1.70 (s, 9H).

6). Synthesis of 4-((6-((1-((6-bromo-1H-indol-2-yl)methyl)piperidin-4-yl)oxy)pyridin-2-yl)methoxy)-3-fluoro-benzonitrile

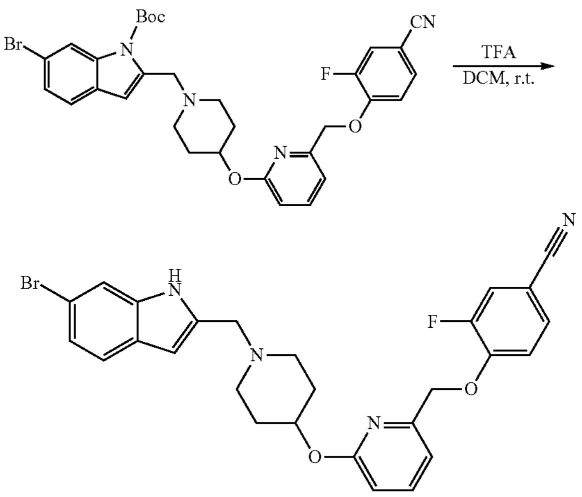

To a solution of tert-butyl 6-bromo-2-((4-((6-((4-cyano-2-fluorophenoxy)methyl)pyridin-2-yl)oxy)piperidin-1-yl)methyl)-1H-indole-1-carboxylate (400 mg, 0.63 mmol) in dichloromethane (10 mL) trifluoroacetic acid (4 mL) was added at room temperature. And the mixture was stirred at room temperature for 3 hours. After completion, the reaction mixture was concentrated in vacuo to obtain a crude product. The crude product was further purified by silica gel column chromatography (dichloromethane/methanol=15/1) to obtain 4-((6-((1-((6-bromo-1H-indol-2-yl)methyl)piperidin-4-yl)oxy)pyridin-2-yl)methoxy)-3-fluorobenzonitrile (280 mg, 82.5% yield).

$^1$HNMR (400 MHZ, $CDCl_3$) δ 11.09 (s, 1H), 7.67-7.62 (m, 2H), 7.42-7.37 (m, 3H), 7.20 (dd, J=8.4, 1.6 Hz, 1H), 7.10-7.03 (m, 2H), 6.70 (d, J-8.4 Hz, 1H), 6.48 (s, 1H), 5.34 (s, 1H), 5.15 (s, 2H), 4.18 (s, 2H), 3.08 (s, 2H), 2.96 (s, 1H), 2.88 (s, 1H), 2.31-2.22 (m, 2H), 1.31-1.24 (m, 2H).

7). Synthesis of 4-((6-((1-((6-bromo-1-(oxetan-2-ylmethyl)-1H-indol-2-yl)methyl)piperidin-4-yl)oxy)pyridin-2-yl)methoxy)-3-fluorobenzonitrile

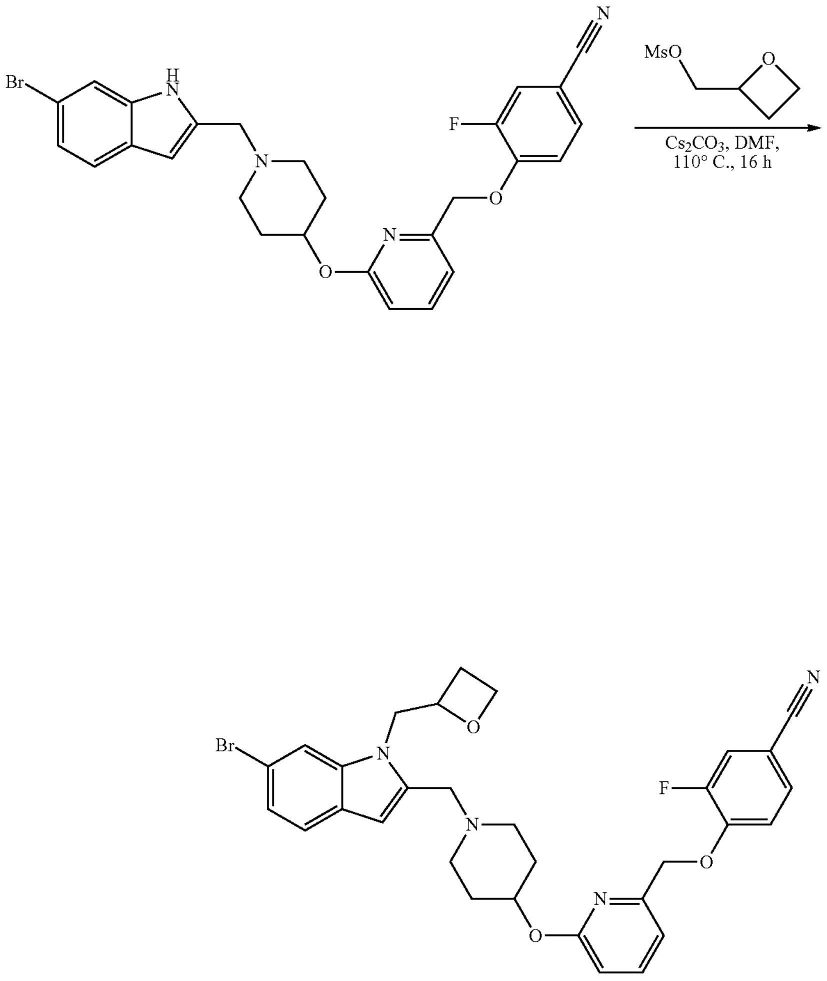

The mixture of 4-((6-((1-((6-bromo-1H-indol-2-yl)methyl)piperidin-4-yl)oxy)pyridin-2-yl)methoxy)-3-fluorobenzonitrile (280 mg, 0.52 mmol), oxetan-2-ylmethanesulfonate (259 mg, 1.56 mmol) and cesium carbonate (509 mg, 1.56 mmol) in N,N-dimethylformamide (5 mL) was stirred at 110° C. for 16 hours. Upon completion of the reaction, the resulting mixture was cooled to room temperature, poured into brine (5 mL) and then extracted with ethyl acetate (2×20 mL). The combined organic layers were washed with brine (2×20 mL) and concentrated to give a residue in vacuo. The residue was purified by silica gel column chromatography (dichloromethane/methanol=10/1) to obtain 4-((6-((1-((6-bromo-1-(oxetan-2-ylmethyl))-1H-indol-2-yl)methyl)piperidin-4-yl)oxy)pyridin-2-yl)methoxy)-3-fluorobenzonitrile (150 mg, 48.0% yield). LC-MS m/z: 607 $[M+H]^+$.

$^1$HNMR (400 MHZ, $CDCl_3$) δ7.60-7.55 (m, 2H), 7.41-7.36 (m, 3H), 7.17 (dd, J=8.4, 1.6 Hz, 1H), 7.09 (t, J=8.0 Hz, 1H), 7.00 (d, J=7.2 Hz, 1H), 6.65 (d, J-8.0 Hz, 1H), 6.36 (s, 1H), 5.18-5.14 (m, 3H), 5.02 (s, 1H), 4.64-4.48 (m, 3H), 4.43-4.38 (m, 1H), 3.75-3.67 (m, 2H), 2.75-2.64 (m, 3H), 2.47-2.42 (m, 1H), 2.32-2.24 (m, 2H), 1.95 (s, 2H), 1.74 (d, J-8.8 Hz, 2H).

8). Synthesis of 2-((4-((6-((4-cyano-2-fluorophenoxy)methyl)pyridin-2-yl)oxy)piperidin-1-yl)methyl)-1-(oxetan-2-ylmethyl)-1H-indole-6-carboxylic acid

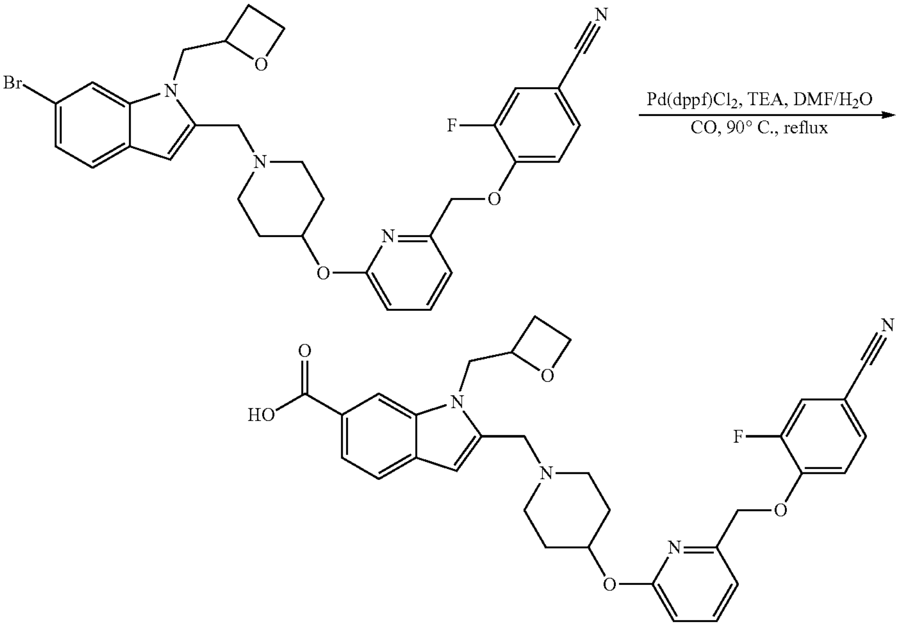

To a mixture of 4-((6-((1-((6-bromo-1-(oxetan-2-ylmethyl)-1H-indole-2-yl)methyl)piperidin-4-yl)oxy)pyridin-2-yl)methoxy)-3-fluorobenzonitrile (150 mg, 0.25 mmol) in N,N-dimethylformamide (5 mL) and water (5 mL) triethylamine (76 mg, 0.75 mmol) and 1,1'-bisdiphenylphosphinoferrocene palladium dichloride (18 mg, 0.025 mmol) were added at room temperature. The resulting mixture was heated to 90° C. under carbon monoxide gas atmosphere. The reaction was stirred for 16 hours. After completion, water (15 mL) was added to quench the reaction, and extracted with ethyl acetate (30 mL×3). The combined organic layers were washed with brine (30 mL×2), dried over anhydrous sodium sulfate, filtered, and concentrated to give a residue in vacuo. The residue was purified by reverse-phase flash chromatography under the following conditions (Column: Spherical C18, 20-40 μm, 40 g; Mobile Phase A: 10 mM $NH_4OH$ in water; Mobile Phase B: acetonitrile; Flow rate: 40 mL/min; Gradient: 20% B-50% B in 20 min; Detector: 254 nm) to obtain 2-((4-((6-((4-cyano-2-fluorophenoxy)methyl)pyridin-2-yl)oxy)piperidin-1-yl)methyl)-1-(oxetan-2-ylmethyl)-1H-indole-6-carboxylic acid (9.07 mg, 6.4% yield). LC-MS m/z: 571 $[M+H]^+$.

$^1$HNMR (400 MHZ, DMSO-$d_6$) δ 8.13 (s, 1H), 7.89 (dd, J=11.2, 2.0 Hz, 1H), 7.73 (t, J=8.0 Hz, 1H), 7.67 (d, J=8.4 Hz, 1H), 7.61 (d, J=8.4 Hz, 1H), 7.52-7.43 (m, 2H), 7.05 (d, J=7.2 Hz, 1H), 6.73 (d, J=8.4 Hz, 1 H), 6.45 (s, 1H), 5.32 (s, 2H), 5.05-5.02 (m, 1H), 4.91-4.87 (m, 1H), 4.71-4.66 (m, 1H), 4.56-4.45 (m, 2H), 4.37-4.32 (m, 1H), 3.80 (d, J=13.6 Hz, 1H), 3.63 (d, J=13.6 Hz, 1H), 2.73-2.65 (m, 3H), 2.43-2.38 (m, 1H), 2.23-2.18 (m 2 H), 1.89-1.88 (m, 2H), 1.62-1.57 (m 2 H).

Example 76. Synthesis of(S)-2-(4-((6-((4-cyano-2-fluorobenzyl)oxy)pyridin-2-yl)oxy)-2,5-difluorobenzyl)-4-fluoro-1-(oxetan-2-ylmethyl)-1H-benzo[d]imidazole-6-carboxylic acid (compound C43)

1). Synthesis of 2-(4-Bromo-2,5-difluorophenoxy)-6-fluoropyridine

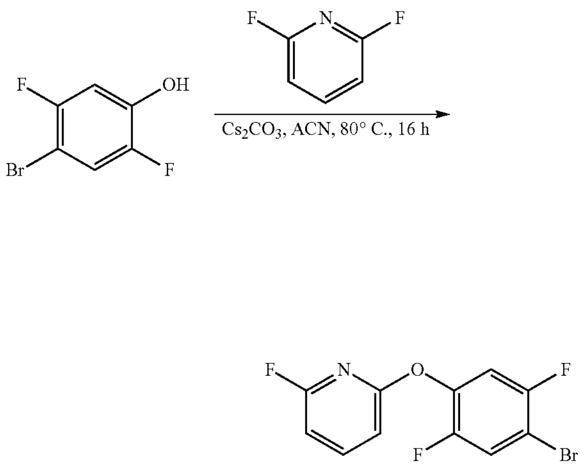

4-Bromo-2,5-difluorophenol (2.00 g, 9.57 mmol), 2,6-difluoropyridine (2.20 g, 19.14 mmol) and cesium carbonate (6.24 g, 19.14 mmol) were dissolved in acetonitrile (50 mL) at room temperature. The resulting mixture was warmed to 80° C. and stirred for 16 hours. After completion, the solvent was removed by concentration to give a residue in vacuo. The residue was purified by silica gel column chromatography (petroleum ether/ethyl acetate=4/1) to obtain 2-(4-bromo-2,5-difluorophenoxy)-6-fluoropyridine (2.00 g, 68.7% yield). LC-MS m/z: 304 [M+H]$^+$.

2). Synthesis of 4-((6-(4-Bromo-2,5-difluorophenoxy)pyridin-2-yl)oxy)methyl)-3-fluorobenzonitrile

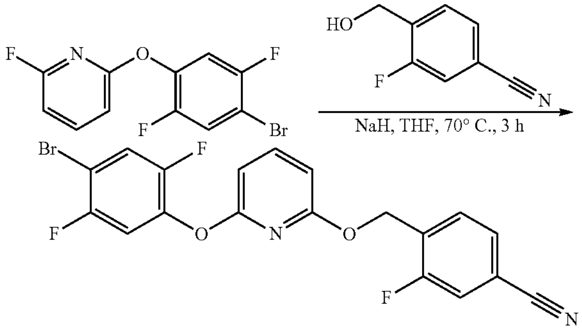

To a solution of 3-fluoro-4-(hydroxymethyl)benzonitrile (1.49 g, 9.87 mmol) in dry tetrahydrofuran (50 mL) sodium hydride (395 mg, 9.87 mmol 60% w/w in mineral oil) was slowly added at 0° C. The resulting mixture was stirred at 0° C. for 30 min, then 2-(4-bromo-2,5-difluorophenoxy)-6-fluoropyridine (2.00 g, 6.58 mmol) was slowly added to above mixture at 0° C. . . . The resulting mixture was stirred for 3 hours at 70° C. After completion, the reaction was quenched with water (100 mL) at 0° C. and then extracted with dichloromethane (3×50 mL). The combined organic layers were washed with brine (20 mL×3), dried over anhydrous sodium sulfate, filtered, and concentrated to give a residue in vacuo. The residue was purified by silica gel column chromatography (petroleum ether/ethyl acetate-4/1) to obtain 4-((6-(4-bromo-2,5-difluorophenoxy)pyridin-2-yl)oxy)methyl)-3-fluorobenzonitrile (2.00 g, 69.9% yield). LC-MS m/z: 437 [M+H]$^+$.

3). Synthesis of tert-butyl 2-(4-((6-((4-cyano-2-fluorobenzyl)oxy)pyridin-2-yl)oxy)-2,5-difluorophenyl)acetate

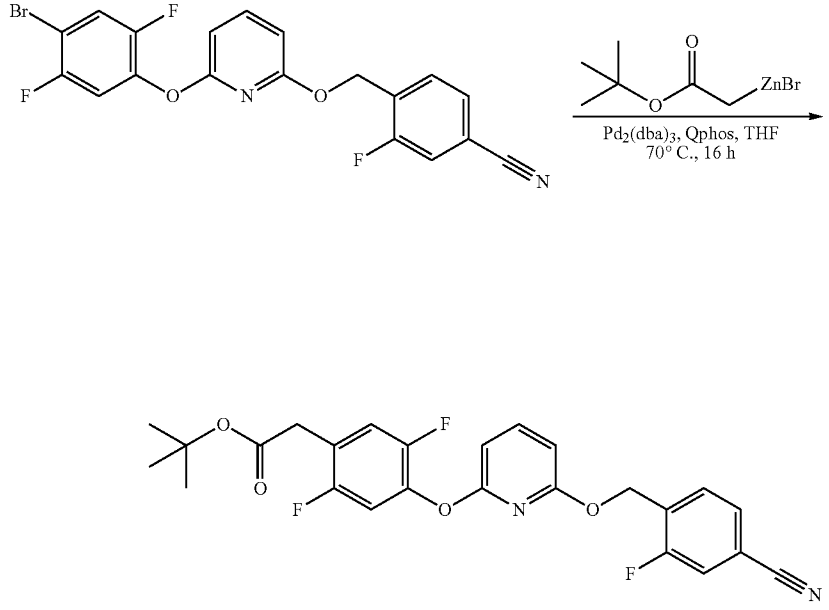

To a mixture of (2-(tert-butoxy)-2-oxoethyl) zinc bromide (1.20 g, 4.60 mmol), 1,2,3,4,5-pentylphenyl-1'-(di-tert-butylphosphonium) ferrocene (164 mg, 0.23 mmol) and tris(dibenzylideneacetone) dipalladium (211 mg, 0.23 mmol) in tetrahydrofuran (20 mL) 4-((6-(4-bromo-2,5-difluorophenoxy)pyridin-2-yl)oxy)methyl)-3-fluorobenzonitrile (1.00 g, 2.30 mmol) was added at room temperature. The resulting mixture was stirred at 70° C. for 16 hours. After completion, the solvent was removed by concentration to give a residue in vacuo. The residue was purified by silica gel column chromatography (petroleum ether/ethyl acetate=5/1) to obtain tert-butyl 2-(4-((6-((4-cyano-2-fluoro)benzyl)oxy)pyridin-2-yl)oxy)-2,5-difluorophenyl) acetate (1.00 g, 92.5% yield). LC-MS m/z: 471 [M+H]$^+$.

4). Synthesis of 2-(4-((6-((4-cyano-2-fluorobenzyl) oxy)pyridin-2-yl)oxy)-2,5-difluorophenyl)acetic acid

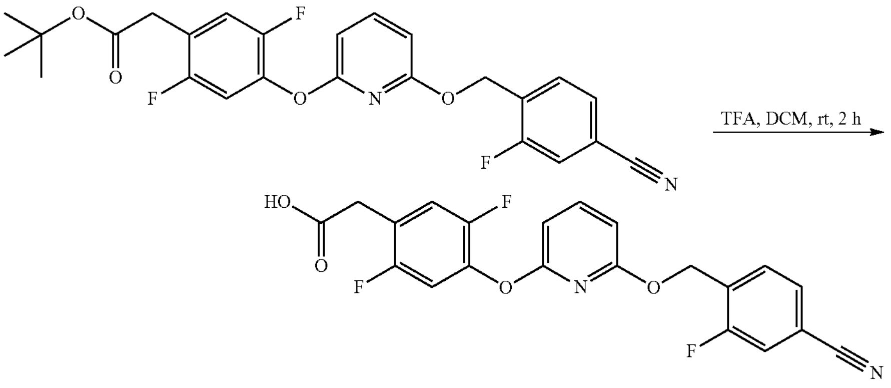

To a solution of tert-butyl 2-(4-((6-((4-cyano-2-fluorobenzyl)oxy)pyridin-2-yl)oxy)-2,5-difluorophenyl)acetate (1.00 g, 2.13 mmol) in dichloromethane (10 mL) trifluoroacetic acid (5 mL) was added at room temperature. The resulting mixture was stirred at room temperature for 2 hours. After completion, the solvent was removed by concentration to give a residue in vacuo. The residue was purified by reverse-phase flash chromatography under the following conditions (Column: Spherical C18, 20-40 μm, 120 g; Mobile Phase A: 10 mM hexachlorocyclohexane in water; Mobile Phase B: acetonitrile; Flow rate: 80 mL/min; Gradient: 5% B-95% B in 30 minutes; Detector: 254 nm). The mobile phase containing the desired product was collected at 82% B and then concentrated in vacuo to give 2-(4-((6-((4-cyano-2-fluorobenzyl)oxy)pyridin-2-yl)oxy)-2,5-difluorophenyl)acetic acid (800 mg, 90.7% yield). LC-MS m/z: 415 [M+H]$^+$.

5). Synthesis of methyl(S)-4-(2-(4-((6-((4-cyano-2-fluorobenzyl)oxy)pyridin-2-yl)oxy)-2,5-difluorophenyl)-acetamido)-3-fluoro-5-((oxetan-2-ylmethyl) amino)benzoate

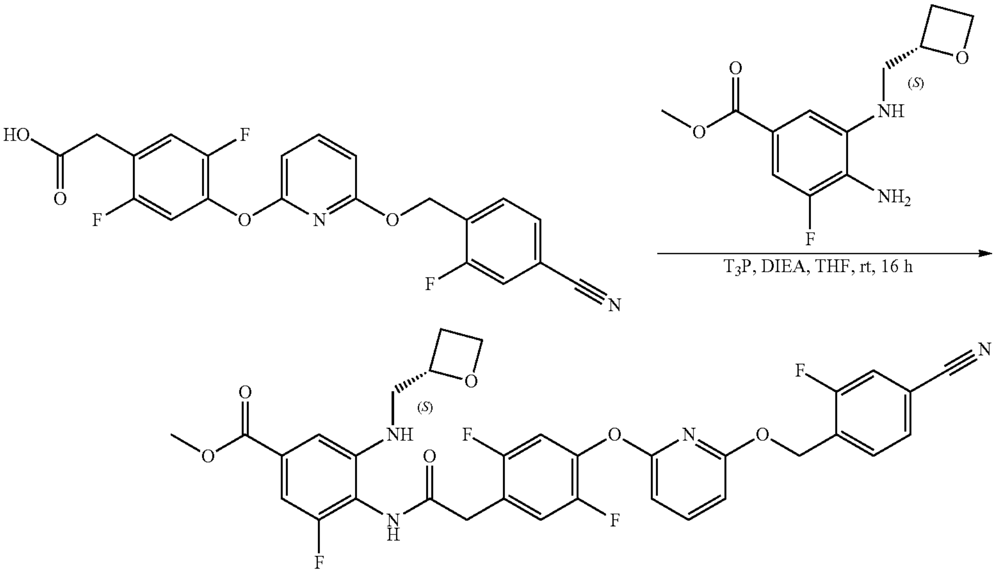

The mixture of 2-(4-((6-((4-cyano-2-fluorobenzyl)oxy)pyridin-2-yl)oxy)-2,5-difluorophenyl)acetic acid (400 mg, 0.97 mmol), methyl(S)-4-amino-3-fluoro-5-((oxetan-2-ylmethyl)amino)benzoate (246 mg, 0.97 mmol), N,N-diisopropylethylamine (250 mg, 1.94 mmol) and 2,4,6-tripropyl-1,3,5,2,4,6-trioxatriphosphinane 2,4,6-trioxide (954 mg, 1.50 mmol, 50% in ethyl acetate) in THF (10 mL) was stirred at room temperature for 16 hours. After completion, the solvent was removed by concentration to give a reissue in vacuo. The residue was purified by silica gel column chromatography (petroleum ether/ethyl acetate=1/1) to obtain methyl(S)-4-(2-(4-((6-((4-cyano-2-fluorobenzyl)oxy)pyridin-2-yl)oxy)-2,5-difluorophenyl)acetamide)-3-fluoro-5-((oxetan-2-ylmethyl)amino)benzoate (400 mg, 63.4% yield). LC-MS m/z: 651 $[M+H]^+$.

6). Synthesis of methyl(S)-2-(4-((6-((4-cyano-2-fluorobenzyl)oxy)pyridin-2-yl)oxy)-2,5-difluorobenzyl)-4-fluoro-1-(oxetan-2-ylmethyl)-1H-benzo[d]imidazole-6-carboxylate

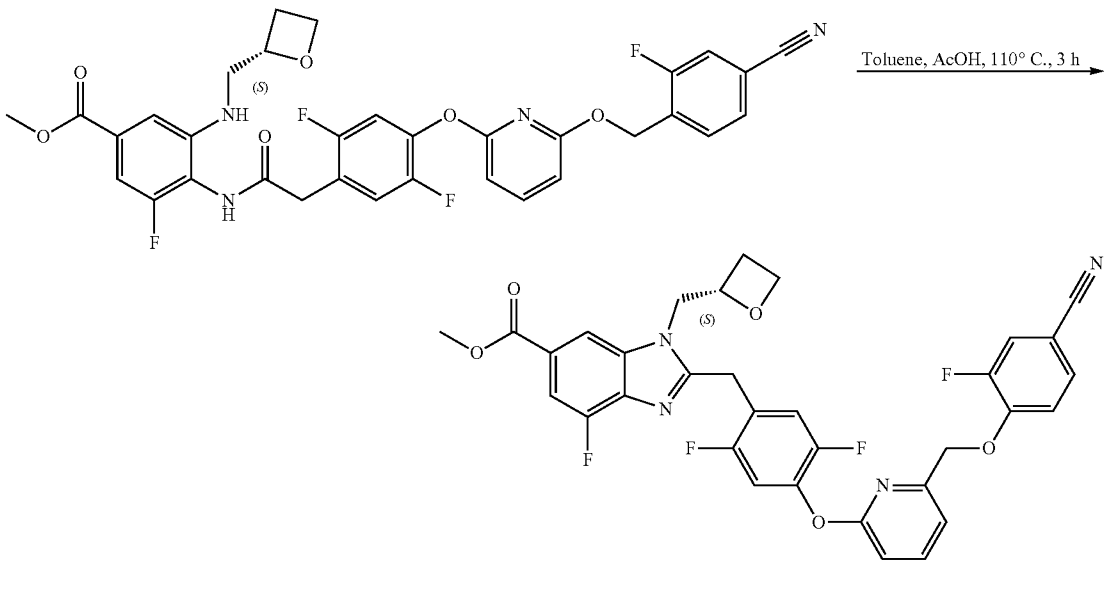

The mixture of methyl(S)-4-(2-(4-((6-((4-cyano-2-fluorobenzyl)oxy)pyridin-2-yl)oxy)-2,5-difluoro-phenyl)acetamido)-3-fluoro-5-((oxetan-2-ylmethyl)amino)benzoate (200 mg, 0.31 mmol) in toluene (5 mL) and acetic acid (0.5 mL) was stirred at 110° C. for 3 hours. After completion, the solvent was removed by concentration to give residue in vacuo. The residue was purified by silica gel column chromatography (petroleum ether/ethyl acetate=1/1) to obtain methyl(S)-2-(4-((6-((4-cyano-2-fluorobenzyl)oxy)pyridin-2-yl)oxy)-2,5-difluoro-benzyl)-4-fluoro-1-(oxetan-2-ylmethyl)-1H-benzo[d]imidazole-6-carboxylate (180 mg, 91.9% yield). LC-MS m/z: 633 $[M+H]^+$.

7). Synthesis of(S)-2-(4-((6-((4-cyano-2-fluorobenzyl)oxy)pyridin-2-yl)oxy)-2,5-difluorobenzyl)-4-.fluoro-1-(oxetan-2-ylmethyl)-1H-benzo[d]imidazole-6-carboxylic acid

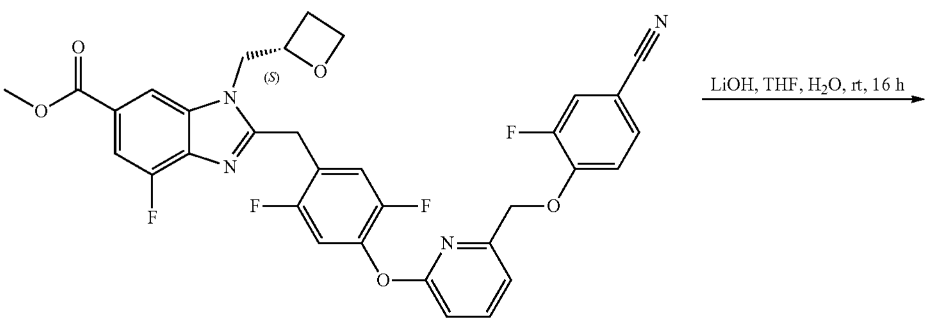

-continued

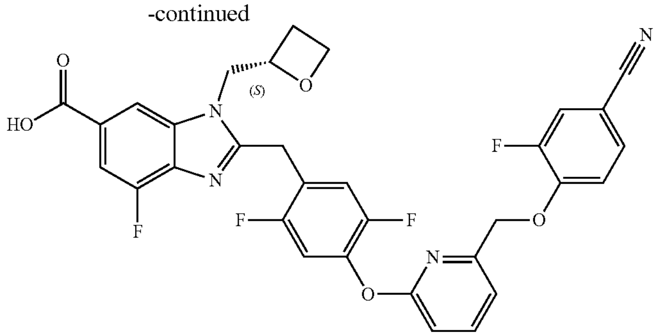

To a mixture of methyl(S)-2-(4-((6-((4-cyano-2-fluorobenzyl)oxy)pyridin-2-yl)oxy)-2,5-difluorobenzyl)-4-fluoro-1-(oxetan-2-ylmethyl)-1H-benzo[d]imidazole-6-carboxylate (180 mg, 0.28 mmol) in water (5 mL) and THF (5 mL), lithium hydroxide (20 mg, 0.84 mmol) was added at room temperature. The resulting mixture was stirred at room temperature for 16 hours. After completion, the reaction mixture was adjusted to pH=5-6 with formic acid. The solvent was removed by concentration to give a residue in vacuo. The residue was purified by prep-HPLC (Waters 2767/2545/2489 system; Column: SunFire Prep C8 OBD 10 um 19×250 mm Column; Gradient elution with ACN/0.1% FA in $H_2O$ solvent system); Detection Wavelength 254 nm/214 nm; Flow rate: 20 mL/min) to obtain(S)-2-(4-((6-((4-cyano-2-fluorobenzyl)oxy)pyridin-2-yl)oxy)-2,5-difluorobenzyl)-4-fluoro-1-(oxetan-2-ylmethyl)-1H-benzo-[d]imidazole-6-carboxylic acid (148.49 mg, 85.8% yield). LC-MS m/z: 619 $[M+H]^+$.

$^1H$ NMR (400 MHZ, DMSO-$d_6$): δ8.13 (d, J=1.2 Hz, 1H), 7.83 (t, J=8.0 Hz, 1H), 7.76 (dd, J=10.0 Hz, 1.2 Hz, 1H), 7.54 (dd, J-8.0 Hz, 1.2 Hz, 1H), 7.47 (dd, J=11.2 Hz, 1.2 Hz, 1H), 7.42-7.38 (m, 1H), 7.26 (t, J=8.0 Hz, 2H), 6.72-6.67 (m, 2H), 5.19 (s, 2H), 5.09-5.04 (m, 1H), 4.81-4.76 (m, 1H), 4.67-4.63 (m, 1H), 4.54-4.42 (m, 3H), 4.38-4.33 (m, 1H), 2.74-2.67 (m, 1H), 2.45-2.33 (m, 1H).

Example 77. Synthesis of Other Compounds

Similar to the synthesis steps in Example 3-74, the following compounds can be obtained from the A-type intermediates and the B-type intermediates:

| Number | Structure | MS m/z: $[M + H]^+$ |
|---|---|---|
| Compound 4 | 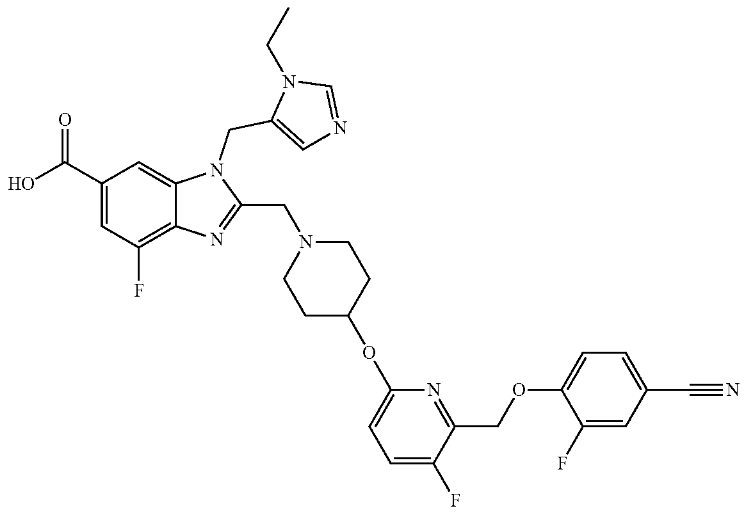 [SMILES: CCn1cncc1Cn1c(CN2CCC(Oc3ccc(F)c(COc4ccc(C#N)cc4F)n3)CC2)nc2c(F)cc(C(=O)O)cc21] | 646 |

-continued
| Number | Structure | MS m/z: [M + H]+ |
|---|---|---|
| Compound 5 | 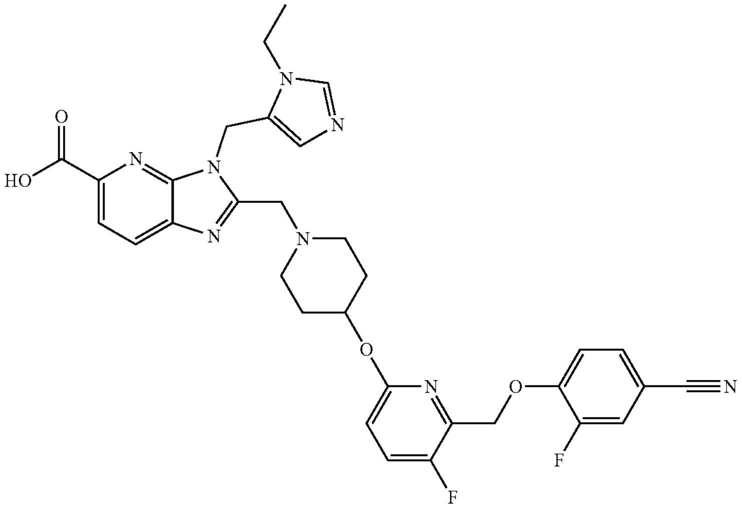 | 629 |
| Compound 8 | 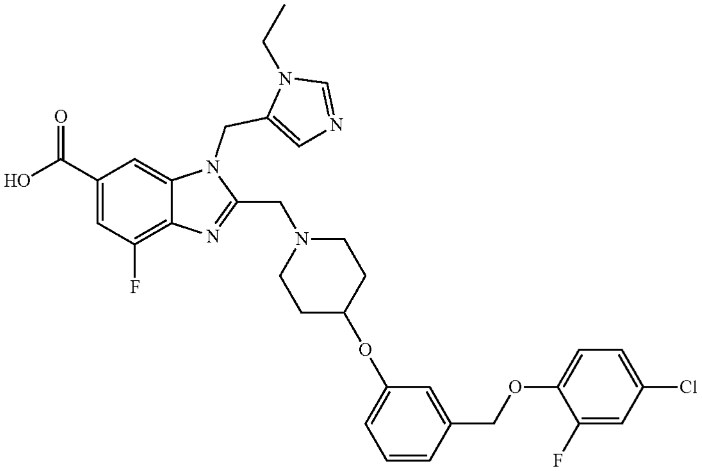 | 636 |
| Compound 9 | 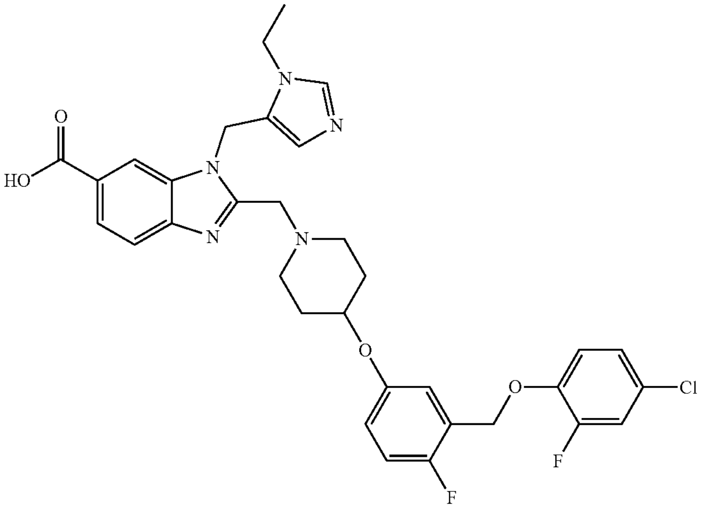 [SMILES: CCn1cncc1Cn1c(CN2CCC(Oc3ccc(F)c(COc4ccc(Cl)cc4F)c3)CC2)nc2ccc(C(=O)O)cc21] | 636 |

-continued
| Number | Structure | MS m/z: [M + H]+ |
|---|---|---|
| Compound 10 | 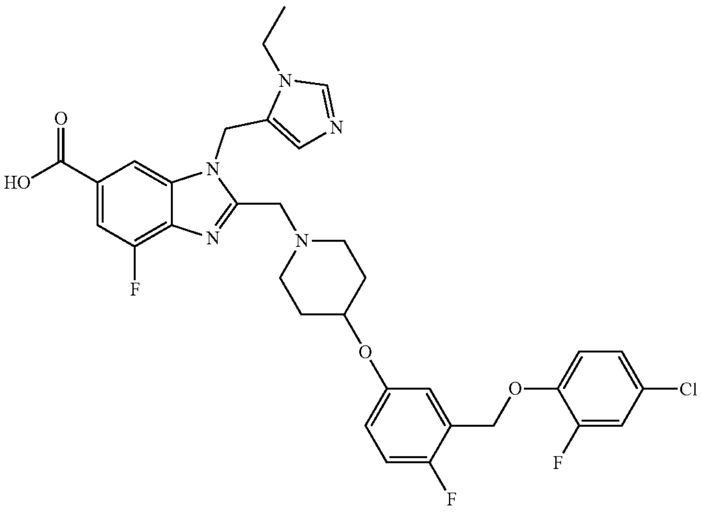 | 654 |
| Compound 11 | 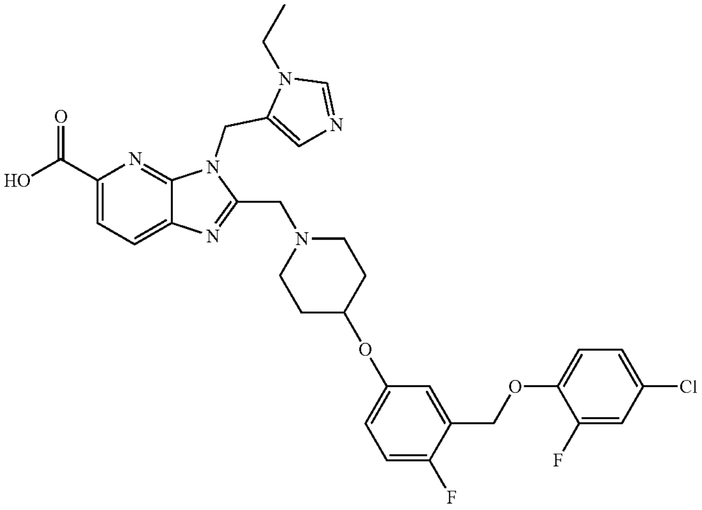 | 637 |
| Compound 12 | 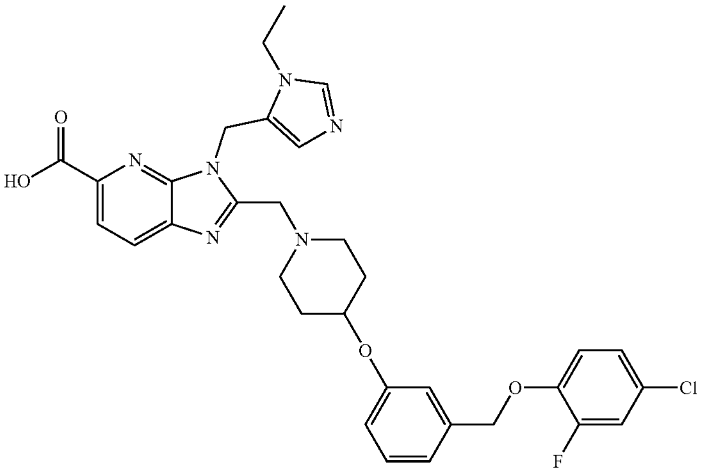 | 619 |

-continued
| Number | Structure | MS m/z: [M + H]+ |
|---|---|---|
| Compound 14 | 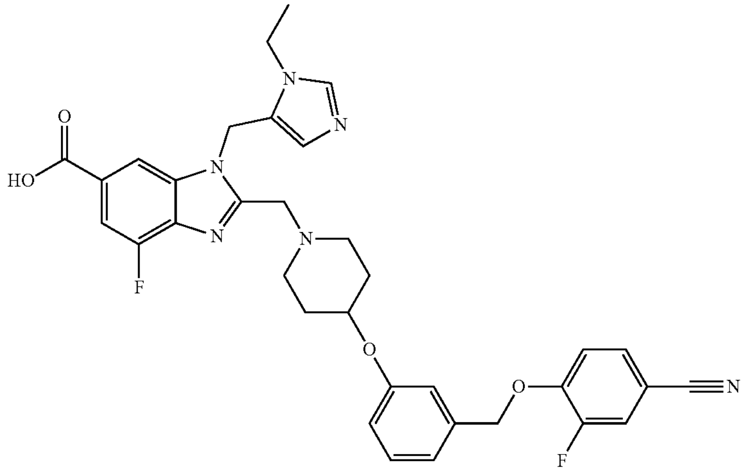 [SMILES: CCn1cncc1Cn1c(CN2CCC(Oc3cccc(COc4ccc(C#N)cc4F)c3)CC2)nc2c(F)cc(C(=O)O)cc21] | 627 |
| Compound 15 | 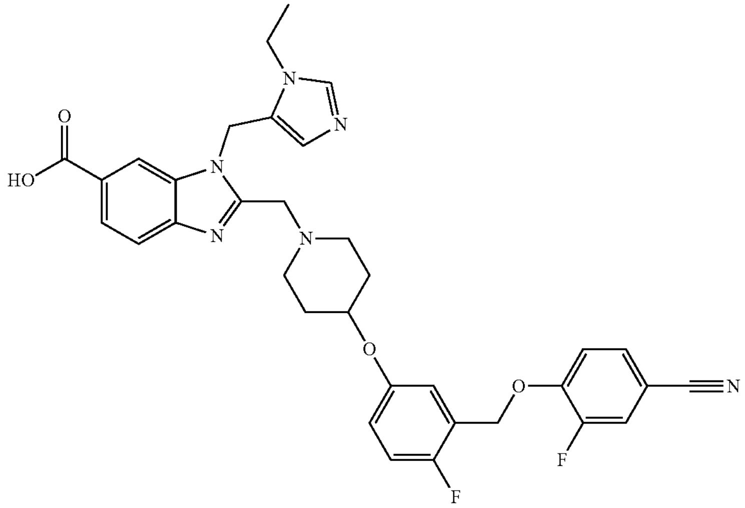 | 627 |
| Compound 16 | 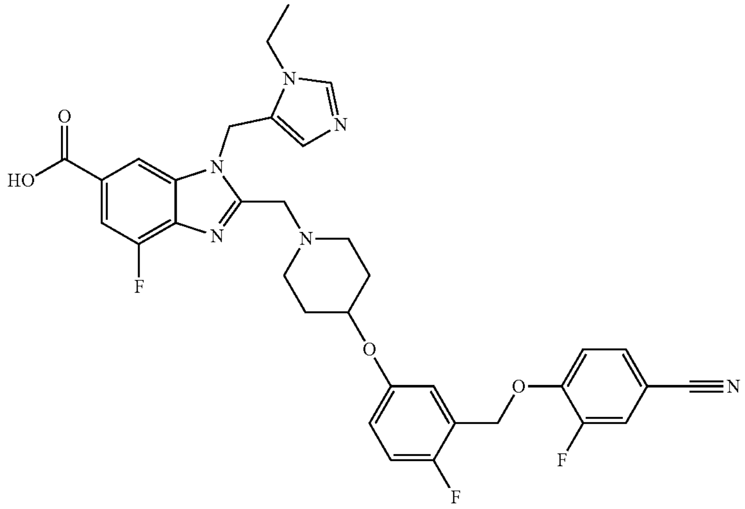 | 645 |

-continued
| Number | Structure | MS m/z: [M + H]+ |
|---|---|---|
| Compound 17 | 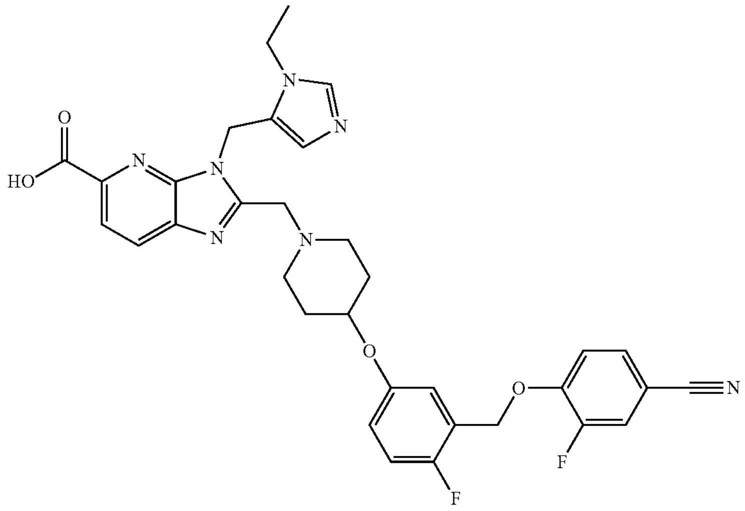 [SMILES: CCn1cncc1Cn1c(CN2CCC(Oc3ccc(F)c(COc4ccc(C#N)cc4F)c3)CC2)nc2ccc(C(=O)O)nc21] | 628 |
| Compound 18 | 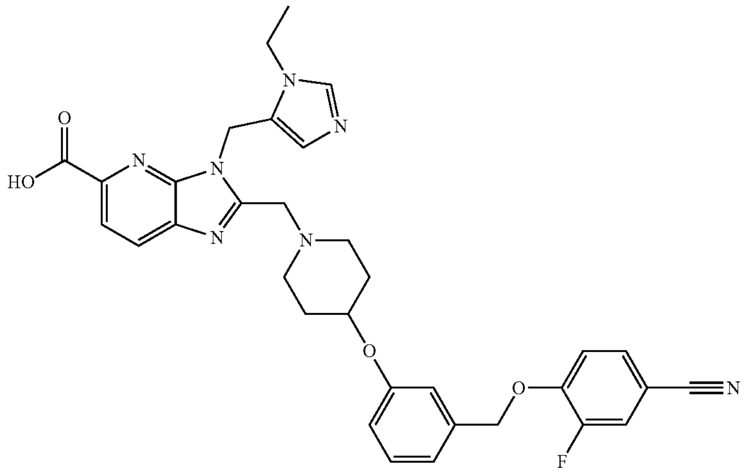 [SMILES: CCn1cncc1Cn1c(CN2CCC(Oc3cccc(COc4ccc(C#N)cc4F)c3)CC2)nc2ccc(C(=O)O)nc21] | 610 |
| Compound 19 | 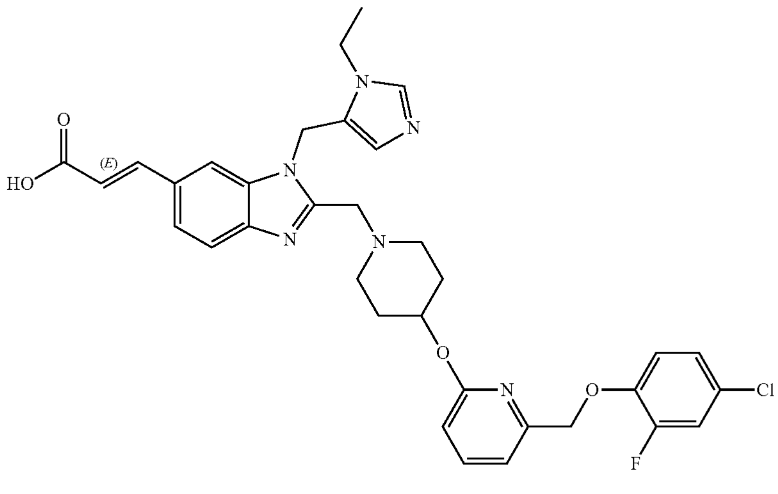 [SMILES: CCn1cncc1Cn1c(CN2CCC(Oc3cccc(COc4ccc(Cl)cc4F)n3)CC2)nc2ccc(/C=C/C(=O)O)cc21] | 645 |

-continued
| Number | Structure | MS m/z: $[M + H]^+$ |
| --- | --- | --- |
| Compound 20 | 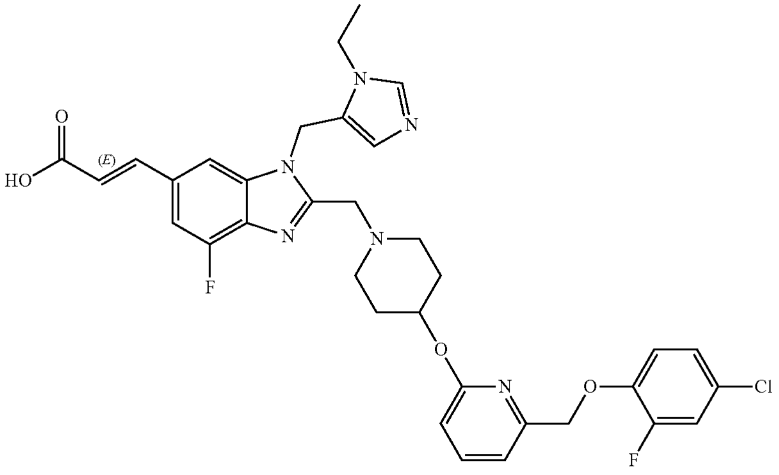 [SMILES: CCn1cncc1Cn1c(CN2CCC(Oc3cccc(COc4ccc(Cl)cc4F)n3)CC2)nc2c(F)cc(/C=C/C(=O)O)cc21] | 663 |
| Compound 21 | 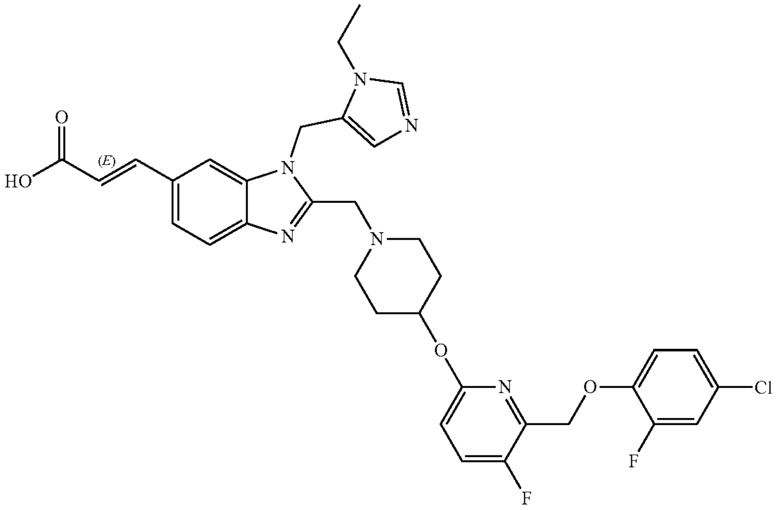 [SMILES: CCn1cncc1Cn1c(CN2CCC(Oc3ccc(F)c(COc4ccc(Cl)cc4F)n3)CC2)nc2ccc(/C=C/C(=O)O)cc21] | 663 |
| Compound 22 | 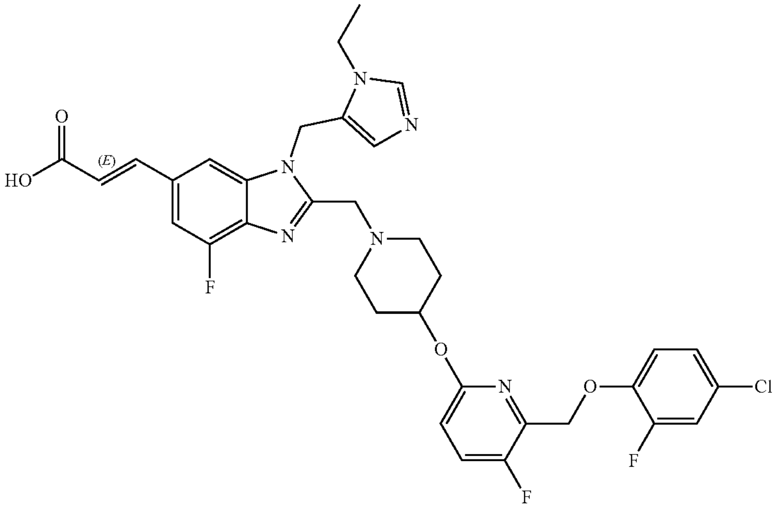 [SMILES: CCn1cncc1Cn1c(CN2CCC(Oc3ccc(F)c(COc4ccc(Cl)cc4F)n3)CC2)nc2c(F)cc(/C=C/C(=O)O)cc21] | 681 |

-continued
| Number | Structure | MS m/z: [M + H]+ |
|---|---|---|
| Compound 23 | 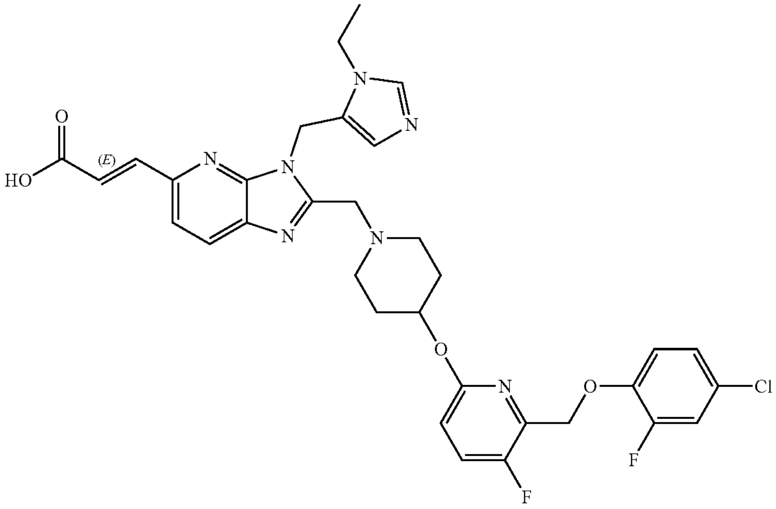 | 664 |
| Compound 24 | 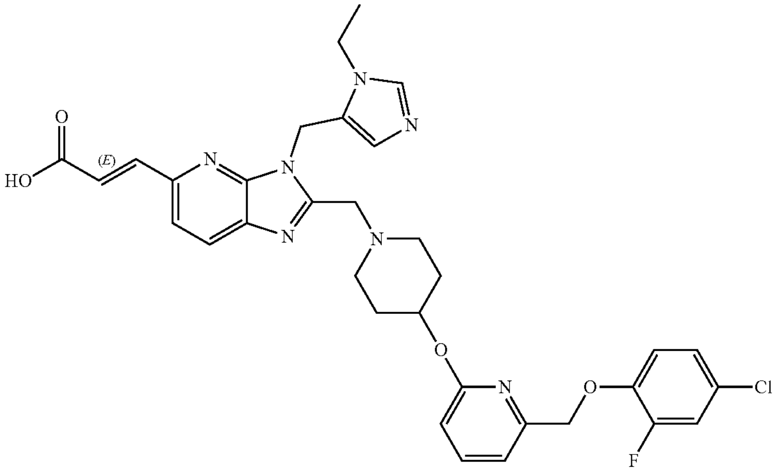 | 646 |
| Compound 25 | 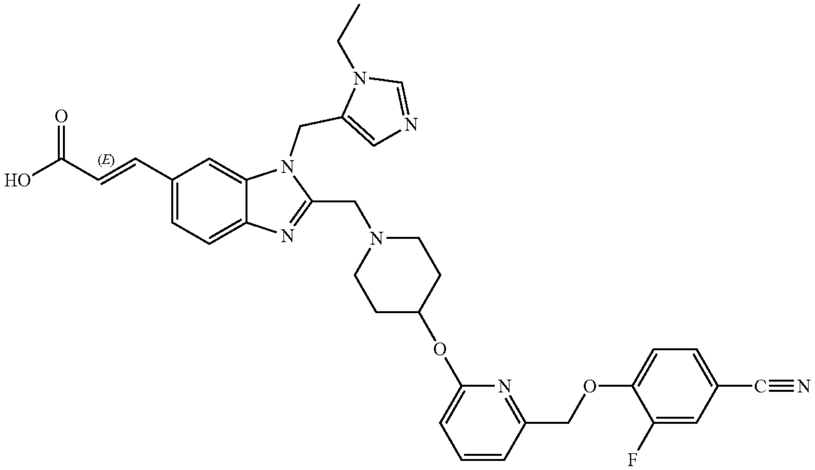 | 636 |

-continued
| Number | Structure | MS m/z: [M + H]+ |
|---|---|---|
| Compound 26 | 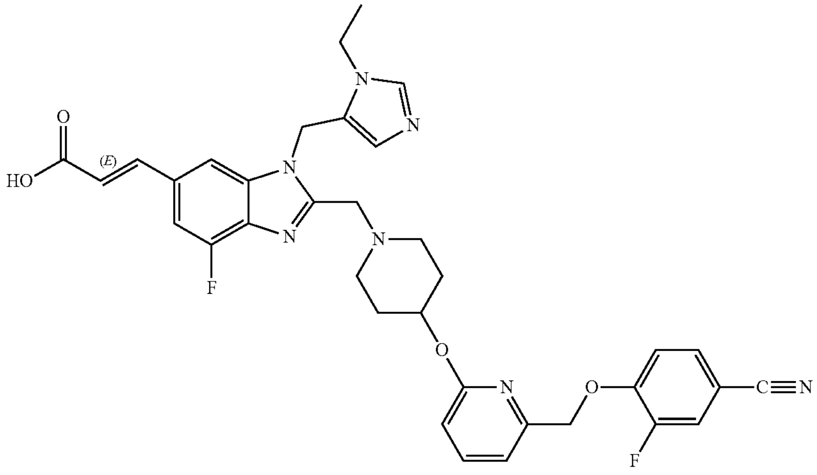 [SMILES: CCn1cncc1Cn1c(CN2CCC(Oc3cccc(COc4ccc(C#N)cc4F)n3)CC2)nc2c(F)cc(/C=C/C(=O)O)cc21] | 654 |
| Compound 27 | 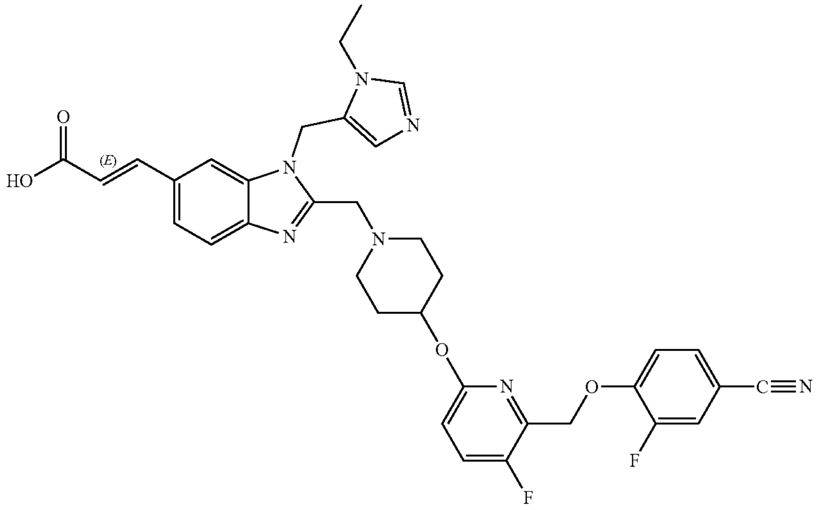 [SMILES: CCn1cncc1Cn1c(CN2CCC(Oc3ccc(F)c(COc4ccc(C#N)cc4F)n3)CC2)nc2ccc(/C=C/C(=O)O)cc21] | 654 |
| Compound 28 | 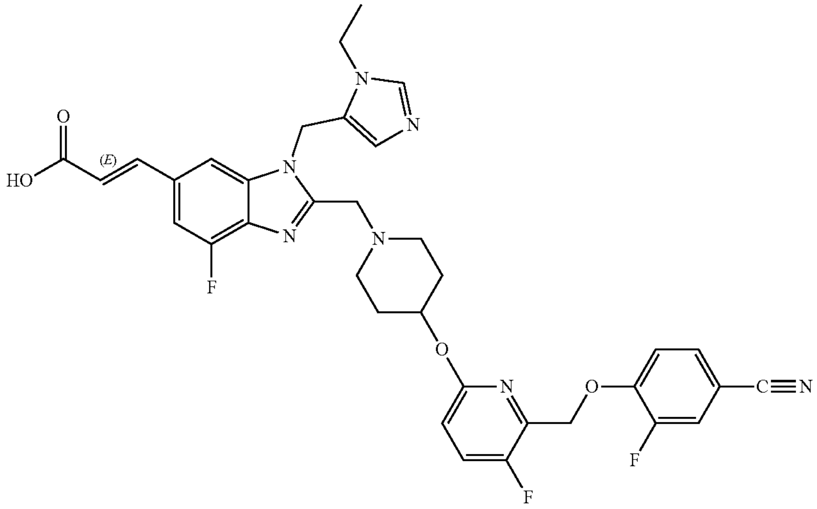 [SMILES: CCn1cncc1Cn1c(CN2CCC(Oc3ccc(F)c(COc4ccc(C#N)cc4F)n3)CC2)nc2c(F)cc(/C=C/C(=O)O)cc21] | 672 |

-continued
| Number | Structure | MS m/z: [M + H]+ |
| --- | --- | --- |
| Compound 29 | 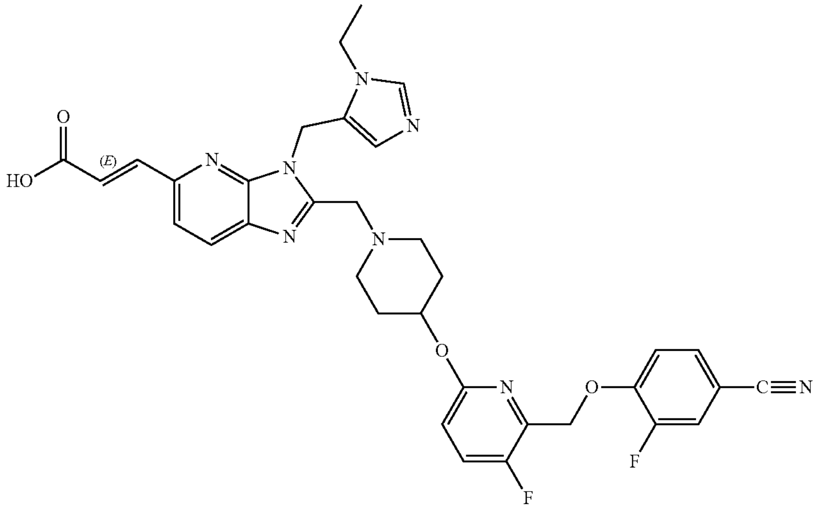 | 655 |
| Compound 30 | 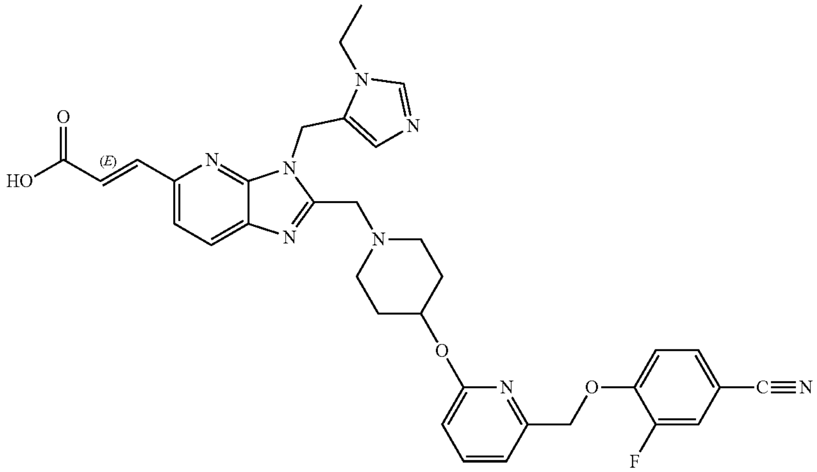 [SMILES: CCn1cncc1Cn1c(CN2CCC(Oc3cccc(COc4ccc(C#N)cc4F)n3)CC2)nc2ccc(/C=C/C(=O)O)nc21] | 637 |
| Compound 31 | 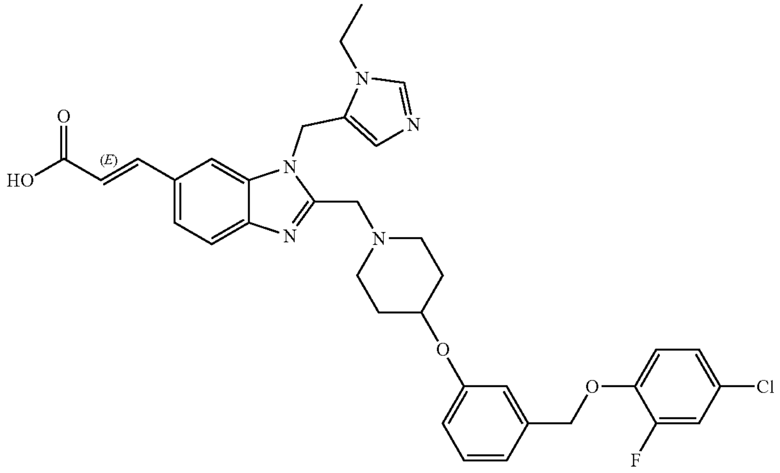 | 644 |

-continued
| Number | Structure | MS m/z: $[M + H]^+$ |
| --- | --- | --- |
| Compound 32 | 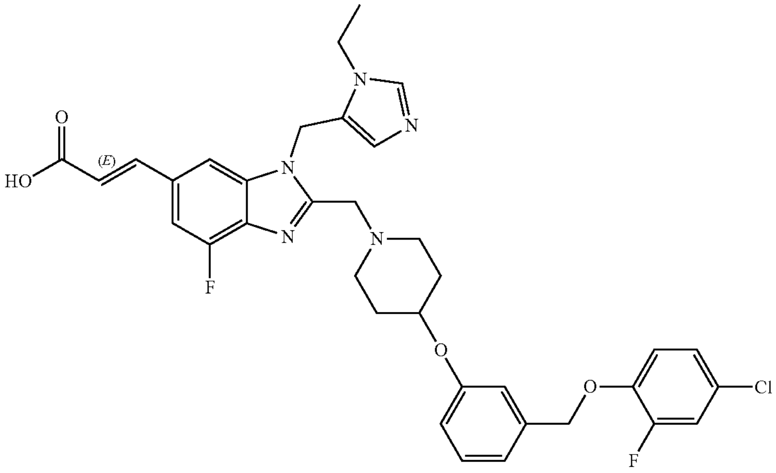 [SMILES: CCn1cncc1Cn1c(CN2CCC(Oc3cccc(COc4ccc(Cl)cc4F)c3)CC2)nc2c(F)cc(/C=C/C(=O)O)cc21] | 662 |
| Compound 33 | 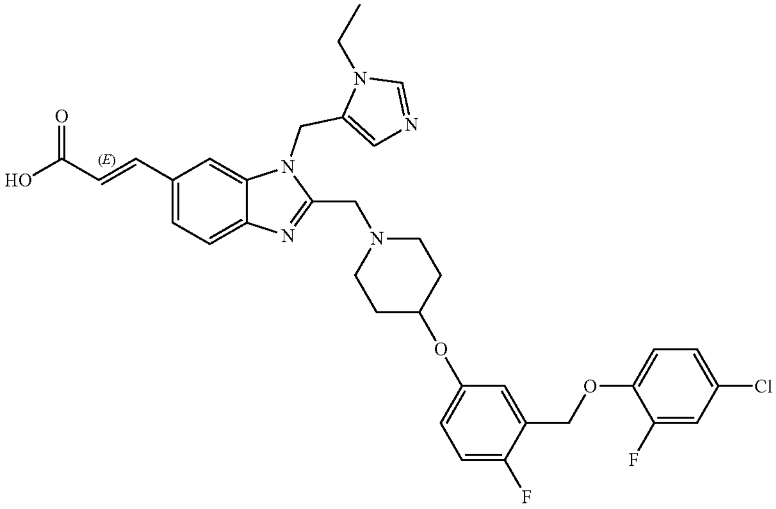 | 662 |
| Compound 34 | 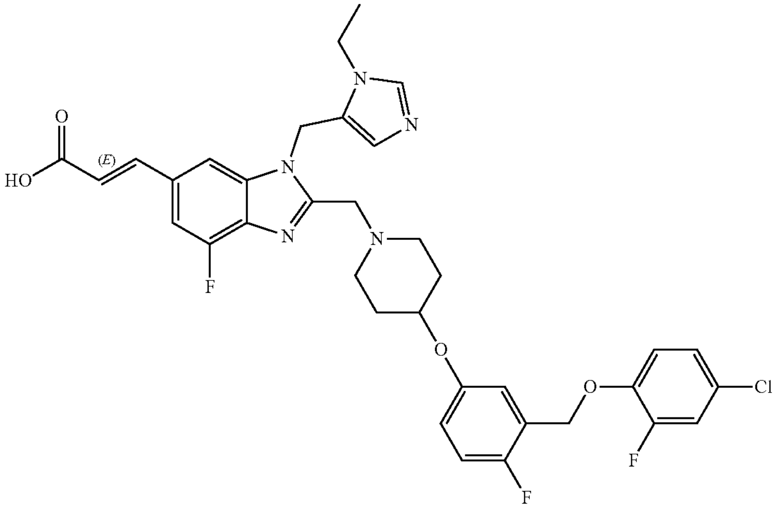 [SMILES: CCn1cncc1Cn1c(CN2CCC(Oc3ccc(F)c(COc4ccc(Cl)cc4F)c3)CC2)nc2c(F)cc(/C=C/C(=O)O)cc21] | 680 |

-continued
| Number | Structure | MS m/z: [M + H]+ |
|---|---|---|
| Compound 35 | 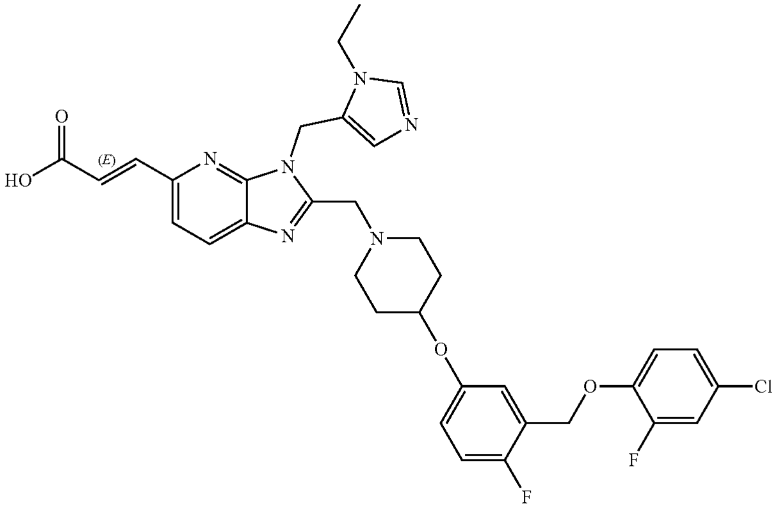 [SMILES: CCn1cncc1Cn1c(CN2CCC(Oc3ccc(F)c(COc4ccc(Cl)cc4F)c3)CC2)nc2ccc(/C=C/C(=O)O)nc21] | 663 |
| Compound 36 | 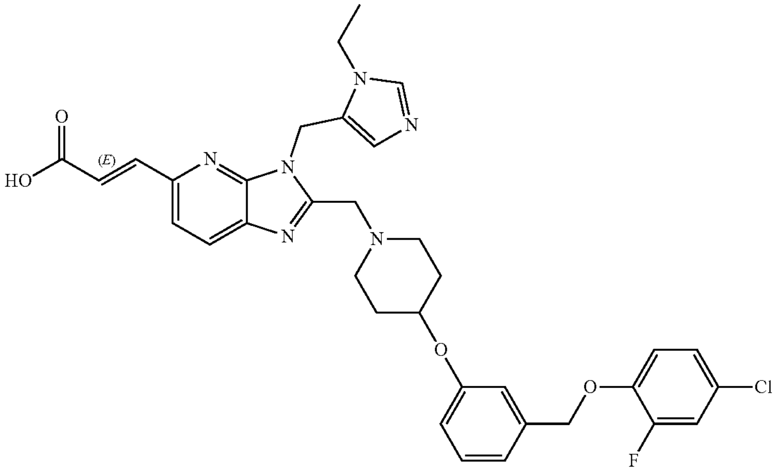 [SMILES: CCn1cncc1Cn1c(CN2CCC(Oc3cccc(COc4ccc(Cl)cc4F)c3)CC2)nc2ccc(/C=C/C(=O)O)nc21] | 645 |
| Compound 37 | 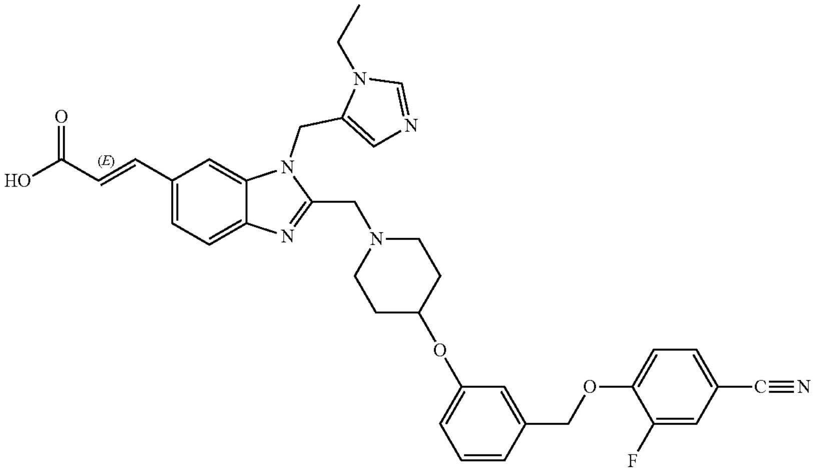 [SMILES: CCn1cncc1Cn1c(CN2CCC(Oc3cccc(COc4ccc(C#N)cc4F)c3)CC2)nc2ccc(/C=C/C(=O)O)cc21] | 635 |

-continued
| Number | Structure | MS m/z: [M + H]+ |
|---|---|---|
| Compound 38 | 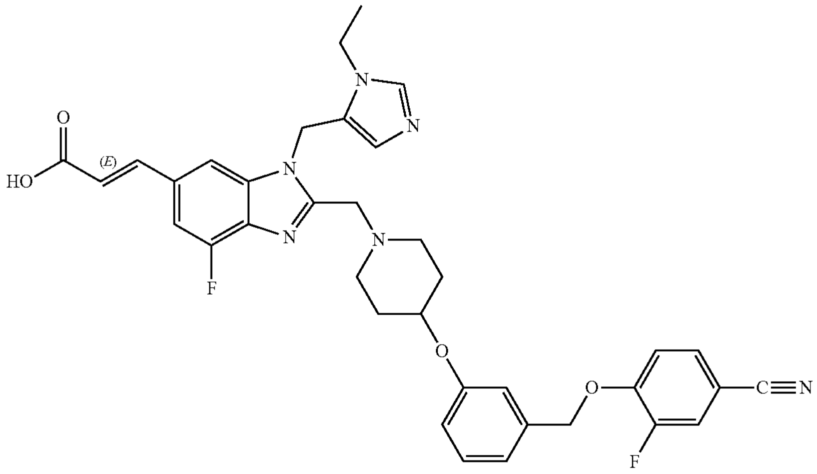 | 653 |
| Compound 39 | 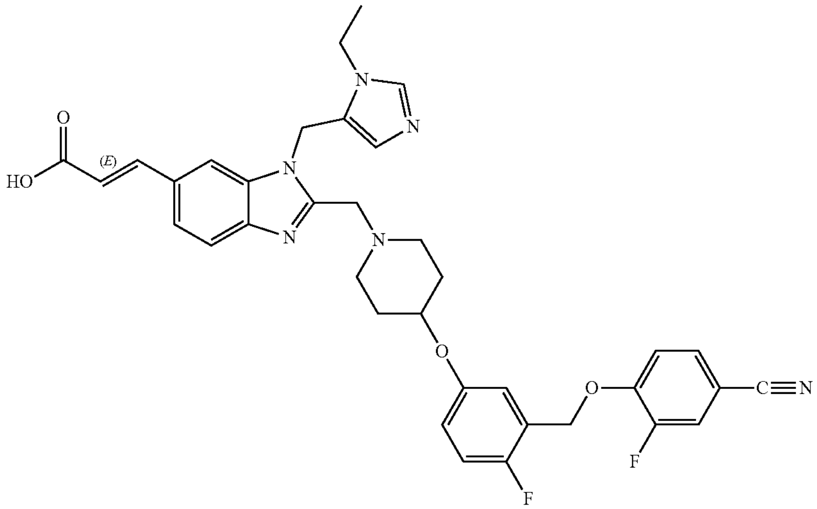 [SMILES: CCn1cncc1Cn1c(CN2CCC(Oc3ccc(F)c(COc4ccc(C#N)cc4F)c3)CC2)nc2ccc(/C=C/C(=O)O)cc21] | 653 |
| Compound 40 | 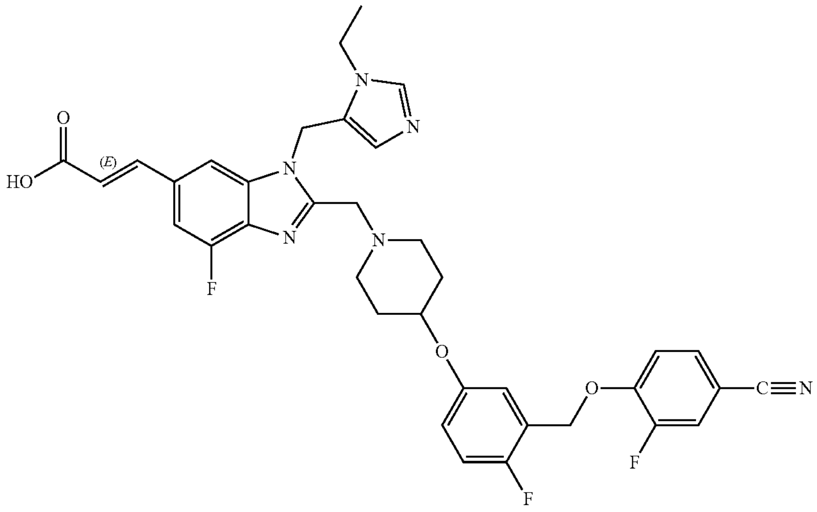 | 671 |

-continued
| Number | Structure | MS m/z: [M + H]+ |
|---|---|---|
| Compound 41 | 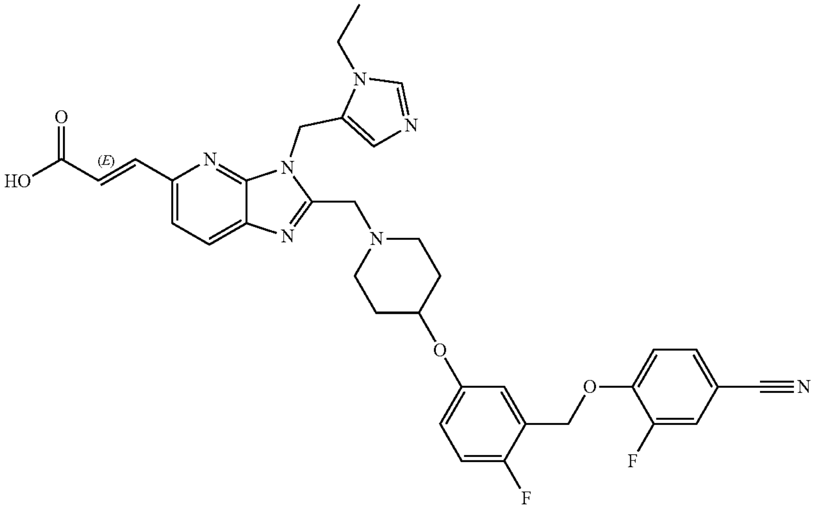 [SMILES: CCn1cncc1Cn1c(CN2CCC(Oc3ccc(F)c(COc4ccc(C#N)cc4F)c3)CC2)nc2ccc(/C=C/C(=O)O)nc21] | 654 |
| Compound 42 | 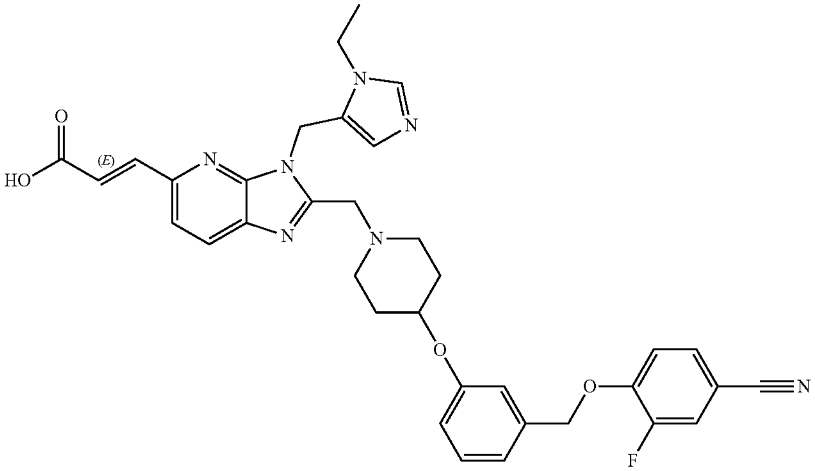 [SMILES: CCn1cncc1Cn1c(CN2CCC(Oc3cccc(COc4ccc(C#N)cc4F)c3)CC2)nc2ccc(/C=C/C(=O)O)nc21] | 636 |
| Compound 44 | 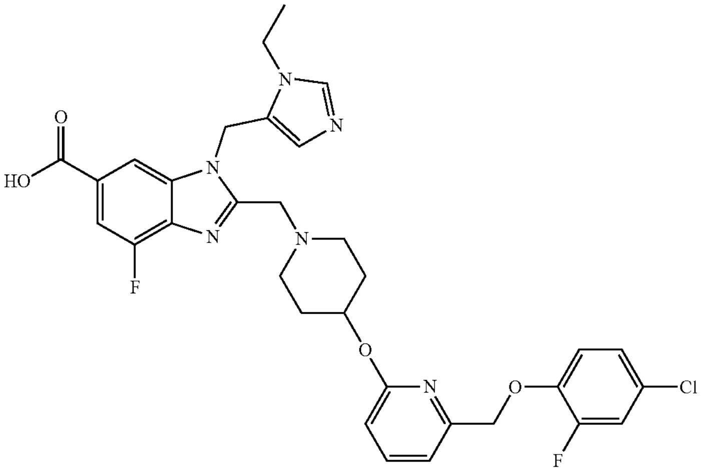 [SMILES: CCn1cncc1Cn1c(CN2CCC(Oc3cccc(COc4ccc(Cl)cc4F)n3)CC2)nc2c(F)cc(C(=O)O)cc21] | 637 |

-continued
| Number | Structure | MS m/z: [M + H]+ |
| --- | --- | --- |
| Compound 45 | 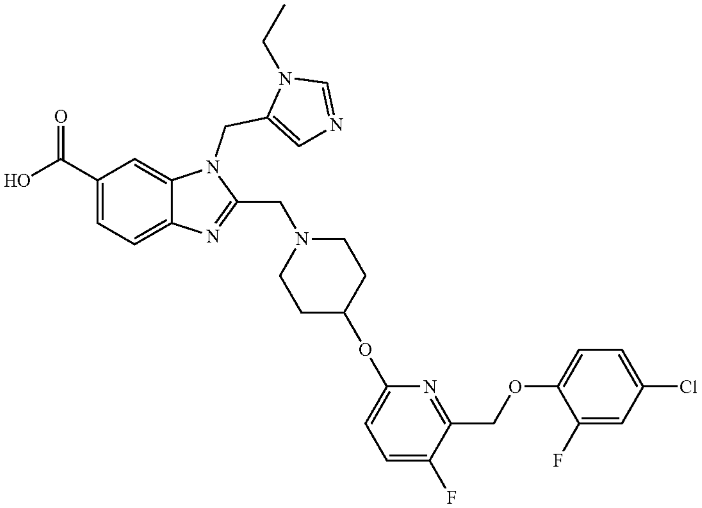 [SMILES: CCn1cncc1Cn1c(CN2CCC(Oc3ccc(F)c(COc4ccc(Cl)cc4F)n3)CC2)nc2ccc(C(=O)O)cc21] | 637 |
| Compound 46 | 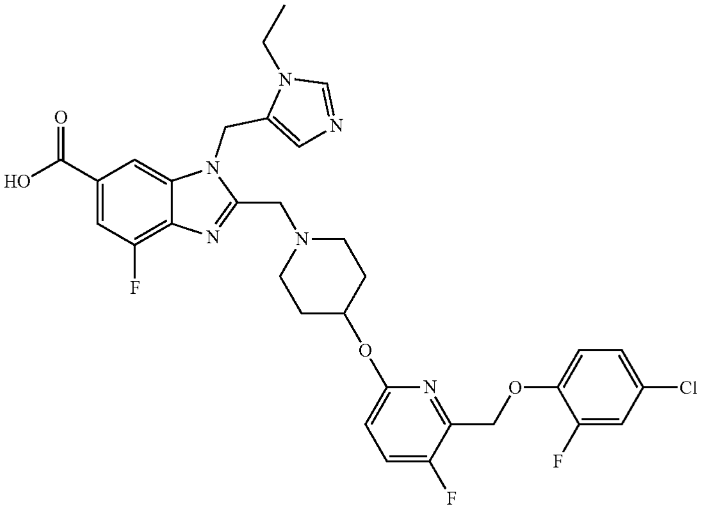 [SMILES: CCn1cncc1Cn1c(CN2CCC(Oc3ccc(F)c(COc4ccc(Cl)cc4F)n3)CC2)nc2c(F)cc(C(=O)O)cc21] | 655 |
| Compound 47 | 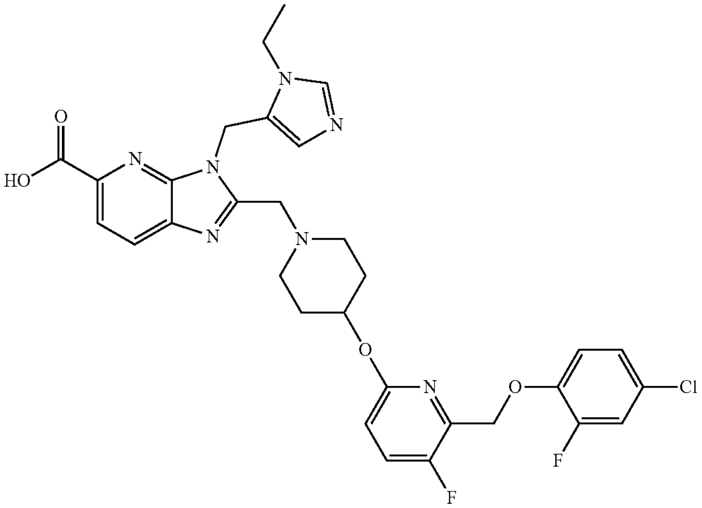 [SMILES: CCn1cncc1Cn1c(CN2CCC(Oc3ccc(F)c(COc4ccc(Cl)cc4F)n3)CC2)nc2ccc(C(=O)O)nc21] | 638 |

-continued
| Number | Structure | MS m/z: [M + H]+ |
|---|---|---|
| Compound 48 | 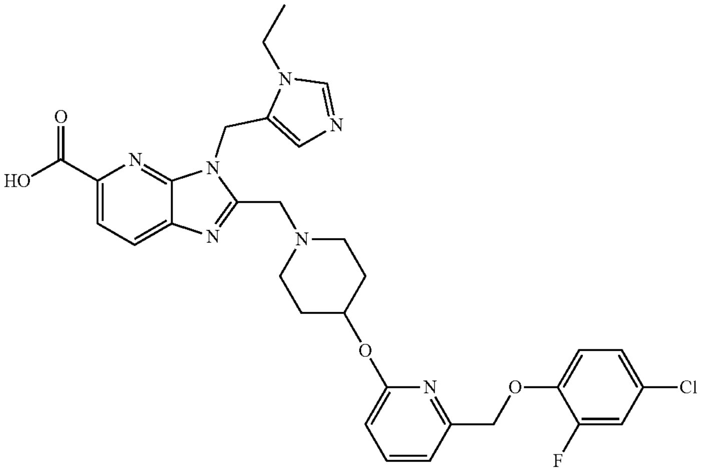 [SMILES: CCn1cncc1Cn1c(CN2CCC(Oc3cccc(COc4ccc(Cl)cc4F)n3)CC2)nc2ccc(C(=O)O)nc21] | 620 |
| Compound 51 | 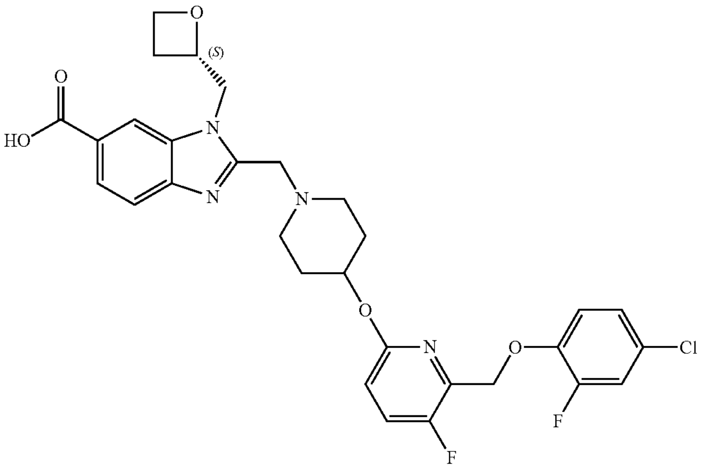 | 599 |
| Compound 52 | 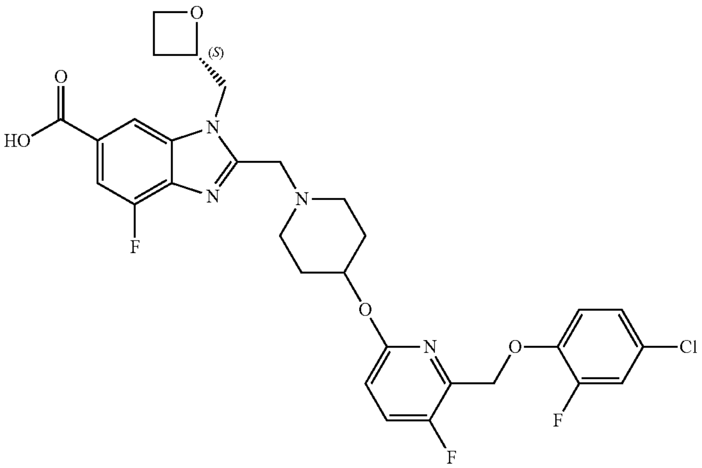 | 617 |

-continued
| Number | Structure | MS m/z: [M + H]+ |
|---|---|---|
| Compound 53 | 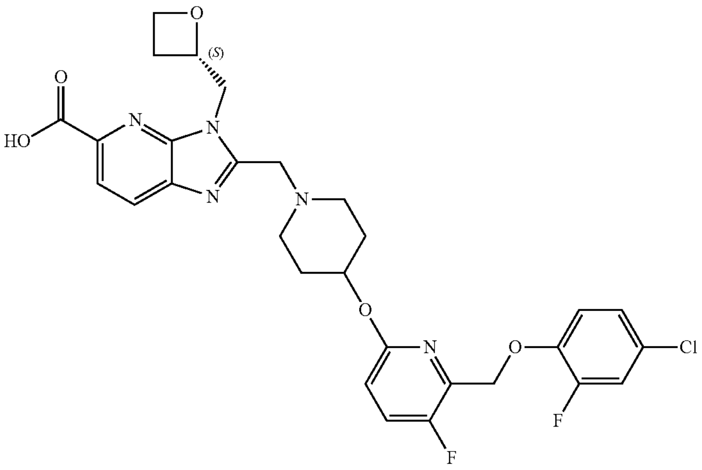 | 600 |
| Compound 54 | 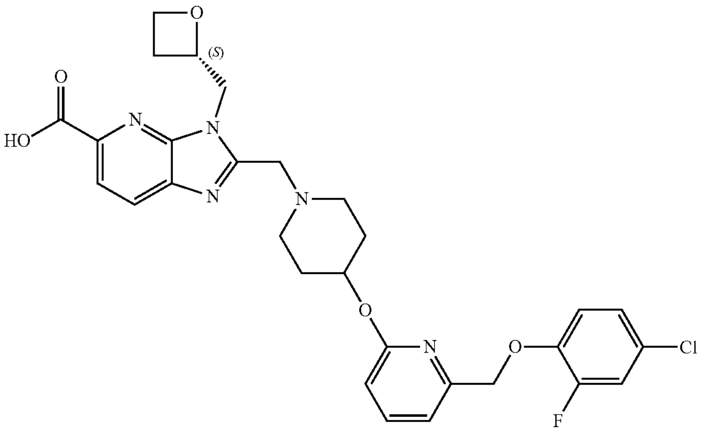 | 582 |
| Compound 58 | 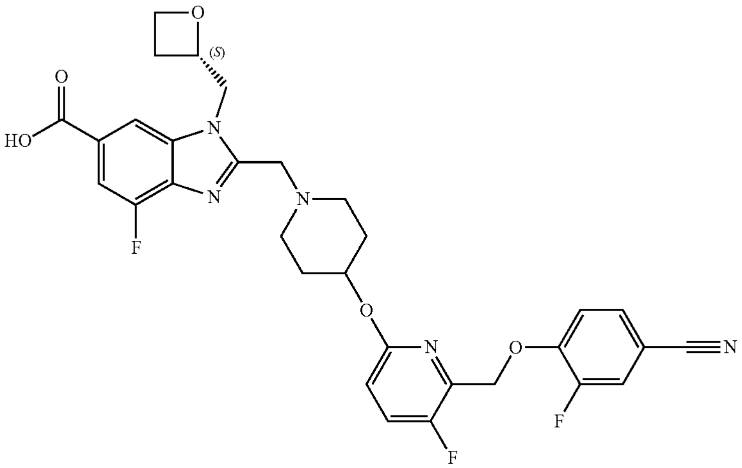 | 608 |

-continued
| Number | Structure | MS m/z: [M + H]+ |
|---|---|---|
| Compound 59 | 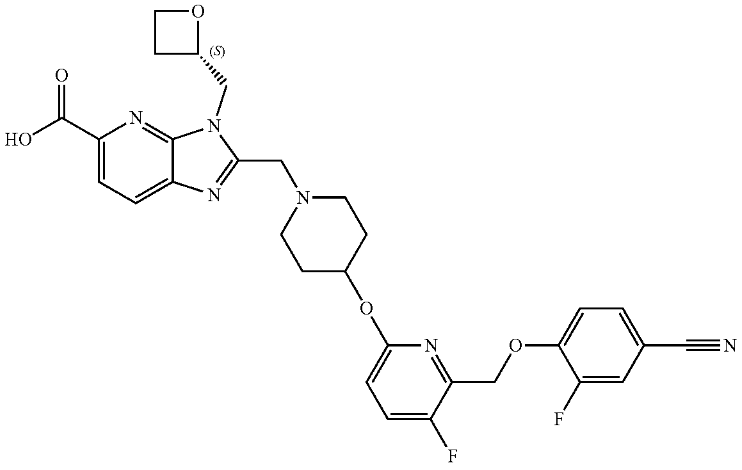 | 591 |
| Compound 61 | 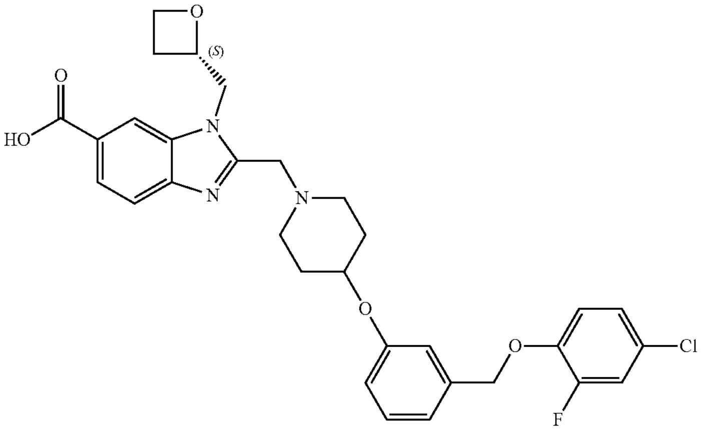 | 580 |
| Compound 62 | 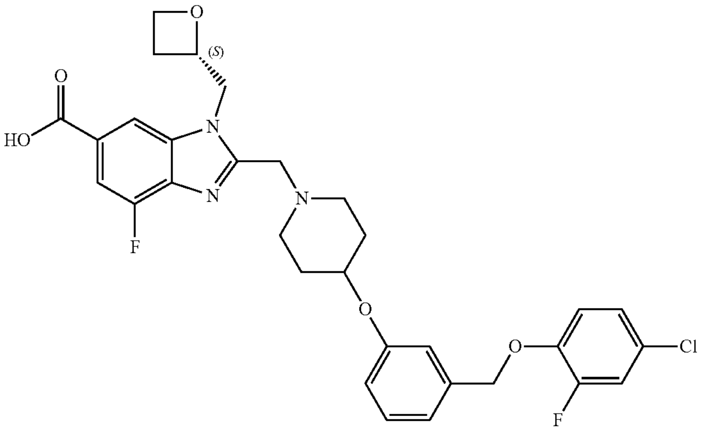 | 598 |

-continued
| Number | Structure | MS m/z: [M + H]$^+$ |
|---|---|---|
| Compound 63 | 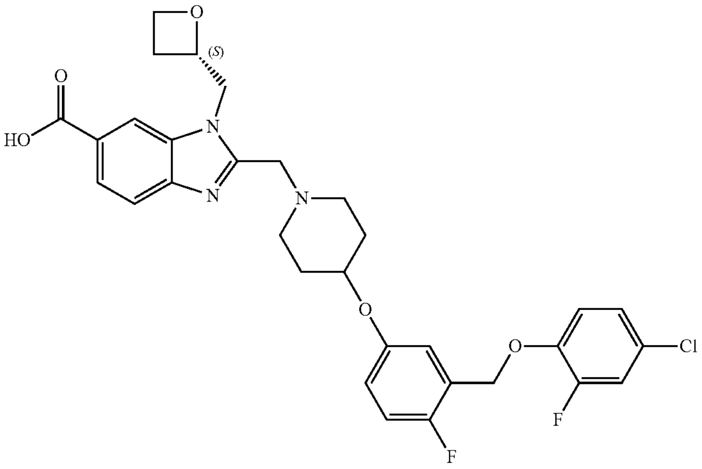 | 598 |
| Compound 64 | 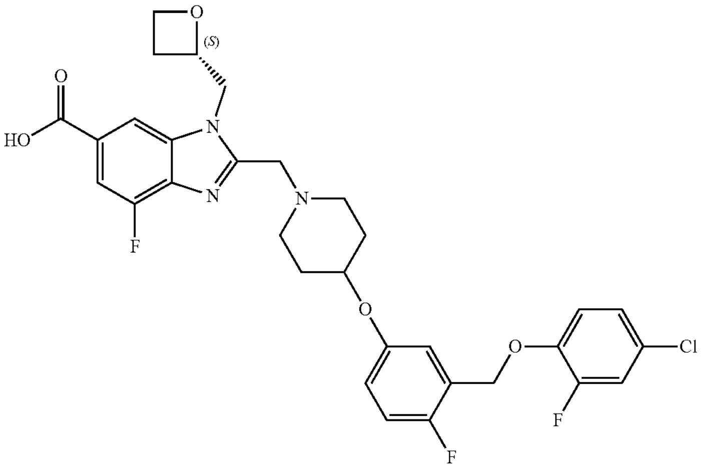 | 616 |
| Compound 65 | 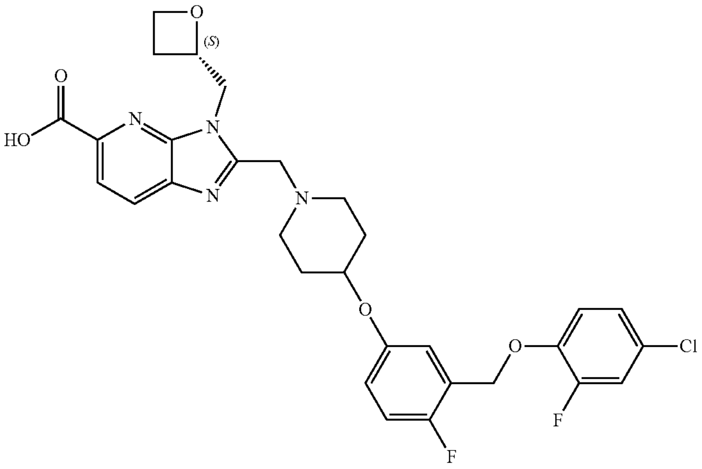 | 599 |

-continued
| Number | Structure | MS m/z: [M + H]+ |
| --- | --- | --- |
| Compound 66 | 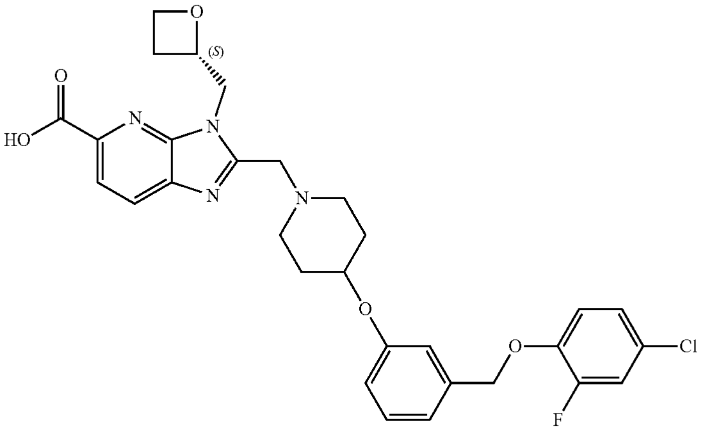 | 581 |
| Compound 68 | 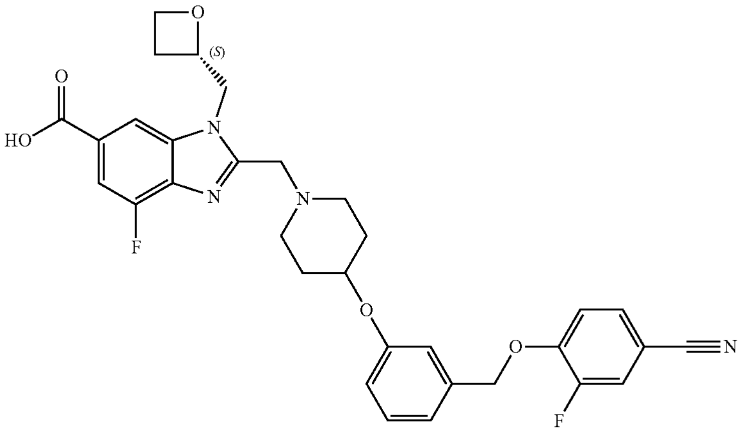 | 589 |
| Compound 69 | 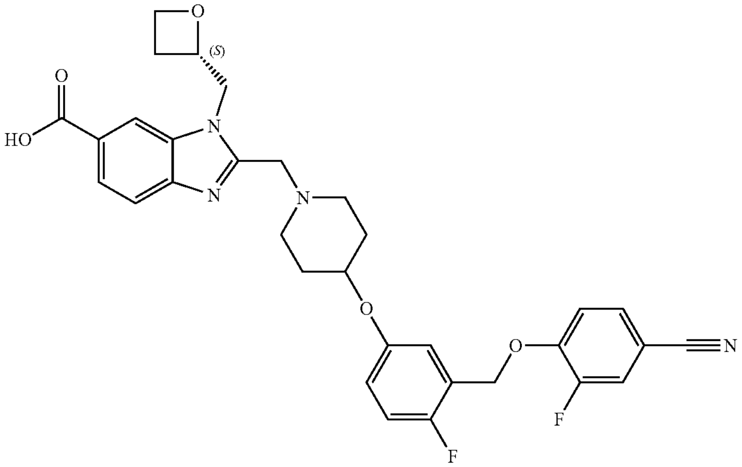 | 589 |

-continued
| Number | Structure | MS m/z: [M + H]$^+$ |
|---|---|---|
| Compound 70 | 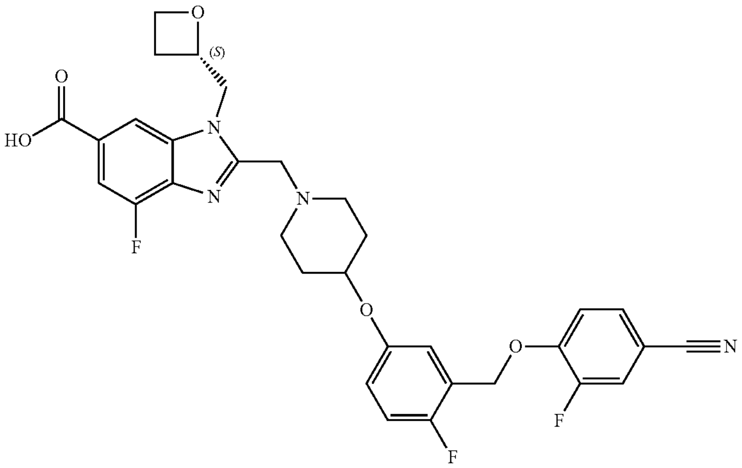 | 607 |
| Compound 71 | 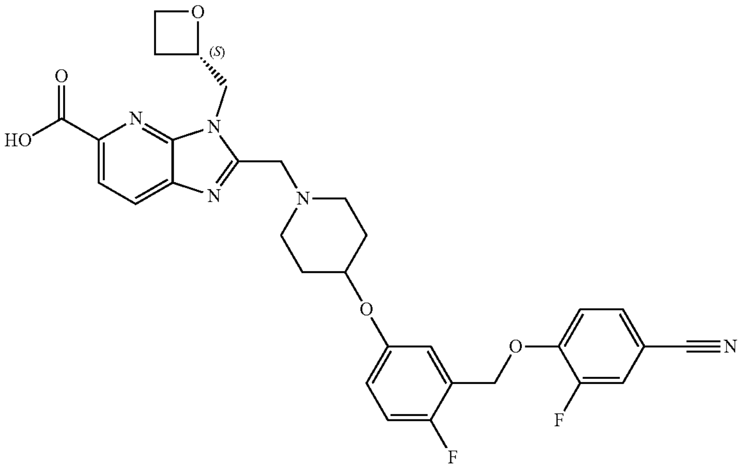 | 590 |
| Compound 72 | 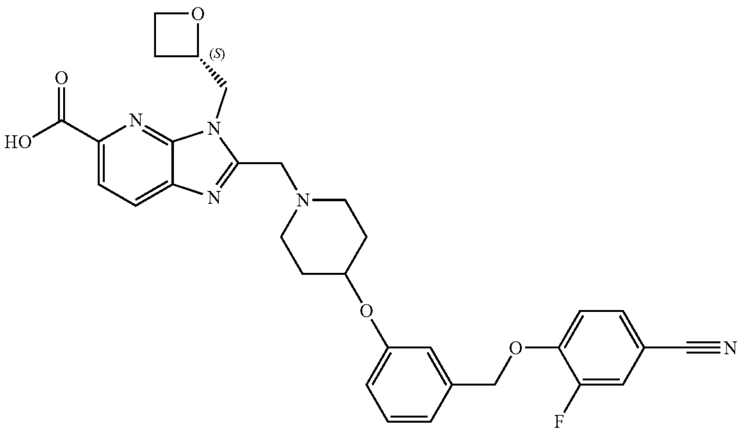 | 572 |

-continued
| Number | Structure | MS m/z: [M + H]+ |
|---|---|---|
| Compound 73 | 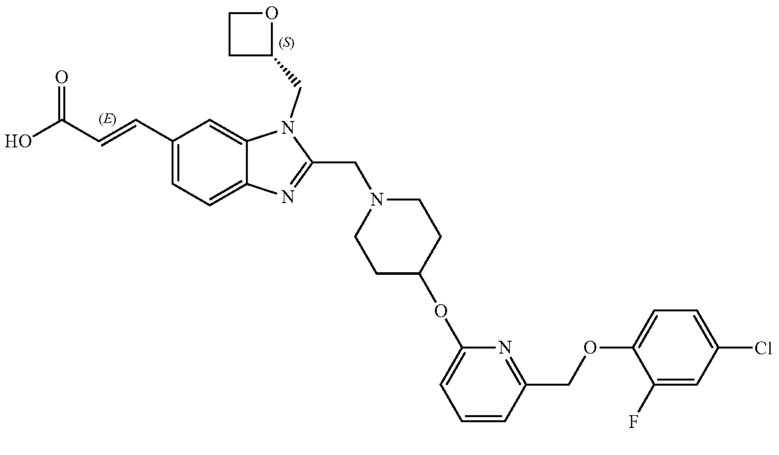 | 607 |
| Compound 74 | 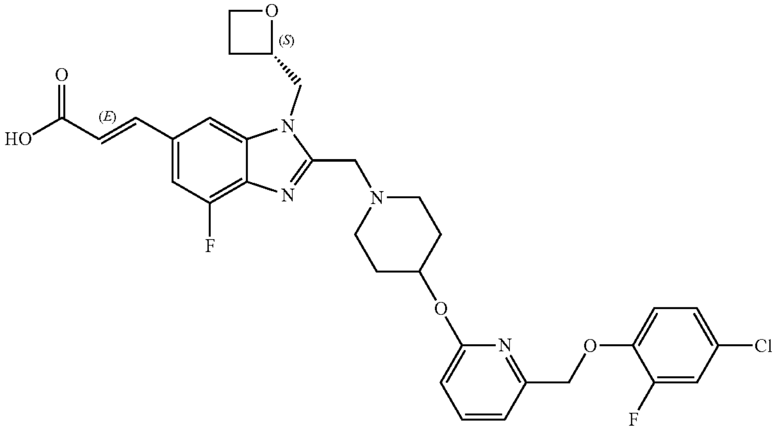 | 625 |
| Compound 75 | 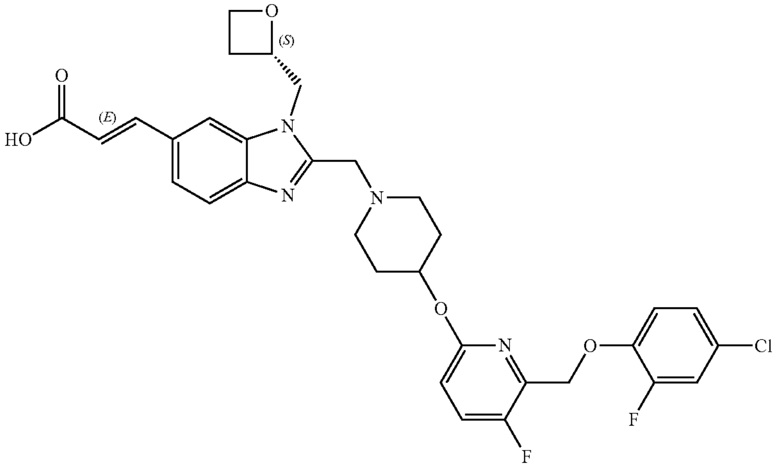 | 625 |

-continued
| Number | Structure | MS m/z: [M + H]+ |
| --- | --- | --- |
| Compound 76 | 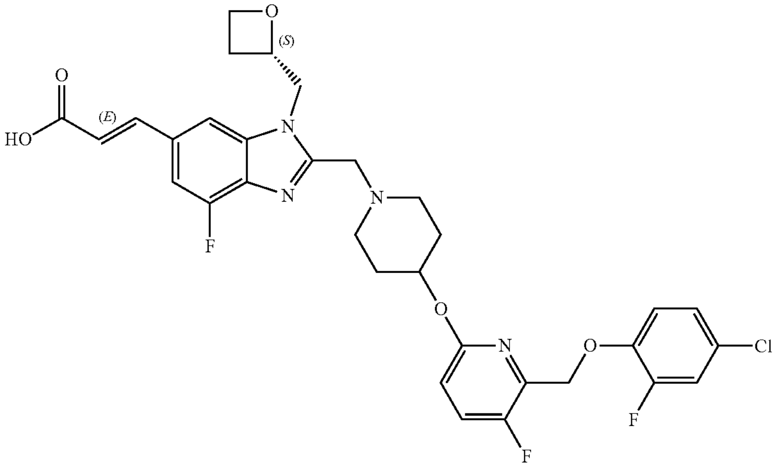 | 643 |
| Compound 77 | 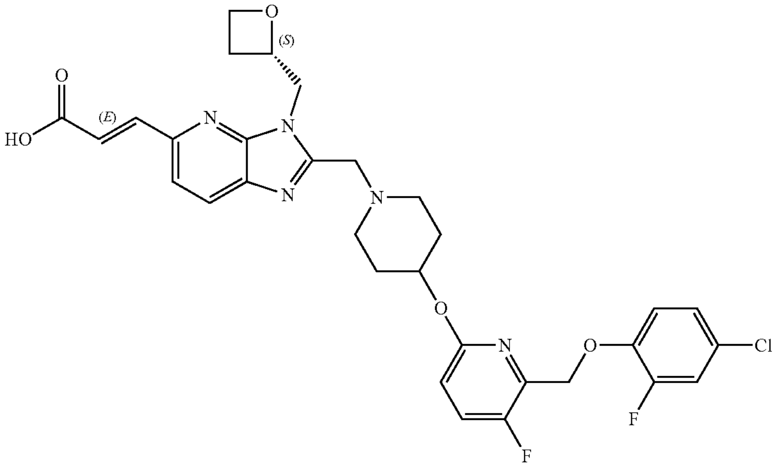 | 626 |
| Compound 78 | 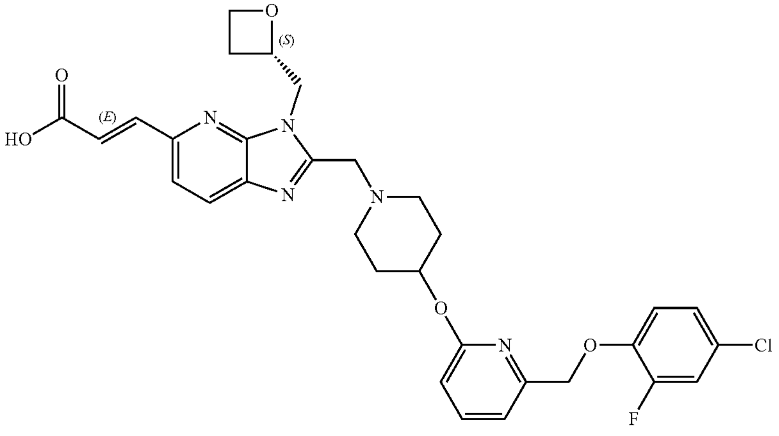 | 608 |

-continued
| Number | Structure | MS m/z: [M + H]+ |
|---|---|---|
| Compound 79 | 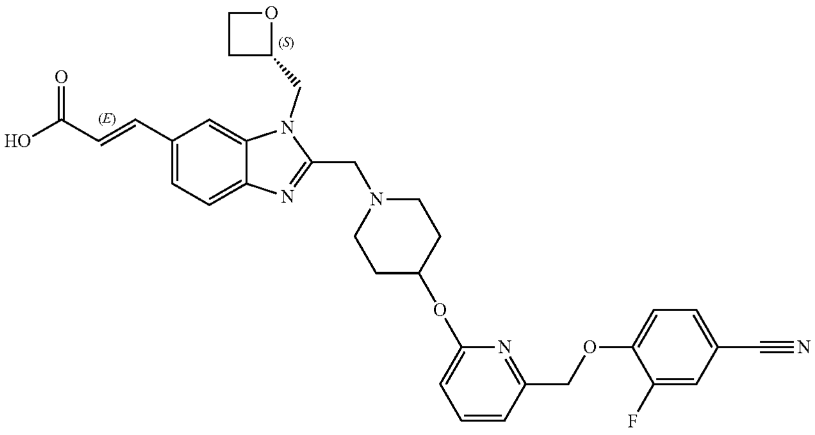 | 598 |
| Compound 80 | 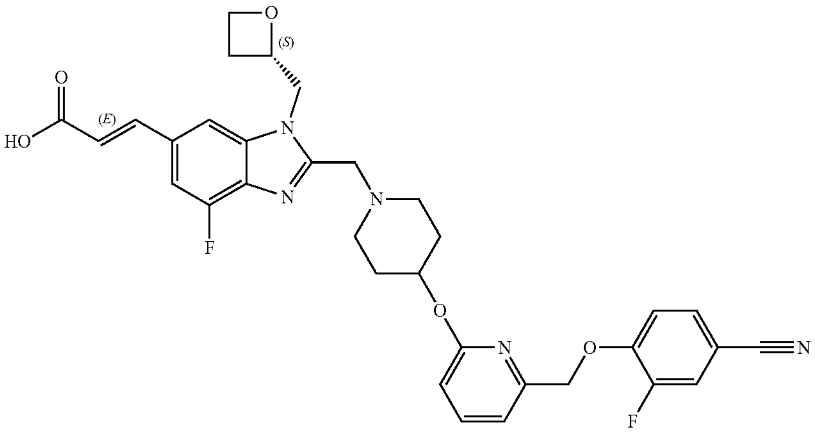 | 616 |
| Compound 81 | 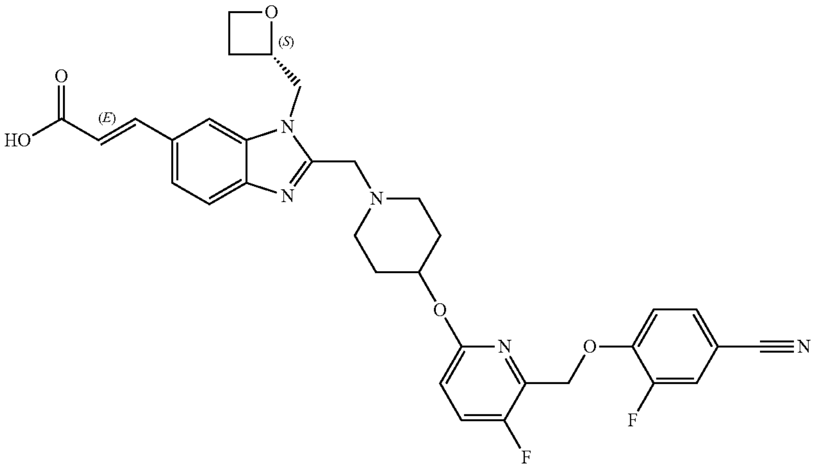 | 616 |

-continued
| Number | Structure | MS m/z: [M + H]+ |
| --- | --- | --- |
| Compound 82 | 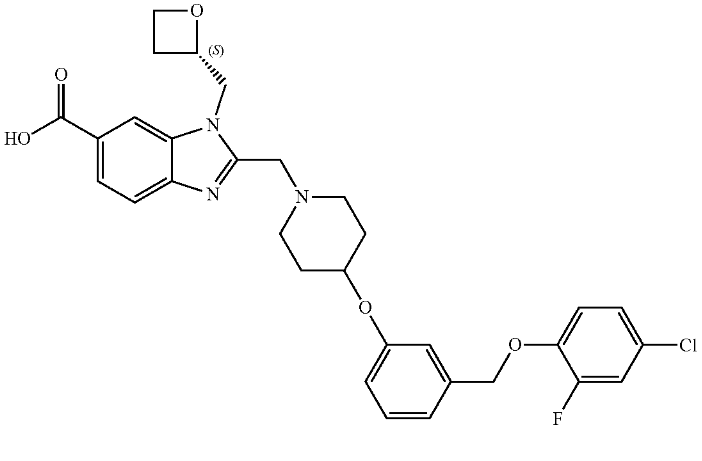 | 634 |
| Compound 83 | 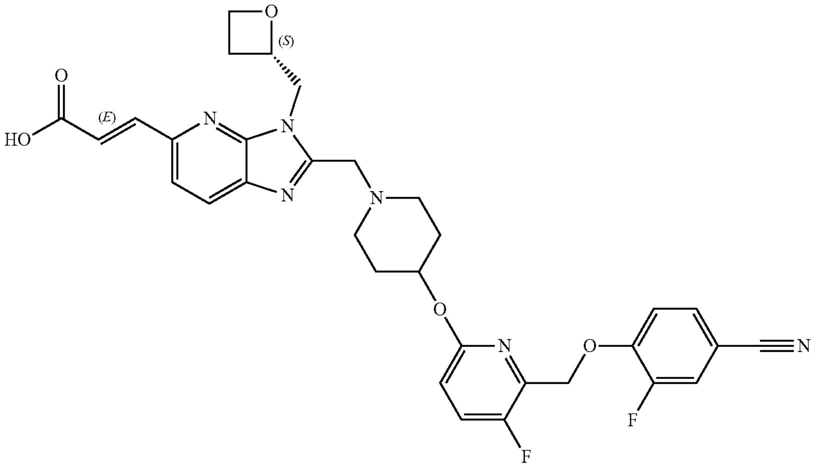 | 617 |
| Compound 84 | 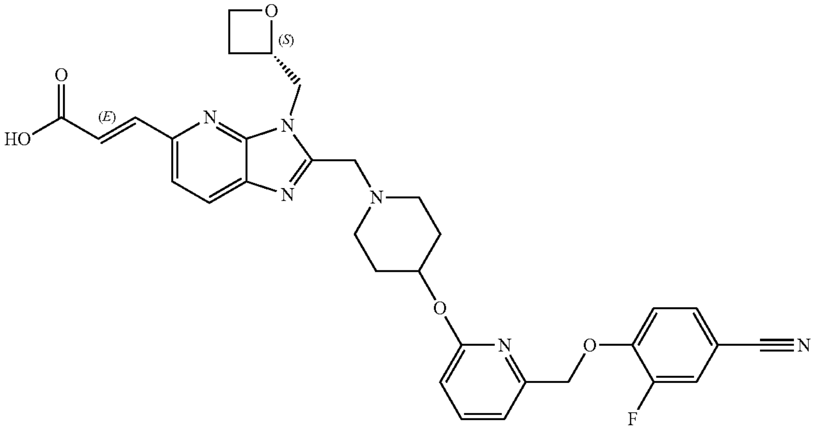 | 599 |

-continued
| Number | Structure | MS m/z: [M + H]+ |
|---|---|---|
| Compound 85 | 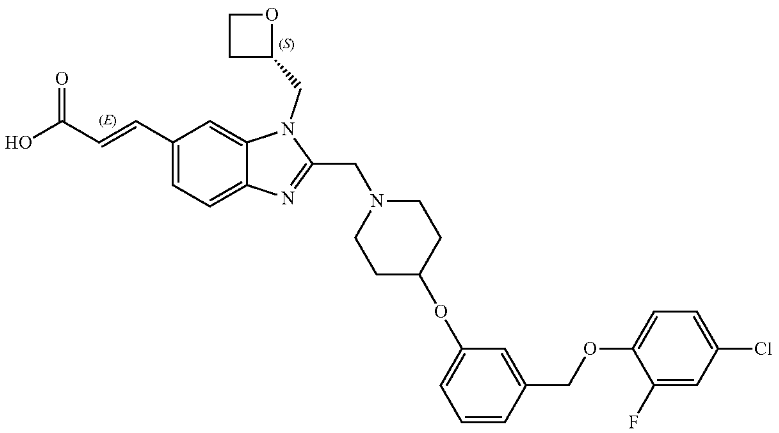 | 606 |
| Compound 86 | 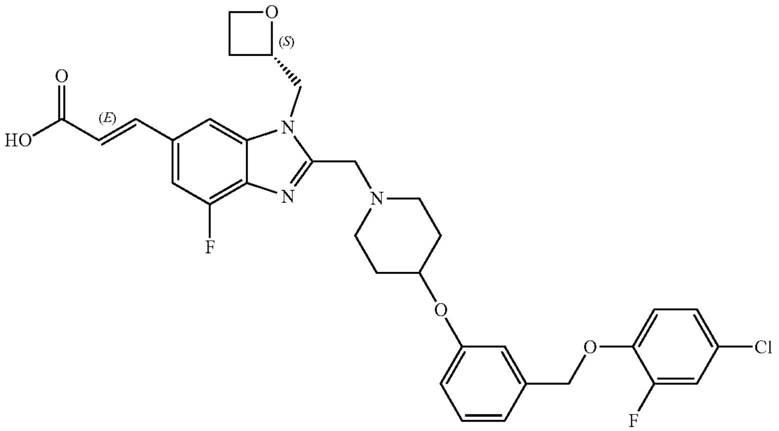 | 624 |
| Compound 87 | 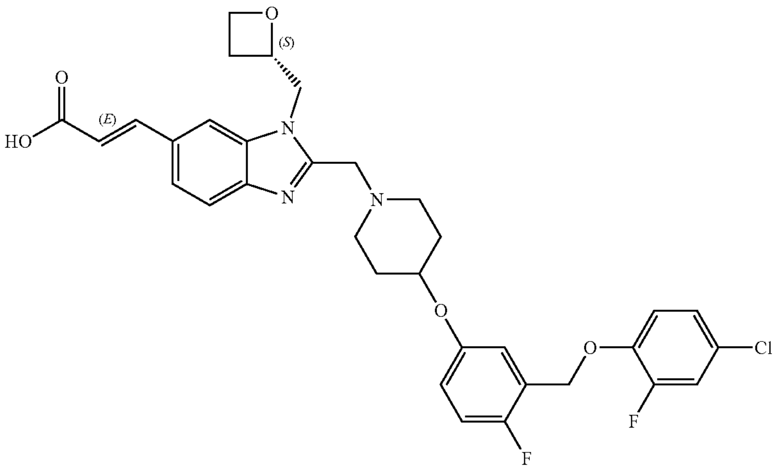 | 624 |

-continued
| Number | Structure | MS m/z: [M + H]+ |
| --- | --- | --- |
| Compound 88 | 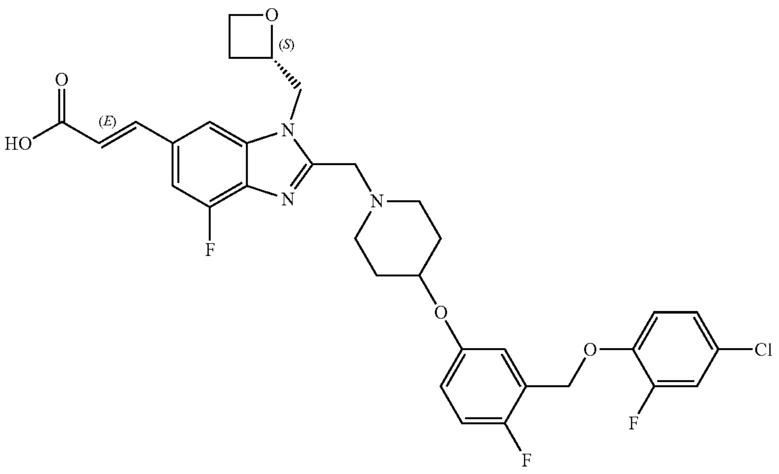 | 642 |
| Compound 89 | 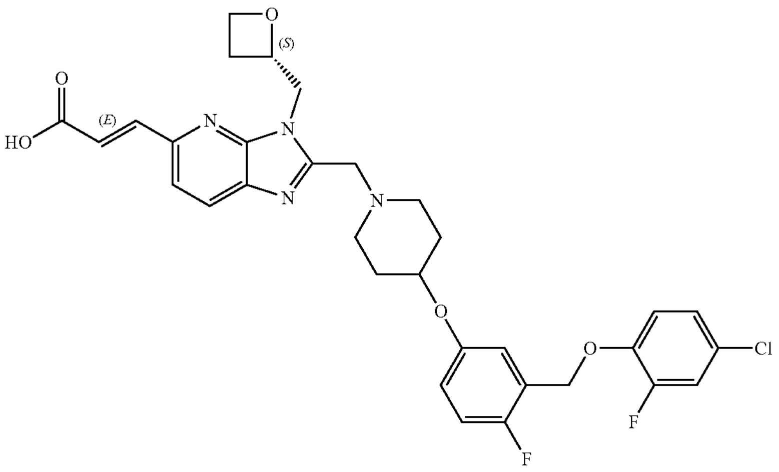 | 625 |
| Compound 90 | 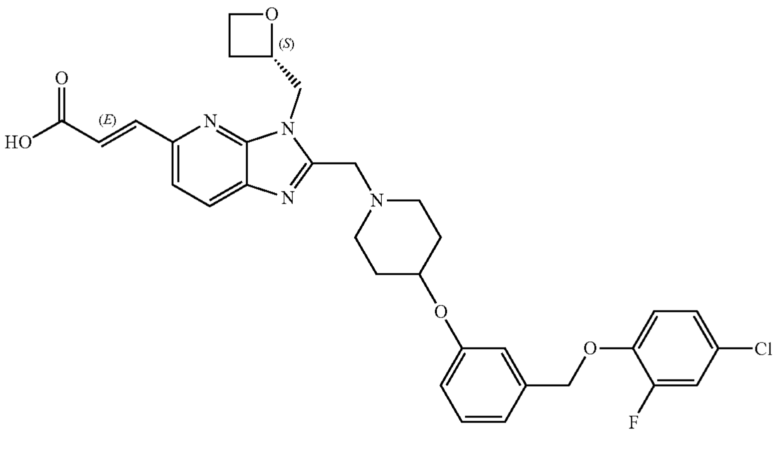 | 607 |

-continued
| Number | Structure | MS m/z: [M + H]+ |
|---|---|---|
| Compound 91 | 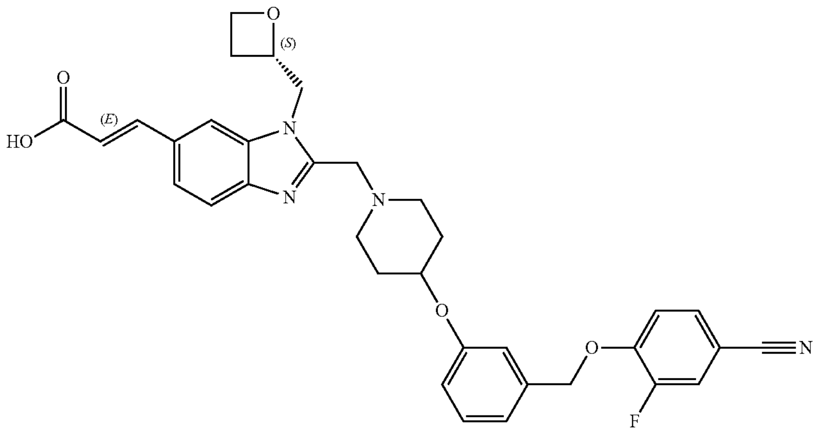 | 597 |
| Compound 92 | 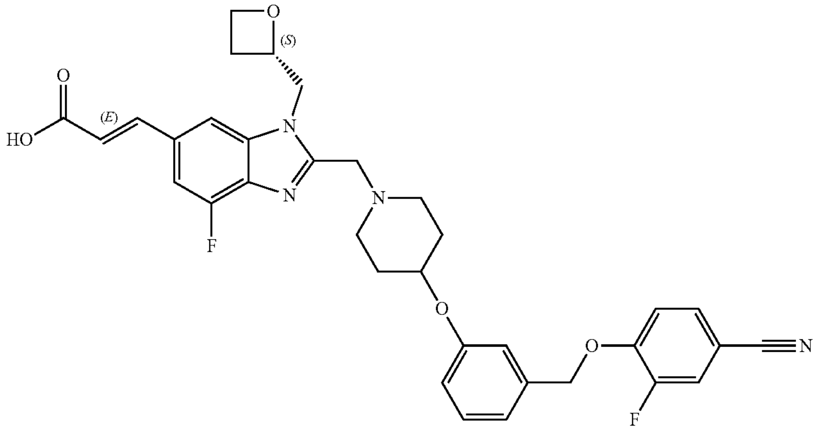 | 615 |
| Compound 93 | 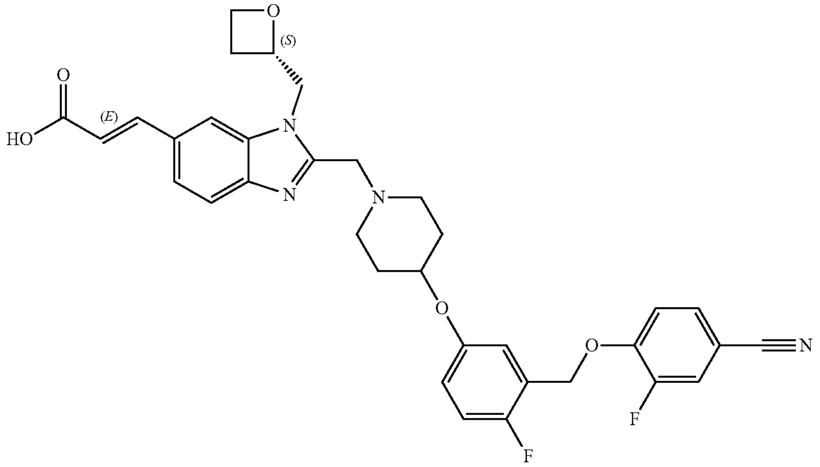 | 615 |

-continued
| Number | Structure | MS m/z: [M + H]+ |
|---|---|---|
| Compound 94 | 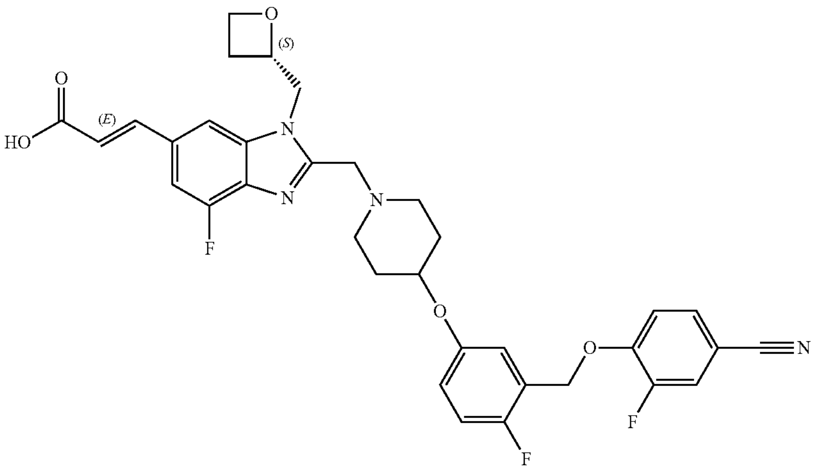 | 633 |
| Compound 95 | 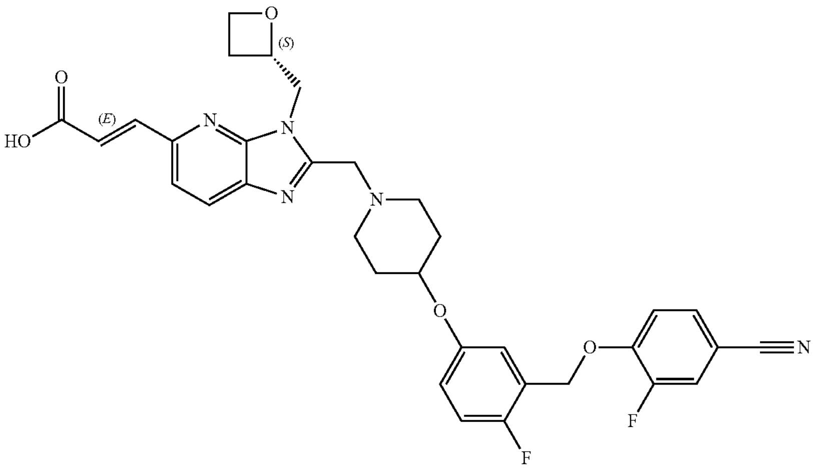 | 616 |
| Compound 96 | 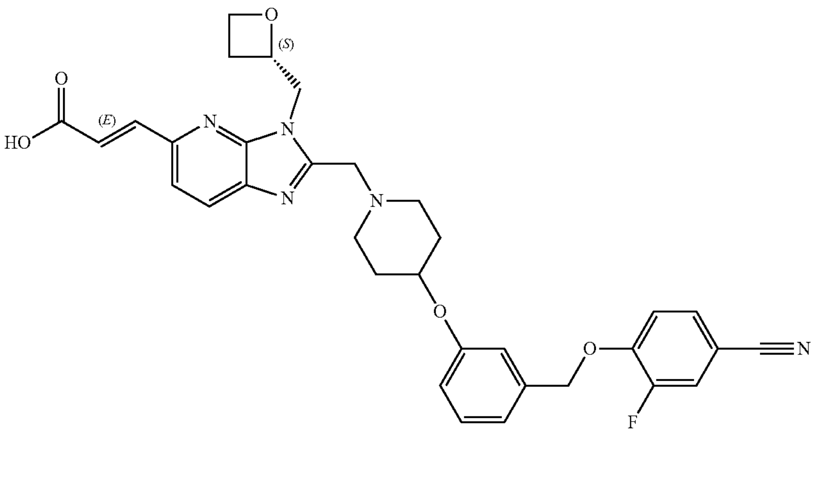 | 598 |

-continued
| Number | Structure | MS m/z: [M + H]+ |
|---|---|---|
| Compound 97 | 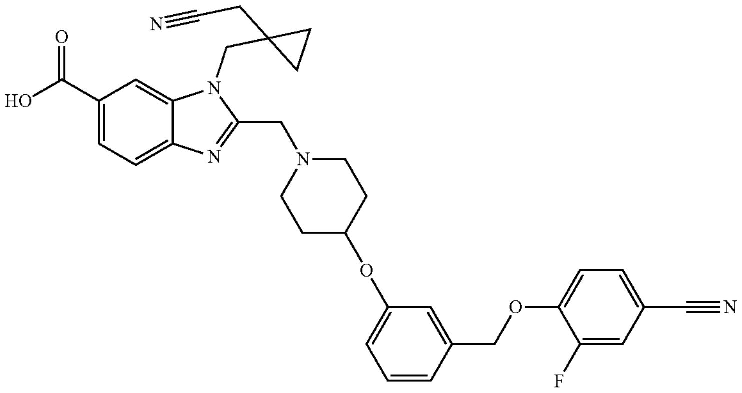 | 594 |
| Compound 98 | 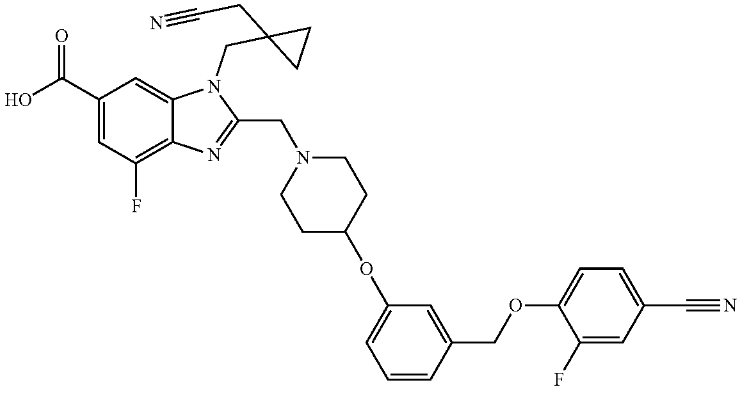 [SMILES: N#CCC1(Cn2c(CN3CCC(Oc4cccc(COc5ccc(C#N)cc5F)c4)CC3)nc3c(F)cc(C(=O)O)cc32)CC1] | 612 |
| Compound 99 | 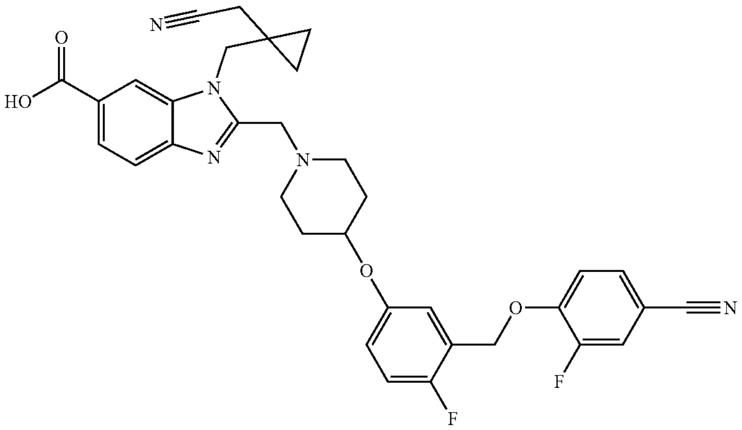 [SMILES: N#CCC1(Cn2c(CN3CCC(Oc4ccc(F)c(COc5ccc(C#N)cc5F)c4)CC3)nc3ccc(C(=O)O)cc32)CC1] | 612 |

-continued
| Number | Structure | MS m/z: [M + H]+ |
|---|---|---|
| Compound 100 | 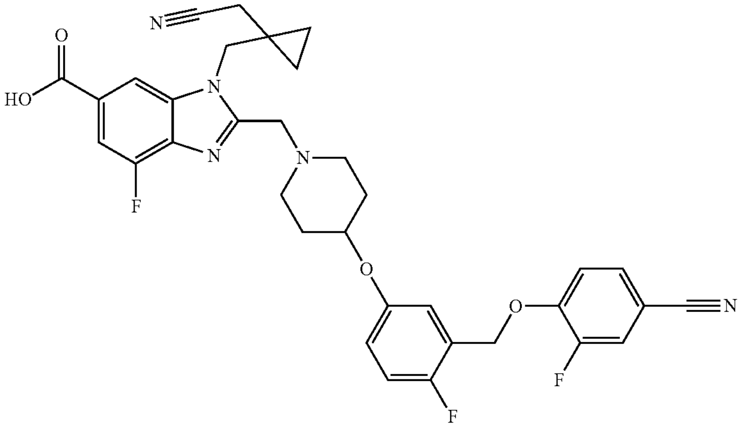 [SMILES: N#CCC1(Cn2c(CN3CCC(Oc4ccc(F)c(COc5ccc(C#N)cc5F)c4)CC3)nc3c(F)cc(C(=O)O)cc32)CC1] | 630 |
| Compound 101 | 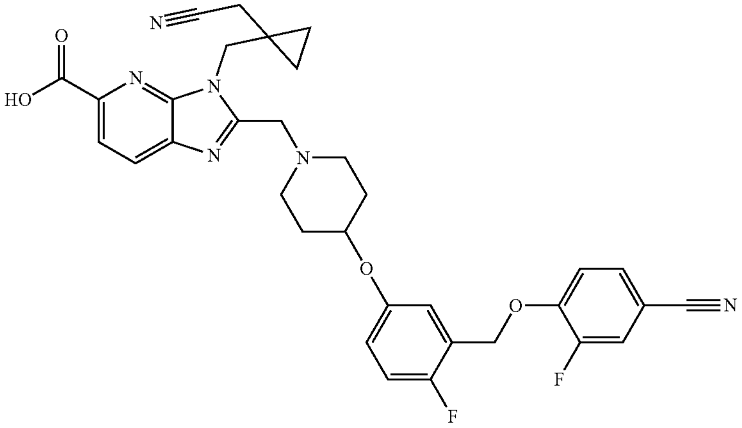 [SMILES: N#CCC1(Cn2c(CN3CCC(Oc4ccc(F)c(COc5ccc(C#N)cc5F)c4)CC3)nc3ccc(C(=O)O)nc32)CC1] | 613 |
| Compound 102 | 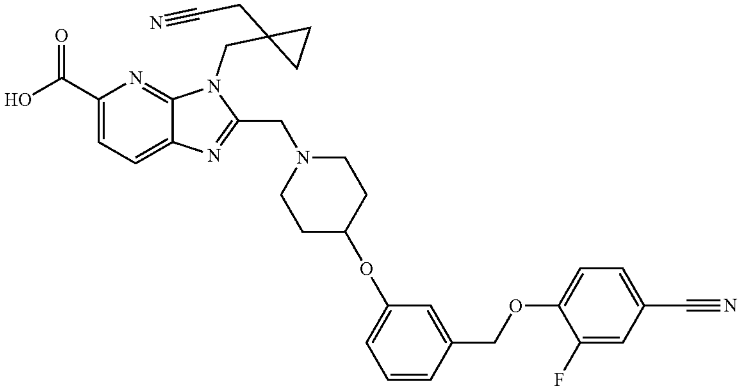 | 595 |

-continued
| Number | Structure | MS m/z: [M + H]+ |
| --- | --- | --- |
| Compound 103 | 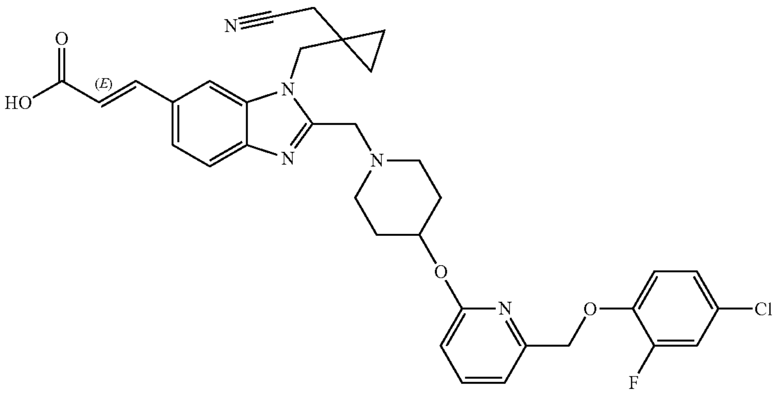 | 630 |
| Compound 104 | 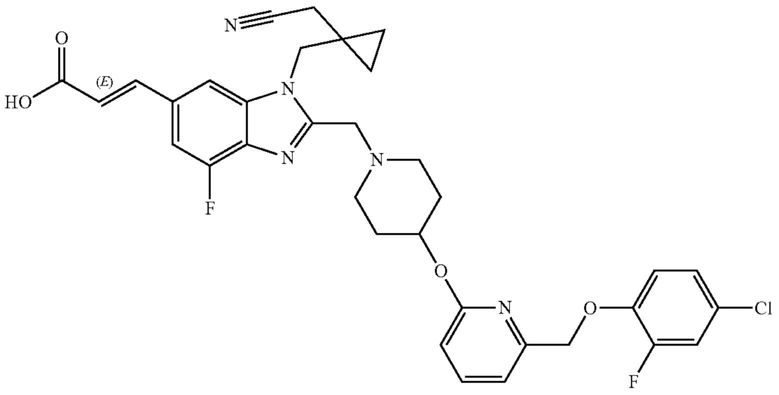 [SMILES: N#CCC1(Cn2c(CN3CCC(Oc4cccc(COc5ccc(Cl)cc5F)n4)CC3)nc3c(F)cc(/C=C/C(=O)O)cc32)CC1] | 648 |
| Compound 105 | 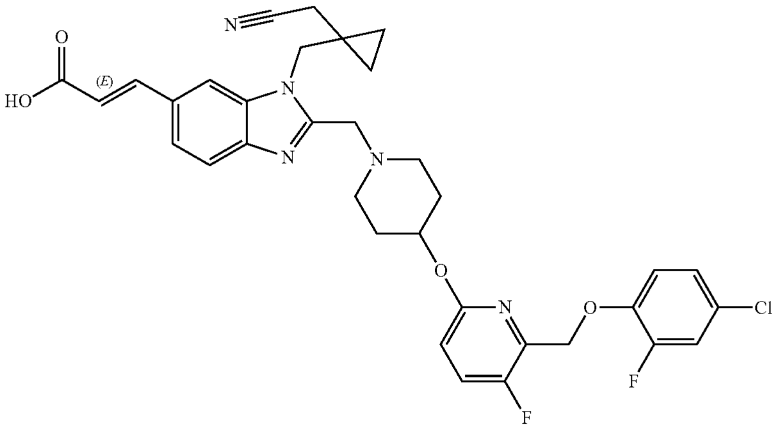 [SMILES: N#CCC1(Cn2c(CN3CCC(Oc4ccc(F)c(COc5ccc(Cl)cc5F)n4)CC3)nc3ccc(/C=C/C(=O)O)cc32)CC1] | 648 |

-continued
| Number | Structure | MS m/z: [M + H]+ |
|---|---|---|
| Compound 106 | 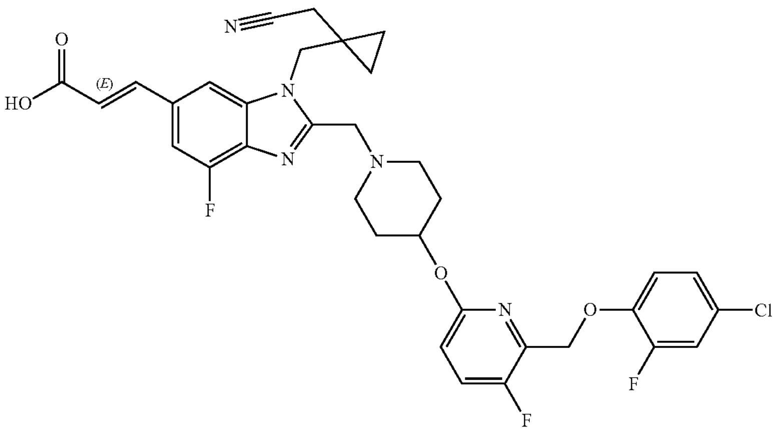 [SMILES: N#CCC1(Cn2c(CN3CCC(Oc4ccc(F)c(COc5ccc(Cl)cc5F)n4)CC3)nc3c(F)cc(/C=C/C(=O)O)cc32)CC1] | 666 |
| Compound 107 | 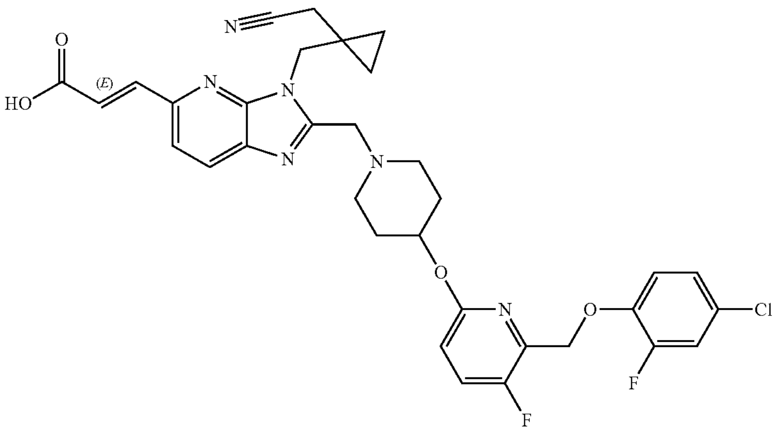 | 649 |
| Compound 108 | 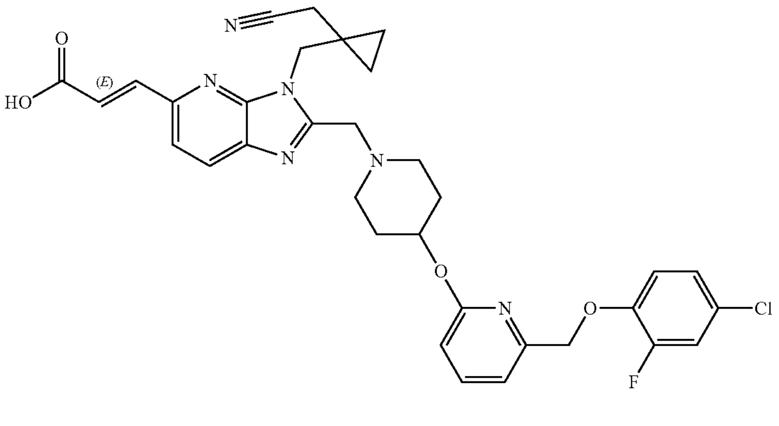 [SMILES: N#CCC1(Cn2c(CN3CCC(Oc4cccc(COc5ccc(Cl)cc5F)n4)CC3)nc3ccc(/C=C/C(=O)O)nc32)CC1] | 631 |

-continued
| Number | Structure | MS m/z: $[M + H]^+$ |
|---|---|---|
| Compound 109 | 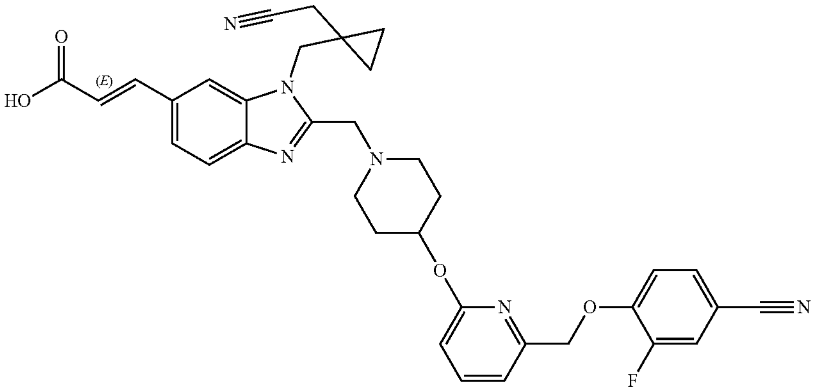 [SMILES: N#CCC1(Cn2c(CN3CCC(Oc4cccc(COc5ccc(C#N)cc5F)n4)CC3)nc3ccc(/C=C/C(=O)O)cc32)CC1] | 621 |
| Compound 110 | 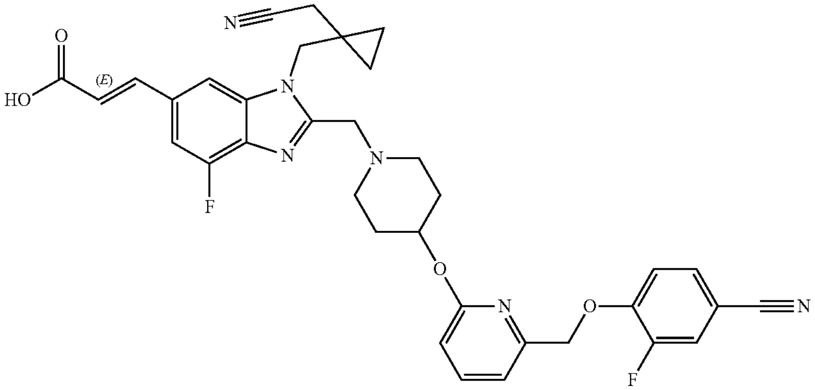 [SMILES: N#CCC1(Cn2c(CN3CCC(Oc4cccc(COc5ccc(C#N)cc5F)n4)CC3)nc3c(F)cc(/C=C/C(=O)O)cc32)CC1] | 639 |
| Compound 111 | 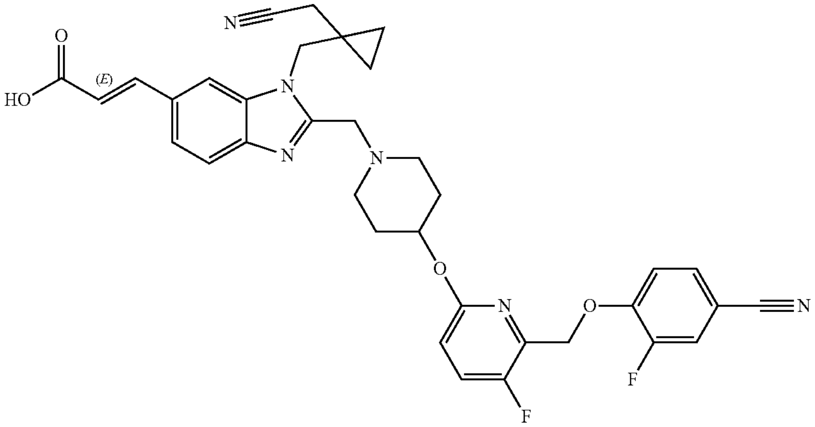 [SMILES: N#CCC1(Cn2c(CN3CCC(Oc4ccc(F)c(COc5ccc(C#N)cc5F)n4)CC3)nc3ccc(/C=C/C(=O)O)cc32)CC1] | 639 |

-continued
| Number | Structure | MS m/z: [M + H]+ |
|---|---|---|
| Compound 112 | 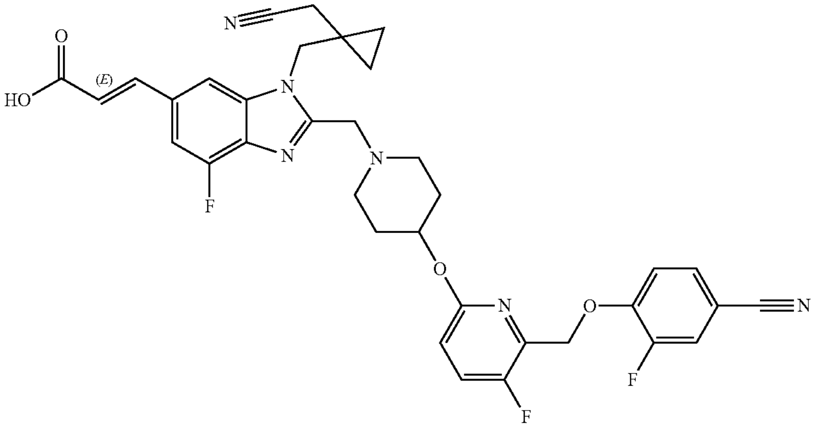 [SMILES: N#CCC1(Cn2c(CN3CCC(Oc4ccc(F)c(COc5ccc(C#N)cc5F)n4)CC3)nc3c(F)cc(/C=C/C(=O)O)cc32)CC1] | 657 |
| Compound 113 | 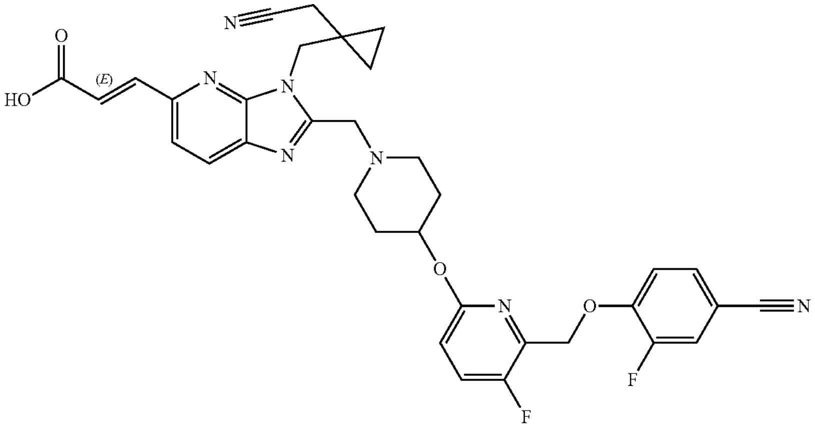 | 640 |
| Compound 114 | 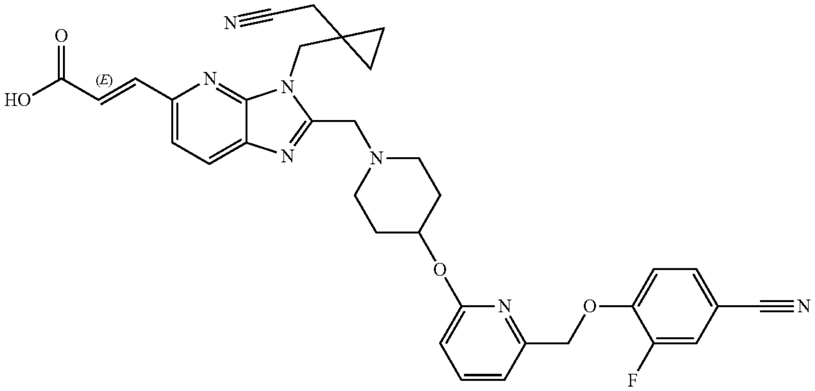 [SMILES: N#CCC1(Cn2c(CN3CCC(Oc4cccc(COc5ccc(C#N)cc5F)n4)CC3)nc3ccc(/C=C/C(=O)O)nc32)CC1] | 622 |

-continued
| Number | Structure | MS m/z: [M + H]+ |
|---|---|---|
| Compound 115 | 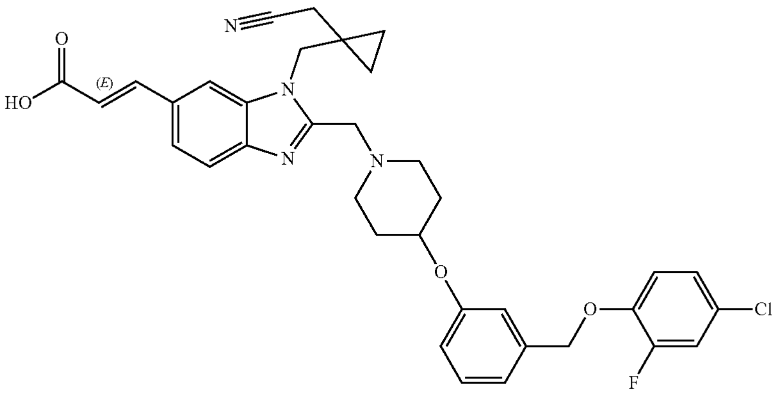 [SMILES: N#CCC1(Cn2c(CN3CCC(Oc4cccc(COc5ccc(Cl)cc5F)c4)CC3)nc3ccc(/C=C/C(=O)O)cc32)CC1] | 629 |
| Compound 116 | 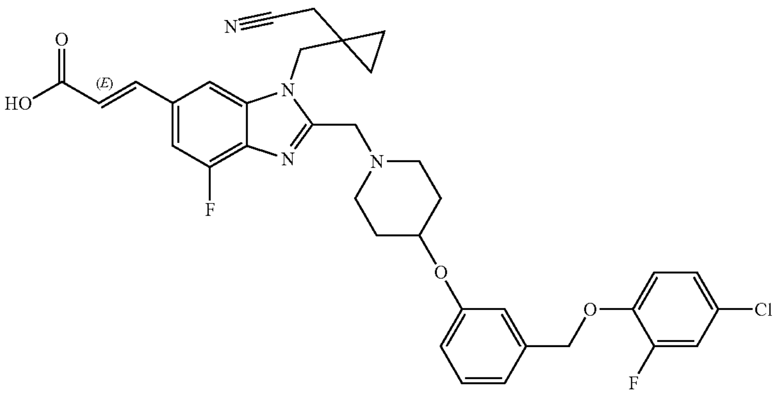 [SMILES: N#CCC1(Cn2c(CN3CCC(Oc4cccc(COc5ccc(Cl)cc5F)c4)CC3)nc3c(F)cc(/C=C/C(=O)O)cc32)CC1] | 647 |
| Compound 117 | 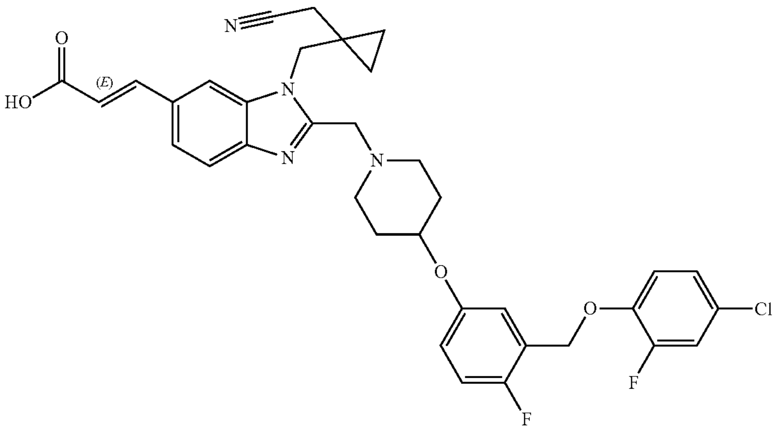 [SMILES: N#CCC1(Cn2c(CN3CCC(Oc4ccc(F)c(COc5ccc(Cl)cc5F)c4)CC3)nc3ccc(/C=C/C(=O)O)cc32)CC1] | 647 |

-continued
| Number | Structure | MS m/z: [M + H]+ |
|---|---|---|
| Compound 118 | 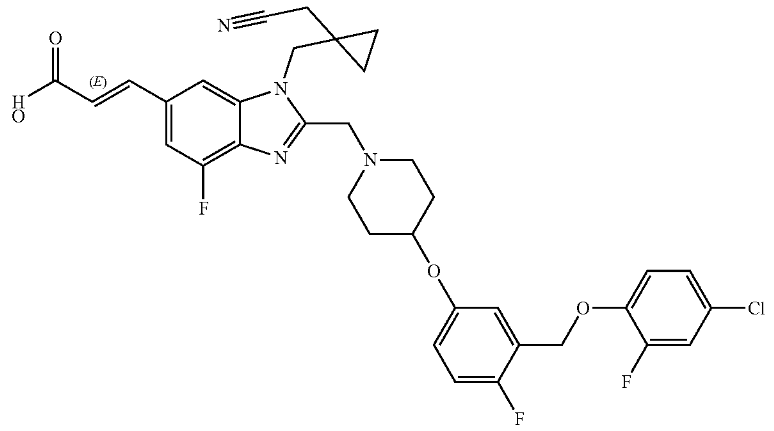 [SMILES: N#CCC1(Cn2c(CN3CCC(Oc4ccc(F)c(COc5ccc(Cl)cc5F)c4)CC3)nc3c(F)cc(/C=C/C(=O)O)cc32)CC1] | 665 |
| Compound 119 | 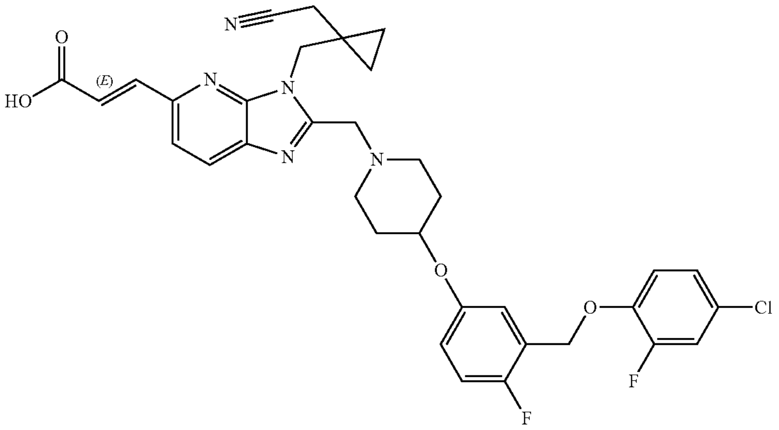 [SMILES: N#CCC1(Cn2c(CN3CCC(Oc4ccc(F)c(COc5ccc(Cl)cc5F)c4)CC3)nc3ccc(/C=C/C(=O)O)nc32)CC1] | 648 |
| Compound 120 | 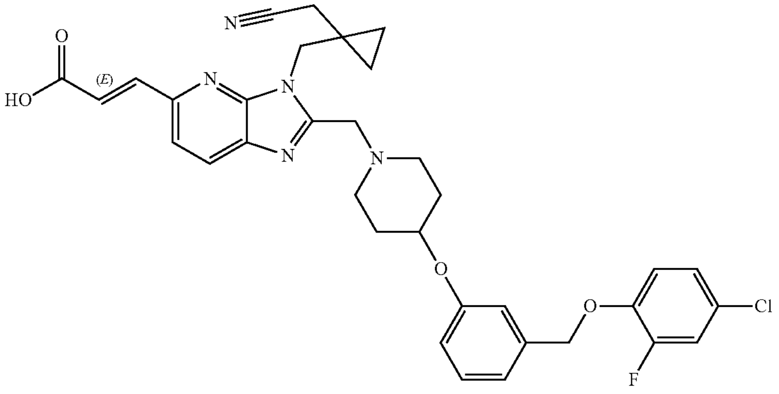 | 630 |

-continued
| Number | Structure | MS m/z: [M + H]+ |
|---|---|---|
| Compound 121 | 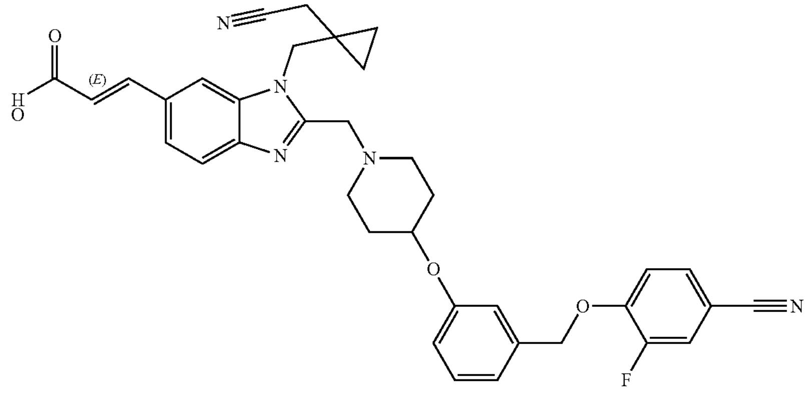 [SMILES: N#CCC1(Cn2c(CN3CCC(Oc4cccc(COc5ccc(C#N)cc5F)c4)CC3)nc3ccc(/C=C/C(=O)O)cc32)CC1] | 620 |
| Compound 122 | 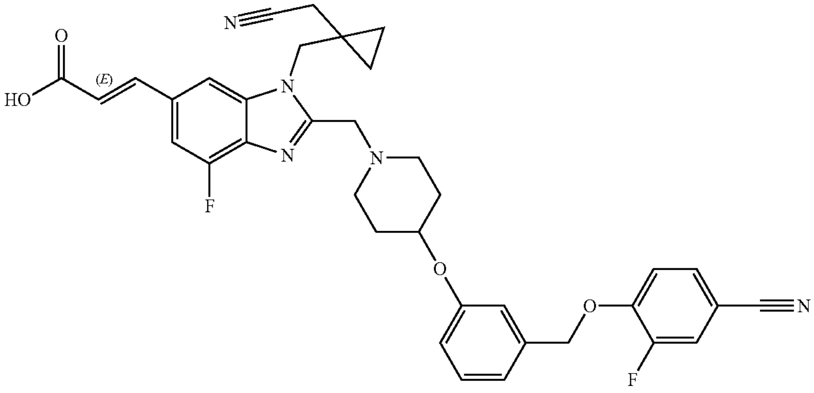 | 638 |
| Compound 123 | 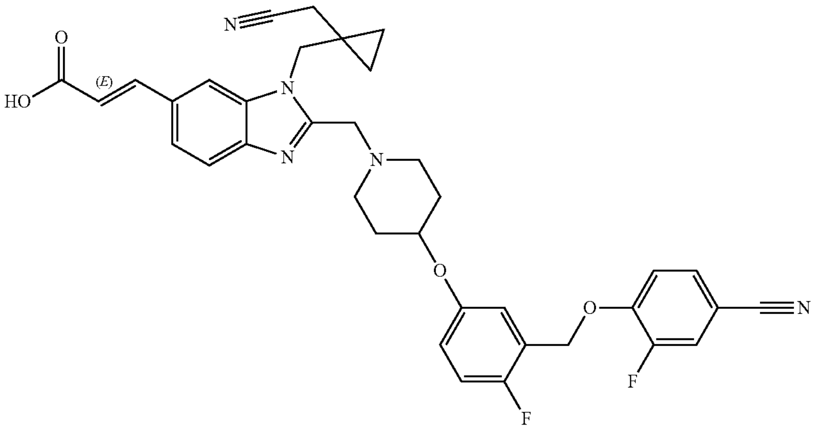 [SMILES: N#CCC1(Cn2c(CN3CCC(Oc4ccc(F)c(COc5ccc(C#N)cc5F)c4)CC3)nc3ccc(/C=C/C(=O)O)cc32)CC1] | 638 |

-continued
| Number | Structure | MS m/z: [M + H]+ |
|---|---|---|
| Compound 124 | 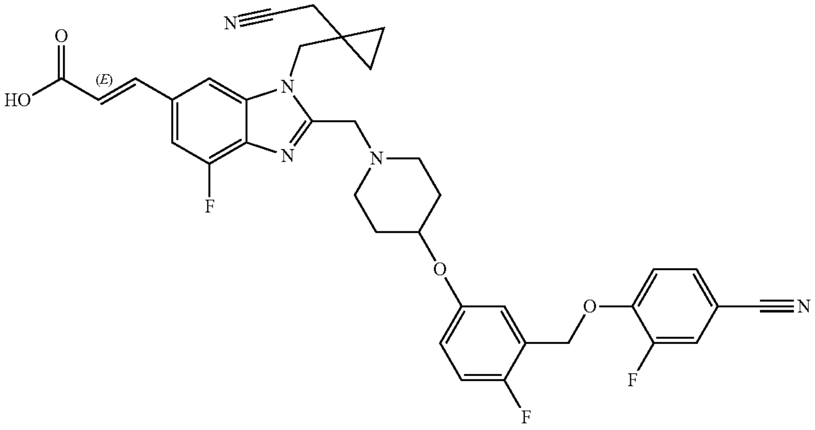 | 656 |
| Compound 125 | 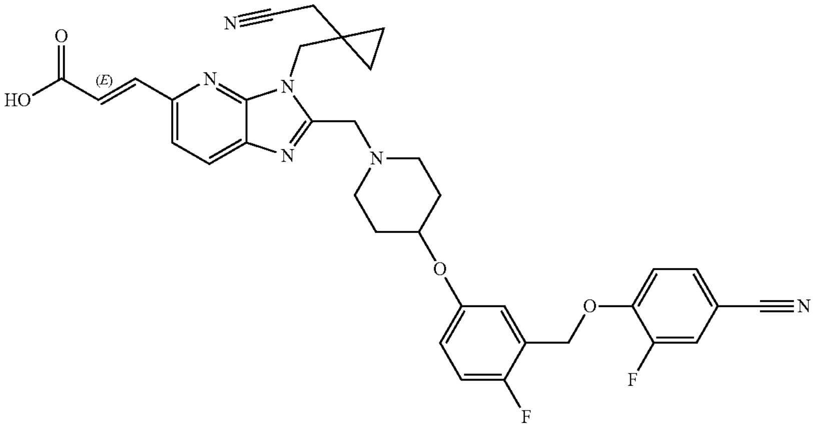 [SMILES: N#CCC1(Cn2c(CN3CCC(Oc4ccc(F)c(COc5ccc(C#N)cc5F)c4)CC3)nc3ccc(/C=C/C(=O)O)nc32)CC1] | 639 |
| Compound 126 | 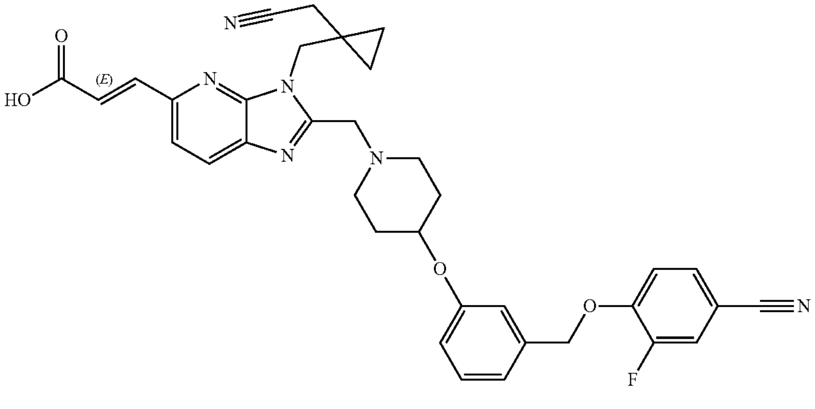 [SMILES: N#CCC1(Cn2c(CN3CCC(Oc4cccc(COc5ccc(C#N)cc5F)c4)CC3)nc3ccc(/C=C/C(=O)O)nc32)CC1] | 621 |

-continued
| Number | Structure | MS m/z: [M + H]+ |
|---|---|---|
| Compound 128 | 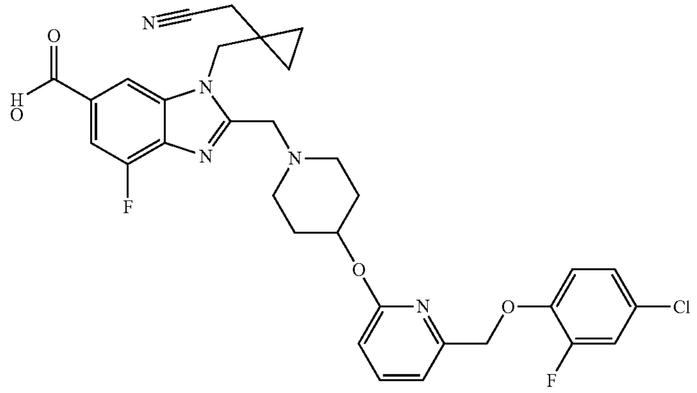 [SMILES: N#CCC1(Cn2c(CN3CCC(Oc4cccc(COc5ccc(Cl)cc5F)n4)CC3)nc3c(F)cc(C(=O)O)cc32)CC1] | 622 |
| Compound 129 | 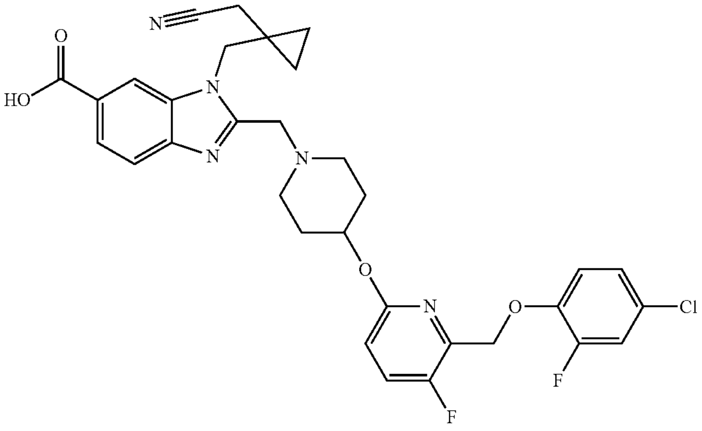 [SMILES: N#CCC1(Cn2c(CN3CCC(Oc4ccc(F)c(COc5ccc(Cl)cc5F)n4)CC3)nc3ccc(C(=O)O)cc32)CC1] | 622 |
| Compound 130 | 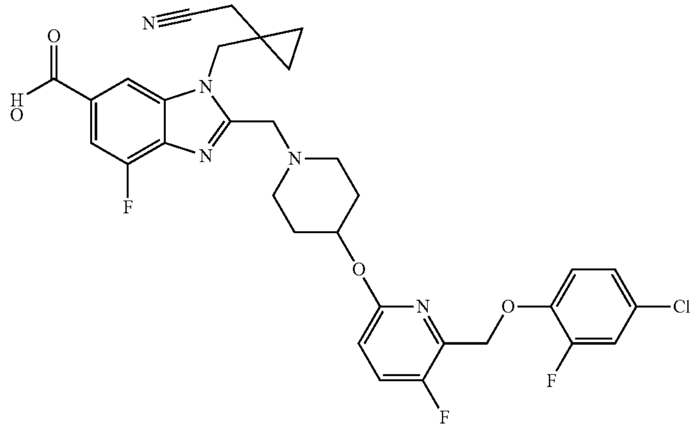 [SMILES: N#CCC1(Cn2c(CN3CCC(Oc4ccc(F)c(COc5ccc(Cl)cc5F)n4)CC3)nc3c(F)cc(C(=O)O)cc32)CC1] | 640 |

-continued
| Number | Structure | MS m/z: [M + H]$^+$ |
|---|---|---|
| Compound 131 | 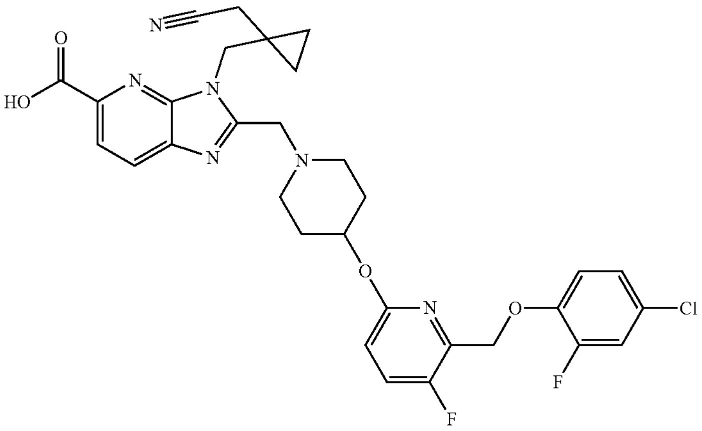 [SMILES: N#CCC1(Cn2c(CN3CCC(Oc4ccc(F)c(COc5ccc(Cl)cc5F)n4)CC3)nc3ccc(C(=O)O)nc32)CC1] | 623 |
| Compound 132 | 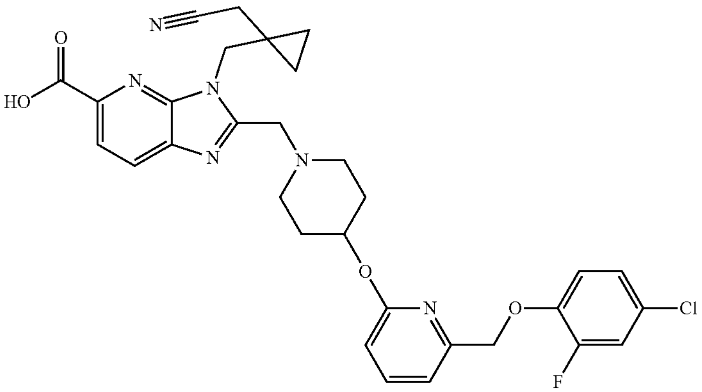 [SMILES: N#CCC1(Cn2c(CN3CCC(Oc4cccc(COc5ccc(Cl)cc5F)n4)CC3)nc3ccc(C(=O)O)nc32)CC1] | 605 |
| Compound 136 | 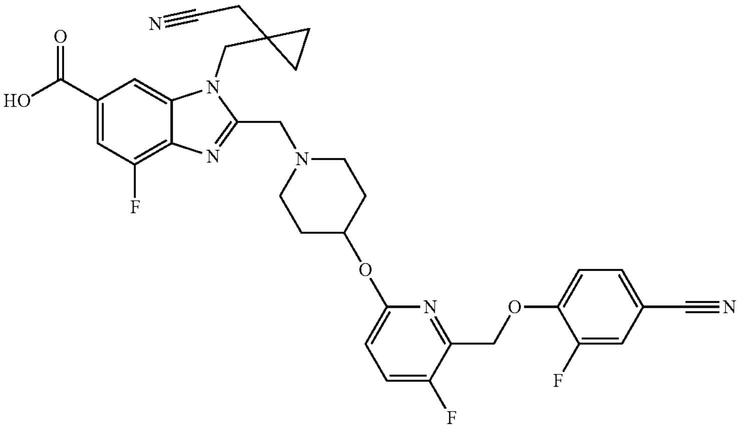 | 631 |

-continued
| Number | Structure | MS m/z: [M + H]+ |
|---|---|---|
| Compound 137 | 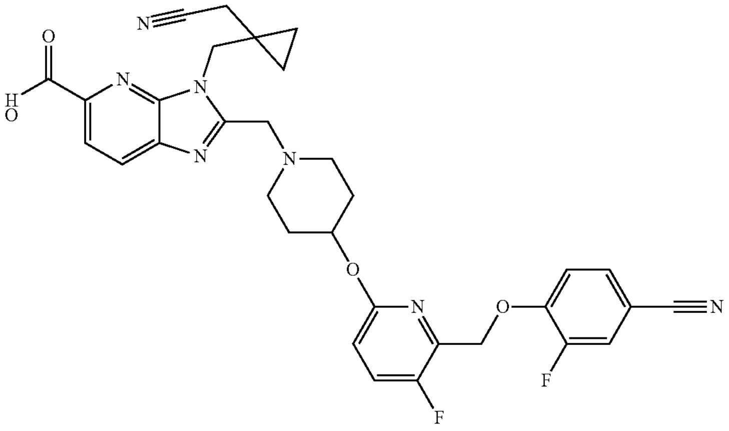 [SMILES: N#CCC1(Cn2c(CN3CCC(Oc4ccc(F)c(COc5ccc(C#N)cc5F)n4)CC3)nc3ccc(C(=O)O)nc32)CC1] | 614 |
| Compound 139 | 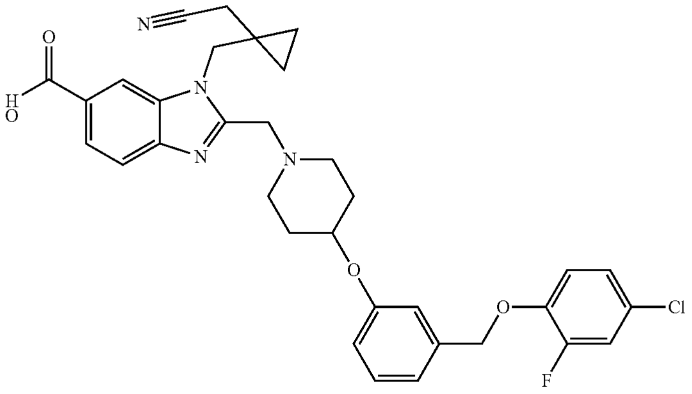 [SMILES: N#CCC1(Cn2c(CN3CCC(Oc4cccc(COc5ccc(Cl)cc5F)c4)CC3)nc3ccc(C(=O)O)cc32)CC1] | 603 |
| Compound 140 | 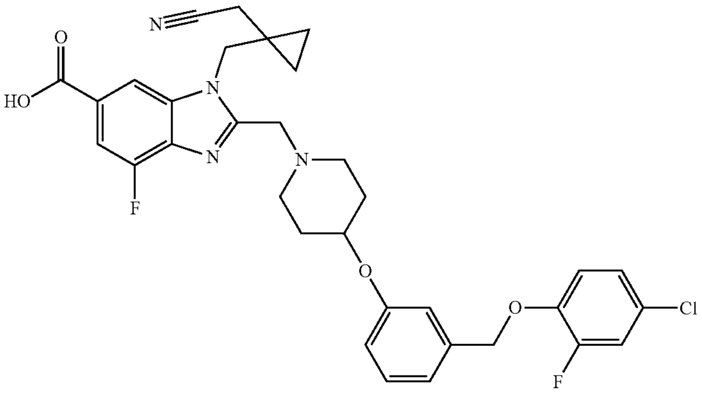 | 621 |

-continued
| Number | Structure | MS m/z: [M + H]$^+$ |
|---|---|---|
| Compound 141 | 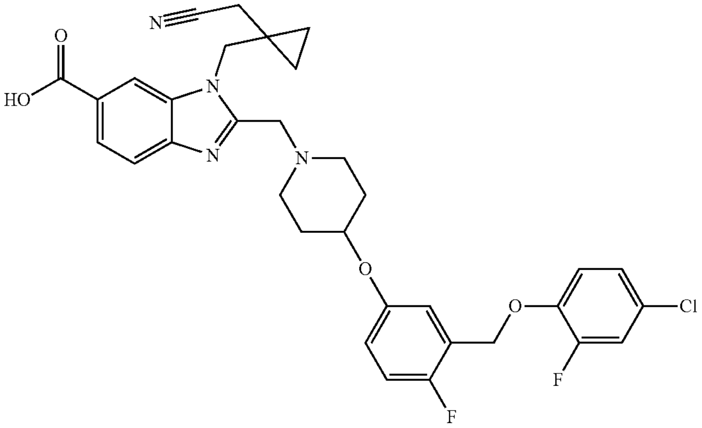 [SMILES: N#CCC1(Cn2c(CN3CCC(Oc4ccc(F)c(COc5ccc(Cl)cc5F)c4)CC3)nc3ccc(C(=O)O)cc32)CC1] | 621 |
| Compound 142 | 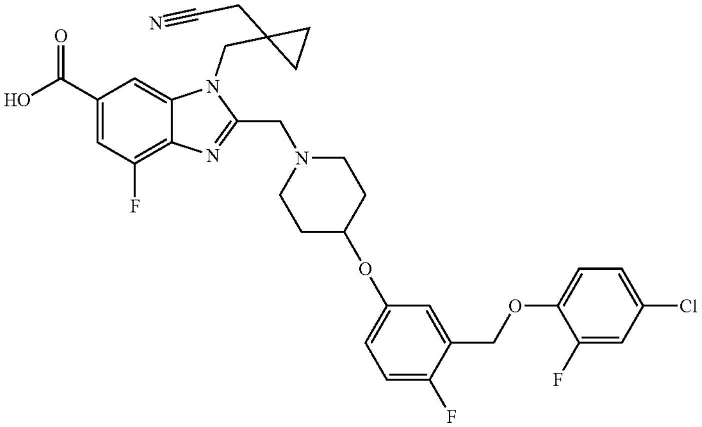 | 639 |
| Compound 143 | 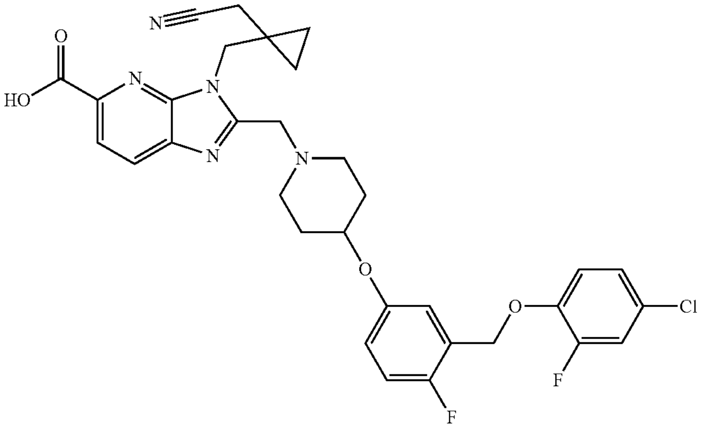 [SMILES: N#CCC1(Cn2c(CN3CCC(Oc4ccc(F)c(COc5ccc(Cl)cc5F)c4)CC3)nc3ccc(C(=O)O)nc32)CC1] | 622 |

-continued
| Number | Structure | MS m/z: [M + H]+ |
|---|---|---|
| Compound 144 | 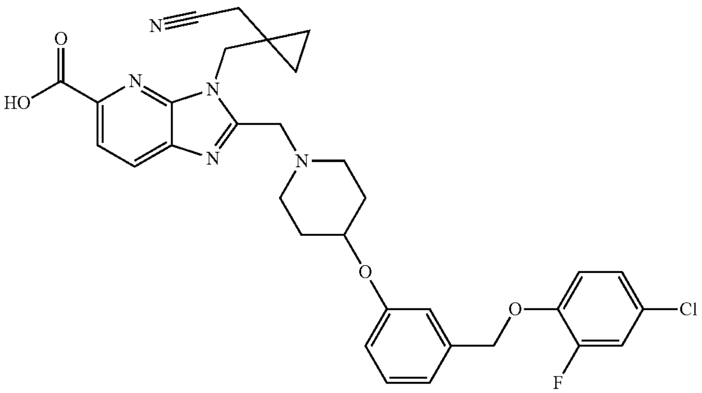 | 604 |
| Compound 145 | 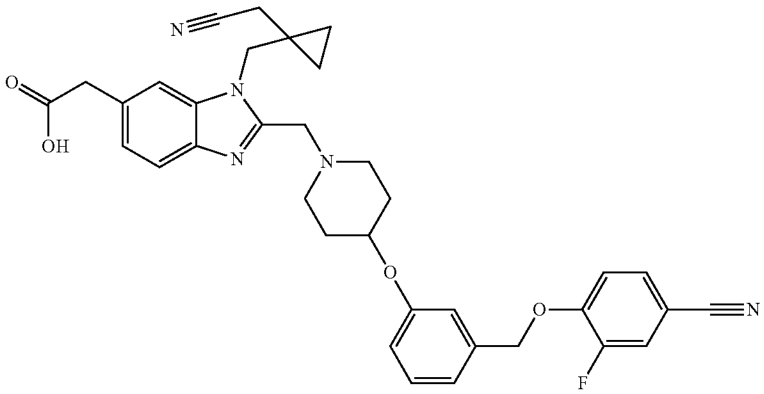 | 608 |
| Compound 146 | 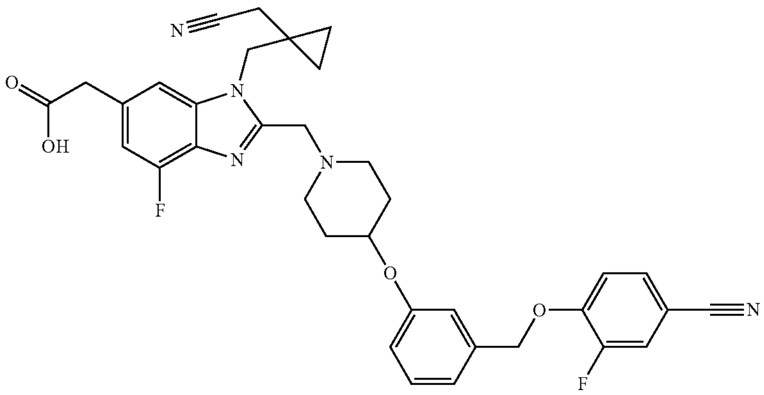 [SMILES: N#CCC1(Cn2c(CN3CCC(Oc4cccc(COc5ccc(C#N)cc5F)c4)CC3)nc3c(F)cc(CC(=O)O)cc32)CC1] | 626 |

-continued
| Number | Structure | MS m/z: [M + H]+ |
|---|---|---|
| Compound 147 | 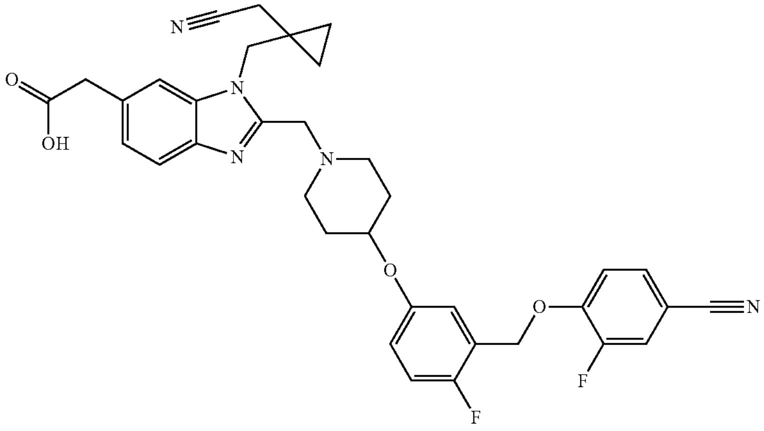 [SMILES: N#CCC1(Cn2c(CN3CCC(Oc4ccc(F)c(COc5ccc(C#N)cc5F)c4)CC3)nc3ccc(CC(=O)O)cc32)CC1] | 626 |
| Compound 148 | 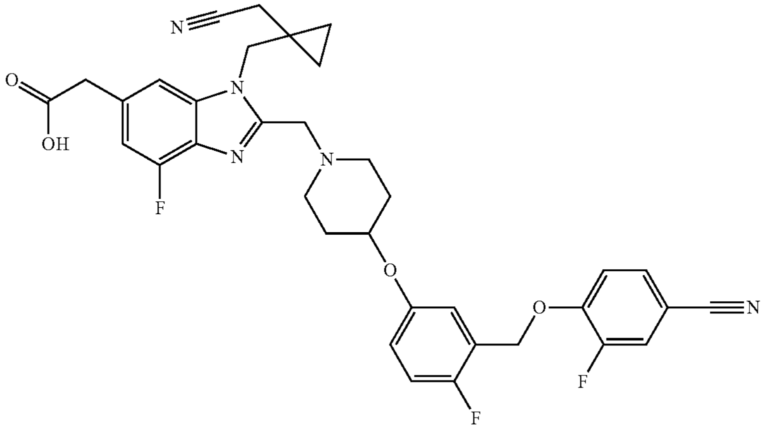 | 644 |
| Compound 149 | 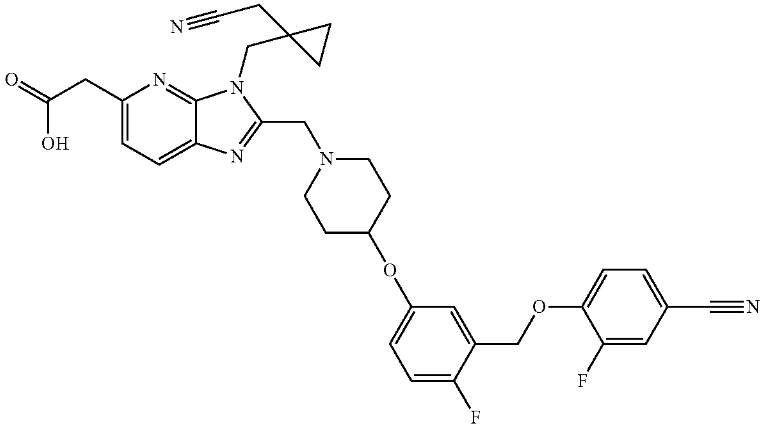 | 627 |

-continued
| Number | Structure | MS m/z: [M + H]+ |
| --- | --- | --- |
| Compound 150 | 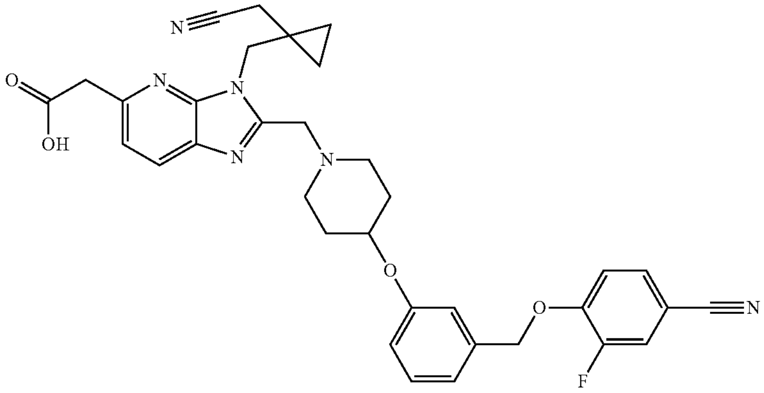 [SMILES: N#CCC1(Cn2c(CN3CCC(Oc4cccc(COc5ccc(C#N)cc5F)c4)CC3)nc3ccc(CC(=O)O)nc32)CC1] | 609 |
| Compound 151 | 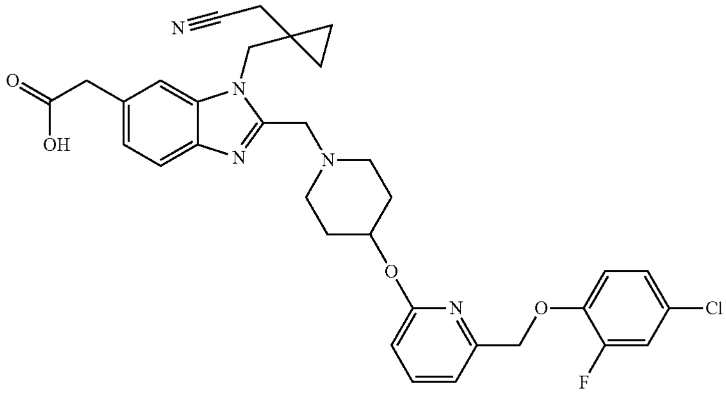 | 618 |
| Compound 152 | 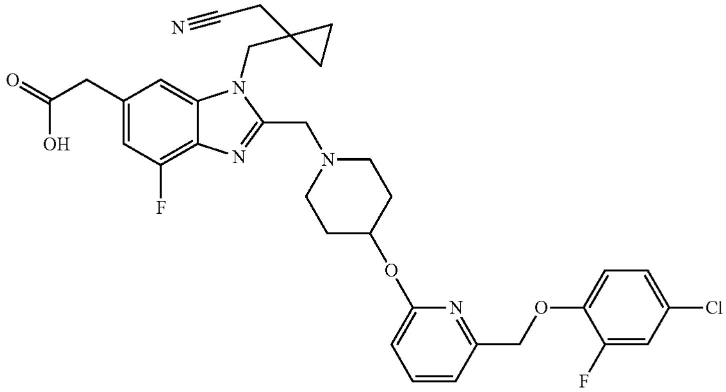 | 636 |

-continued
| Number | Structure | MS m/z: [M + H]$^+$ |
|---|---|---|
| Compound 153 | 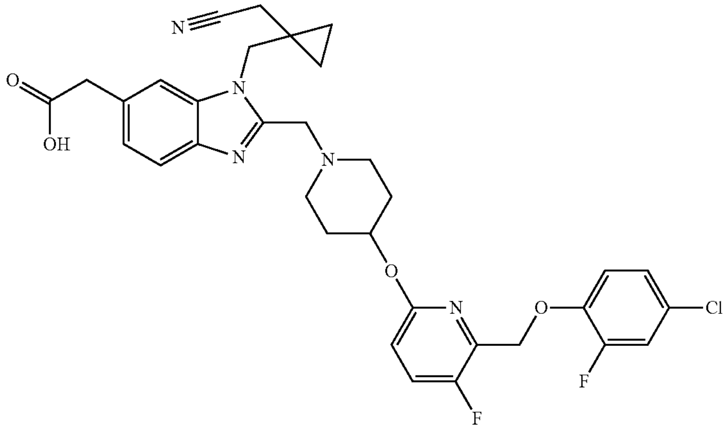 | 636 |
| Compound 154 | 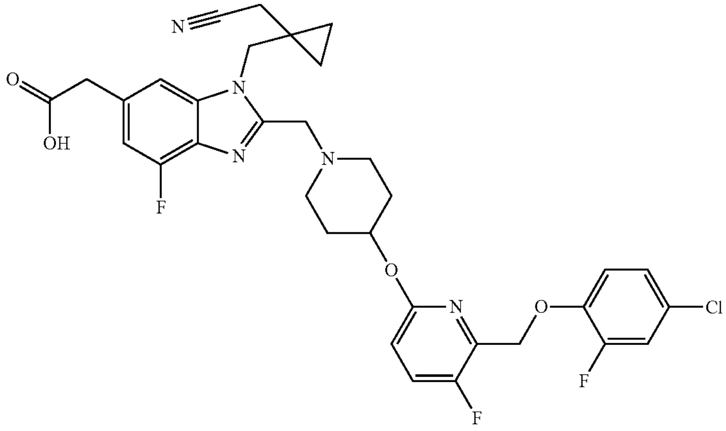 [SMILES: N#CCC1(Cn2c(CN3CCC(Oc4ccc(F)c(COc5ccc(Cl)cc5F)n4)CC3)nc3c(F)cc(CC(=O)O)cc32)CC1] | 654 |
| Compound 155 | 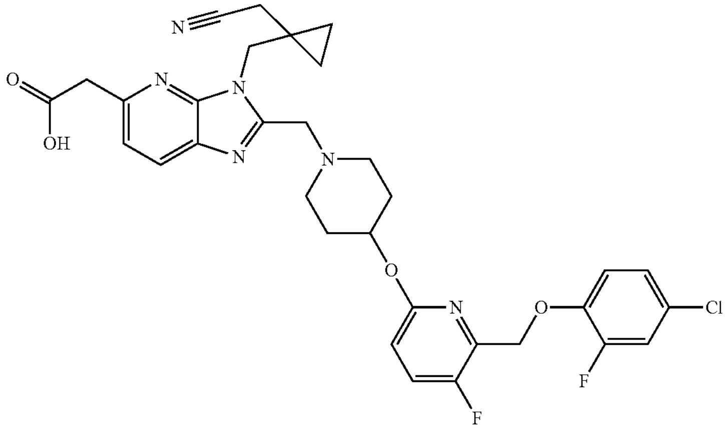 | 637 |

-continued
| Number | Structure | MS m/z: [M + H]$^+$ |
|---|---|---|
| Compound 156 | 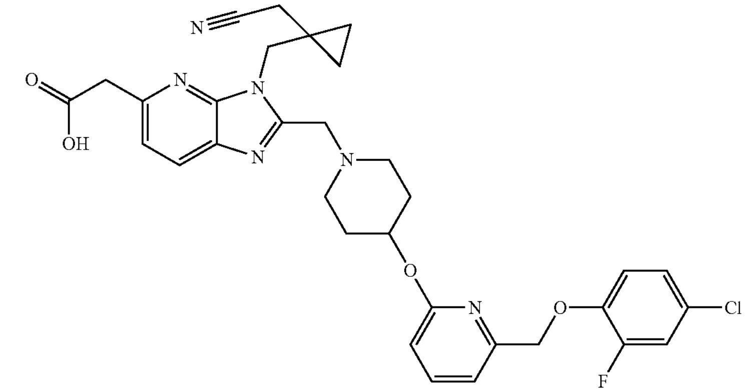 [SMILES: N#CCC1(Cn2c(CN3CCC(Oc4cccc(COc5ccc(Cl)cc5F)n4)CC3)nc3ccc(CC(=O)O)nc32)CC1] | 619 |
| Compound 157 | 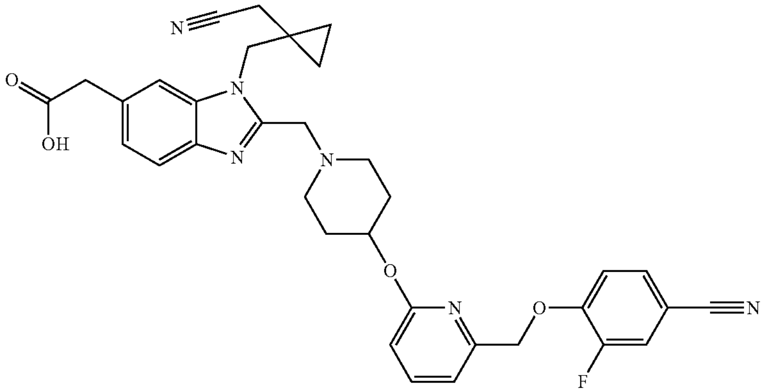 | 609 |
| Compound 158 | 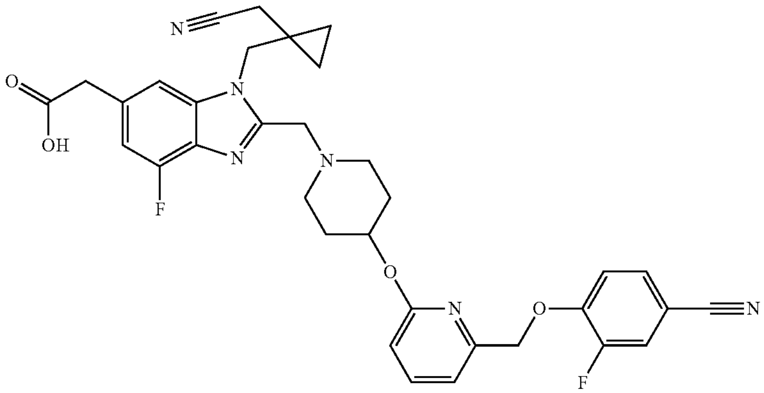 | 627 |

-continued
| Number | Structure | MS m/z: [M + H]+ |
|---|---|---|
| Compound 159 | 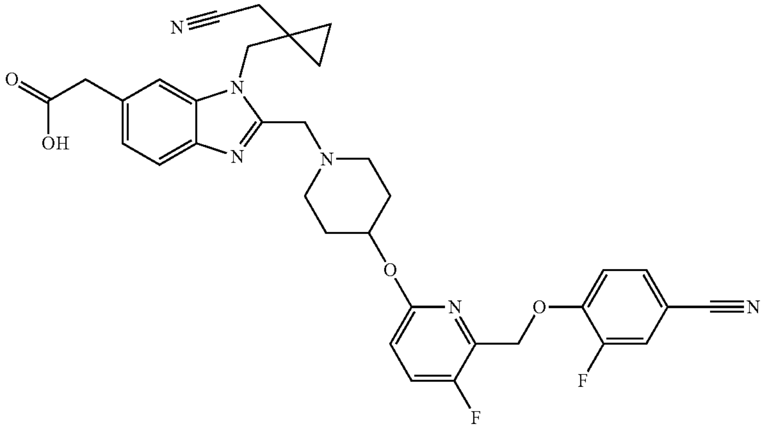 | 627 |
| Compound 160 | 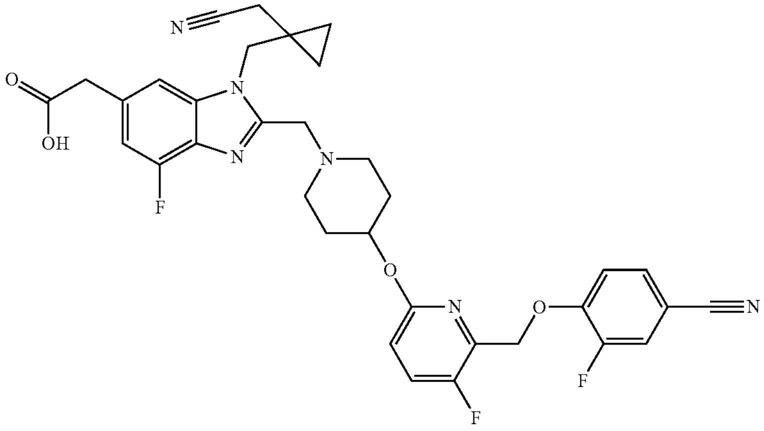 | 645 |
| Compound 161 | 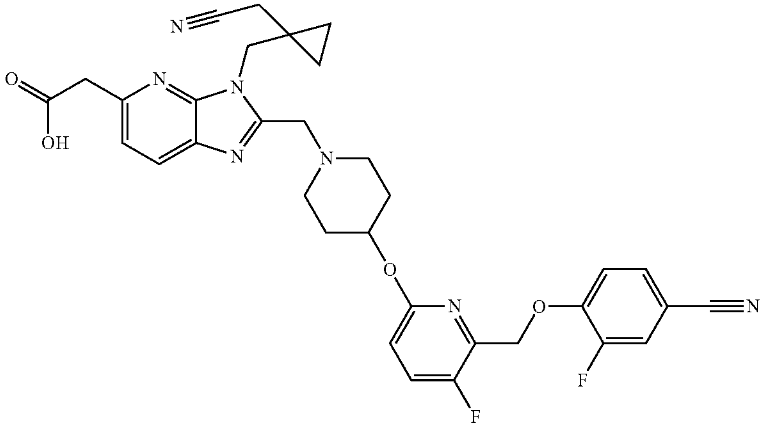 [SMILES: N#CCC1(Cn2c(CN3CCC(Oc4ccc(F)c(COc5ccc(C#N)cc5F)n4)CC3)nc3ccc(CC(=O)O)nc32)CC1] | 628 |

-continued
| Number | Structure | MS m/z: [M + H]$^+$ |
|---|---|---|
| Compound 162 | 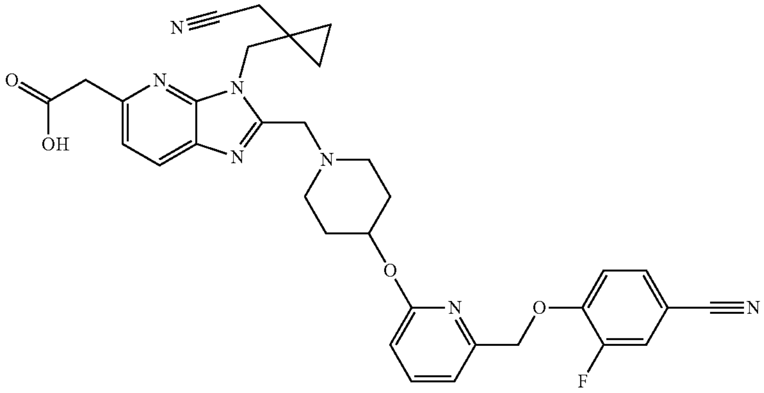 [SMILES: N#CCC1(Cn2c(CN3CCC(Oc4cccc(COc5ccc(C#N)cc5F)n4)CC3)nc3ccc(CC(=O)O)nc32)CC1] | 610 |
| Compound 163 | 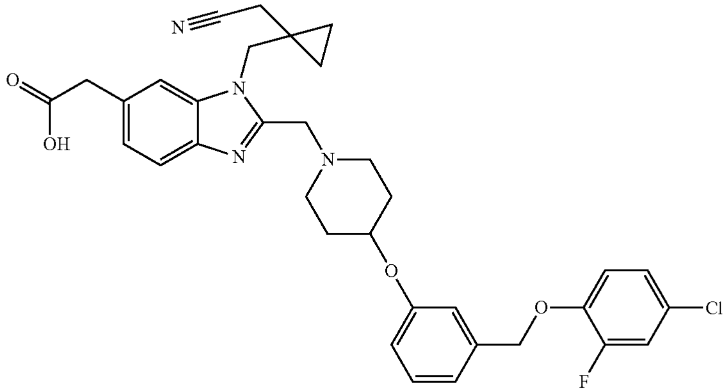 [SMILES: N#CCC1(Cn2c(CN3CCC(Oc4cccc(COc5ccc(Cl)cc5F)c4)CC3)nc3ccc(CC(=O)O)cc32)CC1] | 617 |
| Compound 164 | 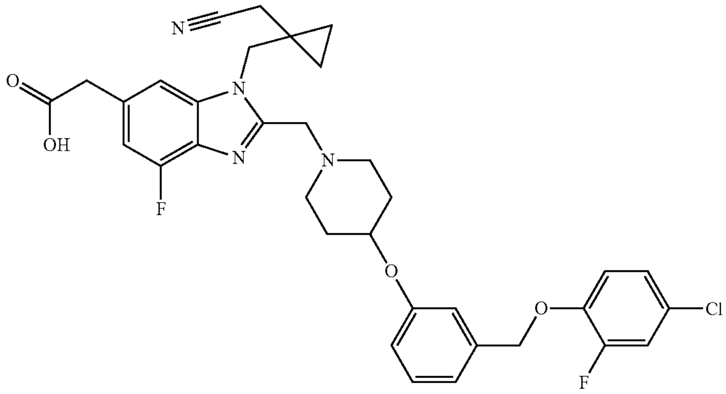 [SMILES: N#CCC1(Cn2c(CN3CCC(Oc4cccc(COc5ccc(Cl)cc5F)c4)CC3)nc3c(F)cc(CC(=O)O)cc32)CC1] | 635 |

-continued
| Number | Structure | MS m/z: [M + H]+ |
|---|---|---|
| Compound 165 | 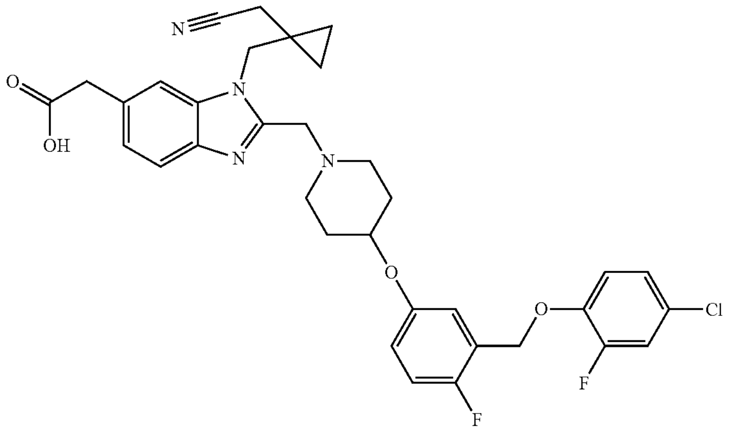 | 635 |
| Compound 166 | 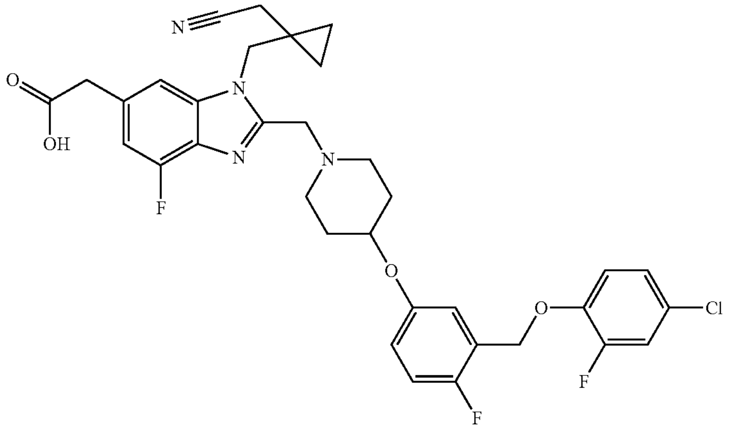 | 653 |
| Compound 167 | 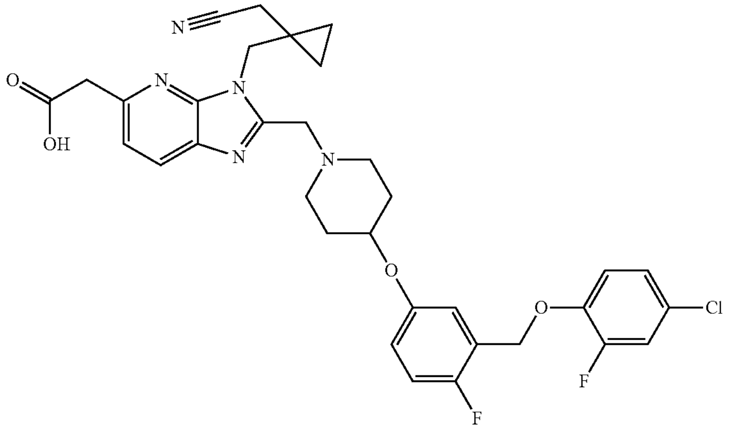 | 636 |

-continued
| Number | Structure | MS m/z: [M + H]+ |
|---|---|---|
| Compound 168 | 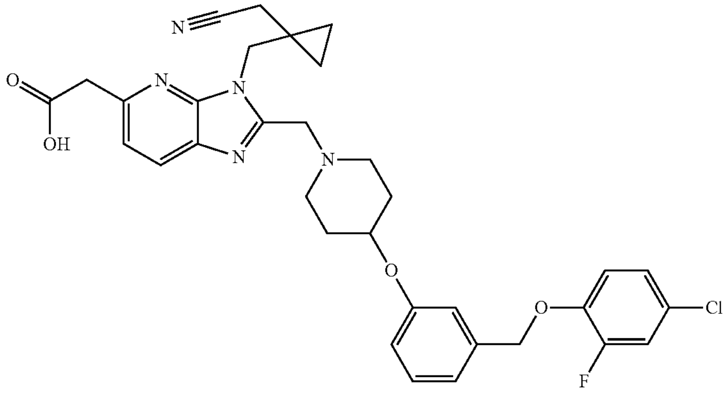 | 618 |
| Compound 169 | 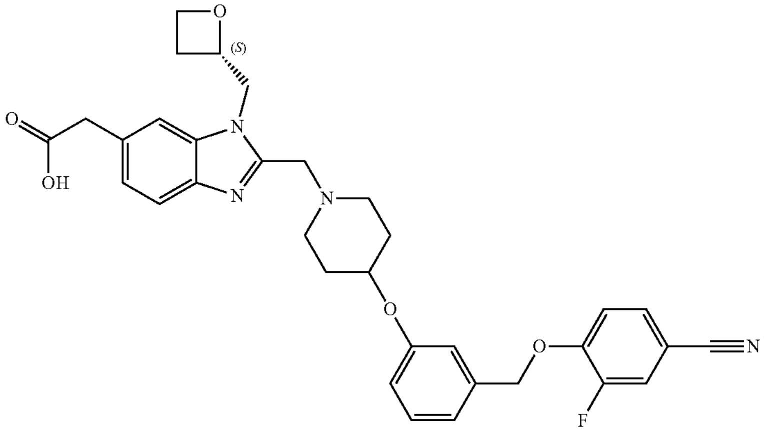 | 585 |
| Compound 170 | 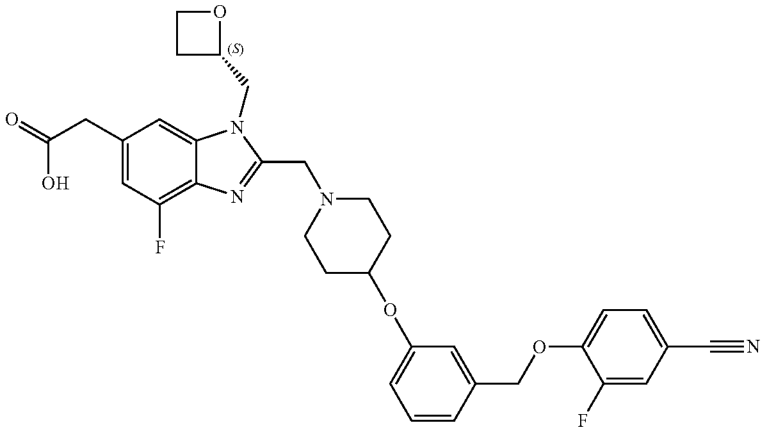 | 603 |

-continued
| Number | Structure | MS m/z: [M + H]+ |
|---|---|---|
| Compound 171 | 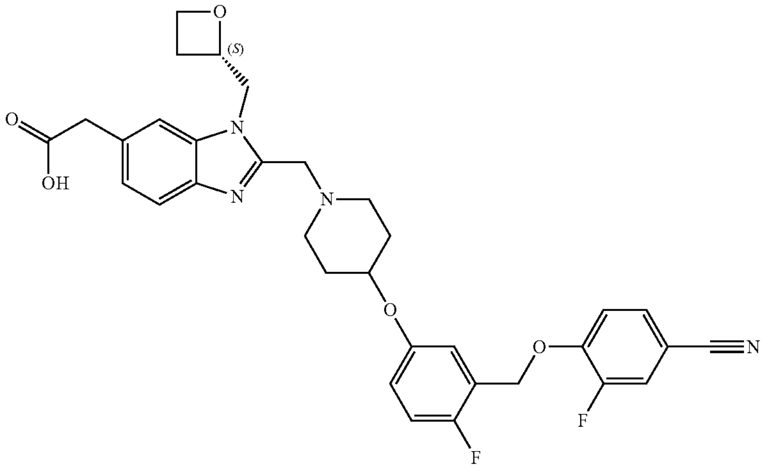 | 603 |
| Compound 172 | 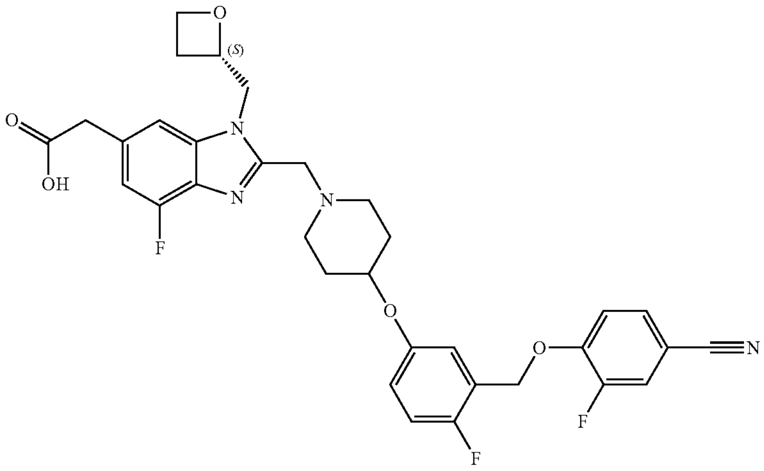 | 621 |
| Compound 173 | 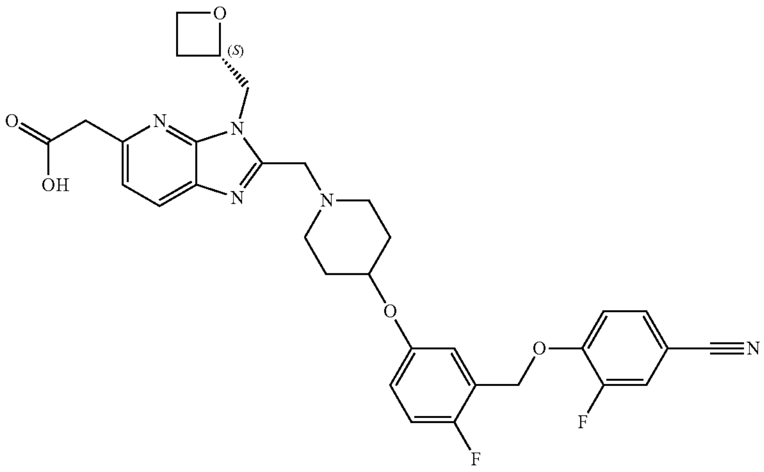 | 604 |

-continued
| Number | Structure | MS m/z: [M + H]+ |
| --- | --- | --- |
| Compound 174 | 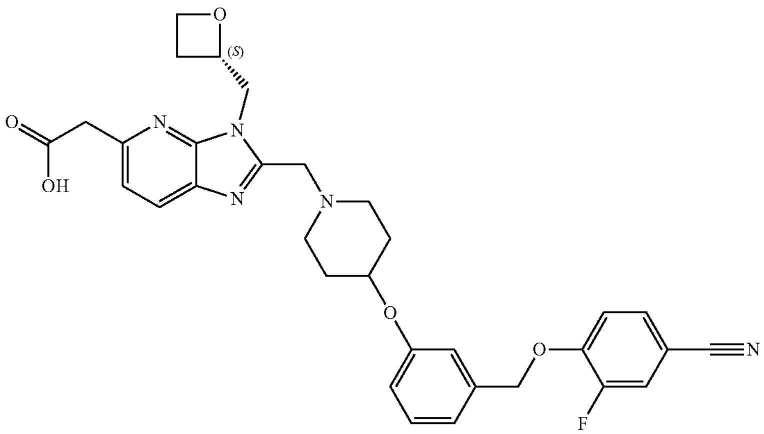 | 586 |
| Compound 175 | 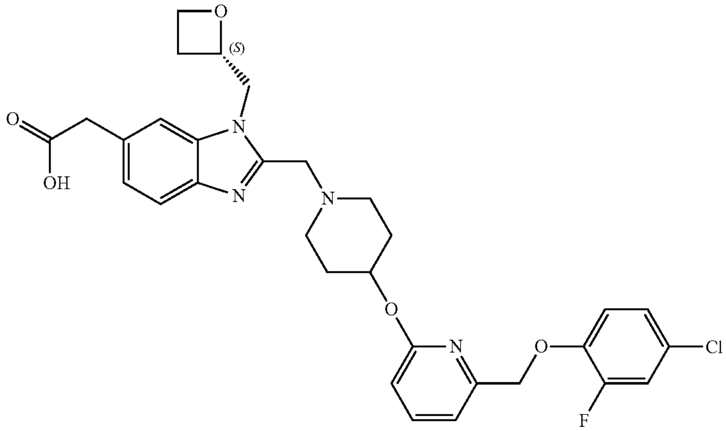 | 595 |
| Compound 176 | 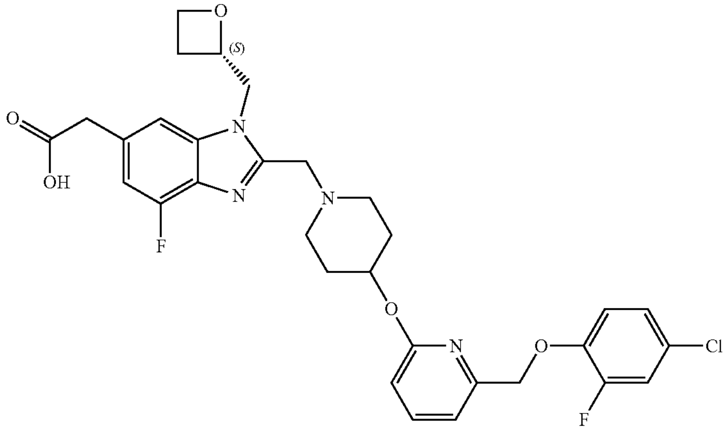 | 613 |

-continued
| Number | Structure | MS m/z: [M + H]+ |
|---|---|---|
| Compound 177 | 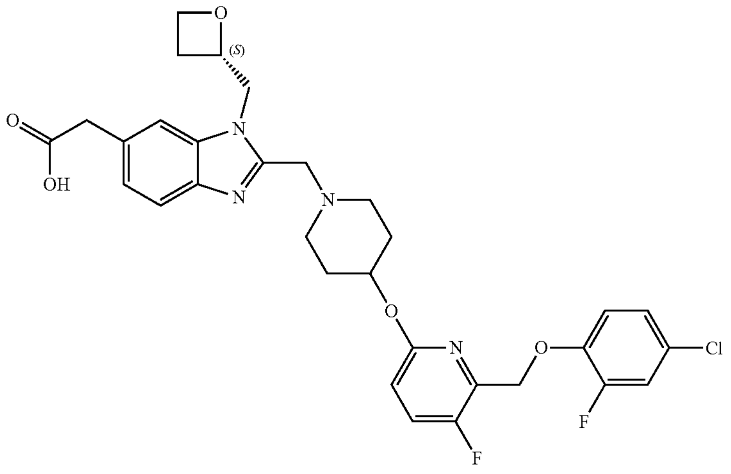 | 613 |
| Compound 179 | 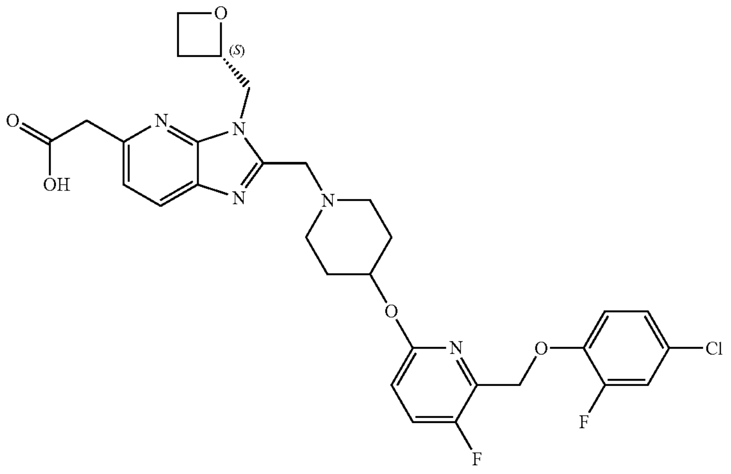 | 614 |
| Compound 180 | 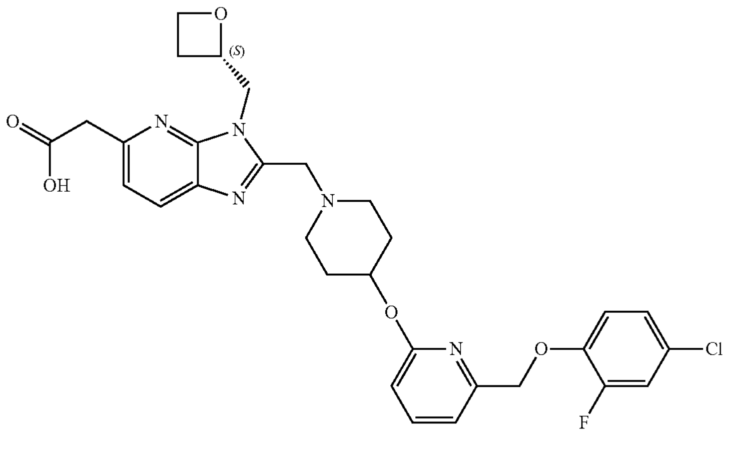 | 596 |

-continued
| Number | Structure | MS m/z: [M + H]+ |
|---|---|---|
| Compound 181 | 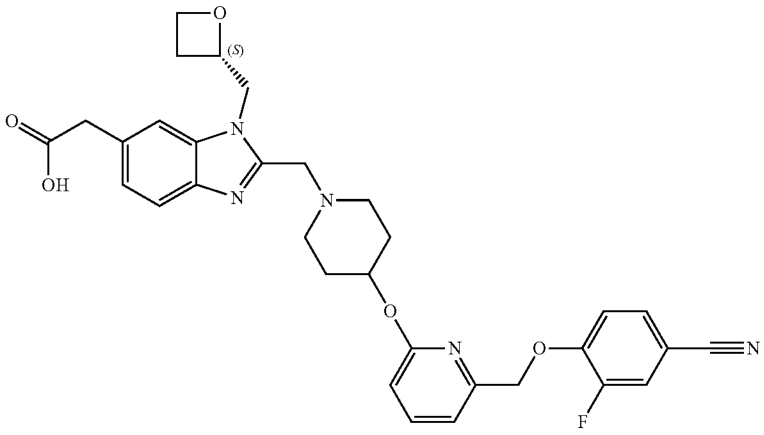 | 586 |
| Compound 182 | 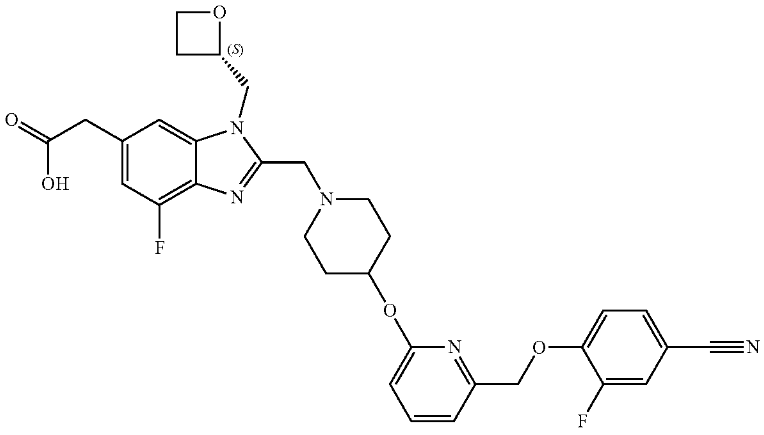 | 604 |
| Compound 183 | 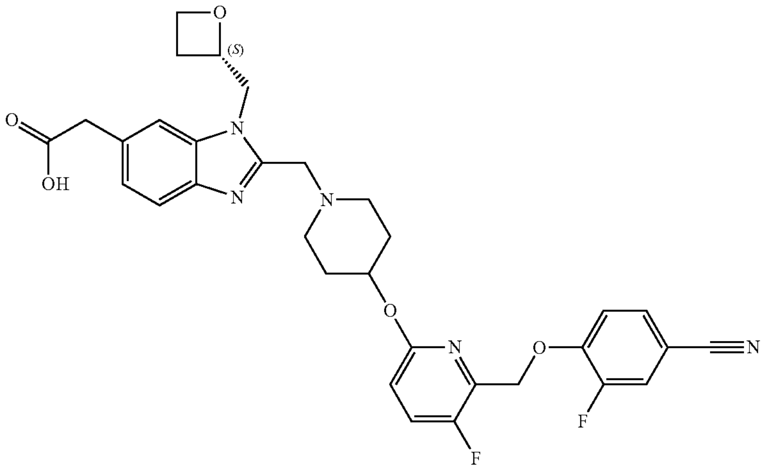 | 604 |

-continued
| Number | Structure | MS m/z: [M + H]+ |
|---|---|---|
| Compound 184 | 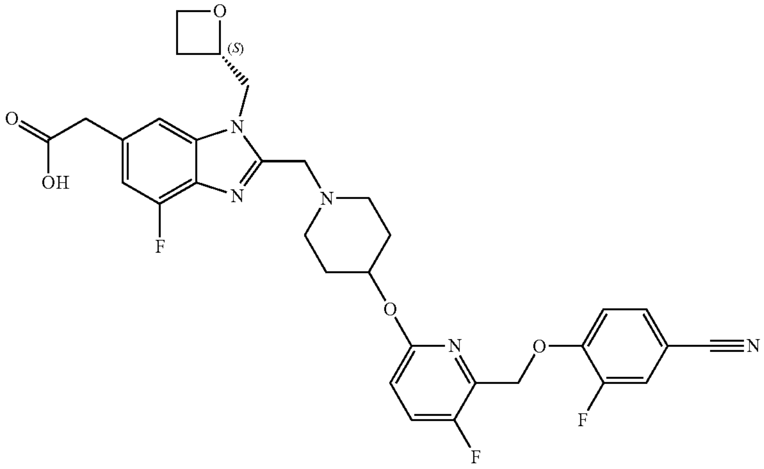 | 622 |
| Compound 185 | 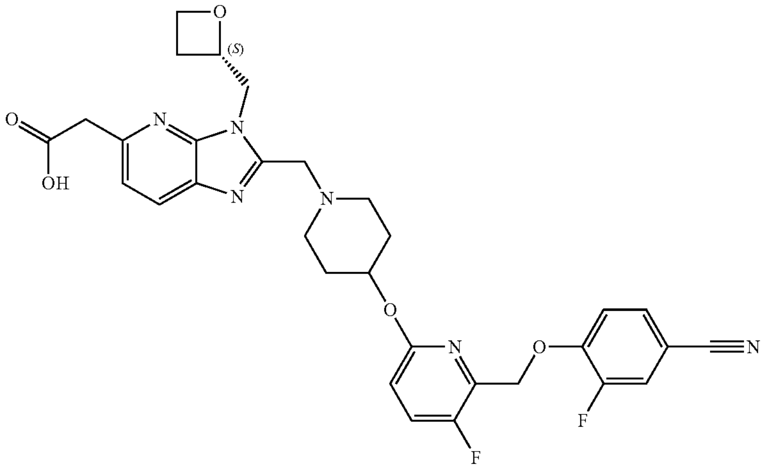 | 605 |
| Compound 186 | 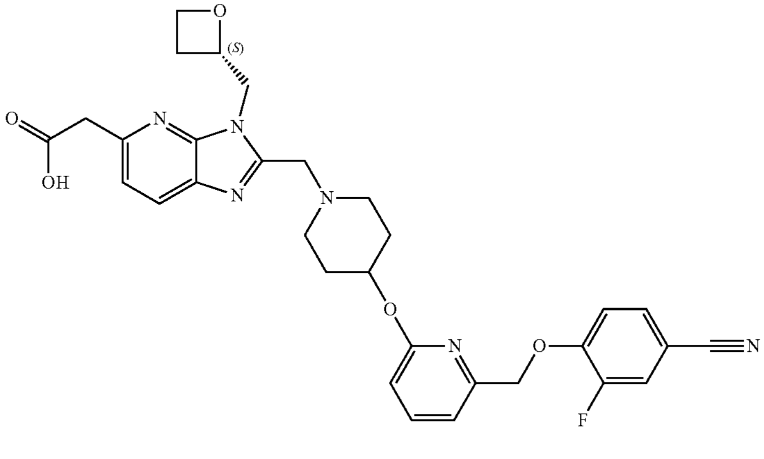 | 587 |

-continued
| Number | Structure | MS m/z: [M + H]+ |
|---|---|---|
| Compound 187 | 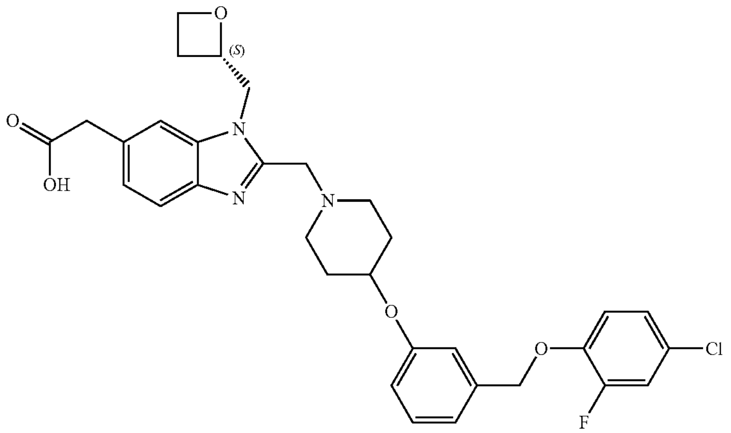 | 594 |
| Compound 188 | 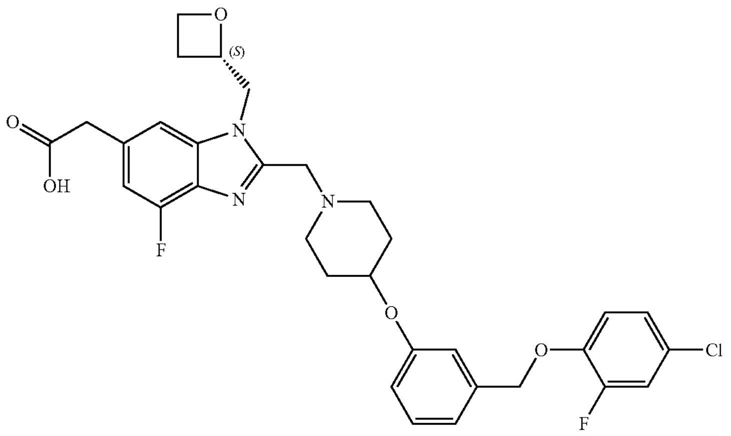 | 612 |
| Compound 189 | 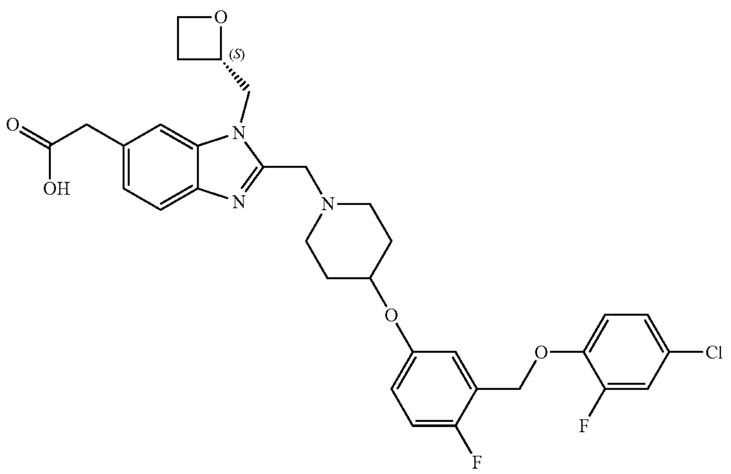 | 612 |

-continued
| Number | Structure | MS m/z: [M + H]+ |
| --- | --- | --- |
| Compound 190 | 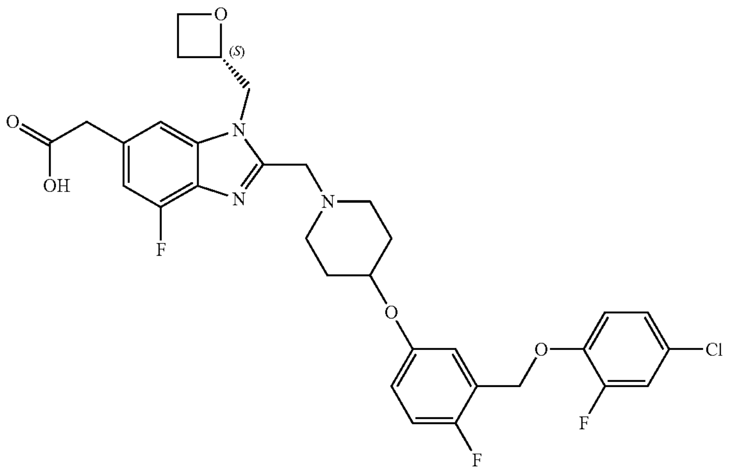 | 630 |
| Compound 191 | 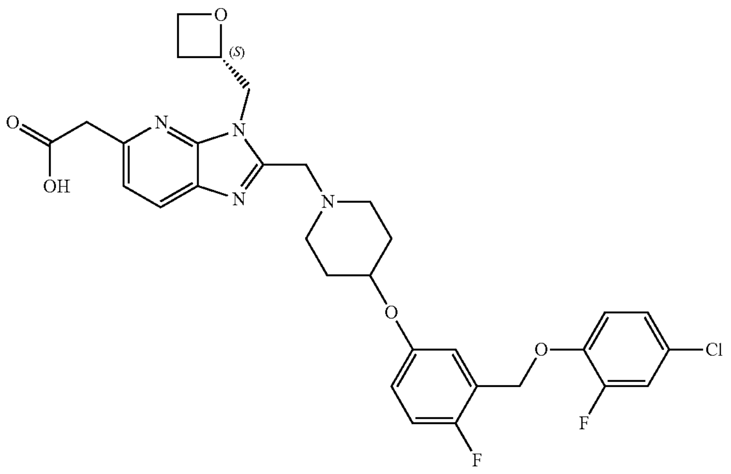 | 613 |
| Compound 192 | 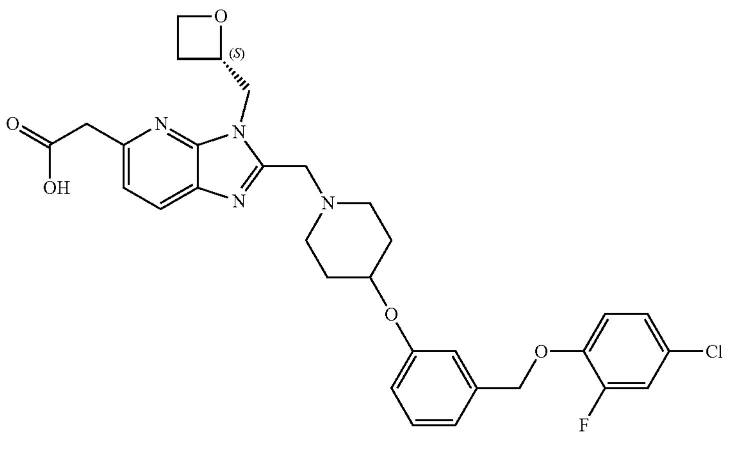 | 595 |

-continued
| Number | Structure | MS m/z: [M + H]+ |
|---|---|---|
| Compound 193 | 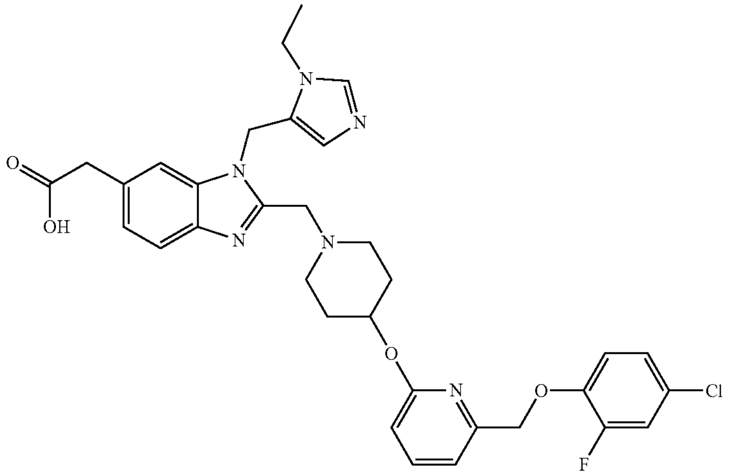 [SMILES: CCn1cncc1Cn1c(CN2CCC(Oc3cccc(COc4ccc(Cl)cc4F)n3)CC2)nc2ccc(CC(=O)O)cc21] | 633 |
| Compound 194 | 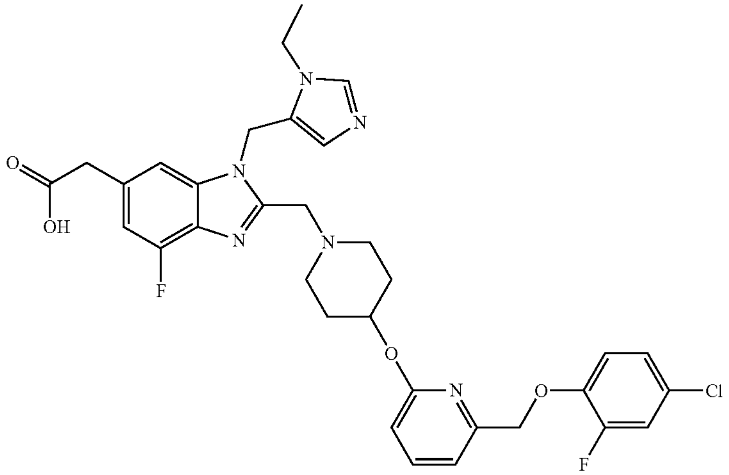 | 651 |
| Compound 195 | 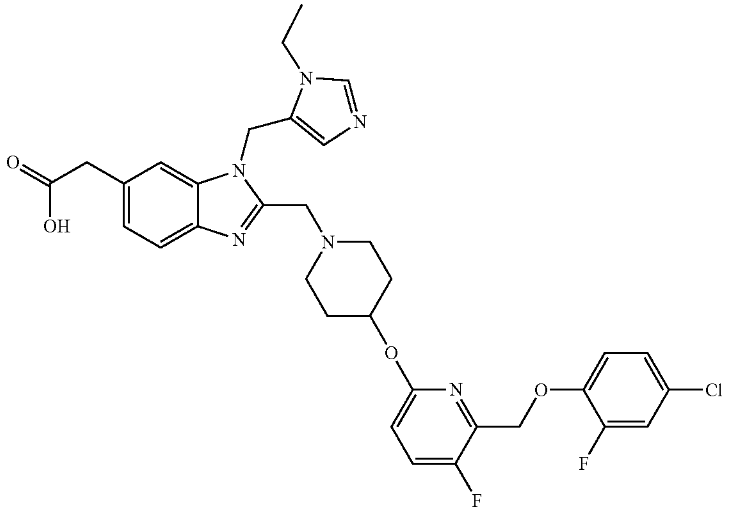 [SMILES: CCn1cncc1Cn1c(CN2CCC(Oc3ccc(F)c(COc4ccc(Cl)cc4F)n3)CC2)nc2ccc(CC(=O)O)cc21] | 651 |

-continued
| Number | Structure | MS m/z: [M + H]+ |
| --- | --- | --- |
| Compound 196 | 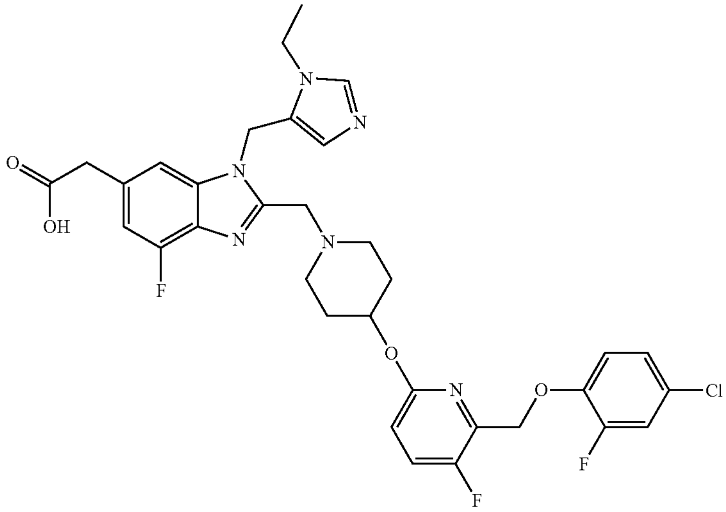 [SMILES: CCn1cncc1Cn1c(CN2CCC(Oc3ccc(F)c(COc4ccc(Cl)cc4F)n3)CC2)nc2c(F)cc(CC(=O)O)cc21] | 669 |
| Compound 197 | 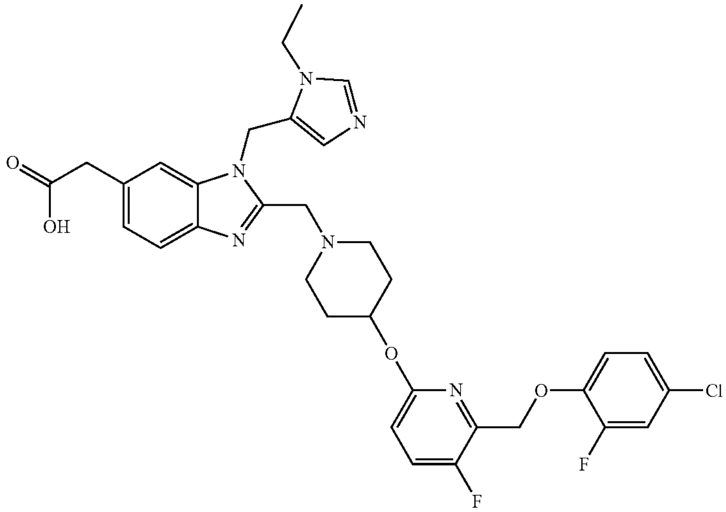 [SMILES: CCn1cncc1Cn1c(CN2CCC(Oc3ccc(F)c(COc4ccc(Cl)cc4F)n3)CC2)nc2ccc(CC(=O)O)cc21] | 652 |
| Compound 198 | 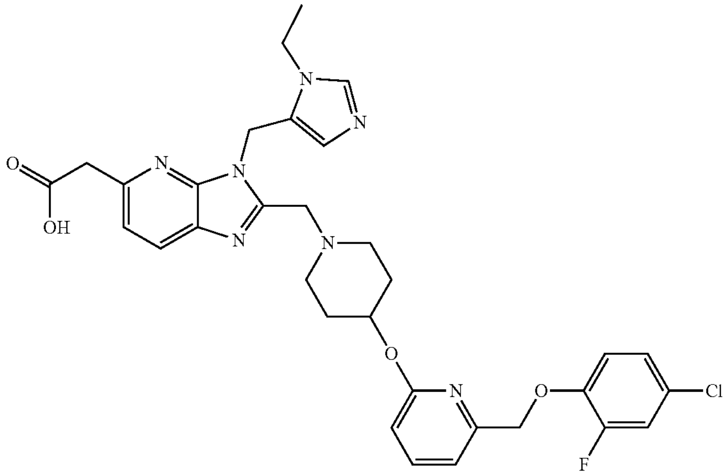 [SMILES: CCn1cncc1Cn1c(CN2CCC(Oc3cccc(COc4ccc(Cl)cc4F)n3)CC2)nc2ccc(CC(=O)O)nc21] | 634 |

-continued
| Number | Structure | MS m/z: [M + H]+ |
|---|---|---|
| Compound 199 | 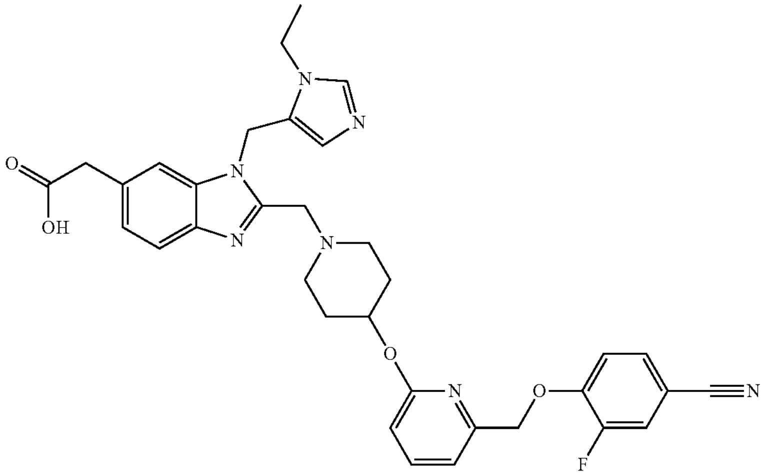 [SMILES: CCn1cncc1Cn1c(CN2CCC(Oc3cccc(COc4ccc(C#N)cc4F)n3)CC2)nc2ccc(CC(=O)O)cc21] | 624 |
| Compound 200 | 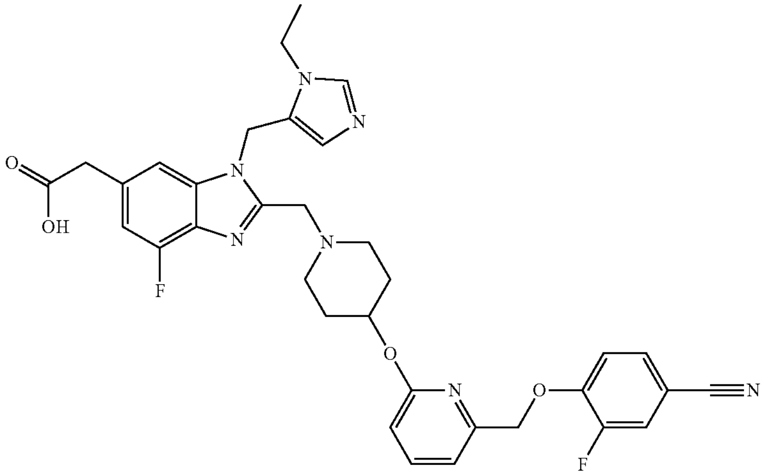 [SMILES: CCn1cncc1Cn1c(CN2CCC(Oc3cccc(COc4ccc(C#N)cc4F)n3)CC2)nc2c(F)cc(CC(=O)O)cc21] | 642 |
| Compound 201 | 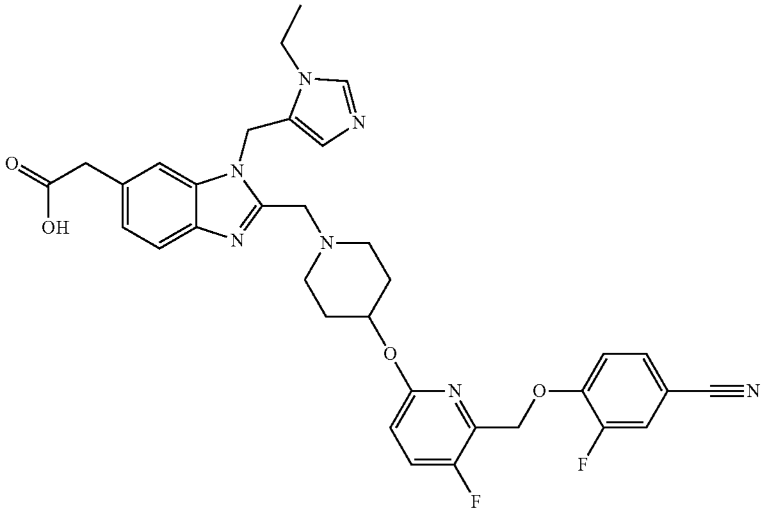 [SMILES: CCn1cncc1Cn1c(CN2CCC(Oc3ccc(F)c(COc4ccc(C#N)cc4F)n3)CC2)nc2ccc(CC(=O)O)cc21] | 642 |

-continued
| Number | Structure | MS m/z: [M + H]+ |
|---|---|---|
| Compound 202 | 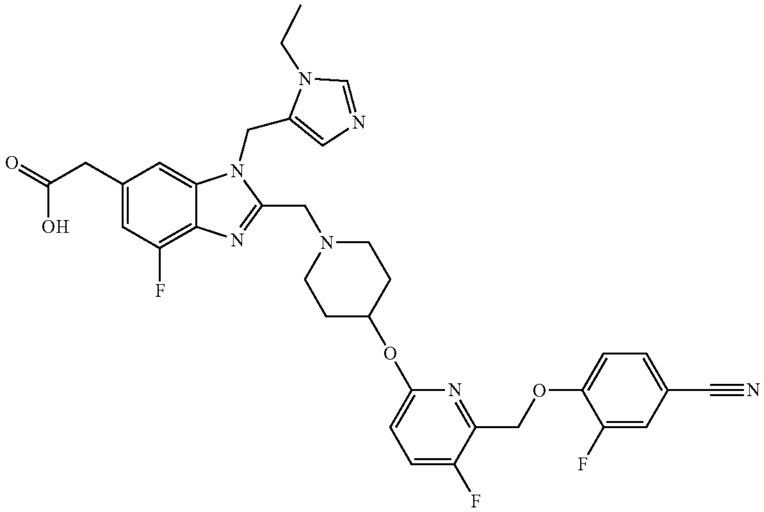 | 660 |
| Compound 203 | 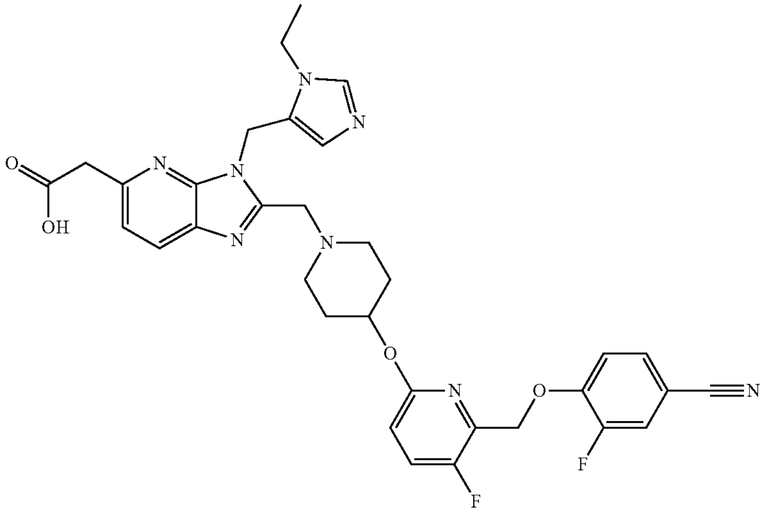 [SMILES: CCn1cncc1Cn1c(CN2CCC(Oc3ccc(F)c(COc4ccc(C#N)cc4F)n3)CC2)nc2ccc(CC(=O)O)nc21] | 643 |
| Compound 204 | 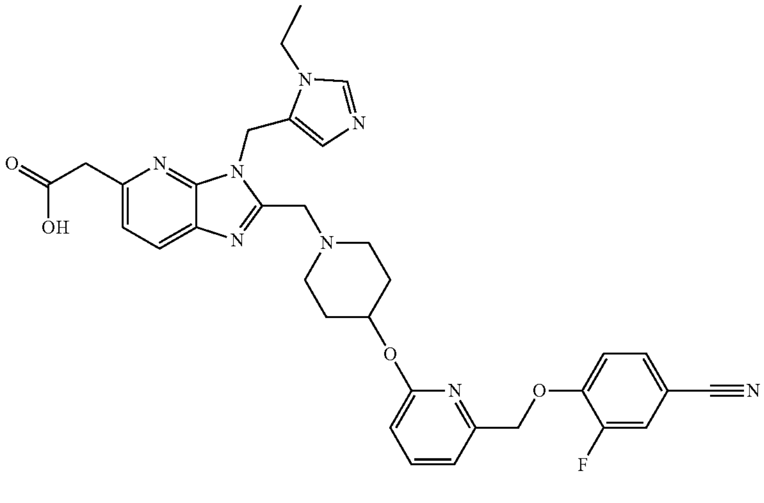 [SMILES: CCn1cncc1Cn1c(CN2CCC(Oc3cccc(COc4ccc(C#N)cc4F)n3)CC2)nc2ccc(CC(=O)O)nc21] | 625 |

-continued
| Number | Structure | MS m/z: [M + H]+ |
|---|---|---|
| Compound 205 | 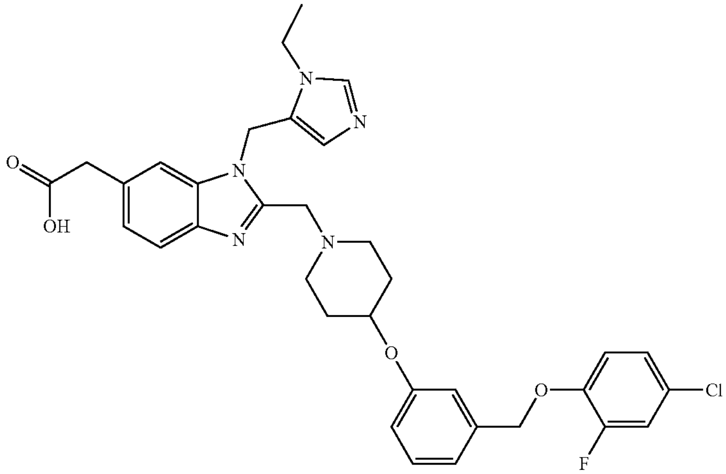 [SMILES: CCn1cncc1Cn1c(CN2CCC(Oc3cccc(COc4ccc(Cl)cc4F)c3)CC2)nc2ccc(CC(=O)O)cc21] | 632 |
| Compound 206 | 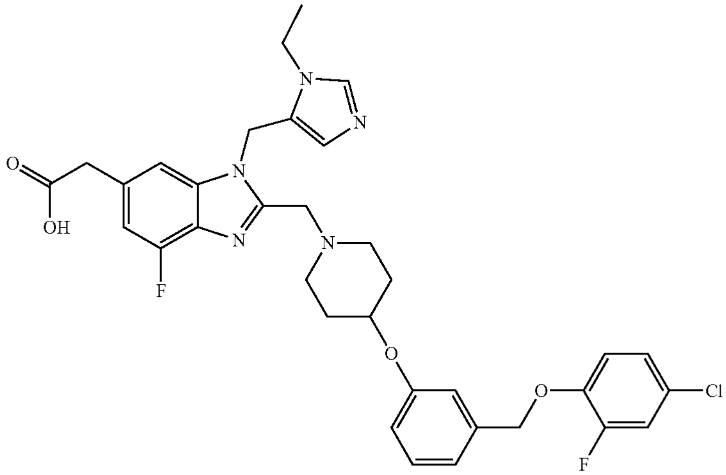 [SMILES: CCn1cncc1Cn1c(CN2CCC(Oc3cccc(COc4ccc(Cl)cc4F)c3)CC2)nc2c(F)cc(CC(=O)O)cc21] | 650 |
| Compound 207 | 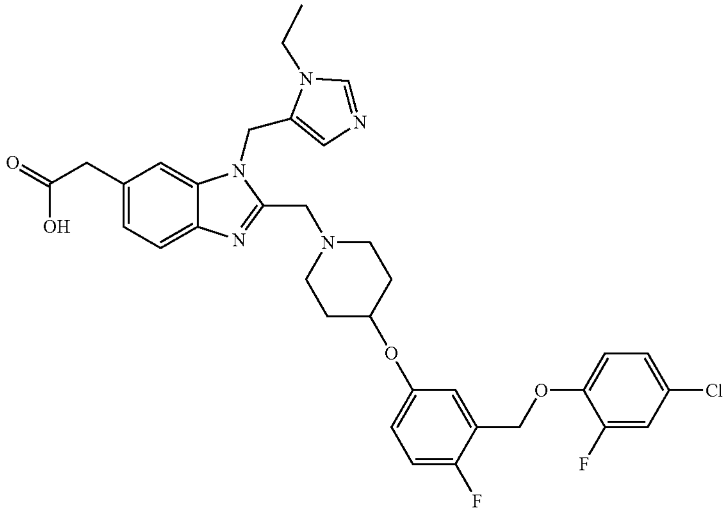 | 650 |

-continued
| Number | Structure | MS m/z: [M + H]$^+$ |
|---|---|---|
| Compound 208 | 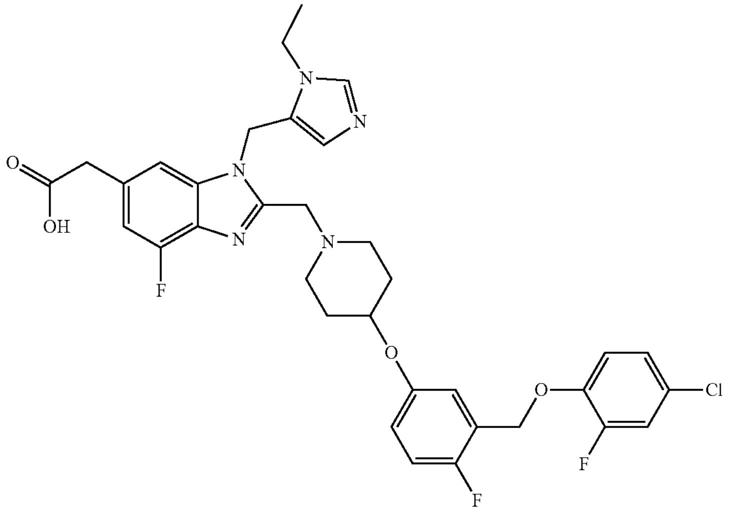 [SMILES: CCn1cncc1Cn1c(CN2CCC(Oc3ccc(F)c(COc4ccc(Cl)cc4F)c3)CC2)nc2c(F)cc(CC(=O)O)cc21] | 668 |
| Compound 209 | 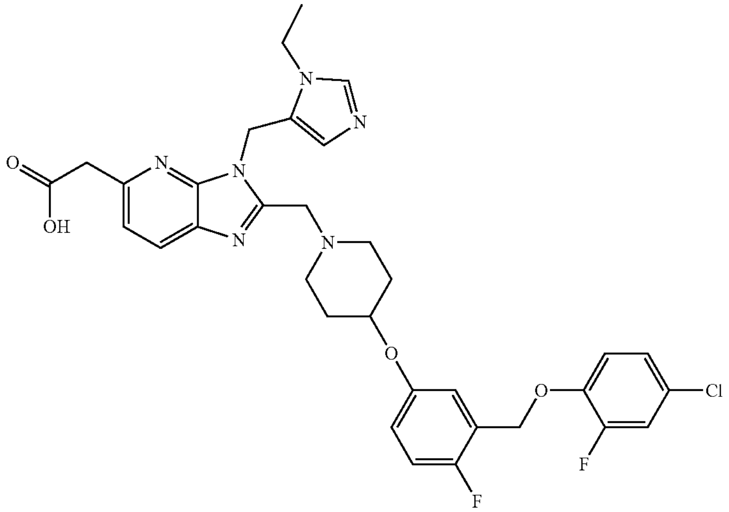 [SMILES: CCn1cncc1Cn1c(CN2CCC(Oc3ccc(F)c(COc4ccc(Cl)cc4F)c3)CC2)nc2ccc(CC(=O)O)nc21] | 651 |
| Compound 210 | 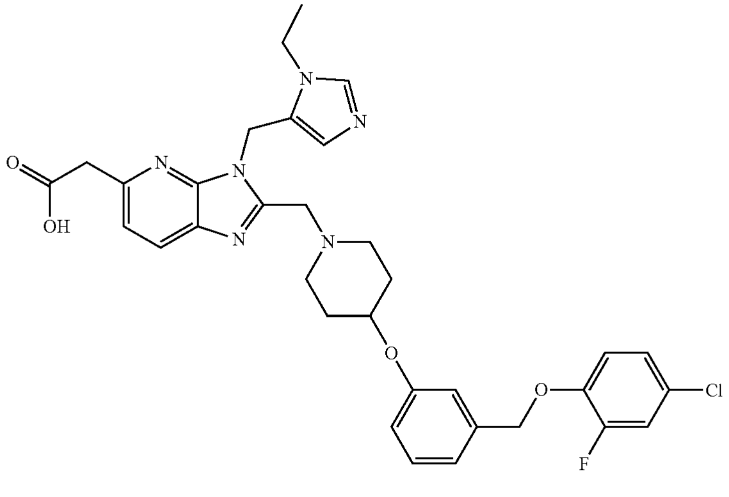 [SMILES: CCn1cncc1Cn1c(CN2CCC(Oc3cccc(COc4ccc(Cl)cc4F)c3)CC2)nc2ccc(CC(=O)O)nc21] | 633 |

-continued
| Number | Structure | MS m/z: [M + H]+ |
| --- | --- | --- |
| Compound 211 | 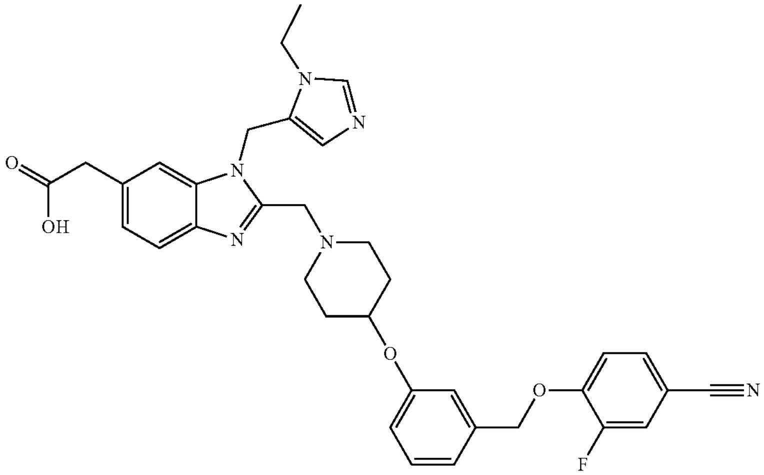 | 623 |
| Compound 212 | 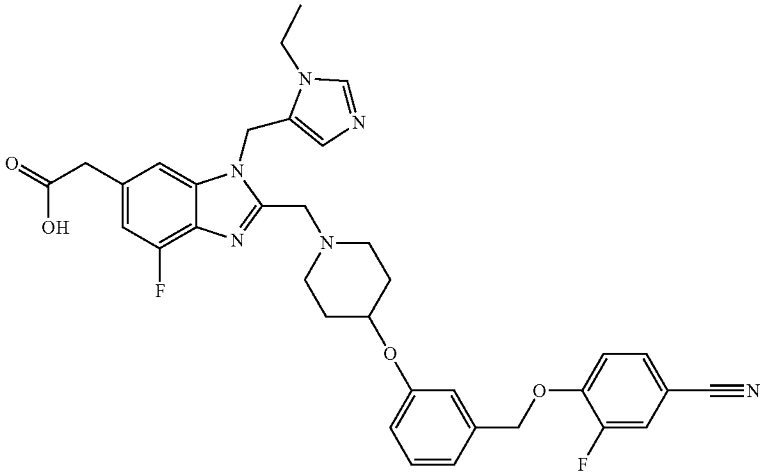 | 641 |
| Compound 213 | 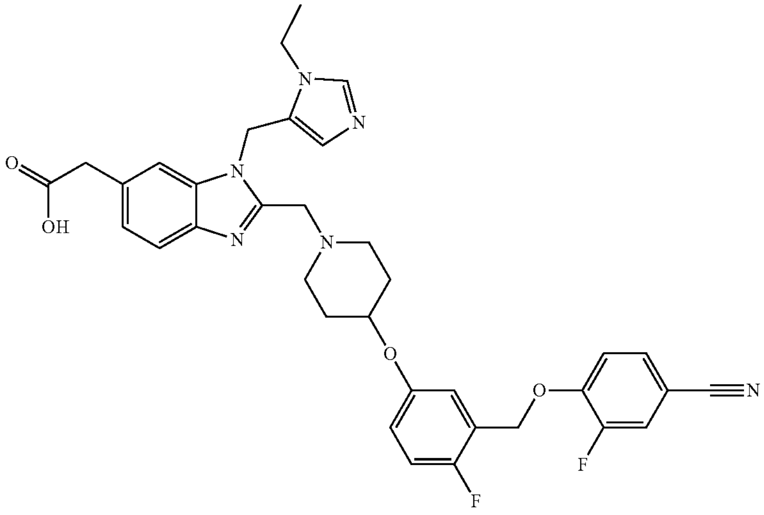 | 641 |

-continued
| Number | Structure | MS m/z: [M + H]+ |
|---|---|---|
| Compound 214 | 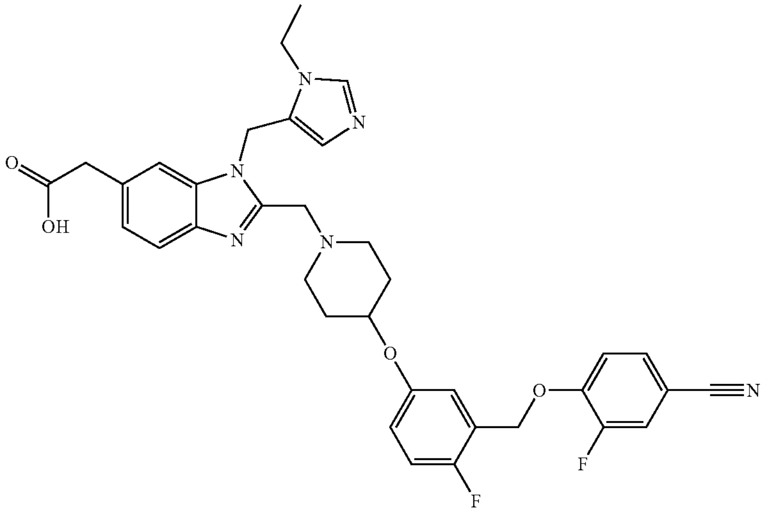 | 659 |
| Compound 215 | 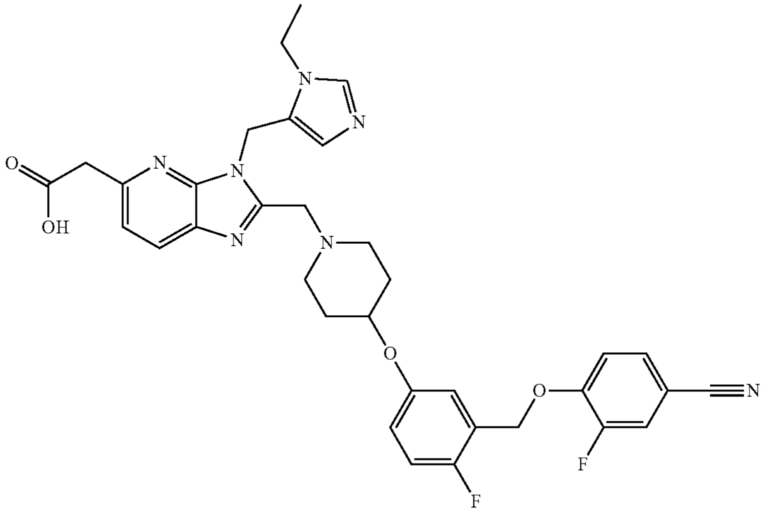 | 642 |
| Compound 216 | 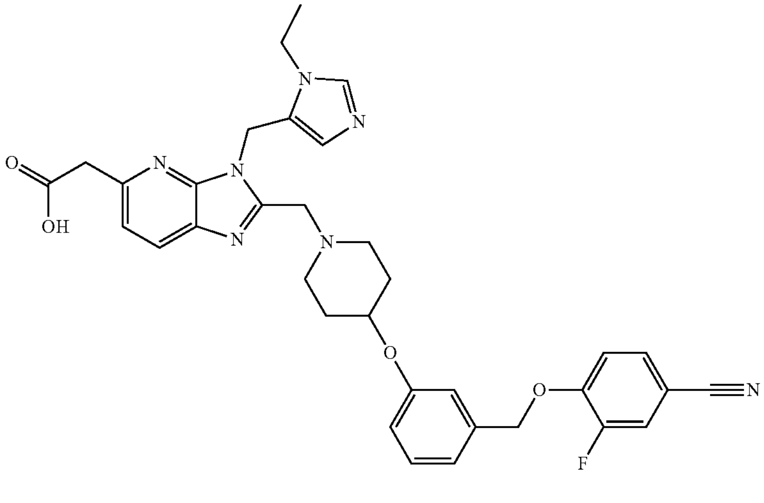 [SMILES: CCn1cncc1Cn1c(CN2CCC(Oc3cccc(COc4ccc(C#N)cc4F)c3)CC2)nc2ccc(CC(=O)O)nc21] | 624 |

-continued
| Number | Structure | MS m/z: [M + H]$^+$ |
|---|---|---|
| Compound S7 | 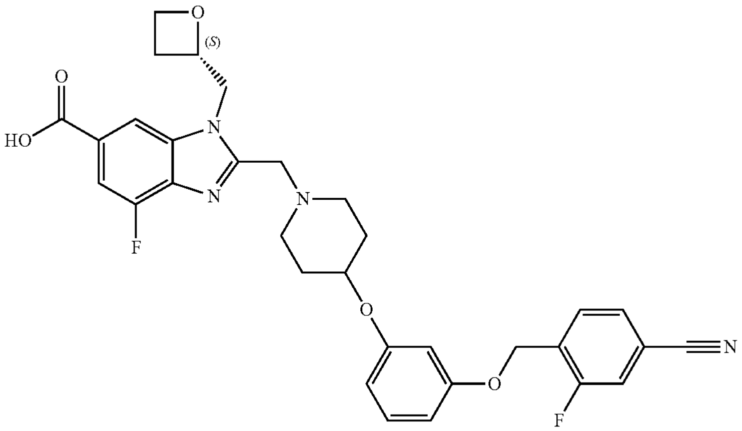 | 589 |
| Compound S8 | 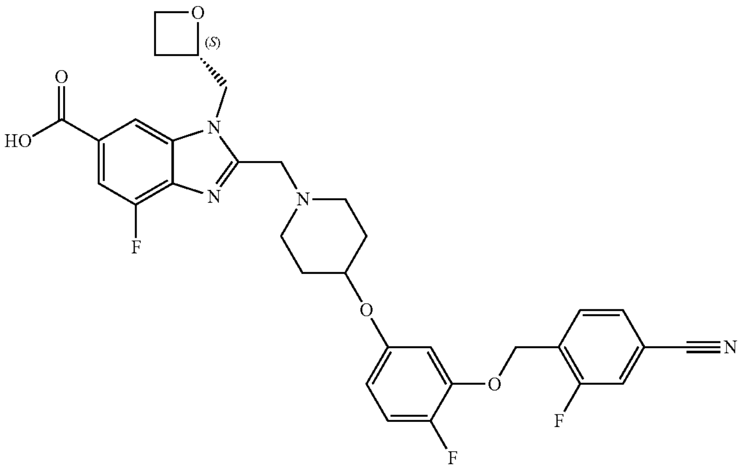 | 607 |
| Compound S9 | 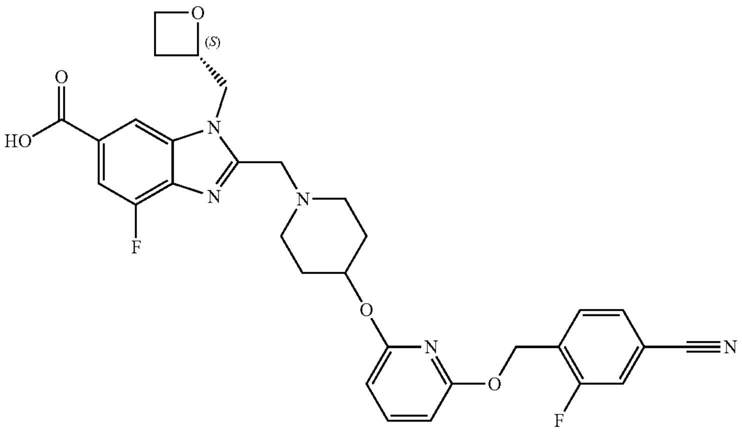 | 590 |

-continued
| Number | Structure | MS m/z: [M + H]+ |
|---|---|---|
| Compound S10 | 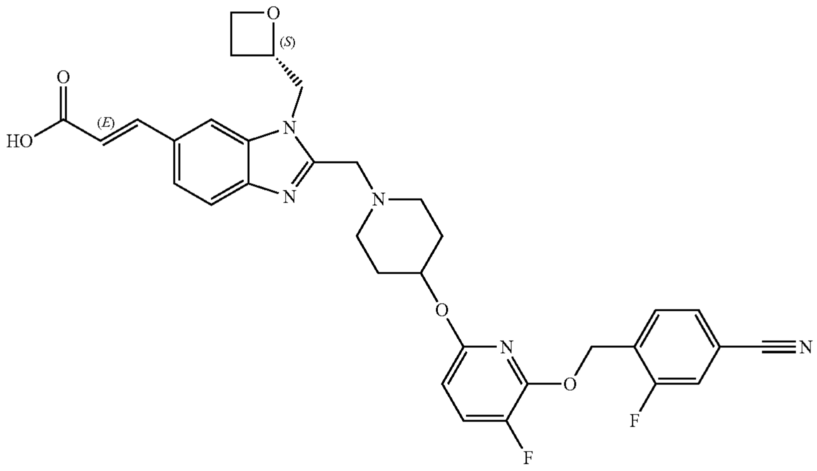 | 616 |
| Compound S11 | 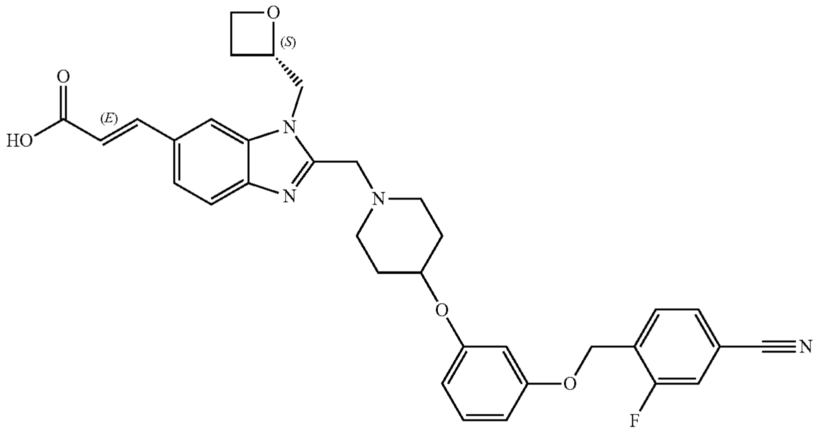 | 597 |
| Compound S14 | 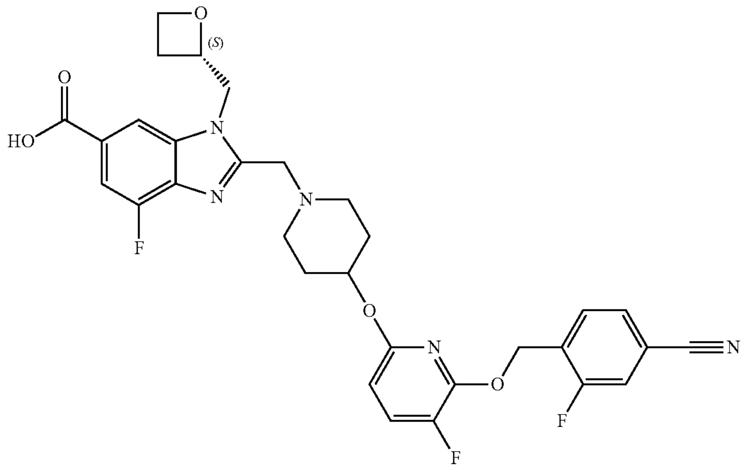 | 608 |

-continued
| Number | Structure | MS m/z: [M + H]+ |
|---|---|---|
| Compound S15 | 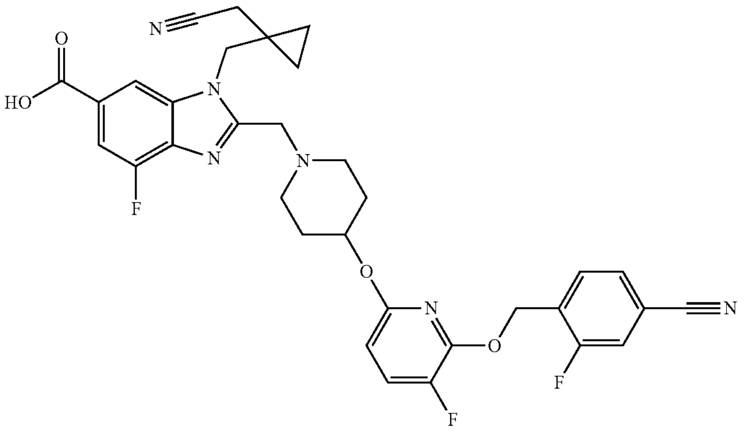 [SMILES: N#CCC1(Cn2c(CN3CCC(Oc4ccc(F)c(OCc5ccc(C#N)cc5F)n4)CC3)nc3c(F)cc(C(=O)O)cc32)CC1] | 631 |
| Compound S16 | 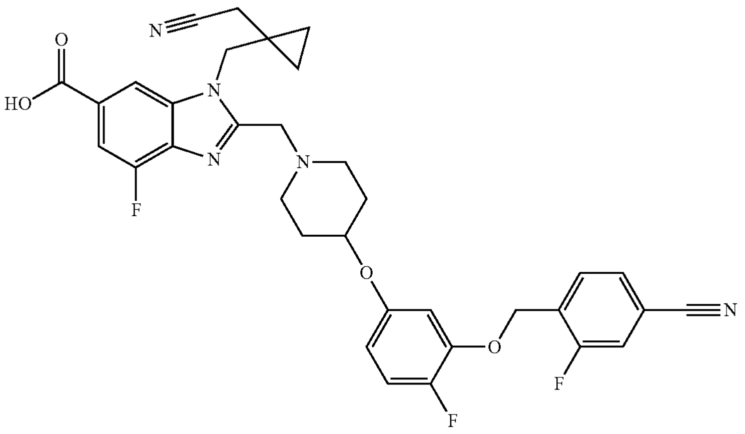 [SMILES: N#CCC1(Cn2c(CN3CCC(Oc4ccc(F)c(OCc5ccc(C#N)cc5F)c4)CC3)nc3c(F)cc(C(=O)O)cc32)CC1] | 630 |
| Compound S17 | 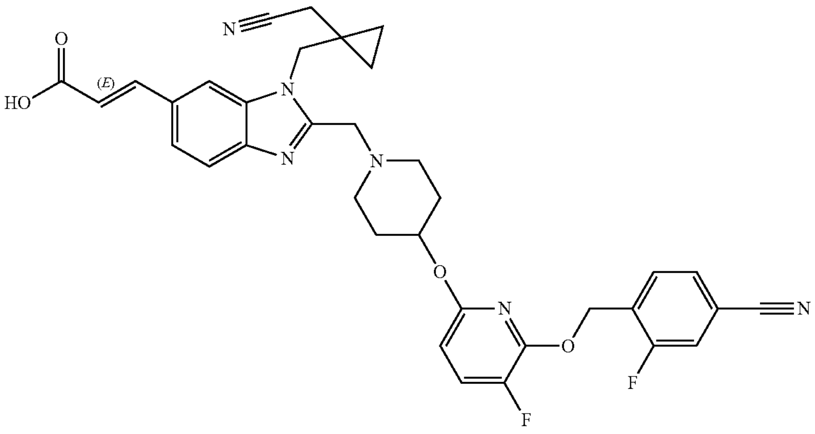 [SMILES: N#CCC1(Cn2c(CN3CCC(Oc4ccc(F)c(OCc5ccc(C#N)cc5F)n4)CC3)nc3ccc(/C=C/C(=O)O)cc32)CC1] | 639 |

-continued
| Number | Structure | MS m/z: [M + H]+ |
| --- | --- | --- |
| Compound S21 | 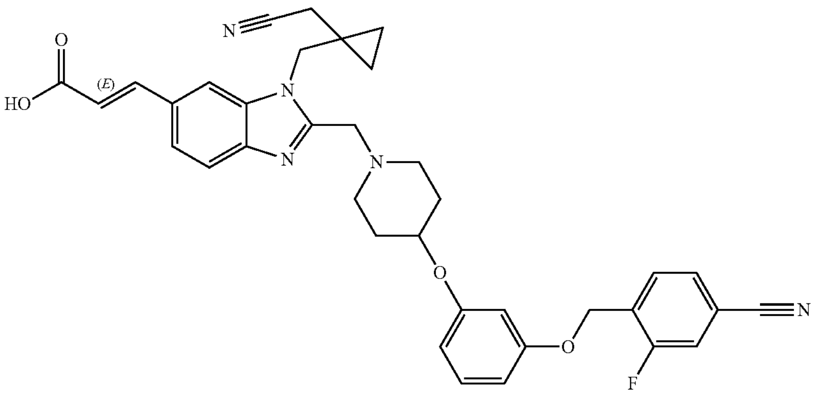 [SMILES: N#CCC1(Cn2c(CN3CCC(Oc4cccc(OCc5ccc(C#N)cc5F)c4)CC3)nc3ccc(/C=C/C(=O)O)cc32)CC1] | 620 |
| Compound S24 | 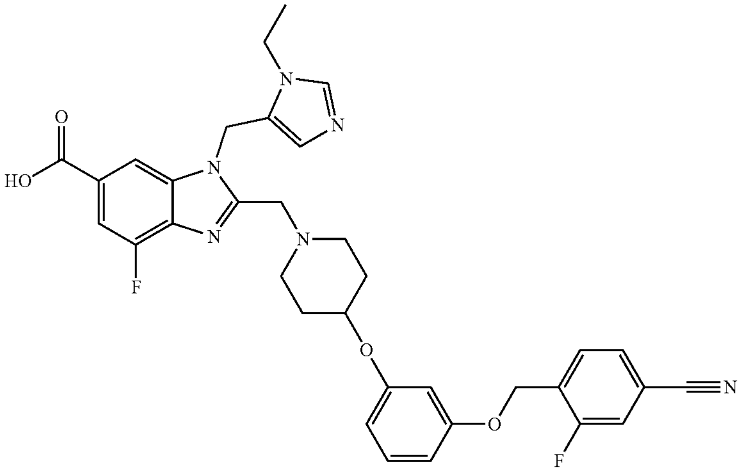 [SMILES: CCn1cncc1Cn1c(CN2CCC(Oc3cccc(OCc4ccc(C#N)cc4F)c3)CC2)nc2c(F)cc(C(=O)O)cc21] | 627 |
| Compound S25 | 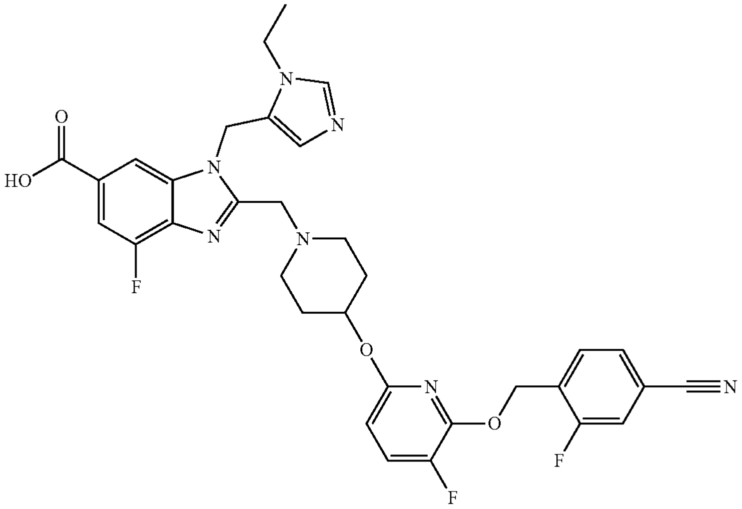 | 646 |

-continued
| Number | Structure | MS m/z: [M + H]+ |
|---|---|---|
| Compound S26 | 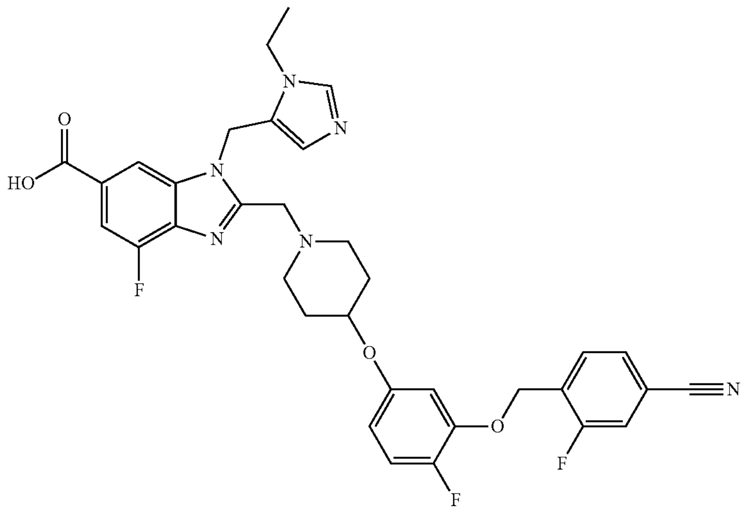 | 645 |
| Compound S27 | 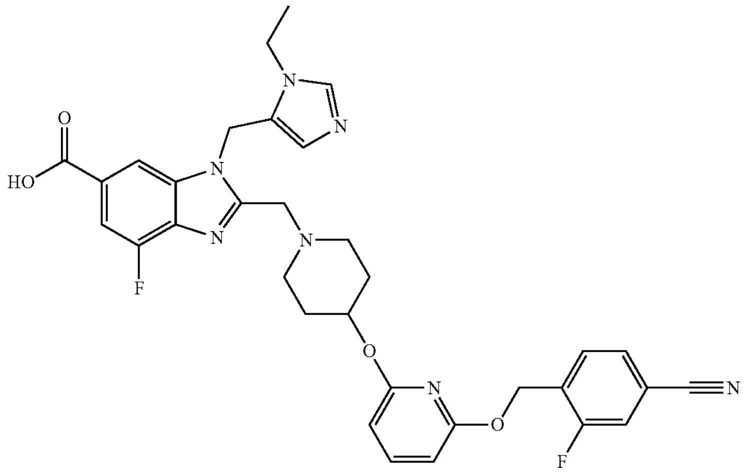 | 628 |
| Compound S28 | 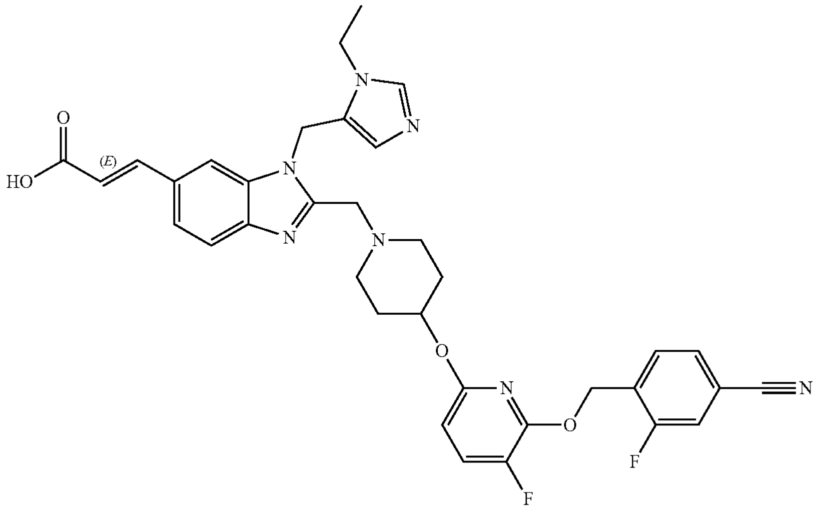 [SMILES: CCn1cncc1Cn1c(CN2CCC(Oc3ccc(F)c(OCc4ccc(C#N)cc4F)n3)CC2)nc2ccc(/C=C/C(=O)O)cc21] | 654 |

-continued
| Number | Structure | MS m/z: [M + H]+ |
|---|---|---|
| Compound S29 | 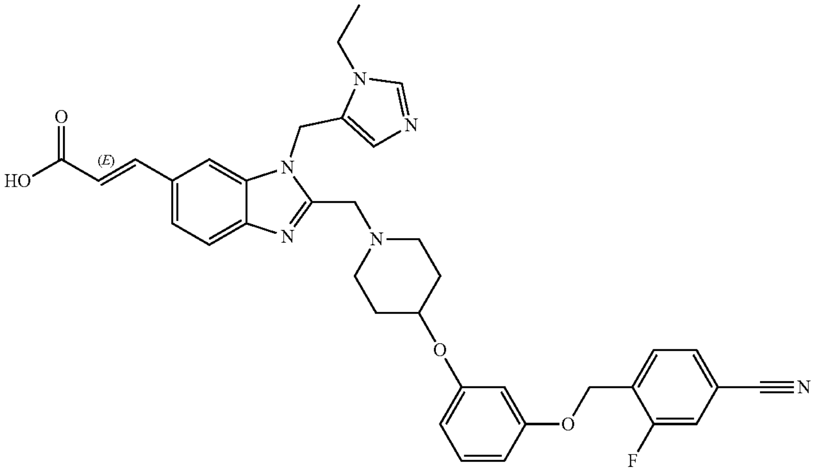 [SMILES: CCn1cncc1Cn1c(CN2CCC(Oc3cccc(OCc4ccc(C#N)cc4F)c3)CC2)nc2ccc(/C=C/C(=O)O)cc21] | 635 |
| Compound S32 | 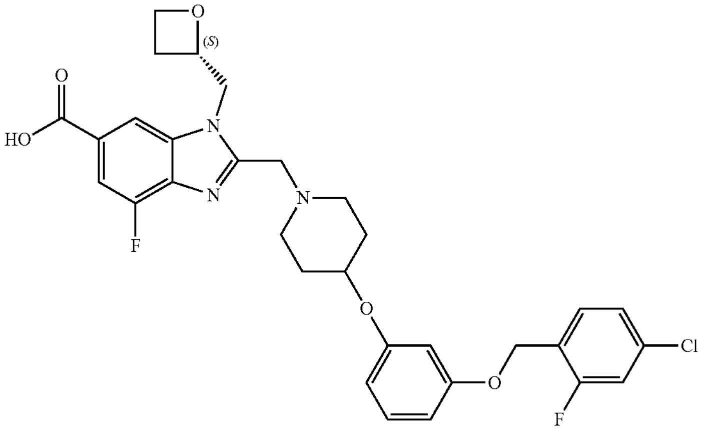 | 598 |
| Compound S33 | 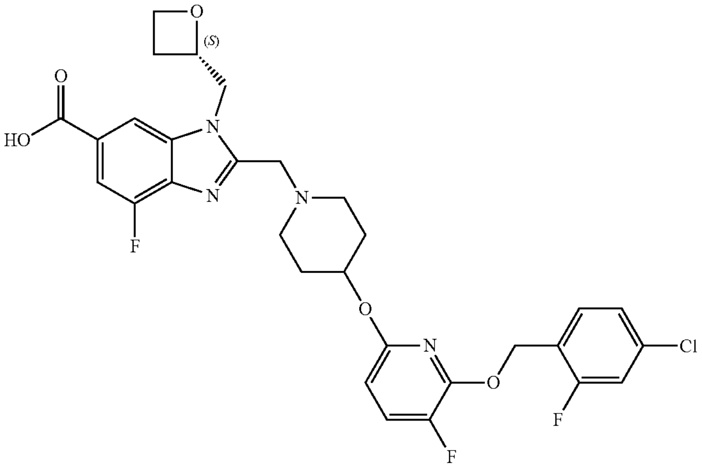 | 617 |

-continued
| Number | Structure | MS m/z: [M + H]+ |
|---|---|---|
| Compound S34 | 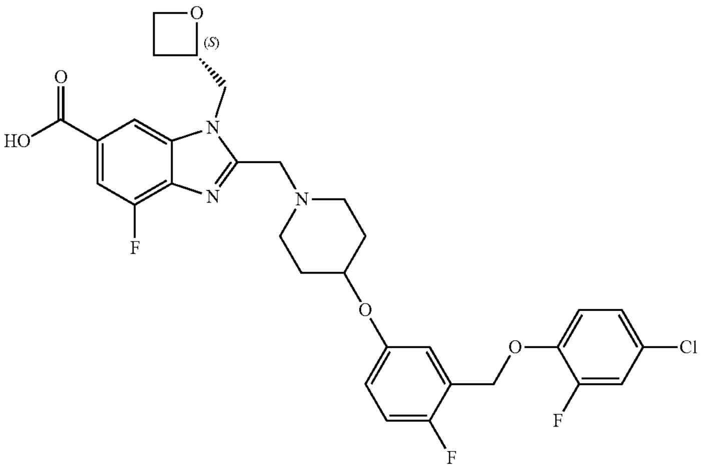 | 616 |
| Compound S35 | 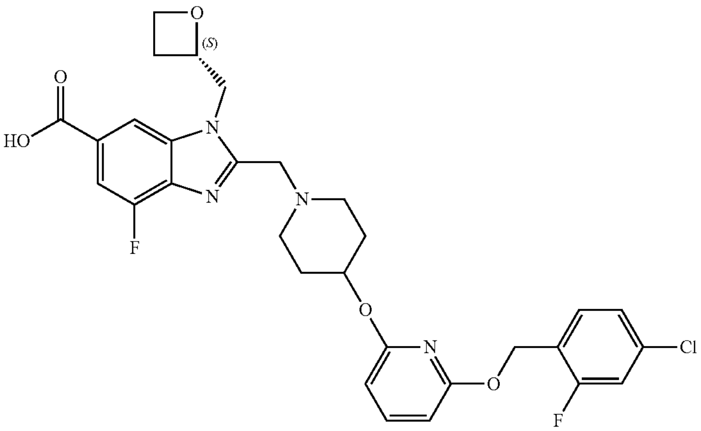 | 599 |
| Compound S37 | 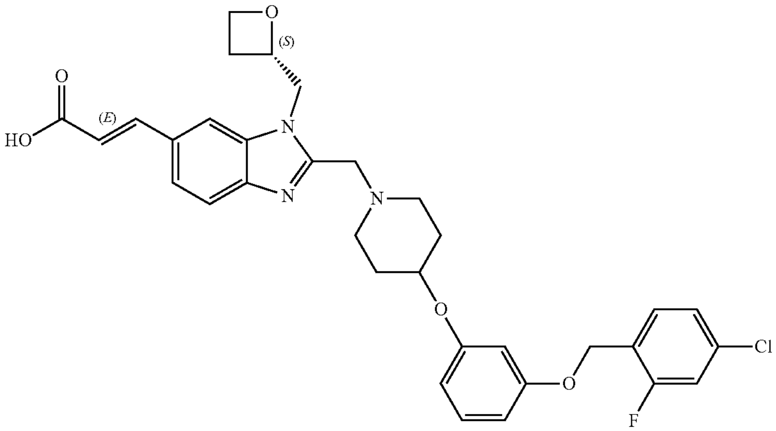 | 606 |

-continued
| Number | Structure | MS m/z: [M + H]+ |
|---|---|---|
| Compound S40 | 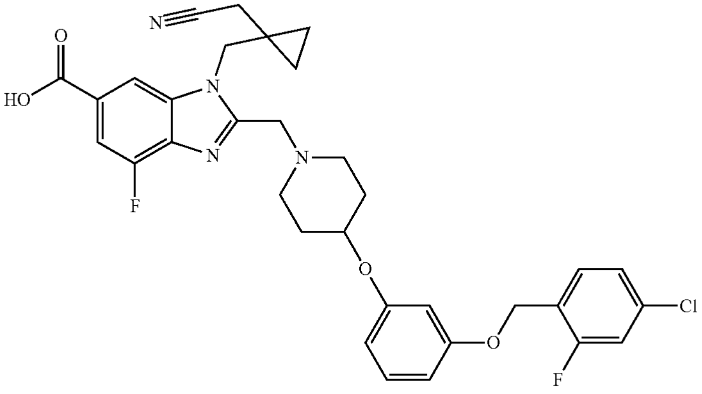 [SMILES: N#CCC1(Cn2c(CN3CCC(Oc4cccc(OCc5ccc(Cl)cc5F)c4)CC3)nc3c(F)cc(C(=O)O)cc32)CC1] | 621 |
| Compound S42 | 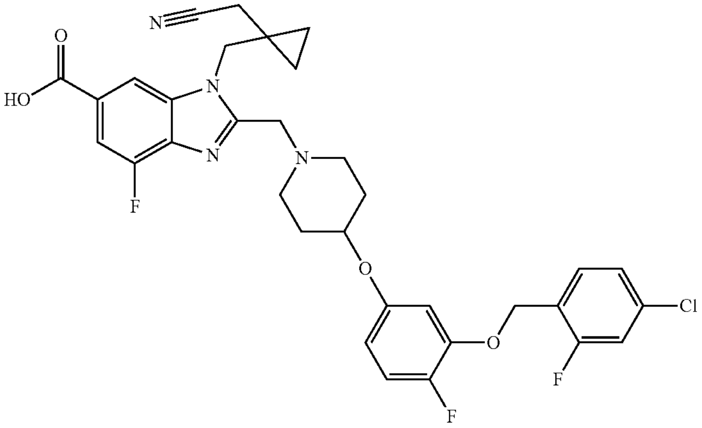 [SMILES: N#CCC1(Cn2c(CN3CCC(Oc4ccc(F)c(OCc5ccc(Cl)cc5F)c4)CC3)nc3c(F)cc(C(=O)O)cc32)CC1] | 639 |
| Compound S43 | 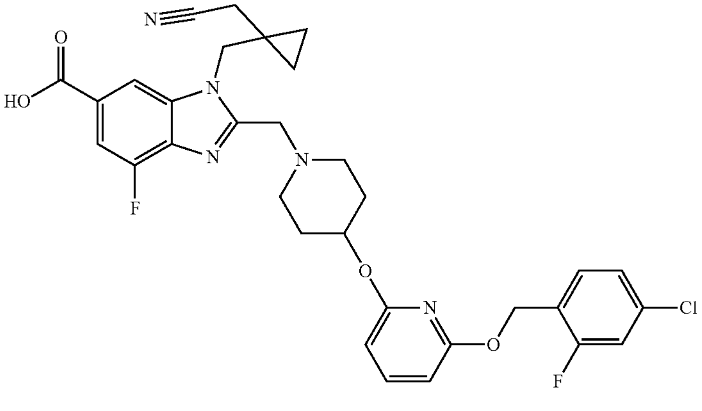 [SMILES: N#CCC1(Cn2c(CN3CCC(Oc4cccc(OCc5ccc(Cl)cc5F)n4)CC3)nc3c(F)cc(C(=O)O)cc32)CC1] | 622 |

-continued
| Number | Structure | MS m/z: [M + H]$^+$ |
|---|---|---|
| Compound S44 | 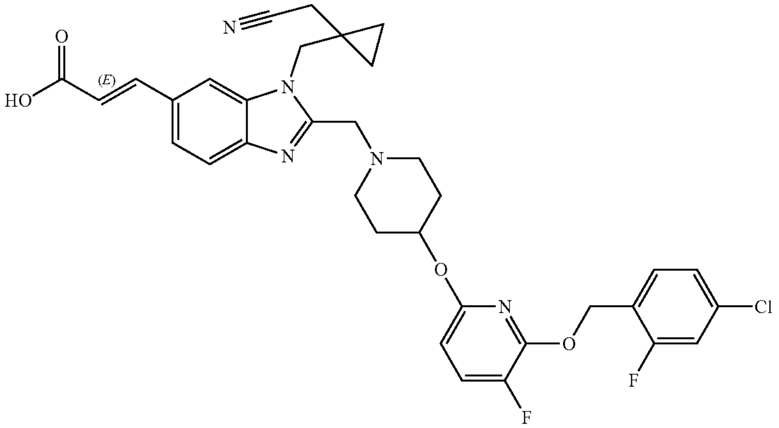 [SMILES: N#CCC1(Cn2c(CN3CCC(Oc4ccc(F)c(OCc5ccc(Cl)cc5F)n4)CC3)nc3ccc(/C=C/C(=O)O)cc32)CC1] | 648 |
| Compound S45 | 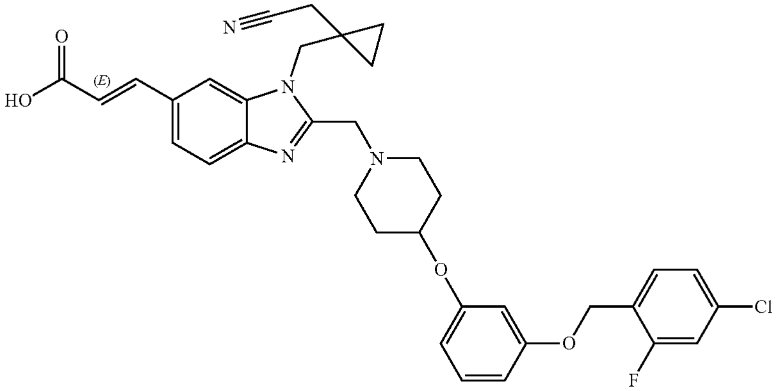 [SMILES: N#CCC1(Cn2c(CN3CCC(Oc4cccc(OCc5ccc(Cl)cc5F)c4)CC3)nc3ccc(/C=C/C(=O)O)cc32)CC1] | 629 |
| Compound S48 | 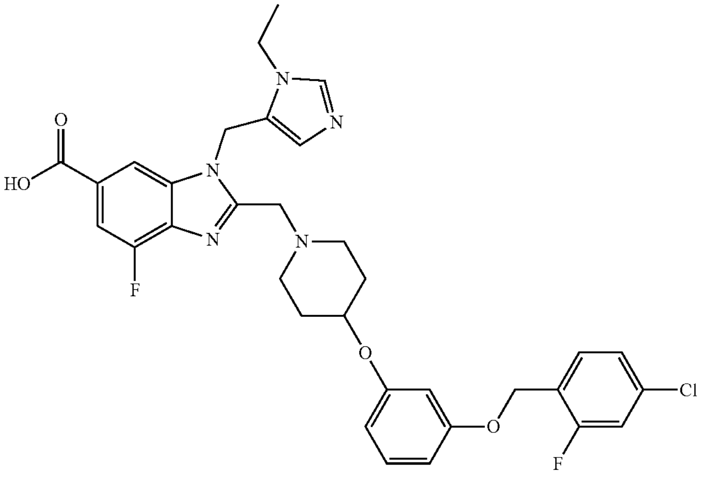 [SMILES: CCn1cncc1Cn1c(CN2CCC(Oc3cccc(OCc4ccc(Cl)cc4F)c3)CC2)nc2c(F)cc(C(=O)O)cc21] | 636 |

-continued
| Number | Structure | MS m/z: [M + H]+ |
|---|---|---|
| Compound S49 | 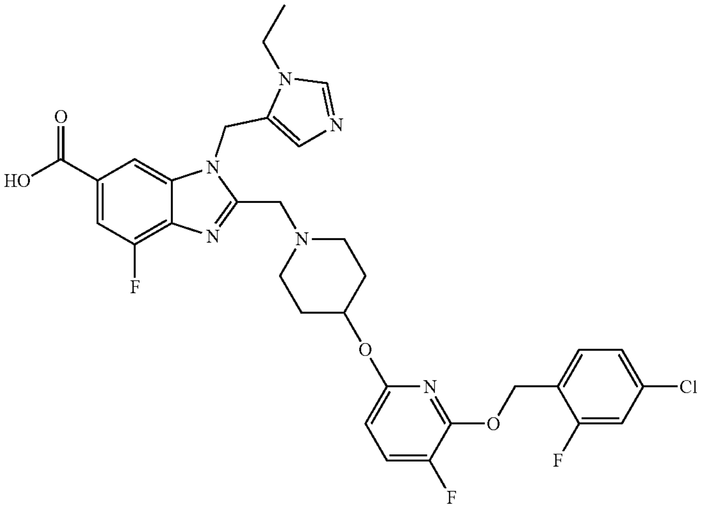 | 655 |
| Compound S50 | 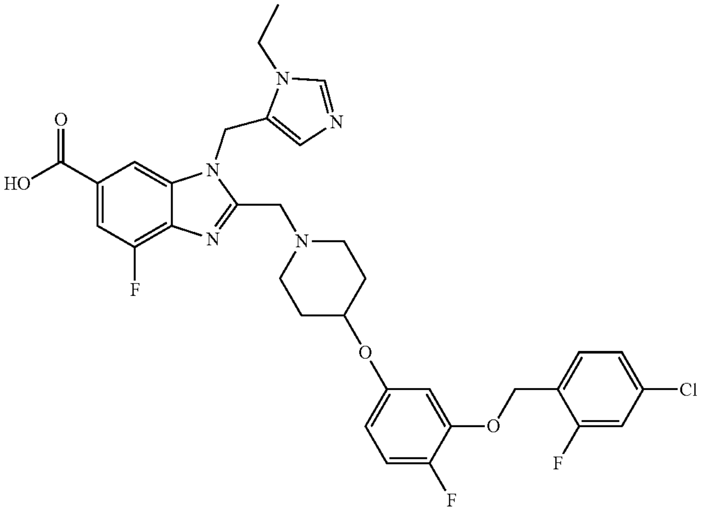 | 654 |
| Compound S51 | 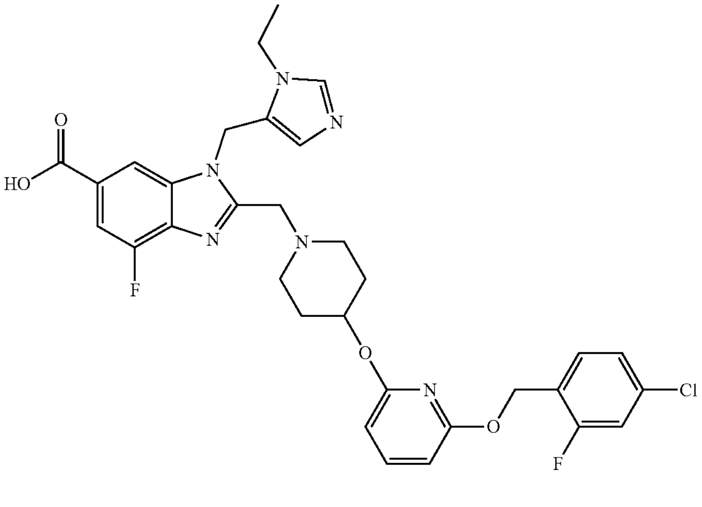 | 637 |

-continued
| Number | Structure | MS m/z: [M + H]$^+$ |
|---|---|---|
| Compound S52 | 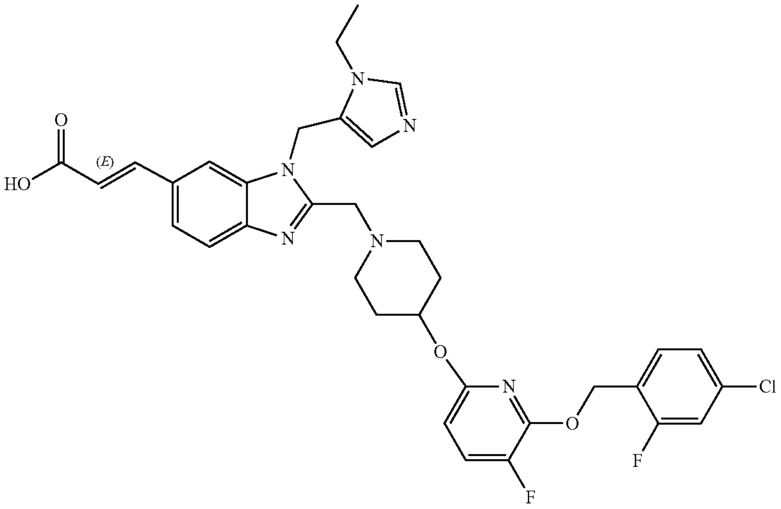 [SMILES: CCn1cncc1Cn1c(CN2CCC(Oc3ccc(F)c(OCc4ccc(Cl)cc4F)n3)CC2)nc2ccc(/C=C/C(=O)O)cc21] | 663 |
| Compound S53 | 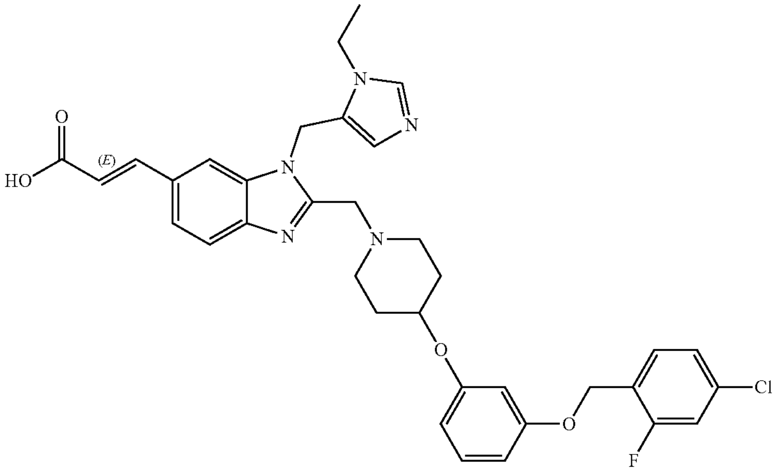 [SMILES: CCn1cncc1Cn1c(CN2CCC(Oc3cccc(OCc4ccc(Cl)cc4F)c3)CC2)nc2ccc(/C=C/C(=O)O)cc21] | 644 |
| Compound S56 | 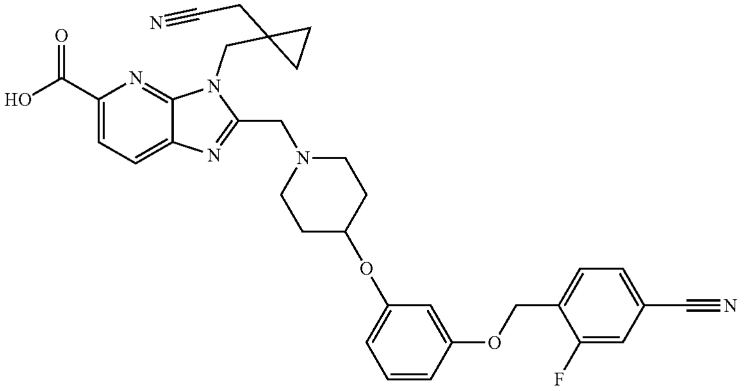 [SMILES: N#CCC1(Cn2c(CN3CCC(Oc4cccc(OCc5ccc(C#N)cc5F)c4)CC3)nc3ccc(C(=O)O)nc32)CC1] | 595 |

-continued
| Number | Structure | MS m/z: [M + H]+ |
|---|---|---|
| Compound S57 | 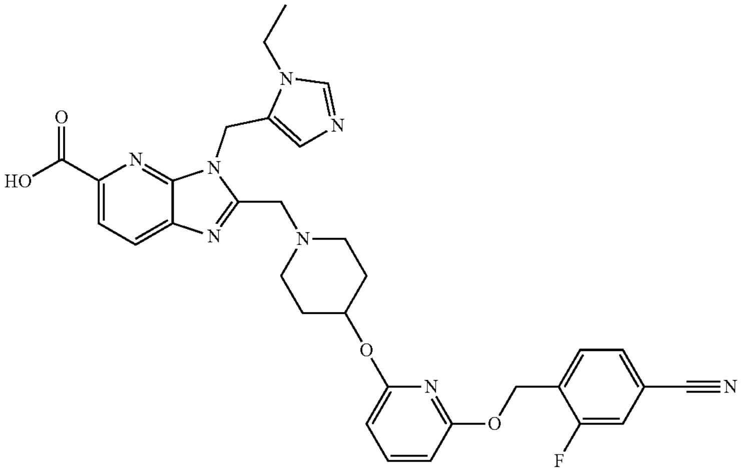 [SMILES: CCn1cncc1Cn1c(CN2CCC(Oc3cccc(OCc4ccc(C#N)cc4F)n3)CC2)nc2ccc(C(=O)O)nc21] | 611 |
| Compound S58 | 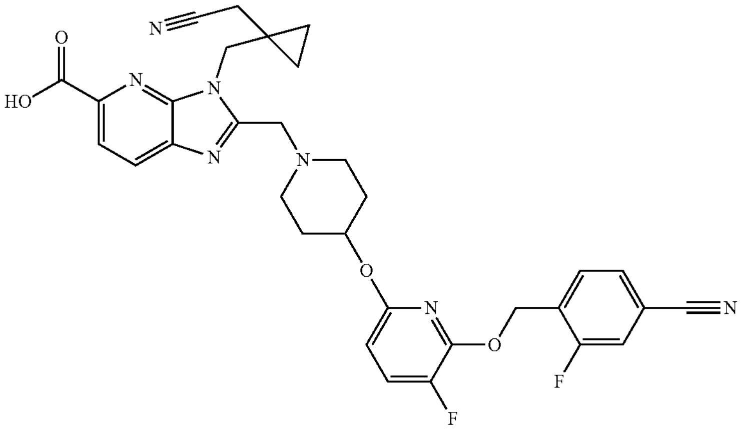 [SMILES: N#CCC1(Cn2c(CN3CCC(Oc4ccc(F)c(OCc5ccc(C#N)cc5F)n4)CC3)nc3ccc(C(=O)O)nc32)CC1] | 614 |
| Compound S59 | 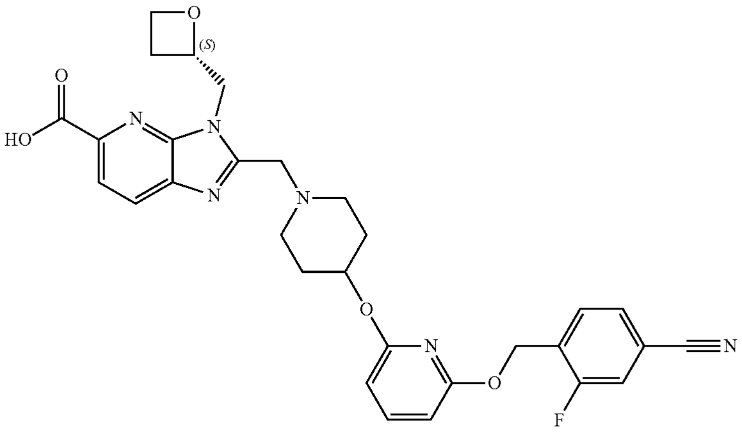 | 573 |

-continued
| Number | Structure | MS m/z: [M + H]+ |
|---|---|---|
| Compound S60 | 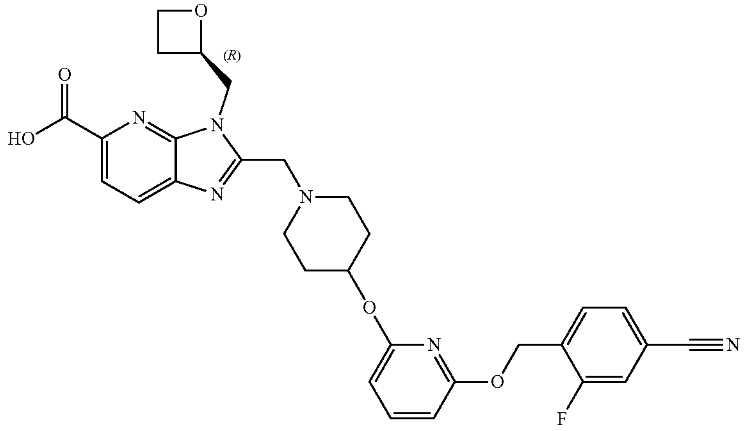 | 573 |
| Compound S61 | 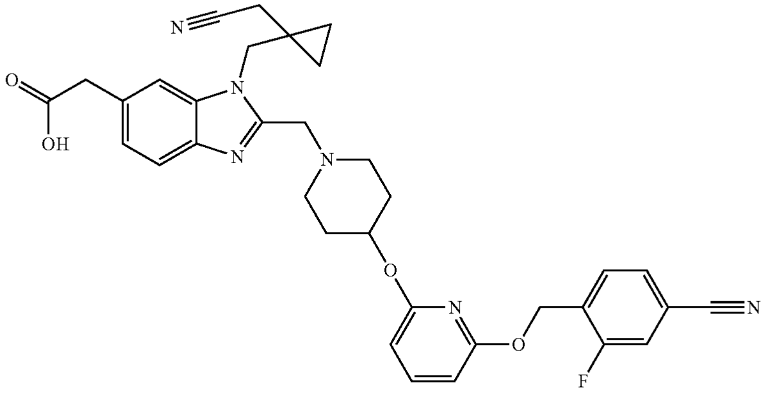 | 609 |
| Compound S62 | 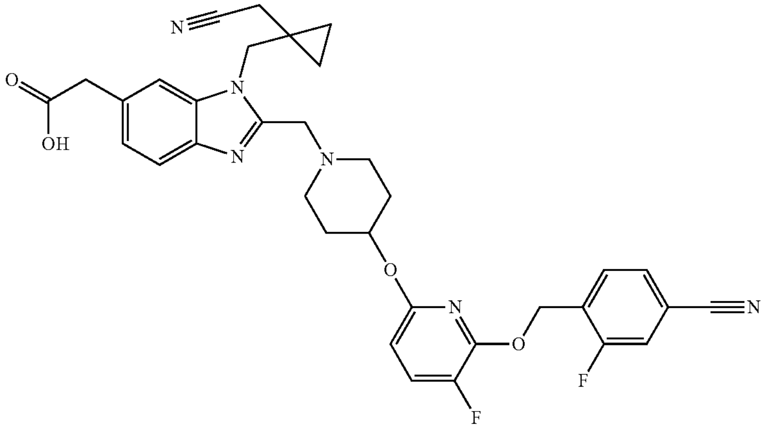 | 627 |

-continued
| Number | Structure | MS m/z: [M + H]+ |
| --- | --- | --- |
| Compound S63 | 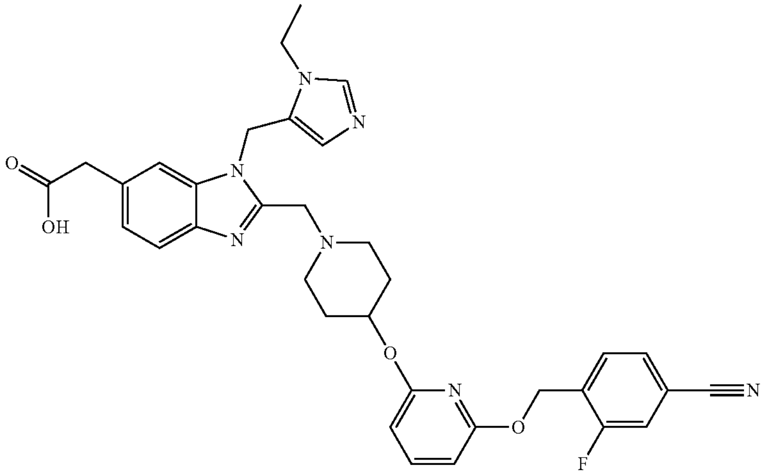 [SMILES: CCn1cncc1Cn1c(CN2CCC(Oc3cccc(OCc4ccc(C#N)cc4F)n3)CC2)nc2ccc(CC(=O)O)cc21] | 624 |
| Compound S64 | 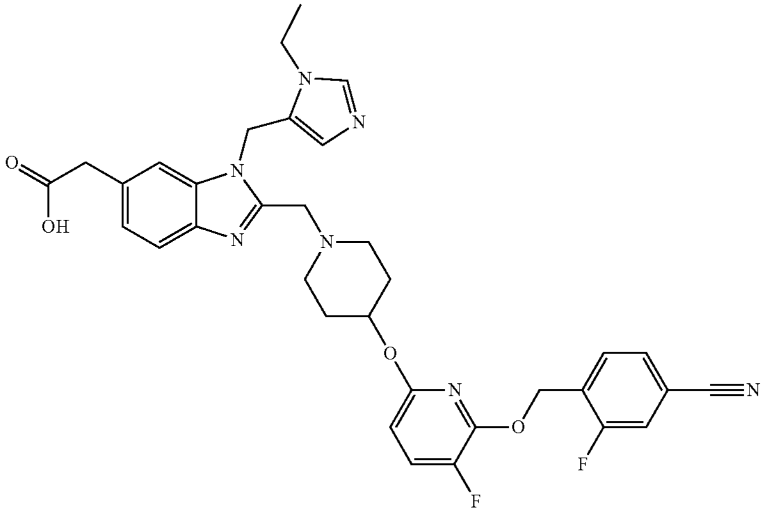 | 642 |
| Compound C44 | 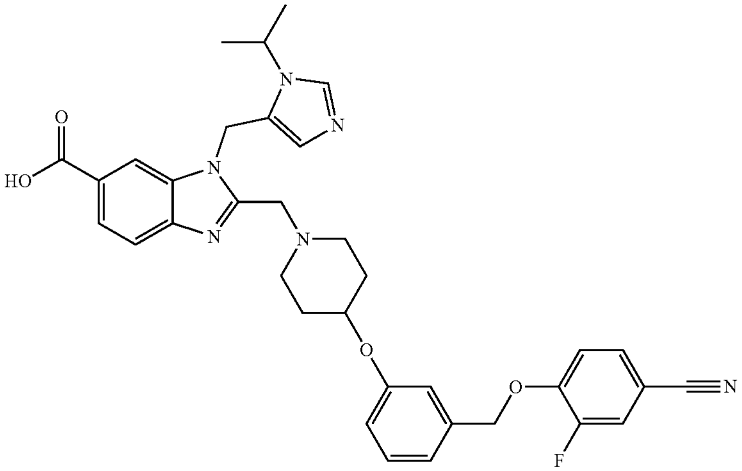 | 641 |

-continued
| Number | Structure | MS m/z: [M + H]+ |
|---|---|---|
| Compound C45 | 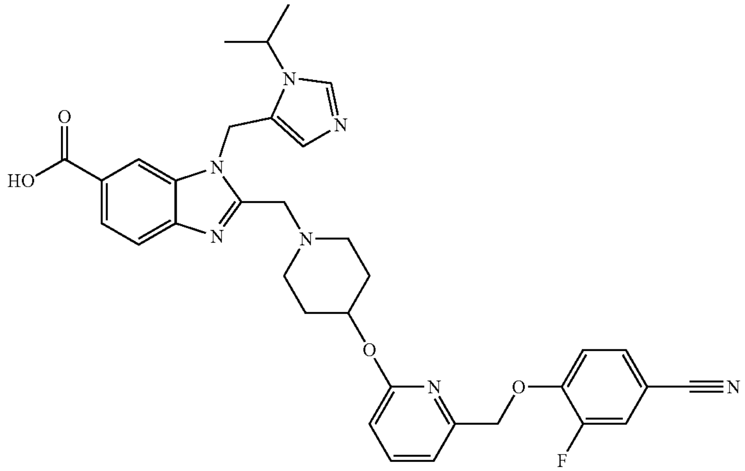 [SMILES: CC(C)n1cncc1Cn1c(CN2CCC(Oc3cccc(COc4ccc(C#N)cc4F)n3)CC2)nc2ccc(C(=O)O)cc21] | 624 |
| Compound C46 | 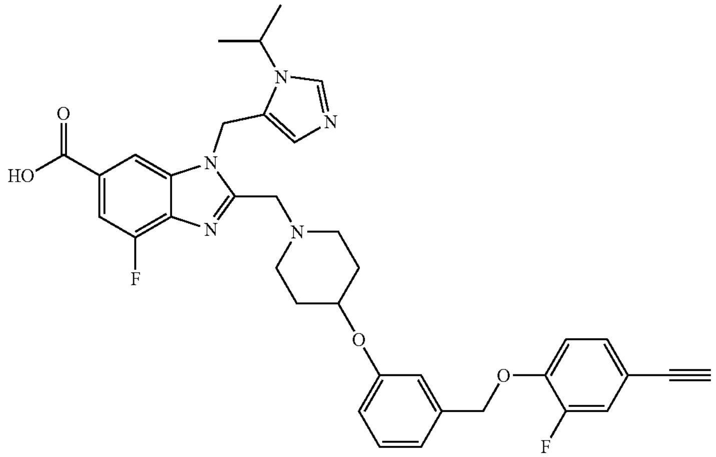 [SMILES: C#Cc1ccc(OCc2cccc(OC3CCN(Cc4nc5c(F)cc(C(=O)O)cc5n4Cc4cncn4C(C)C)CC3)c2)c(F)c1] | 640 |
| Compound C47 | 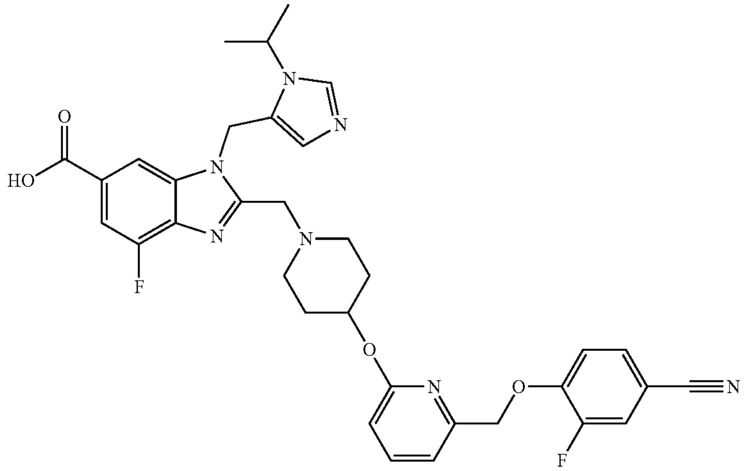 | 642 |

-continued
| Number | Structure | MS m/z: [M + H]+ |
|---|---|---|
| Compound C48 | 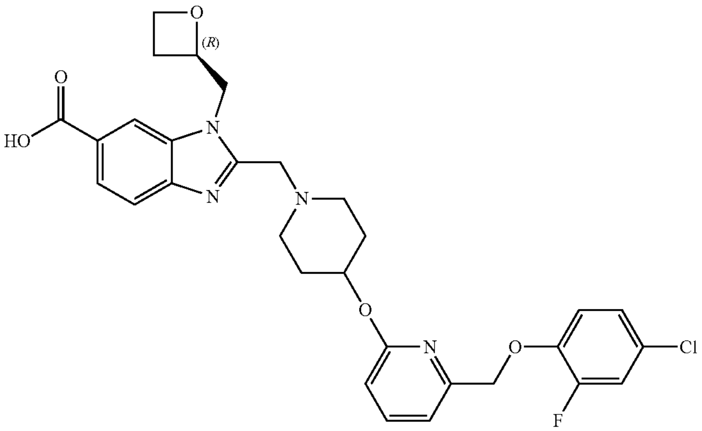 | 581 |
| Compound C49 | 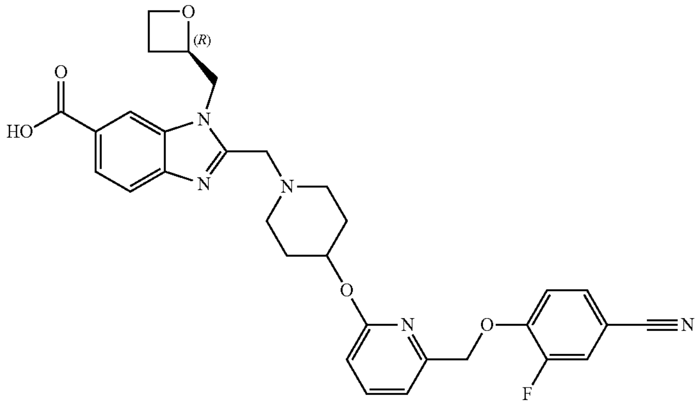 | 572 |
| Compound C50 | 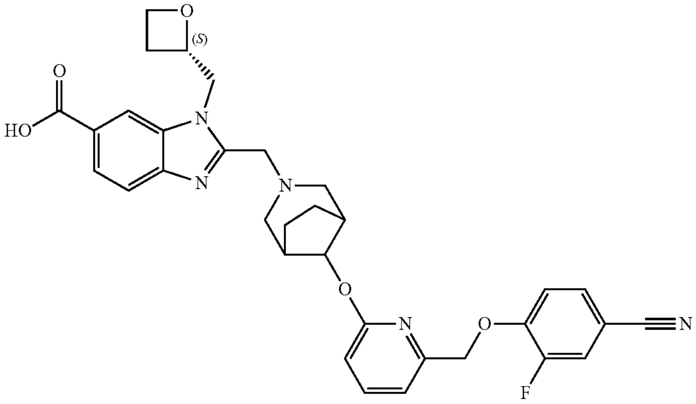 | 598 |

-continued
| Number | Structure | MS m/z: [M + H]+ |
|---|---|---|
| Compound C51 | 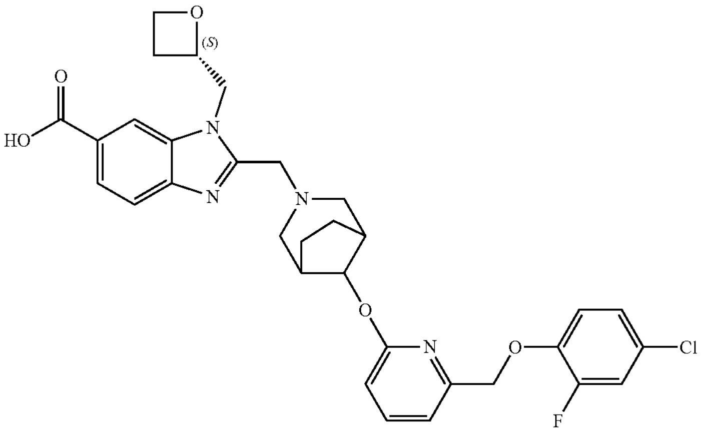 | 607 |
| Compound C52 | 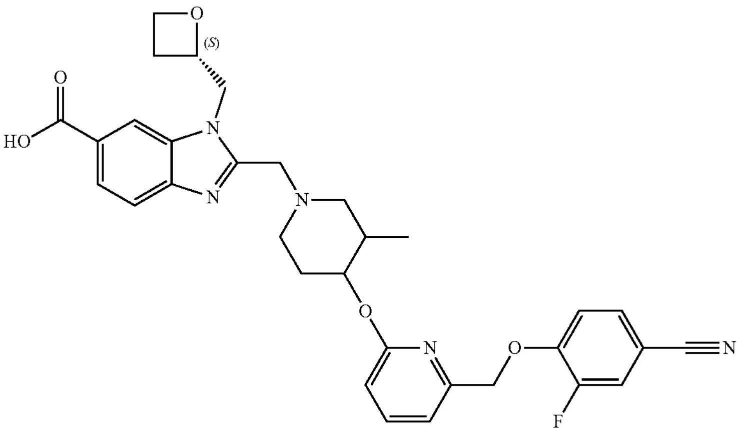 | 586 |
| Compound C53 | 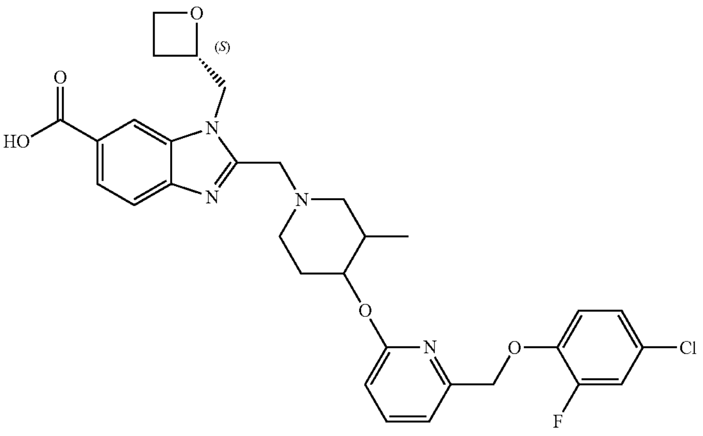 | 595 |

-continued
| Number | Structure | MS m/z: [M + H]+ |
|---|---|---|
| Compound C54 | 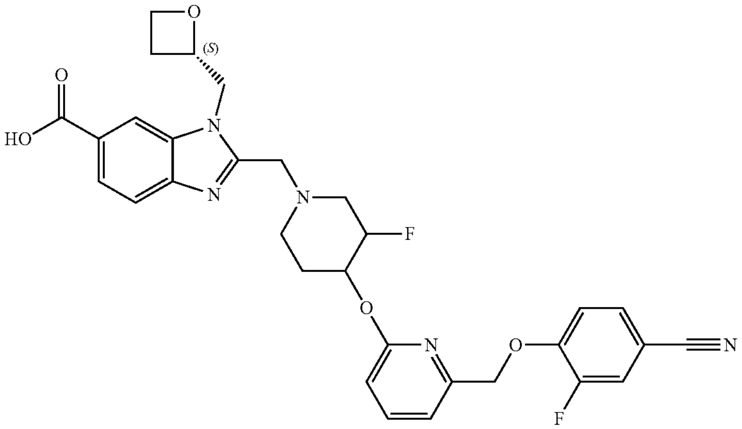 | 590 |
| Compound C55 | 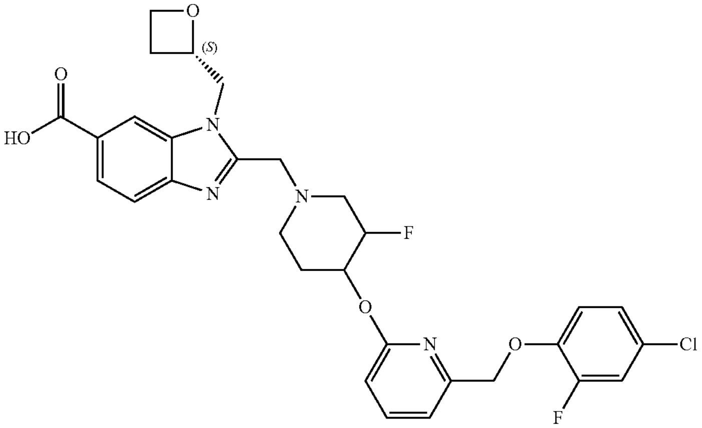 | 599 |
| Compound C56 | 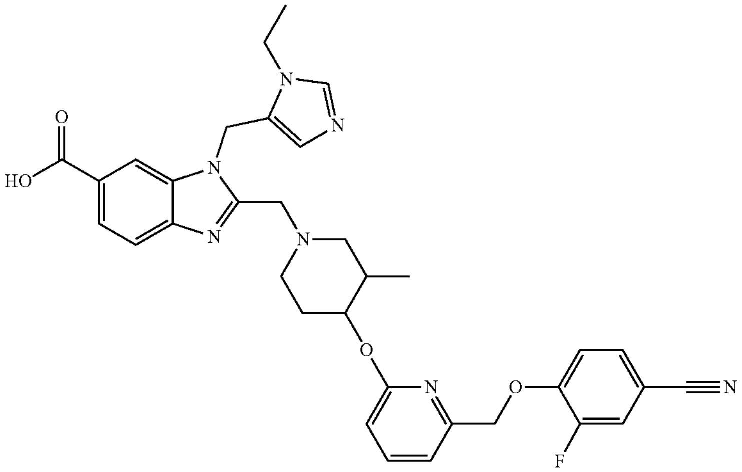 [SMILES: CCn1cncc1Cn1c(CN2CCC(Oc3cccc(COc4ccc(C#N)cc4F)n3)C(C)C2)nc2ccc(C(=O)O)cc21] | 624 |

-continued
| Number | Structure | MS m/z: [M + H]+ |
|---|---|---|
| Compound C57 | 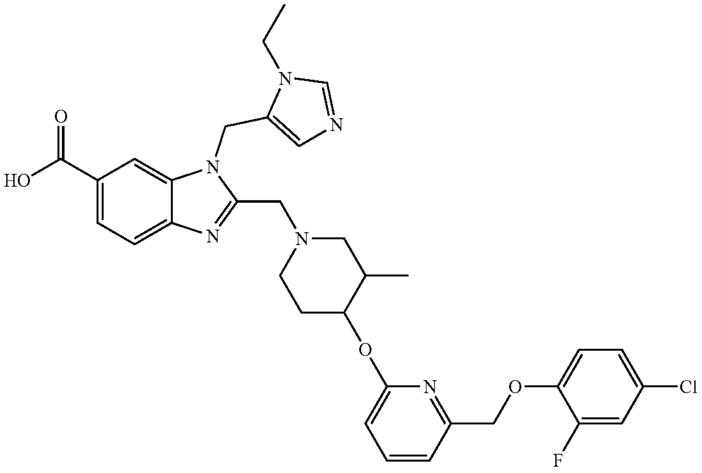 [SMILES: CCn1cncc1Cn1c(CN2CCC(Oc3cccc(COc4ccc(Cl)cc4F)n3)C(C)C2)nc2ccc(C(=O)O)cc21] | 633 |
| Compound C58 | 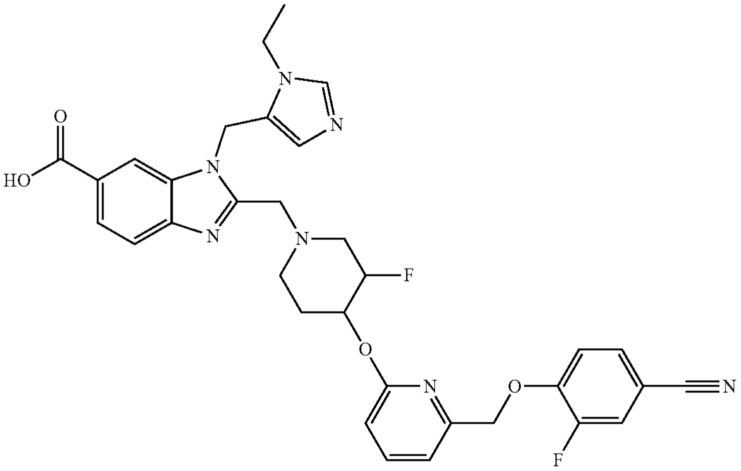 | 628 |
| Compound C59 | 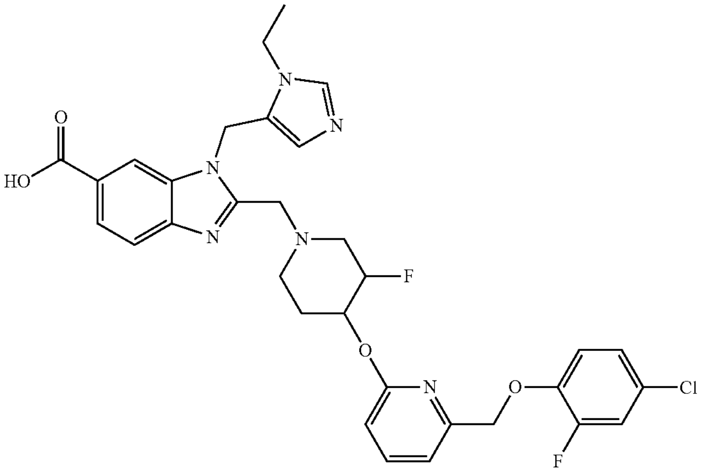 | 637 |

-continued
| Number | Structure | MS m/z: [M + H]$^+$ |
|---|---|---|
| Compound C60 | 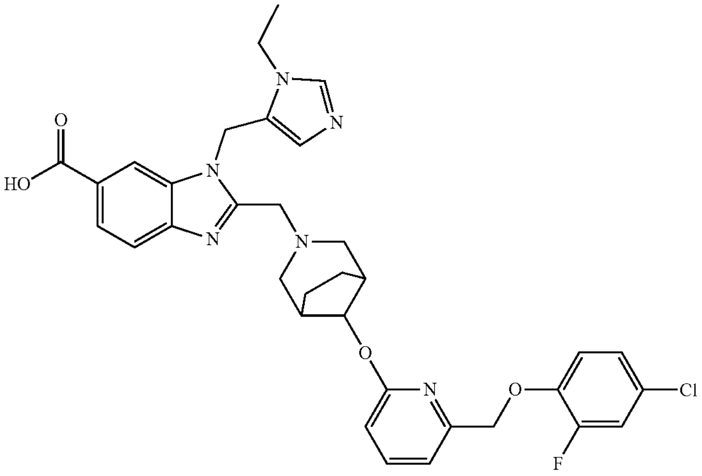 [SMILES: CCn1cncc1Cn1c(CN2CC3CCC(C2)C3Oc2cccc(COc3ccc(Cl)cc3F)n2)nc2ccc(C(=O)O)cc21] | 645 |
| Compound C61 | 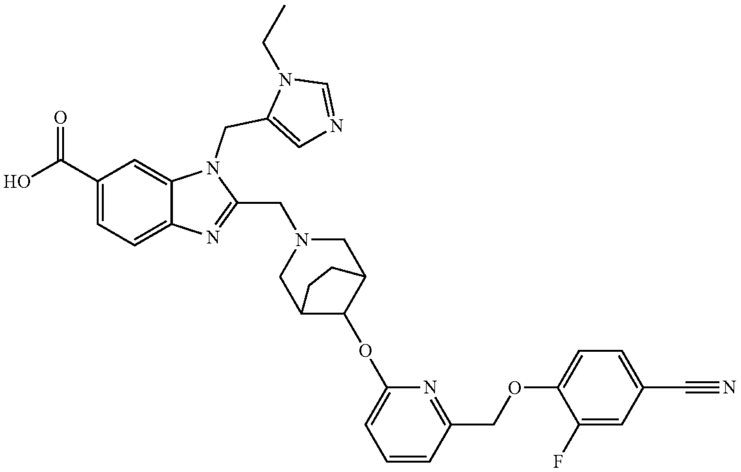 [SMILES: CCn1cncc1Cn1c(CN2CC3CCC(C2)C3Oc2cccc(COc3ccc(C#N)cc3F)n2)nc2ccc(C(=O)O)cc21] | 636 |
| Compound C62 | 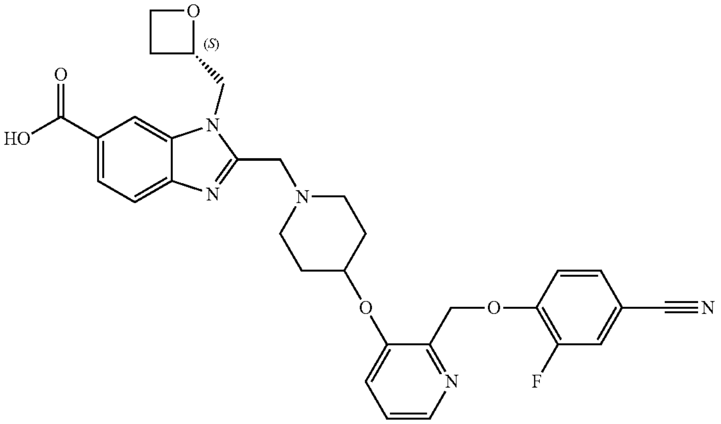 | 572 |

-continued
| Number | Structure | MS m/z: [M + H]+ |
|---|---|---|
| Compound C63 | 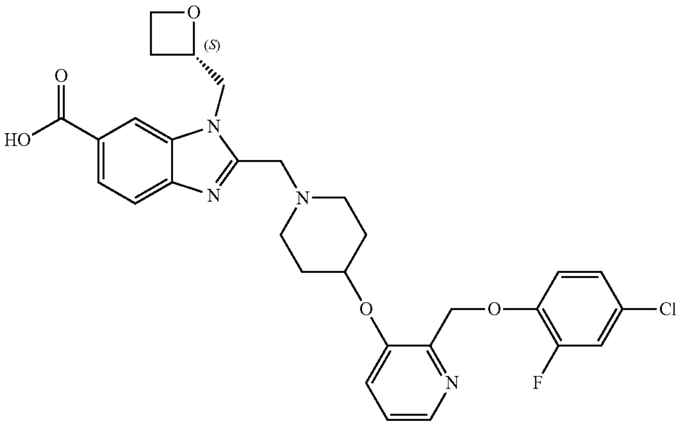 | 581 |
| Compound C64 | 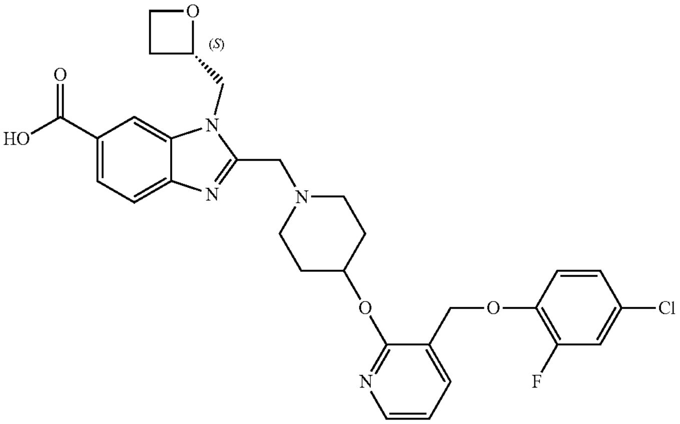 | 581 |
| Compound C65 | 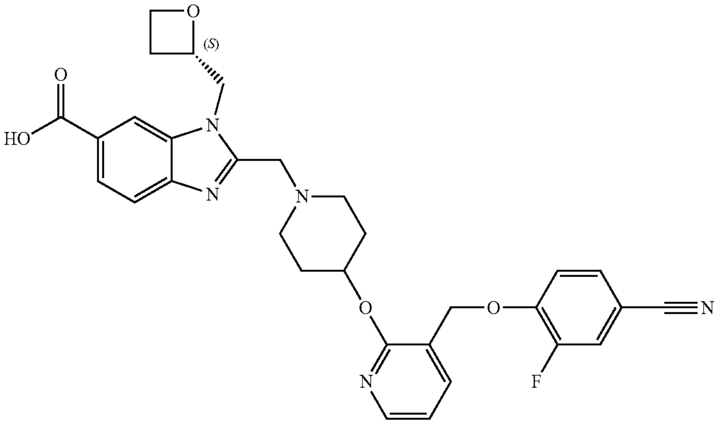 | 572 |

-continued
| Number | Structure | MS m/z: [M + H]+ |
| --- | --- | --- |
| Compound C66 | 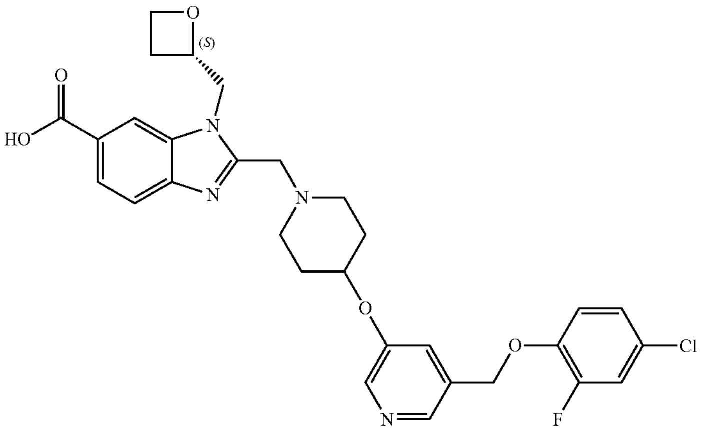 | 581 |
| Compound C67 | 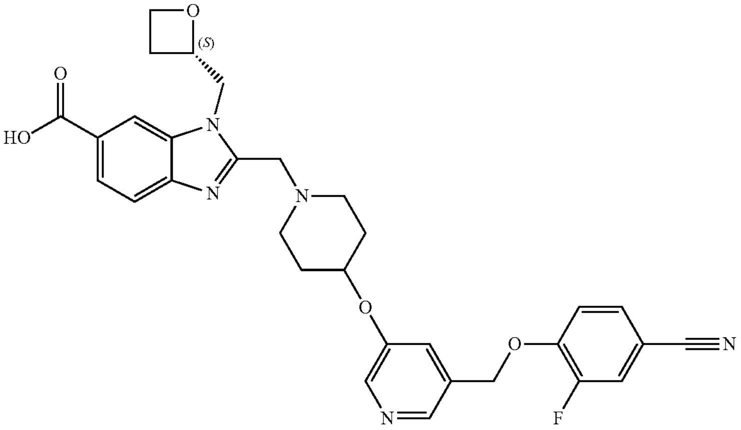 | 572 |
| Compound C68 | 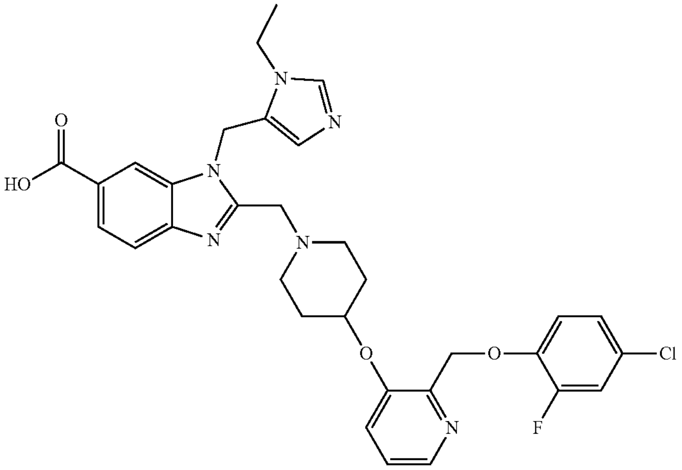 [SMILES: CCn1cncc1Cn1c(CN2CCC(Oc3cccnc3COc3ccc(Cl)cc3F)CC2)nc2ccc(C(=O)O)cc21] | 619 |

-continued
| Number | Structure | MS m/z: [M + H]+ |
| --- | --- | --- |
| Compound C69 | 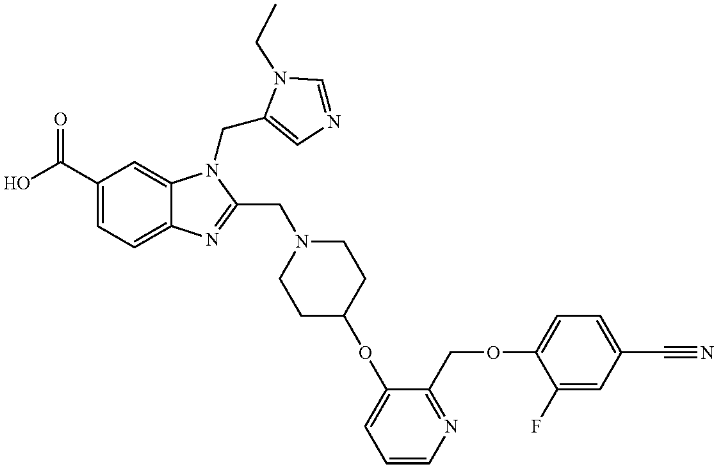 [SMILES: CCn1cncc1Cn1c(CN2CCC(Oc3cccnc3COc3ccc(C#N)cc3F)CC2)nc2ccc(C(=O)O)cc21] | 610 |
| Compound C70 | 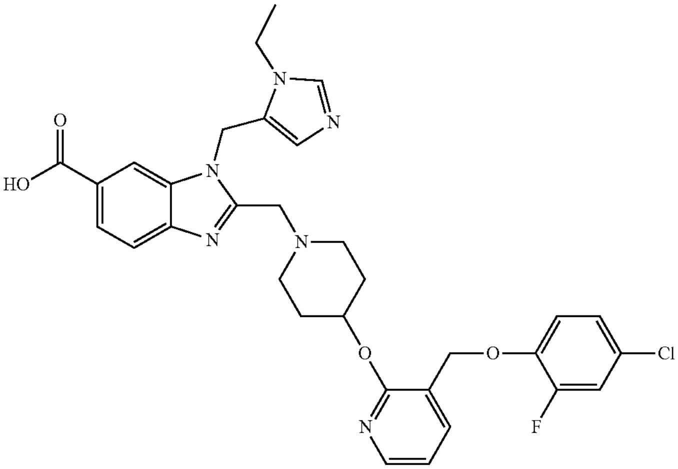 [SMILES: CCn1cncc1Cn1c(CN2CCC(Oc3ncccc3COc3ccc(Cl)cc3F)CC2)nc2ccc(C(=O)O)cc21] | 619 |
| Compound C71 | 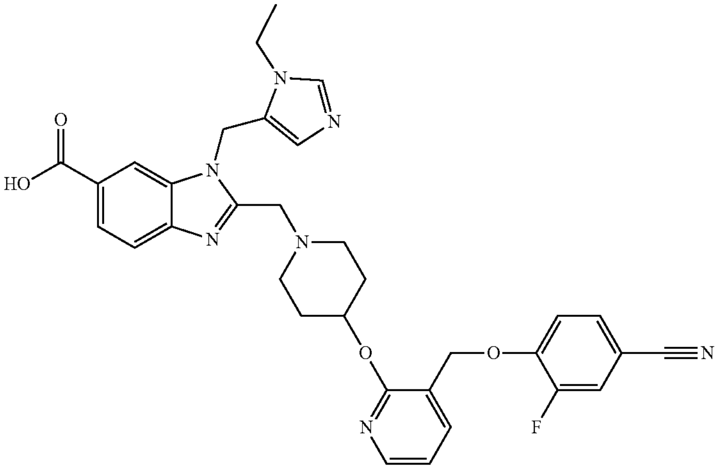 [SMILES: CCn1cncc1Cn1c(CN2CCC(Oc3ncccc3COc3ccc(C#N)cc3F)CC2)nc2ccc(C(=O)O)cc21] | 610 |

-continued
| Number | Structure | MS m/z: [M + H]+ |
| --- | --- | --- |
| Compound C72 | 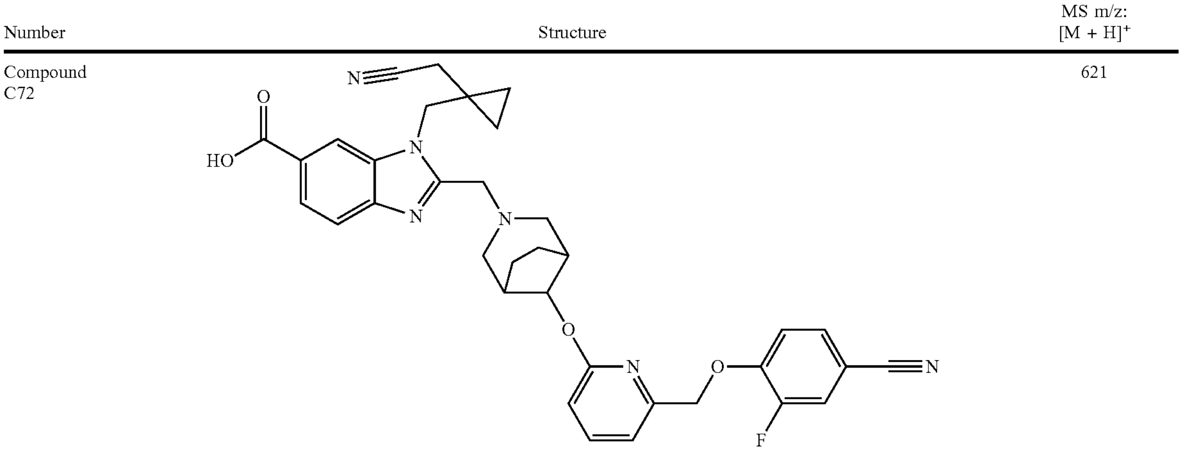 | 621 |
| Compound C73 | 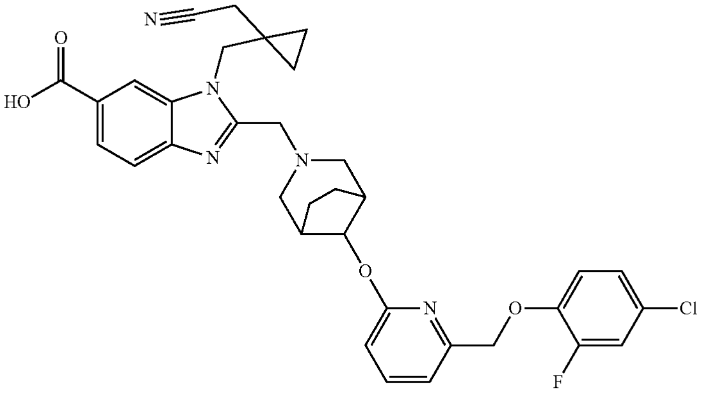 [SMILES: N#CCC1(Cn2c(CN3CC4CCC(C3)C4Oc3cccc(COc4ccc(Cl)cc4F)n3)nc3ccc(C(=O)O)cc32)CC1] | 630 |
| Compound C74 | 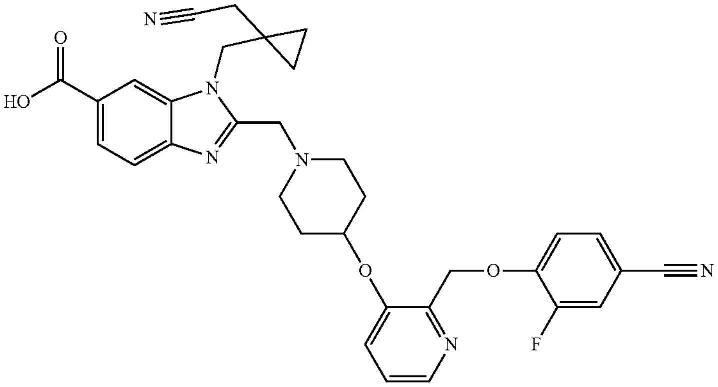 [SMILES: N#CCC1(Cn2c(CN3CCC(Oc4cccnc4COc4ccc(C#N)cc4F)CC3)nc3ccc(C(=O)O)cc32)CC1] | 595 |
| Compound C75 | 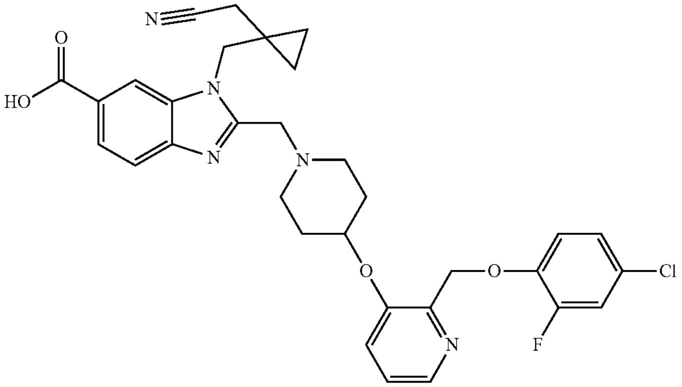 | 604 |

-continued
| Number | Structure | MS m/z: [M + H]$^+$ |
|---|---|---|
| Compound C76 | 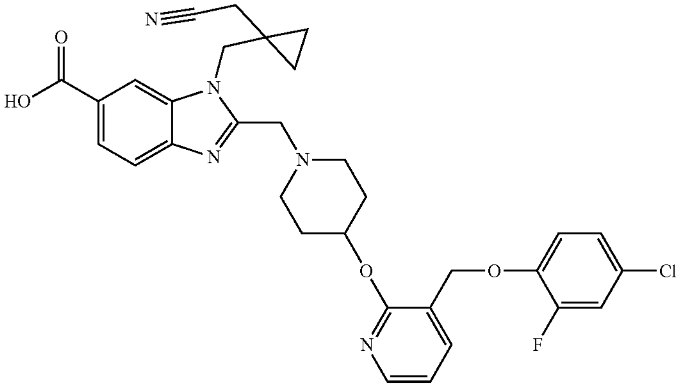 [SMILES: N#CCC1(Cn2c(CN3CCC(Oc4ncccc4COc4ccc(Cl)cc4F)CC3)nc3ccc(C(=O)O)cc32)CC1] | 604 |
| Compound C77 | 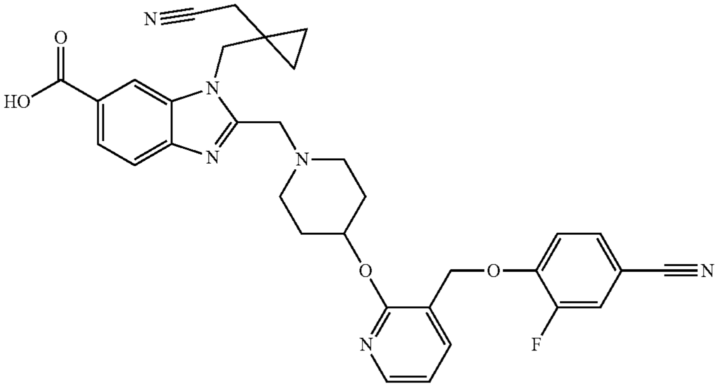 | 595 |
| Compound C78 | 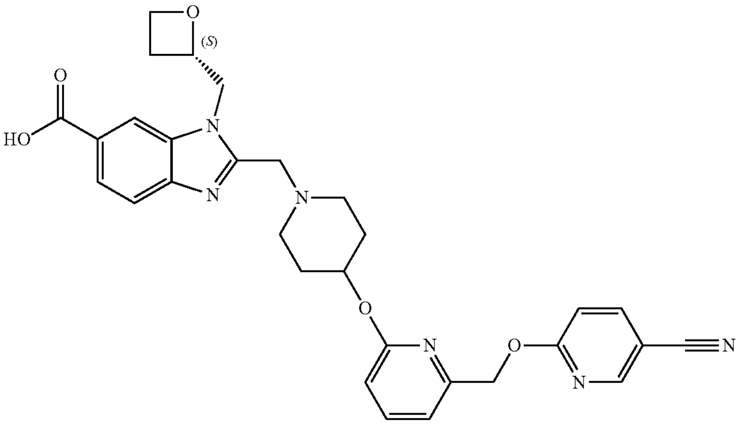 | 555 |

-continued

| Number | Structure | MS m/z: [M + H]$^+$ |
|---|---|---|
| Compound C79 | 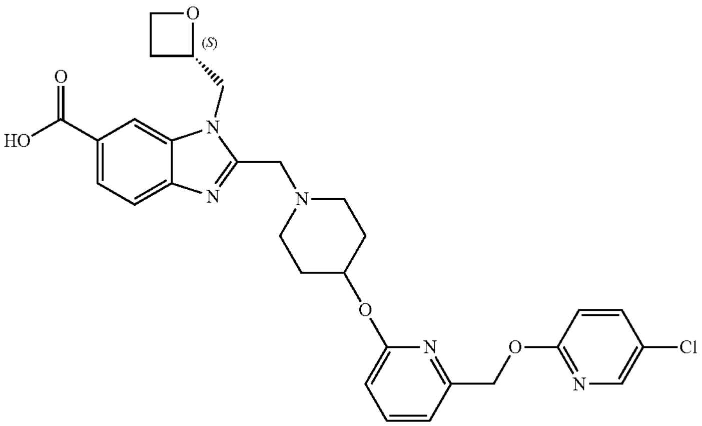 | 564 |
| Compound C80 | 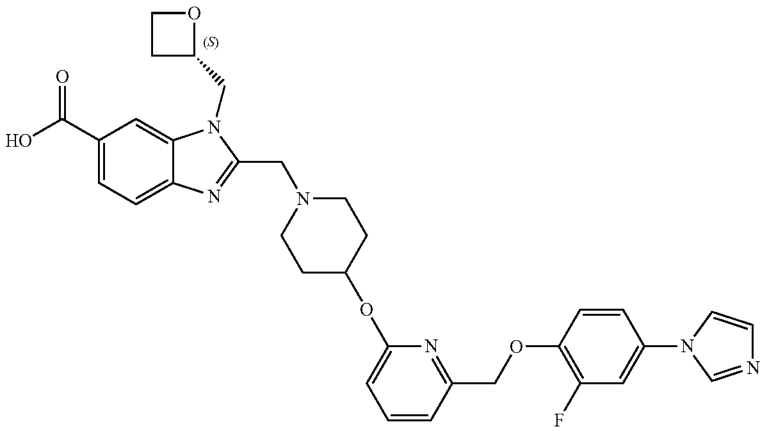 | 613 |
| Compound C81 | 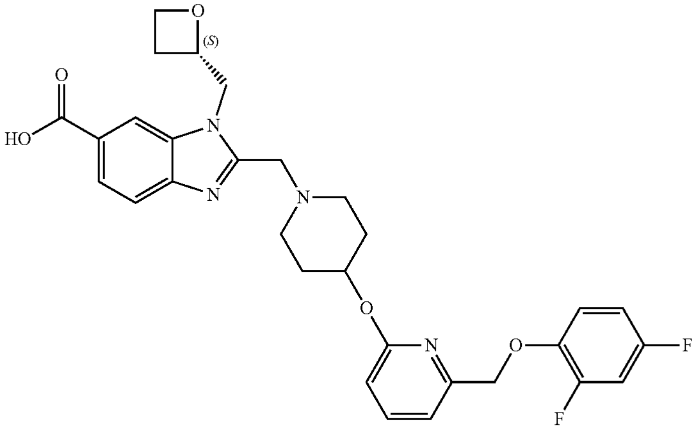 | 565 |

Test Example 1. Detection of agonist activity of the test compounds on GLP-1R

1). Reagents

| Name | Manufacturer |
|---|---|
| cAMP Detection Kit | Cisbio |
| Bovine Serum Albumin(BSA) | Sigma |

-continued

| Name | Manufacturer |
|---|---|
| Hanks' Balanced Salt Solution 1X(HBSS) | Gibco |
| 1M HEPES | Invitrogen |
| 3-Isobutyl-1-methylxanthine(IBMX) | Invitrogen |
| PP-384 well plate | Greiner |
| OptiPlate-384 | PerkinElmer |
| GLP-1(7-37) | Hao Yuan |

2). Equipment

| Instrument | Model | Factory |
|---|---|---|
| EnVision | Envision2014 | PerkinElmer |
| Vi-cell counter | Vi-CELL ™ XR Cell Viability Analyzer | Beckman |
| Bravo | Bravo V11 | Agilent |
| Centrifuge | Allegra ™ 25R Centrifuge | Beckman |
| ECHO | ECHO 555 | Labcyte |

3). Cell line

| Target | Host cell | Source |
|---|---|---|
| GLP-1R | HEK293 | WuXi |

4). Methods and procedures:

1) The test compound was dissolved in DMSO and diluted 4-fold with Bravo for a total of 10 concentration gradients (the starting concentration was 1 mM). The reference compound GLP-1 (7-37) was dissolved in DMSO and diluted 4-fold with Bravo for a total of 10 concentration gradients (starting at 500 nM).

2) The stable transfection GLP-1R/HEK293 cells were resuscitated in a sterile water bath at 37° C. and shaken gently until ice cubes were completely melted.

3) The recovered cells were transferred to a 15 mL sterile centrifuge tube to remove DMSO. HBSS(10 mL) pre-warmed at 37° C. was added, mixed gently, and centrifuged at 1000 rpm for 5 minutes. The supernatant was discarded and another 10 mL of HBSS was added and mixed gently. The cells were counted to measure viability with Vi-cell counter.

4) The cells were re-suspended with assay buffer, counted with a Vi-cell counter, and diluted to $1.0\times10^5$/mL.

5) 10 μL of assay buffer containing cells was added to a 384-well plate with electronic multichannel pipette and the plate was shaken at 1000 rpm for 5 seconds.

6) The diluted test compound solution was transfer to the 384 cell plate with ECHO by 100 nL of transfer volume. The plate was shaken to mix at 2000 rpm for 60 seconds.

7) The cells in the 384-well plate were incubated in $CO_2$ cell incubator at 37° C. for 30 min.

8) 10 μL of HTRF cAMP detection solution was added to the 384-well plate, stick with sealing film, and incubated at room temperature for 1 hour.

9) After 1 hour of incubation, the sealing film was removed. The plate was put into the EnVision microplate reader to read the values of OD665 nm and OD615 nm.

4). Data Analysis a) Calculation formula $$\%\ \text{Activity} = (cAMP\ \text{level of testing sample} - \text{average}\ cAMP\ \text{level of}\ LC)/(\text{average}\ cAMP\ \text{level of}\ HC - \text{average}\ cAMP\ \text{level of}\ LC)\times 100\%$$

$$Z\ \text{factor: } 1-3X(\text{STD\_cAMP level of}\ HC + \text{STD\_cAMP level of}\ HC)/(\text{average}\ cAMP\ \text{level of}\ HC - \text{average}\ cAMP\ \text{level of}\ LC)$$

$$\text{Assay Window: } HC/LC$$

HC: wells with adding the top concentration of reference compound

LC: wells with adding assay buffer b) Using "log (agonist) vs. response--Variable slope" mode of GraphPad Prism 5.0 to fit the dose response curve of each sample and calculate the EC50 value.

TABLE 1

Data And Analysis of Some Representative Compounds

| Numer | $EC_{50}$(nM) | Max activity(%) |
|---|---|---|
| GLP-1(7-37) | 0.02 | 98.1 |
| PF-06882961 | 0.229 | 99.7 |
| Compound 1 | 0.088 | 116.8 |
| Compound 2 | 0.0529 | 98.6 |
| Compound 3 | 0.317 | 128.3 |
| Compound 6 | 0.133 | 114.8 |
| Compound 7 | 0.145 | 91.3 |
| Compound 13 | 0.114 | 99.4 |
| Compound 43 | 0.110 | 109.7 |
| Compound 49 | 0.193 | 129.3 |
| Compound 55 | 0.149 | 111.5 |
| Compound 56 | 0.210 | 124.9 |
| Compound 60 | 0.455 | 112.0 |
| Compound 67 | 1.086 | 106.4 |
| Compound 133 | 0.264 | 126.6 |
| Compound 134 | 0.133 | 117.3 |
| Compound 135 | 0.244 | 109.6 |
| Compound 138 | 0.669 | 125.0 |
| Compound S1 | 1401 | 93.7 |
| Compound S2 | 5.578 | 139.9 |
| Compound S3 | 2170 | 70.1 |
| Compound S4 | 0.29 | 106.9 |
| Compound S5 | 15.44 | 125.2 |
| Compound S6 | 2.6 | 114.9 |
| Compound S20 | 0.962 | 129.1 |
| Compound S22 | 730.8 | 92.7 |
| Compound S23 | 1.472 | 98.0 |
| Compound S36 | 150.2 | 114.2 |
| Compound S41 | 21.68 | 94.8 |
| Compound S66 | 1.253 | 106.7 |
| Compound C1 | 1194 | 76.6 |
| Compound C2 | 0.614 | 123.1 |
| Compound C3 | 0.278 | 122.3 |
| Compound C4 | 0.560 | 147.9 |
| Compound C5 | 2.409 | 112.6 |
| Compound C6 | 13.77 | 99.8 |
| Compound C7 | 23.48 | 90.1 |
| Compound C8 | 25.58 | 117.4 |
| Compound C9 | 3.743 | 97.2 |
| Compound C10 | 4.157 | 110.2 |
| Compound C11 | 1.484 | 114.8 |
| Compound C12 | 0.233 | 125.5 |
| Compound C13 | 1.819 | 141.7 |
| Compound C14 | 0.315 | 101.9 |
| Compound C15 | 0.807 | 109.1 |
| Compound C16 | 2.544 | 99.2 |
| Compound C17 | 0.668 | 127.7 |
| Compound C18 | 0.472 | 103.8 |
| Compound C19 | 1.067 | 134.3 |
| Compound C20 | 0.425 | 137.0 |
| Compound C21 | 46.24 | N/A |
| Compound C22 | 30.37 | N/A |
| Compound C23 | 0.249 | 109.1 |
| Compound C24 | 1.67 | 76.88 |
| Compound C25 | 0.512 | 133.4 |
| Compound C26 | 0.215 | 117.3 |
| Compound C27 | 8.03 | N/A |
| Compound C28 | 5.051 | N/A |
| Compound C29 | 6.831 | 121.6 |
| Compound C30 | 5.851 | 121.2 |
| Compound C31 | 0.833 | 106.6 |
| Compound C32 | 0.768 | 114.3 |
| Compound C33 | 0.068 | 99.1 |
| Compound C34 | 10.98 | 113.6 |
| Compound C35 | >100 | N/A |
| Compound C36 | 3.919 | 104.0 |
| Compound C37 | 0.223 | 121.0 |
| Compound C38 | >100 | N/A |
| Compound C39 | 7.93 | 142.8 |
| Compound C40 | 6.50 | 90.7 |

TABLE 1-continued

| Data And Analysis of Some Representative Compounds | | |
|---|---|---|
| Numer | $EC_{50}$(nM) | Max activity(%) |
| Compound C41 | 4.164 | 122.3 |
| Compound C42 | >100 | N/A |
| Compound C43 | 5.306 | 88.8 |
| Compound C82 | 7.483 | 90.7 |
| Compound C83 | 0.705 | 111.1 |
| Compound C84 | 0.246 | 136.4 |

Data in Table 1 indicated that most of the compounds of the present invention had potent agonistic effects on hGLP1R receptors, and were excellent hGLP1R agonists. Its maximal agonistic effect could reach or even exceed that of GLP1 polypeptide or the control molecule PF-06882961 currently under clinical research.

Test Example 2. Pharmacokinetic Study of the Test Compounds in Mice

The pharmacokinetic properties of some compounds of the present invention were evaluated in mice pharmacokinetic experiments. SPF male CD-1 mice from Beijing Vital River Laboratory Animal Technology Co., Ltd were used with 6 mice in each group. Compounds were dissolved in 10% solutol/90% saline. A single intravenous administration was given at a dose of 1 mg/kg in a volume of 1 mL/kg. A single intragastric administration was given at a dose of 5 mg/kg in a volume of 1 mL/kg. Animals were fasted overnight prior to the administration and resumed feeding 4 hours after administration, ad libitum to water. Blood was collected at 0.0830, 0.25, 0.5, 1, 2, 4, 6, 8 and 24 hours after dosing. About 0.4 mL of whole blood was collected from the saphenous vein of animals and placed in an EDTA-K2 anticoagulation tube. The samples were centrifuged at 4° C. and 4200 rpm for 5 min, and the plasma was transferred into a centrifuge tube and stored at −80° C. until analysis. For plasma sample analysis, the test compounds and internal standards (Labetalol & tolbutamide & Verapamil & dexamethasone & glyburide & Celecoxib) were extracted from mice plasma by protein precipitation method with acetonitrile, and the extracts were analyzed by LC/MS/MS. The measured plasma concentration-time data of individual animals were analyzed with the non-compartmental model of Phoenix WinNonlin 7.0 (Pharsight, USA) software, and the pharmacokinetic parameters of mice were obtained as follows: maximum (peak) plasma drug concentration Cmax; Peak time Tmax; half-life T1/2 and area under the plasma concentration-time curve extrapolated to infinity AUCO-inf.

TABLE 2

| Pharmacokinetic Parameters of Representative Compounds in Mice | | | | | | | |
|---|---|---|---|---|---|---|---|
| Compound | Dose(mg/kg) | Cmax (ng/mL) | AUC0-inf(ng · h/mL) | Cl(mL/min/kg) | Vdss (L/kg) | T1/2 (h) | F (%) |
| PF-06882961 | 1(iv) | — | 370 | 45.1 | 1 | 0.3 | — |
| Compound 55 | | — | 637 | 26.2 | 1.3 | 1.5 | — |
| Compound 49 | | — | 1350 | 12 | 1 | 1 | — |
| Compound 56 | | — | 771 | 21.7 | 1.2 | 2.3 | — |
| Compound C23 | | | 1141 | 15 | 1 | 1 | |
| PF-06882961 | 5(po) | 299 | 366 | — | — | 2.0 | 19.8 |
| Compound 55 | | 483 | 1042 | — | — | 1.7 | 32.7 |
| Compound 49 | | 515 | 1760 | — | — | 3.2 | 20.7 |
| Compound 56 | | 1640 | 2097 | — | — | 1.0 | 54.4 |
| Compound C23 | | 2193 | 2575 | | | 1.4 | 45.1 |

The results in Table2 indicated that compared with the reference molecule PF-06882961, some representative compounds of the present invention such as compounds 56, 49, 55 and C23 had lower clearance rates higher exposure and larger oral bioavailability, and therefore more suitable as candidates for drug development.

Test Example 3. Pharmacokinetic Study of the Test Compounds in Monkeys

The pharmacokinetic properties of compounds of the present invention were evaluated in monkey pharmacokinetic experiments with 3 male Non-naive cynomolgus monkeys per group. Compounds were dissolved in 10% solutol/90% saline. For single intravenous administration, the dose was 1 mg/kg, and the administration volume was 1 mL/kg. For single intragastric administration, the dose was 5 mg/kg, and the administration volume was 1 mL/kg. Animals were fasted overnight with free water before the experiment and resumed feeding 4 hours after administration. Blood was collected at 0.0830, 0.25, 0.5, 1, 2, 4, 6, 8 and 24 hours after dosing. About 0.4 mL of whole blood was collected from the animal's forearm vein and placed in an EDTA-K2 anticoagulant tube. The samples were centrifuged at 4° C. and 4200 rpm for 5 min, and the plasma was transferred to a centrifuge tube and stored at −80° C. until analysis. For plasma sample analysis, the test compounds and internal standards (Labetalol & tolbutamide & Verapamil & dexamethasone & glyburide & Celecoxib) were extracted from monkey plasma by protein precipitation method with acetonitrile, and the extracts were analyzed by LC/MS/MS. Measured plasma concentration-time data in individual animals were analyzed using the non-compartmental model of Phoenix WinNonlin 7.0 (Pharsight, USA) software to obtain the following pharmacokinetic parameters: maximum (peak) plasma drug concentration Cmax; time to peak Tmax; Half-life T1/2 and area under the plasma concentration-time curve extrapolated to infinity AUCO-inf.

TABLE 3

Pharmacokinetic Parameters of Some Representative Compounds in Monkeys

| Compound | Dose(mg/kg) | Cmax (ng/mL) | AUC0-inf(ng · h/mL) | Cl(mL/min/kg) | Vdss (L/kg) | T1/2 (h) | F (%) |
|---|---|---|---|---|---|---|---|
| PF-06882961 | 1(iv) | — | 1167 | 14.4 | 0.3 | 1.1 | — |
| Compound 55 | | — | 1425 | 12.0 | 0.4 | 2.2 | — |
| Compound 49 | | — | 2381 | 7.26 | 0.29 | 1.34 | — |
| PF-06882961 | | 58.8 | 344 | — | — | 2.8 | 5.9 |
| Compound 55 | 5(po) | 214 | 614 | — | — | 5.4 | 8.6 |
| Compound 49 | | 235 | 1244 | — | — | 4.01 | 10.4 |

The results in Table 3 showed that, compared with the reference molecule PF-06882961, some representative compounds of the present invention, such as compound 49 and compound 55, had lower clearance rates, higher exposure, and greater oral bioavailability and half-life, thus more suitable as candidates for drug development.

Test Example 4. Intraperitoneal glucose tolerance (IPGTT) test in h-GLP1-R C57BL6J mice 1) Formulation The compounds to be tested were dissolved in 10% Solutol HS15+90% Saline, and vortexed by ultrasonic to dissolve.

2) Animals

Male SPF h-GLP1-R $C_{57}$BL6J mice, 6-9 weeks old, weighing 20 g-25 g.

3) Animal acclimation and grouping

Upon arrival, animals were acclimated for 7 days before experiments. The body weight and random blood sugar of the animals were measured one day before administration. Animals were divided into 4 groups based on body weight and random blood glucose.

The animal grouping information was as follows

TABLE 4

Animal Grouping Information

| Group | Dose level (mg/kg) | Dose (ml/kg) | Route of administration | Frequency |
|---|---|---|---|---|
| Vehicle | — | 10 | PO | QD |
| PF-06882961 | 0.3 | 10 | PO | QD |
| Compound 55 | 0.3 | 10 | PO | QD |

4) IPGTT test

Mice were overnight fasted before IPGTT. Baseline fasting blood glucose and insulin level were measured before vehicle or compound dosing. 30 min post of compound dosing, glucose were injected intraperitonelly (2 g/kg, 10 ml/kg). Blood glucose levels were measured at −30, 0, 15, 30, 60, 120 min. Plasma 15 ul were collected at 0 and 15 min for insulin analysis by Rat/Mouse Insulin Elisa Kit.

5) Data analysis

AUC $_{0-120}$ min was the area under the blood glucose-time curve. Insulin change was the difference between 15 min and 0 min plasma insulin concentration. Statistical analysis of data was performed with Graphpad Prism 6, and the statistical method was one-way ANOVA Dunnett test. Compared with the vehicle group, $p<0.05$ was considered a significant difference. * means $p<0.05$,  means $p<0.01$, * means $p<0.001$.

6) Experimental Results

Figure 2:
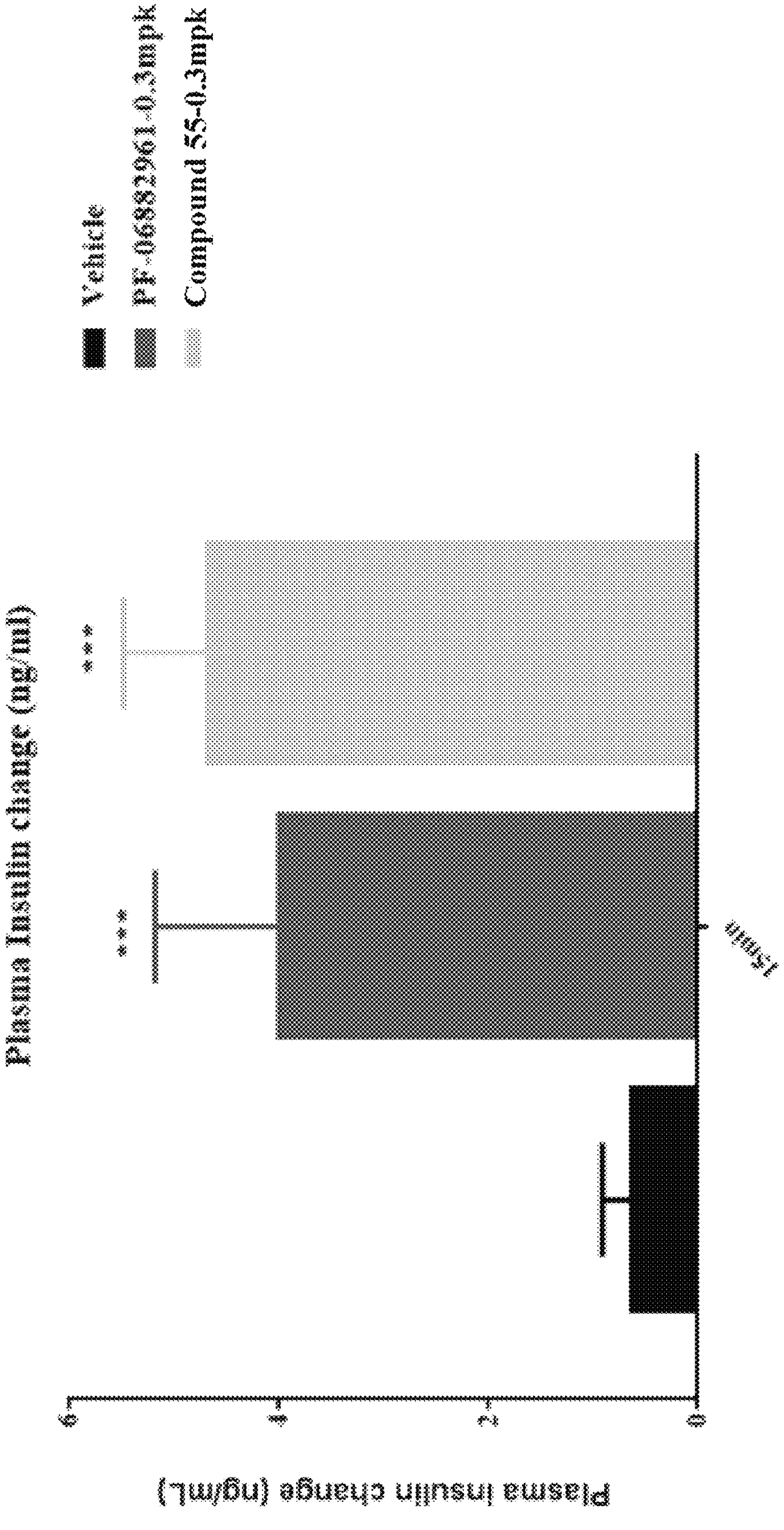
FIG. 2 shows comparison of the effects of the compounds of the present invention and known drugs on the insulin-stimulating release of IPGTT in hGLP1R mice.

As shown in FIGS. 1 and 2, a single oral dose of compound 55 significantly reduced the blood glucose eduring IPGTT. AUC 0-120 min results showed that 0.3 mpk had a significant difference compared with the vehicle group. Insulin change results showed that 0.3 mpk compound 55 could significantly increase insulin secretion. In conclusion, compound 55 showed similar or slightly better hypoglycemic and insulin-releasing effects compared with the control molecule PF-06882961.

Test Example 5. Intravenous Glucose Tolerance (IVGTT) Experiment in Cynomolgus Monkey 1) Formulation The compounds were dissolved in 10% Solutol HS15+90% Saline by vortex ultrasound. Vehicle was 10% Solutol HS15+90% Saline.

2) Animals

Male cynomolgus monkeys, 10-15 years old, weighing 6-13 kg. Healthy animals were selected for efficacy studies according to alanine aminotransferase (ALT), aspartate aminotransferase (AST), triglyceride (TG), total cholesterol (TC), high density lipoprotein (HDL), low density lipoprotein (LDL), glycosylated hemoglobin (HbAlc), body weight (BW).

3) Animal Acclimation and Grouping

After 1 week of acclimation, the IVGTT baseline before administration was measured, and the animals were grouped according to the insulin and blood glucose results of the IVGTT. The detailed information of treatment was as follows

TABLE 5

Animal Grouping Information

| Group | Dose level (mg/kg) | Dose (ml/kg) | Route of administration | Frequency |
|---|---|---|---|---|
| Vehicle | — | 5 | PO | QD |
| PF-06882961 | 100 | 5 | PO | QD |
| Compound 49 | 60 | 5 | PO | QD |
| Compound 49 | 100 | 5 | PO | QD |
| Compound 55 | 100 | 5 | PO | QD |

4) IVGTT Test

IVGTT was started after 2 hours post of compound dosing. Blood were collected—at −15 min, 0 min (before sugar administration), and 2, 5, 7, 10, 20, and 30 min after sugar administration. And the blood glucose level were measured.

5) Data Analysis

Data was analyzed by Graphpad Prism 6 and the statistical method was one-way ANOVA Dunnett's test. Compared with the vehicle group, $p<0.05$ was considered significant difference. * means $p<0.05$,  means $p<0.01$, * means $p<0.001$.

6) Experimental results

Figure 3:
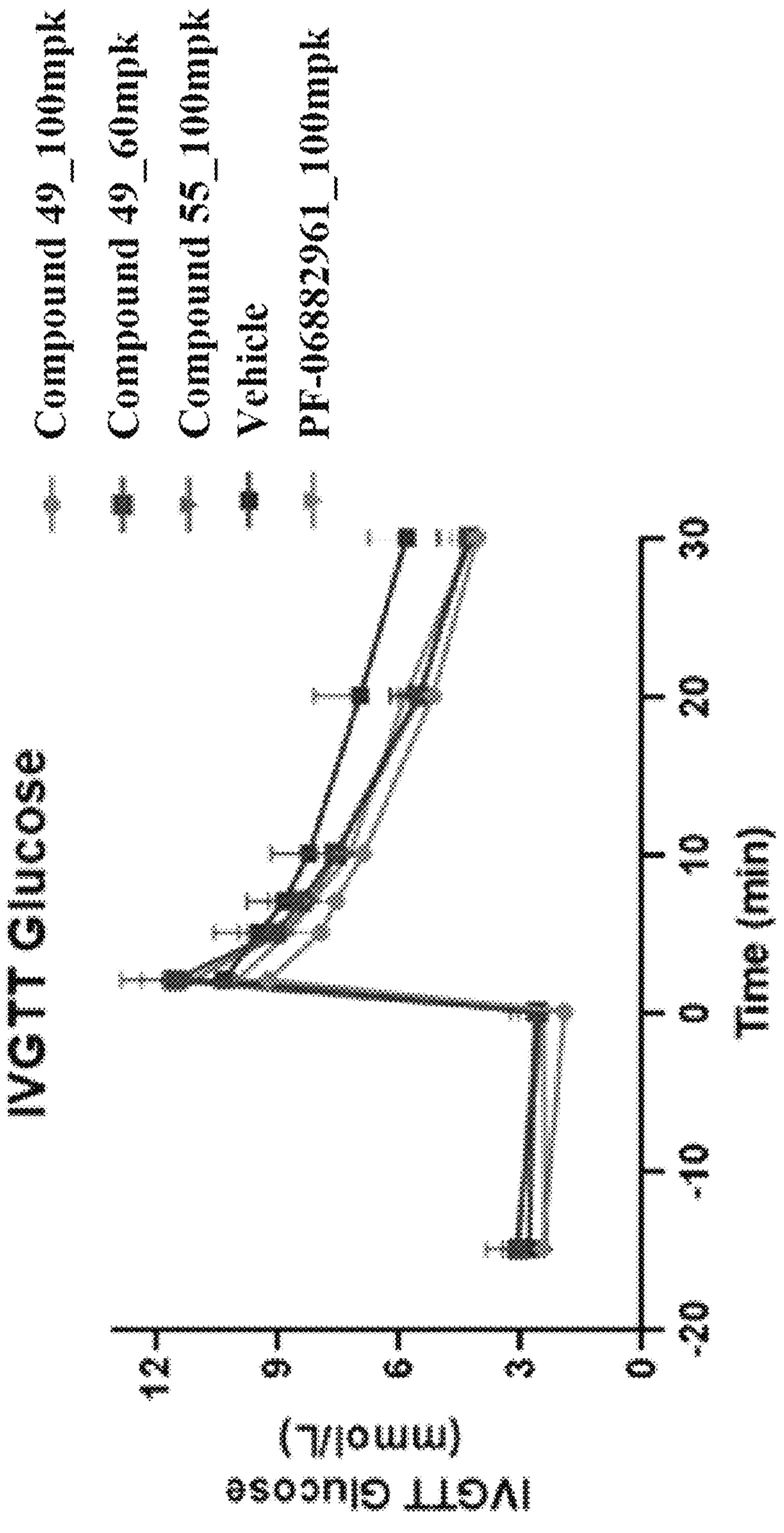
FIG. 3 shows comparison curve of the effect of the compounds of the present invention and known drugs on blood glucose of cynomolgus monkey IVGTT.

As shown in FIG. 3, in the IVGTT experiment, a single oral dose of 100 mg/kg compound 49, 55 or PF-06882961 could significantly lower the blood glucose level. Compared with PF-06882961, compound 49 was slightly more effective, and the effect of compound 55 was equivalent. Furthermore, compound 49 still had a significant hypoglycemic effect in the 60 mg/kg dose group.

The embodiments of the present invention have been described above. However, the present invention is not limited to the above-described embodiments. Any modification, equivalent replacement, improvement, etc. made within the spirit and principle of the present invention shall be included within the protection scope of the present invention.

The invention claimed is:

1. A compound of Formula (IE), pharmaceutically acceptable salts, or enantiomers thereof, Formula (IE)

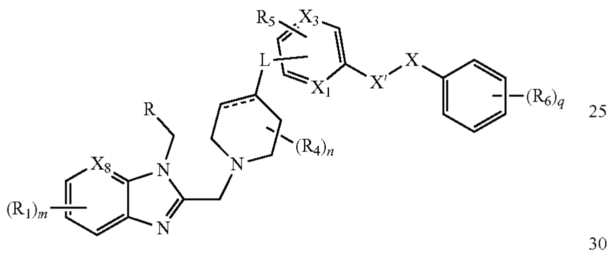

wherein,

------ =represents a single bond;

X represents —O—;

X' represents —C($R_{d1}$)($R_{d2}$)—;

L represents —O—;

$X_1$ represents —N—;

$X_3$ represents —N—;

$X_8$ represents —$CR_5$— or —N—;

R is 5- to 8-membered heteroaryl, 3- to 8-membered saturated or partially saturated heterocyclyl, or 3- to 8-membered saturated or partially saturated cycloalkyl, and wherein the heteroaryl, heterocyclyl, and cycloalkyl are optionally substituted with one to multiple substituent groups independently selected from methyl, ethyl, propyl, butyl, 2-methyl-propyl, 1,1-dimethylethyl, pentyl, and hexyl;

each $R_1$ is the same or different and is independently selected from the group consisting of hydrogen, deuterium, halogen, $C_{1-10}$ alkyl, halogen-substituted $C_{1-10}$ alkyl, deuterium substituted $C_{1-10}$ alkyl, and —COOH;

each $R_4$ is the same or different and is independently selected from hydrogen, deuterium, halogen, $C_{1-10}$ alkyl, and $C_{1-10}$ alkoxy;

$R_5$ is selected from hydrogen, deuterium, halogen, CN, $C_{1-10}$ alkyl, $C_{2-10}$ alkynyl, and $C_{1-10}$ alkoxy;

each $R_6$ is the same or different and is independently selected from hydrogen, deuterium, halogen, CN, $C_{1-10}$ alkyl, $C_{2-10}$ alkynyl, and $C_{1-10}$ alkoxy;

$R_{d1}$ and $R_{d2}$ are independently selected from hydrogen, deuterium, halogen, and $C_{1-10}$ alkyl;

m is an integer selected from 1 and 2;

n is an integer selected from 0, 1 and 2; and q is an integer selected from 0, 1 and 2.

2. The compound according to claim 1, pharmaceutically acceptable salts, or enantiomers thereof, wherein R is oxetanyl or imidazolyl, wherein the oxetanyl or imidazolyl is optionally substituted with methyl, ethyl, propyl, butyl, 2-methyl-propyl, 1,1-dimethylethyl, pentyl, or hexyl.

3. The compound according to claim 1, pharmaceutically acceptable salts, or enantiomers thereof, wherein, each $R_1$ is the same or different and is independently selected from the group consisting of hydrogen, F and —COOH;

each $R_4$ is the same or different and is independently selected from the group consisting of hydrogen, deuterium, F and methyl;

$R_5$ is selected from the group consisting of hydrogen, deuterium and F;

each $R_6$ is the same or different and is independently selected from the group consisting of hydrogen, deuterium, halogen, ethynyl and CN.

4. The compound according to claim 1, pharmaceutically acceptable salts, or enantiomers thereof, wherein, m is 1; n is 0; q is 2.

5. A compound selected from the following compounds, or pharmaceutically acceptable salts, or enantiomers thereof:

| Number | Structure |
|---|---|
| Compound 1 | 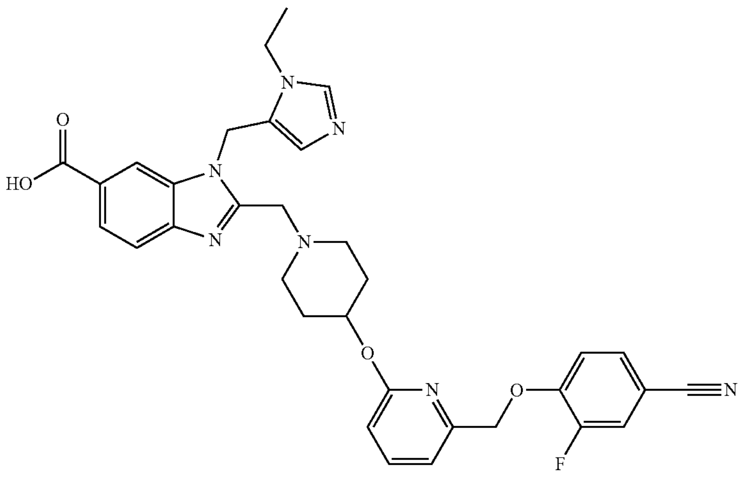 |

-continued
| Number | Structure |
| --- | --- |
| Compound 2 | 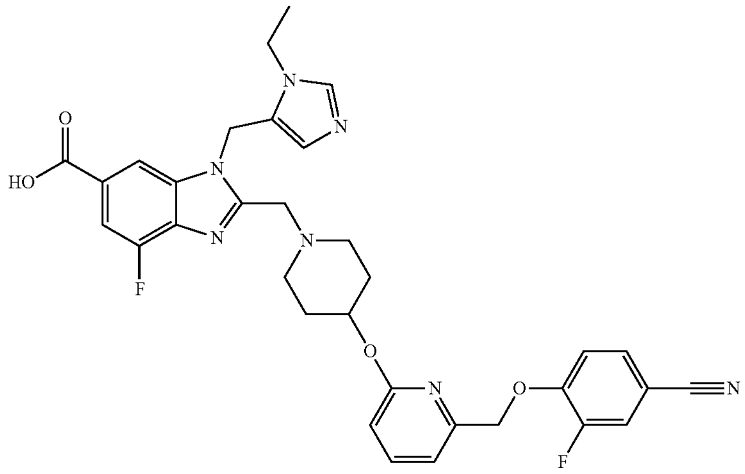 [SMILES: CCn1cncc1Cn1c(CN2CCC(Oc3cccc(COc4ccc(C#N)cc4F)n3)CC2)nc2c(F)cc(C(=O)O)cc21] |
| Compound 3 | 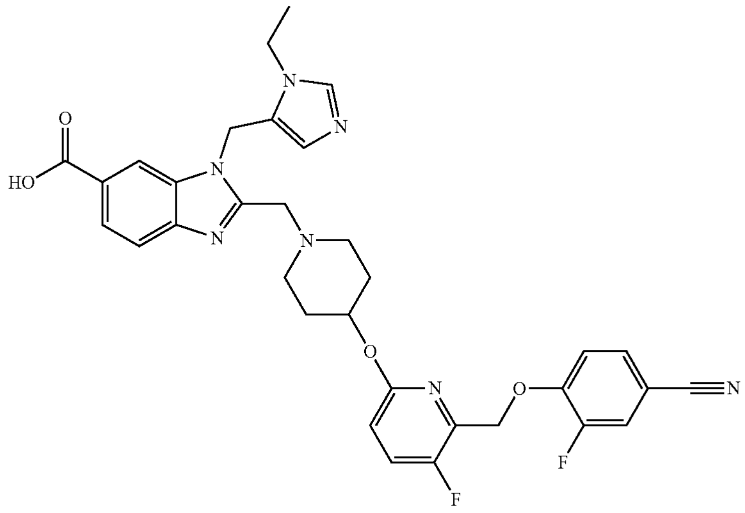 [SMILES: CCn1cncc1Cn1c(CN2CCC(Oc3ccc(F)c(COc4ccc(C#N)cc4F)n3)CC2)nc2ccc(C(=O)O)cc21] |
| Compound 4 | 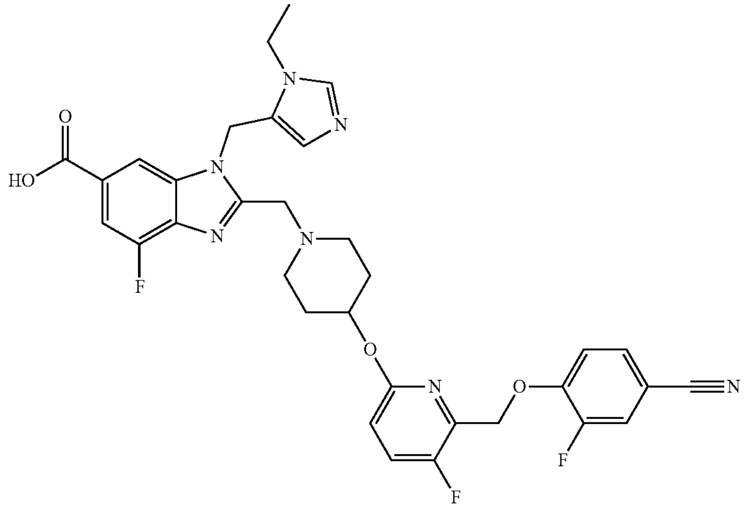 [SMILES: CCn1cncc1Cn1c(CN2CCC(Oc3ccc(F)c(COc4ccc(C#N)cc4F)n3)CC2)nc2c(F)cc(C(=O)O)cc21] |

-continued
| Number | Structure |
|---|---|
| Compound 43 | 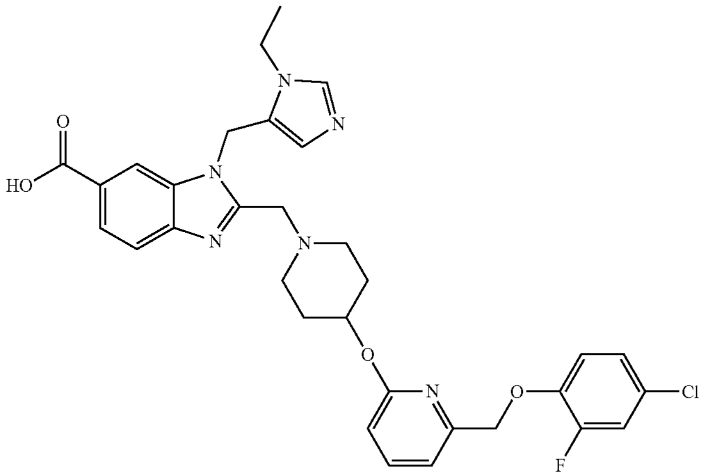 [SMILES: CCn1cncc1Cn1c(CN2CCC(Oc3cccc(COc4ccc(Cl)cc4F)n3)CC2)nc2ccc(C(=O)O)cc21] |
| Compound 44 | 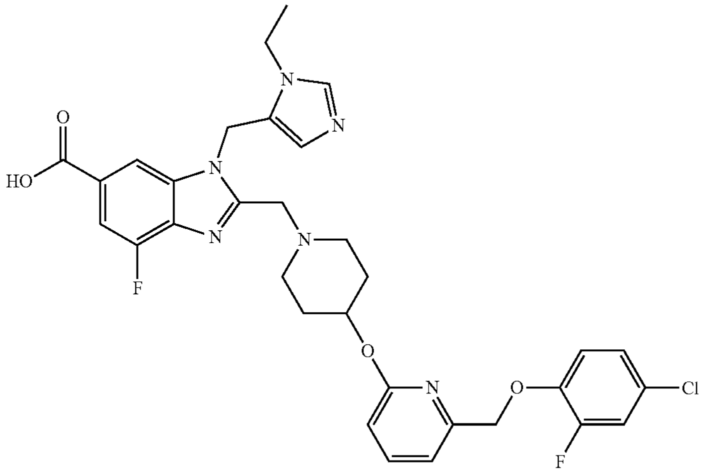 [SMILES: CCn1cncc1Cn1c(CN2CCC(Oc3cccc(COc4ccc(Cl)cc4F)n3)CC2)nc2c(F)cc(C(=O)O)cc21] |
| Compound 45 | 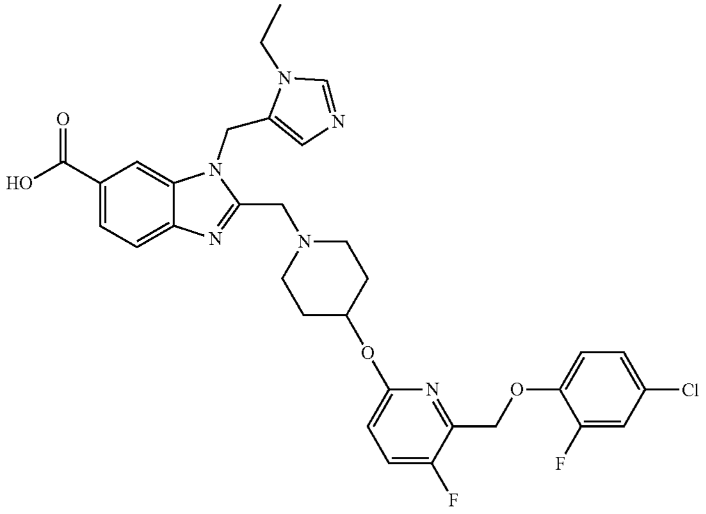 |

-continued
| Number | Structure |
|---|---|
| Compound 46 | 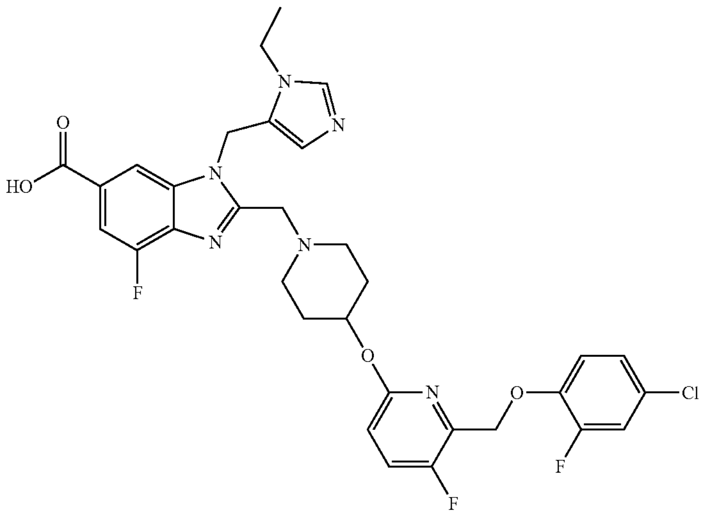 |
| Compound C3 | |
| Compound C5 | 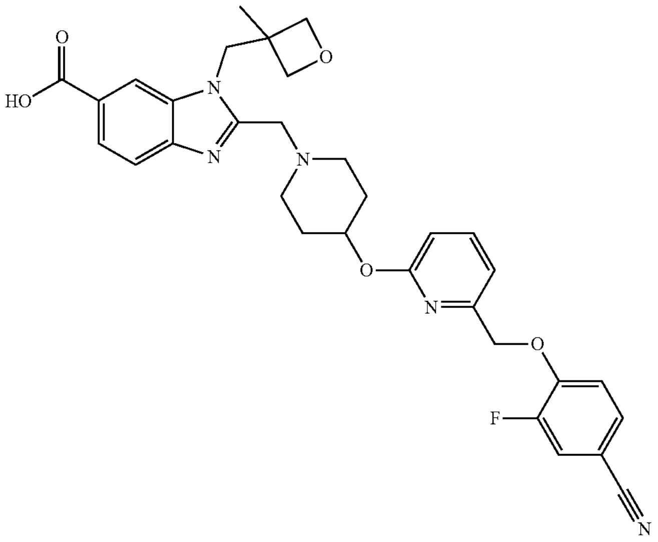 [SMILES: CC1(Cn2c(CN3CCC(Oc4cccc(COc5ccc(C#N)cc5F)n4)CC3)nc3ccc(C(=O)O)cc32)COC1] |
| Compound C6 | 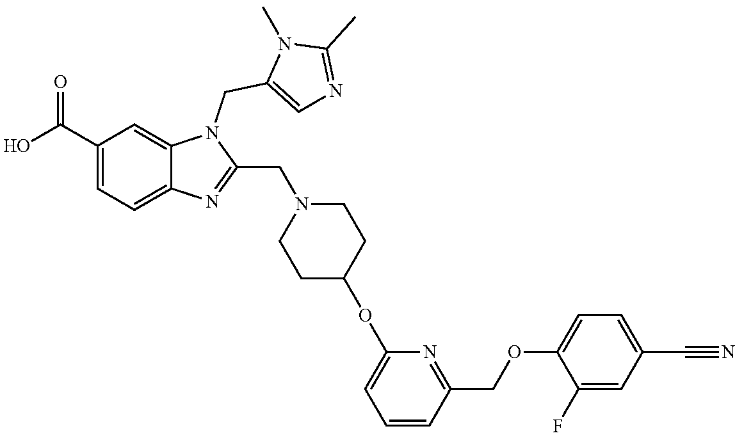 [SMILES: Cc1ncc(Cn2c(CN3CCC(Oc4cccc(COc5ccc(C#N)cc5F)n4)CC3)nc3ccc(C(=O)O)cc32)n1C] |

-continued
| Number | Structure |
|---|---|
| Compound C14 | 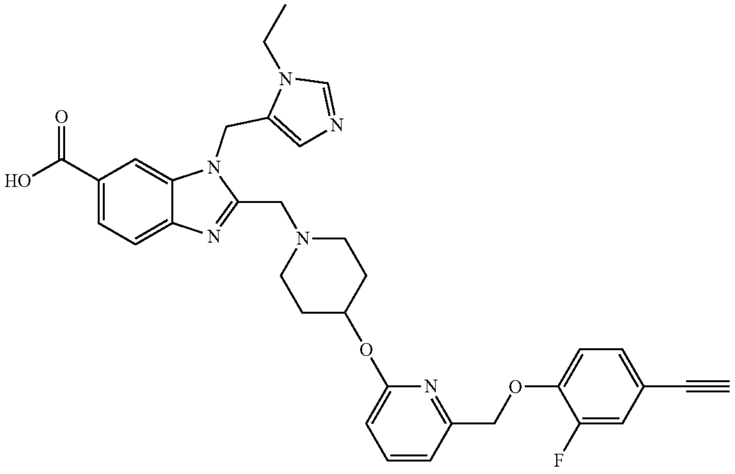 [SMILES: C#Cc1ccc(OCc2cccc(OC3CCN(Cc4nc5ccc(C(=O)O)cc5n4Cc4cncn4CC)CC3)n2)c(F)c1] |
| Compound C19 | 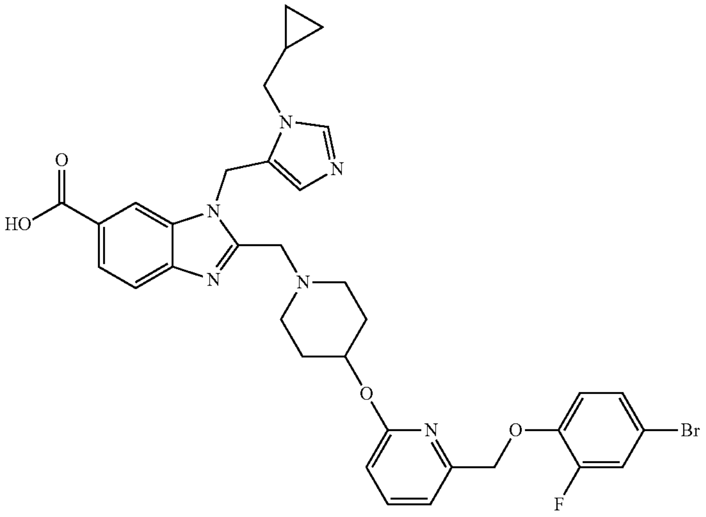 [SMILES: O=C(O)c1ccc2nc(CN3CCC(Oc4cccc(COc5ccc(Br)cc5F)n4)CC3)n(Cc3cncn3CC3CC3)c2c1] |
| Compound C31 | 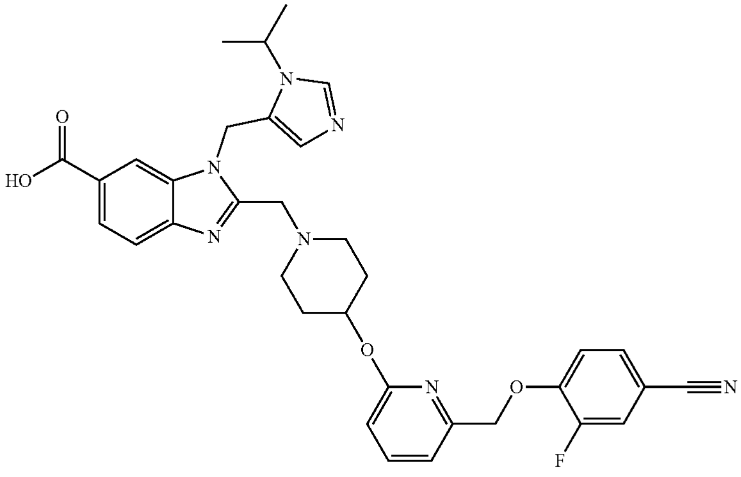 [SMILES: CC(C)n1cncc1Cn1c(CN2CCC(Oc3cccc(COc4ccc(C#N)cc4F)n3)CC2)nc2ccc(C(=O)O)cc21] |

-continued
| Number | Structure |
|---|---|
| Compound C33 | 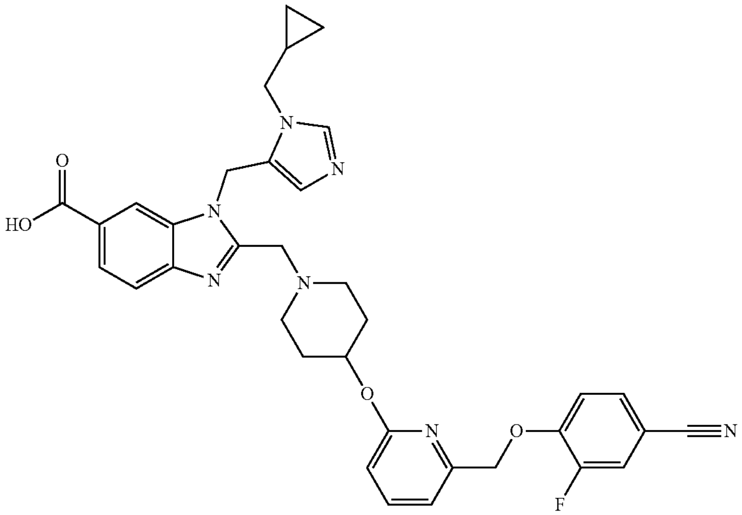 [SMILES: N#Cc1ccc(OCc2cccc(OC3CCN(Cc4nc5ccc(C(=O)O)cc5n4Cc4cncn4CC4CC4)CC3)n2)c(F)c1] |
| Compound C45 | 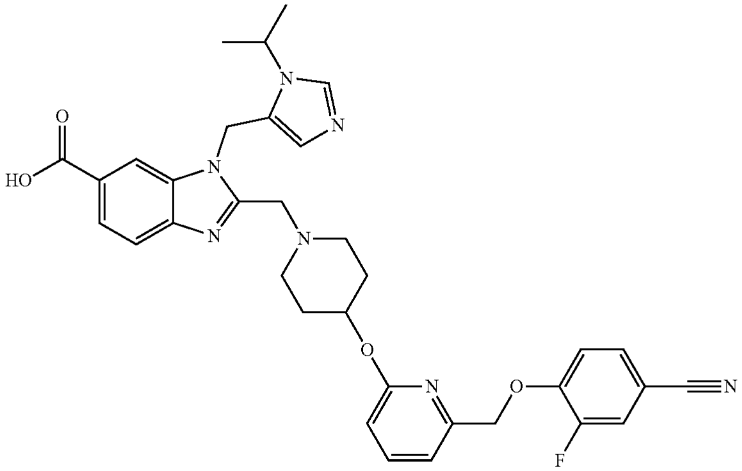 [SMILES: CC(C)n1cncc1Cn1c(CN2CCC(Oc3cccc(COc4ccc(C#N)cc4F)n3)CC2)nc2ccc(C(=O)O)cc21] |
| Compound C56 | 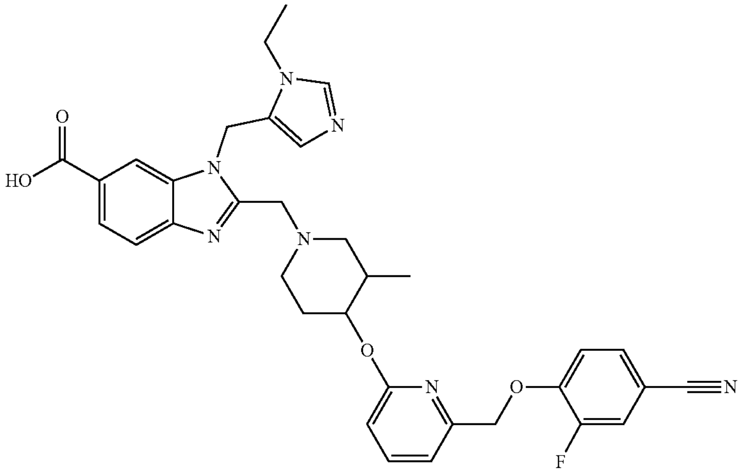 [SMILES: CCn1cncc1Cn1c(CN2CCC(Oc3cccc(COc4ccc(C#N)cc4F)n3)C(C)C2)nc2ccc(C(=O)O)cc21] |

-continued
| Number | Structure |
|---|---|
| Compound C57 | 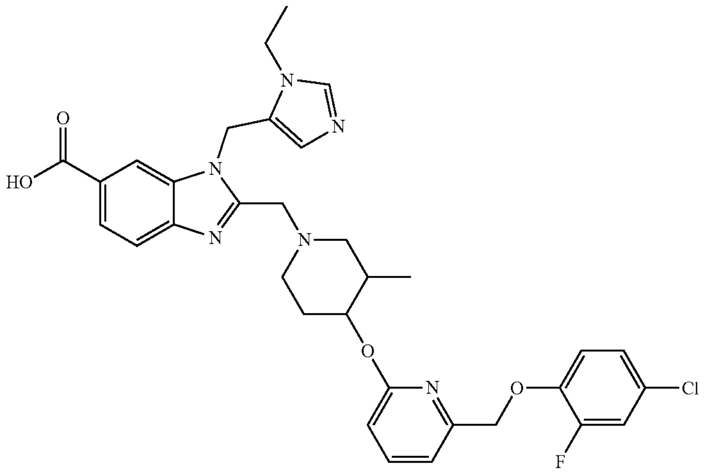 [SMILES: CCn1cncc1Cn1c(CN2CCC(Oc3cccc(COc4ccc(Cl)cc4F)n3)C(C)C2)nc2ccc(C(=O)O)cc21] |
| Compound C58 | 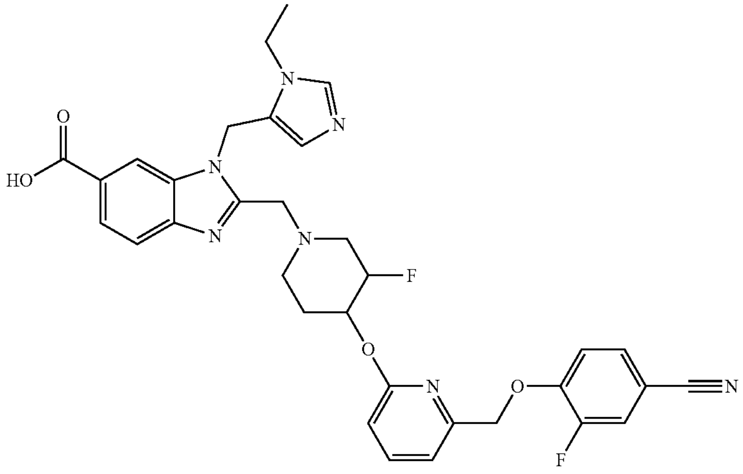 |
| Compound C59 | 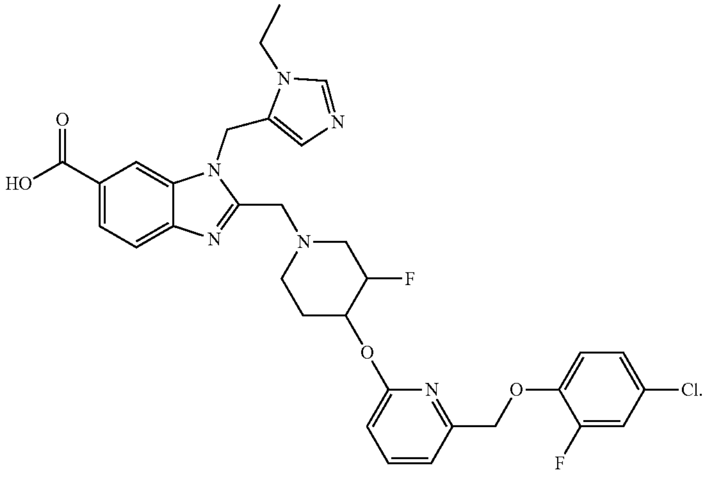 [SMILES: CCn1cncc1Cn1c(CN2CCC(Oc3cccc(COc4ccc(Cl)cc4F)n3)C(F)C2)nc2ccc(C(=O)O)cc21] |

6. A pharmaceutical composition comprising a therapeutically effective amount of a compound of claim 1.

7. A method of treating a disease comprising administering to a patient a therapeutically effective amount of a compound of claim 1, wherein the disease is overweight, diabetes, hyperglycemia, insulin resistance, impaired glucose tolerance, diabetic neuropathy, diabetic nephropathy, diabetic retinopathy, adipocyte dysfunction, visceral fat deposition, sleep apnea, obesity, weight gain due to use of other drugs, dyslipidemia, NAFLD, cardiovascular disease, atherosclerosis sclerosis, or peripheral vascular disease.

8. A method of treating a disease comprising administering to a patient a therapeutically effective amount of a compound of claim 5, or a pharmaceutically acceptable salt or enantiomer thereof, wherein the disease is overweight, diabetes, hyperglycemia, insulin resistance, impaired glucose tolerance, diabetic neuropathy, diabetic nephropathy, diabetic retinopathy, adipocyte dysfunction, visceral fat deposition, sleep apnea, obesity, weight gain due to use of other drugs, dyslipidemia, NAFLD, cardiovascular disease, atherosclerosis sclerosis, or peripheral vascular disease.

9. A pharmaceutical composition comprising a therapeutically effective amount of a compound of claim 5.

10. The method of claim 7, wherein the disease is overweight or obesity.

11. The method of claim 7, wherein the disease is diabetes.

12. The method of claim 8, wherein the disease is overweight or obesity.

13. The method of claim 8, wherein the disease is diabetes.

* * * * *